(12) United States Patent
Ameriks et al.

(10) Patent No.: US 11,820,766 B2
(45) Date of Patent: Nov. 21, 2023

(54) MONOACYLGLYCEROL LIPASE MODULATORS

(71) Applicant: Janssen Pharmaceutica NV, Beerse (BE)

(72) Inventors: Michael K. Ameriks, San Diego, CA (US); Gang Chen, San Diego, CA (US); Chaofeng Huang, San Diego, CA (US); Brian Ngo Laforteza, San Diego, CA (US); Suchitra Ravula, San Diego, CA (US); Emma Helen Southgate, Burlingame, CA (US); Wei Zhang, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/132,313

(22) Filed: Dec. 23, 2020

(65) Prior Publication Data
US 2022/0332713 A1    Oct. 20, 2022

Related U.S. Application Data

(63) Continuation of application No. 16/586,088, filed on Sep. 27, 2019, now abandoned.

(60) Provisional application No. 62/738,600, filed on Sep. 28, 2018.

(51) Int. Cl.
*C07D 471/04* (2006.01)
*C07D 487/04* (2006.01)
*C07D 519/00* (2006.01)

(52) U.S. Cl.
CPC ......... *C07D 471/04* (2013.01); *C07D 487/04* (2013.01); *C07D 519/00* (2013.01)

(58) Field of Classification Search
CPC .. C07D 471/04; C07D 487/04; C07D 498/04; C07D 513/04; C07D 519/00
See application file for complete search history.

(56) References Cited

U.S. PATENT DOCUMENTS

| | | | |
|---|---|---|---|
| 4,812,462 A | 3/1989 | Blankley et al. |
| 4,816,463 A | 3/1989 | Blankley et al. |
| 5,338,744 A | 8/1994 | Dudley et al. |
| 8,431,704 B2 | 4/2013 | Love et al. |
| 8,513,248 B2 | 8/2013 | Dean et al. |
| 8,871,760 B2 | 10/2014 | Brotherton-Pleiss et al. |
| 8,933,236 B2 | 1/2015 | Chowdhury et al. |
| 8,987,249 B2 | 3/2015 | Anderskewitz et al. |
| 9,056,874 B2 | 6/2015 | Adams et al. |
| 9,066,946 B2 | 6/2015 | Alcazar Vaca et al. |
| 9,156,824 B2 | 10/2015 | Dally et al. |
| 9,181,271 B2 | 11/2015 | Li et al. |
| 9,233,974 B2 | 1/2016 | Link et al. |
| 9,242,969 B2 | 1/2016 | Barsanti et al. |
| 9,273,047 B2 | 3/2016 | Hunt et al. |
| 9,273,947 B2 | 3/2016 | Kim et al. |
| 9,290,476 B2 | 3/2016 | Leonard et al. |

(Continued)

FOREIGN PATENT DOCUMENTS

CN    101778850 A    7/2010
FR    2857363 A1    1/2005

(Continued)

OTHER PUBLICATIONS

Alekseev, et al., Use of the Graebe-Ullmann Reaction in the Synthesis of 8-Methyl-Y-Carboline and Isomeric Aromatic Aza-Y-Carbolines, Chemistry of Heterocyclic Compounds, 2012, pp. 1235-1250, vol. 48 Issue 8.

Arbeloa, et al., P2X7 receptor blockade prevents ATP excitotoxicity in neurons and reduces brain damage after schemia, Neurobiology of Disease, 2012, pp. 954-961, vol. 45.

Arulkumaran, et al., A potential therapeutic role for P2X7 receptor (P2X7R) antagonists in the treatment of Inflammatory diseases, Expert Opin Investig, 2011, pp. 897-915, vol. 20 Issue 7.

Avignone, et al., Status Epilepticus Induces a Particular Microglial Activation State Characterized by Enhanced Purinergic Signaling, The Journal of Neuroscience, Sep. 10, 2008, pp. 9133-9144, vol. 28 Issue 37, Society for Neuroscience.

(Continued)

*Primary Examiner* — Valerie Rodriguez-Garcia

(57) ABSTRACT

Fused compounds of Formula (I) and Formula (II), pharmaceutical compositions containing them, methods of making them, and methods of using them including methods for treating disease states, disorders, and conditions associated with MGL modulation, such as those associated with pain, psychiatric disorders, neurological disorders (including, but not limited to major depressive disorder, treatment resistant depression, anxious depression, bipolar disorder), cancers and eye conditions.

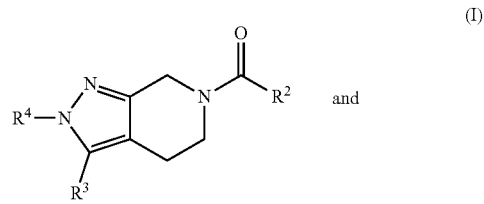

(I) and

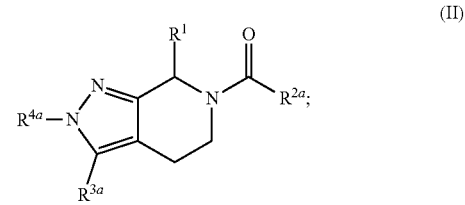

(II)

Wherein $R^1$, $R^2$, $R^{2a}$, $R^3$, $R^{3a}$, $R^4$, and $R^{4a}$ are defined herein.

93 Claims, No Drawings

(56) References Cited

U.S. PATENT DOCUMENTS

| | | | |
|---|---|---|---|
| 9,375,418 | B2 | 6/2016 | Schmidt et al. |
| 9,434,715 | B2 | 9/2016 | Conza et al. |
| 9,447,045 | B2 | 9/2016 | Chen et al. |
| 9,464,084 | B2 | 10/2016 | Alcazar Vaca et al. |
| 9,532,992 | B2 | 1/2017 | Kuntz et al. |
| 9,561,228 | B2 | 2/2017 | Haq et al. |
| 9,617,272 | B2 | 4/2017 | Kumar et al. |
| 9,637,456 | B2 | 5/2017 | Amans et al. |
| 10,112,937 | B2 | 10/2018 | Alcazar Vaca et al. |
| 10,150,765 | B2 | 12/2018 | Alcazar Vaca et al. |
| 10,150,766 | B2 | 12/2018 | Letavic et al. |
| 2005/0096345 | A1 | 5/2005 | Thompson et al. |
| 2006/0217448 | A1 | 9/2006 | Kelly et al. |
| 2006/0293337 | A1 | 12/2006 | Evans et al. |
| 2008/0275052 | A1 | 11/2008 | Dhar et al. |
| 2010/0144758 | A1 | 6/2010 | Dillon et al. |
| 2011/0252717 | A1 | 10/2011 | Graf Fernandez |
| 2011/0294790 | A1 | 12/2011 | Mantegani et al. |
| 2012/0190680 | A1 | 7/2012 | Bakthavatchalam et al. |
| 2014/0213554 | A1 | 7/2014 | Wu et al. |
| 2014/0251902 | A1 | 9/2014 | Solheim et al. |
| 2014/0275015 | A1* | 9/2014 | Alcazar Vaca .......... A61P 13/00 544/405 |
| 2014/0275056 | A1 | 9/2014 | Letavic et al. |
| 2014/0275096 | A1 | 9/2014 | Ameriks et al. |
| 2014/0275120 | A1 | 9/2014 | Alcazar Vaca et al. |
| 2015/0290190 | A1 | 10/2015 | Ameriks et al. |
| 2015/0322062 | A1 | 11/2015 | Alcazar Vaca et al. |
| 2016/0016962 | A1 | 1/2016 | Ameriks et al. |
| 2016/0024082 | A1 | 1/2016 | Alcazar Vaca et al. |
| 2016/0039809 | A1 | 2/2016 | Alcazar Vaca et al. |
| 2016/0039836 | A1 | 2/2016 | Letavic et al. |
| 2016/0046596 | A1 | 2/2016 | Banerjee et al. |
| 2017/0081342 | A1 | 3/2017 | Cheung et al. |
| 2018/0118749 | A1 | 5/2018 | Andres Gil et al. |

FOREIGN PATENT DOCUMENTS

| | | |
|---|---|---|
| JP | 2012525351 A | 10/2012 |
| JP | 2013/505220 A | 2/2013 |
| WO | 2004/014374 A1 | 2/2004 |
| WO | 2004013144 A1 | 2/2004 |
| WO | 2006/023750 A2 | 3/2006 |
| WO | 2006/080884 A1 | 8/2006 |
| WO | 2006/110516 A1 | 10/2006 |
| WO | 2009/002423 A2 | 12/2008 |
| WO | 2009/023623 A1 | 2/2009 |
| WO | 2009095253 A1 | 8/2009 |
| WO | 2010/125101 A1 | 11/2010 |
| WO | 2010/125102 A1 | 11/2010 |
| WO | 2011050202 A1 | 4/2011 |
| WO | 2011/103715 A1 | 9/2011 |
| WO | 2011/121137 A1 | 10/2011 |
| WO | 2012/040048 A2 | 3/2012 |
| WO | 2012145581 A1 | 10/2012 |
| WO | 2014/152589 A1 | 9/2014 |
| WO | 2014/152621 A1 | 9/2014 |
| WO | 2014152604 A1 | 9/2014 |
| WO | 2014/154897 A1 | 10/2014 |
| WO | 2015/025026 A1 | 2/2015 |
| WO | 2016/039977 A1 | 3/2016 |
| WO | 2016/039983 A1 | 3/2016 |
| WO | 2016040789 A1 | 3/2016 |
| WO | 2017087858 A1 | 5/2017 |
| WO | 2020/065613 A1 | 4/2020 |
| WO | 2020065614 A1 | 4/2020 |
| WO | 2020211798 A1 | 10/2020 |
| WO | 2021064569 A1 | 4/2021 |
| WO | 2021/191359 A1 | 9/2021 |

OTHER PUBLICATIONS

Bagshawe, "Antibody-Directed Enzyme prodrug Therapy : A Review", Drug Development Research, , vol. 34; pp. 220-230 (1995).

Bartlett, et al., The P2X7 Receptor Channel: Recent Development and the use of P2X7 antagonists in model of Disease, Pharmocol Rev, 2014, pp. 638-675, vol. 66.

Basso, et al., Behavioral profile of P2X7 receptor knockout mice in animal models of depression and anxiety: Relevance for neuropsychiatric disorders, Behavioural Brain Research, Oct. 18, 2008, pp. 83-90, vol. 198, Elsevier B.V.

Bennet, et al. (Editor), "Part XIV Oncology", Cecil Textbook of Medicine,vol. 1, 20th Edition: pp. 1004-1010 (1996).

Bertolini, et al., "A New Rational Hypothesis for the Pharmacophore of the Active Metabolite of Leflunomide, a Potent Immunosuppressive Drug", Journal of Medicinal Chemistry, vol. 40 (13); pp. 2011-2016 (1997).

Bodor, Nicholas "Novel Approaches to the Design of Safer Drugs: Soft Drugs and Site-Specific Chemical Delivery Systems", Advances in Drug Research, vol. 13; pp. 256-331, (1984).

Bourzac, et al., Glucose Transporter 2 Expression is Down Regulated Following P2X7 Activation in Enterocytes, Journal of Cellular Physiology, 2013, pp. 120-129, vol. 228.

Bundgaard, Hans "Design of Products", Design of Products, pp. 1-3, (1985).

Capuron, et al., Immune system to brain signaling: Neuropsychopharmacological implications, Pharmacology & Therapeutics, 2011, pp. 226-238, vol. 130, Elsevier Inc.

Chessell, et al., Disruption of the P2X7 purinoceptor gene abolishes chronic inflammatory and neuropathic pain, Pain, Jan. 5, 2005, pp. 386-396, vol. 114, Elsevier B.V.

Chu, et al., Inhibition of P2X7 receptor ameliorates transient global cerebral ischemia/reperfusion injury via modulating inflammatory responses in the rat hippocampus, Journal of Neuroinflammation, 2012, pp. 1-10, vol. 9 Issue 69.

Considine, G.D., Van Nostrand's Encyclopedia of Chemistry,, Encyclopedia of Chemistry, 2005, p. 261, Chapter 5.

Dantzer, Robert, Cytokine, Sickness Behavior, and Depression, Immunol Allergy Clin N Am, 2009, pp. 247-264, Volime 29.

Database Chemcats Ambinter Stock Screening Collection Accession No. 2040381923, Feb. 13, 2008.

Database Chemcats Ambinter Stock Screening Collection Accession No. 2040548370, Feb. 13, 2008.

Database Chemcats Ambinter Stock Screening Collection Accession No. 2046454718, Feb. 13, 2008.

Database Chemcats Ambinter Stock Screening Collection Database Accession No. 2040033692, Feb. 13, 2008.

Database Chemcats Aurora Screening Library Accession No. 2037938546, Sep. 6, 2007.

Database Chemcats Enamine Screening Library Accession No. 2035772210, Jan. 17, 2008.

Database Chemcats Ryan Scientific Screening Library Accession No. 2042634059, Jan. 25, 2008.

Database Chemcats Ryan Scientific Screening Library Accession No. 2042637020, Jan. 25, 2008.

Database Chemcats Ryan Scientific Screening Library Accession No. 2042676574, Jan. 25, 2008.

Database Chemcats Ryan Scientific Screening Library Accession No. 2043876860, Jan. 25, 2008.

Database Chemcats Ukrorgsynthesis Screening Collection Accession No. 2033253463, Mar. 6, 2007.

Delarasse, et al., The Purinergic Receptor P2X7 Triggers—Secretasedependent Processing of the Amyloid Precursor Protein, The Journal of Biological Chemistry, Nov. 16, 2010, pp. 2596-2606, vol. 286 Issue 4.

Dermer, Gerald B., "Another Anniversary For the War on Cancer",, Nature Publishing Group, Mar. 12, 1994, p. 320, vol. 12 No 2.

Diaz-Hernandez, et al., Altered P2X7-receptor level and function in mouse models of Huntington's disease and therapeutic efficacy of antagonist administration, The FASEB Journal, 2009, pp. 1893-1906, vol. 23.

Diaz-Hernandez, et al., In vivo P2X7 inhibition reduces amyloid plaques in Alzheimer's disease through GSK3 and secretases, Neurobiology of Aging, 2012, pp. 1816-1828, vol. 33.

(56) References Cited

OTHER PUBLICATIONS

Donnelly-Roberts, et al., [3H]A-804598 ([3H]2-cyano-1-[(1S)-1-phenylethyl]-3-quinolin-5-ylguanidine) is a novel, potent, and selective antagonist radioligand for P2X7 receptors, Neuropharmacology, 2009, pp. 223-229, vol. 56.
Duan, et al., P2X7 Receptors: Properties and Relevance to CNS Function, GLIA, 2006, pp. 738-746, vol. 54.
Dyatkin et al., Determination of the Absolute Configuration of a Key Tricyclic Component of a Novel Vasopressin Receptor Antagonist by Use of Vibrational Circular Dichroism, Chirality, 2002, pp. 215-219, vol. 14.
Engel, et al., Seizure suppression and neuroprotection by targeting the purinergic P2X7 receptor during status epilepticus in mice, The FASEB Journal, 2012, pp. 1616-1628, vol. 26.
Ferrari, et al., The P2X7 Receptor: A Key Player in IL-1 Processing and Release1, The Journal of Immunology,, 2006, pp. 3877-3883, vol. 176.
Fleisher, et al., "Improved oral drug delivery: solubility limitations overcome by the use of prodrugs", Advanced Drug Delivery Reviews, vol. 19; pp. 115-130 (1996).
Freshney, et al., Culture of Animal Cells, Manual of Basic Technique, 1983, pp. 1-6, Chapter 1.
Friedle, et al., Recent Patents on Novel P2X7 Receptor Antagonists and their Potential for Reducing Central Nervous System Inflammation, Recent Patents on CNS Drug Discovery, 2010, pp. 35-45, vol. 5.
Furlan-Freguia, et al., P2X7 receptor signaling contributes to tissue factor-dependent thrombosis in mice, The Journal of Clinical Investigation, 2011, pp. 2932-2944, vol. 121 Issue 7.
Golub, et al., Molecular Classification of cancer: Class Discovery and class prediction by gene expression monitoring. Science, 1999, pp. 531-537, vol. 286.
Grygorowicz, et al., Temporal expression of P2X7 purinergic receptor during the course of experimental autoimmune encephalomyelitis, Neurochemistry International, Sep. 9, 2010, pp. 823-829, vol. 57.
Guile, et al., Antagonists of the P2X7 Receptor. From Lead Identification to Drug Development, Journal of Medicinal Chemistry, May 28, 2009, pp. 3123-3141, vol. 52 Issue 10.
Gunosewoyo, et al., P2X purinergic receptor ligands recently patented compounds, Expert Opin. Ther Patents, 2010, pp. 625-646, vol. 20 Issue 5.
Hackam, et al., "Translation of Research Evidence From animals to Humans", JAMA, vol. 296 (14): pp. 1731-1732 (2006).
Hudson, Derek, Methodological Implications of Simultaneous Solid-Phase peptide Synthesis, J.Org.Chem, 1988, pp. 617-624, vol. 53.
Ji, et al., P2X7 deficiency attenuates hypertension and renal injury in deoxycorticosterone acetate-salt hypertension, Am J Physiol Renal Physiol, 2012, pp. F1207-F1215, vol. 303.
Jordan, "Tamoxifen: A Most Unlikely Pioneering Medicine", Nature Reviews, vol. 2: pp. 205-213, (Mar. 2003).
Keating, et al., P2X7 Receptor-Dependent Intestinal Afferent Hypersensitivity in a Mouse Model of Postinfectious Irritable Bowel Syndrome, The Journal of Immunology, Jun. 22, 2011, pp. 1467-1474, vol. 187.
Killeen, et al., Signaling through purinergic receptors for ATP induce human cutaneous innate and adaptive th17 responses:implications in the pathogenesis of psoriasis, The Journal of Immunology, 2013, pp. 4324-4336, vol. 190.
Kim, et al., Blockade of P2X receptor prevents astroglial death in the dentate gyrus following pilocarpine-induced status epilepticus, Neurological research, 2009, pp. 982-988, vol. 31.
Larsen, et al., "A text book of Drug Design and Development", Index; pp. 1-18 (1991).
Marcellino, et al., On the role of P2X7 receptors in dopamine nerve cell degeneration in a rat model of Parkinson's disease: studies with the P2X7 receptor antagonist A-438079, J Neural Transm, Apr. 13, 2010, pp. 681-687, vol. 117.
Martins, et al., The role of P2X7 purinergic receptors in inflammatory and nociceptive changes accompanying cyclophosphamide-induced haemorrhagic cystitis in mice, British Journal of Pharmacology, 2012, pp. 183-196, vol. 165.
Muller, et al., Apotential role for P2X7r in allergic airway inflammation in mice and humans, American Journal of Respiratory Cell and molecular Biology, 2011, pp. 456-464, vol. 44.
Oyanguren-Desez, et al., Gain-of-function of P2X7 receptor gene variants in multiple sclerosis, Cell Calcium, Sep. 8, 2011, pp. 468-472, vol. 50.
Parvathenani, et al., P2X7 Mediates Superoxide Production in Primary Microglia and Is Up-regulated in a Transgenic Mouse Model of Alzheimer's Disease, The Journal of Biological Chemistry, Jan. 17, 2003, pp. 13309-13317, vol. 278 Issue 15.
Paulekuhn, et al., Trends in Active Pharmaceutical Ingredient Salt Selection based on Analysis of the Orange Book Database, Journal of Medicinal Chemistry, Aug. 20, 2007, pp. 6665-6672, vol. 50 Issue 26.
Robinson, et al., "Discovery of the Hemifumarate and (r-L-Alanyloxy)methyl Ether as Prodrugs of an Antirheumatic Oxindole: Prodrugs for the Enolic OH Group", Journal of Medicinal Chemistry, vol. 39 (1); pp. 10-18 (1996).
Romagnoli, et al., The P2X 7 receptor as a therapeutic target, Expert Opin. Ther., 2008, pp. 647-661, vol. 15 Issue 5.
Rudolph, et al., Novel methyl substituted 1-(5,6-dihydro-[1,2,4]triazolo [4,3-a]pyrazin-7(8H)-yl)methanones are P2X7 antagonists, Bioorganic & Medicinal Chemistry Letters, Jun. 9, 2015, pp. 3157-3163, vol. 25.
Sanz, et al., Activation of Microglia by Amyloid Requires P2X7 Receptor Expression!, The Journal of Immunology, 2009, pp. 4378-4385, vol. 182.
Shan, et al., "Prodrug Strategies Based on Intramolecular Cyclization Reactions", Journal of Pharmaceutical Sciences,vol. 86 (7): pp. 765-767 (Jul. 1977).
Sharp, et al., P2x7 deficiency suppresses development of experimental autoimmune encephalomyelitis, Journal of Neuroinflammation, Aug. 8, 2008, pp. 1-13, vol. 5 Issue 33.
Simone, Part XIV—Oncology, Textbook of Medicine, 1996, 20th edition, pp. 1004-1010, vol. 1.
Skaper, et al., The P2X7 purinergic receptor: from physiology to neurological disorders, The FASEB Journal, 2010, pp. 337-345, vol. 24.
Solini, et al., Enhanced P2X7 Activity in Human Fibroblasts From Diabetic Patients A Possible Pathogenetic Mechanism for Vascular Damage in Diabetes, Arterioscler Thromb Vase Biol., 2004, pp. 1240-1245, vol. 24.
Stahl, et al., "Handbook Of Pharmaceutical Salts", International Union of Pure and Applied Chemistry, Index; pp. 1-3, (2002).
Surprenant, et al., Signaling at Purinergic P2X Receptors, Annu. Rev. Physiol, Oct. 13, 2008, pp. 333-359, vol. 71.
Thiboutot, et al., Inflammasome Activation by propionibacterium acnes: the Story of IL-1 in Acne continues to unfold, Journal Of Investigative Dermatology, 2014, pp. 595-597, vol. 134.
Vergani, et al., Effects of the purinergic Inhibitor Oxidized ATP in a model of Islet Allograft rejection, Diabetes, 2013, pp. 1665-1675, vol. 62.
Vergani, et al., Long term Heart Transplant Survival by targeting the Ionotropic Purinergic receptor P2X7, Circulation, 2013, pp. 463-475, vol. 127.
Carroll et al., "Synthesis and Pharmacological Characterization of Nicotinic Acetylcholine Receptor Properties of (+)- and (−)-Pyrido-[3,4-b]homotropanes", Journal of Medicinal Chemistry, 2006, 3244-3250, vol. 49, No. 11.
Folkes et al., "An endocannabinoid-regulated basolateral amygdala-nucleus accumbens circuit modulates sociability", J Clin Invest., 2020, 1728-1742., vol. 130, Issue 4.
International Search Report and Written Opinion for International Applic No. PCT/IB2020/059099 dated Nov. 24, 2020.
International Search Report and Written Opinion for International Application No. PCT/EP2021/057764 dated Jun. 8, 2021.
International Search Report and Written Opinion for International Application No. PCT/IB2019/058241 dated Jan. 10, 2020.
Jung et al., "Uncoupling of the endocannabinoid signalling complex in a mouse model of fragile X syndrome", Nature Communications, 2012, 1080., vol. 3.

(56) References Cited

OTHER PUBLICATIONS

Wang et al., "Treating a novel plasticity defect rescues episodic memory in Fragile X model mice", Mol Psychiatry, 2018, 1798-1806, vol. 23, No. 8.
Ahn et al., "Enzymatic Pathways That Regulate Endocannabinoid Signaling in the Nervous System", Chemical Reviews, 2008, vol. 108, No. 5, Jan. 28, 2008, pp. 1687-1707.
Alhouayek et al., "Increasing endogenous 2-arachidonoylglycerol levels counteracts colitis and related systemic Inflammation", The FASEB Journal, vol. 25, No. 8, Aug. 2011, pp. 2711-2721.
Bedse et al., "Functional Redundancy Between Canonical Endocannabinoid Signaling Systems in the Modulation of Anxiety", Biological Psychiatry, Oct. 1, 2017, pp. 488-499.
Bedse et al., "Therapeutic endocannabinoid augmentation for mood and anxiety disorders: comparative profiling of FAAH, MAGL and dual inhibitors", Translational Psychiatry (2018) 8:92 DOI 10.1038/s41398-018-0141-7, pp. 1-14.
Benito et al., "Cannabinoid CB2 receptors in human brain inflammation", British Journal of Pharmacology (2008) 153, Oct. 15, 2007, pp. 277-285.
Berge et al., "Pharmaceutical Salts", Journal of Pharmaceutical Sciences, vol. 66, No. 1, Jan. 1977, pp. 1-19.
Bernal-Chico et al., "Blockade of Monoacylglycerol Lipase Inhibits Oligodendrocyte Excitotoxicity and Prevents Demyelination In Vivo", GLIA 2015, vol. 63, No. 1, pp. 163-176, Aug. 8, 2014 Wiley Periodicals, Inc.
Buczynski et al., "Quantification of brain endocannabinoid levels: methods", interpretations and pitfalls, British Journal of Pharmacology (2010) 160, pp. 423-442.
International Search Report and Written Opinion for International Applic No. PCT/IB2019/058240 dated Jan. 10, 2020.
Cavuoto et al., "The expression of receptors for endocannabinoids in human and rodent skeletal muscle", Biochemical and Biophysical Research Communications 364 (2007), Oct. 2, 2007, pp. 105-110.
Chen et al., "Monoacylglycerol Lipase Is a Therapeutic Target for Alzheimer's Disease", Cell Reports 2, Nov. 29, 2012, 1329-1339.
Chinnadurai et al., "Monoacylglycerol lipase inhibition as potential treatment for interstitial cystitis", Med Hypotheses 131, 2019, pp. 1-3.
Christensen et al., "Efficacy and safety of the weight-loss drug rimonabant: a meta-analysis of randomised trials", Lancet 2007, vol. 370, pp. 1706-1713.
Covey et al., "Inhibition of endocannabinoid degradation rectifies motivational and dopaminergic deficits in the Q175 mouse model of Huntington's disease", Neuropsychopharmacology, 2018, vol. 43, pp. 2056-2063.
Curry et al., "Monoacylglycerol Lipase Inhibitors Reverse Paclitaxel-Induced Nociceptive Behavior and Proinflammatory Markers in a Mouse Model of Chemotherapy-Induced Neuropathy", The Journal of Pharmacology and Experimental Therapeutics, 366, Jul. 2018, pp. 169-183.
Devane et al., "Isolation and Structure of a Brain Constituent That Binds to the Cannabinoid Receptor", Science 1992, vol. 258, pp. 1946-1949.
Di Marzo et al., "Endocannabinoids and the regulation of their levels in health and disease", Curr Opin Lipidol, 2007, vol. 18, pp. 129-140.
Di Marzo et al., "Plant, Synthetic, and Endogenous Cannabinoids in Medicine", Annu. Rev. Med. 2006, vol. 57, pp. 553-575.
Dinh et al., "Brain monoglyceride lipase participating in endocannabinoid inactivation", Proc Natl Acad Sci, 2002, vol. 99(16), pp. 10819-10824.
Ghosh et al., "The monoacylglycerol lipase inhibitor JZL184 suppresses inflammatory pain in the mouse carrageenan model", Life Sci., vol. 92, 2013, pp. 498-505.
Greene et al., Chapter 7 Protection for the Amino Group, Protective Groups in Organic Synthesis, Third Edition, John Wiley & Sons, 1999, pp. 518-525; 579-580; 620-621.

Guindon et al., "Peripheral antinociceptive effects of inhibitors of monoacylglycerol lipase in a rat model of Inflammatory pain", British Journal of Pharmacology, 2011, vol. 163(7), pp. 1464-1478.
Hajrasouliha et al., "Endogenous cannabinoids contribute to remote ischemic preconditioning via cannabinoid CB2 receptors in the rat heart", European Journal of Pharmacology (2008), vol. 579, Oct. 5, 2007 pp. 246-252.
Hauer et al., "Glucocorticoid-endocannabinoid interaction in cardiac surgical patients: relationship to early cognitive dysfunction and late depression", Rev Neurosci., 2012, vol. 23(5-6), pp. 681-690.
Hernndez-Torres et al., "A Reversible and Selective Inhibitor of Monoacylglycerol Lipase Ameliorates Multiple Sclerosis", Angew. Chem. Int. Ed., 2014, vol. 53(50) pp. 13765-13770.
Herkenham et al., "Cannabinoid receptor localization in brain", Proc. Natl. Acad. Sci. USA, Mar. 1990, vol. 87, pp. 1932-1936.
Hill et al., "Circulating endocannabinoids and N-acyl ethanolamines are differentially regulated in major depression and following exposure to social stress", Psychoneuroendocrinology, 2009, vol. 34(8), pp. 1257-1262.
Hill et al., "Reductions in Circulating Endocannabinoid Levels in Individuals with Post-Traumatic Stress Disorder Following Exposure to the World Trade Center Attacks", Psychoneuroendocrinology 2013, vol. 38 (12), pp. 1-16.
Hill et al., "Serum Endocannabinoid Content is Altered in Females with Depressive Disorders: A Preliminary Report", Pharmacopsychiatry 2008; vol. 41, pp. 48-53.
Katz et al., "Endocannabinoid Degradation Inhibition Improves Neurobehavioral Function, Blood-Brain Barrier Integrity, and Neuroinflammation following Mild Traumatic Brain Injury", Journal of Neurotrauma, Mar. 1, 2015, vol. 32(5), p. 297-306.
Kinsey et al., "Blockade of Endocannabinoid-Degrading Enzymes Attenuates Neuropathic Pain", The Journal of Pharmacology and Experimental Therapeutics, 2009, vol. 330, No. 3, pp. 902-910.
Ligresti et al., "From endocannabinoid profiling to 'endocannabinoid therapeutics'", Current Opinion in Chemical Biology 2009, vol. 13, pp. 321-331.
Long et al., "Characterization of Monoacylglycerol Lipase Inhibition Reveals Differences in Central and Peripheral Endocannabinoid Metabolism", Chemistry & Biology, 2009, vol. 16(7), pp. 744-753.
Long et al., "Selective blockade of 2-arachidonoylglycerol hydrolysis produces cannabinoid behavioral effects", Nature Chemical Biology, 2009, vol. 5(1), pp. 37-44.
Manske et al., "The SKRAUP Synthesis of Quinolines", Chapter 2 Organic Reactions, vol. 7, 1953, pp. 59-98.
Matsuda et al., "Structure of a cannabinoid receptor and functional expression of the cloned cDNA", Letters To Nature vol. 346, Aug. 9, 1990, pp. 561-564.
Mechoulam et al., "Identification of an Endogenous 2-Monoglyceride, Present in Canine Gut, That Binds To Cannabinoid Receptors", Biochemical Pharmacology, vol. 50. No. 1, 1995, pp. 83-90.
Miller et al., "Controlled-Deactivation CB1 Receptor Ligands as a Novel Strategy to Lower Intraocular Pressure", Pharmaceuticals 2018, 11, 50; doi:10.3390/ph11020050, pp. 1-8.
Mulvihill et al., "Therapeutic potential of monoacylglycerol lipase inhibitors", Life Sciences 92 (2013), pp. 492-497.
Munro et al., "Molecular characterization of a peripheral receptor for cannabinoids", Letters to Nature, vol. 365, Sep. 2, 1993, pp. 61-65.
Nithipatikom et al., "Anti-proliferative effect of a putative endocannabinoid, 2-arachidonylglyceryl ether in prostate carcinoma cells", Prostaglandins and Other Lipid Mediators, 94, 2011, pp. 34-43.
Nikitenko et al., "Selective Hydrolysis of Ethyl 5,6-Dihydro-4H-pyrrolo[1,2-b]pyrazole-2-carboxylate and Ethyl 5,6-Dihydro-4H-pyrrolo[1,2-b]pyrazole-3-carboxylate as a Key Step in the Large-Scale Synthesis of Bicyclic Heteroaryl Carboxyaldehydes", Organic Process Research & Development, vol. 10, No. 4, 2006, pp. 712-716.
Nithipatikom et al., "2-Arachidonoylglycerol: A Novel Inhibitor of Androgen-Independent Prostate Cancer Cell nvasion", Cancer Research 64, Dec. 15, 2004, pp. 8826-8830.

(56) References Cited

OTHER PUBLICATIONS

Nithipatikom et al., "A new class of inhibitors of 2-arachidonoylglycerol hydrolysis and invasion of prostate cancer cells", Biochemical and Biophysical Research Communications 332 (2005), pp. 1028-1033.
Nomura et al., "Endocannabinoid Hydrolysis Generates Brain Prostaglandins That Promote Neuroinflammation", Science, vol. 334, Nov. 11, 2011, pp. 809-813.
Pacher et al., "Pleiotropic effects of the CB2 cannabinoid receptor activation on human monocyte migration: implications for atherosclerosis and inflammatory diseases", Am. J. Physiol Heart Circ Physiol 294, 2008, pp. H1133-H1134.
Pasquarelli et al., "Contrasting effects of selective MAGL and FAAH inhibition on dopamine depletion and GDNF expression in a chronic MPTP mouse model of Parkinson's disease", Neurochem. Int., vol. 110, 2017, pp. 14-24.
Pasquarelli et al., Evaluation of monoacylglycerol lipase as a therapeutic target in a transgenic mouse model of ALS, Neuropharmacology, vol. 124, 2017, pp. 157-169.
Patel et al., "The endocannabinoid system as a target for novel anxiolytic drugs", Neurosci. Biobehav. Rev., vol. 76, 2017, pp. 56-66.
Piomelli, D., "The Molecular Logic of Endocannabinoid Signalling", Nature Reviews Neuroscience, 2003, vol. 4, pp. 873-884.
Piro et al., "A Dysregulated Endocannabinoid-Eicosanoid Network Supports Pathogenesis in a Mouse Model of Alzheimer's Disease", Cell Reports 1, Jun. 28, 2012, pp. 617-623.
Ramesh et al., "Blockade of Endocannabinoid Hydrolytic Enzymes Attenuates Precipitated Opioid Withdrawal Symptoms in Mice", J Pharmacol Exp Ther., 2011, vol. 339, No. 1, pp. 173-185.
Schlosburg et al., "Chronic monoacylglycerol lipase blockade causes functional antagonism of the endocannabinoid system", Nat Neurosci., Sep. 2010, vol. 13(9), pp. 1113-1119.
Sticht et al., "Inhibition of monoacylglycerol lipase attenuates vomiting in Suncus murinus and 2-arachidonoyl glycerol attenuates nausea in rats", British Journal of Pharmacol., 2012, vol. 165, pp. 2425-2435.
Straiker et al., "Monoacylglycerol Lipase Limits the Duration of Endocannabinoid-Mediated Depolarization-Induced Suppression of Excitation in Autaptic Hippocampal Neurons", Molecular Pharmacology, 2009, vol. 76(6), pp. 1220-1227.
Sugiura et al. "Biosynthesis and degradation of anandamide and 2-arachidonoylglycerol and their possible physiological significance", Prostaglandins, Leukotrienes and Essential Fatty Acids., 2002, vol. 66(2&3), pp. 173-192.
Sugiura et al., "2-Arachidonoylgylcerol: A Possible Endogenous Cannabinoid Receptor Ligand in Brain", Biochemical and Biophysical Research Communications, Oct. 4, 1995, vol. 215, No. 1, pp. 89-97.
Suguira et al., "Biochemistry, pharmacology and physiology of 2-arachidonoylglycerol, an endogenous cannabinoid receptor ligand", Progress in Lipid Research, 2006, vol. 45, pp. 405-446.
Terrone et al., "Inhibition of monoacylglycerol lipase terminates diazepam-resistant status epilepticus in mice and its affects are potentiated by a ketogenic diet", Epilepsia, 2018, vol. 59, pp. 79-91.
Tuo et al., "Therapeutic Potential of Fatty Acid Amide Hydrolase, Monoacylglycerol Lipase, and N-Acylethanolamine Acid Amidase Inhibitors", J Med. Chem., 2017, vol. 60, Oct. 21, 2016, pp. 4-46.
Von Ruden et al., "Inhibition of monoacylglycerol lipase mediates a cannabinoid 1-receptor dependent delay of kindling progression in mice", Neurobiology of Disease, 2015, vol. 77, pp. 238-245.
Walter et al., "ATP Induces a Rapid and Pronounced Increase in 2-Arachidonoylglycerol Production by Astrocytes, a Response Limited by Monoacylglycerol Lipase", The Journal of Neuroscience, Sep. 15, 2004, vol. 24(37), pp. 8068-8074.
Wenzel et al., "Novel multi-target directed ligand-based strategies for reducing neuroinflammation in Alzheimer's disease", Life Sciences, 2018, vol. 207, pp. 314-322.
Wilkerson et al., "The Selective Monoacylglycerol Lipase Inhibitor MJN110 Produces Opioid-Sparing Effects in a Mouse Neuropathic Pain Model", Journal of Pharmacology and Experimental Therapeutics, Apr. 2016, vol. 357, pp. 145-156.
Wilson et al., "A high-throughput-compatible assay for determining the activity of fatty acid amide hydrolase", Analytical Biochemistry, 2003, vol. 318, pp. 270-275.
Yi et al., "Reductions in circulating endocannabinoid 2-arachidonoylglycerol levels in healthy human subjects exposed to chronic stressors", Progress in Neuro-Psychopharmacology and Biological Psychiatry, 2016, vol. 67, pp. 92-97.
Zhang et al., "Inhibition of monoacylglycerol lipase prevents chronic traumatic encephalopathy-like neuropathology in a mouse model of repetitive mild closed head injury", Journal of Cerebral Blood Flow & Metabolism, 2015, vol. 35, pp. 443-453, 706.
Keller, et al., "Radiosynthesis and Preclinical Evaluation of [18F]F-DPA, A Novel Pyrazolo[1,5a]pyrimidine Acetamide TSPO Radioligand, in Healthy Sprague Dawley Rats", Molecular Imaging and Biology, 2017, pp. 736-745, vol. 19.
Pike, Victor W., "Hypervalent aryliodine compounds as precursors for radiofluorination", J. Label Compd Radiopharm., 2018, pp. 196-227, vol. 61.

\* cited by examiner

MONOACYLGLYCEROL LIPASE MODULATORS

CROSS-REFERENCE TO RELATED APPLICATIONS

This application is a continuation of U.S. Ser. No. 16/586,088 filed Sep. 27, 2019, pending, which claims priority to U.S. Patent Application No. 62/738,600 filed on Sep. 28, 2018, which are incorporated herein in their entirety.

FIELD OF THE INVENTION

The present invention is related to certain fused chemical entities having MGL modulating properties, pharmaceutical compositions comprising these chemical entities, chemical processes for preparing these chemical entities and their use in the treatment of diseases, disorders or conditions associated with MGL receptor activity in subjects, in particular humans.

BACKGROUND OF THE INVENTION

*Cannabis Sativa* and analogs of $\Delta^9$-tetrahydrocannabinol have been used since the days of folk medicine for therapeutic purposes. The endocannabinoid system consists of two G-protein coupled receptors, cannabinoid receptor type 1 (CB1) (Matsuda et al., *Nature*, 1990, 346, 561-4) and cannabinoid receptor type 2 (CB2) (Munro et al., *Nature*, 1993, 365, 61-5). CB1 receptor is one of the most abundant G-protein coupled receptor expressed in the brain (Herkenam et al., *Proc. Nat. Acad. Sci.*, 1990, 87 (5), 1932-1936). CB1 is also expressed peripherally in the liver, gastrointestinal tract, pancreas, adipose tissue and skeletal muscles (Di Marzo et al., *Curr Opin Lipidol*, 2007, 18, 129-140). CB2 is predominantly expressed in immune cells such as monocytes (Pacher et al., *Amer J Physiol*, 2008, 294, H1133-H1134) and under certain conditions (inflammation) in the brain ((Benito et al., *Brit J Pharmacol*, 2008, 153, 277-285) and in skeletal (Cavuoto et al., *Biochem Biophys Res Commun*, 2007, 364, 105-110) and cardiac muscles (Hajrasouliha et al., *Eur J Pharmacol*, 2008, 579, 246-252).

In 1992, N-arachidonoylethanolamine (AEA or anandamide) was found to be an endogenous ligand for cannabinoid receptors (Devane et al., *Science*, 1992, 258, 1946-9). Subsequently, 2-arachidonoylglycerol (2-AG) was also identified as an additional endogenous ligand for the cannabinoid receptors (Mechoulam et al., *Biochem Pharmacol*, 1995, 50, 83-90; Sugiura et al., *Biochem Biophys Res Commun*, 1995, 215, 89-97). Concentrations of 2-AG were reported to be at least 100 times higher than these of anandamide in the rat brain (Buczynski and Parsons, *Brit J Pharmacol*, 2010, 160 (3), 423-42). Therefore 2-AG may play more essential physiological roles than anandamide in the brain endocannabinoid system (Sugiura et al. *Prostaglandins Leukot Essent Fatty Acids.*, 2002, February-March, 66(2-3):173-92). The endocannabinoid 2-AG is a full agonist for CB1 and CB2 receptors, while anandamide is a partial agonist for both receptors (Suguira et al., *Prog Lipid Res*, 2006, 45(5):405-46). Unlike many classical neurotransmitters, endocannabinoids signal through a retrograde mechanism. They are synthesized on demand in postsynaptic neurons and then rapidly degraded following binding to presynaptic cannabinoid receptors (Ahn et al., *Chem Rev.* 2008, 108(5):1687-707). Monoacylglycerol lipase (MGLL, also known as MAG lipase and MGL) is the serine hydrolase responsible for the degradation of 2-AG into arachidonic acid and glycerol in the central nervous system (Mechoulam et al., *Biochem Pharmacol*, 1995, 50, 83-90; Sugiura et al., *Biochem Biophys Res Commun*, 1995, 215, 89-97; Long et al., *Nat Chem Biol.* 2009 January; 5(1):37-44;), Schlosburg et al, *Nat Neurosci.*, 2010, September; 13(9):1113-9) and peripheral tissues (Long et al., *Chem Biol.*, 2009 Jul. 31; 16(7):744-53). Anandamide is hydrolyzed by fatty acid amide hydrolase (FAAH) (Piomelli, *Nat Rev Neurosci*, 2003, 4, 873-884). MGL exists in both soluble and membrane bound forms (Dinh et al., *Proc Natl Acad Sci USA*, 2002, Aug. 6; 99(16):10819-24). In the brain MGL is located in presynaptic neurons (Straiker et al., *Mol Pharmacol.*, 2009, December; 76(6):1220-7) and astrocytes (Walter et al., *J Neurosci.*, 2004, Sep. 15; 24(37):8068-74) within regions associated with high CB1 receptor density. Compared to wild-type controls, genetic ablation of MGL expression produces 10-fold increase in brain 2-AG levels without affecting anandamide concentration (Schlosburg et al., *Nat Neurosci.*, 2010, September; 13(9):1113-9).

Thus, MGL modulation offers an interesting strategy for potentiating the cannabinoid system. The primary advantage of this approach is that only brain regions where endocannabinoids are actively produced will be modulated, potentially minimizing the side effects associated with exogenous CB1 agonists. Pharmacological inactivation of MGL by covalent inhibitors in animals increase 2-AG content in brain and peripheral tissues and has been found to produce antinociceptive, anxiolytic and anti-inflammatory effects that are dependent on CB1 and/or CB2 receptors (Long et al., *Nat Chem Biol.*, 2009, January, 5(1):37-44; Ghosh et al., *Life Sci.*, 2013, Mar. 19, 92(8-9):498-505; Bedse et al., *Biol Psychiatry.*, 2017, Oct. 1, 82(7):488-499; Bernal-Chico et al., *Glia.*, 2015, January, 63(1):163-76; Patel et al. *Neurosci Biobehav Rev.*, 2017, May, 76(Pt A):56-66; Betse et al., *Transl Psychiatry.*, 2018, Apr. 26, 8(1):92). In addition to the role of MGL in terminating 2-AG signaling, MGL modulation, including MGL inhibition also promotes CB1/2-independent effects on neuroinflammation (Nomura et al., *Science.*, 2011, Nov. 11; 334(6057):809-13). MGL modulation, including MGL inhibition leads to reduction in proinflammatory prostanoid signaling in animal models of traumatic brain injury (Katz et al., *J Neurotrauma.*, 2015, Mar. 1; 32(5):297-306; Zhang et al., *J Cereb Blood Flow Metab.*, 2015, Mar. 31; 35(4):706), neurodegeneration including Alzheimer's disease (Piro et al., *Cell Rep.*, 2012, Jun. 28, 1(6):617-23; Wenzel et al., *Life Sci.*, 2018, Aug. 15, 207: 314-322; Chen et al., *Cell Rep.*, 2012, Nov. 29, 2(5):1329-39), Parkinson's disease (Nomura et al., *Science*, 2011, Nov. 11, 334(6057), 809-13; Pasquarelli et al., *Neurochem Int.*, 2017, November, 110:14-24), amyotrophic lateral sclerosis (Pasquarelli et al., *Neuropharmacology*, 2017, Sep. 15, 124: 157-169), multiple sclerosis (Hernadez-Torres et al., *Angew Chem Int Ed Engl.*, 2014, Dec. 8, 53(50):13765-70; Bernal-Chico et al., *Glia.*, 2015, January, 63(1):163-76), Huntington's disease (Covey et al., *Neuropsychopharmacology*, 2018, 43, 2056-2063), Tourette syndrome and status epilepticus (Terrone et al., *Epilepsia.*, 2018, January, 59(1), 79-91; von Ruden et al., *Neurobiol Dis.*, 2015, May; 77:238-45).

Therefore, by potentiating the cannabinoid system and attenuating proinflammatory cascades, MGL modulation, including MGL inhibition offers a compelling therapeutic approach for the treatment of a vast array of complex diseases. Importantly, MGL modulation, including MGL inhibition in animals does not produces the full spectrum of neurobehavioral effects observed with $\Delta^9$-tetrahydrocannabinol and other CB1 agonists (Tuo et al., *J Med Chem.*, 2017, Jan. 12, 60(1), 4-46; Mulvihill et al., *Life Sci.*, 2013, Mar. 19, 92(8-9), 492-7).

Endocannabinoid hypoactivity is a risk factor for the treatment of depression, anxiety and post-traumatic stress disorders. Millennia of human use of *Cannabis sativa*, and a brief period in which humans were treated with the endocannabinoid antagonist, rimonabant, provide support for that hypothesis. 2-AG levels are decreased in individuals with major depression (Hill et al., *Pharmacopsychiatry.*, 2008, March; 41(2): 48-53; Hill et al., *Psychoneuroendocrinology.*, 2009, September; 34(8): 1257-1262.). Low circulating 2-AG levels predict rates of depression (Hauer et al., *Rev Neurosci.*, 2012, 23(5-6):681-90). Reduced circulating 2-AG has been found in patient with post-traumatic stress disorder (PTSD) (Hill et al., *Psychoneuroendocrinology*, 2013, 38 (12), 2952-2961). Healthy volunteers exposed to chronic stressors exhibited progressively diminished circulating 2-AG levels which correlated with the onset of reductions in measures of positive emotions (Yi et al., *Progress in Neuro-Psychopharmacology and Biological Psychiatry*, 2016, 67 (3), 92-97). The CB1 receptor inverse agonist/antagonist Rimonabant has been withdrawn from the market due to the high incidence of severe depression and suicidal ideation (Christensen et al., *The Lancet*, 2007, 370, 1706-1713). Therefore, MGL modulators are potentially useful for the treatment of mood disorders, anxiety and PTSD.

Cannabinoid receptor agonists are clinically used to treat pain, spasticity, emesis and anorexia (Di Marzo, et al., *Annu Rev Med.*, 2006, 57:553-74; Ligresti et al., *Curr Opin Chem Biol.*, 2009, June; 13(3):321-31). Therefore, MGL modulators, including MGL inhibitors are also potentially useful for these indications. MGL exerts CB1-dependant antinociceptive effects in animal models of noxious chemical, inflammatory, thermal and neuropathic pain (Guindon et al., *Br J Pharmacol.*, 2011, August; 163(7):1464-78; Kinsey et al., *J Pharmacol Exp Ther.*, 2009, September; 330(3):902-10; Long et al., *Nat Chem Biol.*, 2009, January; 5(1):37-44). MGL blockade reduces mechanical and acetone induced cold allodynia in mice subjected to chronic constriction injury of the sciatic nerve (Kinsey et al., *J Pharmacol Exp Ther.*, 2009, September; 330(3):902-10). MGL inhibition produces opiate-sparing events with diminished tolerance, constipation, and cannabimimetic side effects (Wilkerson et al., *J Pharmacol Exp Ther.*, 2016, April; 357(1):145-56). MGL blockade is protective in model of inflammatory bowel disease (Alhouayek et al., *FASEB J.*, 2011, August; 25(8): 2711-21). MGL inhibition also reverse Paclitaxel-induced nociceptive behavior and proinflammatory markers in a mouse model of chemotherapy-induced neuropathy (Curry et al., *J Pharmacol Exp Ther.*, 2018, July; 366(1):169-18). MGL inhibitors are also potentially useful for the treatment of chronic inflammatory condition of the urinary bladder like interstitial cystitis (Chinnadurai et al., Med Hypotheses 2019, October; 131: 109321).

Inhibition of 2-AG hydrolysis exerts anti-proliferative activity and reduction in prostate cancer cell invasiveness (Nithipatikom et al., *Cancer Res.*, 2004, Dec. 15, 64(24): 8826-30; Nithipatikom et al., *Biochem Biophys Res Commun.*, 2005, Jul. 15,332(4):1028-33; Nithipatikom et al., *Prostaglandins Other Lipid Mediat.*, 2011, February, 94(1-2):34-43). MGL is upregulated in aggressive human cancer cells and primary tumors where it has a unique role of providing lipolytic sources of free fatty acids for synthesis of oncogenic signaling lipids that promote cancer aggressiveness. Thus, beyond the physiological roles of MGL in mediated endocannabinoid signaling, MGL in cancer plays a distinct role in modulating the fatty acid precursor pools for synthesis of protumorigenic signaling lipids in malignant human cancer cells.

MGL blockade shows anti-emetic and anti-nausea effects in a lithium chloride model of vomiting in shrews (Sticht et al., *Br J Pharmacol.*, 2012, April, 165(8):2425-35). MGL modulators, including MGL inhibitors may have utility in modulating drug dependence of opiates. MGL blockade reduce the intensity of naloxone-precipitated morphine withdrawal symptoms in mice. MGL blockade also attenuated spontaneous withdrawal signs in morphine-dependent mice (Ramesh et al., *J Pharmacol Exp Ther.*, 2011, October, 339(1):173-85).

MGL modulators are also potentially useful for the treatment of eye conditions, including but not limited to, glaucoma and disease states arising from elevated intraocular pressure (Miller et al., *Pharmaceuticals*, 2018, 11, 50).

SUMMARY OF THE INVENTION

Embodiments of the present invention relate to chemical entities, pharmaceutical compositions containing them, methods of making and purifying them, and methods for using them the treatment of diseases, disorders, and conditions associated with the MGL modulation. An additional embodiment of the invention is a method of treating a subject suffering from or diagnosed with a disease, disorder, or condition associated with the MGL modulation using at least one chemical entity of the invention.

Additional embodiments, features, and advantages of the invention will be apparent from the following detailed description and through practice of the invention.

Embodiments of this invention are compounds of Formula (I),

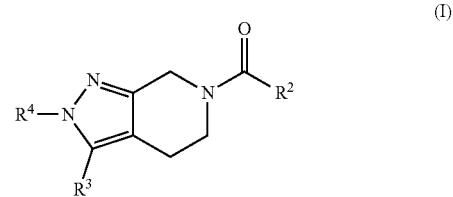

(I)

wherein:
$R^2$ is selected from the group consisting of:

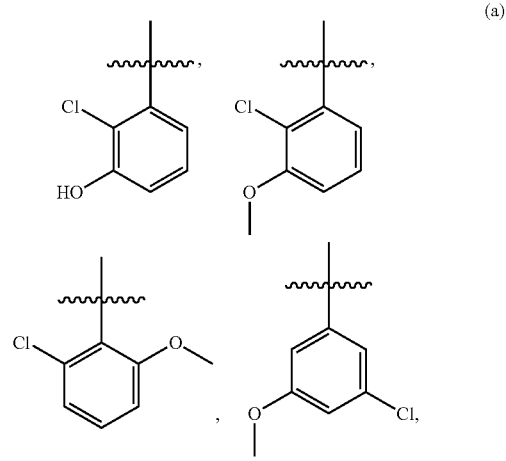

(a)

-continued
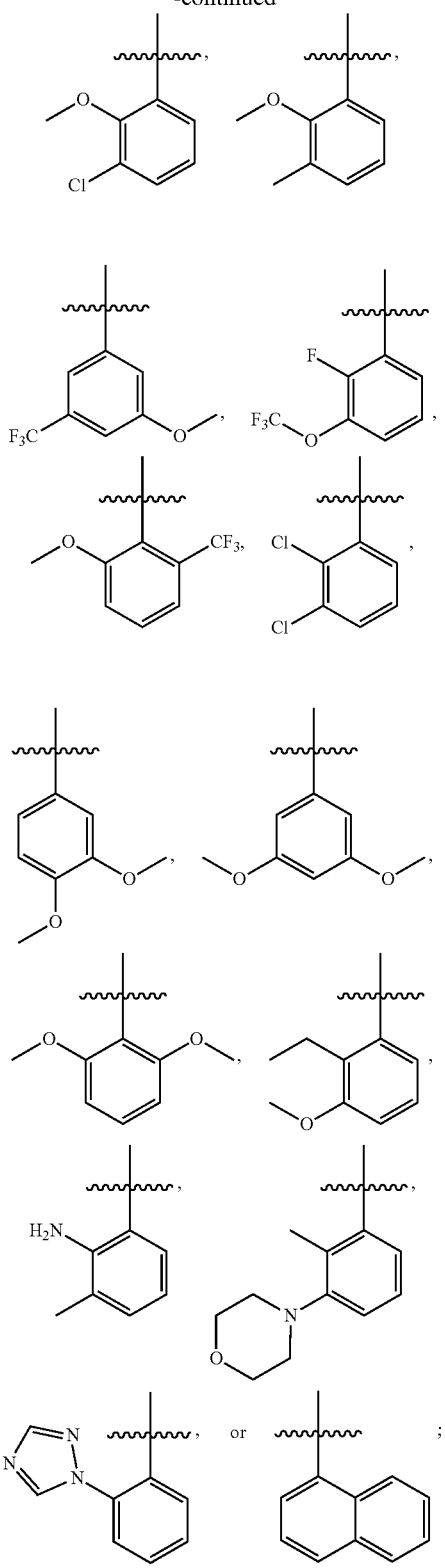
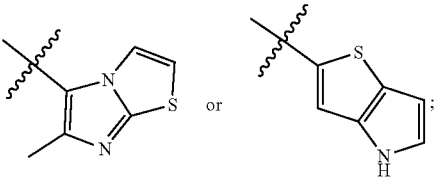
(d)
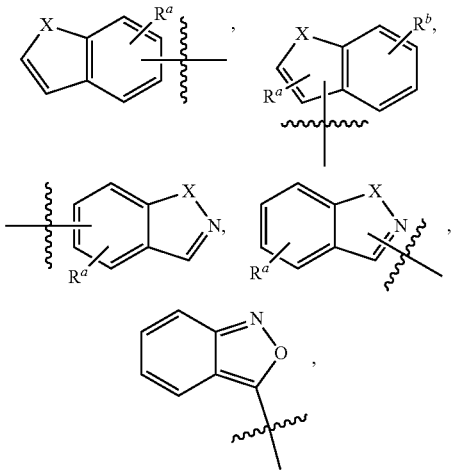
(e)
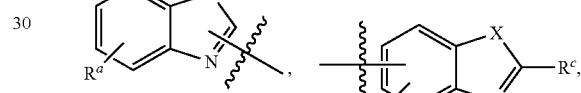

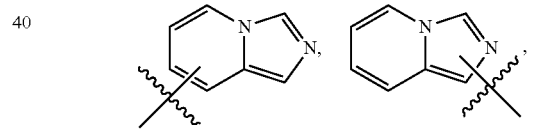
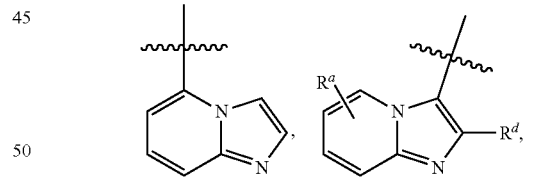
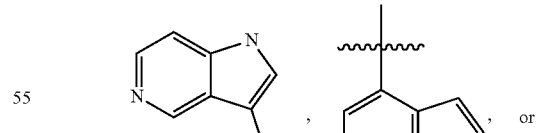
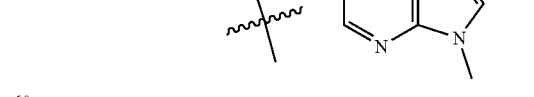
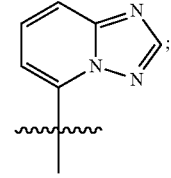
(b) pyridyl substituted with $OC_{1-4}$haloalkyl;
(c) pyrazole or 1H-1,2,4-triazole each substituted with one or two members each independently selected from the group consisting of: H, Cl, $C_{1-4}$alkyl, cyclopropyl and phenyl;

-continued

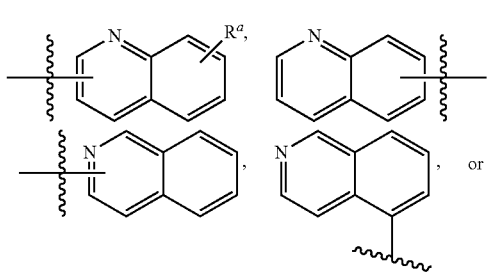
(f)

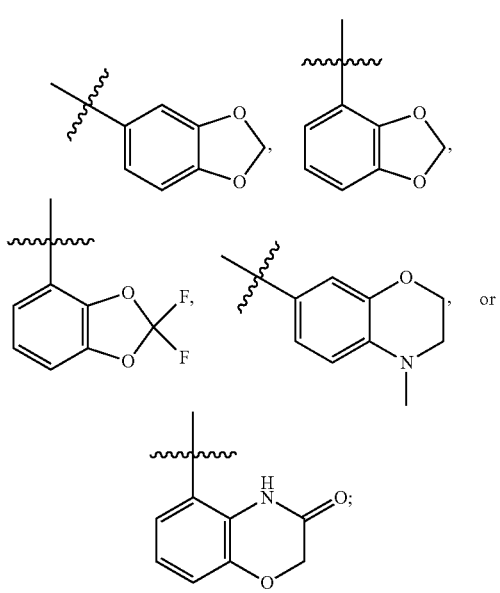
(g)

where X is selected from the group consisting of: O, S, NH, and NCH₃;
$R^a$ is H or halo;
$R^b$ is selected from the group consisting of: H, halo and CH₃;
$R^c$ is H or CF₃; and
$R^d$ is H or CH₃;
$R^3$ is selected from the group consisting of:
(h) Phenyl; or phenyl independently substituted with one or two members selected from the group consisting of: halo and $OC_{1-4}$haloalkyl;

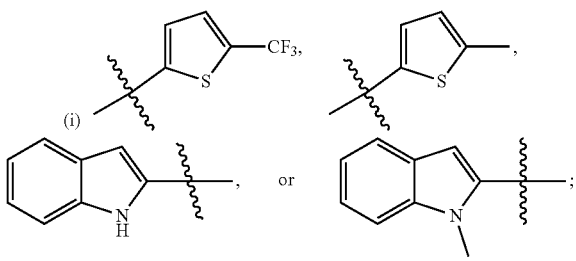
(i)

and
(j) $C_{3-4}$cycloalkyl; and
$R^4$ is selected from the group consisting of: $C_{1-4}$alkyl;
with the proviso that when $R^2$ is

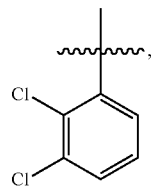

then $R^3$ is cyclopropyl; and pharmaceutically acceptable salts, isotopes, N-oxides, solvates, and stereoisomers thereof.

Embodiments of this invention are also compounds of Formula (II),

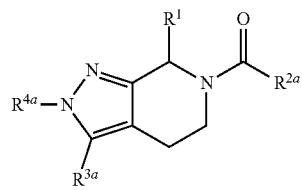
(II)

wherein
$R^1$ is $C_{1-4}$alkyl;
$R^{2a}$ is selected from the group consisting of:
(a)

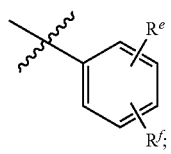

(b) 6-Membered heteroaryl selected from the group consisting of:

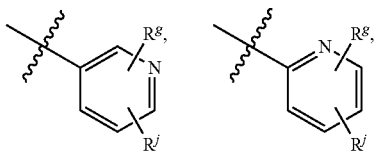

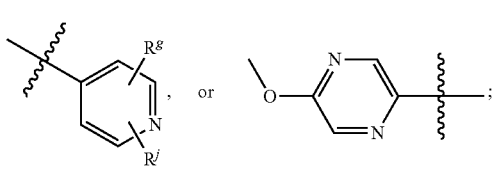

(c) 5-Membered heteroaryl selected from the group consisting of:
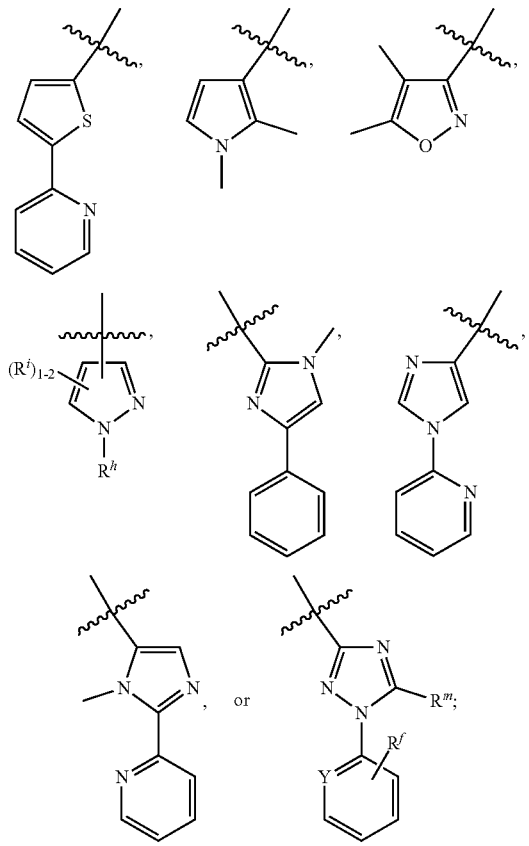
(d) 5,6-Fused or 6,5-fused heteroaryl selected from the group consisting of:
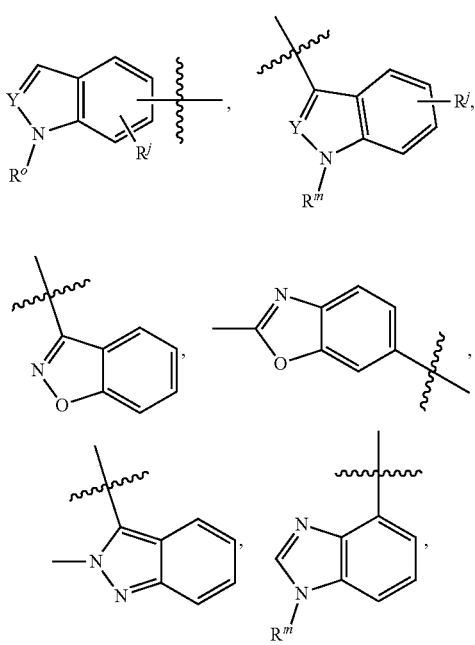
-continued
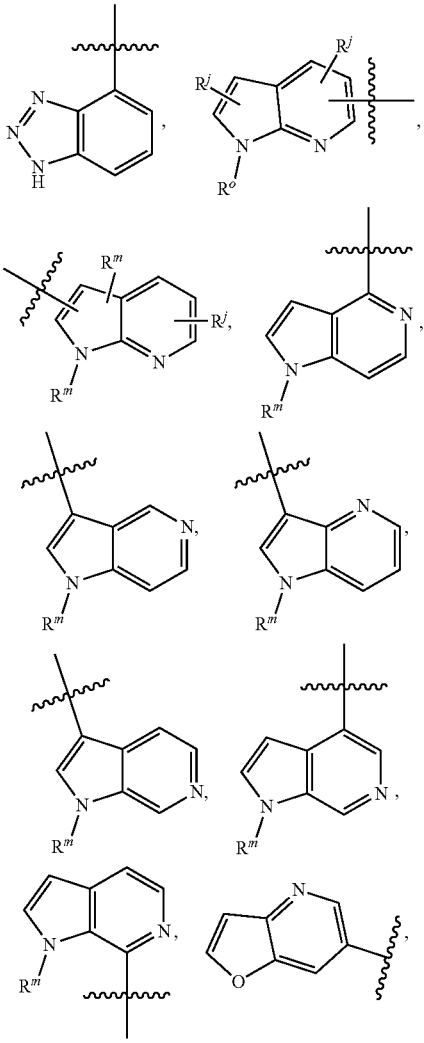
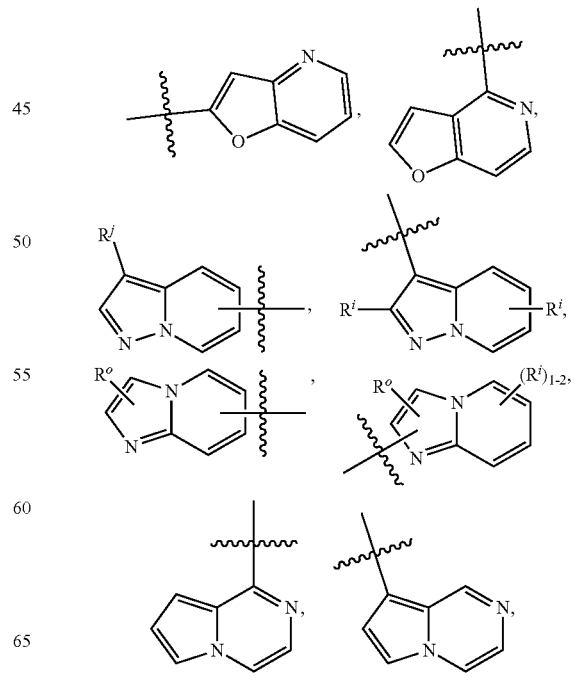

-continued
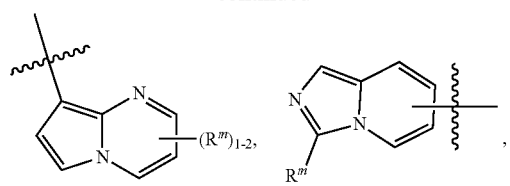 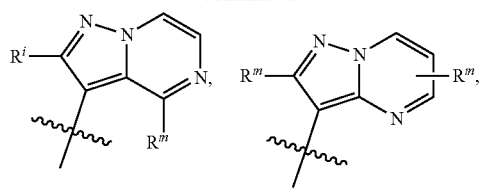
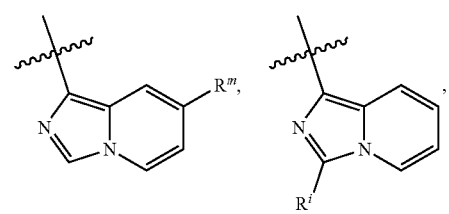 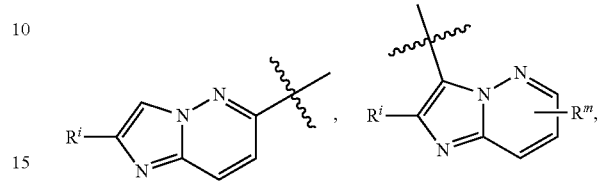
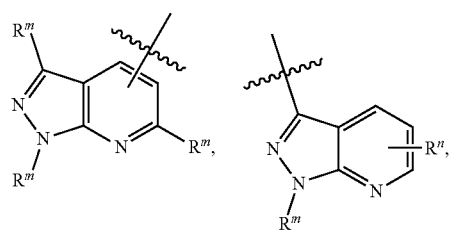 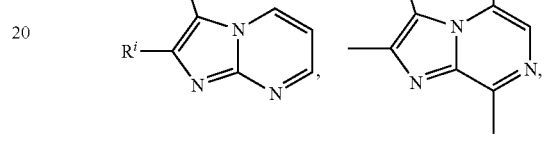
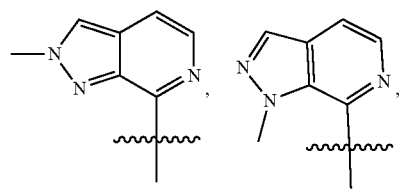 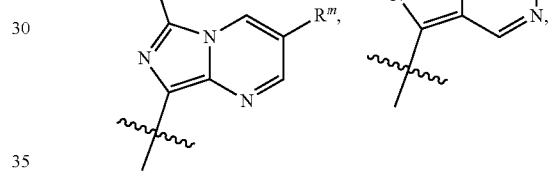
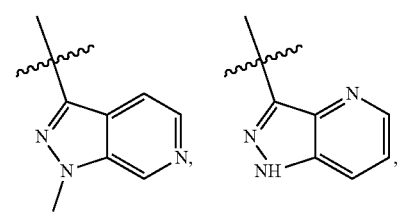 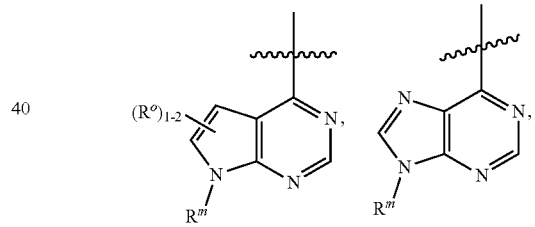
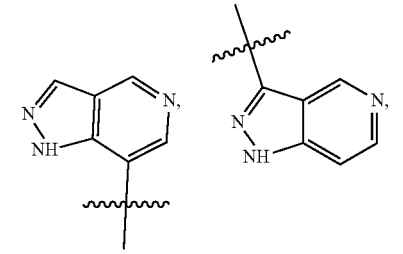 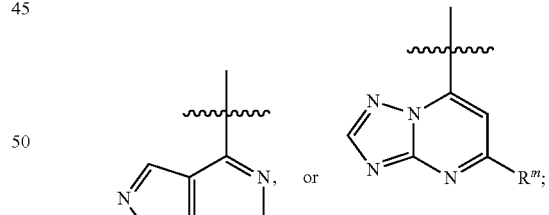
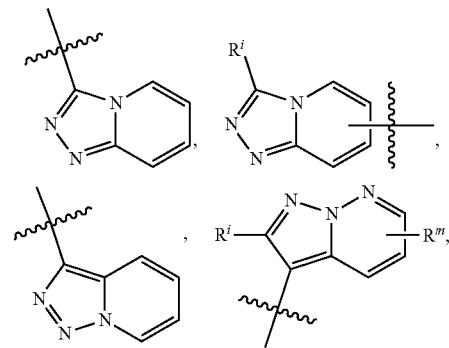
(e) Fused 6,6 heteroaryl selected from the group consisting of:
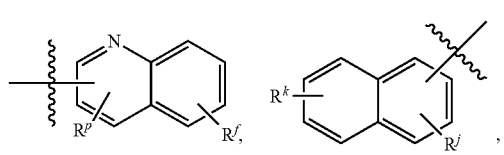

-continued
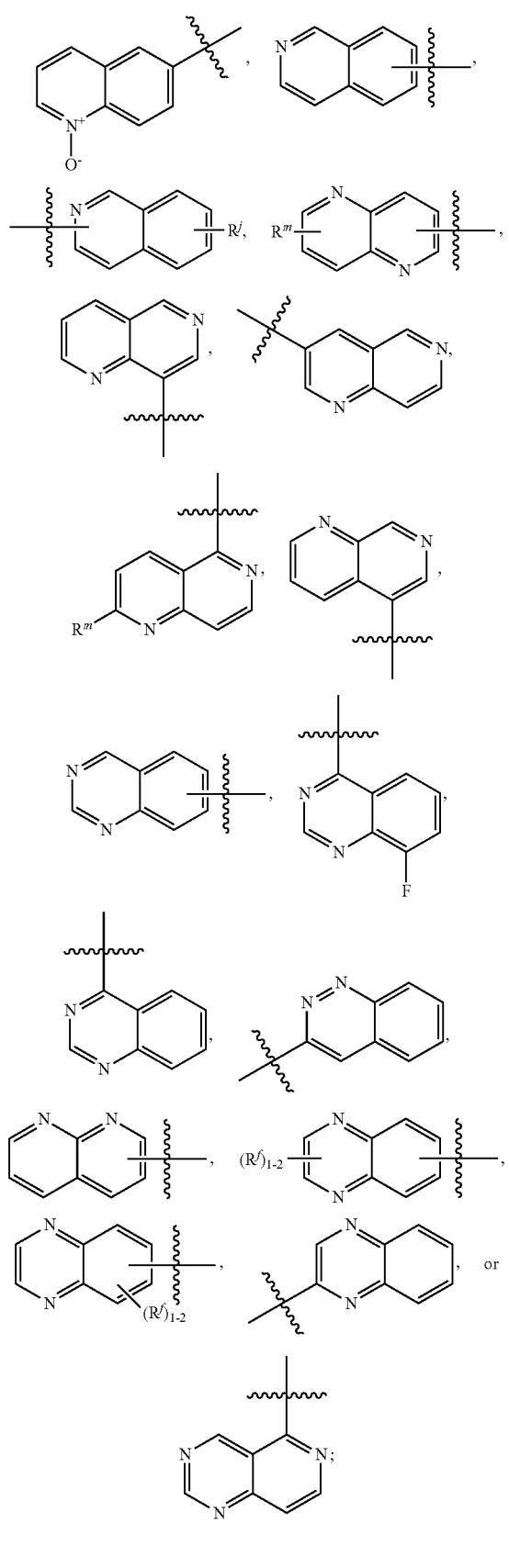
and
(f) Heterocycloalkyl selected from the group consisting of:
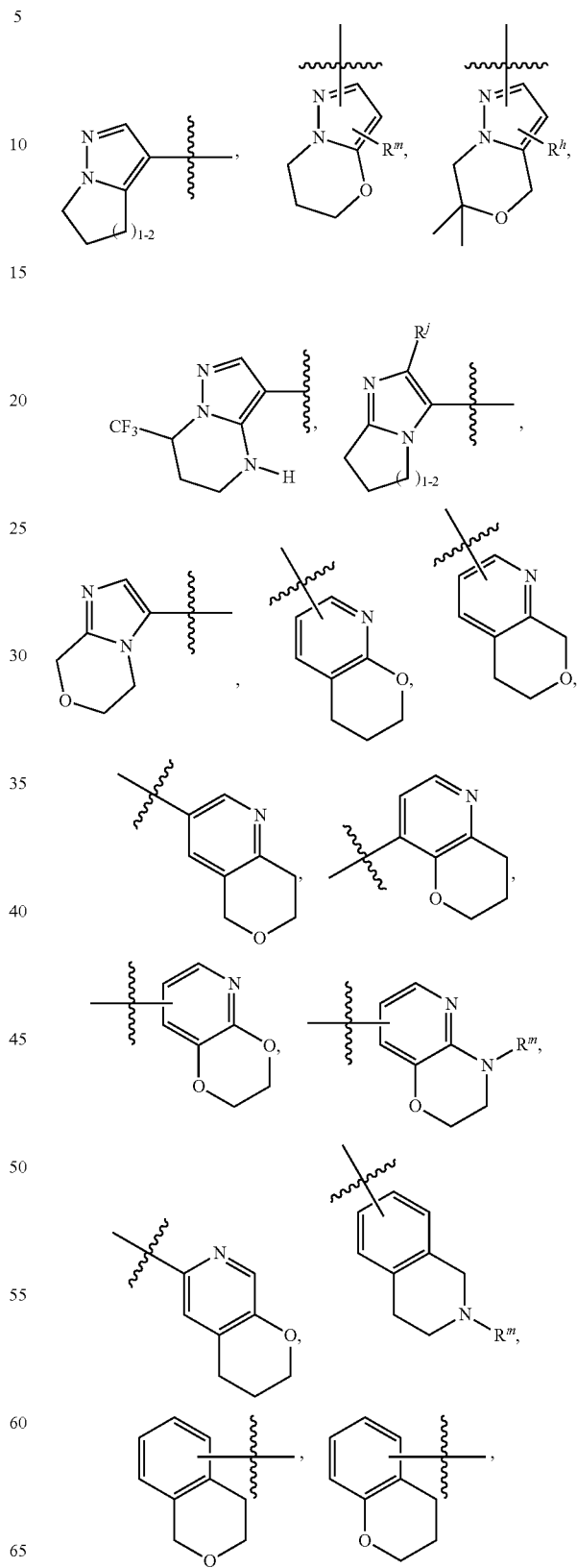

-continued

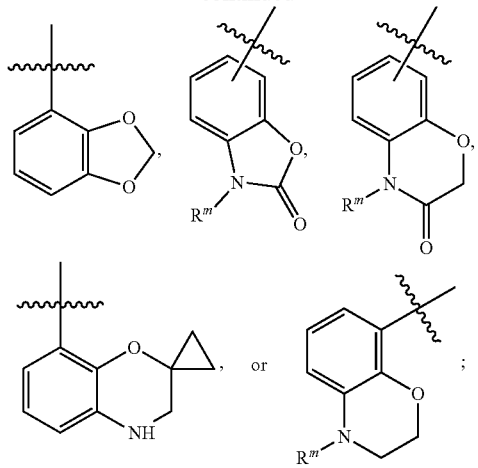

$R^{3a}$ is selected from the group consisting of:
(g) Phenyl; or phenyl substituted with one, two, or three members each independently selected from the group consisting of: halo, $C_{1-4}$alkyl, $C_{1-4}$haloalkyl, $OC_{1-4}$alkyl, and $OC_{1-6}$haloalkyl;
(h) 5-Membered heteroaryl selected from the group consisting of:

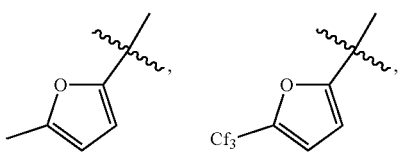

and

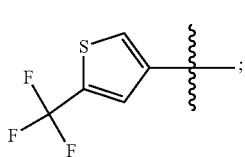

(i) 6-Membered heteroaryl selected from the group consisting of:

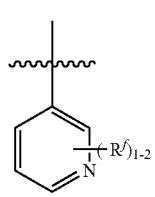

and

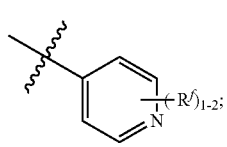

(j) 5,6-Fused or 6,5-fused heteroaryl selected from the group consisting of:

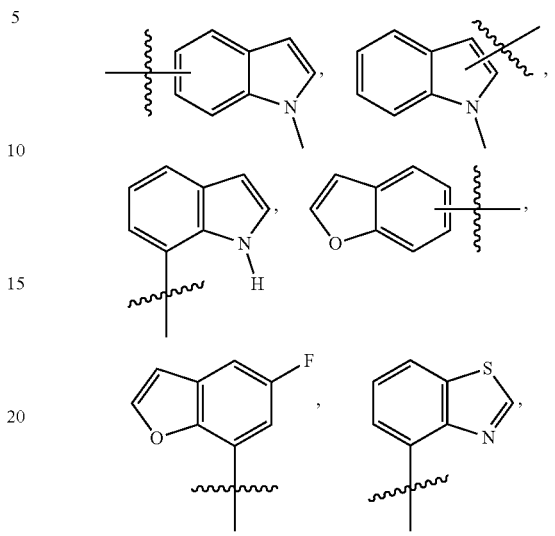

and

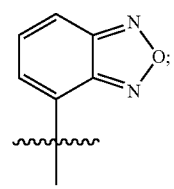 [SMILES: *c1cccc2nonc12]

and
(k) Heterocycloalkyl selected from the group consisting of:

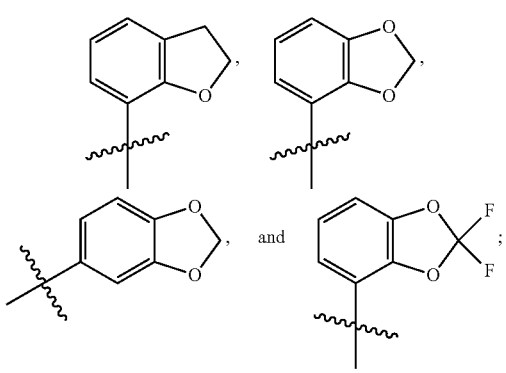

$R^e$ is selected from the group consisting of: $OC_{1-4}$alkyl, $OC_{1-4}$haloalkyl, $(C=O)NHCH_3$, and 5-membered heteroaryl ring containing two or three nitrogen members, wherein the 5-membered heteroaryl ring is optionally substituted with one $R^f$ member;
$R^f$ is selected from the group consisting of: H, halo, $C_{1-4}$alkyl, $C_{1-4}$haloalkyl, $OC_{1-4}$alkyl, and $OC_{1-4}$haloalkyl;
$R^g$ is selected from the group consisting of: $OC_{1-4}$alkyl, $OC_{1-4}$haloalkyl, $CH_2OCH_3$, $CH_2OH$,

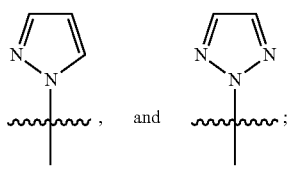 [SMILES: *n1cccn1 ; *n1nccn1]

$R^h$ is selected from the group consisting of: H, $C_{1-4}$alkyl, $C_{1-4}$haloalkyl, and $C_{3-6}$cycloalkyl;

$R^i$ is selected from the group consisting of: H, halo, $C_{1-4}$alkyl, $C_{1-4}$haloalkyl, $OC_{1-4}$alkyl, $C_{3-6}$cycloalkyl, and $C_{3-6}$cycloalkyl substituted with one or two members independently selected from: F and $CH_3$;

$R^j$ is selected from the group consisting of: H, halo, $C_{1-4}$alkyl and $C_{1-4}$haloalkyl;

$R^k$ is selected from the group consisting of: H, halo, OH, $C_{1-4}$alkyl, $C_{1-4}$haloalkyl, $OC_{1-4}$alkyl, and $OC_{1-4}$haloalkyl;

$R^m$ is H or $C_{1-4}$alkyl;

$R^n$ is selected from the group consisting of: H, halo and $OC_{1-4}$alkyl;

$R^o$ is selected from the group consisting of: H, $C_{1-4}$alkyl, and $C_{1-4}$haloalkyl;

$R^p$ is selected from the group consisting of: H, $C_{1-4}$alkyl, and $OC_{1-4}$alkyl;

Y is CH or N; and $R^{4a}$ is selected from the group consisting of: $CH_3$, $CF_2H$, $CF_3$, $C_{3-6}$cycloalkyl, and phenyl; and pharmaceutically acceptable salts, isotopes, N-oxides, solvates, and stereoisomers thereof.

DETAILED DESCRIPTION OF THE INVENTION

As used herein, the terms "including", "containing" and "comprising" are used in their open, non-limiting sense.

Unless qualified specifically in particular instances of use, the term "alkyl" refers to a straight- or branched-chain alkyl group having from 1 to 8 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. "$C_1$-$C_4$alkyl" refers to straight- or branched-chain alkyl group having from 1 to 4 carbon atoms in the chain.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

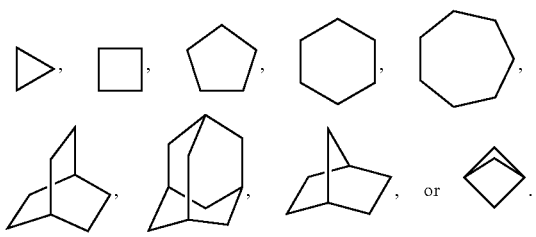

The term "halogen" or "halo" represents chlorine, fluorine, bromine, or iodine.

The term "haloalkyl" refers to a straight- or branched-chain alkyl group having from 1 to 6 carbon atoms in the chain optionally substituting hydrogens with halogens. The term "$C_1$-$C_4$ haloalkyl" as used here refers to a straight- or branched-chain alkyl group having from 1 to 4 carbon atoms in the chain, optionally substituting hydrogens with halogens. Examples of "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl ($CF(CF_3)_2$), and groups that in light of the ordinary skill in the art and the teachings provided herein would be considered equivalent to any one of the foregoing examples.

The term "aryl" refers to a monocyclic, aromatic carbocycle (ring structure having ring atoms that are all carbon) having 6 atoms per ring (Carbon atoms in the aryl groups are sp2 hybridized.)

The term "phenyl" represents the following moiety:

The term "heteroaryl" as used herein, refers to an aromatic monocyclic or multicyclic ring system comprising 5 to 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is monocyclic and has 5 or 6 ring atoms and at least one nitrogen ring atom. A heteroaryl group is joined via a ring carbon atom and any nitrogen atom of a heteroaryl can be optionally oxidized to the corresponding N-oxide. The term "heteroaryl" also encompasses a heteroaryl group, as defined above, which has been fused to a benzene ring.

The term "5-membered heteroaryl" as used herein, refers to a heteroaryl group, as defined above, which has 5 ring atoms. Non-limiting examples of illustrative 5-membered heteroaryls include:

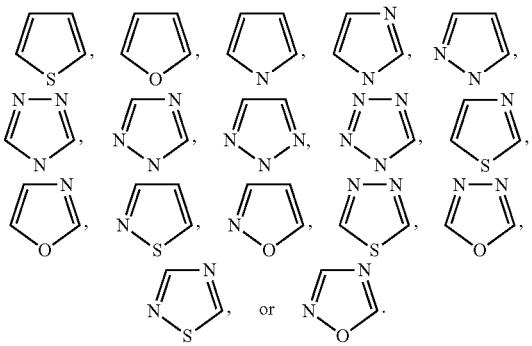

The term "6-membered heteroaryl" as used herein, refers to a heteroaryl group, as defined above, which has 6 ring atoms. Non-limiting examples of illustrative 6-membered heteroaryls include:

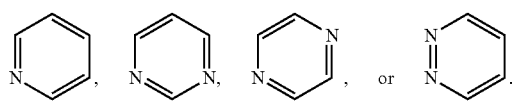

The term "5,6-fused bicyclic heteroaryl or 6,5-fused bicyclic heteroaryl" as used herein, refers to a heteroaryl group, as defined above, which has 9 ring atoms. Non-limiting examples of illustrative 5,6-fused bicyclic heteroaryl or 6,5-fused bicyclic heteroaryl include:

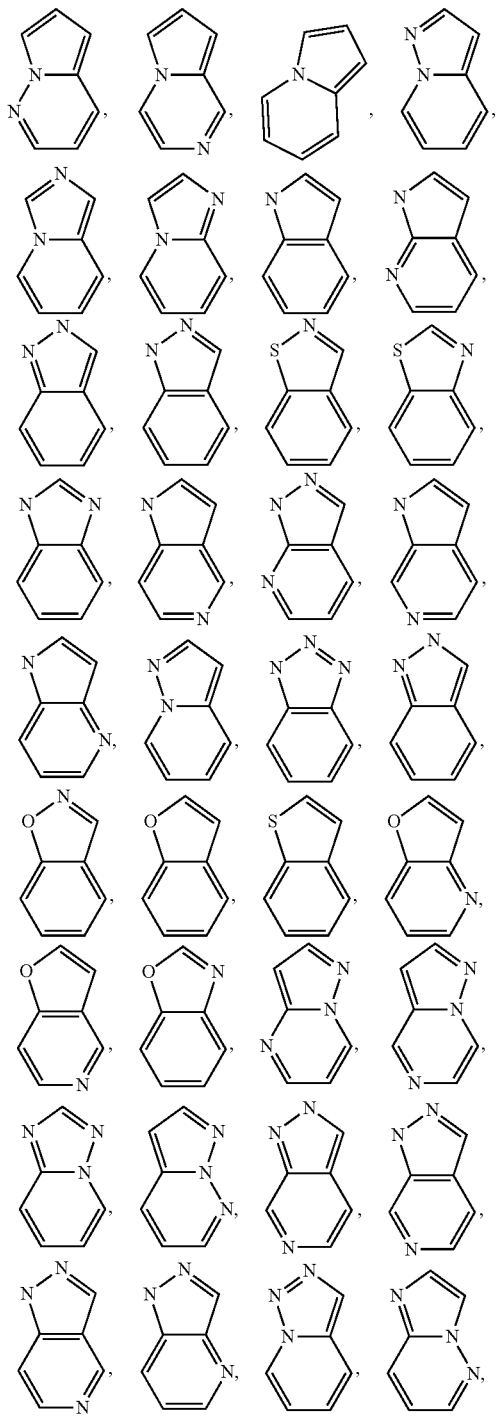

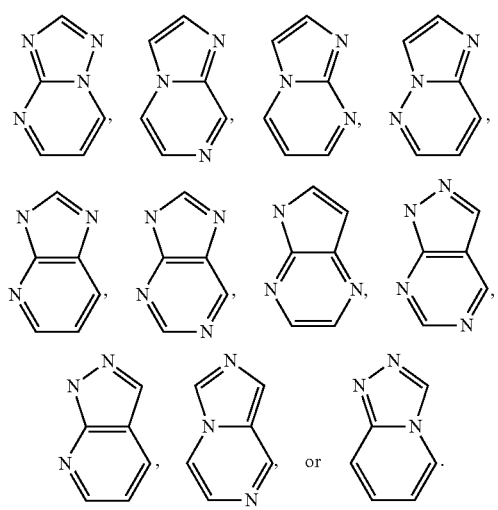

The term "6,6-fused bicyclic heteroaryl" as used herein, refers to a heteroaryl group, as defined above, which has 9 ring atoms. Non-limiting examples of illustrative 6,6-fused bicyclic heteroaryl include:

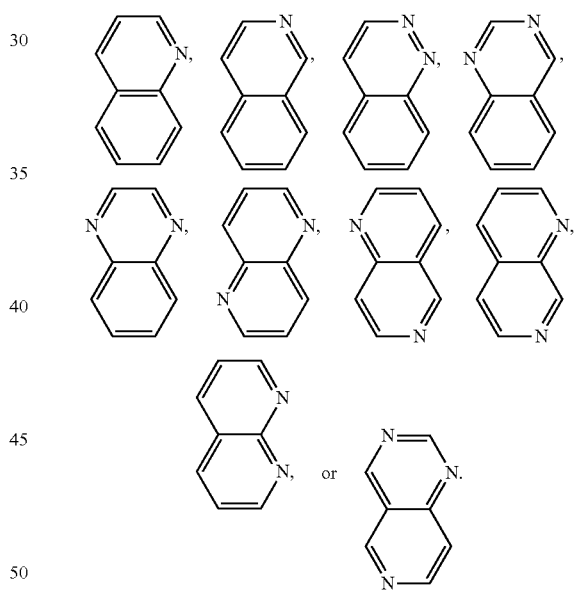

The term "heterocycloalkyl" as used herein, refers to a ring system which is non-aromatic, 1 to 4 of the ring atoms is independently O, N or S and the remaining ring atoms are carbon atoms, which may optionally be fused to another ring (aromatic or heteroaromatic). Non-limiting examples of illustrative 6,6-fused bicyclic heteroaryl include:

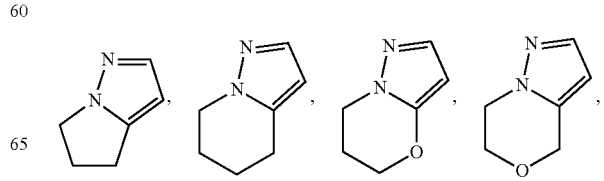

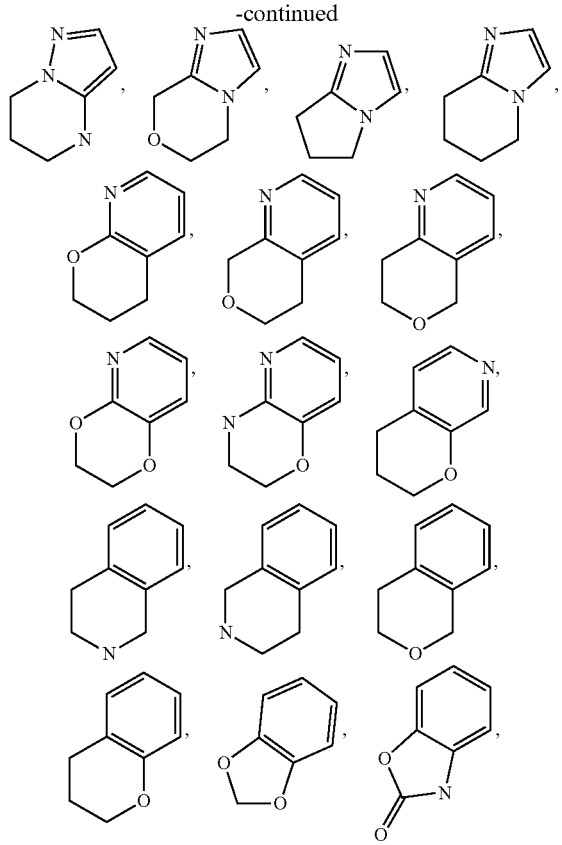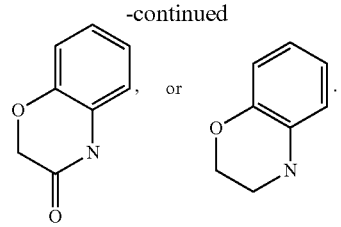

Those skilled in the art will recognize that the species of heteroaryl, cycloalkyl, aryl groups listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

The term "variable point of attachment" means that a group is allowed to be attached at more than one alternative position in a structure. The attachment will always replace a hydrogen atom on one of the ring atoms. In other words, all permutations of bonding are represented by the single diagram, as shown in the illustrations below.

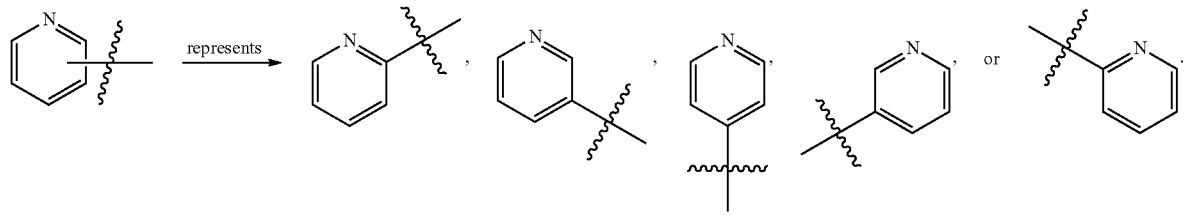

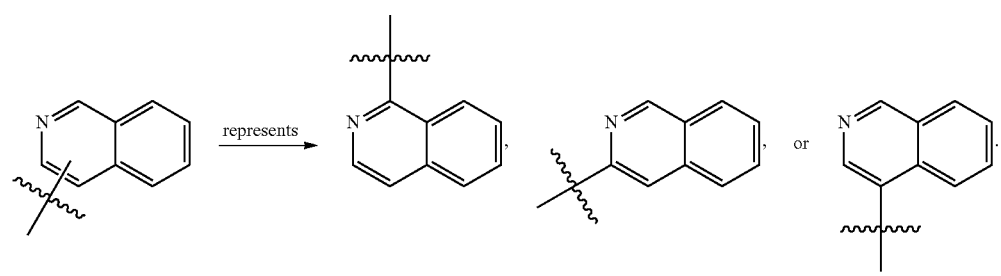

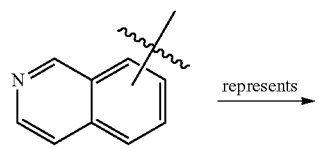

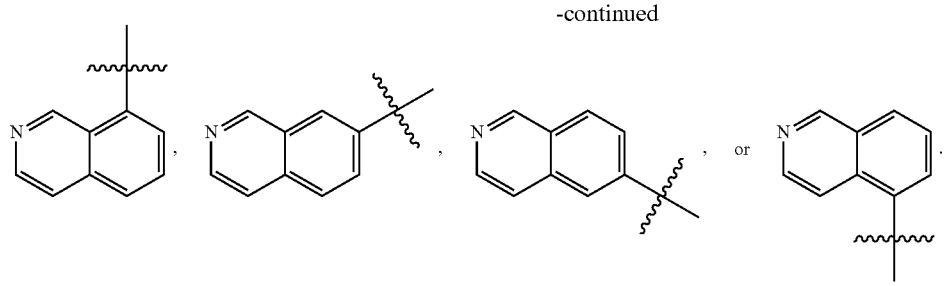

Those skilled in the art will recognize that that if more than one such substituent is present for a given ring, the bonding of each substituent is independent of all of the others. The groups listed or illustrated above are not exhaustive.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of such formula. The compounds of this invention may possess one or more asymmetric centers; such compounds can therefore be produced as individual (R)- or (S)-stereoisomers or as mixtures thereof. Thus, any formula given herein is intended to represent a racemate, one or more of its enantiomeric forms, one or more of its diastereomeric forms, and mixtures thereof. Additionally, any formula given herein is intended to refer also to any one of hydrates, solvates, polymorphs and of such compounds, and mixtures thereof, even if such forms are not listed explicitly.

The term "R" at a stereocenter designates that the stereocenter is purely of the R-configuration as defined in the art; likewise, the term "S" means that the stereocenter is purely of the S-configuration. As used herein, the term "RS" refers to a stereocenter that exists as a mixture of the R- and S-configurations.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Unlabeled stereocenters drawn without stereo bond designations are a mixture of the R- and S-configurations. For unlabeled stereocenters drawn with stereo bond designations, the absolute stereochemistry is as depicted.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number in an enriched form. Examples of isotopes that can be incorporated into compounds of the invention in a form that exceeds natural abundances include isotopes of hydrogen, carbon, nitrogen, oxygen, phosphorous, fluorine, chlorine, and iodine, such as $^{2}$H (or chemical symbol D), $^{3}$H (or chemical symbol T), $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (preferably with $^{14}$C), reaction kinetic studies (with, for example $^{2}$H or $^{3}$H), detection or imaging techniques [such as positron emission tomography (PET) or single-photon emission computed tomography (SPECT)] including drug or substrate tissue distribution assays, or in radioactive treatment of patients. In particular, an F or $^{11}$C labeled compound may be particularly preferred for PET or SPECT studies. Further, substitution with heavier isotopes such as deuterium (i.e., $^{2}$H, or D) may afford certain therapeutic advantages resulting from greater metabolic stability, for example increased in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for such variable appearing elsewhere. In other words, where a variable appears more than once, the choice of the species from a specified list is independent of the choice of the species for the same variable elsewhere in the formula, unless stated otherwise.

The term $C_{n-m}$ alkyl refers to an aliphatic chain, whether straight or branched, with a total number N of carbon members in the chain that satisfies n≤N≤m, with m>n.

When the same plurality of substituents is assigned to various groups, the specific individual substituent assignment to each of such groups is meant to be independently made with respect to the specific individual substituent assignments to the remaining groups. By way of illustration, but not as a limitation, if each of groups Q and R can be H or F, the choice of H or F for Q is made independently of the choice of H or F for R, so the choice of assignment for Q does not determine or condition the choice of assignment for R, or vice-versa, unless it is expressly indicated otherwise. Illustrative claim recitation in this regard would read as "each of Q and R is independently H or F", or "each of Q and R is independently selected from the group consisting of H and F".

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

In another example, a zwitterionic compound would be encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI.27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well-established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$," is accordingly used herein for the sake of brevity, but not by way of limitation. The foregoing first example on substituent terminology, which is stated in generic terms, is meant to illustrate the various substituent assignments described herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$," is accordingly used herein for the sake of brevity, but not by way of limitation. The foregoing second example on substituent terminology, which is stated in generic terms, is meant to illustrate the various substituent assignments described herein.

The nomenclature "$C_i$-$C_j$" with j>i, when applied herein to a class of substituents, is meant to refer to embodiments of this invention for which each and every one of the number of carbon members, from i to j including i and j, is independently realized. By way of example, the term $C_1$-$C_3$ refers independently to embodiments that have one carbon member ($C_1$), embodiments that have two carbon members ($C_2$), and embodiments that have three carbon members ($C_3$).

A "pharmaceutically acceptable salt" is intended to mean a salt of an acid or base of a compound represented by Formula (I) (as well as compounds of Formula (II)) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response.

A compound of Formula (I) (as well as compounds of Formula (II)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

Compounds of Formula (I) (as well as compounds of Formula (II)) may contain at least one nitrogen of basic character, so desired pharmaceutically acceptable salts may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents.

Compounds of Formula (I) (as well as compounds of Formula (II)) may contain a carboxylic acid moiety, a desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, piperazine, N-methyl-glucamine and tromethamine and inorganic salts derived from sodium, calcium, potassium, magnesium, manganese, iron, copper, zinc, aluminum, and lithium.

The compounds of the invention, including their pharmaceutically acceptable salts, whether alone or in combination, (collectively, "active agent" or "active agents") of the present invention are useful as MGL-modulators in the methods of the invention. Such methods for modulating MGL comprise the use of a therapeutically effective amount of at least one chemical entity of the invention.

In some embodiments, the MGL modulator is an inhibitor and is used in a subject diagnosed with or suffering from a disease, disorder, or condition associated with MGL receptor activity, such as those described herein. Symptoms or disease states are intended to be included within the scope of "disease, disorders or conditions."

Accordingly, the invention relates to methods of using the active agents described herein to treat subjects diagnosed with or suffering from a disease, disorder, or condition associated with the MGL receptor activity. The term "treat" or "treating" as used herein is intended to refer to administration of an active agent or composition of the invention to a subject for the purpose of effecting a therapeutic or prophylactic benefit through modulation of MGL receptor activity. Treating includes reversing, ameliorating, alleviating, inhibiting the progress of, lessening the severity of, or preventing a disease, disorder, or condition, or one or more symptoms of such disease, disorder or condition associated with the MGL modulation. The term "subject" refers to a mammalian patient in need of such treatment, such as a human.

The term "composition" refers to a product that includes the specified ingredients in therapeutically effective amounts, as well as any product that results, directly, or indirectly, from combinations of the specified ingredients in the specified amounts.

The term "MGL inhibitor" is intended to encompass a compound that interacts with MGL to substantially reduce or eliminate its catalytic activity, thereby increasing the concentrations of its substrate(s). The term "MGL-modulated" is used to refer to the condition of being affected by the modulation of the MGL enzyme including the condition of being affected by the inhibition of the MGL enzyme. The disclosure is directed to methods for treating, ameliorating and/or preventing diseases, conditions, or disorders associated with pain (including inflammatory pain), and also psychiatric disorders, neurological disorders, cancers and eye conditions by the administration of therapeutically effective amounts of MGL modulators to subjects in need thereof.

The term "modulators" include both inhibitors and activators, where "inhibitors" refer to compounds that decrease, prevent, inactivate, desensitize, or down-regulate the MGL expression or activity, and "activators" are compounds that increase, activate, facilitate, sensitize, or up-regulate MGL expression or activity.

As used herein, unless otherwise noted, the term "affect" or "affected" (when referring to a disease, condition or disorder that is affected by inhibition of MGL) includes a reduction in the frequency and/or severity of one or more symptoms or manifestations of said disease, condition or disorder; and/or include the prevention of the development of one or more symptoms or manifestations of said disease, condition or disorder or the development of the disease, condition or disorder.

In treatment methods according to the invention, a therapeutically effective amount of at least one active agent according to the invention is administered to a subject suffering from or diagnosed as having such a disease, disorder, or condition. A "therapeutically effective amount" means an amount or dose sufficient to generally bring about the desired therapeutic or prophylactic benefit in subjects in need of such treatment for the designated disease, disorder, or condition. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. For a 70-kg human, an illustrative range for a suitable dosage amount is from about 1 to 1000 mg/day in single or multiple dosage units (e.g., BID, TID, QID or as required by modality).

Once improvement of the subject's disease, disorder, or condition has occurred, the dose may be adjusted for preventive or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Subjects may, however, require intermittent treatment on a long-term basis upon any recurrence of symptoms.

In addition, the compounds of the invention are envisaged for use alone, in combination with one or more of other compounds of this invention, or in combination with additional active ingredients in the treatment of the conditions discussed below. The additional active ingredients may be co-administered separately with at least one compound of the invention, with active agents of the invention or included with such an agent in a pharmaceutical composition according to the invention. In an illustrative embodiment, additional active ingredients are those that are known or discovered to be effective in the treatment of conditions, disorders, or diseases associated with the MGL modulation, such as another MGL inhibitor or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

When referring to inhibiting the target, an "effective amount" means an amount sufficient to affect MGL modulation.

The active agents of the invention are envisaged for use, alone or in combination with one or more additional active ingredients, to formulate pharmaceutical compositions of the invention. A pharmaceutical composition of the invention comprises a therapeutically effective amount of at least one active agent in accordance with the invention.

Pharmaceutically acceptable excipients commonly used in pharmaceutical compositions are substances that are non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of such excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using pharmaceutically acceptable excipients and compounding techniques known or that become available to those of ordinary skill in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. The compositions may be formulated for any one of a plurality of administration routes, such as intravenous infusion, topical administration, or oral administration. Preferably, the compositions may be formulated for oral administration.

For oral administration, the active agents of the invention can be provided in the form of tablets or capsules, or as a solution, emulsion, or suspension. To prepare the oral compositions, the active agents may be formulated to yield a dosage of, e.g., for a 70-kg human, an illustrative range for a suitable dosage amount is from about 1 to 1000 mg/day in single or multiple dosage units.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin or (hydroxypropyl)methyl cellulose capsules. To prepare hard gelatin capsules, active ingredient(s) may be mixed with a solid, semi-solid, or liquid diluent. Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository, enema or foam. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.01% to about 20% of drug to vehicle, preferably 0.1% to 10%. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

In a further embodiment, the invention is directed to a method of treating a subject suffering from or diagnosed with a disease, disorder, or condition associated with MGL modulation, comprising administering to the subject in need of such treatment a therapeutically effective amount of the active agent.

The compounds of Formula (I) and Formula (II) are useful in methods for treating, ameliorating and/or preventing a disease, a condition or a disorder that is affected by the inhibition of MGL. Such methods comprise administering to a subject, including an animal, a mammal, and a human in need of such treatment, amelioration and/or prevention, a therapeutically effective amount of a compound of Formula (I), Formula (II), or an enantiomer, diastereomer, solvate or pharmaceutically acceptable salt thereof.

In particular, the compounds of Formula (I), Formula (II), or pharmaceutically acceptable salts, isotopes, N-oxides, solvates and stereoisomers thereof, are useful for treating, ameliorating and/or preventing diseases, conditions, or disorders causing pain, psychiatric disorders, neurological disorders, cancers and eyes conditions. More particularly, the compounds of Formula (I), Formula (II), or pharmaceutically acceptable salts, isotopes, N-oxides, solvates and stereoisomers thereof, are useful for treating, ameliorating and/or preventing inflammatory pain, major depressive disorder, treatment resistant depression, anxious depression or bipolar disorder by administering to a subject in need thereof a therapeutically effective amount of a compound of Formula (I), Formula (II), or a pharmaceutically acceptable salt, isotope, N-oxide, solvate or stereoisomer thereof as herein defined.

1) Pain

Examples of inflammatory pain include, but are not limited to, pain due to a disease, condition, disorder, or a pain state including inflammatory bowel disease, visceral pain, migraine, post-operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect bite, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache, or arachnoiditis.

One type of inflammatory pain is inflammatory hyperalgesia/hypersensitivity. Examples of inflammatory hyperalgesia include a disease, condition, disorder, or pain state including inflammation, osteoarthritis, rheumatoid arthritis, back pain, joint pain, abdominal pain, musculoskeletal diseases, skin diseases, post-operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity and/or dermal allergy, itch, eczema, pharyngitis, enteritis, irritable bowel syndrome, inflammatory bowel diseases including Crohn's Disease, ulcerative colitis, benign prostatic hypertrophy, and nasal hypersensitivity.

In an embodiment, the present invention is directed to a method for treating, ameliorating and/or preventing inflammatory visceral hyperalgesia in which an enhanced visceral irritability exists, comprising, consisting of, and/or consisting essentially of the step of administering to a subject in need of such treatment a therapeutically effective amount of a compound of Formula (I) (as well as compounds of Formula (II)) or a pharmaceutically acceptable salt, isotope, N-oxide, solvate or stereoisomer thereof. In a further embodiment, the present invention is directed to a method for treating inflammatory somatic hyperalgesia in which a hypersensitivity to thermal, mechanical and/or chemical stimuli exists, comprising administering to a subject in need of such treatment a therapeutically effective amount of a compound of Formula (I) (as well as compounds of Formula (II)), or a pharmaceutically acceptable salt, isotope, N-oxide, solvate or stereoisomer thereof.

A further embodiment of the present invention is directed to a method for treating, ameliorating and/or preventing neuropathic pain. Examples of a neuropathic pain include pain due to a disease, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngeal neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, vidian neuralgia or chemotherapy-induced neuropathy.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment, the present invention is directed to a method for treating, ameliorating and/or preventing neuropathic cold allodynia in which a hypersensitivity to a cooling stimuli exists, comprising administering to a subject in need of such treatment a therapeutically effective amount of a compound of Formula (I) (as well as compounds of Formula (II)) or a pharmaceutically acceptable salt, isotope, N-oxide, solvate or stereoisomer thereof.

2) Psychiatric Disorders

Examples of psychiatric disorders include, but are not limited to, anxieties such as, social anxiety, post-traumatic stress disorder, phobias, social phobia, special phobias, panic disorder, obsessive-compulsive disorder, acute stress disorder, separation anxiety disorder, and generalized anxiety disorder, as well as depression such as, major depression, bipolar disorder, seasonal affective disorder, post-natal depression, manic depression, and bipolar depression, mood disorders and mood affective disorders that can be treated according to the present invention include, but are not limited to, bipolar disorder I depressed, hypomanic, manic and mixed form; bipolar disorder II; depressive disorders, such as single depressive episode or recurrent major depressive disorder, minor depressive disorder, treatment-resistant depression, anxious depression, bipolar disorder, depressive disorder with postpartum onset, depressive disorders with psychotic symptoms; persistent mood disorders, such as cyclothymia, dysthymia, euthymia; and premenstrual dysphoric disorder; psychoses.

3) Neurological Disorders

Examples of neurological disorder include, but are not limited to, tremors, dyskinesias, dystonias, spasticity, Tourette's Syndrome; neuromyelitis optica, Parkinson's disease; Alzheimer's disease; senile dementia; Huntington's disease; Epilepsy/seizure disorders and sleep disorders.

4) Cancers:

Examples of cancers include, but are not limited to, benign skin tumors, prostate tumors, ovarian tumors and cerebral tumors (glioblastomas, medulloepitheliomas, medulloblastomas, neuroblastomas, tumors of embryonic origin, astrocytomas, astroblastomas, ependymomas, oligodendrogliomas, neuroepitheliomas, epiphyseal tumor, ependymoblastomas, malignant meningiomas, sarcomatosis, malignant melanomas, schwannomas).

5) Eye Conditions

Examples of eye conditions include, but are not limited to, ocular hypertension, glaucoma, degeneration and apoptosis of retinal ganglion cells and neuroretinal cells.

Other embodiments of this invention provide for a method for modulating MGL receptor activity, including when such receptor is in a subject, comprising exposing MGL receptor to a therapeutically effective amount of at least one compound selected from compounds of the invention.

Embodiments of this invention are compounds of Formula (I),

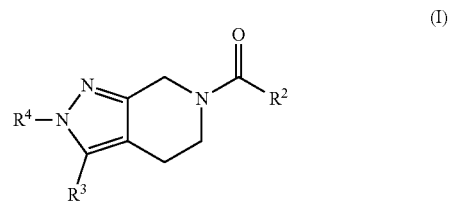

wherein:
$R^2$ is selected from the group consisting of:
(a)

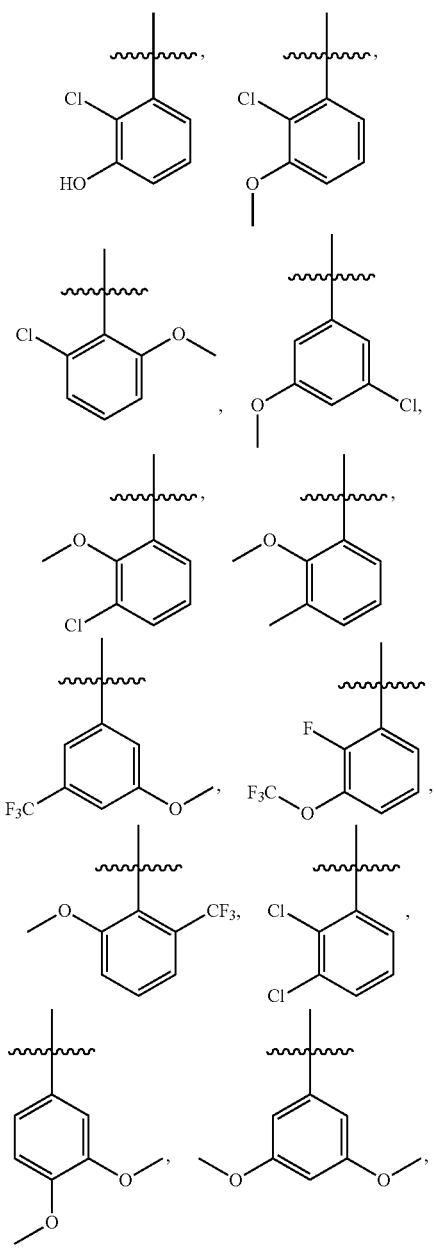

-continued
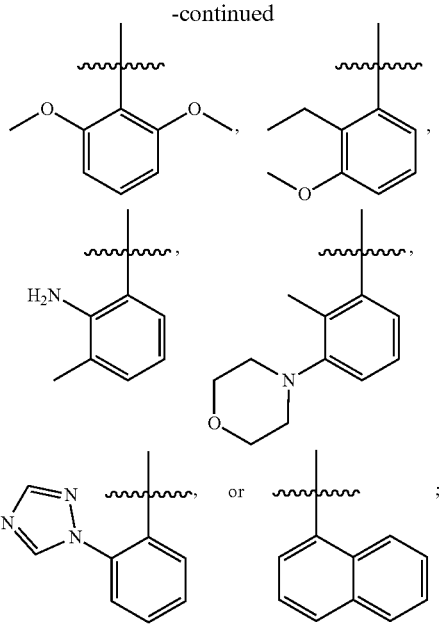
(b) pyridyl substituted with $OC_{1-4}$haloalkyl;
(c) pyrazole or 1H-1,2,4-triazole each substituted with one or two members each independently selected from the group consisting of: H, Cl, $C_{1-4}$alkyl, cyclopropyl and phenyl;
(d)
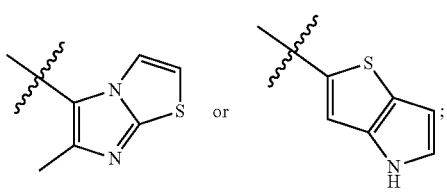
(e)
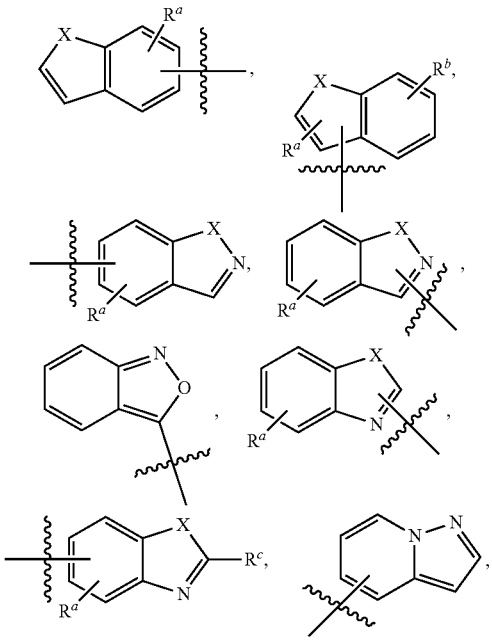
-continued
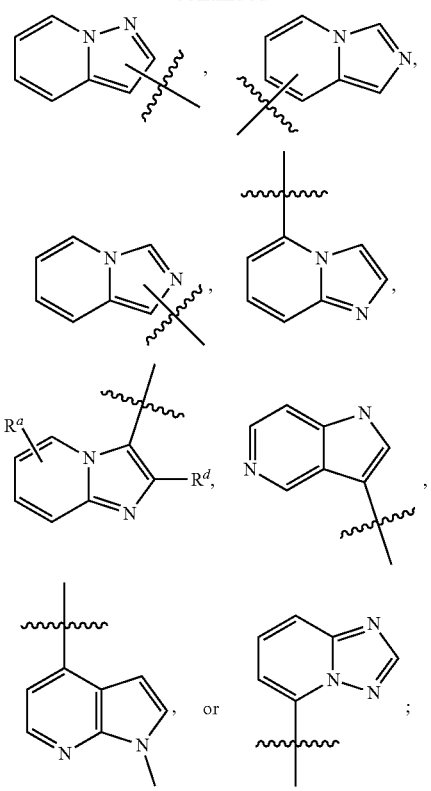
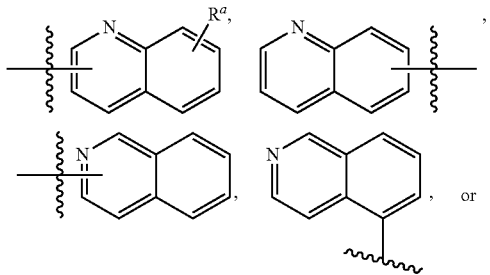
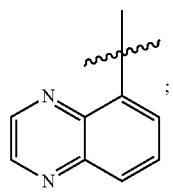; and
(g)
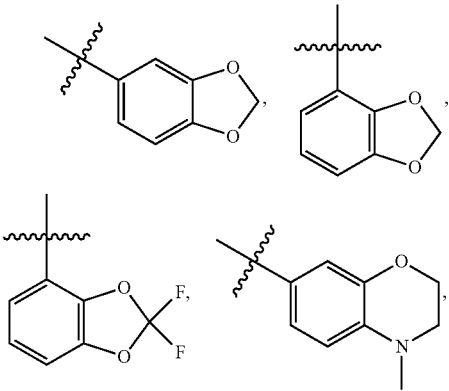

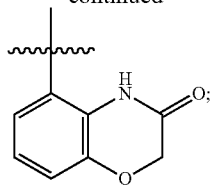

where X is selected from the group consisting of: O, S, NH, and NCH$_3$;

R$^a$ is H or halo;

R$^b$ is selected from the group consisting of: H, halo and CH$_3$;

R$^c$ is H or CF$_3$; and

R$^d$ is H or CH$_3$;

R$^3$ is selected from the group consisting of:

(h) Phenyl; or phenyl independently substituted with one or two members selected from the group consisting of: halo and OC$_{1-4}$haloalkyl;

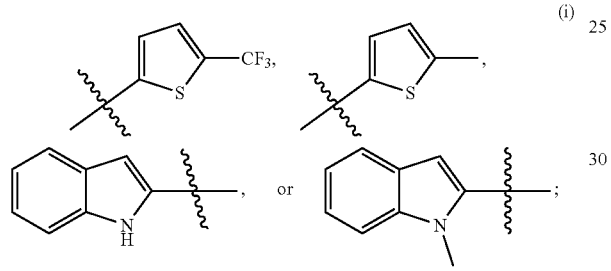

(i)

and (j) C$_{3-4}$cycloalkyl; and

R$^4$ is selected from the group consisting of: C$_{1-4}$alkyl;

with the proviso that when R$^2$ is

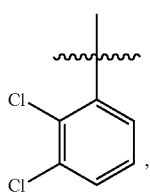 [SMILES: *c1cccc(Cl)c1Cl]

then R$^3$ is cyclopropyl;

and pharmaceutically acceptable salts, isotopes, N-oxides, solvates, and stereoisomers thereof.

An additional embodiment of the invention is a compound of Formula (I) wherein R$^2$ is

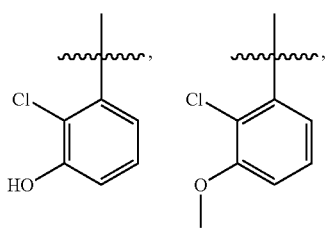

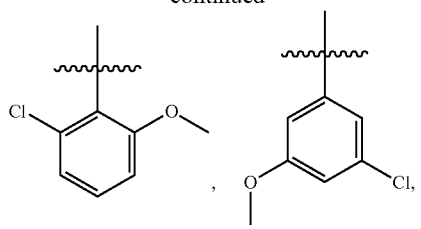

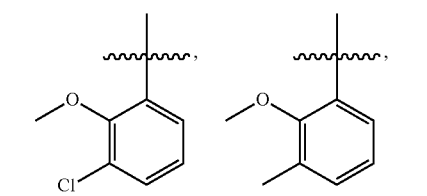

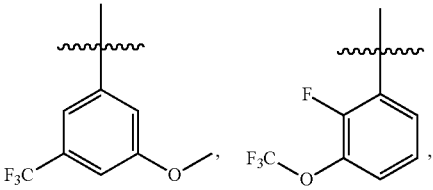

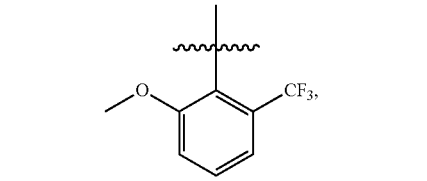

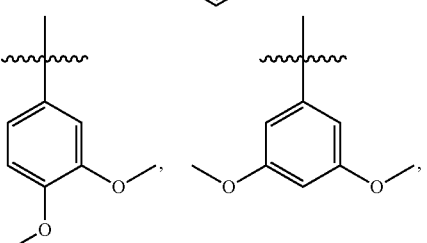

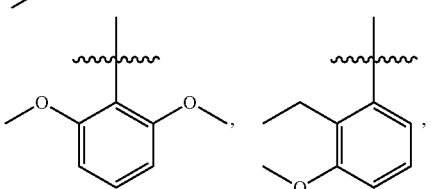

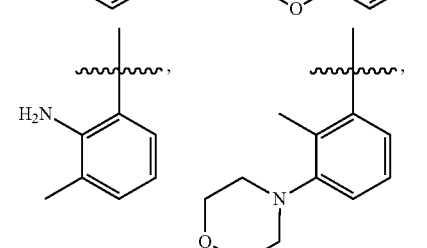

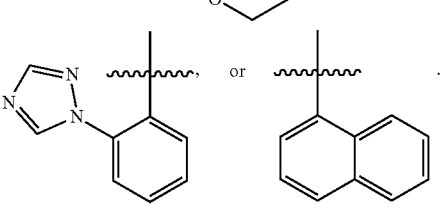

An additional embodiment of the invention is a compound of Formula (I) wherein R² is

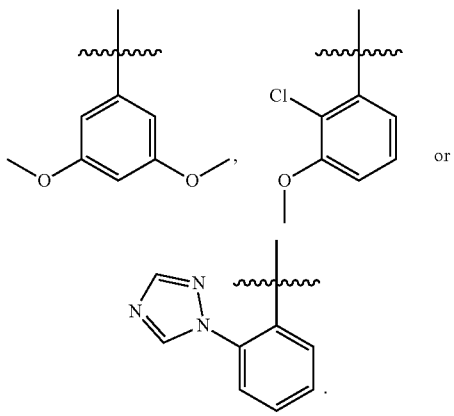

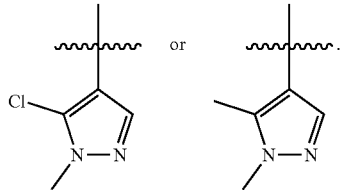 or

An additional embodiment of the invention is a compound of Formula (I) wherein R² is

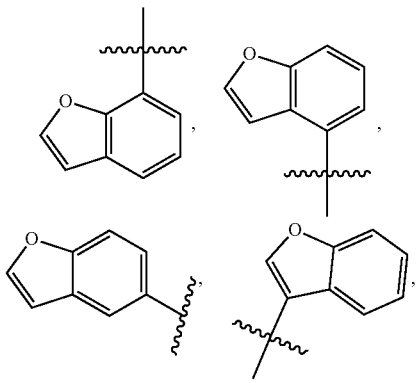

An additional embodiment of the invention is a compound of Formula (I) wherein R² is

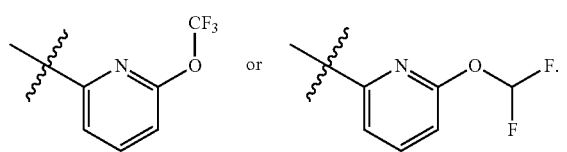 [SMILES: *c1cccc(OC(F)(F)F)n1 ; "or" ; *c1cccc(OC(F)F)n1]

An additional embodiment of the invention is a compound of Formula (I) wherein R² is

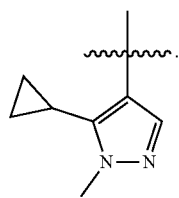 [SMILES: *c1cnn(C)c1C1CC1]

An additional embodiment of the invention is a compound of Formula (I) wherein R² is

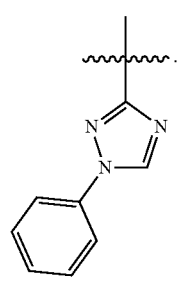 [SMILES: *c1ncn(-c2ccccc2)n1]

An additional embodiment of the invention is a compound of Formula (I) wherein R² is

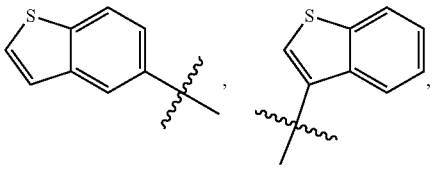

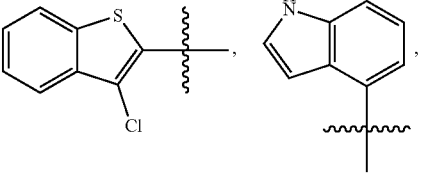

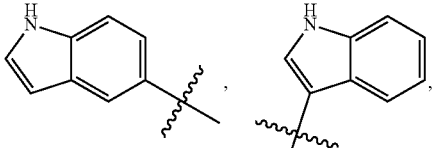

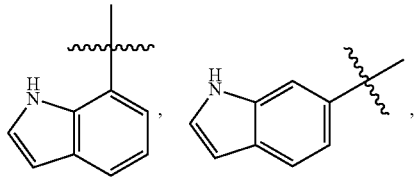

-continued
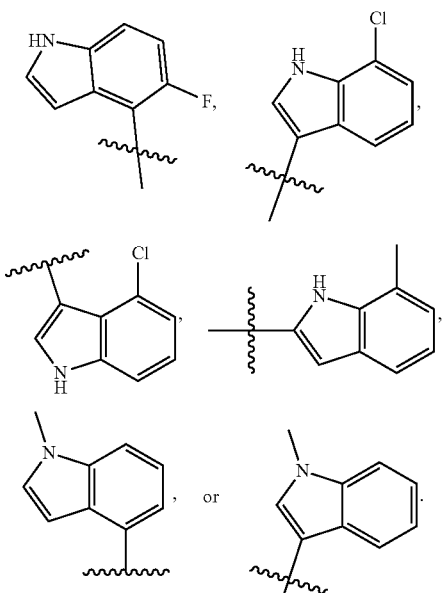
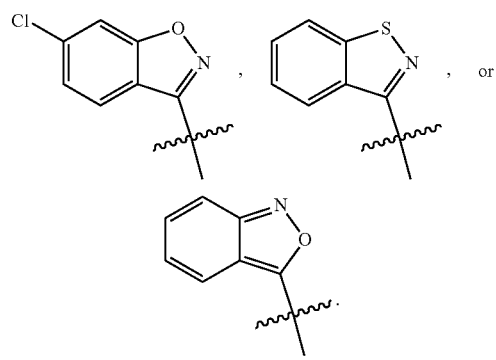
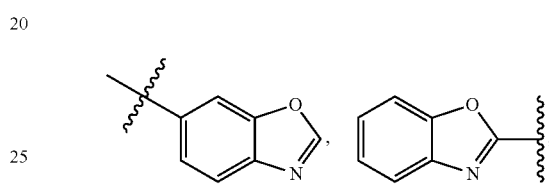
An additional embodiment of the invention is a compound of Formula (I) wherein R² is
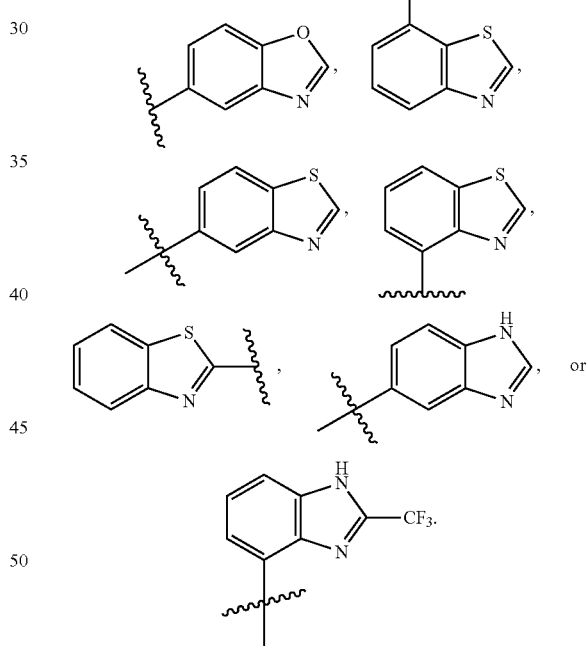
An additional embodiment of the invention is a compound of Formula (I) wherein R² is
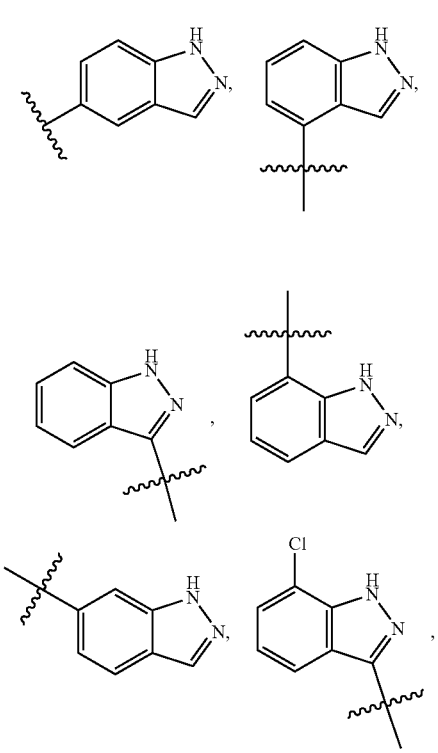
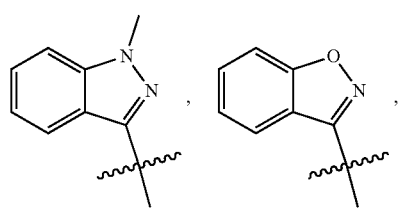
An additional embodiment of the invention is a compound of Formula (I) wherein R² is
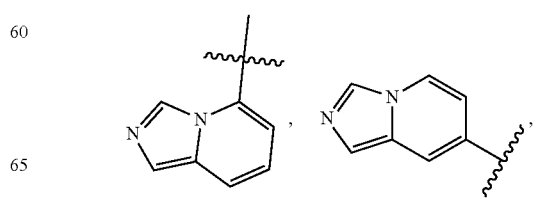

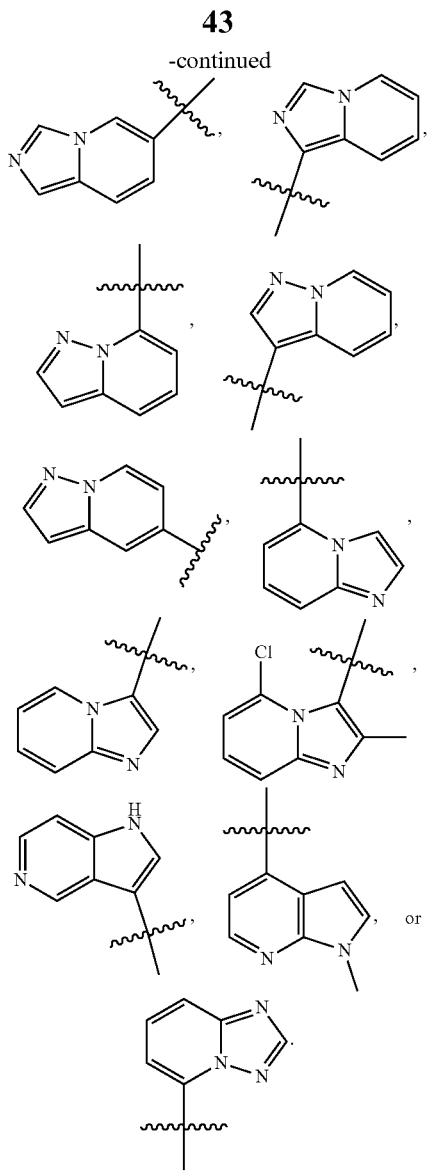

An additional embodiment of the invention is a compound of Formula (I) wherein R² is

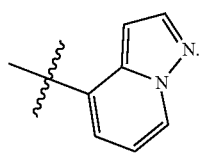 [SMILES: *c1cccn2nccc12]

An additional embodiment of the invention is a compound of Formula (I) wherein R² is

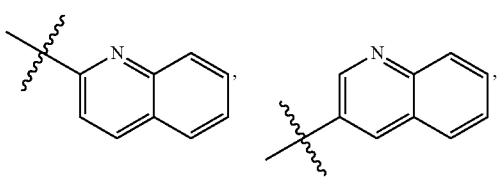

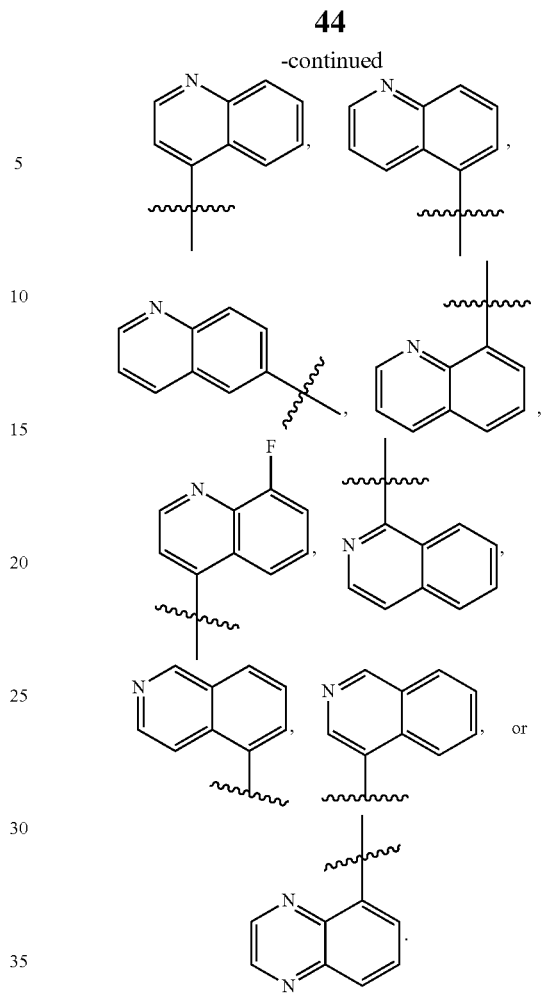

An additional embodiment of the invention is a compound of Formula (I) wherein R² is

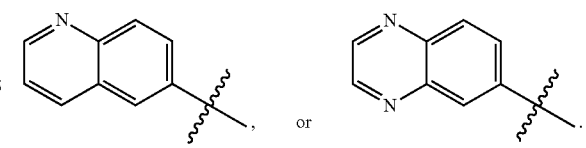

An additional embodiment of the invention is a compound of Formula (I) wherein R³ is phenyl, 3,5-difluorophenyl, 3-chlorophenyl, 3-fluorophenyl, or 3-(difluoromethoxy)phenyl.

An additional embodiment of the invention is a compound of Formula (I) wherein R³ is cyclopropyl.

An additional embodiment of the invention is a compound of Formula (I) wherein R⁴ is CH₃.

An additional embodiment of the invention is a compound of Formula (I) wherein X is O.

An additional embodiment of the invention is a compound of Formula (I) wherein X is S.

An additional embodiment of the invention is a compound of Formula (I) wherein X is NH or NCH₃.

A further embodiment of the current invention is a compound as shown below in Table 1.

| Ex # | Compound Name |
|---|---|
| 1 | (2-Methyl-3-phenyl-2,4,5,7-tetrahydro-6H-pyrazolo[3,4-c]pyridin-6-yl)(naphthalen-1-yl)methanone; |
| 2 | (3-Cyclopropyl-2-methyl-2,4,5,7-tetrahydro-6H-pyrazolo[3,4-c]pyridin-6-yl)(2,3-dichlorophenyl)methanone; |
| 3 | (3-Cyclopropyl-2-methyl-2,4,5,7-tetrahydro-6H-pyrazolo[3,4-c]pyridin-6-yl)(naphthalen-1-yl)methanone; |
| 4 | (2-Fluoro-3-(trifluoromethoxy)phenyl)(2-methyl-3-phenyl-2,4,5,7-tetrahydro-6H-pyrazolo[3,4-c]pyridin-6-yl)methanone; |
| 5 | (2-Methoxy-6-(trifluoromethyl)phenyl)(2-methyl-3-phenyl-2,4,5,7-tetrahydro-6H-pyrazolo[3,4-c]pyridin-6-yl)methanone; |
| 6 | (3-Methoxy-5-(trifluoromethyl)phenyl)(2-methyl-3-phenyl-2,4,5,7-tetrahydro-6H-pyrazolo[3,4-c]pyridin-6-yl)methanone; |
| 7 | (2-Methoxy-3-methylphenyl)(2-methyl-3-phenyl-2,4,5,7-tetrahydro-6H-pyrazolo[3,4-c]pyridin-6-yl)methanone; |
| 8 | (2-Ethyl-3-methoxyphenyl)(2-methyl-3-phenyl-2,4,5,7-tetrahydro-6H-pyrazolo[3,4-c]pyridin-6-yl)methanone; |
| 9 | (3,4-Dimethoxyphenyl)(2-methyl-3-phenyl-2,4,5,7-tetrahydro-6H-pyrazolo[3,4-c]pyridin-6-yl)methanone; |
| 10 | (2,6-Dimethoxyphenyl)(2-methyl-3-phenyl-2,4,5,7-tetrahydro-6H-pyrazolo[3,4-c]pyridin-6-yl)methanone; |
| 11 | (3,5-Dimethoxyphenyl)-(2-methyl-3-phenyl-5,7-dihydro-4H-pyrazolo[3,4-c]pyridin-6-yl)methanone; |
| 12 | (2-Chloro-3-hydroxyphenyl)(2-methyl-3-phenyl-2,4,5,7-tetrahydro-6H-pyrazolo[3,4-c]pyridin-6-yl)methanone; |
| 13 | (2-Chloro-3-methoxyphenyl)(2-methyl-3-phenyl-2,4,5,7-tetrahydro-6H-pyrazolo[3,4-c]pyridin-6-yl)methanone; |
| 14 | (3-Chloro-2-methoxy-phenyl)-(2-methyl-3-phenyl-5,7-dihydro-4H-pyrazolo[3,4-c]pyridin-6-yl)methanone; |
| 15 | (2-Chloro-6-methoxyphenyl)(2-methyl-3-phenyl-2,4,5,7-tetrahydro-6H-pyrazolo[3,4-c]pyridin-6-yl)methanone; |
| 16 | (3-Chloro-5-methoxyphenyl)(2-methyl-3-phenyl-2,4,5,7-tetrahydro-6H-pyrazolo[3,4-c]pyridin-6-yl)methanone; |
| 17 | (2-Amino-3-methylphenyl)(2-methyl-3-phenyl-2,4,5,7-tetrahydro-6H-pyrazolo[3,4-c]pyridin-6-yl)methanone; |
| 18 | (2-(1H-1,2,4-Triazol-1-yl)phenyl)(2-methyl-3-phenyl-2,4,5,7-tetrahydro-6H-pyrazolo[3,4-c]pyridin-6-yl)methanone; |
| 19 | (2-Methyl-3-morpholinophenyl)(2-methyl-3-phenyl-2,4,5,7-tetrahydro-6H-pyrazolo[3,4-c]pyridin-6-yl)methanone; |
| 20 | (5-Chloro-1-methyl-1H-pyrazol-4-yl)(2-methyl-3-phenyl-2,4,5,7-tetrahydro-6H-pyrazolo[3,4-c]pyridin-6-yl)methanone; |
| 21 | (1,5-Dimethyl-1H-pyrazol-4-yl)(2-methyl-3-phenyl-2,4,5,7-tetrahydro-6H-pyrazolo[3,4-c]pyridin-6-yl)methanone; |
| 22 | (5-Cyclopropyl-1-methyl-1H-pyrazol-4-yl)(2-methyl-3-phenyl-2,4,5,7-tetrahydro-6H-pyrazolo[3,4-c]pyridin-6-yl)methanone; |
| 23 | (2-Methyl-3-phenyl-2,4,5,7-tetrahydro-6H-pyrazolo[3,4-c]pyridin-6-yl)(1-phenyl-1H-1,2,4-triazol-3-yl)methanone; |
| 24 | (6-(Difluoromethoxy)pyridin-2-yl)(2-methyl-3-phenyl-2,4,5,7-tetrahydro-6H-pyrazolo[3,4-c]pyridin-6-yl)methanone; |
| 25 | (2-Methyl-3-phenyl-2,4,5,7-tetrahydro-6H-pyrazolo[3,4-c]pyridin-6-yl)(6-(trifluoromethoxy)pyridin-2-yl)methanone; |
| 26 | 5-(2-Methyl-3-phenyl-4,5,6,7-tetrahydro-2H-pyrazolo[3,4-c]pyridine-6-carbonyl)-2H-benzo[b][1,4]oxazin-3(4H)-one; |
| 27 | (4-Methyl-3,4-dihydro-2H-benzo[b][1,4]oxazin-7-yl)(2-methyl-3-phenyl-2,4,5,7-tetrahydro-6H-pyrazolo[3,4-c]pyridin-6-yl)methanone; |
| 28 | Benzo[d][1,3]dioxol-4-yl(2-methyl-3-phenyl-2,4,5,7-tetrahydro-6H-pyrazolo[3,4-c]pyridin-6-yl)methanone; |
| 29 | Benzo[d][1,3]dioxol-5-yl(2-methyl-3-phenyl-2,4,5,7-tetrahydro-6H-pyrazolo[3,4-c]pyridin-6-yl)methanone; |
| 30 | (2,2-Difluorobenzo[d][1,3]dioxol-4-yl)(2-methyl-3-phenyl-2,4,5,7-tetrahydro-6H-pyrazolo[3,4-c]pyridin-6-yl)methanone; |
| 31 | (2-Methyl-3-phenyl-2,4,5,7-tetrahydro-6H-pyrazolo[3,4-c]pyridin-6-yl)(4H-thieno[3,2-b]pyrrol-2-yl)methanone; |
| 32 | (2-Methyl-3-phenyl-2,4,5,7-tetrahydro-6H-pyrazolo[3,4-c]pyridin-6-yl)(6-methylimidazo[2,1-b]thiazol-5-yl)methanone; |
| 33 | Benzofuran-7-yl(2-methyl-3-phenyl-2,4,5,7-tetrahydro-6H-pyrazolo[3,4-c]pyridin-6-yl)methanone; |
| 34 | Benzofuran-4-yl(2-methyl-3-phenyl-2,4,5,7-tetrahydro-6H-pyrazolo[3,4-c]pyridin-6-yl)methanone; |
| 35 | Benzofuran-5-yl(2-methyl-3-phenyl-2,4,5,7-tetrahydro-6H-pyrazolo[3,4-c]pyridin-6-yl)methanone; |
| 36 | Benzofuran-3-yl(2-methyl-3-phenyl-2,4,5,7-tetrahydro-6H-pyrazolo[3,4-c]pyridin-6-yl)methanone; |
| 37 | Benzo[b]thiophen-7-yl(2-methyl-3-phenyl-2,4,5,7-tetrahydro-6H-pyrazolo[3,4-c]pyridin-6-yl)methanone; |
| 38 | Benzo[b]thiophen-4-yl(2-methyl-3-phenyl-2,4,5,7-tetrahydro-6H-pyrazolo[3,4-c]pyridin-6-yl)methanone; |
| 39 | Benzo[b]thiophen-5-yl(2-methyl-3-phenyl-2,4,5,7-tetrahydro-6H-pyrazolo[3,4-c]pyridin-6-yl)methanone; |

-continued

| Ex # | Compound Name |
|---|---|
| 40 | Benzo[b]thiophen-3-yl(2-methyl-3-phenyl-2,4,5,7-tetrahydro-6H-pyrazolo[3,4-c]pyridin-6-yl)methanone; |
| 41 | (3-Chlorobenzo[b]thiophen-2-yl)(2-methyl-3-phenyl-2,4,5,7-tetrahydro-6H-pyrazolo[3,4-c]pyridin-6-yl)methanone; |
| 42 | (1H-Indol-4-yl)(2-methyl-3-phenyl-2,4,5,7-tetrahydro-6H-pyrazolo[3,4-c]pyridin-6-yl)methanone; |
| 43 | (1H-Indol-5-yl)(2-methyl-3-phenyl-2,4,5,7-tetrahydro-6H-pyrazolo[3,4-c]pyridin-6-yl)methanone; |
| 44 | (1H-Indol-3-yl)(2-methyl-3-phenyl-2,4,5,7-tetrahydro-6H-pyrazolo[3,4-c]pyridin-6-yl)methanone; |
| 45 | (1H-Indol-7-yl)(2-methyl-3-phenyl-2,4,5,7-tetrahydro-6H-pyrazolo[3,4-c]pyridin-6-yl)methanone; |
| 46 | (1H-Indol-6-yl)(2-methyl-3-phenyl-2,4,5,7-tetrahydro-6H-pyrazolo[3,4-c]pyridin-6-yl)methanone; |
| 47 | (5-Fluoro-1H-indol-4-yl)(2-methyl-3-phenyl-2,4,5,7-tetrahydro-6H-pyrazolo[3,4-c]pyridin-6-yl)methanone; |
| 48 | (7-Chloro-1H-indol-3-yl)(2-methyl-3-phenyl-2,4,5,7-tetrahydro-6H-pyrazolo[3,4-c]pyridin-6-yl)methanone; |
| 49 | (4-Chloro-1H-indol-3-yl)(2-methyl-3-phenyl-2,4,5,7-tetrahydro-6H-pyrazolo[3,4-c]pyridin-6-yl)methanone; |
| 50 | (7-Methyl-1H-indol-2-yl)(2-methyl-3-phenyl-2,4,5,7-tetrahydro-6H-pyrazolo[3,4-c]pyridin-6-yl)methanone; |
| 51 | (1-Methyl-1H-indol-4-yl)(2-methyl-3-phenyl-2,4,5,7-tetrahydro-6H-pyrazolo[3,4-c]pyridin-6-yl)methanone; |
| 52 | (1-Methyl-1H-indol-3-yl)(2-methyl-3-phenyl-2,4,5,7-tetrahydro-6H-pyrazolo[3,4-c]pyridin-6-yl)methanone; |
| 53 | Benzo[d]isoxazol-3-yl(2-methyl-3-phenyl-2,4,5,7-tetrahydro-6H-pyrazolo[3,4-c]pyridin-6-yl)methanone; |
| 54 | (6-Chlorobenzo[d]isoxazol-3-yl)(2-methyl-3-phenyl-2,4,5,7-tetrahydro-6H-pyrazolo[3,4-c]pyridin-6-yl)methanone; |
| 55 | Benzo[c]isoxazol-3-yl(2-methyl-3-phenyl-2,4,5,7-tetrahydro-6H-pyrazolo[3,4-c]pyridin-6-yl)methanone; |
| 56 | Benzo[d]oxazol-6-yl(2-methyl-3-phenyl-2,4,5,7-tetrahydro-6H-pyrazolo[3,4-c]pyridin-6-yl)methanone; |
| 57 | Benzo[d]oxazol-2-yl(2-methyl-3-phenyl-2,4,5,7-tetrahydro-6H-pyrazolo[3,4-c]pyridin-6-yl)methanone; |
| 58 | Benzo[d]oxazol-5-yl(2-methyl-3-phenyl-2,4,5,7-tetrahydro-6H-pyrazolo[3,4-c]pyridin-6-yl)methanone; |
| 59 | Benzo[d]thiazol-7-yl(2-methyl-3-phenyl-2,4,5,7-tetrahydro-6H-pyrazolo[3,4-c]pyridin-6-yl)methanone; |
| 60 | Benzo[d]thiazol-5-yl(2-methyl-3-phenyl-2,4,5,7-tetrahydro-6H-pyrazolo[3,4-c]pyridin-6-yl)methanone; |
| 61 | Benzo[d]thiazol-4-yl(2-methyl-3-phenyl-2,4,5,7-tetrahydro-6H-pyrazolo[3,4-c]pyridin-6-yl)methanone; |
| 62 | Benzo[d]thiazol-2-yl(2-methyl-3-phenyl-2,4,5,7-tetrahydro-6H-pyrazolo[3,4-c]pyridin-6-yl)methanone; |
| 63 | Benzo[d]isothiazol-3-yl(2-methyl-3-phenyl-2,4,5,7-tetrahydro-6H-pyrazolo[3,4-c]pyridin-6-yl)methanone; |
| 64 | (1H-Indazol-5-yl)(2-methyl-3-phenyl-2,4,5,7-tetrahydro-6H-pyrazolo[3,4-c]pyridin-6-yl)methanone; |
| 65 | (1H-Indazol-4-yl)(2-methyl-3-phenyl-2,4,5,7-tetrahydro-6H-pyrazolo[3,4-c]pyridin-6-yl)methanone; |
| 66 | (1H-Indazol-3-yl)(2-methyl-3-phenyl-2,4,5,7-tetrahydro-6H-pyrazolo[3,4-c]pyridin-6-yl)methanone; |
| 67 | (1H-Indazol-7-yl)(2-methyl-3-phenyl-2,4,5,7-tetrahydro-6H-pyrazolo[3,4-c]pyridin-6-yl)methanone; |
| 68 | (1H-Indazol-6-yl)(2-methyl-3-phenyl-2,4,5,7-tetrahydro-6H-pyrazolo[3,4-c]pyridin-6-yl)methanone; |
| 69 | (7-Chloro-1H-indazol-3-yl)(2-methyl-3-phenyl-2,4,5,7-tetrahydro-6H-pyrazolo[3,4-c]pyridin-6-yl)methanone; |
| 70 | (1-Methyl-1H-indazol-3-yl)(2-methyl-3-phenyl-2,4,5,7-tetrahydro-6H-pyrazolo[3,4-c]pyridin-6-yl)methanone; |
| 71 | (1H-Benzo[d]imidazol-5-yl)(2-methyl-3-phenyl-2,4,5,7-tetrahydro-6H-pyrazolo[3,4-c]pyridin-6-yl)methanone; |
| 72 | (2-Methyl-3-phenyl-2,4,5,7-tetrahydro-6H-pyrazolo[3,4-c]pyridin-6-yl)(2-(trifluoromethyl)-1H-benzo[d]imidazol-4-yl)methanone; |
| 73 | (2-Methyl-3-phenyl-2,4,5,7-tetrahydro-6H-pyrazolo[3,4-c]pyridin-6-yl)(pyrazolo[1,5-a]pyridin-5-yl)methanone; |
| 74 | (2-Methyl-3-phenyl-2,4,5,7-tetrahydro-6H-pyrazolo[3,4-c]pyridin-6-yl)(pyrazolo[1,5-a]pyridin-3-yl)methanone; |
| 75 | (2-Methyl-3-phenyl-2,4,5,7-tetrahydro-6H-pyrazolo[3,4-c]pyridin-6-yl)(pyrazolo[1,5-a]pyridin-7-yl)methanone; |
| 76 | Imidazo[1,5-a]pyridin-1-yl(2-methyl-3-phenyl-2,4,5,7-tetrahydro-6H-pyrazolo[3,4-c]pyridin-6-yl)methanone; |
| 77 | Imidazo[1,5-a]pyridin-6-yl(2-methyl-3-phenyl-2,4,5,7-tetrahydro-6H-pyrazolo[3,4-c]pyridin-6-yl)methanone; |

-continued

| Ex # | Compound Name |
|---|---|
| 78 | Imidazo[1,5-a]pyridin-7-yl(2-methyl-3-phenyl-2,4,5,7-tetrahydro-6H-pyrazolo[3,4-c]pyridin-6-yl)methanone; |
| 79 | Imidazo[1,5-a]pyridin-5-yl(2-methyl-3-phenyl-2,4,5,7-tetrahydro-6H-pyrazolo[3,4-c]pyridin-6-yl)methanone; |
| 80 | Imidazo[1,2-a]pyridin-5-yl(2-methyl-3-phenyl-2,4,5,7-tetrahydro-6H-pyrazolo[3,4-c]pyridin-6-yl)methanone; |
| 81 | Imidazo[1,2-a]pyridin-3-yl(2-methyl-3-phenyl-2,4,5,7-tetrahydro-6H-pyrazolo[3,4-c]pyridin-6-yl)methanone; |
| 82 | (5-Chloro-2-methylimidazo[1,2-a]pyridin-3-yl)(2-methyl-3-phenyl-2,4,5,7-tetrahydro-6H-pyrazolo[3,4-c]pyridin-6-yl)methanone; |
| 83 | (2-Methyl-3-phenyl-2,4,5,7-tetrahydro-6H-pyrazolo[3,4-c]pyridin-6-yl)(1H-pyrrolo[3,2-c]pyridin-3-yl)methanone; |
| 84 | (1-Methyl-1H-pyrrolo[2,3-b]pyridin-4-yl)(2-methyl-3-phenyl-2,4,5,7-tetrahydro-6H-pyrazolo[3,4-c]pyridin-6-yl)methanone; |
| 85 | [1,2,4]Triazolo[1,5-a]pyridin-5-yl(2-methyl-3-phenyl-2,4,5,7-tetrahydro-6H-pyrazolo[3,4-c]pyridin-6-yl)methanone; |
| 86 | (2-Methyl-3-phenyl-2,4,5,7-tetrahydro-6H-pyrazolo[3,4-c]pyridin-6-yl)(quinolin-4-yl)methanone; |
| 87 | Isoquinolin-4-yl(2-methyl-3-phenyl-2,4,5,7-tetrahydro-6H-pyrazolo[3,4-c]pyridin-6-yl)methanone; |
| 88 | Isoquinolin-1-yl(2-methyl-3-phenyl-2,4,5,7-tetrahydro-6H-pyrazolo[3,4-c]pyridin-6-yl)methanone; |
| 89 | (2-Methyl-3-phenyl-2,4,5,7-tetrahydro-6H-pyrazolo[3,4-c]pyridin-6-yl)(quinolin-5-yl)methanone; |
| 90 | (2-Methyl-3-phenyl-2,4,5,7-tetrahydro-6H-pyrazolo[3,4-c]pyridin-6-yl)(quinolin-6-yl)methanone; |
| 91 | (2-Ethyl-3-phenyl-2,4,5,7-tetrahydro-6H-pyrazolo[3,4-c]pyridin-6-yl)(quinolin-6-yl)methanone; |
| 92 | Isoquinolin-5-yl(2-methyl-3-phenyl-2,4,5,7-tetrahydro-6H-pyrazolo[3,4-c]pyridin-6-yl)methanone; |
| 93 | (2-Methyl-3-phenyl-2,4,5,7-tetrahydro-6H-pyrazolo[3,4-c]pyridin-6-yl)(quinolin-8-yl)methanone; |
| 94 | (2-Methyl-3-phenyl-2,4,5,7-tetrahydro-6H-pyrazolo[3,4-c]pyridin-6-yl)(quinolin-2-yl)methanone; |
| 95 | (2-Methyl-3-phenyl-2,4,5,7-tetrahydro-6H-pyrazolo[3,4-c]pyridin-6-yl)(quinolin-3-yl)methanone; |
| 96 | (8-Fluoroquinolin-4-yl)(2-methyl-3-phenyl-2,4,5,7-tetrahydro-6H-pyrazolo[3,4-c]pyridin-6-yl)methanone; |
| 97 | (2-Methyl-3-phenyl-2,4,5,7-tetrahydro-6H-pyrazolo[3,4-c]pyridin-6-yl)(quinoxalin-5-yl)methanone; |
| 98 | (3-(3-(Difluoromethoxy)phenyl)-2-methyl-2,4,5,7-tetrahydro-6H-pyrazolo[3,4-c]pyridin-6-yl)(quinolin-6-yl)methanone; |
| 99 | (3-(3-Chlorophenyl)-2-methyl-2,4,5,7-tetrahydro-6H-pyrazolo[3,4-c]pyridin-6-yl)(quinolin-6-yl)methanone; |
| 100 | (3-(3-Fluorophenyl)-2-methyl-2,4,5,7-tetrahydro-6H-pyrazolo[3,4-c]pyridin-6-yl)(quinolin-6-yl)methanone; |
| 101 | (3-(3,5-Difluorophenyl)-2-methyl-2,4,5,7-tetrahydro-6H-pyrazolo[3,4-c]pyridin-6-yl)(quinolin-6-yl)methanone; |
| 102 | Benzo[d]isoxazol-3-yl(2-methyl-3-(5-methylthiophen-2-yl)-2,4,5,7-tetrahydro-6H-pyrazolo[3,4-c]pyridin-6-yl)methanone; |
| 103 | (2-Methyl-3-(5-(trifluoromethyl)thiophen-2-yl)-2,4,5,7-tetrahydro-6H-pyrazolo[3,4-c]pyridin-6-yl)(quinolin-6-yl)methanone; |
| 104 | (3-(1H-Indol-2-yl)-2-methyl-2,4,5,7-tetrahydro-6H-pyrazolo[3,4-c]pyridin-6-yl)(quinolin-6-yl)methanone;and |
| 105 | (2-Methyl-3-(1-methyl-1H-indol-2-yl)-2,4,5,7-tetrahydro-6H-pyrazolo[3,4-c]pyridin-6-yl)(quinolin-6-yl)methanone; | and pharmaceutically acceptable salts, isotopes, N-oxides, solvates, and stereoisomers thereof.

An additional embodiment of the invention is a pharmaceutical composition comprising:

(A) a therapeutically effective amount of at least one compound selected from compounds of Formula (I)

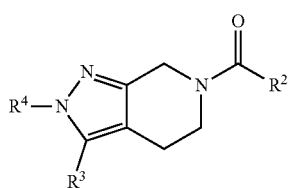

(I)

wherein:

$R^2$ is selected from the group consisting of:

(a)

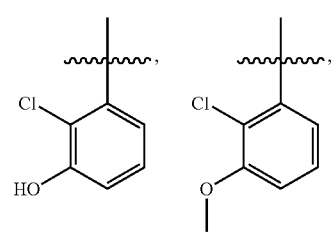

-continued
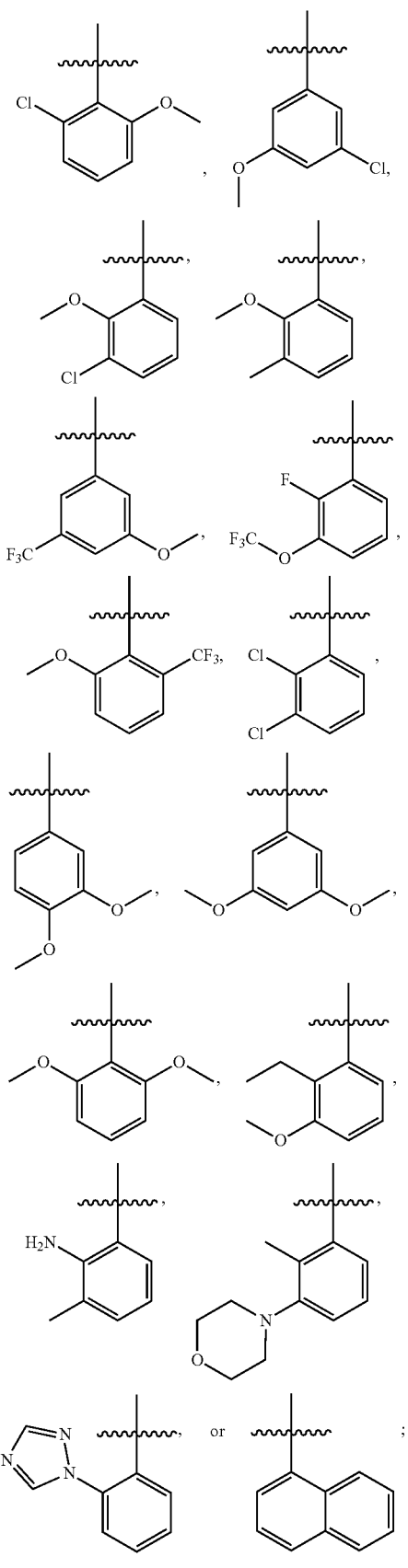
(b) pyridyl substituted with $OC_{1-4}$haloalkyl;
(c) pyrazole or 1H-1,2,4-triazole each substituted with one or two members each independently selected from the group consisting of: H, Cl, $C_{1-4}$alkyl, cyclopropyl and phenyl;
(d)
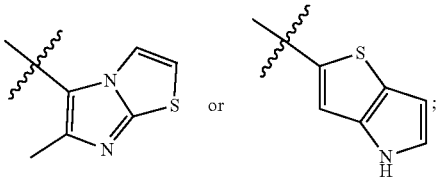
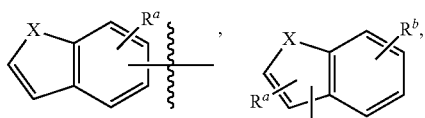
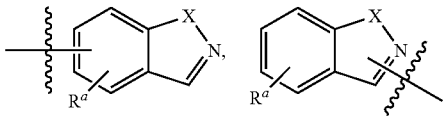
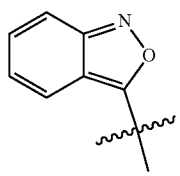
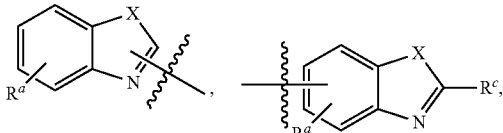
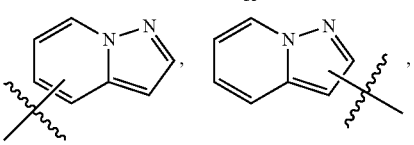
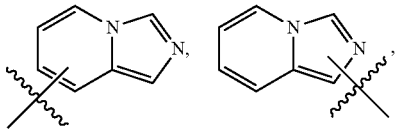
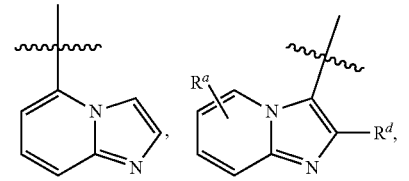

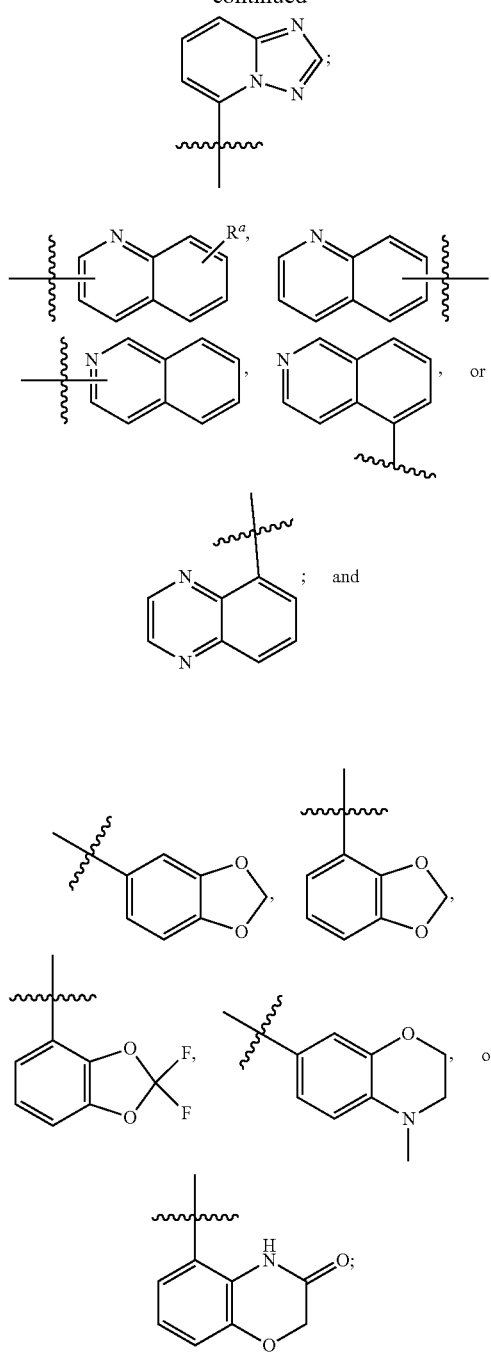

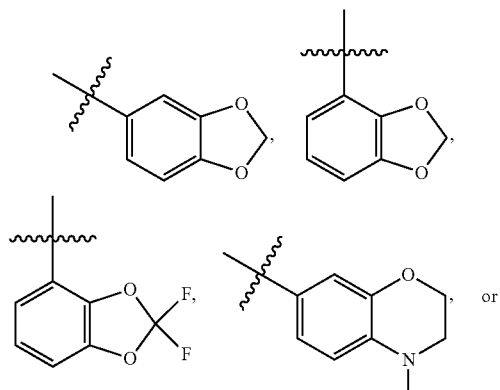

where X is selected from the group consisting of: O, S, NH, and NCH₃;

$R^a$ is H or halo;

$R^b$ is selected from the group consisting of: H, halo and CH₃;

$R^c$ is H or CF₃; and $R^d$ is H or CH₃;

$R^3$ is selected from the group consisting of:

(h) Phenyl; or phenyl independently substituted with one or two members selected from the group consisting of: halo and $OC_{1-4}$haloalkyl;

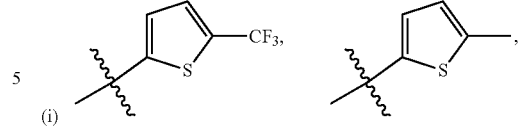

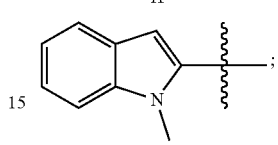

and (j) $C_{3-4}$cycloalkyl; and $R^4$ is selected from the group consisting of: $C_{1-4}$alkyl;

with the proviso that when $R^2$ is

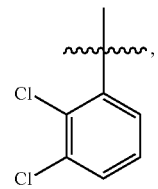 [SMILES: *c1cccc(Cl)c1Cl]

then $R^3$ is cyclopropyl;

and pharmaceutically acceptable salts, isotopes, N-oxides, solvates, and stereoisomers of compounds of Formula (I);

and (B) at least one pharmaceutically acceptable excipient.

An additional embodiment of the invention is a pharmaceutical composition comprising a therapeutically effective amount of at least one compound in Table 1, as well as and pharmaceutically acceptable salts, isotopes, N-oxides, solvates, and stereoisomers of compounds of Table 1, pharmaceutically acceptable prodrugs of compounds of Table 1, and pharmaceutically active metabolites of Table 1; and at least one pharmaceutically acceptable excipient.

An additional embodiment of the invention is a method of treating a subject suffering from or diagnosed with a disease, disorder, or condition mediated by MGL receptor activity, comprising administering to a subject in need of such treatment a therapeutically effective amount of at least one compound selected from compounds of Formula (I):

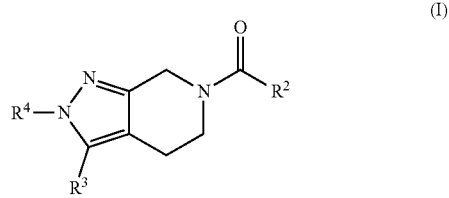

wherein:
$R^2$ is selected from the group consisting of:
(a) 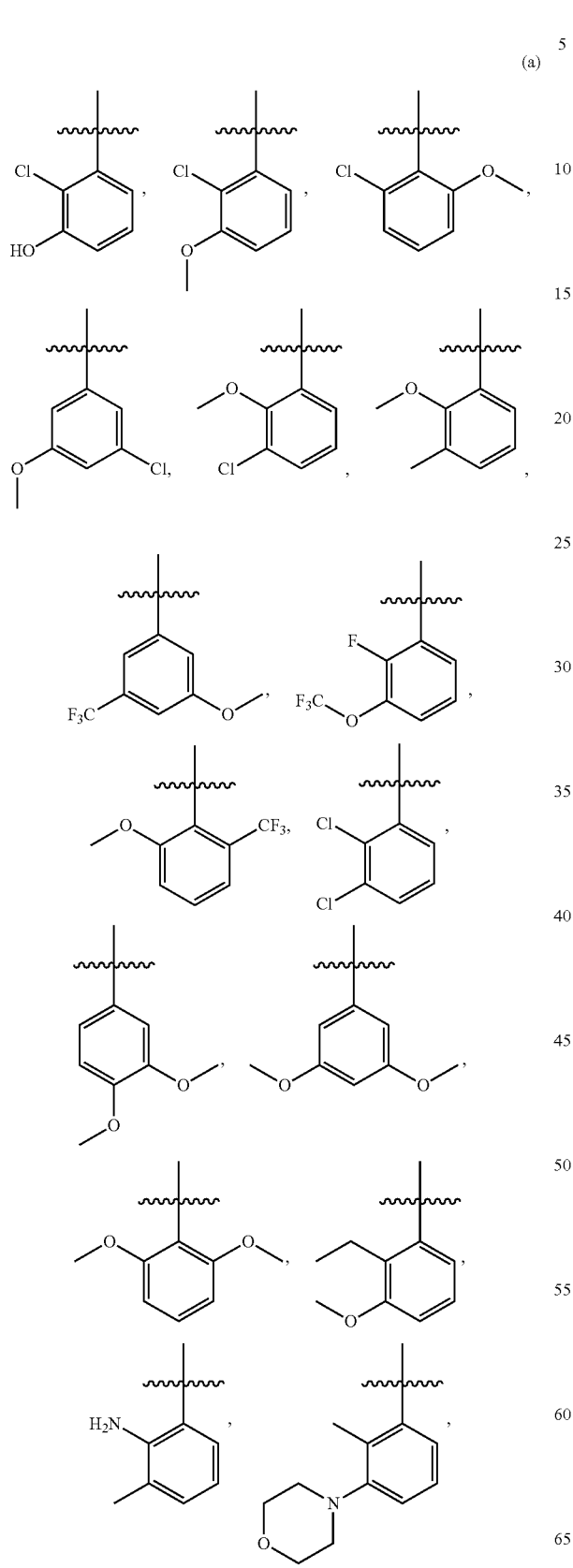
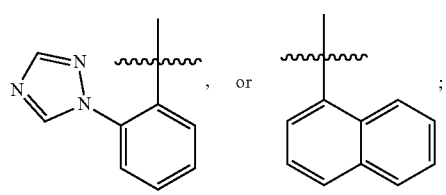 [SMILES: *c1ccccc1-n1cncn1 ; *c1cccc2ccccc12]
(b) pyridyl substituted with $OC_{1-4}$haloalkyl;
(c) pyrazole or 1H-1,2,4-triazole each substituted with one or two members each independently selected from the group consisting of: H, Cl, $C_{1-4}$alkyl, cyclopropyl and phenyl;
(d) 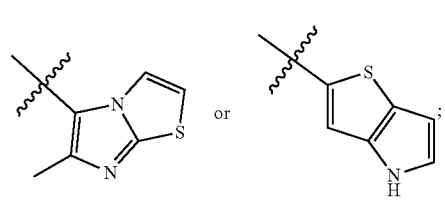
(e) 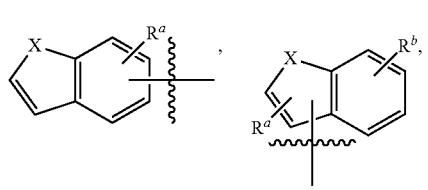
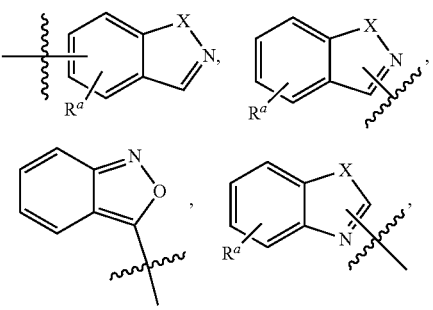
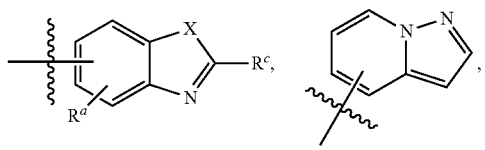
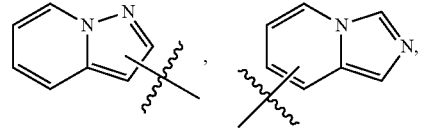
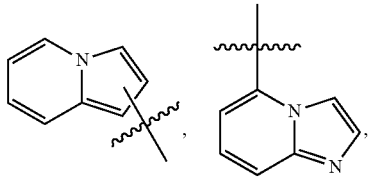

-continued

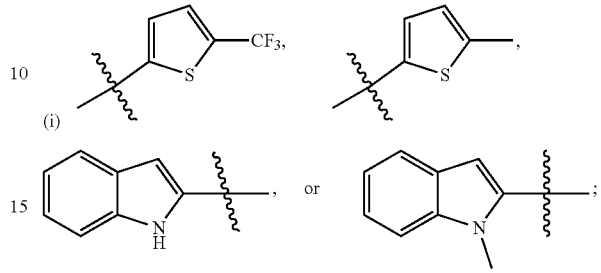

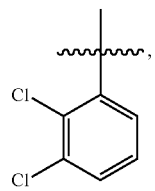

where X is selected from the group consisting of: O, S, NH, and NCH$_3$;
R$^a$ is H or halo;
R$^b$ is selected from the group consisting of: H, halo and CH$_3$;
R$^c$ is H or CF$_3$; and
R$^d$ is H or CH$_3$;

R$^3$ is selected from the group consisting of:
(h) Phenyl; or phenyl independently substituted with one or two members selected from the group consisting of: halo and OC$_{1-4}$haloalkyl;

(i)

and
(j) C$_{3-4}$cycloalkyl; and
R$^4$ is selected from the group consisting of: C$_{1-4}$alkyl;
with the proviso that when R$^2$ is

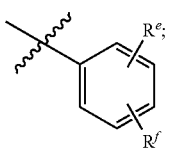

then R$^3$ is cyclopropyl;
and pharmaceutically acceptable salts, isotopes, N-oxides, solvates, and stereoisomers thereof, to a subject in need thereof.

An additional embodiment of the invention is a compound of Formula (II) wherein (II)

wherein
R$^1$ is C$_{1-4}$alkyl;
R$^{2a}$ is selected from the group consisting of:

(a)

(b) 6-Membered heteroaryl selected from the group consisting of:
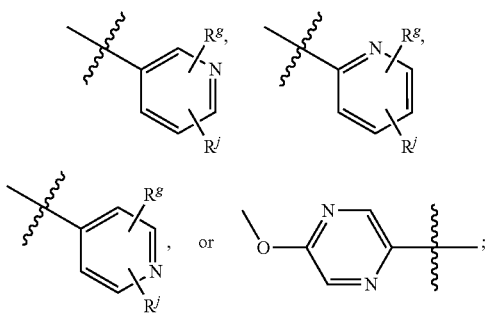
(c) 5-Membered heteroaryl selected from the group consisting of:
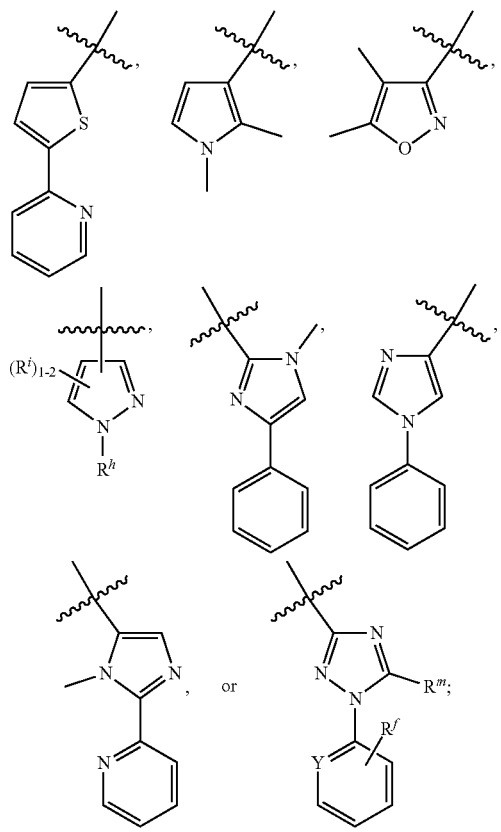
(d) 5,6-Fused or 6,5-fused heteroaryl selected from the group consisting of:
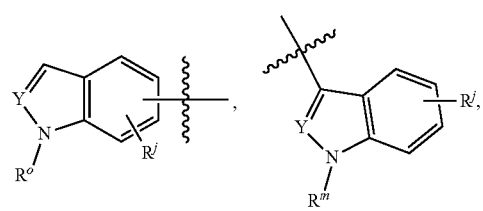
-continued
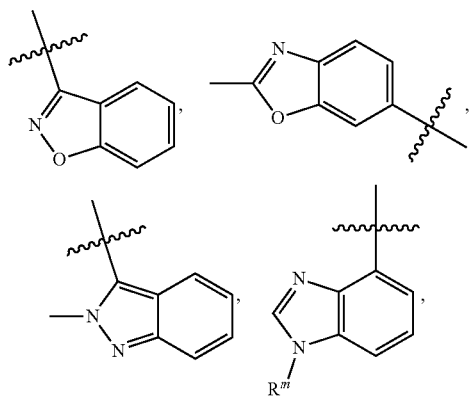
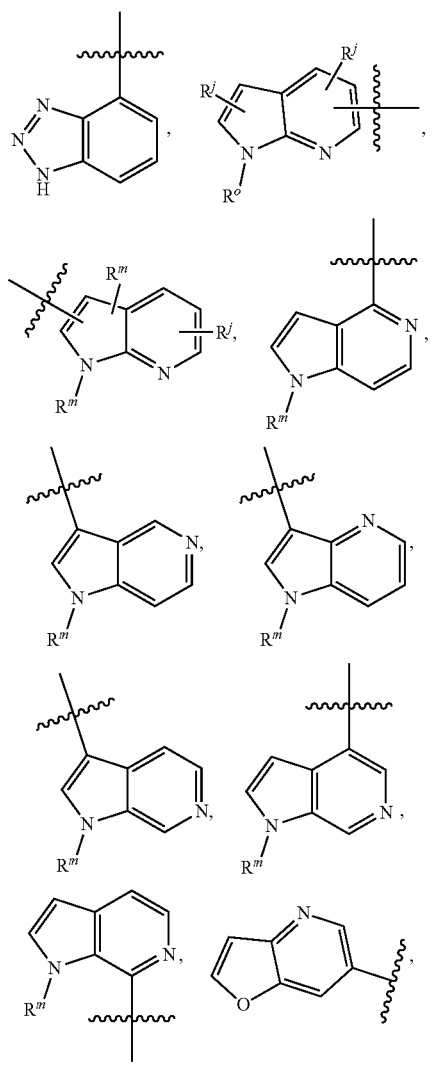
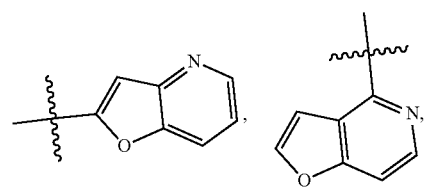

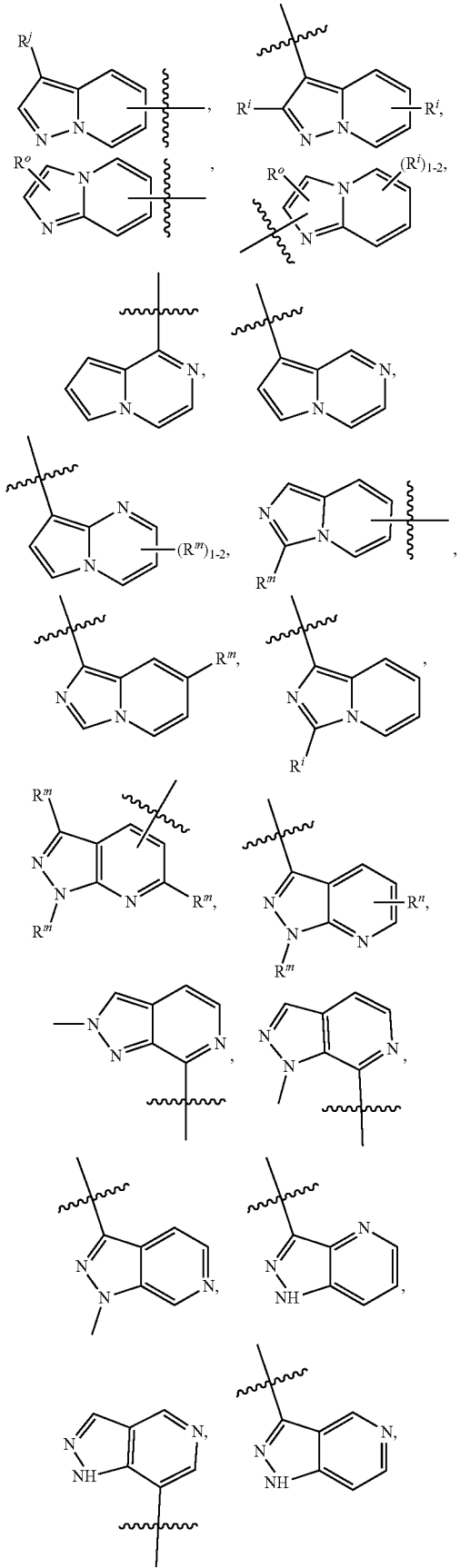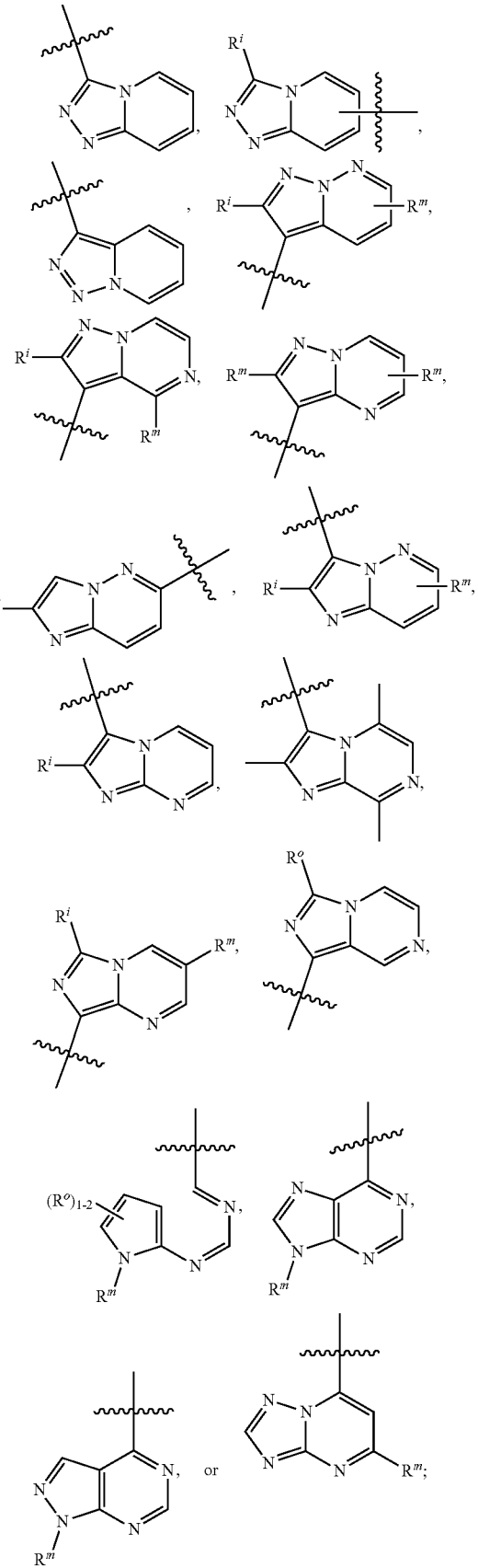

(e) Fused 6,6 heteroaryl selected from the group consisting of:
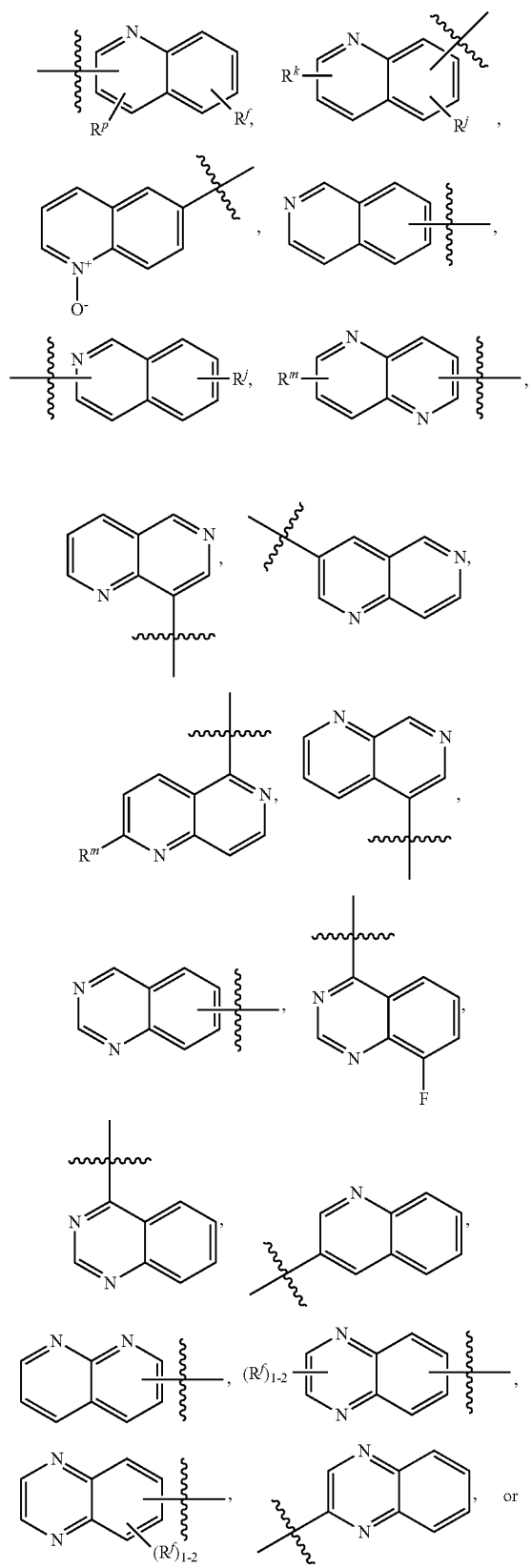
-continued
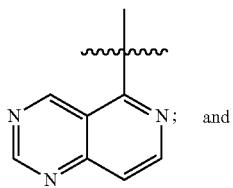
(f) Heterocycloalkyl selected from the group consisting of:

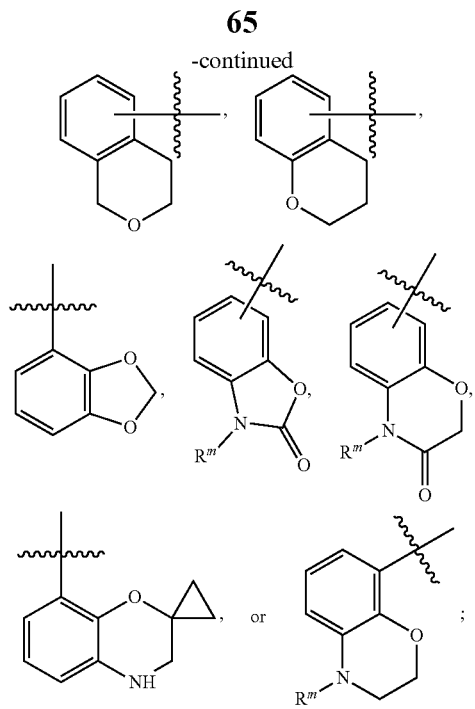

R³ᵃ is selected from the group consisting of:

(g) Phenyl; or phenyl substituted with one, two, or three members each independently selected from the group consisting of: halo, $C_{1-4}$alkyl, $C_{1-4}$haloalkyl, $OC_{1-4}$alkyl, and $OC_{1-6}$haloalkyl;

(h) 5-Membered heteroaryl selected from the group consisting of:

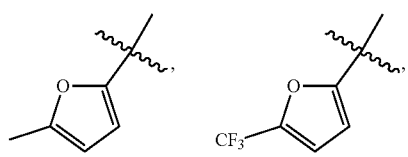

and

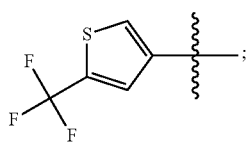

(i) 6-Membered heteroaryl selected from the group consisting of:

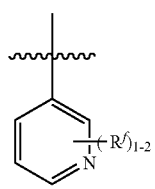

and

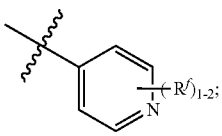

(j) 5,6-Fused or 6,5-fused heteroaryl selected from the group consisting of:

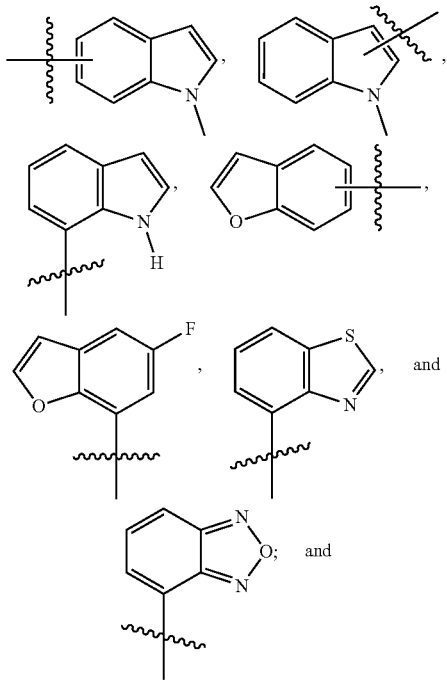

(k) Heterocycloalkyl selected from the group consisting of:

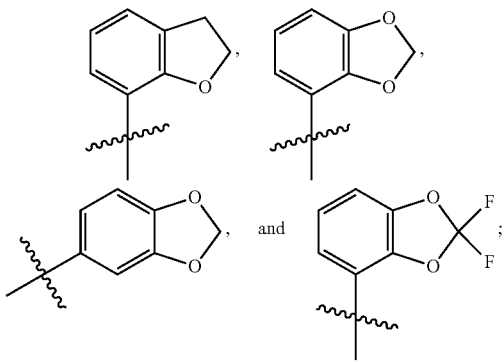

$R^e$ is selected from the group consisting of: $OC_{1-4}$alkyl, $OC_{1-4}$haloalkyl, (C=O)NHCH₃, and 5-membered heteroaryl ring containing two or three nitrogen members, wherein the 5-membered heteroaryl ring is optionally substituted with one $R^f$ member;

$R^f$ is selected from the group consisting of: H, halo, $C_{1-4}$alkyl, $C_{1-4}$haloalkyl, $OC_{1-4}$alkyl, and $OC_{1-4}$haloalkyl;

$R^g$ is selected from the group consisting of: $OC_{1-4}$alkyl, $OC_{1-4}$haloalkyl, $CH_2OCH_3$, $CH_2OH$,

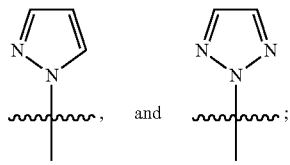 [SMILES: *n1cccn1 ; *n1nccn1]

and;

$R^h$ is selected from the group consisting of: H, $C_{1-4}$alkyl, $C_{1-4}$haloalkyl, and $C_{3-6}$cycloalkyl;

$R^i$ is selected from the group consisting of: H, halo, $C_{1-4}$alkyl, $C_{1-4}$haloalkyl, $OC_{1-4}$alkyl, $C_{3-6}$cycloalkyl, and $C_{3-6}$cycloalkyl substituted with one or two members independently selected from: F and $CH_3$;

$R^j$ is selected from the group consisting of: H, halo, $C_{1-4}$alkyl and $C_{1-4}$haloalkyl;

$R^k$ is selected from the group consisting of: H, halo, OH, $C_{1-4}$alkyl, $C_{1-4}$haloalkyl, $OC_{1-4}$alkyl, and $OC_{1-4}$haloalkyl;

$R^m$ is H or $C_{1-4}$alkyl;

$R^n$ is selected from the group consisting of: H, halo and $OC_{1-4}$alkyl;

$R^o$ is selected from the group consisting of: H, $C_{1-4}$alkyl, and $C_{1-4}$haloalkyl;

$R^p$ is selected from the group consisting of: H, $C_{1-4}$alkyl, and $OC_{1-4}$alkyl;

Y is CH or N; and $R^{4a}$ is selected from the group consisting of: $CH_3$, $CF_2H$, $CF_3$, $C_{3-6}$cycloalkyl, and phenyl; and pharmaceutically acceptable salts, isotopes, N-oxides, solvates, and stereoisomers thereof.

An additional embodiment of the invention is a compound of Formula (II) wherein $R^1$ is $CH_3$.

An additional embodiment of the invention is a compound of Formula (II) wherein $R^1$ is $CH_2CH_3$.

An additional embodiment of the invention is a compound of Formula (II) wherein $R^{2a}$ is

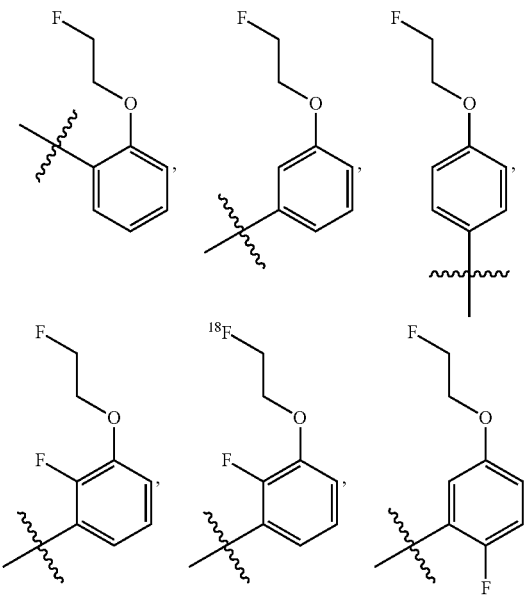

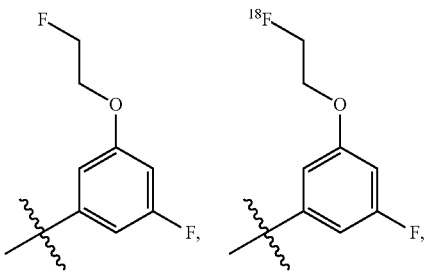

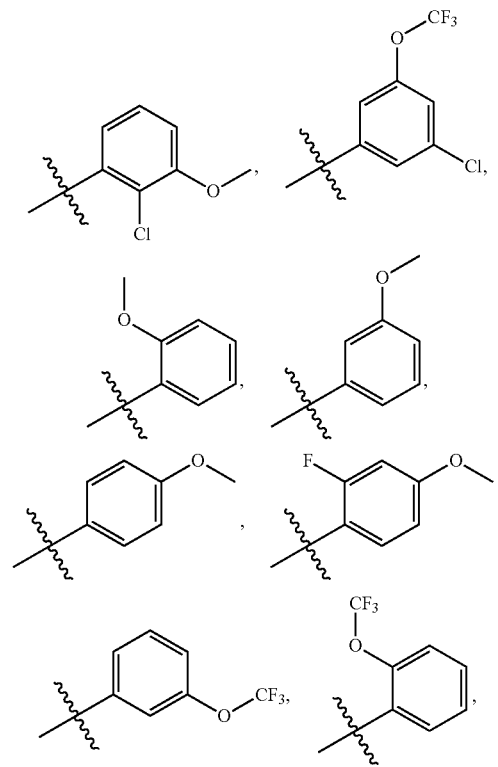

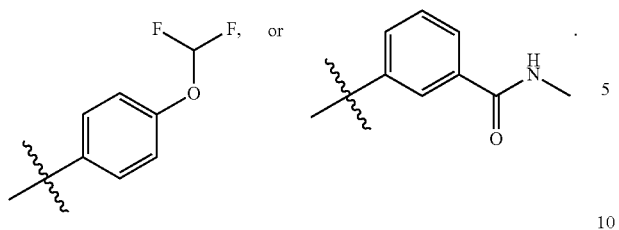
An additional embodiment of the invention is a compound of Formula (II) wherein $R^{2a}$ is
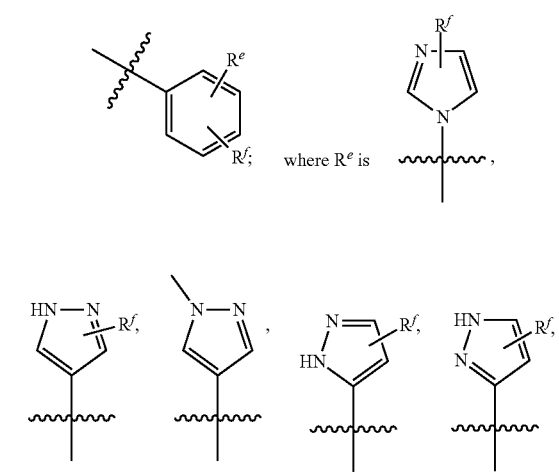
and $R^f$ is H, F, CH$_3$, CF$_3$, or OCH$_3$.
An additional embodiment of the invention is a compound of Formula (II) wherein $R^e$ is
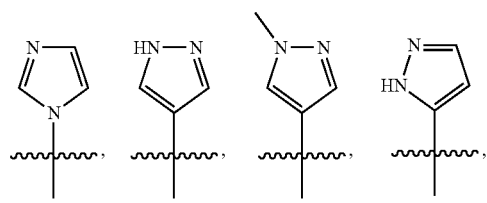
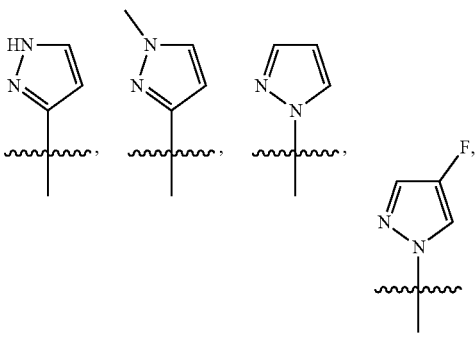
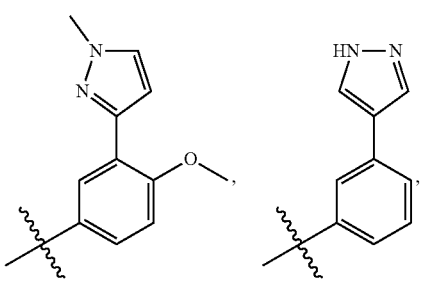
An additional embodiment of the invention is a compound of Formula (II) wherein $R^{2a}$ is
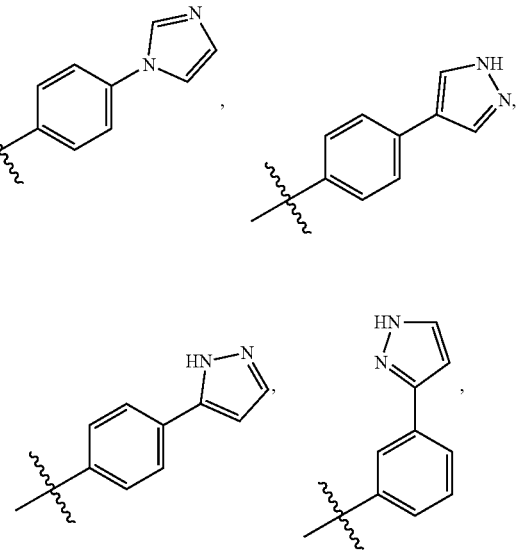

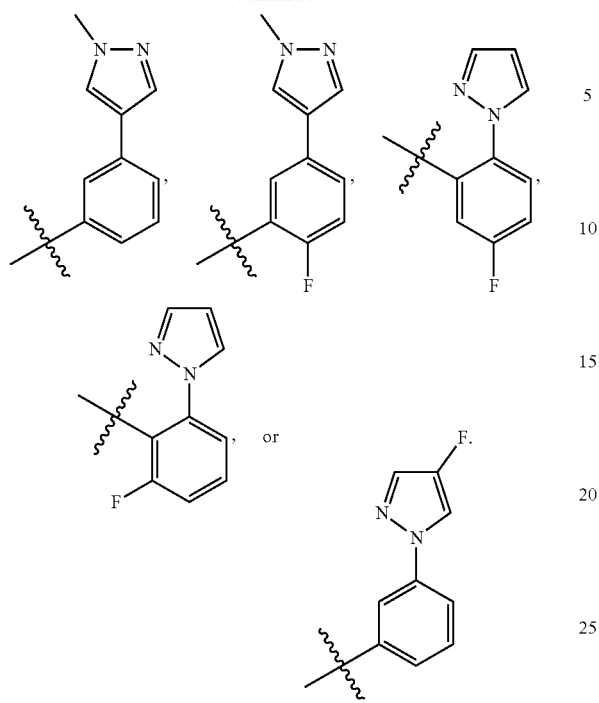
An additional embodiment of the invention is a compound of Formula (II) wherein $R^{2a}$ is
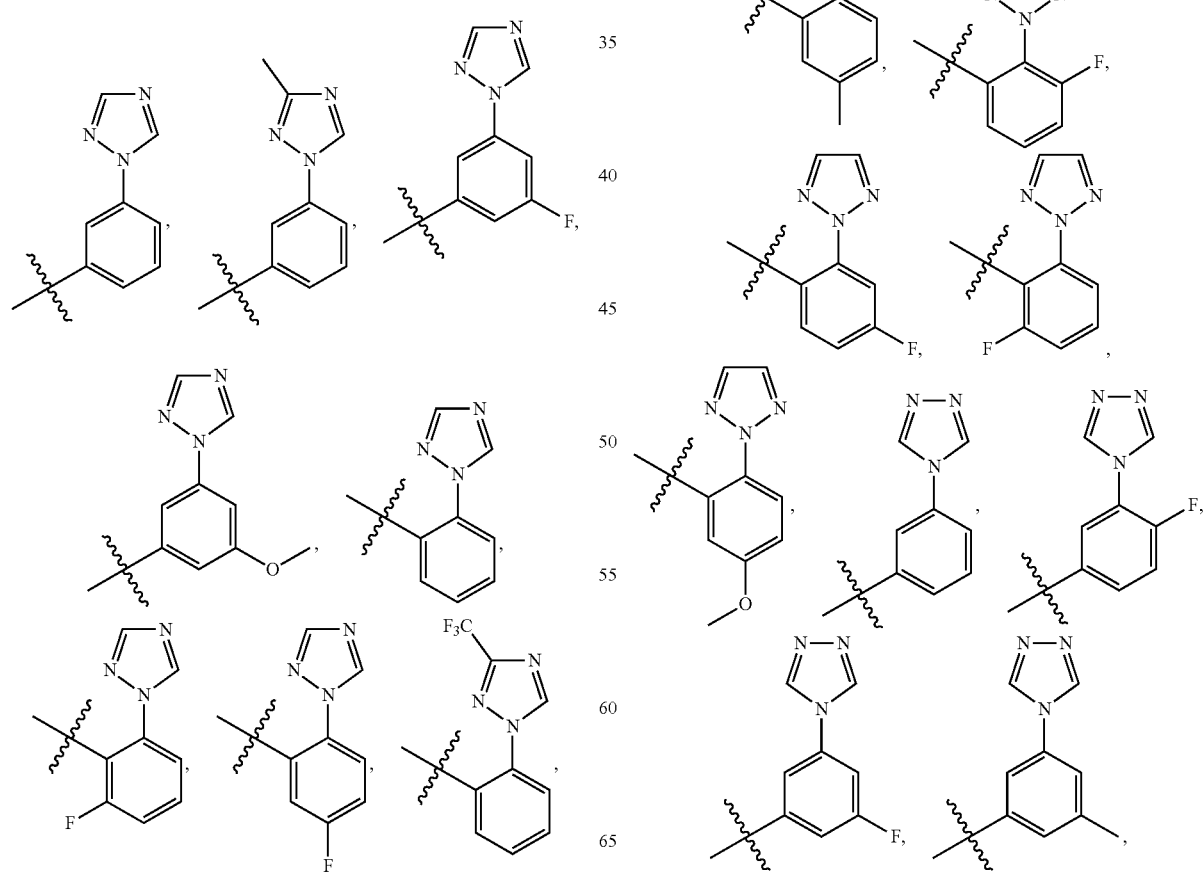

-continued
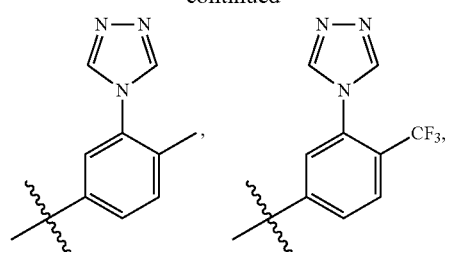
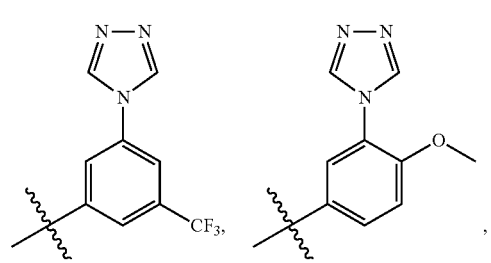
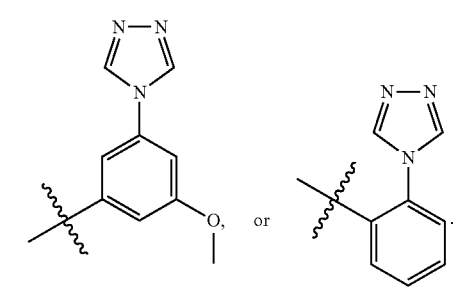 [SMILES: *c1cc(OC)cc(-n2cnnc2)c1 ; *c1ccccc1-n1cnnc1]
An additional embodiment of the invention is a compound of Formula (II) wherein $R^{2a}$ is
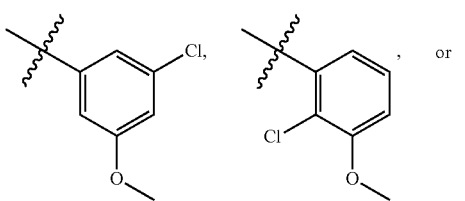
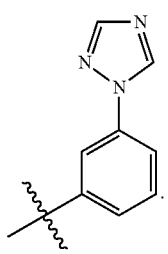
An additional embodiment of the invention is a compound of Formula (II) wherein $R^{2a}$ is
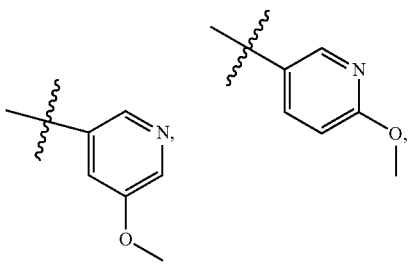
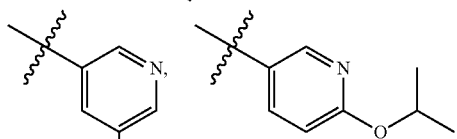
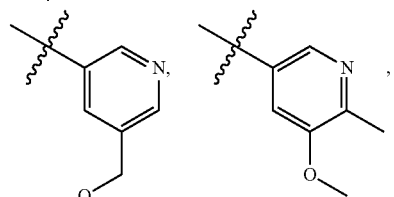
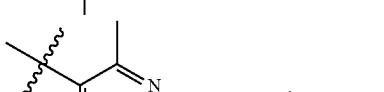
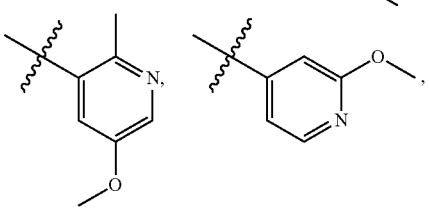
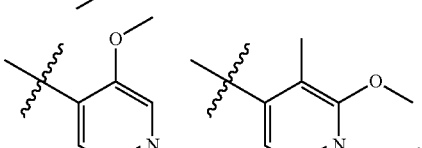
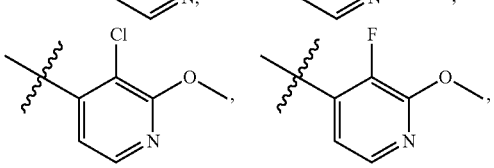
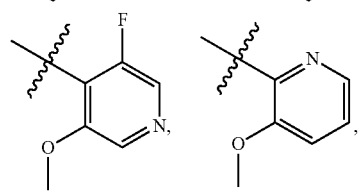

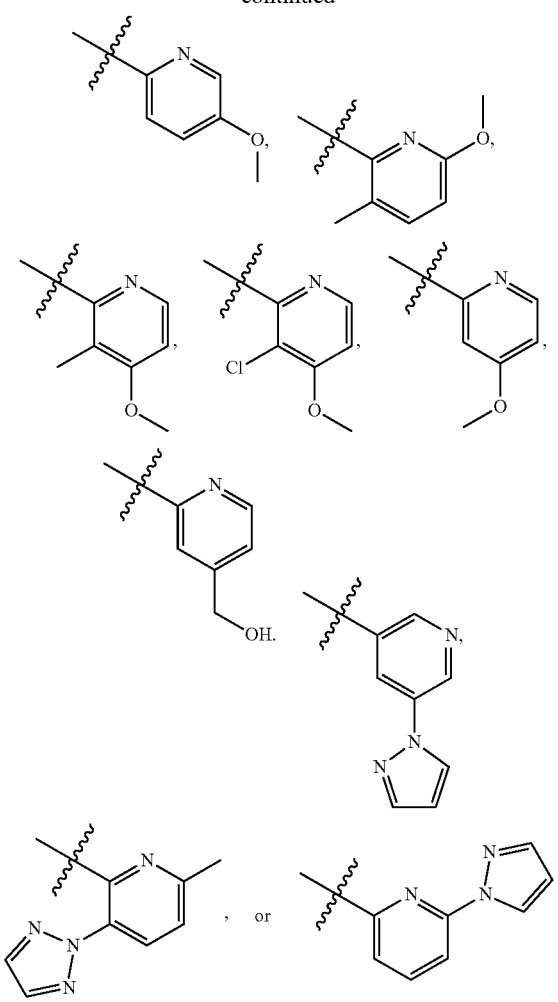
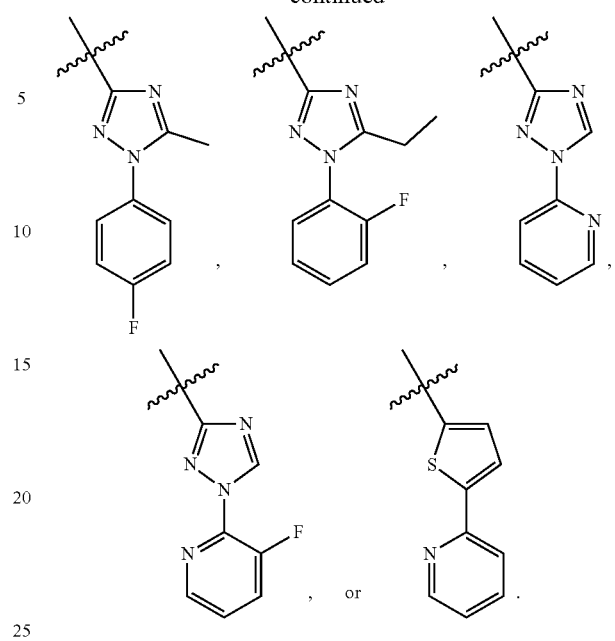
An additional embodiment of the invention is a compound of Formula (II) wherein $R^{2a}$ is
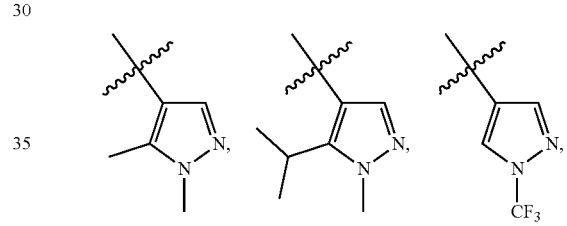
An additional embodiment of the invention is a compound of Formula (II) wherein $R^{2a}$ is
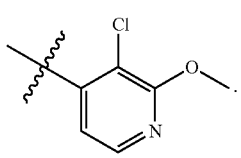 [SMILES: *c1ccnc(OC)c1Cl]
An additional embodiment of the invention is a compound of Formula (II) wherein $R^{2a}$ is
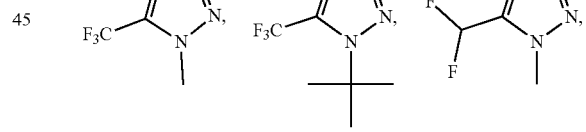
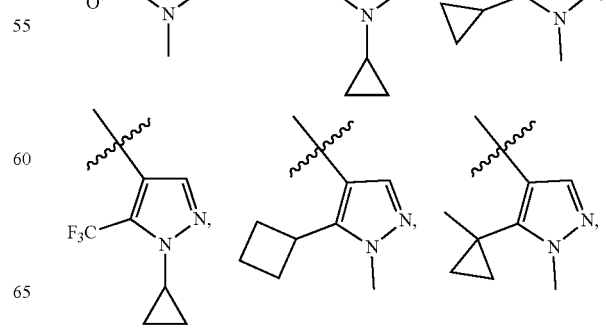

-continued
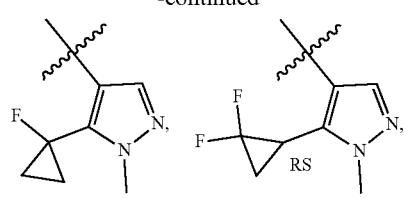
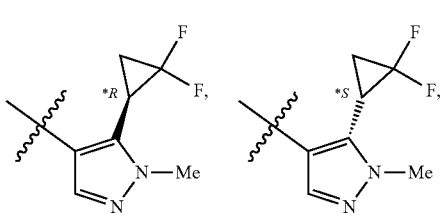
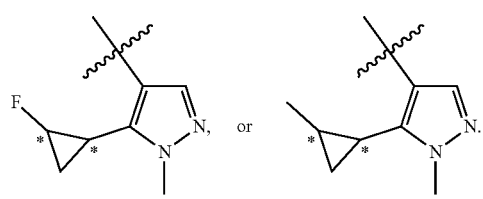
An additional embodiment of the invention is a compound of Formula (II) wherein $R^{2a}$ is
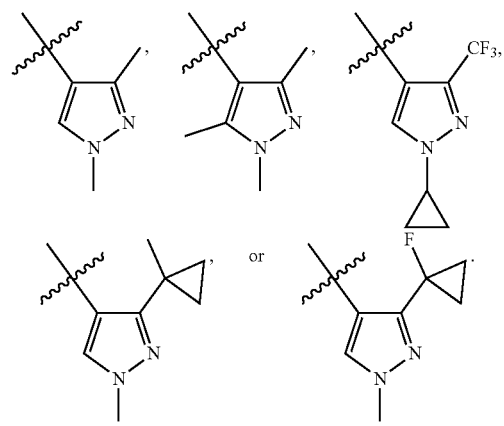
An additional embodiment of the invention is a compound of Formula (II) wherein $R^{2a}$ is
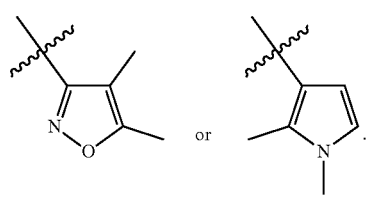
An additional embodiment of the invention is a compound of Formula (II) wherein $R^{2a}$ is
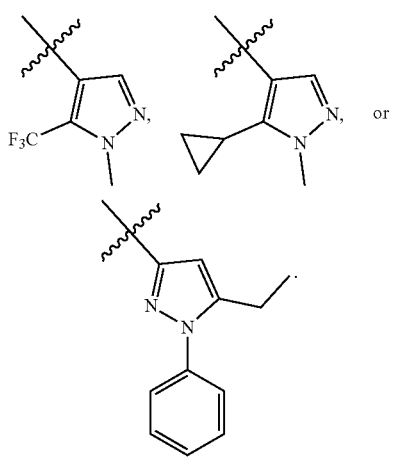
An additional embodiment of the invention is a compound of Formula (II) wherein $R^{2a}$ is
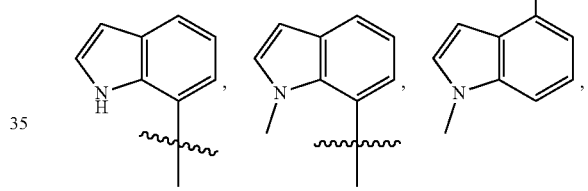
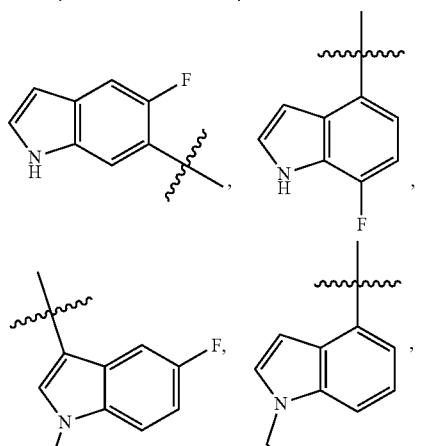
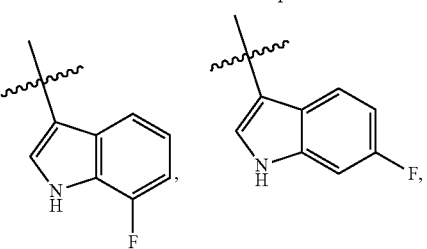

-continued
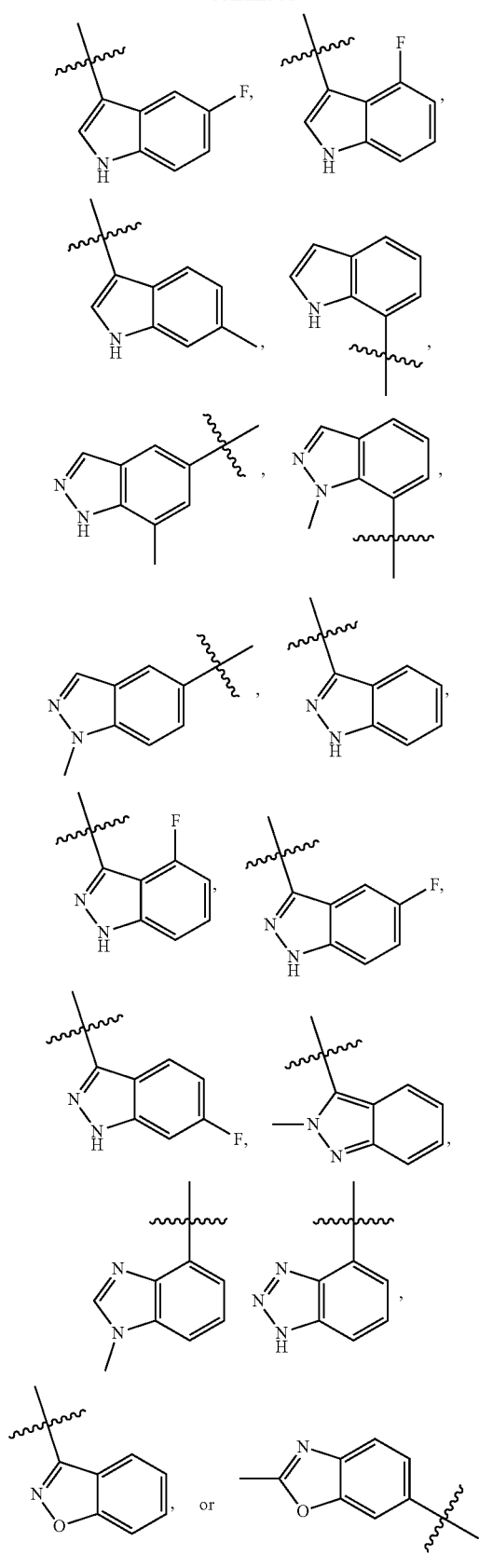
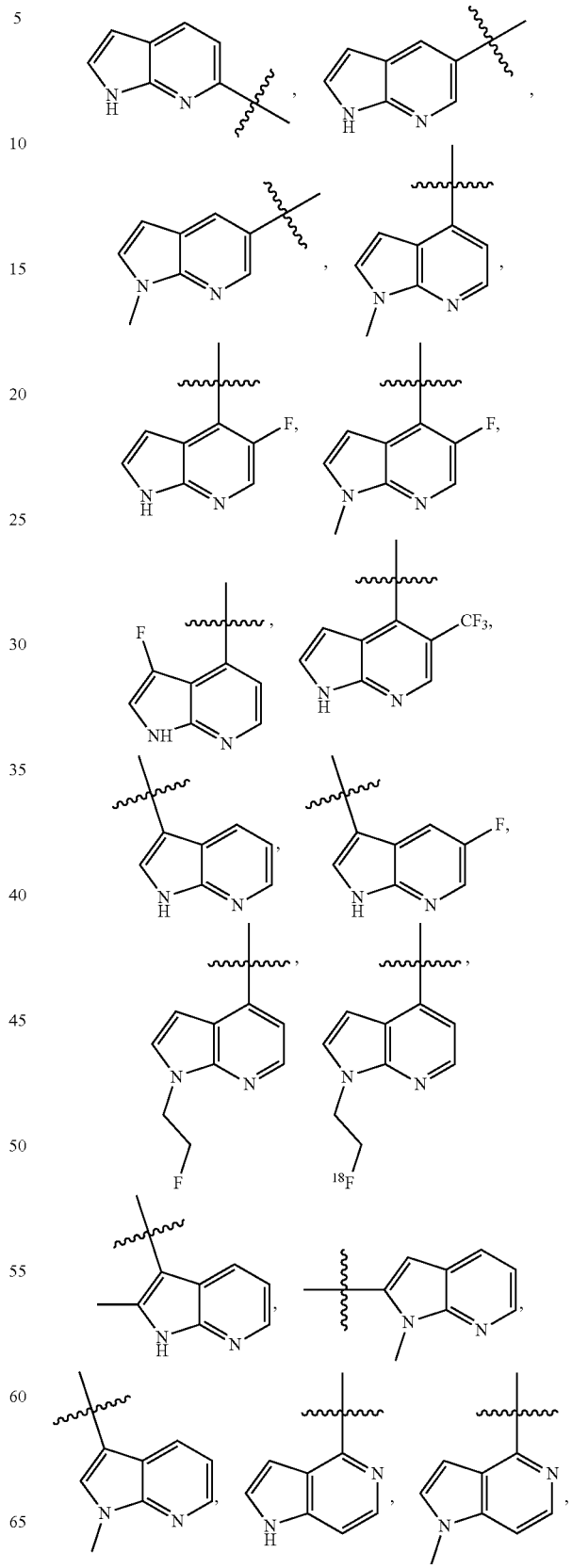
An additional embodiment of the invention is a compound of Formula (II) wherein $R^{2a}$ is -continued
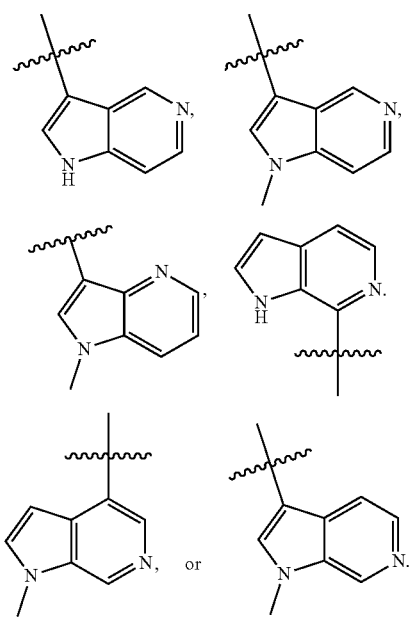
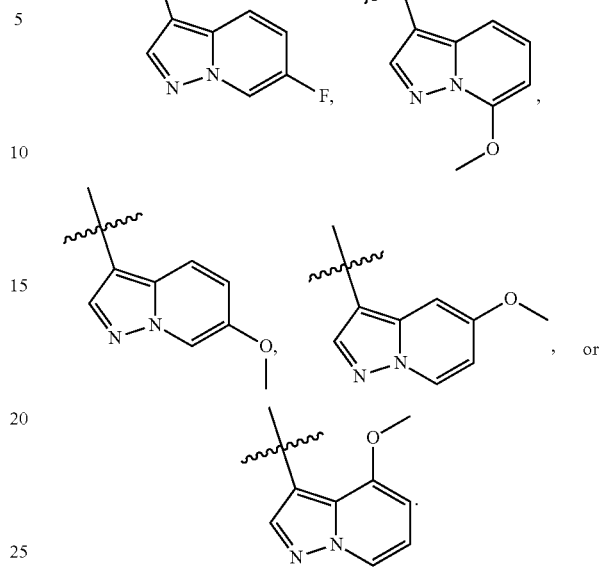
An additional embodiment of the invention is a compound of Formula (II) wherein $R^{2a}$ is
An additional embodiment of the invention is a compound of Formula (II) wherein $R^{2a}$ is
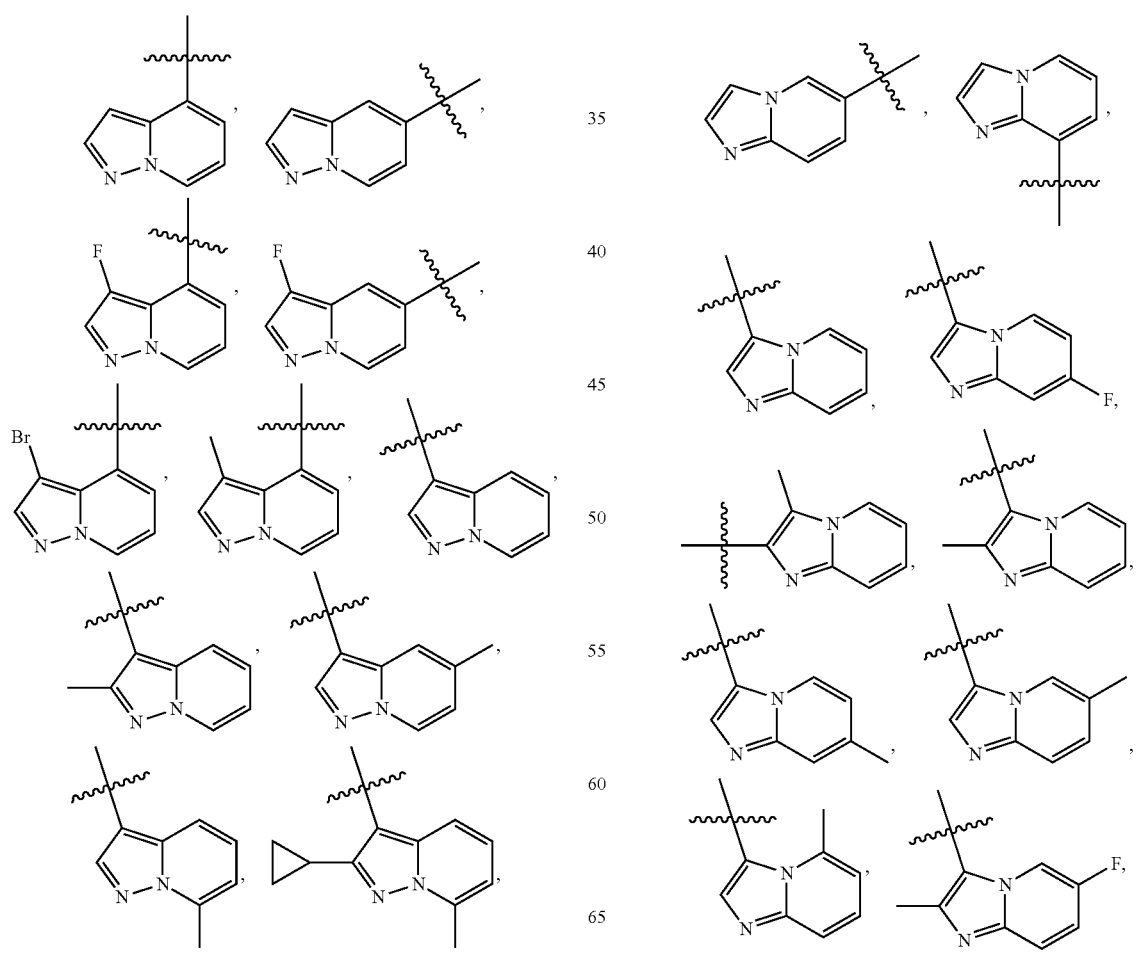

-continued
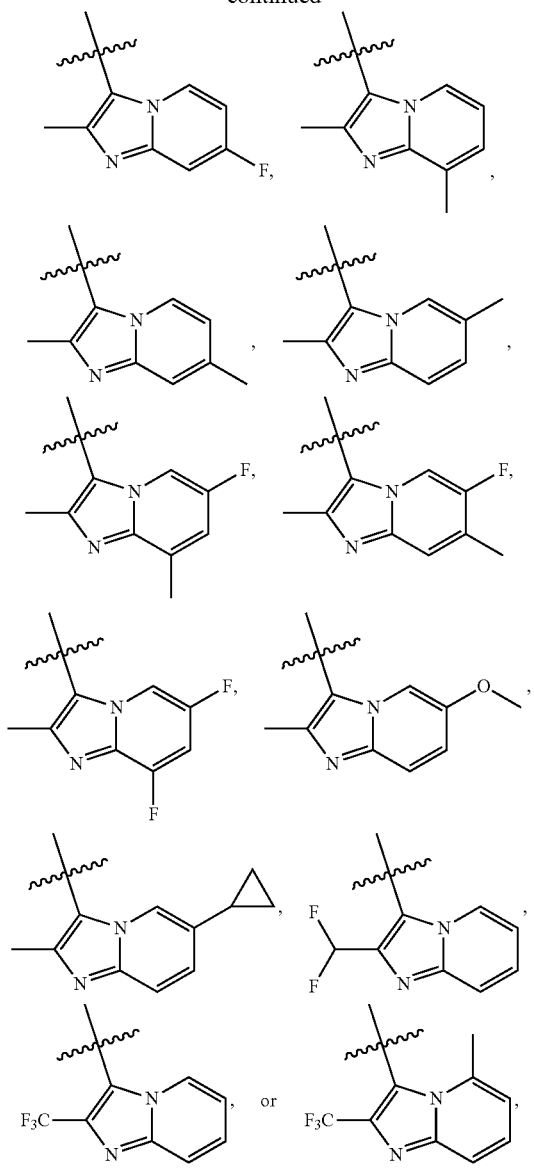
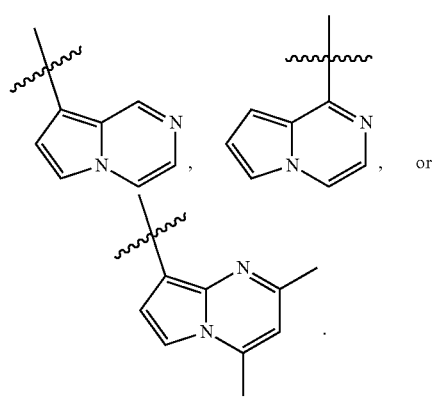
An additional embodiment of the invention is a compound of Formula (II) wherein R$^{2a}$ is
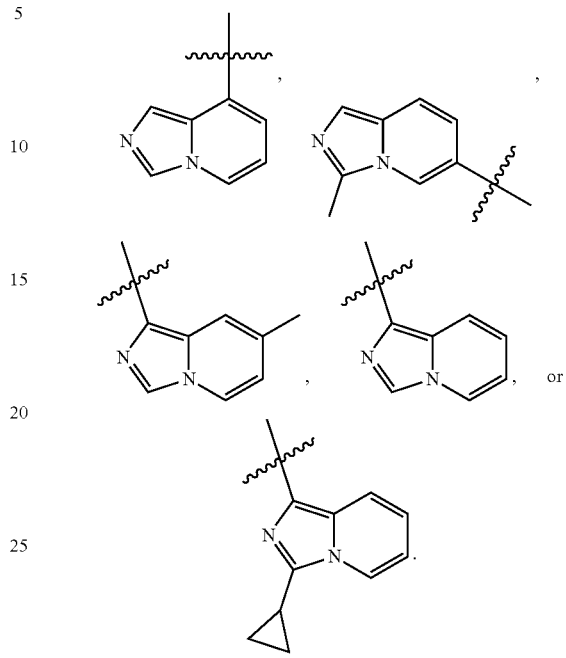
An additional embodiment of the invention is a compound of Formula (II) wherein R$^{2a}$ is
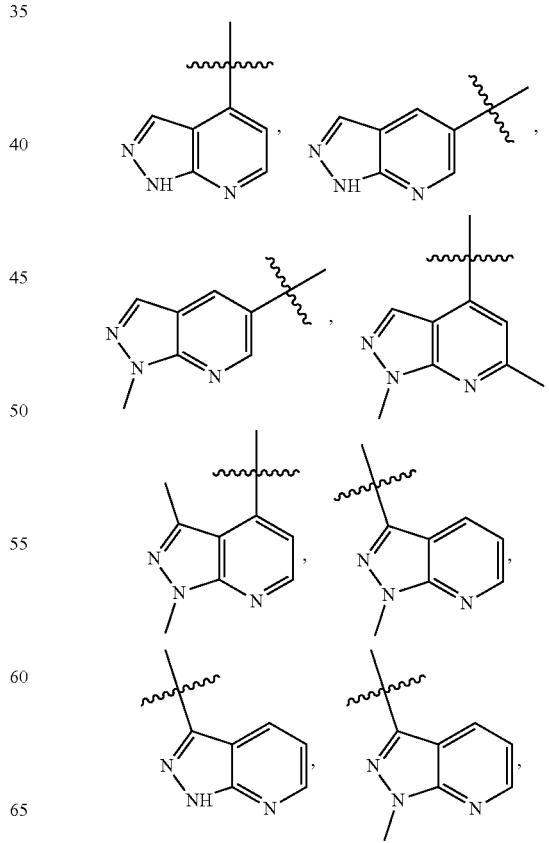

-continued
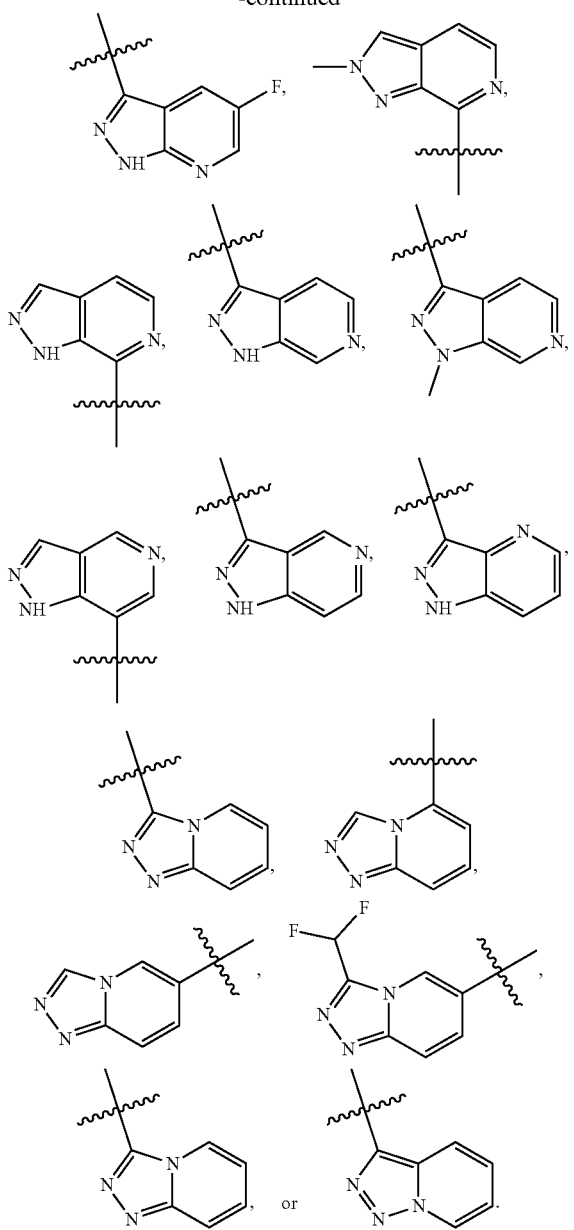
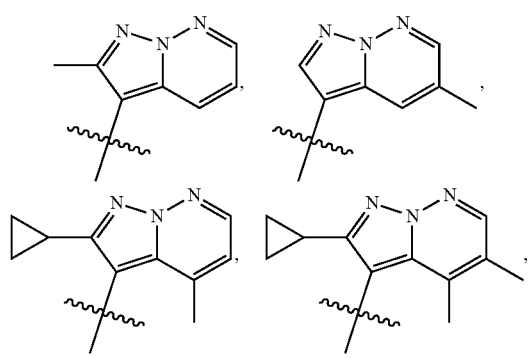
An additional embodiment of the invention is a compound of Formula (II) wherein R$^{2a}$ is
-continued
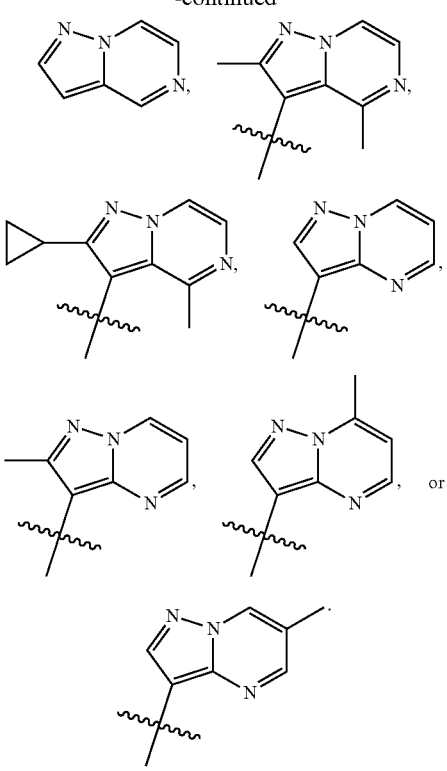
An additional embodiment of the invention is a compound of Formula (II) wherein R$^{2a}$ is
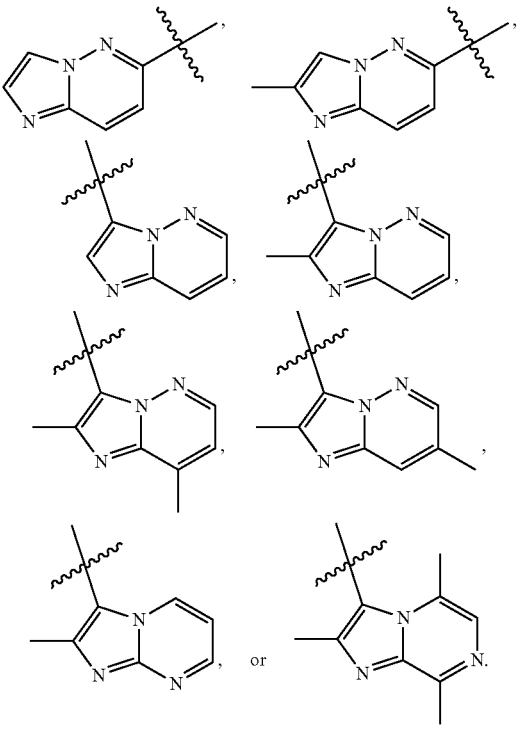
An additional embodiment of the invention is a compound of Formula (II) wherein R$^{2a}$ is

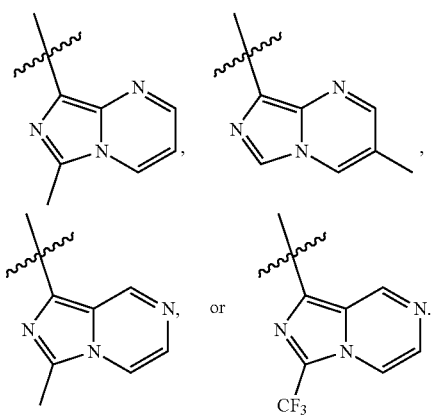
An additional embodiment of the invention is a compound of Formula (II) wherein $R^{2a}$ is
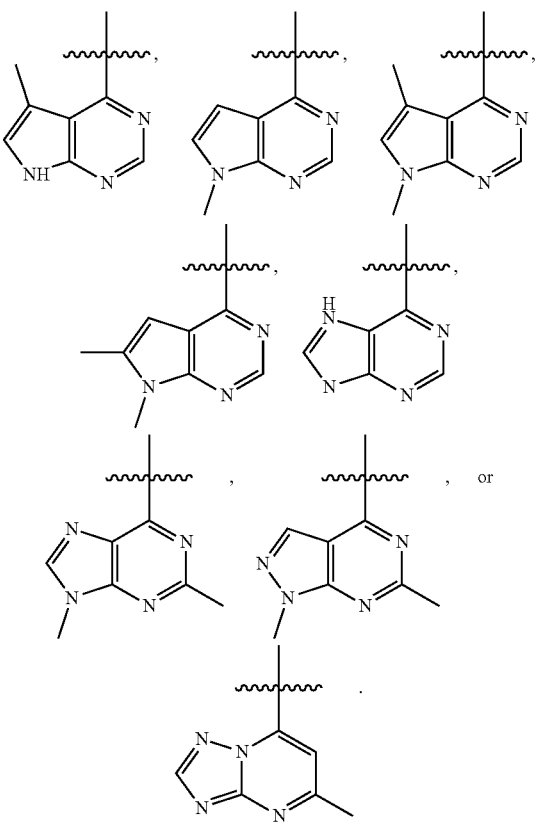
An additional embodiment of the invention is a compound of Formula (II) wherein $R^{2a}$ is
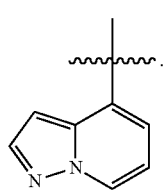
An additional embodiment of the invention is a compound of Formula (II) wherein $R^{2a}$ is
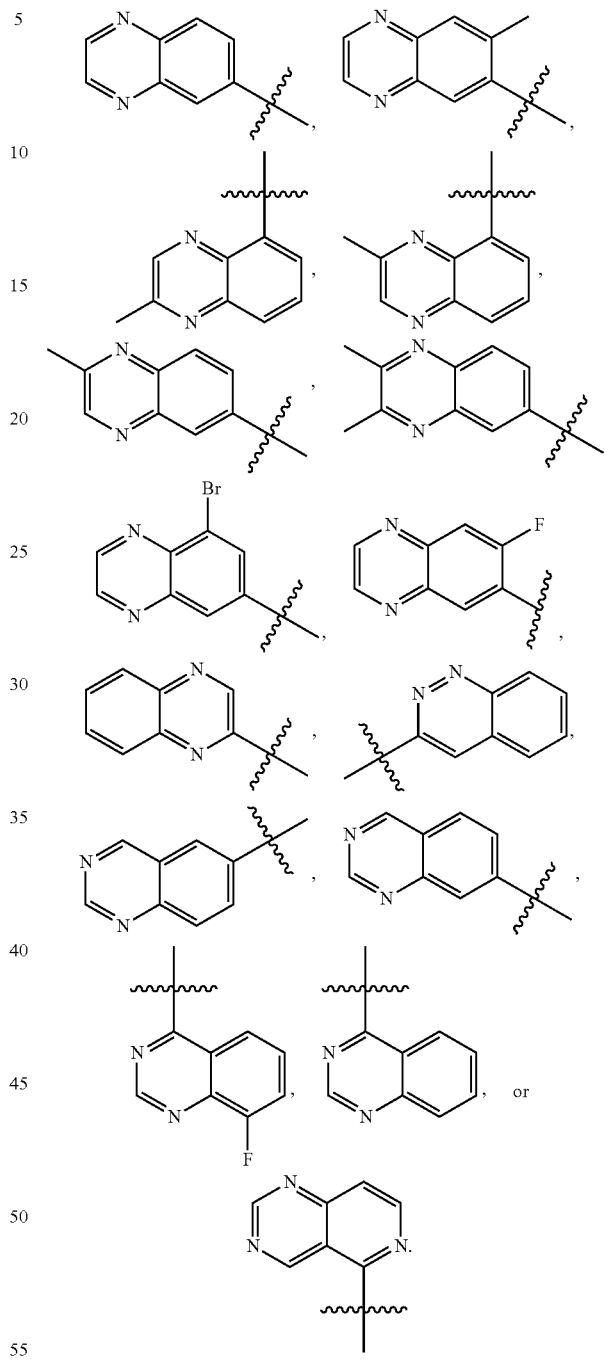
An additional embodiment of the invention is a compound of Formula (II) wherein $R^{2a}$ is
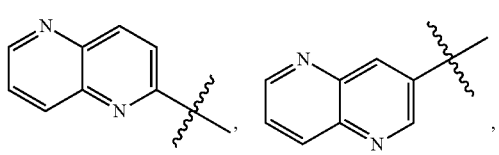

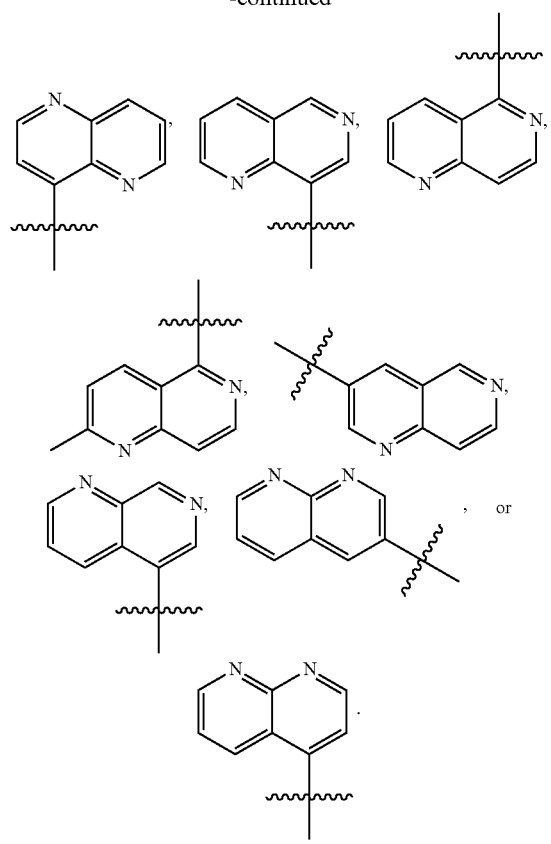
An additional embodiment of the invention is a compound of Formula (II) wherein $R^{2a}$ is
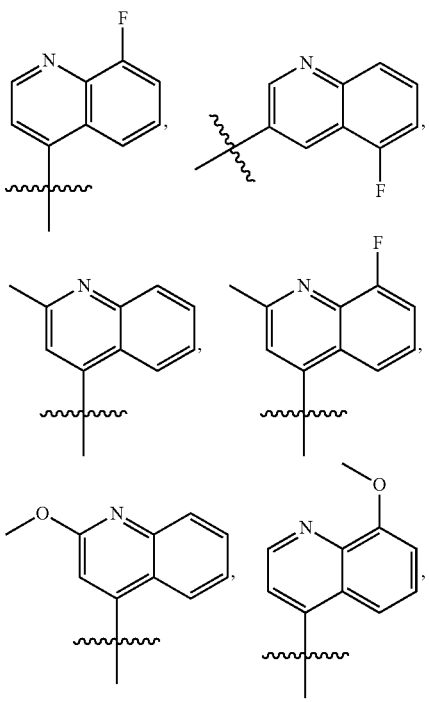
An additional embodiment of the invention is a compound of Formula (II) wherein $R^{2a}$ is
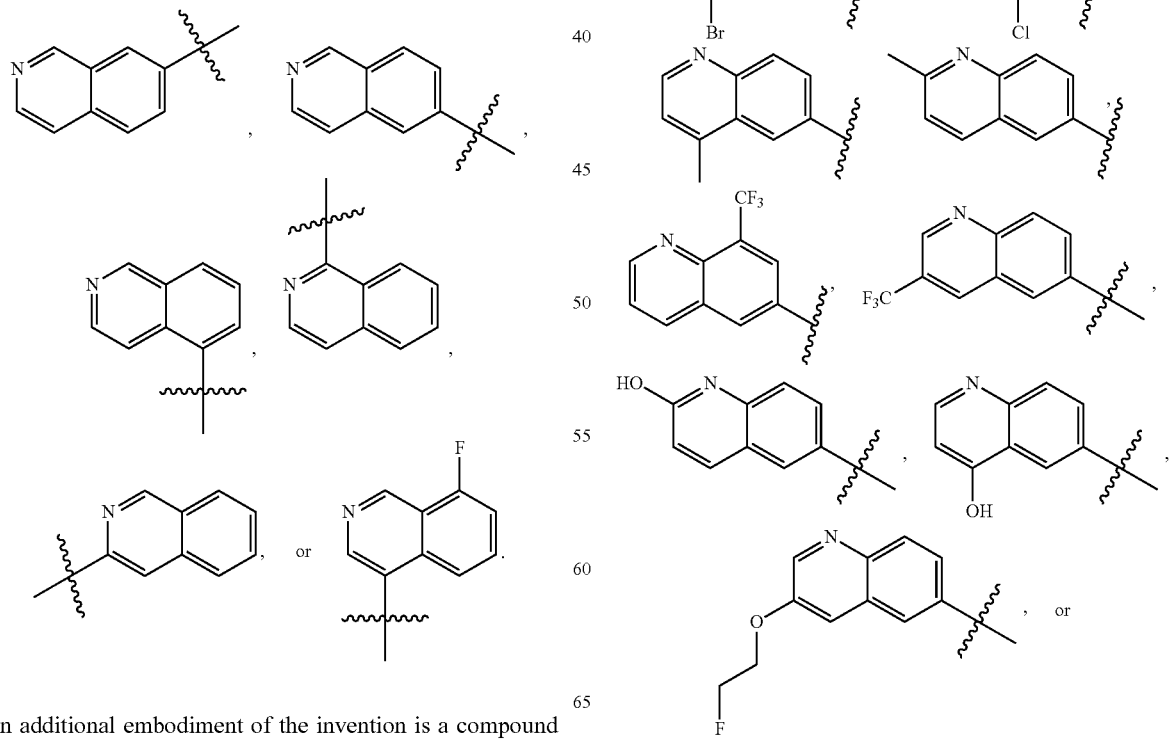

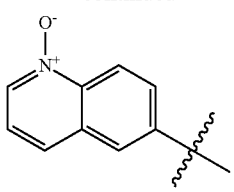
An additional embodiment of the invention is a compound of Formula (II) wherein $R^{2a}$ is
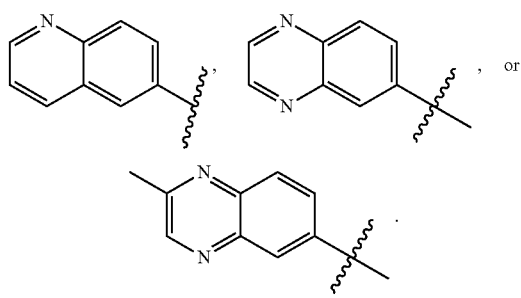
An additional embodiment of the invention is a compound of Formula (II) wherein $R^{2a}$ is
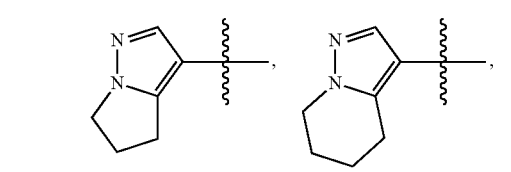
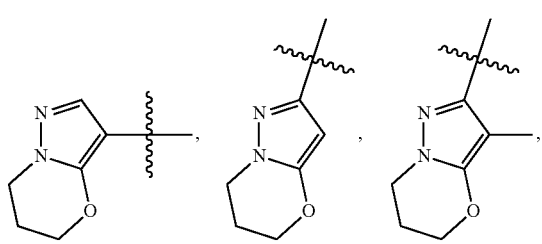
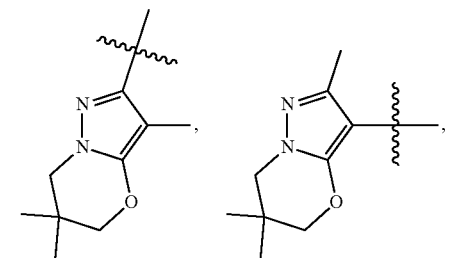
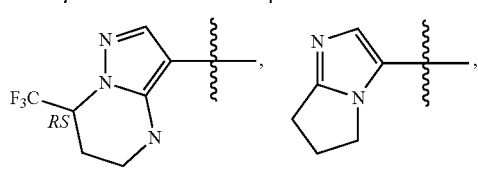
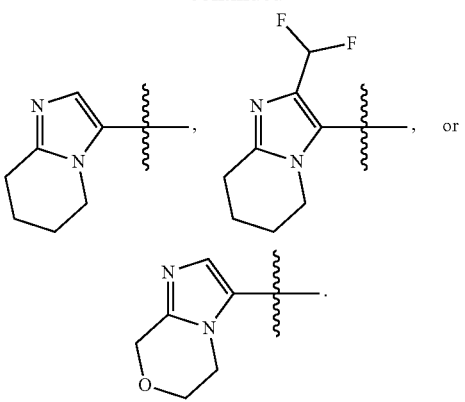
An additional embodiment of the invention is a compound of Formula (II) wherein $R^{2a}$ is
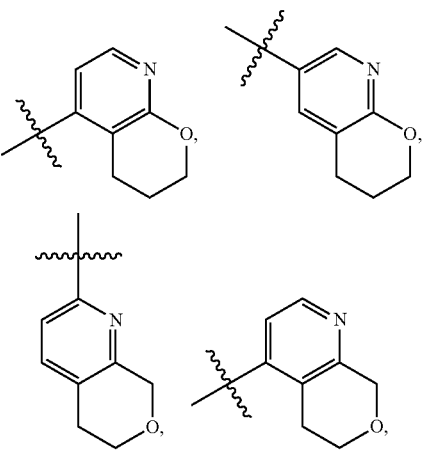
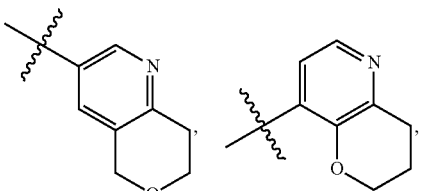
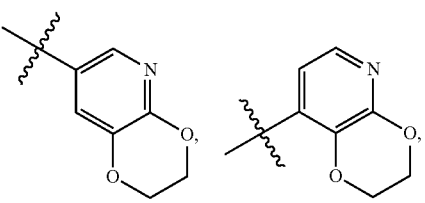
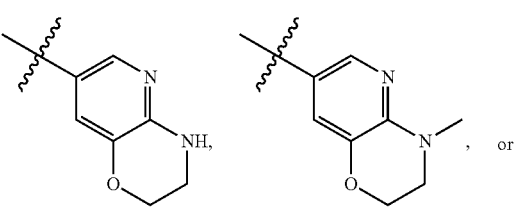

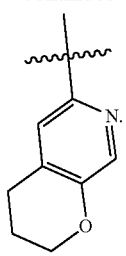

An additional embodiment of the invention is a compound of Formula (II) wherein $R^{2a}$ is

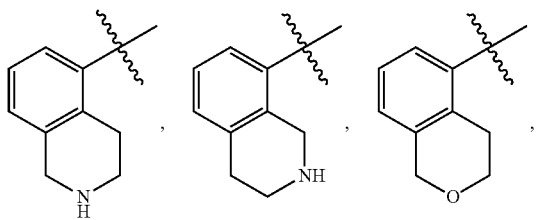

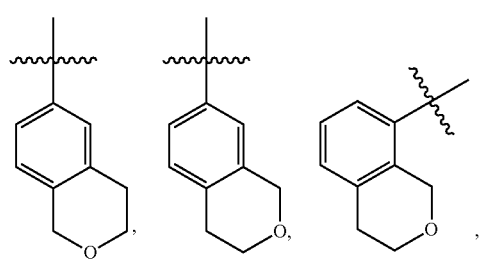

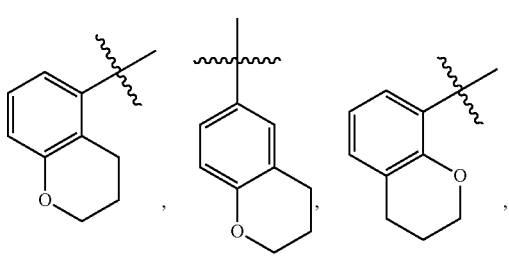

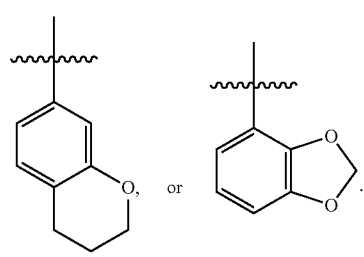

An additional embodiment of the invention is a compound of Formula (II) wherein $R^{2a}$ is

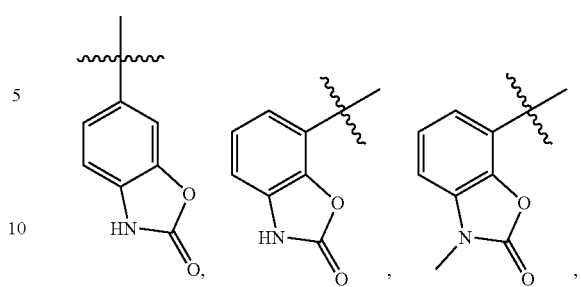

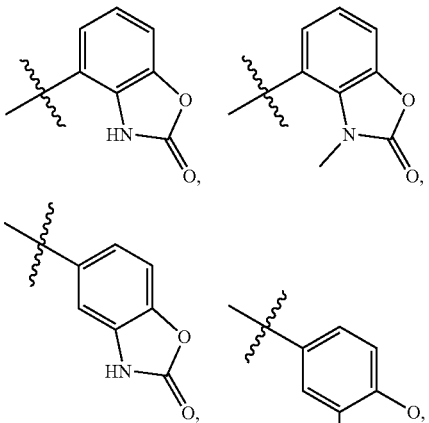

An additional embodiment of the invention is a compound of Formula (II) wherein $R^{3a}$ is phenyl; or phenyl substituted with one member selected from the group consisting of: F, Cl, $OCH_3$, $OCH_2CH_3$, $OCH(CH_3)_2$, $OCHF_2$, $CF_3$, $CF_2CH_3$, $OCF_2H$, and $OCF_3$.

An additional embodiment of the invention is a compound of Formula (II) wherein $R^{3a}$ is phenyl substituted with two or three members independently selected from the group consisting of: F, Cl, $CH_3$, $CF_2H$, $OCF_2H$ and $OCH_3$.

An additional embodiment of the invention is a compound of Formula (II) wherein $R^{3a}$ is

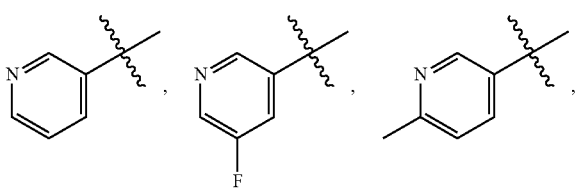

-continued

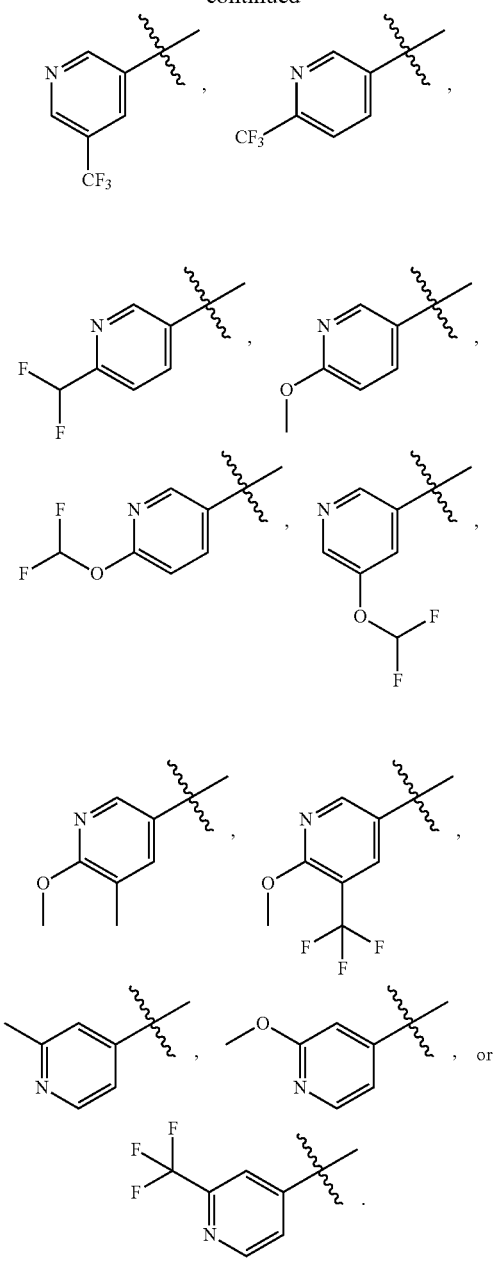

An additional embodiment of the invention is a compound of Formula (II) wherein R$^{3a}$ is

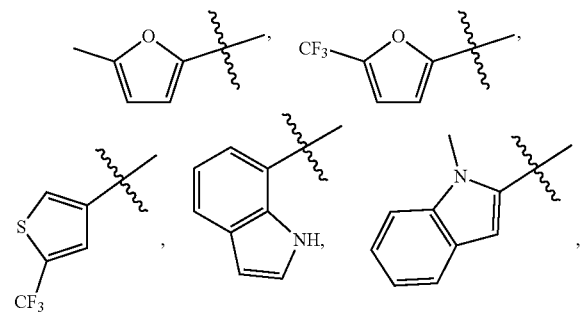

-continued

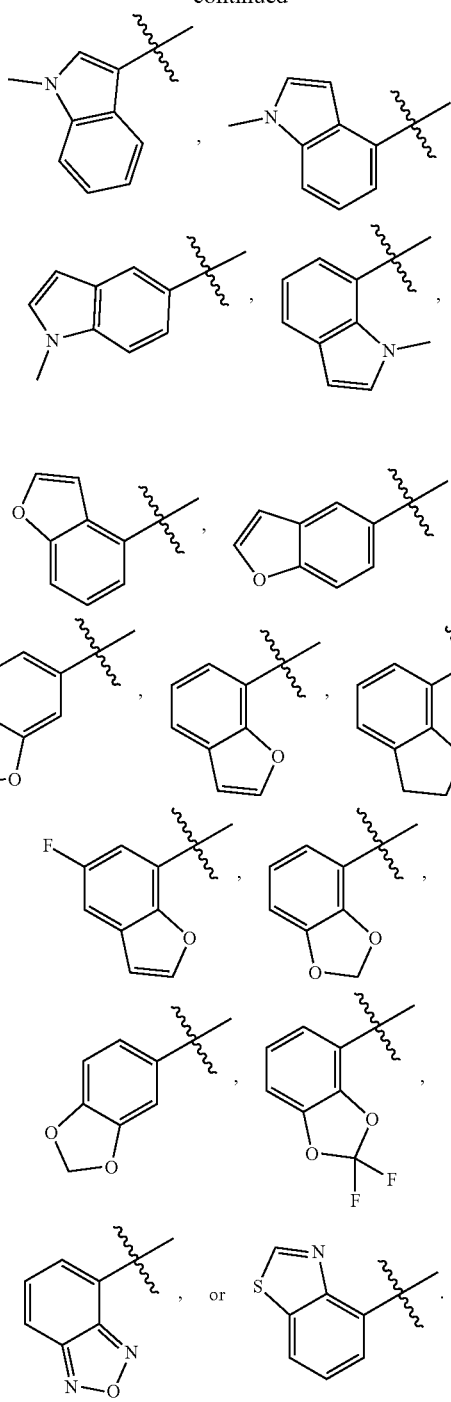

An additional embodiment of the invention is a compound of Formula (II) wherein R$^{4a}$ is CH$_3$.

An additional embodiment of the invention is a compound of Formula (II) wherein R$^{4a}$ is CF$_3$.

An additional embodiment of the invention is a compound of Formula (II) wherein R$^{4a}$ is CF$_2$H.

An additional embodiment of the invention is a compound of Formula (II) wherein R$^{4a}$ is phenyl.

An additional embodiment of the invention is a compound of Formula (II) having the Formula

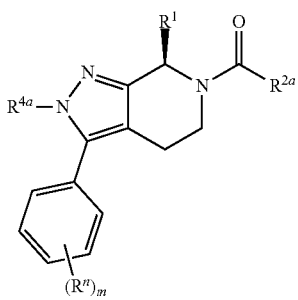

(IIA)

wherein $R^1$ is $CH_3$;

$R^{2a}$ is selected from the group consisting of:

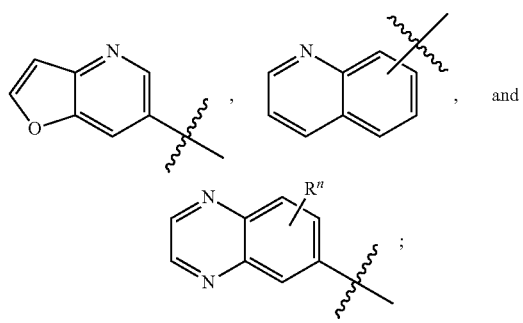

$R^{4a}$ is $CH_3$ or phenyl; and each $R^n$ is independently selected from the group consisting of: H, Cl and F; and m is 1, 2, or 3.

An additional embodiment of the invention is a compound of Formula (II) having the Formula (IIB):

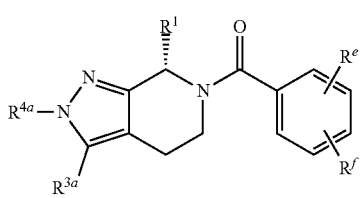

(IIB)

wherein $R^1$ is $CH_3$ or $CH_2CH_3$ $R^e$ is selected from the group consisting of: $OC_{1-4}$alkyl, $OC_{1-4}$haloalkyl, (C=O)NHCH$_3$, and 5-membered heteroaryl ring containing two or three nitrogen members, wherein the 5-membered heteroaryl ring is optionally substituted with one $R^f$ member;

$R^f$ is selected from the group consisting of: H, halo, $C_{1-4}$alkyl, $C_{1-4}$haloalkyl, $OC_{1-4}$alkyl, and $OC_{1-4}$haloalkyl;

$R^{3a}$ is phenyl substituted with one, two, or three members independently selected from halo or $C_{1-4}$alkyl; and $R^{4a}$ is $CH_3$.

An additional embodiment of the invention is a compound of Formula (II) having the Formula (IIB), wherein $R^1$ is $CH_3$;

$R^e$ is selected from the group consisting of: $OC_{1-4}$alkyl, $OC_{1-4}$haloalkyl, (C=O)NHCH$_3$, and 5-membered heteroaryl ring containing two or three nitrogen members, wherein the 5-membered heteroaryl ring is optionally substituted with one $R^f$ member;

$R^f$ is selected from the group consisting of: H, halo, $C_{1-4}$alkyl, $C_{1-4}$haloalkyl, $OC_{1-4}$alkyl, and $OC_{1-4}$haloalkyl;

$R^{3a}$ is 3-chlorophenyl, 3,5-difluorophenyl, 3-fluoro-5-methyl-phenyl, or 3,4,5-trifluorophenyl; and $R^{4a}$ is $CH_3$.

An additional embodiment of the invention is a compound of Formula (II) having the Formula (IIC):

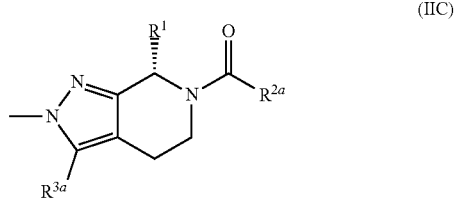

(IIC)

wherein $R^1$ is $CH_3$;

$R^{2a}$ is selected from the group consisting of:

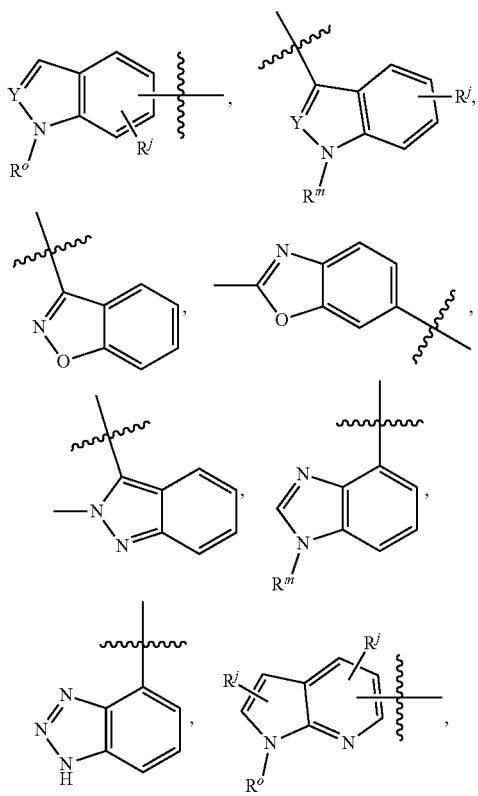

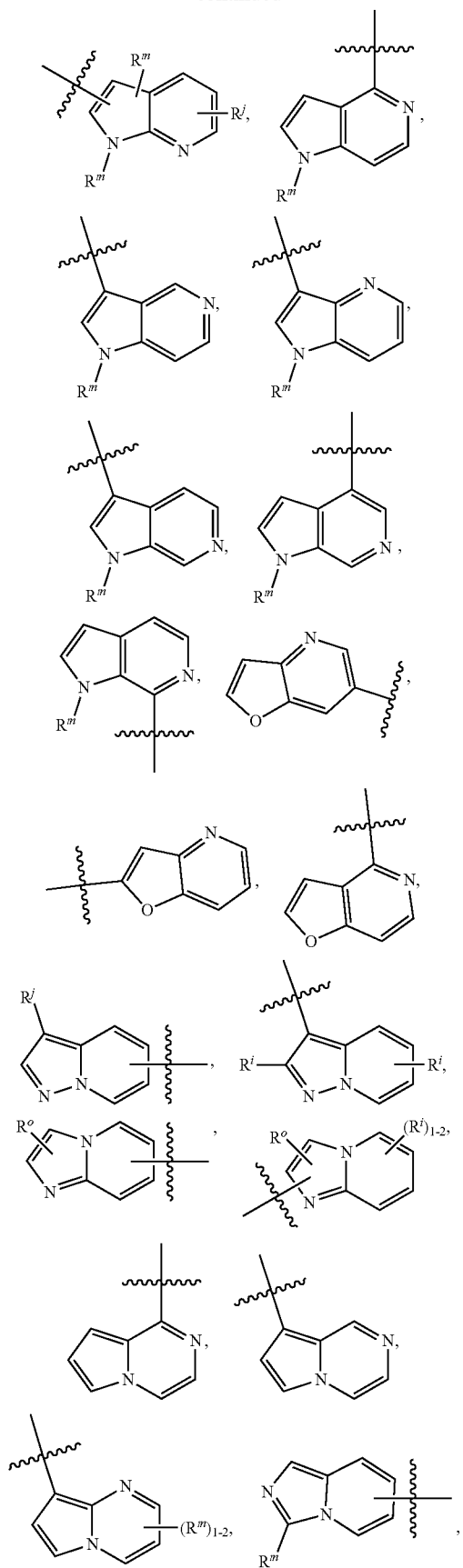
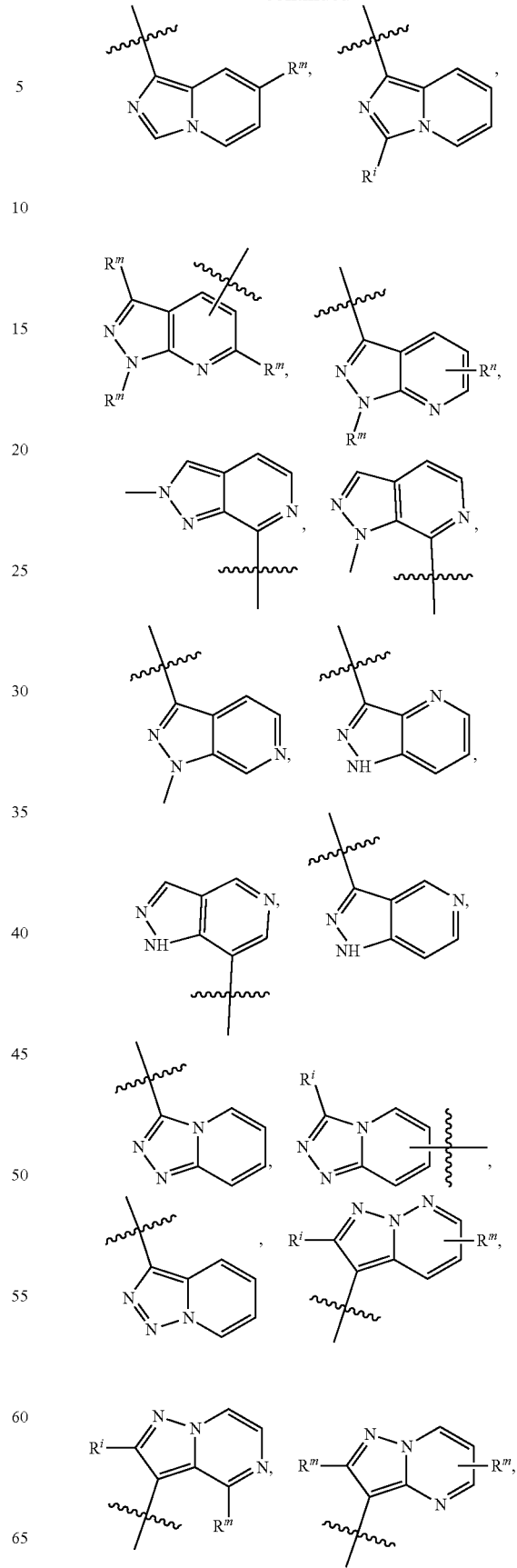

-continued

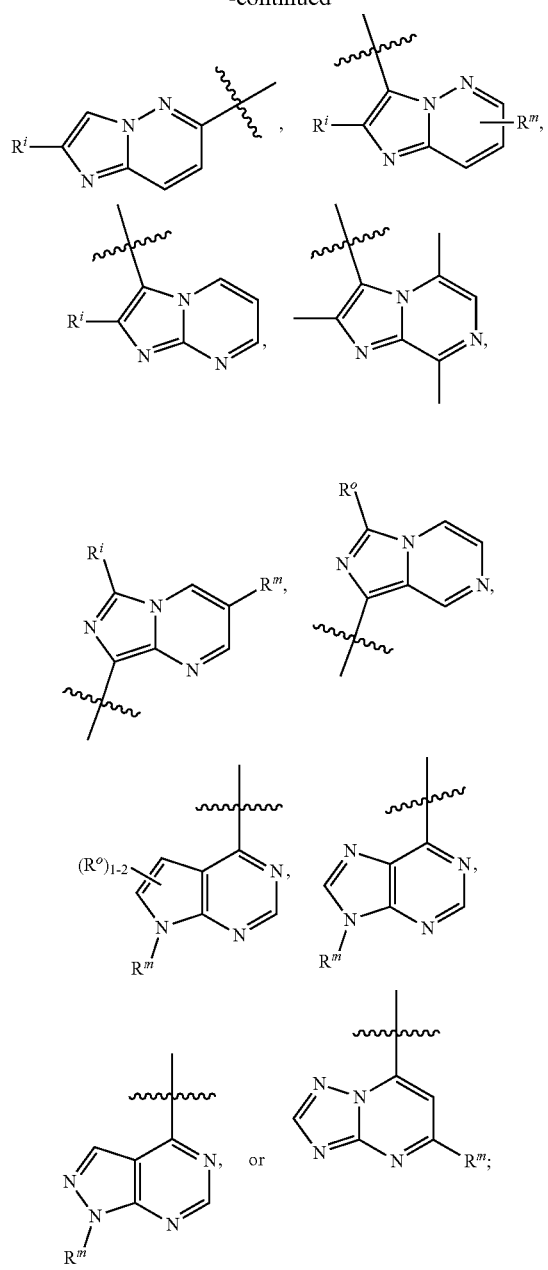

R$^i$ is selected from the group consisting of: H, F, CH$_3$, CF$_3$, CF$_2$H, OCH$_3$, and cyclopropyl;

R$^j$ is selected from the group consisting of: H, Br, F, CH$_3$, and CF$_3$;

R$^m$ is H or CH$_3$;

R$^n$ is selected from the group consisting of: H, halo and OCH$_3$;

R$^o$ is selected from the group consisting of: H, CH$_3$, CF$_3$, CF$_2$H, and CH$_2$CH$_2$F;

Y is CH or N;

and

R$^{3a}$ is phenyl substituted with one, two or three members each independently selected from the group consisting of: Cl, F, CH$_3$, and OCH$_3$.

An additional embodiment of the invention is a compound of Formula (II) having the Formula (IIC), wherein R$^1$ is CH$_3$;

R$^{2a}$ is

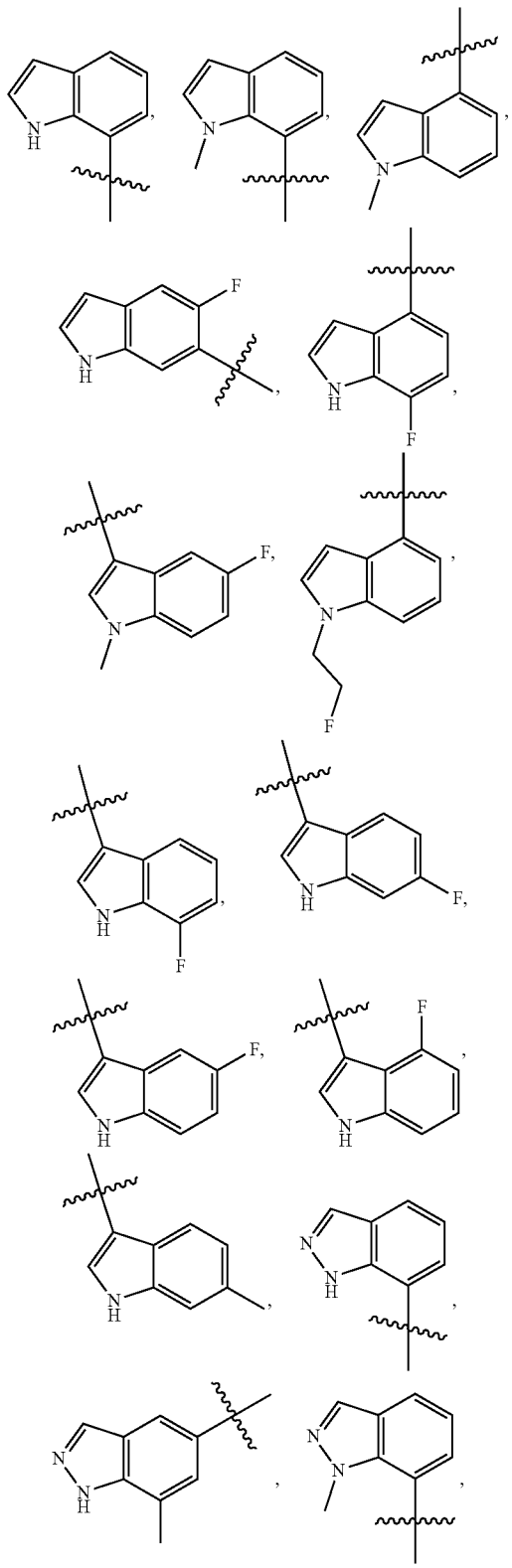

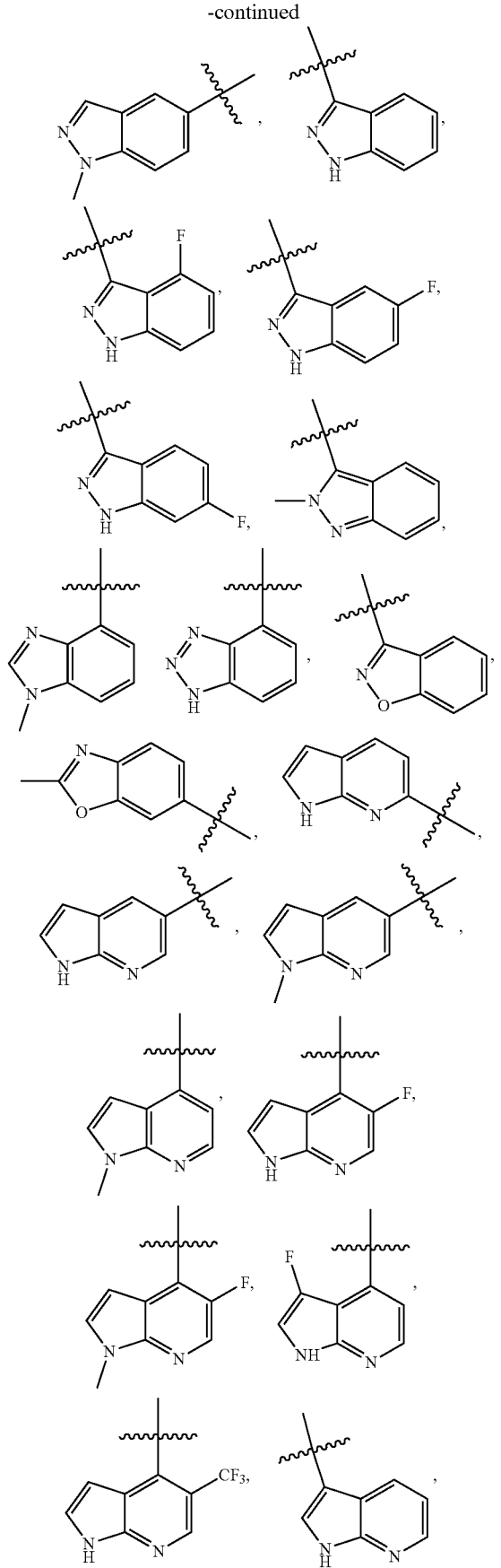
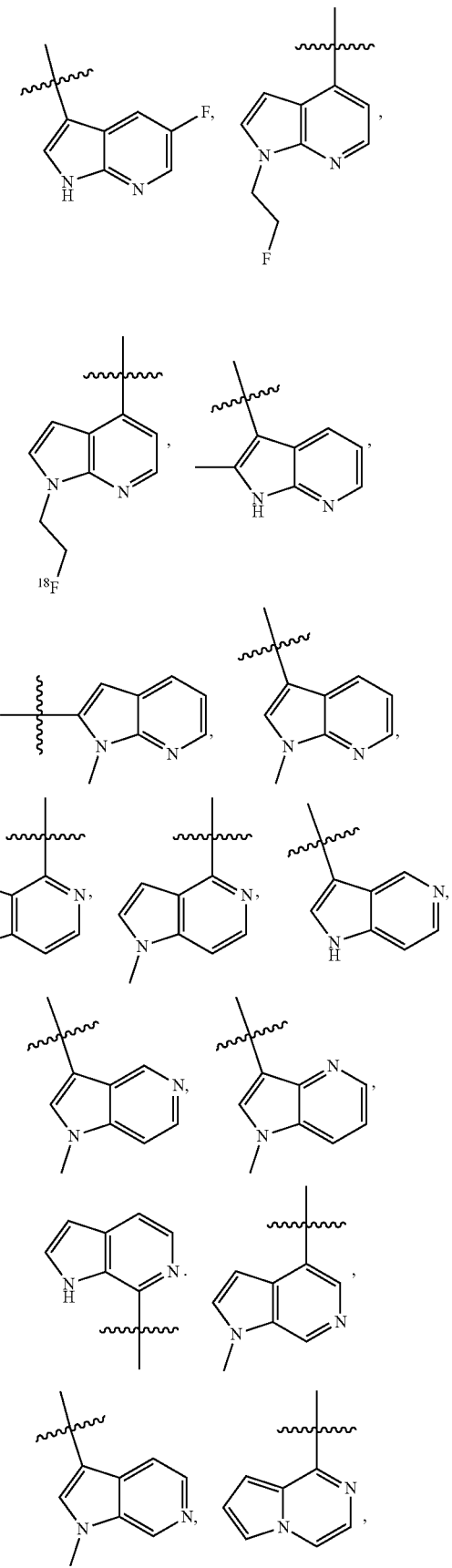

105
-continued
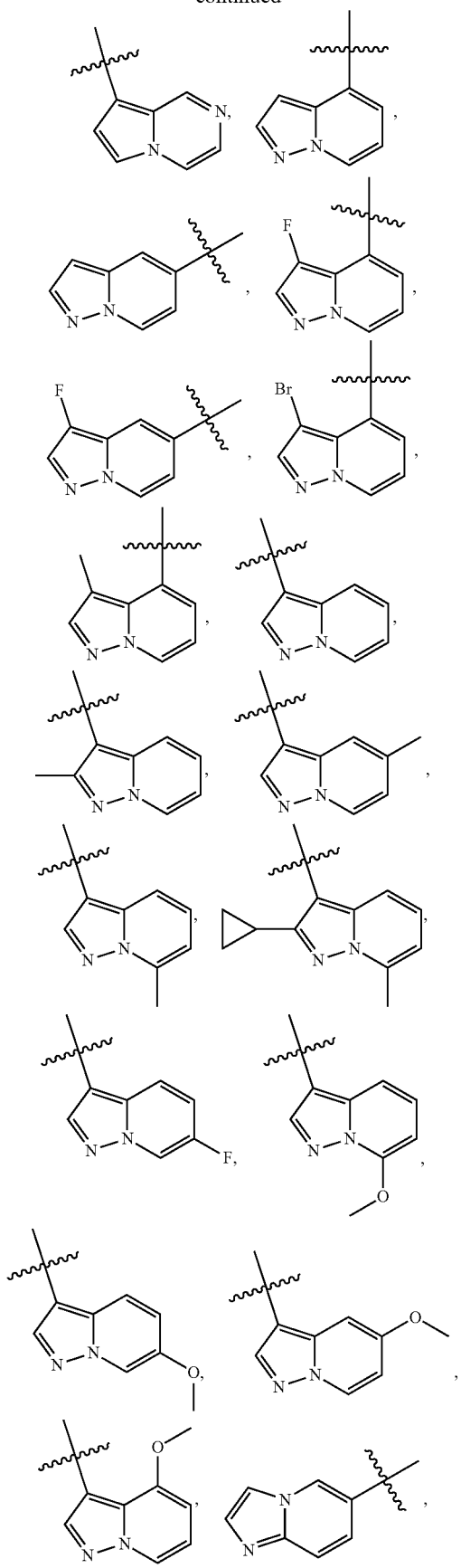
106
-continued
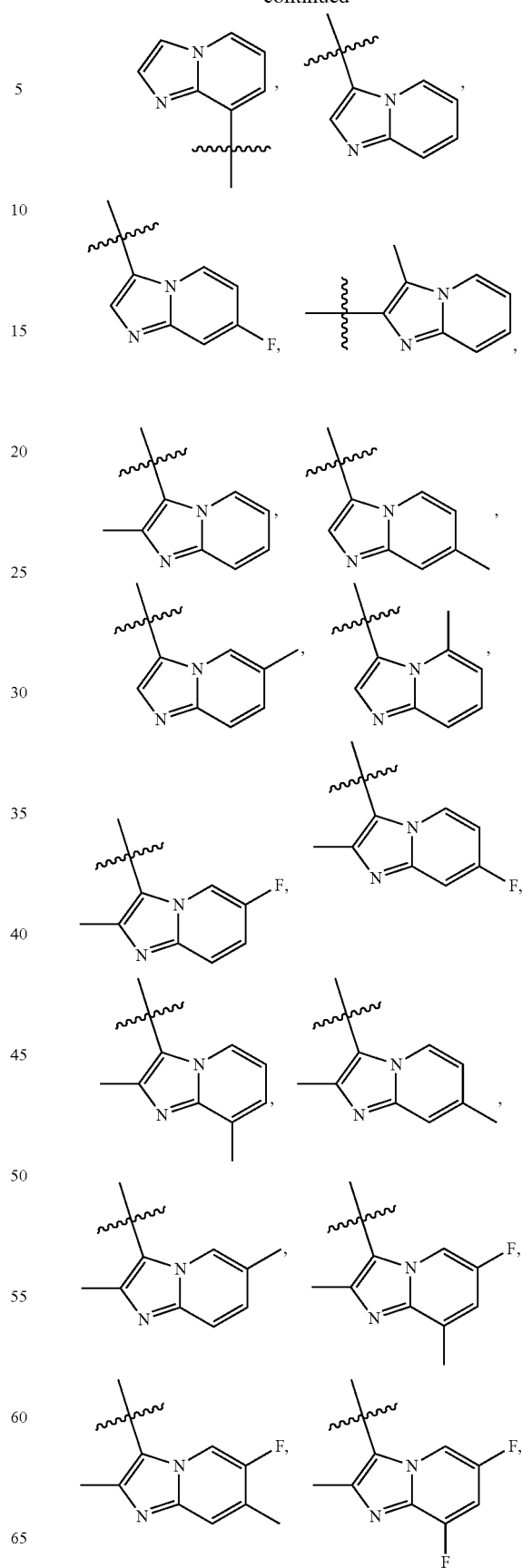

107
-continued

108
-continued

-continued
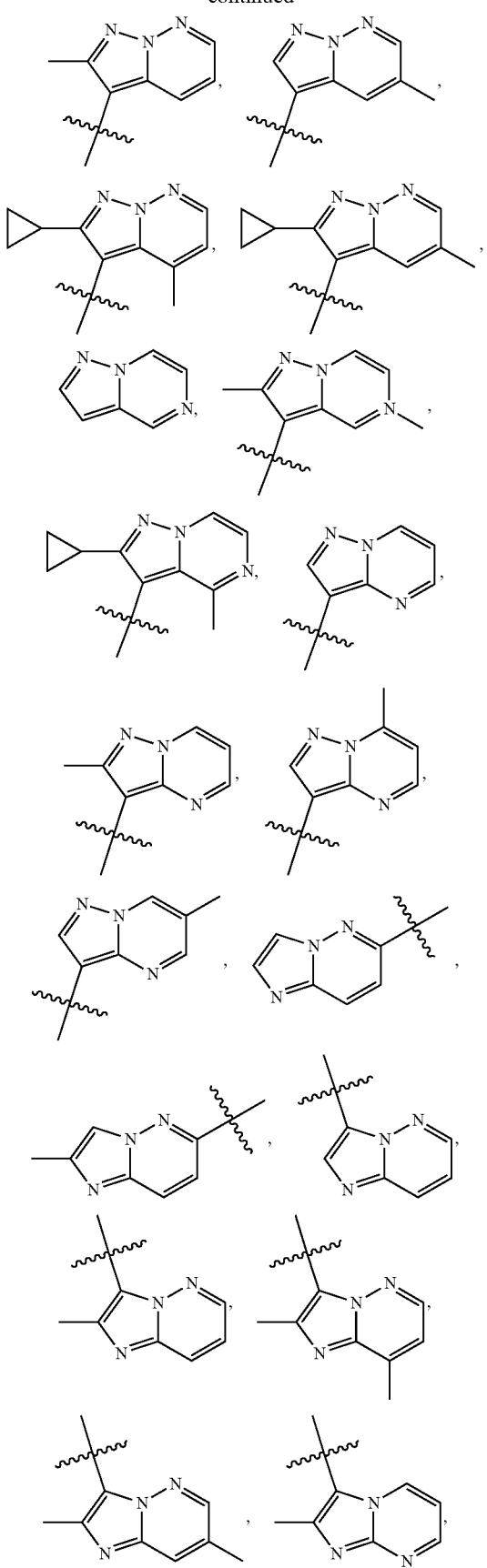
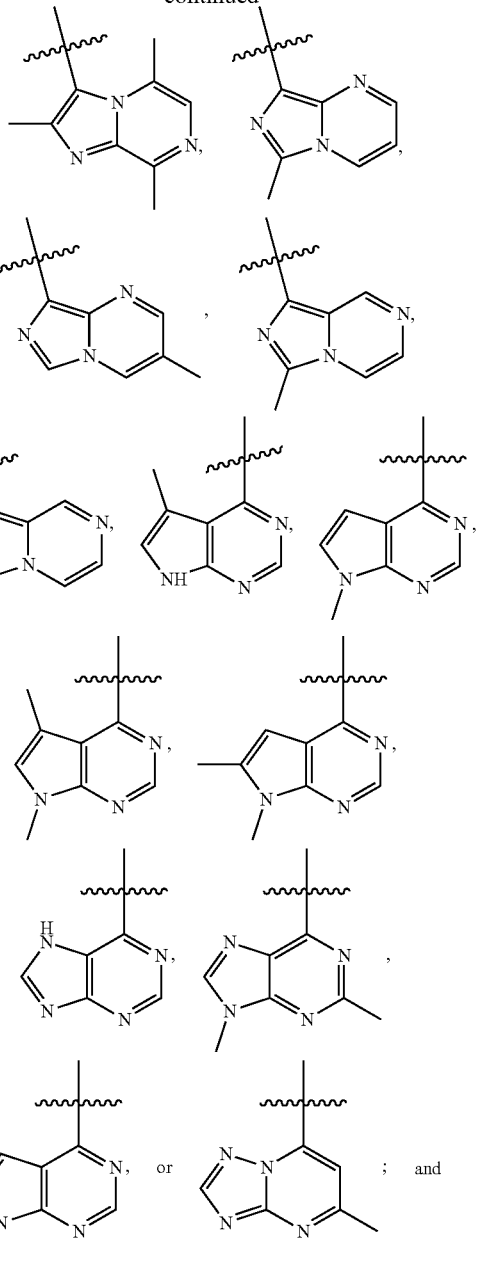
$R^{3a}$ is 3-chlorophenyl, 3,5-difluorophenyl, 3,5-dichlorophenyl, 3-fluoro-5-methylphenyl, 3-chloro-5-methoxyphenyl, or 3,4,5-trifluorophenyl.
An additional embodiment of the invention is a compound of Formula (II) having the Formula (IID):
(IID)
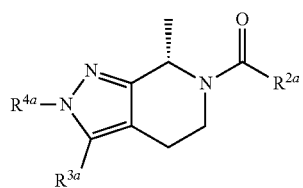

wherein
R$^{2a}$ is selected from the group consisting of:

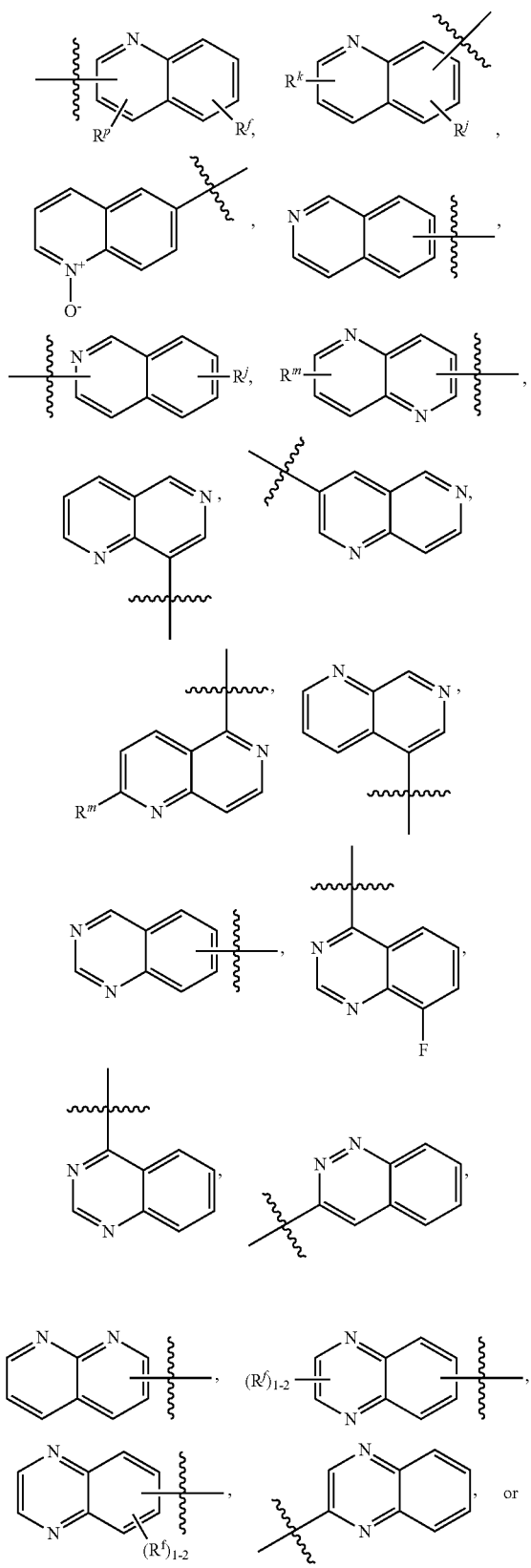

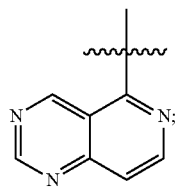

R$^f$ is selected from the group consisting of: H, F and OCH$_3$;

R$^j$ is selected from the group consisting of: H, Cl, F and CF$_3$;

R$^k$ is selected from the group consisting of: H, Br, CH$_3$, CF$_3$, OH, and OCH$_2$CH$_2$F;

R$^m$ is H or CH$_3$; and

R$^p$ is selected from the group consisting of: H, CH$_3$, and OCH$_3$;

R$^{3a}$ is selected from the group consisting of:

(a) phenyl, phenyl substituted with one, two or three members each independently selected from the group consisting of: Cl, F, C$_{1-4}$alkyl, CF$_3$, OC$_{1-4}$alkyl, OCF$_3$, and OCF$_2$H; and (b)

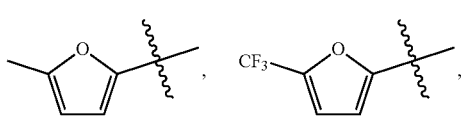

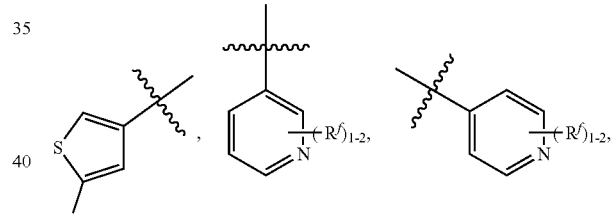

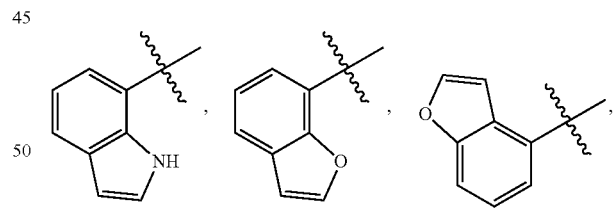

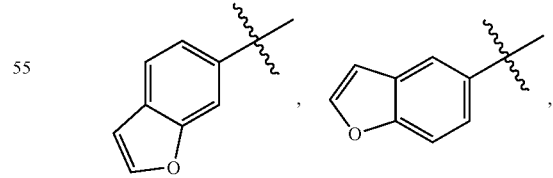

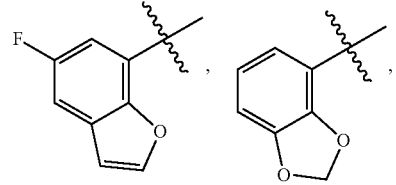

-continued
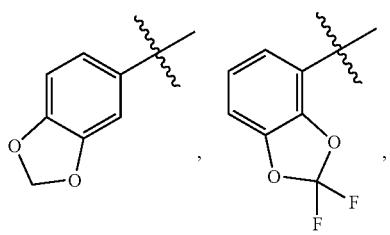
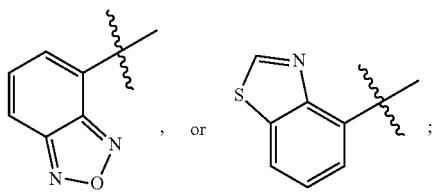
where $R^f$ is H, F, $CH_3$, $CF_2H$, $CF_3$, $OCH_3$, $OCF_2H$; and $R^{4a}$ is $CH_3$ or $CF_2H$.
An additional embodiment of the invention is a compound of Formula (II) having the Formula (IID), wherein: $R^{2a}$ is
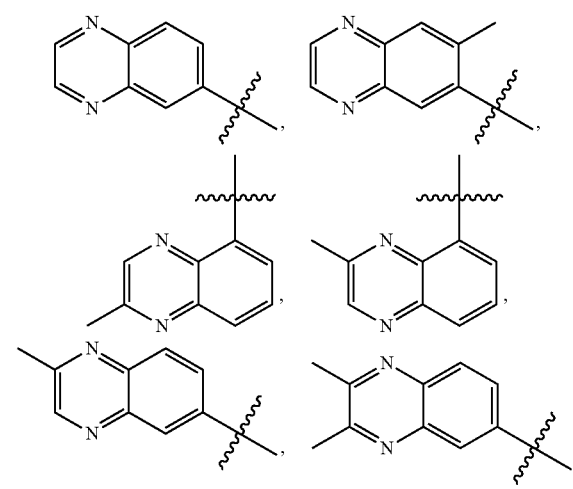
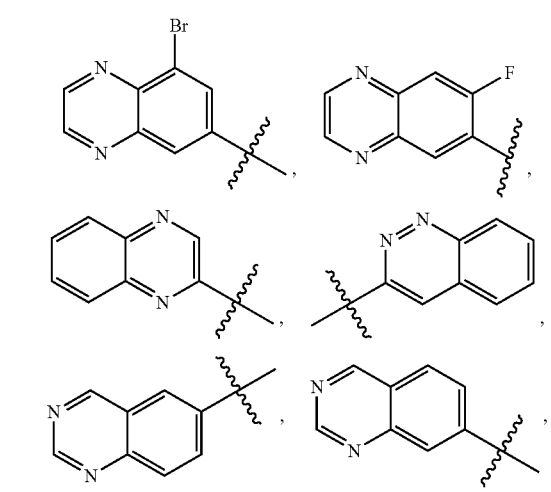
-continued
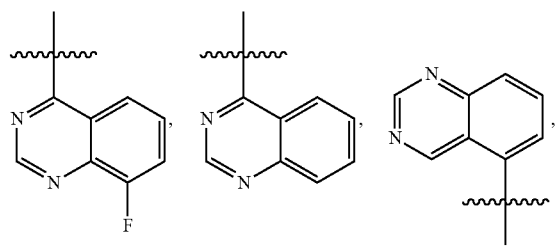
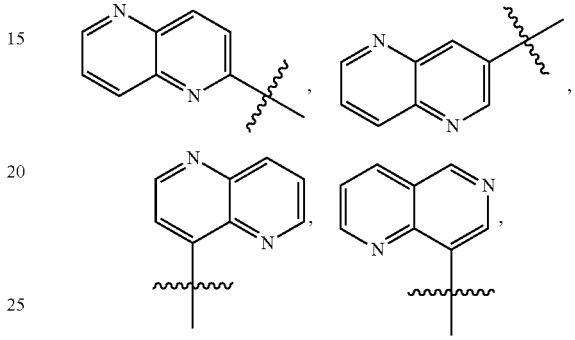
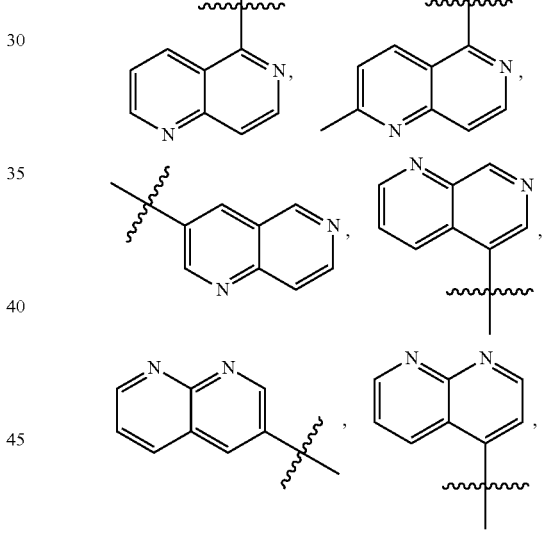
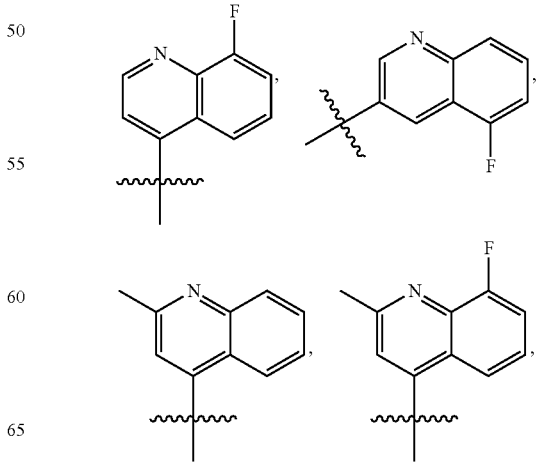

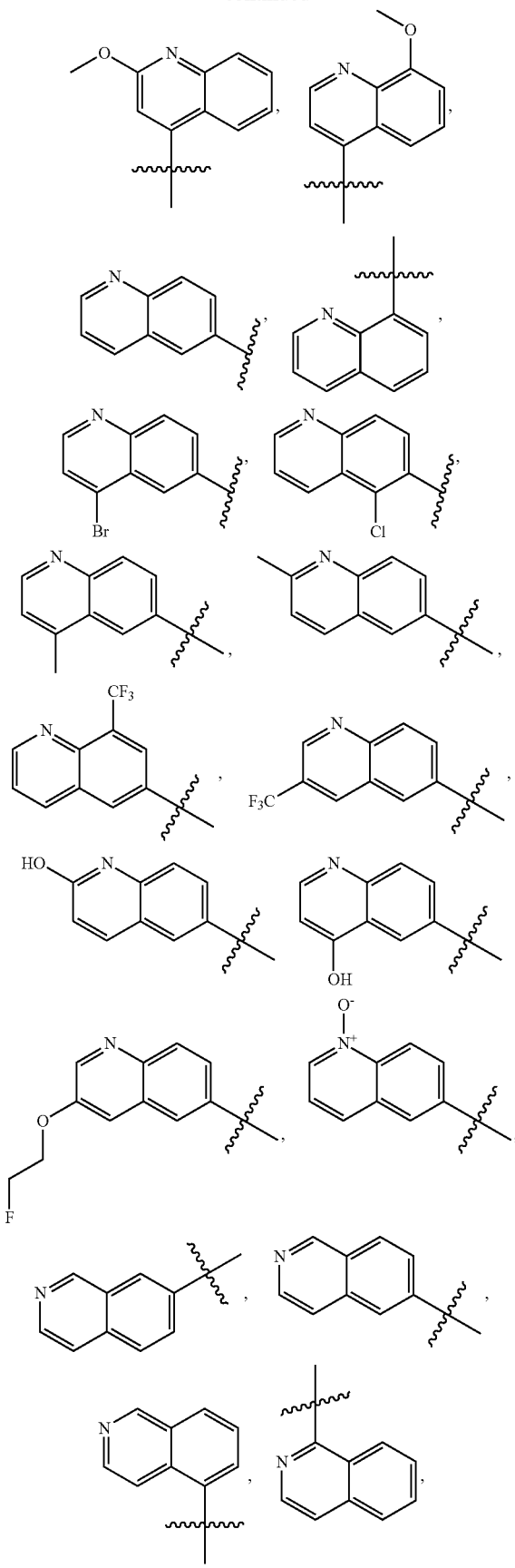

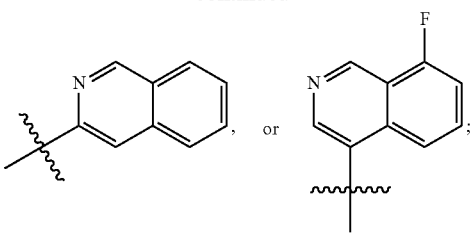

R[3a] is 5-methylfuran-2-yl, 5-(trifluoromethyl)furan-2-yl, pyridin-3-yl, 5-fluoropyridin-3-yl, 5-(trifluoromethyl)pyridin-3-yl, phenyl, 3-chlorophenyl, 3,5-difluorophenyl, 3,5-dichlorophenyl, 3-chloro-5-fluorophenyl, 3-fluoro-4-methoxyphenyl, 4-(difluoromethoxy)-3-fluorophenyl, 3-fluoro-5-(trifluoromethyl)phenyl, 3-chloro-4-methoxyphenyl, 3-fluoro-5-methoxyphenyl, 3-chloro-4-methylphenyl, 3,5-difluoro-4-methylphenyl, or 3,4,5-trifluorophenyl; and R[4a] is CH$_3$.

An additional embodiment of the invention is a compound of Formula (II) having the Formula (IIE):

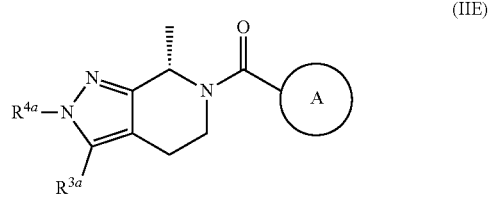

(IIE)

wherein ring

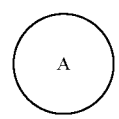

is selected from the group consisting of:

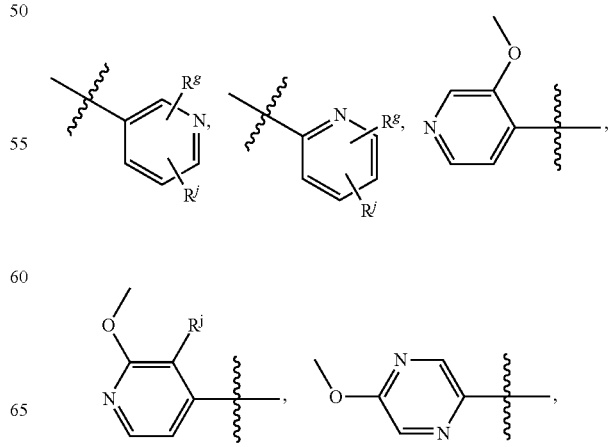

-continued

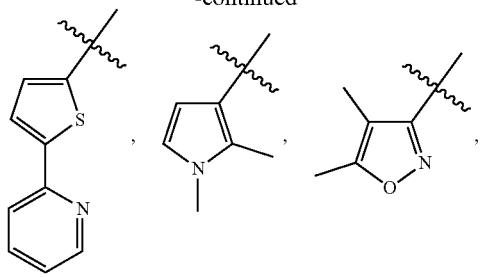

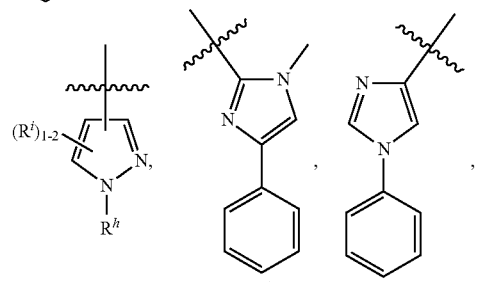

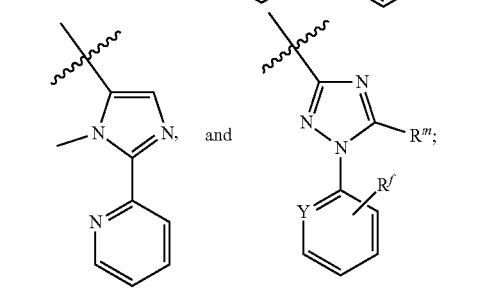

where
Y is CH or N;
$R^f$ is H or F;
$R^g$ is selected from the group consisting of: $OC_{1-4}alkyl$, $CH_2OCH_3$, $CH_2OH$,

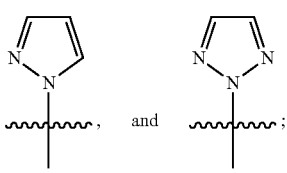 [SMILES: *n1cccn1 ; *n1nccn1]

$R^h$ is selected from the group consisting of: $C_{1-4}alkyl$, $CF_3$, and cyclopropyl;
$R^i$ is selected from the group consisting of: H, halo, $C_{1-4}alkyl$, $CF_2H$, $CF_3$, $OCH_3$, cyclopropyl, cyclobutyl, and cyclopropyl substituted with one or two members independently selected from: F and $CH_3$;
$R^j$ is selected from the group consisting of: H, Cl, F, and $CH_3$;
$R^m$ is H, $CH_3$, or $CH_2CH_3$;
$R^{3a}$ is selected from the group consisting of: phenyl, 3,3-chlorophenyl, 5-difluorophenyl, 3-fluoro-5-methylphenyl, 3,4,5-trifluorophenyl; and
$R^{4a}$ is selected from the group consisting of: $CH_3$, $C_{3-6}$cycloalkyl, and phenyl.

An additional embodiment of the invention is a compound of Formula (II) having the Formula (IIF):

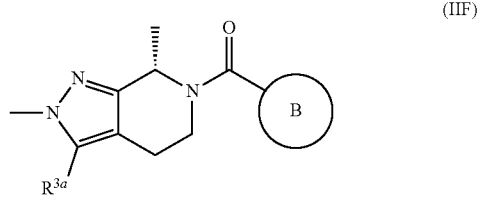

(IIF)

wherein ring

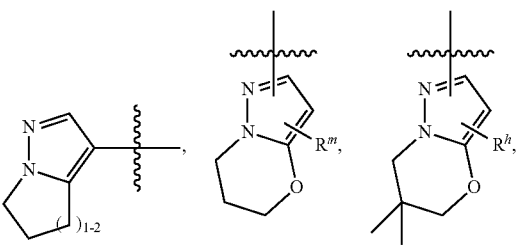

is selected from the group consisting of:

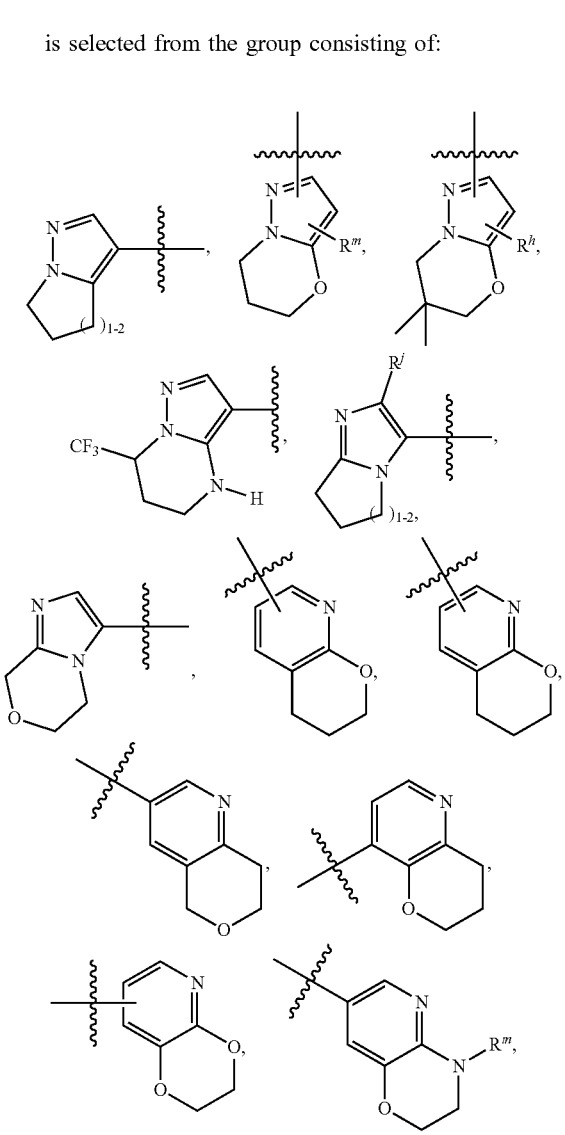

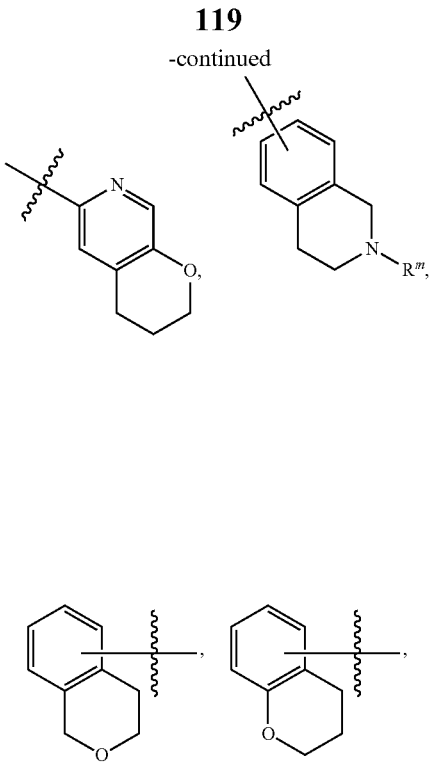
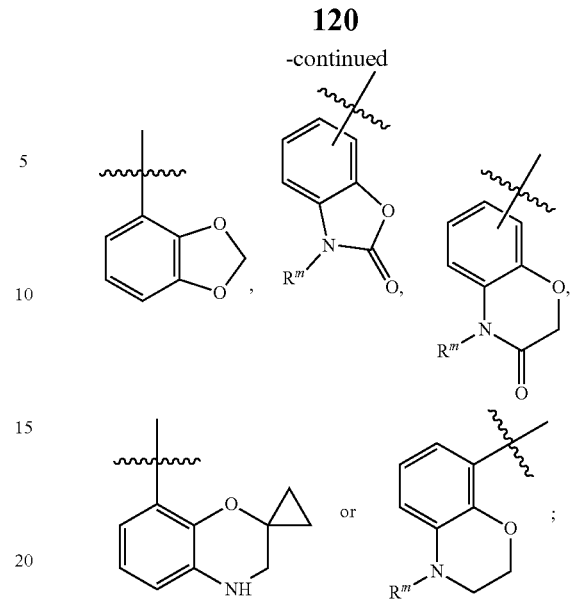

where
$R^h$ is $CH_3$;
$R^j$ is H or $CF_2H$;
$R^m$ is H or $CH_3$;
$R^{3a}$ is 3-chlorophenyl or 3,4,5-trifluorophenyl.

A further embodiment of the current invention is a compound as shown below in Table 2.

TABLE 2

| Example # | Compound Name |
|---|---|
| 106 | (3-(3,5-Difluorophenyl)-2,7-dimethyl-2,4,5,7-tetrahydro-6H-pyrazolo[3,4-c]pyridin-6-yl)(quinolin-6-yl)methanone; |
| 107 | (S)-(2,7-Dimethyl-3-(5-methylfuran-2-yl)-2,4,5,7-tetrahydro-6H-pyrazolo[3,4-c]pyridin-6-yl)(quinoxalin-6-yl)methanone; |
| 108 | (S)-(2,7-Dimethyl-3-(pyridin-3-yl)-2,4,5,7-tetrahydro-6H-pyrazolo[3,4-c]pyridin-6-yl)(quinoxalin-6-yl)methanone; |
| 109 | (S)-(3-(5-Fluoropyridin-3-yl)-2,7-dimethyl-2,4,5,7-tetrahydro-6H-pyrazolo[3,4-c]pyridin-6-yl)(quinoxalin-6-yl)methanone; |
| 110 | (2,7-Dimethyl-3-phenyl-2,4,5,7-tetrahydro-6H-pyrazolo[3,4-c]pyridin-6-yl)(quinolin-6-yl)methanone; |
| 111 | (R)-(2,7-Dimethyl-3-phenyl-2,4,5,7-tetrahydro-6H-pyrazolo[3,4-c]pyridin-6-yl)(quinolin-6-yl)methanone; |
| 112 | (S)-(2,7-Dimethyl-3-phenyl-2,4,5,7-tetrahydro-6H-pyrazolo[3,4-c]pyridin-6-yl)(quinolin-6-yl)methanone; |
| 113 | (7-Methyl-2,3-diphenyl-2,4,5,7-tetrahydro-6H-pyrazolo[3,4-c]pyridin-6-yl)(quinolin-6-yl)methanone; |
| 114 | (R)-(7-Methyl-2,3-diphenyl-2,4,5,7-tetrahydro-6H-pyrazolo[3,4-c]pyridin-6-yl)(quinolin-6-yl)methanone; |
| 115 | (S)-(7-Methyl-2,3-diphenyl-2,4,5,7-tetrahydro-6H-pyrazolo[3,4-c]pyridin-6-yl)(quinolin-6-yl)methanone; |
| 116 | (S)-(3-Chloro-5-(trifluoromethoxy)phenyl)(3-(3-chlorophenyl)-2,7-dimethyl-2,4,5,7-tetrahydro-6H-pyrazolo[3,4-c]pyridin-6-yl)methanone; |
| 117 | (S)-(3-(3-Chlorophenyl)-2,7-dimethyl-2,4,5,7-tetrahydro-6H-pyrazolo[3,4-c]pyridin-6-yl)(1-phenyl-1H-1,2,4-triazol-3-yl)methanone; |
| 118 | (S)-(3-(3-Chlorophenyl)-2,7-dimethyl-2,4,5,7-tetrahydro-6H-pyrazolo[3,4-c]pyridin-6-yl)(5-ethyl-1-(2-fluorophenyl)-1H-1,2,4-triazol-3-yl)methanone; |
| 119 | (S)-(3-(3-Chlorophenyl)-2,7-dimethyl-2,4,5,7-tetrahydro-6H-pyrazolo[3,4-c]pyridin-6-yl)(4-(hydroxymethyl)pyridin-2-yl)methanone; |
| 120 | (S)-(3-(3-Chlorophenyl)-2,7-dimethyl-2,4,5,7-tetrahydro-6H-pyrazolo[3,4-c]pyridin-6-yl)(5-(methoxymethyl)pyridin-3-yl)methanone; |
| 121 | (S)-(3-(3-Chlorophenyl)-2,7-dimethyl-2,4,5,7-tetrahydro-6H-pyrazolo[3,4-c]pyridin-6-yl)(6-isopropoxypyridin-3-yl)methanone; |
| 122 | (S)-(3-(3-Chlorophenyl)-2,7-dimethyl-2,4,5,7-tetrahydro-6H-pyrazolo[3,4-c]pyridin-6-yl)(5-isopropoxypyridin-3-yl)methanone; |
| 123 | (S)-Benzo[d][1,3]dioxol-4-yl(3-(3-chlorophenyl)-2,7-dimethyl-2,4,5,7-tetrahydro-6H-pyrazolo[3,4-c]pyridin-6-yl)methanone; |
| 124 | (S)-6-(3-(3-Chlorophenyl)-2,7-dimethyl-4,5,6,7-tetrahydro-2H-pyrazolo[3,4-c]pyridine-6-carbonyl)benzo[d]oxazol-2(3H)-one |

TABLE 2-continued

| Example # | Compound Name |
|---|---|
| 125 | (S)-(3-(3-Chlorophenyl)-2,7-dimethyl-2,4,5,7-tetrahydro-6H-pyrazolo[3,4-c]pyridin-6-yl)(2-methylbenzo[d]oxazol-6-yl)methanone; |
| 126 | (3-(3-Chlorophenyl)-2,7-dimethyl-2,4,5,7-tetrahydro-6H-pyrazolo[3,4-c]pyridin-6-yl)(furo[3,2-b]pyridin-6-yl)methanone; |
| 127 | (R)-(3-(3-Chlorophenyl)-2,7-dimethyl-2,4,5,7-tetrahydro-6H-pyrazolo[3,4-c]pyridin-6-yl)(furo[3,2-b]pyridin-6-yl)methanone; |
| 128 | (S)-(3-(3-Chlorophenyl)-2,7-dimethyl-2,4,5,7-tetrahydro-6H-pyrazolo[3,4-c]pyridin-6-yl)(furo[3,2-b]pyridin-6-yl)methanone; |
| 129 | (S)-(3-(3-Chlorophenyl)-2,7-dimethyl-2,4,5,7-tetrahydro-6H-pyrazolo[3,4-c]pyridin-6-yl)(furo[3,2-b]pyridin-2-yl)methanone; |
| 130 | (S)-(3-(3-Chlorophenyl)-2,7-dimethyl-2,4,5,7-tetrahydro-6H-pyrazolo[3,4-c]pyridin-6-yl)(1H-pyrrolo[2,3-b]pyridin-6-yl)methanone; |
| 131 | (S)-(3-(3-Chlorophenyl)-2,7-dimethyl-2,4,5,7-tetrahydro-6H-pyrazolo[3,4-c]pyridin-6-yl)(1,5-naphthyridin-2-yl)methanone; |
| 132 | (3-(3-Chlorophenyl)-2,7-dimethyl-2,4,5,7-tetrahydro-6H-pyrazolo[3,4-c]pyridin-6-yl)(quinoxalin-6-yl)methanone; |
| 133 | (R)-(3-(3-Chlorophenyl)-2,7-dimethyl-2,4,5,7-tetrahydro-6H-pyrazolo[3,4-c]pyridin-6-yl)(quinoxalin-6-yl)methanone; |
| 134 | (S)-(3-(3-Chlorophenyl)-2,7-dimethyl-2,4,5,7-tetrahydro-6H-pyrazolo[3,4-c]pyridin-6-yl)(quinoxalin-6-yl)methanone; |
| 135 | (S)-(8-Bromoquinoxalin-6-yl)(3-(3-chlorophenyl)-2,7-dimethyl-2,4,5,7-tetrahydro-6H-pyrazolo[3,4-c]pyridin-6-yl)methanone; |
| 136 | (7-Ethyl-3-(3-fluorophenyl)-2-methyl-2,4,5,7-tetrahydro-6H-pyrazolo[3,4-c]pyridin-6-yl)(quinolin-6-yl)methanone; |
| 137 | [(7S)-3-(3,5-Difluorophenyl)-2,7-dimethyl-5,7-dihydro-4H-pyrazolo[3,4-c]pyridin-6-yl]-[2-(2-fluoroethoxy)phenyl]methanone; |
| 138 | (S)-(3-(3,5-Difluorophenyl)-2,7-dimethyl-2,4,5,7-tetrahydro-6H-pyrazolo[3,4-c]pyridin-6-yl)(4-(2-fluoroethoxy)phenyl)methanone; |
| 139 | (S)-(3-(3,5-Difluorophenyl)-2,7-dimethyl-2,4,5,7-tetrahydro-6H-pyrazolo[3,4-c]pyridin-6-yl)(3-(2-fluoroethoxy)phenyl)methanone; |
| 140 | (S)-(3-(3,5-Difluorophenyl)-2,7-dimethyl-2,4,5,7-tetrahydro-6H-pyrazolo[3,4-c]pyridin-6-yl)(3-(2-(fluoro-$^{18}$F)ethoxy)phenyl)methanone; |
| 141 | (S)-(3-(3,5-Difluorophenyl)-2,7-dimethyl-2,4,5,7-tetrahydro-6H-pyrazolo[3,4-c]pyridin-6-yl)(2-fluoro-3-(2-fluoroethoxy)phenyl)methanone; |
| 142 | (S)-(3-(3,5-Difluorophenyl)-2,7-dimethyl-2,4,5,7-tetrahydro-6H-pyrazolo[3,4-c]pyridin-6-yl)(2-fluoro-5-(2-fluoroethoxy)phenyl)methanone; |
| 143 | (S)-(3-(3,5-Difluorophenyl)-2,7-dimethyl-2,4,5,7-tetrahydro-6H-pyrazolo[3,4-c]pyridin-6-yl)(3-fluoro-5-(2-fluoroethoxy)phenyl)methanone; |
| 144 | (S)-(3-(3,5-Difluorophenyl)-2,7-dimethyl-2,4,5,7-tetrahydro-6H-pyrazolo[3,4-c]pyridin-6-yl)(4-fluoro-3-(2-fluoroethoxy)phenyl)methanone; |
| 145 | [2-Chloro-3-(2-fluoroethoxy)phenyl]-[(7S)-3-(3,5-difluorophenyl)-2,7-dimethyl-5,7-dihydro-4H-pyrazolo[3,4-c]pyridin-6-yl]methanone; |
| 146 | [(2-Chloro-5-(2-fluoroethoxy)phenyl)(3-(3,5-difluorophenyl)-2,7-dimethyl-2,4,5,7-tetrahydro-6H-pyrazolo[3,4-c]pyridin-6-yl)methanone; |
| 147 | (S)-(2-(2H-1,2,3-Triazol-2-yl)phenyl)(3-(3,5-difluorophenyl)-2,7-dimethyl-2,4,5,7-tetrahydro-6H-pyrazolo[3,4-c]pyridin-6-yl)methanone; |
| 148 | (3-(3,5-Difluorophenyl)-2,7-dimethyl-2,4,5,7-tetrahydro-6H-pyrazolo[3,4-c]pyridin-6-yl)(1-phenyl-1H-1,2,4-triazol-3-yl)methanone; |
| 149 | (S)-(3-(3,5-Difluorophenyl)-2,7-dimethyl-2,4,5,7-tetrahydro-6H-pyrazolo[3,4-c]pyridin-6-yl)(5-ethyl-1-phenyl-1H-1,2,4-triazol-3-yl)methanone; |
| 150 | (S)-(3-(3,5-Difluorophenyl)-2,7-dimethyl-2,4,5,7-tetrahydro-6H-pyrazolo[3,4-c]pyridin-6-yl)(1-(2-fluoroethyl)-1H-indol-4-yl)methanone; |
| 151 | [(7S)-3-(3,5-Difluorophenyl)-2,7-dimethyl-5,7-dihydro-4H-pyrazolo[3,4-c]pyridin-6-yl]-[1-(2-fluoranylethyl)indol-5-yl]methanone; |
| 152 | (S)-(3-(3,5-Difluorophenyl)-2,7-dimethyl-2,4,5,7-tetrahydro-6H-pyrazolo[3,4-c]pyridin-6-yl)(1-(2-fluoroethyl)-1H-pyrrolo[2,3-b]pyridin-4-yl)methanone; |
| 153 | (S)-(3-(3,5-Difluorophenyl)-2,7-dimethyl-2,4,5,7-tetrahydro-6H-pyrazolo[3,4-c]pyridin-6-yl)(furo[3,2-b]pyridin-6-yl)methanone; |
| 154 | (R)-(3-(3,5-Difluorophenyl)-2,7-dimethyl-2,4,5,7-tetrahydro-6H-pyrazolo[3,4-c]pyridin-6-yl)(furo[3,2-b]pyridin-6-yl)methanone; |
| 155 | (2-(Difluoromethyl)-3-(3,5-difluorophenyl)-7-methyl-2,4,5,7-tetrahydro-6H-pyrazolo[3,4-c]pyridin-6-yl)(quinolin-6-yl)methanone; |
| 156 | (3-(3,5-Difluorophenyl)-7-methyl-2-(trifluoromethyl)-2,4,5,7-tetrahydro-6H-pyrazolo[3,4-c]pyridin-6-yl)(quinolin-6-yl)methanone; |
| 157 | (3-(3,5-Difluorophenyl)-7-methyl-2-(methyl-d3)-2,4,5,7-tetrahydro-6H-pyrazolo[3,4-c]pyridin-6-yl)(quinolin-6-yl)methanone; |
| 158 | (R)-(3-(3,5-Difluorophenyl)-2,7-dimethyl-2,4,5,7-tetrahydro-6H-pyrazolo[3,4-c]pyridin-6-yl)(quinolin-6-yl)methanone; |
| 159 | (S)-(3-(3,5-Difluorophenyl)-2,7-dimethyl-2,4,5,7-tetrahydro-6H-pyrazolo[3,4-c]pyridin-6-yl)(quinolin-6-yl)methanone; |
| 160 | (3-(3,5-Difluorophenyl)-2,7-dimethyl-2,4,5,7-tetrahydro-6H-pyrazolo[3,4-c]pyridin-6-yl)(isoquinolin-3-yl)methanone; |
| 161 | (3-(3,5-Difluorophenyl)-2,7-dimethyl-2,4,5,7-tetrahydro-6H-pyrazolo[3,4-c]pyridin-6-yl)(isoquinolin-7-yl)methanone; |
| 162 | (4-Bromoquinolin-6-yl)(3-(3,5-difluorophenyl)-2,7-dimethyl-2,4,5,7-tetrahydro-6H-pyrazolo[3,4-c]pyridin-6-yl)methanone; |
| 163 | (5-Chloroquinolin-6-yl)(3-(3,5-difluorophenyl)-2,7-dimethyl-2,4,5,7-tetrahydro-6H-pyrazolo[3,4-c]pyridin-6-yl)methanone; |

TABLE 2-continued

| Example # | Compound Name |
|---|---|
| 164 | (S)-(3-(3,5-Difluorophenyl)-2,7-dimethyl-2,4,5,7-tetrahydro-6H-pyrazolo[3,4-c]pyridin-6-yl)(8-(trifluoromethyl)quinolin-6-yl)methanone; |
| 165 | (S)-(3-(3,5-Difluorophenyl)-2,7-dimethyl-2,4,5,7-tetrahydro-6H-pyrazolo[3,4-c]pyridin-6-yl)(3-(trifluoromethyl)quinolin-6-yl)methanone; |
| 166 | (S)-(3-(3,5-Difluorophenyl)-2,7-dimethyl-2,4,5,7-tetrahydro-6H-pyrazolo[3,4-c]pyridin-6-yl)(3-(2-fluoroethoxy)quinolin-6-yl)methanone; |
| 167 | (3-(3,5-Difluorophenyl)-2,7-dimethyl-2,4,5,7-tetrahydro-6H-pyrazolo[3,4-c]pyridin-6-yl)(quinoxalin-6-yl)methanone; |
| 168 | (S)-(3-(3,5-Difluorophenyl)-2,7-dimethyl-2,4,5,7-tetrahydro-6H-pyrazolo[3,4-c]pyridin-6-yl)(quinoxalin-6-yl)methanone; |
| 169 | (R)-(3-(3,5-Difluorophenyl)-2,7-dimethyl-2,4,5,7-tetrahydro-6H-pyrazolo[3,4-c]pyridin-6-yl)(quinoxalin-6-yl)methanone; |
| 170 | (S)-(3-(3,5-Difluorophenyl)-2,7-dimethyl-2,4,5,7-tetrahydro-6H-pyrazolo[3,4-c]pyridin-6-yl)(1,5-naphthyridin-2-yl)methanone; |
| 171 | (S)-(3-(3,5-Difluorophenyl)-2,7-dimethyl-2,4,5,7-tetrahydro-6H-pyrazolo[3,4-c]pyridin-6-yl)(7-fluoroquinoxalin-6-yl)methanone; |
| 172 | (S)-(3-(3,5-Dichlorophenyl)-2,7-dimethyl-2,4,5,7-tetrahydro-6H-pyrazolo[3,4-c]pyridin-6-yl)(2-methylbenzo[d]oxazol-6-yl)methanone; |
| 173 | (S)-(3-(3,5-Dichlorophenyl)-2,7-dimethyl-2,4,5,7-tetrahydro-6H-pyrazolo[3,4-c]pyridin-6-yl)(1-methyl-1H-pyrazolo[3,4-b]pyridin-3-yl)methanone; |
| 174 | (S)-(3-(3,5-Dichlorophenyl)-2,7-dimethyl-2,4,5,7-tetrahydro-6H-pyrazolo[3,4-c]pyridin-6-yl)(quinolin-6-yl)methanone; |
| 175 | (S)-(3-(3,5-Dichlorophenyl)-2,7-dimethyl-2,4,5,7-tetrahydro-6H-pyrazolo[3,4-c]pyridin-6-yl)(quinoxalin-6-yl)methanone; |
| 176 | (S)-(3-(3,5-Dichlorophenyl)-2,7-dimethyl-2,4,5,7-tetrahydro-6H-pyrazolo[3,4-c]pyridin-6-yl)(2-methylquinoxalin-6-yl)methanone; |
| 177 | (3-(3-Chloro-5-fluorophenyl)-2,7-dimethyl-2,4,5,7-tetrahydro-6H-pyrazolo[3,4-c]pyridin-6-yl)(quinolin-6-yl)methanone; |
| 178 | (S)-(3-(3-Chloro-5-fluorophenyl)-2,7-dimethyl-2,4,5,7-tetrahydro-6H-pyrazolo[3,4-c]pyridin-6-yl)(quinolin-6-yl)methanone; |
| 179 | (R)-(3-(3-Chloro-5-fluorophenyl)-2,7-dimethyl-2,4,5,7-tetrahydro-6H-pyrazolo[3,4-c]pyridin-6-yl)(quinolin-6-yl)methanone; |
| 180 | (3-(3-Chloro-5-fluorophenyl)-2,7-dimethyl-2,4,5,7-tetrahydro-6H-pyrazolo[3,4-c]pyridin-6-yl)(quinoxalin-6-yl)methanone; |
| 181 | (S)-(3-(3-Chloro-5-fluorophenyl)-2,7-dimethyl-2,4,5,7-tetrahydro-6H-pyrazolo[3,4-c]pyridin-6-yl)(quinoxalin-6-yl)methanone; |
| 182 | (R)-(3-(3-Chloro-5-fluorophenyl)-2,7-dimethyl-2,4,5,7-tetrahydro-6H-pyrazolo[3,4-c]pyridin-6-yl)(quinoxalin-6-yl)methanone; |
| 183 | (S)-(3-(3-Chloro-4-methylphenyl)-2,7-dimethyl-2,4,5,7-tetrahydro-6H-pyrazolo[3,4-c]pyridin-6-yl)(quinoxalin-6-yl)methanone; |
| 184 | (S)-(3-(3-Fluoro-5-(trifluoromethyl)phenyl)-2,7-dimethyl-2,4,5,7-tetrahydro-6H-pyrazolo[3,4-c]pyridin-6-yl)(quinoxalin-6-yl)methanone; |
| 185 | (S)-(3-(3-Fluoro-4-methoxyphenyl)-2,7-dimethyl-2,4,5,7-tetrahydro-6H-pyrazolo[3,4-c]pyridin-6-yl)(quinoxalin-6-yl)methanone; |
| 186 | (S)-(3-(3-Fluoro-5-methoxyphenyl)-2,7-dimethyl-2,4,5,7-tetrahydro-6H-pyrazolo[3,4-c]pyridin-6-yl)(quinoxalin-6-yl)methanone; |
| 187 | (S)-(3-(3-Fluoro-5-methoxyphenyl)-2,7-dimethyl-2,4,5,7-tetrahydro-6H-pyrazolo[3,4-c]pyridin-6-yl)(7-fluoroquinoxalin-6-yl)methanone; |
| 188 | (S)-(3-(3-Chloro-4-methoxyphenyl)-2,7-dimethyl-2,4,5,7-tetrahydro-6H-pyrazolo[3,4-c]pyridin-6-yl)(quinoxalin-6-yl)methanone; |
| 189 | (S)-(3-(4-(Difluoromethoxy)-3-fluorophenyl)-2,7-dimethyl-2,4,5,7-tetrahydro-6H-pyrazolo[3,4-c]pyridin-6-yl)(quinoxalin-6-yl)methanone; |
| 190 | (S)-(3-(3,5-Difluoro-4-methylphenyl)-2,7-dimethyl-2,4,5,7-tetrahydro-6H-pyrazolo[3,4-c]pyridin-6-yl)(quinoxalin-6-yl)methanone; |
| 191 | (S)-(2-Chloro-3-methoxyphenyl)(2,7-dimethyl-3-(3,4,5-trifluorophenyl)-2,4,5,7-tetrahydro-6H-pyrazolo[3,4-c]pyridin-6-yl)methanone; |
| 192 | (S)-(3-Chloro-5-methoxyphenyl)(2,7-dimethyl-3-(3,4,5-trifluorophenyl)-2,4,5,7-tetrahydro-6H-pyrazolo[3,4-c]pyridin-6-yl)methanone; |
| 193 | (S)-(2,7-Dimethyl-3-(3,4,5-trifluorophenyl)-2,4,5,7-tetrahydro-6H-pyrazolo[3,4-c]pyridin-6-yl)(5-fluoro-2-(1H-pyrazol-1-yl)phenyl)methanone; |
| 194 | (S)-(3-(1H-1,2,4-Triazol-1-yl)phenyl)(2,7-dimethyl-3-(3,4,5-trifluorophenyl)-2,4,5,7-tetrahydro-6H-pyrazolo[3,4-c]pyridin-6-yl)methanone; |
| 195 | (S)-(2,7-Dimethyl-3-(3,4,5-trifluorophenyl)-2,4,5,7-tetrahydro-6H-pyrazolo[3,4-c]pyridin-6-yl)(3-fluoro-2-(2H-1,2,3-triazol-2-yl)phenyl)methanone; |
| 196 | (S)-(2,7-Dimethyl-3-(3,4,5-trifluorophenyl)-2,4,5,7-tetrahydro-6H-pyrazolo[3,4-c]pyridin-6-yl)(4-fluoro-2-(2H-1,2,3-triazol-2-yl)phenyl)methanone; |
| 197 | (S)-(2,7-Dimethyl-3-(3,4,5-trifluorophenyl)-2,4,5,7-tetrahydro-6H-pyrazolo[3,4-c]pyridin-6-yl)(5-methyl-2-(2H-1,2,3-triazol-2-yl)phenyl)methanone; |
| 198 | (S)-(2,7-Dimethyl-3-(3,4,5-trifluorophenyl)-2,4,5,7-tetrahydro-6H-pyrazolo[3,4-c]pyridin-6-yl)(1-methyl-5-(trifluoromethyl)-1H-pyrazol-4-yl)methanone; |
| 199 | (S)-(1-(tert-Butyl)-5-(trifluoromethyl)-1H-pyrazol-4-yl)(2,7-dimethyl-3-(3,4,5-trifluorophenyl)-2,4,5,7-tetrahydro-6H-pyrazolo[3,4-c]pyridin-6-yl)methanone; |
| 200 | (S)-(2,7-Dimethyl-3-(3,4,5-trifluorophenyl)-2,4,5,7-tetrahydro-6H-pyrazolo[3,4-c]pyridin-6-yl)(5-methoxy-1-methyl-1H-pyrazol-3-yl)methanone; |
| 201 | (S)-(5-Cyclopropyl-1-methyl-1H-pyrazol-4-yl)(2,7-dimethyl-3-(3,4,5-trifluorophenyl)-2,4,5,7-tetrahydro-6H-pyrazolo[3,4-c]pyridin-6-yl)methanone; |
| 202 | (S)-(2,7-Dimethyl-3-(3,4,5-trifluorophenyl)-2,4,5,7-tetrahydro-6H-pyrazolo[3,4-c]pyridin-6-yl)(5-ethyl-1-phenyl-1H-1,2,4-triazol-3-yl)methanone; |

TABLE 2-continued

| Example # | Compound Name |
|---|---|
| 203 | (S)-(2,7-Dimethyl-3-(3,4,5-trifluorophenyl)-2,4,5,7-tetrahydro-6H-pyrazolo[3,4-c]pyridin-6-yl)(5-methoxypyridin-3-yl)methanone; |
| 204 | (S)-6-(2,7-Dimethyl-3-(3,4,5-trifluorophenyl)-4,5,6,7-tetrahydro-2H-pyrazolo[3,4-c]pyridine-6-carbonyl)-4-methyl-2H-benzo[b][1,4]oxazin-3(4H)-one; |
| 205 | (S)-(2,7-Dimethyl-3-(3,4,5-trifluorophenyl)-2,4,5,7-tetrahydro-6H-pyrazolo[3,4-c]pyridin-6-yl)(1H-indol-7-yl)methanone; |
| 206 | (S)-(2,7-Dimethyl-3-(3,4,5-trifluorophenyl)-2,4,5,7-tetrahydro-6H-pyrazolo[3,4-c]pyridin-6-yl)(1-methyl-1H-indol-7-yl)methanone; |
| 207 | (S)-(2,7-Dimethyl-3-(3,4,5-trifluorophenyl)-2,4,5,7-tetrahydro-6H-pyrazolo[3,4-c]pyridin-6-yl)(1-methyl-1H-indol-4-yl)methanone; |
| 208 | (S)-(2,7-Dimethyl-3-(3,4,5-trifluorophenyl)-2,4,5,7-tetrahydro-6H-pyrazolo[3,4-c]pyridin-6-yl)(1H-indazol-7-yl)methanone; |
| 209 | (S)-(2,7-Dimethyl-3-(3,4,5-trifluorophenyl)-2,4,5,7-tetrahydro-6H-pyrazolo[3,4-c]pyridin-6-yl)(1-methyl-1H-indazol-7-yl)methanone; |
| 210 | (S)-(2,7-Dimethyl-3-(3,4,5-trifluorophenyl)-2,4,5,7-tetrahydro-6H-pyrazolo[3,4-c]pyridin-6-yl)(7-methyl-1H-indazol-5-yl)methanone; |
| 211 | (S)-(2,7-Dimethyl-3-(3,4,5-trifluorophenyl)-2,4,5,7-tetrahydro-6H-pyrazolo[3,4-c]pyridin-6-yl)(1-methyl-1H-indazol-5-yl)methanone; |
| 212 | (S)-(2,7-Dimethyl-3-(3,4,5-trifluorophenyl)-2,4,5,7-tetrahydro-6H-pyrazolo[3,4-c]pyridin-6-yl)(imidazo[1,5-a]pyridin-8-yl)methanone; |
| 213 | (S)-(2,7-Dimethyl-3-(3,4,5-trifluorophenyl)-2,4,5,7-tetrahydro-6H-pyrazolo[3,4-c]pyridin-6-yl)(imidazo[1,2-a]pyridin-3-yl)methanone; |
| 214 | (S)-(2,7-Dimethyl-3-(3,4,5-trifluorophenyl)-2,4,5,7-tetrahydro-6H-pyrazolo[3,4-c]pyridin-6-yl)(furo[3,2-c]pyridin-4-yl)methanone; |
| 215 | (S)-Benzo[d]isoxazol-3-yl(2,7-dimethyl-3-(3,4,5-trifluorophenyl)-2,4,5,7-tetrahydro-6H-pyrazolo[3,4-c]pyridin-6-yl)methanone; |
| 216 | (S)-(2,7-Dimethyl-3-(3,4,5-trifluorophenyl)-2,4,5,7-tetrahydro-6H-pyrazolo[3,4-c]pyridin-6-yl)(1H-pyrrolo[3,2-c]pyridin-4-yl)methanone; |
| 217 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[3,2-c]pyridin-4-yl)methanone; |
| 218 | (S)-(2,7-Dimethyl-3-(3,4,5-trifluorophenyl)-2,4,5,7-tetrahydro-6H-pyrazolo[3,4-c]pyridin-6-yl)(1H-pyrrolo[3,2-c]pyridin-3-yl)methanone; |
| 219 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[3,2-c]pyridin-3-yl)methanone; |
| 220 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[3,2-b]pyridin-3-yl)methanone; |
| 221 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-c]pyridin-3-yl)methanone; |
| 222 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-2-yl)methanone; |
| 223 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-3-yl)methanone; |
| 224 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-c]pyridin-4-yl)methanone; |
| 225 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-4-yl)methanone; |
| 226 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-5-yl)methanone; |
| 227 | (S)-(2,7-Dimethyl-3-(3,4,5-trifluorophenyl)-2,4,5,7-tetrahydro-6H-pyrazolo[3,4-c]pyridin-6-yl)(pyrazolo[1,5-a]pyridin-4-yl)methanone; |
| 228 | (S)-(2,7-Dimethyl-3-(3,4,5-trifluorophenyl)-2,4,5,7-tetrahydro-6H-pyrazolo[3,4-c]pyridin-6-yl)(pyrazolo[1,5-a]pyridin-5-yl)methanone; |
| 229 | (S)-(2,7-Dimethyl-3-(3,4,5-trifluorophenyl)-2,4,5,7-tetrahydro-6H-pyrazolo[3,4-c]pyridin-6-yl)(pyrazolo[1,5-a]pyrazin-3-yl)methanone; |
| 230 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrazolo[3,4-b]pyridin-3-yl)methanone; |
| 231 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrazolo[3,4-b]pyridin-5-yl)methanone; |
| 232 | (S)-(2-(Difluoromethyl)-7-methyl-3-(3,4,5-trifluorophenyl)-2,4,5,7-tetrahydro-6H-pyrazolo[3,4-c]pyridin-6-yl)(quinolin-6-yl)methanone; |
| 233 | (R)-(2-(Difluoromethyl)-7-methyl-3-(3,4,5-trifluorophenyl)-2,4,5,7-tetrahydro-6H-pyrazolo[3,4-c]pyridin-6-yl)(quinolin-6-yl)methanone; |
| 234 | (S)-(2,7-Dimethyl-3-(3,4,5-trifluorophenyl)-2,4,5,7-tetrahydro-6H-pyrazolo[3,4-c]pyridin-6-yl)(quinolin-6-yl)methanone; |
| 235 | (R)-(2,7-Dimethyl-3-(3,4,5-trifluorophenyl)-2,4,5,7-tetrahydro-6H-pyrazolo[3,4-c]pyridin-6-yl)(quinolin-6-yl)methanone; |
| 236 | (S)-(2,7-Dimethyl-3-(3,4,5-trifluorophenyl)-2,4,5,7-tetrahydro-6H-pyrazolo[3,4-c]pyridin-6-yl)(quinolin-8-yl)methanone; |
| 237 | (S)-(2,7-Dimethyl-3-(3,4,5-trifluorophenyl)-2,4,5,7-tetrahydro-6H-pyrazolo[3,4-c]pyridin-6-yl)(isoquinolin-1-yl)methanone; |
| 238 | (S)-(2,7-Dimethyl-3-(3,4,5-trifluorophenyl)-2,4,5,7-tetrahydro-6H-pyrazolo[3,4-c]pyridin-6-yl)(8-fluoroquinolin-4-yl)methanone; |
| 239 | (S)-(2,7-Dimethyl-3-(3,4,5-trifluorophenyl)-2,4,5,7-tetrahydro-6H-pyrazolo[3,4-c]pyridin-6-yl)(2-methylquinolin-4-yl)methanone; |
| 240 | (S)-(2,7-Dimethyl-3-(3,4,5-trifluorophenyl)-2,4,5,7-tetrahydro-6H-pyrazolo[3,4-c]pyridin-6-yl)(2-methoxyquinolin-4-yl)methanone; |

TABLE 2-continued

| Example # | Compound Name |
|---|---|
| 241 | (S)-(2,7-Dimethyl-3-(3,4,5-trifluorophenyl)-2,4,5,7-tetrahydro-6H-pyrazolo[3,4-c]pyridin-6-yl)(8-fluoro-2-methylquinolin-4-yl)methanone; |
| 242 | (S)-(2,7-Dimethyl-3-(3,4,5-trifluorophenyl)-2,4,5,7-tetrahydro-6H-pyrazolo[3,4-c]pyridin-6-yl)(quinoxalin-6-yl)methanone; |
| 243 | (S)-(2,7-Dimethyl-3-(3,4,5-trifluorophenyl)-2,4,5,7-tetrahydro-6H-pyrazolo[3,4-c]pyridin-6-yl)(2-methylquinoxalin-6-yl)methanone; |
| 244 | (S)-(2,7-Dimethyl-3-(3,4,5-trifluorophenyl)-2,4,5,7-tetrahydro-6H-pyrazolo[3,4-c]pyridin-6-yl)(1,5-naphthyridin-2-yl)methanone; |
| 245 | (S)-(2,7-Dimethyl-3-(3,4,5-trifluorophenyl)-2,4,5,7-tetrahydro-6H-pyrazolo[3,4-c]pyridin-6-yl)(1,5-naphthyridin-3-yl)methanone; |
| 246 | (S)-(2,7-Dimethyl-3-(3,4,5-trifluorophenyl)-2,4,5,7-tetrahydro-6H-pyrazolo[3,4-c]pyridin-6-yl)(1,6-naphthyridin-8-yl)methanone; |
| 247 | (S)-(2,7-Dimethyl-3-(5-(trifluoromethyl)furan-2-yl)-2,4,5,7-tetrahydro-6H-pyrazolo[3,4-c]pyridin-6-yl)(quinoxalin-6-yl)methanone; |
| 248 | (S)-(2,7-Dimethyl-3-(5-(trifluoromethyl)pyridin-3-yl)-2,4,5,7-tetrahydro-6H-pyrazolo[3,4-c]pyridin-6-yl)(quinoxalin-6-yl)methanone; |
| 249 | (2,7-Dimethyl-3-(1-methyl-1H-indol-4-yl)-2,4,5,7-tetrahydro-6H-pyrazolo[3,4-c]pyridin-6-yl)(quinolin-6-yl)methanone; |
| 250 | (2,7-Dimethyl-3-(1-methyl-1H-indol-2-yl)-2,4,5,7-tetrahydro-6H-pyrazolo[3,4-c]pyridin-6-yl)(quinolin-6-yl)methanone; |
| 251 | (2,7-Dimethyl-3-(1-methyl-1H-indol-3-yl)-2,4,5,7-tetrahydro-6H-pyrazolo[3,4-c]pyridin-6-yl)(quinolin-6-yl)methanone; |
| 252 | (2,7-Dimethyl-3-(1-methyl-1H-indol-5-yl)-2,4,5,7-tetrahydro-6H-pyrazolo[3,4-c]pyridin-6-yl)(quinolin-6-yl)methanone;and |
| 253 | (2,7-Dimethyl-3-(1-methyl-1H-indol-7-yl)-2,4,5,7-tetrahydro-6H-pyrazolo[3,4-c]pyridin-6-yl)(quinolin-6-yl)methanone; |
| 254 | (S)-(3-(3,5-Difluorophenyl)-2,7-dimethyl-5,7-dihydro-4H-pyrazolo[3,4-c]pyridin-6-yl]-[3-(2-fluoranylethoxy)-2-fluoro-phenyl]methanone; |
| 255 | [2-Chloro-3-(2-fluoranylethoxy)phenyl]-[(7S)-3-(3,5-difluorophenyl)-2,7-dimethyl-5,7-dihydro-4H-pyrazolo[3,4-c]pyridin-6-yl]methanone; |
| 256 | (S)-[3-(3,5-Difluorophenyl)-2,7-dimethyl-5,7-dihydro-4H-pyrazolo[3,4-c]pyridin-6-yl]-[3-(2-fluoranylethoxy)-5-fluoro-phenyl]methanone; |
| 257 | (3-Methoxyphenyl)-[(7S)-7-methyl-2,3-diphenyl-5,7-dihydro-4H-pyrazolo[3,4-c]pyridin-6-yl]methanone; |
| 258 | [(7S)-3-(3-Fluoro-5-methyl-phenyl)-2,7-dimethyl-5,7-dihydro-4H-pyrazolo[3,4-c]pyridin-6-yl]-(4-methoxyphenyl)methanone; |
| 259 | [(7S)-2,7-Dimethyl-3-(3,4,5-trifluorophenyl)-5,7-dihydro-4H-pyrazolo[3,4-c]pyridin-6-yl]-(2-methoxyphenyl)methanone; |
| 260 | [(7S)-2,7-Dimethyl-3-(3,4,5-trifluorophenyl)-5,7-dihydro-4H-pyrazolo[3,4-c]pyridin-6-yl]-(3-methoxyphenyl)methanone; |
| 261 | [(7S)-2,7-Dimethyl-3-(3,4,5-trifluorophenyl)-5,7-dihydro-4H-pyrazolo[3,4-c]pyridin-6-yl]-(4-methoxyphenyl)methanone; |
| 262 | [(7S)-2,7-Dimethyl-3-(3,4,5-trifluorophenyl)-5,7-dihydro-4H-pyrazolo[3,4-c]pyridin-6-yl]-[3-(trifluoromethoxy)phenyl]methanone; |
| 263 | [(7S)-2,7-Dimethyl-3-(3,4,5-trifluorophenyl)-5,7-dihydro-4H-pyrazolo[3,4-c]pyridin-6-yl]-[2-(trifluoromethoxy)phenyl]methanone; |
| 264 | [4-(Difluoromethoxy)phenyl]-[(7S)-2,7-dimethyl-3-(3,4,5-trifluorophenyl)-5,7-dihydro-4H-pyrazolo[3,4-c]pyridin-6-yl]methanone; |
| 265 | [(7S)-2,7-Dimethyl-3-(3,4,5-trifluorophenyl)-5,7-dihydro-4H-pyrazolo[3,4-c]pyridin-6-yl]-(2-fluoro-4-methoxy-phenyl)methanone; |
| 266 | 3-[(7S)-2,7-Dimethyl-3-(3,4,5-trifluorophenyl)-5,7-dihydro-4H-pyrazolo[3,4-c]pyridine-6-carbonyl]-N-methyl-benzamide; |
| 267 | [(7S)-2,7-Dimethyl-3-(3,4,5-trifluorophenyl)-5,7-dihydro-4H-pyrazolo[3,4-c]pyridin-6-yl]-(4-imidazol-1-ylphenyl)methanone; |
| 268 | [(7S)-2,7-Dimethyl-3-(3,4,5-trifluorophenyl)-5,7-dihydro-4H-pyrazolo[3,4-c]pyridin-6-yl]-[4-(1H-pyrazol-4-yl)phenyl]methanone; |
| 269 | [(7S)-2,7-Dimethyl-3-(3,4,5-trifluorophenyl)-5,7-dihydro-4H-pyrazolo[3,4-c]pyridin-6-yl]-[4-(1H-pyrazol-5-yl)phenyl]methanone; |
| 270 | [(7S)-2,7-Dimethyl-3-(3,4,5-trifluorophenyl)-5,7-dihydro-4H-pyrazolo[3,4-c]pyridin-6-yl]-[3-(1H-pyrazol-3-yl)phenyl]methanone; |
| 271 | [(7S)-2,7-Dimethyl-3-(3,4,5-trifluorophenyl)-5,7-dihydro-4H-pyrazolo[3,4-c]pyridin-6-yl]-[4-methoxy-3-(1-methylpyrazol-3-yl)phenyl]methanone; |
| 272 | [(7S)-2,7-Dimethyl-3-(3,4,5-trifluorophenyl)-5,7-dihydro-4H-pyrazolo[3,4-c]pyridin-6-yl]-[3-(1H-pyrazol-4-yl)phenyl]methanone; |
| 273 | [(7S)-2,7-Dimethyl-3-(3,4,5-trifluorophenyl)-5,7-dihydro-4H-pyrazolo[3,4-c]pyridin-6-yl]-[3-(1-methylpyrazol-4-yl)phenyl]methanone; |
| 274 | [(7S)-2,7-Dimethyl-3-(3,4,5-trifluorophenyl)-5,7-dihydro-4H-pyrazolo[3,4-c]pyridin-6-yl]-[2-fluoro-5-(1-methylpyrazol-4-yl)phenyl]methanone; |
| 275 | [(7S)-2,7-Dimethyl-3-(3,4,5-trifluorophenyl)-5,7-dihydro-4H-pyrazolo[3,4-c]pyridin-6-yl]-[3-(4-fluoropyrazol-1-yl)phenyl]methanone; |
| 276 | [(7S)-2,7-Dimethyl-3-(3,4,5-trifluorophenyl)-5,7-dihydro-4H-pyrazolo[3,4-c]pyridin-6-yl]-[3-(3-methyl-1,2,4-triazol-1-yl)phenyl]methanone; |
| 277 | [(7S)-2,7-Dimethyl-3-(3,4,5-trifluorophenyl)-5,7-dihydro-4H-pyrazolo[3,4-c]pyridin-6-yl]-[3-fluoro-5-(1,2,4-triazol-1-yl)phenyl]methanone; |
| 278 | [(7S)-2,7-Dimethyl-3-(3,4,5-trifluorophenyl)-5,7-dihydro-4H-pyrazolo[3,4-c]pyridin-6-yl]-[3-methoxy-5-(1,2,4-triazol-1-yl)phenyl]methanone; |
| 279 | [(7S)-2,7-Dimethyl-3-(3,4,5-trifluorophenyl)-5,7-dihydro-4H-pyrazolo[3,4-c]pyridin-6-yl]-[2-(1,2,4-triazol-1-yl)phenyl]methanone; |

TABLE 2-continued

| Example # | Compound Name |
|---|---|
| 280 | [(7S)-2,7-Dimethyl-3-(3,4,5-trifluorophenyl)-5,7-dihydro-4H-pyrazolo[3,4-c]pyridin-6-yl]-[2-fluoro-6-(1,2,4-triazol-1-yl)phenyl]methanone; |
| 281 | [(7S)-2,7-Dimethyl-3-(3,4,5-trifluorophenyl)-5,7-dihydro-4H-pyrazolo[3,4-c]pyridin-6-yl]-[5-fluoro-2-(1,2,4-triazol-1-yl)phenyl]methanone; |
| 282 | [(7S)-2,7-Dimethyl-3-(3,4,5-trifluorophenyl)-5,7-dihydro-4H-pyrazolo[3,4-c]pyridin-6-yl]-[2-[3-(trifluoromethyl)-1,2,4-triazol-1-yl]phenyl]methanone; |
| 283 | [(7S)-2,7-Dimethyl-3-(3,4,5-trifluorophenyl)-5,7-dihydro-4H-pyrazolo[3,4-c]pyridin-6-yl]-[3-(triazol-2-yl)phenyl]methanone; |
| 284 | [(7S)-2,7-Dimethyl-3-(3,4,5-trifluorophenyl)-5,7-dihydro-4H-pyrazolo[3,4-c]pyridin-6-yl]-[3-fluoro-5-(triazol-2-yl)phenyl]methanone; |
| 285 | [(7S)-2,7-Dimethyl-3-(3,4,5-trifluorophenyl)-5,7-dihydro-4H-pyrazolo[3,4-c]pyridin-6-yl]-[2-fluoro-5-(triazol-2-yl)phenyl]methanone; |
| 286 | [(7S)-2,7-Dimethyl-3-(3,4,5-trifluorophenyl)-5,7-dihydro-4H-pyrazolo[3,4-c]pyridin-6-yl]-[3-methyl-5-(triazol-2-yl)phenyl]methanone; |
| 287 | [(7S)-2,7-Dimethyl-3-(3,4,5-trifluorophenyl)-5,7-dihydro-4H-pyrazolo[3,4-c]pyridin-6-yl]-[3-(triazol-2-yl)-5-(trifluoromethyl)phenyl]methanone; |
| 288 | [(7S)-2,7-Dimethyl-3-(3,4,5-trifluorophenyl)-5,7-dihydro-4H-pyrazolo[3,4-c]pyridin-6-yl]-[2-fluoro-6-(triazol-2-yl)phenyl]methanone; |
| 289 | [(7S)-2,7-Dimethyl-3-(3,4,5-trifluorophenyl)-5,7-dihydro-4H-pyrazolo[3,4-c]pyridin-6-yl]-[5-methoxy-2-(triazol-2-yl)phenyl]methanone; |
| 290 | [(7S)-2,7-Dimethyl-3-(3,4,5-trifluorophenyl)-5,7-dihydro-4H-pyrazolo[3,4-c]pyridin-6-yl]-[3-(1,2,4-triazol-4-yl)phenyl]methanone; |
| 291 | [(7S)-2,7-Dimethyl-3-(3,4,5-trifluorophenyl)-5,7-dihydro-4H-pyrazolo[3,4-c]pyridin-6-yl]-[4-fluoro-3-(1,2,4-triazol-4-yl)phenyl]methanone; |
| 292 | [(7S)-2,7-Dimethyl-3-(3,4,5-trifluorophenyl)-5,7-dihydro-4H-pyrazolo[3,4-c]pyridin-6-yl]-[3-fluoro-5-(1,2,4-triazol-4-yl)phenyl]methanone; |
| 293 | [(7S)-2,7-Dimethyl-3-(3,4,5-trifluorophenyl)-5,7-dihydro-4H-pyrazolo[3,4-c]pyridin-6-yl]-[3-methyl-5-(1,2,4-triazol-4-yl)phenyl]methanone; |
| 294 | [(7S)-2,7-Dimethyl-3-(3,4,5-trifluorophenyl)-5,7-dihydro-4H-pyrazolo[3,4-c]pyridin-6-yl]-[4-methyl-3-(1,2,4-triazol-4-yl)phenyl]methanone; |
| 295 | [(7S)-2,7-Dimethyl-3-(3,4,5-trifluorophenyl)-5,7-dihydro-4H-pyrazolo[3,4-c]pyridin-6-yl]-[3-(1,2,4-triazol-4-yl)-4-(trifluoromethyl)phenyl]methanone; |
| 296 | [(7S)-2,7-Dimethyl-3-(3,4,5-trifluorophenyl)-5,7-dihydro-4H-pyrazolo[3,4-c]pyridin-6-yl]-[3-(1,2,4-triazol-4-yl)-5-(trifluoromethyl)phenyl]methanone; |
| 297 | [(7S)-2,7-Dimethyl-3-(3,4,5-trifluorophenyl)-5,7-dihydro-4H-pyrazolo[3,4-c]pyridin-6-yl]-[4-methoxy-3-(1,2,4-triazol-4-yl)phenyl]methanone; |
| 298 | [(7S)-2,7-Dimethyl-3-(3,4,5-trifluorophenyl)-5,7-dihydro-4H-pyrazolo[3,4-c]pyridin-6-yl]-[3-methoxy-5-(1,2,4-triazol-4-yl)phenyl]methanone; |
| 299 | [(7S)-2,7-Dimethyl-3-(3,4,5-trifluorophenyl)-5,7-dihydro-4H-pyrazolo[3,4-c]pyridin-6-yl]-[2-(1,2,4-triazol-4-yl)phenyl]methanone; |
| 300 | [(7S)-2,7-Dimethyl-3-(3,4,5-trifluorophenyl)-5,7-dihydro-4H-pyrazolo[3,4-c]pyridin-6-yl]-(6-methoxy-3-pyridyl)methanone; |
| 301 | [(7S)-2,7-Dimethyl-3-(3,4,5-trifluorophenyl)-5,7-dihydro-4H-pyrazolo[3,4-c]pyridin-6-yl]-(5-methoxy-2-pyridyl)methanone; |
| 302 | [(7S)-2,7-Dimethyl-3-(3,4,5-trifluorophenyl)-5,7-dihydro-4H-pyrazolo[3,4-c]pyridin-6-yl]-(6-methoxy-3-methyl-2-pyridyl)methanone; |
| 303 | [(7S)-2,7-Dimethyl-3-(3,4,5-trifluorophenyl)-5,7-dihydro-4H-pyrazolo[3,4-c]pyridin-6-yl]-(3-methoxy-2-pyridyl)methanone; |
| 304 | [(7S)-2,7-Dimethyl-3-(3,4,5-trifluorophenyl)-5,7-dihydro-4H-pyrazolo[3,4-c]pyridin-6-yl]-[5-(methoxymethyl)-3-pyridyl]methanone; |
| 305 | [(7S)-2,7-Dimethyl-3-(3,4,5-trifluorophenyl)-5,7-dihydro-4H-pyrazolo[3,4-c]pyridin-6-yl]-(5-isopropoxy-3-pyridyl)methanone; |
| 306 | [(7S)-2,7-Dimethyl-3-(3,4,5-trifluorophenyl)-5,7-dihydro-4H-pyrazolo[3,4-c]pyridin-6-yl]-(6-methoxy-2-methyl-3-pyridyl)methanone; |
| 307 | [(7S)-2,7-Dimethyl-3-(3,4,5-trifluorophenyl)-5,7-dihydro-4H-pyrazolo[3,4-c]pyridin-6-yl]-(4-methoxy-3-methyl-2-pyridyl)methanone; |
| 308 | [(7S)-2,7-Dimethyl-3-(3,4,5-trifluorophenyl)-5,7-dihydro-4H-pyrazolo[3,4-c]pyridin-6-yl]-(5-methoxy-2-methyl-3-pyridyl)methanone; |
| 309 | [(7S)-2,7-Dimethyl-3-(3,4,5-trifluorophenyl)-5,7-dihydro-4H-pyrazolo[3,4-c]pyridin-6-yl]-(4-methoxy-2-pyridyl)methanone; |
| 310 | [(7S)-2,7-Dimethyl-3-(3,4,5-trifluorophenyl)-5,7-dihydro-4H-pyrazolo[3,4-c]pyridin-6-yl]-(5-methoxy-6-methyl-3-pyridyl)methanone; |
| 311 | [(7S)-2,7-Dimethyl-3-(3,4,5-trifluorophenyl)-5,7-dihydro-4H-pyrazolo[3,4-c]pyridin-6-yl]-(3-methoxy-4-pyridyl)methanone; |
| 312 | [(7S)-2,7-Dimethyl-3-(3,4,5-trifluorophenyl)-5,7-dihydro-4H-pyrazolo[3,4-c]pyridin-6-yl]-(2-methoxy-4-pyridyl)methanone; |
| 313 | [(7S)-2,7-Dimethyl-3-(3,4,5-trifluorophenyl)-5,7-dihydro-4H-pyrazolo[3,4-c]pyridin-6-yl]-(5-methoxy-4-methyl-3-pyridyl)methanone; |
| 314 | [(7S)-2,7-Dimethyl-3-(3,4,5-trifluorophenyl)-5,7-dihydro-4H-pyrazolo[3,4-c]pyridin-6-yl]-(2-methoxy-3-methyl-4-pyridyl)methanone; |
| 315 | [(7S)-2,7-Dimethyl-3-(3,4,5-trifluorophenyl)-5,7-dihydro-4H-pyrazolo[3,4-c]pyridin-6-yl]-(3-fluoro-2-methoxy-4-pyridyl)methanone; |
| 316 | (3-Chloro-2-methoxy-4-pyridyl)-[(7S)-2,7-dimethyl-3-(3,4,5-trifluorophenyl)-5,7-dihydro-4H-pyrazolo[3,4-c]pyridin-6-yl]methanone; |
| 317 | (3-Chloro-4-methoxy-2-pyridyl)-[(7S)-2,7-dimethyl-3-(3,4,5-trifluorophenyl)-5,7-dihydro-4H-pyrazolo[3,4-c]pyridin-6-yl]methanone; |
| 318 | [(7S)-2,7-Dimethyl-3-(3,4,5-trifluorophenyl)-5,7-dihydro-4H-pyrazolo[3,4-c]pyridin-6-yl]-(5-pyrazol-1-yl-3-pyridyl)methanone; |

TABLE 2-continued

| Example # | Compound Name |
|---|---|
| 319 | [(7S)-2,7-Dimethyl-3-(3,4,5-trifluorophenyl)-5,7-dihydro-4H-pyrazolo[3,4-c]pyridin-6-yl]-[6-methyl-3-(triazol-2-yl)-2-pyridyl]methanone; |
| 320 | [(7S)-2,7-Dimethyl-3-(3,4,5-trifluorophenyl)-5,7-dihydro-4H-pyrazolo[3,4-c]pyridin-6-yl]-(6-pyrazol-1-yl-2-pyridyl)methanone; |
| 321 | [(7S)-2,7-Dimethyl-3-(3,4,5-trifluorophenyl)-5,7-dihydro-4H-pyrazolo[3,4-c]pyridin-6-yl]-(5-methyl-1-phenyl-1,2,4-triazol-3-yl)methanone; |
| 322 | [(7S)-2,7-Dimethyl-3-(3,4,5-trifluorophenyl)-5,7-dihydro-4H-pyrazolo[3,4-c]pyridin-6-yl]-[1-(4-fluorophenyl)-5-methyl-1,2,4-triazol-3-yl]methanone; |
| 323 | [(7S)-2,7-Dimethyl-3-(3,4,5-trifluorophenyl)-5,7-dihydro-4H-pyrazolo[3,4-c]pyridin-6-yl]-[1-(2-pyridyl)-1,2,4-triazol-3-yl]methanone; |
| 324 | [(7S)-2,7-Dimethyl-3-(3,4,5-trifluorophenyl)-5,7-dihydro-4H-pyrazolo[3,4-c]pyridin-6-yl]-[1-(3-fluoro-2-pyridyl)-1,2,4-triazol-3-yl]methanone; |
| 325 | [(7S)-2,7-Dimethyl-3-(3,4,5-trifluorophenyl)-5,7-dihydro-4H-pyrazolo[3,4-c]pyridin-6-yl]-[5-(2-pyridyl)-2-thienyl]methanone; |
| 326 | [(7S)-2,7-Dimethyl-3-(3,4,5-trifluorophenyl)-5,7-dihydro-4H-pyrazolo[3,4-c]pyridin-6-yl]-(5-methoxypyrazin-2-yl)methanone; |
| 327 | (1,5-Dimethylpyrazol-4-yl)-[(7S)-3-(3-fluoro-5-methyl-phenyl)-2,7-dimethyl-5,7-dihydro-4H-pyrazolo[3,4-c]pyridin-6-yl]methanone; |
| 328 | [(7S)-2,7-Dimethyl-3-(3,4,5-trifluorophenyl)-5,7-dihydro-4H-pyrazolo[3,4-c]pyridin-6-yl]-(5-isopropyl-1-methyl-pyrazol-4-yl)methanone; |
| 329 | [(7S)-2,7-Dimethyl-3-(3,4,5-trifluorophenyl)-5,7-dihydro-4H-pyrazolo[3,4-c]pyridin-6-yl]-[1-(trifluoromethyl)pyrazol-4-yl]methanone; |
| 330 | [5-(Difluoromethyl)-1-methyl-pyrazol-4-yl]-[(7S)-2,7-dimethyl-3-(3,4,5-trifluorophenyl)-5,7-dihydro-4H-pyrazolo[3,4-c]pyridin-6-yl]methanone; |
| 331 | (1-Cyclopropylpyrazol-4-yl)-[(7S)-2,7-dimethyl-3-(3,4,5-trifluorophenyl)-5,7-dihydro-4H-pyrazolo[3,4-c]pyridin-6-yl]methanone; |
| 332 | [1-Cyclopropyl-3-(trifluoromethyl)pyrazol-4-yl]-[(7S)-2,7-dimethyl-3-(3,4,5-trifluorophenyl)-5,7-dihydro-4H-pyrazolo[3,4-c]pyridin-6-yl]methanone; |
| 333 | (5-Cyclobutyl-1-methyl-pyrazol-4-yl)-[(7S)-2,7-dimethyl-3-(3,4,5-trifluorophenyl)-5,7-dihydro-4H-pyrazolo[3,4-c]pyridin-6-yl]methanone; |
| 334 | [(7S)-2,7-Dimethyl-3-(3,4,5-trifluorophenyl)-5,7-dihydro-4H-pyrazolo[3,4-c]pyridin-6-yl]-[1-methyl-5-(1-methylcyclopropyl)pyrazol-4-yl]methanone; |
| 335 | [(7S)-2,7-Dimethyl-3-(3,4,5-trifluorophenyl)-5,7-dihydro-4H-pyrazolo[3,4-c]pyridin-6-yl]-[5-(1-fluorocyclopropyl)-1-methyl-pyrazol-4-yl]methanone; |
| 336 | (5-(2,2-Difluorocyclopropyl)-1-methyl-1H-pyrazol-4-yl)((S)-2,7-dimethyl-3-(3,4,5-trifluorophenyl)-4,5-dihydro-2H-pyrazolo[3,4-c]pyridin-6-yl)methanone; |
| 337 | (5-((R*)-2,2-difluorocyclopropyl)-1-methyl-1H-pyrazol-4-yl)((S)-2,7-dimethyl-3-(3,4,5-trifluorophenyl)-2,4,5,7-tetrahydro-6H-pyrazolo[3,4-c]pyridin-6-yl)methanone; |
| 338 | (5-((S*)-2,2-Difluorocyclopropyl)-1-methyl-1H-pyrazol-4-yl)((S)-2,7-dimethyl-3-(3,4,5-trifluorophenyl)-2,4,5,7-tetrahydro-6H-pyrazolo[3,4-c]pyridin-6-yl)methanone; |
| 339 | ((S)-2,7-Dimethyl-3-(3,4,5-trifluorophenyl)-2,4,5,7-tetrahydro-6H-pyrazolo[3,4-c]pyridin-6-yl)(cis-5-(2-fluorocyclopropyl)-1-methyl-1H-pyrazol-4-yl)methanone; |
| 340 | ((S)-2,7-Dimethyl-3-(3,4,5-trifluorophenyl)-2,4,5,7-tetrahydro-6H-pyrazolo[3,4-c]pyridin-6-yl)(trans-5-(2-fluorocyclopropyl)-1-methyl-1H-pyrazol-4-yl)methanone; |
| 341 | ((S)-2,7-Dimethyl-3-(3,4,5-trifluorophenyl)-2,4,5,7-tetrahydro-6H-pyrazolo[3,4-c]pyridin-6-yl)(1-methyl-cis-5-(2-methylcyclopropyl)-1H-pyrazol-4-yl)methanone; |
| 342 | (S*)-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone; |
| 343 | (1,3-Dimethylpyrazol-4-yl)-[(7S)-2,7-dimethyl-3-(3,4,5-trifluorophenyl)-5,7-dihydro-4H-pyrazolo[3,4-c]pyridin-6-yl]methanone; |
| 344 | [(7S)-2,7-Dimethyl-3-(3,4,5-trifluorophenyl)-5,7-dihydro-4H-pyrazolo[3,4-c]pyridin-6-yl]-(1,3,5-trimethylpyrazol-4-yl)methanone; |
| 345 | (1,5-Dimethylpyrazol-4-yl)-[(7S)-2,7-dimethyl-3-(3,4,5-trifluorophenyl)-5,7-dihydro-4H-pyrazolo[3,4-c]pyridin-6-yl]methanone; |
| 346 | [1-Cyclopropyl-5-(trifluoromethyl)pyrazol-4-yl]-[(7S)-2,7-dimethyl-3-(3,4,5-trifluorophenyl)-5,7-dihydro-4H-pyrazolo[3,4-c]pyridin-6-yl]methanone; |
| 347 | [(7S)-2,7-Dimethyl-3-(3,4,5-trifluorophenyl)-5,7-dihydro-4H-pyrazolo[3,4-c]pyridin-6-yl]-[1-methyl-3-(1-methylcyclopropyl)pyrazol-4-yl]methanone; |
| 348 | [(7S)-2,7-Dimethyl-3-(3,4,5-trifluorophenyl)-5,7-dihydro-4H-pyrazolo[3,4-c]pyridin-6-yl]-[3-(1-fluorocyclopropyl)-1-methyl-pyrazol-4-yl]methanone; |
| 349 | (R)-(5-cyclopropyl-1-methyl-1H-pyrazol-4-yl)(7-methyl-2,3-diphenyl-2,4,5,7-tetrahydro-6H-pyrazolo[3,4-c]pyridin-6-yl)methanone; |
| 350 | (S)-(5-cyclopropyl-1-methyl-1H-pyrazol-4-yl)(7-methyl-2,3-diphenyl-2,4,5,7-tetrahydro-6H-pyrazolo[3,4-c]pyridin-6-yl)methanone; |
| 351 | (1,2-Dimethylpyrrol-3-yl)-[(7S)-2,7-dimethyl-3-(3,4,5-trifluorophenyl)-5,7-dihydro-4H-pyrazolo[3,4-c]pyridin-6-yl]methanone; |
| 352 | (4,5-Dimethylisoxazol-3-yl)-[(7S)-2,7-dimethyl-3-(3,4,5-trifluorophenyl)-5,7-dihydro-4H-pyrazolo[3,4-c]pyridin-6-yl]methanone; |
| 353 | [(7S)-2,7-Dimethyl-3-(3,4,5-trifluorophenyl)-5,7-dihydro-4H-pyrazolo[3,4-c]pyridin-6-yl]-(5-fluoro-1H-indol-6-yl)methanone; |
| 354 | [(7S)-2,7-Dimethyl-3-(3,4,5-trifluorophenyl)-5,7-dihydro-4H-pyrazolo[3,4-c]pyridin-6-yl]-(7-fluoro-1H-indol-4-yl)methanone; |

TABLE 2-continued

| Example # | Compound Name |
|---|---|
| 355 | [(7S)-2,7-Dimethyl-3-(3,4,5-trifluorophenyl)-5,7-dihydro-4H-pyrazolo[3,4-c]pyridin-6-yl]-(5-fluoro-1H-indol-3-yl)methanone; |
| 356 | [(7S)-2,7-Dimethyl-3-(3,4,5-trifluorophenyl)-5,7-dihydro-4H-pyrazolo[3,4-c]pyridin-6-yl]-(5-fluoro-1-methyl-indol-3-yl)methanone; |
| 357 | [(7S)-2,7-Dimethyl-3-(3,4,5-trifluorophenyl)-5,7-dihydro-4H-pyrazolo[3,4-c]pyridin-6-yl]-(4-fluoro-1H-indol-3-yl)methanone; |
| 358 | [(7S)-2,7-Dimethyl-3-(3,4,5-trifluorophenyl)-5,7-dihydro-4H-pyrazolo[3,4-c]pyridin-6-yl]-(6-fluoro-1H-indol-3-yl)methanone; |
| 359 | [(7S)-2,7-Dimethyl-3-(3,4,5-trifluorophenyl)-5,7-dihydro-4H-pyrazolo[3,4-c]pyridin-6-yl]-(7-fluoro-1H-indol-3-yl)methanone; |
| 360 | [(7S)-2,7-Dimethyl-3-(3,4,5-trifluorophenyl)-5,7-dihydro-4H-pyrazolo[3,4-c]pyridin-6-yl]-(6-methyl-1H-indol-3-yl)methanone; |
| 361 | [(7S)-2,7-Dimethyl-3-(3,4,5-trifluorophenyl)-5,7-dihydro-4H-pyrazolo[3,4-c]pyridin-6-yl]-(1H-indazol-3-yl)methanone; |
| 362 | [(7S)-2,7-Dimethyl-3-(3,4,5-trifluorophenyl)-5,7-dihydro-4H-pyrazolo[3,4-c]pyridin-6-yl]-(4-fluoro-1H-indazol-3-yl)methanone; |
| 363 | [(7S)-2,7-Dimethyl-3-(3,4,5-trifluorophenyl)-5,7-dihydro-4H-pyrazolo[3,4-c]pyridin-6-yl]-(6-fluoro-1H-indazol-3-yl)methanone; |
| 364 | [(7S)-2,7-Dimethyl-3-(3,4,5-trifluorophenyl)-5,7-dihydro-4H-pyrazolo[3,4-c]pyridin-6-yl]-(5-fluoro-1H-indazol-3-yl)methanone; |
| 365 | [(7S)-2,7-Dimethyl-3-(3,4,5-trifluorophenyl)-5,7-dihydro-4H-pyrazolo[3,4-c]pyridin-6-yl]-(2-methylindazol-3-yl)methanone; |
| 366 | [(7S)-2,7-Dimethyl-3-(3,4,5-trifluorophenyl)-5,7-dihydro-4H-pyrazolo[3,4-c]pyridin-6-yl]-(1-methylbenzimidazol-4-yl)methanone; |
| 367 | 1H-Benzotriazol-4-yl-[(7S)-2,7-dimethyl-3-(3,4,5-trifluorophenyl)-5,7-dihydro-4H-pyrazolo[3,4-c]pyridin-6-yl]methanone; |
| 368 | [(7S)-2,7-Dimethyl-3-(3,4,5-trifluorophenyl)-5,7-dihydro-4H-pyrazolo[3,4-c]pyridin-6-yl]-(1H-pyrrolo[2,3-b]pyridin-5-yl)methanone; |
| 369 | [(7S)-2,7-Dimethyl-3-(3,4,5-trifluorophenyl)-5,7-dihydro-4H-pyrazolo[3,4-c]pyridin-6-yl]-(5-fluoro-1H-pyrrolo[2,3-b]pyridin-4-yl)methanone; |
| 370 | [(7S)-2,7-Dimethyl-3-(3,4,5-trifluorophenyl)-5,7-dihydro-4H-pyrazolo[3,4-c]pyridin-6-yl]-(5-fluoro-1-methyl-pyrrolo[2,3-b]pyridin-4-yl)methanone; |
| 371 | [(7S)-2,7-Dimethyl-3-(3,4,5-trifluorophenyl)-5,7-dihydro-4H-pyrazolo[3,4-c]pyridin-6-yl]-[5-(trifluoromethyl)-1H-pyrrolo[2,3-b]pyridin-4-yl]methanone; |
| 372 | [(7S)-3-(3,5-Difluorophenyl)-2,7-dimethyl-5,7-dihydro-4H-pyrazolo[3,4-c]pyridin-6-yl]-[1-(2-fluoranylethyl)pyrrolo[2,3-b]pyridin-4-yl]methanone; |
| 373 | [(7S)-2,7-Dimethyl-3-(3,4,5-trifluorophenyl)-5,7-dihydro-4H-pyrazolo[3,4-c]pyridin-6-yl]-(1H-pyrrolo[2,3-b]pyridin-3-yl)methanone; |
| 374 | [(7S)-2,7-Dimethyl-3-(3,4,5-trifluorophenyl)-5,7-dihydro-4H-pyrazolo[3,4-c]pyridin-6-yl]-(5-fluoro-1H-pyrrolo[2,3-b]pyridin-3-yl)methanone; |
| 375 | [(7S)-2,7-Dimethyl-3-(3,4,5-trifluorophenyl)-5,7-dihydro-4H-pyrazoIo[3,4-c]pyridin-6-yl]-(2-methyl-1H-pyrrolo[2,3-b]pyridin-3-yl)methanone; |
| 376 | [(7S)-2,7-Dimethyl-3-(3,4,5-trifluorophenyl)-5,7-dihydro-4H-pyrazolo[3,4-c]pyridin-6-yl]-(1H-pyrrolo[2,3-c]pyridin-7-yl)methanone; |
| 377 | [(7S)-2,7-Dimethyl-3-(3,4,5-trifluorophenyl)-5,7-dihydro-4H-pyrazolo[3,4-c]pyridin-6-yl]-(3-fluoropyrazolo[1,5-a]pyridin-4-yl)methanone; |
| 378 | [(7S)-2,7-Dimethyl-3-(3,4,5-trifluorophenyl)-5,7-dihydro-4H-pyrazolo[3,4-c]pyridin-6-yl]-(3-fluoropyrazolo[1,5-a]pyridin-5-yl)methanone; |
| 379 | (3-Bromopyrazolo[1,5-a]pyridin-4-yl)-[(7S)-2,7-dimethyl-3-(3,4,5-trifluorophenyl)-5,7-dihydro-4H-pyrazolo[3,4-c]pyridin-6-yl]methanone; |
| 380 | [(7S)-2,7-Dimethyl-3-(3,4,5-trifluorophenyl)-5,7-dihydro-4H-pyrazolo[3,4-c]pyridin-6-yl]-(3-methylpyrazolo[1,5-a]pyridin-4-yl)methanone; |
| 381 | [(7S)-2,7-Dimethyl-3-(3,4,5-trifluorophenyl)-5,7-dihydro-4H-pyrazolo[3,4-c]pyridin-6-yl]-pyrazolo[1,5-a]pyridin-3-yl-methanone; |
| 382 | [(7S)-2,7-Dimethyl-3-(3,4,5-trifluorophenyl)-5,7-dihydro-4H-pyrazolo[3,4-c]pyridin-6-yl]-(2-methylpyrazolo[1,5-a]pyridin-3-yl)methanone; |
| 383 | [(7S)-2,7-Dimethyl-3-(3,4,5-trifluorophenyl)-5,7-dihydro-4H-pyrazolo[3,4-c]pyridin-6-yl]-(5-methylpyrazolo[1,5-a]pyridin-3-yl)methanone; |
| 384 | [(7S)-2,7-Dimethyl-3-(3,4,5-trifluorophenyl)-5,7-dihydro-4H-pyrazolo[3,4-c]pyridin-6-yl]-(6-fluoropyrazolo[1,5-a]pyridin-3-yl)methanone; |
| 385 | (2-Cyclopropyl-7-methyl-pyrazolo[1,5-a]pyridin-3-yl)-[(7S)-2,7-dimethyl-3-(3,4,5-trifluorophenyl)-5,7-dihydro-4H-pyrazolo[3,4-c]pyridin-6-yl]methanone; |
| 386 | [(7S)-2,7-Dimethyl-3-(3,4,5-trifluorophenyl)-5,7-dihydro-4H-pyrazolo[3,4-c]pyridin-6-yl]-(7-methylpyrazolo[1,5-a]pyridin-3-yl)methanone; |
| 387 | [(7S)-2,7-Dimethyl-3-(3,4,5-trifluorophenyl)-5,7-dihydro-4H-pyrazolo[3,4-c]pyridin-6-yl]-(7-methoxypyrazolo[1,5-a]pyridin-3-yl)methanone; |
| 388 | [(7S)-2,7-Dimethyl-3-(3,4,5-trifluorophenyl)-5,7-dihydro-4H-pyrazolo[3,4-c]pyridin-6-yl]-(6-methoxypyrazolo[1,5-a]pyridin-3-yl)methanone; |
| 389 | [(7S)-2,7-Dimethyl-3-(3,4,5-trifluorophenyl)-5,7-dihydro-4H-pyrazolo[3,4-c]pyridin-6-yl]-(5-methoxypyrazolo[1,5-a]pyridin-3-yl)methanone; |
| 390 | [(7S)-2,7-Dimethyl-3-(3,4,5-trifluorophenyl)-5,7-dihydro-4H-pyrazolo[3,4-c]pyridin-6-yl]-(4-methoxypyrazolo[1,5-a]pyridin-3-yl)methanone; |
| 391 | [(7S)-2,7-Dimethyl-3-(3,4,5-trifluorophenyl)-5,7-dihydro-4H-pyrazolo[3,4-c]pyridin-6-yl]-imidazo[1,2-a]pyridin-6-yl-methanone; |
| 392 | [(7S)-2,7-Dimethyl-3-(3,4,5-trifluorophenyl)-5,7-dihydro-4H-pyrazolo[3,4-c]pyridin-6-yl]-imidazo[1,2-a]pyridin-8-yl-methanone; |
| 393 | [(7S)-2,7-Dimethyl-3-(3,4,5-trifluorophenyl)-5,7-dihydro-4H-pyrazolo[3,4-c]pyridin-6-yl]-(7-fluoroimidazo[1,2-a]pyridin-3-yl)methanone; |

TABLE 2-continued

| Example # | Compound Name |
|---|---|
| 394 | [(7S)-2,7-Dimethyl-3-(3,4,5-trifluorophenyl)-5,7-dihydro-4H-pyrazolo[3,4-c]pyridin-6-yl]-(2-methylimidazo[1,2-a]pyridin-5-yl)methanone; |
| 395 | [(7S)-3-(3-Chloro-5-methoxy-phenyl)-2,7-dimethyl-5,7-dihydro-4H-pyrazolo[3,4-c]pyridin-6-yl]-(2-methylimidazo[1,2-a]pyridin-3-yl)methanone; |
| 396 | [(7S)-3-(3-Fluoro-5-methyl-phenyl)-2,7-dimethyl-5,7-dihydro-4H-pyrazolo[3,4-c]pyridin-6-yl]-(2-methylimidazo[1,2-a]pyridin-3-yl)methanone; |
| 397 | [(7S)-2,7-Dimethyl-3-(3,4,5-trifluorophenyl)-5,7-dihydro-4H-pyrazolo[3,4-c]pyridin-6-yl]-(2-methylimidazo[1,2-a]pyridin-3-yl)methanone; |
| 398 | [(7S)-2,7-Dimethyl-3-(3,4,5-trifluorophenyl)-5,7-dihydro-4H-pyrazolo[3,4-c]pyridin-6-yl]-(3-methylimidazo[1,2-a]pyridin-2-yl)methanone; |
| 399 | [(7S)-2,7-Dimethyl-3-(3,4,5-trifluorophenyl)-5,7-dihydro-4H-pyrazolo[3,4-c]pyridin-6-yl]-(7-methylimidazo[1,2-a]pyridin-3-yl)methanone; |
| 400 | [(7S)-2,7-Dimethyl-3-(3,4,5-trifluorophenyl)-5,7-dihydro-4H-pyrazolo[3,4-c]pyridin-6-yl]-(6-methylimidazo[1,2-a]pyridin-3-yl)methanone; |
| 401 | [(7S)-2,7-Dimethyl-3-(3,4,5-trifluorophenyl)-5,7-dihydro-4H-pyrazolo[3,4-c]pyridin-6-yl]-(5-methylimidazo[1,2-a]pyridin-3-yl)methanone; |
| 402 | [(7S)-2,7-Dimethyl-3-(3,4,5-trifluorophenyl)-5,7-dihydro-4H-pyrazolo[3,4-c]pyridin-6-yl]-(7-fluoro-2-methyl-imidazo[1,2-a]pyridin-3-yl)methanone; |
| 403 | (2,8-Dimethylimidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone; |
| 404 | (2,7-Dimethylimidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone; |
| 405 | (2,6-Dimethylimidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone; |
| 406 | [(7S)-3-(3-Chloro-5-methoxy-phenyl)-2,7-dimethyl-5,7-dihydro-4H-pyrazolo[3,4-c]pyridin-6-yl]-(6-fluoro-2-methyl-imidazo[1,2-a]pyridin-3-yl)methanone; |
| 407 | [(7S)-2,7-Dimethyl-3-(3,4,5-trifluorophenyl)-5,7-dihydro-4H-pyrazolo[3,4-c]pyridin-6-yl]-(6-fluoro-2-methyl-imidazo[1,2-a]pyridin-3-yl)methanone; |
| 408 | [(7S)-2,7-Dimethyl-3-(3,4,5-trifluorophenyl)-5,7-dihydro-4H-pyrazolo[3,4-c]pyridin-6-yl]-(6-fluoro-2,8-dimethyl-imidazo[1,2-a]pyridin-3-yl)methanone; |
| 409 | [(7S)-2,7-Dimethyl-3-(3,4,5-trifluorophenyl)-5,7-dihydro-4H-pyrazolo[3,4-c]pyridin-6-yl]-(6-fluoro-2,7-dimethyl-imidazo[1,2-a]pyridin-3-yl)methanone; |
| 410 | (6,8-Difluoro-2-methyl-imidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone; |
| 411 | [(7S)-2,7-Dimethyl-3-(3,4,5-trifluorophenyl)-5,7-dihydro-4H-pyrazolo[3,4-c]pyridin-6-yl]-(6-methoxy-2-methyl-imidazo[1,2-a]pyridin-3-yl)methanone; |
| 412 | [2-(Difluoromethyl)imidazo[1,2-a]pyridin-3-yl]-[(7S)-2,7-dimethyl-3-(3,4,5-trifluorophenyl)-5,7-dihydro-4H-pyrazolo[3,4-c]pyridin-6-yl]methanone; |
| 413 | [(7S)-2,7-Dimethyl-3-(3,4,5-trifluorophenyl)-5,7-dihydro-4H-pyrazolo[3,4-c]pyridin-6-yl]-[2-(trifluoromethyl)imidazo[1,2-a]pyridin-3-yl]methanone; |
| 414 | [(7S)-2,7-Dimethyl-3-(3,4,5-trifluorophenyl)-5,7-dihydro-4H-pyrazolo[3,4-c]pyridin-6-yl]-[5-methyl-2-(trifluoromethyl)imidazo[1,2-a]pyridin-3-yl]methanone; |
| 415 | [(7S)-2,7-Dimethyl-3-(3,4,5-trifluorophenyl)-5,7-dihydro-4H-pyrazolo[3,4-c]pyridin-6-yl]-pyrrolo[1,2-a]pyrazin-1-yl-methanone; |
| 416 | [(7S)-2,7-Dimethyl-3-(3,4,5-trifluorophenyl)-5,7-dihydro-4H-pyrazolo[3,4-c]pyridin-6-yl]-pyrrolo[1,2-a]pyrazin-8-yl-methanone; |
| 417 | (2,4-Dimethylpyrrolo[1,2-a]pyrimidin-8-yl)-[(7S)-2,7-dimethyl-3-(3,4,5-trifluorophenyl)-5,7-dihydro-4H-pyrazolo[3,4-c]pyridin-6-yl]methanone; |
| 418 | [(7S)-2,7-Dimethyl-3-(3,4,5-trifluorophenyl)-5,7-dihydro-4H-pyrazolo[3,4-c]pyridin-6-yl]-(3-methylimidazo[1,5-a]pyridin-6-yl)methanone; |
| 419 | [(7S)-2,7-Dimethyl-3-(3,4,5-trifluorophenyl)-5,7-dihydro-4H-pyrazolo[3,4-c]pyridin-6-yl]-(7-methylimidazo[1,5-a]pyridin-1-yl)methanone; |
| 420 | [(7S)-2,7-Dimethyl-3-(3,4,5-trifluorophenyl)-5,7-dihydro-4H-pyrazolo[3,4-c]pyridin-6-yl]-imidazo[1,5-a]pyridin-1-yl-methanone; |
| 421 | (3-Cyclopropylimidazo[1,5-a]pyridin-1-yl)-[(7S)-2,7-dimethyl-3-(3,4,5-trifluorophenyl)-5,7-dihydro-4H-pyrazolo[3,4-c]pyridin-6-yl]methanone; |
| 422 | [(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-4-yl)methanone; |
| 423 | [(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-5-yl)methanone; |
| 424 | (1,6-Dimethylpyrazolo[3,4-b]pyridin-4-yl)-[(7S)-2,7-dimethyl-3-(3,4,5-trifluorophenyl)-5,7-dihydro-4H-pyrazolo[3,4-c]pyridin-6-yl]methanone; |
| 425 | (1,3-Dimethylpyrazolo[3,4-b]pyridin-4-yl)-[(7S)-2,7-dimethyl-3-(3,4,5-trifluorophenyl)-5,7-dihydro-4H-pyrazolo[3,4-c]pyridin-6-yl]methanone; |
| 426 | [(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-3-yl)methanone; |
| 427 | [(7S)-2,7-Dimethyl-3-(3,4,5-trifluorophenyl)-5,7-dihydro-4H-pyrazolo[3,4-c]pyridin-6-yl]-(1-methylpyrazolo[3,4-b]pyridin-3-yl)methanone; |
| 428 | [(7S)-2,7-Dimethyl-3-(3,4,5-trifluorophenyl)-5,7-dihydro-4H-pyrazolo[3,4-c]pyridin-6-yl]-(5-fluoro-1H-pyrazolo[3,4-b]pyridin-3-yl)methanone; |
| 429 | [(7S)-2,7-Dimethyl-3-(3,4,5-trifluorophenyl)-5,7-dihydro-4H-pyrazolo[3,4-c]pyridin-6-yl]-(2-methylpyrazolo[3,4-c]pyridin-7-yl)methanone; |
| 430 | [(7S)-2,7-Dimethyl-3-(3,4,5-trifluorophenyl)-5,7-dihydro-4H-pyrazolo[3,4-c]pyridin-6-yl]-(1H-pyrazolo[3,4-c]pyridin-3-yl)methanone; |
| 431 | [(7S)-2,7-Dimethyl-3-(3,4,5-trifluorophenyl)-5,7-dihydro-4H-pyrazolo[3,4-c]pyridin-6-yl]-(1-methylpyrazolo[3,4-c]pyridin-3-yl)methanone; |

TABLE 2-continued

| Example # | Compound Name |
|---|---|
| 432 | [(7S)-2,7-Dimethyl-3-(3,4,5-trifluorophenyl)-5,7-dihydro-4H-pyrazolo[3,4-c]pyridin-6-yl]-(1H-pyrazolo[3,4-c]pyridin-7-yl)methanone; |
| 433 | [(7S)-2,7-Dimethyl-3-(3,4,5-trifluorophenyl)-5,7-dihydro-4H-pyrazolo[3,4-c]pyridin-6-yl]-(1-methylpyrazolo[3,4-c]pyridin-7-yl)methanone; |
| 434 | [(7S)-2,7-Dimethyl-3-(3,4,5-trifluorophenyl)-5,7-dihydro-4H-pyrazolo[3,4-c]pyridin-6-yl]-(1H-pyrazolo[4,3-c]pyridin-7-yl)methanone; |
| 435 | [(7S)-2,7-Dimethyl-3-(3,4,5-trifluorophenyl)-5,7-dihydro-4H-pyrazolo[3,4-c]pyridin-6-yl]-(1H-pyrazolo[4,3-c]pyridin-3-yl)methanone; |
| 436 | [(7S)-2,7-Dimethyl-3-(3,4,5-trifluorophenyl)-5,7-dihydro-4H-pyrazolo[3,4-c]pyridin-6-yl]-(1H-pyrazolo[4,3-b]pyridin-3-yl)methanone; |
| 437 | [(7S)-2,7-Dimethyl-3-(3,4,5-trifluorophenyl)-5,7-dihydro-4H-pyrazolo[3,4-c]pyridin-6-yl]-([1,2,4]triazolo[4,3-a]pyridin-3-yl)methanone; |
| 438 | [(7S)-2,7-Dimethyl-3-(3,4,5-trifluorophenyl)-5,7-dihydro-4H-pyrazolo[3,4-c]pyridin-6-yl]-([1,2,4]triazolo[4,3-a]pyridin-5-yl)methanone; |
| 439 | [(7S)-2,7-Dimethyl-3-(3,4,5-trifluorophenyl)-5,7-dihydro-4H-pyrazolo[3,4-c]pyridin-6-yl]-([1,2,4]triazolo[4,3-a]pyridin-6-yl)methanone; |
| 440 | [3-(Difluoromethyl)-[1,2,4]triazolo[4,3-a]pyridin-6-yl]-[(7S)-2,7-dimethyl-3-(3,4,5-trifluorophenyl)-5,7-dihydro-4H-pyrazolo[3,4-c]pyridin-6-yl]methanone; |
| 441 | [(7S)-2,7-Dimethyl-3-(3,4,5-trifluorophenyl)-5,7-dihydro-4H-pyrazolo[3,4-c]pyridin-6-yl]-(triazolo[1,5-a]pyridin-3-yl)methanone; |
| 442 | [(7S)-2,7-Dimethyl-3-(3,4,5-trifluorophenyl)-5,7-dihydro-4H-pyrazolo[3,4-c]pyridin-6-yl]-(2-methylpyrazolo[1,5-b]pyridazin-3-yl)methanone; |
| 443 | [(7S)-2,7-Dimethyl-3-(3,4,5-trifluorophenyl)-5,7-dihydro-4H-pyrazolo[3,4-c]pyridin-6-yl]-(5-methylpyrazolo[1,5-b]pyridazin-3-yl)methanone; |
| 444 | (2-Cyclopropyl-4-methyl-pyrazolo[1,5-b]pyridazin-3-yl)-[(7S)-2,7-dimethyl-3-(3,4,5-trifluorophenyl)-5,7-dihydro-4H-pyrazolo[3,4-c]pyridin-6-yl]methanone; |
| 445 | (2-Cyclopropyl-5-methyl-pyrazolo[1,5-b]pyridazin-3-yl)-[(7S)-2,7-dimethyl-3-(3,4,5-trifluorophenyl)-5,7-dihydro-4H-pyrazolo[3,4-c]pyridin-6-yl]methanone; |
| 446 | (2,4-Dimethylpyrazolo[1,5-a]pyrazin-3-yl)-[(7S)-2,7-dimethyl-3-(3,4,5-trifluorophenyl)-5,7-dihydro-4H-pyrazolo[3,4-c]pyridin-6-yl]methanone; |
| 447 | (2-Cyclopropyl-4-methyl-pyrazolo[1,5-a]pyrazin-3-yl)-[(7S)-2,7-dimethyl-3-(3,4,5-trifluorophenyl)-5,7-dihydro-4H-pyrazolo[3,4-c]pyridin-6-yl]methanone; |
| 448 | [(7S)-2,7-Dimethyl-3-(3,4,5-trifluorophenyl)-5,7-dihydro-4H-pyrazolo[3,4-c]pyridin-6-yl]-pyrazolo[1,5-a]pyrimidin-3-yl-methanone; |
| 449 | [(7S)-2,7-Dimethyl-3-(3,4,5-trifluorophenyl)-5,7-dihydro-4H-pyrazolo[3,4-c]pyridin-6-yl]-(2-methylpyrazolo[1,5-a]pyrimidin-3-yl)methanone; |
| 450 | [(7S)-2,7-Dimethyl-3-(3,4,5-trifluorophenyl)-5,7-dihydro-4H-pyrazolo[3,4-c]pyridin-6-yl]-(7-methylpyrazolo[1,5-a]pyrimidin-3-yl)methanone; |
| 451 | [(7S)-2,7-Dimethyl-3-(3,4,5-trifluorophenyl)-5,7-dihydro-4H-pyrazolo[3,4-c]pyridin-6-yl]-(6-methylpyrazolo[1,5-a]pyrimidin-3-yl)methanone; |
| 452 | [(7S)-2,7-Dimethyl-3-(3,4,5-trifluorophenyl)-5,7-dihydro-4H-pyrazolo[3,4-c]pyridin-6-yl]-imidazo[1,2-b]pyridazin-6-yl-methanone; |
| 453 | [(7S)-2,7-Dimethyl-3-(3,4,5-trifluorophenyl)-5,7-dihydro-4H-pyrazolo[3,4-c]pyridin-6-yl]-(2-methylimidazo[1,2-b]pyridazin-6-yl)methanone; |
| 454 | [(7S)-2,7-Dimethyl-3-(3,4,5-trifluorophenyl)-5,7-dihydro-4H-pyrazolo[3,4-c]pyridin-6-yl]-imidazo[1,2-b]pyridazin-3-yl-methanone; |
| 455 | [(7S)-2,7-Dimethyl-3-(3,4,5-trifluorophenyl)-5,7-dihydro-4H-pyrazolo[3,4-c]pyridin-6-yl]-(2-methylimidazo[1,2-b]pyridazin-3-yl)methanone; |
| 456 | (2,8-Dimethylimidazo[1,2-b]pyridazin-3-yl)-[(7S)-2,7-dimethyl-3-(3,4,5-trifluorophenyl)-5,7-dihydro-4H-pyrazolo[3,4-c]pyridin-6-yl]methanone; |
| 457 | (2,7-Dimethylimidazo[1,2-b]pyridazin-3-yl)-[(7S)-2,7-dimethyl-3-(3,4,5-trifluorophenyl)-5,7-dihydro-4H-pyrazolo[3,4-c]pyridin-6-yl]methanone; |
| 458 | [(7S)-2,7-Dimethyl-3-(3,4,5-trifluorophenyl)-5,7-dihydro-4H-pyrazolo[3,4-c]pyridin-6-yl]-(2-methylimidazo[1,2-a]pyrimidin-3-yl)methanone; |
| 459 | [(7S)-2,7-Dimethyl-3-(3,4,5-trifluorophenyl)-5,7-dihydro-4H-pyrazolo[3,4-c]pyridin-6-yl]-(2,5,8-trimethylimidazo[1,2-a]pyrazin-3-yl)methanone; |
| 460 | [(7S)-2,7-Dimethyl-3-(3,4,5-trifluorophenyl)-5,7-dihydro-4H-pyrazolo[3,4-c]pyridin-6-yl]-(6-methylimidazo[1,5-a]pyrimidin-8-yl)methanone; |
| 461 | [(7S)-2,7-Dimethyl-3-(3,4,5-trifluorophenyl)-5,7-dihydro-4H-pyrazolo[3,4-c]pyridin-6-yl]-(3-methylimidazo[1,5-a]pyrimidin-8-yl)methanone; |
| 462 | [(7S)-2,7-Dimethyl-3-(3,4,5-trifluorophenyl)-5,7-dihydro-4H-pyrazolo[3,4-c]pyridin-6-yl]-(3-methylimidazo[1,5-a]pyrazin-1-yl)methanone; |
| 463 | [(7S)-2,7-Dimethyl-3-(3,4,5-trifluorophenyl)-5,7-dihydro-4H-pyrazolo[3,4-c]pyridin-6-yl]-[3-(trifluoromethyl)imidazo[1,5-a]pyrazin-1-yl]methanone; |
| 464 | [(7S)-2,7-Dimethyl-3-(3,4,5-trifluorophenyl)-5,7-dihydro-4H-pyrazolo[3,4-c]pyridin-6-yl]-(5-methyl-7H-pyrrolo[2,3-d]pyrimidin-4-yl)methanone; |
| 465 | [(7S)-3-(3-Fluoro-5-methyl-phenyl)-2,7-dimethyl-5,7-dihydro-4H-pyrazolo[3,4-c]pyridin-6-yl]-(7-methylpyrrolo[2,3-d]pyrimidin-4-yl)methanone; |
| 466 | [(7S)-2,7-Dimethyl-3-(3,4,5-trifluorophenyl)-5,7-dihydro-4H-pyrazolo[3,4-c]pyridin-6-yl]-(7-methylpyrrolo[2,3-d]pyrimidin-4-yl)methanone; |
| 467 | (5,7-Dimethylpyrrolo[2,3-d]pyrimidin-4-yl)-[(7S)-2,7-dimethyl-3-(3,4,5-trifluorophenyl)-5,7-dihydro-4H-pyrazolo[3,4-c]pyridin-6-yl]methanone; |
| 468 | [(7S)-2,7-Dimethyl-3-[3-(trifluoromethyl)phenyl]-5,7-dihydro-4H-pyrazolo[3,4-c]pyridin-6-yl]-(6-quinolyl)methanone; |
| 469 | (6,7-Dimethylpyrrolo[2,3-d]pyrimidin-4-yl)-[(7S)-2,7-dimethyl-3-(3,4,5-trifluorophenyl)-5,7-dihydro-4H-pyrazolo[3,4-c]pyridin-6-yl]methanone; |
| 470 | [(7S)-2,7-Dimethyl-3-(3,4,5-trifluorophenyl)-5,7-dihydro-4H-pyrazolo[3,4-c]pyridin-6-yl]-(7H-purin-6-yl)methanone; |

TABLE 2-continued

| Example # | Compound Name |
|---|---|
| 471 | [(7S)-2,7-Dimethyl-3-(3,4,5-trifluorophenyl)-5,7-dihydro-4H-pyrazolo[3,4-c]pyridin-6-yl]-(1-methylpyrazolo[3,4-d]pyrimidin-4-yl)methanone; |
| 472 | [(7S)-2,7-Dimethyl-3-(3,4,5-trifluorophenyl)-5,7-dihydro-4H-pyrazolo[3,4-c]pyridin-6-yl]-(5-methyl-[1,2,4]triazolo[1,5-a]pyrimidin-7-yl)methanone; |
| 473 | [(7S)-2,7-Dimethyl-3-(3,4,5-trifluorophenyl)-5,7-dihydro-4H-pyrazolo[3,4-c]pyridin-6-yl]-(7-methylquinoxalin-6-yl)methanone; |
| 474 | [(7S)-2,7-Dimethyl-3-(3,4,5-trifluorophenyl)-5,7-dihydro-4H-pyrazolo[3,4-c]pyridin-6-yl]-(2-methylquinoxalin-5-yl)methanone; |
| 475 | [(7S)-2,7-Dimethyl-3-(3,4,5-trifluorophenyl)-5,7-dihydro-4H-pyrazolo[3,4-c]pyridin-6-yl]-(3-methylquinoxalin-5-yl)methanone; |
| 476 | (2,3-Dimethylquinoxalin-6-yl)-[(7S)-2,7-dimethyl-3-(3,4,5-trifluorophenyl)-5,7-dihydro-4H-pyrazolo[3,4-c]pyridin-6-yl]methanone; |
| 477 | [(7S)-2,7-Dimethyl-3-(3,4,5-trifluorophenyl)-5,7-dihydro-4H-pyrazolo[3,4-c]pyridin-6-yl]-quinoxalin-2-yl-methanone; |
| 478 | Cinnolin-3-yl-[(7S)-2,7-dimethyl-3-(3,4,5-trifluorophenyl)-5,7-dihydro-4H-pyrazolo[3,4-c]pyridin-6-yl]methanone; |
| 479 | [(7S)-2,7-Dimethyl-3-(3,4,5-trifluorophenyl)-5,7-dihydro-4H-pyrazolo[3,4-c]pyridin-6-yl]-quinazolin-6-yl-methanone; |
| 480 | [(7S)-2,7-Dimethyl-3-(3,4,5-trifluorophenyl)-5,7-dihydro-4H-pyrazolo[3,4-c]pyridin-6-yl]-quinazolin-7-yl-methanone; |
| 481 | [(7S)-2,7-Dimethyl-3-(3,4,5-trifluorophenyl)-5,7-dihydro-4H-pyrazolo[3,4-c]pyridin-6-yl]-(8-fluoroquinazolin-4-yl)methanone; |
| 482 | [(7S)-2,7-Dimethyl-3-(3,4,5-trifluorophenyl)-5,7-dihydro-4H-pyrazolo[3,4-c]pyridin-6-yl]-quinazolin-4-yl-methanone; |
| 483 | (2-Deuterioquinoxalin-6-yl)-[(7S)-2,7-dimethyl-3-(3,4,5-trifluorophenyl)-5,7-dihydro-4H-pyrazolo[3,4-c]pyridin-6-yl]methanone; |
| 484 | [(7S)-2,7-Dimethyl-3-(3,4,5-trifluorophenyl)-5,7-dihydro-4H-pyrazolo[3,4-c]pyridin-6-yl]-pyrido[4,3-d]pyrimidin-5-yl-methanone; |
| 485 | [(7S)-2,7-Dimethyl-3-(3,4,5-trifluorophenyl)-5,7-dihydro-4H-pyrazolo[3,4-c]pyridin-6-yl]-(1,5-naphthyridin-4-yl)methanone; |
| 486 | [(7S)-2,7-Dimethyl-3-(3,4,5-trifluorophenyl)-5,7-dihydro-4H-pyrazolo[3,4-c]pyridin-6-yl]-(1,6-naphthyridin-5-yl)methanone; |
| 487 | [(7S)-2,7-Dimethyl-3-(3,4,5-trifluorophenyl)-5,7-dihydro-4H-pyrazolo[3,4-c]pyridin-6-yl]-(2-methyl-1,6-naphthyridin-5-yl)methanone; |
| 488 | [(7S)-2,7-Dimethyl-3-(3,4,5-trifluorophenyl)-5,7-dihydro-4H-pyrazolo[3,4-c]pyridin-6-yl]-(1,6-naphthyridin-3-yl)methanone; |
| 489 | [(7S)-2,7-Dimethyl-3-(3,4,5-trifluorophenyl)-5,7-dihydro-4H-pyrazolo[3,4-c]pyridin-6-yl]-(1,7-naphthyridin-5-yl)methanone; |
| 490 | [(7S)-2,7-Dimethyl-3-(3,4,5-trifluorophenyl)-5,7-dihydro-4H-pyrazolo[3,4-c]pyridin-6-yl]-(1,8-naphthyridin-3-yl)methanone; |
| 491 | [(7S)-2,7-Dimethyl-3-(3,4,5-trifluorophenyl)-5,7-dihydro-4H-pyrazolo[3,4-c]pyridin-6-yl]-(1,8-naphthyridin-4-yl)methanone; |
| 492 | [(7S)-2,7-Dimethyl-3-(o-tolyl)-5,7-dihydro-4H-pyrazolo[3,4-c]pyridin-6-yl]-(6-quinolyl)methanone; |
| 493 | [(7S)-2,7-Dimethyl-3-[2-(trifluoromethyl)phenyl]-5,7-dihydro-4H-pyrazolo[3,4-c]pyridin-6-yl]-(6-quinolyl)methanone; |
| 494 | [(7S)-2,7-Dimethyl-3-[4-(trifluoromethyl)phenyl]-5,7-dihydro-4H-pyrazolo[3,4-c]pyridin-6-yl]-(6-quinolyl)methanone; |
| 495 | [(7S)-3-(3-Methoxyphenyl)-2,7-dimethyl-5,7-dihydro-4H-pyrazolo[3,4-c]pyridin-6-yl]-(6-quinolyl)methanone; |
| 496 | [(7S)-3-(2-Methoxyphenyl)-2,7-dimethyl-5,7-dihydro-4H-pyrazolo[3,4-c]pyridin-6-yl]-(6-quinolyl)methanone; |
| 497 | [(7S)-3-(4-Ethoxyphenyl)-2,7-dimethyl-5,7-dihydro-4H-pyrazolo[3,4-c]pyridin-6-yl]-(6-quinolyl)methanone; |
| 498 | [(7S)-3-(3-Isopropoxyphenyl)-2,7-dimethyl-5,7-dihydro-4H-pyrazolo[3,4-c]pyridin-6-yl]-(6-quinolyl)methanone; |
| 499 | [(7S)-3-[3-(Difluoromethoxy)phenyl]-2,7-dimethyl-5,7-dihydro-4H-pyrazolo[3,4-c]pyridin-6-yl]-(6-quinolyl)methanone; |
| 500 | [(7S)-2,7-Dimethyl-3-[4-(trifluoromethoxy)phenyl]-5,7-dihydro-4H-pyrazolo[3,4-c]pyridin-6-yl]-(6-quinolyl)methanone; |
| 501 | [(7S)-2,7-Dimethyl-3-[3-(trifluoromethoxy)phenyl]-5,7-dihydro-4H-pyrazolo[3,4-c]pyridin-6-yl]-(6-quinolyl)methanone; |
| 502 | [(7S)-3-(2,4-Difluorophenyl)-2,7-dimethyl-5,7-dihydro-4H-pyrazolo[3,4-c]pyridin-6-yl]-(6-quinolyl)methanone; |
| 503 | [(7S)-3-(2,3-Difluorophenyl)-2,7-dimethyl-5,7-dihydro-4H-pyrazolo[3,4-c]pyridin-6-yl]-(6-quinolyl)methanone; |
| 504 | [(7S)-3-(4-Chloro-3-fluoro-phenyl)-2,7-dimethyl-5,7-dihydro-4H-pyrazolo[3,4-c]pyridin-6-yl]-(6-quinolyl)methanone; |
| 505 | [(7S)-3-(3-Chloro-4-fluoro-phenyl)-2,7-dimethyl-5,7-dihydro-4H-pyrazolo[3,4-c]pyridin-6-yl]-(6-quinolyl)methanone; |
| 506 | [(7S)-3-(2-Chloro-4-fluoro-phenyl)-2,7-dimethyl-5,7-dihydro-4H-pyrazolo[3,4-c]pyridin-6-yl]-(6-quinolyl)methanone; |
| 507 | [(7S)-3-(3,4-Dichlorophenyl)-2,7-dimethyl-5,7-dihydro-4H-pyrazolo[3,4-c]pyridin-6-yl]-(6-quinolyl)methanone; |
| 508 | [(7S)-3-(5-Fluoro-2-methoxy-phenyl)-2,7-dimethyl-5,7-dihydro-4H-pyrazolo[3,4-c]pyridin-6-yl]-(6-quinolyl)methanone; |
| 509 | [(7S)-3-(4-Fluoro-3-methoxy-phenyl)-2,7-dimethyl-5,7-dihydro-4H-pyrazolo[3,4-c]pyridin-6-yl]-(6-quinolyl)methanone; |

TABLE 2-continued

| Example # | Compound Name |
|---|---|
| 510 | [(7S)-3-(2-Fluoro-3-methoxy-phenyl)-2,7-dimethyl-5,7-dihydro-4H-pyrazolo[3,4-c]pyridin-6-yl]-(6-quinolyl)methanone; |
| 511 | [(7S)-3-(3-Fluoro-5-methyl-phenyl)-2,7-dimethyl-5,7-dihydro-4H-pyrazolo[3,4-c]pyridin-6-yl]-(6-quinolyl)methanone; |
| 512 | [(7S)-3-(4-Methoxy-3-methyl-phenyl)-2,7-dimethyl-5,7-dihydro-4H-pyrazolo[3,4-c]pyridin-6-yl]-(6-quinolyl)methanone; |
| 513 | [(7S)-3-(3-Chloro-5-methoxy-phenyl)-2,7-dimethyl-5,7-dihydro-4H-pyrazolo[3,4-c]pyridin-6-yl]-(6-quinolyl)methanone; |
| 514 | [(7S)-3-(4-Chloro-2,3-difluoro-phenyl)-2,7-dimethyl-5,7-dihydro-4H-pyrazolo[3,4-c]pyridin-6-yl]-(6-quinolyl)methanone; |
| 515 | [(7S)-2,7-Dimethyl-3-(2,3,4-trifluorophenyl)-5,7-dihydro-4H-pyrazolo[3,4-c]pyridin-6-yl]-(6-quinolyl)methanone; |
| 516 | [(7S)-2,7-Dimethyl-3-(3,4,5-trifluorophenyl)-5,7-dihydro-4H-pyrazolo[3,4-c]pyridin-6-yl]-(1-oxidoquinolin-1-ium-6-yl)methanone; |
| 517 | [(7S)-2,7-Dimethyl-3-(3,4,5-trifluorophenyl)-5,7-dihydro-4H-pyrazolo[3,4-c]pyridin-6-yl]-(2-hydroxy-6-quinolyl)methanone; |
| 518 | [(7S)-2,7-Dimethyl-3-(3,4,5-trifluorophenyl)-5,7-dihydro-4H-pyrazolo[3,4-c]pyridin-6-yl]-(4-hydroxy-6-quinolyl)methanone; |
| 519 | [(7S)-2,7-Dimethyl-3-(6-methyl-3-pyridyl)-5,7-dihydro-4H-pyrazolo[3,4-c]pyridin-6-yl]-(6-quinolyl)methanone; |
| 520 | [(7S)-2,7-Dimethyl-3-(2-methyl-4-pyridyl)-5,7-dihydro-4H-pyrazolo[3,4-c]pyridin-6-yl]-(6-quinolyl)methanone; |
| 521 | [(7S)-3-[6-(Difluoromethyl)-3-pyridyl]-2,7-dimethyl-5,7-dihydro-4H-pyrazolo[3,4-c]pyridin-6-yl]-(6-quinolyl)methanone; |
| 522 | [(7S)-2,7-Dimethyl-3-[6-(trifluoromethyl)-3-pyridyl]-5,7-dihydro-4H-pyrazolo[3,4-c]pyridin-6-yl]-(6-quinolyl)methanone; |
| 523 | [(7S)-2,7-Dimethyl-3-[2-(trifluoromethyl)-4-pyridyl]-5,7-dihydro-4H-pyrazolo[3,4-c]pyridin-6-yl]-(6-quinolyl)methanone; |
| 524 | [(7S)-2,7-Dimethyl-3-[5-(trifluoromethyl)-3-thienyl]-5,7-dihydro-4H-pyrazolo[3,4-c]pyridin-6-yl]-(6-quinolyl)methanone; |
| 525 | [(7S)-3-(6-Methoxy-3-pyridyl)-2,7-dimethyl-5,7-dihydro-4H-pyrazolo[3,4-c]pyridin-6-yl]-(6-quinolyl)methanone; |
| 526 | [(7S)-3-(2-Methoxy-4-pyridyl)-2,7-dimethyl-5,7-dihydro-4H-pyrazolo[3,4-c]pyridin-6-yl]-(6-quinolyl)methanone; |
| 527 | [(7S)-3-[6-(Difluoromethoxy)-3-pyridyl]-2,7-dimethyl-5,7-dihydro-4H-pyrazolo[3,4-c]pyridin-6-yl]-(6-quinolyl)methanone; |
| 528 | [(7S)-3-[5-(Difluoromethoxy)-3-pyridyl]-2,7-dimethyl-5,7-dihydro-4H-pyrazolo[3,4-c]pyridin-6-yl]-(6-quinolyl)methanone; |
| 529 | [(7S)-3-(6-Methoxy-5-methyl-3-pyridyl)-2,7-dimethyl-5,7-dihydro-4H-pyrazolo[3,4-c]pyridin-6-yl]-(6-quinolyl)methanone; |
| 530 | [(7S)-3-[6-Methoxy-5-(trifluoromethyl)-3-pyridyl]-2,7-dimethyl-5,7-dihydro-4H-pyrazolo[3,4-c]pyridin-6-yl]-(6-quinolyl)methanone; |
| 531 | [(7S)-3-(1H-Indol-7-yl)-2,7-dimethyl-5,7-dihydro-4H-pyrazolo[3,4-c]pyridin-6-yl]-(6-quinolyl)methanone; |
| 532 | [(7S)-3-(Benzofuran-6-yl)-2,7-dimethyl-5,7-dihydro-4H-pyrazolo[3,4-c]pyridin-6-yl]-(6-quinolyl)methanone; |
| 533 | [(7S)-3-(Benzofuran-5-yl)-2,7-dimethyl-5,7-dihydro-4H-pyrazolo[3,4-c]pyridin-6-yl]-(6-quinolyl)methanone; |
| 534 | [(7S)-3-(Benzofuran-7-yl)-2,7-dimethyl-5,7-dihydro-4H-pyrazolo[3,4-c]pyridin-6-yl]-(6-quinolyl)methanone; |
| 535 | [(7S)-3-(Benzofuran-4-yl)-2,7-dimethyl-5,7-dihydro-4H-pyrazolo[3,4-c]pyridin-6-yl]-(6-quinolyl)methanone; |
| 536 | [(7S)-3-(5-Fluorobenzofuran-7-yl)-2,7-dimethyl-5,7-dihydro-4H-pyrazolo[3,4-c]pyridin-6-yl]-(6-quinolyl)methanone; |
| 537 | [(7S)-3-(1,3-Benzothiazol-4-yl)-2,7-dimethyl-5,7-dihydro-4H-pyrazolo[3,4-c]pyridin-6-yl]-(6-quinolyl)methanone; |
| 538 | [(7S)-3-(2,1,3-Benzoxadiazol-4-yl)-2,7-dimethyl-5,7-dihydro-4H-pyrazolo[3,4-c]pyridin-6-yl]-(6-quinolyl)methanone; |
| 539 | [(7S)-3-(2,3-Dihydrobenzofuran-7-yl)-2,7-dimethyl-5,7-dihydro-4H-pyrazolo[3,4-c]pyridin-6-yl]-(6-quinolyl)methanone; |
| 540 | [(7S)-3-(1,3-Benzodioxol-5-yl)-2,7-dimethyl-5,7-dihydro-4H-pyrazolo[3,4-c]pyridin-6-yl]-(6-quinolyl)methanone; |
| 541 | [(7S)-3-(1,3-Benzodioxol-4-yl)-2,7-dimethyl-5,7-dihydro-4H-pyrazolo[3,4-c]pyridin-6-yl]-(6-quinolyl)methanone; |
| 542 | [(7S)-3-(2,2-Difluoro-1,3-benzodioxol-4-yl)-2,7-dimethyl-5,7-dihydro-4H-pyrazolo[3,4-c]pyridin-6-yl]-(6-quinolyl)methanone; |
| 543 | [(7S)-2,7-Dimethyl-3-(3,4,5-trifluorophenyl)-5,7-dihydro-4H-pyrazolo[3,4-c]pyridin-6-yl]-(5-isoquinolyl)methanone; |
| 544 | [(7S)-2,7-Dimethyl-3-(3,4,5-trifluorophenyl)-5,7-dihydro-4H-pyrazolo[3,4-c]pyridin-6-yl]-(6-isoquinolyl)methanone; |
| 545 | [(7S)-2,7-Dimethyl-3-(3,4,5-trifluorophenyl)-5,7-dihydro-4H-pyrazolo[3,4-c]pyridin-6-yl]-(5-fluoro-3-quinolyl)methanone; |
| 546 | [(7S)-2,7-Dimethyl-3-(3,4,5-trifluorophenyl)-5,7-dihydro-4H-pyrazolo[3,4-c]pyridin-6-yl]-(8-fluoro-4-isoquinolyl)methanone; |
| 547 | (4-Bromo-6-quinolyl)-[(7S)-2,7-dimethyl-3-(3,4,5-trifluorophenyl)-5,7-dihydro-4H-pyrazolo[3,4-c]pyridin-6-yl]methanone; |
| 548 | [(7S)-2,7-Dimethyl-3-(3,4,5-trifluorophenyl)-5,7-dihydro-4H-pyrazolo[3,4-c]pyridin-6-yl]-(2-methyl-6-quinolyl)methanone; |

TABLE 2-continued

| Example # | Compound Name |
|---|---|
| 549 | [(7S)-2,7-Dimethyl-3-(3,4,5-trifluorophenyl)-5,7-dihydro-4H-pyrazolo[3,4-c]pyridin-6-yl]-(4-methyl-6-quinolyl)methanone; |
| 550 | [(7S)-2,7-Dimethyl-3-(3,4,5-trifluorophenyl)-5,7-dihydro-4H-pyrazolo[3,4-c]pyridin-6-yl]-(8-methoxy-4-quinolyl)methanone; |
| 551 | 5,6-Dihydro-4H-pyrrolo[1,2-b]pyrazol-3-yl-[(7S)-2,7-dimethyl-3-(3,4,5-trifluorophenyl)-5,7-dihydro-4H-pyrazolo[3,4-c]pyridin-6-yl]methanone; |
| 552 | [(7S)-2,7-Dimethyl-3-(3,4,5-trifluorophenyl)-5,7-dihydro-4H-pyrazolo[3,4-c]pyridin-6-yl]-(4,5,6,7-tetrahydropyrazolo[1,5-a]pyridin-3-yl)methanone; |
| 553 | 6,7-Dihydro-5H-pyrazolo[5,1-b][1,3]oxazin-2-yl-[(7S)-2,7-dimethyl-3-(3,4,5-trifluorophenyl)-5,7-dihydro-4H-pyrazolo[3,4-c]pyridin-6-yl]methanone; |
| 554 | 6,7-Dihydro-5H-pyrazolo[5,1-b][1,3]oxazin-3-yl-[(7S)-2,7-dimethyl-3-(3,4,5-trifluorophenyl)-5,7-dihydro-4H-pyrazolo[3,4-c]pyridin-6-yl]methanone; |
| 555 | [(7S)-2,7-Dimethyl-3-(3,4,5-trifluorophenyl)-5,7-dihydro-4H-pyrazolo[3,4-c]pyridin-6-yl]-(3-methyl-6,7-dihydro-5H-pyrazolo[5,1-b][1,3]oxazin-2-yl)methanone; |
| 556 | [(7S)-2,7-Dimethyl-3-(3,4,5-trifluorophenyl)-5,7-dihydro-4H-pyrazolo[3,4-c]pyridin-6-yl]-(2,6,6-trimethyl-4,7-dihydropyrazolo[5,1-c][1,4]oxazin-3-yl)methanone; |
| 557 | [(7S)-2,7-Dimethyl-3-(3,4,5-trifluorophenyl)-5,7-dihydro-4H-pyrazolo[3,4-c]pyridin-6-yl]-(3,6,6-trimethyl-4,7-dihydropyrazolo[5,1-c][1,4]oxazin-2-yl)methanone; |
| 558 | ((S)-2,7-Dimethyl-3-(3,4,5-trifluorophenyl)-4,5-dihydro-2H-pyrazolo[3,4-c]pyridin-6(7H)-yl)(7-(trifluoromethyl)-4,5,6,7-tetrahydropyrazolo[1,5-a]pyrimidin-3-yl)methanone; |
| 559 | 6,7-Dihydro-5H-pyrrolo[1,2-a]imidazol-3-yl-[(7S)-2,7-dimethyl-3-(3,4,5-trifluorophenyl)-5,7-dihydro-4H-pyrazolo[3,4-c]pyridin-6-yl]methanone; |
| 560 | [(7S)-2,7-Dimethyl-3-(3,4,5-trifluorophenyl)-5,7-dihydro-4H-pyrazolo[3,4-c]pyridin-6-yl]-(5,6,7,8-tetrahydroimidazo[1,2-a]pyridin-3-yl)methanone; |
| 561 | [2-(Difluoromethyl)-5,6,7,8-tetrahydroimidazo[1,2-a]pyridin-3-yl]-[(7S)-2,7-dimethyl-3-(3,4,5-trifluorophenyl)-5,7-dihydro-4H-pyrazolo[3,4-c]pyridin-6-yl]methanone; |
| 562 | 6,8-Dihydro-5H-imidazo[2,1-c][1,4]oxazin-3-yl-[(7S)-2,7-dimethyl-3-(3,4,5-trifluorophenyl)-5,7-dihydro-4H-pyrazolo[3,4-c]pyridin-6-yl]methanone; |
| 563 | 3,4-Dihydro-2H-pyrano[2,3-b]pyridin-6-yl-[(7S)-2,7-dimethyl-3-(3,4,5-trifluorophenyl)-5,7-dihydro-4H-pyrazolo[3,4-c]pyridin-6-yl]methanone; |
| 564 | 3,4-Dihydro-2H-pyrano[2,3-b]pyridin-5-yl-[(7S)-2,7-dimethyl-3-(3,4,5-trifluorophenyl)-5,7-dihydro-4H-pyrazolo[3,4-c]pyridin-6-yl]methanone; |
| 565 | 6,8-Dihydro-5H-pyrano[3,4-b]pyridin-4-yl-[(7S)-2,7-dimethyl-3-(3,4,5-trifluorophenyl)-5,7-dihydro-4H-pyrazolo[3,4-c]pyridin-6-yl]methanone; |
| 566 | 6,8-Dihydro-5H-pyrano[3,4-b]pyridin-2-yl-[(7S)-2,7-dimethyl-3-(3,4,5-trifluorophenyl)-5,7-dihydro-4H-pyrazolo[3,4-c]pyridin-6-yl]methanone; |
| 567 | 7,8-Dihydro-5H-pyrano[4,3-b]pyridin-3-yl-[(7S)-2,7-dimethyl-3-(3,4,5-trifluorophenyl)-5,7-dihydro-4H-pyrazolo[3,4-c]pyridin-6-yl]methanone; |
| 568 | 3,4-Dihydro-2H-pyrano[3,2-b]pyridin-8-yl-[(7S)-2,7-dimethyl-3-(3,4,5-trifluorophenyl)-5,7-dihydro-4H-pyrazolo[3,4-c]pyridin-6-yl]methanone; |
| 569 | 2,3-Dihydro-[1,4]dioxino[2,3-b]pyridin-8-yl-[(7S)-2,7-dimethyl-3-(3,4,5-trifluorophenyl)-5,7-dihydro-4H-pyrazolo[3,4-c]pyridin-6-yl]methanone; |
| 570 | 2,3-Dihydro-[1,4]dioxino[2,3-b]pyridin-7-yl-[(7S)-2,7-dimethyl-3-(3,4,5-trifluorophenyl)-5,7-dihydro-4H-pyrazolo[3,4-c]pyridin-6-yl]methanone; |
| 571 | 3,4-Dihydro-2H-pyrido[3,2-b][1,4]oxazin-7-yl-[(7S)-2,7-dimethyl-3-(3,4,5-trifluorophenyl)-5,7-dihydro-4H-pyrazolo[3,4-c]pyridin-6-yl]methanone; |
| 572 | [(7S)-2,7-Dimethyl-3-(3,4,5-trifluorophenyl)-5,7-dihydro-4H-pyrazolo[3,4-c]pyridin-6-yl]-(4-methyl-2,3-dihydropyrido[3,2-b][1,4]oxazin-7-yl)methanone; |
| 573 | 3,4-Dihydro-2H-pyrano[2,3-c]pyridin-6-yl-[(7S)-2,7-dimethyl-3-(3,4,5-trifluorophenyl)-5,7-dihydro-4H-pyrazolo[3,4-c]pyridin-6-yl]methanone; |
| 574 | [(7S)-2,7-Dimethyl-3-(3,4,5-trifluorophenyl)-5,7-dihydro-4H-pyrazolo[3,4-c]pyridin-6-yl]-(1,2,3,4-tetrahydroisoquinolin-5-yl)methanone; |
| 575 | [(7S)-2,7-Dimethyl-3-(3,4,5-trifluorophenyl)-5,7-dihydro-4H-pyrazolo[3,4-c]pyridin-6-yl]-(1,2,3,4-tetrahydroisoquinolin-8-yl)methanone; |
| 576 | [(7S)-2,7-Dimethyl-3-(3,4,5-trifluorophenyl)-5,7-dihydro-4H-pyrazolo[3,4-c]pyridin-6-yl]-isochroman-5-yl-methanone; |
| 577 | [(7S)-2,7-Dimethyl-3-(3,4,5-trifluorophenyl)-5,7-dihydro-4H-pyrazolo[3,4-c]pyridin-6-yl]-isochroman-7-yl-methanone; |
| 578 | [(7S)-2,7-Dimethyl-3-(3,4,5-trifluorophenyl)-5,7-dihydro-4H-pyrazolo[3,4-c]pyridin-6-yl]-isochroman-6-yl-methanone; |
| 579 | [(7S)-2,7-Dimethyl-3-(3,4,5-trifluorophenyl)-5,7-dihydro-4H-pyrazolo[3,4-c]pyridin-6-yl]-isochroman-8-yl-methanone; |
| 580 | Chroman-6-yl-[(7S)-2,7-dimethyl-3-(3,4,5-trifluorophenyl)-5,7-dihydro-4H-pyrazolo[3,4-c]pyridin-6-yl]methanone; |
| 581 | Chroman-5-yl-[(7S)-2,7-dimethyl-3-(3,4,5-trifluorophenyl)-5,7-dihydro-4H-pyrazolo[3,4-c]pyridin-6-yl]methanone; |
| 582 | Chroman-7-yl-[(7S)-2,7-dimethyl-3-(3,4,5-trifluorophenyl)-5,7-dihydro-4H-pyrazolo[3,4-c]pyridin-6-yl]methanone; |
| 583 | Chroman-8-yl-[(7S)-2,7-dimethyl-3-(3,4,5-trifluorophenyl)-5,7-dihydro-4H-pyrazolo[3,4-c]pyridin-6-yl]methanone; |
| 584 | 4-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one; |

TABLE 2-continued

| Example # | Compound Name |
|---|---|
| 585 | 4-[(7S)-2,7-Dimethyl-3-(3,4,5-trifluorophenyl)-5,7-dihydro-4H-pyrazolo[3,4-c]pyridine-6-carbonyl]-3-methyl-1,3-benzoxazol-2-one; |
| 586 | 5-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one; |
| 587 | 7-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one; |
| 588 | 6-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one; |
| 589 | 7-[(7S)-2,7-dimethyl-3-(3,4,5-trifluorophenyl)-5,7-dihydro-4H-pyrazolo[3,4-c]pyridine-6-carbonyl]-3-methyl-1,3-benzoxazol-2-one; |
| 590 | 7-[(7S)-2,7-Dimethyl-3-(3,4,5-trifluorophenyl)-5,7-dihydro-4H-pyrazolo[3,4-c]pyridine-6-carbonyl]-4-methyl-1,4-benzoxazin-3-one; |
| 591 | [(7S)-2,7-8-[(7S)-2,7-Dimethyl-3-(3,4,5-trifluorophenyl)-5,7-dihydro-4H-pyrazolo[3,4-c]pyridine-6-carbonyl]-4-methyl-1,4-benzoxazin-3-one; |
| 592 | 3,4-Dihydro-2H-1,4-benzoxazin-8-yl-[(7S)-2,7-dimethyl-3-(3,4,5-trifluorophenyl)-5,7-dihydro-4H-pyrazolo[3,4-c]pyridin-6-yl]methanone; |
| 593 | [(7S)-3-[3-(Difluoromethyl)-4-fluoro-phenyl]-2,7-dimethyl-5,7-dihydro-4H-pyrazolo[3,4-c]pyridin-6-yl]-(2-methoxy-3-methyl-4-pyridyl)methanone; |
| 594 | [(7S)-3-[3-(1,1-Difluoroethyl)phenyl]-2,7-dimethyl-5,7-dihydro-4H-pyrazolo[3,4-c]pyridin-6-yl]-(2-methoxy-3-methyl-4-pyridyl)methanone; |
| 595 | [(7S)-3-[3-(Difluoromethoxy)-4-fluoro-phenyl]-2,7-dimethyl-5,7-dihydro-4H-pyrazolo[3,4-c]pyridin-6-yl]-(2-methoxy-3-methyl-4-pyridyl)methanone; |
| 596 | Chroman-7-yl-[(7S)-3-[3-(difluoromethoxy)-5-fluoro-phenyl]-2,7-dimethyl-5,7-dihydro-4H-pyrazolo[3,4-c]pyridin-6-yl]methanone; |
| 597 | [(7S)-3-[3-(Difluoromethoxy)-5-fluoro-phenyl]-2,7-dimethyl-5,7-dihydro-4H-pyrazolo[3,4-c]pyridin-6-yl]-(2-methoxy-3-methyl-4-pyridyl)methanone; |
| 598 | [(7S)-3-(4-Fluoro-3-methyl-phenyl)-2,7-dimethyl-5,7-dihydro-4H-pyrazolo[3,4-c]pyridin-6-yl]-(2-methoxy-3-methyl-4-pyridyl)methanone; |
| 599 | [(7S)-2,7-Dimethyl-3-(3,4,5-trifluorophenyl)-5,7-dihydro-4H-pyrazolo[3,4-c]pyridin-6-yl]-(3-methoxy-2-methyl-4-pyridyl)methanone; |
| 600 | [(7S)-2,7-Dimethyl-3-(3,4,5-trifluorophenyl)-5,7-dihydro-4H-pyrazolo[3,4-c]pyridin-6-yl]-(1-methyl-4-phenyl-imidazol-2-yl)methanone; |
| 601 | [(7S)-2,7-Dimethyl-3-(3,4,5-trifluorophenyl)-5,7-dihydro-4H-pyrazolo[3,4-c]pyridin-6-yl]-(1-phenylimidazol-4-yl)methanone; |
| 602 | [(7S)-2,7-Dimethyl-3-(3,4,5-trifluorophenyl)-5,7-dihydro-4H-pyrazolo[3,4-c]pyridin-6-yl]-[3-methyl-2-(2-pyridyl)imidazol-4-yl]methanone; |
| 603 | [(7S)-2,7-Dimethyl-3-(3,4,5-trifluorophenyl)-5,7-dihydro-4H-pyrazolo[3,4-c]pyridin-6-yl]-(2-fluoro-6-pyrazol-1-yl-phenyl)methanone; |
| 604 | [(7S)-2,7-Dimethyl-3-(3,4,5-trifluorophenyl)-5,7-dihydro-4H-pyrazolo[3,4-c]pyridin-6-yl]-spiro[3,4-dihydro-1,4-benzoxazine-2,1'-cyclopropane]-8-yl-methanone; |
| 605 | [(7S)-2,7-Dimethyl-3-(3,4,5-trifluorophenyl)-5,7-dihydro-4H-pyrazolo[3,4-c]pyridin-6-yl]-(3-fluoro-1H-pyrrolo[2,3-b]pyridin-4-yl)methanone; |
| 606 | [(7S)-2,7-Dimethyl-3-(3,4,5-trifluorophenyl)-5,7-dihydro-4H-pyrazolo[3,4-c]pyridin-6-yl]-(9-methylpurin-6-yl)methanone; |
| 607 | [(7S)-2,7-Dimethyl-3-(3,4,5-trifluorophenyl)-5,7-dihydro-4H-pyrazolo[3,4-c]pyridin-6-yl]-(3-fluoro-5-methoxy-4-pyridyl)methanone; |
| 608 | (3-Chloro-4-methoxy-2-pyridyl)-[(7S)-3-[3-(difluoromethyl)-5-fluoro-phenyl]-2,7-dimethyl-5,7-dihydro-4H-pyrazolo[3,4-c]pyridin-6-yl]methanone; |
| 609 | [(7S)-3-[3-(Difluoromethyl)-5-fluoro-phenyl]-2,7-dimethyl-5,7-dihydro-4H-pyrazolo[3,4-c]pyridin-6-yl]-(2-methoxy-3-methyl-4-pyridyl)methanone; |
| 610 | Chroman-7-yl-[(7S)-3-[3-(difluoromethyl)-5-fluoro-phenyl]-2,7-dimethyl-5,7-dihydro-4H-pyrazolo[3,4-c]pyridin-6-yl]methanone; |
| 611 | Chroman-7-yl-[(7S)-3-(3-fluoro-5-methoxy-phenyl)-2,7-dimethyl-5,7-dihydro-4H-pyrazolo[3,4-c]pyridin-6-yl]methanone; |
| 612 | (3-Chloro-4-methoxy-2-pyridyl)-[(7S)-3-[3-(difluoromethoxy)-5-fluoro-phenyl]-2,7-dimethyl-5,7-dihydro-4H-pyrazolo[3,4-c]pyridin-6-yl]methanone; |
| 613 | [(7S)-3-(3-Fluoro-5-methoxy-phenyl)-2,7-dimethyl-5,7-dihydro-4H-pyrazolo[3,4-c]pyridin-6-yl]-(2-methoxy-3-methyl-4-pyridyl)methanone; |
| 614 | (3-Chloro-4-methoxy-2-pyridyl)-[(7S)-3-(3-fluoro-5-methoxy-phenyl)-2,7-dimethyl-5,7-dihydro-4H-pyrazolo[3,4-c]pyridin-6-yl]methanone; |
| 615 | racemic-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone; |
| 616 | (R*)-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone; |
| 617 | (S)-(1,6-Dimethyl-1H-pyrazolo[3,4-d]pyrimidin-4-yl)(2,7-dimethyl-3-(3,4,5-trifluorophenyl)-2,4,5,7-tetrahydro-6H-pyrazolo[3,4-c]pyridin-6-yl)methanone; and |
| 618 | Cyclopropyl-2-methyl-imidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone; | and pharmaceutically acceptable salts, isotopes, N-oxides, solvates, and stereoisomers thereof.

An additional embodiment of the invention is a compound selected from the group consisting of compounds of Formula (I), Formula (II), Formula (IIA), Formula (IIB), or Formula (IIC), or Formula (IID), or Formula (IIE), or Formula (IIF), or a combination thereof.

A further embodiment of the current invention is a compound selected from the group consisting of:

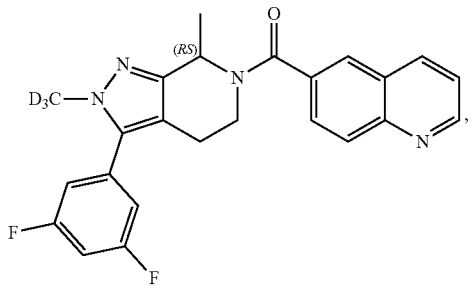

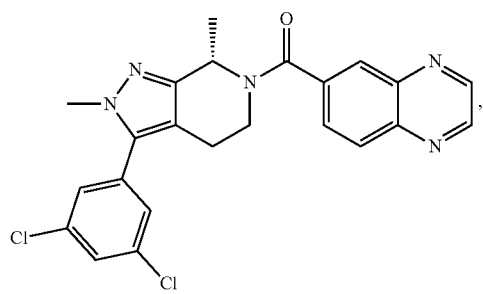

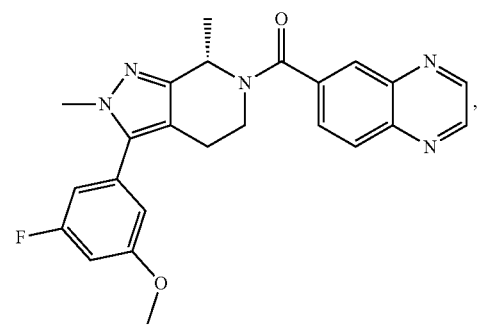

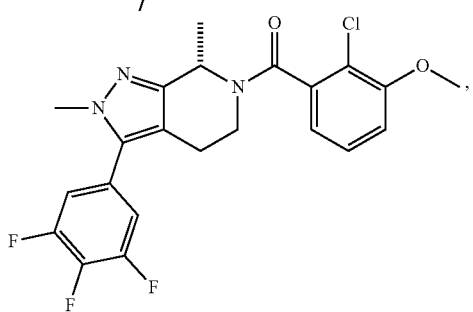

-continued

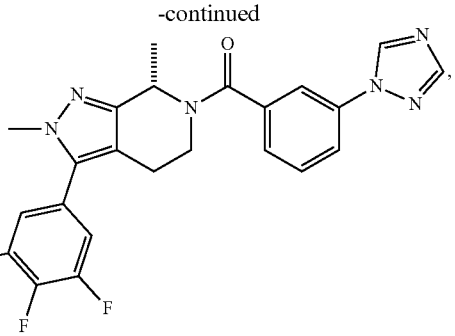

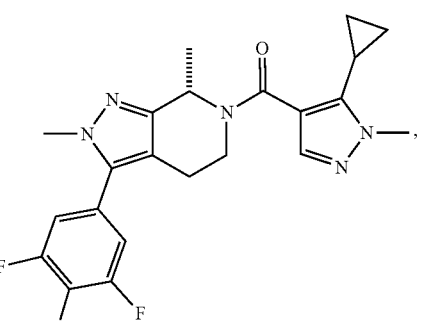

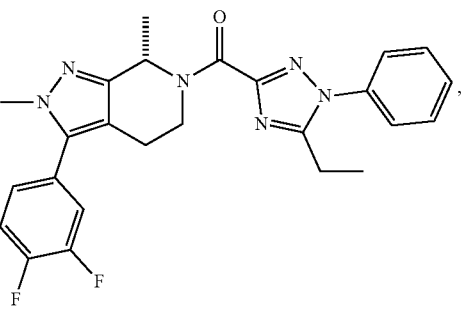

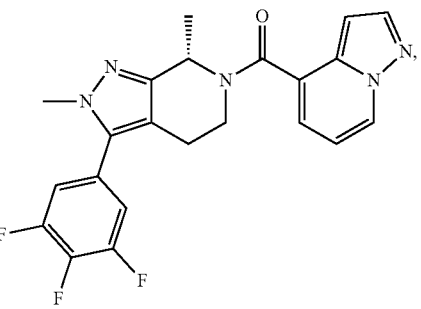

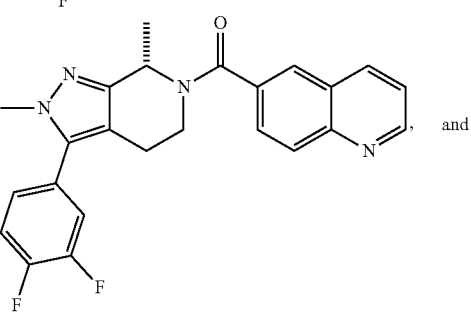, and

-continued

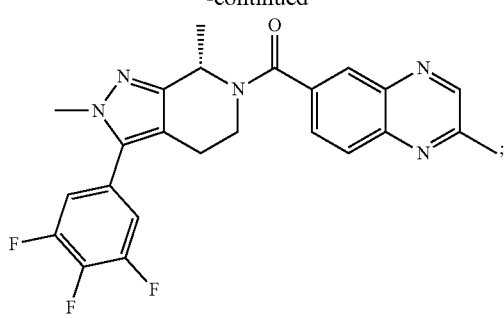

and pharmaceutically acceptable salts, isotopes, N-oxides, solvates, and stereoisomers thereof.

An additional embodiment of the invention is a pharmaceutical composition comprising:

(A) a therapeutically effective amount of at least one compound selected from compounds of Formula (II):

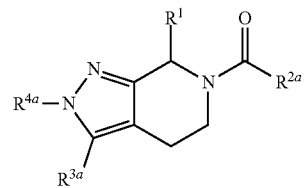

wherein

R$^1$ is C$_{1-4}$alkyl;

R$^{2a}$ is selected from the group consisting of:

(a)

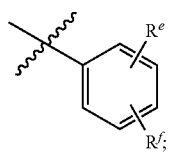

(b) 6-Membered heteroaryl selected from the group consisting of:

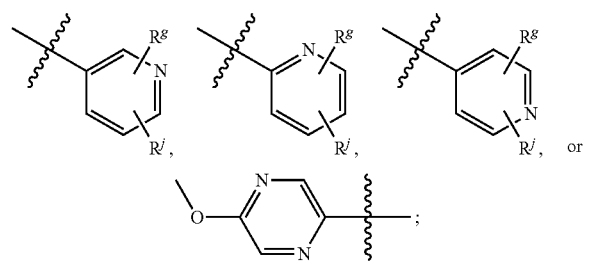

(c) 5-Membered heteroaryl selected from the group consisting of:

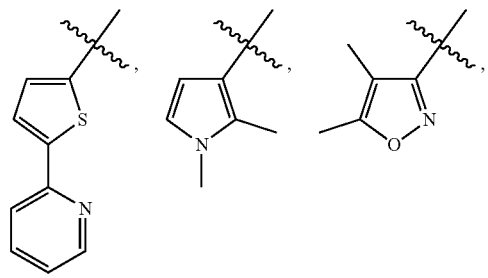

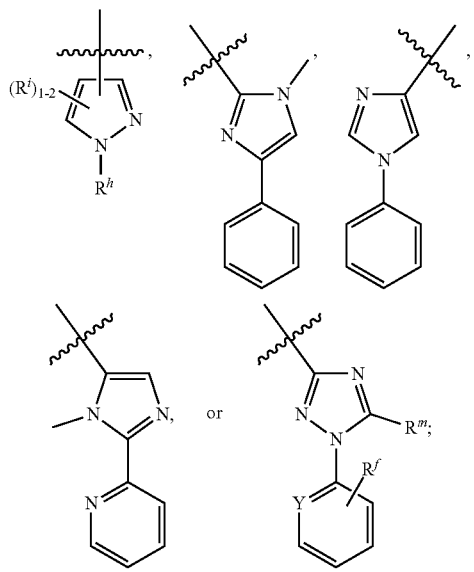

(d) 5,6-Fused or 6,5-fused heteroaryl selected from the group consisting of:

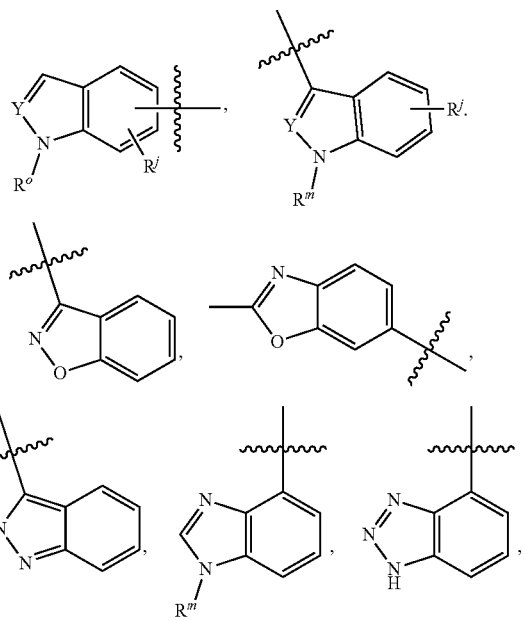

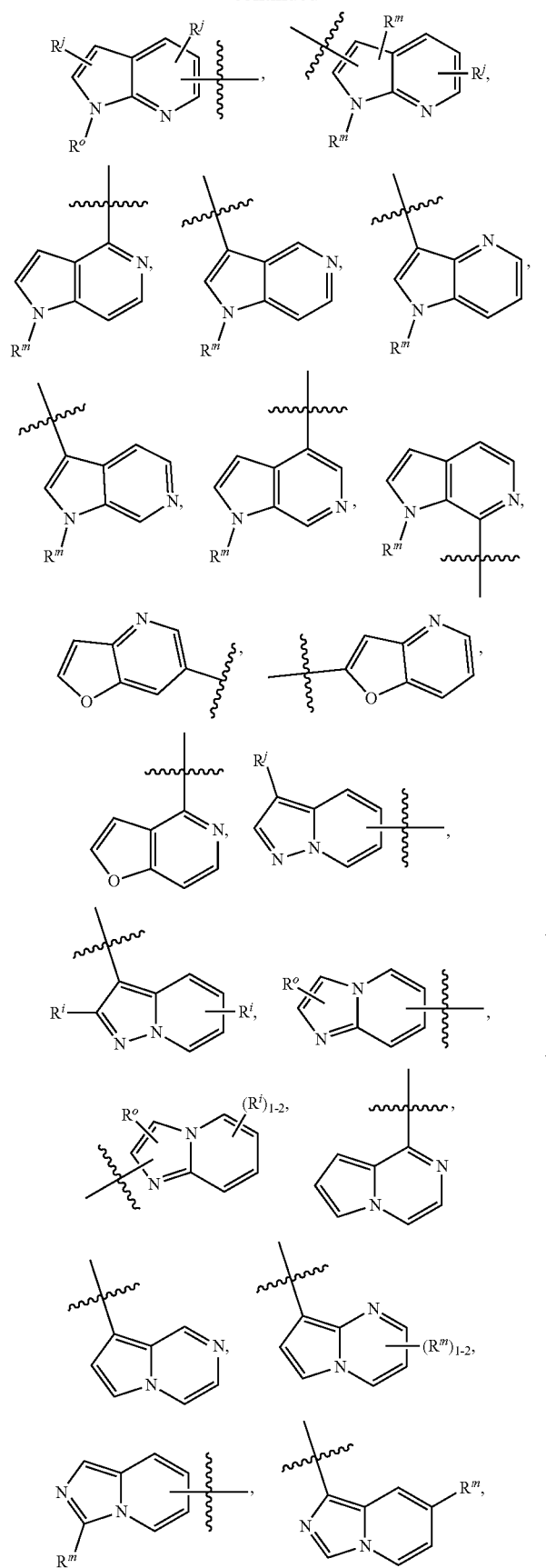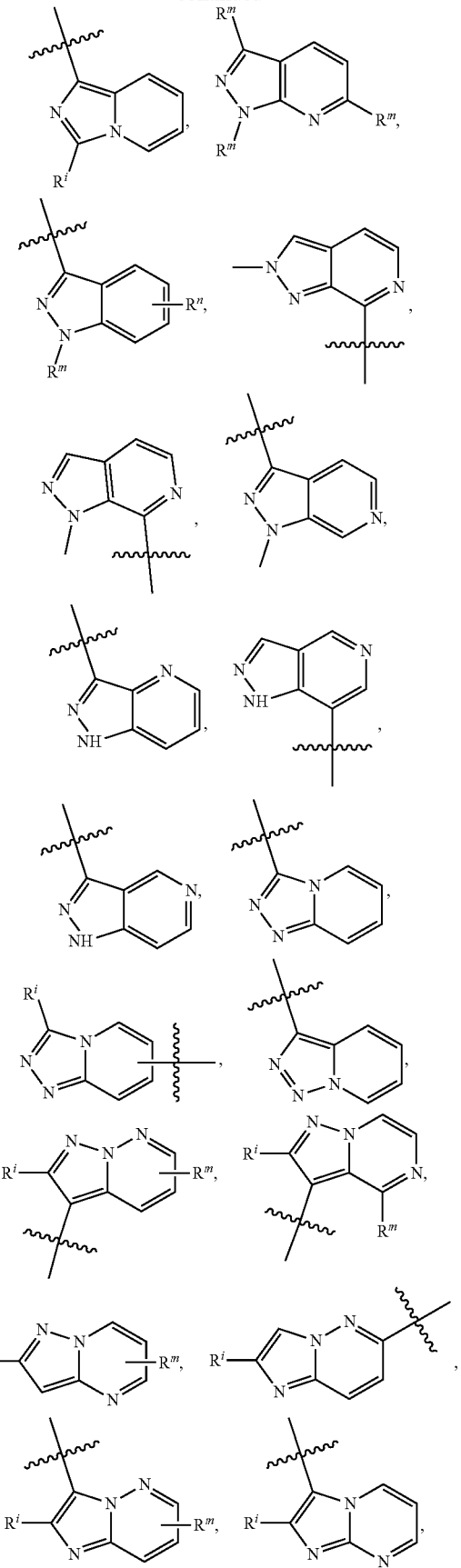

-continued
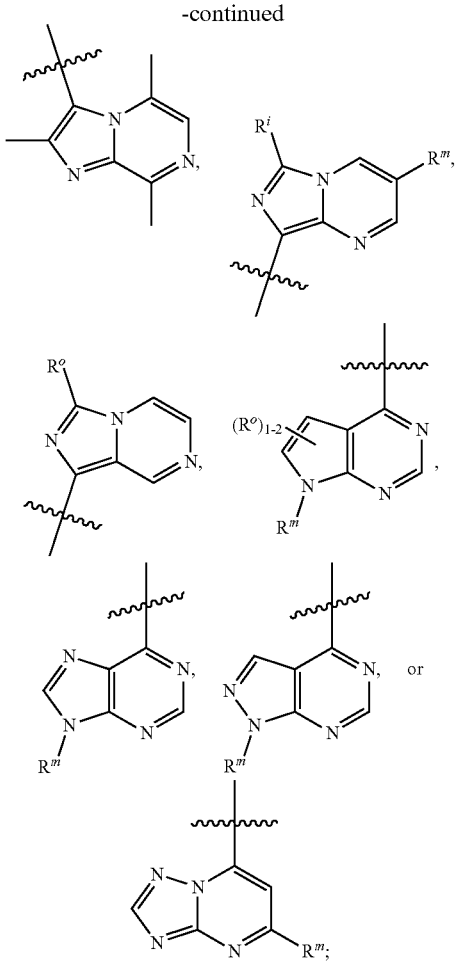
(e) Fused 6,6 heteroaryl selected from the group consisting of:
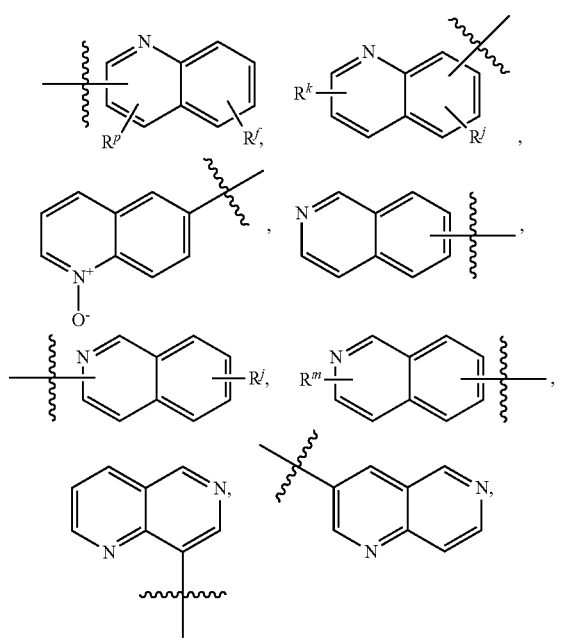
-continued
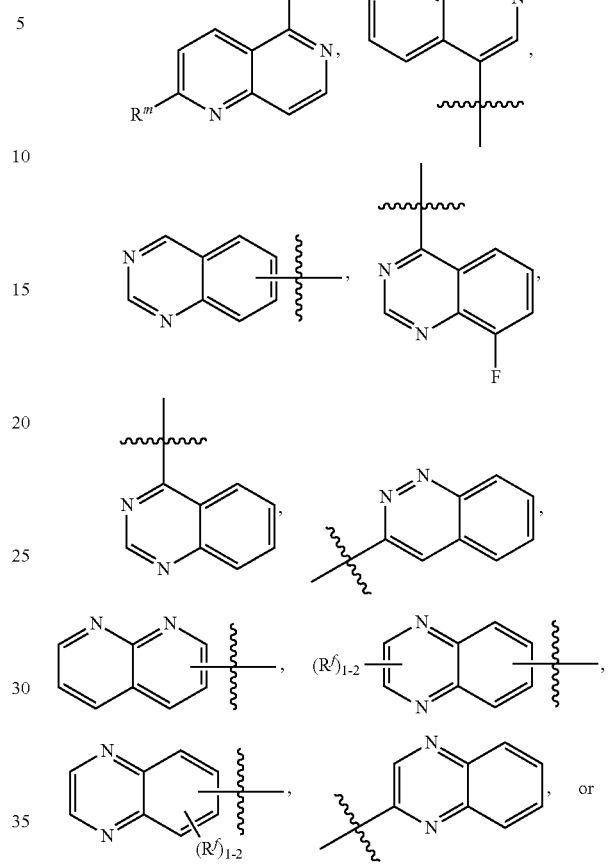
(f) Heterocycloalkyl selected from the group consisting of:
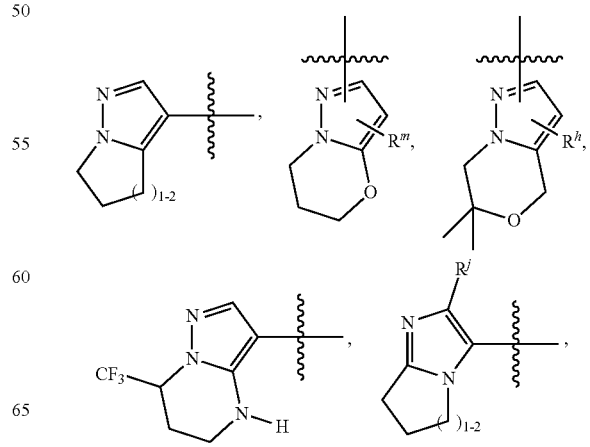

-continued

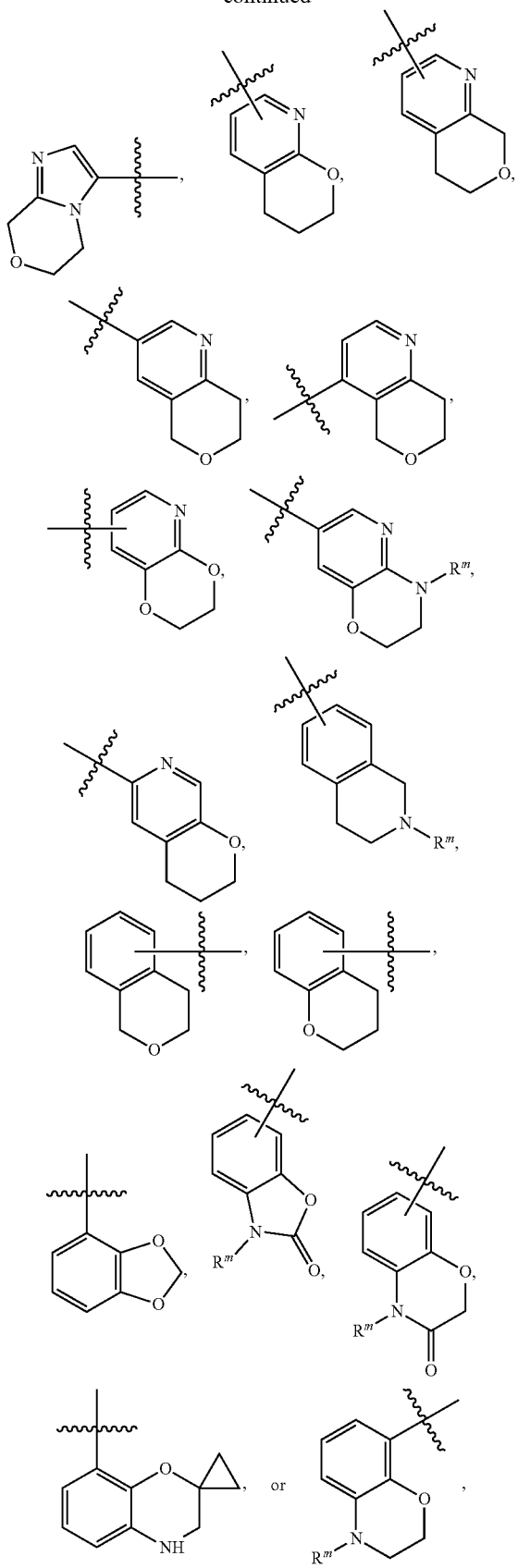

$R^{3a}$ is selected from the group consisting of:
(g) Phenyl; or phenyl substituted with one, two, or three members each independently selected from the group consisting of: halo, $C_{1-4}$alkyl, $C_{1-4}$haloalkyl, $OC_{1-4}$alkyl, and $OC_{1-6}$haloalkyl;
(h) 5-Membered heteroaryl selected from the group consisting of:

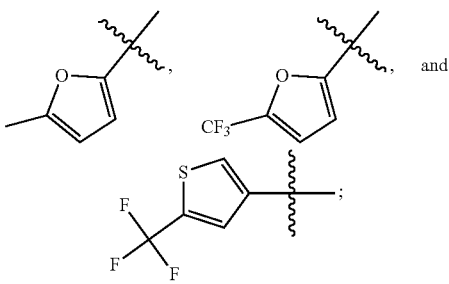

(i) 6-Membered heteroaryl selected from the group consisting of:

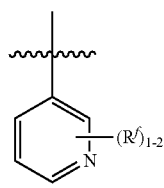

and

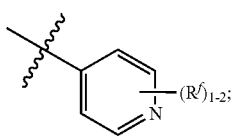

(j) 5,6-Fused or 6,5-fused heteroaryl selected from the group consisting of:

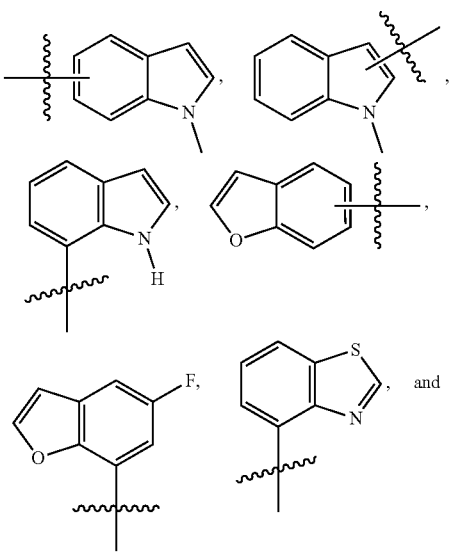

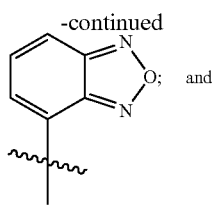

and (k) Heterocycloalkyl selected from the group consisting of:

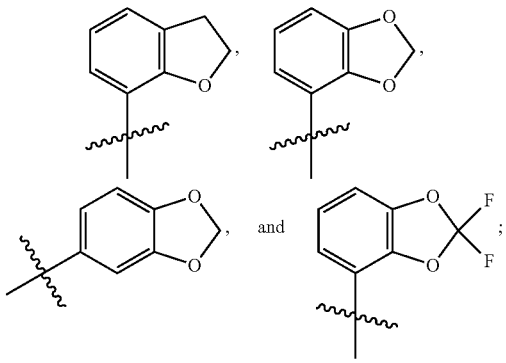

$R^e$ is selected from the group consisting of: $OC_{1-4}$alkyl, $OC_{1-4}$haloalkyl, (C=O)$NHCH_3$, and 5-membered heteroaryl ring containing two or three nitrogen members, wherein the 5-membered heteroaryl ring is optionally substituted with one $R^f$ member;

$R^f$ is selected from the group consisting of: H, halo, $C_{1-4}$alkyl, $C_{1-4}$haloalkyl, $OC_{1-4}$alkyl, and $OC_{1-4}$haloalkyl;

$R^g$ is selected from the group consisting of: $OC_{1-4}$alkyl, $OC_{1-4}$haloalkyl, $CH_2OCH_3$, $CH_2OH$,

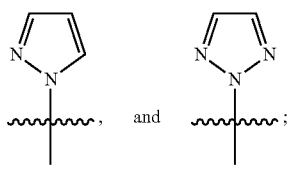 [SMILES: *n1cccn1 ; *n1nccn1]

$R^h$ is selected from the group consisting of: H, $C_{1-4}$alkyl, $C_{1-4}$haloalkyl, and $C_{3-6}$cycloalkyl;

$R^i$ is selected from the group consisting of: H, halo, $C_{1-4}$alkyl, $C_{1-4}$haloalkyl, $OC_{1-4}$alkyl, $C_{3-6}$cycloalkyl, and $C_{3-6}$cycloalkyl substituted with one or two members independently selected from: F and $CH_3$;

$R^j$ is selected from the group consisting of: H, halo, $C_{1-4}$alkyl and $C_{1-4}$haloalkyl;

$R^k$ is selected from the group consisting of: H, halo, OH, $C_{1-4}$alkyl, $C_{1-4}$haloalkyl, $OC_{1-4}$alkyl, and $OC_{1-4}$haloalkyl;

$R^m$ is H or $C_{1-4}$alkyl;

$R^n$ is selected from the group consisting of: H, halo and $OC_{1-4}$alkyl;

$R^o$ is selected from the group consisting of: H, $C_{1-4}$alkyl, and $C_{1-4}$haloalkyl;

$R^p$ is selected from the group consisting of: H, $C_{1-4}$alkyl, and $OC_{1-4}$alkyl;

Y is CH or N; and $R^{4a}$ is selected from the group consisting of: $CH_3$, $CF_2H$, $CF_3$, $C_{3-6}$cycloalkyl, and phenyl;

and pharmaceutically acceptable salts, isotopes, N-oxides, solvates, and stereoisomers of compounds of Formula (II); and (B) at least one pharmaceutically acceptable excipient.

An additional embodiment of the invention is a pharmaceutical composition comprising a therapeutically effective amount of at least one compound of Formula (IIA), as well as pharmaceutically acceptable salts, N-oxides or solvates of compounds of Formula (IIA), pharmaceutically acceptable prodrugs of compounds of Formula (IIA), and pharmaceutically active metabolites of Formula (IIA); and at least one pharmaceutically acceptable excipient.

An additional embodiment of the invention is a pharmaceutical composition comprising a therapeutically effective amount of at least one compound of Formula (IIB), as well as pharmaceutically acceptable salts, N-oxides or solvates of compounds of Formula (IIB), pharmaceutically acceptable prodrugs of compounds of Formula (IIB), and pharmaceutically active metabolites of Formula (IIB); and at least one pharmaceutically acceptable excipient.

An additional embodiment of the invention is a pharmaceutical composition comprising a therapeutically effective amount of at least one compound of Formula (IIC), as well as pharmaceutically acceptable salts, N-oxides or solvates of compounds of Formula (IIC), pharmaceutically acceptable prodrugs of compounds of Formula (IIC), and pharmaceutically active metabolites of Formula (IIC); and at least one pharmaceutically acceptable excipient.

An additional embodiment of the invention is a pharmaceutical composition comprising a therapeutically effective amount of at least one compound of Formula (IID), as well as pharmaceutically acceptable salts, N-oxides or solvates of compounds of Formula (IID), pharmaceutically acceptable prodrugs of compounds of Formula (IID), and pharmaceutically active metabolites of Formula (IID); and at least one pharmaceutically acceptable excipient.

An additional embodiment of the invention is a pharmaceutical composition comprising a therapeutically effective amount of at least one compound of Formula (IIE), as well as pharmaceutically acceptable salts, N-oxides or solvates of compounds of Formula (IIE), pharmaceutically acceptable prodrugs of compounds of Formula (IIE), and pharmaceutically active metabolites of Formula (IIE); and at least one pharmaceutically acceptable excipient.

An additional embodiment of the invention is a pharmaceutical composition comprising a therapeutically effective amount of at least one compound of Formula (IIF), as well as pharmaceutically acceptable salts, N-oxides or solvates of compounds of Formula (IIF), pharmaceutically acceptable prodrugs of compounds of Formula (IIF), and pharmaceutically active metabolites of Formula (IIF); and at least one pharmaceutically acceptable excipient.

An additional embodiment of the invention is a pharmaceutical composition comprising a therapeutically effective amount of at least one compound in Table 2, as well as pharmaceutically acceptable salts, N-oxides or solvates of compounds of Table 2, pharmaceutically acceptable prodrugs of compounds of Table 2, and pharmaceutically active metabolites of Table 2; and at least one pharmaceutically acceptable excipient.

Also within the scope of the invention are enantiomers and diastereomers of the compounds of Formula (I) (as well as Formulas (II), (IIA), (IIB), (IIC), (IID), (IIE) and (IIF)) Also within the scope of the invention are the pharmaceutically acceptable salts, N-oxides or solvates of the compounds of Formula (I) (as well as Formulas (II), (IIA), (IIB), (IIC), (IID), (IIE) and (IIF)). Also within the scope of the invention are the pharmaceutically acceptable prodrugs of compounds of Formula (I) (as well as Formulas (II), (IIA), (IIB), (IIC), (IID), (IIE) and (IIF)), and pharmaceutically active metabolites of the compounds of Formula (I) (as well as Formulas (II), (IIA), (IIB), (IIC), (IID), (IIE) and (IIF)).

Also within the scope of the invention are isotopic variations of compounds of Formula (I) (as well as Formulas (II), (IIA), (IIB), (IIC), (IID), (IIE) and (IIF)), such as, e.g., deuterated compounds of Formula (I), or Formula (II). Also within the scope of the invention are the pharmaceutically acceptable salts, N-oxides or solvates of the isotopic variations of the compounds of Formula (I) (as well as Formulas (II), (IIA), (IIB), (IIC), (IID), (IIE) and (IIF)). Also within the scope of the invention are the pharmaceutically acceptable prodrugs of the isotopic variations of the compounds of Formula (I) (as well as Formulas (II), (IIA), (IIB), (IIC), (IID), (IIE) and (IIF)), and pharmaceutically active metabolites of the isotopic variations of the compounds of Formula (I) (as well as Formulas (II), (IIA), (IIB), (IIC), (IID), (IIE) and (IIF)).

An additional embodiment of the invention is a method of treating a subject suffering from or diagnosed with a disease, disorder, or condition mediated by MGL receptor activity, comprising administering to a subject in need of such treatment a therapeutically effective amount of at least one compound selected from compounds of Formula (II):

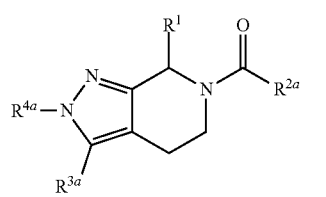

(II)

wherein
$R^1$ is $C_{1-4}$alkyl;
$R^{2a}$ is selected from the group consisting of:
(a)

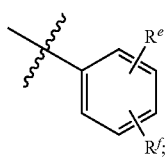

(b) 6-Membered heteroaryl selected from the group consisting of:

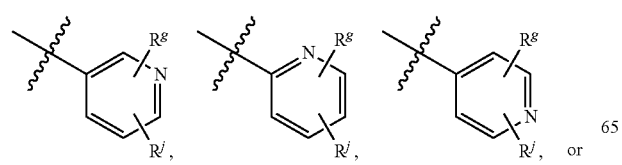

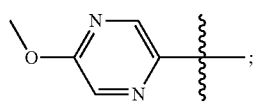

(c) 5-Membered heteroaryl selected from the group consisting of:

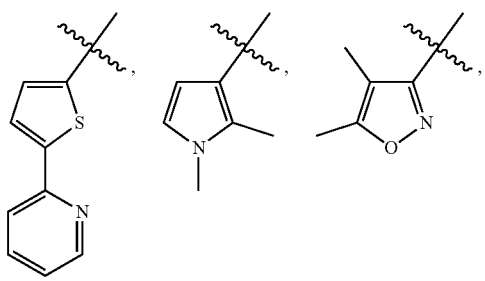

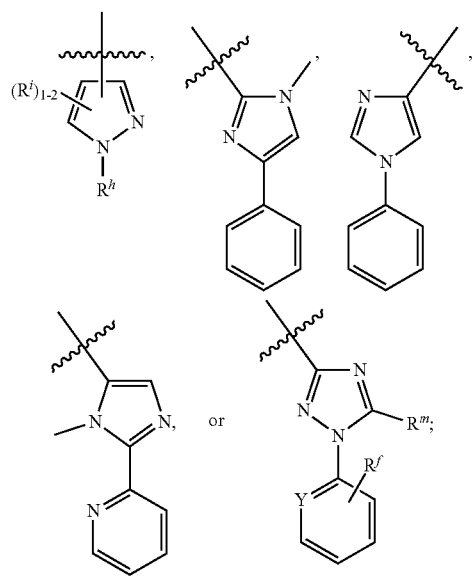

(d) 5,6-Fused or 6,5-fused heteroaryl selected from the group consisting of:

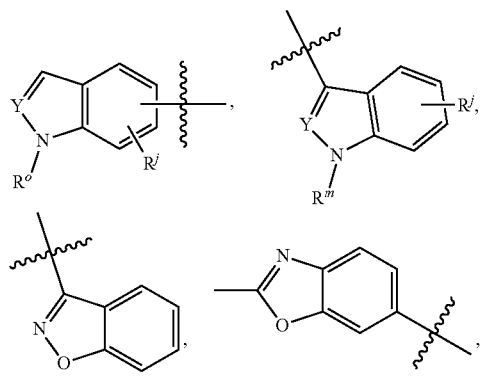

-continued
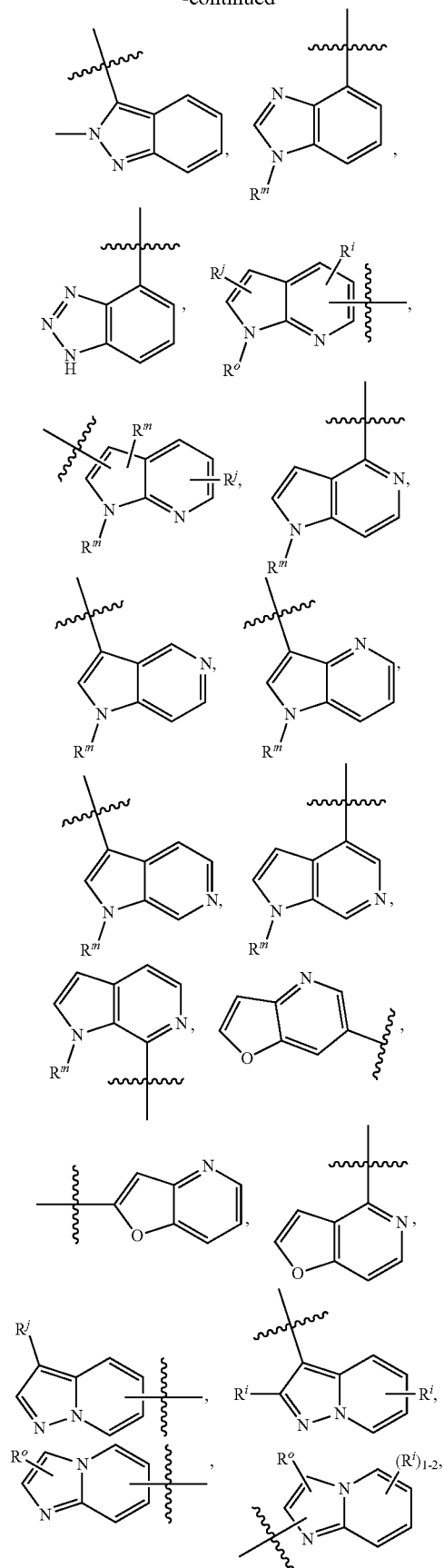
-continued
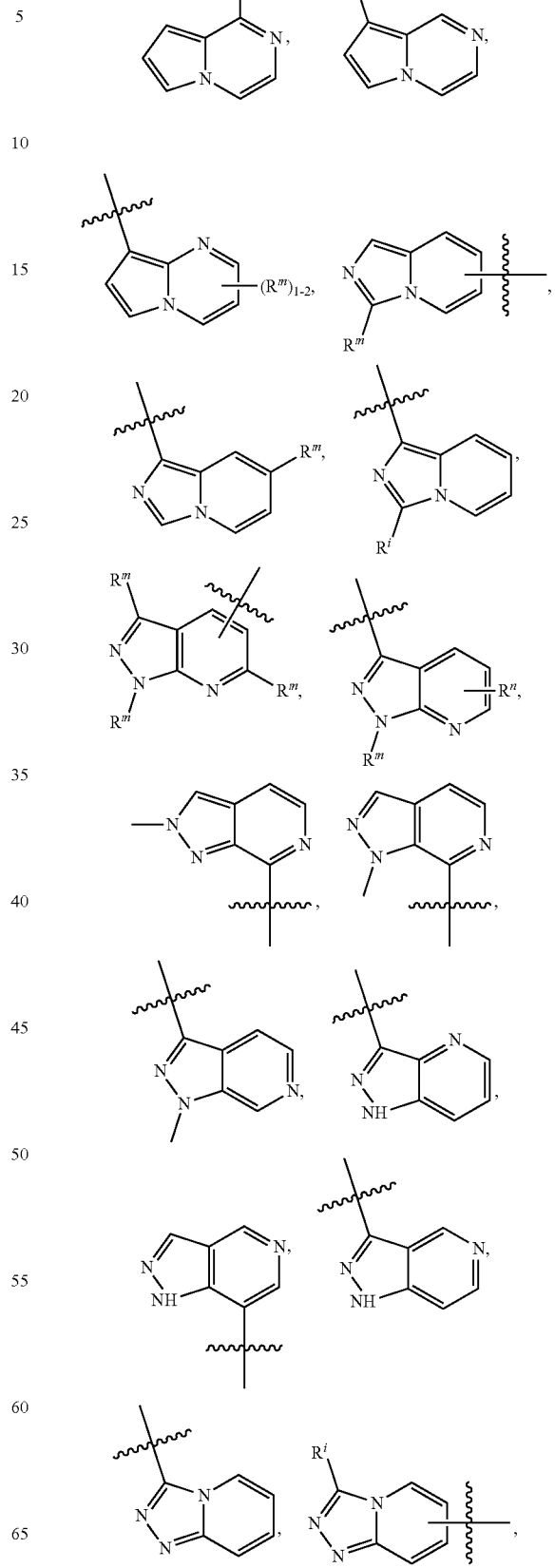

163
-continued
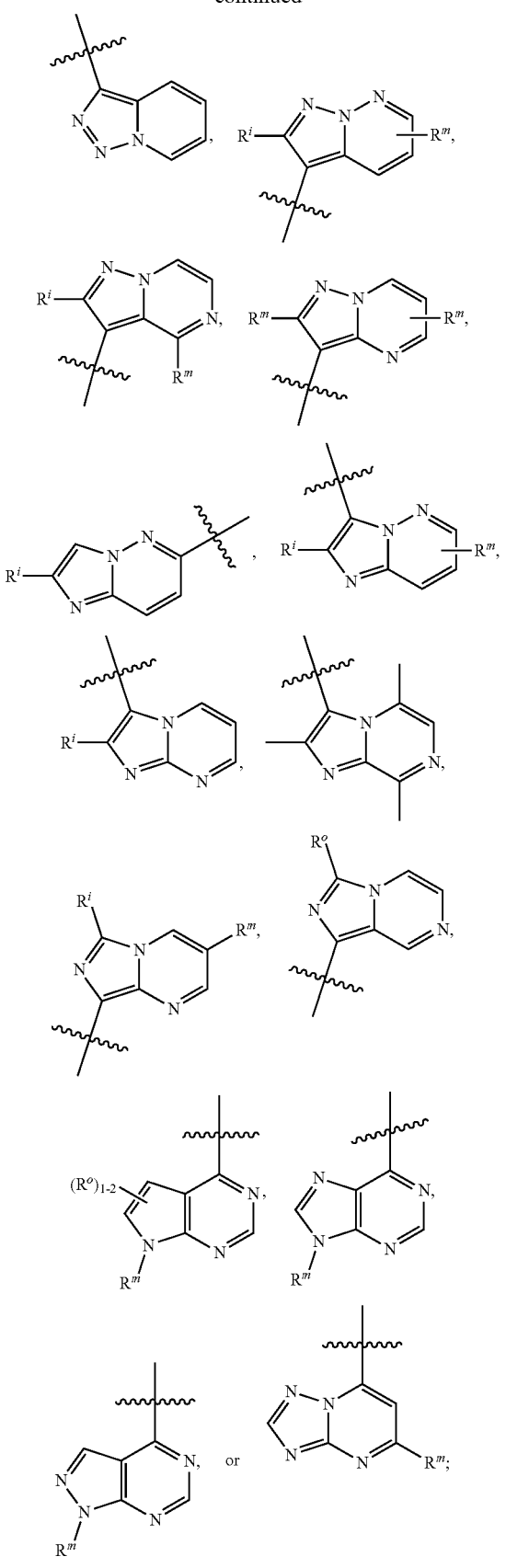
164
(e) Fused 6,6 heteroaryl selected from the group consisting of:
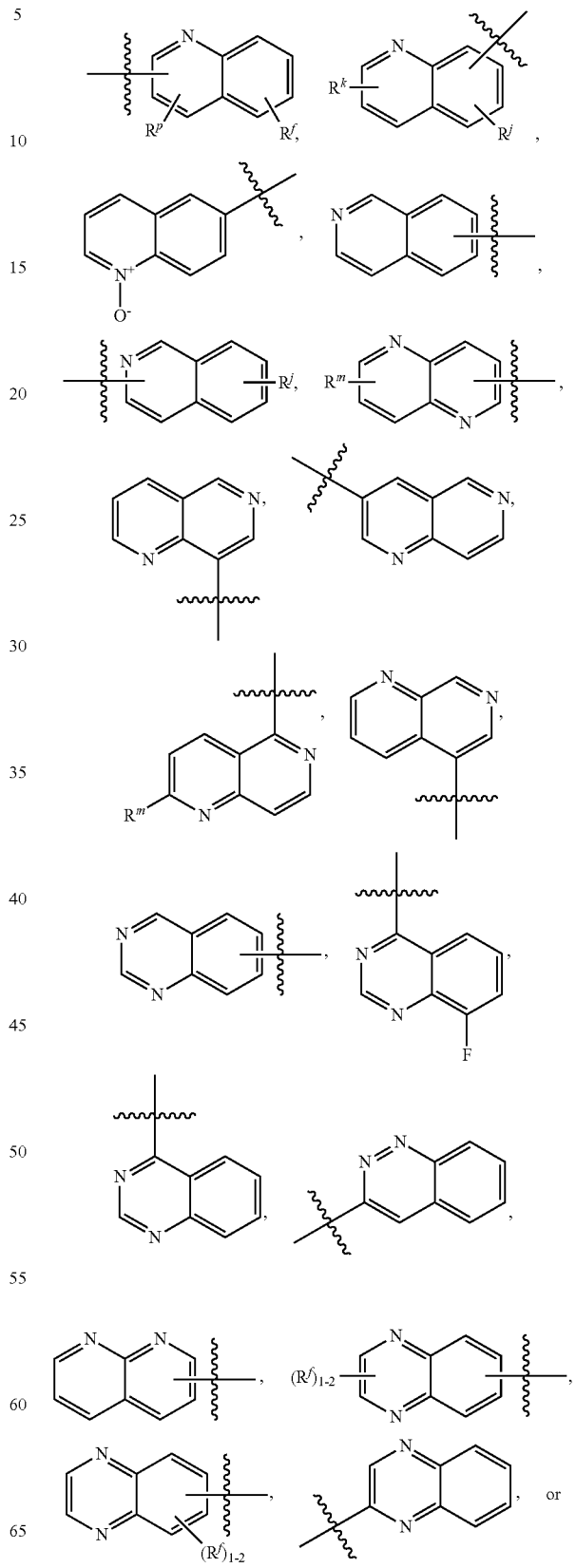

-continued

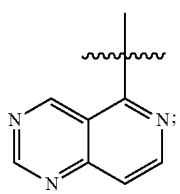 and (f) Heterocycloalkyl selected from the group consisting of:

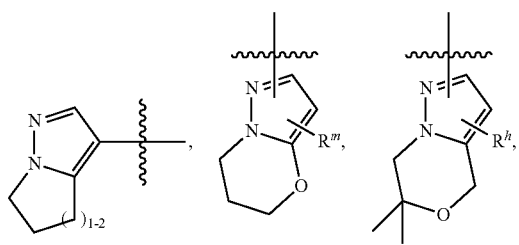

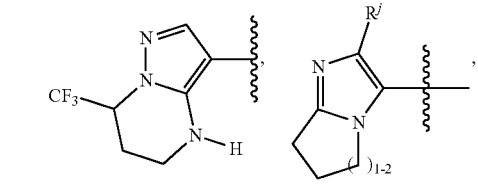

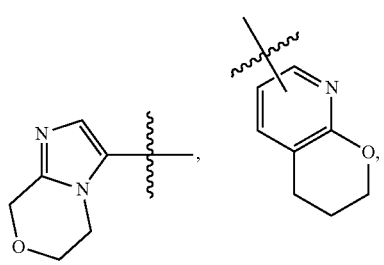

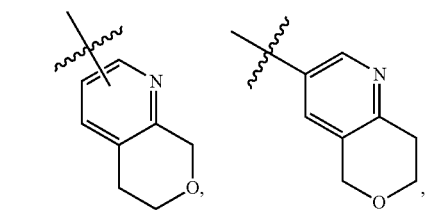

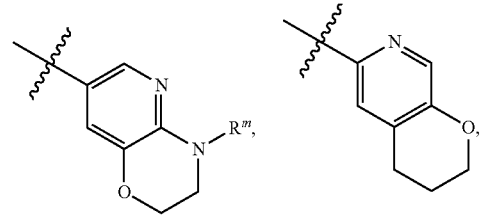

-continued

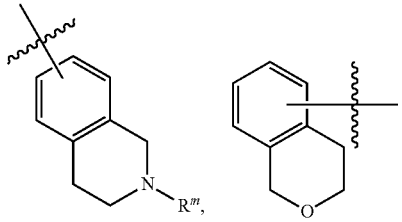

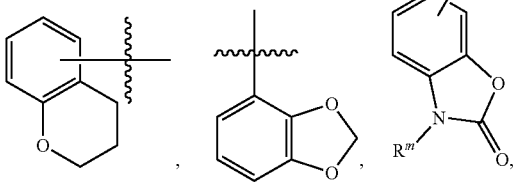

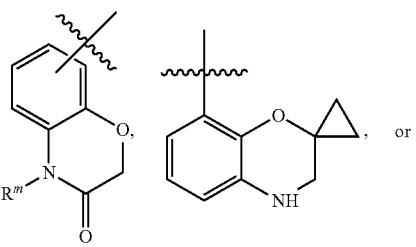 or

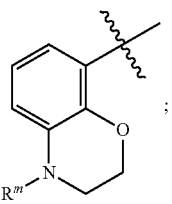

$R^{3a}$ is selected from the group consisting of:

(g) Phenyl; or phenyl substituted with one, two, or three members each independently selected from the group consisting of: halo, $C_{1-4}$alkyl, $C_{1-4}$haloalkyl, $OC_{1-4}$alkyl, and $OC_{1-6}$haloalkyl;

(h) 5-Membered heteroaryl selected from the group consisting of:

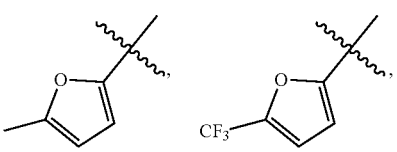

and

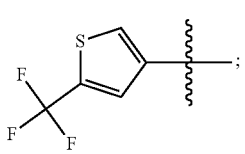 [SMILES: *c1csc(C(F)(F)F)c1] ;

(i) 6-Membered heteroaryl selected from the group consisting of:

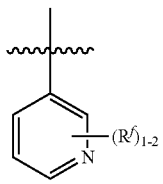

and

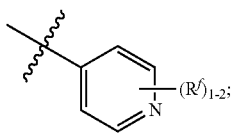

(j) 5,6-Fused or 6,5-fused heteroaryl selected from the group consisting of:

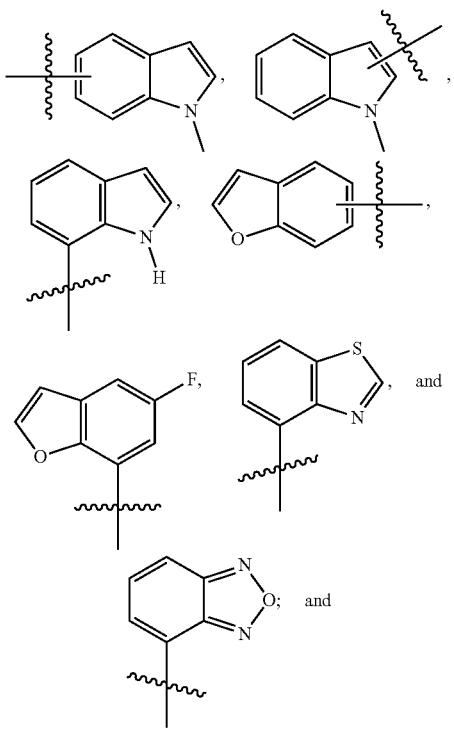

(k) Heterocycloalkyl selected from the group consisting of:

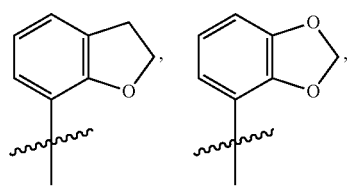

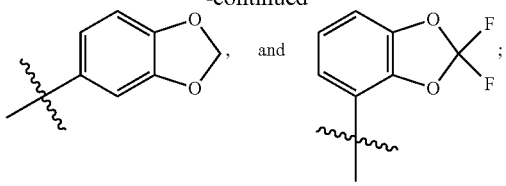

$R^e$ is selected from the group consisting of: $OC_{1-4}$alkyl, $OC_{1-4}$haloalkyl, (C=O)$NHCH_3$, and 5-membered heteroaryl ring containing two or three nitrogen members, wherein the 5-membered heteroaryl ring is optionally substituted with one R member;

$R^f$ is selected from the group consisting of: H, halo, $C_{1-4}$alkyl, $C_{1-4}$haloalkyl, $OC_{1-4}$alkyl, and $OC_{1-4}$haloalkyl;

$R^g$ is selected from the group consisting of: $OC_{1-4}$alkyl, $OC_{1-4}$haloalkyl, $CH_2OCH_3$, $CH_2OH$,

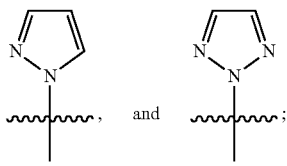 [SMILES: *n1cccn1 ; *n1nccn1]

$R^h$ is selected from the group consisting of: H, $C_{1-4}$alkyl, $C_{1-4}$haloalkyl, and $C_{3-6}$cycloalkyl;

$R^i$ is selected from the group consisting of: H, halo, $C_{1-4}$alkyl, $C_{1-4}$haloalkyl, $OC_{1-4}$alkyl, $C_{3-6}$cycloalkyl, and $C_{3-6}$cycloalkyl substituted with one or two members independently selected from: F and $CH_3$;

$R^j$ is selected from the group consisting of: H, halo, $C_{1-4}$alkyl and $C_{1-4}$haloalkyl;

$R^k$ is selected from the group consisting of: H, halo, OH, $C_{1-4}$alkyl, $C_{1-4}$haloalkyl, $OC_{1-4}$alkyl, and $OC_{1-4}$haloalkyl;

$R^m$ is H or $C_{1-4}$alkyl;

$R^n$ is selected from the group consisting of: H, halo and $OC_{1-4}$alkyl;

$R^o$ is selected from the group consisting of: H, $C_{1-4}$alkyl, and $C_{1-4}$haloalkyl;

$R^p$ is selected from the group consisting of: H, $C_{1-4}$alkyl, and $OC_{1-4}$alkyl;

Y is CH or N; and $R^{4a}$ is selected from the group consisting of: $CH_3$, $CF_2H$, $CF_3$, $C_{3-6}$cycloalkyl, and phenyl; and pharmaceutically acceptable salts, isotopes, N-oxides, solvates, and stereoisomers thereof, to a subject in need thereof.

An additional embodiment of the invention is a method of treating a subject suffering from or diagnosed with a disease, disorder, or condition mediated by MGL receptor activity, comprising administering to a subject in need of such treatment a therapeutically effective amount of at least one compound selected from compounds of Formula (I) (as well as Formulas (II), (IIA), (IIB), (IIC), (IID), (IIE) and (IIF)), enantiomers and diastereomers of the compounds of Formula (I) (as well as Formulas (II), (IIA), (IIB), (IIC), (IID), (IIE) and (IIF)), isotopic variations of the compounds of Formula (I) (as well as Formulas (II), (IIA), (IIB), (IIC), (IID), (IIE) and (IIF)), and pharmaceutically acceptable salts of all of the foregoing.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I) or Formula (II). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

TABLE 3

| Term | Acronym |
| --- | --- |
| Aqueous | aq |
| Acetonitrile | ACN, MeCN |
| Atmosphere | atm |
| Broad | br |
| Diatomaceous Earth | Celite ® |
| Dimethylsulfoxide | DMSO |
| Diethyl ether | Ether, Et$_2$O |
| Ethyl Acetate | EtOAc, or EA |
| Ethanol | EtOH |
| Electrospray ionization | ESI |
| Normal-phase silica gel chromatography | FCC |
| Grams | g |
| Hours | H, hr, hrs |
| High-pressure liquid chromatography | HPLC |
| Hertz | Hz |
| Isopropyl alcohol | iPrOH, IPA |
| Liquid chromatography and mass spectrometry | LCMS |
| Molar | M |
| Mass to charge ratio | m/z |
| Methanol | MeOH |
| Milligrams | mg |
| Minute | min |
| Milliliter | mL |
| Microliter | µL |
| Millimoles | mmol |
| Mass spectrometry | MS |
| Normal | N |
| Nuclear magnetic resonance | NMR |
| CF$_3$SO$_3$– or triflate | OTf |
| Parts per million | ppm |
| Precipitate | ppt |
| Polytetrafluoroethylene | PTFE |
| Retention time | R$_t$ |
| Room temperature | rt |
| Saturated | sat |
| Supercritical Fluid Chromatography | SFC |
| Temperature | T |
| Thin layer chromatography | TLC |
| Volume in milliliters of solvent per gram of substrate | V, or volumes |

PREPARATIVE EXAMPLES

Exemplary compounds useful in methods of the invention will now be described by reference to the illustrative synthetic schemes for their general preparation below and the specific examples to follow.

SCHEME 1

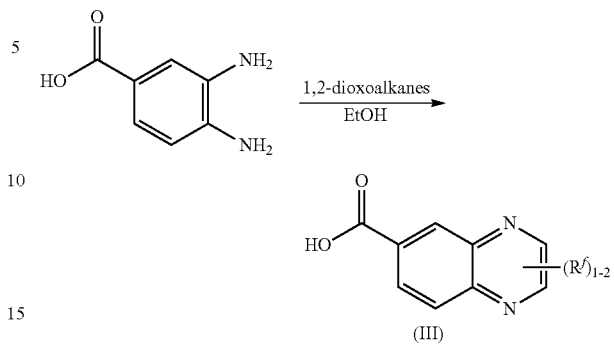

According to SCHEME 1, a compound of formula (III) is prepared by condensation of commercially available or synthetically accessible 2-amino-4-aminobenzoic acid; with 1,2-dioxoalkanes such as 2-oxopropanal, 2,3-butanedione, and the like; in a suitable solvent such as EtOH and the like; at a temperature of 80° C.; for a period of about 1-16 hours; to provide a compound of formula (III), where R$^f$ is H or CH$_3$.

SCHEME 2

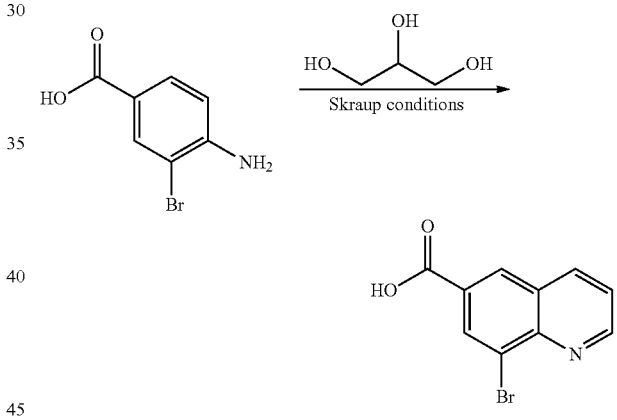

According to SCHEME 2, treatment of 4-amino-3-bromobenzoic acid with excess glycerol; under Skraup conditions known to one skilled in the art (R. H. F. Manske and M. Kulka, "The Skraup Synthesis of Quinolines"; Org. Reaction, vol. 7, p. 59-98, 1953); affords 6-carboxy-8-bromoquinoline. For example, 4-amino-3-bromobenzoic acid is reacted with sulfuric acid; glycerol; an oxidizing agent such as nitrobenzene; in the presence of ferrous sulfate; at a temperature of 140° C.; to provide 6-carboxy-8-bromoquinoline.

SCHEME 3

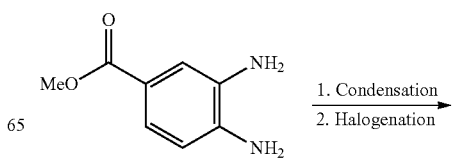

171
-continued

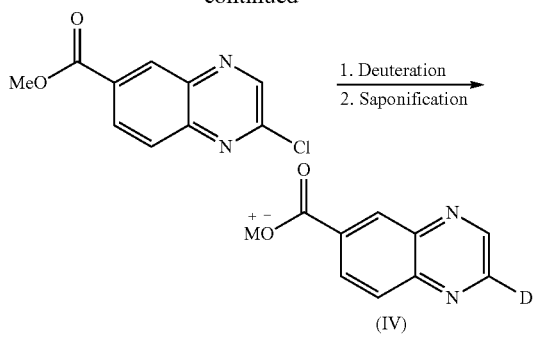

(IV)

According to SCHEME 3, methyl 2-hydroxyquinoxaline-6-carboxylate is prepared by condensation of commercially available or synthetically accessible 2-amino-4-aminobenzoic acid; with ethyl 2-oxoacetate; in a suitable solvent such as ethanol (EtOH) and the like; at room temperature; for a period of 1 hour. Halogenation of methyl 2-hydroxyquinoxaline-6-carboxylate is achieved with a chlorinating reagent, such as thionyl chloride; neat, or in a suitable solvent such as toluene, and the like; followed by catalytic amount of N,N-dimethylformamide (DMF); at reflux temperature; to provide methyl 2-chloroquinoxaline-6-carboxylate. A compound of formula (IV) is prepared in two steps. In a first step, palladium catalyzed reductive deuteration of methyl 2-chloroquinoxaline-6-carboxylate; using a commercially available deuterated reagent such as sodium borodeuteride; in presence of a palladium catalyst such as [1,1'-bis(diphenylphosphino)ferrocene]dichloropalladium(II) (PdCl$_2$(dppf)), and the like; a base such as tetramethylethylenediamine (TMEDA or TEMED); in a suitable solvent such as tetrahydrofuran (THF), and the like; at room temperature; for a period of 1 hour. In a second step, saponification of the ester to the acid is achieved employing conditions known to one skilled in the art. For example, employing a suitable base such as NaOH, LiOH, and the like; in a suitable solvent such as water, THF, methanol (MeOH), or a mixture thereof, at room temperature; for a period of about 1 h; provides a compound of formula (IV), where M is lithium.

SCHEME 4

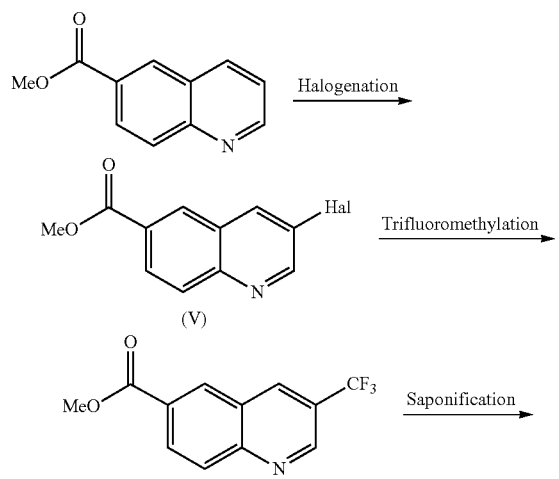

172
-continued

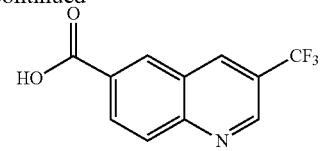

According to SCHEME 4, methyl quinoline-6-carboxylate is halogenated under conditions known to one skilled in the art. For example, reaction of methyl quinoline-6-carboxylate; with a halogenating agent such as N-bromosuccinimide (NBS), N-iodosuccinimide (NIS), and the like; in a suitable solvent such as acetic acid (AcOH); at a temperature of about 100° C.; for a period of 2-4 h; provides a compound of formula (V). In a preferred method, the halogenating agent is NIS, for a compound of formula (V), where Hal is I. In another approach, the iodo-substituent allows the insertion of the trifluoromethyl moiety via (trifluoromethyl)copper-mediated trifluoromethylation, employing a trifluormethylating agent such as trifluoromethyl iodide, sodium trifluoroacetate, methyl 2,2-difluoro-2-(fluorosulfonyl)acetate, trifluoromethyl-trimethylsilane, trifluoromethyl-triethylsilane, methyl chlorodifluoroacetate-potassium fluoride, and the like, (methyl2,2-difluoro-2-(fluorosulfonyl)acetate is preferred); a catalyst such as copper iodide, copper bromide, or other such copper salts, and copper powder (copper iodide is preferred), in an inert solvent such as N,N-dimethylformamide, N,N-dimethylacetamide, dimethyl sulfoxide, N-methylpyrrolidone, and other such aprotic polar solvents; (N,N-dimethylformamide is preferred) and a base such as N,N'-Dimethylpropyleneurea (DMPU); a temperatures ranging from 100 to 130° C., employing microwave or conventional heating; to provide methyl 3-(trifluoromethyl)quinoline-6-carboxylate.

Saponification of the ester to the acid is achieved employing conditions known to one skilled in the art, for example, using a suitable base such as NaOH, LiOH, and the like, in a suitable solvent such as water/THF/MeOH, at a temperature of about 60° C., for a period of about 2 h, to provide 3-(trifluoromethyl)quinoline-6-carboxylic acid.

SCHEME 5

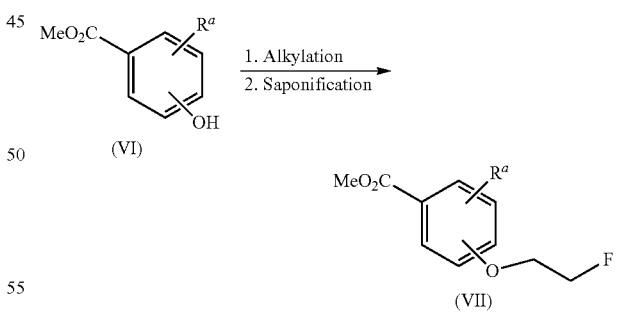

According to SCHEME 5, a compound of formula (VI), where R$^a$ is H or halo, is alkylated with a suitable alkyl halide such as 1-iodoethane, fluoro-2-iodoethane, and the like; a suitable base such as Cs$_2$CO$_3$, K$_2$CO$_3$, and the like; in a suitable solvent such as N,N-dimethylformamide. Subsequent saponification employing conditions previously described, provides a compound of formula (VII). In a similar fashion, 3-hydroxyquinoline-6-carboxylic acid, and methyl indole-4-carboxylic acid are alkylated and saponified.

SCHEME 6

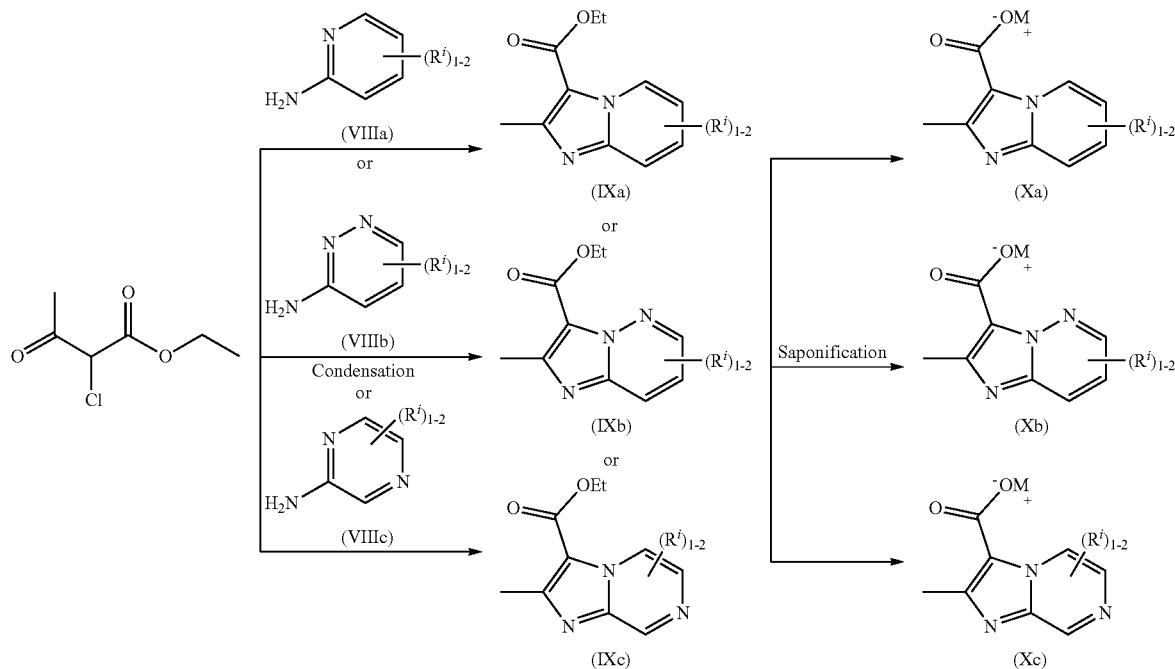

According to SCHEME 6, compounds of formulas (IXa), (IXb) and (IXc) are prepared under conditions known to one skilled in the art, by condensation of commercially available or synthetically accessible substituted pyridine, pyridazine and pyrazine amines of formulas (VIIIa), (VIIIb) and (VIIIc) where $R^i$ is independently H, $C_{1-4}$alkyl, $C_{1-4}$haloalkyl, $OC_{1-4}$ alkyl, and $C_{3-6}$cycloalkyl; using ethyl 2-chloro-3-oxobutanoate in suitable solvents such as 1,2-dimethoxy ethane (DME), and the like; at temperature of 90° C., for a period of about 2-16 hours. Saponification of the esters (IXa), (IXb) and (IXc) to the corresponding acid is achieved employing conditions known to one skilled in the art, for example, using a suitable base such as potassium trimethylsilanolate (TMSOK), NaOH, LiOH, and the like, in a suitable solvent such as water/THF/MeOH, at a temperature of about 60° C., for a period of about 24 h, to provide compounds of formulas (Xa), (Xb), and (Xc), where M is potassium, Na, or Li, preferably potassium.

SCHEME 7

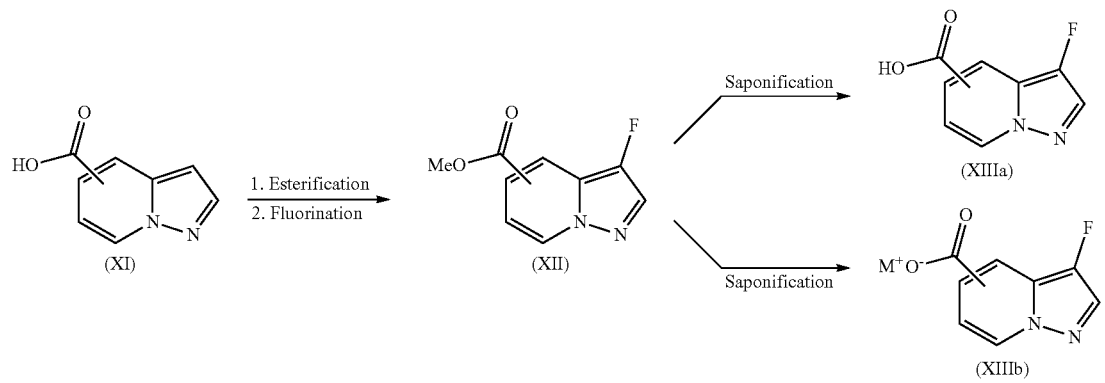

According to SCHEME 7, a commercially available or synthetically accessible acid compound of (XI) is converted to its corresponding methyl ester by employing thionyl chloride in methanol, at a temperature of about 65° C. Subsequent fluorination using 1-chloromethyl-4-fluoro-1,4-diazoniabicyclo[2.2.2]octane bis(tetrafluoroborate) (Selectfluor®) provides a compound of formula (XII). Saponification of the ester, employing conditions previously described, then treatment under acidic conditions provides a compound of formula (XIIIa). Saponification employing basic conditions, using a suitable base such as TMSOK, NaOH, LiOH, and the like; in a suitable solvent such as water, THF, MeOH, or a mixture thereof; at a temperature of about 60° C.; for a period of about 24 h; provides a compound of formula (XIIIb) where M is potassium, Na, or Li; preferably potassium.

SCHEME 8

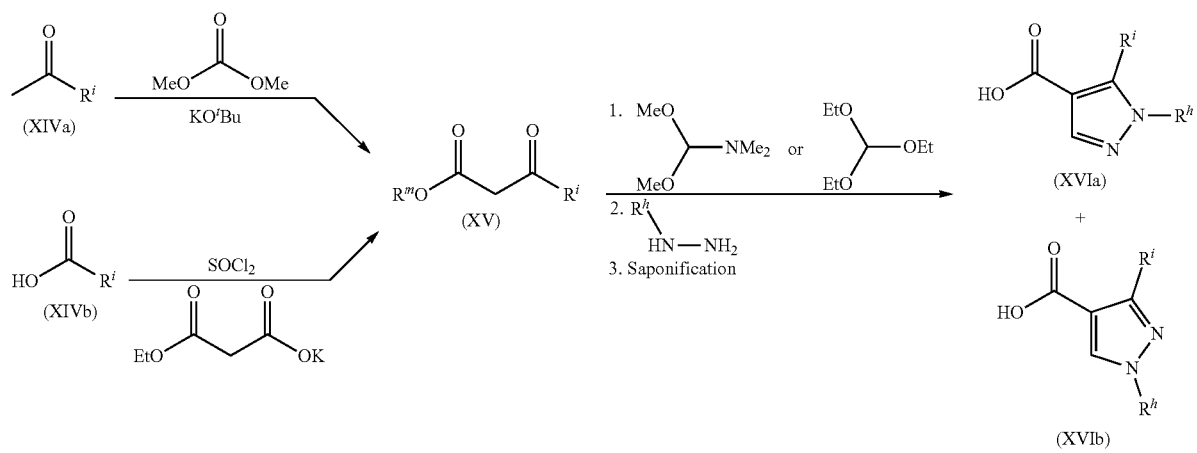

According to SCHEME 8, a compound of formula (XIVa), where $R^i$ is $C_{3-6}$cycloalkyl substituted with $C_{1-4}$alkyl, is treated with dimethylcarbonate; and a suitable base such as potassium tert-butoxide, and the like; in a suitable solvent such as toluene, and the like; at a temperature of about 75° C.; to provide a compound of (XV), where $R^m$ is methyl. Alternatively, a compound of formula (XIVb), where $R^i$ is an optionally substituted $C_{3-6}$cycloalkyl, is reacted with oxalyl chloride; ethyl potassium malonate; in the presence of magnesium chloride; a suitable base such as triethylamine, and the like; in a suitable solvent such as ethyl acetate, THF, or a mixture thereof, to provide a compound of formula (XV), where $R^m$ is ethyl.

A commercially available or synthetically accessible compound of formula (XV), where $R^i$ is $C_{1-4}$haloalkyl, $C_{3-6}$cycloalkyl optionally substituted with one or two halo, or $C_{1-4}$alkyl; is reacted with N,N-dimethylformamide dimethyl acetal or triethyl orthoformate; neat or in a suitable solvent such as acetic anhydride; at temperatures ranging from room temperature or 135° C. The resulting mixture is then reacted with commercially available or synthetically accessible hydrazine of formula $R^hNHNH_2$, where $R^h$ is either $C_{1-4}$alkyl or $C_{3-6}$cycloalkyl; in a suitable solvent such as ethanol, and the like; to afford the pyrazole intermediates which are subsequently saponified under conditions previously described to provides regioisomeric compounds of formula (XVIa) and formula (XVIb). It is known that depending on the saponification conditions and the purification method, the resulting compounds of formula (XVIa) and (XVIb), which may be metal salts, are obtained.

SCHEME 9

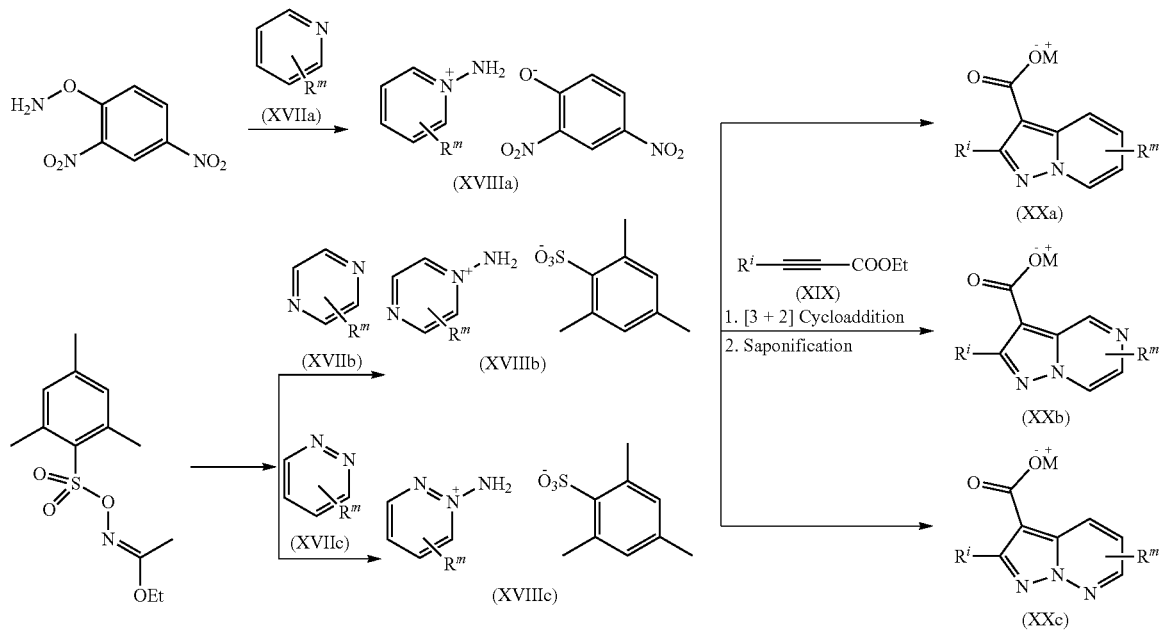

According to SCHEME 9, a commercially available or synthetically accessible compound of formula (XVIIa) where $R^m$ is Me; is dissolved in a suitable solvent such as acetonitrile (ACN) and the like; and reacted with an aminating reagent such as O-(2,4-dinitrophenyl)hydroxylamine; at a temperature of 40° C.; for a period of 18 h; to provide a pyridinium compound of formula (XVIIIa).

In an alternate method, commercially available or synthetically accessible compounds of formulas (XVIIb), and (XVIIc), where $R^m$ is $C_{1-4}$alkyl; are dissolved in a solvent such as dichloromethane (DCM), and the like; and reacted with an aminating reagent (formed by treatment of (E)-N-((mesitylsulfonyl)oxy)acetimidate; with an acid such as perchloric acid, and the like); in a suitable solvent such as dioxane, water, or a mixture thereof; at a temperature ranging from 0° C. to room temperature; to provide corresponding amino pyrazinium and amino pyridazinium salts of formulas (XVIIIb) and (XVIIIc). Compounds of formulas (XVIIIa), (XVIIIb), and (XVIIIc). undergo a [3+2] cycloaddition; in the presence of an alkynoate of formula (XIX), where $R^i$ is $C_{1-4}$alkyl or $C_{3-6}$cycloalkyl; a suitable base such as $K_2CO_3$, and the like; in a solvent such as DMF. Subsequent saponification of the ester moiety to the corresponding acid is achieved employing conditions known to one skilled in the art. For example, using a suitable base such as NaOH, LiOH, KOH, and the like, preferably LiOH; in a suitable solvent such as water, THF, MeOH, or a mixture thereof, at a temperature of about 60° C.; for a period of about 24 h; to provide compounds of formulas (XXa), (XXb), and (XXc), where M is potassium, Na, or Li, preferably potassium.

SCHEME 10

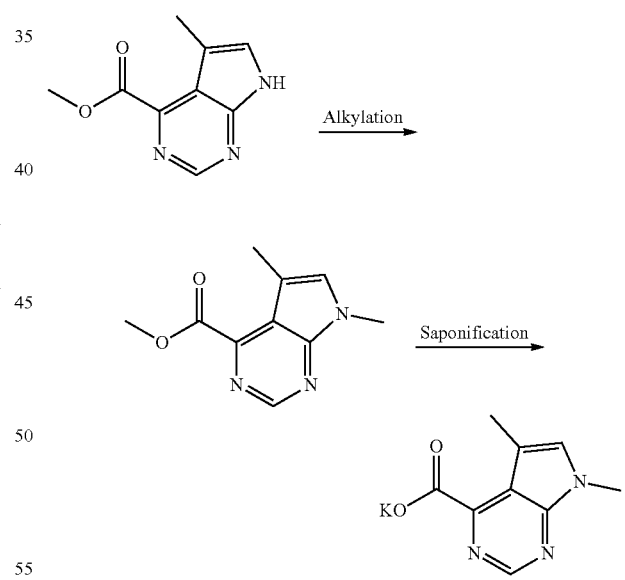

According to SCHEME 10, alkylation of methyl 5-methyl-7H-pyrrolo[2,3-d]pyrimidine-4-carboxylate with a suitable alkylating agent such as methyl iodide (MeI); a suitable base such as NaH, and the like; in a suitable solvent such as THF, and the like; provides methyl 5,7-dimethyl-7H-pyrrolo[2,3-d]pyrimidine-4-carboxylate. Subsequent hydrolysis of methyl 5,7-dimethyl-7H-pyrrolo[2,3-d]pyrimidine-4-carboxylate is achieved employing conditions previously described, to provide potassium 5,7-dimethyl-7H-pyrrolo[2,3-d]pyrimidine-4-carboxylate.

SCHEME 11

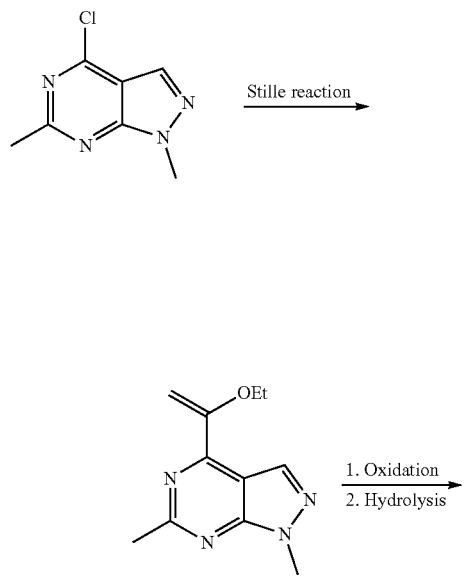

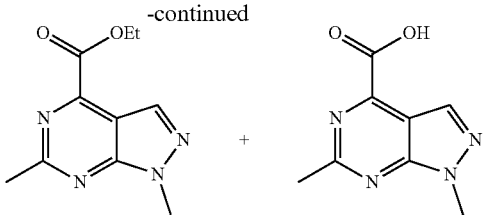

According to SCHEME 11, reaction of 4-chloro-1,6-dimethyl-1H-pyrazolo[3,4-d]pyrimidine in a Stille cross coupling reaction with an alkyl stannane such as tributyl(1-ethoxyvinyl)stannane; a palladium catalyst such as bis(triphenylphosphine)palladium(II) dichloride ($Pd(PPh_3)_2Cl_2$), and the like; in suitable solvent such as DMF, and the like; at a temperature of 60° C.; for a period of 16 h; provides 4-(1-ethoxyvinyl)-1,6-dimethyl-1H-pyrazolo[3,4-d]pyrimidine. Oxidation of 4-(1-ethoxyvinyl)-1,6-dimethyl-1H-pyrazolo[3,4-d]pyrimidine employing oxidation conditions such as sodium periodate; potassium permanganate; in suitable solvent such as 1,4 dioxane, and the like; at a temperature of about room temperature; for a period of 18 h; and neutralized with aqueous potassium carbonate solution; provides a mixture of ethyl 1,6-dimethyl-1H-pyrazolo[3,4-d]pyrimidine-4-carboxylate and 1,6-dimethyl-1H-pyrazolo[3,4-d]pyrimidine-4-carboxylic acid (WO 2015/025026; Page-96).

SCHEME 12

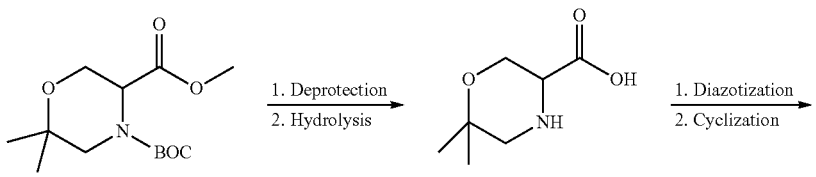

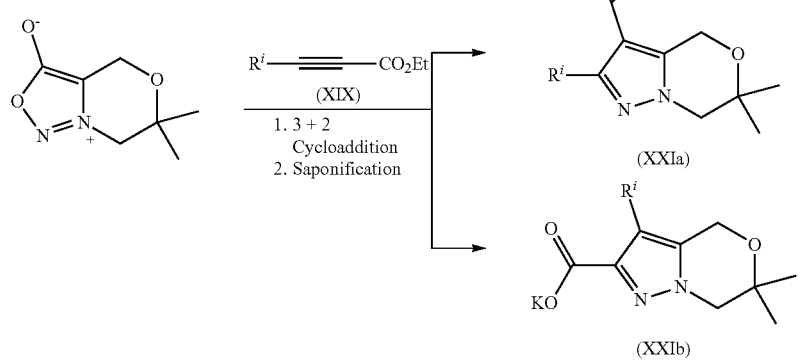

181

According to SCHEME 12, 6,6-dimethylmorpholine-3-carboxylic acid is prepared in two steps from 4-(tert-butyl) 3-methyl 6,6-dimethylmorpholine-3,4-dicarboxylate. In a first step, deprotection of BOC group is achieved according to procedures known to one skilled in the art and employing established methodologies, such as those described in T. W. Greene and P. G. M. Wuts, "Protective Groups in Organic Synthesis," 3 ed., John Wiley & Sons, 1999, pgs 518-525. For example, deprotection under acidic conditions such as trifluoroacetic acid (TFA)/CH$_2$Cl$_2$, HCl/Dioxane, and the like, at room temperature for a period of 2 h. Subsequent hydrolysis in situ, with suitable base such as NaOH and the like, in a solvent such as MeOH/water provides 6,6-dimethylmorpholine-3-carboxylic acid. Diazotization of 6,6-dimethylmorpholine-3-carboxylic acid is achieved employing sodium nitrite; in water; under acidic conditions such as conc. HCl; at temperatures ranging from 0° C. to room temperature; for a period of 16 h. The resulting nitroso acid is treated with trifluoroacetic anhydride (TFAA) in a suitable solvent such as acetonitrile (ACN) and the like; at room temperature; for a period of 2 h; to provide 6,6-dimethyl-6,7-dihydro-4H-[1,2,3]oxadiazolo[4,3-c][1,4]oxazin-8-ium-3-olate (Reference: Nikitenko, A. A., et al. Org. Process Res. Dev., 2006, 10 (4), pp 712-716)

6,6-Dimethyl-6,7-dihydro-4H-[1,2,3]oxadiazolo[4,3-c][1,4]oxazin-8-ium-3-olate undergoes a [3+2] cycloaddition reaction with an alkynoate of formula (XIX), where R$^i$ is C$_{1-4}$alkyl; in a suitable solvent such as xylene, and the like; at a temperature of about 140° C.; for a period of 2 h. Subsequent saponification of the resulting two regioisomeric esters to the corresponding acids is achieved employing conditions previously described. For example, employing a suitable base such as NaOH, LiOH, KOH, and the like; in a suitable solvent such as water, THF, MeOH, or a mixture thereof, at a temperature of about 60° C.; for a period of about 24 h; to provide compounds of formulas (XXIa) and (XXIb), where M is K, Na, or Li.

SCHEME 13

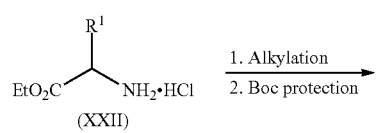
(XXII)

1. Alkylation
2. Boc protection

-continued

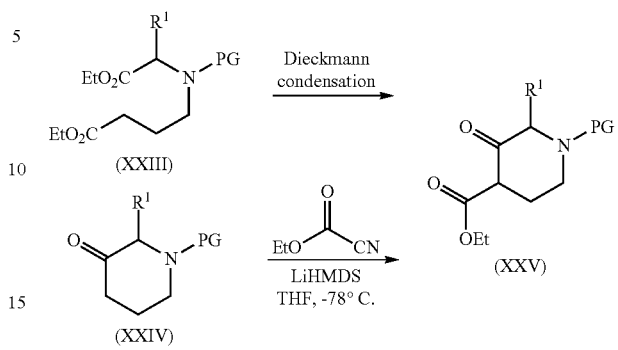

According to SCHEME 13, a keto-ester compound of formula (XXV), where PG is a suitable protecting group such as BOC (tert-butyloxycarbonyl), and R$^1$ is C$_{1-4}$alkyl is prepared from a commercially available or synthetically accessible compound of formula (XXIV). For example, a compound of formula (XXIV), where PG is BOC, is converted to compound (XXV), by treatment with a strong base such as LHMDS, in a suitable solvent such as THF, and the like, at a temperature of about −78° C.; for 30 minutes, followed by treatment with ethyl cyanoformate at −78° C., for a period of about 2 hours.

In an alternate method, a compound of formula (XXIII) is prepared in two steps from a compound of formula (XXII), where R$^1$ is C$_{1-4}$alkyl. In a first step, a compound of formula (XXII) is alkylated with ethyl 4-bromobutanoate; employing potassium iodide; a suitable base such as dibasic potassium phosphate. In a second step, BOC protection employing established methodologies, such as those described in T. W. Greene and P. G. M. Wuts, "Protective Groups in Organic Synthesis," 3 ed., John Wiley & Sons, 1999, pgs 518-525, provides a compound of formula (XXIII). Cyclization under Dieckmann condensation conditions of a compound of formula (XXIII) using a suitable base such as LiHMDS or potassium tert-butoxide; in a suitable solvent such as tetrahydrofuran and the like; at temperatures between −40° C. to 20° C.; provides a keto-ester of formula (XXV).

In a similar fashion, ethyl L-alaninate hydrochloride is alkylated by treatment with bromobutanoate and potassium iodide in the presence of a suitable base such as dibasic potassium phosphate in a suitable solvent such as DMF. The amine moiety is protected with a carbamate protecting group such as tert-butyloxycarbonyl (BOC). Cyclization of the diester occurs under Dieckmann condensation conditions known to one skilled in the art. For example ethyl (S)-4-((tert-butoxycarbonyl)(1-ethoxy-1-oxopropan-2-yl)amino) butanoate is treated with lithium bis(trimethylsilyl)amide (LiHMDS) at a suitable temperature range such as between −40° C. to 20° C. to provide 1-(tert-butyl) 4-ethyl (2S)-2-methyl-3-oxopiperidine-1,4-dicarboxylate.

SCHEME 14

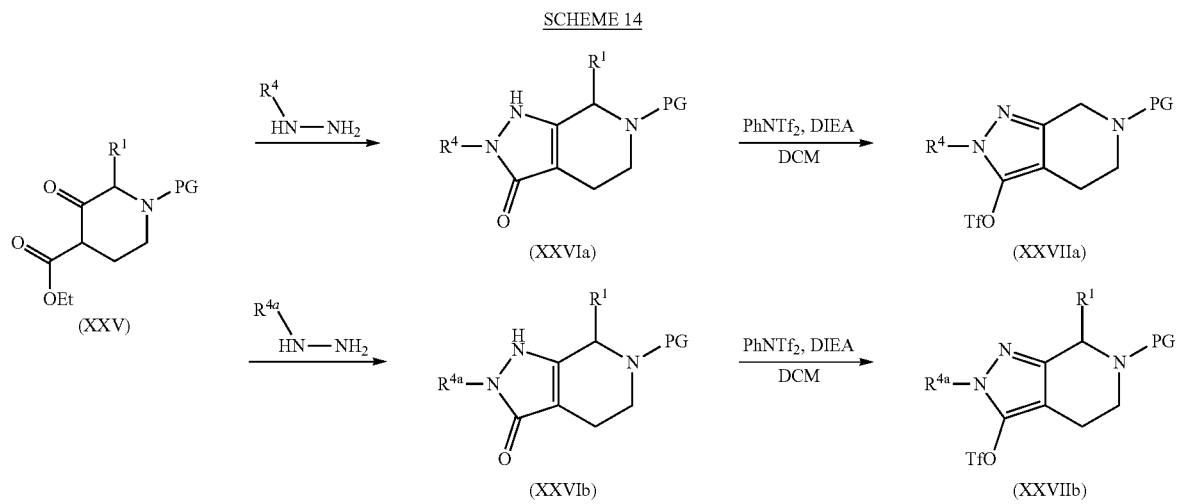

According to SCHEME 14, a commercially available or synthetically accessible compound of formula (XXV), where $R^1$ is H, and PG is BOC (tert-butyloxycarbonyl) is reacted with a commercially available or synthetically accessible hydrazine compound of formula $R^4NHNH_2$, where $R^4$ is $C_{1-4}$alkyl, in AcOH, at a temperature of about 80° C., to provide a pyrazolone compound of formula (XXVIa), where $R^4$ is $C_{1-4}$alkyl. A commercially available or synthetically accessible compound of formula (XXV), where $R^1$ is $C_{1-4}$alkyl, and PG is BOC (tert-butyloxycarbonyl) is reacted with a commercially available or synthetically accessible hydrazine compound of formula $R^{4a}NHNH_2$, or salt thereof, where $R^{4a}$ is $C_{1-4}$alkyl, $C_{3-6}$cycloalkyl or phenyl, in a suitable solvent such as toluene or ethanol with a suitable base such as N,N-diisopropylethylamine (Hünig's base or DIEA), at a temperature of between 80 and 110° C., to provide a pyrazolone compound of formula (XXVIb), where $R^{4a}$ is $C_{1-4}$alkyl, $C_{3-6}$cycloalkyl or phenyl.

Derivation of pyrazolone compounds of formulas (XXVIa) and (XXVIb) with a sulfonate-based leaving group such as trifluoromethanesulfonyl (triflate) is achieved by is by reaction with a triflating agent such as trifluoromethanesulfonic anhydride ($Tf_2O$); a base such as triethylamine (TEA), pyridine, N-ethyldiisopropylamine (DIEA, DIPEA), and the like; in a suitable solvent such as DCM and the like. Milder triflating agents such as N-phenylbis(trifluoromethanesufonimide) ($Tf_2NPh$), a base such as TEA, DIEA, and the like, in a suitable solvent such as DCM, and the like; are used for better selectivity, to provide compounds of formulas (XXVIIa) and (XXVIIb).

In a similar fashion a compound of formula (XXV), where PG is BOC, is reacted with hydrazine hydrate, to provide tert-butyl 7-methyl-3-oxo-1,2,3,4,5,7-hexahydro-6H-pyrazolo[3,4-c]pyridine-6-carboxylate. tert-Butyl 7-methyl-3-oxo-1,2,3,4,5,7-hexahydro-6H-pyrazolo[3,4-c]pyridine-6-carboxylate is reacted with a triflating agent as previously described to provide tert-butyl 7-methyl-3-(((trifluoromethyl)sulfonyl)oxy)-2,4,5,7-tetrahydro-6H-pyrazolo[3,4-c]pyridine-6-carboxylate.

SCHEME 15

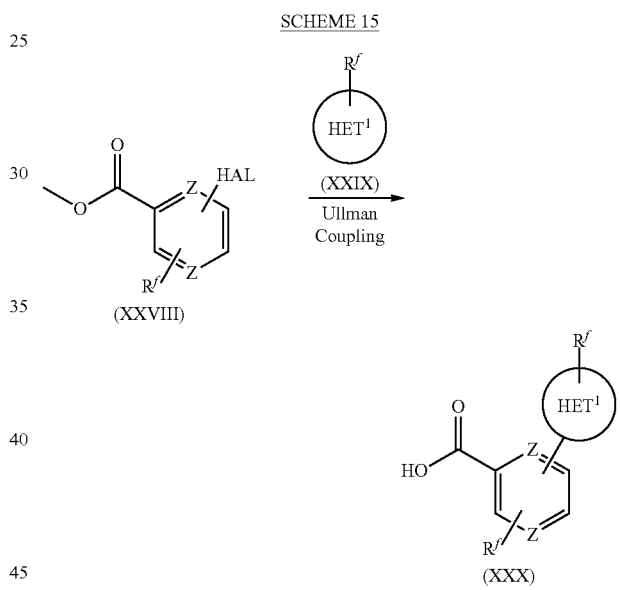

According to SCHEME 15, Ullmann-type copper-mediated displacement of an optionally substituted aryl halide compound of formula (XXVIII), where R is independently selected from the group consisting of: halo, $C_{1-4}$alkyl, $C_{1-4}$haloalkyl, and $OC_{1-4}$alkyl; HAL is I, or Br; and Z is CH or N, wherein only one Z can be N; with an nitrogen containing nucleophile such as a 5 membered heteroaryl containing 2 or 3 nitrogen members of formula (XXIX), where $R^a$ is independently selected from the group consisting of: halo, $C_{1-4}$alkyl, $C_{1-4}$haloalkyl, and $OC_{1-4}$alkyl; in the presence of a copper catalyst such as copper powder, copper (I) iodide, and the like; an inorganic base such as cesium carbonate, potassium carbonate, $K_3PO_4$, and the like; an auxiliary bidentate amine ligand such as trans-N,N'-dimethylcyclohexane-1,2-diamine; in an inert high boiling solvent such as nitrobenzene, toluene, xylene, N-methylpyrrolidone (NMP), dimethylformamide (DMF), and the like, at temperatures ranging from 100-200° C.; employing conventional or microwave heating; provides a compound of formula (XXX). For example, 3-iodobenzoic acid is reacted with 3-(trifluoromethyl)pyrazole, a base such as cesium carbonate, a copper catalyst such as CuI, a ligand such as trans-N,N'-dimethylcyclohexane-1,2-diamine, in a suitable solvent such as DMF, at temperatures ranging from 100-140° C., under microwave irradiation, to provide 3-[3-(trifluoromethyl)pyrazol-1-yl]benzoic acid.

SCHEME 16

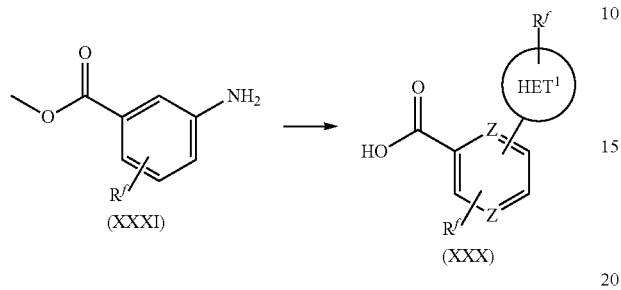

According to SCHEME 16, a compound of formula (XXX), where Z is CH, and HET$^1$ is 1,2,4-triazol-4-yl, is prepared in two steps from a compound of formula (XXXI) where R$^f$ is halo, C$_{1-4}$alkyl, C$_{1-4}$haloalkyl or OC$_{1-4}$alkyl. In a first step, a compound of formula (XXXI) where R$^f$ is halo, C$_{1-4}$alkyl, C$_{1-4}$haloalkyl or OC$_{1-4}$alkyl is reacted with diformylhydrazine, in the presence of trimethylsilyl chloride as a Lewis acid, triethylamine, in a suitable solvent such as pyridine, at a temperature of about 100° C., for a period of about 16 h, to provide the 1,2,4-triazol-4-yl intermediate; in a second step, saponification is achieved according to conditions known to one skilled in the art, or as previously described.

SCHEME 17

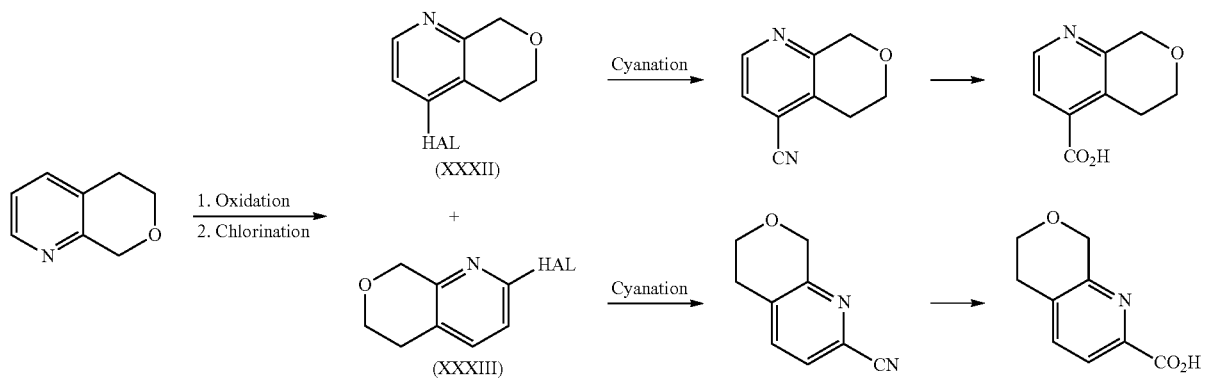

According to SCHEME 17, 5,8-dihydro-6H-pyrano[3,4-b]pyridine 1-oxide is prepared by oxidizing 5,8-dihydro-6H-pyrano[3,4-b]pyridine (prepared according to procedures described in Tetrahedron, 45(19), 6211-20; 1989) employing conditions known to one skilled in the art. For example, 5,8-dihydro-6H-pyrano[3,4-b]pyridine, is reacted with an oxidizing agent such as meta-chloroperoxybenzoic acid (mCPBA), in a suitable solvent such as DCM, at a temperature ranging from 0° C. to 25° C. to provide 5,8-dihydro-6H-pyrano[3,4-b]pyridine 1-oxide. Halogenation employing a chlorinating agent such as POCl$_3$, and the like, in a suitable solvent such as chloroform, and the like, at temperatures ranging from 70-90° C., to affords a mixture of compounds of formula (XXXII) and (XXXIII), where HAL is Cl. Palladium-catalyzed cyanation of (hetero)aryl halide compounds of formula (XXXII) and (XXXIII) is achieved employing zinc cyanide as the nucleophile, zinc, tris(dibenzylideneacetone)dipalladium(0), and 1,1'-bis(diphenylphosphino)ferrocene, in a suitable solvent, at a temperature of about 90° C., for a period of 4 days, to provide 5,8-dihydro-6H-pyrano[3,4-b]pyridine-4-carbonitrile and 5,8-dihydro-6H-pyrano[3,4-b]pyridine-2-carbonitrile. Hydrolysis of 5,8-dihydro-6H-pyrano[3,4-b]pyridine-4-carbonitrile employing a suitable base such as NaOH, LiOH, and the like; in a suitable solvent such as water, THF, MeOH, ethanol (EtOH), or a mixture thereof; at room temperature; for a period of about 16 h; provides 5,8-dihydro-6H-pyrano[3,4-b]pyridine-4-carboxylic acid. Hydrolysis of 5,8-dihydro-6H-pyrano[3,4-b]pyridine-2-carbonitrile employing similar conditions previously described provides 5,8-dihydro-6H-pyrano[3,4-b]pyridine-2-carboxamide, which is subsequently treated with LiOH, in THF to provide 5,8-dihydro-6H-pyrano[3,4-b]pyridine-2-carboxylic acid.

3,4-Dihydro-2H-pyrano[2,3-b]pyridine-5-carboxylic acid is prepared according to methods previously described starting from 3,4-dihydro-2H-pyrano[2,3-b]pyridine.

According to SCHEME 18, a compound of formula (XXVIIa) where $R^4$ is $C_{1-4}$alkyl and PG is BOC; is reacted in a metal mediated cross coupling reaction to provide a compound of formula (XXXVIa), where PG is BOC, and $R^3$ is $C_{3-4}$cycloalkyl, 5-methylthiophen-2-yl, 5-(trifluoromethyl)thiophen-2-yl, 1H-indol-2-yl, 1-methyl-1H-indol-2-yl phenyl, or phenyl substituted with one or two members independently selected from the group consisting of: halo or $OC_{1-4}$haloalkyl; For example, a compound of formula (XXVIIa), where $R^4$ is $C_{1-4}$alkyl and PG is BOC; is reacted with a suitably substituted commercially available or synthetically accessible alkyl, cycloalkyl, aryl or heteroaryl boronic acid, boronate ester, and the like, in the presence of a palladium catalyst such as [1,1'-bis(di-tert-butylphosphino)ferrocene]dichloropalladium(II) ($PdCl_2$(dtbpf)), tetrakis(triphenylphosphine)palladium(0) (Pd($PPh_3$)$_4$), [1,1'-bis(diphenylphosphino)ferrocene]dichloropalladium(II) ($PdCl_2$(dppf)), palladium(II)bis(triphenylphosphine) dichloride (Pd($PPh_3$)$_2Cl_2$), XPhos-Pd-G2 precatalyst (chloro(2-dicyclohexylphosphino-2',4',6'-triisopropyl-1,1'-biphenyl) [2-(2'-amino-1,1'-biphenyl)]palladium(II)), and the like, a base such as $K_3PO_4$, aq. $Na_2CO_3$, $Na_2CO_3$, $Cs_2CO_3$, and the like, in a suitable solvent such as 1,2-dimethoxyethane, 1,4-dioxane, DMF, water, or a mixture thereof, at a temperature ranging from 60 to 180° C., employing microwave or conventional heating, for a period of about 30 min to 16 h, to provide a compound of formula (XXXVIa). In a similar fashion, a compound of formula (XXVIIb), where $R^1$ and $R^{4a}$ are as defined in Claim 28, is reacted with commercially available or synthetically accessible alkyl, cycloalkyl, aryl or heteroaryl boronic acid, boronate ester, and the like, in a metal mediated cross coupling as previously described to provide a compound of formula (XXXVIb), where $R^{3a}$ is as defined in Claim 28.

Cleavage of the BOC protecting group on a compound of formula (XXXVIa) or (XXXVIb) is achieved according to procedures known to one skilled in the art and employing established methodologies, such as those described in T. W. Greene and P. G. M. Wuts, "Protective Groups in Organic Synthesis," 3 ed., John Wiley & Sons, 1999, pgs 518-525. For example, under acidic conditions such as TFA/$CH_2Cl_2$, HCl/Dioxane, and the like, provides compounds of formula (XXXVIIa) and (XXXVIIb).

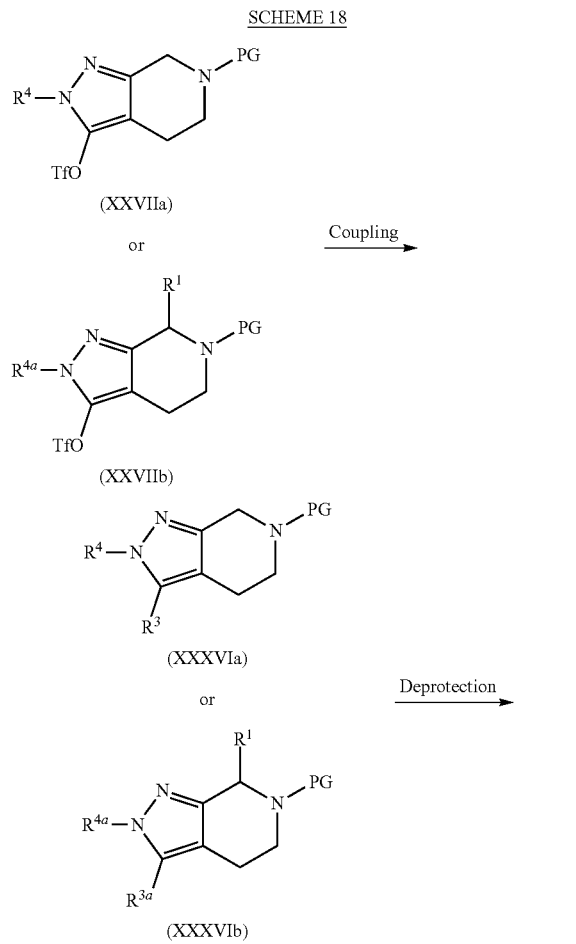

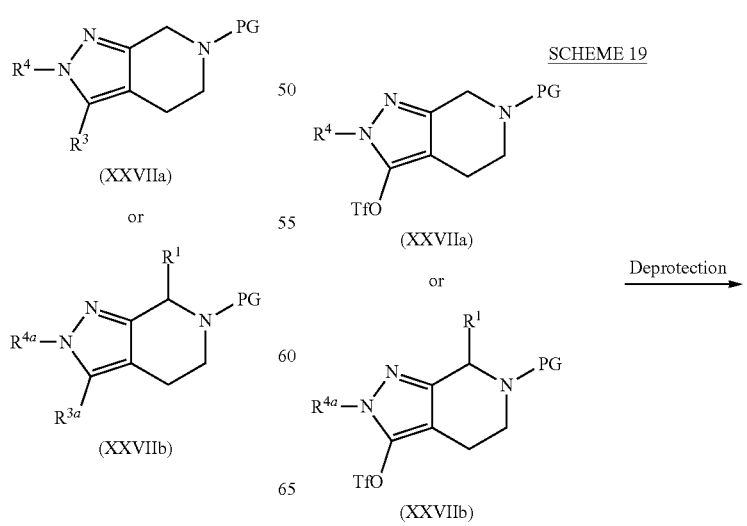

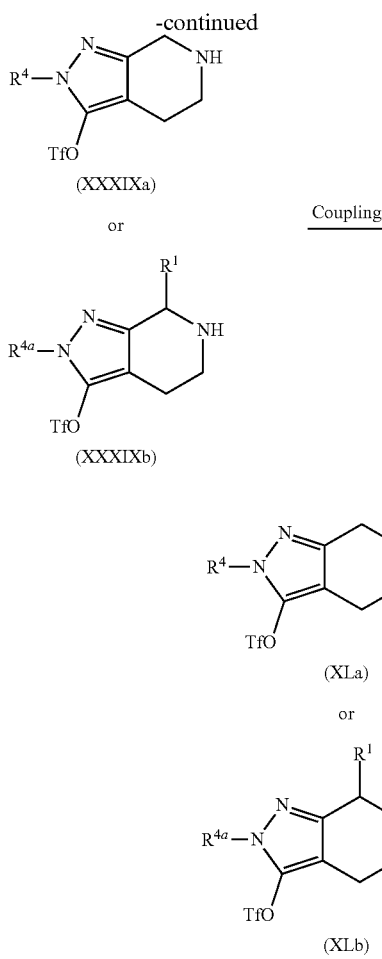

(XXXIXa)

or (XXXIXb)

Coupling →

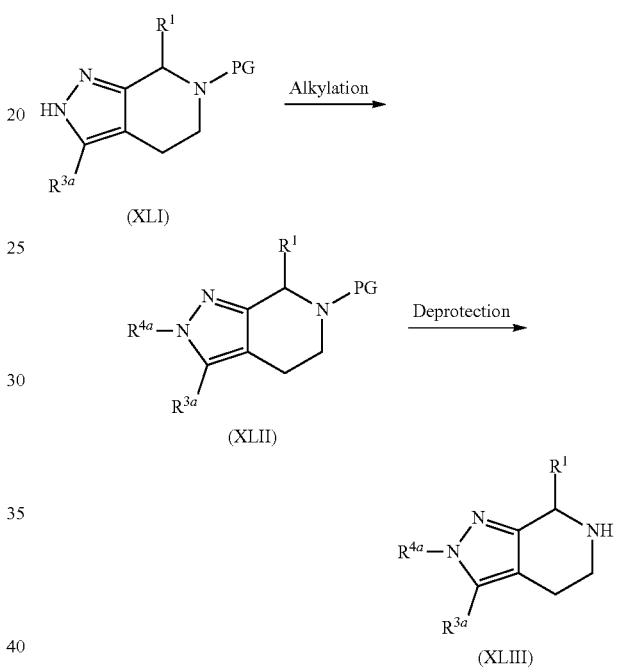

(XLa)

or (XLb)

According to SCHEME 19, cleavage of the BOC protecting group on compounds of formulas (XXVIIa) and (XXVIIb) according to methods previously described, provides compounds of formula (XXXIXa) and (XXXIXb). A compound of formula (XLa), where $R^4$ is $C_{1-4}$alkyl; and $R^2$ is quinoline; is prepared by conventional amide bond forming techniques such as coupling reactions which are well known to those skilled in the art (such as HATU (1-[bis(dimethylamino)methylene]-1H-1,2,3-triazolo[4,5-b]pyridinium 3-oxid hexafluorophosphate), BOP (benzotriazol-1-yloxy-tris(dimethylamino)phosphonium hexafluorophosphate), or conversion of the acid to an acid chloride). For example, reaction of a compound of formula (XXXIXa) where $R^4$ is $C_{1-4}$alkyl or phenyl; with a commercially available or synthetically accessible (according to the schemes above) suitably substituted aryl, or heteroaryl carboxylic acid, where the acid is activated with an appropriate activating reagent, for example a carbodiimide, such as N,N'-dicyclohexylcarbodiimide (DCC) or 1-ethyl-3-(3-dimethylaminopropyl)carbodiimide (EDC, EDAC or EDCI) optionally in the presence of hydroxybenzotriazole (HOBt) and/or a catalyst such as 4-dimethylaminopyridine (DMAP); a halotrisaminophosphonium salt such as (benzotriazol-1-yloxy)tris(dimethylamino)phosphonium hexafluorophosphate (BOP), or bromotripyrrolidinophosphonium hexafluorophosphate (PyBroP®); a suitable pyridinium salt such as 2-chloro-1-methyl pyridinium chloride; or another suitable coupling agent such as N,N,N',N'-tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxid hexafluorophosphate (HATU), 2,4,6-tripropyl-1,3,5,2,4,6-trioxatriphosphorinane-2,4,6-trioxide (T3P®) and the like. Coupling reactions are conducted in a suitable solvent such as DCM, THF, DMF and the like, optionally in the presence of a tertiary amine such as N-methylmorpholine, N-ethyldiisopropylamine (DIEA, DIPEA), or triethylamine (TEA), at a temperature ranging from about 0° C. to rt, to provide compound a of formula (XLa). Similarly, a compound of (XXXIXb) is reacted in the same fashion as described above to provide compounds of formula (XLb).

SCHEME 20

According to SCHEME 20, a compound of formula (XLI), where $R^1$ is $C_{1-4}$alkyl, and $R^{3a}$ is phenyl substituted with one, two, or three halo members, is prepared by reacting tert-butyl 7-methyl-3-(((trifluoromethyl)sulfonyl)oxy)-2,4,5,7-tetrahydro-6H-pyrazolo[3,4-c]pyridine-6-carboxylate is in metal-mediated cross coupling reaction employing conditions previously described with a commercially available or synthetically accessible suitably substituted phenyl boronic acid. Alkylation of a compound of formula (XLI), with a suitable alkylating agent such as $CD_3I$, a suitable base such as NaH, and the like, in a suitable solvent such as THF, and the like, provides a compound of formula (XLII), where $R^{4a}$ is $CD_3$.

Diflouromethylation of a compound of formula (XLI) is achieved employing sodium 2-chloro-2,2-difluoroacetate, a suitable base such as NaH, in a solvent such as DMF, and the like, to provide a compound of formula (XLII), where $R^{4a}$ is $CF_2H$.

Trifluoromethylation of a compound of formula (XLI) is achieved in two steps. In a first step, reaction with dibromodifluoromethane, in a suitable solvent such as DMF, in the presence of a suitable base such as NaH, at elevated temperature, provides the 1-bromodifluoromethylated intermediate. Subsequent reaction with silver(I) tetrafluoroborate, in a suitable solvent such as DCM, at temperatures ranging from 0° C. to room temperature, provides a compound of formula (XLII), where $R^{4a}$ is $CF_3$.

Cleavage of the BOC protecting group according to methods previously described, provides a compound of formula (XLIII).

Scheme 21

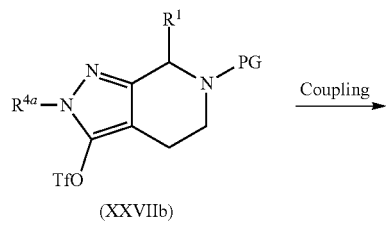

(XXVIIb)

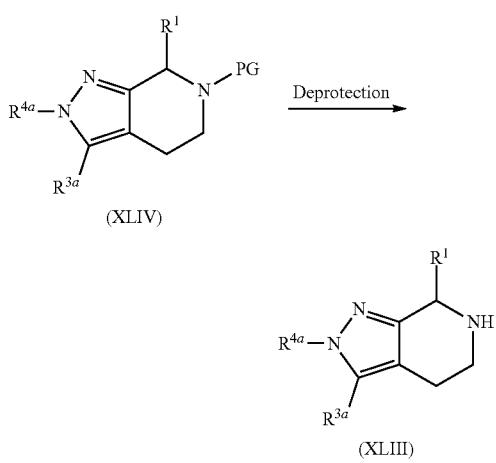

According to SCHEME 21, a compound of formula (XXVIIb), is coupled in a metal mediated cross coupling reaction as previously described, with a suitably substituted commercially available or synthetically accessible aryl, alkyl, or heteroaryl boronic acid, to provide a compound of formula (XLIV), where $R^{3a}$ and $R^{4a}$ are as described in claim 28. Subsequent deprotection employing methods previously described provides a compound of formula (XLIII).

SCHEME 22

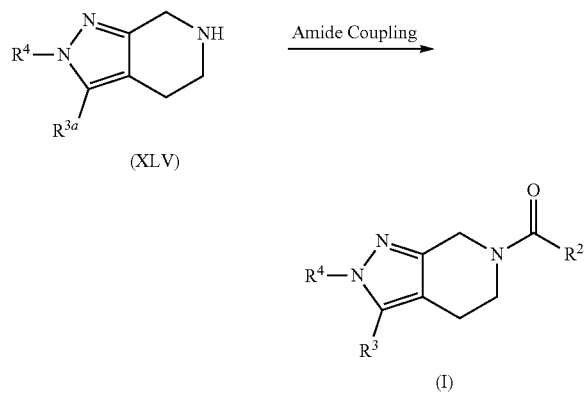

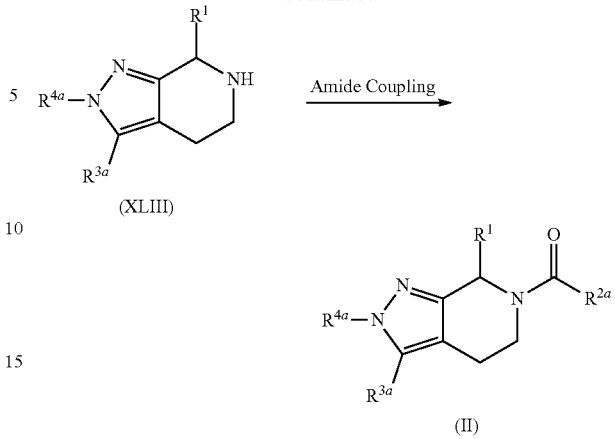

According to SCHEME 22, compounds of Formula (I), or Formula (II), where $R^1$, $R^2$, $R^{2a}$, $R^3$, $R^{3a}$, $R^4$ and $R^{4a}$ are as defined in claim 1 and claim 28, are prepared from compounds of formula (XLV) or (XLIII), according to conventional amide bond forming techniques such as coupling reactions with a suitably substituted aryl or heteroaryl carboxylic acid, which are previously described, or by reaction of suitably substituted aryl or heteroaryl acid chlorides (conversion of the acid to an acid chloride), employing a base such as TEA (triethylamine), and the like, in a suitable solvent such as DCM, THF, ethyl acetate (EtOAc), and the like.

A compound of Formula (II), where $R^{2a}$ is a phenyl substituted with a reactive functional group such as $CH_2CH_2O$-Ts, is fluorinated with [$^{18}F$]fluoride, a base such as $K_2CO_3$, in a solvent such as acetonitrile/water, to provide a compound of Formula (II), where $R^{2a}$ is phenyl substituted with $CH_2CH_2{}^{18}F$.

A compound of Formula (II), where $R^{2a}$ is an indole substituted with a reactive functional group such as $CH_2CH_2O$-THP, is deprotected with HCl/MeOH, to provide the free $CH_2CH_2OH$ intermediate. Subsequent tosylation of the OH moiety employing toluene-p-sulphonic anhydride ($Ts_2O$), a base such as TEA (triethylamine), in a suitable solvent, provides a tosylated compound which is subsequently fluorinated with [$^{18}F$]fluoride, as previously described, to provide a compound of Formula (II), where $R^{2a}$ is an indole substituted with $CH_2CH_2{}^{18}F$.

A compound of Formula (II), where $R^{2a}$ is 1H-pyrrolo[2,3-b]pyridin-4-yl, is alkylated with fluoro-2-iodoethane; a suitable base such as $Cs_2CO_3$, $K_2CO_3$, NaH, and the like; in a suitable solvent such as N,N-dimethylformamide, and the like, to provide a compound of Formula (II) where $R^{2a}$ is 1-(2-fluoroethyl)-1H-pyrrolo[2,3-b]pyridin-4-yl. In a similar fashion a compound of Formula (II), where $R^{2a}$ is 1H-indol-7-yl, 1H-pyrrolo[2,3-c]pyridin-3-yl, or 1H-pyrrolo[2,3-c]pyridin-4-yl, is alkylated with MeI, NaH, in a suitable solvent such as tetrahydrofuan, N,N-dimethylformamide, and the like, to provide compounds of Formula (II), where $R^{2a}$ is 1-methyl-1H-indol-7-yl, 1-methyl-1H-pyrrolo[2,3-c]pyridin-3-yl, 1-methyl-1H-pyrrolo[2,3-c]pyridin-4-yl, 1-methyl-1H-pyrrolo[3,2-c]pyridin-4-yl, 1-methyl-1H-pyrrolo[3,2-c]pyridin-3-yl, 2-methylpyrazolo[3,4-c]pyridin-7-yl, 1-methylpyrazolo[3,4-c]pyridin-7-yl, or 3-methyl-1,3-benzoxazol-2-one.

A compound of Formula (II), where $R^{2a}$ is 3-bromopyrazolo[1,5-a]pyridin-4-yl is reacted with trimethylboroxine, a suitable catalyst such as tetrakis(triphenylphosphine)palladium(0), and a suitable base such as potassium carbonate, in a suitable solvent such as N,N-dimethylformamide at 100° C. to provide a compound of Formula (II), where $R^{2a}$ is 3-methylpyrazolo[1,5-a]pyridin-4-yl.

SCHEME 23

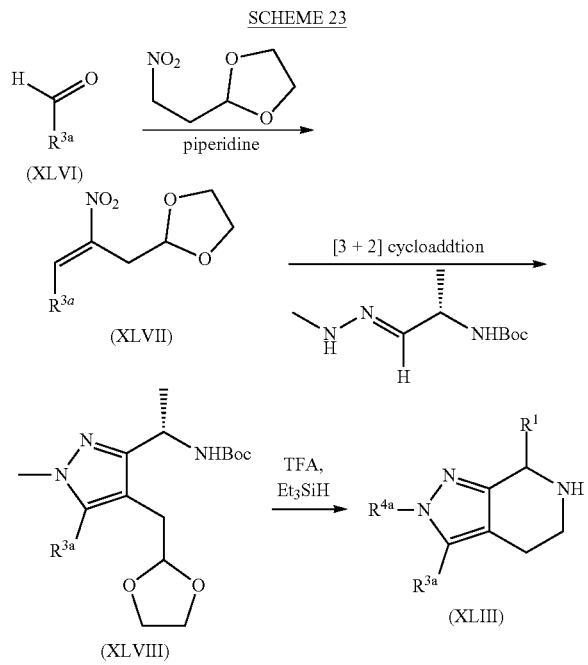

According to SCHEME 23, tert-butyl (S)-(1-oxopropan-2-yl)carbamate and methylhydrazine can be condensed in a suitable solvent such as THF to afford tert-butyl (S,E)-(1-(2-methylhydrazineylidene)propan-2-yl)carbamate. A commercially available or synthetically accessible suitably substituted aryl aldehyde of formula (XLVI) is treated with 2-(2-nitroethyl)-1,3-dioxolane in the presence of a catalytic amount of suitable base such as piperidine; in a suitable solvent such as toluene; at a temperature of 110° C. to provide a compound of formula (XLVII), where $R^{3a}$ and $R^{4a}$ are as defined in Formula (II).

Pyrazole ring formation is accomplished through [3+2] cycloaddition of tert-butyl (S,E)-(1-(2-methylhydraziney-lidene)propan-2-yl)carbamate and a compound of formula (XLVII) at a temperature of 40° C. Subsequent global deprotection and cyclization by treatment with trifluoro-acetic acid and triethylsilane at 55° C. affords a compound of formula (XLIII).

Compounds of Formula (I) (as well as compounds of Formula (II)) may be converted to their corresponding salts using methods known to one of ordinary skill in the art. For example, an amine of Formula (I) (as well as compounds of Formula (II)) is treated with trifluoroacetic acid, HCl, or citric acid in a solvent such as $Et_2O$, $CH_2Cl_2$, THF, MeOH, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) (as well as compounds of Formula (II)) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16" PTFE tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

METHOD A. An Agilent HPLC with an Xterra Prep RP18 column (5 µM, 30×100 or 50×150 mm) or an XBridge C18 OBD column (5 µM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

METHOD B. A Shimadzu LC-8A Series HPLC with an Inertsil ODS-3 column (3 m, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

METHOD C. A Shimadzu LC-8A Series HPLC with an XBridge C18 OBD column (5 µm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

METHOD D. A Gilson HPLC with an XBridge C18 column (5 μm, 100×50 mm), mobile phase of 5-99% ACN in 20 mM $NH_4OH$ over 10 min and then hold at 99 ACN for 2 min, at a flow rate of 80 mL/min.

or

METHOD E. An ACCQ Prep HPLC with an XBridge C18 OBD column (5 μM, 50×100), mobile phase of 5% ACN in $H_2O$ (both with 0.05% TFA) was held for 1 min, then a gradient of 5-95% ACN over 12 min, then held at 95% ACN for 2 min, with a flow rate of 80 mL/min.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100 to 150 bar with a flow rate ranging from 40 to 60 mL/min. The column was heated to 35 to 40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 17.1 (CambridgeSoft Corp., Cambridge, Mass.) or OEMetaChem V1.4.0.4 (Open Eye).

Compounds designated as R* or S* are enantiopure compounds where the absolute configuration was not determined.

Intermediate 1: 2-Methyl-3-phenyl-4,5,6,7-tetrahydropyrazolo[3,4-c]pyridine

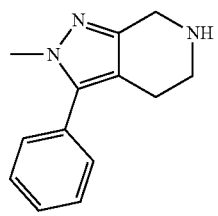 [SMILES: Cn1nc2c(c1-c1ccccc1)CCNC2]

Step A: tert-Butyl 2-methyl-3-oxo-1,4,5,7-tetrahydropyrazolo[3,4-c]pyridine-6-carboxylate. To a mixture of 1-tert-butyl 4-ethyl-3-oxopiperidine-1,4-dicarboxylate (8.89 g, 32.8 mmol) in acetic acid (100 mL) was added methylhydrazine (2.6 mL, 49.7 mmol, 0.88 g/mL) and the reaction was stirred at 80° C. for 1 h. The reaction mixture was concentrated under reduced pressure. Purification (FCC, silica gel ($SiO_2$) column chromatography, eluting with ethyl acetate (EtOAc):methanol (MeOH)(10:1) afforded the title compound (8.11 g, 32.0 mmol, 97%) as a yellow foam. MS (ESI): mass calcd. for $C_{12}H_9N_3O_3$, 253.1; m/z found, 254.2 $[M+H]^+$.

Step B: tert-Butyl 2-methyl-3-(trifluoromethylsulfonyloxy)-5,7-dihydro-4H-pyrazolo[3,4-c]pyridine-6-carboxylate. To a solution of tert-butyl 2-methyl-3-oxo-1,4,5,7-tetrahydropyrazolo[3,4-c]pyridine-6-carboxylate (8.70 g, 34.3 mmol) in dichloromethane (100 mL) was added N,N-diisopropylethylamine (DIEA/DIPEA) (6.55 mL, 37.9 mmol, 0.747 g/mL) and N-phenyl bis(trifluoromethanesulfonimide) (13.5 g, 37.8 mmol). The reaction mixture was stirred at room temperature (rt) for 8 h and concentrated under reduced pressure. Purification (FCC, silica gel ($SiO_2$) column chromatography, eluting with heptane:ethyl acetate (6:1→4:1) afforded the title compound (9.55 g, 24.8 mmol, 72%) as a colorless oil. MS (ESI): mass calcd. for $C_{13}H_{18}F_3N_3O_5S$, 385.1; m/z found, 330.0 $[M+2H-tBu]^+$.

Step C: tert-Butyl 2-methyl-3-phenyl-5,7-dihydro-4H-pyrazolo[3,4-c]pyridine-6-carboxylate. To a solution of tert-butyl 2-methyl-3-(trifluoromethylsulfonyloxy)-5,7-dihydro-4H-pyrazolo[3,4-c]pyridine-6-carboxylate (2.14 g, 5.55 mmol) in 1,4-dioxane (60 mL) was added phenylboronic acid (940 mg, 7.71 mmol), aqueous sodium carbonate (2 M, 8.3 mL, 16.6 mmol) and tetrakis(triphenylphosphine)palladium(0) (320 mg, 0.277 mmol). The reaction mixture was stirred at 65° C. for 18 h under argon and concentrated under reduced pressure. The residue was taken up in ethyl acetate (EtOAc) (50 mL), washed with 1 M sodium hydroxide (2×60 mL), brine (1×90 mL, dried over sodium sulfate, filtered and concentrated under reduced pressure. The residue was purified by silica gel column chromatography, eluting with heptane:ethyl acetate (4:1) to give the title compound (1.51 g, 4.42 mmol, 86%) as a yellow powder. MS (ESI): mass calcd. for $C_{18}H_{23}N_3O_2$, 313.2; m/z found, 314.2 $[M+H]^+$. $^1H$ NMR (300 MHz, DMSO-$d_6$) δ 7.57-7.39 (m, 5H), 4.44 (s, 2H), 3.74 (s, 3H), 3.53 (t, J=5.8 Hz, 2H), 2.55-2.43 (m, 2H), 1.43 (s, 9H).

Step D: 2-Methyl-3-phenyl-4,5,6,7-tetrahydropyrazolo[3,4-c]pyridine. To a mixture of tert-butyl 2-methyl-3-phenyl-5,7-dihydro-4H-pyrazolo[3,4-c]pyridine-6-carboxylate (6.41 g, 20.5 mmol) in dichloromethane (65 mL) was added trifluoroacetic acid (TFA) (15.5 mL, 203 mmol, 1.49 g/mL) at 0° C. and the reaction was stirred at room temperature for 18 h. The reaction mixture was poured into saturated sodium carbonate (250 mL) and the layers were separated. The aqueous layer was extracted with dichloromethane (2×200 mL). The combined organic layers were washed with brine (2×150 mL). The organic layer was dried over sodium sulfate, filtered and evaporated to give the title compound (4.00 g, 18.8 mmol, 91%) as a yellow powder. MS (ESI): mass calcd. for $C_{13}H_{15}N_3$, 213.1; m/z=214.3 $[M+H]^+$. $^1H$ NMR (500 MHz, DMSO-$d_6$) δ 7.53-7.48 (m, 2H), 7.44-7.39 (m, 3H), 3.74-3.69 (m, 5H), 3.35-3.27 (m, 1H), 2.83 (t, J=5.7 Hz, 2H), 2.41 (t, J=5.7 Hz, 2H).

Intermediate 2: 3-Cyclopropyl-2-methyl-4,5,6,7-tetrahydro-2H-pyrazolo[3,4-c]pyridine

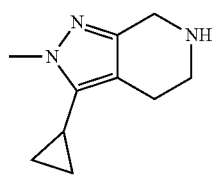

The title compound was prepared in a manner analogous to Intermediate 1, using cyclopropylboronic acid instead of phenylboronic acid in Step C. MS (ESI): mass calcd. for $C_{10}H_{15}N_3$, 177.1; m/z found, 178.1 $[M+H]^+$.

Intermediate 3: 2-Methyl-3-(5-methylthiophen-2-yl)-4,5,6,7-tetrahydro-2H-pyrazolo[3,4-c]pyridine

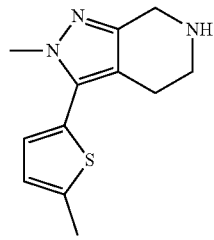 [SMILES: Cc1ccc(-c2c3c(nn2C)CNCC3)s1]

The title compound was prepared in a manner analogous to Intermediate 1, using 4,4,5,5-tetramethyl-2-(5-methylthiophen-2-yl)-1,3,2-dioxaborolane instead of phenylboronic acid in Step C. MS (ESI): mass calcd. for $C_{12}H_{15}N_3S$, 233.1; m/z found, 234.1 $[M+H]^+$.

Intermediate 4: 3-(3-Fluorophenyl)-2-methyl-4,5,6,7-tetrahydro-2H-pyrazolo[3,4-c]pyridine

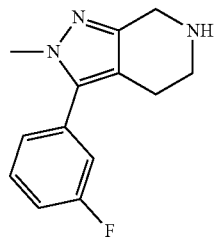 [SMILES: Cn1nc2c(c1-c1cccc(F)c1)CCNC2]

The title compound was prepared in a manner analogous to Intermediate 1, using 3-fluorophenylboronic acid instead of phenylboronic acid in Step C. MS (ESI): mass calcd. for $C_{13}H_{14}FN_3$, 231.1; m/z found, 232.1 $[M+H]^+$.

Intermediate 5: 3-(3,5-Difluorophenyl)-2-methyl-4,5,6,7-tetrahydro-2H-pyrazolo[3,4-c]pyridine

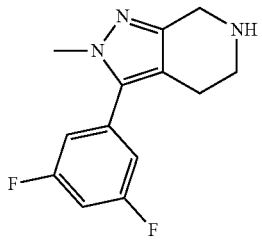 [SMILES: Cn1nc2c(c1-c1cc(F)cc(F)c1)CCNC2]

The title compound was prepared in a manner analogous to Intermediate 1, using 3,5-difluorophenylboronic acid instead of phenylboronic acid in Step C. MS (ESI): mass calcd. for $C_{13}H_{13}F_2N_3$, 249.1; m/z found, 250.1 $[M+H]^+$.

Intermediate 6: 2-Ethyl-3-phenyl-4,5,6,7-tetrahydro-2H-pyrazolo[3,4-c]pyridine

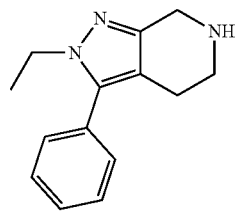 [SMILES: CCn1nc2c(c1-c1ccccc1)CCNC2]

The title compound was prepared in a manner analogous to Intermediate 1, using ethylhydrazine hydrochloride instead of methylhydrazine in Step A. MS (ESI): mass calcd. for $C_{13}H_{21}N_3O_3$, 267.2; m/z found, 268.2 $[M+H]^+$.

Intermediate 7: tert-Butyl 2,7-dimethyl-3-(((trifluoromethyl)sulfonyl)oxy)-2,4,5,7-tetrahydro-6H-pyrazolo[3,4-c]pyridine-6-carboxylate

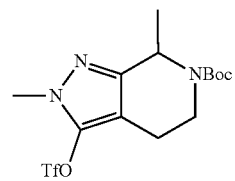 [SMILES: CC1c2nn(C)c(OS(=O)(=O)C(F)(F)F)c2CCN1C(=O)OC(C)(C)C]

Step A: 1-(tert-Butyl) 4-ethyl 2-methyl-3-oxopiperidine-1,4-dicarboxylate. To a cooled (−78° C.) solution of tert-butyl 2-methyl-3-oxopiperidine-1-carboxylate (5 g, 23.4 mmol) in tetrahydrofuran (THF) (35 mL), was added lithium bis(trimethylsilyl)amide (1.0 M in THF, 28.1 mL, 28.1 mmol) dropwise over a period of 10 minutes. Stirring was maintained at −78° C. for 30 minutes, and then a solution of ethyl cyanoformate (3.0 mL, 30.4 mmol) in THF (15 mL) was added dropwise at −78° C. over a period of 10 minutes. The reaction mixture was allowed to stir at −78° C. for 2 h and then quenched with saturated aqueous $NH_4Cl$. The aqueous layer was extracted with EtOAc (2×100 mL), the combined organics dried over $Na_2SO_4$ and concentrated in vacuo. The residue was purified by flash chromatography ($SiO_2$; 0-30% EtOAc/hexanes) to give the title compound as an oil (3.5 g, 52% yield). $^1$H NMR (500 MHz, $CDCl_3$) δ 4.26-4.10 (m, 2H), 2.79 (s, 1H), 2.34-2.14 (m, 2H), 1.47 (d, J=27.0 Hz, 2H), 1.40 (s, 9H), 1.36 (s, 1H), 1.29 (d, J=6.9 Hz, 3H), 1.23 (t, J=7.1 Hz, 3H).

Step B: tert-Butyl 2,7-dimethyl-3-oxo-1,2,3,4,5,7-hexahydro-6H-pyrazolo[3,4-c]pyridine-6-carboxylate. To a solution of [1-(tert-butyl) 4-ethyl 2-methyl-3-oxopiperidine-1,4-dicarboxylate](3.5 g, 12.1 mmol) in toluene (40.0 mL) was added methylhydrazine (0.96 mL, 18.1 mmol). The reaction mixture was refluxed at 110° C. for 3 h. The reaction mixture was cooled to room temperature and the solvent was removed in vacuo. Purification (FCC, $SiO_2$; 0-10% DCM-MeOH) afforded the title compound as an oil (2.7 g, 83% yield). MS (ESI): mass calcd. for $C_{13}H_{21}N_3O_3$, 267.2; m/z found, 268.1 $[M+H]^+$.

Step C: tert-Butyl-2,7-dimethyl-3-(((trifluoromethyl)sulfonyl)oxy)-2,4,5,7-tetrahydro-6H-pyrazolo[3,4-c]pyridine-6-carboxylate. To a solution of tert-butyl 2,7-dimethyl-3-oxo-1,2,3,4,5,7-hexahydro-6H-pyrazolo[3,4-c]pyridine- 6-carboxylate (2.7 g, 10.1 mmol) in dichloromethane (45.0 mL) was added diisopropylethylamine (1.9 mL, 11.1 mmol) followed by 1,1,1-trifluoro-N-phenyl-N-((trifluoromethyl)sulfonyl)methanesulfonamide (4.0 g, 11.1 mmol). The reaction mixture was stirred at room temperature for 5 h and concentrated in vacuo. The crude residue was purified by flash chromatography (SiO$_2$; 0-20% hexanes-EtOAc) to give the title compound as an oil (3.8 g, 86% yield). MS (ESI): mass calcd. for $C_{14}H_{20}F_3N_3O_5S$, 399.1; m/z found, 344.0 [M+2H-$^t$Bu]$^+$. $^1$H NMR (500 MHz, CDCl$_3$) δ 5.23 (s, 1H), 4.25 (s, 1H), 3.70 (s, 3H), 2.85 (s, 1H), 2.47 (dtd, J=30.7, 15.4, 4.0 Hz, 2H), 1.41 (s, 9H), 1.34 (d, J=6.8 Hz, 3H).

Intermediate 8: (S)-tert-Butyl 2,7-dimethyl-3-(((trifluoromethyl)sulfonyl) oxy)-2,4,5,7-tetrahydro-6H-pyrazolo[3,4-c] pyridine-6-carboxylate

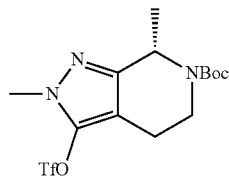 [SMILES: C[C@H]1c2nn(C)c(OS(=O)(=O)C(F)(F)F)c2CCN1C(=O)OC(C)(C)C]

Method A:

Purification of racemic tert-butyl 2,7-dimethyl-3-(((trifluoromethyl)sulfonyl)oxy)-2,4,5,7-tetrahydro-6H-pyrazolo[3,4-c]pyridine-6-carboxylate, Intermediate 7 (8.1 g, 18.5 mmol) by chiral SFC chromatography (Stationary phase: Whelk-O1 (S, S) 5 µm 250*21.2 mm, Mobile phase: 90% CO$_2$, 10% iPrOH) provided 3.6 g of the title compound. $[α]^{20}_D$=+100.3 (c=1.0, MeOH).

MS (ESI): mass calcd. for $C_{14}H_{20}F_3N_3O_5S$, 399.1; m/z found, 344.0 [M+2H-$^t$Bu]$^+$. $^1$H NMR (500 MHz, CDCl$_3$) δ 5.23 (s, 1H), 4.25 (s, 1H), 3.70 (s, 3H), 2.85 (s, 1H), 2.47 (dtd, J=30.7, 15.4, 4.0 Hz, 2H), 1.41 (s, 9H), 1.34 (d, J=6.8 Hz, 3H).

Method B:

Step A: Ethyl (S)-4-((1-ethoxy-1-oxopropan-2-yl) amino) butanoate. Into a 50 L reactor were added DMF (21 L, 6 V), ethyl L-alaninate hydrochloride (6.13 kg, 2.0 eq. 90% w/w), K$_2$HPO$_4$ (10.94 kg, 3.5 eq.) and KI (2.98 kg, 1.0 eq.) successively at 20-30° C. The resulting mixture was warmed to 50-55° C. and held at this temperature for 30 min. Then a solution of ethyl 4-bromobutanoate (3.50 kg, 1.0 eq.) in dimethylformamide (DMF) (7 L, 2 V) was added dropwise over 1 h while keeping the temperature at 50-55° C. The mixture was stirred at 50-55° C. for 3 h. After the completion of the reaction, the reaction mixture was cooled to 20-30° C. and transferred into another reactor followed by adding water (87.5 L, 25 V). The resulting mixture was extracted with tert-butyl methyl ether (MTBE) (17.5 L×4). The organic phase was collected and washed with brine (17.5 L). The organic phase was combined with the organic phases from other two batches (1.00 kg batch and 2.50 kg batch). Then the solution was concentrated under vacuum at 40-45° C. to give 6.8 kg of the title compound as a light-yellow oil (94% w/w assay by Q-NMR) in the yield of 82.2%. $^1$H NMR (CDCl$_3$, 300 MHz) δ 4.26-4.12 (m, 3H), 4.12 (d, J=7.1 Hz, 1H), 3.35 (q, J=7.0 Hz, 1H), 2.68 (dt, J=11.4, 7.0 Hz, 1H), 2.55 (dt, J=11.4, 7.1 Hz, 1H), 2.38 (t, J=7.3 Hz, 2H), 1.84 (q, J=6.9 Hz, 1H), 1.36-1.17 (m, 9H).

Step B: Ethyl (S)-4-((tert-butoxycarbonyl)(1-ethoxy-1-oxopropan-2-yl)amino)butanoate. Into a 20 L reactor were added crude ethyl (S)-4-((1-ethoxy-1-oxopropan-2-yl) amino)butanoate (3.5 kg, 1.0 eq.), tetrahydrofuran (THF) (10 L, 3 V), and di-tert-butyl dicarbonate (3.5 kg, 1.05 eq.) at 20-30° C. The resulting mixture was warmed to 55-60° C. and held at this temperature for 3 h. After the completion of the reaction, the reaction mixture was concentrated under vacuum at 40-45° C. to give 5624 g of the title compound as a yellow oil with purity of 87.2% (GC) and 99.1% ee. The crude product was used in the next step without further purification. $^1$H NMR (CDCl$_3$, 400 MHz,) δ 4.43-3.92 (m, 5H), 3.53-3.31 (m, 1H), 3.24-3.03 (m, 1H), 2.47-2.28 (m, 2H), 1.98-1.87 (m, 2H), 1.54 (s, 3H), 1.51-1.40 (m, 11H), 1.33-1.22 (m, 7H).

Step C: 1-(tert-Butyl) 4-ethyl (2S)-2-methyl-3-oxopiperidine-1,4-dicarboxylate. Into a 10 L four-necked flask were added crude ethyl(S)-4-((tert-butoxycarbonyl)(1-ethoxy-1-oxopropan-2-yl)amino)butanoate (450 g, 87% pure, 1.9 mol, 1.0 eq.) and THF (2.25 L, 5 V) at 20-30° C. After the mixture was cooled to −40° C. to −30° C., lithium bis(trimethylsilyl)amide (LiHMDS) (1 M in THF, 2.9 L, 2.9 mol, 1.5 eq.) was added dropwise while keeping the temperature at −40° C. to −30° C. The resulting reaction mixture was warmed to 10-20° C. and held at this temperature for 1 h. After the completion of the reaction, the reaction mixture was combined with other two batches then poured into aq. citric acid (408.6 g in 2250 mL H$_2$O, 2.9 mol, 1.5 eq.). After phase separation, the aqueous layer was re-extracted with MTBE (12 L, 10 V), the combined organic layers were sequentially washed with brine (9 L×2). The organic phase was dried over Na$_2$SO$_4$, then concentrated under vacuum to give crude product. The crude product was purified by silica gel chromatography (petroleum ether/ethyl acetate=1/0 to 20/1) to give the title compound (1100 g) with 99% purity in the yield of 70% over two steps. $^1$H NMR (500 MHz, CDCl$_3$) δ 4.26-4.10 (m, 2H), 2.79 (s, 1H), 2.34-2.14 (m, 2H), 1.47 (d, J=27.0 Hz, 2H), 1.40 (s, 9H), 1.36 (s, 1H), 1.29 (d, J=6.9 Hz, 3H), 1.23 (t, J=7.1 Hz, 3H).

Step D: tert-Butyl (7S)-2,7-dimethyl-3-oxo-2,3,3a,4,5,7-hexahydro-6H-pyrazolo[3,4-c]pyridine-6-carboxylate. Into a 10 L four-necked flask were added methylhydrazine sulfate (360 g, 2.5 mol, 1.5 eq.), EtOH (5 L, 10.6 V) and DIEA (399 mL, 2.4 mol, 1.45 eq.) at 20-30° C. The resulting mixture was warmed to 75-80° C. over 30 min. Then a solution of 1-(tert-butyl) 4-ethyl (2S)-2-methyl-3-oxopiperidine-1,4-dicarboxylate (495 g crude, assay weight 470 g, 1.6 mol, 1.0 eq.) in EtOH (500 mL) was added dropwise over 20 min while keeping the temperature at 75-80° C. The resulting mixture was stirred at 75-80° C. for 4 h. After the completion of the reaction, the reaction mixture was concentrated under vacuum. The resulting residue was combined with the residue from another 470 g batch. To the combined residues were diluted with DCM (8 L, 8.5 V), H$_2$O (2 L, 2.7 V) and brine (2.5 L, 2.7 V). After phase separation, the aqueous layers were re-extracted with DCM (2 L×2). The combined organic layers were dried over Na$_2$SO$_4$, then concentrated under vacuum to give the title compound, which was used in the next step without further purification. MS (ESI): mass calcd. for $C_{13}H_{21}N_3O_3$, 267.2; m/z found, 268.1 [M+H]$^+$.

Step E: (S)-tert-Butyl 2,7-dimethyl-3-(trifluoromethylsulfonyloxy)-4,5-dihydro-2H-pyrazolo[3,4-c]pyridine-6 (7H)-carboxylate. Into a 10 L four-necked flask were added tert-butyl (7S)-2,7-dimethyl-3-oxo-2,3,3a,4,5,7-hexahydro- 6H-pyrazolo[3,4-c]pyridine-6-carboxylate (940 g, 3.3 mol, 1.0 eq.), DCM (6 L, 6.4 V) and DIEA (550 mL, 3.3 mol, 1.0 eq.) at 20-30° C.

After the mixture was cooled to 10-20° C., N-(5-chloro-2-pyridyl)bis(trifluoromethanesulfonimide) (902 g, 2.3 mol, 0.7 eq.) was added batch-wise while keeping the temperature at 10-20° C. Additional N-(5-chloro-2-pyridyl)bis(trifluoromethanesulfonimide) (232 g, 0.6 mol, 0.18 eq.) was added. After stirring overnight, HPLC indicated the reaction was completed. Then the reaction mixture was concentrated under vacuum, followed by purification with silica gel chromatography (petroleum ether/ethyl acetate=1/0 to 8/1) to give 1106 g of the title compound with a purity of 99% (84% yield over two steps). $^1$H NMR (400 MHz, CDCl$_3$) δ 5.19 (br, 1H), 4.30 (br, 1H), 3.78 (s, 3H), 2.99-2.85 (m, 1H), 2.59-2.52 (m, 1H), 1.48 (s, 10H), 1.41 (d, J=6.4 Hz, 3H).

Intermediate 9: (R)-tert-Butyl 2,7-dimethyl-3-(((trifluoromethyl)sulfonyl) oxy)-2,4,5,7-tetrahydro-6H-pyrazolo[3,4-c]pyridine-6-carboxylate

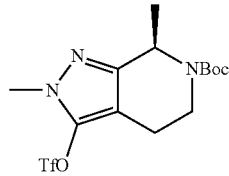 [SMILES: C[C@@H]1c2nn(C)c(OS(=O)(=O)C(F)(F)F)c2CCN1C(=O)OC(C)(C)C]

Purification of racemic tert-butyl 2,7-dimethyl-3-(((trifluoromethyl)sulfonyl)oxy)-2,4,5,7-tetrahydro-6H-pyrazolo[3,4-c]pyridine-6-carboxylate, Intermediate 7 (8.1 g, 18.5 mmol) by chiral SFC chromatography (Stationary phase: Whelk-O1 (S, S) 5 μm 250*21.2 mm, Mobile phase: 90% CO$_2$, 10% iPrOH) provided 3.8 g of the title compound. [α]$^{20}_D$=−92.6 (c=1.0, MeOH). MS (ESI): mass calcd. for C$_{14}$H$_{20}$F$_3$N$_3$O$_5$S, 399.1; m/z found, 344.0 [M+2H-$^t$Bu]$^+$. $^1$H NMR (500 MHz, CDCl$_3$) δ 5.23 (s, 1H), 4.25 (s, 1H), 3.70 (s, 3H), 2.85 (s, 1H), 2.47 (dtd, J=30.7, 15.4, 4.0 Hz, 2H), 1.41 (s, 9H), 1.34 (d, J=6.8 Hz, 3H).

Intermediate 10: 2-Methyl-6-(quinoline-6-carbonyl)-4,5,6,7-tetrahydro-2H-pyrazolo[3,4-c]pyridin-3-yl trifluoromethanesulfonate

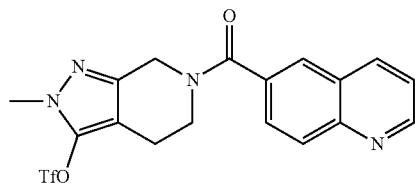 [SMILES: Cn1nc2c(c1OS(=O)(=O)C(F)(F)F)CCN(C(=O)c1ccc3ncccc3c1)C2]

Step A: 2-Methyl-4,5,6,7-tetrahydro-2H-pyrazolo[3,4-c]pyridin-3-yl trifluoromethanesulfonate. To a solution of [tert-butyl 2-methyl-3-(((trifluoromethyl)sulfonyl)oxy)-2,4,5,7-tetrahydro-6H-pyrazolo[3,4-c]pyridine-6-carboxylate] Intermediate 1, Step C, (1 g, 2.60 mmol) in dichloromethane (7.8 mL) was added trifluoroacetic acid (TFA) (7.8 mL, 101 mmol). The reaction mixture was stirred at room temperature for 30 min, and then concentrated in vacuo. The residue was purified by preparative HPLC (High Pressure Liquid Chromatography) to afford the title compound as a yellow solid (354 mg, 48% yield). MS (ESI): mass calcd. for C$_8$H$_{10}$F$_3$N$_3$O$_3$S, 285.0; m/z found, 286.1 [M+H]$^+$.

Step B: 2-Methyl-6-(quinoline-6-carbonyl)-4,5,6,7-tetrahydro-2H-pyrazolo[3,4-c]pyridin-3-yl trifluoromethanesulfonate. To a solution of 2-methyl-4,5,6,7-tetrahydro-2H-pyrazolo[3,4-c]pyridin-3-yl trifluoromethanesulfonate (354 mg, 1.24 mmol) and quinoline-6-carboxylic acid (236 mg, 1.37 mmol) in dichloromethane (5.3 mL) was added HATU (708 mg, 1.86 mmol) followed by DIPEA (0.64 mL, 3.72 mmol). The reaction mixture was stirred at 36° C. for 4.5 h, and then diluted with dichloromethane (DCM) and H$_2$O. The layers were separated, and the aqueous layer extracted with DCM (×2). The combined organics were washed with brine, dried over Na$_2$SO$_4$, filtered, and concentrated in vacuo. The residue was purified by silica gel chromatography (0-20% MeOH in DCM) to afford the title compound as an amorphous solid (241 mg, 44% yield). MS (ESI): mass calcd. for C$_{18}$H$_{15}$F$_3$N$_4$O$_4$S, 440.1; m/z found, 441.0 [M+H]$^+$.

Intermediate 11: 2,7-Dimethyl-6-(quinoline-6-carbonyl)-4,5,6,7-tetrahydro-2H-pyrazolo[3,4-c]pyridin-3-yl trifluoromethanesulfonate

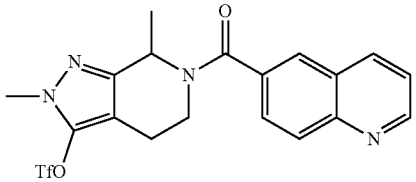 [SMILES: CC1c2nn(C)c(OS(=O)(=O)C(F)(F)F)c2CCN1C(=O)c1ccc2ncccc2c1]

The title compound was prepared in a manner analogous to Intermediate 10, using tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) instead of [tert-butyl 2-methyl-3-(((trifluoromethyl)sulfonyl)oxy)-2,4,5,7-tetrahydro-6H-pyrazolo[3,4-c]pyridine-6-carboxylate] in Step A. MS (ESI): mass calcd. for C$_{19}$H$_{17}$F$_3$N$_4$O$_4$S, 454.1; m/z found, 455.0 [M+H]$^+$.

Intermediate 12: 2-Chloro-3-(2-fluoroethoxy)benzoic acid

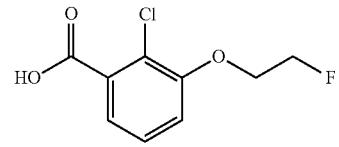 [SMILES: O=C(O)c1cccc(OCCF)c1Cl]

A solution of methyl 2-chloro-3-hydroxybenzoate (150 mg, 0.80 mmol), 1-fluoro-2-iodoethane (167 mg, 0.97 mmol) and cesium carbonate (392 mg, 1.2 mmol) in dimethylformamide (DMF) (3.1 mL) was stirred at rt for 16 h. The reaction mixture was diluted with water and extracted with ethyl acetate (EtOAc) (20 mL×3). The combined organic layers were washed with brine, dried, filtered and concentrated under reduced pressure. Purification (FCC SiO$_2$, EtOAc in hexanes (0 to 25%) afforded a yellow oil (183 mg, 98%). The oil (183 mg, 0.79 mmol) was further diluted in tetrahydrofuran (THF) (6.4 mL) and water (0.28 mL). Lithium hydroxide monohydrate (264 mg, 6.3 mmol)

was added. The reaction mixture was sealed and heated to 85° C. for 19 h then cooled. The reaction mixture was concentrated under reduced pressure and the resulting crude product was neutralized with HCl (1M, aq, 6.3 mL, 6.3 mmol). The resulting crude solid was filtered and dried to yield the title product (102 mg, 59%), which was used without further purification. MS (ESI): mass calcd. for $C_9H_8ClFO_3$, 218.0; m/z found, 217.0 [M−H]⁻.

Intermediate 13: 2-(2-Fluoroethoxy)benzoic acid

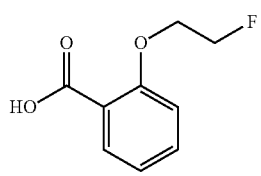 [SMILES: O=C(O)c1ccccc1OCCF]

The title compound was prepared in a manner analogous to Intermediate 12, using methyl 2-hydroxybenzoate in place of methyl 2-chloro-3-hydroxybenzoate. The crude product was used directly without purification.

Intermediate 14:
2-Chloro-5-(2-fluoroethoxy)benzoic acid

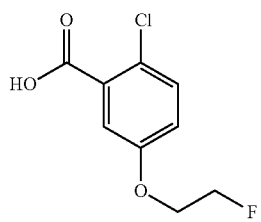 [SMILES: O=C(O)c1cc(OCCF)ccc1Cl]

The title compound was prepared in a manner analogous to Intermediate 12, using methyl 2-chloro-5-hydroxybenzoate in place of methyl 2-chloro-3-hydroxybenzoate. MS (ESI): mass calcd. for $C_9H_8ClFO_3$, 218.0; m/z found, 217.0 [M−H]⁻.

Intermediate 15: 3-(2-Fluoroethoxy)benzoic acid

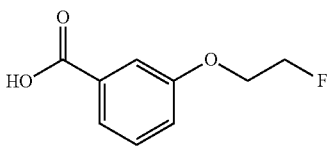 [SMILES: O=C(O)c1cccc(OCCF)c1]

The title compound was prepared in a manner analogous to Intermediate 12, using methyl 3-hydroxybenzoate in place of methyl 2-chloro-3-hydroxybenzoate. MS (ESI): mass calcd. for $C_9H_9FO_3$, 184.1; m/z found, 183.0 [M−H]⁻.

Intermediate 16: 4-(2-Fluoroethoxy)benzoic acid

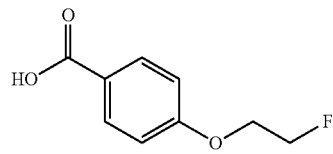 [SMILES: O=C(O)c1ccc(OCCF)cc1]

The title compound was prepared in a manner analogous to Intermediate 12, using methyl 4-hydroxybenzoate in place of methyl 2-chloro-3-hydroxybenzoate. MS (ESI): mass calcd. for $C_9H_9FO_3$, 184.1; m/z found, 183.0 [M−H]⁻.

Intermediate 17:
1-(2-Fluoroethyl)-1H-indole-4-carboxylic acid

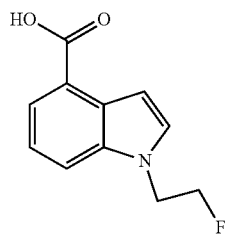 [SMILES: O=C(O)c1cccc2c1ccn2CCF]

The title compound was prepared in a manner analogous to Intermediate 12, using methyl indole-4-carboxylic acid in place of methyl 2-chloro-3-hydroxybenzoate. MS (ESI): mass calcd. for $C_{11}H_{10}FNO_2$, 207.1; m/z found, 208.1 [M+H]⁺.

Intermediate 18:
3-(2-Fluoroethoxy)quinoline-6-carboxylic acid

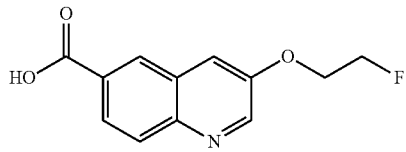 [SMILES: O=C(O)c1ccc2ncc(OCCF)cc2c1]

The title compound was prepared in a manner analogous to Intermediate 12, using 3-hydroxyquinoline-6-carboxylic acid in place of methyl 2-chloro-3-hydroxybenzoate and NaOH in place of LiOH. MS (ESI): mass calcd. for $C_{12}H_{10}FNO_3$, 235.1; m/z found, 236.2 [M+H]⁺.

Intermediate 19:
2-Fluoro-3-(2-fluoroethoxy)benzoic acid

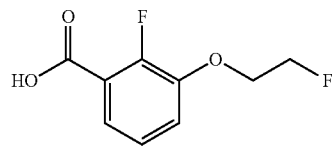 [SMILES: O=C(O)c1cccc(OCCF)c1F]

The title compound was prepared in a manner analogous to Intermediate 12, using methyl 2-fluoro-3-hydroxybenzoate in place of methyl 2-chloro-3-hydroxybenzoate and NaOH in place of LiOH. MS (ESI): mass calcd. for $C_9H_8F_2O_3$, 202.0; m/z found, 201.0 [M–H]$^-$.

Intermediate 20:
4-Fluoro-3-(2-fluoroethoxy)benzoic acid

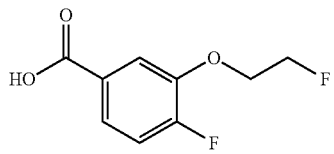 [SMILES: O=C(O)c1ccc(F)c(OCCF)c1]

The title compound was prepared in a manner analogous to Intermediate 12, using methyl 4-fluoro-3-hydroxybenzoate in place of methyl 2-chloro-3-hydroxybenzoate and NaOH in place of LiOH. MS (ESI): mass calcd. for $C_9H_8F_2O_3$, 202.0; m/z found, 201.0 [M–H]$^-$.

Intermediate 21:
5-Fluoro-3-(2-fluoroethoxy)benzoic acid

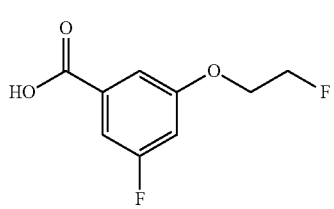 [SMILES: O=C(O)c1cc(F)cc(OCCF)c1]

The title compound was prepared in a manner analogous to Intermediate 12, using methyl 5-fluoro-3-hydroxybenzoate in place of methyl 2-chloro-3-hydroxybenzoate and NaOH in place of LiOH. MS (ESI): mass calcd. for $C_9H_8F_2O_3$, 202.0; m/z found, 201.0 [M–H]$^-$.

Intermediate 22:
2-Fluoro-5-(2-fluoroethoxy)benzoic acid

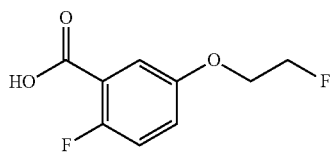 [SMILES: O=C(O)c1cc(OCCF)ccc1F]

The title compound was prepared in a manner analogous to Intermediate 12, using methyl 2-fluoro-5-hydroxybenzoate in place of methyl 2-chloro-3-hydroxybenzoate and NaOH in place of LiOH. MS (ESI): mass calcd. for $C_9H_8F_2O_3$, 202.0; m/z found, 201.0 [M–H]$^-$.

Intermediate 23:
8-(Trifluoromethyl)quinoline-6-carboxylic acid

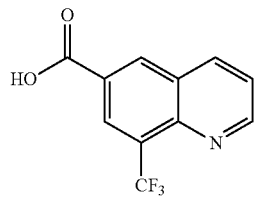

A mixture of 4-amino-3-(trifluoromethyl)benzoic acid (870 mg, 4.24 mmol), glycerol (0.62 mL, 8.49 mmol), and 3-nitrobenzenesulfonic acid sodium salt (4.30 g, 19.1 mmol) in 75% aqueous $H_2SO_4$ was heated to 100° C. for 3 h, then 140° C. for an additional 1 h. The reaction mixture was cooled to room temperature, and the pH of the reaction mixture was adjusted to pH 7 with careful addition of 20% aqueous NaOH solution. The resulting suspension was filtered, and the solid collected to afford the title compound as a brown solid. The filtrate was extracted with EtOAc (×3), and the combined organics were dried over $Na_2SO_4$, filtered, and concentrated under reduced pressure to afford additional material as a brown solid. MS (ESI): mass calcd. for $C_{11}H_6F_3NO_2$, 241.0; m/z found, 242.0 [M+H]$^+$.

Intermediate 24:
3-(Trifluoromethyl)quinoline-6-carboxylic acid

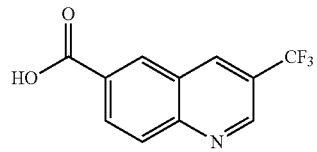 [SMILES: O=C(O)c1ccc2ncc(C(F)(F)F)cc2c1]

Step A: Methyl 3-iodoquinoline-6-carboxylate. To a solution of methyl quinoline-6-carboxylate (4.0 g, 21.4 mmol) in acetic acid (AcOH) (35 mL) was added N-iodosuccinimide (NIS) (7.21 g, 35.1 mmol). The reaction mixture was heated to 100° C. for 2 h. After cooling to room temperature, the reaction mixture was poured into a solution of saturated aqueous $Na_2CO_3$ cooled in an ice bath. The resulting precipitate was collected via vacuum filtration and triturated in hot methanol (MeOH) to afford the title compound as a white solid (2.86 g, 43% yield). MS (ESI): mass calcd. for $C_{11}H_8INO_2$, 313.0; m/z found, 314.0 [M+H]$^+$.

Step B: Methyl 3-(trifluoromethyl)quinoline-6-carboxylate. A microwave vial was charged with methyl 3-iodoquinoline-6-carboxylate (150 mg, 0.48 mmol), methyl 2,2-difluoro-2-(fluorosulfonyl)acetate (0.15 mL, 1.20 mmol), copper(I) iodide (228 mg, 1.20 mmol), DMPU (0.33 mL, 2.71 mmol), and DMF (3.0 mL). The head space was evacuated under vacuum and refilled with $N_2$ (×3), and then the reaction mixture was heated under microwave irradiation at 130° C. for 30 min. The reaction mixture was filtered over a pad of diatomaceous earth (Celite©), eluting with MeOH. The filtrate was concentrated, the residue dissolved in EtOAc, and the solution washed with saturated aqueous $NH_4Cl$. The aqueous layer was extracted with EtOAc (×3) and the combined organics were washed with brine (×3), dried over $Na_2SO_4$, filtered, and concentrated under reduced pressure. Purification (FCC, SiO$_2$, 0-50% EtOAc in hexanes) afforded the title compound (16 mg, 13% yield). MS (ESI): mass calcd. for C$_{12}$H$_8$F$_3$NO$_2$, 255.1; m/z found, 256.1 [M+H]$^+$.

Step C: 3-(Trifluoromethyl)quinoline-6-carboxylic acid. A mixture of methyl 3-(trifluoromethyl)quinoline-6-carboxylate (25 mg, 98.0 µmol), NaOH (7.8 mg, 0.2 mmol), and H$_2$O (20 µL, 1.11 mmol) in 1:1 THF:MeOH (0.4 mL) was heated to 60° C. for 2 h. The reaction was allowed to cool to room temperature and the solvent removed in vacuo. The resulting crude product was dissolved in H$_2$O and the reaction mixture was acidified to pH 5 with 2N HCl. The resulting precipitate was collected via vacuum filtration to afford the title compound as a white solid. MS (ESI): mass calcd. for C$_{11}$H$_6$F$_3$NO$_2$, 241.0; m/z found, 242.0 [M+H]$^+$.

Intermediate 25: 2-Methylquinoxaline-6-carboxylic acid

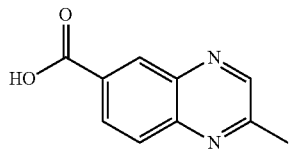

To a solution of 3,4-diaminobenzoic acid (500 mg, 3.3 mmol) in ethanol (EtOH) (4.0 mL) was added 2-oxopropanal (0.45 mL, 6.6 mmol). The reaction mixture was refluxed at 80° C. for 16 hours (h/hrs). The reaction mixture was cooled to room temperature and the solvent was removed in vacuo. The crude product was used in the next step without further purification. MS (ESI): mass calcd. for C$_{10}$H$_8$N$_2$O$_2$, 188.0 m/z found, 189.0 [M+H]$^+$. $^1$H NMR (500 MHz, DMSO-d$_6$) δ 13.38 (s, 1H), 8.96 (s, 1H), 8.62-8.49 (m, 1H), 8.31-8.19 (m, 1H), 8.17-7.95 (m, 1H), 2.75 (d, J=1.6 Hz, 3H).

Intermediate 26: 7-Methyl-2,3-diphenyl-4,5,6,7-tetrahydro-2H-pyrazolo[3,4-c]pyridine

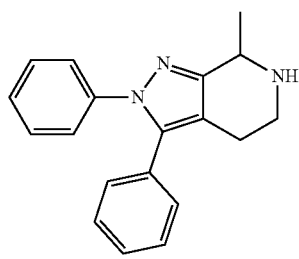 [SMILES: CC1NCCc2c1nn(-c1ccccc1)c2-c1ccccc1]

The title compound was prepared in a manner analogous to Intermediate 1, using 1-(tert-butyl) 4-ethyl 2-methyl-3-oxopiperidine-1,4-dicarboxylate instead of 1-tert-butyl 4-ethyl-3-oxopiperidine-1,4-dicarboxylate and phenylhydrazine instead of methylhydrazine in Step A. MS(ESI): mass calcd. for C$_{19}$H$_{19}$N$_3$, 289.1; m/z found, 290.1 [M+H]$^+$.

Intermediate 27: tert-Butyl 7-ethyl-2-methyl-3-(((trifluoromethyl)sulfonyl) oxy)-2,4,5,7-tetrahydro-6H-pyrazolo[3,4-c] pyridine-6-carboxylate

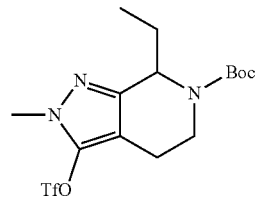 [SMILES: CCC1c2nn(C)c(OS(=O)(=O)C(F)(F)F)c2CCN1C(=O)OC(C)(C)C]

The title compound was prepared in a manner analogous to Intermediate 7, using tert-butyl 2-ethyl-3-oxopiperidine-1-carboxylate instead of tert-butyl 2-methyl-3-oxopiperidine-1-carboxylate in Step A. $^1$H NMR (500 MHz, CDCl$_3$) δ 5.20-4.96 (m, 1H), 4.48-4.14 (m, 1H), 3.78 (s, 3H), 3.05-2.85 (m, 1H), 2.67-2.53 (m, 1H), 2.52-2.44 (m, 1H), 1.90-1.82 (m, 1H), 1.78-1.68 (m, 1H), 1.48 (s, 9H), 1.03 (t, J=7.4 Hz, 3H).

Intermediate 28: tert-Butyl 7-methyl-3-(((trifluoromethyl)sulfonyl)oxy)-2,4,5,7-tetrahydro-6H-pyrazolo[3,4-c]pyridine-6-carboxylate

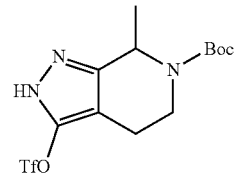 [SMILES: CC1c2n[nH]c(OS(=O)(=O)C(F)(F)F)c2CCN1C(=O)OC(C)(C)C]

The title compound was prepared in a manner analogous to Intermediate 7, using hydrazine hydrate instead of methyl hydrazine in Step B. The crude residue was purified by silica gel chromatography (0-20% EtOAc/hexanes @ 220 nm wavelength) to give the title compound as an oil (550 mg, 51% yield). MS (ESI): mass calcd. for C$_{13}$H$_{18}$F$_3$N$_3$O$_5$S, 385.1; m/z found, 329.1 [M+2H-$^t$Bu]$^+$.

Intermediate 29: tert-Butyl (S)-7-methyl-3-(((trifluoromethyl)sulfonyl)oxy)-2,4,5,7-tetrahydro-6H-pyrazolo[3,4-c]pyridine-6-carboxylate

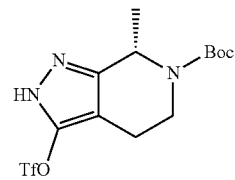 [SMILES: C[C@H]1c2n[nH]c(OS(=O)(=O)C(F)(F)F)c2CCN1C(=O)OC(C)(C)C]

Purification of tert-butyl 7-methyl-3-(((trifluoromethyl)sulfonyl)oxy)-2,4,5,7-tetrahydro-6H-pyrazolo[3,4-c]pyridine-6-carboxylate, Intermediate 28, by chiral SFC chromatography (Stationary phase: CHIRALPAK IC 5 µm 250*30 mm, Mobile phase: 87% CO$_2$, 13% MeOH, retention time=0.86 min) afforded the title compound as a pure enantiomer. MS (ESI): mass calcd. for $C_{13}H_{18}F_3N_3O_5S$, 385.1; m/z found, 329.1 $[M+2H-^tBu]^+$.

Intermediate 30: tert-Butyl (R)-7-methyl-3-(((trifluoromethyl)sulfonyl)oxy)-2,4,5,7-tetrahydro-6H-pyrazolo[3,4-c]pyridine-6-carboxylate

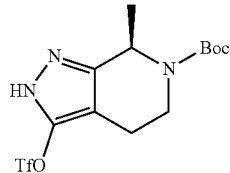 [SMILES: C[C@@H]1c2n[nH]c(OS(=O)(=O)C(F)(F)F)c2CCN1C(=O)OC(C)(C)C]

Purification of tert-butyl 7-methyl-3-(((trifluoromethyl)sulfonyl)oxy)-2,4,5,7-tetrahydro-6H-pyrazolo[3,4-c]pyridine-6-carboxylate, Intermediate 28 by chiral SFC chromatography (Stationary phase: CHIRALPAK IC 5 μm 250*30 mm, Mobile phase: 87% $CO_2$, 13% MeOH, retention time=1.79 min) afforded the title compound as a pure enantiomer. MS (ESI): mass calcd. for $C_{13}H_{18}F_3N_3O_5S$, 385.1; m/z found, 329.1 $[M+2H-^tBu]^+$.

Intermediate 31: 3-(3,5-Difluorophenyl)-7-methyl-2-(methyl-d3)-4,5,6,7-tetrahydro-2H-pyrazolo[3,4-c]pyridine

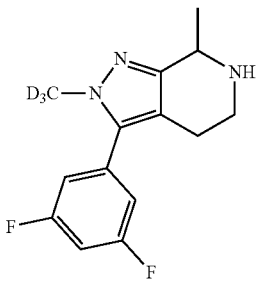 [SMILES: [2H]C([2H])([2H])n1nc2c(c1-c1cc(F)cc(F)c1)CCNC2C]

Step A: tert-Butyl 3-(3,5-difluorophenyl)-7-methyl-2,4,5,7-tetrahydro-6H-pyrazolo[3,4-c]pyridine-6-carboxylate.
The title compound was prepared in a manner analogous to Intermediate 1, using tert-butyl 7-methyl-3-(((trifluoromethyl)sulfonyl)oxy)-2,4,5,7-tetrahydro-6H-pyrazolo[3,4-c]pyridine-6-carboxylate (Intermediate 28) instead of tert-butyl 2-methyl-3-(trifluoromethylsulfonyloxy)-5,7-dihydro-4H-pyrazolo[3,4-c]pyridine-6-carboxylate and 3,5-difluorophenylboronic acid instead of phenylboronic acid in Step C. MS (ESI): mass calcd. for $C_{18}H_{21}F_2N_3O_2$, 349.1; m/z found, 294.0 $[M+2H-^tBu]^+$.

Step B: tert-Butyl 3-(3,5-difluorophenyl)-7-methyl-2-(methyl-d3)-2,4,5,7-tetrahydro-6H-pyrazolo[3,4-c]pyridine-6-carboxylate. To an ice-cold solution of tert-butyl 3-(3,5-difluorophenyl)-7-methyl-2,4,5,7-tetrahydro-6H-pyrazolo[3,4-c]pyridine-6-carboxylate (200 mg, 0.6 mmol) in THF (2.0 mL) was added 60 wt % sodium hydride/mineral oil (24 mg, 0.6 mmol). The reaction mixture was stirred for 30 min at 0° C., and then iodomethane-$d_3$ (40 μL, 0.6 mmol) was added. Stirring was maintained at 0° C. for 1 h and the crude mixture was quenched with water then extracted with EtOAc (×3). The combined organic layers were dried over $Na_2SO_4$, concentrated in vacuo and purified by reverse-phase HPLC (XBridge $C_{18}$ column (5 μm, 100× 4.6 mm), mobile phase of 10-100% ACN in 20 mM $NH_4OH$) to afford the title compound as white solid (33 mg, 16% yield). MS (ESI): mass calcd. for $C_{19}H_{20}D_3F_2N_3O_2$, 366.1; m/z found, 311.1 $[M+2H-tBu]^+$. $^1H$ NMR (500 MHz, DMSO-$d_6$) δ 7.39-7.20 (m, 3H), 5.09 (s, 1H), 4.12 (s, 1H), 2.92 (s, 1H), 2.70-2.57 (m, 1H), 2.44-2.30 (m, 1H), 1.43 (s, 9H), 1.35 (d, J=6.7 Hz, 3H).

Step C: 3-(3,5-Difluorophenyl)-7-methyl-2-(methyl-d3)-4,5,6,7-tetrahydro-2H-pyrazolo[3,4-c]pyridine. To a solution of tert-butyl 3-(3,5-difluorophenyl)-7-methyl-2-(methyl-d3)-2,4,5,7-tetrahydro-6H-pyrazolo[3,4-c]pyridine-6-carboxylate (28 mg, 0.075 mmol) in DCM (1 mL) was added TFA and the mixture was stirred at room temperature for 1 h. The solvent was concentrated in vacuo and the crude residue taken onto the next step without further purification. MS (ESI): mass calcd. for $C_{14}H_{12}D_3F_2N_3$, 266.1; m/z found, 267.1 $[M+H]^+$.

Intermediate 32: 2-(Difluoromethyl)-3-(3,5-difluorophenyl)-7-methyl-4,5,6,7-tetrahydro-2H-pyrazolo[3,4-c]pyridine

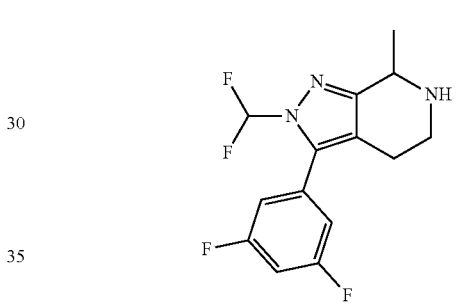

Step A: tert-Butyl 2-(difluoromethyl)-3-(3,5-difluorophenyl)-7-methyl-2,4,5,7-tetrahydro-6H-pyrazolo[3,4-c]pyridine-6-carboxylate. To an ice-cold solution of tert-butyl 3-(3,5-difluorophenyl)-7-methyl-2,4,5,7-tetrahydro-6H-pyrazolo[3,4-c]pyridine-6-carboxylate, Intermediate 31, Step A, (125 mg, 0.36 mmol) in DMF (5.0 mL) was added 60 wt % sodium hydride/mineral oil (36 mg, 0.9 mmol). The mixture was stirred for 30 minutes at 0° C., and then sodium 2-chloro-2,2-difluoroacetate (136 mg, 0.9 mmol) was added. The reaction was heated to 80° C. for 2 h, and then cooled to room temperature before quenching with water and extracting the aqueous layer with EtOAc (×3). The combined organic extracts were dried over $Na_2SO_4$, concentrated in vacuo and purified by reverse-phase HPLC (XBridge C18 column; 5 μm, 100×4.6 mm; mobile phase of 10-100% ACN in 20 mM $NH_4OH$) to afford the title compound as a white solid (47 mg, 33% yield). MS (ESI): mass calcd. for $C_{19}H_{21}F_4N_3O_2$, 399.1; m/z found, 400.1 $[M+H]^+$. $^1H$ NMR (500 MHz, DMSO-$d_6$) δ 7.70 (t, J=57.6 Hz, 1H), 7.44 (m, 1H), 7.32-7.19 (m, 2H), 5.20 (s, 1H), 4.12 (d, J=22.4 Hz, 1H), 2.97 (s, 1H), 2.62 (q, J=8.5, 4.9 Hz, 1H), 2.39 (d, J=14.8 Hz, 1H), 1.44 (s, 9H), 1.40 (d, J=6.8 Hz, 3H).

Step B: 2-(Difluoromethyl)-3-(3,5-difluorophenyl)-7-methyl-4,5,6,7-tetrahydro-2H-pyrazolo[3,4-c]pyridine. To a solution of tert-butyl 2-(difluoromethyl)-3-(3,5-difluorophenyl)-7-methyl-2,4,5,7-tetrahydro-6H-pyrazolo[3,4-c]pyridine-6-carboxylate (38 mg, 0.05 mmol) in DCM (1 mL) was added TFA (1 mL) and the mixture was stirred at rt for 1 h. The solvent was concentrated in vacuo and the crude residue was taken onto the next step without further purification. MS (ESI): mass calcd. for $C_{14}H_{12}D_3F_2N_3$, 266.1; m/z found, 267.1 $[M+H]^+$.

Intermediate 33: (S)-2-(Difluoromethyl)-7-methyl-3-(3,4,5-trifluorophenyl)-4,5,6,7-tetrahydro-2H-pyrazolo[3,4-c]pyridine

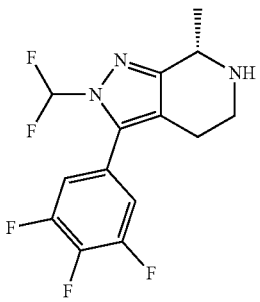 [SMILES: C[C@@H]1NCCc2c1nn(C(F)F)c2-c1cc(F)c(F)c(F)c1]

Step A: tert-Butyl (S)-7-methyl-3-(3,4,5-trifluorophenyl)-2,4,5,7-tetrahydro-6H-pyrazolo[3,4-c]pyridine-6-carboxylate. The title compound was prepared in a manner analogous to Intermediate 1, using tert-butyl (S)-7-methyl-3-(((trifluoromethyl)sulfonyl)oxy)-2,4,5,7-tetrahydro-6H-pyrazolo[3,4-c]pyridine-6-carboxylate (Intermediate 29) instead of tert-butyl 2-methyl-3-(trifluoromethylsulfonyloxy)-5,7-dihydro-4H-pyrazolo[3,4-c]pyridine-6-carboxylate and (3,4,5-trifluorophenyl)boronic acid instead of phenylboronic acid in Step C. MS (ESI): mass calcd. for $C_{18}H_{20}F_3N_3O_2$, 367.2; m/z found, 312.0 $[M+2H-^tBu]^+$.

Step B: (S)-2-(Difluoromethyl)-7-methyl-3-(3,4,5-trifluorophenyl)-4,5,6,7-tetrahydro-2H-pyrazolo[3,4-c]pyridine. The title compound was prepared in a manner analogous to Intermediate 32, using tert-butyl (S)-7-methyl-3-(3,4,5-trifluorophenyl)-2,4,5,7-tetrahydro-6H-pyrazolo[3,4-c]pyridine-6-carboxylate in place of tert-butyl 3-(3,5-difluorophenyl)-7-methyl-2,4,5,7-tetrahydro-6H-pyrazolo[3,4-c]pyridine-6-carboxylate in Step A. MS (ESI): mass calcd. for $C_{14}H_{12}F_5N_3$, 317.1 m/z found, 318.1 $[M+H]^+$.

Intermediate 34: (R)-2-(Difluoromethyl)-7-methyl-3-(3,4,5-trifluorophenyl)-4,5,6,7-tetrahydro-2H-pyrazolo[3,4-c]pyridine

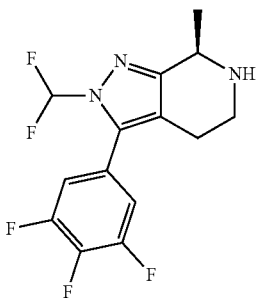 [SMILES: C[C@H]1NCCc2c1nn(C(F)F)c2-c1cc(F)c(F)c(F)c1]

Step A: tert-Butyl (R)-7-methyl-3-(3,4,5-trifluorophenyl)-2,4,5,7-tetrahydro-6H-pyrazolo[3,4-c]pyridine-6-carboxylate. The title compound was prepared in a manner analogous to Intermediate 1, using tert-butyl (R)-7-methyl-3-(((trifluoromethyl)sulfonyl)oxy)-2,4,5,7-tetrahydro-6H-pyrazolo[3,4-c]pyridine-6-carboxylate (Intermediate 30) instead of tert-butyl 2-methyl-3-(trifluoromethylsulfonyloxy)-5,7-dihydro-4H-pyrazolo[3,4-c]pyridine-6-carboxylate and (3,4,5-trifluorophenyl)boronic acid instead of phenylboronic acid in Step C. MS (ESI): mass calcd. for $C_{18}H_{20}F_3N_3O_2$, 367.2; m/z found, 312.0 $[M+2H-^tBu]^+$.

Step B: (R)-2-(Difluoromethyl)-7-methyl-3-(3,4,5-trifluorophenyl)-4,5,6,7-tetrahydro-2H-pyrazolo[3,4-c]pyridine. The title compound was prepared in a manner analogous to Intermediate 32, using tert-butyl (R)-7-methyl-3-(3,4,5-trifluorophenyl)-2,4,5,7-tetrahydro-6H-pyrazolo[3,4-c]pyridine-6-carboxylate in place of tert-butyl 3-(3,5-difluorophenyl)-7-methyl-2,4,5,7-tetrahydro-6H-pyrazolo[3,4-c]pyridine-6-carboxylate in Step A. MS (ESI): mass calcd. for $C_{14}H_{12}F_5N_3$, 317.1 m/z found, 318.1 $[M+H]^+$.

Intermediate 35: 3-(3,5-Difluorophenyl)-7-methyl-2-(trifluoromethyl)-4,5,6,7-tetrahydro-2H-pyrazolo[3,4-c]pyridine

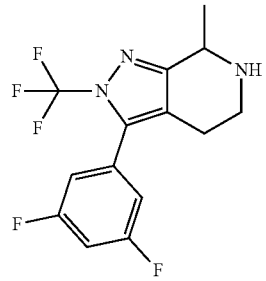 [SMILES: CC1NCCc2c1nn(C(F)(F)F)c2-c1cc(F)cc(F)c1]

Step A: tert-butyl 2-(bromodifluoromethyl)-3-(3,5-difluorophenyl)-7-methyl-2,4,5,7-tetrahydro-6H-pyrazolo[3,4-c]pyridine-6-carboxylate. The title compound was prepared in a manner analogous to Intermediate 32, using dibromo difluoromethane instead of sodium 2-chloro-2,2-difluoroacetate in Step A. MS(ESI): mass calcd. for $C_{19}H_{20}BrF_4N_3O_2$, 477.1; m/z found, 423.9 $[M+2H-^tBu]^+$.

Step B: 3-(3,5-Difluorophenyl)-7-methyl-2-(trifluoromethyl)-4,5,6,7-tetrahydro-2H-pyrazolo[3,4-c]pyridine. To a cooled (−78° C.) solution of tert-butyl 2-(bromodifluoromethyl)-3-(3,5-difluorophenyl)-7-methyl-2,4,5,7-tetrahydro-6H-pyrazolo[3,4-c]pyridine-6-carboxylate (90 mg, 0.2 mmol) in DCM (3.0 mL) was added silver tetrafluoroborate (81 mg, 0.4 mmol) portion-wise. The reaction mixture was then warmed to room temperature and stirred for 20 h. Saturated aqueous $NaHCO_3$(5 mL) was added and the mixture filtered. The aqueous layer of the filtrate was extracted with DCM (×2) and the combined organics were dried over $Na_2SO_4$ and concentrated in vacuo. Purification by reverse-phase HPLC (XBridge C18 column; 5 μm, 100× 4.6 mm; mobile phase of 10-100% ACN in 20 mM $NH_4OH$) provided the title compound as a white solid (25 mg, 42% yield). MS(ESI): mass calcd. for $C_{14}H_{12}F_5N_3$, 317.1; m/z found, 318.1 $[M+H]^+$.

Intermediate 36: 3-(2-(Tosyloxy)ethoxy)benzoic acid

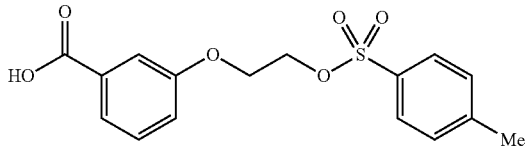 [SMILES: Cc1ccc(S(=O)(=O)OCCOc2cccc(C(=O)O)c2)cc1]

The title compound was prepared in a manner analogous to Intermediate 12, using methyl 3-hydroxybenzoate in place of methyl 2-chloro-3-hydroxybenzoate, ethane-1,2-diyl bis(4-methylbenzenesulfonate) in place of 1-fluoro-2-iodoethane, and NaOH in place of LiOH. MS (ESI): mass calcd. for $C_{16}H_{16}O_6S$, 336.1; m/z found, 337.1 [M+H]$^+$.

Intermediate 37: 1-(2-((Tetrahydro-2H-pyran-2-yl)oxy)ethyl)-1H-indole-5-carboxylic acid

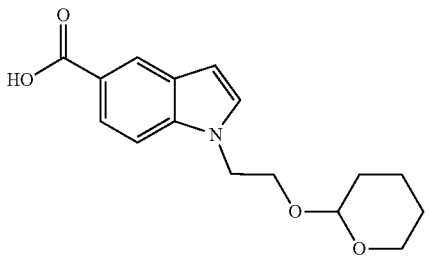 [SMILES: O=C(O)c1ccc2c(ccn2CCOC2CCCCO2)c1]

The title compound was prepared in a manner analogous to Intermediate 12, using methyl 1H-indole-5-carboxylate in place of methyl 2-chloro-3-hydroxybenzoate and 2-(2-bromoethoxy)tetrahydro-2H-pyran in place of ethane-1,2-diyl bis(4-methylbenzenesulfonate) in place of 1-fluoro-2-iodoethane. MS (ESI): mass calcd. for $C_{16}H_{19}NO_4$, 289.1; m/z found, 290.1 [M+H]$^+$.

Intermediate 38: 3-[3-(Trifluoromethyl)pyrazol-1-yl]benzoic acid

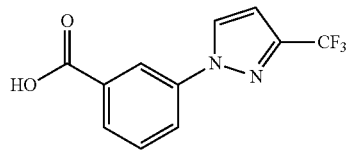 [SMILES: O=C(O)c1cccc(-n2ccc(C(F)(F)F)n2)c1]

A mixture of 3-iodobenzoic acid (300 mg, 1.21 mmol), 3-(trifluoromethyl)pyrazole (247 mg, 1.82 mmol), cesium carbonate (670 mg, 2.06 mmol), trans-N,N-dimethylcyclohexane-1,2-diamine (32 μL, 0.203 mmol) and copper(I) iodide (25 mg, 0.131 mmol) in N,N-dimethylformamide (1.25 mL) was stirred at 100° C. for 30 min, then at 140° C. for 70 min under microwave irradiation. The reaction mixture was taken up in water (5 mL), acidified to pH 3 with 1 M hydrochloric acid and extracted with ethyl acetate (3×5 mL). The combined organic layers were dried over sodium sulfate, filtered and evaporated. The crude product was purified by preparative HPLC to afford the title compound (140 mg, 45% yield) as a tan powder. MS (ESI): mass calcd. for $C_{11}H_7F_3N_2O_2$, 256.0; m/z found, 257.1 [M+H]$^+$.

Intermediate 39: (S)-3-(3,5-Difluorophenyl)-2,7-dimethyl-4,5,6,7-tetrahydro-2H-pyrazolo[3,4-c]pyridine. Hydrochloride salt

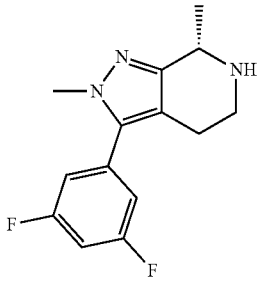 [SMILES: C[C@@H]1NCCc2c1nn(C)c2-c1cc(F)cc(F)c1]

Step A: (E)-2-(3-(3,5-Difluorophenyl)-2-nitroallyl)-1,3-dioxolane. Dilute 2-(2-nitroethyl)-1,3-dioxolane (20.26 g, 137.72 mmol), 3,5-difluorobenzaldehyde (19.57 g, 137.72 mmol) and catalytic piperidine (2 mL, 20.25 mmol) in toluene (150 mL). Heat to reflux overnight. The reaction mixture was cooled to room temperature then quenched with saturated NaCl solution (150 mL). The extracted organic layer was dried with Na$_2$SO$_4$, filtered and concentrated to dark oil to recover quantitative crude yield of the title compound. The compound was used in the next step without further purification.

Step B: tert-Butyl (S,E)-(1-(2-methylhydrazineylidene)propan-2-yl)carbamate. A solution of methylhydrazine (3.04 mL, 57.73 mmol) and tert-butyl (S)-(1-oxopropan-2-yl)carbamate (10 g, 57.73 mmol) in THF (150 mL) was stirred for 4 hours at room temperature. The reaction mixture was dried over Na$_2$SO$_4$, filtered and evaporated under reduced pressure overnight. The title compound was isolated as a light oil in quantitative crude yield. The crude product was used in the next reaction without further purification.

Step C: tert-Butyl (S)-(1-(4-((1,3-dioxolan-2-yl)methyl)-5-(3,5-difluorophenyl)-1-methyl-1H-pyrazol-3-yl)ethyl)carbamate. To a solution of tert-Butyl (S,E)-(1-(2-methylhydrazineylidene)propan-2-yl)carbamate (11.62 g, 57.73 mmol) in EtOH (500 mL) was added (E)-2-(3-(3,5-difluorophenyl)-2-nitroallyl)-1,3-dioxolane (16.27 g, 59.98 mmol). The reaction was stirred overnight at room temperature under open air. The reaction mixture was mildly heated to 40° C. overnight to drive the reaction to completion. The reaction was concentrated to an oil then quenched with EtOAc (250 mL) and NaCl solution (250 mL). The extracted organic layer was washed with water then dried with Na$_2$SO$_4$, filtered and concentrated to dark orange oil. Purification (FCC, SiO$_2$, 7/3 hexane/EtOAc) afforded the title compound (13.32 g, 54.5%).

Step D: (S)-3-(3,5-Difluorophenyl)-2,7-dimethyl-4,5,6,7-tetrahydro-2H-pyrazolo[3,4-c]pyridine. A solution of tert-Butyl (S)-(1-(4-((1,3-dioxolan-2-yl)methyl)-5-(3,5-difluorophenyl)-1-methyl-1H-pyrazol-3-yl)ethyl)carbamate (4 g, 9.446 mmol) in CH$_2$C$_2$ (30 mL), TFA (8 mL, 104.54 mmol) and triethylsilane (23 mL, 144.0 mmol) was stirred for 30 minutes then heated to 55° C. overnight. The reaction mixture was concentrated to an oil then quenched with EtOAc and 1 N NaOH to pH 11-12. The extracted organic layer was dried with Na$_2$SO$_4$, filtered and evaporated to light brown oil. The crude product was diluted in EtOH and 1.1

Intermediate 40: (S)-2,7-dimethyl-3-(3,4,5-trifluorophenyl)-4,5,6,7-tetrahydro-2H-pyrazolo[3,4-c]pyridine

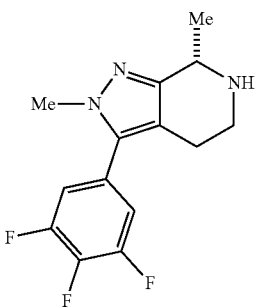 [SMILES: C[C@@H]1NCCc2c1nn(C)c2-c1cc(F)c(F)c(F)c1]

The title compound was prepared in a manner analogous to Intermediate 1, using (S)-tert-Butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of tert-butyl 2-methyl-3-(trifluoromethylsulfonyloxy)-5,7-dihydro-4H-pyrazolo[3,4-c]pyridine-6-carboxylate, 3,4,5-trifluorophenylboronic acid instead of phenylboronic acid, and XPhos-Pd-G2 instead of tetrakis(triphenylphosphine)palladium(0) in Step C. MS (ESI): mass calcd. for $C_{14}H_{14}F_3N_3$, 281.1; m/z found, 282.0 [M+H]$^+$. $^1$H NMR (600 MHz, CDCl$_3$) δ 7.00-6.92 (m, 2H), 4.04 (q, J=6.6 Hz, 1H), 3.80 (s, 3H), 3.31-3.23 (m, 1H), 2.96-2.86 (m, 1H), 2.64-2.54 (m, 1H), 2.47-2.38 (m, 1H), 1.49 (d, J=6.6 Hz, 3H).

Intermediate 41: (S)-3-(3-Chloro-5-methoxyphenyl)-2,7-dimethyl-4,5,6,7-tetrahydro-2H-pyrazolo[3,4-c] pyridine

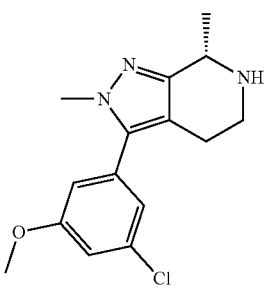 [SMILES: COc1cc(Cl)cc(-c2c3c(nn2C)[C@H](C)NCC3)c1]

The title compound was prepared in a manner analogous to Intermediate 40, using (3-chloro-5-methoxy phenyl) boronic acid instead of (3,4,5-trifluorophenyl) boronic acid. MS (ESI): mass calcd. for $C_{15}H_{18}ClN_3O$, 291.1; m/z found, 292.0 [M+H]$^+$.

Intermediate 42: (S)-3-(3-fluoro-5-methylphenyl)-2,7-dimethyl-4,5,6,7-tetrahydro-2H-pyrazolo[3,4-c]pyridine

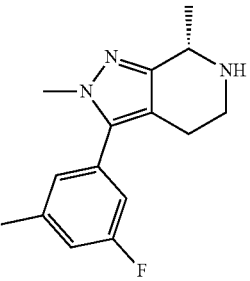 [SMILES: Cc1cc(F)cc(-c2c3c(nn2C)[C@H](C)NCC3)c1]

The title compound was prepared in a manner analogous to Intermediate 40, using (3-fluoro-5-methyl phenyl) boronic acid instead of (3,4,5-trifluorophenyl) boronic acid. MS (ESI): mass calcd. for $C_{15}H_{18}FN_3$, 259.2; m/z found, 260.1 [M+H]$^+$.

Intermediate 43: (S)-3-(2,2-difluorobenzo[d][1,3]dioxol-4-yl)-2,7-dimethyl-4,5,6,7-tetrahydro-2H-pyrazolo[3,4-c]pyridine

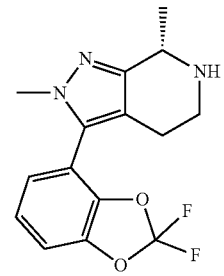 [SMILES: C[C@@H]1NCCc2c1nn(C)c2-c1cccc2c1OC(F)(F)O2]

The title compound was prepared in a manner analogous to Intermediate 40 using (2,2-difluorobenzo[d][1,3]dioxol-4-yl)boronic acid instead of (3,4,5-trifluorophenyl) boronic acid. MS (ESI): mass calcd. for $C_{15}H_{15}F_2N_3O_2$, 307.1.1; m/z found, 308.1 [M+H]$^+$.

Intermediate 44: (S)-2,7-dimethyl-3-(3-(trifluoromethoxy)phenyl)-4,5,6,7-tetrahydro-2H-pyrazolo[3,4-c]pyridine

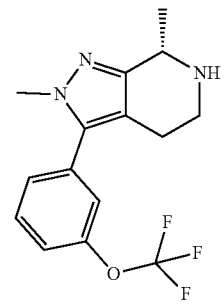 [SMILES: C[C@@H]1NCCc2c1nn(C)c2-c1cccc(OC(F)(F)F)c1]

The title compound was prepared in a manner analogous to Intermediate 40 using (3-(trifluoromethoxy)phenyl)boronic acid instead of (3,4,5-trifluorophenyl) boronic acid. MS (ESI): mass calcd. for $C_{15}H_{16}F_3N_3O$, 311.1; m/z found, 312.0 $[M+H]^+$.

Intermediate 45: (S)-3-(3-(difluoromethoxy)phenyl)-2,7-dimethyl-4,5,6,7-tetrahydro-2H-pyrazolo[3,4-c]pyridine

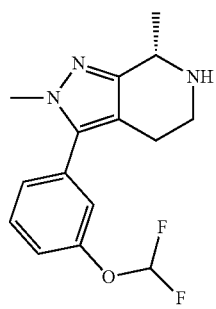 [SMILES: C[C@@H]1NCCc2c1nn(C)c2-c1cccc(OC(F)F)c1]

The title compound was prepared in a manner analogous to Intermediate 40 using (3-(difluoromethoxy)phenyl)boronic acid instead of (3,4,5-trifluorophenyl) boronic acid. MS (ESI): mass calcd. for $C_{15}H_{17}F_2N_3O$, 293.1; m/z found, 294.1 $[M+H]^+$.

Intermediate 46: (S)-3-(3-isopropoxyphenyl)-2,7-dimethyl-4,5,6,7-tetrahydro-2H-pyrazolo[3,4-c]pyridine

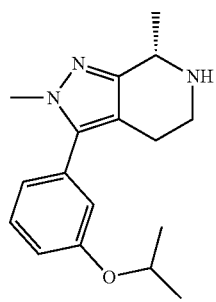 [SMILES: CC(C)Oc1cccc(-c2c3c(nn2C)[C@H](C)NCC3)c1]

The title compound was prepared in a manner analogous to Intermediate 40 using (3-isopropoxyphenyl)boronic acid instead of (3,4,5-trifluorophenyl) boronic acid. MS (ESI): mass calcd. for $C_{15}H_{23}N_3O$, 285.2; m/z found, 286.1 $[M+H]^+$.

Intermediate 47: (S)-3-(2-methoxyphenyl)-2,7-dimethyl-4,5,6,7-tetrahydro-2H-pyrazolo[3,4-c]pyridine

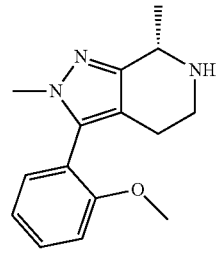 [SMILES: COc1ccccc1-c1c2c(nn1C)[C@H](C)NCC2]

The title compound was prepared in a manner analogous to Intermediate 40 using (2-methoxyphenyl)boronic acid instead of (3,4,5-trifluorophenyl) boronic acid. MS (ESI): mass calcd. for $C_{15}H_{19}N_3O$, 257.2; m/z found, 258.1 $[M+H]^+$.

Intermediate 48: (S)-3-(3-methoxyphenyl)-2,7-dimethyl-4,5,6,7-tetrahydro-2H-pyrazolo[3,4-c]pyridine

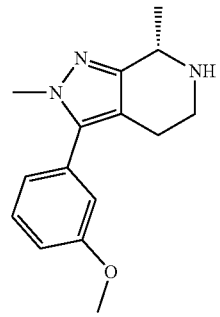 [SMILES: COc1cccc(-c2c3c(nn2C)[C@H](C)NCC3)c1]

The title compound was prepared in a manner analogous to Intermediate 40 using (3-methoxy phenyl)boronic acid instead of (3,4,5-trifluorophenyl) boronic acid. MS (ESI): mass calcd. for $C_{15}H_{23}N_3O$, 285.2; m/z found, 286.1 $[M+H]^+$.

Intermediate 49: (S)-2,7-Dimethyl-6-(quinoline-6-carbonyl)-4,5,6,7-tetrahydro-2H-pyrazolo[3,4-c]pyridin-3-yl trifluoromethanesulfonate

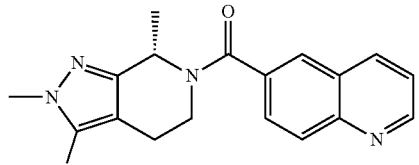

The title compound was prepared in a manner analogous to Intermediate 10, using (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of [tert-butyl 2-methyl-3-(((trifluoromethyl)sulfonyl)oxy)-2,4,5,7-tetrahydro-6H-pyrazolo[3,4-c]pyridine-6- carboxylate] in Step A, and 1-propanephosphonic anhydride (T3P©, 50% in ethyl acetate) instead of HATU in Step B. MS (ESI): mass calcd. for $C_{19}H_{17}F_3N_4O_4S$, 454.1; m/z found, 455.1 $[M+H]^+$.

Intermediate 50: (S)-2,7-dimethyl-3-(3-(trifluoromethyl) phenyl)-4,5,6,7-tetrahydro-2H-pyrazolo[3,4-c] pyridine

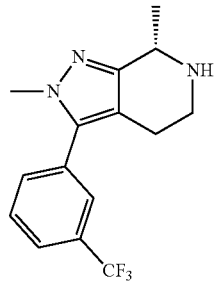 [SMILES: C[C@@H]1NCCc2c1nn(C)c2-c1cccc(C(F)(F)F)c1]

The title compound was prepared in a manner analogous to Intermediate 40 using (3-(trifluoromethyl) phenyl) boronic acid instead of (3,4,5-trifluorophenyl) boronic acid. MS (ESI): mass calcd. for $C_{15}H_{16}F_3N_3$, 295.1; m/z found, 296.1 $[M+H]^+$.

Intermediate 51: 2-(Bicyclo[1.1.1]pentan-1-yl)-7-methyl-3-phenyl-4,5,6,7-tetrahydro-2H-pyrazolo[3,4-c]pyridine

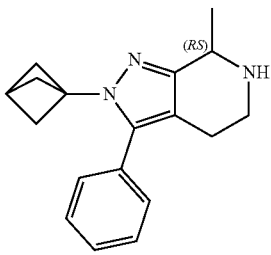 [SMILES: CC1NCCc2c1nn(C13CC(C1)C3)c2-c1ccccc1]

Step A: tert-butyl 2-(bicyclo[1.1.1]pentan-1-yl)-7-methyl-3-oxo-1,2,3,4,5,7-hexahydro-6H-pyrazolo[3,4-c]pyridine-6-carboxylate. To a solution of 1-(tert-butyl) 4-ethyl 2-methyl-3-oxopiperidine-1,4-dicarboxylate (Intermediate 7, Step A) (224 mg, 0.79 mmol) and bicyclo[1.1.1]pentan-1-ylhydrazine dihydrochloride (148 mg, 0.87 mmol) in EtOH (1.5 mL) was added triethylamine (0.24 mL, 1.73 mmol), and the reaction stirred at 80° C. overnight. After cooling to room temperature, the mixture was diluted in hexanes, the solids filtered away, and the filtrate concentrated in vacuo. The crude residue was purified by silica gel chromatography (0-20% MeOH/DCM) to afford the title compound as a yellow oil (164 mg, 65% yield). MS (ESI): mass calcd. for $C_{17}H_{25}N_3O_3$, 319.2; m/z found, 320.1 $[M+H]^+$.

Step B: 2-(bicyclo[1.1.1]pentan-1-yl)-7-methyl-3-phenyl-4,5,6,7-tetrahydro-2H-pyrazolo[3,4-c]pyridine. The title compound was prepared in a manner analogous to Intermediate 1, Steps B-D using tert-butyl 2-(bicyclo[1.1.1]pentan-1-yl)-7-methyl-3-oxo-1,2,3,4,5,7-hexahydro-6H-pyrazolo[3,4-c]pyridine-6-carboxylate instead of tert-butyl 2-methyl-3-oxo-1,4,5,7-tetrahydropyrazolo[3,4-c]pyridine-6-carboxylate in Step B, and XPhos-Pd-G2 instead of tetrakis (triphenylphosphine)palladium(0) in Step C. MS (ESI): mass calcd. for $C_{18}H_{21}N_3$, 279.2; m/z found, 280.2 $[M+H]^+$.

Intermediate 52: tert-Butyl 7-methyl-2-phenyl-3-(((trifluoromethyl)sulfonyl) oxy)-2,4,5,7-tetrahydro-6H-pyrazolo[3,4-c] pyridine-6-carboxylate

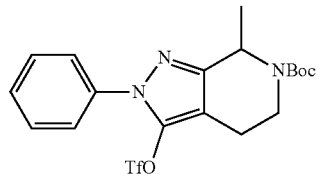

The title compound was prepared in a manner analogous to Intermediate 7, using phenylhydrazine instead of methylhydrazine in Step B. MS(ESI): mass calcd. for $C_{19}H_{22}F_3N_3O_5S$, 461.5; m/z found, 406.0 $[M+2H-tBu]^+$.

Intermediate 53: tert-Butyl (S)-7-methyl-2-phenyl-3-(((trifluoromethyl)sulfonyl) oxy)-2,4,5,7-tetrahydro-6H-pyrazolo[3,4-c] pyridine-6-carboxylate

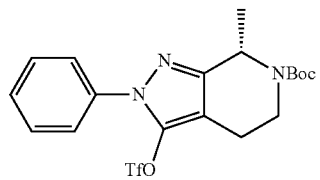 [SMILES: C[C@H]1c2nn(-c3ccccc3)c(OS(=O)(=O)C(F)(F)F)c2CCN1C(=O)OC(C)(C)C]

Purification of racemic tert-butyl 7-methyl-2-phenyl-3-(((trifluoromethyl)sulfonyl) oxy)-2,4,5,7-tetrahydro-6H-pyrazolo[3,4-c] pyridine-6-carboxylate (Intermediate 52) (2.4 g, 5.2 mmol) by chiral SFC chromatography (Stationary phase: Whelk-O1 (S, S) 3 µm 100*4.6 mm, 10% iPrOH, neat, 3.5 ml/min) provided 861 mg of the title compound. (ESI): mass calcd. for $C_{19}H_{22}F_3N_3O_5S$, 461.5; m/z found, 406.0 $[M+2H-^tBu]$. $^1H$ NMR (400 MHz, DMSO-$d_6$) δ 7.64-7.45 (m, 5H), 5.17 (s, 1H), 4.20 (s, 1H), 3.03 (s, 1H), 2.69-2.57 (m, 1H), 2.54 (d, J=5.4 Hz, 1H), 1.45 (s, 9H), 1.40 (d, J=6.8 Hz, 3H).

Intermediate 54: tert-Butyl (R)-7-methyl-2-phenyl-3-(((trifluoromethyl)sulfonyl) oxy)-2,4,5,7-tetrahydro-6H-pyrazolo[3,4-c] pyridine-6-carboxylate

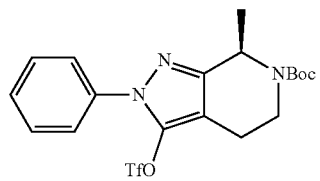 [SMILES: C[C@@H]1c2nn(-c3ccccc3)c(OS(=O)(=O)C(F)(F)F)c2CCN1C(=O)OC(C)(C)C]

Purification of racemic tert-butyl 7-methyl-2-phenyl-3-(((trifluoromethyl)sulfonyl) oxy)-2,4,5,7-tetrahydro-6H-pyrazolo[3,4-c] pyridine-6-carboxylate (Intermediate 52)

Intermediate 55: (S)-7-Methyl-2,3-diphenyl-4,5,6,7-tetrahydro-2H-pyrazolo[3,4-c] pyridine

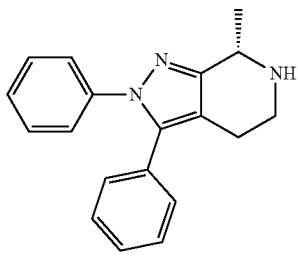

The title compound was prepared in a manner analogous to Intermediate 1, using tert-butyl (S)-7-methyl-2-phenyl-3-(((trifluoromethyl)sulfonyl) oxy)-2,4,5,7-tetrahydro-6H-pyrazolo[3,4-c]pyridine-6-carboxylate (Intermediate 53) instead of tert-butyl 2-methyl-3-(trifluoromethylsulfonyloxy)-5,7-dihydro-4H-pyrazolo[3,4-c]pyridine-6-carboxylate in Step C. MS(ESI): mass calcd. for $C_{19}H_{19}N_3$, 289.1; m/z found, 290.1 [M+H]$^+$.

Intermediate 56: (R)-7-Methyl-2,3-diphenyl-4,5,6,7-tetrahydro-2H-pyrazolo[3,4-c] pyridine

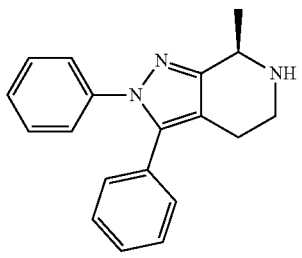 [SMILES: C[C@H]1NCCc2c1nn(-c1ccccc1)c2-c1ccccc1]

The title compound was prepared in a manner analogous to Intermediate 1, using tert-butyl (R)-7-methyl-2-phenyl-3-(((trifluoromethyl)sulfonyl) oxy)-2,4,5,7-tetrahydro-6H-pyrazolo[3,4-c]pyridine-6-carboxylate (Intermediate 54) instead of tert-butyl 2-methyl-3-(trifluoromethylsulfonyloxy)-5,7-dihydro-4H-pyrazolo[3,4-c]pyridine-6-carboxylate in Step C. MS(ESI): mass calcd. for $C_{19}H_{19}N_3$, 289.1; m/z found, 290.1 [M+H]$^+$.

Intermediate 57: 5,8-Dihydro-6H-pyrano[3,4-b]pyridine-4-carboxylic acid

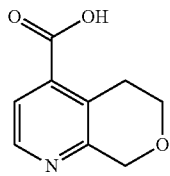 [SMILES: O=C(O)c1ccnc2c1CCOC2]

(2.4 g, 5.2 mmol) by chiral SFC chromatography (Stationary phase: Whelk-O1 (S, S) 3 µm 100*4.6 mm, 10% iPrOH, neat, 3.5 ml/min) provided 778 mg of the title compound. (ESI): mass calcd. for $C_{19}H_{22}F_3N_3O_5S$, 461.5; m/z found, 406.0 [M+2H-$^t$Bu]$^+$.

Step A: 2-(Chloromethyl)pyrazine. A solution of thionyl chloride (30.9 mL, 435.9 mmol) in DCM (250 mL) was added dropwise to a mixture of 2-pyrazinylmethanol (16 g, 145.3 mmol) in DCM (250 mL) under a nitrogen atmosphere at 0° C. The reaction mixture was stirred at room temperature overnight. Saturated aqueous NaHCO$_3$ was added and the mixture was extracted with DCM. The organic layer was separated, dried over MgSO$_4$, filtered and concentrated under reduced pressure. Purification (FCC, SiO$_2$, 0-50% Et$_2$O in pentane) afforded the title compound (18.7 g, 100%). The title compound is volatile and unstable. MS (ESI): mass calcd. for $C_5H_5ClN_2$, 128.0; m/z found, 129 [M+H]$^+$. $^1$H NMR (300 MHz, CDCl$_3$) δ 8.75 (s, 1H), 8.55 (s, 2H), 4.70 (s, 2H).

Step B: 2-((But-3-yn-1-yloxy)methyl)pyrazine. Sodium (4 g, 174.4 mmol) was added to a solution of 3-butyn-1-ol (16.5 mL, 218.0 mmol) in THF (300 mL) under a nitrogen atmosphere at room temperature. After 2 hours, a solution of 2-(chloromethyl)pyrazine (18.7 g, 145.3 mmol) in THF (300 mL) was added to the suspension and the reaction mixture was heated to 40° C. for 2 hours. Then, the reaction mixture was stirred at room temperature overnight. A mixture of EtOAc and water (5:1) was added to the reaction mixture. The organic layer was separated, dried over MgSO$_4$, filtered and concentrated under reduced pressure. Purification (FCC, SiO$_2$, 0-40% EtOAc in heptane) afforded the title compound (14.7 g, 62%). MS (ESI): mass calcd. for $C_9H_{10}N_2O$, 162.1; m/z found, 163 [M+H]$^+$. $^1$H NMR (300 MHz, CDCl$_3$) δ 8.76 (s, 1H), 8.50 (s, 2H), 4.73 (s, 2H), 3.73 (t, J=6.8 Hz, 2H), 2.56 (td, J=6.7, 2.5 Hz, 2H), 2.01 (t, J=2.1 Hz, 1H).

Step C: 5,8-Dihydro-6H-pyrano[3,4-b]pyridine.

A mixture of 2-((but-3-yn-1-yloxy)methyl)pyrazine (8.3 g, 51.0 mmol) in undecane (33 mL) was stirred at 195° C. for 7 days. Purification (FCC, SiO$_2$, 0-90% EtOAc in heptane) afforded the title compound (1.5 g, 22%). MS (ESI): mass calcd. for $C_8H_9NO$, 135.1; m/z found, 136 [M+H]$^+$. $^1$H NMR (300 MHz, CDCl$_3$) δ 8.38 (d, J=4.5 Hz, 1H), 7.42 (d, J=7.7 Hz, 1H), 7.10 (dd, J=7.4, 5.0 Hz, 1H), 4.79 (s, 2H), 3.98 (t, J=5.6 Hz, 2H), 2.88 (t, J=5.6 Hz, 2H).

Step D: 5,8-Dihydro-6H-pyrano[3,4-b]pyridine 1-oxide.

m-CPBA (3.1 g, 18.0 mmol) was added to mixture of 5,8-dihydro-6H-pyrano[3,4-b]pyridine (1.5 g, 11.2 mmol) in DCM (22 mL). The reaction mixture was stirred overnight at room temperature. Purification (FCC, SiO$_2$, 0-3% MeOH in DCM) afforded the title compound (1.5 g, 86%). MS (ESI): mass calcd. for $C_8H_9NO_2$, 151.1; m/z found, 152 [M+H]$^+$. $^1$H NMR (300 MHz, CDCl$_3$) δ 8.12 (d, J=6.2 Hz, 1H), 7.20-6.96 (m, 2H), 4.89 (s, 2H), 3.93 (t, J=5.5 Hz, 2H), 2.87 (t, J=5.3 Hz, 2H).

Step E: 4-Chloro-5,8-dihydro-6H-pyrano[3,4-b]pyridine.

Phosphorus(V) oxychloride (6.3 mL, 67.6 mmol) was added to a mixture of 5,8-dihydro-6H-pyrano[3,4-b]pyridine 1-oxide (1.5 g, 9.7 mmol) in chloroform (55 mL). The reaction mixture was refluxed at 80° C. overnight. Then, iced water and aqueous ammonia was added until basic pH was reached. DCM was added to the mixture. The organic layer was separated, dried over MgSO$_4$, filtered and concentrated under reduced pressure. Purification (FCC, SiO$_2$, 0-20% EtOAc in heptane) afforded the title compound (860 mg, 52%) and 2-chloro-5,8-dihydro-6H-pyrano[3,4-b]pyridine (370 mg, 23%). MS (ESI): mass calcd. for $C_8H_8ClNO$, 169.0; m/z found, 170 [M+H]$^+$. $^1$H NMR (300 MHz, CDCl$_3$) δ 8.29 (d, J=5.2 Hz, 1H), 7.20 (d, J=5.2 Hz, 1H), 4.77 (s, 2H), 4.02 (t, J=5.7 Hz, 2H), 2.88 (t, J=5.6 Hz, 2H).

Step F: 5,8-Dihydro-6H-pyrano[3,4-b]pyridine-4-carbonitrile.

A mixture of 4-chloro-5,8-dihydro-6H-pyrano[3,4-b]pyridine (100 mg, 0.6 mmol), zinc cyanide (69 mg, 0.6 mmol), 1,1'-bis(diphenylphosphino)ferrocene (26.1 mg, 0.05 mmol), tris(dibenzylideneacetone)dipalladium(0) (27 mg, 0.03 mmol) and zinc (19 mg, 0.3 mmol) in DMF (5 mL) was stirred at 90° C. under a nitrogen atmosphere. After 16 h, zinc cyanide (69 mg, 0.6 mmol), zinc (19 mg, 0.3 mmol), 1,1'-bis(diphenylphosphino)ferrocene (26.1 mg, 0.05 mmol) and tris(dibenzylideneacetone)dipalladium(0) (27 mg, 0.03 mmol) were added to the reaction mixture. The reaction mixture was heated to 90° C. for 4 days. Then, the reaction mixture was cooled to room temperature. Saturated aqueous NaHCO$_3$(20 mL) was added and the mixture was extracted using EtOAc (3×30 mL). The combined organics were dried over MgSO$_4$, filtered and concentrated under reduced pressure to afford the crude title product 1-P1. The title compound was carried as is to the next step. MS (ESI): mass calcd. for C$_9$H$_8$N$_2$O, 160.1; m/z found, 161.1 [M+H]$^+$.

Step G: 5,8-Dihydro-6H-pyrano[3,4-b]pyridine-4-carboxylic acid. A mixture of 5,8-dihydro-6H-pyrano[3,4-b]pyridine-4-carbonitrile (94.4 mg, 0.6 mmol) and LiOH (4N in water, 0.7 mL, 2.9 mmol) in THF (9 mL) was refluxed at 90° C. After 16 hours, the reaction mixture was concentrated under reduced pressure. Purification (preparative HPLC, METHOD A) afforded the title compound (82 mg, 78%). MS (ESI): mass calcd. for C$_9$H$_9$NO$_3$, 179.1; m/z found, 180.1 [M+H]$^+$.

Intermediate 58: 3,4-Dihydro-2H-pyrano[2,3-b]pyridine-5-carboxylic acid

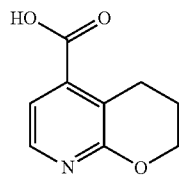

The title compound was prepared in a manner analogous to Intermediate 57, Steps D-G, using 3,4-dihydro-2H-pyrano[2,3-B]pyridine in Step D instead of 5,8-dihydro-6H-pyrano[3,4-b]pyridine; and MeOH was used instead of THF in Step G. MS (ESI): mass calcd. for C$_9$H$_9$NO$_3$, 179.1; m/z found, 180.1 [M+H]$^+$.

Intermediate 59: 5,8-Dihydro-6H-pyrano[3,4-b]pyridine-2-carboxylic acid

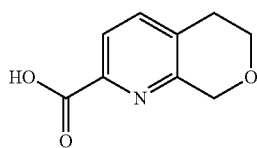 [SMILES: O=C(O)c1ccc2c(n1)COCC2]

Step A: 5,8-Dihydro-6H-pyrano[3,4-b]pyridine-2-carbonitrile. The title compound was prepared in a manner analogous to Intermediate 57, Step F, using 2-chloro-5,8-dihydro-6H-pyrano[3,4-b]pyridine (side Product from Intermediate 57, Step E) instead of 4-chloro-5,8-dihydro-6H-pyrano[3,4-b]pyridine (Intermediate 57, Step E). MS (ESI): mass calcd. for C$_9$H$_8$N$_2$O, 160.1; m/z found, 161.1 [M+H]$^+$.

Step B: 5,8-Dihydro-6H-pyrano[3,4-b]pyridine-2-carboxamide. NaOH (48.5 mg, 1.2 mmol) was added to a mixture of 5,8-dihydro-6H-pyrano[3,4-b]pyridine-2-carbonitrile (38.9 mg, 0.2 mmol) in EtOH (2 mL). The mixture was heated to 50° C. overnight. Then, volatiles were removed and water (3.0 mL) followed by conc. HCl (0.65 mL) was added to the crude material. After 20 minutes, the solids were filtered off. The filtrate was extracted using EtOAc (3×). The combined organics were dried over MgSO$_4$, filtered and concentrated under reduced pressure to afford the title compound. The compound was carried as is to the next step without further purification.

Step C: 5,8-Dihydro-6H-pyrano[3,4-b]pyridine-2-carboxylic acid. 4N LiOH (0.3 mL, 1.2 mmol) was added to a mixture of 5,8-dihydro-6H-pyrano[3,4-b]pyridine-2-carboxamide (43.0 mg, 0.2 mmol) in THF (2 mL). The mixture was heated to 50° C. for 3 days. Then, volatiles were removed and EtOAc was added. The mixture was stirred at room temperature. The solvent was pipetted out and DCM was added to the crude mixture. The mixture was stirred at room temperature overnight. Then, the solvent was pipetted out and MeOH was added to the crude mixture. The mixture was stirred at room temperature. The solids were filtered off and the filtrate was concentrated under reduced pressure to afford the title compound. MS (ESI): mass calcd. for C$_9$H$_9$NO$_3$, 179.1; m/z found, 180.1 [M+H]$^+$.

Intermediate 60: 5-Trifluoromethyl)-1-((2-(trimethylsilyl)ethoxy)methyl)-1H-pyrrolo[2,3-b]pyridine-4-carboxylic acid

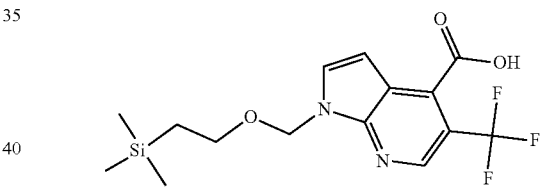

Step A: (2-(Trimethylsilyl)ethoxy)methyl 5-(trifluoromethyl)-1-((2-(trimethylsilyl)ethoxy)methyl)-1H-pyrrolo[2,3-b]pyridine-4-carboxylate. 5-(Trifluoromethyl)-1H-pyrrolo[2,3-b]pyridine-4-carboxylic acid (150 mg, 0.7 mmol) was added to a suspension of NaH (60% dispersion in mineral oil, 65.2 mg, 1.6 mmol) in THF (7 mL) under a nitrogen atmosphere at room temperature. After 5 minutes, 2-(trimethylsilyl)ethoxymethyl chloride (0.36 mL, 2.0 mmol) was added to the reaction mixture. After 16 hours, water (20 mL) was added to the reaction mixture. The mixture was extracted with EtOAc (3×30 mL). The combined organics were dried over MgSO$_4$, filtered and concentrated under reduced pressure to afford the title compound. The compound was carried as is to the next step without further purification.

Step B: 5-Trifluoromethyl)-1-((2-(trimethylsilyl)ethoxy)methyl)-1H-pyrrolo[2,3-b]pyridine-4-carboxylic acid. Lithium hydroxide (4N in water, 1.6 mL, 6.5 mmol) was added to a mixture of (2-(trimethylsilyl)ethoxy)methyl 5-(trifluoromethyl)-1-((2-(trimethylsilyl)ethoxy)methyl)-1H-pyrrolo[2,3-b]pyridine-4-carboxylate (320 mg, 0.7 mmol) in THF (5 mL) at room temperature. After completion, the reaction mixture was concentrated under reduced pressure. Purification (preparative HPLC, METHOD A)

afforded the title compound (65 mg, 28%). MS (ESI): mass calcd. for $C_{15}H_{19}F_3N_2O_3Si$, 360.1; m/z found, 361.2 $[M+H]^+$.

Intermediate 61: 1-((2-(Trimethylsilyl)ethoxy)methyl)-1H-pyrazolo[3,4-b]pyridine-5-carboxylic acid

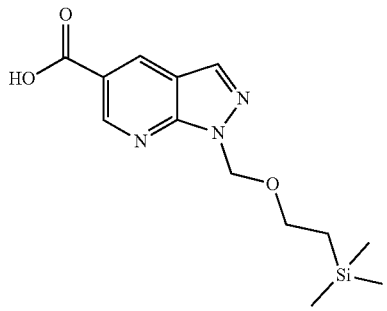 [SMILES: C[Si](C)(C)CCOCn1ncc2cc(C(=O)O)cnc21]

Step A: Methyl 1-((2-(trimethylsilyl)ethoxy)methyl)-1H-pyrazolo[3,4-b]pyridine-5-carboxylate. The title compound was prepared in a manner analogous to Intermediate 60, Step A, using methyl 1H-pyrazolo[3,4-b]pyridine-5-carboxylate instead of 5-(trifluoromethyl)-1H-pyrrolo[2,3-b]pyridine-4-carboxylic acid. MS (ESI): mass calcd. for $C_{14}H_{21}N_3O_3Si$, 307.1; m/z found, 308.2 $[M+H]^+$.

Step B: 1-((2-(Trimethylsilyl)ethoxy)methyl)-1H-pyrazolo[3,4-b]pyridine-5-carboxylic acid. The title compound was prepared in a manner analogous to Intermediate 60, Step B, using methyl 1-((2-(trimethylsilyl)ethoxy)methyl)-1H-pyrazolo[3,4-b]pyridine-5-carboxylate instead of (2-(trimethylsilyl)ethoxy)methyl 5-(trifluoromethyl)-1-((2-(trimethylsilyl)ethoxy)methyl)-1H-pyrrolo[2,3-b]pyridine-4-carboxylate. MS (ESI): mass calcd. for $C_{14}H_{21}N_3O_3Si$, 293.1; m/z found, 294.1 $[M+H]^+$.

Intermediate 62: 3-Fluoro-1-((2-(trimethylsilyl)ethoxy)methyl)-1H-pyrrolo[2,3-b]pyridine-4-carboxylic acid

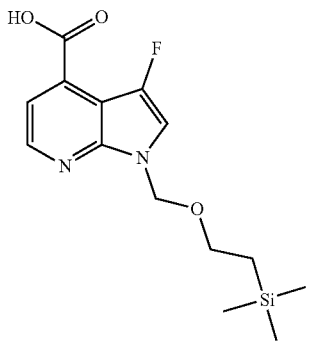 [SMILES: C[Si](C)(C)CCOCn1cc(F)c2c(C(=O)O)ccnc21]

The title compound was prepared in a manner analogous to Intermediate 60, Step A-B, using 3-fluoro-1H-pyrrolo[2,3-b]pyridine-4-carboxylic acid instead of 5-(trifluoromethyl)-1H-pyrrolo[2,3-b]pyridine-4-carboxylic acid, and using DMF instead of THF in Step A. MS (ESI): mass calcd. for $C_{14}H_{19}FN_2O_3Si$, 310.1; m/z found, 311.1 $[M+H]^+$.

Intermediate 63: 5-Methoxy-2-(2H-1,2,3-triazol-2-yl)benzoic acid

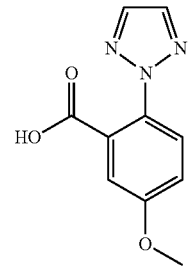 [SMILES: COc1ccc(-n2nccn2)c(C(=O)O)c1]

The title compound was prepared in a manner analogous to Intermediate 38 using 2-iodo-5-methoxybenzoic acid instead of 3-iodobenzoic acid and 1,2,3-triazole instead of 3-(trifluoromethyl)pyrazole. MS (ESI): mass calcd. for $C_{10}H_9N_3O_3$, 219.1; m/z found, 220.1 $[M+H]^+$.

Intermediate 64: 2-(2H-1,2,3-Triazol-2-yl)benzoic acid

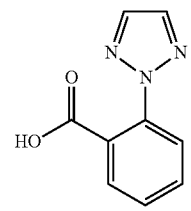 [SMILES: O=C(O)c1ccccc1-n1nccn1]

The title compound was prepared in a manner analogous to Intermediate 38, using 2-iodobenzoic acid instead of 3-iodobenzoic acid and 1,2,3-triazole instead of 3-(trifluoromethyl)pyrazole. MS (ESI): mass calcd. for $C_9H_7N_3O_2$, 189.1; m/z found, 190.1 $[M+H]^+$. (prepared according to methods described in Pat. Pub. No. WO2016040789, Mar. 17, 2016)

Intermediate 65: 3-(2H-1,2,3-Triazol-2-yl)benzoic acid

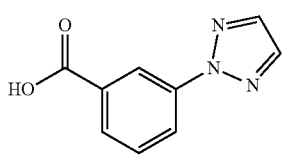 [SMILES: O=C(O)c1cccc(-n2nccn2)c1]

The title compound was prepared in a manner analogous to Intermediate 38 using 1,2,3-triazole instead of 3-(trifluoromethyl)pyrazole. MS (ESI): mass calcd. for $C_9H_7N_3O_2$, 189.1; m/z found, 190.1 $[M+H]^+$.

Intermediate 66: 2-(3-(Trifluoromethyl)-1H-1,2,4-triazol-1-yl)benzoic acid

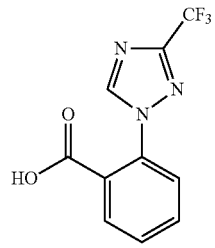

The title compound was prepared in a manner analogous to Intermediate 38 using 2-iodobenzoic acid instead of 3-iodobenzoic acid and 3-(trifluoromethyl)-1H-1,2,4-triazole instead of 3-(trifluoromethyl)pyrazole. MS (ESI): mass calcd. for $C_{10}H_6F_3N_3O_2$, 257.0; m/z found, 258.1 [M+H]$^+$.

Intermediate 67:
5-Fluoro-2-(1H-1,2,4-triazol-1-yl)benzoic acid

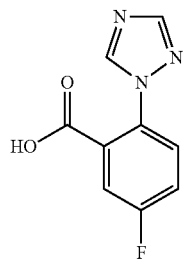 [SMILES: O=C(O)c1cc(F)ccc1-n1cncn1]

The title compound was prepared in a manner analogous to Intermediate 38 using 5-fluoro-2-iodobenzoic acid instead of 3-iodobenzoic acid and 1,2,4-triazole instead of 3-(trifluoromethyl)pyrazole. MS (ESI): mass calcd. for $C_9H_6FN_3O_2$, 207.0; m/z found, 208.1 [M+H]$^+$.

Intermediate 68:
3-(4-Fluoro-1H-pyrazol-1-yl)benzoic acid

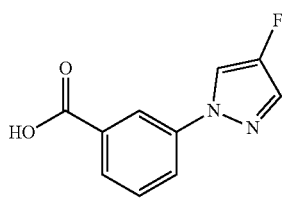 [SMILES: O=C(O)c1cccc(-n2cc(F)cn2)c1]

The title compound was prepared in a manner analogous to Intermediate 38 using 4-fluoropyrazole instead of 3-(trifluoromethyl)pyrazole. MS (ESI): mass calcd. for $C_{10}H_7F_1N_2O_2$, 206.0; m/z found, 207.1 [M+H]$^+$.

Intermediate 69: 3-Fluoropyrazolo[1,5-a]pyridine-4-carboxylic acid

Step A: Methyl pyrazolo[1,5-a]pyridine-4-carboxylate. To a suspension of pyrazolo[1,5-a]pyridine-4-carboxylic acid (500 mg, 3.08 mmol) in MeOH (4.8 mL) at 0° C. was added thionyl chloride (0.9 mL, 12.3 mmol) carefully dropwise via syringe. The reaction was stirred at reflux overnight, then cooled to room temperature and diluted with EtOAc. The mixture was carefully basified with sat. aq. NaHCO$_3$ and the layers separated. The aqueous layer was separated and extracted with EtOAc (×3), then the combined organic layers washed with brine, dried over Na$_2$SO$_4$, filtered, and concentrated in vacuo. MS (ESI): mass calcd. for $C_9H_8N_2O_2$, 176.1; m/z found, 177.0 [M+H]$^+$.

Step B: Methyl 3-fluoropyrazolo[1,5-a]pyridine-4-carboxylate. Methyl pyrazolo[1,5-a]pyridine-4-carboxylate (200 mg, 1.14 mmol) and Selectfluor (442 mg, 1.25 mmol) were stirred in MeCN (4.4 mL) at room temperature for 1 h. The reaction was diluted with EtOAc and H$_2$O, then the aqueous layer separated and extracted with EtOAc (×3). The combined organics were washed with brine, dried over Na$_2$SO$_4$, filtered, and concentrated in vacuo. The crude residue was purified by silica gel chromatography (0-100% EtOAc in hexanes) to afford a yellow solid. MS (ESI): mass calcd. for $C_9H_7FN_2O_2$, 194.0; m/z found, 195.0 [M+H]$^+$. $^1$H NMR (600 MHz, Chloroform-d) δ 8.44-8.41 (m, 1H), 7.94 (d, J=3.5 Hz, 1H), 7.83 (dd, J=7.1, 1.1 Hz, 1H), 6.75 (t, J=7.1 Hz, 1H), 3.99 (s, 3H).

Step C: 3-Fluoropyrazolo[1,5-a]pyridine-4-carboxylic acid. A mixture of methyl 3-fluoropyrazolo[1,5-a]pyridine-4-carboxylate (55 mg, 0.28 mmol), NaOH (22.7 mg, 0.57 mmol), and H$_2$O (58 µL, 3.21 mmol) in 1:1 THF/MeOH (1.2 mL) was stirred at 60° C. for 30 min. The reaction was then cooled to room temperature, concentrated in vacuo and re-dissolved in H$_2$O. The mixture was acidified to pH 5 with 2 N HCl, and the precipitate collected via vacuum filtration to afford the title compound as a white solid. MS (ESI): mass calcd. for $C_8H_5FN_2O_2$, 180.0; m/z found, 181.1 [M+H]$^+$.

Intermediate 70: Potassium 3-fluoropyrazolo[1,5-a]pyridine-5-carboxylate

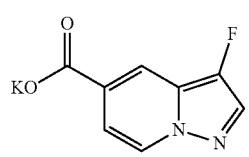

Step A: Methyl pyrazolo[1,5-a] pyridine-5-carboxylate. The title compound was prepared in a manner analogous Intermediate 69 Step A, using pyrazolo[1,5-a] pyridine-5-carboxylic acid instead of pyrazolo[1,5-a] pyridine-4-carboxylic acid. MS(ESI): mass calcd. for $C_9H_8N_2O_2$, 176.1;

m/z found, 177.0 [M+H]⁺. ¹H NMR (500 MHz, DMSO-$d_6$) δ 8.78 (dt, J=7.3, 1.0 Hz, 1H), 8.41 (dd, J=1.9, 1.0 Hz, 1H), 8.14 (d, J=2.3 Hz, 1H), 7.26 (ddd, J=7.3, 1.9, 0.4 Hz, 1H), 6.93 (dd, J=2.4, 1.0 Hz, 1H), 3.90 (s, 3H).

Step B: Methyl 3-fluoropyrazolo[1,5-a]pyridine-5-carboxylate. The title compound was prepared in a manner analogous Intermediate 69 Step B, using methyl pyrazolo[1,5-a] pyridine-5-carboxylate instead of methyl pyrazolo[1,5-a] pyridine-4-carboxylate. MS(ESI): mass calcd. for $C_9H_7FN_2O_2$, 194.1; m/z found, 195.0 [M+H]⁺. ¹H NMR (500 MHz, DMSO-$d_6$) δ 8.68 (ddd, J=7.4, 1.6, 1.0 Hz, 1H), 8.33-8.18 (m, 2H), 7.25 (dd, J=7.3, 1.9 Hz, 1H), 3.90 (s, 3H).

Step C: Potassium 3-fluoropyrazolo[1,5-a]pyridine-5-carboxylate. To a solution of methyl 3-fluoropyrazolo[1,5-a]pyridine-5-carboxylate (50 mg, 0.26 mmol) in THF (2.0 mL) was added potassium trimethylsilanolate (50 mg, 0.40 mmol) and the resulting mixture was heated to 60° C. for 24 h. The reaction mixture was then filtered and washed with THF to obtain the title compound as white solid which was taken to next step without purification. MS (ESI): mass calcd. for $C_8H_4KFN_2O_2$, 218.0; m/z found, 181.0[M−K+2H]⁺.

Intermediate 71: 1-Methyl-5-(1-methylcyclopropyl)-1H-pyrazole-4-carboxylic acid

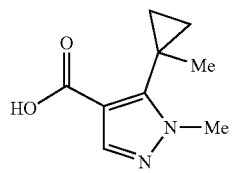 [SMILES: Cn1ncc(C(=O)O)c1C1(C)CC1]

Step A: Methyl 1-methyl-S-(1-methylcyclopropyl)-1H-pyrazole-4-carboxylate and Methyl 1-methyl-3-(1-methylcyclopropyl)-1H-pyrazole-4-carboxylate. Methyl 3-(1-methylcyclopropyl)-3-oxopropanoate (500 mg, 3.20 mmol) and N,N-dimethylformamide dimethyl acetal (0.51 mL, 3.84 mmol) were stirred together for 1.5 h, then the mixture concentrated in vacuo. EtOH (3.0 mL) and methylhydrazine (0.17 mL, 3.20 mmol) were then added, and the reaction heated to reflux for 1 h before being allowed to stir overnight at room temperature. The mixture was diluted with EtOAc and $H_2O$, then the aqueous layer separated and extracted with EtOAc (×2). The combined organics were washed with brine, dried over $Na_2SO_4$, filtered, and concentrated in vacuo, then the crude residue purified by silica gel chromatography (0-25% EtOAc in hexanes) to afford methyl 1-methyl-5-(1-methylcyclopropyl)-1H-pyrazole-4-carboxylate (183 mg, 29% yield). MS (ESI): mass calcd. for $C_{10}H_{14}N_2O_2$, 194.1; m/z found, 195.2 [M+H]⁺. ¹H NMR (500 MHz, Chloroform-d) δ 7.79 (s, 1H), 3.92 (s, 3H), 3.82 (s, 3H), 1.35 (s, 3H), 0.95-0.86 (m, 4H). Methyl 1-methyl-3-(1-methylcyclopropyl)-1H-pyrazole-4-carboxylate was isolated as a second regioisomer (200 mg, 32% yield): MS (ESI): mass calcd. for $C_{10}H_{14}N_2O_2$, 194.1; m/z found, 195.2 [M+H]⁺. ¹H NMR (500 MHz, Chloroform-d) δ 7.77 (s, 1H), 3.83-3.81 (m, 6H), 1.41 (s, 3H), 0.95-0.91 (m, 2H), 0.72-0.69 (m, 2H)

Step B: 1-Methyl-S-(1-methylcyclopropyl)-1H-pyrazole-4-carboxylic acid. To a solution of methyl 1-methyl-5-(1-methylcyclopropyl)-1H-pyrazole-4-carboxylate (169 mg, 0.87 mmol) in EtOH (1.8 mL) was added 10 N NaOH (0.35 mL), and the reaction stirred at room temperature overnight. The mixture was concentrated in vacuo, the crude residue re-dissolved in a small amount of $H_2O$, and the mixture acidified with 6 N HCl. The product was collected via vacuum filtration as a white solid, and the filtrate extracted with 20% i-PrOH/DCM (×2). The combined organics were dried over $Na_2SO_4$, filtered and concentrated in vacuo to afford additional product. The combined material afforded the title compound in 82% yield. MS (ESI): mass calcd. for $C_9H_{12}N_2O_2$, 180.1; m/z found, 181.1 [M+H]⁺.

Intermediate 72: 1-Methyl-3-(1-methylcyclopropyl)-1H-pyrazole-4-carboxylic acid

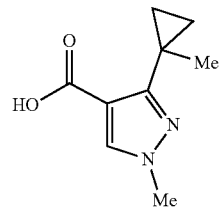 [SMILES: Cn1cc(C(=O)O)c(C2(C)CC2)n1]

The title compound was prepared in a manner analogous to Intermediate 71, Step B, using methyl 1-methyl-3-(1-methylcyclopropyl)-1H-pyrazole-4-carboxylate (isolated as a second regioisomer in Step A) instead of methyl 1-methyl-5-(1-methylcyclopropyl)-1H-pyrazole-4-carboxylate. MS (ESI): mass calcd. for $C_9H_{12}N_2O_2$, 180.1; m/z found, 181.1 [M+H]⁺.

Intermediate 73: Potassium 5-(1-fluorocyclopropyl)-1-methyl-1H-pyrazole-4-carboxylate

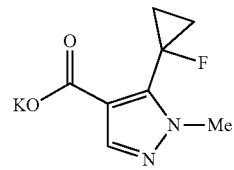

Step A: Ethyl 3-(1-fluorocyclopropyl)-3-oxopropanoate. To a solution of ethyl potassium malonate (0.82 g, 4.80 mmol) in EtOAc (5 mL) at 0° C. was added $MgCl_2$ (1.37 g, 14.4 mmol) followed by triethylamine (3.3 mL, 24.0 mmol). The heterogenous mixture was allowed to warm to room temperature and stirred overnight. In a separate flask, oxalyl chloride (0.41 mL, 4.80 mmol) and DMF (0.4 μL, 5.1 μmol) were added to a 0° C. solution of 1-fluorocyclopropanecarboxylic acid (500 mg, 4.80 mmol) in THF (5.1 mL). The mixture was then maintained at 0° C. for 1 h, then the ice bath was removed and the reaction allowed to warm to room temperature and stirred for an additional 2 h. Afterwards, the solution was carefully added dropwise to the reaction vessel containing ethyl potassium malonate at 0° C. The combined mixtures were then stirred at room temperature overnight before being carefully quenched with a 10% aq. citric acid solution. The layers were separated and the aqueous layer extracted with $CH_2Cl_2$ (×2), after which the combined organic layers were washed once with sat. aq. $NaHCO_3$, dried over $Na_2SO_4$, filtered, and concentrated in vacuo at ca. 90 torr, 23° C. The crude residue was purified by silica gel chromatography (0-100% CH$_2$C$_2$ in hexanes) to afford a pale brown oil (674 mg, 81% yield).

Step B: Ethyl 5-(1-fluorocyclopropyl)-1-methyl-1H-pyrazole-4-carboxylate and Ethyl 3-(1-fluorocyclopropyl)-1-methyl-1H-pyrazole-4-carboxylate. The title compounds were prepared in a manner analogous to Intermediate 71, Step A, using ethyl 3-(1-fluorocyclopropyl)-3-oxopropanoate instead of methyl 3-(1-methylcyclopropyl)-3-oxopropanoate.

Ethyl 5-(1-fluorocyclopropyl)-1-methyl-1H-pyrazole-4-carboxylate: MS (ESI): mass calcd. for C$_{10}$H$_{13}$FN$_2$O$_2$, 212.1; m/z found, 213.1 [M+H]$^+$. $^1$H NMR (600 MHz, Chloroform-d) δ 7.88 (s, 1H), 4.31 (q, J=7.1 Hz, 2H), 4.04 (d, J=0.5 Hz, 3H), 1.67-1.57 (m, 2H), 1.36 (t, J=7.1 Hz, 3H), 1.19-1.14 (m, 2H).

Ethyl 3-(1-fluorocyclopropyl)-1-methyl-1H-pyrazole-4-carboxylate: MS (ESI): mass calcd. for C$_{10}$H$_{13}$FN$_2$O$_2$, 212.1; m/z found, 213.1 [M+H]$^+$. $^1$H NMR (600 MHz, Chloroform-d) δ 7.87 (s, 1H), 4.30 (q, J=7.1 Hz, 2H), 3.88 (d, J=0.7 Hz, 3H), 1.43-1.37 (m, 2H), 1.34 (t, J=7.1 Hz, 3H), 1.18-1.13 (m, 2H).

Step C: Potassium 5-(1-fluorocyclopropyl)-1-methyl-1H-pyrazole-4-carboxylate. To a solution of ethyl 5-(1-fluorocyclopropyl)-1-methyl-1H-pyrazole-4-carboxylate (50 mg, 0.24 mmol) in THF (1.6 mL) was added potassium trimethylsilanoate (67.2 mg, 0.47 mmol), and the reaction stirred at room temperature overnight. The mixture was then diluted with hexanes, and the white solid collected by vacuum filtration, washing with additional hexanes. MS (ESI): mass calcd. for C$_8$H$_8$FKN$_2$O$_2$, 222.0; m/z found, 185.1 [M−K+2H]$^+$.

Intermediate 74: Potassium 3-(1-fluorocyclopropyl)-1-methyl-1H-pyrazole-4-carboxylate

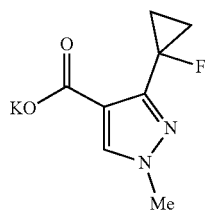

The title compound was prepared in a manner analogous to Intermediate 73, Step C, using ethyl 3-(1-fluorocyclopropyl)-1-methyl-1H-pyrazole-4-carboxylate (isolated as a second regioisomer in Step B) instead of ethyl 5-(1-fluorocyclopropyl)-1-methyl-1H-pyrazole-4-carboxylate. MS (ESI): mass calcd. for C$_8$H$_8$FKN$_2$O$_2$, 222.0; m/z found, 185.1 [M−K+2H]$^+$.

Intermediate 75: 5-(2,2-Difluorocyclopropyl)-1-methyl-1H-pyrazole-4-carboxylic acid

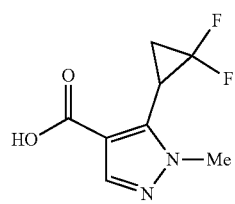 [SMILES: Cn1ncc(C(=O)O)c1C1CC1(F)F]

The title compound was prepared in a manner analogous to Intermediate 73, using 2,2-difluorocyclopropane-1-carboxylic acid instead of 1-fluorocyclopropanecarboxylic acid in Step A. MS (ESI): mass calcd. for C$_8$H$_8$F$_2$N$_2$O$_2$, 202.1; m/z found, 203.1 [M+H]$^+$.

Intermediate 76: Potassium 1-methyl-cis-5-(2-methylcyclopropyl)-1H-pyrazole-4-carboxylate

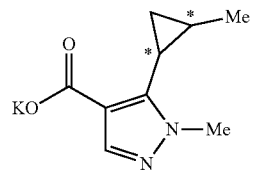

Step A: Methyl 3-(2-methylcyclopropyl)-3-oxopropanoate. To a solution dimethyl carbonate (1.35 mL, 16.0 mmol) in PhMe (5 mL) was added 1-(2-methylcyclopropyl)ethan-1-one (0.5 g, 5.10 mmol), and the mixture stirred at room temperature for 15 min. After cooling to 0° C., potassium tert-butoxide (0.4 g, 3.57 mmol) was added in one portion, and the reaction heated to 75° C. overnight. After cooling to room temperature, the mixture was poured into cooled (0° C.) H$_2$O, and the pH was adjusted to 2-3 with 6 N HCl. The layers were separated, the aqueous layer extracted with EtOAc, then the combined organics washed with H$_2$O, dried over Na$_2$SO$_4$, filtered and concentrated in vacuo (ca. 65 torr, 28° C.) to afford the title compound, which was used directly in the next step without further purification.

Step B: Potassium 1-methyl-cis-5-(2-methylcyclopropyl)-1H-pyrazole-4-carboxylate. The title compound was prepared in the same manner as Intermediate 73, Steps B-C, using methyl 3-(2-methylcyclopropyl)-3-oxopropanoate instead of ethyl 3-(1-fluorocyclopropyl)-3-oxopropanoate in Step B. MS (ESI): mass calcd. for C$_9$H$_{11}$KN$_2$O$_2$, 218.0; m/z found, 181.1 [M−K+2H]$^+$. (Mixture of isomers with relative cis-configuration at starred stereocenters).

Intermediate 77: Potassium cis-5-(2-fluorocyclopropyl)-1-methyl-1H-pyrazole-4-carboxylate

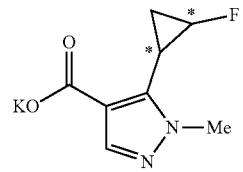

The title compound was prepared in the same manner as Intermediate 73, Steps B-C, using ethyl cis-3-(-2-fluorocyclopropyl)-3-oxopropanoate instead of ethyl 3-(1-fluorocyclopropyl)-3-oxopropanoate in Step B. MS (ESI): mass calcd. for C$_8$H$_8$FKN$_2$O$_2$, 222.0; m/z found, 185.1 [M−K+2H]$^+$. (Mixture of isomers with relative cis-configuration at starred stereocenters).

Intermediate 78: Potassium trans-5-(2-fluorocyclopropyl)-1-methyl-1H-pyrazole-4-carboxylate

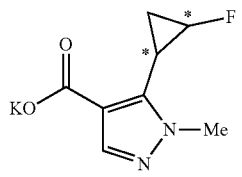

The title compound was prepared in the same manner as Intermediate 73, Steps B-C, using ethyl trans-3-(-2-fluorocyclopropyl)-3-oxopropanoate instead of ethyl 3-(1-fluorocyclopropyl)-3-oxopropanoate in Step B. MS (ESI): mass calcd. for $C_8H_8FKN_2O_2$, 222.0; m/z found, 185.1 [M−K+ 2H]$^+$. (Mixture of isomers with relative trans-configuration at starred stereocenters).

Intermediate 79: trans-5-(2-fluorocyclopropyl)-1-methyl-1H-pyrazole-4-carboxylic acid

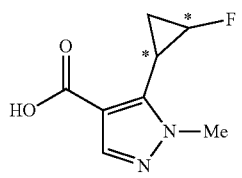

The title compound was prepared in the same manner as Intermediate 73 Steps B-C, using ethyl trans-3-(-2-fluorocyclopropyl)-3-oxopropanoate instead of ethyl 3-(1-fluorocyclopropyl)-3-oxopropanoate in Step B, and then purifying under acidic conditions: ACCQPrep HPLC system with XBridge $C_{18}$ OBD column (5 µm, 50×100 mm); mobile phase of 5% MeCN in $H_2O$ (both phases containing 0.05% TFA) was held for 1 min, then gradient of 5-95% MeCN in $H_2O$ (both containing 0.05% TFA) over 12 min with a flow rate of 80 mL/min. MS (ESI): mass calcd. for $C_8H_9FN_2O_2$, 184.1; m/z found, 185.1 [M+H]$^+$. (Mixture of isomers with relative trans-configuration at starred stereocenters).

Intermediate 80: Potassium 5-cyclobutyl-1-methyl-1H-pyrazole-4-carboxylate

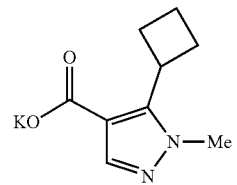

The title compound was prepared in the same manner as Intermediate 73, Steps B-C using ethyl 3-cyclobutyl-3-oxopropanoate instead of ethyl 5-(1-fluorocyclopropyl)-1-methyl-1H-pyrazole-4-carboxylate in Step B. MS (ESI): mass calcd. for $C_9H_{11}KN_2O_2$, 218.0; m/z found, 181.1 [M−K+2H]$^+$.

Intermediate 81: potassium 1-cyclopropyl-5-(trifluoromethyl)-1H-pyrazole-4-carboxylate

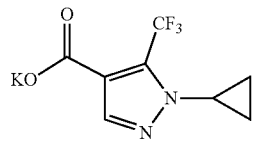

Step A: Ethyl 1-cyclopropyl-5-(trifluoromethyl)-1H-pyrazole-4-carboxylate and Ethyl 1-cyclopropyl-3-(trifluoromethyl)-1H-pyrazole-4-carboxylate. To a solution of triethyl orthoformate (0.34 mL, 2.05 mmol) in acetic anhydride (0.63 mL, 6.66 mmol) was added ethyl 4,4,4-trifluoroacetoacetate (0.1 mL, 0.68 mmol), and the reaction heated to 135° C. overnight. After cooling to room temperature, the mixture was concentrated in vacuo and then re-dissolved in EtOH (0.63 mL). Cyclopropylhydrazine hydrochloride (164 mg, 0.68 mmol) was then added, and the reaction heated to 78° C. for 1 h, then room temperature overnight. The mixture was diluted with EtOAc and $H_2O$, then the aqueous layer separated and extracted with EtOAc (×2). The combined organics were washed with brine, dried over $Na_2SO_4$, filtered, and concentrated in vacuo, and the crude residue was purified by silica gel chromatography (0-50% EtOAc in hexanes) to afford ethyl 1-cyclopropyl-5-(trifluoromethyl)-1H-pyrazole-4-carboxylate (38 mg, 22% yield) MS (ESI): mass calcd. for $C_{10}H_{11}F_3N_2O_2$, 248.1; m/z found, 249.0 [M+H]$^+$. $^1$H NMR (600 MHz, Chloroform-d) δ 7.83 (s, 1H), 4.31 (q, J=7.1 Hz, 2H), 3.75-3.69 (m, 1H), 1.36-1.29 (m, 5H), 1.15-1.10 (m, 2H). Ethyl 1-cyclopropyl-3-(trifluoromethyl)-1H-pyrazole-4-carboxylate was also isolated as a second regioisomer (39 mg, 27% yield): MS (ESI): mass calcd. for $C_{10}H_{11}F_3N_2O_2$, 248.1; m/z found, 249.0 [M+H]$^+$. $^1$H NMR (600 MHz, Chloroform-d) δ 8.03 (s, 1H), 4.31 (q, J=7.1 Hz, 2H), 3.69-3.64 (m, 1H), 1.34 (t, J=7.1 Hz, 3H), 1.21-1.17 (m, 2H), 1.14-1.09 (m, 2H).

Step B: Potassium 1-cyclopropyl-5-(trifluoromethyl)-1H-pyrazole-4-carboxylate. The title compound was prepared in a manner analogous to Intermediate 73, Step C using ethyl 1-cyclopropyl-5-(trifluoromethyl)-1H-pyrazole-4-carboxylate instead of ethyl 5-(1-fluorocyclopropyl)-1-methyl-1H-pyrazole-4-carboxylate. MS (ESI): mass calcd. for $C_8H_6F_3KN_2O_2$, 258.0; m/z found, 220.1 [M−K+2H]$^+$.

Intermediate 82: Potassium 1-cyclopropyl-3-(trifluoromethyl)-1H-pyrazole-4-carboxylate

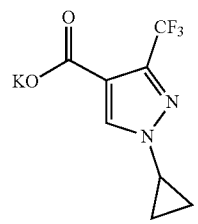

The title compound was prepared in the same manner as Intermediate 73, Step C, using ethyl 1-cyclopropyl-3-(trifluoromethyl)-1H-pyrazole-4-carboxylate (Intermediate 81, isolated as a second regioisomer in Step A) instead of ethyl 5-(1-fluorocyclopropyl)-1-methyl-1H-pyrazole-4-carboxylate. MS (ESI): mass calcd. for $C_8H_6F_3KN_2O_2$, 258.0; m/z found, 220.1 [M−K+2H]$^+$.

Intermediate 83: Potassium 2-cyclopropyl-7-methylpyrazolo[1,5-a]pyridine-3-carboxylate

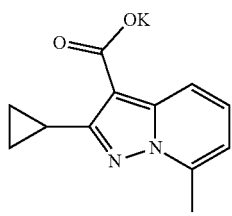

Step A: Ethyl 2-cyclopropyl-7-methylpyrazolo[1,5-a]pyridine-3-carboxylate. To a solution of O-(2,4-dinitrophenyl) hydroxylamine in acetonitrile (25 mL) was added 2-methylpyridine (466 mg, 5.0 mmol) and the resulting mixture was heated to 40° C. for 18 h. The solution mixture was evaporated to dryness using rotary evaporator and re-dissolved in DMF (25 mL). To this mixture was then added ethyl 3-cyclopropylpropiolate (1.0 g, 7.5 mmol) and potassium carbonate (2.1 g, 15 mmol) and was stirred for another 24 h at room temperature. The crude mixture was then diluted with EtOAc (2×), and the combined organics washed with brine (4×), dried over $Na_2SO_4$, filtered, and concentrated. The residue was purified by silica gel chromatography (0-50% EtOAc/hexanes) to afford the title compound as yellow solid (470 mg, 38.5% yield). MS(ESI): mass calcd. for $C_{14}H_{16}N_2O_2$, 244.1; m/z found, 245.1 [M+H]$^+$. $^1$H NMR (400 MHz, DMSO-d$_6$) δ 7.95-7.86 (m, 1H), 7.46 (dd, J=8.9, 7.0 Hz, 1H), 6.98 (dt, J=7.0, 1.2 Hz, 1H), 4.32 (q, J=7.1 Hz, 2H), 2.82 (tt, J=7.9, 5.4 Hz, 1H), 2.63 (s, 3H), 1.36 (t, J=7.1 Hz, 3H), 1.11-0.99 (m, 4H).

Step B: Potassium 2-cyclopropyl-7-methylpyrazolo[1,5-a] pyridine-3-carboxylate. The title compound was prepared in a manner analogous to Intermediate 70, Step C using ethyl 2-cyclopropyl-7-methylpyrazolo[1,5-a] pyridine-3-carboxylate instead of methyl 3-fluoropyrazolo[1,5-a] pyridine-5-carboxylate. MS (ESI): mass calcd. for $C_{12}H_{11}KN_2O_2$, 254.1; m/z found, 217.1[M−K+2H]$^+$.

Intermediate 84: Potassium 7-fluoroimidazo[1,2-a]pyridine-3-carboxylate

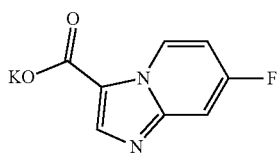

To a solution of ethyl 7-fluoroimidazo[1,2-a] pyridine-3-carboxylate (100 mg, 0.5 mmol) in THF (4.0 mL) was added potassium trimethylsilanolate (92.4 mg, 0.72 mmol) and the resulting mixture was stirred at rt for 16 h. The reaction mixture was then filtered and washed with THF to obtain the title compound as white solid which was taken to next step without purification. MS (ESI): mass calcd. for $C_8H_4FKN_2O_2$, 218.0; m/z found, 181.1 [M+H]$^+$.

Intermediate 85: Potassium 7-fluoro-2-methylimidazo[1,2-a]pyridine-3-carboxylate

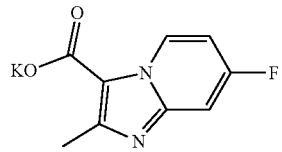

Step A: ethyl 7-fluoro-2-methylimidazo[1,2-a] pyridine-3-carboxylate. To a solution of 4-fluoropyridin-2-amine (250 mg, 2.2 mmol) in 1,2-dimethoxyethane (2.1 mL, 20.2 mmol) was added ethyl 2-chloro-3-oxobutanoate (2.3 mL, 2.7 mmol) and the mixture was heated to 90° C. for 16 h. The reaction mixture was concentrated under reduced pressure, diluted with EtOAc, washed the organic layer with water (×2). The combined organic extracts were dried over anhydrous $Na_2SO_4$ and concentrated under vacuo. Purification by flash chromatography (SiO$_2$; 0-100% EtOAc/hexanes) afforded the title compound as a white solid (66.4 mg, 14% yield). MS (ESI): mass calcd. for $C_{11}H_{11}FN_2O_2$, 222.2; m/z found, 223.1 [M+H]$^+$.

Step B: Potassium 7-fluoro-2-methylimidazo[1,2-a] pyridine-3-carboxylate. The title compound was prepared in a manner analogous to Intermediate 70, Step C, using ethyl 7-fluoro-2-methylimidazo[1,2-a] pyridine-3-carboxylate instead of methyl 3-fluoropyrazolo[1,5-a] pyridine-5-carboxylate. MS (ESI): mass calcd. for $C_9H_6FKN_2O_2$, 232.0; m/z found, 195.1[M−K+2H]$^+$.

Intermediate 86: Potassium 6-fluoro-2,8-dimethylimidazo[1,2-a]pyridine-3-carboxylate

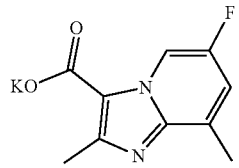

The title compound was prepared in a manner analogous to Intermediate 85, using 5-fluoro-3-methylpyridin-2-amine instead of 4-fluoropyridin-2-amine in step A. MS (ESI): mass calcd. for $C_{10}H_8FKN_2O_2$, 246.0; m/z found, 209.1 [M−K+2H]$^+$.

Intermediate 87: Potassium 6-fluoro-2,7-dimethylimidazo[1,2-a]pyridine-3-carboxylate

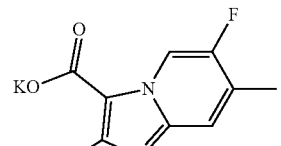

The title compound was prepared in a manner analogous to Intermediate 85 using 5-fluoro-4-methylpyridin-2-amine instead of 4-fluoropyridin-2-amine in step A. MS (ESI): mass calcd. for $C_{10}H_8FKN_2O_2$, 246.0; m/z found, 209.1 [M−K+2H]$^+$.

Intermediate 88: Potassium 6,8-difluoro-2-methylimidazo[1,2-a] pyridine-3-carboxylate

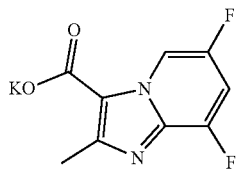

The title compound was prepared in a manner analogous to Intermediate 85 using 3,5-difluoropyridin-2-amine instead of 4-fluoropyridin-2-amine and heating at 90° C. for 3 h in Step A. MS (ESI): mass calcd. for $C_9H_5F_2KN_2O_2$, 250.0; m/z found, 213.1 [M−K+2H]$^+$.

Intermediate 89: Potassium 7-methoxy-2-methylimidazo[1,2-a] pyridine-3-carboxylate

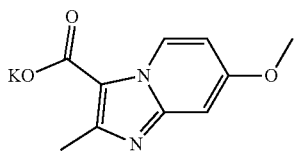

The title compound was prepared in a manner analogous to Intermediate 85 using 5-methoxypyridin-2-amine instead of 4-fluoropyridin-2-amine in Step A. MS (ESI): mass calcd. for $C_{10}H_9KN_2O_3$, 244.0; m/z found, 207.0 [M−K+2H]$^+$.

Intermediate 90: Potassium 6-cyclopropyl-2-methylimidazo[1,2-a] pyridine-3-carboxylate

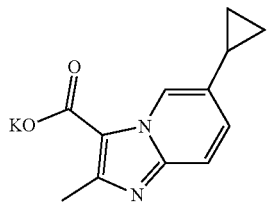

The title compound was prepared in a manner analogous to Intermediate 85 using 5-cyclopropylpyridin-2-amine instead of 4-fluoropyridin-2-amine and heating at 90° C. for 2 h in Step A. MS (ESI): mass calcd. for $C_{12}H_{11}KN_2O_2$, 254.0; m/z found, 217.1 [M−K+2H]$^+$.

Intermediate 91: Potassium pyrrolo[1,2-a] pyrazine-1-carboxylate

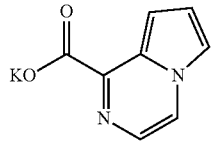

The title compound was prepared in a manner analogous to Intermediate 70, Step C, using ethyl pyrrolo[1,2-a] pyrazine-1-carboxylate instead of methyl 3-fluoropyrazolo[1,5-a] pyridine-5-carboxylate. MS (ESI): mass calcd. for $C_5H_5KN_2O_2$, 200.0; m/z found, 163.1[M−K+2H]$^+$.

Intermediate 92: Potassium [1,2,4] triazolo[4,3-a] pyridine-3-carboxylate

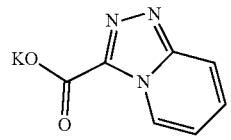

The title compound was prepared in a manner analogous to Intermediate 84, using ethyl [1,2,4]triazolo[4,3-a] pyridine-3-carboxylate instead of ethyl 7-fluoroimidazo[1,2-a] pyridine-3-carboxylate and stirred for 1 h at rt. MS (ESI): mass calcd. for $C_7H_4KN_3O_2$, 201.0; m/z found, 164.1[M−K+2H]$^+$.

Intermediate 93: Potassium 5-methylpyrazolo[1,5-b] pyridazine-3-carboxylate

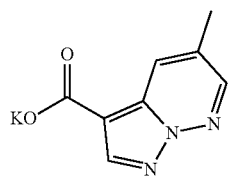

The title compound was prepared in a manner analogous to Intermediate 70, Step C, using methyl 5-methylpyrazolo [1,5-b] pyridazine-3-carboxylate instead of methyl 3-fluoropyrazolo[1,5-a] pyridine-5-carboxylate. MS (ESI): mass calcd. for $C_8H_6KN_3O_2$, 215.0; m/z found, 178.1 [M−K+2H]$^+$.

Intermediate 94: Potassium 2,4-dimethylpyrazolo[1,5-a] pyrazine-3-carboxylate

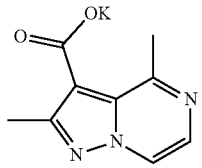

Step A: 1-Amino-2-methylpyrazin-1-ium 2,4,6-trimethylbenzenesulfonate. To a cooled (0° C.) solution of ethyl (E)-N-((mesitylsulfonyl)oxy) acetimidate (3.9 g, 13.8 mmol) in dioxane (6.0 mL) was added 70% perchloric acid (2.8 mL, 33.3 mmol) dropwise. Following the addition, the temperature was maintained at 0° C. for 10 minutes and then ice-cold water (13 mL) was added at once. The resulting precipitate was collected by vacuum filtration and washed with water (caution: this compound has been reported to be potentially explosive when dry). The white solid was immediately dissolved in DCM (5.0 mL), dried over $Na_2SO_4$, and filtered. The filtrate was then added dropwise to a cooled (0° C.) solution of 2-methylpyrazine (1.0 g, 11.0 mmol) in DCM (10 mL). The reaction was allowed to warm to room temperature and stirred for 2 h. The resulting crude mixture was concentrated in vacuo to afford the title compound as a yellow oil. MS (ESI): mass calcd. for $C_5H_8N_3$, 110.1; m/z found, 111.1 [M+H]$^+$.

Step B: Ethyl 2,4-dimethylpyrazolo[1,5-a] pyrazine-3-carboxylate. To the crude solution of a 1-amino-2-methylpyrazin-1-ium 2,4,6-trimethylbenzenesulfonate (0.5 g, 1.6 mmol) in DMF (8.0 mL) was added ethyl but-2-ynoate (0.27 g, 2.4 mmol) and potassium carbonate (0.67 g, 4.8 mmol) and the resulting mixture was stirred for 16 h at rt. The crude mixture was then diluted with EtOAc (2×), and the combined organics washed with brine (4×), dried over $Na_2SO_4$, filtered, and concentrated. The residue was purified by silica gel chromatography (0-50% EtOAc/hexanes) to afford the title compound as yellow solid (65 mg, 18% yield). MS(ESI): mass calcd. for $C_{11}H_{13}N_3O_2$, 219.1; m/z found, 220.1 [M+H]$^+$.

Step C: Potassium 2,4-dimethylpyrazolo[1,5-a] pyrazine-3-carboxylate. The title compound was prepared in a manner analogous to Intermediate 70, Step C, using ethyl 2,4-dimethylpyrazolo[1,5-a] pyrazine-3-carboxylate instead of methyl 3-fluoropyrazolo[1,5-a]pyridine-5-carboxylate. MS (ESI): mass calcd. for $C_9H_8KN_3O_2$, 229.0; m/z found, 192.0 [M−K+2H]$^+$.

Intermediate 95: Potassium 2-cyclopropyl-4-methylpyrazolo[1,5-a] pyrazine-3-carboxylate

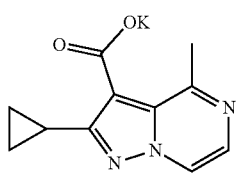

The title compound was prepared in a manner analogous to Intermediate 94, using ethyl 3-cyclopropylpropiolate instead of ethyl but-2-ynoate in Step B. MS (ESI): mass calcd. for $C_{11}H_{10}KN_3O_2$, 255.0; m/z found, 218.1 [M−K+2H].

Intermediate 96: Potassium 2-methylimidazo[1,2-b]pyridazine-6-carboxylate

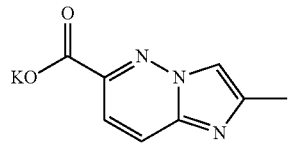

The title compound was prepared in a manner analogous to Intermediate 70, Step C, using methyl 2-methylimidazo[1,2-b] pyridazine-6-carboxylate instead of ethyl 7-fluoroimidazo[1,2-a]pyridine-3-carboxylate. MS (ESI): mass calcd. for $C_8H_6KN_3O_2$, 215.0; m/z found, 178.1 [M−K+2H]$^+$.

Intermediate 97: Potassium 2,8-dimethylimidazo[1,2-b]pyridazine-3-carboxylate

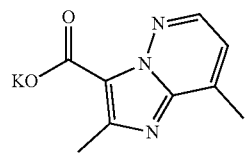

The title compound was prepared in a manner analogous to Intermediate 85 using 4-methylpyridazin-3-amine instead of 4-fluoropyridin-2-amine in Step A. MS (ESI): mass calcd. for $C_9H_8KN_3O_2$, 229.1; m/z found, 192.0 [M−K+2H]$^+$.

Intermediate 98: Potassium 2,7-dimethylimidazo[1,2-b]pyridazine-3-carboxylate

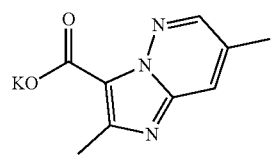

The title compound was prepared in a manner analogous to Intermediate 85 using 5-methylpyridazin-3-amine instead of 4-fluoropyridin-2-amine in Step A. MS (ESI): mass calcd. for $C_9H_8KN_3O_2$, 229.1; m/z found, 192.0 [M−K+2H]$^+$.

Intermediate 99: Potassium 2,5,8-trimethylimidazo[1,2-a]pyrazine-3-carboxylate

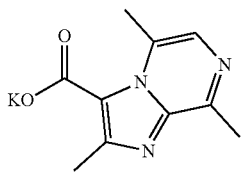

The title compound was prepared in a manner analogous to Intermediate 85 using 3,6-dimethylpyrazin-2-amine instead of 4-fluoropyridin-2-amine in Step A. MS (ESI): mass calcd. for $C_{10}H_{10}KN_3O_2$, 243.1; m/z found, 206.1 [M−K+2H]⁺.

Intermediate 100: Sodium 3-methylimidazo[1,5-a]pyrazine-1-carboxylate

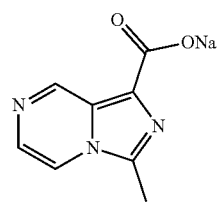

To a stirred solution of methyl 3-methylimidazo[1,5-a]pyrazine-1-carboxylate (53 mg, 0.275 mmol) in ethanol (3.0 mL) and water (1.0 mL) were added sodium hydroxide (33 mg, 0.82 mmol) and the resulting mixture was heated at 80° C. for 16 h. The mixture was then cooled and filtered to obtain the title compound as white solid which was taken to next step without purification. MS (ESI): mass calcd. for $C_8H_6N_3NaO_2$, 199.0; m/z found, 178.1 [M−Na+2H]⁺.

Intermediate 101: Potassium 2-cyclopropyl-4-methylpyrazolo[1,5-a]pyrazine-3-carboxylate

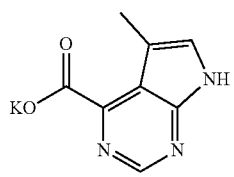

The title compound was prepared in a manner analogous to Intermediate 70, Step C, using methyl 5-methyl-7H-pyrrolo[2,3-d] pyrimidine-4-carboxylate instead of ethyl 7-fluoroimidazo[1,2-a] pyridine-3-carboxylate. MS (ESI): mass calcd. for $C_8H_6KN_3O_2$, 215.0; m/z found, 178.1 [M−K+2H]⁺.

Intermediate 102: Potassium 5-methyl-7H-pyrrolo[2,3-d]pyrimidine-4-carboxylate

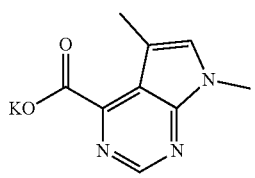

Step A: methyl 5,7-dimethyl-7H-pyrrolo[2,3-d] pyrimidine-4-carboxylate. To a cooled (0° C.) solution of methyl 5-methyl-7H-pyrrolo[2,3-d] pyrimidine-4-carboxylate (0.25 g, 1.3 mmol) in THF (7.5 mL) was added sodium hydride (60% in mineral oil, 105 mg, 2.62 mmol). The reaction mixture was warmed to rt and stirred for 1 h. After 1 h, the mixture was cooled to 0° C., then iodomethane (0.25 mL, 4.0 mmol) was added, and the reaction mixture was stirred for 16 h.

The reaction was then quenched with water, diluted with EtOAc (2×), and the combined organics washed with brine (4×), dried over $Na_2SO_4$, filtered, and concentrated. The crude residue was taken to next step without further purification. MS(ESI): mass calcd. for $C_{10}H_{11}N_3O_2$, 205.1; m/z found, 206.1 [M+H]⁺.

Step B: Potassium 5,7-dimethyl-7H-pyrrolo[2,3-d]pyrimidine-4-carboxylate. The title compound was prepared in a manner analogous to Intermediate 70, Step C, using methyl 5-methyl-7H-pyrrolo[2,3-d] pyrimidine-4-carboxylate instead of methyl 3-fluoropyrazolo[1,5-a]pyridine-5-carboxylate. MS (ESI): mass calcd. for $C_9H_8KN_3O_2$, 229.0; m/z found, 192.0 [M−K+2H]⁺.

Intermediate 103: 2,3-Dimethylquinoxaline-6-carboxylic acid

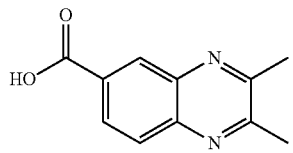

To a stirred solution of 3,4-diaminobenzoic acid (0.25 g, 1.64 mmol) in ethanol (2.0 mL) was added 2,3-butanedione (0.2 mL, 2.0 mmol) and the resulting mixture was heated at 80° C. for 1 h. The mixture was then cooled and concentrated the solvent to obtain the title compound as brown solid which was taken to next step without further purification. MS (ESI): mass calcd. for $C_{11}H_{10}N_2O_2$, 202.2; m/z found, 202.9 [M+H]⁺.

Intermediate 104: Lithium(I) quinoxaline-6-carboxylate-2-d

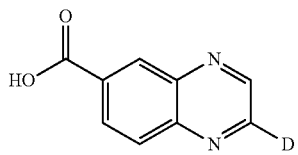 [SMILES: [2H]c1cnc2cc(C(=O)O)ccc2n1]

Step A: Methyl 2-hydroxyquinoxaline-6-carboxylate. A solution of methyl 3,4-diaminobenzoate (2.0 g, 12 mmol) in ethanol (6.0 mL) was added ethyl 2-oxoacetate (1.4 mL, 14.4 mmol) and the mixture was stirred at rt for 1 h. Concentrated the solvent and recrystallized the crude mixture with ethyl acetate (10.0 mL). The resulting yellow solid was filtered and dried on vacuum to afford the title compound (1.5 g, 63% yield). MS (ESI): mass calcd. for $C_{10}H_8N_2O_3$, 204.2; m/z found, 205.1 [M+H]⁺.

Step B: Methyl 2-chloroquinoxaline-6-carboxylate. To a solution of methyl 2-hydroxyquinoxaline-6-carboxylate (655 mg, 3.2 mmol) in toluene (20.0 mL) was added thionyl chloride (5.0 mL, 64.1 mmol) followed by N, N-dimethylformamide (0.3 mL, 3.8 mmol). The resulting solution was heated to reflux temperature for 3 h. After cooling the mixture, concentrated the solvent under vacuum and triturated with ethyl acetate. The resulting brown solid was filtered and dried on vacuum to afford the title compound (426 mg, 60% yield). MS (ESI): mass calcd. for $C_{10}H_7ClN_2O_2$, 222.1; m/z found, 222.9 $[M+H]^+$.

Step C: methyl quinoxaline-6-carboxylate-2-d. To a solution of methyl 2-chloroquinoxaline-6-carboxylate (225 mg, 1.0 mmol) in THF (20.0 mL) was added $PdCl_2(dppf)$ (37 mg, 0.05 mmol), $N^1$, $N^1$, $N^2$, $N^2$-tetramethylethane-1,2-diamine (0.26 mL, 1.72 mmol) and sodium borodeuteride (72 mg, 1.72 mmol). The mixture was degassed with nitrogen and then stirred at rt for 2 h. The reaction mixture was diluted with water and extracted with ethyl acetate (×2). The combined organic extracts were dried over $Na_2SO_4$ and concentrated. Purification by flash chromatography ($SiO_2$; 0-100% EtOAc/hexanes) afforded the title compound as a white solid (130 mg, 68% yield). MS (ESI): mass calcd. for $C_{10}H_7DN_2O_2$, 189.2; m/z found, 190.1 $[M+H]^+$. $^1$H NMR (400 MHz, DMSO-$d_6$) δ 9.08 (d, J=1.2 Hz, 1H), 8.64 (dd, J=2.0, 0.6 Hz, 1H), 8.32 (dd, J=8.7, 1.9 Hz, 1H), 8.22 (dd, J=8.7, 0.6 Hz, 1H), 3.97 (s, 3H).

Step D: Lithium(I) quinoxaline-6-carboxylate-2-d. To a solution of methyl quinoxaline-6-carboxylate-2-d (100 mg, 0.53 mmol) in THF (3.5 mL) was added a solution of lithium hydroxide (25.0 mg, 1.05 mmol) in water (1.5 mL). The mixture was stirred at rt for 1 h, then concentrated the solvent to afford the title compound as white solid which was further taken to next step without purification (quantitative yield). MS (ESI): mass calcd. for $C_9H_4DLiN_2O$, 181.1 m/z found, 176.0 $[M-Li+2H]^+$.

Intermediate 105: Potassium 2,6,6-trimethyl-6,7-dihydro-4H-pyrazolo[5,1-c][1,4]oxazine-3-carboxylate

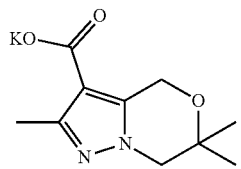

Step A: 6,6-Dimethylmorpholine-3-carboxylic acid. To a solution of 4-(tert-butyl) 3-methyl 6,6-dimethylmorpholine-3,4-dicarboxylate (5 g, 18.3 mmol) in DCM (18.3 mL) was added trifluoroacetic acid (6.0 mL) and the mixture was stirred at rt for 2 h. Concentrated the solvent, dissolved the crude residue in MeOH (9.2 mL) followed by addition of sodium hydroxide (3.0 g, 73.2 mmol) in water. Concentrated solvent using a rotary evaporator and the crude product was taken to next step without purification. MS (ESI): mass calcd. for $C_7H_{13}NO_3$, 159.1; m/z found, 160.2 $[M+H]^+$.

Step B: 6,6-Dimethyl-6,7-dihydro-4H-[1,2,3]oxadiazolo[4,3-c][1,4]oxazin-8-ium-3-olate. To a solution of 6,6-dimethylmorpholine-3-carboxylic acid (2.9 g, 18.3 mmol) in water (1.8 mL, 95.2 mmol) was added sodium nitrite (1.9 g, 27.4 mmol) and hydrochloric acid (37% in water) (1.24 mL, 14.8 mmol). The mixture was stirred at rt for 16 h, diluted with water and extracted 3× with 20% iPrOH/chloroform mixture. The combined organic extracts were dried over anhydrous $Na_2SO_4$ and concentrated under vacuo. The crude residue was then dissolved in acetonitrile (7.5 mL) followed by addition of 2,2,2-trifluoroacetic anhydride (1.5 mL, 11.1 mmol). The resulting mixture was stirred at rt for 2 h. The reaction mixture was quenched with potassium carbonate (2.0 g, 14.8 mmol), added water and filtered to obtain the title compound as crystalline precipitate extracted 3× with 20% iPrOH/chloroform. The solid was used in next step without further purification. MS (ESI): mass calcd. for $C_7H_{12}N_2O_4$, 170.2; m/z found, 171.1 $[M+H]^+$. $^1$H NMR (500 MHz, DMSO-$d_6$) δ ppm 4.6 (s, 2H) 4.3 (s, 2H) 1.3 (s, 6H).

Step C: Ethyl 2,6,6-trimethyl-6,7-dihydro-4H-pyrazolo[5,1-c][1,4]oxazine-3-carboxylate and ethyl 3,6,6-trimethyl-6,7-dihydro-4H-pyrazolo[5,1-c][1,4]oxazine-2-carboxylate To a solution of 6,6-dimethyl-6,7-dihydro-4H-[1,2,3]oxadiazole[4,3-c] [1,4]oxazin-8-ium-3-olate (200 mg, 1.2 mmol) in xylene (4.0 mL) was added ethyl but-2-ynoate (0.28 mL, 2.4 mmol) and the mixture was stirred at 145° C. for 16 h. Concentrated the solvent and purified by flash chromatography ($SiO_2$; 0-100% EtOAc/hexanes) to obtain mixture of regio isomers (91 mg; 52 mg, 33%; 18% yield). MS (ESI): mass calcd. for $C_{12}H_{18}N_2O_3$, 238.3; m/z found, 239.1 $[M+H]^+$.

Step D: (A). Potassium 2,6,6-trimethyl-6,7-dihydro-4H-pyrazolo[5,1-c][1,4]oxazine-3-carboxylate and (B). Potassium 3,6,6-trimethyl-6,7-dihydro-4H-pyrazolo[5,1-c][1,4]oxazine-2-carboxylate: The title compound was prepared in a manner analogous to Intermediate 6 using ethyl 2,6,6-trimethyl-6,7-dihydro-4H-pyrazolo[5,1-c] [1,4] oxazine-3-carboxylate and ethyl 3,6,6-trimethyl-6,7-dihydro-4H-pyrazolo[5,1-c][1,4]oxazine-2-carboxylate (Step C) instead of methyl 3-fluoropyrazolo[1,5-a] pyridine-5-carboxylate. MS (ESI): mass calcd. for $C_{10}H_{13}KN_2O_3$, 248.2; m/z found, 211.1 $[M-K+2H]^+$.

Intermediate 106: Potassium 3,6,6-trimethyl-6,7-dihydro-4H-pyrazolo[5,1-c][1,4]oxazine-2-carboxylate

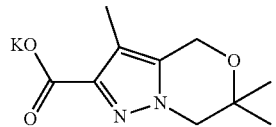

The title compound was isolated from Intermediate 105, Step C. MS (ESI): mass calcd. for $C_{10}H_{13}KN_2O_3$, 248.2; m/z found, 211.1 $[M-K+2H]^+$.

Intermediate 107: 3-Fluoro-5-methoxyisonicotinic acid

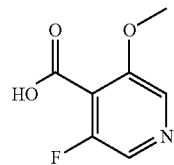

Under a nitrogen atmosphere was added n-BuLi (2.5M in hexanes, 0.21 mL, 0.53 mmol) to a mixture of 4-bromo-3-fluoro-5-methoxypyridine (100 mg, 0.5 mmol) in THF (2.3 mL) at −78 C. After 1 hour, $CO_2$ was cannulated and bubbled through the reaction mixture from dry ice. Then, the reaction mixture slowly warmed to room temperature. After 16 hours, water (20 mL) was added and the mixture was acidified using 6N HCl. The mixture was extracted using DCM (3×30 mL). The combined organics were discarded. The aqueous layer was concentrated under reduced pressure. Purification (preparative HPLC, METHOD A) afforded the title compound (133 mg, 64%). MS (ESI): mass calcd. for $C_7H_6FNO_3$, 171.0; m/z found, 172.1 $[M+H]^+$.

Intermediate 108: Potassium 2-cyclopropyl-4-methylpyrazolo[1,5-b]pyridazine-3-carboxylate

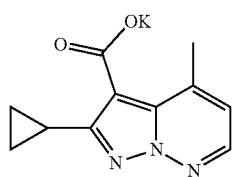

The title compound was prepared in a manner analogous to Intermediate 94, using 4-methyl pyridazine in Step A and ethyl 3-cyclopropylpropiolate instead of ethyl but-2-ynoate in Step B. MS (ESI): mass calcd. for $C_{11}H_{10}KN_3O_2$, 255.0; m/z found, 218.1 $[M-K+2H]^+$.

Intermediate 109: Potassium 2-cyclopropyl-5-methylpyrazolo[1,5-b]pyridazine-3-carboxylate

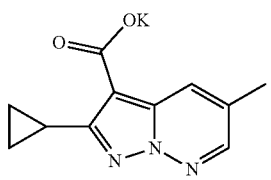

The title compound was prepared in a manner analogous to Intermediate 94, using 4-methyl pyridazine in Step A and ethyl 3-cyclopropylpropiolate instead of ethyl but-2-ynoate in Step B. MS (ESI): mass calcd. for $C_{11}H_{10}KN_3O_2$, 255.0; m/z found, 218.1 $[M-K+2H]^+$.

Intermediate 110: 1,6-Dimethyl-1H-pyrazolo[3,4-d]pyrimidine-4-carboxylic acid

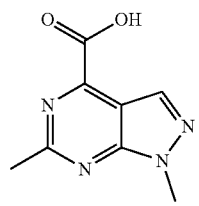

Step A: 4-(1-Ethoxyvinyl)-1,6-dimethyl-1H-pyrazolo[3,4-d]pyrimidine. To a solution of 4-chloro-1,6-dimethyl-1H-pyrazolo[3,4-d]pyrimidine (500 mg, 2.74 mmol) in N,N-dimethylformamide (4.0 mL) was added tributyl(1-ethoxyvinyl)stannane (0.92 mL, 2.74 mmol), and bis(triphenylphosphine)palladium chloride (192 mg, 0.27 mmol). The reaction mixture was stirred at 60° C. for 18 h under nitrogen and concentrated under reduced pressure. After cooling, the reaction was quenched by saturated potassium fluoride aqueous solution and diluted with ethyl acetate (EtOAc). The resulting precipitate was filtered off and filtrate was collected and washed with water and brine solution. The organic layer is dried over sodium sulfate, filtered and concentrated under reduced pressure. The residue was purified by silica gel column chromatography, eluting with hexanes:ethyl acetate (4:1) to give the title compound (177 mg, 30% yield) as white solid. MS (ESI): mass calcd. for $C_{11}H_{14}N_4O$, 218.1; m/z found, 219.1 $[M+H]^+$. $^1$H NMR (400 MHz, DMSO-d$_6$) δ 8.27 (s, 1H), 5.74 (d, J=2.0 Hz, 1H), 4.76 (d, J=2.0 Hz, 1H), 4.05 (t, J=6.9 Hz, 2H), 3.99 (s, 3H), 2.71 (s, 3H), 1.48 (t, J=7.0 Hz, 3H).

Step B: 1,6-Dimethyl-1H-pyrazolo[3,4-d]pyrimidine-4-carboxylic acid. To a solution of 4-(1-ethoxyvinyl)-1,6-dimethyl-1H-pyrazolo[3,4-d]pyrimidine (50 mg, 0.23 mmol) in 1,4 dioxane (1.5 mL) was added a solution of sodium periodate (98 mg, 0.46 mmol) in water (0.5 mL) followed by addition of potassium permanganate (18.1 mg, 0.11 mmol) and the mixture was stirred at room temperature for 16 h. After completion, the reaction mixture was adjusted to pH 7-8 with saturated potassium carbonate solution. The precipitate was filtered off and washed with dichloromethane to afford the title compound as white solid. (28 mg, 64% yield). MS (ESI): mass calcd. for $C_8H_8N_4O_2$, 192.1; m/z found, 193.1 $[M+H]^+$.

Intermediate 111: 3-Fluoro-5-(triazol-2-yl)benzoic acid

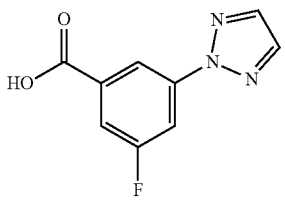 [SMILES: O=C(O)c1cc(F)cc(-n2nccn2)c1]

To a mixture of 3-fluoro-5-iodobenzoic acid (270 mg, 1.02 mmol) in N,N-dimethylformamide (2.7 mL) was added 1H-1,2,3-triazole (88 μL, 1.52 mmol, 1.192 g/mL), cesium carbonate (562 mg, 1.72 mmol), trans-N,N-dimethylcyclohexane-1,2-diamine (27 μL, 0.171 mmol, 0.902 g/mL) and copper(I) iodide (19 mg, 0.0998 mmol). The reaction mixture was stirred at 140° C. for 80 min under microwave irradiation. The reaction mixture was filtered through a pad of Celite® and the Celite® was washed with ethyl acetate (2×5 mL). The combined filtrates were extracted with water (1×5 mL). The aqueous layer was acidified to pH 3 with 1 M hydrochloric acid. The aqueous layer was extracted with ethyl acetate (2×5 mL). The combined organic layers were dried over magnesium sulfate, filtered and evaporated. The crude product was purified by preparative HPLC to afford the title compound (57 mg, 27% yield) as an off-white powder. MS (ESI): mass calcd. for $C_9H_6FN_3O_2$, 207.0; m/z found, 208.1 $[M+H]^+$. $^1$H NMR (500 MHz, DMSO-d$_6$) δ 13.75 (br s, 1H), 9.01 (d, J=1.2 Hz, 1H), 8.38-8.30 (m, 1H), 8.16 (dt, J=9.4, 2.2 Hz, 1H), 8.03 (d, J=1.2 Hz, 1H), 7.82-7.74 (m, 1H).

Intermediate 112:
3-(3-methyl-1H-1,2,4-triazol-1-yl)benzoic acid

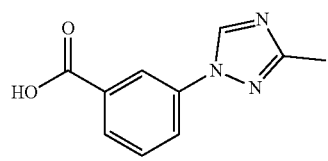

The compound was made in a manner analogous to Intermediate 111 (3-fluoro-5-(triazol-2-yl)benzoic acid) using 3-iodobenzoic acid instead of 3-fluoro-5-iodobenzoic acid and 3-methyl-1H-1,2,4-triazole instead of 1H-1,2,3-triazole. MS (ESI): mass calcd. for $C_{10}H_9N_3O_2$, 203.1; m/z found, 204.1 [M+H]$^+$.

Intermediate 113:
3-fluoro-5-(1H-1,2,4-triazol-1-yl)benzoic acid

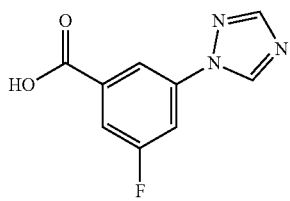 [SMILES: O=C(O)c1cc(F)cc(-n2cncn2)c1]

The compound was made in a manner analogous to Intermediate 111 (3-fluoro-5-(triazol-2-yl)benzoic acid) using 1H-1,2,4-triazole instead of 1H-1,2,3-triazole. MS (ESI): mass calcd. for $C_9H_6FN_3O_2$, 207.0; m/z found, 208.1 [M+H]$^+$.

Intermediate 114:
3-methoxy-5-(1H-1,2,4-triazol-1-yl)benzoic acid

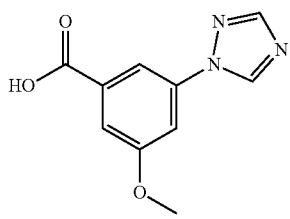 [SMILES: COc1cc(C(=O)O)cc(-n2cncn2)c1]

The compound was made in a manner analogous to Intermediate 111 (3-fluoro-5-(triazol-2-yl)benzoic acid) using 3-iodo-5-methoxybenzoic acid instead of 3-fluoro-5-iodobenzoic acid and 1H-1,2,4-triazole instead of 1H-1,2,3-triazole. MS (ESI): mass calcd. for $C_{10}H_9N_3O_3$, 219.1; m/z found, 220.1 [M+H]$^+$.

Intermediate 115:
2-fluoro-6-(1H-1,2,4-triazol-1-yl)benzoic acid

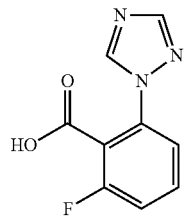 [SMILES: O=C(O)c1c(F)cccc1-n1cncn1]

The compound was made in a manner analogous to Intermediate 111 (3-fluoro-5-(triazol-2-yl)benzoic acid) using 2-fluoro-6-iodobenzoic acid instead of 3-fluoro-5-iodobenzoic acid and 1H-1,2,4-triazole instead of 1H-1,2,3-triazole. MS (ESI): mass calcd. for $C_9H_6FN_3O_2$, 207.0; m/z found, 208.1 [M+H]$^+$.

Intermediate 116:
2-fluoro-5-(2H-1,2,3-triazol-2-yl)benzoic acid

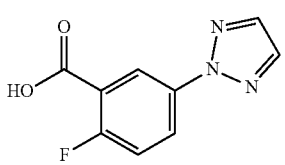 [SMILES: O=C(O)c1cc(-n2nccn2)ccc1F]

The compound was made in a manner analogous to Intermediate 111 (3-fluoro-5-(triazol-2-yl)benzoic acid) using 2-fluoro-5-iodobenzoic acid instead of 3-fluoro-5-iodobenzoic acid. MS (ESI): mass calcd. for $C_9H_6FN_3O_2$, 207.0; m/z found, 208.1 [M+H]$^+$.

Intermediate 117:
3-methyl-5-(2H-1,2,3-triazol-2-yl)benzoic acid

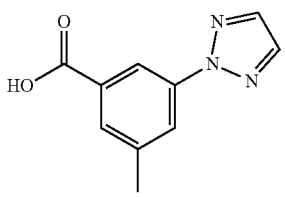

The compound was made in a manner analogous to Intermediate 111 (3-fluoro-5-(triazol-2-yl)benzoic acid) using 3-iodo-5-methylbenzoic acid instead of 3-fluoro-5-iodobenzoic acid. MS (ESI): mass calcd. for $C_9H_6FN_3O_2$, 203.1; m/z found, 204.1 [M+H]$^+$.

Intermediate 118: 3-(2H-1,2,3-triazol-2-yl)-5-(trifluoromethyl)benzoic acid

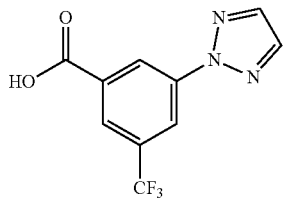 [SMILES: O=C(O)c1cc(-n2nccn2)cc(C(F)(F)F)c1]

The compound was made in a manner analogous to Intermediate 111 (3-fluoro-5-(triazol-2-yl)benzoic acid) using 3-iodo-5-(trifluoromethyl)benzoic acid instead of 3-fluoro-5-iodobenzoic acid. MS (ESI): mass calcd. for $C_{10}H_6F_3N_3O_2$, 257.0; m/z found, 256.1 [M−H]⁻.

Intermediate 119: 5-(1H-pyrazol-1-yl)nicotinic acid

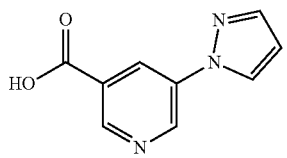 [SMILES: O=C(O)c1cncc(-n2cccn2)c1]

The compound was made in a manner analogous to Intermediate 111 (3-fluoro-5-(triazol-2-yl)benzoic acid) using 5-iodonicotinic acid instead of 3-fluoro-5-iodobenzoic acid and 1H-pyrazole instead of 1H-1,2,3-triazole. MS (ESI): mass calcd. for $C_9H_7N_3O_2$, 189.1; m/z found, 190.1 [M+H]⁺.

Intermediate 120: 3-Fluoro-5-(4H-1,2,4-triazol-4-yl)benzoic acid

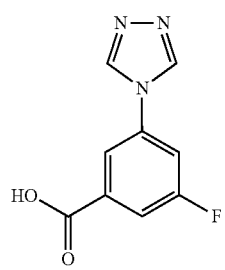 [SMILES: O=C(O)c1cc(F)cc(-n2cnnc2)c1]

Step A: Methyl 3-fluoro-5-(1,2,4-triazol-4-yl)benzoate. To a solution of methyl 3-amino-5-fluorobenzoate (250 mg, 1.48 mmol) in pyridine (8 mL) was added 1,2-diformylhydrazine (325 mg, 3.69 mmol) and triethylamine (1 mL, 7.16 mmol). To the mixture was added chlorotrimethylsilane (375 μL, 2.96 mmol) dropwise. The reaction mixture was stirred at 100° C. for 16 h and evaporated. The residue was diluted with dichloromethane (8 mL) and water (10 mL). The aqueous layer was extracted with dichloromethane (2×10 mL). The combined organic layers were washed with 10% potassium bisulfate (1×15 mL) and 1 M sodium hydroxide (1×15 mL), dried over sodium sulfate, filtered and evaporated to give the title compound (131 mg, 0.592 mmol, 40%) as a white powder. MS (ESI): mass calcd. for $C_{10}H_8FN_3O_2$, 221.1; m/z found, 222.1 [M+H]⁺.

Step B: 3-Fluoro-5-(1,2,4-triazol-4-yl)benzoic acid. To a solution of methyl 3-fluoro-5-(1,2,4-triazol-4-yl)benzoate (130 mg, 0.588 mmol) in 1,4-dioxane (1 mL) and water (1 mL) was added sodium hydroxide (48 mg, 1.20 mmol) and the reaction was stirred at room temperature for 16 h. The reaction was quenched with 6 M hydrochloric acid (0.20 mL). The precipitate was collected and washed with water (1×1 mL) to afford the title compound (80 mg, 0.386 mmol, 65%) as a white powder. MS (ESI): mass calcd. for $C_9H_6FN_3O_2$, 207.0; m/z found, 208.1 [M+H]⁺.

Intermediate 121: 4-Fluoro-3-(4H-1,2,4-triazol-4-yl)benzoic acid

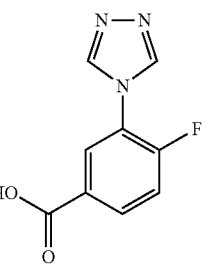

The title compound was prepared in a manner analogous to Intermediate 120 using methyl 3-amino-4-fluorobenzoate instead of methyl 3-amino-5-fluorobenzoate in Step A. MS (ESI): mass calcd. for $C_9H_6FN_3O_2$, 207.0; m/z found, 206.0 [M−H]⁻.

Intermediate 122: 3-Methyl-5-(4H-1,2,4-triazol-4-yl)benzoic acid

The title compound was prepared in a manner analogous to Intermediate 120 using methyl 3-amino-5-methylbenzoate instead of methyl 3-amino-5-fluorobenzoate in Step A. MS (ESI): mass calcd. for $C_{10}H_9N_3O_2$, 203.1; m/z found, 204.1 [M+H]⁺.

Intermediate 123:
4-Methyl-3-(4H-1,2,4-triazol-4-yl)benzoic acid

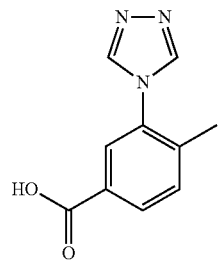

The title compound was prepared in a manner analogous to Intermediate 120 using methyl 3-amino-4-methylbenzoate instead of methyl 3-amino-5-fluorobenzoate in Step A. MS (ESI): mass calcd. for $C_{10}H_9N_3O_2$, 203.1; m/z found, 204.1 [M+H]$^+$.

Intermediate 124:
4-Methoxy-3-(1,2,4-triazol-4-yl)benzoic acid

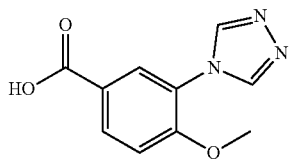 [SMILES: COc1ccc(C(=O)O)cc1-n1cnnc1]

The title compound was prepared in a manner analogous to Intermediate 120 using methyl 3-amino-4-methoxybenzoate instead of methyl 3-amino-5-fluorobenzoate in Step A. MS (ESI): mass calcd. for $C_{10}H_9N_3O_3$, 219.1; m/z found 220.1 [M+H]$^+$.

Intermediate 125:
3-methoxy-5-(4H-1,2,4-triazol-4-yl)benzoic acid

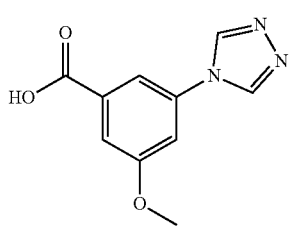 [SMILES: COc1cc(C(=O)O)cc(-n2cnnc2)c1]

The title compound was prepared in a manner analogous to Intermediate 120 using methyl 3-amino-5-methoxybenzoate instead of methyl 3-amino-5-fluorobenzoate in Step A. MS (ESI): mass calcd. for $C_{10}H_9N_3O_3$, 219.1; m/z found 220.1 [M+H]V.

Intermediate 126: 3-(4H-1,2,4-triazol-4-yl)-4-(trifluoromethyl)benzoic acid

The title compound was prepared in a manner analogous to Intermediate 120 using methyl 3-amino-4-(trifluoromethyl)benzoic acid instead of methyl 3-amino-5-fluorobenzoate in Step A. MS (ESI): mass calcd. for $C_{10}H_6F_3N_3O_2$, 257.1; m/z found 258.1 [M+H]$^+$.

Intermediate 127: 3-(4H-1,2,4-triazol-4-yl)-5-(trifluoromethyl)benzoic acid

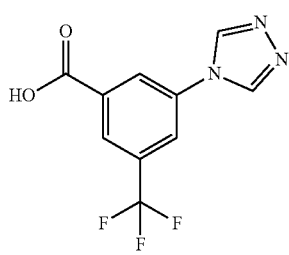 [SMILES: O=C(O)c1cc(-n2cnnc2)cc(C(F)(F)F)c1]

The title compound was prepared in a manner analogous to Intermediate 120 using methyl 3-amino-5-(trifluoromethyl)benzoate instead of methyl 3-amino-5-fluorobenzoate in Step A. MS (ESI): mass calcd. for $C_{10}H_6F_3N_3O_2$, 257.1; m/z found 258.1 [M+H]$^+$.

Intermediate 128:
2-Fluoro-3-(2-(tosyloxy)ethoxy)benzoic acid

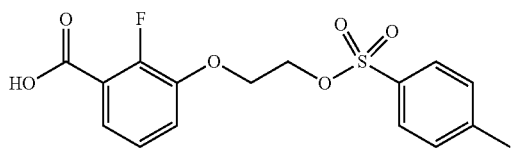 [SMILES: Cc1ccc(S(=O)(=O)OCCOc2cccc(C(=O)O)c2F)cc1]

The title compound was prepared in a manner analogous to Intermediate 12, using methyl 2-fluoro-3-hydroxybenzoate in place of methyl 2-chloro-3-hydroxybenzoate, ethane-1,2-diyl bis(4-methylbenzenesulfonate) in place of 1-fluoro-2-iodoethane, and NaOH in place of LiOH. MS (ESI): mass calcd. for $C_{16}H_{15}FO_6S$, 354.1; m/z found, 376.9 [M–H+Na]$^+$.

Intermediate 129: 2-chloro-3-(2-((Tetrahydro-2H-pyran-2-yl)oxy)ethoxy)benzoic

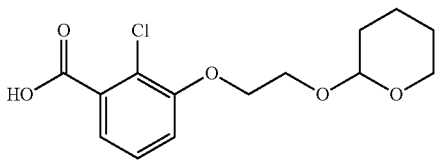 [SMILES: O=C(O)c1cccc(OCCOC2CCCCO2)c1Cl]

The title compound was prepared in a manner analogous to Intermediate 12, using 2-(2-bromoethoxy)tetrahydro-2H-pyran in place of 1-fluoro-2-iodoethane.

Intermediate 130: 3-Fluoro-5-(2-(tosyloxy)ethoxy)benzoic acid

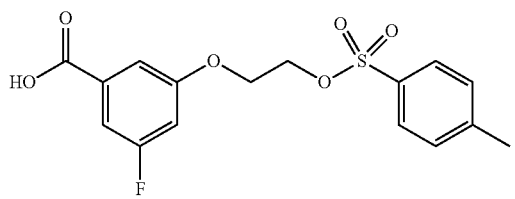 [SMILES: Cc1ccc(S(=O)(=O)OCCOc2cc(F)cc(C(=O)O)c2)cc1]

The title compound was prepared in a manner analogous to Intermediate 12, using methyl 3-fluoro-5-hydroxybenzoate in place of methyl 2-chloro-3-hydroxybenzoate, ethane-1,2-diyl bis(4-methylbenzenesulfonate) in place of 1-fluoro-2-iodoethane, and NaOH in place of LiOH. MS (ESI): mass calcd. for $C_{16}H_{15}FO_6S$, 354.1; m/z found, 354.9 [M+H]$^+$.

Intermediate 131: (S)-2-(4-(3-(3,5-Difluorophenyl)-2,7-dimethyl-4,5,6,7-tetrahydro-2H-pyrazolo[3,4-c]pyridine-6-carbonyl)-1H-pyrrolo[2,3-b]pyridin-1-yl)ethyl 4-methylbenzenesulfonate

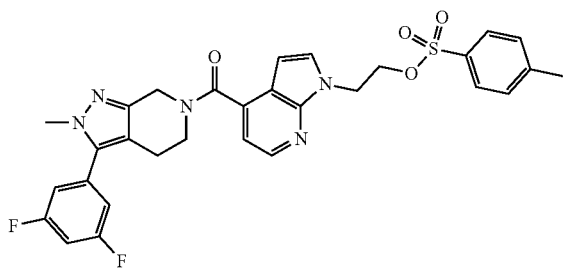 [SMILES: Cc1ccc(S(=O)(=O)OCCn2ccc3c(C(=O)N4CCc5c(nn(C)c5-c5cc(F)cc(F)c5)C4)ccnc32)cc1]

Step A: (S)-(3-(3,5-Difluorophenyl)-2,7-dimethyl-2,4,5,7-tetrahydro-6H-pyrazolo[3,4-c]pyridin-6-yl)(1H-pyrrolo[2,3-b]pyridin-4-yl)methanone. To a solution of (S)-3-(3,5-difluorophenyl)-2,7-dimethyl-4,5,6,7-tetrahydro-2H-pyrazolo[3,4-c]pyridine, Intermediate 39, (50 mg, 0.19 mmol) in dichloromethane (DCM) (1.5 mL) was added HATU (144 mg, 0.38 mmol), followed by DIPEA (0.1 mL, 0.66 mmol) and 1H-pyrrolo[2,3-b]pyridine-4-carboxylic acid (62 mg, 0.38 mmol), and the mixture was stirred at room temperature for 1 h. The reaction mixture was diluted with water and the aqueous layer extracted with DCM (×2). The combined organics were washed with brine, dried over $Na_2SO_4$, filtered, and concentrated in vacuo. The crude residue was purified by flash column chromatography (SiO$_2$; 0-15% MeOH in DCM) to afford the title compound (76 mg, 99% yield). MS (ESI): mass calcd. for $C_{22}H_{19}F_2N_5O$, 407.2; m/z found, 408.2 [M+H]$^+$.

Step B: (S)-2-(4-(3-(3,5-Difluorophenyl)-2,7-dimethyl-4,5,6,7-tetrahydro-2H-pyrazolo[3,4-c]pyridine-6-carbonyl)-1H-pyrrolo[2,3-b]pyridin-1-yl)ethyl 4-methylbenzenesulfonate. A solution of (S)-(3-(3,5-difluorophenyl)-2,7-dimethyl-2,4,5,7-tetrahydro-6H-pyrazolo[3,4-c]pyridin-6-yl)(1H-pyrrolo[2,3-b]pyridin-4-yl)methanone (140 mg, 0.34 mmol), ethane-1,2-diyl bis(4-methylbenzenesulfonate) (255 mg, 0.69 mmol) and cesium carbonate (230 mg, 0.70 mmol) in DMF (2.7 mL) was stirred at rt for 30 minutes. The reaction mixture was diluted with saturated aq. NaHCO$_3$ and extracted with EtOAc (×3). The combined organic layers were concentrated under reduced pressure and purified by flash column chromatography (SiO$_2$, 0-5% MeOH in DCM) to afford the title compound. MS (ESI): mass calcd. for $C_{31}H_{29}F_2N_5O_4S$, 605.2; m/z found, 606.0 [M+H]$^+$.

Example 1: (2-Methyl-3-phenyl-2,4,5,7-tetrahydro-6H-pyrazolo[3,4-c]pyridin-6-yl)(naphthalen-1-yl)methanone

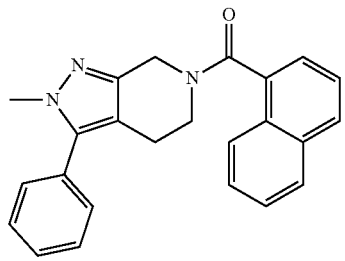 [SMILES: Cn1nc2c(c1-c1ccccc1)CCN(C(=O)c1cccc3ccccc13)C2]

To a solution of 2-methyl-3-phenyl-4,5,6,7-tetrahydro-2H-pyrazolo[3,4-c]pyridine, Intermediate 1, (150 mg, 0.7 mmol) in dichloromethane (DCM) (5.0 mL) was added HATU (348 mg, 0.91 mmol), followed by DIPEA (0.6 mL, 3.5 mmol) and 1-naphthoic acid (222 mg, 1.3 mmol), and the mixture stirred at room temperature for 1 h. The reaction mixture was diluted with water and the aqueous layer extracted with DCM (×2). The combined organics were washed with brine, dried over Na$_2$SO$_4$, filtered, and concentrated in vacuo. The crude residue was purified by reverse-phase HPLC (Method A) to afford the title compound as a white solid (94 mg, 36% yield). MS (ESI): mass calcd. for $C_{24}H_{21}N_3O$, 367.1; m/z found, 368.1 [M+H]$^+$. $^1$H NMR (400 MHz, Methanol-d$_4$) δ 8.12-7.93 (m, 2H), 7.89-7.74 (m, 1H), 7.67-7.35 (m, 9H), 5.20-4.92 (m, 2H), 4.46-4.22 (m, 1H), 4.13-3.98 (m, 0.3H), 3.76 (d, J=54.9 Hz, 3H), 3.52-3.41 (m, 1H), 2.93-2.75 (m, 0.7H), 2.57-2.30 (m, 1H).

Example 2: (3-Cyclopropyl-2-methyl-2,4,5,7-tetrahydro-6H-pyrazolo[3,4-c]pyridin-6-yl)(2,3-dichlorophenyl)methanone

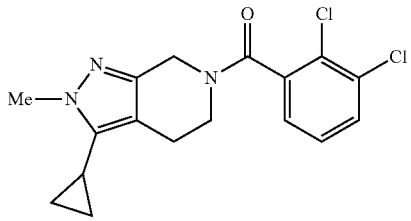 [SMILES: Cn1nc2c(c1C1CC1)CCN(C(=O)c1cccc(Cl)c1Cl)C2]

The title compound was prepared in a manner analogous to Example 1, using 3-cyclopropyl-2-methyl-4,5,6,7-tetrahydro-2H-pyrazolo[3,4-c]pyridine (Intermediate 2) and 2,3-dichlorobenzoic acid instead of 1-naphthoic acid. MS (ESI): mass calcd. for $C_{17}H_{17}Cl_2N_3O$, 349.0; m/z found, 350.0 [M+H]$^+$. $^1$H NMR (500 MHz, DMSO-d$_6$) δ 7.82-7.69 (m, 1H), 7.52-7.24 (m, 2H), 4.64 (dd, J=116.8, 16.1 Hz, 2H), 4.13 (s, 0.5H), 3.91-3.82 (m, 0.5H), 3.74 (d, J=31.1 Hz, 3H), 3.33-3.27 (m, 1H), 2.64-2.57 (m, 1H), 2.45 (t, J=5.8 Hz, 1H), 1.74 (td, J=8.4, 4.3 Hz, 1H), 0.97-0.85 (m, 2H), 0.69-0.56 (m, 2H).

Example 3: (3-Cyclopropyl-2-methyl-2,4,5,7-tetrahydro-6H-pyrazolo[3,4-c]pyridin-6-yl)(naphthalen-1-yl)methanone

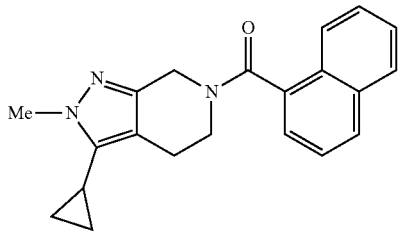 [SMILES: Cn1nc2c(c1C1CC1)CCN(C(=O)c1cccc3ccccc13)C2]

The title compound was prepared in a manner analogous to Example 1, using 3-cyclopropyl-2-methyl-4,5,6,7-tetrahydro-2H-pyrazolo[3,4-c]pyridine (Intermediate 2) instead of 3-(phenyl)-2-methyl-4,5,6,7-tetrahydro-2H-pyrazolo[3,4-c]pyridine (Intermediate 1). MS (ESI): mass calcd. for $C_{21}H_{21}N_3O$, 331.1; m/z found, 332.1 [M+H]$^+$. $^1$H NMR (400 MHz, Methanol-d$_4$) δ 8.06-7.91 (m, 2H), 7.87-7.66 (m, 1H), 7.63-7.40 (m, 4H), 5.06-4.90 (m, 1H), 4.41-3.94 (m, 2H), 3.82 (d, J=54.2 Hz, 3H), 3.46-3.38 (m, 1H), 2.91-2.76 (m, 1H), 2.56-2.33 (m, 1H), 1.82-1.69 (m, 1H), 1.09-0.91 (m, 2H), 0.84-0.60 (m, 2H).

Example 4: (2-Fluoro-3-(trifluoromethoxy)phenyl)(2-methyl-3-phenyl-2,4,5,7-tetrahydro-6H-pyrazolo[3,4-c]pyridin-6-yl)methanone

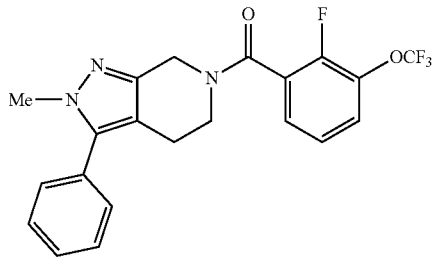 [SMILES: Cn1nc2c(c1-c1ccccc1)CCN(C(=O)c1cccc(OC(F)(F)F)c1F)C2]

The title compound was prepared in a manner analogous to Example 1, using 2-fluoro-3-(trifluoromethoxy) benzoic acid instead of 1-naphthoic acid. MS (ESI): mass calcd. for $C_{21}H_{17}F_4N_3O_2$, 419.1; m/z found, 420.1 [M+H]$^+$. $^1$H NMR (400 MHz, DMSO-d$_6$) δ 7.79-7.62 (m, 1H), 7.62-7.37 (m, 7H), 4.77 (s, 1H), 4.38 (s, 1H), 3.97-3.86 (m, 1H), 3.81-3.69 (m, 3H), 3.45 (t, J=5.8 Hz, 1H), 2.63 (t, J=5.8 Hz, 1H), 2.55-2.52 (m, 1H).

Example 5: (2-Methoxy-6-(trifluoromethyl)phenyl)(2-methyl-3-phenyl-2,4,5,7-tetrahydro-6H-pyrazolo[3,4-c]pyridin-6-yl)methanone

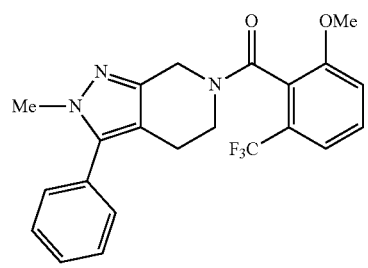 [SMILES: COc1cccc(C(F)(F)F)c1C(=O)N1CCc2c(nn(C)c2-c2ccccc2)C1]

The title compound was prepared in a manner analogous to Example 1, using 2-methoxy-6-trifluoromethylbenzoic acid instead of 1-naphthoic acid, triethylamine instead of DIPEA, and ethyl acetate instead of DCM. MS (ESI): mass calcd. for $C_{22}H_{20}F_3N_3O_2$, 415.2; m/z found, 416.3 [M+H]$^+$. $^1$H NMR (500 MHz, DMSO-d$_6$) δ 7.66-7.60 (m, 1H), 7.55-7.48 (m, 2H), 7.48-7.40 (m, 4H), 7.40-7.34 (m, 1H), 4.86 (d, J=16.3 Hz, 1H), 4.56 (d, J=16.3 Hz, 1H), 3.85 (s, 3H), 3.78 (s, 3H), 3.38-3.30 (m, 2H), 2.51-2.34 (m, 2H).

Example 6: (3-Methoxy-5-(trifluoromethyl)phenyl)(2-methyl-3-phenyl-2,4,5,7-tetrahydro-6H-pyrazolo[3,4-c]pyridin-6-yl)methanone

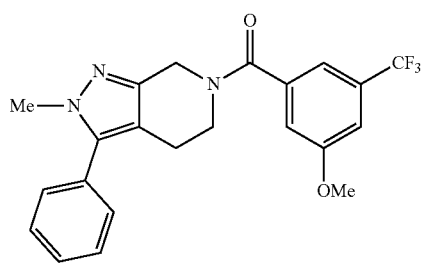 [SMILES: COc1cc(C(=O)N2CCc3c(nn(C)c3-c3ccccc3)C2)cc(C(F)(F)F)c1]

The title compound was prepared in a manner analogous to Example 1, using 3-methoxy-5-trifluoromethylbenzoic acid instead of 1-naphthoic acid, triethylamine instead of DIPEA, and ethyl acetate instead of DCM. MS (ESI): mass calcd. for $C_{22}H_{20}F_3N_3O_2$, 415.2; m/z found, 416.2 [M+H]$^+$. $^1$H NMR (500 MHz, DMSO-d$_6$) δ 7.56-7.49 (m, 2H), 7.49-7.41 (m, 3H), 7.39-7.28 (m, 3H), 4.72 (s, 2H), 3.88 (s, 3H), 3.79 (s, 3H), 3.55-3.41 (m, 2H), 2.61-2.53 (m, 2H).

Example 7: (2-Methoxy-3-methylphenyl)(2-methyl-3-phenyl-2,4,5,7-tetrahydro-6H-pyrazolo[3,4-c]pyridin-6-yl)methanone

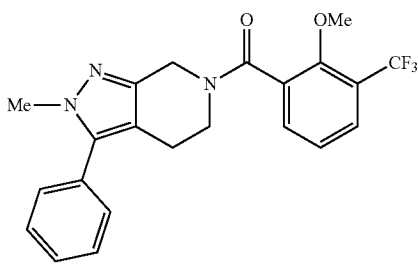 [SMILES: COc1c(C(=O)N2CCc3c(nn(C)c3-c3ccccc3)C2)cccc1C(F)(F)F]

The title compound was prepared in a manner analogous to Example 1, using 2-methoxy-3-methylbenzoic acid instead of 1-naphthoic acid, triethylamine instead of DIPEA, and ethyl acetate instead of DCM. MS (ESI): mass calcd. for $C_{22}H_{23}N_3O_2$, 361.2; m/z found, 362.2 [M+H]$^+$. $^1$H NMR (300 MHz, DMSO-d$_6$) δ 7.58-7.35 (m, 5H), 7.31-7.19 (m, 1H), 7.06-6.95 (m, 1H), 6.81 (d, J=7.5 Hz, 1H), 4.90 (d, J=16.2 Hz, 1H), 4.61 (d, J=16.2 Hz, 1H), 3.81 (s, 3H), 3.78 (s, 3H), 3.46-3.21 (m, 2H), 2.57-2.29 (m, 2H), 2.05 (s, 3H).

Example 8: (2-Ethyl-3-methoxyphenyl)(2-methyl-3-phenyl-2,4,5,7-tetrahydro-6H-pyrazolo[3,4-c]pyridin-6-yl)methanone

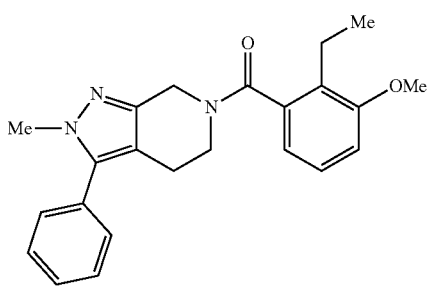 [SMILES: CCc1c(OC)cccc1C(=O)N1CCc2c(nn(C)c2-c2ccccc2)C1]

The title compound was prepared in a manner analogous to Example 1, using 2-ethyl-3-methoxybenzoic acid instead of 1-naphthoic acid, triethylamine instead of DIPEA, and ethyl acetate instead of DCM. MS (ESI): mass calcd. for $C_{23}H_{25}N_3O_2$, 375.2; m/z found, 376.2 [M+H]$^+$. $^1$H NMR (500 MHz, DMSO-d$_6$) δ 7.55-7.40 (m, 5H), 7.26-7.22 (m, 1H), 7.03-6.99 (m, 1H), 6.80 (dd, J=7.6, 1.1 Hz, 1H), 4.95 (d, J=16.1 Hz, 1H), 4.55 (d, J=16.2 Hz, 1H), 3.82 (s, 3H), 3.78 (s, 3H), 3.41-3.34 (m, 1H), 3.33-3.24 (m, 1H), 2.69-2.52 (m, 2H), 2.42-2.28 (m, 2H), 1.05 (t, J=7.4 Hz, 3H).

Example 9: (3,4-Dimethoxyphenyl)(2-methyl-3-phenyl-2,4,5,7-tetrahydro-6H-pyrazolo[3,4-c]pyridin-6-yl)methanone

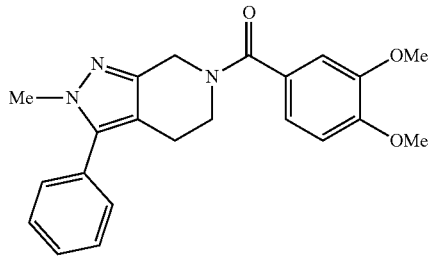 [SMILES: COc1ccc(C(=O)N2CCc3c(nn(C)c3-c3ccccc3)C2)cc1OC]

The title compound was prepared in a manner analogous to Example 1, using 3,4-dimethoxybenzoic acid instead of 1-naphthoic acid, triethylamine instead of DIPEA, and ethyl acetate instead of DCM. MS (ESI): mass calcd. for $C_{22}H_{23}N_3O_3$, 377.2; m/z found, 378.3 [M+H]$^+$. $^1$H NMR (300 MHz, DMSO-d$_6$) δ 7.59-7.39 (m, 5H), 7.09-6.96 (m, 3H), 4.62 (s, 2H), 3.80 (s, 3H), 3.78 (s, 3H), 3.75 (s, 3H), 3.74-3.46 (m, 2H), 2.67-2.54 (m, 2H).

Example 10: (2,6-Dimethoxyphenyl)(2-methyl-3-phenyl-2,4,5,7-tetrahydro-6H-pyrazolo[3,4-c]pyridin-6-yl)methanone

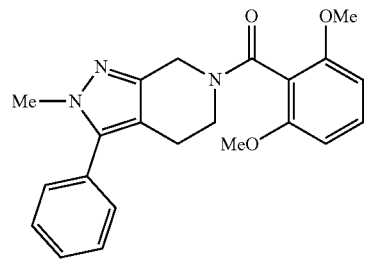 [SMILES: COc1cccc(OC)c1C(=O)N1CCc2c(nn(C)c2-c2ccccc2)C1]

The title compound was prepared in a manner analogous to Example 1, using 2,6-dimethoxybenzoic acid instead of 1-naphthoic acid, triethylamine instead of DIPEA, and ethyl acetate instead of DCM. MS (ESI): mass calcd. for $C_{22}H_{23}N_3O_3$, 377.2; m/z found, 378.2 [M+H]$^+$. $^1$H NMR (500 MHz, DMSO-d$_6$) δ 7.55-7.48 (m, 2H), 7.48-7.40 (m, 3H), 7.33 (t, J=8.4 Hz, 1H), 6.72 (d, J=8.5 Hz, 2H), 4.70 (s, 2H), 3.74 (s, 6H), 3.67 (s, 3H), 3.35-3.30 (m, 2H), 2.44-2.37 (m, 2H).

Example 11: (3,5-Dimethoxyphenyl)-(2-methyl-3-phenyl-5,7-dihydro-4H-pyrazolo[3,4-c]pyridin-6-yl)methanone

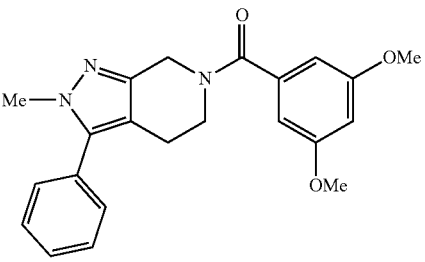 [SMILES: COc1cc(OC)cc(C(=O)N2CCc3c(nn(C)c3-c3ccccc3)C2)c1]

To a suspension of 2-methyl-3-phenyl-4,5,6,7-tetrahydro-pyrazolo[3,4-c]pyridine, Intermediate 1, (60 mg, 0.281 mmol) in ethyl acetate (1 mL) was added triethylamine (87 μL, 0.624 mmol, 0.726 g/mL) and 3,5-dimethoxybenzoyl chloride (67 mg, 0.334 mmol). The reaction mixture was stirred at room temperature for 1 h and diluted with ethyl acetate (5 mL). The organic layer was washed with water (2×3 mL), dried over magnesium sulfate, filtered and evaporated. The residue was purified by preparative HPLC to afford the title compound (38 mg, 0.101 mmol, 36%) as an off-white powder. MS (ESI): mass calcd. for $C_{22}H_{23}N_3O_3$, 377.2; m/z found, 378.2 [M+H]$^+$. $^1$H NMR (500 MHz, DMSO-d$_6$) δ 7.56-7.40 (m, 5H), 6.62-6.55 (m, 1H), 6.57-6.53 (m, 2H), 4.68 (br s, 2H), 3.77 (s, 9H), 3.54-3.43 (m, 2H), 2.63-2.53 (m, 2H).

Example 12: (2-Chloro-3-hydroxyphenyl)(2-methyl-3-phenyl-2,4,5,7-tetrahydro-6H-pyrazolo[3,4-c]pyridin-6-yl)methanone

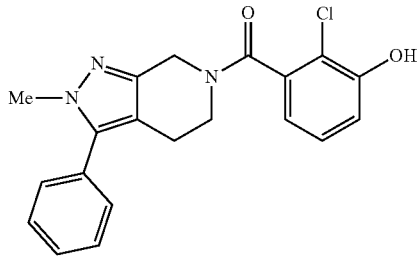

The title compound was prepared in a manner analogous to Example 1, using 2-chloro-3-hydroxybenzoic acid instead of 1-naphthoic acid, triethylamine instead of DIPEA, and ethyl acetate instead of DCM. MS (ESI): mass calcd. for $C_{20}H_{18}ClN_3O_2$, 367.1; m/z found, 368.2 [M+H]$^+$. $^1$H NMR (500 MHz, DMSO-d$_6$) δ 10.48 (br s, 1H), 7.56-7.40 (m, 5H), 7.23-7.18 (m, 1H), 7.01 (dd, J=8.1, 1.4 Hz, 1H), 6.80 (dd, J=7.5, 1.4 Hz, 1H), 4.87 (d, J=16.2 Hz, 1H), 4.61 (d, J=16.2 Hz, 1H), 3.78 (s, 3H), 3.41-3.31 (m, 2H), 2.51-2.40 (m, 2H).

Example 13: (2-Chloro-3-methoxyphenyl)(2-methyl-3-phenyl-2,4,5,7-tetrahydro-6H-pyrazolo[3,4-c]pyridin-6-yl)methanone

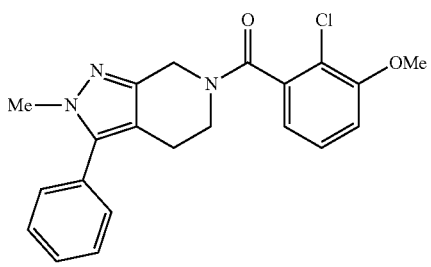 [SMILES: COc1cccc(C(=O)N2CCc3c(nn(C)c3-c3ccccc3)C2)c1Cl]

The title compound was prepared in a manner analogous to Example 1, using 2-chloro-3-methoxybenzoic acid instead of 1-naphthoic acid. MS (ESI): mass calcd. for $C_{21}H_{20}ClN_3O$, 381.1; m/z found, 382.0 [M+H]$^+$. $^1$H NMR (400 MHz, DMSO-d$_6$) δ 7.61-7.33 (m, 6H), 7.28-7.18 (m, 1H), 7.07-6.85 (m, 1H), 4.96-4.78 (m, 1H), 4.69-4.58 (m, 1H), 4.24 (s, 1H), 3.94-3.85 (m, 3H), 3.81-3.69 (m, 3H), 3.39-3.34 (m, 1H), 2.70-2.58 (m, 1H), 2.48-2.40 (m, 1H).

Example 14: (3-Chloro-2-methoxy-phenyl)-(2-methyl-3-phenyl-5,7-dihydro-4H-pyrazolo[3,4-c]pyridin-6-yl)methanone

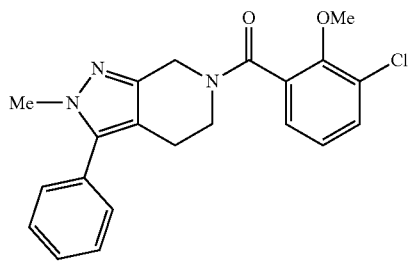 [SMILES: COc1c(Cl)cccc1C(=O)N1CCc2c(nn(C)c2-c2ccccc2)C1]

The title compound was prepared in a manner analogous to Example 1, using 3-chloro-2-methoxybenzoic acid instead of 1-naphthoic acid, triethylamine instead of DIPEA, and ethyl acetate instead of DCM. MS (ESI): mass calcd. for $C_{21}H_{20}ClN_3O_2$, 381.1; m/z found, 382.1 [M+H]$^+$. $^1$H NMR (300 MHz, DMSO-d$_6$) δ 7.63-7.38 (m, 6H), 7.34-7.17 (m, 2H), 4.91 (d, J=16.3 Hz, 1H), 4.61 (d, J=16.2 Hz, 1H), 3.78 (s, 6H), 3.45-3.28 (m, 2H), 2.66-2.37 (m, 2H).

Example 15: (2-Chloro-6-methoxyphenyl)(2-methyl-3-phenyl-2,4,5,7-tetrahydro-6H-pyrazolo[3,4-c]pyridin-6-yl)methanone

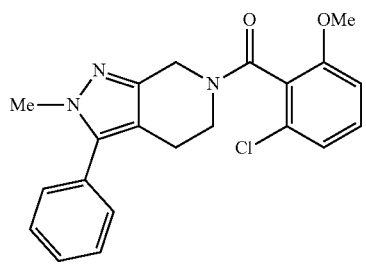 [SMILES: COc1cccc(Cl)c1C(=O)N1CCc2c(nn(C)c2-c2ccccc2)C1]

The title compound was prepared in a manner analogous to Example 1, using 2-chloro-6-methoxybenzoic acid instead of 1-naphthoic acid. MS (ESI): mass calcd. for $C_{21}H_{20}ClN_3O$, 381.1; m/z found, 382.0 [M+H]$^+$. $^1$H NMR (600 MHz, DMSO-d$_6$) δ 7.54-7.33 (m, 6H), 7.07 (d, J=8.2 Hz, 2H), 4.82-4.66 (m, 1H), 4.21 (s, 1H), 3.79 (d, J=3.3 Hz, 2H), 3.76-3.71 (m, 3H), 3.68 (s, 1H), 3.36 (t, J=5.8 Hz, 1H), 2.59 (t, J=5.8 Hz, 1H), 2.50 (t, J=5.7 Hz, 1H), 2.45 (d, J=5.9 Hz, 1H).

Example 16: (3-Chloro-5-methoxyphenyl)(2-methyl-3-phenyl-2,4,5,7-tetrahydro-6H-pyrazolo[3,4-c]pyridin-6-yl)methanone

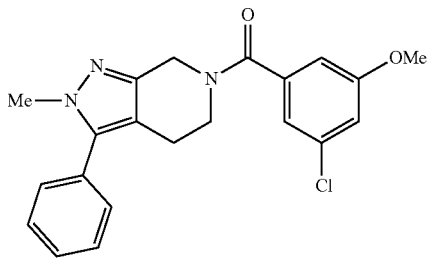 [SMILES: COc1cc(Cl)cc(C(=O)N2CCc3c(nn(C)c3-c3ccccc3)C2)c1]

The title compound was prepared in a manner analogous to Example 1, using 3-chloro-5-methoxybenzoic acid instead of 1-naphthoic acid. MS (ESI): mass calcd. for $C_{21}H_{20}ClN_3O_2$, 381.1; m/z found, 382.1 [M+H]$^+$. $^1$H NMR (600 MHz, Methanol-$d_4$) δ 7.53 (t, J=7.5 Hz, 2H), 7.49-7.42 (m, 3H), 7.08 (d, J=27.0 Hz, 2H), 6.96 (s, 1H), 4.61-4.51 (m, 1.5H), 3.98 (s, 0.73H), 3.89-3.74 (m, 6.24H), 3.63 (s, 1H), 3.37-3.33 (m, 0.53H), 2.76-2.61 (m, 2H).

Example 17: (2-Amino-3-methylphenyl)(2-methyl-3-phenyl-2,4,5,7-tetrahydro-6H-pyrazolo[3,4-c]pyridin-6-yl)methanone

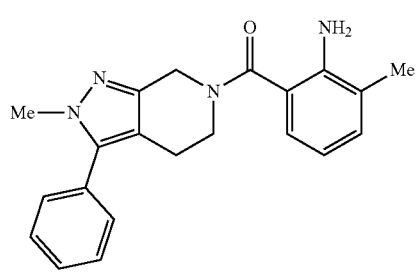 [SMILES: Cc1cccc(C(=O)N2CCc3c(nn(C)c3-c3ccccc3)C2)c1N]

The title compound was prepared in a manner analogous to Example 1, using 2-amino-3-methylbenzoic acid instead of 1-naphthoic acid, triethylamine instead of DIPEA, and ethyl acetate instead of DCM. MS (ESI): mass calcd. for $C_{21}H_{22}N_4O$, 346.2; m/z found, 347.3 [M+H]$^+$. $^1$H NMR (500 MHz, DMSO-$d_6$) δ 7.55-7.49 (m, 2H), 7.48-7.41 (m, 3H), 7.06-7.01 (m, 1H), 6.96-6.91 (m, 1H), 6.55 (t, J=7.5 Hz, 1H), 4.88 (s, 2H), 4.76-4.42 (m, 2H), 3.75 (s, 3H), 3.73-3.45 (m, 2H), 2.62-2.53 (m, 2H), 2.12 (s, 3H).

Example 18: (2-(1H-1,2,4-Triazol-1-yl)phenyl)(2-methyl-3-phenyl-2,4,5,7-tetrahydro-6H-pyrazolo[3,4-c]pyridin-6-yl)methanone

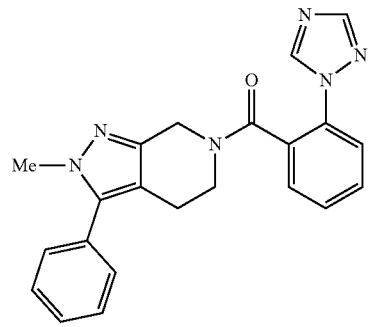 [SMILES: Cn1nc2c(c1-c1ccccc1)CCN(C(=O)c1ccccc1-n1cncn1)C2]

The title compound was prepared in a manner analogous to Example 1, using 2-(1H-1,2,4-triazol-1-yl) benzoic acid instead of 1-naphthoic acid. MS (ESI): mass calcd. for $C_{22}H_{20}N_6O$, 384.1; m/z found, 385.1 [M+H]$^+$. $^1$H NMR (400 MHz, DMSO-$d_6$) δ 8.87 (d, J=28.1 Hz, 1H), 8.11 (d, J=56.1 Hz, 1H), 7.80-7.41 (m, 9H), 4.81 (d, J=16.8 Hz, 1H), 4.35 (dd, J=45.8, 16.1 Hz, 2H), 4.05 (d, J=16.1 Hz, 1H), 3.84-3.64 (m, 3H), 2.46-2.14 (m, 2H).

Example 19: (2-Methyl-3-morpholinophenyl)(2-methyl-3-phenyl-2,4,5,7-tetrahydro-6H-pyrazolo[3,4-c]pyridin-6-yl)methanone

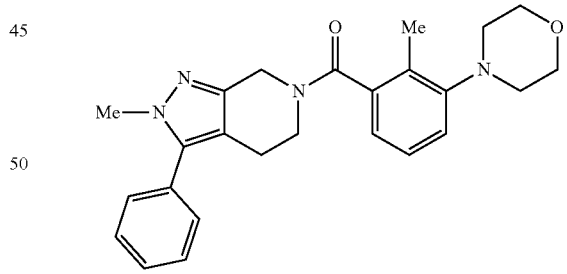

The title compound was prepared in a manner analogous to Example 1, using 2-methyl-3-morphilinobenzoic acid instead of 1-naphthoic acid, triethylamine instead of DIPEA, and ethyl acetate instead of DCM. MS (ESI): mass calcd. for $C_{25}H_{28}N_4O_2$, 416.2; m/z found, 417.3 [M+H]$^+$. $^1$H NMR (500 MHz, DMSO-$d_6$) δ 7.57-7.39 (m, 5H), 7.26-7.22 (m, 1H), 7.12-7.08 (m, 1H), 6.96-6.92 (m, 1H), 4.92 (d, J=16.1 Hz, 1H), 4.59 (d, J=16.2 Hz, 1H), 3.80-3.76 (m, 2H), 3.76-3.71 (m, 4H), 3.72-3.69 (m, 1H), 3.36-3.31 (m, 2H), 2.92-2.77 (m, 3H), 2.57-2.48 (m, 2H), 2.43-2.32 (m, 1H), 2.17 (s, 3H).

Example 20: (5-Chloro-1-methyl-1H-pyrazol-4-yl)(2-methyl-3-phenyl-2,4,5,7-tetrahydro-6H-pyrazolo[3,4-c]pyridin-6-yl)methanone

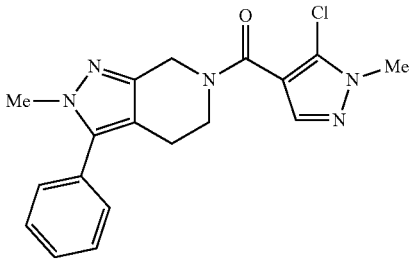

The title compound was prepared in a manner analogous to Example 1, using 5-chloro-1-methyl-1H-pyrazole-4-carboxylic acid instead of 1-naphthoic acid. MS (ESI): mass calcd. for $C_{18}H_{18}ClN_5O$, 355.1; m/z found, 356.1 [M+H]$^+$. $^1$H NMR (400 MHz, DMSO-d$_6$) δ 7.79 (s, 1H), 7.58-7.37 (m, 5H), 4.64 (s, 2H), 3.84 (s, 3H), 3.76 (s, 3H), 3.66 (s, 2H), 2.62 (s, 2H).

Example 21: (1,5-Dimethyl-1H-pyrazol-4-yl)(2-methyl-3-phenyl-2,4,5,7-tetrahydro-6H-pyrazolo[3,4-c]pyridin-6-yl)methanone

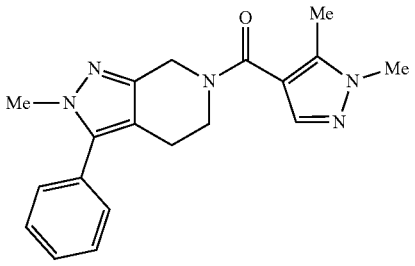 [SMILES: Cc1c(C(=O)N2CCc3c(nn(C)c3-c3ccccc3)C2)cnn1C]

The title compound was prepared in a manner analogous to Example 1, using 1,5-dimethyl-1H-pyrazole-4-carboxylic acid instead of 1-naphthoic acid. MS (ESI): mass calcd. for $C_{19}H_{21}N_5O$, 335.1; m/z found, 336.1 [M+H]$^+$. $^1$H NMR (400 MHz, DMSO-d$_6$) δ 7.60-7.39 (m, 6H), 4.64 (s, 2H), 3.75 (s, 6H), 3.71 (d, J=6.0 Hz, 2H), 2.61 (d, J=5.4 Hz, 2H), 2.32 (s, 3H).

Example 22: (5-Cyclopropyl-1-methyl-1H-pyrazol-4-yl)(2-methyl-3-phenyl-2,4,5,7-tetrahydro-6H-pyrazolo[3,4-c]pyridin-6-yl)methanone

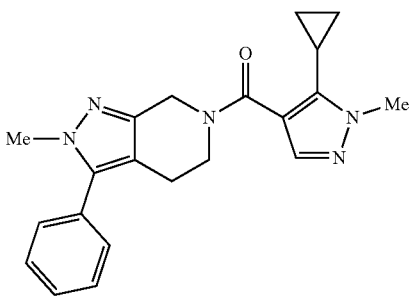 [SMILES: Cn1nc2c(c1-c1ccccc1)CCN(C(=O)c1cnn(C)c1C1CC1)C2]

The title compound was prepared in a manner analogous to Example 1, using 5-cyclopropyl-1-methyl-1H-pyrazole-4-carboxylic acid instead of 1-naphthoic acid. MS (ESI): mass calcd. for $C_{21}H_{23}N_5O$, 361.1; m/z found, 362.1 [M+H]$^+$. $^1$H NMR (400 MHz, DMSO-d$_6$) δ 7.57-7.34 (m, 6H), 4.63 (s, 2H), 3.84 (s, 3H), 3.75 (s, 3H), 3.57 (s, 2H), 2.56 (t, J=5.8 Hz, 2H), 1.98-1.81 (m, 1H), 0.89 (d, J=8.2 Hz, 2H), 0.59 (s, 2H).

Example 23: (2-Methyl-3-phenyl-2,4,5,7-tetrahydro-6H-pyrazolo[3,4-c]pyridin-6-yl)(1-phenyl-1H-1,2,4-triazol-3-yl)methanone

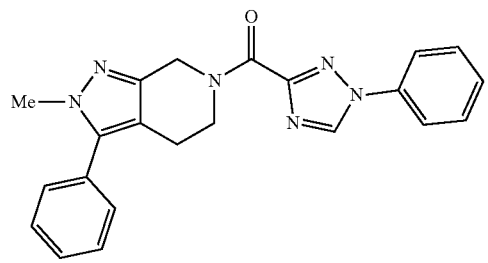 [SMILES: Cn1nc2c(c1-c1ccccc1)CCN(C(=O)c1ncn(-c3ccccc3)n1)C2]

The title compound was prepared in a manner analogous to Example 1, using 1-phenyl-1H-1,2,4-triazole-3-carboxylic acid instead of 1-naphthoic acid. MS (ESI): mass calcd. for $C_{22}H_{20}N_6O$, 384.1; m/z found, 385.1 [M+H]$^+$. $^1$H NMR (600 MHz, DMSO-d$_6$) δ 9.42 (d, J=4.3 Hz, 1H), 7.96-7.87 (m, 2H), 7.64-7.56 (m, 2H), 7.57-7.40 (m, 6H), 4.79 (d, J=16.5 Hz, 2H), 3.92 (t, J=5.8 Hz, 1H), 3.81-3.78 (m, 3H), 3.73 (s, 1H), 2.71-2.60 (m, 2H).

Example 24: (6-(Difluoromethoxy)pyridin-2-yl)(2-methyl-3-phenyl-2,4,5,7-tetrahydro-6H-pyrazolo[3,4-c]pyridin-6-yl)methanone

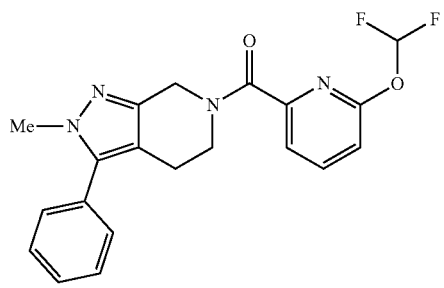 [SMILES: Cn1nc2c(c1-c1ccccc1)CCN(C(=O)c1cccc(OC(F)F)n1)C2]

The title compound was prepared in a manner analogous to Example 1, using 6-(difluoromethoxy)picolinic acid instead of 1-naphthoic acid. MS (ESI): mass calcd. for $C_{20}H_{18}F_2N_4O_2$, 384.1; m/z found, 385.1 [M+H]$^+$. $^1$H NMR (400 MHz, DMSO-d$_6$) δ 8.12-8.00 (m, 1H), 7.92-7.67 (m, 1H), 7.59-7.42 (m, 6H), 7.29-7.18 (m, 1H), 4.65 (d, J=58.2 Hz, 2H), 3.87 (t, J=5.8 Hz, 1H), 3.82-3.70 (m, 3H), 3.57 (t, J=5.7 Hz, 1H), 2.67-2.57 (m, 2H).

Example 25: (2-Methyl-3-phenyl-2,4,5,7-tetrahydro-6H-pyrazolo[3,4-c]pyridin-6-yl)(6-(trifluoromethoxy)pyridin-2-yl)methanone

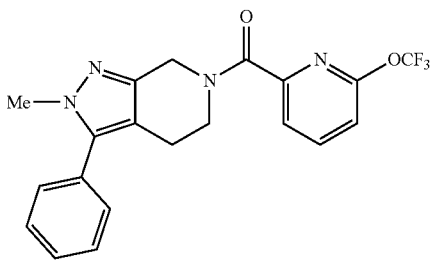 [SMILES: Cn1nc2c(c1-c1ccccc1)CCN(C(=O)c1cccc(OC(F)(F)F)n1)C2]

The title compound was prepared in a manner analogous to Example 1, using 6-(trifluoromethoxy)picolinic acid instead of 1-naphthoic acid. MS (ESI): mass calcd. for $C_{20}H_{17}F_3N_4O_2$, 402.1; m/z found, 403.0 [M+H]$^+$. $^1$H NMR (400 MHz, DMSO-d$_6$) δ 8.19 (dd, J=8.2, 7.5 Hz, 1H), 7.70 (dd, J=7.6, 0.9 Hz, 1H), 7.59-7.40 (m, 6H), 4.74 (s, 1H), 4.58 (s, 1H), 3.89 (t, J=5.8 Hz, 1H), 3.79-3.70 (m, 3H), 3.57 (t, J=5.7 Hz, 1H), 2.61 (dt, J=15.5, 5.8 Hz, 2H).

Example 26: 5-(2-Methyl-3-phenyl-4,5,6,7-tetrahydro-2H-pyrazolo[3,4-c]pyridine-6-carbonyl)-2H-benzo[b][1,4]oxazin-3(4H)-one

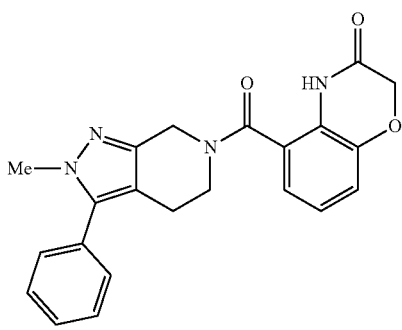 [SMILES: Cn1nc2c(c1-c1ccccc1)CCN(C(=O)c1cccc3c1NC(=O)CO3)C2]

The title compound was prepared in a manner analogous to Example 1, using 3-oxo-3,4-dihydro-2H-benzo[b][1,4]oxazine-5-carboxylic acid instead of 1-naphthoic acid. MS (ESI): mass calcd. for $C_{22}H_{20}N_4O_3$, 388.1; m/z found, 389.1 [M+H]$^+$. $^1$H NMR (500 MHz, DMSO-d$_6$) δ 10.36 (s, 1H), 7.67-7.34 (m, 5H), 7.24-6.81 (m, 3H), 4.65 (d, J=26.7 Hz, 3H), 4.41 (s, 1H), 3.95-3.64 (m, 3H), 3.42 (s, 2H), 2.66 (d, J=10.9 Hz, 1H), 2.49 (s, 1H).

Example 27: (4-Methyl-3,4-dihydro-2H-benzo[b][1,4]oxazin-7-yl)(2-methyl-3-phenyl-2,4,5,7-tetrahydro-6H-pyrazolo[3,4-c]pyridin-6-yl)methanone

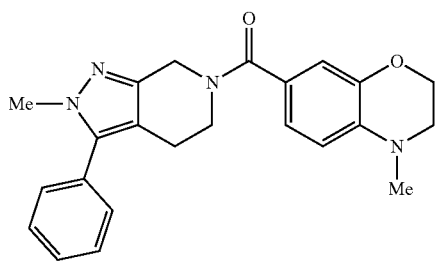 [SMILES: CN1CCOc2cc(C(=O)N3CCc4c(nn(C)c4-c4ccccc4)C3)ccc21]

The title compound was prepared in a manner analogous to Example 1, using 4-methyl-3,4-dihydro-2H-benzo[b][1,4]oxazine-7-carboxylic acid instead of 1-naphthoic acid. MS (ESI): mass calcd. for $C_{23}H_{24}N_4O_2$, 388.2; m/z found, 389.1 [M+H]$^+$. $^1$H NMR (600 MHz, DMSO-d$_6$) δ 7.57-7.39 (m, 5H), 6.94 (dt, J=8.3, 1.5 Hz, 1H), 6.83-6.66 (m, 2H), 4.59 (s, 2H), 4.28-4.21 (m, 2H), 3.75 (s, 3H), 3.65 (s, 2H), 3.30 (d, J=4.3 Hz, 2H), 2.89 (d, J=1.1 Hz, 3H), 2.59 (t, J=5.8 Hz, 2H).

Example 28: Benzo[d][1,3]dioxol-4-yl(2-methyl-3-phenyl-2,4,5,7-tetrahydro-6H-pyrazolo[3,4-c]pyridin-6-yl)methanone

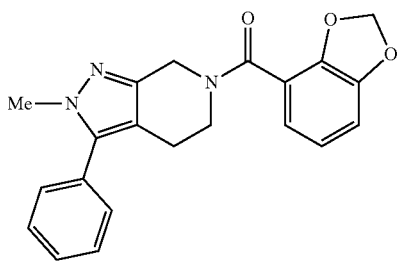 [SMILES: Cn1nc2c(c1-c1ccccc1)CCN(C(=O)c1cccc3c1OCO3)C2]

The title compound was prepared in a manner analogous to Example 1, using benzo[d][1,3]dioxole-4-carboxylic acid instead of 1-naphthoic acid, triethylamine instead of DIPEA, and ethyl acetate instead of DCM. MS (ESI): mass calcd. for $C_{21}H_{19}N_3O_3$, 361.1; m/z found, 362.2 [M+H]$^+$. $^1$H NMR (500 MHz, DMSO-d$_6$) δ 7.59-7.37 (m, 5H), 7.03-7.00 (m, 1H), 6.92 (t, J=7.7 Hz, 1H), 6.89-6.86 (m, 1H), 6.08 (s, 2H), 4.69 (s, 2H), 3.78 (s, 3H), 3.56-3.47 (m, 2H), 2.63-2.52 (m, 2H).

Example 29: Benzo[d][1,3]dioxol-5-yl(2-methyl-3-phenyl-2,4,5,7-tetrahydro-6H-pyrazolo[3,4-c]pyridin-6-yl)methanone

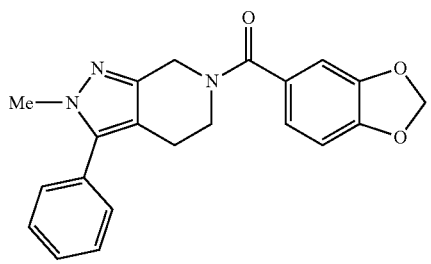 [SMILES: Cn1nc2c(c1-c1ccccc1)CCN(C(=O)c1ccc3c(c1)OCO3)C2]

The title compound was prepared in a manner analogous to Example 1, using benzo[d][1,3]dioxole-5-carboxylic acid instead of 1-naphthoic acid, triethylamine instead of DIPEA, and ethyl acetate instead of DCM. MS (ESI): mass calcd. for $C_{21}H_{19}N_3O_3$, 361.1; m/z found, 362.2 [M+H]$^+$. $^1$H NMR (300 MHz, DMSO-$d_6$) δ 7.63-7.37 (m, 5H), 7.06-7.01 (m, 1H), 7.00-6.94 (m, 2H), 6.09 (s, 2H), 4.60 (br s, 2H), 3.76 (s, 3H), 3.77-3.39 (m, 2H), 2.70-2.52 (m, 2H).

Example 30: (2,2-Difluorobenzo[d][1,3]dioxol-4-yl)(2-methyl-3-phenyl-2,4,5,7-tetrahydro-6H-pyrazolo[3,4-c]pyridin-6-yl)methanone

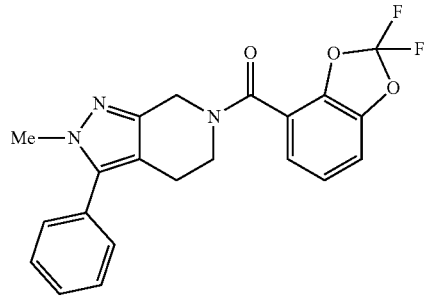 [SMILES: Cn1nc2c(c1-c1ccccc1)CCN(C(=O)c1cccc3c1OC(F)(F)O3)C2]

The title compound was prepared in a manner analogous to Example 1, using 2,2-difluorobenzo[d][1,3]dioxole-4-carboxylic acid instead of 1-naphthoic acid. MS (ESI): mass calcd. for $C_{21}H_{17}F_2N_3O_3$, 397.1; m/z found, 398.1 [M+H]$^+$. $^1$H NMR (400 MHz, DMSO-$d_6$) δ 7.58-7.40 (m, 6H), 7.36-7.23 (m, 2H), 4.79-4.47 (m, 2H), 3.89 (s, 1H), 3.75 (d, J=25.6 Hz, 3H), 3.53 (t, J=5.8 Hz, 1H), 2.70-2.54 (m, 2H).

Example 31: (2-Methyl-3-phenyl-2,4,5,7-tetrahydro-6H-pyrazolo[3,4-c]pyridin-6-yl)(4H-thieno[3,2-b]pyrrol-2-yl)methanone

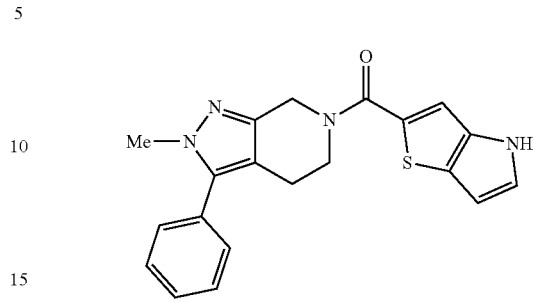

The title compound was prepared in a manner analogous to Example 1, using 4H-thieno[3,2-b]pyrrole-2-carboxylic acid instead of 1-naphthoic acid. MS (ESI): mass calcd. for $C_{20}H_{18}N_4OS$, 362.1; m/z found, 363.1 [M+H]$^+$. $^1$H NMR (400 MHz, DMSO-$d_6$) δ 11.32 (s, 1H), 7.57-7.39 (m, 6H), 7.24 (d, J=3.0 Hz, 1H), 6.41 (d, J=3.0 Hz, 1H), 4.78 (s, 2H), 3.88 (t, J=5.7 Hz, 2H), 3.76 (s, 3H), 2.68 (t, J=5.5 Hz, 2H).

Example 32: (2-Methyl-3-phenyl-2,4,5,7-tetrahydro-6H-pyrazolo[3,4-c]pyridin-6-yl)(6-methylimidazo[2,1-b]thiazol-5-yl)methanone

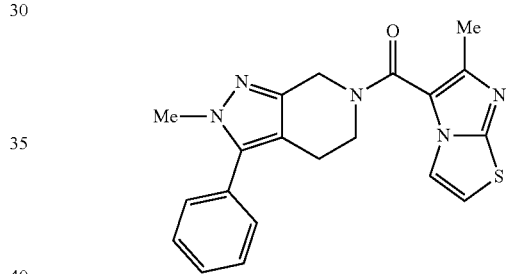

The title compound was prepared in a manner analogous to Example 1, using 6-methylimidazo[2,1-b]thiazole-5-carboxylic acid instead of 1-naphthoic acid. MS (ESI): mass calcd. for $C_{20}H_{19}N_5OS$, 377.1; m/z found, 378.1 [M+H]$^+$. $^1$H NMR (400 MHz, DMSO-$d_6$) δ 7.78 (d, J=4.4 Hz, 1H), 7.54-7.41 (m, 5H), 7.30 (d, J=4.4 Hz, 1H), 4.67 (s, 2H), 3.77 (s, 1H), 3.75 (s, 3H), 3.27 (s, 1H), 2.70-2.59 (m, 2H), 2.35 (s, 3H).

Example 33: Benzofuran-7-yl(2-methyl-3-phenyl-2,4,5,7-tetrahydro-6H-pyrazolo[3,4-c]pyridin-6-yl)methanone

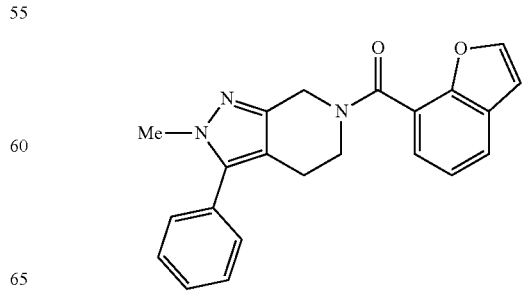

The title compound was prepared in a manner analogous to Example 1, using benzofuran-7-carboxylic acid instead of 1-naphthoic acid, triethylamine instead of DIPEA, and ethyl acetate instead of DCM. MS (ESI): mass calcd. for $C_{22}H_{19}N_3O_2$, 357.1; m/z found, 358.1 [M+H]$^+$. $^1$H NMR (500 MHz, DMSO-d$_6$) δ 8.07 (d, J=2.2 Hz, 1H), 7.80-7.75 (m, 1H), 7.56-7.40 (m, 5H), 7.39-7.30 (m, 2H), 7.07-7.03 (m, 1H), 4.81 (s, 2H), 3.79 (s, 3H), 3.48-3.36 (m, 2H), 2.58-2.44 (m, 2H).

Example 34: Benzofuran-4-yl(2-methyl-3-phenyl-2,4,5,7-tetrahydro-6H-pyrazolo[3,4-c]pyridin-6-yl)methanone

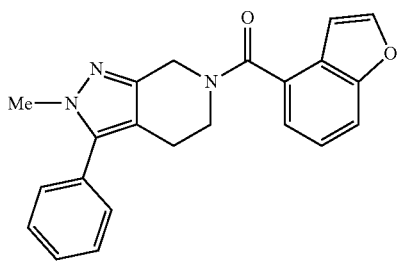

The title compound was prepared in a manner analogous to Example 1, using benzofuran-4-carboxylic acid instead of 1-naphthoic acid, triethylamine instead of DIPEA, and ethyl acetate instead of DCM. MS (ESI): mass calcd. for $C_{22}H_{19}N_3O_2$, 357.1; m/z found, 358.3 [M+H]$^+$. $^1$H NMR (500 MHz, DMSO-d$_6$) δ 8.09 (d, J=2.2 Hz, 1H), 7.77-7.67 (m, 1H), 7.58-7.38 (m, 6H), 7.36-7.30 (m, 1H), 7.01-6.84 (m, 1H), 4.89-4.71 (m, 2H), 3.78 (br s, 3H), 3.58-3.38 (m, 2H), 2.76-2.48 (m, 2H).

Example 35: Benzofuran-5-yl(2-methyl-3-phenyl-2,4,5,7-tetrahydro-6H-pyrazolo[3,4-c]pyridin-6-yl)methanone

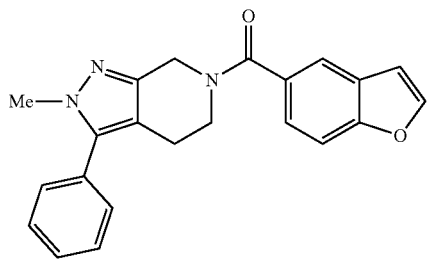 [SMILES: Cn1nc2c(c1-c1ccccc1)CCN(C(=O)c1ccc3occc3c1)C2]

The title compound was prepared in a manner analogous to Example 1, using benzofuran-5-carboxylic acid instead of 1-naphthoic acid, triethylamine instead of DIPEA, and ethyl acetate instead of DCM. MS (ESI): mass calcd. for $C_{22}H_{19}N_3O_2$, 357.1; m/z found, 358.2 [M+H]$^+$. $^1$H NMR (500 MHz, DMSO-d$_6$) δ 8.09 (d, J=2.2 Hz, 1H), 7.80-7.77 (m, 1H), 7.71-7.66 (m, 1H), 7.55-7.39 (m, 6H), 7.05-7.01 (m, 1H), 4.79-4.61 (m, 2H), 3.76 (br s, 3H), 3.64-3.42 (m, 2H), 2.69-2.55 (m, 2H).

Example 36: Benzofuran-3-yl(2-methyl-3-phenyl-2,4,5,7-tetrahydro-6H-pyrazolo[3,4-c]pyridin-6-yl)methanone

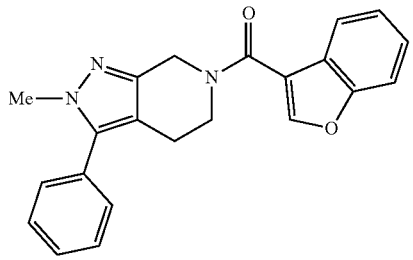 [SMILES: Cn1nc2c(c1-c1ccccc1)CCN(C(=O)c1coc3ccccc13)C2]

The title compound was prepared in a manner analogous to Example 1, using benzofuran-3-carboxylic acid instead of 1-naphthoic acid, triethylamine instead of DIPEA, and ethyl acetate instead of DCM. MS (ESI): mass calcd. for $C_{22}H_{19}N_3O_2$, 357.1; m/z found, 358.2 [M+H]$^+$. $^1$H NMR (300 MHz, DMSO-d$_6$) δ 8.44 (s, 1H), 7.77-7.71 (m, 1H), 7.72-7.65 (m, 1H), 7.59-7.30 (m, 7H), 4.76 (s, 2H), 3.93-3.59 (m, 2H), 3.76 (s, 3H), 2.72-2.58 (m, 2H).

Example 37: Benzo[b]thiophen-7-yl(2-methyl-3-phenyl-2,4,5,7-tetrahydro-6H-pyrazolo[3,4-c]pyridin-6-yl)methanone

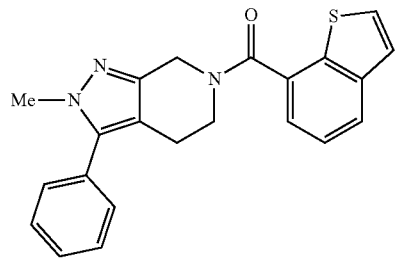 [SMILES: Cn1nc2c(c1-c1ccccc1)CCN(C(=O)c1cccc3ccsc13)C2]

The title compound was prepared in a manner analogous to Example 1, using benzo[b]thiophene-7-carboxylic acid instead of 1-naphthoic acid, triethylamine instead of DIPEA, and ethyl acetate instead of DCM. MS (ESI): mass calcd. for $C_{22}H_{19}N_3OS$, 373.1; m/z found, 374.2 [M+H]$^+$. $^1$H NMR (500 MHz, DMSO-d$_6$) δ 8.04-7.97 (m, 1H), 7.83 (d, J=5.4 Hz, 1H), 7.57-7.40 (m, 8H), 4.96-4.45 (m, 2H), 3.76 (br s, 3H), 4.00-3.38 (m, 2H), 2.71-2.55 (m, 2H).

Example 38: Benzo[b]thiophen-4-yl(2-methyl-3-phenyl-2,4,5,7-tetrahydro-6H-pyrazolo[3,4-c]pyridin-6-yl)methanone

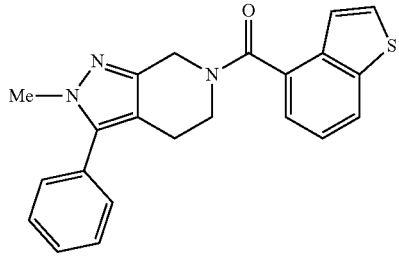

The title compound was prepared in a manner analogous to Example 1, using benzo[b]thiophene-4-carboxylic acid instead of 1-naphthoic acid, triethylamine instead of DIPEA, and ethyl acetate instead of DCM. MS (ESI): mass calcd. for $C_{22}H_{19}N_3OS$, 373.1; m/z found, 374.3 [M+H]$^+$. $^1$H NMR (300 MHz, DMSO-$d_6$) δ 8.19-8.02 (m, 1H), 7.87 (d, J=5.5 Hz, 1H), 7.60-7.23 (m, 8H), 4.84 (s, 2H), 3.80 (s, 3H), 3.49-3.30 (m, 2H), 2.81-2.46 (m, 2H).

Example 39: Benzo[b]thiophen-5-yl(2-methyl-3-phenyl-2,4,5,7-tetrahydro-6H-pyrazolo[3,4-c]pyridin-6-yl)methanone

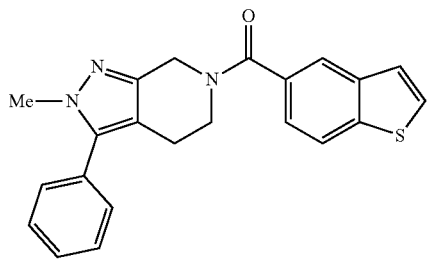 [SMILES: Cn1nc2c(c1-c1ccccc1)CCN(C(=O)c1ccc3sccc3c1)C2]

The title compound was prepared in a manner analogous to Example 1, using benzo[b]thiophene-5-carboxylic acid instead of 1-naphthoic acid, triethylamine instead of DIPEA, and ethyl acetate instead of DCM. MS (ESI): mass calcd. for $C_{22}H_{19}N_3OS$, 373.1; m/z found, 374.2 [M+H]$^+$. $^1$H NMR (500 MHz, DMSO-$d_6$) δ 8.13-8.08 (m, 1H), 8.02-7.98 (m, 1H), 7.87 (d, J=5.4 Hz, 1H), 7.56-7.53 (m, 1H), 7.53-7.47 (m, 4H), 7.47-7.41 (m, 2H), 4.84-4.62 (m, 2H), 3.77 (s, 3H), 3.64-3.43 (m, 2H), 2.67-2.54 (m, 2H).

Example 40: Benzo[b]thiophen-3-yl(2-methyl-3-phenyl-2,4,5,7-tetrahydro-6H-pyrazolo[3,4-c]pyridin-6-yl)methanone

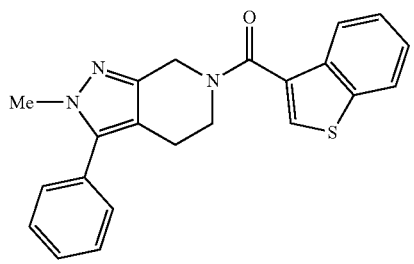 [SMILES: Cn1nc2c(c1-c1ccccc1)CCN(C(=O)c1csc3ccccc13)C2]

The title compound was prepared in a manner analogous to Example 1, using benzo[b]thiophene-3-carboxylic acid instead of 1-naphthoic acid, triethylamine instead of DIPEA, and ethyl acetate instead of DCM. MS (ESI): mass calcd. for $C_{22}H_{19}N_3O_2S$, 373.1; m/z found, 374.2 [M+H]$^+$. $^1$H NMR (300 MHz, DMSO-$d_6$) δ 8.14-8.04 (m, 1H), 8.06 (s, 1H), 7.87-7.73 (m, 1H), 7.62-7.35 (m, 7H), 4.93-4.59 (m, 2H), 3.76 (br s, 3H), 3.70-3.41 (m, 2H), 2.71-2.53 (m, 2H).

Example 41: (3-Chlorobenzo[b]thiophen-2-yl)(2-methyl-3-phenyl-2,4,5,7-tetrahydro-6H-pyrazolo[3,4-c]pyridin-6-yl)methanone

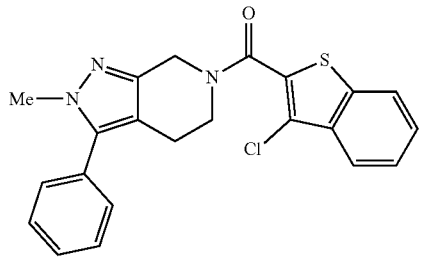 [SMILES: Cn1nc2c(c1-c1ccccc1)CCN(C(=O)c1sc3ccccc3c1Cl)C2]

The title compound was prepared in a manner analogous to Example 1, using 3-chlorobenzo[b]thiophene-2-carboxylic acid instead of 1-naphthoic acid. MS (ESI): mass calcd. for $C_{22}H_{18}ClN_3OS$, 407.0; m/z found, 408.0 [M+H]$^+$. $^1$H NMR (600 MHz, DMSO-$d_6$) δ 8.17-8.09 (m, 1H), 7.88 (d, J=7.6 Hz, 1H), 7.66-7.38 (m, 7H), 4.85-4.52 (m, 2H), 3.78 (s, 3H), 3.63 (s, 1H), 2.61 (d, J=10.5 Hz, 2H), 3.98-3.87 (m, 1H).

Example 42: (1H-Indol-4-yl)(2-methyl-3-phenyl-2,4,5,7-tetrahydro-6H-pyrazolo[3,4-c]pyridin-6-yl)methanone

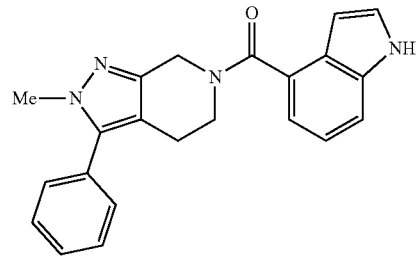 [SMILES: Cn1nc2c(c1-c1ccccc1)CCN(C(=O)c1cccc3[nH]ccc13)C2]

The title compound was prepared in a manner analogous to Example 1, using 1H-indole-4-carboxylic acid instead of 1-naphthoic acid. MS (ESI): mass calcd. for $C_{22}H_{20}N_4O$, 356.1; m/z found, 357.1 [M+H]$^+$. $^1$H NMR (400 MHz, DMSO-$d_6$) δ 11.34 (s, 1H), 7.59-7.38 (m, 8H), 7.16 (d, J=7.4 Hz, 1H), 7.04 (dd, J=7.2, 0.9 Hz, 1H), 6.36 (s, 1H), 4.79 (s, 2H), 3.99-3.64 (m, 4H), 3.44 (s, 1H), 2.67 (dd, J=3.8, 1.8 Hz, 1H).

Example 43: (1H-Indol-5-yl)(2-methyl-3-phenyl-2,4,5,7-tetrahydro-6H-pyrazolo[3,4-c]pyridin-6-yl)methanone

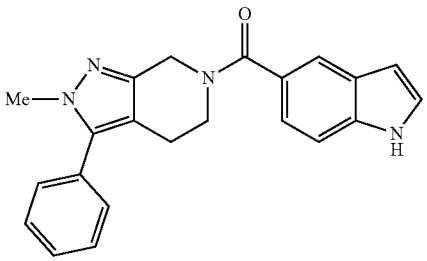

The title compound was prepared in a manner analogous to Example 1, using 1H-indole-5-carboxylic acid instead of 1-naphthoic acid, triethylamine instead of DIPEA, and ethyl acetate instead of DCM. MS (ESI): mass calcd. for $C_{22}H_{20}N_4O$, 356.2; m/z found, 357.3 [M+H]$^+$. $^1$H NMR (500 MHz, DMSO-d$_6$) δ 11.30 (br s, 1H), 7.71-7.67 (m, 1H), 7.57-7.39 (m, 7H), 7.20 (dd, J=8.3, 1.6 Hz, 1H), 6.55-6.48 (m, 1H), 4.65 (s, 2H), 3.75 (s, 3H), 3.90-3.49 (m, 2H), 2.69-2.56 (m, 2H).

Example 44: (1H-Indol-3-yl)(2-methyl-3-phenyl-2,4,5,7-tetrahydro-6H-pyrazolo[3,4-c]pyridin-6-yl)methanone

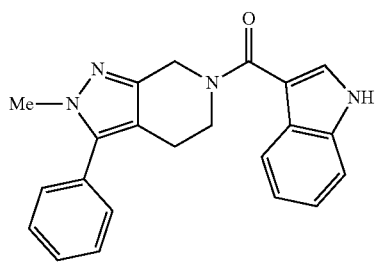 [SMILES: Cn1nc2c(c1-c1ccccc1)CCN(C(=O)c1c[nH]c3ccccc13)C2]

The title compound was prepared in a manner analogous to Example 1, using 1H-indole-3-carboxylic acid instead of 1-naphthoic acid. MS (ESI): mass calcd. for $C_{22}H_{20}N_4O$, 356.1; m/z found, 357.1 [M+H]$^+$. $^1$H NMR (500 MHz, DMSO-d$_6$) δ 11.64 (s, 1H), 7.73 (d, J=7.9 Hz, 1H), 7.58-7.42 (m, 7H), 7.23-7.06 (m, 2H), 4.75 (s, 2H), 3.83 (t, J=5.7 Hz, 2H), 3.75 (s, 3H), 2.67 (q, J=7.1, 5.7 Hz, 2H).

Example 45: (1H-Indol-7-yl)(2-methyl-3-phenyl-2,4,5,7-tetrahydro-6H-pyrazolo[3,4-c]pyridin-6-yl)methanone

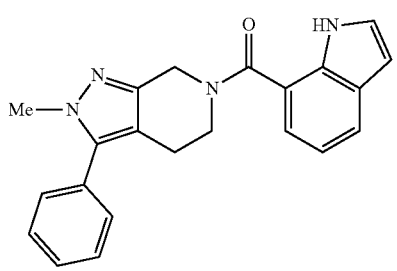

The title compound was prepared in a manner analogous to Example 1, using 1H-indole-7-carboxylic acid instead of 1-naphthoic acid, triethylamine instead of DIPEA, and DMA instead of DCM. MS (ESI): mass calcd. for $C_{22}H_{20}N_4O$, 356.2; m/z found, 357.3 [M+H]$^+$. $^1$H NMR (500 MHz, DMSO-d$_6$) δ 11.11 (br s, 1H), 7.70-7.63 (m, 1H), 7.55-7.48 (m, 2H), 7.48-7.40 (m, 3H), 7.39-7.32 (m, 1H), 7.18-7.12 (m, 1H), 7.06 (t, J=7.5 Hz, 1H), 6.54-6.49 (m, 1H), 4.93-4.40 (m, 2H), 4.09-3.40 (m, 2H), 3.75 (br s, 3H), 2.69-2.49 (m, 2H).

Example 46: (1H-Indol-6-yl)(2-methyl-3-phenyl-2,4,5,7-tetrahydro-6H-pyrazolo[3,4-c]pyridin-6-yl)methanone The title compound was prepared in a manner analogous to Example 1, using 1H-indole-6-carboxylic acid instead of 1-naphthoic acid. MS (ESI): mass calcd. for $C_{22}H_{20}N_4O$, 356.1; m/z found, 357.1 [M+H]$^+$. $^1$H NMR (600 MHz, DMSO-d$_6$) δ 11.26 (s, 1H), 7.60 (d, J=8.1 Hz, 1H), 7.57-7.40 (m, 6H), 7.10 (dd, J=8.1, 1.5 Hz, 1H), 6.59-6.43 (m, 1H), 5.75 (s, 2H), 4.65 (s, 2H), 3.75 (s, 4H), 2.62 (t, J=5.7 Hz, 2H).

Example 47: (5-Fluoro-1H-indol-4-yl)(2-methyl-3-phenyl-2,4,5,7-tetrahydro-6H-pyrazolo[3,4-c]pyridin-6-yl)methanone

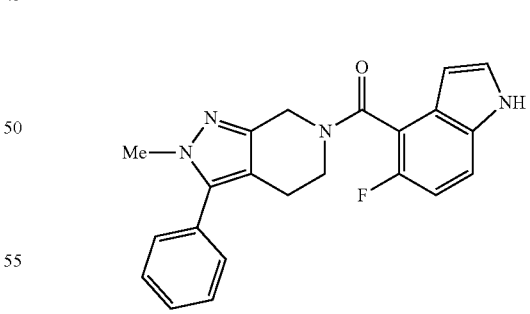

The title compound was prepared in a manner analogous to Example 1, using 5-fluoro-1H-indole-4-carboxylic acid instead of 1-naphthoic acid. MS (ESI): mass calcd. for $C_{22}H_{19}FN_4O$, 374.1; m/z found, 375.1 [M+H]$^+$. $^1$H NMR (400 MHz, DMSO-d$_6$) δ 11.41 (s, 1H), 7.59-7.37 (m, 6H), 7.07-6.95 (m, 1H), 6.34-6.20 (m, 1H), 4.94-4.75 (m, 1H), 4.34 (s, 1H), 4.19-4.06 (m, 1H), 3.85-3.66 (m, 3H), 3.50-3.39 (m, 1H), 3.17 (d, J=4.9 Hz, 1H), 2.78-2.55 (m, 1H), 2.46-2.31 (m, 1H).

Example 48: (7-Chloro-1H-indol-3-yl)(2-methyl-3-phenyl-2,4,5,7-tetrahydro-6H-pyrazolo[3,4-c]pyridin-6-yl)methanone

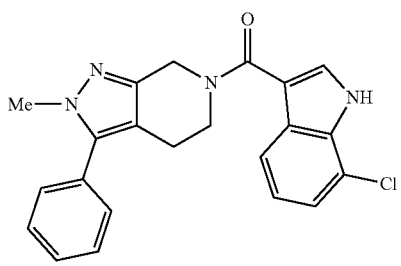 [SMILES: Cn1nc2c(c1-c1ccccc1)CCN(C(=O)c1c[nH]c3c(Cl)cccc13)C2]

The title compound was prepared in a manner analogous to Example 1, using 7-chloro-1H-indole-3-carboxylic acid instead of 1-naphthoic acid. MS (ESI): mass calcd. for $C_{22}H_{19}ClN_4O$, 390.1; m/z found, 391.0 [M+H]$^+$. $^1$H NMR (400 MHz, DMSO-d$_6$) δ 12.15-11.94 (m, 1H), 7.82 (d, J=2.4 Hz, 1H), 7.71 (dd, J=8.0, 0.9 Hz, 1H), 7.60-7.40 (m, 5H), 7.27 (dd, J=7.6, 0.9 Hz, 1H), 7.12 (t, J=7.8 Hz, 1H), 4.76 (s, 2H), 3.83 (t, J=5.7 Hz, 2H), 3.75 (s, 3H), 2.66 (t, J=5.8 Hz, 2H).

Example 49: (4-Chloro-1H-indol-3-yl)(2-methyl-3-phenyl-2,4,5,7-tetrahydro-6H-pyrazolo[3,4-c]pyridin-6-yl)methanone

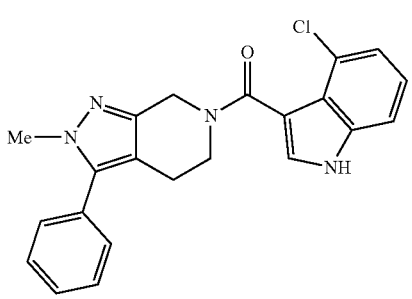 [SMILES: Cn1nc2c(c1-c1ccccc1)CCN(C(=O)c1c[nH]c3cccc(Cl)c13)C2]

The title compound was prepared in a manner analogous to Example 1, using 4-chloro-1H-indole-3-carboxylic acid instead of 1-naphthoic acid, triethylamine instead of DIPEA, and ethyl acetate instead of DCM. MS (ESI): mass calcd. for $C_{22}H_{19}ClN_4O$, 390.1; m/z found, 391.1 [M+H]$^+$. $^1$H NMR (300 MHz, DMSO-d$_6$) δ 11.76 (br s, 1H), 7.62 (s, 1H), 7.56-7.36 (m, 6H), 7.16 (t, J=7.6 Hz, 1H), 7.11 (dd, J=7.6, 1.3 Hz, 1H), 4.88-4.62 (m, 2H), 3.76 (br s, 3H), 3.59-3.37 (m, 2H), 2.68-2.44 (m, 2H).

Example 50: (7-Methyl-1H-indol-2-yl)(2-methyl-3-phenyl-2,4,5,7-tetrahydro-6H-pyrazolo[3,4-c]pyridin-6-yl)methanone

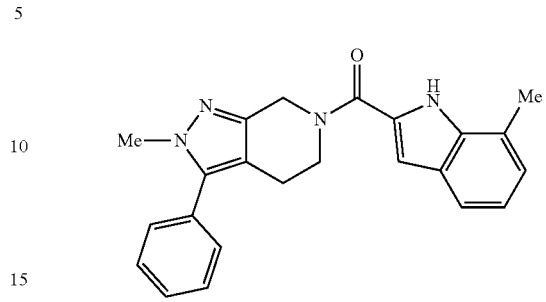

The title compound was prepared in a manner analogous to Example 1, using 7-methyl-1H-indole-2-carboxylic acid instead of 1-naphthoic acid. MS (ESI): mass calcd. for $C_{23}H_{22}N_4O$, 370.1; m/z found, 371.1 [M+H]$^+$. $^1$H NMR (600 MHz, DMSO-d$_6$) δ 11.46 (s, 1H), 7.56-7.43 (m, 6H), 7.02-6.83 (m, 3H), 4.83 (s, 2H), 3.93 (t, J=5.7 Hz, 2H), 3.77 (s, 3H), 3.33 (s, 3H), 2.70 (s, 2H).

Example 51: (1-Methyl-1H-indol-4-yl)(2-methyl-3-phenyl-2,4,5,7-tetrahydro-6H-pyrazolo[3,4-c]pyridin-6-yl)methanone

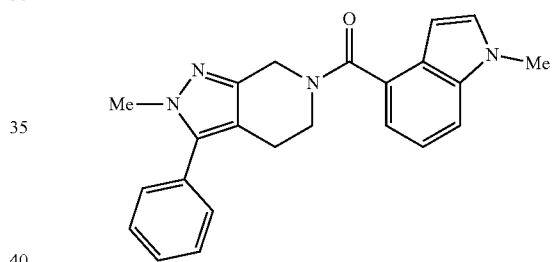

The title compound was prepared in a manner analogous to Example 1, using 1-methyl-1H-indole-4-carboxylic acid instead of 1-naphthoic acid. MS (ESI): mass calcd. for $C_{23}H_{22}N_4O$, 370.1; m/z found, 371.1 [M+H]$^+$. $^1$H NMR (400 MHz, DMSO-d$_6$) δ 7.59-7.35 (m, 7H), 7.22 (dd, J=8.2, 7.1 Hz, 1H), 7.07 (dd, J=7.2, 0.9 Hz, 1H), 6.35 (s, 1H), 4.91-4.22 (m, 2H), 3.83 (s, 3H), 3.78 (s, 3H), 3.42 (s, 1H), 2.72-2.53 (m, 2H), 2.47-2.30 (m, 1H).

Example 52: (1-Methyl-1H-indol-3-yl)(2-methyl-3-phenyl-2,4,5,7-tetrahydro-6H-pyrazolo[3,4-c]pyridin-6-yl)methanone

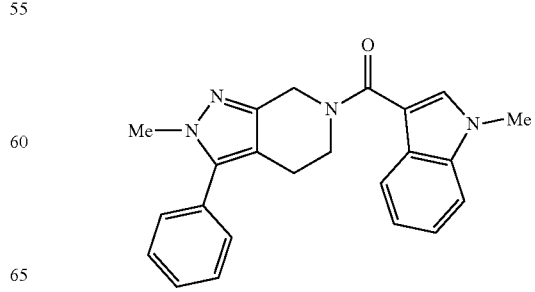

The title compound was prepared in a manner analogous to Example 1, using 1-methyl-1H-indole-3-carboxylic acid instead of 1-naphthoic acid. MS (ESI): mass calcd. for $C_{23}H_{22}N_4O$, 370.1; m/z found, 371.1 [M+H]$^+$. $^1$H NMR (600 MHz, DMSO-d$_6$) δ 7.84-7.74 (m, 2H), 7.56-7.41 (m, 6H), 7.29-7.12 (m, 2H), 4.75 (s, 2H), 3.85 (s, 3H), 3.84 (d, J=5.9 Hz, 2H), 3.75 (s, 3H), 2.67 (t, J=5.8 Hz, 2H).

Example 53: Benzo[d]isoxazol-3-yl(2-methyl-3-phenyl-2,4,5,7-tetrahydro-6H-pyrazolo[3,4-c]pyridin-6-yl)methanone

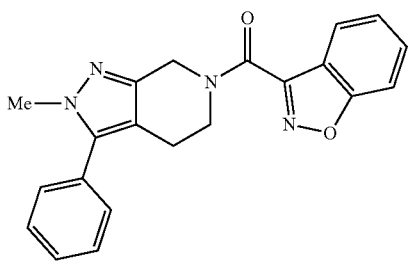 [SMILES: Cn1nc2c(c1-c1ccccc1)CCN(C(=O)c1noc3ccccc13)C2]

The title compound was prepared in a manner analogous to Example 1, using benzo[d]isoxazole-3-carboxylic acid instead of 1-naphthoic acid. MS (ESI): mass calcd. for $C_{21}H_{18}N_4O_2$, 358.1; m/z found, 359.1 [M+H]$^+$. $^1$H NMR (600 MHz, Methanol-d$_4$) δ 7.97-7.89 (m, 1H), 7.76-7.69 (m, 2H), 7.56-7.50 (m, 2H), 7.49-7.41 (m, 4H), 4.97 (d, J=4.7 Hz, 2H), 4.17-3.96 (m, 2H), 3.85-3.74 (m, 3H), 2.81-2.70 (m, 2H).

Example 54: (6-Chlorobenzo[d]isoxazol-3-yl)(2-methyl-3-phenyl-2,4,5,7-tetrahydro-6H-pyrazolo[3,4-c]pyridin-6-yl)methanone

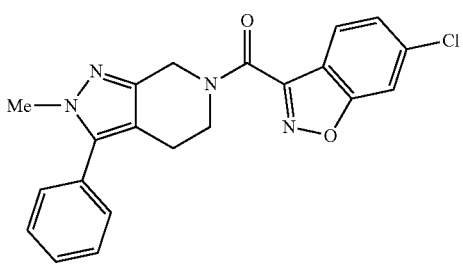 [SMILES: Cn1nc2c(c1-c1ccccc1)CCN(C(=O)c1noc3cc(Cl)ccc13)C2]

To a solution of 6-chlorobenzo[d]isoxazole-3-carboxylic acid (52 mg, 0.263 mmol) in dichloromethane (600 μL) was added N,N-dimethylformamide (10 μL, 0.13 mmol, 0.948 g/mL) and oxalyl chloride (25 μL, 0.287 mmol, 1.45 g/mL) at 0° C. The reaction mixture was stirred at 0° C. for 5 min. To the reaction mixture was added 2-methyl-3-phenyl-4,5,6,7-tetrahydropyrazolo[3,4-c]pyridine, Intermediate 1 (55 mg, 0.258 mmol) at 0° C. The reaction mixture was allowed to warm to room temperature and stirred for 18 h. The reaction mixture was diluted with water (2 mL) and extracted with ethyl acetate (2×5 mL). The combined organic layers were washed with 10% potassium bisulfate (1×5 mL), 1 M sodium carbonate (1×5 mL) and brine (1×5 mL), dried over magnesium sulfate, filtered and evaporated. The residue was purified by reverse phase HPLC to afford the title compound (14 mg, 0.036 mmol, 13%) as an off-white powder. MS (ESI): mass calcd. for $C_{21}H_{17}ClN_4O_2$, 392.1; m/z found, 393.1 [M+H]$^+$. $^1$H NMR (500 MHz, DMSO-d$_6$) δ 8.15-8.12 (m, 1H), 7.96 (d, J=8.5 Hz, 1H), 7.58-7.42 (m, 6H), 4.86 (s, 2H), 3.88-3.83 (m, 2H), 3.79 (s, 3H), 2.67-2.60 (m, 2H).

Example 55: Benzo[c]isoxazol-3-yl(2-methyl-3-phenyl-2,4,5,7-tetrahydro-6H-pyrazolo[3,4-c]pyridin-6-yl)methanone

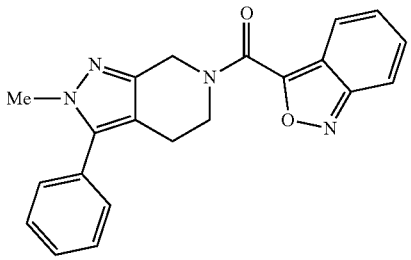 [SMILES: Cn1nc2c(c1-c1ccccc1)CCN(C(=O)c1onc3ccccc13)C2]

The title compound was prepared in a manner analogous to Example 1, using benzo[c]isoxazole-3-carboxylic acid instead of 1-naphthoic acid, triethylamine instead of DIPEA, and ethyl acetate instead of DCM. MS (ESI): mass calcd. for $C_{21}H_{18}N_4O_2$, 358.1; m/z found, 359.2 [M+H]$^+$. $^1$H NMR (500 MHz, DMSO-d$_6$) δ 7.88-7.80 (m, 1H), 7.80-7.74 (m, 1H), 7.56-7.43 (m, 6H), 7.30-7.24 (m, 1H), 4.83 (s, 2H), 3.96-3.87 (m, 2H), 3.79 (s, 3H), 2.78-2.69 (m, 2H).

Example 56: Benzo[d]oxazol-6-yl(2-methyl-3-phenyl-2,4,5,7-tetrahydro-6H-pyrazolo[3,4-c]pyridin-6-yl)methanone

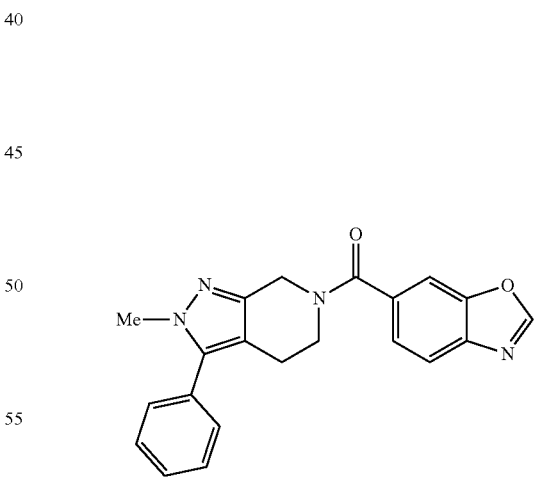

The title compound was prepared in a manner analogous to Example 1, using benzo[d]oxazole-6-carboxylic acid instead of 1-naphthoic acid, triethylamine instead of DIPEA, and ethyl acetate instead of DCM. MS (ESI): mass calcd. for $C_{21}H_{18}N_4O_2$, 358.1; m/z found, 359.1 [M+H]$^+$. $^1$H NMR (500 MHz, DMSO-d$_6$) δ 8.86 (s, 1H), 7.95-7.91 (m, 1H), 7.89 (d, J=8.1 Hz, 1H), 7.58-7.41 (m, 6H), 4.79-4.62 (m, 2H), 3.78 (br s, 3H), 3.59-3.42 (m, 2H), 2.68-2.55 (m, 2H).

Example 57: Benzo[d]oxazol-2-yl(2-methyl-3-phenyl-2,4,5,7-tetrahydro-6H-pyrazolo[3,4-c]pyridin-6-yl)methanone

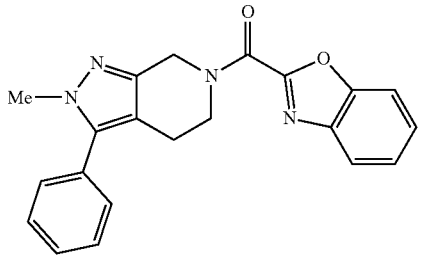 [SMILES: Cn1nc2c(c1-c1ccccc1)CCN(C(=O)c1nc3ccccc3o1)C2]

The title compound was prepared in a manner analogous to Example 1, using benzo[d]oxazole-2-carboxylic acid instead of 1-naphthoic acid, triethylamine instead of DIPEA, and ethyl acetate instead of DCM. MS (ESI): mass calcd. for $C_{21}H_{18}N_4O_2$, 358.1; m/z found, 359.1 [M+H]$^+$. $^1$H NMR (500 MHz, DMSO-d$_6$) δ 7.94-7.91 (m, 1H), 7.90-7.86 (m, 1H), 7.61-7.43 (m, 7H), 4.82 (s, 2H), 4.14-4.05 (m, 2H), 3.79 (s, 3H), 2.77-2.71 (m, 2H).

Example 58: Benzo[d]oxazol-5-yl(2-methyl-3-phenyl-2,4,5,7-tetrahydro-6H-pyrazolo[3,4-c]pyridin-6-yl)methanone

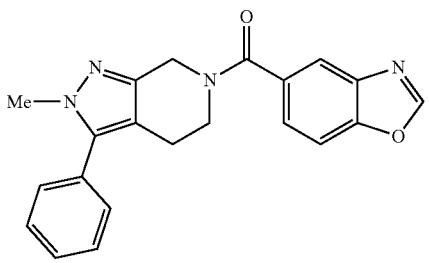

The title compound was prepared in a manner analogous to Example 1, using benzo[d]oxazole-5-carboxylic acid instead of 1-naphthoic acid, triethylamine instead of DIPEA, and ethyl acetate instead of DCM. MS (ESI): mass calcd. for $C_{21}H_{18}N_4O_2$, 358.1; m/z found, 359.1 [M+H]$^+$. $^1$H NMR (300 MHz, DMSO-d$_6$) δ 8.86 (s, 1H), 7.94-7.89 (m, 1H), 7.87 (d, J=8.4 Hz, 1H), 7.60-7.38 (m, 6H), 4.86-4.61 (m, 2H), 3.77 (br s, 3H), 3.63-3.40 (m, 2H), 2.71-2.53 (m, 2H).

Example 59: Benzo[d]thiazol-7-yl(2-methyl-3-phenyl-2,4,5,7-tetrahydro-6H-pyrazolo[3,4-c]pyridin-6-yl)methanone

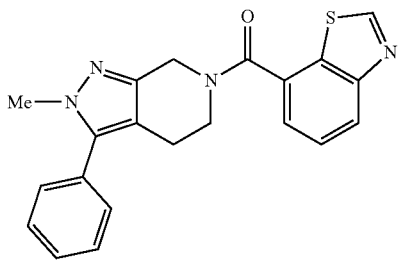 [SMILES: Cn1nc2c(c1-c1ccccc1)CCN(C(=O)c1cccc3ncsc13)C2]

The title compound was prepared in a manner analogous to Example 1, using benzo[d]thiazole-7-carboxylic acid instead of 1-naphthoic acid, triethylamine instead of DIPEA, and ethyl acetate instead of DCM. MS (ESI): mass calcd. for $C_{21}H_{18}N_4OS$, 374.1; m/z found, 375.1 [M+H]$^+$. $^1$H NMR (500 MHz, DMSO-d$_6$) δ 9.47 (s, 1H), 8.25-8.20 (m, 1H), 7.69-7.63 (m, 2H), 7.55-7.42 (m, 5H), 4.71 (br s, 2H), 3.94-3.47 (m, 2H), 3.76 (br s, 3H), 2.70-2.60 (m, 2H).

Example 60: Benzo[d]thiazol-5-yl(2-methyl-3-phenyl-2,4,5,7-tetrahydro-6H-pyrazolo[3,4-c]pyridin-6-yl)methanone

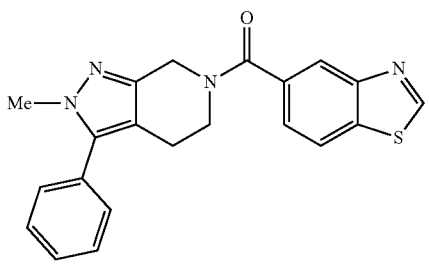

The title compound was prepared in a manner analogous to Example 1, using benzo[d]thiazole-5-carboxylic acid instead of 1-naphthoic acid, triethylamine instead of DIPEA, and ethyl acetate instead of DCM. MS (ESI): mass calcd. for $C_{21}H_{18}N_4OS$, 374.1; m/z found, 375.1 [M+H]$^+$. $^1$H NMR (500 MHz, DMSO-d$_6$) δ 9.50 (s, 1H), 8.28 (d, J=8.2 Hz, 1H), 8.16 (d, J=1.5 Hz, 1H), 7.61-7.55 (m, 1H), 7.55-7.47 (m, 4H), 7.47-7.41 (m, 1H), 4.75 (br s, 2H), 3.79 (br s, 3H), 3.63-3.44 (m, 2H), 2.68-2.55 (m, 2H).

Example 61: Benzo[d]thiazol-4-yl(2-methyl-3-phenyl-2,4,5,7-tetrahydro-6H-pyrazolo[3,4-c]pyridin-6-yl)methanone

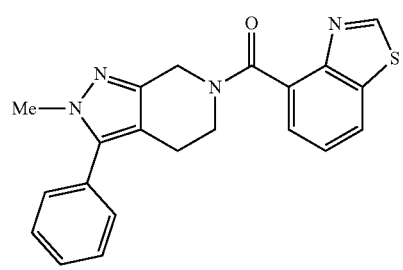

The title compound was prepared in a manner analogous to Example 1, using benzo[d]thiazole-4-carboxylic acid instead of 1-naphthoic acid, triethylamine instead of DIPEA, and ethyl acetate instead of DCM. MS (ESI): mass calcd. for $C_{21}H_{18}N_4OS$, 374.1; m/z found, 375.2 [M+H]$^+$. $^1$H NMR (500 MHz, DMSO-d$_6$) δ 9.45 (s, 1H), 8.26 (dd, J=7.8, 1.5 Hz, 1H), 7.62-7.37 (m, 7H), 4.96-4.71 (m, 2H), 3.79 (s, 3H), 3.36-3.28 (m, 2H), 2.47-2.40 (m, 2H).

Example 62: Benzo[d]thiazol-2-yl(2-methyl-3-phenyl-2,4,5,7-tetrahydro-6H-pyrazolo[3,4-c]pyridin-6-yl)methanone

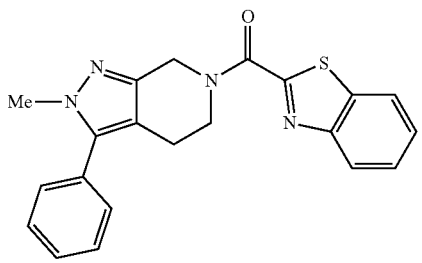 [SMILES: Cn1nc2c(c1-c1ccccc1)CCN(C(=O)c1nc3ccccc3s1)C2]

The title compound was prepared in a manner analogous to Example 1, using benzo[d]thiazole-2-carboxylic acid instead of 1-naphthoic acid, triethylamine instead of DIPEA, and ethyl acetate instead of DCM. MS (ESI): mass calcd. for $C_{21}H_{18}N_4OS$, 374.1; m/z found, 375.3 [M+H]$^+$. $^1$H NMR (300 MHz, DMSO-d$_6$) δ 8.30-8.06 (m, 2H), 7.72-7.35 (m, 7H), 4.82 (s, 2H), 4.49-4.31 (m, 2H), 3.79 (s, 3H), 2.80-2.69 (m, 2H).

Example 63: Benzo[d]isothiazol-3-yl(2-methyl-3-phenyl-2,4,5,7-tetrahydro-6H-pyrazolo[3,4-c]pyridin-6-yl)methanone

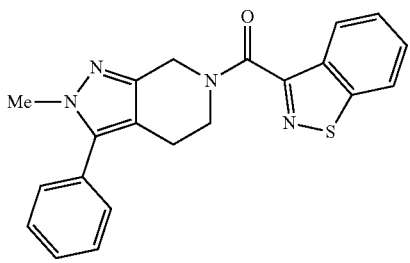

The title compound was prepared in a manner analogous to Example 1, using benzo[d]isothiazole-3-carboxylic acid instead of 1-naphthoic acid, triethylamine instead of DIPEA, and ethyl acetate instead of DCM. MS (ESI): mass calcd. for $C_{21}H_{18}N_4OS$, 374.1; m/z found, 375.2 [M+H]$^+$. $^1$H NMR (500 MHz, DMSO-d$_6$) δ 8.33-8.30 (m, 1H), 8.17-8.11 (m, 1H), 7.71-7.65 (m, 1H), 7.60-7.41 (m, 6H), 4.87 (s, 2H), 3.80 (s, 3H), 3.69-3.60 (m, 2H), 2.64-2.56 (m, 2H).

Example 64: (1H-Indazol-5-yl)(2-methyl-3-phenyl-2,4,5,7-tetrahydro-6H-pyrazolo[3,4-c]pyridin-6-yl)methanone

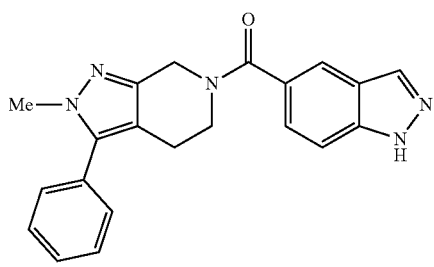 [SMILES: Cn1nc2c(c1-c1ccccc1)CCN(C(=O)c1ccc3[nH]ncc3c1)C2]

The title compound was prepared in a manner analogous to Example 1, using 1H-indazole-5-carboxylic acid instead of 1-naphthoic acid, triethylamine instead of DIPEA, and DMA instead of DCM. MS (ESI): mass calcd. for $C_{21}H_{19}N_5O$, 357.2; m/z found, 358.3 [M+H]$^+$. $^1$H NMR (300 MHz, DMSO-d$_6$) δ 13.26 (br s, 1H), 8.16 (s, 1H), 7.99-7.86 (m, 1H), 7.61 (d, J=8.6 Hz, 1H), 7.56-7.39 (m, 6H), 4.66 (s, 2H), 3.96-3.45 (m, 2H), 3.76 (s, 3H), 2.69-2.56 (m, 2H).

Example 65: (1H-Indazol-4-yl)(2-methyl-3-phenyl-2,4,5,7-tetrahydro-6H-pyrazolo[3,4-c]pyridin-6-yl)methanone

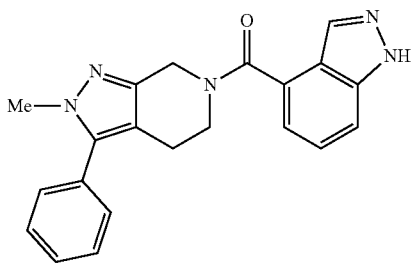 [SMILES: Cn1nc2c(c1-c1ccccc1)CCN(C(=O)c1cccc3[nH]ncc13)C2]

The title compound was prepared in a manner analogous to Example 1, using 1H-indazole-4-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.3 [M+H]$^+$. $^1$H NMR (500 MHz, DMSO-d$_6$) δ 13.31 (br s, 1H), 8.02 (br s, 1H), 7.72-7.60 (m, 1H), 7.60-7.34 (m, 6H), 7.19 (d, J=6.9 Hz, 1H), 4.94-4.65 (m, 2H), 3.84-3.70 (m, 3H), 3.61-3.39 (m, 2H), 2.75-2.48 (m, 2H).

Example 66: (1H-Indazol-3-yl)(2-methyl-3-phenyl-2,4,5,7-tetrahydro-6H-pyrazolo[3,4-c]pyridin-6-yl)methanone

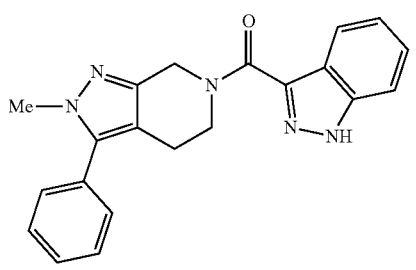 [SMILES: Cn1nc2c(c1-c1ccccc1)CCN(C(=O)c1n[nH]c3ccccc13)C2]

The title compound was prepared in a manner analogous to Example 1, using 1H-indazole-3-carboxylic acid instead of 1-naphthoic acid. MS (ESI): mass calcd. for $C_{21}H_{19}N_5O$, 357.1; m/z found, 358.1 [M+H]$^+$. $^1$H NMR (600 MHz, DMSO-d$_6$) δ 13.55 (s, 1H), 8.00 (d, J=8.2 Hz, 1H), 7.62 (d, J=8.5 Hz, 1H), 7.57-7.39 (m, 6H), 7.27-7.20 (m, 1H), 5.20 (s, 1H), 4.81 (s, 1H), 4.16 (s, 1H), 3.95 (s, 1H), 3.81-3.71 (m, 3H), 2.68 (s, 2H).

Example 67: (1H-Indazol-7-yl)(2-methyl-3-phenyl-2,4,5,7-tetrahydro-6H-pyrazolo[3,4-c]pyridin-6-yl)methanone

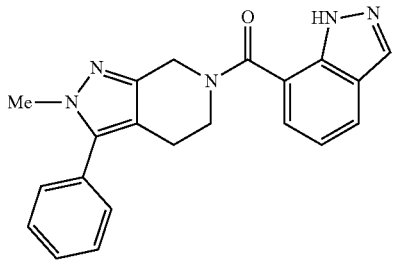 [SMILES: Cn1nc2c(c1-c1ccccc1)CCN(C(=O)c1cccc3cn[nH]c13)C2]

The title compound was prepared in a manner analogous to Example 1, using 1H-indazole-7-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.3 [M+H]$^+$. $^1$H NMR (500 MHz, DMSO-d$_6$) δ 13.25 (br s, 1H), 8.17 (s, 1H), 7.93-7.84 (m, 1H), 7.56-7.48 (m, 2H), 7.49-7.37 (m, 4H), 7.24-7.15 (m, 1H), 4.98-4.61 (m, 2H), 3.76 (s, 3H), 3.67-3.42 (m, 2H), 2.73-2.48 (m, 2H).

Example 68: (1H-Indazol-6-yl)(2-methyl-3-phenyl-2,4,5,7-tetrahydro-6H-pyrazolo[3,4-c]pyridin-6-yl)methanone

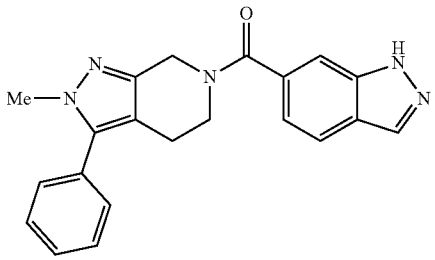 [SMILES: Cn1nc2c(c1-c1ccccc1)CCN(C(=O)c1ccc3cn[nH]c3c1)C2]

The title compound was prepared in a manner analogous to Example 1, using 1H-indazole-6-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.3 [M+H]$^+$. $^1$H NMR (500 MHz, DMSO-d$_6$) δ 13.22 (br s, 1H), 8.18-8.11 (m, 1H), 7.85 (d, J=8.2 Hz, 1H), 7.61 (s, 1H), 7.55-7.50 (m, 2H), 7.50-7.41 (m, 3H), 7.22-7.11 (m, 1H), 4.88-4.59 (m, 2H), 3.77 (br s, 3H), 3.65-3.45 (m, 2H), 2.67-2.53 (m, 2H).

Example 69: (7-Chloro-1H-indazol-3-yl)(2-methyl-3-phenyl-2,4,5,7-tetrahydro-6H-pyrazolo[3,4-c]pyridin-6-yl)methanone

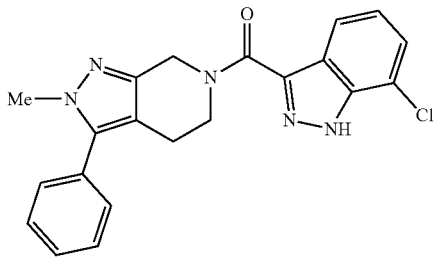 [SMILES: Cn1nc2c(c1-c1ccccc1)CCN(C(=O)c1n[nH]c3c(Cl)cccc13)C2]

The title compound was prepared in a manner analogous to Example 1, using 7-chloro-1H-indazole-3-carboxylic acid instead of 1-naphthoic acid, triethylamine instead of DIPEA, and DMA instead of DCM. MS (ESI): mass calcd. for $C_{21}H_{18}ClN_5O$, 391.1; m/z found, 392.3 [M+H]$^+$. $^1$H NMR (500 MHz, DMSO-d$_6$) δ 14.10 (s, 1H), 8.01-7.92 (m, 1H), 7.57-7.49 (m, 3H), 7.50-7.41 (m, 3H), 7.27-7.20 (m, 1H), 4.82 (s, 2H), 4.21-4.07 (m, 2H), 3.79 (s, 3H), 2.73-2.60 (m, 2H).

Example 70: (1-Methyl-1H-indazol-3-yl)(2-methyl-3-phenyl-2,4,5,7-tetrahydro-6H-pyrazolo[3,4-c]pyridin-6-yl)methanone

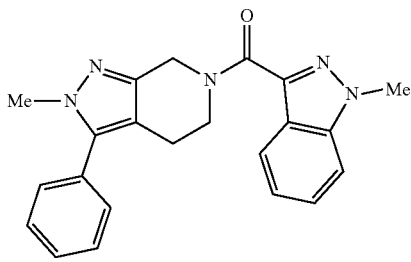 [SMILES: Cn1nc2c(c1-c1ccccc1)CCN(C(=O)c1nn(C)c3ccccc13)C2]

The title compound was prepared in a manner analogous to Example 1, using 1-methyl-1H-indazole-3-carboxylic acid instead of 1-naphthoic acid. MS (ESI): mass calcd. for $C_{22}H_{21}N_5O$, 371.1; m/z found, 372.1 [M+H]$^+$. $^1$H NMR (400 MHz, DMSO-d$_6$) δ 8.01 (d, J=8.2 Hz, 1H), 7.74 (d, J=8.5 Hz, 1H), 7.59-7.38 (m, 5H), 7.34-7.21 (m, 1H), 5.20 (s, 1H), 4.81 (s, 1H), 4.20-4.11 (m, 3H), 3.95 (s, 1H), 3.86-3.70 (m, 3H), 3.41-3.35 (m, 1H), 3.30 (s, 1H), 2.68 (s, 2H).

Example 71: (1H-Benzo[d]imidazol-5-yl)(2-methyl-3-phenyl-2,4,5,7-tetrahydro-6H-pyrazolo[3,4-c]pyridin-6-yl)methanone

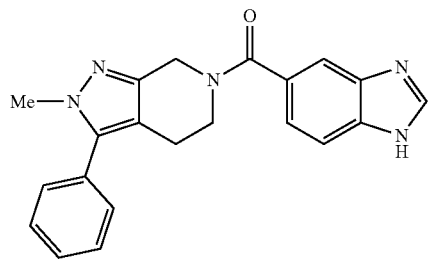

The title compound was prepared in a manner analogous to Example 1, using 1H-benzo[d]imidazole-5-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.2 [M+H]$^+$. $^1$H NMR (300 MHz, DMSO-d$_6$) δ 13.15-12.02 (m, 1H), 8.32 (s, 1H), 7.72-7.67 (m, 1H), 7.65 (d, J=8.3 Hz, 1H), 7.57-7.39 (m, 5H), 7.30 (dd, J=8.3, 1.6 Hz, 1H), 4.66 (s, 2H), 3.76 (s, 3H), 3.80-3.47 (m, 2H), 2.68-2.52 (m, 2H).

Example 72: (2-Methyl-3-phenyl-2,4,5,7-tetrahydro-6H-pyrazolo[3,4-c]pyridin-6-yl)(2-(trifluoromethyl)-1H-benzo[d]imidazol-4-yl)methanone

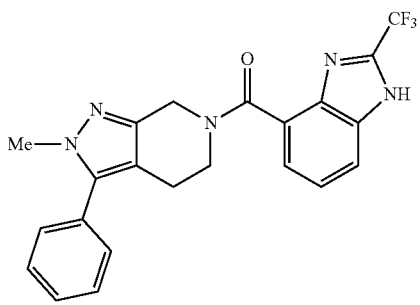 [SMILES: Cn1nc2c(c1-c1ccccc1)CCN(C(=O)c1cccc3[nH]c(C(F)(F)F)nc13)C2]

The title compound was prepared in a manner analogous to Example 1, using 2-(trifluoromethyl)-1H-benzo[d]imidazole-4-carboxylic acid instead of 1-naphthoic acid. MS (ESI): mass calcd. for $C_{22}H_{18}F_3N_5O$, 425.1; m/z found, 426.1 [M+H]$^+$. $^1$H NMR (400 MHz, DMSO-d$_6$) δ 14.18 (s, 1H), 7.79 (s, 1H), 7.61-7.20 (m, 7H), 4.82 (s, 1H), 4.36 (s, 1H), 3.97 (s, 1H), 3.86-3.59 (m, 3H), 3.40 (s, 1H), 2.74-2.62 (m, 1H), 2.49 (s, 1H).

Example 73: (2-Methyl-3-phenyl-2,4,5,7-tetrahydro-6H-pyrazolo[3,4-c]pyridin-6-yl)(pyrazolo[1,5-a]pyridin-5-yl)methanone

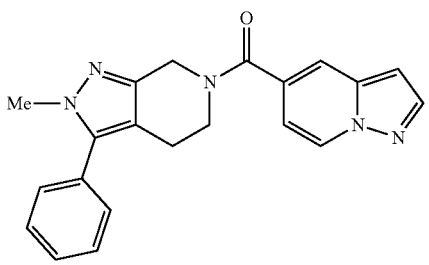 [SMILES: Cn1nc2c(c1-c1ccccc1)CCN(C(=O)c1ccn3nccc3c1)C2]

The title compound was prepared in a manner analogous to Example 1, using pyrazolo[1,5-a]pyridine-5-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.2 [M+H]$^+$. $^1$H NMR (300 MHz, DMSO-d$_6$) δ 8.75 (d, J=7.1 Hz, 1H), 8.08 (d, J=2.3 Hz, 1H), 7.92-7.81 (m, 1H), 7.60-7.37 (m, 5H), 6.93 (dd, J=7.2, 1.9 Hz, 1H), 6.78-6.70 (m, 1H), 4.89-4.44 (m, 2H), 3.77 (br s, 3H), 3.70-3.49 (m, 2H), 2.70-2.56 (m, 2H).

Example 74: (2-Methyl-3-phenyl-2,4,5,7-tetrahydro-6H-pyrazolo[3,4-c]pyridin-6-yl)(pyrazolo[1,5-a]pyridin-3-yl)methanone

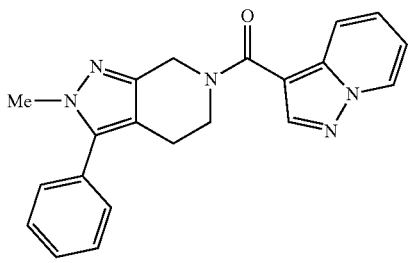 [SMILES: Cn1nc2c(c1-c1ccccc1)CCN(C(=O)c1cnn3ccccc13)C2]

The title compound was prepared in a manner analogous to Example 1, using pyrazolo[1,5-a]pyridine-3-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.2 [M+H]$^+$. $^1$H NMR (500 MHz, DMSO-d$_6$) δ 8.83-8.77 (m, 1H), 8.37 (s, 1H), 7.97-7.90 (m, 1H), 7.55-7.47 (m, 4H), 7.48-7.42 (m, 2H), 7.07 (td, J=6.9, 1.4 Hz, 1H), 4.77 (s, 2H), 3.89-3.81 (m, 2H), 3.76 (s, 3H), 2.76-2.65 (m, 2H).

Example 75: (2-Methyl-3-phenyl-2,4,5,7-tetrahydro-6H-pyrazolo[3,4-c]pyridin-6-yl)(pyrazolo[1,5-a]pyridin-7-yl)methanone

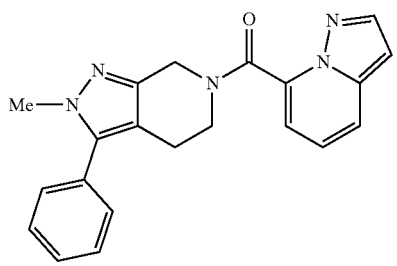 [SMILES: Cn1nc2c(c1-c1ccccc1)CCN(C(=O)c1cccc3ccnn13)C2]

The title compound was prepared in a manner analogous to Example 1, using pyrazolo[1,5-a]pyridine-7-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.3 [M+H]$^+$. $^1$H NMR (500 MHz, DMSO-d$_6$) δ 8.05 (d, J=2.3 Hz, 1H), 7.79 (dd, J=8.9, 1.3 Hz, 1H), 7.57-7.45 (m, 3H), 7.46-7.41 (m, 2H), 7.32-7.25 (m, 1H), 7.02 (dd, J=6.8, 1.3 Hz, 1H), 6.73 (d, J=2.3 Hz, 1H), 4.94 (d, J=16.2 Hz, 1H), 4.73 (d, J=16.1 Hz, 1H), 3.79 (s, 3H), 3.37-3.19 (m, 2H), 2.56-2.41 (m, 2H).

Example 76: Imidazo[1,5-a]pyridin-1-yl(2-methyl-3-phenyl-2,4,5,7-tetrahydro-6H-pyrazolo[3,4-c]pyridin-6-yl)methanone

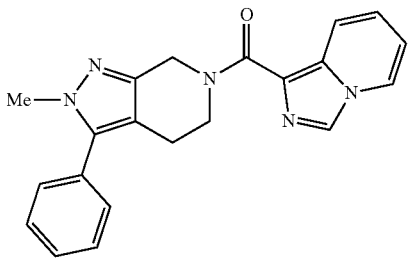 [SMILES: Cn1nc2c(c1-c1ccccc1)CCN(C(=O)c1ncn3ccccc13)C2]

The title compound was prepared in a manner analogous to Example 1, using imidazo[1,5-a]pyridine-1-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.2 [M+H]$^+$. $^1$H NMR (300 MHz, DMSO-d$_6$) δ 8.58-8.41 (m, 2H), 8.13-7.98 (m, 1H), 7.60-7.34 (m, 5H), 7.18-7.04 (m, 1H), 6.95-6.83 (m, 1H), 5.73-5.11 (m, 1H), 4.98-4.55 (m, 1H), 4.59-4.22 (m, 1H), 4.15-3.61 (m, 1H), 3.76 (s, 3H), 2.81-2.58 (m, 2H).

Example 77: Imidazo[1,5-a]pyridin-6-yl(2-methyl-3-phenyl-2,4,5,7-tetrahydro-6H-pyrazolo[3,4-c]pyridin-6-yl)methanone

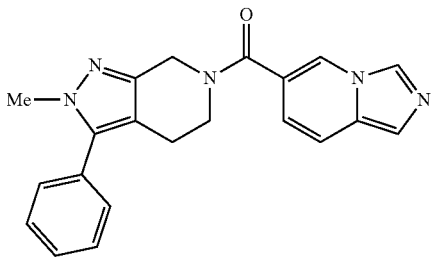 [SMILES: Cn1nc2c(c1-c1ccccc1)CCN(C(=O)c1ccc3cncn3c1)C2]

The title compound was prepared in a manner analogous to Example 1, using imidazo[1,5-a]pyridine-6-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.2 [M+H]$^+$. $^1$H NMR (300 MHz, DMSO-$d_6$) δ 8.60 (br s, 1H), 8.44 (s, 1H), 7.68-7.57 (m, 1H), 7.57-7.39 (m, 6H), 6.88-6.79 (m, 1H), 4.67 (s, 2H), 3.77 (s, 3H), 3.90-3.58 (m, 2H), 2.74-2.57 (m, 2H).

Example 78: Imidazo[1,5-a]pyridin-7-yl(2-methyl-3-phenyl-2,4,5,7-tetrahydro-6H-pyrazolo[3,4-c]pyridin-6-yl)methanone

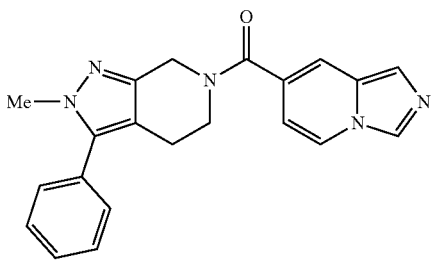 [SMILES: Cn1nc2c(c1-c1ccccc1)CCN(C(=O)c1ccn3cncc3c1)C2]

The title compound was prepared in a manner analogous to Example 1, using imidazo[1,5-a]pyridine-7-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.2 [M+H]$^+$. $^1$H NMR (500 MHz, DMSO-$d_6$) δ 8.47 (s, 1H), 8.39 (d, J=7.2 Hz, 1H), 7.74 (s, 1H), 7.58-7.38 (m, 6H), 6.75-6.68 (m, 1H), 4.66 (s, 2H), 3.76 (s, 3H), 3.75-3.51 (m, 2H), 2.70-2.57 (m, 2H).

Example 79: Imidazo[1,5-a]pyridin-5-yl(2-methyl-3-phenyl-2,4,5,7-tetrahydro-6H-pyrazolo[3,4-c]pyridin-6-yl)methanone

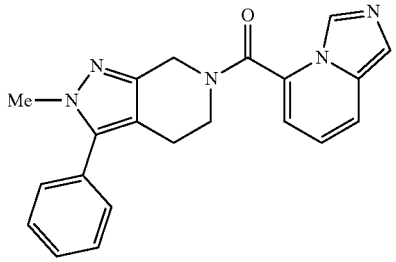 [SMILES: Cn1nc2c(c1-c1ccccc1)CCN(C(=O)c1cccc3cncn13)C2]

The title compound was prepared in a manner analogous to Example 1, using imidazo[1,5-a]pyridine-5-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.2 [M+H]$^+$. $^1$H NMR (300 MHz, DMSO-$d_6$) δ 8.29 (br s, 1H), 7.77-7.65 (m, 1H), 7.59-7.38 (m, 6H), 6.95-6.81 (m, 2H), 4.94-4.46 (m, 2H), 4.06-3.43 (m, 2H), 3.77 (s, 3H), 2.73-2.58 (m, 2H).

Example 80: Imidazo[1,2-a]pyridin-5-yl(2-methyl-3-phenyl-2,4,5,7-tetrahydro-6H-pyrazolo[3,4-c]pyridin-6-yl)methanone

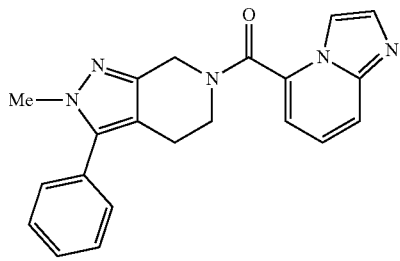 [SMILES: Cn1nc2c(c1-c1ccccc1)CCN(C(=O)c1cccc3nccn13)C2]

The title compound was prepared in a manner analogous to Example 1, using imidazo[1,2-a]pyridine-5-carboxylic acid instead of 1-naphthoic acid. MS (ESI): mass calcd. for $C_{21}H_{19}N_5O$, 357.1; m/z found, 358.1 [M+H]$^+$. $^1$H NMR (400 MHz, DMSO-$d_6$) δ 7.84 (s, 1H), 7.75-7.65 (m, 2H), 7.60-7.42 (m, 5H), 7.33 (dd, J=9.1, 6.9 Hz, 1H), 7.12 (dd, J=6.9, 1.1 Hz, 1H), 4.94-4.53 (m, 2H), 4.15-3.95 (m, 1H), 3.78 (s, 3H), 3.54 (s, 1H), 2.61 (s, 2H).

Example 81: Imidazo[1,2-a]pyridin-3-yl(2-methyl-3-phenyl-2,4,5,7-tetrahydro-6H-pyrazolo[3,4-c]pyridin-6-yl)methanone

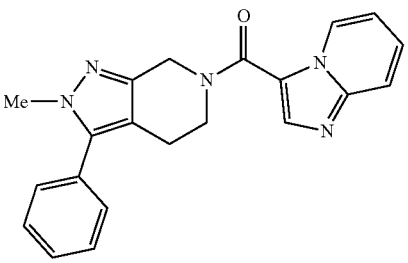 [SMILES: Cn1nc2c(c1-c1ccccc1)CCN(C(=O)c1cnc3ccccn13)C2]

The title compound was prepared in a manner analogous to Example 1, using imidazo[1,2-a]pyridine-3-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.2 [M+H]$^+$. $^1$H NMR (500 MHz, DMSO-$d_6$) δ 8.97-8.92 (m, 1H), 8.13 (s, 1H), 7.74-7.70 (m, 1H), 7.56-7.48 (m, 4H), 7.48-7.43 (m, 2H), 7.09 (td, J=6.9, 1.3 Hz, 1H), 4.84 (s, 2H), 3.98-3.88 (m, 2H), 2.80-2.69 (m, 2H).

Example 82: (5-Chloro-2-methylimidazo[1,2-a]pyridin-3-yl)(2-methyl-3-phenyl-2,4,5,7-tetrahydro-6H-pyrazolo[3,4-c]pyridin-6-yl)methanone

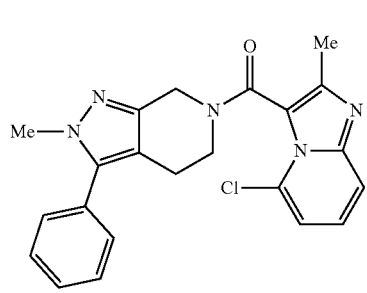 [SMILES: Cc1nc2cccc(Cl)n2c1C(=O)N1CCc2c(nn(C)c2-c2ccccc2)C1]

The title compound was prepared in a manner analogous to Example 1, using 5-chloro-2-methylimidazo[1,2-a]pyridine-3-carboxylic acid instead of 1-naphthoic acid. MS (ESI): mass calcd. for $C_{22}H_{20}ClN_5O$, 405.1; m/z found, 406.1 [M+H]$^+$. $^1$H NMR (400 MHz, DMSO-$d_6$) δ 8.60-8.52 (m, 1H), 7.68-7.59 (m, 1H), 7.58-7.38 (m, 6H), 4.71 (s, 2H), 3.80-3.72 (m, 4H), 3.18 (s, 1H), 2.71-2.60 (m, 2H), 2.43 (s, 3H).

Example 83: (2-Methyl-3-phenyl-2,4,5,7-tetrahydro-6H-pyrazolo[3,4-c]pyridin-6-yl)(1H-pyrrolo[3,2-c]pyridin-3-yl)methanone

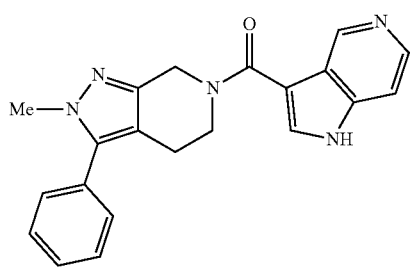 [SMILES: Cn1nc2c(c1-c1ccccc1)CCN(C(=O)c1c[nH]c3ccncc13)C2]

The title compound was prepared in a manner analogous to Example 1, using 1H-pyrrolo[3,2-c]pyridine-3-carboxylic acid instead of 1-naphthoic acid, triethylamine instead of DIPEA, and ethyl acetate instead of DCM. MS (ESI): mass calcd. for $C_{21}H_{19}N_5O$, 357.2; m/z found, 358.3 [M+H]$^+$. $^1$H NMR (500 MHz, DMSO-$d_6$) δ 12.51-11.44 (m, 1H), 9.02-8.91 (m, 1H), 8.25-8.14 (m, 1H), 7.94-7.79 (m, 1H), 7.56-7.36 (m, 6H), 4.75 (s, 2H), 3.93-3.77 (m, 2H), 3.73 (s, 3H), 2.72-2.59 (m, 2H).

Example 84: (1-Methyl-1H-pyrrolo[2,3-b]pyridin-4-yl)(2-methyl-3-phenyl-2,4,5,7-tetrahydro-6H-pyrazolo[3,4-c]pyridin-6-yl)methanone

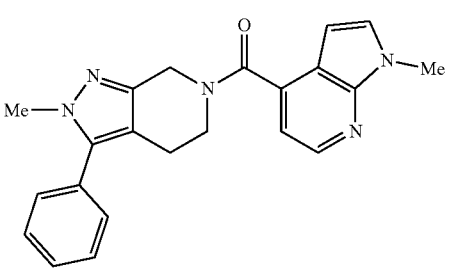 [SMILES: Cn1nc2c(c1-c1ccccc1)CCN(C(=O)c1ccnc3c1ccn3C)C2]

The title compound was prepared in a manner analogous to Example 1, using 1-methyl-1H-pyrrolo[2,3-b]pyridine-4-carboxylic acid instead of 1-naphthoic acid. MS (ESI): mass calcd. for $C_{22}H_{21}N_5O$, 371.1; m/z found, 372.1 [M+H]$^+$. $^1$H NMR (400 MHz, DMSO-$d_6$) δ 8.35 (d, J=4.7 Hz, 1H), 7.67-7.36 (m, 4H), 7.30 (t, J=7.8 Hz, 1H), 7.22-7.02 (m, 2H), 6.47-6.29 (m, 1H), 4.82 (s, 1H), 4.46 (d, J=85.4 Hz, 1H), 3.91-3.75 (m, 3H), 3.74-3.51 (m, 1H), 3.40 (d, J=5.6 Hz, 1H), 2.49-2.31 (m, 1H), 1.41 (d, J=3.8 Hz, 1H), 1.29-1.21 (m, 3H).

Example 85: [1,2,4]Triazolo[1,5-a]pyridin-5-yl(2-methyl-3-phenyl-2,4,5,7-tetrahydro-6H-pyrazolo[3,4-c]pyridin-6-yl)methanone

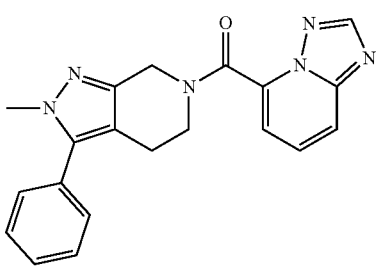 [SMILES: Cn1nc2c(c1-c1ccccc1)CCN(C(=O)c1cccc3ncnn13)C2]

The title compound was prepared in a manner analogous to Example 1, using [1,2,4]triazolo[1,5-a]pyridine-5-carboxylic acid instead of 1-naphthoic acid, triethylamine instead of DIPEA, and ethyl acetate instead of DCM. MS (ESI): mass calcd. for $C_{20}H_{18}N_6O$, 358.2; m/z found, 359.2 [M+H]$^+$. $^1$H NMR (300 MHz, DMSO-$d_6$) δ 8.56 (br s, 1H), 8.02-7.91 (m, 1H), 7.83-7.70 (m, 1H), 7.60-7.29 (m, 6H), 5.05-4.66 (m, 2H), 3.80 (s, 3H), 3.48-3.25 (m, 2H), 2.63-2.40 (m, 2H).

Example 86: (2-Methyl-3-phenyl-2,4,5,7-tetrahydro-6H-pyrazolo[3,4-c]pyridin-6-yl)(quinolin-4-yl)methanone

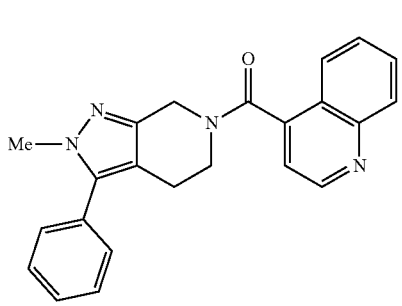 [SMILES: Cn1nc2c(c1-c1ccccc1)CCN(C(=O)c1ccnc3ccccc13)C2]

The title compound was prepared in a manner analogous to Example 1, using quinoline-4-carboxylic acid instead of 1-naphthoic acid. MS (ESI): mass calcd. for $C_{23}H_{20}N_4O$, 368.2; m/z found, 369.2 [M+H]$^+$. $^1$H NMR (600 MHz, Methanol-d$_4$) δ 8.96 (dd, J=8.6, 4.4 Hz, 1H), 8.17-8.11 (m, 1H), 7.93-7.79 (m, 2H), 7.73-7.64 (m, 1H), 7.58-7.37 (m, 6H), 5.18-4.94 (m, 1.55H), 4.43-4.21 (m, 1H), 4.04 (m, 0.35H), 3.87-3.67 (m, 3H), 3.48-3.44 (m, 1.1H), 2.91-2.37 (m, 2H).

Example 87: Isoquinolin-4-yl(2-methyl-3-phenyl-2,4,5,7-tetrahydro-6H-pyrazolo[3,4-c]pyridin-6-yl)methanone

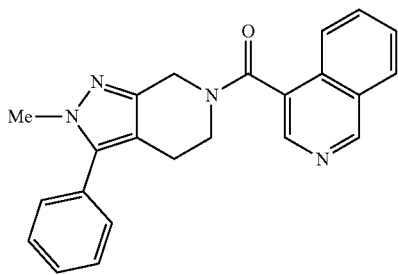 [SMILES: Cn1nc2c(c1-c1ccccc1)CCN(C(=O)c1cncc3ccccc13)C2]

The title compound was prepared in a manner analogous to Example 1, using isoquinoline-4-carboxylic acid instead of 1-naphthoic acid. MS (ESI): mass calcd. for $C_{23}H_{20}N_4O$, 368.2; m/z found, 369.2 [M+H]$^+$. $^1$H NMR (600 MHz, Methanol-d$_4$) δ 9.36 (d, J=10.0 Hz, 1H), 8.49 (d, J=19.7 Hz, 1H), 8.25-8.20 (m, 1H), 7.94-7.77 (m, 3H), 7.57-7.38 (m, 5H), 5.19-4.94 (m, 1.2H), 4.48-4.25 (m, 1.21H), 4.03 (s, 0.44H), 3.86-3.68 (m, 3H), 3.55-3.48 (m, 1.14H), 2.91-2.38 (m, 2H).

Example 88: Isoquinolin-1-yl(2-methyl-3-phenyl-2,4,5,7-tetrahydro-6H-pyrazolo[3,4-c]pyridin-6-yl)methanone

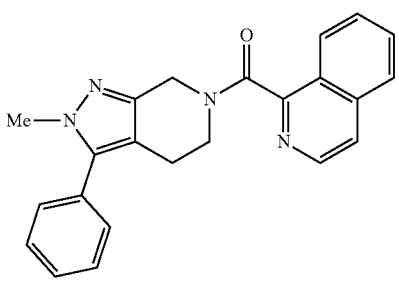 [SMILES: Cn1nc2c(c1-c1ccccc1)CCN(C(=O)c1nccc3ccccc13)C2]

The title compound was prepared in a manner analogous to Example 1, using isoquinoline-1-carboxylic acid instead of 1-naphthoic acid. MS (ESI): mass calcd. for $C_{23}H_{20}N_4O$, 368.2; m/z found, 369.2 [M+H]$^+$. $^1$H NMR (600 MHz, Methanol-d$_4$) δ 8.51 (m, 1H), 8.07-7.91 (m, 3H), 7.87-7.81 (m, 1H), 7.76-7.69 (m, 1H), 7.56-7.38 (m, 5H), 5.06 (s, 1.28H), 4.33-4.15 (m, 1.45H), 3.86-3.68 (m, 3H), 3.42 (t, J=5.8 Hz, 1.27H), 2.88-2.49 (m, 2H).

Example 89: (2-Methyl-3-phenyl-2,4,5,7-tetrahydro-6H-pyrazolo[3,4-c]pyridin-6-yl)(quinolin-5-ylmethanone

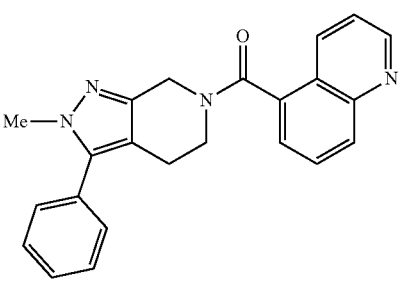 [SMILES: Cn1nc2c(c1-c1ccccc1)CCN(C(=O)c1cccc3ncccc13)C2]

The title compound was prepared in a manner analogous to Example 1, using quinoline-5-carboxylic acid instead of 1-naphthoic acid. MS (ESI): mass calcd. for $C_{23}H_{20}N_4O$, 368.2; m/z found, 369.2 [M+H]$^+$. $^1$H NMR (600 MHz, Methanol-d$_4$) δ 8.93 (td, J=4.6, 1.6 Hz, 1H), 8.37-8.25 (m, 1H), 8.19-8.14 (m, 1H), 7.87 (m, 1H), 7.71-7.38 (m, 7H), 5.22-4.91 (m, 1.54H), 4.48-3.94 (m, 1.41H), 3.76 (m, 3H), 3.48 (d, J=15.2 Hz, 1.24H), 2.93-2.30 (m, 1.81H).

Example 90: (2-Methyl-3-phenyl-2,4,5,7-tetrahydro-6H-pyrazolo[3,4-c]pyridin-6-yl)(quinolin-6-yl)methanone

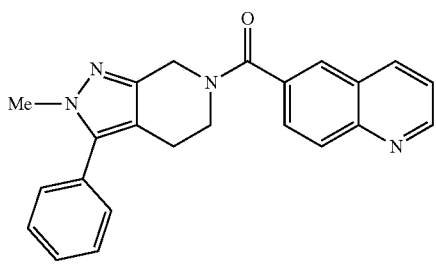 [SMILES: Cn1nc2c(c1-c1ccccc1)CCN(C(=O)c1ccc3ncccc3c1)C2]

The title compound was prepared in a manner analogous to Example 1, using quinoline-6-carboxylic acid instead of 1-naphthoic acid. MS (ESI): mass calcd. for $C_{23}H_{20}N_4O$, 368.2; m/z found, 369.2 [M+H]$^+$. $^1$H NMR (600 MHz, Methanol-d$_4$) δ 8.96 (s, 1H), 8.49 (d, J=8.3 Hz, 1H), 8.17 (d, J=8.7 Hz, 1H), 8.13 (d, J=1.8 Hz, 1H), 7.88 (d, J=8.6 Hz, 1H), 7.68-7.61 (m, 1H), 7.57-7.43 (m, 5H), 4.93 (s, 1.23H), 4.66 (s, 0.81H), 4.08 (s, 0.72H), 3.89-3.64 (m, 4.24H), 2.80-2.65 (m, 2H).

Example 91: (2-Ethyl-3-phenyl-2,4,5,7-tetrahydro-6H-pyrazolo[3,4-c]pyridin-6-yl)(quinolin-6-yl)methanone

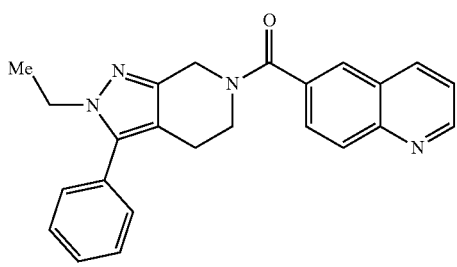 [SMILES: CCn1nc2c(c1-c1ccccc1)CCN(C(=O)c1ccc3ncccc3c1)C2]

The title compound was prepared in a manner analogous to Example 1, using 2-ethyl-3-phenyl-4,5,6,7-tetrahydro-2H-pyrazolo[3,4-c]pyridine (Intermediate 6) instead of 3-(phenyl)-2-methyl-4,5,6,7-tetrahydro-2H-pyrazolo[3,4-c]pyridine (Intermediate 1) and quinoline-6-carboxylic acid instead of 1-naphthoic acid. MS (ESI): mass calcd. for $C_{24}H_{22}N_4O$, 382.2; m/z found, 383.1 [M+H]$^+$. $^1$H NMR (600 MHz, Methanol-d$_4$) δ 8.94 (s, 1H), 8.47 (d, J=8.5 Hz, 1H), 8.19-8.10 (m, 2H), 7.89-7.84 (m, 1H), 7.66-7.58 (m, 1H), 7.57-7.36 (m, 5H), 4.93 (s, 1.2H), 4.66 (s, 0.8H), 4.21-3.99 (m, 3H), 3.67 (s, 1H), 2.76-2.60 (m, 2H), 1.41-1.21 (m, 3H).

Example 92: Isoquinolin-5-yl(2-methyl-3-phenyl-2,4,5,7-tetrahydro-6H-pyrazolo[3,4-c]pyridin-6-yl)methanone

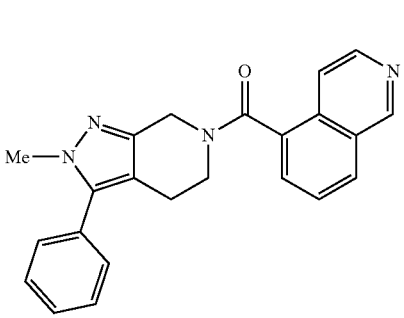 [SMILES: Cn1nc2c(c1-c1ccccc1)CCN(C(=O)c1cccc3cnccc13)C2]

The title compound was prepared in a manner analogous to Example 1, using isoquinoline-5-carboxylic acid instead of 1-naphthoic acid. MS (ESI): mass calcd. for $C_{23}H_{20}N_4O$, 368.2; m/z found, 369.2 [M+H]$^+$. $^1$H NMR (600 MHz, Methanol-d$_4$) δ 9.35 (d, J=5.8 Hz, 1H), 8.51 (dd, J=24.1, 6.0 Hz, 1H), 8.31-8.23 (m, 1H), 7.89-7.70 (m, 3H), 7.57-7.39 (m, 5H), 5.19-4.91 (m, 1.51H), 4.44-3.98 (m, 1.52H), 3.87-3.69 (m, 3H), 3.48 (s, 1.13H), 2.95-2.36 (m, 1.84H).

Example 93: (2-Methyl-3-phenyl-2,4,5,7-tetrahydro-6H-pyrazolo[3,4-c]pyridin-6-yl)(quinolin-8-ylmethanone

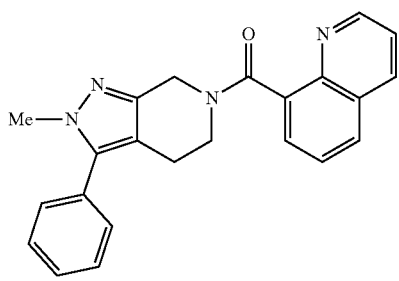 [SMILES: Cn1nc2c(c1-c1ccccc1)CCN(C(=O)c1cccc3cccnc13)C2]

The title compound was prepared in a manner analogous to Example 1, using quinoline-8-carboxylic acid instead of 1-naphthoic acid. MS (ESI): mass calcd. for $C_{23}H_{20}N_4O$, 368.2; m/z found, 369.1 [M+H]$^+$. $^1$H NMR (500 MHz, DMSO-d$_6$) δ 8.96-8.91 (m, 1H), 8.51-8.43 (m, 1H), 8.12-8.03 (m, 1H), 7.78-7.59 (m, 3H), 7.56-7.39 (m, 5H), 4.95 (d, J=16.1 Hz, 1H), 4.79 (d, J=16.1 Hz, 1H), 4.38 (dt, J=12.5, 4.8 Hz, 0.3H), 4.26-3.95 (m, 0.7H), 3.80 (s, 2H), 3.66 (s, 1H), 3.25 (t, J=5.8 Hz, 1H), 2.77-2.59 (m, 0.6H), 2.39 (q, J=5.5 Hz, 1.4H).

Example 94: (2-Methyl-3-phenyl-2,4,5,7-tetrahydro-6H-pyrazolo[3,4-c]pyridin-6-yl)(quinolin-2-yl)methanone

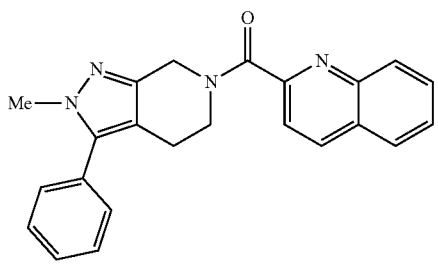 [SMILES: Cn1nc2c(c1-c1ccccc1)CCN(C(=O)c1ccc3ccccc3n1)C2]

The title compound was prepared in a manner analogous to Example 1, using quinoline-2-carboxylic acid instead of 1-naphthoic acid. MS (ESI): mass calcd. for $C_{23}H_{20}N_4O$, 368.2; m/z found, 369.2 [M+H]$^+$. $^1$H NMR (600 MHz, Methanol-$d_4$) δ 8.52-8.47 (m, 1H), 8.12-8.06 (m, 1H), 8.01 (t, J=8.9, 8.2, 1.5 Hz, 1H), 7.89-7.82 (m, 1H), 7.75-7.67 (m, 2H), 7.56-7.50 (m, 2H), 7.49-7.42 (m, 3H), 4.95 (s, 1.4H), 4.73 (s, 0.7H), 4.09 (t, J=5.9 Hz, 0.73H), 3.83 (s, 1.8H), 3.76-3.69 (m, 2.37H), 2.80-2.72 (m, 2H).

Example 95: (2-Methyl-3-phenyl-2,4,5,7-tetrahydro-6H-pyrazolo[3,4-c]pyridin-6-yl)(quinolin-3-yl)methanone

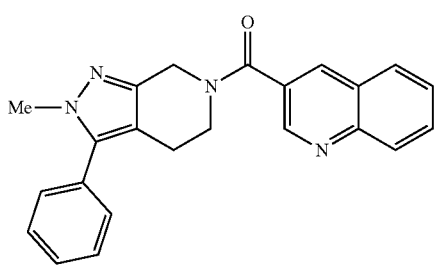 [SMILES: Cn1nc2c(c1-c1ccccc1)CCN(C(=O)c1cnc3ccccc3c1)C2]

The title compound was prepared in a manner analogous to Example 1, using quinoline-3-carboxylic acid instead of 1-naphthoic acid. MS (ESI): mass calcd. for $C_{23}H_{20}N_4O$, 368.2; m/z found, 369.2 [M+H]$^+$. $^1$H NMR (600 MHz, Methanol-$d_4$) δ 8.96 (d, J=2.1 Hz, 1H), 8.55-8.51 (m, 1H), 8.11 (d, J=8.5 Hz, 1H), 8.08-8.05 (m, 1H), 7.89 (t, J=7.7 Hz, 1H), 7.71 (t, J=7.5 Hz, 1H), 7.53 (t, J=7.5 Hz, 2H), 7.45 (t, J=5.2 Hz, 3H), 4.93 (s, 1.4H), 4.73 (s, 0.6H), 4.17-3.66 (m, 5H), 2.82-2.67 (m, 2H).

Example 96: (8-Fluoroquinolin-4-yl)(2-methyl-3-phenyl-2,4,5,7-tetrahydro-6H-pyrazolo[3,4-c]pyridin-6-yl)methanone

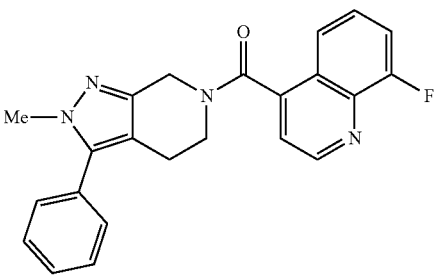 [SMILES: Cn1nc2c(c1-c1ccccc1)CCN(C(=O)c1ccnc3c(F)cccc13)C2]

The title compound was prepared in a manner analogous to Example 1, using 8-fluoroquinoline-4-carboxylic acid instead of 1-naphthoic acid. MS (ESI): mass calcd. for $C_{23}H_{19}FN_4O$, 386.1; m/z found, 387.1 [M+H]$^+$. $^1$H NMR (400 MHz, DMSO-$d_6$) δ 9.04 (dd, J=5.6, 4.2 Hz, 1H), 7.77-7.36 (m, 9H), 5.12-4.68 (m, 2H), 4.37-4.05 (m, 1H), 4.02-3.83 (m, 1H), 3.85-3.62 (m, 3H), 2.85-2.55 (m, 1H), 2.33 (s, 1H).

Example 97: (2-Methyl-3-phenyl-2,4,5,7-tetrahydro-6H-pyrazolo[3,4-c]pyridin-6-yl)(quinoxalin-5-yl)methanone

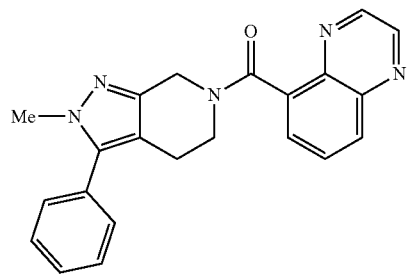 [SMILES: Cn1nc2c(c1-c1ccccc1)CCN(C(=O)c1cccc3nccnc13)C2]

The title compound was prepared in a manner analogous to Example 1, using quinoxaline-5-carboxylic acid instead of 1-naphthoic acid. MS (ESI): mass calcd. for $C_{22}H_{19}N_5O$, 369.1; m/z found, 370.1 [M+H]$^+$. $^1$H NMR (400 MHz, DMSO-$d_6$) δ 9.09-8.94 (m, 2H), 8.19 (td, J=8.6, 1.4 Hz, 1H), 7.99-7.77 (m, 2H), 7.67-7.32 (m, 5H), 4.97-4.78 (m, 1H), 4.37-4.08 (m, 1H), 3.82-3.65 (m, 3H), 3.27 (t, J=5.7 Hz, 1H), 2.80-2.53 (m, 1H), 2.49-2.28 (m, 2H).

Example 98: (3-(3-(Difluoromethoxy)phenyl)-2-methyl-2,4,5,7-tetrahydro-6H-pyrazolo[3,4-c]pyridin-6-yl)(quinolin-6-yl)methanone

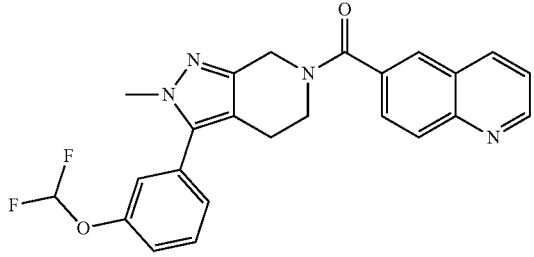 [SMILES: Cn1nc2c(c1-c1cccc(OC(F)F)c1)CCN(C(=O)c1ccc3ncccc3c1)C2]

A microwave vial was charged with [2-methyl-6-(quinoline-6-carbonyl)-4,5,6,7-tetrahydro-2H-pyrazolo[3,4-c]pyridin-3-yl trifluoromethanesulfonate] (Intermediate 10, 30 mg, 68.1 μmol), 3-(difluoromethoxy)phenylboronic acid (15.4 mg, 81.7 μmol), XPhos-Pd-G2 precatalyst (5.4 mg, 6.81 μmol), saturated aqueous $Na_2CO_3$ (0.23 mL), and 1,4-dioxane (0.93 mL). The head space was evacuated under vacuum and refilled with $N_2$ (×3), and then the reaction stirred in a microwave reactor at 110° C. for 30 min. After cooling to room temperature, the mixture was diluted with DCM and $H_2O$, the layers separated, and the aqueous layer extracted with DCM (×2). The combined organics were washed with brine, dried over $Na_2SO_4$, filtered, and concentrated in vacuo. The residue was purified by preparative HPLC to afford a white foam (13.7 mg, 46% yield). MS (ESI): mass calcd. for $C_{24}H_{20}F_2N_4O_2$, 434.2; m/z found, 435.2 [M+H]$^+$. $^1$H NMR (500 MHz, Methanol-$d_4$) δ 8.93 (dd, J=4.3, 1.7 Hz, 1H), 8.43 (d, J=8.4 Hz, 1H), 8.15 (d, J=8.6 Hz, 1H), 8.07 (d, J=1.9 Hz, 1H), 7.83 (dd, J=8.7, 1.9 Hz, 1H), 7.61-7.53 (m, 2H), 7.31-7.19 (m, 3H), 6.85 (t, J=73.8 Hz, 1H), 4.79 (s, 2H), 4.10-3.58 (m, 5H), 2.70 (s, 2H).

Example 99: (3-(3-Chlorophenyl)-2-methyl-2,4,5,7-tetrahydro-6H-pyrazolo[3,4-c]pyridin-6-yl)(quinolin-6-yl)methanone

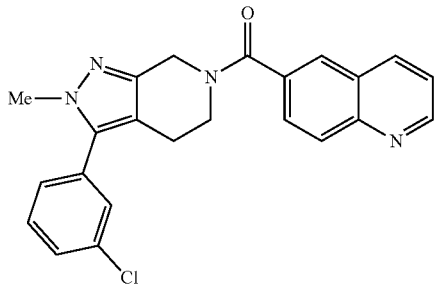 [SMILES: Cn1nc2c(c1-c1cccc(Cl)c1)CCN(C(=O)c1ccc3ncccc3c1)C2]

The title compound was prepared in a manner analogous to Example 98, using 3-chlorophenylboronic acid instead of 3-(difluoromethoxy)phenylboronic acid. MS (ESI): mass calcd. for $C_{23}H_{19}ClN_4O$, 402.1; m/z found, 403.1 [M+H]$^+$. $^1$H NMR (500 MHz, Methanol-$d_4$) δ 8.93 (dd, J=4.3, 1.7 Hz, 1H), 8.44 (d, J=8.3 Hz, 1H), 8.15 (d, J=8.7 Hz, 1H), 8.07 (d, J=1.9 Hz, 1H), 7.84 (dd, J=8.7, 1.9 Hz, 1H), 7.62-7.58 (m, 1H), 7.52-7.44 (m, 3H), 7.36 (d, J=7.4 Hz, 1H), 4.79 (s, 2H), 3.77 (s, 5H), 2.69 (s, 2H).

Example 100: (3-(3-Fluorophenyl)-2-methyl-2,4,5,7-tetrahydro-6H-pyrazolo[3,4-c]pyridin-6-yl)(quinolin-6-yl)methanone

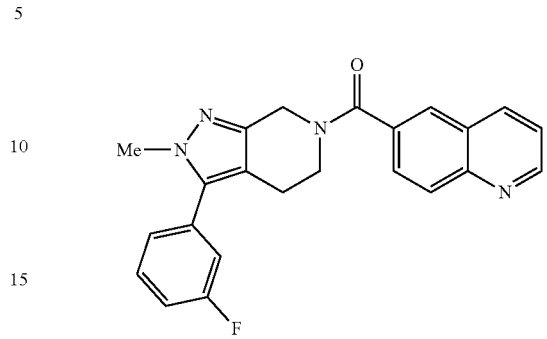

The title compound was prepared in a manner analogous to Example 1, using quinoline-6-carboxylic acid instead of 1-naphthoic acid and 3-(3-fluorophenyl)-2-methyl-4,5,6,7-tetrahydro-2H-pyrazolo[3,4-c]pyridine (Intermediate 4) instead of 3-(phenyl)-2-methyl-4,5,6,7-tetrahydro-2H-pyrazolo[3,4-c]pyridine (Intermediate 1). MS (ESI): mass calcd. for $C_{23}H_{19}FN_4O$, 386.2; m/z found, 387.2 [M+H]$^+$. $^1$H NMR (400 MHz, CDCl$_3$) δ 8.98 (dd, J=4.3, 1.7 Hz, 1H), 8.24 (d, J=8.3 Hz, 1H), 8.19 (d, J=8.6 Hz, 1H), 7.99 (d, J=1.8 Hz, 1H), 7.80 (dd, J=8.7, 1.9 Hz, 1H), 7.52-7.41 (m, 2H), 7.17-7.09 (m, 2H), 7.05 (ddd, J=9.4, 2.6, 1.6 Hz, 1H), 4.95 (s, 1H), 4.67 (s, 1H), 4.11-3.43 (m, 5H), 2.69 (d, J=37.1 Hz, 2H).

Example 101: (3-(3,5-Difluorophenyl)-2-methyl-2,4,5,7-tetrahydro-6H-pyrazolo[3,4-c]pyridin-6-yl)(quinolin-6-yl)methanone

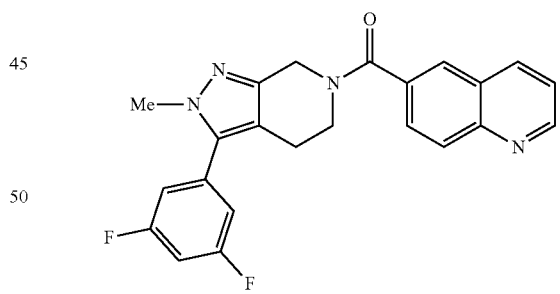

The title compound was prepared in a manner analogous to Example 1, using quinoline-6-carboxylic acid instead of 1-naphthoic acid and 3-(3,5-difluorophenyl)-2-methyl-4,5,6,7-tetrahydro-2H-pyrazolo[3,4-c]pyridine (Intermediate 5) instead of 3-(phenyl)-2-methyl-4,5,6,7-tetrahydro-2H-pyrazolo[3,4-c]pyridine (Intermediate 1). MS (ESI): mass calcd. for $C_{23}H_{18}F_2N_4O$, 404.1; m/z found, 404.9 [M+H]$^+$. $^1$H NMR (500 MHz, CDCl$_3$) δ 8.99 (dd, J=4.2, 1.7 Hz, 1H), 8.21 (d, J=8.3 Hz, 1H), 8.17 (d, J=8.7 Hz, 1H), 7.98 (d, J=1.8 Hz, 1H), 7.79 (dd, J=8.6, 1.9 Hz, 1H), 7.47 (dd, J=8.3, 4.2 Hz, 1H), 6.91-6.83 (m, 3H), 5.06-4.56 (m, 2H), 4.08-3.56 (m, 5H), 2.70 (d, J=48.8 Hz, 2H).

Example 102: Benzo[d]isoxazol-3-yl(2-methyl-3-(5-methylthiophen-2-yl)-2,4,5,7-tetrahydro-6H-pyrazolo[3,4-c]pyridin-6-yl)methanone

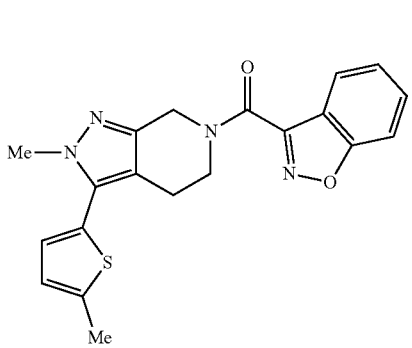 [SMILES: Cc1ccc(-c2c3c(nn2C)CN(C(=O)c2noc4ccccc24)CC3)s1]

The title compound was prepared in a manner analogous to Example 1, using benzo[d]isoxazole-3-carboxylic acid instead of 1-naphthoic acid and 2-methyl-3-(5-methylthiophen-2-yl)-4,5,6,7-tetrahydro-2H-pyrazolo[3,4-c]pyridine (Intermediate 3) instead of 3-(phenyl)-2-methyl-4,5,6,7-tetrahydro-2H-pyrazolo[3,4-c]pyridine (Intermediate 1). MS (ESI): mass calcd. for $C_{20}H_{18}N_4O_2S$, 378.1; m/z found, 379.1 [M+H]$^+$. $^1$H NMR (600 MHz, Methanol-$d_4$) δ 7.95-7.88 (m, 1H), 7.77-7.68 (m, 2H), 7.49-7.43 (m, 1H), 7.04 (t, J=3.3 Hz, 1H), 6.90-6.85 (m, 1H), 4.94 (s, 2H), 4.16-3.96 (m, 2H), 3.92-3.82 (m, 3H), 2.81 (dt, J=22.4, 5.8 Hz, 2H), 2.56-2.51 (m, 3H).

Example 103: (2-Methyl-3-(5-(trifluoromethyl)thiophen-2-yl)-2,4,5,7-tetrahydro-6H-pyrazolo[3,4-c]pyridin-6-yl)(quinolin-6-yl)methanone

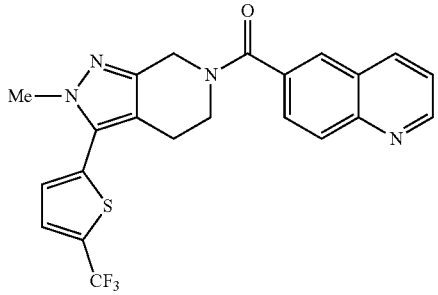 [SMILES: Cn1nc2c(c1-c1ccc(C(F)(F)F)s1)CCN(C(=O)c1ccc3ncccc3c1)C2]

The title compound was prepared in a manner analogous to Example 98, using 5-trifluoromethyl-thiophene-2-boronic acid instead of 3-(difluoromethoxy)phenylboronic acid. MS (ESI): mass calcd. for $C_{22}H_{17}F_3N_4OS$, 442.1; m/z found, 443.1 [M+H]$^+$. $^1$H NMR (600 MHz, Methanol-$d_4$) δ 8.95 (dd, J=4.4, 1.7 Hz, 1H), 8.48 (d, J=7.7 Hz, 1H), 8.18-8.09 (m, 2H), 7.86 (s, 1H), 7.68-7.61 (m, 2H), 7.34 (d, J=3.8 Hz, 1H), 4.90 (s, 1.15H), 4.64 (s, 0.67H), 4.18-3.62 (m, 5.2H), 2.94-2.69 (m, 2H).

Example 104: (3-(1H-Indol-2-yl)-2-methyl-2,4,5,7-tetrahydro-6H-pyrazolo[3,4-c]pyridin-6-yl)(quinolin-6-yl)methanone

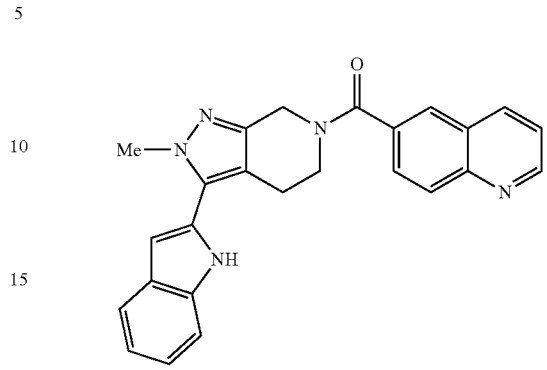

The title compound was prepared in a manner analogous to Example 98, using 2-(4,4,5,5-tetramethyl-1,3,2-dioxaborolan-2-yl)-1H-indole instead of 3-(difluoromethoxy)phenylboronic acid. MS (ESI): mass calcd. for $C_{25}H_{21}N_5O$, 407.2; m/z found, 408.2 [M+H]$^+$. $^1$H NMR (600 MHz, Methanol-$d_4$) δ 8.93 (d, J=4.3 Hz, 1H), 8.44 (d, J=8.3 Hz, 1H), 8.14 (d, J=8.7 Hz, 1H), 8.09 (s, 1H), 7.85 (s, 1H), 7.64-7.57 (m, 2H), 7.42 (s, 1H), 7.16 (t, J=7.6 Hz, 1H), 7.06 (t, J=7.5 Hz, 1H), 6.65 (s, 1H), 4.91 (s, 1.1H), 4.63 (s, 0.63H), 4.14-3.84 (m, 4.3H), 3.67 (s, 1H), 2.95-2.73 (m, 2H).

Example 105: (2-Methyl-3-(1-methyl-1H-indol-2-yl)-2,4,5,7-tetrahydro-6H-pyrazolo[3,4-c]pyridin-6-yl)(quinolin-6-yl)methanone

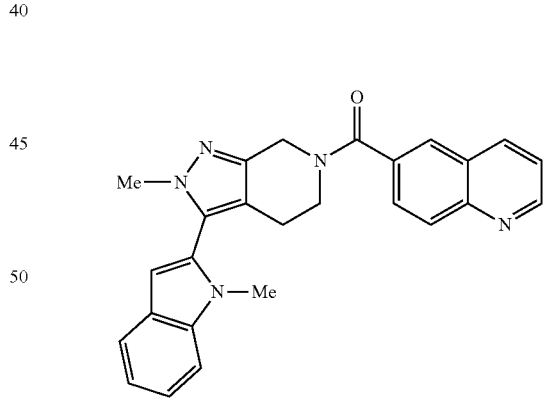

The title compound was prepared in a manner analogous to Example 98, using 1-methyl-2-(4,4,5,5-tetramethyl-1,3,2-dioxaborolan-2-yl)-1H-indole instead of 3-(difluoromethoxy)phenylboronic acid. MS (ESI): mass calcd. for $C_{26}H_{23}N_5O$, 421.2; m/z found, 422.1 [M+H]$^+$. $^1$H NMR (600 MHz, Methanol-$d_4$) δ 8.93 (s, 1H), 8.48-8.43 (m, 1H), 8.18-8.10 (m, 2H), 7.86 (dd, J=8.7, 1.9 Hz, 1H), 7.60 (d, J=7.5 Hz, 2H), 7.44 (d, J=8.1 Hz, 1H), 7.25 (t, J=7.5 Hz, 1H), 7.11 (t, J=7.3 Hz, 1H), 6.61 (d, J=0.8 Hz, 1H), 4.95 (s, 1H), 4.68 (s, 1H), 4.07 (s, 0.64H), 3.82-3.63 (m, 7.36H), 2.75-2.55 (m, 2H).

Example 106: (3-(3,5-Difluorophenyl)-2,7-dimethyl-2,4,5,7-tetrahydro-6H-pyrazolo[3,4-c]pyridin-6-yl)(quinolin-6-yl)methanone

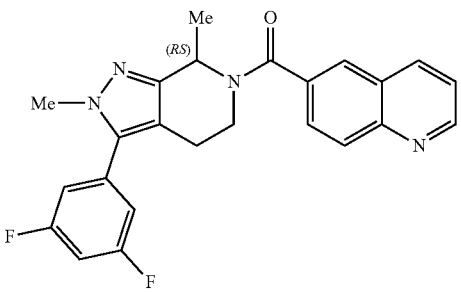 [SMILES: CC1c2nn(C)c(-c3cc(F)cc(F)c3)c2CCN1C(=O)c1ccc2ncccc2c1]

Step A: tert-Butyl 3-(3,5-difluorophenyl)-2,7-dimethyl-2,4,5,7-tetrahydro-6H-pyrazolo[3,4-c]pyridine-6-carboxylate. A microwave vial was charged with racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) (1.0 g, 2.5 mmol), 3,5-difluorophenylboronic acid (475 mg, 3.0 mmol), XPhos-Pd-G2 precatalyst (197 mg, 0.25 mmol), saturated aqueous $Na_2CO_3$ (2 mL), and 1,4-dioxane (8 mL). The head space was evacuated under vacuum and refilled with $N_2$ (×3), and then the reaction stirred in a microwave reactor at 110° C. for 30 min. After cooling to room temperature, the mixture was diluted with DCM and $H_2O$, the layers separated, and the aqueous layer extracted with DCM (×2). The combined organics were washed with brine, dried over $Na_2SO_4$, filtered, and concentrated in vacuo. The residue was purified by flash chromatography ($SiO_2$; 0-50% hexanes-EtOAc) to yield the title compound (538 mg, 60% yield). MS (ESI): mass calcd. for $C_{19}H_{23}F_2N_3O_2$, 363.2; m/z found, 308.1 [M+H-$^t$Bu]$^+$.

Step B: racemic 3-(3,5-Difluorophenyl)-2,7-dimethyl-4,5,6,7-tetrahydro-2H-pyrazolo[3,4-c]pyridine. A solution of tert-butyl 3-(3,5-difluorophenyl)-2,7-dimethyl-2,4,5,7-tetrahydro-6H-pyrazolo[3,4-c]pyridine-6-carboxylate (538 mg, 1.48 mmol) in 1:1 $CH_2Cl_2$:TFA (4 mL) was stirred at room temperature for 1 h and then concentrated in vacuo. The residue was purified by preparative HPLC (XBridge C18 column (5 μm, 100×4.6 mm), mobile phase of 10-100% ACN in 20 mM $NH_4OH$) to afford the title compound as a white solid (312 mg, 80% yield). MS (ESI): mass calcd. for $C_{14}H_{15}F_2N_3$, 263.1; m/z found, 264.1 [M+H]$^+$.

Step C: (3-(3,5-Difluorophenyl)-2,7-dimethyl-2,4,5,7-tetrahydro-6H-pyrazolo[3,4-c]pyridin-6-yl)(quinolin-6-yl)methanone. To a solution of racemic 3-(3,5-difluorophenyl)-2,7-dimethyl-4,5,6,7-tetrahydro-2H-pyrazolo[3,4-c]pyridine (50 mg, 0.19 mmol) in DCM (2.0 mL) was added HATU (94 mg, 0.25 mmol), followed by DIPEA (0.098 mL, 0.57 mmol) and quinoline-6-carboxylic acid (36 mg, 0.21 mmol), and the mixture was stirred at room temperature for 1 h. The reaction mixture was diluted with water and the aqueous layer extracted with DCM (×2). The combined organics were washed with brine, dried over $Na_2SO_4$, filtered, and concentrated in vacuo. The crude residue was purified by reverse-phase HPLC (XBridge C18 column; 5 μm, 100×4.6 mm; mobile phase of 10-100% ACN in 20 mM $NH_4OH$) to afford the title compound as a white solid (45 mg, 56% yield). MS (ESI): mass calcd. for $C_{24}H_{20}F_2N_4O$, 418.1; m/z found, 419.1 [M+H]$^+$. $^1$H NMR (500 MHz, DMSO-$d_6$) δ 8.98 (dd, J=4.2, 1.8 Hz, 1H), 8.49 (dd, J=8.3, 1.7 Hz, 1H), 8.16-8.06 (m, 2H), 7.80 (d, J=8.3 Hz, 1H), 7.62 (dd, J=8.3, 4.2 Hz, 1H), 7.46-7.23 (m, 3H), 5.69 (d, J=63.7 Hz, 1H), 4.75 (s, 1H), 3.85 (s, 3H), 3.71 (s, 1H), 2.91 (s, 1H), 2.35 (s, 1H), 1.51 (s, 3H).

Example 107: (S)-(2,7-Dimethyl-3-(5-methylfuran-2-yl)-2,4,5,7-tetrahydro-6H-pyrazolo[3,4-c]pyridin-6-yl)(quinoxalin-6-yl)methanone

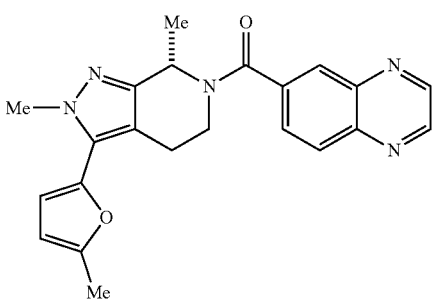 [SMILES: Cc1ccc(-c2c3c(nn2C)[C@H](C)N(C(=O)c2ccc4nccnc4c2)CC3)o1]

The title compound was prepared in a manner analogous to Example 106, using 4,4,5,5-tetramethyl-2-(5-methylfuran-2-yl)-1,3,2-dioxaborolane instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{22}H_{21}N_5O_2$, 387.2; m/z found, 388.1 [M+H]$^+$. $^1$H NMR (500 MHz, $CDCl_3$) δ 8.91 (s, 2H), 8.24-8.13 (m, 2H), 7.85 (s, 1H), 6.45-5.80 (m, 2.13H), 4.94 (s, 0.76H), 4.23-3.80 (m, 3.67H), 3.47-3.13 (m, 1H), 3.04-2.60 (m, 1H), 2.37 (s, 2.7H), 1.85-1.49 (m, 4.74H).

Example 108: (S)-(2,7-Dimethyl-3-(pyridin-3-yl)-2,4,5,7-tetrahydro-6H-pyrazolo[3,4-c]pyridin-6-yl)(quinoxalin-6-yl)methanone

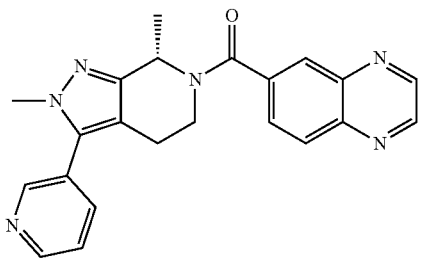 [SMILES: C[C@H]1c2nn(C)c(-c3cccnc3)c2CCN1C(=O)c1ccc2nccnc2c1]

The title compound was prepared in a manner analogous to Example 106, using pyridin-3-ylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{22}H_{20}N_6O$, 384.1; m/z found, 385.1 $[M+H]^+$. $^1H$ NMR (500 MHz, DMSO-$d_6$) δ 9.03 (d, J=1.0 Hz, 2H), 8.81-8.55 (m, 2H), 8.28-8.08 (m, 2H), 8.06-7.86 (m, 2H), 7.55 (dd, J=7.8, 4.8 Hz, 1H), 5.67 (s, 1H), 4.73 (s, 1H), 3.79 (d, J=44.9 Hz, 3H), 3.67 (d, J=13.4 Hz, 1H), 2.88 (s, 1H), 2.32 (s, 1H), 1.54 (s, 3H).

Example 109: (S)-(3-(5-Fluoropyridin-3-yl)-2,7-dimethyl-2,4,5,7-tetrahydro-6H-pyrazolo[3,4-c]pyridin-6-yl)(quinoxalin-6-yl)methanone

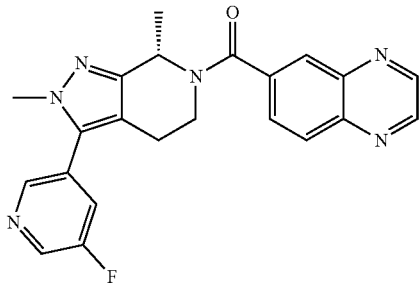 [SMILES: C[C@H]1c2nn(C)c(-c3cncc(F)c3)c2CCN1C(=O)c1ccc2nccnc2c1]

The title compound was prepared in a manner analogous to Example 106, using (5-fluoropyridin-3-yl)boronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{22}H_{19}FN_6O$, 402.1; m/z found, 403.1 $[M+H]^+$. $^1H$ NMR (500 MHz, DMSO-$d_6$) δ 9.03 (d, J=0.7 Hz, 2H), 8.72-8.56 (m, 2H), 8.25-8.09 (m, 2H), 8.04-7.83 (m, 2H), 5.71 (d, J=44.2 Hz, 1H), 4.67 (s, 1H), 3.86 (s, 3H), 3.66 (s, 1H), 2.92 (s, 1H), 2.41-2.33 (m, 1H), 1.54 (s, 3H).

Example 110: (2,7-Dimethyl-3-phenyl-2,4,5,7-tetrahydro-6H-pyrazolo[3,4-c]pyridin-6-yl)(quinolin-6-yl)methanone

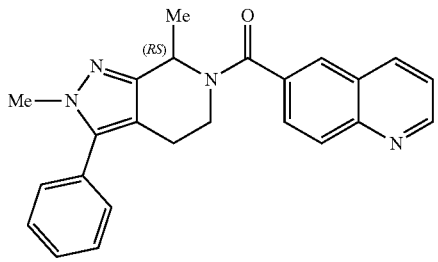 [SMILES: CC1c2nn(C)c(-c3ccccc3)c2CCN1C(=O)c1ccc2ncccc2c1]

The title compound was prepared in a manner analogous to Example 106, using phenylboronic acid instead of 3,5-difluorophenylboronic acid in Step A. MS (ESI): mass calcd. for $C_{24}H_{22}N_4O$, 382.2; m/z found, 383.1 $[M+H]^+$. $^1H$ NMR (500 MHz, DMSO-$d_6$) δ 8.97 (d, J=4.3 Hz, 1H), 8.48 (d, J=8.1 Hz, 1H), 8.13-8.07 (m, 2H), 7.80 (d, J=8.6 Hz, 1H), 7.63-7.58 (m, 1H), 7.56-7.40 (m, 5H), 5.74-4.54 (m, 1H), 3.80 (s, 4H), 3.34-3.05 (m, 1H), 2.85 (s, 1H), 2.33 (d, J=15.4 Hz, 1H), 1.52 (s, 3H).

Example 111: (R)-(2,7-Dimethyl-3-phenyl-2,4,5,7-tetrahydro-6H-pyrazolo[3,4-c]pyridin-6-yl)(quinolin-6-yl)methanone

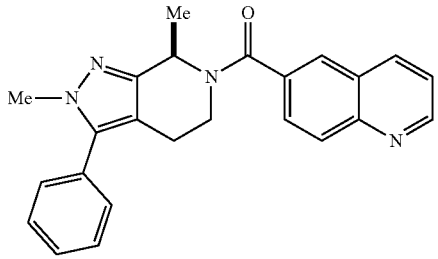

The title compound was obtained as a single enantiomer by chiral SFC purification of racemic (2,7-dimethyl-3-phenyl-2,4,5,7-tetrahydro-6H-pyrazolo[3,4-c]pyridin-6-yl)(quinolin-6-yl)methanone, Example 110 (Stationary phase: Chiralcel OD-H 5 um 250×20 mm, Mobile phase: 30% methanol, 70% $CO_2$, retention time=5.90 min). MS (ESI): mass calcd. for $C_{24}H_{22}N_4O$, 382.2; m/z found, 383.1 $[M+H]^+$. $^1H$ NMR (500 MHz, DMSO-$d_6$) δ 8.97 (d, J=4.3 Hz, 1H), 8.48 (d, J=8.1 Hz, 1H), 8.13-8.07 (m, 2H), 7.80 (d, J=8.6 Hz, 1H), 7.63-7.58 (m, 1H), 7.56-7.40 (m, 5H), 5.74-4.54 (m, 1H), 3.80 (s, 4H), 3.34-3.05 (m, 1H), 2.85 (s, 1H), 2.33 (d, J=15.4 Hz, 1H), 1.52 (s, 3H).

Example 112: (S)-(2,7-Dimethyl-3-phenyl-2,4,5,7-tetrahydro-6H-pyrazolo[3,4-c]pyridin-6-yl)(quinolin-6-yl)methanone

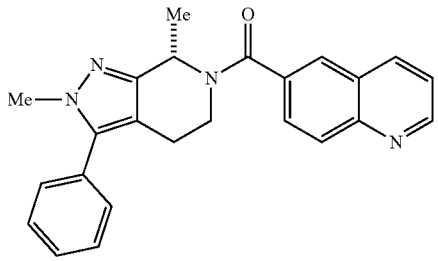 [SMILES: C[C@H]1c2nn(C)c(-c3ccccc3)c2CCN1C(=O)c1ccc2ncccc2c1]

The title compound was obtained as a single enantiomer by chiral SFC purification of racemic (2,7-dimethyl-3-phenyl-2,4,5,7-tetrahydro-6H-pyrazolo[3,4-c]pyridin-6-yl)(quinolin-6-yl)methanone, Example 110 (Stationary phase: Chiralcel OD-H 5 um 250×20 mm, Mobile phase: 30% methanol, 70% $CO_2$, retention time=4.58 min). MS (ESI): mass calcd. for $C_{24}H_{22}N_4O$, 382.2; m/z found, 383.1 $[M+H]^+$. $^1H$ NMR (500 MHz, DMSO-$d_6$) δ 8.97 (d, J=4.3 Hz, 1H), 8.48 (d, J=8.1 Hz, 1H), 8.13-8.07 (m, 2H), 7.80 (d, J=8.6 Hz, 1H), 7.63-7.58 (m, 1H), 7.56-7.40 (m, 5H), 5.74-4.54 (m, 1H), 3.80 (s, 4H), 3.34-3.05 (m, 11H), 2.85 (s, 1H), 2.33 (d, J=15.4 Hz, 1H), 1.52 (s, 3H).

Example 113: (7-Methyl-2,3-diphenyl-2,4,5,7-tetrahydro-6H-pyrazolo[3,4-c]pyridin-6-yl)(quinolin-6-yl)methanone

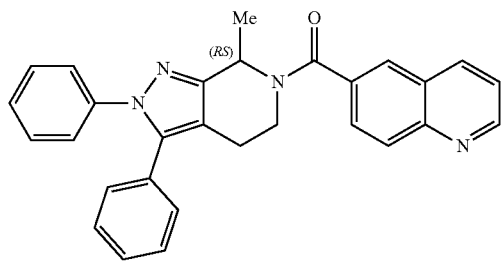 [SMILES: CC1c2nn(-c3ccccc3)c(-c3ccccc3)c2CCN1C(=O)c1ccc2ncccc2c1]

The title compound was prepared in a manner analogous to Example 1, using 7-methyl-2,3-diphenyl-4,5,6,7-tetrahydro-2H-pyrazolo[3,4-c]pyridine (Intermediate 26) and quinoline-6-carboxylic acid instead of 1-naphthoic acid. MS (ESI): mass calcd. for $C_{29}H_{24}N_4O$, 444.2; m/z found, 445.1 [M+H]$^+$. $^1$H NMR (400 MHz, DMSO-d$_6$) δ 8.99 (dd, J=4.2, 1.7 Hz, 1H), 8.50 (dd, J=8.4, 1.7 Hz, 1H), 8.26-8.06 (m, 2H), 7.84 (dd, J=8.6, 1.9 Hz, 1H), 7.62 (dd, J=8.3, 4.2 Hz, 1H), 7.46-7.10 (m, 10H), 5.76 (s, 1H), 4.13-3.39 (m, 2H), 2.95 (s, 1H), 2.21 (s, 1H), 1.61 (d, J=6.7 Hz, 3H).

Example 114: (R)-(7-Methyl-2,3-diphenyl-2,4,5,7-tetrahydro-6H-pyrazolo[3,4-c]pyridin-6-yl)(quinolin-6-yl)methanone

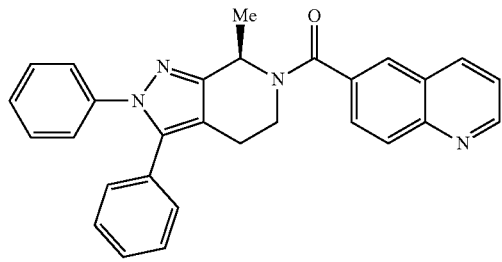 [SMILES: C[C@@H]1c2nn(-c3ccccc3)c(-c3ccccc3)c2CCN1C(=O)c1ccc2ncccc2c1]

The title compound was obtained as a single enantiomer by chiral SFC purification (Chiralcel OD, 5 um, 250×20 mm, Mobile phase: 40% methanol, 60% CO$_2$; 100% single (R) enantiomer; 9.0 min retention time) of Example 113 [(7-methyl-2,3-diphenyl-2,4,5,7-tetrahydro-6H-pyrazolo[3,4-c]pyridin-6-yl)(quinolin-6-yl)methanone]. MS (ESI): mass calcd. for $C_{29}H_{24}N_4O$, 444.2; m/z found, 445.1 [M+H]$^+$. $^1$H NMR (400 MHz, DMSO-d$_6$) δ 8.99 (dd, J=4.2, 1.7 Hz, 1H), 8.50 (dd, J=8.4, 1.7 Hz, 1H), 8.26-8.06 (m, 2H), 7.84 (dd, J=8.6, 1.9 Hz, 1H), 7.62 (dd, J=8.3, 4.2 Hz, 1H), 7.46-7.10 (m, 10H), 5.76 (s, 1H), 4.13-3.39 (m, 2H), 2.95 (s, 1H), 2.21 (s, 1H), 1.61 (d, J=6.7 Hz, 3H).

Example 115: (S)-(7-Methyl-2,3-diphenyl-2,4,5,7-tetrahydro-6H-pyrazolo[3,4-c]pyridin-6-yl)(quinolin-6-yl)methanone

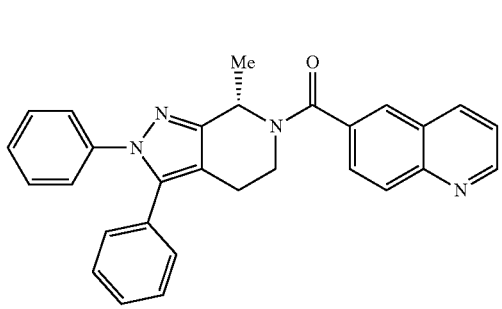 [SMILES: C[C@H]1c2nn(-c3ccccc3)c(-c3ccccc3)c2CCN1C(=O)c1ccc2ncccc2c1]

The title compound was obtained as a single enantiomer by chiral SFC purification (Chiralcel OD, 5 um, 250×20 mm, Mobile phase: 40% methanol, 60% CO$_2$; 100% single (S) enantiomer; 4.6 min retention time) of Example 113 [(7-methyl-2,3-diphenyl-2,4,5,7-tetrahydro-6H-pyrazolo[3,4-c]pyridin-6-yl)(quinolin-6-yl)methanone]. MS (ESI): mass calcd. for $C_{29}H_{24}N_4O$, 444.2; m/z found, 445.1 [M+H]$^+$. $^1$H NMR (400 MHz, DMSO-d$_6$) δ 8.99 (dd, J=4.2, 1.7 Hz, 1H), 8.50 (dd, J=8.4, 1.7 Hz, 1H), 8.26-8.06 (m, 2H), 7.84 (dd, J=8.6, 1.9 Hz, 1H), 7.62 (dd, J=8.3, 4.2 Hz, 1H), 7.46-7.10 (m, 10H), 5.76 (s, 1H), 4.13-3.39 (m, 2H), 2.95 (s, 1H), 2.21 (s, 1H), 1.61 (d, J=6.7 Hz, 3H).

Example 116: (S)-(3-Chloro-5-(trifluoromethoxy)phenyl)(3-(3-chlorophenyl)-2,7-dimethyl-2,4,5,7-tetrahydro-6H-pyrazolo[3,4-c]pyridin-6-yl)methanone

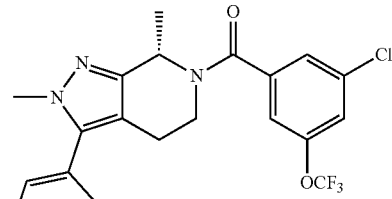

The title compound was prepared in a manner analogous to Example 106, using 3-chlorophenylboronic acid instead of 3,5-difluorophenylboronic acid and (S)-tert-butyl 2,7-dimethyl-3-((((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-((((trifluoromethyl)sulfonyl)oxy)-2,4,5,7-tetrahydro-6H-pyrazolo[3,4-c]pyridine-6-carboxylate (Intermediate 7) in Step A, and 3-chloro-5-(trifluoromethoxy)benzoic acid instead of quinoline 6-carboxylic acid in Step C. MS (ESI): mass calcd. for $C_{22}H_{18}C_{12}F_3N_3O_2$, 484.1; m/z found, 485.1 [M+H]$^+$. $^1$H NMR (500 MHz, DMSO-d$_6$) δ 7.69 (s, 1H), 7.60 (s, 1H), 7.58-7.50 (m, 3H), 7.50-7.41 (m, 2H), 5.54 (d, J=7.5 Hz, 1H), 4.58 (s, 1H), 3.77 (d, J=29.7 Hz, 3H), 3.23-2.68 (m, 2H), 2.31 (d, J=15.3 Hz, 1H), 1.47 (d, J=6.7 Hz, 3H).

Example 117: (S)-(3-(3-Chlorophenyl)-2,7-dimethyl-2,4,5,7-tetrahydro-6H-pyrazolo[3,4-c]pyridin-6-yl)(1-phenyl-1H-1,2,4-triazol-3-yl)methanone

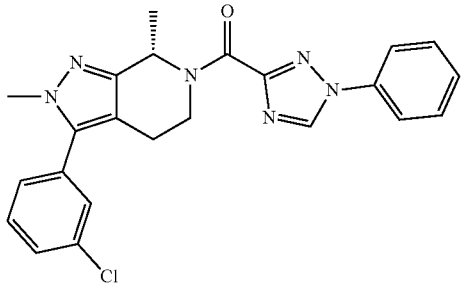 [SMILES: C[C@H]1c2nn(C)c(-c3cccc(Cl)c3)c2CCN1C(=O)c1ncn(-c2ccccc2)n1]

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 1-phenyl-1H-1,2,4-triazole-3-carboxylic acid instead of quinoline 6-carboxylic acid in Step C. MS (ESI): mass calcd. for $C_{23}H_{21}ClN_6O$, 432.15; m/z found, 433.2 [M+H]$^+$. $^1$H NMR (500 MHz, DMSO-d$_6$) δ 9.42 (d, J=3.4 Hz, 1H), 7.96-7.84 (m, 2H), 7.65-7.42 (m, 8H), 5.59 (q, J=6.7 Hz, 1H), 3.77 (d, J=31.8 Hz, 3H), 3.35-3.08 (m, 1H), 2.87-2.66 (m, 1H), 2.47-2.33 (m, 1H), 1.53 (dd, J=34.2, 6.8 Hz, 3H).

Example 118: (S)-(3-(3-Chlorophenyl)-2,7-dimethyl-2,4,5,7-tetrahydro-6H-pyrazolo[3,4-c]pyridin-6-yl)(5-ethyl-1-(2-fluorophenyl)-1H-1,2,4-triazol-3-yl)methanone

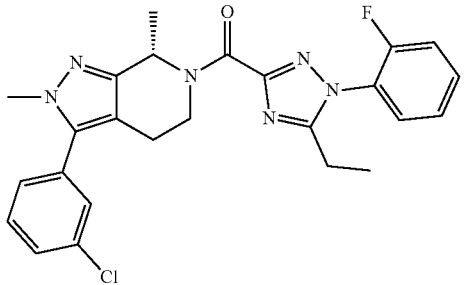 [SMILES: CCc1nc(C(=O)N2CCc3c(nn(C)c3-c3cccc(Cl)c3)[C@@H]2C)nn1-c1ccccc1F]

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 5-ethyl-1-(2-fluorophenyl)-1H-1,2,4-triazole-3-carboxylic acid instead of quinoline 6-carboxylic acid in Step C. MS (ESI): mass calcd. for $C_{25}H_{24}ClFN_6O$, 478.1; m/z found, 479.1 [M+H]$^+$. $^1$H NMR (500 MHz, DMSO-d$_6$) δ 7.82-7.65 (m, 2H), 7.63-7.41 (m, 6H), 5.57 (q, J=6.8 Hz, 1H), 3.77 (d, J=22.4 Hz, 3H), 3.38-3.01 (m, 2H), 2.79-2.61 (m, 3H), 2.48-2.29 (m, 1H), 1.50 (dd, J=27.7, 6.7 Hz, 3H), 1.20 (td, J=7.5, 4.9 Hz, 3H).

Example 119: (S)-(3-(3-Chlorophenyl)-2,7-dimethyl-2,4,5,7-tetrahydro-6H-pyrazolo[3,4-c]pyridin-6-yl)(4-(hydroxymethyl)pyridin-2-yl)methanone

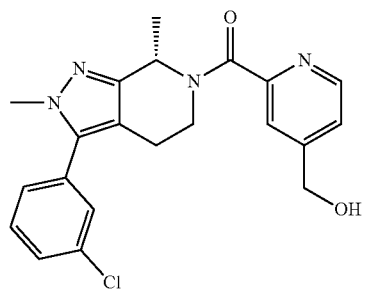 [SMILES: C[C@H]1c2nn(C)c(-c3cccc(Cl)c3)c2CCN1C(=O)c1cc(CO)ccn1]

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 4-(hydroxymethyl)picolinic acid instead of quinoline 6-carboxylic acid in Step C. MS (ESI): mass calcd. for $C_{21}H_{21}ClN_4O_2$, 396.1; m/z found, 397.0 [M+H]$^+$. $^1$H NMR (500 MHz, DMSO-d$_6$) δ 8.58-8.44 (m, 1H), 7.64-7.37 (m, 6H), 5.58 (q, J=6.7 Hz, 1H), 4.59 (s, 2H), 3.83-3.69 (m, 4H), 3.31-3.01 (m, 2H), 2.86-2.59 (m, 1H), 2.47-2.25 (m, 1H), 1.46 (dd, J=9.6, 6.8 Hz, 3H).

Example 120: (S)-(3-(3-Chlorophenyl)-2,7-dimethyl-2,4,5,7-tetrahydro-6H-pyrazolo[3,4-c]pyridin-6-yl)(5-(methoxymethyl)pyridin-3-yl)methanone

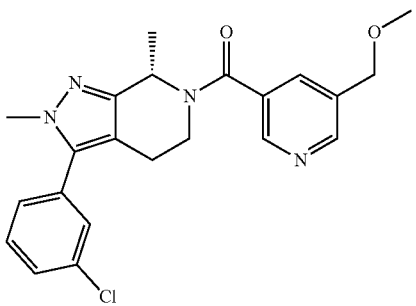 [SMILES: COCc1cncc(C(=O)N2CCc3c(nn(C)c3-c3cccc(Cl)c3)[C@@H]2C)c1]

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 5-(methoxymethyl)nicotinic acid instead of quinoline 6-carboxylic acid in Step C. MS (ESI): mass calcd. for C$_{22}$H$_{23}$ClN$_4$O$_2$, 410.1; m/z found, 411.1 [M+H]$^+$. $^1$H NMR (500 MHz, DMSO-d$_6$) δ 8.65-8.54 (m, 2H), 7.79 (s, 1H), 7.64-7.42 (m, 4H), 5.57 (d, J=6.8 Hz, 1H), 4.51 (s, 2H), 3.54-3.6 (m, 1H), 3.80 (s, 3H), 3.49 (s, 3H), 3.29-2.71 (m, 2H), 2.33 (d, J=15.6 Hz, 1H), 1.48 (d, J=6.8 Hz, 3H).

Example 121: (S)-(3-(3-Chlorophenyl)-2,7-dimethyl-2,4,5,7-tetrahydro-6H-pyrazolo[3,4-c]pyridin-6-yl)(6-isopropoxypyridin-3-yl)methanone

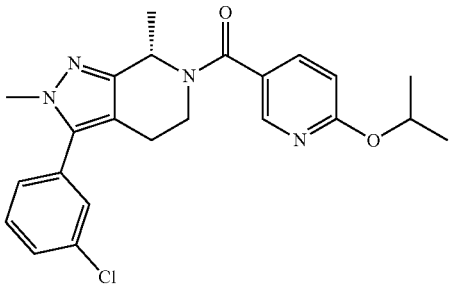 [SMILES: CC(C)Oc1ccc(C(=O)N2CCc3c(nn(C)c3-c3cccc(Cl)c3)[C@@H]2C)cn1]

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 6-isopropoxynicotinic acid instead of quinoline 6-carboxylic acid in Step C. MS (ESI): mass calcd. for C$_{23}$H$_{25}$ClN$_4$O$_2$, 424.1; m/z found, 425.1 [M+H]$^+$. $^1$H NMR (500 MHz, DMSO-d$_6$) δ 8.28 (s, 1H), 7.78 (d, J=8.2 Hz, 1H), 7.63-7.41 (m, 4H), 6.81 (dd, J=8.5, 0.8 Hz, 1H), 5.46 (d, J=38.2 Hz, 1H), 5.41-5.21 (m, 1H), 3.78 (d, J=3.9 Hz, 4H), 3.33-2.81 (m, 2H), 2.41-2.29 (m, 1H), 1.46 (d, J=6.8 Hz, 3H), 1.30 (dd, J=6.2, 1.8 Hz, 6H).

Example 122: (S)-(3-(3-Chlorophenyl)-2,7-dimethyl-2,4,5,7-tetrahydro-6H-pyrazolo[3,4-c]pyridin-6-yl)(5-isopropoxypyridin-3-yl)methanone

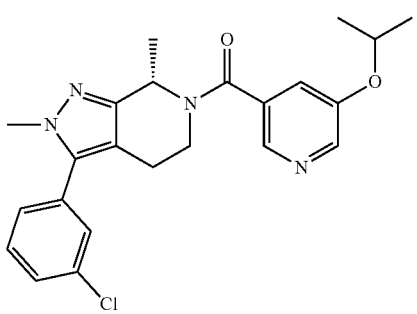 [SMILES: CC(C)Oc1cncc(C(=O)N2CCc3c(nn(C)c3-c3cccc(Cl)c3)[C@@H]2C)c1]

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 5-isopropoxynicotinic acid instead of quinoline 6-carboxylic acid in Step C. MS (ESI): mass calcd. for C$_{23}$H$_{25}$ClN$_4$O$_2$, 424.1; m/z found, 425.1 [M+H]$^+$. $^1$H NMR (500 MHz, DMSO-d$_6$) δ 8.33 (d, J=2.8 Hz, 1H), 8.17 (d, J=17.5 Hz, 1H), 7.63-7.37 (m, 5H), 5.56 (d, J=7.4 Hz, 1H), 4.83-4.58 (m, 1H), 3.80 (s, 3H), 3.63-3.53 (m, 1H), 3.35-2.76 (m, 2H), 2.31 (d, J=15.2 Hz, 1H), 1.47 (d, J=6.9 Hz, 3H), 1.28 (dd, J=6.0, 2.3 Hz, 6H).

Example 123: (S)-Benzo[d][1,3]dioxol-4-yl(3-(3-chlorophenyl)-2,7-dimethyl-2,4,5,7-tetrahydro-6H-pyrazolo[3,4-c]pyridin-6-yl)methanone

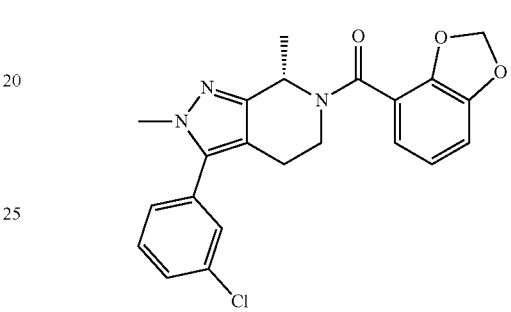

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and benzo[d][1,3]dioxole-4-carboxylic acid instead of quinoline 6-carboxylic acid in Step C. MS (ESI): mass calcd. for C$_{22}$H$_{20}$ClN$_3$O$_3$, 409.1; m/z found, 410.1 [M+H]$^+$. $^1$H NMR (500 MHz, DMSO-d$_6$) δ 7.60-7.41 (m, 4H), 7.06-6.78 (m, 3H), 6.07 (d, J=12.4 Hz, 2H), 5.55 (q, J=6.8 Hz, 1H), 3.76 (d, J=25.2 Hz, 3H), 3.65 (dd, J=13.9, 5.1 Hz, 1H), 3.36-3.00 (m, 1H), 2.76-2.57 (m, 1H), 2.35 (d, J=14.1 Hz, 1H), 1.42 (dd, J=23.3, 6.7 Hz, 3H).

Example 124: (S)-6-(3-(3-Chlorophenyl)-2,7-dimethyl-4,5,6,7-tetrahydro-2H-pyrazolo[3,4-c]pyridine-6-carbonyl)benzo[d]oxazol-2(3H)-one

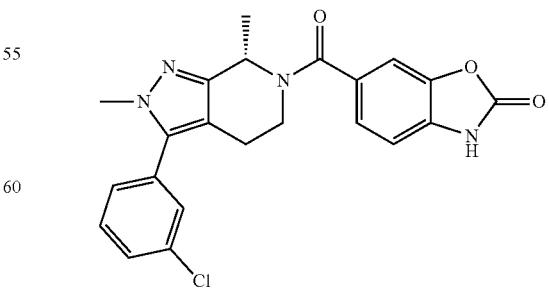

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 2-oxo-2,3-dihydrobenzo[d]oxazole-6-carboxylic acid instead of quinoline 6-carboxylic acid in Step C. MS (ESI): mass calcd. for C$_{22}$H$_{19}$ClN$_4$O$_3$, 422.1; m/z found, 423.1 [M+H]$^+$. $^1$H NMR (500 MHz, DMSO-d$_6$) δ 7.61-7.43 (m, 4H), 7.37 (s, 1H), 7.27-7.09 (m, 2H), 5.49 (s, 1H), 3.78 (s, 5H), 2.82 (s, 2H), 2.32 (s, 1H), 1.46 (d, J=6.8 Hz, 3H).

Example 125: (S)-(3-(3-Chlorophenyl)-2,7-dimethyl-2,4,5,7-tetrahydro-6H-pyrazolo[3,4-c]pyridin-6-yl)(2-methylbenzo[d]oxazol-6-yl)methanone

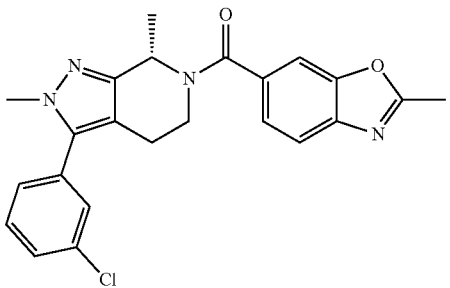 [SMILES: Cc1nc2ccc(C(=O)N3CCc4c(nn(C)c4-c4cccc(Cl)c4)[C@@H]3C)cc2o1]

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 2-methylbenzo[d]oxazole-6-carboxylic acid instead of quinoline 6-carboxylic acid in Step C. MS (ESI): mass calcd. for C$_{23}$H$_{21}$ClN$_4$O$_2$, 420.1; m/z found, 421.1 [M+H]$^+$. $^1$H NMR (500 MHz, DMSO-d$_6$) δ 7.83-7.64 (m, 2H), 7.63-7.52 (m, 2H), 7.50-7.33 (m, 2H), 5.56 (s, 1H), 4.40 (s, 1H), 3.79 (s, 3H), 3.62 (s, 1H), 3.24 (s, 1H), 2.98-2.73 (m, 1H), 2.64 (s, 3H), 2.35 (d, J=42.4 Hz, 1H), 1.47 (d, J=6.7 Hz, 3H).

Example 126: (3-(3-Chlorophenyl)-2,7-dimethyl-2,4,5,7-tetrahydro-6H-pyrazolo[3,4-c]pyridin-6-yl)(furo[3,2-b]pyridin-6-yl)methanone

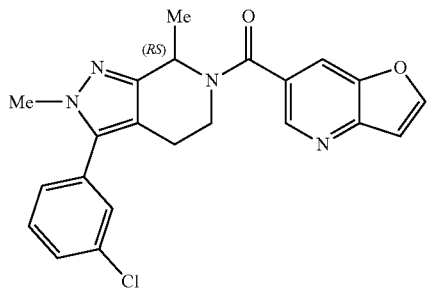 [SMILES: CC1c2nn(C)c(-c3cccc(Cl)c3)c2CCN1C(=O)c1cnc2ccoc2c1]

The title compound was prepared in a manner analogous to Example 106, using 3-chloroboronic acid instead of 3,5-difluorophenylboronic acid in Step A and furo[3,2-b]pyridine-6-carboxylic acid instead of quinoline-6-carboxylic acid in Step C. MS (ESI): mass calcd. for C$_{22}$H$_{19}$ClN$_4$O$_2$, 406.1; m/z found, 407.1 [M+H]$^+$. $^1$H NMR (500 MHz, CDCl$_3$) δ 8.67 (d, J=1.8 Hz, 1H), 7.95 (d, J=2.3 Hz, 1H), 7.89 (s, 1H), 7.46-7.37 (m, 2H), 7.36-7.32 (m, 1H), 7.23 (dt, J=6.9, 1.8 Hz, 1H), 7.04 (dd, J=2.3, 1.0 Hz, 1H), 5.87 (s, 0.47H), 5.15-4.65 (m, 0.72H), 3.81 (s, 3.66H), 3.34 (s, 1H), 2.83 (s, 1H), 2.54-2.38 (m, 1H), 1.61 (s, 3.15H).

Example 127: (R)-(3-(3-Chlorophenyl)-2,7-dimethyl-2,4,5,7-tetrahydro-6H-pyrazolo[3,4-c]pyridin-6-yl)(furo[3,2-b]pyridin-6-yl)methanone

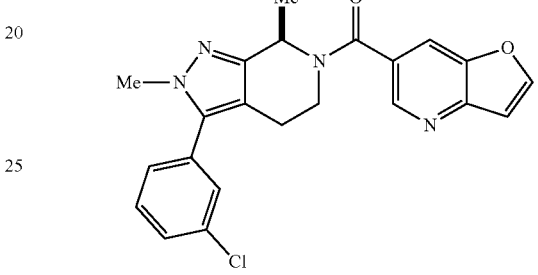

The title compound was obtained as a single enantiomer by chiral SFC purification of racemic (3-(3-chlorophenyl)-2,7-dimethyl-2,4,5,7-tetrahydro-6H-pyrazolo[3,4-c]pyridin-6-yl)(furo[3,2-b]pyridin-6-yl)methanone, Example 126 (Stationary phase: Lux 5μ Cellulose-1 5 um 250×21 mm, Mobile phase: 25% methanol, 75% CO$_2$, retention time=8.19 min). MS (ESI): mass calcd. for C$_{22}$H$_{19}$ClN$_4$O$_2$, 406.1; m/z found, 407.1 [M+H]$^+$. $^1$H NMR (500 MHz, CDCl$_3$) δ 8.67 (d, J=1.8 Hz, 1H), 7.95 (d, J=2.3 Hz, 1H), 7.89 (s, 1H), 7.46-7.37 (m, 2H), 7.36-7.32 (m, 1H), 7.23 (dt, J=6.9, 1.8 Hz, 1H), 7.04 (dd, J=2.3, 1.0 Hz, 1H), 5.87 (s, 0.47H), 5.15-4.65 (m, 0.72H), 3.81 (s, 3.66H), 3.34 (s, 1H), 2.83 (s, 1H), 2.54-2.38 (m, 1H), 1.61 (s, 3.15H).

Example 128: (S)-(3-(3-Chlorophenyl)-2,7-dimethyl-2,4,5,7-tetrahydro-6H-pyrazolo[3,4-c]pyridin-6-yl)(furo[3,2-b]pyridin-6-yl)methanone

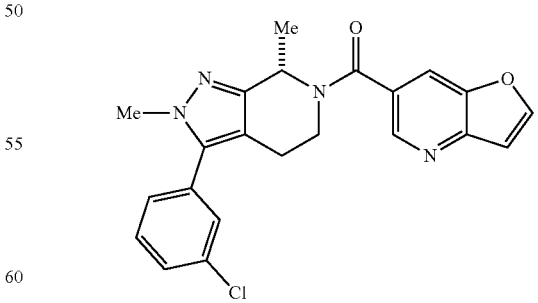

The title compound was obtained as a single enantiomer by chiral SFC purification of racemic (3-(3-chlorophenyl)-2,7-dimethyl-2,4,5,7-tetrahydro-6H-pyrazolo[3,4-c]pyridin-6-yl)(furo[3,2-b]pyridin-6-yl)methanone, Example 126 (Stationary phase: Lux 5μ Cellulose-1 5 um 250×21 mm, Mobile phase: 25% methanol, 75% $CO_2$, retention time=5.57 min). MS (ESI): mass calcd. for $C_{22}H_{19}ClN_4O_2$, 406.1; m/z found, 407.1 [M+H]$^+$. $^1$H NMR (500 MHz, CDCl$_3$) δ 8.67 (d, J=1.8 Hz, 1H), 7.95 (d, J=2.3 Hz, 1H), 7.89 (s, 1H), 7.46-7.37 (m, 2H), 7.36-7.32 (m, 1H), 7.23 (dt, J=6.9, 1.8 Hz, 1H), 7.04 (dd, J=2.3, 1.0 Hz, 1H), 5.87 (s, 0.47H), 5.15-4.65 (m, 0.72H), 3.81 (s, 3.66H), 3.34 (s, 1H), 2.83 (s, 1H), 2.54-2.38 (m, 1H), 1.61 (s, 3.15H).

Example 129: (S)-(3-(3-Chlorophenyl)-2,7-dimethyl-2,4,5,7-tetrahydro-6H-pyrazolo[3,4-c]pyridin-6-yl)(furo[3,2-b]pyridin-2-yl)methanone

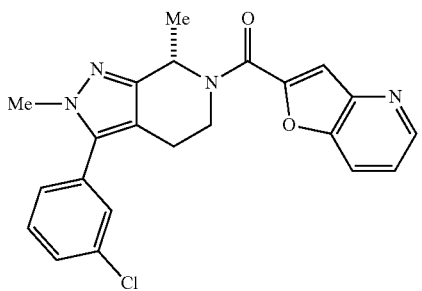 [SMILES: C[C@H]1c2nn(C)c(-c3cccc(Cl)c3)c2CCN1C(=O)c1cc2ncccc2o1]

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and furo[3,2-b]pyridine-2-carboxylic acid instead of quinoline 6-carboxylic acid in Step C. MS (ESI): mass calcd. for $C_{22}H_{19}ClN_4O_2$, 406.1; m/z found, 407.0 [M+H]$^+$. $^1$H NMR (600 MHz, Methanol-d$_4$) δ 8.61 (d, J=4.1 Hz, 1H), 8.12 (d, J=8.1 Hz, 1H), 7.57-7.46 (m, 5H), 7.44-7.38 (m, 1H), 5.74-5.37 (m, 1H), 4.79-4.32 (m, 1.15H), 3.88-3.74 (m, 3H), 3.60-3.46 (m, 0.64H), 3.08-2.77 (m, 1.2H), 2.66-2.55 (m, 1H), 1.70 (d, J=94.5 Hz, 3H).

Example 130: (S)-(3-(3-Chlorophenyl)-2,7-dimethyl-2,4,5,7-tetrahydro-6H-pyrazolo[3,4-c]pyridin-6-yl)(1H-pyrrolo[2,3-b]pyridin-6-yl)methanone

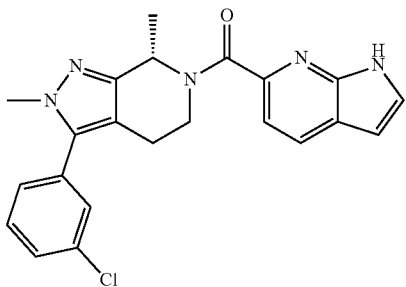 [SMILES: C[C@H]1c2nn(C)c(-c3cccc(Cl)c3)c2CCN1C(=O)c1ccc2cc[nH]c2n1]

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 1H-pyrrolo[2,3-b]pyridine-6-carboxylic acid instead of quinoline 6-carboxylic acid in Step C. MS (ESI): mass calcd. for $C_{22}H_{20}ClN_5O$, 405.1; m/z found, 406.1 [M+H]$^+$. $^1$H NMR (500 MHz, DMSO-d$_6$) δ 11.82 (s, 1H), 8.07 (d, J=7.8 Hz, 1H), 7.61-7.44 (m, 5H), 7.29 (d, J=8.0 Hz, 1H), 6.54 (d, J=7.6 Hz, 1H), 5.75-5.49 (m, 1H), 5.24-5.01 (m, 1H), 3.82-3.67 (m, 3H), 3.24 (d, J=12.3 Hz, 1H), 2.95-2.67 (m, 1H), 2.34 (d, J=15.4 Hz, 1H), 1.50 (d, J=6.7 Hz, 3H).

Example 131: (S)-(3-(3-Chlorophenyl)-2,7-dimethyl-2,4,5,7-tetrahydro-6H-pyrazolo[3,4-c]pyridin-6-yl)(1,5-naphthyridin-2-yl)methanone

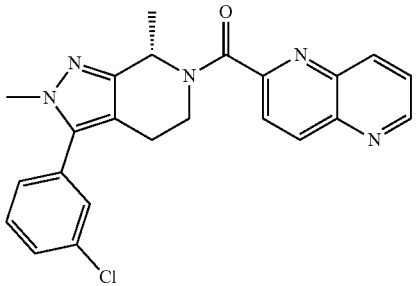 [SMILES: C[C@H]1c2nn(C)c(-c3cccc(Cl)c3)c2CCN1C(=O)c1ccc2ncccc2n1]

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 1,5-naphthyridine-2-carboxylic acid instead of quinoline 6-carboxylic acid in Step C. MS (ESI): mass calcd. for $C_{23}H_{20}ClN_5O$, 417.14; m/z found, 418.2 [M+H]$^+$. $^1$H NMR (500 MHz, DMSO-d$_6$) δ 9.14-9.03 (m, 1H), 8.67-8.41 (m, 2H), 8.02-7.80 (m, 2H), 7.63-7.44 (m, 4H), 5.73-5.53 (m, 1H), 3.81 (s, 3H), 3.71 (s, 1H), 3.20-3.10 (m, 1H), 2.93-2.74 (m, 1H), 2.38-2.28 (m, 1H), 1.54 (dd, J=6.8, 2.1 Hz, 3H).

Example 132: (3-(3-Chlorophenyl)-2,7-dimethyl-2,4,5,7-tetrahydro-6H-pyrazolo[3,4-c]pyridin-6-yl)(quinoxalin-6-yl)methanone

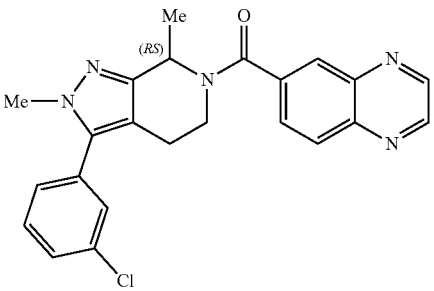 [SMILES: CC1c2nn(C)c(-c3cccc(Cl)c3)c2CCN1C(=O)c1ccc2nccnc2c1]

The title compound was prepared in a manner analogous to Example 106, using 3-chloroboronic acid instead of 3,5-difluorophenylboronic acid in Step A and quinoxaline-6-carboxylic acid instead of quinoline-6-carboxylic acid in Step C. MS (ESI): mass calcd. for $C_{23}H_{20}ClN_5O$, 417.1; m/z found, 418.1 [M+H]$^+$. $^1$H NMR (600 MHz, Methanol-$d_4$) δ 8.98 (s, 2H), 8.27-8.17 (m, 2H), 7.98-7.88 (m, 1H), 7.57-7.46 (m, 3H), 7.42-7.38 (m, 1H), 5.82 (s, 0.66H), 4.96-4.85 (m, 0.75H), 3.81 (m, 3.89H), 3.55-3.44 (m, 0.7H), 2.87 (s, 1H), 2.65-2.37 (m, 1H), 1.71-1.51 (m, 3H).

Example 133: (R)-(3-(3-Chlorophenyl)-2,7-dimethyl-2,4,5,7-tetrahydro-6H-pyrazolo[3,4-c]pyridin-6-yl)(quinoxalin-6-yl)methanone

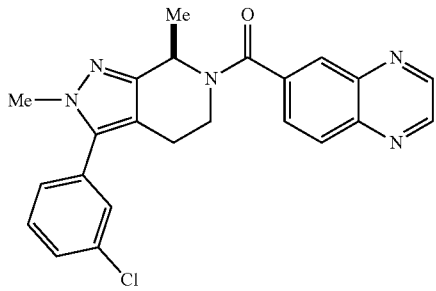 [SMILES: C[C@@H]1c2nn(C)c(-c3cccc(Cl)c3)c2CCN1C(=O)c1ccc2nccnc2c1]

The title compound was obtained as a single enantiomer by chiral SFC purification of racemic (3-(3-chlorophenyl)-2,7-dimethyl-2,4,5,7-tetrahydro-6H-pyrazolo[3,4-c]pyridin-6-yl)(quinoxalin-6-yl)methanone, Example 132 (Stationary phase: Lux 5μ Cellulose-1 5 um 250×21 mm, Mobile phase: 35% methanol, 65% CO$_2$, retention time=7.84 min). MS (ESI): mass calcd. for $C_{23}H_{20}ClN_5O$, 417.1; m/z found, 418.1 [M+H]$^+$. $^1$H NMR (600 MHz, Methanol-$d_4$) δ 8.98 (s, 2H), 8.27-8.17 (m, 2H), 7.98-7.88 (m, 1H), 7.57-7.46 (m, 3H), 7.42-7.38 (m, 1H), 5.82 (s, 0.66H), 4.96-4.85 (m, 0.75H), 3.81 (m, 3.89H), 3.55-3.44 (m, 0.7H), 2.87 (s, 1H), 2.65-2.37 (m, 1H), 1.71-1.51 (m, 3H).

Example 134: (S)-(3-(3-Chlorophenyl)-2,7-dimethyl-2,4,5,7-tetrahydro-6H-pyrazolo[3,4-c]pyridin-6-yl)(quinoxalin-6-yl)methanone

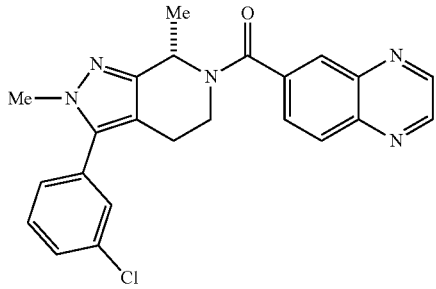 [SMILES: C[C@H]1c2nn(C)c(-c3cccc(Cl)c3)c2CCN1C(=O)c1ccc2nccnc2c1]

The title compound was obtained as a single enantiomer by chiral SFC purification of racemic (3-(3-chlorophenyl)-2,7-dimethyl-2,4,5,7-tetrahydro-6H-pyrazolo[3,4-c]pyridin-6-yl)(quinoxalin-6-yl)methanone, Example 132 (Stationary phase: Lux 5μ Cellulose-1 5 um 250×21 mm, Mobile phase: 35% methanol, 65% CO$_2$, retention time=5.11 min). MS (ESI): mass calcd. for $C_{23}H_{20}ClN_5O$, 417.1; m/z found, 418.1 [M+H]$^+$. $^1$H NMR (600 MHz, Methanol-$d_4$) δ 8.98 (s, 2H), 8.27-8.17 (m, 2H), 7.98-7.88 (m, 1H), 7.57-7.46 (m, 3H), 7.42-7.38 (m, 1H), 5.82 (s, 0.66H), 4.96-4.85 (m, 0.75H), 3.81 (m, 3.89H), 3.55-3.44 (m, 0.7H), 2.87 (s, 1H), 2.65-2.37 (m, 1H), 1.71-1.51 (m, 3H).

Example 135: (S)-(8-Bromoquinoxalin-6-yl)(3-(3-chlorophenyl)-2,7-dimethyl-2,4,5,7-tetrahydro-6H-pyrazolo[3,4-c]pyridin-6-yl)methanone

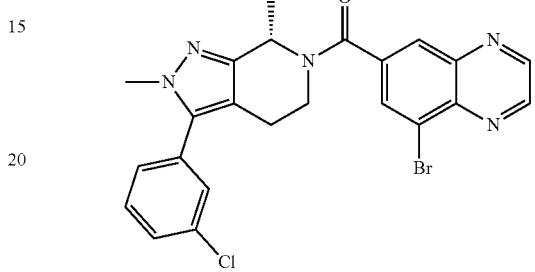

The title compound was prepared in a manner analogous to Example 106, using 3-chlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 8-bromoquinoxaline-6-carboxylic acid instead of quinoline 6-carboxylic acid in Step C. MS (ESI): mass calcd. for $C_{23}H_{19}BrClN_5O$, 495.0; m/z found, 496.0 [M+H]$^+$. $^1$H NMR (500 MHz, DMSO-$d_6$) δ 9.10 (dd, J=14.1, 1.8 Hz, 2H), 8.22 (d, J=45.8 Hz, 2H), 7.71-7.38 (m, 4H), 5.63 (d, J=7.0 Hz, 1H), 4.72 (d, J=43.0 Hz, 1H), 3.81 (s, 3H), 3.69 (d, J=19.3 Hz, 1H), 2.85 (s, 1H), 2.30 (d, J=15.5 Hz, 1H), 1.53 (d, J=6.7 Hz, 3H).

Example 136: (7-Ethyl-3-(3-fluorophenyl)-2-methyl-2,4,5,7-tetrahydro-6H-pyrazolo[3,4-c]pyridin-6-yl)(quinolin-6-yl)methanone

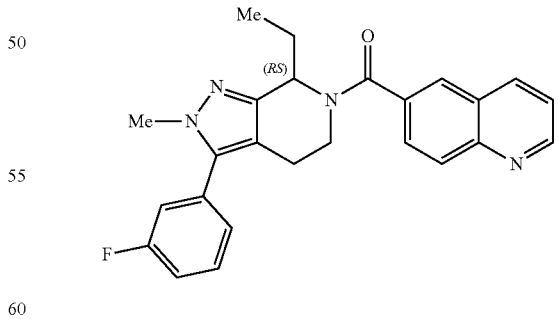

The title compound was prepared in a manner analogous to Example 106, using tert-butyl 7-ethyl-2-methyl-3-(((trifluoromethyl)sulfonyl)oxy)-2,4,5,7-tetrahydro-6H-pyrazolo[3,4-c]pyridine-6-carboxylate (Intermediate 27) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) and 3-fluorophenylboronic acid instead of 3,5-difluorophenylboronic acid in Step A. MS (ESI): mass calcd. for $C_{25}H_{23}FN_4O$, 414.2; m/z found, 415.2 [M+H]$^+$. $^1$H NMR (500 MHz, CDCl$_3$) δ 8.96 (dd, J=4.2, 1.7 Hz, 1H), 8.25-8.10 (m, 2H), 7.94-7.85 (m, 1H), 7.78-7.68 (m, 1H), 7.51-7.38 (m, 2H), 7.18-6.99 (m, 3H), 5.92-5.83 (m, 0.54H), 5.02-4.78 (m, 0.79H), 3.91-3.64 (m, 3.81H), 3.44-3.07 (m, 1H), 2.99-2.61 (m, 1H), 2.59-2.32 (m, 1H), 2.16-1.78 (m, 3H), 1.25-1.18 (m, 1H), 0.97-0.90 (m, 1H).

Example 137: [(7S)-3-(3,5-Difluorophenyl)-2,7-dimethyl-5,7-dihydro-4H-pyrazolo[3,4-c]pyridin-6-yl]-[2-(2-fluoroethoxy)phenyl]methanone

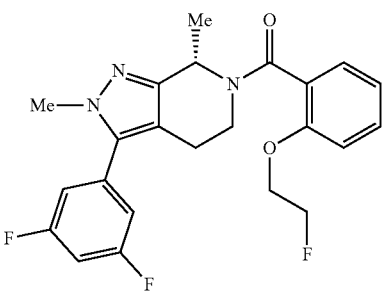 [SMILES: C[C@H]1c2nn(C)c(-c3cc(F)cc(F)c3)c2CCN1C(=O)c1ccccc1OCCF]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 2-(2-fluoroethoxy)benzoic acid (Intermediate 13) instead of 1-naphthoic acid. MS (ESI): mass calcd. for $C_{23}H_{22}F_3N_3O_2$, 429.2; m/z found, 430.1 [M+H]$^+$. $^1$H NMR (CDCl$_3$): δ 7.37-7.27 (m, 2H), 7.07-7.02 (m, 1H), 6.94-6.82 (m, 4H), 5.98-5.91 and 4.99-4.95 (m, 1H), 4.89-4.60 (m, 2H), 4.49-4.38 and 3.63-3.55 (m, 1H), 4.37-4.05 (m, 2H), 3.86 and 3.79 (s, 3H), 3.39-3.32 and 2.55-2.44 (m, 1H), 3.22-3.16 and 2.32-2.22 (m, 1H), 3.12-2.97 and 2.95-2.88 (m, 1H), 1.62-1.58, 1.47-1.45 and 1.39-1.37 (m, 3H).

Example 138: (S)-(3-(3,5-Difluorophenyl)-2,7-dimethyl-2,4,5,7-tetrahydro-6H-pyrazolo[3,4-c]pyridin-6-yl)(4-(2-fluoroethoxy)phenyl)methanone

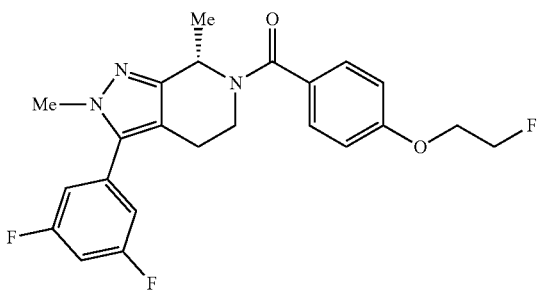 [SMILES: C[C@H]1c2nn(C)c(-c3cc(F)cc(F)c3)c2CCN1C(=O)c1ccc(OCCF)cc1]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 4-(2-fluoroethoxy)benzoic acid (Intermediate 16) instead of 1-naphthoic acid. MS (ESI): mass calcd. for $C_{23}H_{22}F_3N_3O_2$, 429.2; m/z found, 430.3 [M+H]$^+$. $^1$H NMR (400 MHz, CDCl$_3$) δ 7.43 (d, J=8.7 Hz, 2H), 6.97 (d, J=8.7 Hz, 2H), 6.94-6.85 (m, 3H), 5.55 (s, 1H), 4.87-4.81 (m, 1H), 4.75-4.70 (m, 1H), 4.32-4.27 (m, 1H), 4.25-4.21 (m, 1H), 3.85 (s, 3H), 3.21 (s, 1H), 2.87-2.73 (m, 2H), 2.45 (dd, J=15.2, 3.5 Hz, 1H), 2.31 (s, 1H) 1.59 (d, J=6.8 Hz, 3H).

Example 139: (S)-(3-(3,5-Difluorophenyl)-2,7-dimethyl-2,4,5,7-tetrahydro-6H-pyrazolo[3,4-c]pyridin-6-yl)(3-(2-fluoroethoxy)phenyl)methanone

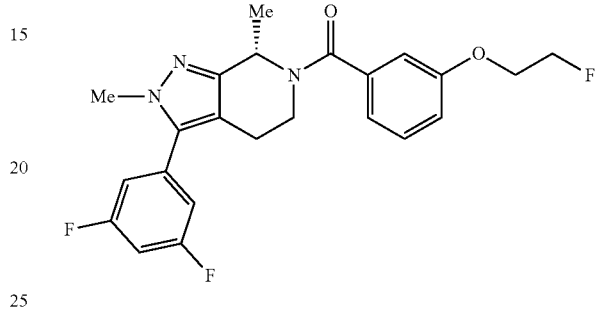

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 3-(2-fluoroethoxy)benzoic acid (Intermediate 15) instead of 1-naphthoic acid. MS (ESI): mass calcd. for $C_{23}H_{22}F_3N_3O_2$, 429.2; m/z found, 430.3 [M+H]$^+$. $^1$H NMR (400 MHz, CDCl$_3$) δ 7.33-7.26 (m, 1H), 6.99-6.90 (m, 3H), 6.88-6.75 (m, 3H), 5.80 (s, 0.5H), 4.95 (s, 0.5H), 4.82-4.52 (m, 1H), 4.75 (m, 1H), 4.63 (m, 1H), 4.17 (m, 1H), 4.15-4.12 (m, 1H), 3.79 (s, 3H), 3.21-3.05 (m, 1H), 2.76-2.63 (m, 1H), 2.37 (m, 1H), 1.54 (s, 3H).

Example 140: (S)-(3-(3,5-Difluorophenyl)-2,7-dimethyl-2,4,5,7-tetrahydro-6H-pyrazolo[3,4-c]pyridin-6-yl)(3-(2-(fluoro-$^{18}$F)ethoxy)phenyl)methanone

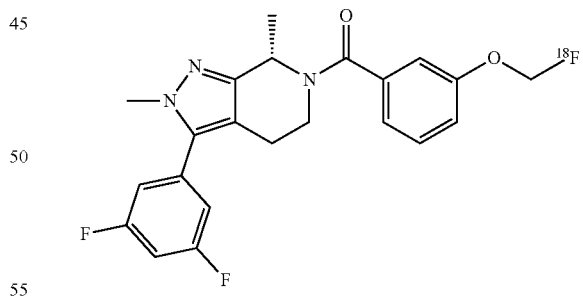

Step A: (S)-2-(3-(3-(3,5-Difluorophenyl)-2,7-dimethyl-4,5,6,7-tetrahydro-2H-pyrazolo[3,4-c]pyridine-6-carbonyl)phenoxy)ethyl 4-methylbenzenesulfonate. The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 3-(2-(tosyloxy)ethoxy)benzoic acid (Intermediate 36) instead of 1-naphthoic acid. MS (ESI): mass calcd. for $C_{30}H_{29}F_2N_3O_5S$, 581.2; m/z found, 582.0 [M+H]$^+$.

Step B: (S)-(3-(3,5-difluorophenyl)-2,7-dimethyl-2,4,5,7-tetrahydro-6H-pyrazolo[3,4-c]pyridin-6-yl)(3-(2-(fluoro-$^{18}$F)ethoxy)phenyl)methanone. [$^{18}$F]fluoride in a shipping vial from PETNET Solutions Inc. (San Diego, Calif. USA) is transferred onto and trapped on an ion exchange cartridge. It is then eluted into the reaction vessel (RV1) of the Synthra RNPlus® module with a solution of potassium carbonate (0.75 mg) and Kryptofix 222 (7.2 mg) in 0.8 mL of acetonitrile/water (6/2, v/v). After the solvent was evaporated under a stream of nitrogen at 85° C. and under vacuum, anhydrous CH$_3$CN (0.5 mL) was added, this process was repeated, and the temperature increased to 110° C. for 3.5 min. The reaction vial was then cooled to 70° C. before a solution of 3.0 mg of (S)-2-(3-(3-(3,5-difluorophenyl)-2,7-dimethyl-4,5,6,7-tetrahydro-2H-pyrazolo[3,4-c]pyridine-6-carbonyl)phenoxy)ethyl 4-methylbenzenesulfonate in 0.7 mL anhydrous MeCN was added to reaction vessel. The reaction mixture is heated at 95° C. for 10 min. The reactor is cooled to 40° C. and diluted with water (4.3 mL) and the contents is transferred into the HPLC injector loop for purification. Purification is performed by HPLC using a semi-preparative Eclipse XDB-C18 column (5 µm, 9.4 mm×250 mm) with a mixture of 10 mM NH$_4$OAc and MeCN (50:50 v/v) at a flow rate of 4 mL/min with UV detection at 254 nm. The purified radiotracer solution was diluted with 30 mL of water and passed through a SepPak Light C-18 cartridge. The C-18 cartridge was further washed with 10 mL of water before 0.5 mL EtOH was used to elute the tracer. The tracer solution was further diluted with 4.5 mL of saline. The final formulation contains an ethanol concentration of 10%, suitable for intravenous (IV) injection.

Example 141: (S)-(3-(3,5-Difluorophenyl)-2,7-dimethyl-2,4,5,7-tetrahydro-6H-pyrazolo[3,4-c]pyridin-6-yl)(2-fluoro-3-(2-fluoroethoxy)phenyl)methanone

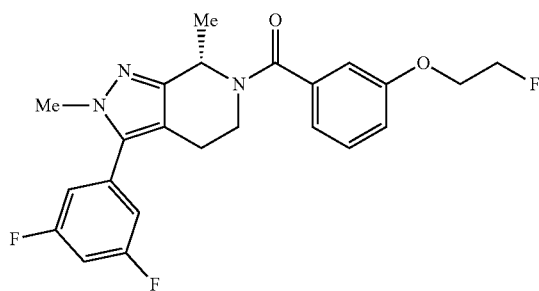 [SMILES: C[C@H]1c2nn(C)c(-c3cc(F)cc(F)c3)c2CCN1C(=O)c1cccc(OCCF)c1]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 2-fluoro-3-(2-fluoroethoxy)benzoic acid (Intermediate 19) instead of 1-naphthoic acid. MS (ESI): mass calcd. for C$_{23}$H$_{22}$F$_4$N$_3$O$_2$, 447.1; m/z found, 448.0 [M+H]$^+$. $^1$H NMR (500 MHz, CDCl$_3$) δ 7.15 (t, J=7.9 Hz, 1H), 7.09-7.05 (m, 1H), 7.05-6.97 (m, 1H), 6.91-6.86 (m, 3H), 5.93 (d, J=7.1 Hz, 0.6H), 4.95 (dd, J=13.1, 5.3 Hz, 0.4H), 4.85 (m, 1H), 4.76-4.73 (m, 1H), 4.36 (t, J=4.2 Hz, 1H), 4.32-4.27 (m, 1H), 3.89 (s, 1.9H), 3.83 (s, 1.1H), 3.69 (dd, J=13.9, 5.2 Hz, 0.6H), 3.33 (s, 0.6H), 3.09 (s, 0.4H), 2.56-2.47 (m, 0.4H), 2.41-2.15 (m, 2H), 1.63 (d, J=6.8 Hz, 1.9H), 1.49 (s, 1.1H). (Fractions of H's that overlap with solvent are not reported).

Example 142: (S)-(3-(3,5-Difluorophenyl)-2,7-dimethyl-2,4,5,7-tetrahydro-6H-pyrazolo[3,4-c]pyridin-6-yl)(2-fluoro-5-(2-fluoroethoxy)phenyl)methanone

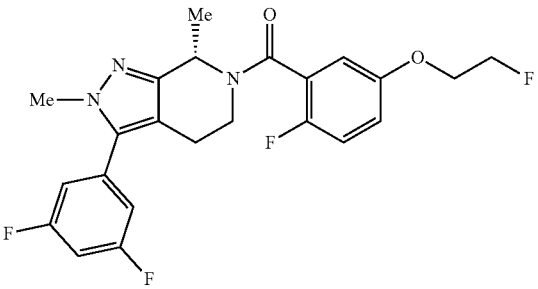 [SMILES: C[C@H]1c2nn(C)c(-c3cc(F)cc(F)c3)c2CCN1C(=O)c1cc(OCCF)ccc1F]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 2-fluoro-5-(2-fluoroethoxy)benzoic acid (Intermediate 22) instead of 1-naphthoic acid. MS (ESI): mass calcd. for C$_{23}$H$_{22}$F$_4$N$_3$O$_2$, 447.1; m/z found, 448.0 [M+H]$^+$. $^1$H NMR (400 MHz, CDCl$_3$) δ 7.06 (t, J=8.7 Hz, 1H), 7.00-6.80 (m, 5H), 5.92 (d, J=6.9 Hz, 0.5H), 5.04-4.85 (m, 0.5H), 4.73-4.66 (m, 1H), 4.31-4.22 (m, 1H), 4.22-4.16 (m, 1H), 3.89 (s, 1.8H), 3.83 (s, 1.2H), 3.71 (dd, J=13.8, 5.1 Hz, 0.7H), 3.35 (m, 0.7H), 3.10 (t, J=12.7 Hz, 0.3H), 2.84 (ddd, J=17.5, 12.3, 5.4 Hz, 0.3H), 2.53 (m, 0.4H), 2.40 (dd, J=15.4, 3.4 Hz, 0.6H), 2.23 (s, 1H), 1.63 (d, J=6.8 Hz, 1.8H), 1.51 (d, J=6.8 Hz, 1.2H). (Fractions of H's that overlap with solvent are not reported).

Example 143: (S)-(3-(3,5-Difluorophenyl)-2,7-dimethyl-2,4,5,7-tetrahydro-6H-pyrazolo[3,4-c]pyridin-6-yl)(3-fluoro-5-(2-fluoroethoxy)phenyl)methanone

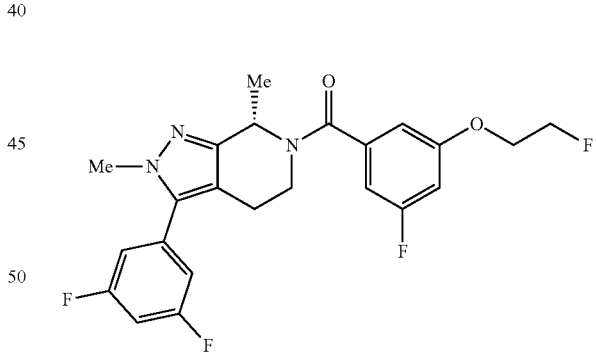

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 5-fluoro-3-(2-fluoroethoxy)benzoic acid (Intermediate 21) instead of 1-naphthoic acid. MS (ESI): mass calcd. for C$_{23}$H$_{22}$F$_4$N$_3$O$_2$, 447.1; m/z found, 448.0 [M+H]$^+$. $^1$H NMR (400 MHz, CDCl$_3$) δ 6.95-6.85 (m, 3H), 6.80-6.71 (m, 3H), 5.85 (s, 0.5H), 4.98 (s, 0.5H), 4.88-4.80 (m, 1H), 4.74-4.68 (m, 1H), 4.35-4.25 (m, 1H), 4.24-4.18 (m, 1H), 3.87 (s, 3H), 3.28-3.12 (m, 1H), 3.82-3.72 (m, 1H), 2.82 (s, 0.5H), 2.47 (s, 1H), 2.25 (s, 1H), 1.60 (s, 3H).

Example 144: (S)-(3-(3,5-Difluorophenyl)-2,7-dimethyl-2,4,5,7-tetrahydro-6H-pyrazolo[3,4-c]pyridin-6-yl)(4-fluoro-3-(2-fluoroethoxy)phenyl)methanone

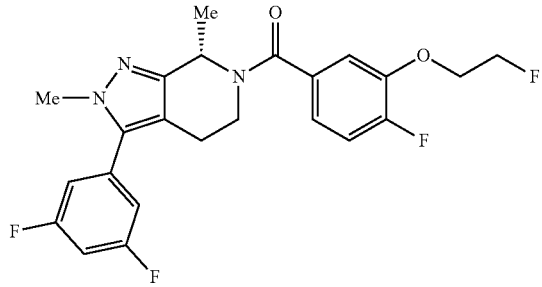 [SMILES: C[C@H]1c2nn(C)c(-c3cc(F)cc(F)c3)c2CCN1C(=O)c1ccc(F)c(OCCF)c1]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 4-fluoro-3-(2-fluoroethoxy)benzoic acid (Intermediate 20) instead of 1-naphthoic acid. MS (ESI): mass calcd. for $C_{23}H_{22}F_4N_3O_2$, 447.1; m/z found, 448.0 [M+H]$^+$. $^1$H NMR (400 MHz, CDCl$_3$) δ 7.19-7.11 (m, 2H), 7.04 (m, 1H), 6.94-6.87 (m, 3H), 5.82 (s, 0.6H), 5.06 (s, 0.4H), 4.89-4.81 (m, 1H), 4.80-4.68 (m, 1H), 4.41-4.33 (m, 1H), 4.33-4.28 (m, 1H), 3.86 (s, 3H), 3.23 (s, 1H), 2.78 (s, 1H), 2.49-2.45 (m, 1H), 2.21 (s, 1H), 1.60 (d, J=6.8 Hz, 3H). (Fractions of H's that overlap with solvent are not reported).

Example 145: [2-Chloro-3-(2-fluoroethoxy)phenyl]-[(7S)-3-(3,5-difluorophenyl)-2,7-dimethyl-5,7-dihydro-4H-pyrazolo[3,4-c]pyridin-6-yl]methanone

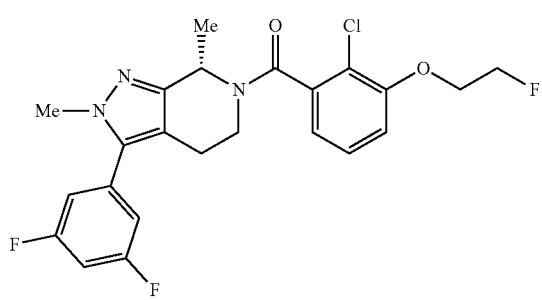 [SMILES: C[C@H]1c2nn(C)c(-c3cc(F)cc(F)c3)c2CCN1C(=O)c1cccc(OCCF)c1Cl]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 2-chloro-3-(2-fluoroethoxy)benzoic acid (Intermediate 12) instead of 1-naphthoic acid. MS (ESI): mass calcd. for $C_{23}H_{21}ClF_3N_3O_2$, 463.1; m/z found, 464.1 [M+H]$^+$. $^1$H NMR (CDCl$_3$): δ 7.33-7.21 (m, 1H), 7.01-6.92 (m, 2H), 6.89-6.81 (m, 3H), 5.96-5.89 and 5.00-4.95 (m, 1H), 4.90-4.72 (m, 2H), 4.70-4.65 and 3.57-3.49 (m, 1H), 4.37-4.25 (m, 2H), 3.86 and 3.80 (s, 3H), 3.38-3.31 and 2.91-2.78 (m, 1H), 3.26-3.20 and 2.57-2.48 (m, 1H), 3.13-2.99 and 2.33-2.28 (m, 1H), 1.64-1.60, 1.49-1.48 and 1.41-1.39 (m, 3H).

Example 146: (2-Chloro-5-(2-fluoroethoxy)phenyl)(3-(3,5-difluorophenyl)-2,7-dimethyl-2,4,5,7-tetrahydro-6H-pyrazolo[3,4-c]pyridin-6-yl)methanone

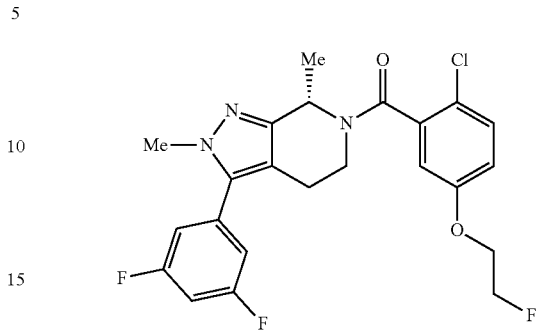

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 2-chloro-5-(2-fluoroethoxy)benzoic acid (Intermediate 14) instead of 1-naphthoic acid. MS (ESI): mass calcd. for $C_{23}H_{21}ClF_3N_3O_2$, 463.1; m/z found, 464.1 [M+H]$^+$. $^1$H NMR (CDCl$_3$): δ 7.37-7.29 (m, 1H), 6.92-6.83 (m, 5H), 5.93-5.87 and 4.97-4.94 (m, 1H), 4.84-4.69 (m, 2H), 4.74-4.64 and 3.60-3.50 (m, 1H), 4.26-4.15 (m, 2H), 3.85 and 3.81 (s, 3H), 3.41-3.33 and 2.87-2.80 (m, 1H), 3.25-3.19 and 2.54-2.47 (m, 1H), 3.14-2.88 (m, 1H), 1.63-1.40 (m, 3H).

Example 147: (S)-(2-(2H-1,2,3-Triazol-2-yl)phenyl)(3-(3,5-difluorophenyl)-2,7-dimethyl-2,4,5,7-tetrahydro-6H-pyrazolo[3,4-c]pyridin-6-yl)methanone

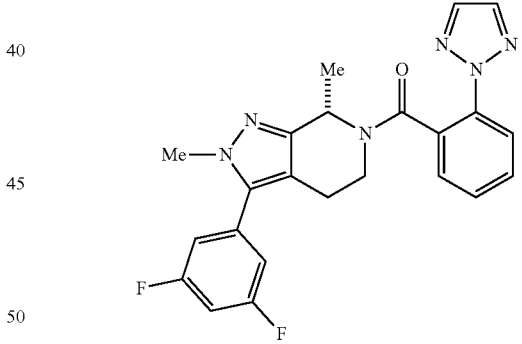

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine and 2-(2H-1,2,3-triazol-2-yl)benzoic acid (Intermediate 64, prepared according to methods described in Pat. Pub. No. WO2016040789, Mar. 17, 2016) instead of 1-naphthoic acid. MS (ESI): mass calcd. for $C_{23}H_{20}F_2N_6O$, 434.2; m/z found, 435.1 [M+H]$^+$. $^1$H NMR (500 MHz, CDCl$_3$) δ 8.10-7.98 (m, 1H), 7.85-7.72 (m, 1.5H), 7.58-7.39 (m, 3.5H), 6.93-6.70 (m, 3H), 5.95-5.76 (m, 0.63H), 5.02-4.72 (m, 0.63H), 3.89-3.72 (m, 2.96H), 3.62-3.52 (m, 0.63H), 3.28-2.80 (m, 1.23H), 2.66-2.42 (m, 0.78H), 2.35-2.26 (m, 0.47H), 2.11-1.85 (m, 0.28H), 1.65-1.41 (m, 3.15H), 1.07-1.03 (m, 0.25H).

Example 148: (3-(3,5-Difluorophenyl)-2,7-dimethyl-2,4,5,7-tetrahydro-6H-pyrazolo[3,4-c]pyridin-6-yl)(1-phenyl-1H-1,2,4-triazol-3-yl)methanone

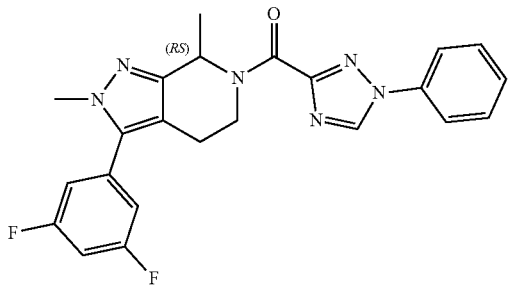 [SMILES: CC1c2nn(C)c(-c3cc(F)cc(F)c3)c2CCN1C(=O)c1ncn(-c2ccccc2)n1]

The title compound was prepared in a manner analogous to Example 106, using 1-phenyl-1H-1,2,4-triazole-3-carboxylic acid instead of quinoline-6-carboxylic acid in Step C. MS (ESI): mass calcd. for $C_{23}H_{20}F_2N_6O$, 434.1; m/z found, 435.1 [M+H]$^+$. $^1$H NMR (500 MHz, DMSO-$d_6$) δ 9.43 (s, 1H), 7.96-7.85 (m, 2H), 7.64-7.54 (m, 2H), 7.54-7.44 (m, 1H), 7.41-7.26 (m, 3H), 5.67-5.13 (m, 1H), 4.72-4.10 (m, 1H), 3.80 (d, J=30.8 Hz, 3H), 3.20-2.72 (m, 2H), 2.47-2.41 (m, 1H), 1.53 (dd, J=32.7, 6.7 Hz, 3H).

Example 149: (S)-(3-(3,5-Difluorophenyl)-2,7-dimethyl-2,4,5,7-tetrahydro-6H-pyrazolo[3,4-c]pyridin-6-yl)(5-ethyl-1-phenyl-1H-1,2,4-triazol-3-yl)methanone

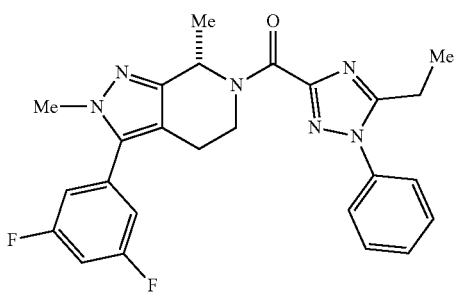 [SMILES: CCc1nc(C(=O)N2CCc3c(nn(C)c3-c3cc(F)cc(F)c3)[C@@H]2C)nn1-c1ccccc1]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine and 5-ethyl-1-phenyl-1H-1,2,4-triazole-3-carboxylic acid instead of 1-naphthoic acid. MS (ESI): mass calcd. for $C_{25}H_{24}F_2N_6O$, 462.2; m/z found, 463.2 [M+H]$^+$. $^1$H NMR (600 MHz, Methanol-$d_4$) δ 7.64-7.54 (m, 5H), 7.12-7.04 (m, 3H), 5.80-5.57 (m, 1H), 4.78-4.76 (m, 0.38H), 4.51-4.45 (m, 0.55H), 3.86-3.78 (m, 3H), 3.50-3.40 (m, 0.6H), 3.32-3.20 (m, 0.48H), 2.95-2.76 (m, 3H), 2.61-2.46 (m, 1H), 1.68-1.57 (m, 3H), 1.35-1.26 (m, 3H).

Example 150: (S)-(3-(3,5-Difluorophenyl)-2,7-dimethyl-2,4,5,7-tetrahydro-6H-pyrazolo[3,4-c]pyridin-6-yl)(1-(2-fluoroethyl)-1H-indol-4-yl)methanone

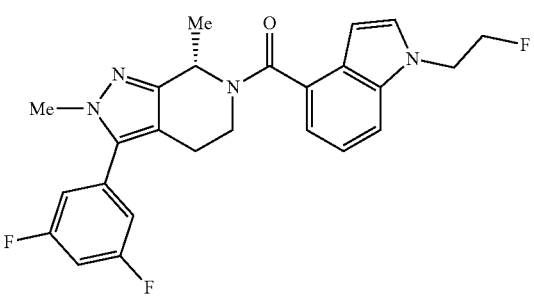 [SMILES: C[C@H]1c2nn(C)c(-c3cc(F)cc(F)c3)c2CCN1C(=O)c1cccc2c1ccn2CCF]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 1-(2-fluoroethyl)-1H-indole-4-carboxylic acid (Intermediate 17) instead of 1-naphthoic acid. MS (ESI): mass calcd. for $C_{25}H_{23}F_3N_4O$, 429.2; m/z found, 430.3 [M+H]$^+$. $^1$H NMR (400 MHz, Methanol-$d_4$) δ 7.51 (d, J=8.3 Hz, 1H), 7.31-7.27 (m, 1H), 7.21 (dd, J=8.3, 7.2 Hz, 1H), 7.10-6.97 (m, 4H), 6.39 (s, 0.6H), 6.25 (s, 0.4H), 5.84 (s, 0.5H), 4.84 (s, 0.5H), 4.72 (t, J=4.6 Hz, 1H), 4.60 (t, J=4.6 Hz, 1H), 4.50 (t, J=4.7 Hz, 1H), 4.43 (t, J=4.6 Hz, 1H), 3.81 (s, 2H), 3.71 (s, 1H), 3.35-3.23 (m, 1H), 2.92-2.74 (m, 1H), 2.58 (m, 1H), 2.30-2.27 (m, 1H), 1.60 (d, J=6.8 Hz, 2H), 1.35 (s, 1H).

Example 151: (S)-(3-(3,5-Difluorophenyl)-2,7-dimethyl-2,4,5,7-tetrahydro-6H-pyrazolo[3,4-c]pyridin-6-yl)(1-(2-(fluoro-$^{18}$F)ethyl)-1H-indol-5-yl)methanone

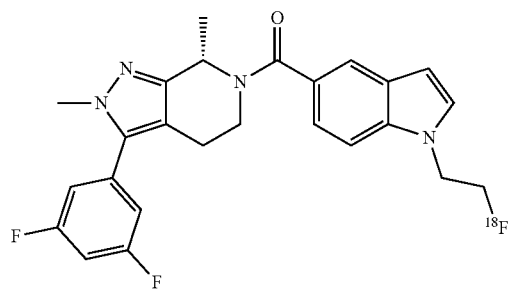 [SMILES: C[C@H]1c2nn(C)c(-c3cc(F)cc(F)c3)c2CCN1C(=O)c1ccc2c(ccn2CC[18F])c1]

Step A: ((S)-3-(3,5-Difluorophenyl)-2,7-dimethyl-2,4,5,7-tetrahydro-6H-pyrazolo[3,4-c]pyridin-6-yl)(1-(2-((tetrahydro-2H-pyran-2-yl)oxy)ethyl)-1H-indol-5-yl)methanone. The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 1-(2-((tetrahydro-2H-pyran-2-yl)oxy)ethyl)-1H-indole-5-carboxylic acid (Intermediate 37) instead of 1-naphthoic acid.

Step B: (S)-(3-(3,5-Difluorophenyl)-2,7-dimethyl-2,4,5,7-tetrahydro-6H-pyrazolo[3,4-c]pyridin-6-yl)(1-(2-hydroxyethyl)-1H-indol-5-yl)methanone. To a solution of ((S)-3-(3,5-difluorophenyl)-2,7-dimethyl-2,4,5,7-tetrahydro-6H-pyrazolo[3,4-c]pyridin-6-yl)(1-(2-((tetrahydro-2H-pyran-2-yl)oxy)ethyl)-1H-indol-5-yl)methanone (150 mg, 0.28 mmol) in methanol (11 mL) was added HCl (1.25M in EtOH, 0.22 mL, 0.28 mmol). The reaction mixture was stirred overnight and then concentrated in vacuo. The residue was taken up in EtOAc and washed with sat. aq NaHCO$_3$. The organic layer was concentrated and used directly in the next step. MS (ESI): mass calcd. for C$_{25}$H$_{24}$F$_2$N$_4$O$_2$, 450.2; m/z found, 451.3 [M+H]$^+$.

Step C: (S)-2-(5-(3-(3,5-Difluorophenyl)-2,7-dimethyl-4,5,6,7-tetrahydro-2H-pyrazolo[3,4-c]pyridine-6-carbonyl)-1H-indol-1-yl)ethyl 4-methylbenzenesulfonate. A solution of (S)-(3-(3,5-difluorophenyl)-2,7-dimethyl-2,4,5,7-tetrahydro-6H-pyrazolo[3,4-c]pyridin-6-yl)(1-(2-hydroxyethyl)-1H-indol-5-yl)methanone (200 mg, 0.80 mmol), 4-methylbenzenesulfonic anhydride (217 mg, 0.67 mmol) and triethylamine (0.19 mL, 1.33 mmol) in DCM (2.8 mL) was stirred at rt for 3 h. The reaction mixture was washed with saturated aqueous NaHCO$_3$ and the organic layer was concentrated in vacuo. Purification (FCC (flash column chromatography), SiO$_2$, MeOH in DCM (0 to 5%) afforded the title compound (60 mg, 22%). MS (ESI): mass calcd. for C$_{32}$H$_{30}$CF$_2$N$_4$O$_4$S, 604.2; m/z found, 605.3 [M+H]$^+$.

Step D: (S)-(3-(3,5-difluorophenyl)-2,7-dimethyl-2,4,5,7-tetrahydro-6H-pyrazolo[3,4-c]pyridin-6-yl)(1-(2-(fluoro-$^{18}$F)ethyl)-1H-indol-5-yl)methanone. [$^{18}$F]fluoride in a shipping vial from PETNET Solutions Inc. (San Diego, Calif. USA) is transferred onto and trapped on an ion exchange cartridge. It is then eluted into the reaction vessel (RV1) of the Synthra RNPlus* module with a solution of potassium carbonate (0.75 mg) and Kryptofix 222 (7.2 mg) in 0.8 mL of acetonitrile/water (6/2, v/v). After the solvent was evaporated under a stream of nitrogen at 85° C. and under vacuum, anhydrous CH$_3$CN (0.5 mL) was added, this process was repeated and the temperature increased to 110° C. for 3.5 min. The reaction vial was then cooled to 70° C. before a solution of 3.0 mg of (S)-2-(5-(3-(3,5-difluorophenyl)-2,7-dimethyl-4,5,6,7-tetrahydro-2H-pyrazolo[3,4-c]pyridine-6-carbonyl)-1H-indol-1-yl)ethyl 4-methylbenzenesulfonate in 0.7 ml anhydrous MeCN was added to reaction vessel. The reaction mixture is heated at 95° C. for 10 min. The reactor is cooled to 40° C. and diluted with water (4.3 mL) and the contents is transferred into the HPLC injector loop for purification. Purification is performed by HPLC using a semi-preparative Eclipse XDB-C18 column (5 μm, 9.4 mm×250 mm) with a mixture of 10 mM NH$_4$OAc and MeCN (50:50 v/v) at a flow rate of 4 mL/min with UV detection at 254 nm. The purified radiotracer solution was diluted with 30 mL of water and passed through a SepPak Light C-18 cartridge. The C-18 cartridge was further washed with 10 mL of water before 0.5 mL EtOH was used to elute the tracer. The tracer solution was further diluted with 4.5 mL of saline. The final formulation contains an ethanol concentration of 10%, suitable for intravenous injection (IV).

Example 152: (S)-(3-(3,5-Difluorophenyl)-2,7-dimethyl-2,4,5,7-tetrahydro-6H-pyrazolo[3,4-c]pyridin-6-yl)(1-(2-fluoroethyl)-1H-pyrrolo[2,3-b]pyridin-4-yl)methanone

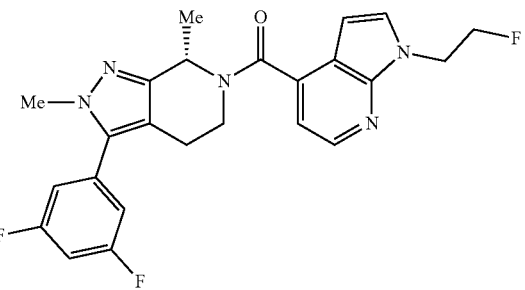

Step A: (S)-(3-(3,5-Difluorophenyl)-2,7-dimethyl-2,4,5,7-tetrahydro-6H-pyrazolo[3,4-c]pyridin-6-yl)(1H-pyrrolo[2,3-b]pyridin-4-yl)methanone. The title compound was prepared in a manner analogous to Example 1 using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 1H-pyrrolo[2,3-b]pyridine-4-carboxylic acid instead of 1-naphthoic acid. MS (ESI): mass calcd. for C$_{22}$H$_{19}$F$_2$N$_5$O, 407.2; m/z found, 408.2 [M+H]$^+$.

Step B: (S)-(3-(3,5-Difluorophenyl)-2,7-dimethyl-2,4,5,7-tetrahydro-6H-pyrazolo[3,4-c]pyridin-6-yl)(1-(2-fluoroethyl)-1H-pyrrolo[2,3-b]pyridin-4-yl)methanone. To an ice-cold solution of (S)-(3-(3,5-difluorophenyl)-2,7-dimethyl-2,4,5,7-tetrahydro-6H-pyrazolo[3,4-c]pyridin-6-yl)(1H-pyrrolo[2,3-b]pyridin-4-yl)methanone (82 mg, 0.2 mmol) in DMF (2 mL) was added NaH (24 mg, 0.6 mmol. 60% in mineral oil). The mixture was stirred at 0° C. for 20 min. To this mixture was added 1-fluoro-2-iodoethane (52 mg, 0.3 mmol) and the reaction was stirred at rt for 30 min. The reaction was quenched by adding 2 g of dry ice and 3 drops of water and then diluted with ether (30 mL). The mixture was washed with brine (3×20 mL) and the organic layer was dried over Na$_2$SO$_4$ and concentrated. The crude product was purified by silica chromatography (0 to 5% MeOH in DCM) to afford the title compound as a clear oil. MS (ESI): mass calcd. for C$_{24}$H$_{22}$F$_3$N$_5$O, 453.2; m/z found, 454.3 [M+H]$^+$. $^1$H NMR (400 MHz, CDCl$_3$) δ 8.39 (d, J=4.9 Hz, 1H), 7.40 (m, 1H), 7.13 (d, J=4.9 Hz, 1H), 6.85-6.84 (m, 3H), 6.53-6.45 (m, 1H), 6.01 (d, J=7.0 Hz, 0.5H), 5.03 (d, J=13.8 Hz, 0.5H), 4.87 (t, J=4.7 Hz, 1H), 4.76-4.72 (m, 2H), 4.66 (t, J=4.4 Hz, 1H), 3.89-3.79 (m, 3H), 3.88-3.62 (m, 1H), 3.38-3.07 (m, 1H), 2.70-2.54 (m, 1H), 2.41-2.26 (m, 1H), 1.70 (d, J=6.8 Hz, 1.8H), 1.46 (d, J=6.5 Hz, 1.2H).

Example 153: (S)-(3-(3,5-Difluorophenyl)-2,7-dimethyl-2,4,5,7-tetrahydro-6H-pyrazolo[3,4-c]pyridin-6-yl)(furo[3,2-b]pyridin-6-yl)methanone

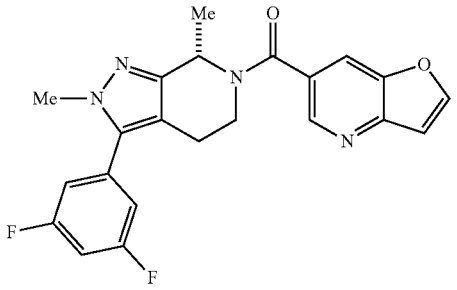 [SMILES: C[C@H]1c2nn(C)c(-c3cc(F)cc(F)c3)c2CCN1C(=O)c1cnc2ccoc2c1]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine and furo[3,2-b]pyridine-6-carboxylic acid instead of 1-naphthoic acid. MS (ESI): mass calcd. for $C_{22}H_{18}F_2N_4O_2$, 408.1; m/z found, 409.1 [M+H]$^+$. $^1$H NMR (500 MHz, CDCl$_3$) δ 8.67 (d, J=1.7 Hz, 1H), 7.95 (d, J=2.3 Hz, 1H), 7.89 (s, 1H), 7.04 (dd, J=2.3, 1.0 Hz, 1H), 6.93-6.84 (m, 3H), 5.86 (s, 0.4H), 5.17-4.64 (m, 0.68H), 3.83 (s, 3.62H), 3.49-3.05 (m, 1H), 2.96-2.38 (m, 2H), 1.62 (s, 3.3H).

Example 154: (R)-(3-(3,5-Difluorophenyl)-2,7-dimethyl-2,4,5,7-tetrahydro-6H-pyrazolo[3,4-c]pyridin-6-yl)(furo[3,2-b]pyridin-6-yl)methanone

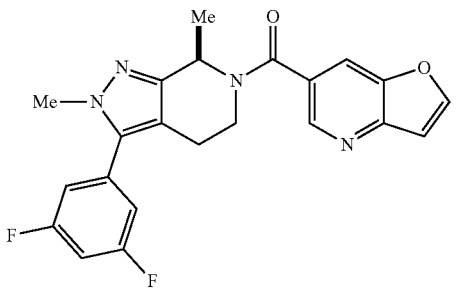 [SMILES: C[C@@H]1c2nn(C)c(-c3cc(F)cc(F)c3)c2CCN1C(=O)c1cnc2ccoc2c1]

The title compound was prepared in a manner analogous to Example 1, using (R)-3-(3,5-difluorophenyl)-2,7-dimethyl-4,5,6,7-tetrahydro-2H-pyrazolo[3,4-c]pyridine (Intermediate 9) instead of 2-methyl-3-phenyl-4,5,6,7-tetrahydro-2H-pyrazolo[3,4-c]pyridine and furo[3,2-b]pyridine-6-carboxylic acid instead of 1-naphthoic acid. MS (ESI): mass calcd. for $C_{22}H_{18}F_2N_4O_2$, 408.1; m/z found, 409.1 [M+H]$^+$. $^1$H NMR (500 MHz, CDCl$_3$) δ 8.67 (d, J=1.7 Hz, 1H), 7.95 (d, J=2.3 Hz, 1H), 7.89 (s, 1H), 7.04 (dd, J=2.3, 1.0 Hz, 1H), 6.93-6.84 (m, 3H), 5.86 (s, 0.4H), 5.17-4.64 (m, 0.68H), 3.83 (s, 3.62H), 3.49-3.05 (m, 1H), 2.96-2.38 (m, 2H), 1.62 (s, 3.3H).

Example 155: (2-(Difluoromethyl)-3-(3,5-difluorophenyl)-7-methyl-2,4,5,7-tetrahydro-6H-pyrazolo[3,4-c]pyridin-6-yl)(quinolin-6-yl)methanone

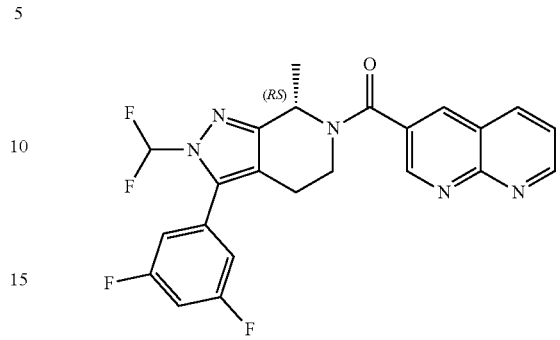

The title compound was prepared in a manner analogous to Example 1, using 2-(difluoromethyl)-3-(3,5-difluorophenyl)-7-methyl-4,5,6,7-tetrahydro-2H-pyrazolo[3,4-c]pyridine (Intermediate 32) instead of 2-methyl-3-phenyl-4,5,6,7-tetrahydro-2H-pyrazolo[3,4-c]pyridine, and quinoline-6-carboxylic acid instead of 1-naphthoic acid. MS (ESI): mass calcd. for $C_{24}H_{18}F_4N_4O$, 454.1; m/z found, 455.1 [M+H]$^+$. $^1$H NMR (500 MHz, DMSO-d$_6$) δ 8.99 (dd, J=4.2, 1.8 Hz, 1H), 8.53-8.43 (m, 1H), 8.20-8.05 (m, 2H), 7.94-7.71 (m, 2H), 7.62 (dd, J=8.3, 4.2 Hz, 1H), 7.52-7.42 (m, 1H), 7.34-7.25 (m, 2H), 5.74 (s, 1H), 4.79 (d, J=95.0 Hz, 1H), 3.92 (d, J=185.0 Hz, 1H), 2.92 (s, 1H), 2.48-2.30 (m, 1H), 1.57 (d, J=6.8 Hz, 3H).

Example 156: (3-(3,5-Difluorophenyl)-7-methyl-2-(trifluoromethyl)-2,4,5,7-tetrahydro-6H-pyrazolo[3,4-c]pyridin-6-yl)(quinolin-6-yl)methanone

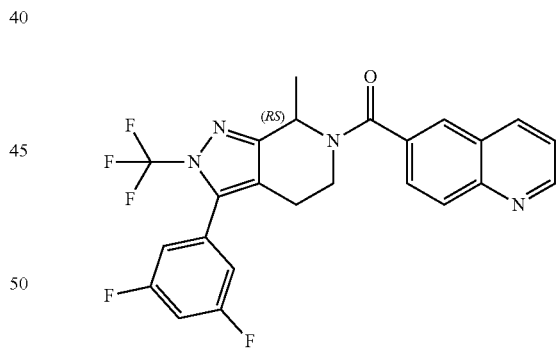

The title compound was prepared in a manner analogous to Example 1, using 3-(3,5-difluorophenyl)-7-methyl-2-(trifluoromethyl)-4,5,6,7-tetrahydro-2H-pyrazolo[3,4-c]pyridine (Intermediate 35) instead of 2-methyl-3-phenyl-4,5,6,7-tetrahydro-2H-pyrazolo[3,4-c]pyridine, and quinoline-6-carboxylic acid instead of 1-naphthoic acid. MS (ESI): mass calcd. for $C_{24}H_{17}F_5N_4O$, 472.1; m/z found, 473.1 [M+H]$^+$. $^1$H NMR (500 MHz, DMSO-d$_6$) δ 8.98 (dd, J=4.2, 1.7 Hz, 1H), 8.48 (dd, J=8.4, 1.7 Hz, 1H), 8.18-8.02 (m, 2H), 7.81 (dd, J=8.6, 2.0 Hz, 1H), 7.62 (dd, J=8.3, 4.2 Hz, 1H), 7.57-7.42 (m, 1H), 7.41-7.29 (m, 2H), 5.76 (s, 1H), 3.65 (d, J=72.5 Hz, 1H), 3.98-3.48 (m, 1H), 2.83 (s, 1H), 2.48-2.28 (m, 1H), 1.57 (d, J=6.9 Hz, 3H).

Example 157: (3-(3,5-Difluorophenyl)-7-methyl-2-(methyl-d3)-2,4,5,7-tetrahydro-6H-pyrazolo[3,4-c]pyridin-6-yl)(quinolin-6-yl)methanone

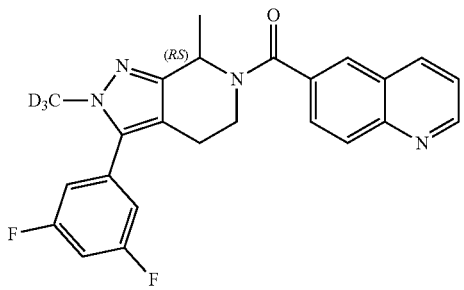 [SMILES: [2H]C([2H])([2H])n1nc2c(c1-c1cc(F)cc(F)c1)CCN(C(=O)c1ccc3ncccc3c1)C2C]

The title compound was prepared in a manner analogous to Example 1, using racemic 3-(3,5-difluorophenyl)-7-methyl-2-(methyl-d3)-4,5,6,7-tetrahydro-2H-pyrazolo[3,4-c]pyridine (Intermediate 31) instead of 2-methyl-3-phenyl-4,5,6,7-tetrahydro-2H-pyrazolo[3,4-c]pyridine, and quinoline-6-carboxylic acid instead of 1-naphthoic acid. MS (ESI): mass calcd. for $C_{24}H_{17}D_3F_2N_4O$, 421.1; m/z found, 422.1 [M+H]$^+$. $^1$H NMR (500 MHz, DMSO-d$_6$) δ 8.98 (dd, J=4.2, 1.7 Hz, 1H), 8.57-8.40 (m, 1H), 8.17-8.07 (m, 2H), 7.80 (d, J=8.9 Hz, 1H), 7.62 (dd, J=8.3, 4.2 Hz, 1H), 7.43-7.24 (m, 3H), 5.63 (s, 1H), 4.70 (s, 1H), 3.77 (d, J=75.2 Hz, 1H), 2.91 (s, 1H), 2.47-2.29 (m, 1H), 1.51 (s, 3H).

Example 158: (R)-(3-(3,5-Difluorophenyl)-2,7-dimethyl-2,4,5,7-tetrahydro-6H-pyrazolo[3,4-c]pyridin-6-yl)(quinolin-6-yl)methanone

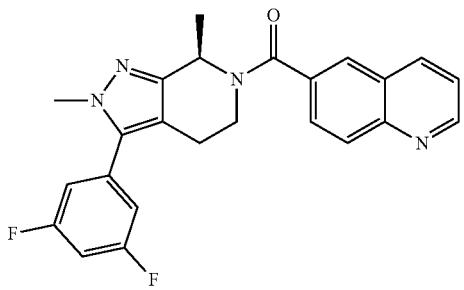

The title compound was obtained as a single enantiomer by Chiral SFC purification (Whelk 01 SS 5 μm 250×20 mm, Mobile phase: 45% methanol, 55% CO$_2$) of (3-(3,5-difluorophenyl)-2,7-dimethyl-2,4,5,7-tetrahydro-6H-pyrazolo[3,4-c]pyridin-6-yl)(quinolin-6-yl)methanone (Example 106) to provide the title compound (retention time=11.3 min). MS (ESI): mass calcd. for $C_{24}H_{20}F_2N_4O$, 418.1; m/z found, 419.1 [M+H]$^+$. $^1$H NMR (500 MHz, DMSO-d$_6$) δ 8.98 (dd, J=4.2, 1.8 Hz, 1H), 8.49 (dd, J=8.3, 1.7 Hz, 1H), 8.16-8.06 (m, 2H), 7.80 (d, J=8.3 Hz, 1H), 7.62 (dd, J=8.3, 4.2 Hz, 1H), 7.46-7.23 (m, 3H), 5.69 (d, J=63.7 Hz, 1H), 4.75 (s, 1H), 3.85 (s, 3H), 3.71 (s, 1H), 2.91 (s, 1H), 2.35 (s, 1H), 1.51 (s, 3H).

Example 159: (S)-(3-(3,5-Difluorophenyl)-2,7-dimethyl-2,4,5,7-tetrahydro-6H-pyrazolo[3,4-c]pyridin-6-yl)(quinolin-6-yl)methanone

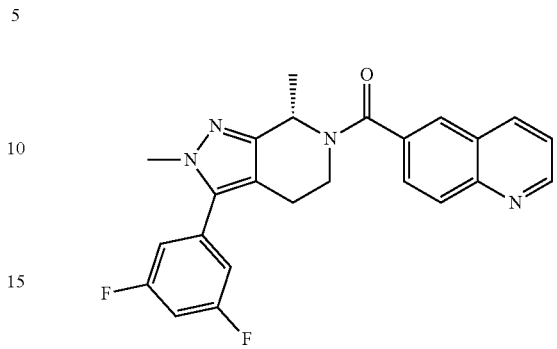

The title compound was obtained as a single enantiomer by Chiral SFC purification (Whelk 01 SS 5 μm 250×20 mm, Mobile phase: 45% methanol, 55% CO$_2$) of (3-(3,5-difluorophenyl)-2,7-dimethyl-2,4,5,7-tetrahydro-6H-pyrazolo[3,4-c]pyridin-6-yl)(quinolin-6-yl)methanone (Example 106) to provide the title compound (retention time=14.5 min). MS (ESI): mass calcd. for $C_{24}H_{20}F_2N_4O$, 418.1; m/z found, 419.1 [M+H]$^+$. $^1$H NMR (500 MHz, DMSO-d$_6$) δ 8.98 (dd, J=4.2, 1.8 Hz, 1H), 8.54-8.41 (m, 1H), 8.16-8.04 (m, 2H), 7.80 (d, J=8.7 Hz, 1H), 7.62 (dd, J=8.3, 4.2 Hz, 1H), 7.43-7.26 (m, 3H), 5.63 (s, 1H), 4.73 (s, 1H), 3.85 (s, 3H), 3.71 (s, 1H), 2.91 (s, 1H), 2.36 (S, 1H), 1.51 (s, 3H).

Example 160: (3-(3,5-Difluorophenyl)-2,7-dimethyl-2,4,5,7-tetrahydro-6H-pyrazolo[3,4-c]pyridin-6-yl)(isoquinolin-3-yl)methanone

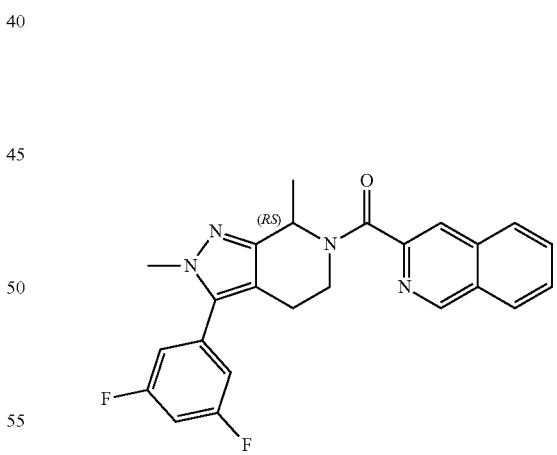

The title compound was prepared in a manner analogous to Example 106, using isoquinoline-3-carboxylic acid instead of quinoline-6-carboxylic acid in Step C. MS (ESI): mass calcd. for $C_{24}H_{20}F_2N_4O$, 418.1; m/z found, 419.1 [M+H]$^+$. $^1$H NMR (500 MHz, DMSO-d$_6$) δ 9.37 (d, J=5.9 Hz, 1H), 8.22 (d, J=8.2 Hz, 1H), 8.17-8.06 (m, 2H), 7.92-7.74 (m, 2H), 7.32 (dd, J=29.8, 7.5 Hz, 3H), 4.87 (dd, J=157.2, 8.6 Hz, 1H), 3.84 (s, 3H), 3.75 (s, 1H), 3.21-2.74 (m, 2H), 2.33 (s, 1H), 1.51 (t, J=8.7 Hz, 3H).

Example 161: (3-(3,5-Difluorophenyl)-2,7-dimethyl-2,4,5,7-tetrahydro-6H-pyrazolo[3,4-c]pyridin-6-yl)(isoquinolin-7-yl)methanone

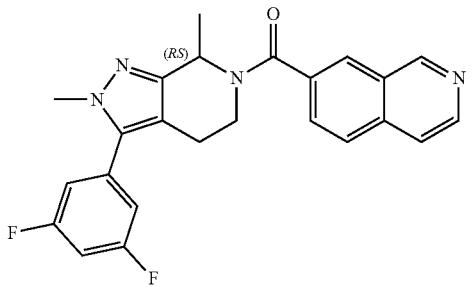 [SMILES: CC1c2nn(C)c(-c3cc(F)cc(F)c3)c2CCN1C(=O)c1ccc2ccncc2c1]

The title compound was prepared in a manner analogous to Example 106, using isoquinoline-7-carboxylic acid instead of quinoline-6-carboxylic acid in Step C. MS (ESI): mass calcd. for $C_{24}H_{20}F_2N_4O$, 418.1; m/z found, 419.1 [M+H]$^+$. $^1$H NMR (500 MHz, DMSO-$d_6$) δ 9.43 (d, J=1.0 Hz, 1H), 8.58 (d, J=5.7 Hz, 1H), 8.24 (s, 1H), 8.08 (d, J=8.5 Hz, 1H), 7.94-7.75 (m, 2H), 7.42-7.22 (m, 3H), 5.69-5.53 (m, 1H), 4.72 (s, 1H), 3.85 (s, 3H), 3.68 (s, 1H), 3.04 (d, J=127.6 Hz, 2H), 1.51 (s, 3H).

Example 162: (4-Bromoquinolin-6-yl)(3-(3,5-difluorophenyl)-2,7-dimethyl-2,4,5,7-tetrahydro-6H-pyrazolo[3,4-c]pyridin-6-yl)methanone

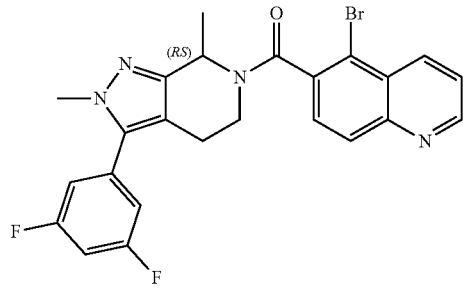 [SMILES: CC1c2nn(C)c(-c3cc(F)cc(F)c3)c2CCN1C(=O)c1ccc2ncccc2c1Cl]

The title compound was prepared in a manner analogous to Example 106, using 4-bromoquinoline-6-carboxylic acid instead of quinoline-6-carboxylic acid in Step C. MS (ESI): mass calcd. for $C_{24}H_{19}BrF_2N_4O$, 496.1; m/z found, 497.1 [M+H]$^+$. $^1$H NMR (500 MHz, DMSO-$d_6$) δ 8.81 (d, J=4.7 Hz, 1H), 8.24-8.14 (m, 2H), 8.04 (d, J=4.7 Hz, 1H), 7.92 (d, J=8.6 Hz, 1H), 7.44-7.23 (m, 3H), 5.60 (d, J=30.1 Hz, 1H), 4.73 (s, 1H), 3.80 (d, J=43.7 Hz, 3H), 3.65 (s, 1H), 2.96-2.79 (m, 1H), 2.39 (s, 1H), 1.53 (d, J=6.7 Hz, 3H).

Example 163: (5-Chloroquinolin-6-yl)(3-(3,5-difluorophenyl)-2,7-dimethyl-2,4,5,7-tetrahydro-6H-pyrazolo[3,4-c]pyridin-6-yl)methanone

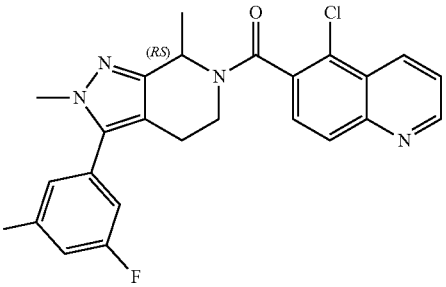

The title compound was prepared in a manner analogous to Example 106, using 5-chloroquinoline-6-carboxylic acid instead of quinoline-6-carboxylic acid in Step C. MS (ESI): mass calcd. for $C_{24}H_{19}ClF_2N_4O$, 452.1; m/z found, 453.1 [M+H]$^+$. $^1$H NMR (500 MHz, DMSO-$d_6$) δ 9.15-9.02 (m, 1H), 8.79-8.55 (m, 1H), 8.23-8.08 (m, 1H), 7.91-7.71 (m, 2H), 7.46-7.16 (m, 3H), 5.75-5.65 (m, 1H), 4.88-4.47 (m, 1H), 3.88-3.73 (m, 3H), 3.21-2.64 (m, 2H), 2.45-2.18 (m, 1H), 1.58-1.30 (m, 3H).

Example 164: (S)-(3-(3,5-Difluorophenyl)-2,7-dimethyl-2,4,5,7-tetrahydro-6H-pyrazolo[3,4-c]pyridin-6-yl)(8-(trifluoromethyl)quinolin-6-yl)methanone

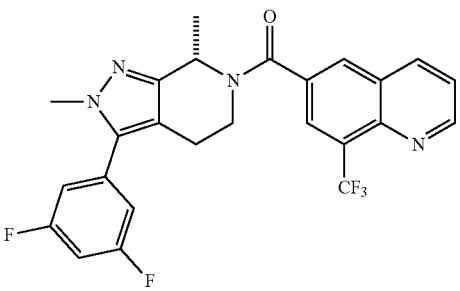 [SMILES: C[C@H]1c2nn(C)c(-c3cc(F)cc(F)c3)c2CCN1C(=O)c1cc(C(F)(F)F)c2ncccc2c1]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 3-(trifluoromethyl)quinoline-6-carboxylic acid (Intermediate 23) instead of 1-naphthoic acid. MS (ESI): mass calcd. for $C_{25}H_{19}F_5N_4O$, 486.1; m/z found, 487.1 [M+H]$^+$. $^1$H NMR (500 MHz, CDCl$_3$) δ 9.14 (dd, J=4.2, 1.8 Hz, 1H), 8.27 (d, J=8.0 Hz, 1H), 8.18-8.09 (m, 2H), 7.58 (dd, J=8.3, 4.2 Hz, 1H), 6.94-6.85 (m, 3H), 5.90 (s, 0.51H), 4.93 (s, 0.81H), 3.83 (s, 3.68H), 3.52-3.07 (m, 1H), 3.03-2.65 (m, 1H), 2.49 (s, 1H), 1.64 (s, 3H).

Example 165: (S)-(3-(3,5-Difluorophenyl)-2,7-dimethyl-2,4,5,7-tetrahydro-6H-pyrazolo[3,4-c]pyridin-6-yl)(3-(trifluoromethyl)quinolin-6-yl)methanone

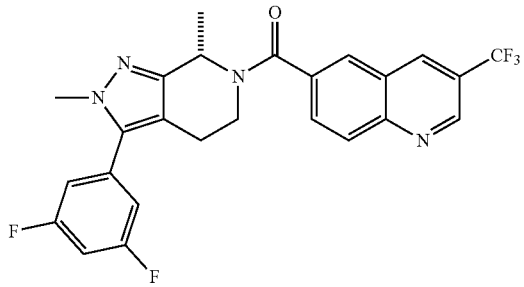 [SMILES: C[C@H]1c2nn(C)c(-c3cc(F)cc(F)c3)c2CCN1C(=O)c1ccc2ncc(C(F)(F)F)cc2c1]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine and 3-(trifluoromethyl)quinoline-6-carboxylic acid (Intermediate 24) instead of 1-naphthoic acid. MS (ESI): mass calcd. for $C_{25}H_{19}F_5N_4O$, 486.1; m/z found, 487.1 [M+H]$^+$. $^1$H NMR (500 MHz, CDCl$_3$) δ 9.16 (d, J=2.2 Hz, 1H), 8.48 (s, 1H), 8.26 (d, J=8.6 Hz, 1H), 8.02 (d, J=1.8 Hz, 1H), 7.90 (dd, J=8.7, 1.8 Hz, 1H), 6.93-6.83 (m, 3H), 5.91 (s, 0.5H), 4.94 (s, 0.81H), 3.96-3.74 (m, 3.69H), 3.49-2.35 (m, 3H), 1.74-1.47 (m, 3H).

Example 166: (S)-(3-(3,5-Difluorophenyl)-2,7-dimethyl-2,4,5,7-tetrahydro-6H-pyrazolo[3,4-c]pyridin-6-yl)(3-(2-fluoroethoxy)quinolin-6-yl)methanone

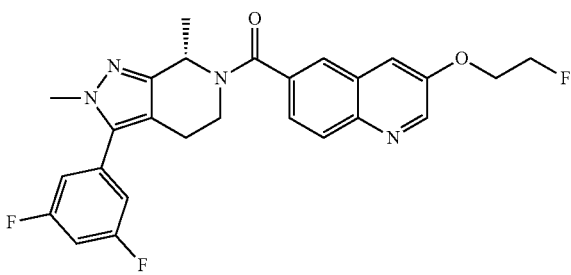 [SMILES: C[C@H]1c2nn(C)c(-c3cc(F)cc(F)c3)c2CCN1C(=O)c1ccc2ncc(OCCF)cc2c1]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine, and 3-(2-fluoroethoxy)quinoline-6-carboxylic acid (Intermediate 18) instead of 1-naphthoic acid. MS (ESI): mass calcd. for $C_{26}H_{23}F_3N_4O_2$, 480.2; m/z found, 481.3 [M+H]$^+$. $^1$H NMR (400 MHz, CDCl$_3$) δ 8.80 (d, J=2.9 Hz, 1H), 8.21 (d, J=8.6 Hz, 1H), 7.87 (d, J=1.9 Hz, 1H), 7.65 (dd, J=8.6, 1.8 Hz, 1H), 7.52 (d, J=2.8 Hz, 1H), 6.93-6.88 (m, 3H), 5.91 (s, 0.5H), 4.98 (s, 0.5H), 4.98-4.89 (m, 1H), 4.86-4.77 (m, 1H), 4.44 (dd, J=5.4, 2.9 Hz, 1H), 4.37 (dd, J=5.2, 3.0 Hz, 1H), 3.85 (m, 3H), 3.42-2.66 (m, 3H), 2.56 (m, 1H), 1.63 (s, 3H).

Example 167: (3-(3,5-Difluorophenyl)-2,7-dimethyl-2,4,5,7-tetrahydro-6H-pyrazolo[3,4-c]pyridin-6-yl)(quinoxalin-6-yl)methanone

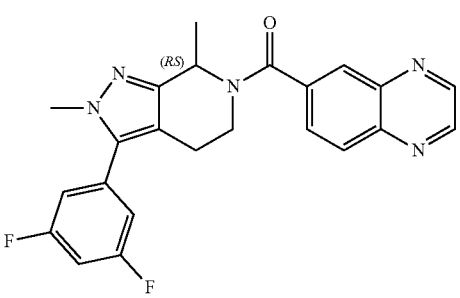 [SMILES: CC1c2nn(C)c(-c3cc(F)cc(F)c3)c2CCN1C(=O)c1ccc2nccnc2c1]

The title compound was prepared in a manner analogous to Example 106, using quinoxaline-6-carboxylic acid instead of quinoline-6-carboxylic acid in Step C. MS (ESI): mass calcd. for $C_{23}H_{19}F_2N_5O$, 419.1; m/z found, 420.1 [M+H]$^+$. $^1$H NMR (500 MHz, DMSO-d$_6$) δ 7.97-7.85 (m, 2H), 7.68-7.59 (m, 2H), 7.55-7.42 (m, 1H), 7.39-7.25 (m, 3H), 5.60 (q, J=6.7 Hz, 0.6H), 5.20 (q, J=6.7 Hz, 0.4H), 4.75-4.61 (m, 0.4H), 4.13 (dd, J=13.7, 4.9 Hz, 0.6H), 3.80 (d, J=30.8 Hz, 3H), 3.11 (td, J=12.7, 4.0 Hz, 1H), 2.92-2.71 (m, 1H), 2.50-2.31 (m, 1H), 1.53 (dd, J=32.7, 6.7 Hz, 3H).

Example 168: (S)-(3-(3,5-Difluorophenyl)-2,7-dimethyl-2,4,5,7-tetrahydro-6H-pyrazolo[3,4-c]pyridin-6-yl)(quinoxalin-6-yl)methanone

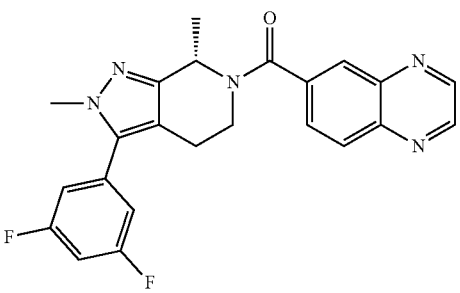 [SMILES: C[C@H]1c2nn(C)c(-c3cc(F)cc(F)c3)c2CCN1C(=O)c1ccc2nccnc2c1]

The title compound was obtained as a single enantiomer by Chiral SFC purification of racemic (3-(3,5-difluorophenyl)-2,7-dimethyl-2,4,5,7-tetrahydro-6H-pyrazolo[3,4-c]pyridin-6-yl)(quinoxalin-6-yl)methanone, Example 167: (Chiralcel OX 5 um 250×20 mm, Mobile phase: 30% isopropanol, 70% CO$_2$; 11.1 min retention time). MS (ESI): mass calcd. for $C_{23}H_{19}F_2N_5O$, 419.1; m/z found, 420.1 [M+H]$^+$. $^1$H NMR (500 MHz, DMSO-d$_6$) δ 9.04 (s, 2H), 8.27-8.08 (m, 2H), 7.91 (d, J=8.8 Hz, 1H), 7.42-7.22 (m, 3H), 5.65 (s, 1H), 5.04-4.34 (m, 1H), 3.80 (d, J=49.4 Hz, 3H), 3.67 (d, J=13.5 Hz, 1H), 2.91 (s, 1H), 2.33 (d, J=15.6 Hz, 1H), 1.53 (d, J=6.8 Hz, 3H).

Example 169: (R)-(3-(3,5-Difluorophenyl)-2,7-dimethyl-2,4,5,7-tetrahydro-6H-pyrazolo[3,4-c]pyridin-6-yl)(quinoxalin-6-yl)methanone

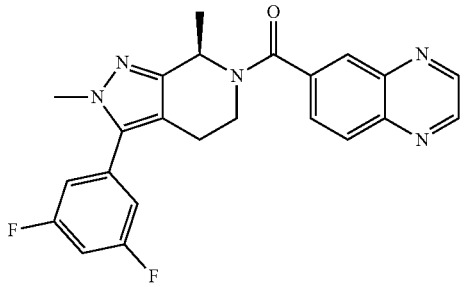

The title compound was obtained as a single enantiomer by Chiral SFC purification of racemic (3-(3,5-difluorophenyl)-2,7-dimethyl-2,4,5,7-tetrahydro-6H-pyrazolo[3,4-c]pyridin-6-yl)(quinoxalin-6-yl)methanone, Example 167: (Chiralcel OX 5 um 250×20 mm, Mobile phase: 30% isopropanol, 70% $CO_2$; 9.6 min retention time). MS (ESI): mass calcd. for $C_{23}H_{19}F_2N_5O$, 419.1; m/z found, 420.1 [M+H]$^+$. $^1$H NMR (500 MHz, DMSO-$d_6$) δ 7.97-7.85 (m, 2H), 7.68-7.59 (m, 2H), 7.55-7.42 (m, 1H), 7.39-7.25 (m, 3H), 5.60 (q, J=6.7 Hz, 0.6H), 5.20 (q, J=6.7 Hz, 0.4H), 4.75-4.61 (m, 0.4H), 4.13 (dd, J=13.7, 4.9 Hz, 0.6H), 3.80 (d, J=30.8 Hz, 3H), 3.11 (td, J=12.7, 4.0 Hz, 1H), 2.92-2.71 (m, 1H), 2.50-2.31 (m, 1H), 1.53 (dd, J=32.7, 6.7 Hz, 3H).

Example 170: (S)-(3-(3,5-Difluorophenyl)-2,7-dimethyl-2,4,5,7-tetrahydro-6H-pyrazolo[3,4-c]pyridin-6-yl)(1,5-naphthyridin-2-yl)methanone

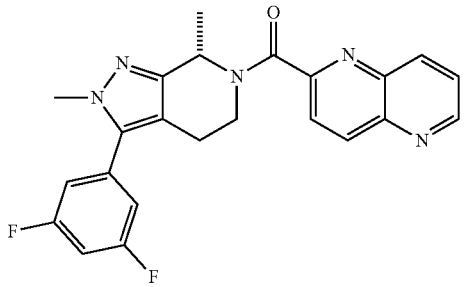 [SMILES: C[C@H]1c2nn(C)c(-c3cc(F)cc(F)c3)c2CCN1C(=O)c1ccc2ncccc2n1]

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine and 1,5-naphthyridine-2-carboxylic acid instead of 1-naphthoic acid. MS (ESI): mass calcd. for $C_{23}H_{19}F_2N_5O$, 419.2; m/z found, 420.2 [M+H]$^+$. $^1$H NMR (500 MHz, CDCl$_3$) δ 9.07-9.02 (m, 1H), 8.55-8.41 (m, 2H), 7.99 (dd, J=8.7, 2.7 Hz, 1H), 7.73-7.67 (m, 1H), 6.93-6.85 (m, 3H), 6.02-5.28 (m, 1H), 5.00-4.06 (m, 1H), 3.91-3.74 (m, 3H), 3.40-3.13 (m, 1H), 3.11-2.87 (m, 1H), 2.62-2.36 (m, 1H), 1.77-1.65 (m, 3H).

Example 171: (S)-(3-(3,5-Difluorophenyl)-2,7-dimethyl-2,4,5,7-tetrahydro-6H-pyrazolo[3,4-c]pyridin-6-yl)(7-fluoroquinoxalin-6-yl)methanone

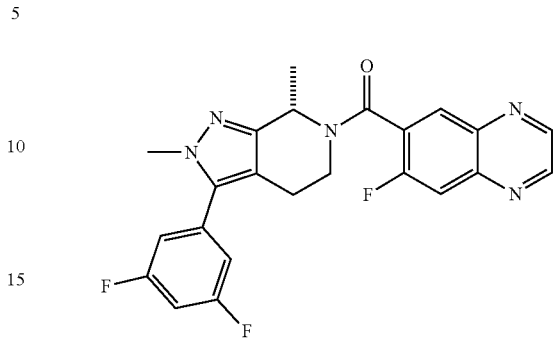

The title compound was prepared in a manner analogous to Example 1, using (S)-3-(3,5-difluorophenyl)-2,7-dimethyl-4,5,6,7-tetrahydro-2H-pyrazolo[3,4-c]pyridine (Intermediate 39) instead of 2-methyl-3-phenyl-4,5,6,7-tetrahydro-2H-pyrazolo[3,4-c]pyridine and 7-fluoroquinoxaline-6-carboxylic acid instead of 1-naphthoic acid. MS (ESI): mass calcd. for $C_{23}H_{18}F_3N_5O$, 437.1; m/z found, 438.2 [M+H]$^+$. $^1$H NMR (500 MHz, CDCl$_3$) δ 8.91-8.85 (m, 2H), 8.16 (s, 1H), 7.84 (d, J=9.4 Hz, 1H), 6.93-6.83 (m, 3H), 6.02-5.93 (m, 0.6H), 5.00 (dd, J=13.1, 5.3 Hz, 0.42H), 4.88-4.77 (m, 0.38H), 3.92-3.75 (m, 3H), 3.64 (dd, J=13.9, 5.2 Hz, 0.61H), 3.47-3.09 (m, 1H), 2.96-2.29 (m, 2H), 1.69-1.47 (m, 3H).

Example 172: (S)-(3-(3,5-Dichlorophenyl)-2,7-dimethyl-2,4,5,7-tetrahydro-6H-pyrazolo[3,4-c]pyridin-6-yl)(2-methylbenzo[d]oxazol-6-yl)methanone

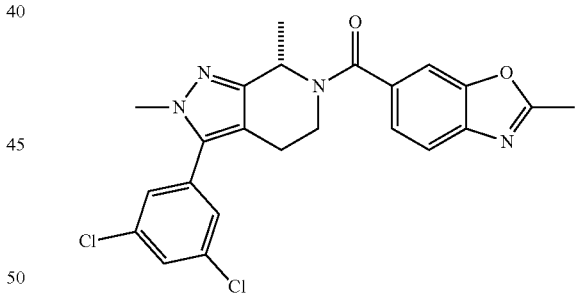

The title compound was prepared in a manner analogous to Example 106, using 3,5-dichlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 2-methylbenzo[d]oxazole-6-carboxylic acid instead of quinoline 6-carboxylic acid in Step C. MS (ESI): mass calcd. for $C_{23}H_{2}Cl_{12}N_4O_2$, 454.1; m/z found, 455.0 [M+H]$^+$. $^1$H NMR (600 MHz, Methanol-$d_4$) δ 7.75-7.69 (m, 2H), 7.57-7.55 (m, 1H), 7.48-7.43 (m, 3H), 5.74 (s, 0.63H), 3.82 (s, 3.86H), 3.44-3.35 (m, 1.19H), 2.87-2.76 (m, 1H), 2.68 (s, 3.15H), 2.43 (s, 1H), 1.59 (s, 3.18H).

Example 173: (S)-(3-(3,5-Dichlorophenyl)-2,7-dimethyl-2,4,5,7-tetrahydro-6H-pyrazolo[3,4-c]pyridin-6-yl)(1-methyl-1H-pyrazolo[3,4-b]pyridin-3-yl)methanone

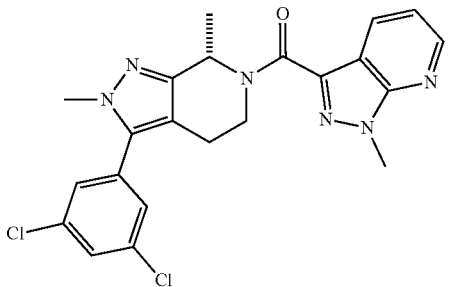 [SMILES: C[C@H]1c2nn(C)c(-c3cc(Cl)cc(Cl)c3)c2CCN1C(=O)c1nn(C)c2ncccc12]

The title compound was prepared in a manner analogous to Example 106, using 3,5-dichlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 1-methyl-1H-pyrazolo[3,4-b]pyridine-3-carboxylic acid instead of quinoline 6-carboxylic acid in Step C. MS (ESI): mass calcd. for $C_{22}H_{20}Cl_2N_6O$, 454.1; m/z found, 455.0 [M+H]$^+$. $^1$H NMR (500 MHz, CDCl$_3$) δ 8.61-8.53 (m, 2H), 7.42 (t, J=1.9 Hz, 1H), 7.26 (s, 3H), 6.44-5.87 (m, 1H), 5.30-4.90 (m, 1H), 4.21 (s, 3H), 3.90-3.76 (m, 3H), 3.46-3.11 (m, 1H), 3.04-2.82 (m, 1H), 2.57-2.47 (m, 1H), 1.83-1.62 (m, 3H).

Example 174: (S)-(3-(3,5-Dichlorophenyl)-2,7-dimethyl-2,4,5,7-tetrahydro-6H-pyrazolo[3,4-c]pyridin-6-yl)(quinolin-6-yl)methanone

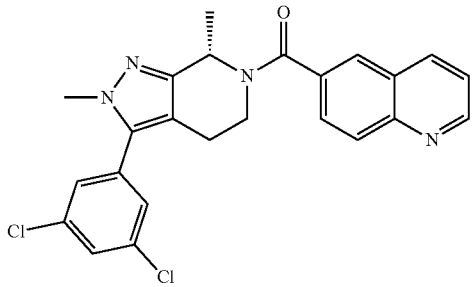 [SMILES: C[C@H]1c2nn(C)c(-c3cc(Cl)cc(Cl)c3)c2CCN1C(=O)c1ccc2ncccc2c1]

The title compound was prepared in a manner analogous to Example 106, using 3,5-dichlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A. MS (ESI): mass calcd. for $C_{24}H_{20}Cl_2N_4O$, 450.1; m/z found, 451.1 [M+H]$^+$. $^1$H NMR (600 MHz, CDCl$_3$) δ 8.98 (dd, J=4.2, 1.7 Hz, 1H), 8.23-8.14 (m, 2H), 7.93 (d, J=1.8 Hz, 1H), 7.76 (dd, J=8.6, 1.9 Hz, 1H), 7.50-7.41 (m, 2H), 7.23 (d, J=1.9 Hz, 2H), 5.91 (s, 0.54H), 5.15-4.78 (m, 0.82H), 3.82 (s, 3.61H), 3.45-2.30 (m, 3.06H), 1.73-1.49 (m, 3H).

Example 175: (S)-(3-(3,5-Dichlorophenyl)-2,7-dimethyl-2,4,5,7-tetrahydro-6H-pyrazolo[3,4-c]pyridin-6-yl)(quinoxalin-6-yl)methanone

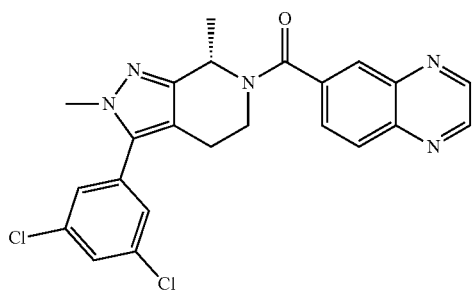 [SMILES: C[C@H]1c2nn(C)c(-c3cc(Cl)cc(Cl)c3)c2CCN1C(=O)c1ccc2nccnc2c1]

The title compound was prepared in a manner analogous to Example 106, using 3,5-dichlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{23}H_{19}Cl_2N_5O$, 451.1; m/z found, 452.0 [M+H]$^+$. $^1$H NMR (500 MHz, DMSO-d$_6$) δ 9.04 (s, 2H), 8.23-8.10 (m, 2H), 7.97-7.83 (m, 1H), 7.71 (s, 1H), 7.62 (d, J=1.9 Hz, 2H), 5.65 (s, 0.74H), 4.72 (s, 0.46H), 3.89-3.62 (m, 3.77H), 3.33-3.05 (m, 1.23H), 2.98-2.76 (m, 1H), 2.38-2.23 (m, 0.8H), 1.60-1.39 (m, 3H).

Example 176: (S)-(3-(3,5-Dichlorophenyl)-2,7-dimethyl-2,4,5,7-tetrahydro-6H-pyrazolo[3,4-c]pyridin-6-yl)(2-methylquinoxalin-6-yl)methanone

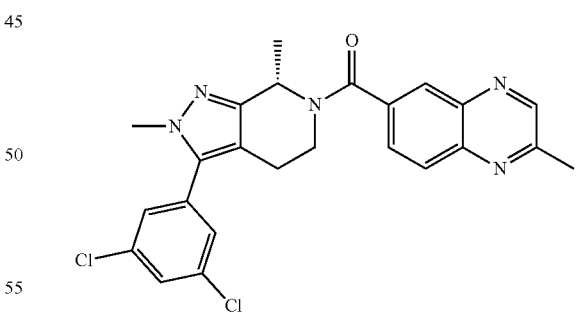

The title compound was prepared in a manner analogous to Example 106, using 3,5-dichlorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 2-methylquinoxaline-6-carboxylic acid (Intermediate 25) instead of 1-naphthoic acid in Step C. MS (ESI):

mass calcd. for $C_{24}H_{21}Cl_2N_5O$, 465.1; m/z found, 466.1 [M+H]$^+$. $^1$H NMR (500 MHz, DMSO-d$_6$) δ 8.93 (d, J=2.8 Hz, 1H), 8.12 (dd, J=28.4, 8.5 Hz, 2H), 7.92-7.76 (m, 1H), 7.70 (t, J=1.9 Hz, 1H), 7.61 (t, J=1.9 Hz, 2H), 5.64 (s, 1H), 4.40 (d, J=309.7 Hz, 1H), 3.83 (s, 3H), 3.66 (s, 1H), 2.89 (d, J=15.2 Hz, 1H), 2.74 (d, J=1.3 Hz, 3H), 2.32 (d, J=15.1 Hz, 1H), 1.51 (s, 3H).

Example 177: (3-(3-Chloro-5-fluorophenyl)-2,7-dimethyl-2,4,5,7-tetrahydro-6H-pyrazolo[3,4-c]pyridin-6-yl)(quinolin-6-yl)methanone

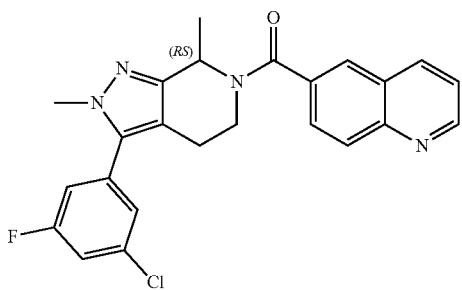 [SMILES: CC1c2nn(C)c(-c3cc(F)cc(Cl)c3)c2CCN1C(=O)c1ccc2ncccc2c1]

The title compound was prepared in a manner analogous to Example 106, using 3-chloro-5-fluoroboronic acid instead of 3,5-difluorophenylboronic acid in Step A. MS (ESI): mass calcd. for $C_{24}H_{20}ClFN_4O$, 434.1; m/z found, 435.1 [M+H]$^+$. $^1$H NMR (500 MHz, DMSO-d$_6$) δ 8.97 (dd, J=4.2, 1.8 Hz, 1H), 8.51-8.46 (m, 1H), 8.11 (d, J=8.3 Hz, 2H), 7.80 (s, 1H), 7.61 (dd, J=8.3, 4.2 Hz, 1H), 7.55-7.51 (m, 1H), 7.48-7.39 (m, 2H), 5.62 (s, 1H), 3.83 (s, 3H), 3.70 (s, 1H), 3.25 (s, 1H) 2.89 (s, 1H), 2.34 (s, 1H), 1.50 (s, 3H).

Example 178: (S)-(3-(3-Chloro-5-fluorophenyl)-2,7-dimethyl-2,4,5,7-tetrahydro-6H-pyrazolo[3,4-c]pyridin-6-yl)(quinolin-6-yl)methanone

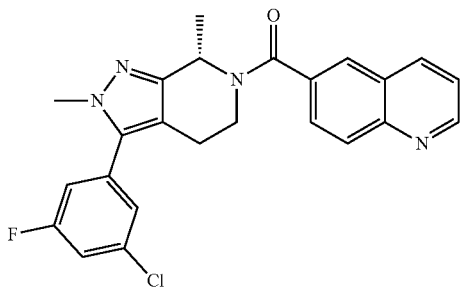 [SMILES: C[C@H]1c2nn(C)c(-c3cc(F)cc(Cl)c3)c2CCN1C(=O)c1ccc2ncccc2c1]

The title compound was obtained as a single enantiomer by chiral SFC purification of racemic [(3-(3-chloro-5-fluorophenyl)-2,7-dimethyl-2,4,5,7-tetrahydro-6H-pyrazolo[3,4-c]pyridin-6-yl)(quinolin-6-yl)methanone], Example 177 (Chiralcel OD 5 μm 250×20 mm, Mobile phase: 16% methanol, 84% CO$_2$. The enantiomeric purity was confirmed by analytical SFC using a Chiralcel OD, 5 μm, 250×4.6 mm, Mobile phase: 20% methanol, 80% CO$_2$ (100% single (S) enantiomer; 9.2 min retention time). MS (ESI): mass calcd. for $C_{24}H_{20}ClFN_4O$, 434.1; m/z found, 435.0 [M+H]$^+$. $^1$H NMR (500 MHz, DMSO-d$_6$) δ 8.97 (dd, J=4.2, 1.8 Hz, 1H), 8.51-8.46 (m, 1H), 8.11 (d, J=8.3 Hz, 2H), 7.80 (s, 1H), 7.61 (dd, J=8.3, 4.2 Hz, 1H), 7.55-7.51 (m, 1H), 7.48-7.39 (m, 2H), 5.62 (s, 1H), 3.83 (s, 3H), 3.70 (s, 1H), 3.25 (s, 1H) 2.89 (s, 1H), 2.34 (s, 1H), 1.50 (s, 3H).

Example 179: (R)-(3-(3-Chloro-5-fluorophenyl)-2,7-dimethyl-2,4,5,7-tetrahydro-6H-pyrazolo[3,4-c]pyridin-6-yl)(quinolin-6-yl)methanone

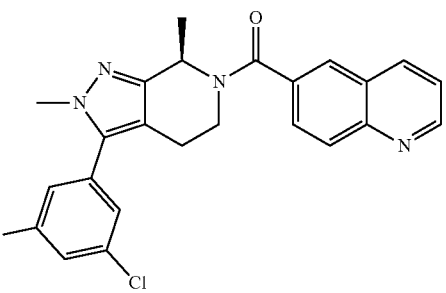

The title compound was obtained as a single enantiomer by chiral SFC purification of racemic [(3-(3-chloro-5-fluorophenyl)-2,7-dimethyl-2,4,5,7-tetrahydro-6H-pyrazolo[3,4-c]pyridin-6-yl)(quinolin-6-yl)methanone], Example 177 Chiralcel OD 5 μm 250×20 mm, Mobile phase: 16% methanol, 84% CO$_2$. The enantiomeric purity was confirmed by analytical SFC using a Chiralcel OD, 5 μm, 250×4.6 mm, Mobile phase: 20% methanol, 80% CO$_2$ (100% single (R) enantiomer). MS (ESI): mass calcd. for $C_{24}H_{20}ClFN_4O$, 434.1; m/z found, 435.0 [M+H]$^+$.

Example 180: (3-(3-Chloro-5-fluorophenyl)-2,7-dimethyl-2,4,5,7-tetrahydro-6H-pyrazolo[3,4-c]pyridin-6-yl)(quinoxalin-6-yl)methanone

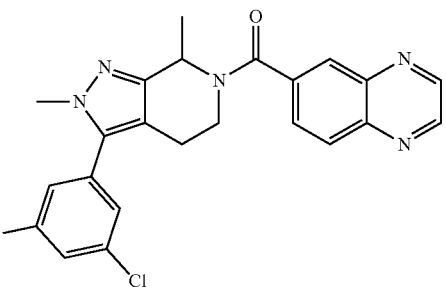

The title compound was prepared in a manner analogous to Example 106, using 3-chloro-5-fluoroboronic acid instead of 3,5-difluorophenylboronic acid in Step A and quinoxaline-6-carboxylic acid instead of quinolone-6-carboxylic acid in Step C. MS (ESI): mass calcd. for $C_{23}H_{19}ClFN_5O$, 435.1; m/z found, 436.1 [M+H]$^+$. $^1$H NMR (500 MHz, DMSO-d$_6$) δ 9.03 (d, J=1.9 Hz, 2H), 8.26-8.08 (m, 2H), 7.91 (d, J=8.8 Hz, 1H), 7.64-7.35 (m, 3H), 5.65 (s, 0.56H), 4.71 (s, 0.44H), 3.84 (s, 3H), 3.66 (d, J=13.7 Hz, 1H), 3.34-2.82 (m, 2H), 2.47-2.24 (m, 1H), 1.52 (d, J=6.7 Hz, 3H).

Example 181: (S)-(3-(3-Chloro-5-fluorophenyl)-2,7-dimethyl-2,4,5,7-tetrahydro-6H-pyrazolo[3,4-c]pyridin-6-yl)(quinoxalin-6-yl)methanone

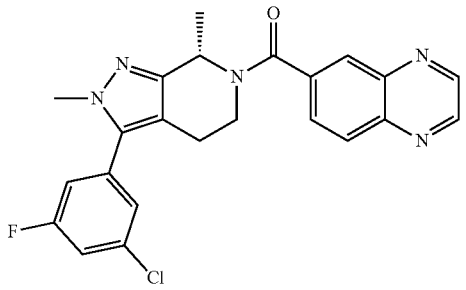 [SMILES: CC1c2nn(C)c(-c3cc(F)cc(Cl)c3)c2CCN1C(=O)c1ccc2nccnc2c1]

The title compound was obtained as a single enantiomer by chiral SFC purification of racemic (3-(3-chloro-5-fluorophenyl)-2,7-dimethyl-2,4,5,7-tetrahydro-6H-pyrazolo[3,4-c]pyridin-6-yl)(quinoxalin-6-yl)methanone, Example 180 (Stationary Phase: Chiralcel OD 5 μm 250×20 mm, Mobile phase: 16% methanol, 84% $CO_2$. The enantiomeric purity was confirmed by analytical SFC using a Chiralcel OD, 5 μm, 250×4.6 mm, Mobile phase: 20% methanol, 80% $CO_2$ (100% single (S) enantiomer; 7.2 min retention time). MS (ESI): mass calcd. for $C_{23}H_{19}ClFN_5O$, 435.1; m/z found, 436.1 [M+H]$^+$. $^1$H NMR (500 MHz, DMSO-$d_6$) δ 9.03 (d, J=1.9 Hz, 2H), 8.26-8.08 (m, 2H), 7.91 (d, J=8.8 Hz, 1H), 7.64-7.35 (m, 3H), 5.65 (s, 0.56H), 4.71 (s, 0.44H), 3.84 (s, 3H), 3.66 (d, J=13.7 Hz, 1H), 3.34-2.82 (m, 2H), 2.47-2.24 (m, 1H), 1.52 (d, J=6.7 Hz, 3H).

Example 182: (R)-(3-(3-Chloro-5-fluorophenyl)-2,7-dimethyl-2,4,5,7-tetrahydro-6H-pyrazolo[3,4-c]pyridin-6-yl)(quinoxalin-6-yl)methanone

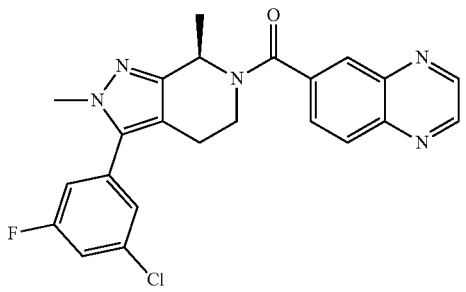 [SMILES: C[C@@H]1c2nn(C)c(-c3cc(F)cc(Cl)c3)c2CCN1C(=O)c1ccc2nccnc2c1]

The title compound was obtained as a single enantiomer by chiral SFC purification of racemic (3-(3-chloro-5-fluorophenyl)-2,7-dimethyl-2,4,5,7-tetrahydro-6H-pyrazolo[3,4-c]pyridin-6-yl)(quinoxalin-6-yl)methanone, Example 180 (Stationary Phase: Chiralcel OD 5 μm 250×20 mm, Mobile phase: 16% methanol, 84% $CO_2$. The enantiomeric purity was confirmed by analytical SFC using a Chiralcel OD, 5 μm, 250×4.6 mm, Mobile phase: 20% methanol, 80% $CO_2$ (100% single (R) enantiomer. MS (ESI): mass calcd. for $C_{23}H_{19}ClFN_5O$, 435.1; m/z found, 436.1 [M+H]$^+$.

Example 183: (S)-(3-(3-Chloro-4-methylphenyl)-2,7-dimethyl-2,4,5,7-tetrahydro-6H-pyrazolo[3,4-c]pyridin-6-yl)(quinoxalin-6-yl)methanone

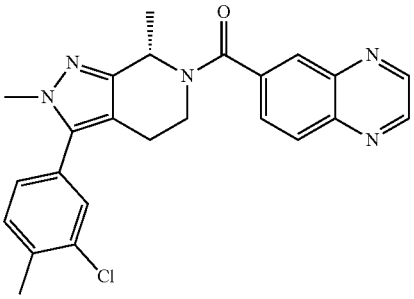 [SMILES: Cc1ccc(-c2c3c(nn2C)[C@H](C)N(C(=O)c2ccc4nccnc4c2)CC3)cc1Cl]

The title compound was prepared in a manner analogous to Example 106, using 3-chloro-4-methylphenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{24}H_{22}ClN_5O$, 431.1; m/z found, 432.1 [M+H]$^+$. $^1$H NMR (400 MHz, DMSO-$d_6$) δ 9.04 (s, 2H), 8.29-8.11 (m, 2H), 7.91 (d, J=8.7 Hz, 1H), 7.64-7.33 (m, 3H), 5.65 (s, 1H), 4.72 (s, 1H), 3.76 (d, J=37.7 Hz, 3H), 2.85 (s, 1H), 2.39 (s, 3H), 2.31 (d, J=17.1 Hz, 2H), 1.53 (s, 3H).

Example 184: (S)-(3-(3-Fluoro-5-(trifluoromethyl)phenyl)-2,7-dimethyl-2,4,5,7-tetrahydro-6H-pyrazolo[3,4-c]pyridin-6-yl)(quinoxalin-6-yl)methanone

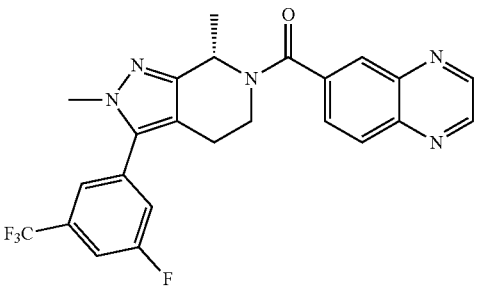 [SMILES: C[C@H]1c2nn(C)c(-c3cc(F)cc(C(F)(F)F)c3)c2CCN1C(=O)c1ccc2nccnc2c1]

The title compound was prepared in a manner analogous to Example 106, using (3-fluoro-5-(trifluoromethyl)phenyl)boronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{24}H_{19}F_4N_5O$, 469.1; m/z found, 470.1 [M+H]$^+$. $^1$H NMR (400 MHz, DMSO-$d_6$) δ 9.04 (d, J=2.4 Hz, 2H), 8.28-8.10 (m, 2H), 7.99-7.65 (m, 4H), 5.67

(s, 1H), 4.74 (s, 1H), 3.82 (d, J=33.4 Hz, 3H), 3.69 (d, J=12.9 Hz, 1H), 2.92 (s, 1H), 2.34 (d, J=13.1 Hz, 1H), 1.54 (d, J=6.7 Hz, 3H).

Example 185: (S)-(3-(3-Fluoro-4-methoxyphenyl)-2,7-dimethyl-2,4,5,7-tetrahydro-6H-pyrazolo[3,4-c]pyridin-6-yl)(quinoxalin-6-yl)methanone

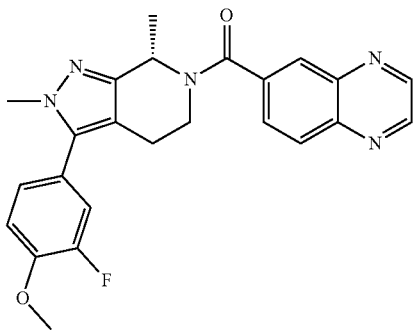 [SMILES: COc1ccc(-c2c3c(nn2C)[C@H](C)N(C(=O)c2ccc4nccnc4c2)CC3)cc1F]

The title compound was prepared in a manner analogous to Example 106, using 3-fluoro-4-methoxyphenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{24}H_{22}FN_5O_2$, 431.1; m/z found, 432.1 [M+H]$^+$. $^1$H NMR (400 MHz, DMSO-d$_6$) δ 9.04 (s, 2H), 8.26-8.09 (m, 2H), 7.97-7.82 (m, 1H), 7.42 (d, J=12.3 Hz, 1H), 7.29 (d, J=8.2 Hz, 2H), 5.64 (s, 1H), 4.72 (s, 1H), 3.90 (s, 3H), 3.75 (d, J=37.5 Hz, 3H), 3.24-2.74 (m, 2H), 2.30 (d, J=16.3 Hz, 1H), 1.53 (s, 3H).

Example 186: (S)-(3-(3-Fluoro-5-methoxyphenyl)-2,7-dimethyl-2,4,5,7-tetrahydro-6H-pyrazolo[3,4-c]pyridin-6-yl)(quinoxalin-6-yl)methanone

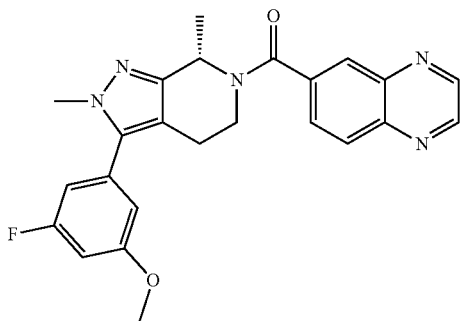 [SMILES: COc1cc(F)cc(-c2c3c(nn2C)[C@H](C)N(C(=O)c2ccc4nccnc4c2)CC3)c1]

The title compound was prepared in a manner analogous to Example 106, using 3-fluoro-5-methoxyphenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{24}H_{22}FN_5O_2$, 431.1; m/z found, 432.1 [M+H]$^+$. $^1$H NMR (500 MHz, DMSO-d$_6$) δ 9.02 (s, 2H), 8.26-8.02 (m, 2H), 7.98-7.80 (m, 1H), 7.00-6.84 (m, 3H), 5.63 (d, J=7.6 Hz, 1H), 4.71 (s, 1H), 3.81 (d, J=8.3 Hz, 6H), 3.37-2.82 (m, 2H), 2.31 (d, J=15.0 Hz, 1H), 1.59-1.37 (m, 3H).

Example 187: (S)-(3-(3-Fluoro-5-methoxyphenyl)-2,7-dimethyl-2,4,5,7-tetrahydro-6H-pyrazolo[3,4-c]pyridin-6-yl)(7-fluoroquinoxalin-6-yl)methanone

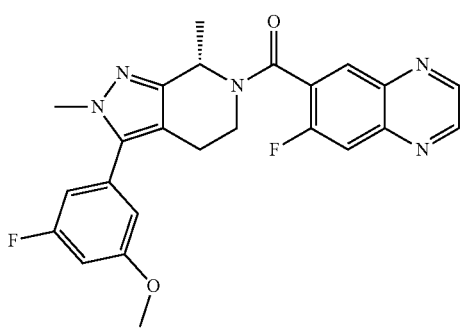 [SMILES: COc1cc(F)cc(-c2c3c(nn2C)[C@H](C)N(C(=O)c2cc4nccnc4cc2F)CC3)c1]

The title compound was prepared in a manner analogous to Example 106, using 3-fluoro-5-methoxyphenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 7-fluoroquinoxaline-6-carboxylic acid instead of quinoline 6-carboxylic acid in Step C. MS (ESI): mass calcd. for $C_{24}H_{21}F_2N_5O_2$, 449.1; m/z found, 450.1 [M+H]$^+$. $^1$H NMR (400 MHz, DMSO-d$_6$) δ 9.09-8.95 (m, 2H), 8.25 (d, J=6.9 Hz, 1H), 8.07 (d, J=9.9 Hz, 1H), 7.02-6.83 (m, 3H), 5.69 (d, J=6.9 Hz, 1H), 4.84-4.53 (m, 1H), 3.89-3.50 (m, 6H), 3.27-2.71 (m, 2H), 2.16 (s, 1H), 1.47 (dd, J=53.8, 6.7 Hz, 3H).

Example 188: (S)-(3-(3-Chloro-4-methoxyphenyl)-2,7-dimethyl-2,4,5,7-tetrahydro-6H-pyrazolo[3,4-c]pyridin-6-yl)(quinoxalin-6-yl)methanone

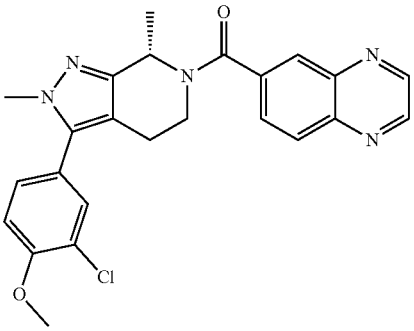 [SMILES: COc1ccc(-c2c3c(nn2C)[C@H](C)N(C(=O)c2ccc4nccnc4c2)CC3)cc1Cl]

The title compound was prepared in a manner analogous to Example 106, using 3-chloro-4-methoxyphenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{24}H_{22}ClN_5O_2$, 447.1; m/z found, 448.1 [M+H]$^+$. $^1$H NMR (400 MHz, DMSO-d$_6$) δ 9.04 (s, 2H), 8.23-8.09 (m, 2H), 7.91 (d, J=8.7 Hz, 1H), 7.58 (d, J=2.1 Hz, 1H), 7.45 (dd, J=8.5, 2.2 Hz, 1H), 7.28 (d, J=8.6 Hz, 1H), 5.64 (s, 1H), 4.72 (s, 1H), 3.92 (s, 3H), 3.74 (d, J=41.4 Hz, 3H), 3.22-2.75 (m, 2H), 2.29 (d, J=14.9 Hz, 1H), 1.53 (s, 3H).

Example 189: (S)-(3-(4-(Difluoromethoxy)-3-fluorophenyl)-2,7-dimethyl-2,4,5,7-tetrahydro-6H-pyrazolo[3,4-c]pyridin-6-yl)(quinoxalin-6-yl)methanone

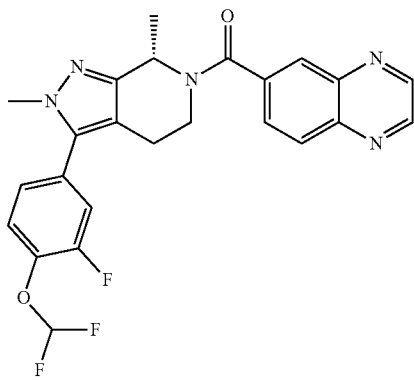 [SMILES: C[C@H]1c2nn(C)c(-c3ccc(OC(F)F)c(F)c3)c2CCN1C(=O)c1ccc2nccnc2c1]

The title compound was prepared in a manner analogous to Example 106, using (4-(difluoromethoxy)-3-fluorophenyl)boronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{24}H_{20}F_3N_5O_2$, 467.1; m/z found, 468.1 [M+H]$^+$. $^1$H NMR (400 MHz, DMSO-d$_6$) δ 9.04 (d, J=2.2 Hz, 2H), 8.26-8.09 (m, 2H), 7.91 (d, J=8.0 Hz, 1H), 7.64 (d, J=11.5 Hz, 1H), 7.58-7.47 (m, 1H), 7.44-7.13 (m, 2H), 5.66 (s, 1H), 4.73 (s, 1H), 3.83 (s, 3H), 3.02 (d, J=121.3 Hz, 2H), 2.32 (d, J=13.5 Hz, 1H), 1.53 (s, 3H).

Example 190: (S)-(3-(3,5-Difluoro-4-methylphenyl)-2,7-dimethyl-2,4,5,7-tetrahydro-6H-pyrazolo[3,4-c]pyridin-6-yl)(quinoxalin-6-yl)methanone

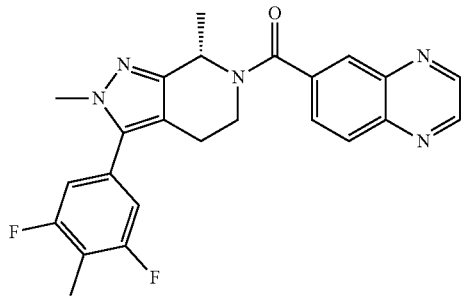 [SMILES: Cc1c(F)cc(-c2c3c(nn2C)[C@H](C)N(C(=O)c2ccc4nccnc4c2)CC3)cc1F]

The title compound was prepared in a manner analogous to Example 106, using (3,5-difluoro-4-methylphenyl)boronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{24}H_{21}F_2N_5O$, 433.1; m/z found, 434.1 [M+H]$^+$. $^1$H NMR (400 MHz, DMSO-d$_6$) δ 9.04 (d, J=2.3 Hz, 2H), 8.30-8.05 (m, 2H), 7.91 (d, J=8.6 Hz, 1H), 7.28 (d, J=7.0 Hz, 2H), 5.65 (s, 1H), 4.72 (s, 1H), 3.80 (d, J=34.7 Hz, 3H), 2.90 (s, 2H), 2.32 (d, J=15.0 Hz, 1H), 2.21 (s, 3H), 1.53 (s, 3H).

Example 191: (S)-(2-Chloro-3-methoxyphenyl)(2,7-dimethyl-3-(3,4,5-trifluorophenyl)-2,4,5,7-tetrahydro-6H-pyrazolo[3,4-c]pyridin-6-yl)methanone

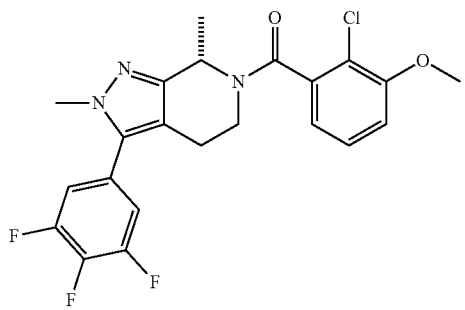

The title compound was prepared in a manner analogous to Example 288, using 2-chloro-3-methoxybenzoic acid instead of 2-fluoro-6-(2H-1,2,3-triazol-2-yl)benzoic acid. MS (ESI): mass calcd. for $C_{22}H_{19}ClF_3N_3O_2$, 449.1; m/z found, 450.0 [M+H]$^+$. $^1$H NMR (500 MHz, CDCl$_3$) δ 7.34-7.20 (m, 1H), 7.01-6.74 (m, 4H), 5.98-5.87 (m, 0.63H), 5.04-4.93 (m, 0.4H), 4.86-4.63 (m, 0.4H), 3.96-3.87 (m, 3H), 3.85-3.76 (m, 3H), 3.61-3.29 (m, 1H), 3.26-2.94 (m, 0.59H), 2.89-2.75 (m, 0.61H), 2.57-2.43 (m, 0.76H), 2.32-2.22 (m, 0.61H), 1.67-1.36 (m, 3H).

Example 192: (S)-(3-Chloro-5-methoxyphenyl)(2,7-dimethyl-3-(3,4,5-trifluorophenyl)-2,4,5,7-tetrahydro-6H-pyrazolo[3,4-c]pyridin-6-yl)methanone

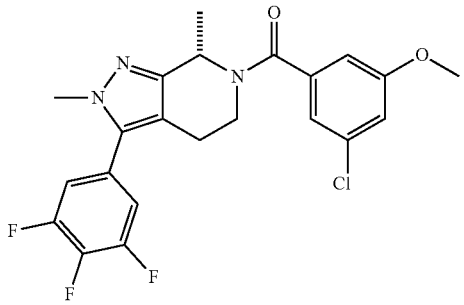 [SMILES: COc1cc(Cl)cc(C(=O)N2CCc3c(nn(C)c3-c3cc(F)c(F)c(F)c3)[C@@H]2C)c1]

The title compound was prepared in a manner analogous to Example 288, using 3-chloro-5-methoxybenzoic acid instead of 2-fluoro-6-(2H-1,2,3-triazol-2-yl)benzoic acid. MS (ESI): mass calcd. for $C_{22}H_{19}ClF_3N_3O_2$, 449.1; m/z found, 450.0 [M+H]$^+$. $^1$H NMR (600 MHz, Methanol-d$_4$) δ 7.36-7.29 (m, 2H), 7.14-6.87 (m, 3H), 5.70 (d, J=7.3 Hz, 0.67H), 4.86-4.71 (m, 0.54H), 3.91-3.71 (m, 6.84H), 3.46-3.18 (m, 0.95H), 2.88-2.70 (m, 1H), 2.58-2.39 (m, 1H), 1.61-1.47 (m, 3H).

Example 193: (S)-(2,7-Dimethyl-3-(3,4,5-trifluorophenyl)-2,4,5,7-tetrahydro-6H-pyrazolo[3,4-c]pyridin-6-yl)(5-fluoro-2-(1H-pyrazol-1-yl)phenyl)methanone

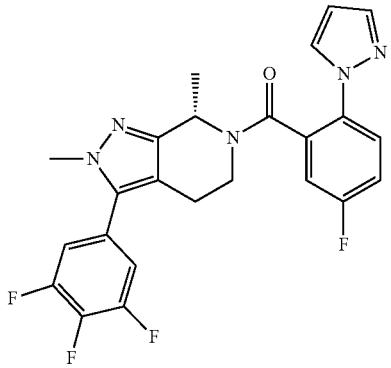 [SMILES: C[C@H]1c2nn(C)c(-c3cc(F)c(F)c(F)c3)c2CCN1C(=O)c1cc(F)ccc1-n1cccn1]

The title compound was prepared in a manner analogous to Example 288, using 5-fluoro-2-(1H-pyrazol-1-yl)benzoic acid instead of 2-fluoro-6-(2H-1,2,3-triazol-2-yl)benzoic acid. MS (ESI): mass calcd. for $C_{24}H_{19}F_4N_5O$, 469.1; m/z found, 470.1 [M+H]$^+$. $^1$H NMR (500 MHz, DMSO-d$_6$) δ 8.16-7.93 (m, 1H), 7.80-7.60 (m, 2H), 7.59-7.42 (m, 3H), 7.40-7.29 (m, 1H), 6.57-6.24 (m, 1H), 5.45 (q, J=6.7 Hz, 1H), 3.85-3.67 (m, 3H), 3.50-3.35 (m, 1H), 3.24-2.69 (m, 2H), 2.38-2.08 (m, 1H), 1.38 (dd, J=60.1, 6.8 Hz, 3H).

Example 194: (S)-(3-(1H-1,2,4-Triazol-1-yl)phenyl)(2,7-dimethyl-3-(3,4,5-trifluorophenyl)-2,4,5,7-tetrahydro-6H-pyrazolo[3,4-c]pyridin-6-yl)methanone

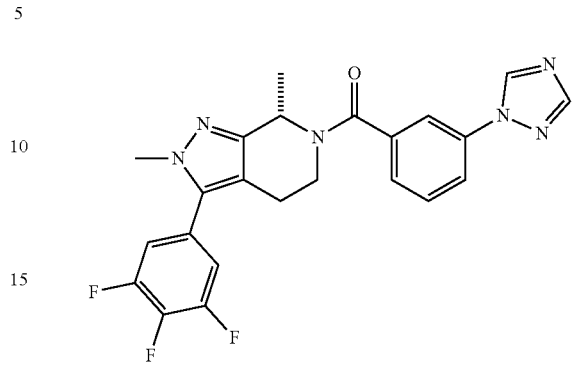

The title compound was prepared in a manner analogous to Example 288, using 3-(1H-1,2,4-triazol-1-yl)benzoic acid instead of 2-fluoro-6-(2H-1,2,3-triazol-2-yl)benzoic acid. MS (ESI): mass calcd. for $C_{23}H_{19}F_3N_6O$, 452.2; m/z found, 453.1 [M+H]$^+$. $^1$H NMR (600 MHz, CDCl$_3$) δ 8.59 (s, 1H), 8.12 (s, 1H), 7.81-7.75 (m, 2H), 7.58 (t, J=7.8 Hz, 1H), 7.45 (d, J=7.7 Hz, 1H), 7.02-6.94 (m, 2H), 5.86 (s, 0.48H), 5.08-4.77 (m, 0.89H), 3.82 (s, 3.66H), 3.45-3.01 (m, 1H), 2.92-2.64 (m, 1H), 2.43 (s, 1H), 1.66-1.56 (m, 3H).

Example 195: (S)-(2,7-Dimethyl-3-(3,4,5-trifluorophenyl)-2,4,5,7-tetrahydro-6H-pyrazolo[3,4-c]pyridin-6-yl)(3-fluoro-2-(2H-1,2,3-triazol-2-yl)phenyl)methanone

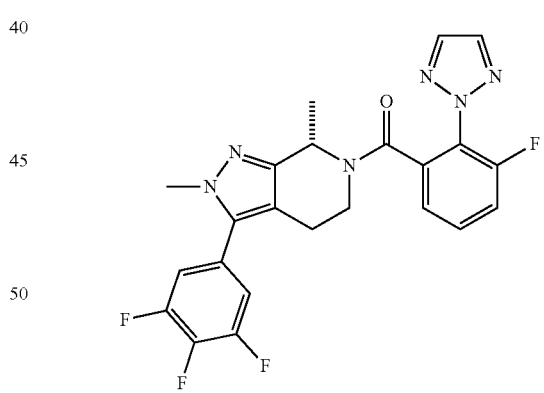

The title compound was prepared in a manner analogous to Example 288, using 3-fluoro-2-(2H-1,2,3-triazol-2-yl)benzoic acid (prepared according to methods described in Pat. Pub. No. WO2011050202, Apr. 28, 2011) instead of 2-fluoro-6-(2H-1,2,3-triazol-2-yl)benzoic acid. MS (ESI): mass calcd. for $C_{23}H_{18}F_4N_6O$, 470.1; m/z found, 471.1 [M+H]$^+$. $^1$H NMR (500 MHz, CDCl$_3$) δ 7.89-7.78 (m, 1.52H), 7.61-7.48 (m, 1.36H), 7.39-7.32 (m, 1.09H), 7.23 (d, J=7.6, 1.2 Hz, 0.73H), 6.99-6.88 (m, 2H), 5.68 (q, J=6.7 Hz, 0.7H), 4.93-4.66 (m, 0.51H), 3.84-3.76 (m, 3.09H), 3.67 (dd, J=13.9, 5.3 Hz, 0.75H), 3.27-2.89 (m, 1H), 2.67-2.27 (m, 2H), 1.57-1.31 (m, 3.25H).

Example 196: (S)-(2,7-Dimethyl-3-(3,4,5-trifluorophenyl)-2,4,5,7-tetrahydro-6H-pyrazolo[3,4-c]pyridin-6-yl)(4-fluoro-2-(2H-1,2,3-triazol-2-yl)phenyl)methanone

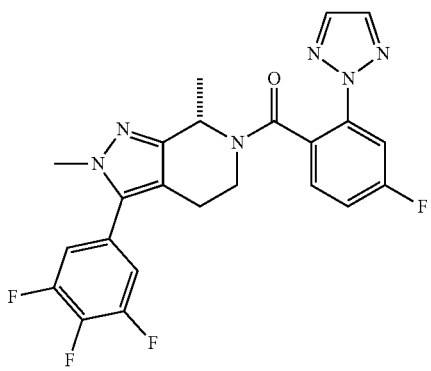 [SMILES: C[C@H]1c2nn(C)c(-c3cc(F)c(F)c(F)c3)c2CCN1C(=O)c1ccc(F)cc1-n1nccn1]

The title compound was prepared in a manner analogous to Example 288, using 4-fluoro-2-(2H-1,2,3-triazol-2-yl)benzoic acid instead of 2-fluoro-6-(2H-1,2,3-triazol-2-yl)benzoic acid. MS (ESI): mass calcd. for $C_{23}H_{18}F_4N_6O$, 470.1; m/z found, 471.2 [M+H]$^+$. $^1$H NMR (500 MHz, CDCl$_3$) δ 7.89-7.73 (m, 2.63H), 7.53-7.34 (m, 1.46H), 7.20-7.11 (m, 0.92H), 7.01-6.81 (m, 2H), 5.96-5.78 (m, 0.67H), 5.02-4.69 (m, 0.66H), 3.90-3.71 (m, 3.11H), 3.65-3.49 (m, 0.67H), 3.30-2.76 (m, 1.34H), 2.65-2.39 (m, 0.86H), 2.32-2.23 (m, 0.51H), 2.14-1.84 (m, 0.35H), 1.68-1.53 (m, 1.75H), 1.44 (d, J=6.8 Hz, 0.73H), 1.06 (d, J=6.7 Hz, 0.34H).

Example 197: (S)-(2,7-Dimethyl-3-(3,4,5-trifluorophenyl)-2,4,5,7-tetrahydro-6H-pyrazolo[3,4-c]pyridin-6-yl)(5-methyl-2-(2H-1,2,3-triazol-2-yl)phenyl)methanone

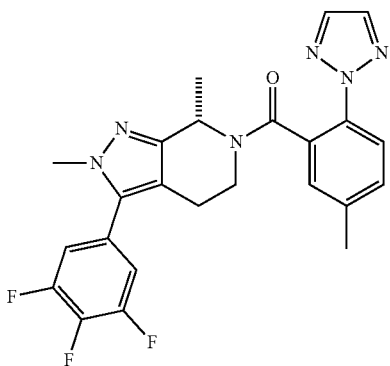 [SMILES: Cc1ccc(-n2nccn2)c(C(=O)N2CCc3c(nn(C)c3-c3cc(F)c(F)c(F)c3)[C@@H]2C)c1]

The title compound was prepared in a manner analogous to Example 288, using 5-methyl-2-(2H-1,2,3-triazol-2-yl)benzoic acid instead of 2-fluoro-6-(2H-1,2,3-triazol-2-yl)benzoic acid. MS (ESI): mass calcd. for $C_{24}H_{21}F_3N_6O$, 466.2; m/z found, 467.1 [M+H]$^+$. $^1$H NMR (600 MHz, Methanol-d$_4$) δ 8.01-7.86 (m, 2H), 7.82-7.62 (m, 1H), 7.50-7.44 (m, 1H), 7.38-7.09 (m, 3H), 5.74-5.62 (m, 0.66H), 4.82-4.60 (m, 0.78H), 3.86-3.80 (m, 2H), 3.79-3.72 (m, 1H), 3.67-3.58 (m, 0.64H), 3.39-3.11 (m, 1.12H), 2.91-2.66 (m, 0.8H), 2.52-2.44 (m, 3H), 2.41-1.90 (m, 1H), 1.61-1.38 (m, 3H).

Example 198: (S)-(2,7-Dimethyl-3-(3,4,5-trifluorophenyl)-2,4,5,7-tetrahydro-6H-pyrazolo[3,4-c]pyridin-6-yl)(1-methyl-5-(trifluoromethyl)-1H-pyrazol-4-yl)methanone

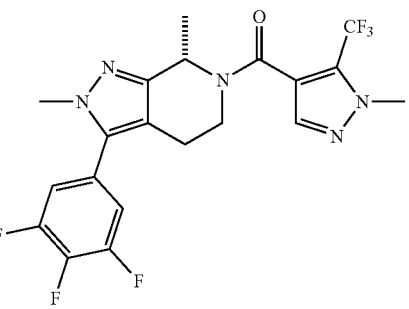

The title compound was prepared in a manner analogous to Example 288, using 1-methyl-5-(trifluoromethyl)-1H-pyrazole-4-carboxylic acid instead of 2-fluoro-6-(2H-1,2,3-triazol-2-yl)benzoic acid. MS (ESI): mass calcd. for $C_{20}H_{17}F_6N_5O$, 457.1; m/z found, 458.0 [M+H]$^+$. $^1$H NMR (600 MHz, Methanol-d$_4$) δ 7.68-7.63 (m, 1H), 7.27 (t, J=7.3 Hz, 2H), 5.72 (q, J=6.8 Hz, 0.68H), 4.05 (s, 3H), 3.85-3.74 (m, 3.8H), 3.45-3.32 (m, 0.91H), 3.16 (s, 0.43H), 2.73-2.60 (m, 1H), 2.58-2.40 (m, 1H), 1.55-1.43 (m, 3.16H).

Example 199: (S)-(1-(tert-Butyl)-5-(trifluoromethyl)-1H-pyrazol-4-yl)(2,7-dimethyl-3-(3,4,5-trifluorophenyl)-2,4,5,7-tetrahydro-6H-pyrazolo[3,4-c]pyridin-6-yl)methanone

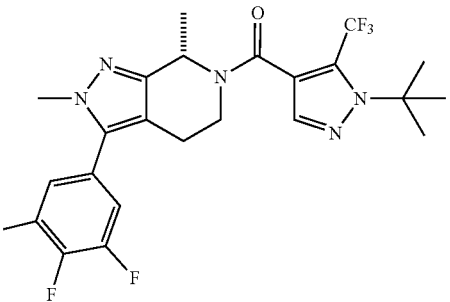

The title compound was prepared in a manner analogous to Example 288, using 1-(tert-butyl)-5-(trifluoromethyl)-1H-pyrazole-4-carboxylic acid instead of 2-fluoro-6-(2H-1,2,3-triazol-2-yl)benzoic acid. MS (ESI): mass calcd. for $C_{23}H_{23}F_6N_5O$, 499.2; m/z found, 500.1 [M+H]$^+$. $^1$H NMR (600 MHz, Methanol-d$_4$) δ 7.64-7.60 (m, 1H), 7.31-7.24 (m, 2H), 5.71 (q, J=6.8 Hz, 0.7H), 4.80-4.73 (m, 0.62H), 3.85-3.76 (m, 3H), 3.72-3.64 (m, 0.71H), 3.45-3.34 (m, 0.93H), 3.22-3.12 (m, 0.24H), 2.75-2.59 (m, 0.91H), 2.57-2.50 (m, 0.26H), 2.47-2.39 (m, 0.65H), 1.70 (s, 9H), 1.54-1.44 (m, 3H).

Example 200: (S)-(2,7-Dimethyl-3-(3,4,5-trifluorophenyl)-2,4,5,7-tetrahydro-6H-pyrazolo[3,4-c]pyridin-6-yl)(5-methoxy-1-methyl-1H-pyrazol-3-yl)methanone

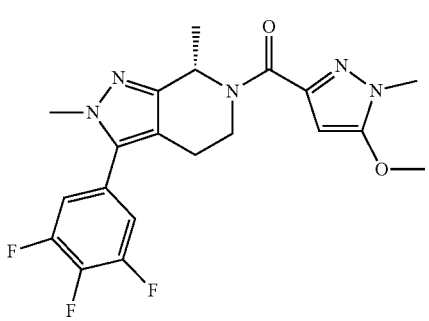 [SMILES: COc1cc(C(=O)N2CCc3c(nn(C)c3-c3cc(F)c(F)c(F)c3)[C@@H]2C)nn1C]

The title compound was prepared in a manner analogous to Example 288, using 5-methoxy-1-methyl-1H-pyrazole-3-carboxylic acid instead of 2-fluoro-6-(2H-1,2,3-triazol-2-yl)benzoic acid. MS (ESI): mass calcd. for $C_{20}H_{20}F_3N_5O_2$, 419.1; m/z found, 420.1 [M+H]$^+$. $^1$H NMR (500 MHz, DMSO-$d_6$) δ 7.54 (dd, J=8.6, 6.6 Hz, 2H), 6.02 (s, 2H), 5.00-4.52 (m, 1H), 3.90 (s, 3H), 3.78 (d, J=17.2 Hz, 3H), 3.61 (s, 3H), 3.26-2.68 (m, 2H), 2.41 (d, J=15.5 Hz, 1H), 1.54-1.32 (m, 3H).

Example 201: (S)-(5-Cyclopropyl-1-methyl-1H-pyrazol-4-yl)(2,7-dimethyl-3-(3,4,5-trifluorophenyl)-2,4,5,7-tetrahydro-6H-pyrazolo[3,4-c]pyridin-6-yl)methanone

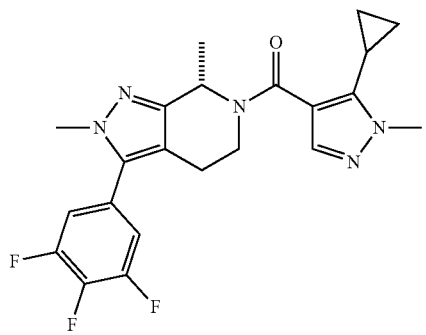 [SMILES: C[C@H]1c2nn(C)c(-c3cc(F)c(F)c(F)c3)c2CCN1C(=O)c1cnn(C)c1C1CC1]

The title compound was prepared in a manner analogous to Example 288, using 5-cyclopropyl-1-methyl-1H-pyrazole-4-carboxylic acid instead of 2-fluoro-6-(2H-1,2,3-triazol-2-yl)benzoic acid. MS (ESI): mass calcd. for $C_{22}H_{22}F_3N_5O$, 429.2; m/z found, 430.1 [M+H]$^+$. $^1$H NMR (500 MHz, DMSO-$d_6$) δ 7.58-7.50 (m, 2H), 7.41 (s, 1H), 5.55 (s, 0.68H), 4.99-4.46 (m, 0.36H), 3.88-3.74 (m, 7.14H), 3.27-3.13 (m, 0.95H), 2.73 (s, 1H), 2.38-2.26 (m, 0.87H), 1.85 (s, 1H), 1.47-1.36 (m, 3H), 0.90 (s, 2H), 0.59 (s, 2H).

Example 202: (S)-(2,7-Dimethyl-3-(3,4,5-trifluorophenyl)-2,4,5,7-tetrahydro-6H-pyrazolo[3,4-c]pyridin-6-yl)(5-ethyl-1-phenyl-1H-1,2,4-triazol-3-yl)methanone

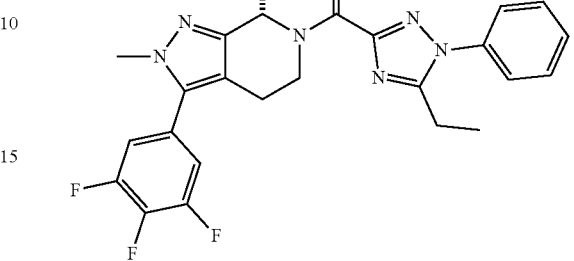

The title compound was prepared in a manner analogous to Example 288, using 5-ethyl-1-phenyl-1H-1,2,4-triazole-3-carboxylic acid instead of 2-fluoro-6-(2H-1,2,3-triazol-2-yl)benzoic acid. MS (ESI): mass calcd. for $C_{25}H_{23}F_3N_6O$, 480.2; m/z found, 481.2 [M+H]$^+$. $^1$H NMR (500 MHz, CDCl$_3$) δ 7.56-7.43 (m, 5H), 7.00-6.91 (m, 2H), 5.93-5.55 (m, 1H), 4.95-4.48 (m, 1H), 3.85-3.74 (m, 3H), 3.39-3.06 (m, 1H), 2.99-2.78 (m, 3H), 2.49-2.36 (m, 1H), 1.73-1.57 (m, 3H), 1.39-1.32 (m, 3H).

Example 203: (S)-(2,7-Dimethyl-3-(3,4,5-trifluorophenyl)-2,4,5,7-tetrahydro-6H-pyrazolo[3,4-c]pyridin-6-yl)(5-methoxypyridin-3-yl)methanone

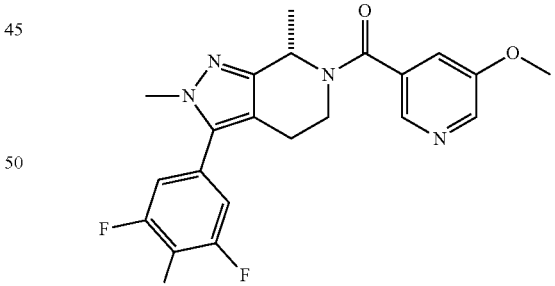

The title compound was prepared in a manner analogous to Example 288, using 5-methoxynicotinic acid instead of 2-fluoro-6-(2H-1,2,3-triazol-2-yl)benzoic acid. MS (ESI): mass calcd. for $C_{21}H_{19}F_3N_4O_2$, 416.1; m/z found, 417.1 [M+H]$^+$. $^1$H NMR (600 MHz, Methanol-$d_4$) δ 8.36 (s, 1H), 8.26-8.17 (m, 1H), 7.53-7.44 (m, 1H), 7.31 (t, J=7.3 Hz, 2H), 5.73 (d, J=7.4 Hz, 0.7H), 4.85-4.68 (m, 0.55H), 3.93 (s, 3H), 3.81 (d, J=38.5 Hz, 3.78H), 3.47-3.37 (m, 0.68H), 3.29-3.21 (m, 0.31H), 2.89-2.76 (m, 1H), 2.60-2.42 (m, 1H), 1.63-1.50 (m, 3H).

Example 204: (S)-6-(2,7-Dimethyl-3-(3,4,5-trifluorophenyl)-4,5,6,7-tetrahydro-2H-pyrazolo[3,4-c]pyridine-6-carbonyl)-4-methyl-2H-benzo[b][1,4]oxazin-3(4H)-one

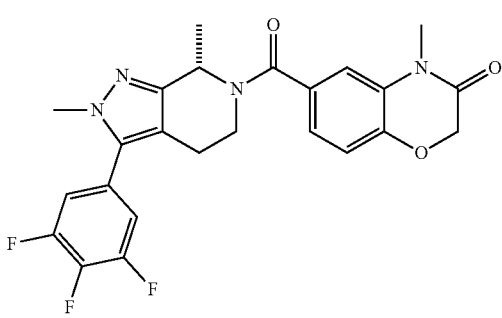 [SMILES: C[C@H]1c2nn(C)c(-c3cc(F)c(F)c(F)c3)c2CCN1C(=O)c1ccc2c(c1)N(C)C(=O)CO2]

The title compound was prepared in a manner analogous to Example 288, using 4-methyl-3-oxo-3,4-dihydro-2H-benzo[b][1,4]oxazine-6-carboxylic acid instead of 2-fluoro-6-(2H-1,2,3-triazol-2-yl)benzoic acid. MS (ESI): mass calcd. for $C_{24}H_{21}F_3N_4O_3$, 470.2; m/z found, 471.1 [M+H]$^+$. $^1$H NMR (600 MHz, Methanol-d$_4$) δ 7.32 (t, J=7.3 Hz, 2H), 7.25 (s, 1H), 7.16 (d, J=8.2 Hz, 1H), 7.10 (d, J=8.2 Hz, 1H), 5.70 (s, 0.72H), 4.70 (s, 2.25H), 3.98-3.71 (m, 3.81H), 3.40 (s, 4.03H), 2.91-2.79 (m, 1H), 2.55-2.42 (m, 1H), 1.62-1.56 (m, 3.18H).

Example 205: (S)-(2,7-Dimethyl-3-(3,4,5-trifluorophenyl)-2,4,5,7-tetrahydro-6H-pyrazolo[3,4-c]pyridin-6-yl)(1H-indol-7-yl)methanone

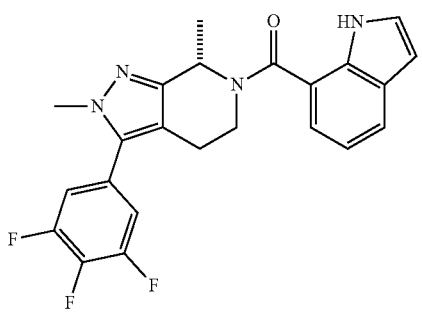 [SMILES: C[C@H]1c2nn(C)c(-c3cc(F)c(F)c(F)c3)c2CCN1C(=O)c1cccc2cc[nH]c12]

The title compound was prepared in a manner analogous to Example 288, using indole-7-carboxylic acid instead of 2-fluoro-6-(2H-1,2,3-triazol-2-yl)benzoic acid. MS (ESI): mass calcd. for $C_{23}H_{19}F_3N_4O$, 424.2; m/z found, 425.1 [M+H]$^+$. $^1$H NMR (500 MHz, CDCl$_3$) δ 9.17 (s, 1H), 7.73 (d, J=7.9 Hz, 1H), 7.33-7.23 (m, 2H), 7.15-7.09 (m, 1H), 7.03-6.94 (m, 2H), 6.59-6.55 (m, 1H), 5.69 (s, 0.79H), 4.50 (s, 0.81H), 3.81 (s, 3H), 3.28 (t, J=12.6 Hz, 1H), 2.94-2.82 (m, 1H), 2.51-2.43 (m, 1H), 1.69-1.61 (m, 3.42H).

Example 206: (S)-(2,7-Dimethyl-3-(3,4,5-trifluorophenyl)-2,4,5,7-tetrahydro-6H-pyrazolo[3,4-c]pyridin-6-yl)(1-methyl-1H-indol-7-yl)methanone

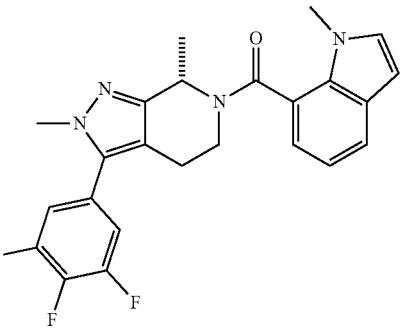

To a solution of [(S)-(2,7-dimethyl-3-(3,4,5-trifluorophenyl)-2,4,5,7-tetrahydro-6H-pyrazolo[3,4-c]pyridin-6-yl)(1H-indol-7-yl)methanone] (Example 205) (19.3 mg, 45.5 μmol) in THF (0.78 mL) at 0° C. was added NaH (60% dispersion, 1.83 mg, 45.9 μmol). After stirring for 15 minutes, MeI (3.1 μL, 50.1 μmol) was added and the cold bath removed. The reaction was stirred at room temperature for 3 h, and then quenched with saturated aqueous NH$_4$Cl. EtOAc was added, the layers separated, and the aqueous layer extracted with EtOAc (×2). The combined organics were washed with brine, dried over Na$_2$SO$_4$, filtered, and concentrated. The residue was purified by preparative HPLC to yield the title compound (17.1 mg, 86% yield). MS (ESI): mass calcd. for $C_{24}H_{21}F_3N_4O$, 438.2; m/z found, 439.1 [M+H]$^+$. $^1$H NMR (500 MHz, CDCl$_3$) δ 7.69-7.60 (m, 1H), 7.18-6.88 (m, 5H), 6.55-6.45 (m, 1H), 6.10-5.94 (m, 0.65H), 5.24-4.98 (m, 0.48H), 4.87-4.79 (m, 0.25H), 3.91-3.67 (m, 5.78H), 3.59 (s, 0.73H), 3.36-3.04 (m, 1.03H), 2.93-2.65 (m, 0.88H), 2.58-2.48 (m, 0.36H), 2.46-2.36 (m, 0.18H), 2.33-2.17 (m, 0.66H), 1.71-1.46 (m, 3H).

Example 207: (S)-(2,7-dimethyl-3-(3,4,5-trifluorophenyl)-2,4,5,7-tetrahydro-6H-pyrazolo[3,4-c]pyridin-6-yl)(1-methyl-1H-indol-4-yl)methanone

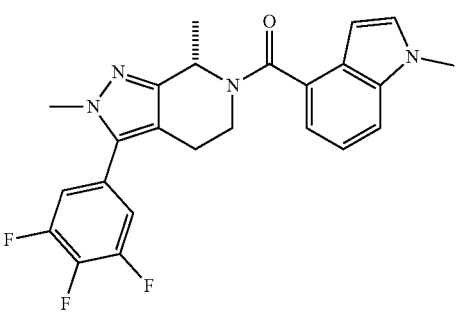 [SMILES: C[C@H]1c2nn(C)c(-c3cc(F)c(F)c(F)c3)c2CCN1C(=O)c1cccc2c1ccn2C]

The title compound was prepared in a manner analogous to Example 288, using 1-methyl-1H-indole-4-carboxylic acid instead of 2-fluoro-6-(2H-1,2,3-triazol-2-yl)benzoic acid. MS (ESI): mass calcd. for $C_{24}H_{21}F_3N_4O$, 438.2; m/z found, 439.1 [M+H]$^+$. $^1$H NMR (500 MHz, CDCl$_3$) δ 7.37 (d, J=8.2 Hz, 1H), 7.26-7.21 (m, 1H), 7.14-6.90 (m, 3.77H), 6.55-5.90 (m, 1.25H), 5.01 (s, 0.48H), 3.91-3.68 (m, 6.28H), 3.33-2.08 (m, 2.54H), 1.75-1.34 (m, 4.68H).

Example 208: (S)-(2,7-Dimethyl-3-(3,4,5-trifluorophenyl)-2,4,5,7-tetrahydro-6H-pyrazolo[3,4-c]pyridin-6-yl)(1H-indazol-7-yl)methanone

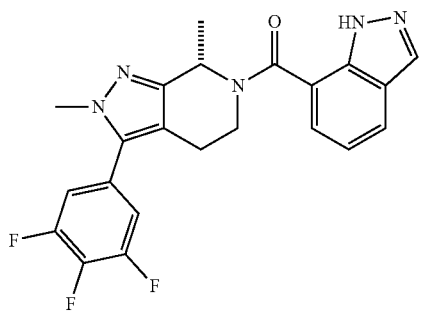 [SMILES: C[C@H]1c2nn(C)c(-c3cc(F)c(F)c(F)c3)c2CCN1C(=O)c1cccc2cn[nH]c12]

The title compound was prepared in a manner analogous to Example 288, using 1H-indazole-7-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.0 [M+H]$^+$. $^1$H NMR (600 MHz, Methanol-$d_4$) δ 8.15 (s, 1H), 7.93 (d, J=8.1 Hz, 1H), 7.46 (d, J=7.0 Hz, 1H), 7.34-7.24 (m, 3H), 5.98-5.63 (m, 0.56H), 3.94-3.76 (m, 3.4H), 3.47-3.35 (m, 0.76H), 2.66 (d, J=215.4 Hz, 2.15H), 1.73-1.48 (m, 3.35H), 1.38-1.32 (m, 0.78H).

Example 209: (S)-(2,7-Dimethyl-3-(3,4,5-trifluorophenyl)-2,4,5,7-tetrahydro-6H-pyrazolo[3,4-c]pyridin-6-yl)(1-methyl-1H-indazol-7-yl)methanone

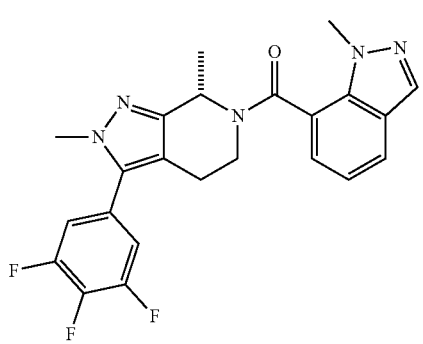 [SMILES: C[C@H]1c2nn(C)c(-c3cc(F)c(F)c(F)c3)c2CCN1C(=O)c1cccc2cnn(C)c12]

The title compound was prepared in a manner analogous to Example 288, using 1-methyl-1H-indazole-7-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (600 MHz, Methanol-$d_4$) δ 8.15-8.05 (m, 1H), 7.93-7.87 (m, 1H), 7.49-7.16 (m, 4H), 6.02-5.78 (m, 0.66H), 5.12-4.90 (m, 0.52H), 4.71-4.58 (m, 0.25H), 4.07 (s, 1.66H), 3.94 (s, 0.62H), 3.89-3.71 (m, 4.1H), 3.65 (m, 0.42H), 3.52-3.40 (m, 0.62H), 2.94-2.74 (m, 0.9H), 2.68-2.58 (m, 0.35H), 2.52-2.31 (m, 0.91H), 1.70-1.47 (m, 3H).

Example 210: (S)-(2,7-Dimethyl-3-(3,4,5-trifluorophenyl)-2,4,5,7-tetrahydro-6H-pyrazolo[3,4-c]pyridin-6-yl)(7-methyl-1H-indazol-5-yl)methanone

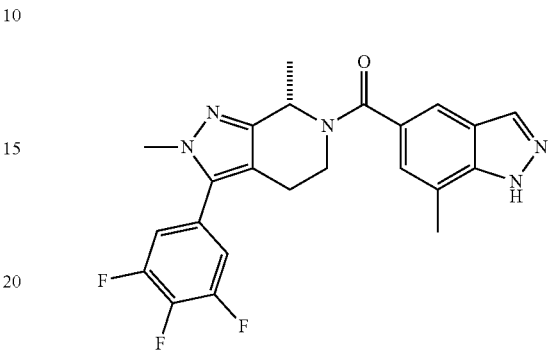

The title compound was prepared in a manner analogous to Example 288, using 7-methyl-1H-indazole-5-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (500 MHz, CDCl$_3$) δ 10.9 (s, 1H), 8.12 (s, 1H), 7.67 (s, 1H), 7.22 (s, 1H), 7.06-6.93 (m, 2H), 5.85 (s, 0.35H), 5.23-4.62 (m, 0.65H), 3.80 (s, 3.49H), 3.21 (s, 1H), 2.79 (s, 1H), 2.60-2.35 (m, 4.29H), 1.93-1.47 (m, 3.23H).

Example 211: (S)-(2,7-Dimethyl-3-(3,4,5-trifluorophenyl)-2,4,5,7-tetrahydro-6H-pyrazolo[3,4-c]pyridin-6-yl)(1-methyl-1H-indazol-5-yl)methanone

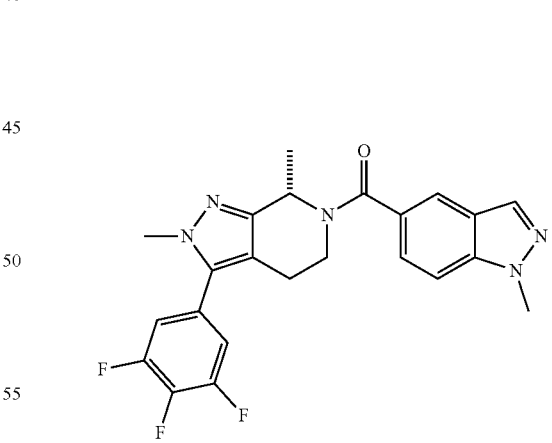

The title compound was prepared in a manner analogous to Example 288, using 1-methyl-1H-indazole-5-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (500 MHz, CDCl$_3$) δ 8.03 (d, J=0.9 Hz, 1H), 7.84 (s, 1H), 7.51-7.42 (m, 2H), 7.02-6.95 (m, 2H), 6.11-4.47 (m, 1.1H), 4.11 (s, 3.15H), 3.80 (s, 3.13H), 3.22 (s, 1H), 2.79 (s, 1H), 2.46-2.34 (m, 1H), 1.60 (d, J=9.8 Hz, 3.61H).

Example 212: (S)-(2,7-Dimethyl-3-(3,4,5-trifluorophenyl)-2,4,5,7-tetrahydro-6H-pyrazolo[3,4-c]pyridin-6-yl)(imidazo[1,5-a]pyridin-8-yl)methanone

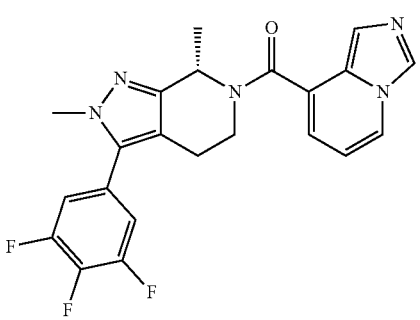 [SMILES: C[C@H]1c2nn(C)c(-c3cc(F)c(F)c(F)c3)c2CCN1C(=O)c1cccn2cncc12]

The title compound was prepared in a manner analogous to Example 288, using imidazo[1,5-a]pyridine-8-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.1 [M+H]+. $^1$H NMR (500 MHz, DMSO-$d_6$) δ 8.51-8.38 (m, 2H), 7.55 (s, 2H), 7.24 (s, 1H), 6.84 (dd, J=6.5, 0.9 Hz, 1H), 6.74 (t, J=6.8 Hz, 1H), 5.64 (s, 1H), 4.40 (d, J=307.0 Hz, 1H), 3.80 (s, 4H), 2.64 (t, J=1.9 Hz, 1H), 2.45-2.24 (m, 1H), 1.50 (s, 3H).

Example 213: (S)-(2,7-Dimethyl-3-(3,4,5-trifluorophenyl)-2,4,5,7-tetrahydro-6H-pyrazolo[3,4-c]pyridin-6-yl)(imidazo[1,2-a]pyridin-3-yl)methanone

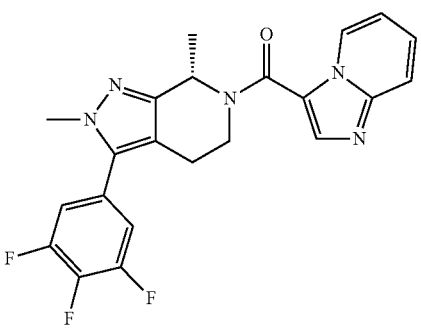 [SMILES: C[C@H]1c2nn(C)c(-c3cc(F)c(F)c(F)c3)c2CCN1C(=O)c1cnc2ccccn12]

The title compound was prepared in a manner analogous to Example 288, using imidazo[1,2-a]pyridine-3-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.1 [M+H]+. $^1$H NMR (500 MHz, DMSO-$d_6$) δ 8.92 (dt, J=7.0, 1.2 Hz, 1H), 8.09 (s, 1H), 7.80-7.67 (m, 1H), 7.58 (dd, J=8.7, 6.6 Hz, 2H), 7.54-7.41 (m, 1H), 7.22-7.01 (m, 1H), 5.52 (q, J=6.7 Hz, 1H), 4.45 (dd, J=14.0, 5.0 Hz, 1H), 3.81 (s, 3H), 3.12 (d, J=50.9 Hz, 2H), 2.49-2.44 (m, 1H), 1.56 (d, J=6.7 Hz, 3H).

Example 214: (S)-(2,7-Dimethyl-3-(3,4,5-trifluorophenyl)-2,4,5,7-tetrahydro-6H-pyrazolo[3,4-c]pyridin-6-yl)(furo[3,2-c]pyridin-4-yl)methanone

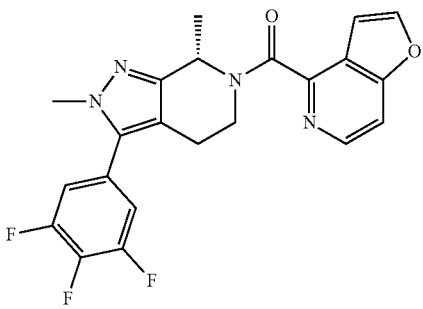

The title compound was prepared in a manner analogous to Example 288, using furo[3,2-c]pyridine-4-carboxylic acid instead of 2-fluoro-6-(2H-1,2,3-triazol-2-yl)benzoic acid. MS (ESI): mass calcd. for $C_{22}H_{17}F_3N_4O_2$, 426.1; m/z found, 427.1 [M+H]+. $^1$H NMR (600 MHz, Methanol-$d_4$) δ 8.54-8.48 (m, 1H), 7.99 (dd, J=13.6, 2.3 Hz, 1H), 7.74-7.71 (m, 1H), 7.35-7.27 (m, 2H), 7.06-6.97 (m, 1H), 5.83 (q, J=6.8 Hz, 0.65H), 5.02 (q, J=6.8 Hz, 0.36H), 3.90-3.82 (m, 2.73H), 3.76 (s, 1H), 3.46-3.36 (m, 0.7H), 3.30-3.24 (m, 0.58H), 2.94-2.79 (m, 1H), 2.66-2.33 (m, 1H), 1.70-1.50 (m, 3H).

Example 215: (S)-Benzo[d]isoxazol-3-yl(2,7-dimethyl-3-(3,4,5-trifluorophenyl)-2,4,5,7-tetrahydro-6H-pyrazolo[3,4-c]pyridin-6-yl)methanone

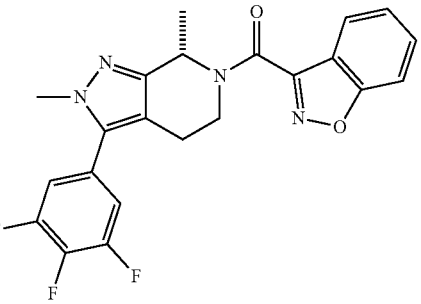

The title compound was prepared in a manner analogous to Example 288, using benzo[d]isoxazole-3-carboxylic acid instead of 2-fluoro-6-(2H-1,2,3-triazol-2-yl)benzoic acid. MS (ESI): mass calcd. for $C_{22}H_{17}F_3N_4O_2$, 426.1; m/z found, 427.1 [M+H]+. $^1$H NMR (500 MHz, CDCl$_3$) δ 8.04-7.93 (m, 1H), 7.67-7.57 (m, 2H), 7.44-7.36 (m, 1H), 7.03-6.94 (m, 2H), 6.00-5.60 (m, 1H), 5.06-4.56 (m, 1H), 3.89-3.73 (m, 3H), 3.45-3.15 (m, 1H), 2.99-2.81 (m, 1H), 2.60-2.44 (m, 1H), 1.75-1.64 (m, 3H).

Example 216: (S)-(2,7-Dimethyl-3-(3,4,5-trifluorophenyl)-2,4,5,7-tetrahydro-6H-pyrazolo[3,4-c]pyridin-6-yl)(1H-pyrrolo[3,2-c]pyridin-4-yl)methanone

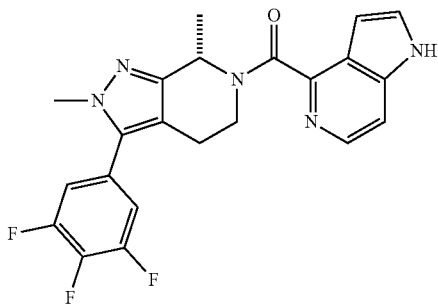 [SMILES: C[C@H]1c2nn(C)c(-c3cc(F)c(F)c(F)c3)c2CCN1C(=O)c1nccc2[nH]ccc12]

The title compound was prepared in a manner analogous to Example 288, using 1H-pyrrolo[3,2-c]pyridine-4-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.2 [M+H]$^+$. $^1$H NMR (500 MHz, Methanol-$d_4$) δ 8.22 (dd, J=5.8, 2.0 Hz, 1H), 7.59-7.45 (m, 2H), 7.38-7.24 (m, 2H), 6.64-6.51 (m, 1H), 5.89 (q, J=6.8 Hz, 0.66H), 4.98-4.91 (m, 0.57H), 4.84-4.73 (m, 0.25H), 3.89-3.74 (m, 3H), 3.67-3.56 (m, 0.64H), 3.41-3.23 (m, 0.88H), 2.96-2.69 (m, 1H), 2.66-2.30 (m, 1H), 1.71-1.41 (m, 3H).

Example 217: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[3,2-c]pyridin-4-yl)methanone

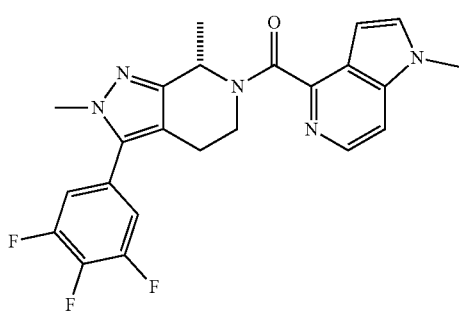 [SMILES: C[C@H]1c2nn(C)c(-c3cc(F)c(F)c(F)c3)c2CCN1C(=O)c1nccc2c1ccn2C]

The title compound was prepared in a manner analogous to Example 206, using Example 216 [(S)-(2,7-dimethyl-3-(3,4,5-trifluorophenyl)-2,4,5,7-tetrahydro-6H-pyrazolo[3,4-c]pyridin-6-yl)(1H-pyrrolo[3,2-c]pyridin-4-yl)methanone] instead of [(S)-(2,7-dimethyl-3-(3,4,5-trifluorophenyl)-2,4,5,7-tetrahydro-6H-pyrazolo[3,4-c]pyridin-6-yl)(1H-indol-7-yl)methanone]. MS (ESI): mass calcd. for $C_{23}H_{20}F_3N_5O$, 439.2; m/z found, 440.1 [M+H]$^+$. $^1$H NMR (600 MHz, Methanol-$d_4$) δ 8.29-8.22 (m, 1H), 7.62-7.55 (m, 1H), 7.47-7.38 (m, 1H), 7.35-7.24 (m, 2H), 6.61-6.51 (m, 1H), 5.90-5.82 (m, 0.66H), 4.98-4.92 (m, 0.27H), 4.79-4.73 (m, 0.33H), 3.94-3.73 (m, 6.41H), 3.61-3.55 (m, 0.65H), 3.38-3.22 (m, 0.7H), 2.96-2.67 (m, 1H), 2.63-2.29 (m, 1H), 1.70-1.39 (m, 3H).

Example 218: (S)-(2,7-Dimethyl-3-(3,4,5-trifluorophenyl)-2,4,5,7-tetrahydro-6H-pyrazolo[3,4-c]pyridin-6-yl)(1H-pyrrolo[3,2-c]pyridin-3-yl)methanone

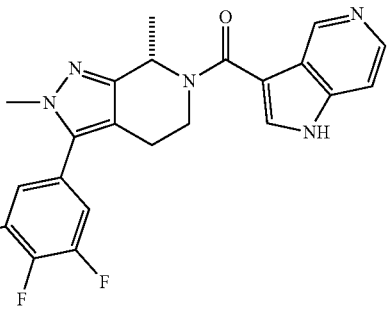

The title compound was prepared in a manner analogous to Example 288, using 1H-pyrrolo[3,2-c]pyridine-3-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.1 [M+H]$^+$. $^1$H NMR (500 MHz, Methanol-$d_4$) δ 8.98 (s, 1H), 8.24 (d, J=5.9 Hz, 1H), 7.82 (s, 1H), 7.52 (dd, J=5.8, 1.1 Hz, 1H), 7.35-7.27 (m, 2H), 5.66 (s, 1H), 4.52 (s, 1H), 3.82 (s, 3H), 3.50-3.36 (m, 1H), 2.94-2.84 (m, 1H), 2.60-2.50 (m, 1H), 1.65-1.60 (m, 3H).

Example 219: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[3,2-c]pyridin-3-yl)methanone

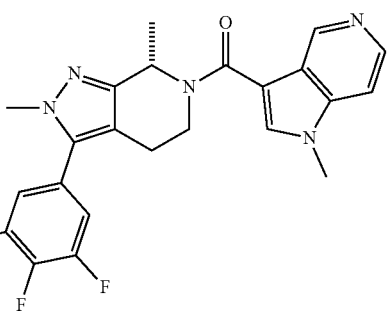

The title compound was prepared in a manner analogous to Example 206, using Example 218 [(S)-(2,7-dimethyl-3-(3,4,5-trifluorophenyl)-2,4,5,7-tetrahydro-6H-pyrazolo[3,4-c]pyridin-6-yl)(1H-pyrrolo[3,2-c]pyridin-3-yl)methanone] instead of [(S)-(2,7-dimethyl-3-(3,4,5-trifluorophenyl)-2,4,5,7-tetrahydro-6H-pyrazolo[3,4-c]pyridin-6-yl)(1H-indol-7-yl)methanone]. MS (ESI): mass calcd. for $C_{23}H_{20}F_3N_5O$, 439.2; m/z found, 440.1 [M+H]$^+$. $^1$H NMR (500 MHz, Methanol-$d_4$) δ 8.98 (s, 1H), 8.29 (d, J=6.0 Hz, 1H), 7.79 (s, 1H), 7.56 (dd, J=6.0, 1.1 Hz, 1H), 7.36-7.28 (m, 2H), 5.66 (s, 0.89H), 4.51 (s, 0.81H), 3.93 (s, 3.19H), 3.82 (s, 3.13H), 3.44 (d, J=9.0 Hz, 1H), 2.99-2.85 (m, 1H), 2.59-2.50 (m, 1H), 1.68-1.59 (m, 3H).

Example 220: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[3,2-b]pyridin-3-yl)methanone

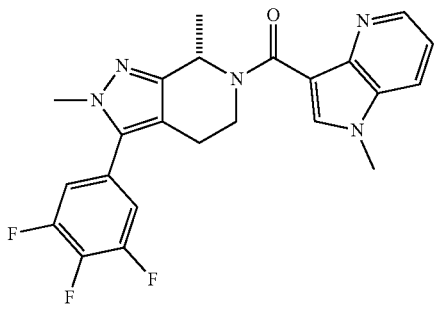 [SMILES: C[C@H]1c2nn(C)c(-c3cc(F)c(F)c(F)c3)c2CCN1C(=O)c1cn(C)c2cccnc12]

The title compound was prepared in a manner analogous to Example 288, using 1-methyl-1H-pyrrolo[3,2-b]pyridine-3-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (600 MHz, CDCl$_3$) δ 8.57-8.52 (m, 1H), 7.79-7.61 (m, 2H), 7.20-7.16 (m, 1H), 7.02-6.96 (m, 2H), 5.81 (s, 0.82H), 4.99-4.22 (m, 0.81H), 3.93-3.70 (m, 6H), 3.29 (s, 1.9H), 2.38 (d, J=15.2 Hz, 1H), 1.71-1.60 (m, 3.45H).

Example 221: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-c]pyridin-3-yl)methanone

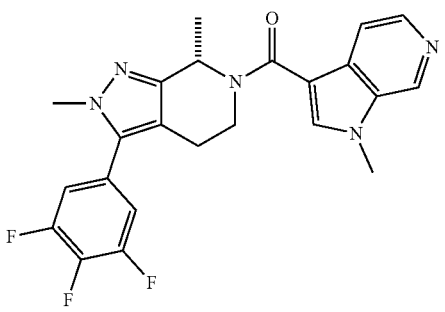 [SMILES: C[C@H]1c2nn(C)c(-c3cc(F)c(F)c(F)c3)c2CCN1C(=O)c1cn(C)c2cnccc12]

Step A: (S)-(2,7-Dimethyl-3-(3,4,5-trifluorophenyl)-2,4,5,7-tetrahydro-6H-pyrazolo[3,4-c]pyridin-6-yl)(1H-pyrrolo[2,3-c]pyridin-3-yl)methanone. The title compound was prepared in a manner analogous to Example 288, using 1H-pyrrolo[2,3-c]pyridine-3-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.0 [M+H]$^+$.

Step B: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-c]pyridin-3-yl)methanone. The title compound was prepared in a manner analogous to Example 206, using (S)-(2,7-dimethyl-3-(3,4,5-trifluorophenyl)-2,4,5,7-tetrahydro-6H-pyrazolo[3,4-c]pyridin-6-yl)(1H-pyrrolo[2,3-c]pyridin-3-yl)methanone instead of [(S)-(2,7-dimethyl-3-(3,4,5-trifluorophenyl)-2,4,5,7-tetrahydro-6H-pyrazolo[3,4-c]pyridin-6-yl)(1H-indol-7-yl)methanone]. MS (ESI): mass calcd. for $C_{23}H_{20}F_3N_5O$, 439.2; m/z found, 440.1 [M+H]$^+$. $^1$H NMR (500 MHz, Methanol-d$_4$) δ 9.34 (s, 1H), 8.50 (s, 1H), 8.35 (d, J=6.5 Hz, 1H), 8.28 (d, J=6.5 Hz, 1H), 7.36-7.27 (m, 2H), 5.65 (s, 0.9H), 4.41 (s, 0.91H), 4.18 (s, 3.14H), 3.83 (s, 3.16H), 3.49 (s, 0.88H), 2.99-2.88 (m, 1H), 2.65-2.51 (m, 1H), 1.69-1.61 (m, 3H).

Example 222: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-2-yl)methanone

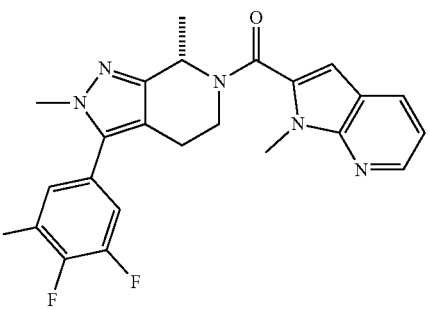

The title compound was prepared in a manner analogous to Example 288, using 1-methyl-1H-pyrrolo[2,3-b]pyridine-2-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (500 MHz, CDCl$_3$) δ 8.41 (dd, J=4.7, 1.6 Hz, 1H), 7.93 (dd, J=7.8, 1.6 Hz, 1H), 7.11 (dd, J=7.8, 4.7 Hz, 1H), 7.02-6.94 (m, 2H), 6.61 (s, 1H), 6.05-4.12 (m, 1.32H), 3.99-3.72 (m, 6.18H), 3.29 (s, 1H), 2.90-2.73 (m, 1H), 2.48 (d, J=15.3 Hz, 1H), 1.71-1.55 (m, 3.5H).

Example 223: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-3-yl)methanone

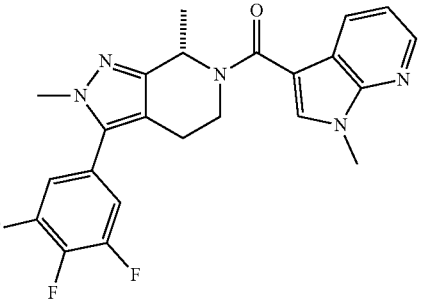

The title compound was prepared in a manner analogous to Example 288, using 1-methyl-1H-pyrrolo[2,3-b]pyridine-3-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (600 MHz, Methanol-d$_4$) δ 8.35 (dd, J=4.7, 1.6 Hz, 1H), 8.19 (d, J=7.9 Hz, 1H), 7.85 (s, 1H), 7.33 (dd, J=8.1, 6.4 Hz, 2H), 7.25 (dd, J=7.9, 4.7 Hz, 1H), 5.65 (s, 1H), 4.51 (s, 1H), 3.95 (s, 3H), 3.83 (s, 3H), 3.42 (p, J=1.6 Hz, 1H), 2.96-2.88 (m, 1H), 2.54 (dd, J=15.4, 3.8 Hz, 1H), 1.62 (d, J=6.8 Hz, 3H).

Example 224: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-c]pyridin-4-yl)methanone

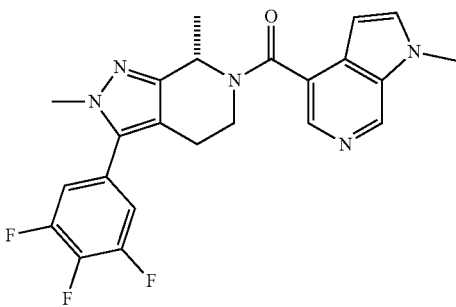 [SMILES: C[C@H]1c2nn(C)c(-c3cc(F)c(F)c(F)c3)c2CCN1C(=O)c1cncc2c1ccn2C]

Step A: (S)-(2,7-Dimethyl-3-(3,4,5-trifluorophenyl)-2,4,5,7-tetrahydro-6H-pyrazolo[3,4-c]pyridin-6-yl)(1H-pyrrolo[2,3-c]pyridin-4-yl)methanone. The title compound was prepared in a manner analogous to Example 288, using 1H-pyrrolo[2,3-c]pyridine-4-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.0 [M+H]$^+$.

Step B: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-c]pyridin-4-yl)methanone. The title compound was prepared in a manner analogous to Example 206, using (S)-(2,7-dimethyl-3-(3,4,5-trifluorophenyl)-2,4,5,7-tetrahydro-6H-pyrazolo[3,4-c]pyridin-6-yl)(1H-pyrrolo[2,3-c]pyridin-4-yl)methanone instead of [(S)-(2,7-dimethyl-3-(3,4,5-trifluorophenyl)-2,4,5,7-tetrahydro-6H-pyrazolo[3,4-c]pyridin-6-yl)(1H-indol-7-yl)methanone]. MS (ESI): mass calcd. for $C_{23}H_{20}F_3N_5O$, 439.2; m/z found, 440.1 [M+H]$^+$. $^1$H NMR (500 MHz, Methanol-d$_4$) δ 8.86 (s, 1H), 8.16 (s, 1H), 7.59 (s, 1H), 7.30 (s, 2H), 6.59-6.35 (m, 1H), 5.88 (s, 0.61H), 4.99-4.87 (m, 1.21H), 4.00 (s, 3H), 3.92-3.66 (m, 3.75H), 3.45-3.37 (m, 0.54H), 2.98-2.29 (m, 1.88H), 1.75-1.38 (m, 3H).

Example 225: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-4-yl)methanone

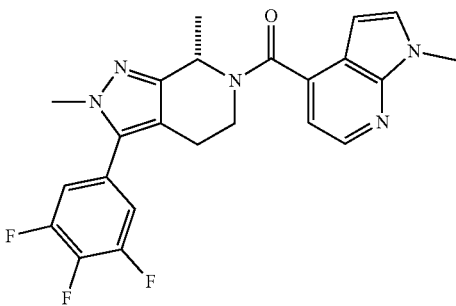 [SMILES: C[C@H]1c2nn(C)c(-c3cc(F)c(F)c(F)c3)c2CCN1C(=O)c1ccnc2c1ccn2C]

The title compound was prepared in a manner analogous to Example 288, using 1-methyl-7-azaindole-4-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (600 MHz, Methanol-d$_4$) δ 8.37 (d, J=4.8 Hz, 1H), 7.54-7.44 (m, 1H), 7.39-7.24 (m, 2H), 7.17-7.10 (m, 1H), 6.50-6.31 (m, 1H), 5.87 (q, J=6.8 Hz, 0.66H), 4.98-4.90 (m, 0.36H), 4.80-4.73 (m, 0.34H), 3.92 (s, 3H), 3.88-3.74 (m, 3H), 3.66-3.58 (m, 0.64H), 3.45-3.35 (m, 0.59H), 3.30-3.22 (m, 0.4H), 2.96-2.30 (m, 2H), 1.73-1.38 (m, 3H).

Example 226: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-5-yl)methanone

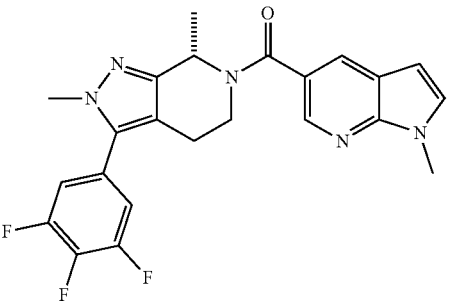 [SMILES: C[C@H]1c2nn(C)c(-c3cc(F)c(F)c(F)c3)c2CCN1C(=O)c1cnc2c(ccn2C)c1]

The title compound was prepared in a manner analogous to Example 288, using 1-methyl-1H-pyrrolo[2,3-b]pyridine-5-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (500 MHz, CDCl$_3$) δ 8.46 (d, J=2.0 Hz, 1H), 8.03 (d, J=2.0 Hz, 1H), 7.25 (s, 1H), 7.01-6.94 (m, 2H), 6.50 (d, J=3.5 Hz, 1H), 6.11-4.31 (m, 0.9H), 3.92 (s, 6.97H), 3.25 (s, 1H), 2.83 (s, 1H), 2.41 (d, J=15.3 Hz, 1H), 1.68-1.53 (m, 3.13H).

Example 227: (S)-(2,7-Dimethyl-3-(3,4,5-trifluorophenyl)-2,4,5,7-tetrahydro-6H-pyrazolo[3,4-c]pyridin-6-yl)(pyrazolo[1,5-a]pyridin-4-yl)methanone

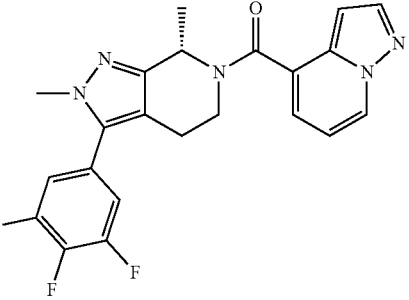

The title compound was prepared in a manner analogous to Example 288, using pyrazolo[1,5-a]pyridine-4-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.1 [M+H]$^+$. $^1$H NMR (500 MHz, DMSO-d$_6$) δ 8.84-8.73 (m, 1H), 8.07 (s, 1H), 7.54 (s, 2H), 7.28 (dd, J=6.9, 1.0 Hz, 1H), 6.97 (t, J=7.0 Hz, 1H), 6.50 (s, 1H), 5.66 (s, 1H), 3.81 (s, 3H), 3.55 (s, 1H), 2.71 (d, J=20.5 Hz, 2H), 2.33 (s, 1H), 1.52 (s, 3H).

Example 228: (S)-(2,7-Dimethyl-3-(3,4,5-trifluorophenyl)-2,4,5,7-tetrahydro-6H-pyrazolo[3,4-c]pyridin-6-yl)(pyrazolo[1,5-a]pyridin-5-yl)methanone

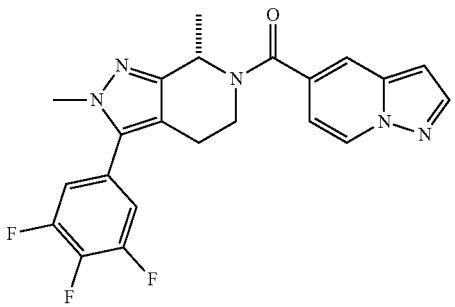 [SMILES: C[C@H]1c2nn(C)c(-c3cc(F)c(F)c(F)c3)c2CCN1C(=O)c1ccn2nccc2c1]

The title compound was prepared in a manner analogous to Example 288, using pyrazolo[1,5-a]pyridine-5-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.0 [M+H]$^+$. $^1$H NMR (600 MHz, Methanol-$d_4$) δ 8.63 (d, J=7.2 Hz, 1H), 8.04 (d, J=2.3 Hz, 1H), 7.80 (s, 1H), 7.33-7.27 (m, 2H), 6.93 (s, 1H), 6.76 (d, J=2.3 Hz, 1H), 5.72 (s, 0.65H), 4.94 (s, 0.46H), 3.83 (s, 3.77H), 3.51-3.36 (m, 0.96H), 2.90-2.78 (m, 1H), 2.48 (s, 0.94H), 1.59 (d, J=6.7 Hz, 3.21H).

Example 229: (S)-(2,7-Dimethyl-3-(3,4,5-trifluorophenyl)-2,4,5,7-tetrahydro-6H-pyrazolo[3,4-c]pyridin-6-yl)(pyrazolo[1,5-a]pyrazin-3-yl)methanone

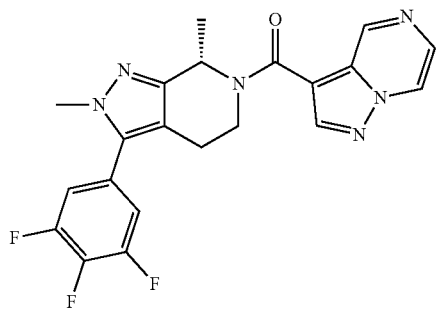 [SMILES: C[C@H]1c2nn(C)c(-c3cc(F)c(F)c(F)c3)c2CCN1C(=O)c1cnn2ccncc12]

The title compound was prepared in a manner analogous to Example 288, using pyrazolo[1,5-a]pyrazine-3-carboxylic acid instead of 2-fluoro-6-(2H-1,2,3-triazol-2-yl)benzoic acid. MS (ESI): mass calcd. for $C_{21}H_{17}F_3N_6O_2$, 426.1; m/z found, 427.1 [M+H]$^+$. $^1$H NMR (500 MHz, DMSO-$d_6$) δ 9.33 (d, J=1.4 Hz, 1H), 8.91 (dd, J=4.7, 1.5 Hz, 1H), 8.50 (s, 1H), 8.08 (d, J=4.7 Hz, 1H), 7.57 (dd, J=8.7, 6.6 Hz, 2H), 5.53 (s, 1H), 4.33 (s, 1H), 3.81 (s, 3H), 3.01 (s, 1H), 2.49-2.29 (m, 2H), 1.54 (d, J=6.7 Hz, 3H).

Example 230: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrazolo[3,4-b]pyridin-3-yl)methanone

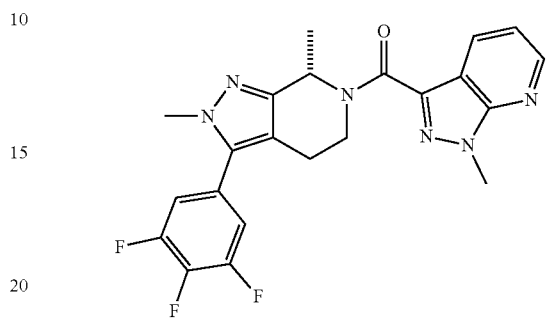

The title compound was prepared in a manner analogous to Example 288, using 1-methyl-1H-pyrazolo[3,4-b]pyridine-3-carboxylic acid instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]$^+$. $^1$H NMR (500 MHz, CDCl$_3$) δ 8.61-8.53 (m, 2H), 7.26-7.20 (m, 1H), 6.98 (s, 2H), 6.46-5.88 (m, 1H), 5.33-4.89 (m, 1H), 4.21 (s, 3H), 3.88-3.78 (m, 3H), 3.43-3.10 (m, 1H), 3.02-2.79 (m, 1H), 2.50 (d, J=15.5 Hz, 1H), 1.80-1.62 (m, 3H).

Example 231: (S)-(2,7-Dimethyl-3-(3,4,5-trifluorophenyl)-2,4,5,7-tetrahydro-6H-pyrazolo[3,4-c]pyridin-6-yl)(1-methyl-1H-pyrazolo[3,4-b]pyridin-5-yl)methanone

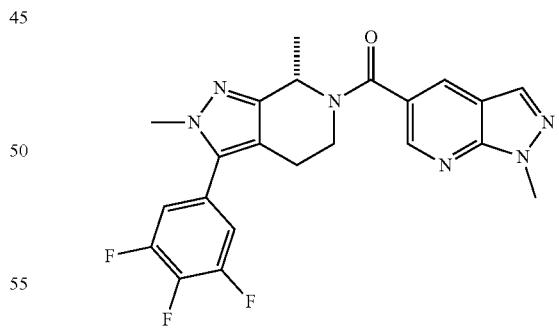

The title compound was prepared in a manner analogous to Example 288, using 1-methyl-1H-pyrazolo[3,4-b]pyridine-5-carboxylic acid instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]$^+$. $^1$H NMR (500 MHz, CDCl$_3$) δ 8.66 (d, J=2.0 Hz, 1H), 8.19 (d, J=2.0 Hz, 1H), 8.07 (s, 1H), 7.03-6.94 (m, 2H), 6.23-4.48 (m, 1.22H), 4.19 (s, 3.12H), 3.80 (s, 3.23H), 3.28 (s, 1H), 2.82 (s, 1H), 2.45 (d, J=15.3 Hz, 1H), 1.70-1.57 (m, 3.43H).

Example 232: (S)-(2-(Difluoromethyl)-7-methyl-3-(3,4,5-trifluorophenyl)-2,4,5,7-tetrahydro-6H-pyrazolo[3,4-c]pyridin-6-yl)(quinolin-6-yl)methanone

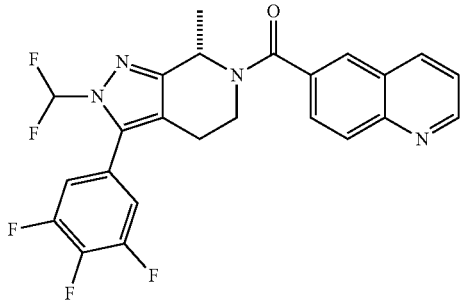 [SMILES: C[C@H]1c2nn(C(F)F)c(-c3cc(F)c(F)c(F)c3)c2CCN1C(=O)c1ccc2ncccc2c1]

The title compound was prepared in a manner analogous to Example 1, using (S)-2-(difluoromethyl)-7-methyl-3-(3,4,5-trifluorophenyl)-4,5,6,7-tetrahydro-2H-pyrazolo[3,4-c]pyridine (Intermediate 33) instead of 2-methyl-3-phenyl-4,5,6,7-tetrahydro-2H-pyrazolo[3,4-c]pyridine and using quinoline-6-carboxylic acid instead of 1-naphthoic acid. MS (ESI): mass calcd. for $C_{24}H_{18}F_4N_4O$, 454.1; m/z found, 455.1 [M+H]$^+$. $^1$H NMR (500 MHz, DMSO-d$_6$) δ 8.99 (dd, J=4.2, 1.7 Hz, 1H), 8.52-8.43 (m, 1H), 8.15-8.07 (m, 2H), 7.89-7.68 (m, 2H), 7.67-7.42 (m, 4H), 5.74 (s, 1H), 4.79 (d, J=94.0 Hz, 1H), 3.74 (s, 1H), 2.88 (s, 1H), 2.42 (s, 1H), 1.56 (d, J=6.8 Hz, 3H).

Example 233: (R)-(2-(Difluoromethyl)-7-methyl-3-(3,4,5-trifluorophenyl)-2,4,5,7-tetrahydro-6H-pyrazolo[3,4-c]pyridin-6-yl)(quinolin-6-yl)methanone

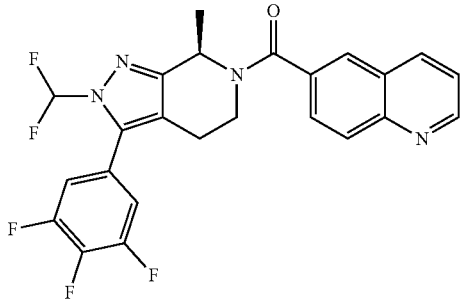

The title compound was prepared in a manner analogous to Example 1, using (R)-2-(difluoromethyl)-7-methyl-3-(3,4,5-trifluorophenyl)-4,5,6,7-tetrahydro-2H-pyrazolo[3,4-c]pyridine (Intermediate 34) instead of 2-methyl-3-phenyl-4,5,6,7-tetrahydro-2H-pyrazolo[3,4-c]pyridine and using quinoline-6-carboxylic acid instead of 1-naphthoic acid. MS (ESI): mass calcd. for $C_{24}H_{18}F_4N_4O$, 454.1; m/z found, 455.1 [M+H]$^+$. $^1$H NMR (500 MHz, DMSO-d$_6$) δ 8.99 (dd, J=4.2, 1.7 Hz, 1H), 8.56-8.40 (m, 1H), 8.18-8.03 (m, 2H), 7.90-7.67 (m, 2H), 7.68-7.36 (m, 4H), 5.74 (s, 1H), 4.85 (s, 1H), 3.73 (s, 1H), 2.89 (s, 1H), 2.41 (s, 1H), 1.56 (d, J=6.8 Hz, 3H).

Example 234: (S)-(2,7-Dimethyl-3-(3,4,5-trifluorophenyl)-2,4,5,7-tetrahydro-6H-pyrazolo[3,4-c]pyridin-6-yl)(quinolin-6-yl)methanone

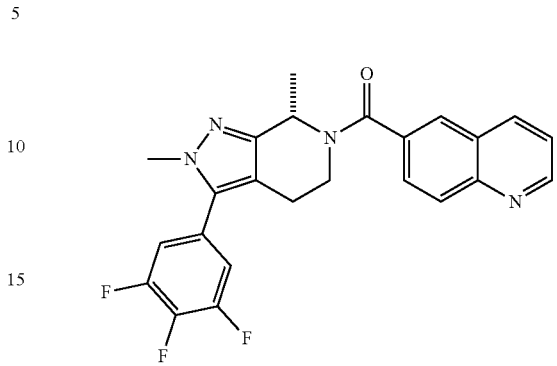

The title compound was prepared in a manner analogous to Example 288, using quinoline-6-carboxylic acid instead of 2-fluoro-6-(2H-1,2,3-triazol-2-yl)benzoic acid. MS (ESI): mass calcd. for $C_{24}H_{19}F_3N_4O$, 436.2; m/z found, 437.1 [M+H]$^+$. $^1$H NMR (500 MHz, CDCl$_3$) δ 8.98 (dd, J=4.2, 1.7 Hz, 1H), 8.23-8.14 (m, 2H), 7.93 (d, J=1.8 Hz, 1H), 7.75 (dd, J=8.6, 1.9 Hz, 1H), 7.47 (dd, J=8.3, 4.2 Hz, 1H), 7.02-6.94 (m, 2H), 5.90 (s, 0.46H), 5.17-4.71 (m, 0.75H), 3.81 (s, 3.57H), 3.40-3.04 (m, 1H), 2.93-2.66 (m, 1H), 2.44 (s, 1H), 1.61 (s, 3.22H).

Example 235: (R)-(2,7-Dimethyl-3-(3,4,5-trifluorophenyl)-2,4,5,7-tetrahydro-6H-pyrazolo[3,4-c]pyridin-6-yl)(quinolin-6-yl)methanone

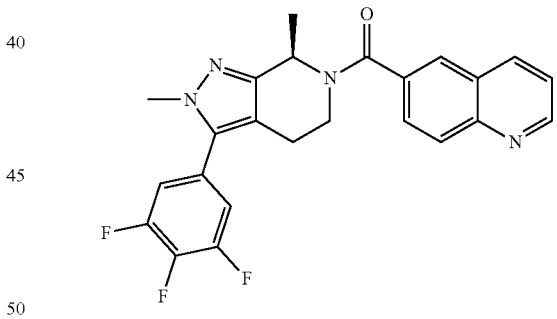

The title compound was prepared in a manner analogous to Example 106, using 3,4,5-trifluorophenylboronic acid instead of 3,5-difluorophenylboronic acid and (R)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 9) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A. MS (ESI): mass calcd. for $C_{24}H_{19}F_3N_4O$, 436.1; m/z found, 437.1 [M+H]$^+$. $^1$H NMR (500 MHz, CDCl$_3$) δ 8.98 (dd, J=4.2, 1.7 Hz, 1H), 8.23-8.14 (m, 2H), 7.93 (d, J=1.8 Hz, 1H), 7.75 (dd, J=8.6, 1.9 Hz, 1H), 7.47 (dd, J=8.3, 4.2 Hz, 1H), 7.02-6.94 (m, 2H), 5.90 (s, 0.46H), 5.17-4.71 (m, 0.75H), 3.81 (s, 3.57H), 3.40-3.04 (m, 1H), 2.93-2.66 (m, 1H), 2.44 (s, 1H), 1.61 (s, 3.22H).

Example 236: (S)-(2,7-Dimethyl-3-(3,4,5-trifluorophenyl)-2,4,5,7-tetrahydro-6H-pyrazolo[3,4-c]pyridin-6-yl)(quinolin-8-yl)methanone

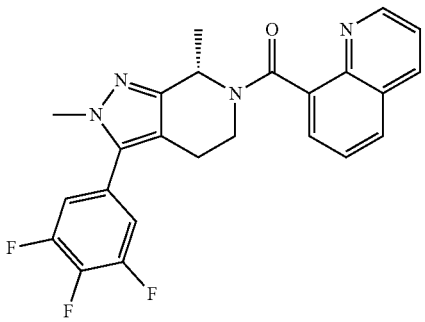 [SMILES: C[C@H]1c2nn(C)c(-c3cc(F)c(F)c(F)c3)c2CCN1C(=O)c1cccc2cccnc12]

The title compound was prepared in a manner analogous to Example 288, using quinoline-8-carboxylic acid instead of 2-fluoro-6-(2H-1,2,3-triazol-2-yl)benzoic acid. MS (ESI): mass calcd. for $C_{24}H_{19}F_3N_4O$, 436.1; m/z found, 437.1 [M+H]$^+$. $^1$H NMR (500 MHz, DMSO-d$_6$) δ 9.04-8.73 (m, 1H), 8.54-8.39 (m, 1H), 8.13-7.96 (m, 1H), 7.84-7.42 (m, 5H), 5.84-5.65 (m, 1H), 3.88-3.64 (m, 3H), 3.26-3.06 (m, 2H), 2.93-2.57 (m, 1H), 2.26-2.07 (m, 1H), 1.63-1.09 (m, 3H).

Example 237: (S)-(2,7-Dimethyl-3-(3,4,5-trifluorophenyl)-2,4,5,7-tetrahydro-6H-pyrazolo[3,4-c]pyridin-6-yl)(isoquinolin-1-yl)methanone

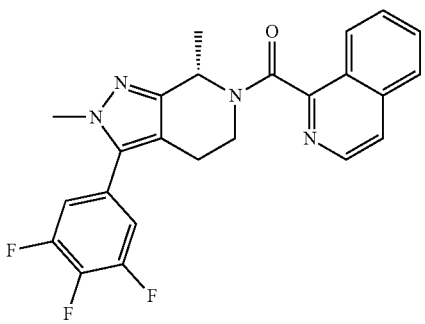 [SMILES: C[C@H]1c2nn(C)c(-c3cc(F)c(F)c(F)c3)c2CCN1C(=O)c1nccc2ccccc12]

The title compound was prepared in a manner analogous to Example 288, using isoquinoline-1-carboxylic acid instead of 2-fluoro-6-(2H-1,2,3-triazol-2-yl)benzoic acid. MS (ESI): mass calcd. for $C_{24}H_{19}F_3N_4O$, 436.1; m/z found, 437.1 [M+H]$^+$. $^1$H NMR (500 MHz, DMSO-d$_6$) δ 8.54 (t, J=5.4 Hz, 1H), 8.08 (dt, J=8.3, 1.0 Hz, 1H), 7.99-7.78 (m, 3H), 7.80-7.66 (m, 1H), 7.63-7.49 (m, 2H), 5.78 (q, J=6.7 Hz, 1H), 3.77 (d, J=61.0 Hz, 3H), 3.29-3.11 (m, 2H), 2.66-2.54 (m, 1H), 2.32-2.20 (m, 1H), 1.46 (dd, J=134.2, 6.8 Hz, 3H).

Example 238: (S)-(2,7-Dimethyl-3-(3,4,5-trifluorophenyl)-2,4,5,7-tetrahydro-6H-pyrazolo[3,4-c]pyridin-6-yl)(8-fluoroquinolin-4-yl)methanone

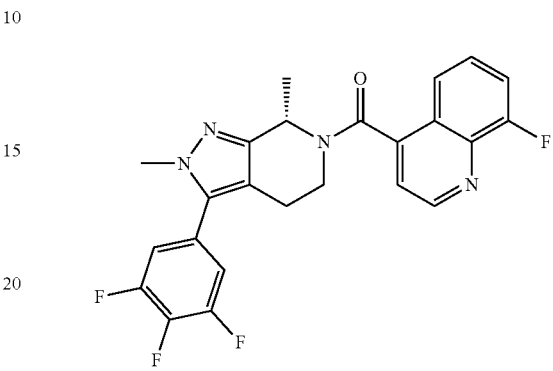

The title compound was prepared in a manner analogous to Example 288, using 8-fluoroquinoline-4-carboxylic acid instead of 2-fluoro-6-(2H-1,2,3-triazol-2-yl)benzoic acid. MS (ESI): mass calcd. for $C_{24}H_{18}F_4N_4O$, 454.1; m/z found, 455.1 [M+H]$^+$. $^1$H NMR (500 MHz, DMSO-d$_6$) δ 9.05 (d, J=4.3 Hz, 1H), 7.81-7.39 (m, 6H), 5.76 (d, J=6.3 Hz, 1H), 4.85 (s, 1H), 3.83 (s, 3H), 3.25 (d, J=8.4 Hz, 1H), 3.18-2.74 (m, 1H), 2.25 (d, J=14.7 Hz, 1H), 1.69-1.24 (m, 3H).

Example 239: (S)-(2,7-Dimethyl-3-(3,4,5-trifluorophenyl)-2,4,5,7-tetrahydro-6H-pyrazolo[3,4-c]pyridin-6-yl)(2-methylquinolin-4-yl)methanone

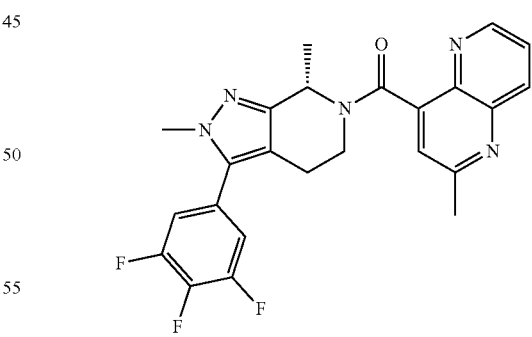

The title compound was prepared in a manner analogous to Example 288, using 2-methylquinoline-4-carboxylic acid instead of 2-fluoro-6-(2H-1,2,3-triazol-2-yl)benzoic acid. MS (ESI): mass calcd. for $C_{25}H_{21}F_3N_4O$, 450.1; m/z found, 451.0 [M+H]$^+$. $^1$H NMR (500 MHz, DMSO-d$_6$) δ 8.01 (d, J=8.7 Hz, 1H), 7.85-7.66 (m, 2H), 7.66-7.38 (m, 4H), 5.77 (dd, J=13.9, 7.0 Hz, 1H), 3.76 (d, J=70.7 Hz, 3H), 3.28-3.20 (m, 1H), 2.99 (s, 1H), 2.70 (s, 3H), 2.62 (d, J=47.3 Hz, 1H), 2.27 (d, J=16.7 Hz, 1H), 1.64-1.36 (m, 3H).

Example 240: (S)-(2,7-Dimethyl-3-(3,4,5-trifluorophenyl)-2,4,5,7-tetrahydro-6H-pyrazolo[3,4-c]pyridin-6-yl)(2-methoxyquinolin-4-yl)methanone

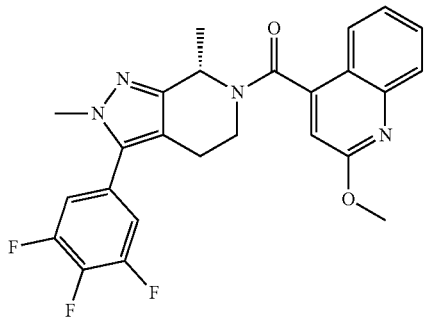 [SMILES: COc1cc(C(=O)N2CCc3c(nn(C)c3-c3cc(F)c(F)c(F)c3)[C@@H]2C)c2ccccc2n1]

The title compound was prepared in a manner analogous to Example 288, using 2-methoxyquinoline-4-carboxylic acid instead of 2-fluoro-6-(2H-1,2,3-triazol-2-yl)benzoic acid. MS (ESI): mass calcd. for $C_{25}H_{21}F_3N_4O_2$, 466.1; m/z found, 467.1 [M+H]⁺. ¹H NMR (500 MHz, DMSO-d₆) δ 7.86 (t, J=9.8 Hz, 1H), 7.74 (t, J=7.4 Hz, 1H), 7.70-7.58 (m, 1H), 7.58-7.31 (m, 3H), 7.21-6.94 (m, 1H), 5.74 (q, J=6.9 Hz, 1H), 4.08 (q, J=5.2 Hz, 1H), 4.03 (s, 3H), 3.87-3.66 (m, 3H), 3.30-3.22 (m, 1H), 3.05-2.66 (m, 1H), 2.24 (dd, J=15.1, 3.1 Hz, 1H), 1.65-1.36 (m, 3H).

Example 241: (S)-(2,7-Dimethyl-3-(3,4,5-trifluorophenyl)-2,4,5,7-tetrahydro-6H-pyrazolo[3,4-c]pyridin-6-yl)(8-fluoro-2-methylquinolin-4-yl)methanone

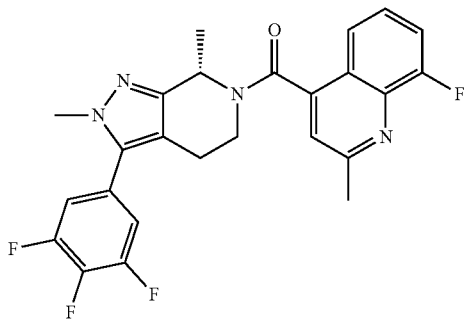 [SMILES: Cc1cc(C(=O)N2CCc3c(nn(C)c3-c3cc(F)c(F)c(F)c3)[C@@H]2C)c2cccc(F)c2n1]

The title compound was prepared in a manner analogous to Example 288, using 8-fluoro-2-methylquinoline-4-carboxylic acid instead of 2-fluoro-6-(2H-1,2,3-triazol-2-yl)benzoic acid. MS (ESI): mass calcd. for $C_{25}H_{20}F_4N_4O$, 468.1; m/z found, 469.1 [M+H]⁺. ¹H NMR (500 MHz, DMSO-d₆) δ 7.61 (t, J=7.9 Hz, 2H), 7.58-7.28 (m, 4H), 5.85-5.65 (m, 1H), 3.77 (d, J=68.7 Hz, 3H), 3.27-3.06 (m, 2H), 2.73 (s, 3H), 2.25 (t, J=18.4 Hz, 2H), 1.68-1.37 (m, 3H).

Example 242: (S)-(2,7-Dimethyl-3-(3,4,5-trifluorophenyl)-2,4,5,7-tetrahydro-6H-pyrazolo[3,4-c]pyridin-6-yl)(quinoxalin-6-yl)methanone

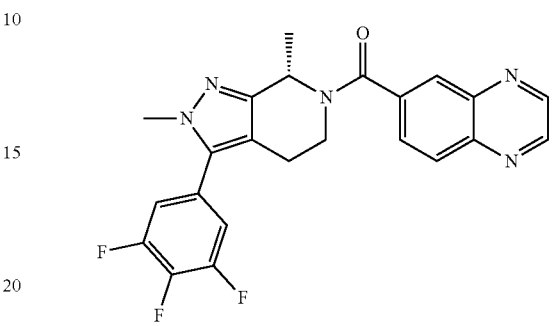

The title compound was prepared in a manner analogous to Example 288, using quinoxaline-6-carboxylic acid instead of 2-fluoro-6-(2H-1,2,3-triazol-2-yl)benzoic acid. MS (ESI): mass calcd. for $C_{23}H_{18}F_3N_5O$, 437.1; m/z found, 438.1 [M+H]⁺. ¹H NMR (400 MHz, DMSO-d₆) δ 9.04 (d, J=2.4 Hz, 2H), 8.33-8.07 (m, 2H), 8.00-7.77 (m, 1H), 7.57 (t, J=7.6 Hz, 2H), 5.65 (s, 1H), 4.73 (s, 1H), 3.84 (s, 3H), 3.68 (d, J=14.7 Hz, 1H), 3.23-2.76 (m, 1H), 2.33 (d, J=14.7 Hz, 1H), 1.53 (d, J=6.6 Hz, 3H).

Example 243: (S)-(2,7-Dimethyl-3-(3,4,5-trifluorophenyl)-2,4,5,7-tetrahydro-6H-pyrazolo[3,4-c]pyridin-6-yl)(2-methylquinoxalin-6-yl)methanone

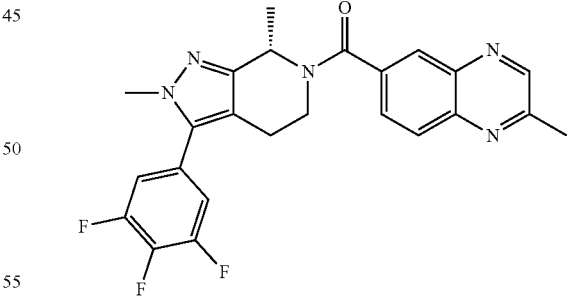

The title compound was prepared in a manner analogous to Example 288, using 2-methylquinoxaline-6-carboxylic acid (Intermediate 25) instead of 2-fluoro-6-(2H-1,2,3-triazol-2-yl)benzoic acid. MS (ESI): mass calcd. for $C_{24}H_{20}F_3N_5O$, 451.1; m/z found, 452.1 [M+H]⁺. ¹H NMR (500 MHz, DMSO-d₆) δ 8.93 (d, J=2.6 Hz, 1H), 8.17-7.96 (m, 2H), 7.84 (d, J=8.8 Hz, 1H), 7.68-7.49 (m, 2H), 5.64 (s, 1H), 4.40 (d, J=310.5 Hz, 1H), 3.79 (d, J=43.5 Hz, 3H), 3.68 (s, 1H), 3.00-2.82 (m, 1H), 2.74 (d, J=1.7 Hz, 3H), 2.41-2.27 (m, 1H), 1.51 (s, 3H).

Example 244: (S)-(2,7-Dimethyl-3-(3,4,5-trifluorophenyl)-2,4,5,7-tetrahydro-6H-pyrazolo[3,4-c]pyridin-6-yl)(1,5-naphthyridin-2-yl)methanone

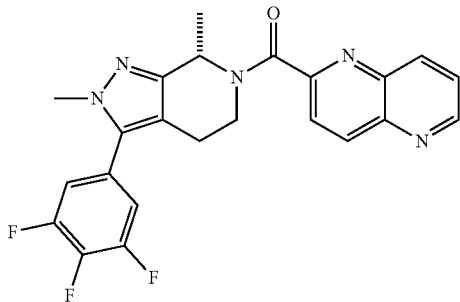 [SMILES: C[C@H]1c2nn(C)c(-c3cc(F)c(F)c(F)c3)c2CCN1C(=O)c1ccc2ncccc2n1]

The title compound was prepared in a manner analogous to Example 288, using 1,5-naphthyridine-2-carboxylic acid instead of 2-fluoro-6-(2H-1,2,3-triazol-2-yl)benzoic acid. MS (ESI): mass calcd. for $C_{23}H_{18}F_3N_5O$, 437.1; m/z found, 438.1 [M+H]$^+$. $^1$H NMR (600 MHz, Methanol-d$_4$) δ 9.08-9.02 (m, 1H), 8.62-8.50 (m, 2H), 8.03-7.97 (m, 1H), 7.90-7.83 (m, 1H), 7.35-7.27 (m, 2H), 5.81 (q, J=6.8 Hz, 0.66H), 5.13 (q, J=6.8 Hz, 0.37H), 4.93-4.85 (m, 0.44H), 3.96 (dd, J=13.9, 5.2 Hz, 0.69H), 3.90-3.72 (m, 3.1H), 3.48-3.36 (m, 0.76H), 3.05-2.81 (m, 1H), 2.66-2.39 (m, 1H), 1.70-1.59 (m, 3H).

Example 245: (S)-(2,7-Dimethyl-3-(3,4,5-trifluorophenyl)-2,4,5,7-tetrahydro-6H-pyrazolo[3,4-c]pyridin-6-yl)(1,5-naphthyridin-3-yl)methanone

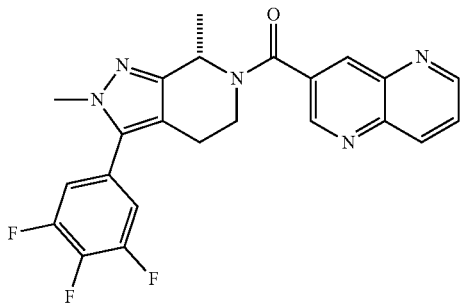 [SMILES: C[C@H]1c2nn(C)c(-c3cc(F)c(F)c(F)c3)c2CCN1C(=O)c1cnc2cccnc2c1]

The title compound was prepared in a manner analogous to Example 288, using 1,5-naphthyridine-3-carboxylic acid instead of 2-fluoro-6-(2H-1,2,3-triazol-2-yl)benzoic acid. MS (ESI): mass calcd. for $C_{23}H_{18}F_3N_5O$, 437.1; m/z found, 438.0 [M+H]$^+$. $^1$H NMR (600 MHz, Methanol-d$_4$) δ 9.11-9.02 (m, 2H), 8.57-8.50 (m, 2H), 7.92-7.87 (m, 1H), 7.36-7.29 (m, 2H), 5.81 (s, 0.69H), 4.84 (s, 0.66H), 3.85 (s, 3.9H), 3.51 (s, 0.75H), 2.90 (m, 1H), 2.47 (m, 1H), 1.67 (s, 3H).

Example 246: (S)-(2,7-Dimethyl-3-(3,4,5-trifluorophenyl)-2,4,5,7-tetrahydro-6H-pyrazolo[3,4-c]pyridin-6-yl)(1,6-naphthyridin-8-yl)methanone

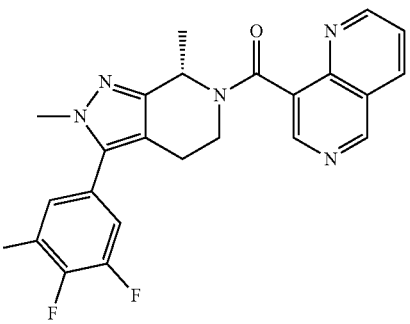

The title compound was prepared in a manner analogous to Example 288, using 1,6-naphthyridine-8-carboxylic acid instead of 2-fluoro-6-(2H-1,2,3-triazol-2-yl)benzoic acid. MS (ESI): mass calcd. for $C_{23}H_{18}F_3N_5O$, 437.14; m/z found, 438.0 [M+H]$^+$. $^1$H NMR (500 MHz, DMSO-d$_6$) δ 9.49 (d, J=7.6 Hz, 1H), 9.23-9.01 (m, 1H), 8.79-8.58 (m, 2H), 7.86-7.40 (m, 3H), 5.83-5.64 (m, 1H), 5.03-4.40 (m, 1H), 3.92-3.68 (m, 3H), 3.09-2.57 (m, 2H), 2.32-2.02 (m, 1H), 1.62-1.19 (m, 3H).

Example 247: (S)-(2,7-Dimethyl-3-(5-(trifluoromethyl)furan-2-yl)-2,4,5,7-tetrahydro-6H-pyrazolo[3,4-c]pyridin-6-yl)(quinoxalin-6-yl)methanone

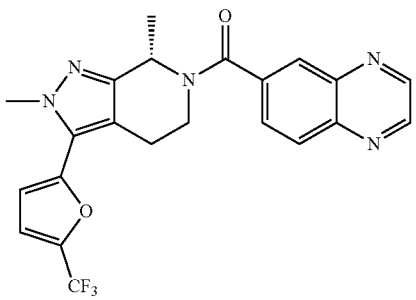 [SMILES: C[C@H]1c2nn(C)c(-c3ccc(C(F)(F)F)o3)c2CCN1C(=O)c1ccc2nccnc2c1]

The title compound was prepared in a manner analogous to Example 106, using (5-(trifluoromethyl)furan-2-yl)boronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{22}H_{18}F_3N_5O_2$, 441.1; m/z found, 442.1 [M+H]$^+$. $^1$H NMR (500 MHz, CDCl$_3$) δ 8.91 (s, 2H), 8.23-8.14 (m, 2H), 7.84 (s, 1H), 6.93 (s, 1H), 6.53 (s, 1H), 5.91 (s, 0.46H), 4.96 (s, 0.77H), 4.20-3.77 (m, 3.77H), 3.53-2.60 (m, 3H), 1.61 (s, 3H).

Example 248: (S)-(2,7-Dimethyl-3-(5-(trifluoromethyl)pyridin-3-yl)-2,4,5,7-tetrahydro-6H-pyrazolo[3,4-c]pyridin-6-yl)(quinoxalin-6-yl)methanone

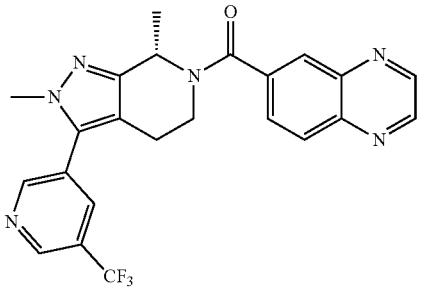 [SMILES: C[C@H]1c2nn(C)c(-c3cncc(C(F)(F)F)c3)c2CCN1C(=O)c1ccc2nccnc2c1]

The title compound was prepared in a manner analogous to Example 106, using 5-(trifluoromethyl)pyridin-3-yl)boronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and quinoxaline-6-carboxylic acid instead of quinoline 6-carboxylic acid in Step C. MS (ESI): mass calcd. for $C_{23}H_{19}F_3N_6O$, 452.1; m/z found, 453.1 [M+H]$^+$. $^1$H NMR (500 MHz, DMSO-d$_6$) δ 9.11-8.97 (m, 4H), 8.49-8.32 (m, 1H), 8.26-8.09 (m, 2H), 7.91 (d, J=8.9 Hz, 1H), 5.68 (s, 1H), 4.74 (s, 1H), 3.82 (d, J=47.3 Hz, 3H), 3.68 (s, 1H), 2.93 (s, 1H), 2.35 (s, 1H), 1.54 (s, 3H).

Example 249: (2,7-Dimethyl-3-(1-methyl-1H-indol-4-yl)-2,4,5,7-tetrahydro-6H-pyrazolo[3,4-c]pyridin-6-yl)(quinolin-6-yl)methanone

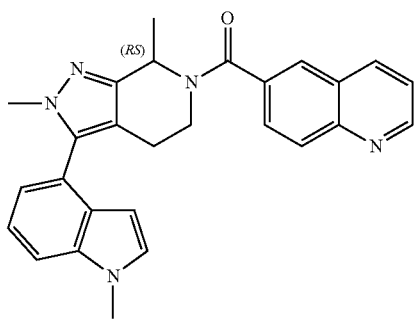 [SMILES: CC1c2nn(C)c(-c3cccc4c3ccn4C)c2CCN1C(=O)c1ccc2ncccc2c1]

The title compound was prepared in a manner analogous to Example 98, using 2,7-dimethyl-6-(quinoline-6-carbonyl)-4,5,6,7-tetrahydro-2H-pyrazolo[3,4-c]pyridin-3-yl trifluoromethanesulfonate (Intermediate 11) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 1-methyl-4-(4,4,5,5-tetramethyl-1,3,2-dioxaborolan-2-yl)-1H-indole instead of 3-(difluoromethoxy)phenylboronic acid. MS (ESI): mass calcd. for $C_{27}H_{25}N_5O$, 435.2; m/z found, 436.1 [M+H]$^+$. $^1$H NMR (500 MHz, CDCl$_3$) δ 8.95 (s, 1H), 8.22-8.10 (m, 2H), 7.93 (s, 1H), 7.82-7.73 (m, 1H), 7.49-7.38 (m, 2H), 7.34-7.27 (m, 1H), 7.18-7.02 (m, 2H), 6.28 (d, J=17.6 Hz, 1H), 5.95 (s, 0.51H), 5.13-4.78 (m, 0.71H), 3.88-3.60 (m, 6.76H), 3.45-3.06 (m, 1H), 2.92-2.23 (m, 2H), 1.79-1.49 (m, 3H).

Example 250: (2,7-Dimethyl-3-(1-methyl-1H-indol-2-yl)-2,4,5,7-tetrahydro-6H-pyrazolo[3,4-c]pyridin-6-yl)(quinolin-6-yl)methanone

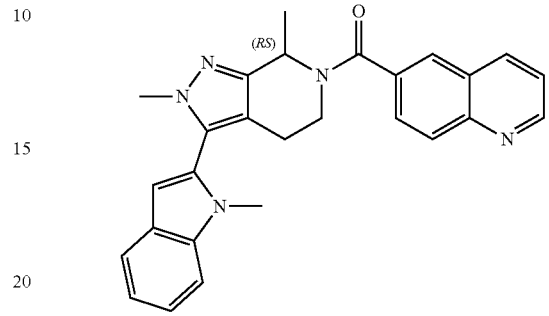

The title compound was prepared in a manner analogous to Example 106, using 1-methyl-2-(4,4,5,5-tetramethyl-1,3,2-dioxaborolan-2-yl)-1H-indole instead of 3,5-difluorophenylboronic acid in Step A. MS (ESI): mass calcd. for $C_{27}H_{25}N_5O$, 435.2; m/z found, 436.2 [M+H]$^+$. $^1$H NMR (500 MHz, CDCl$_3$) δ 8.98 (d, J=4.4 Hz, 1H), 8.23-8.14 (m, 2H), 7.94 (s, 1H), 7.77 (d, J=8.7 Hz, 1H), 7.68 (d, J=7.9 Hz, 1H), 7.47 (dd, J=8.3, 4.2 Hz, 1H), 7.40 (d, J=8.3 Hz, 1H), 7.35-7.29 (m, 1H), 7.23-7.17 (m, 1H), 6.59 (s, 1H), 5.95 (s, 0.47H), 5.14-4.80 (m, 0.73H), 3.94-3.55 (m, 6.79H), 3.44-3.01 (m, 1H), 2.95-2.28 (m, 2H), 1.75-1.53 (m, 3H).

Example 251: (2,7-Dimethyl-3-(1-methyl-1H-indol-3-yl)-2,4,5,7-tetrahydro-6H-pyrazolo[3,4-c]pyridin-6-yl)(quinolin-6-yl)methanone

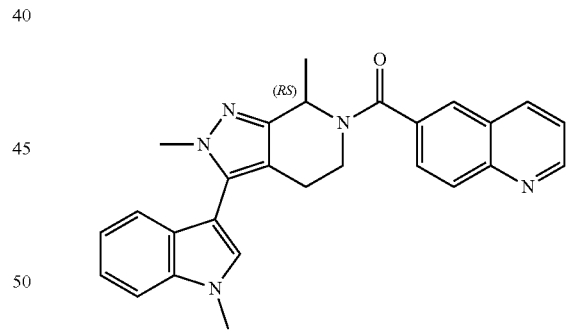

The title compound was prepared in a manner analogous to Example 98, using 2,7-dimethyl-6-(quinoline-6-carbonyl)-4,5,6,7-tetrahydro-2H-pyrazolo[3,4-c]pyridin-3-yl trifluoromethanesulfonate (Intermediate 11) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 1-methyl-3-(4,4,5,5-tetramethyl-1,3,2-dioxaborolan-2-yl)-1H-indole instead of 3-(difluoromethoxy)phenylboronic acid. MS (ESI): mass calcd. for $C_{27}H_{25}N_5O$, 435.2; m/z found, 436.2 [M+H]$^+$. $^1$H NMR (500 MHz, Methanol-d$_4$) δ 8.93 (s, 1H), 8.46 (d, J=8.4 Hz, 1H), 8.14 (d, J=8.7 Hz, 1H), 8.08 (d, J=1.8 Hz, 1H), 7.84 (d, J=8.6 Hz, 1H), 7.62 (s, 1H), 7.47 (d, J=8.2 Hz, 1H), 7.41-7.37 (m, 2H), 7.26 (t, J=7.6 Hz, 1H), 7.15 (t, J=7.5 Hz, 1H), 5.91-5.78 (m, 0.62H), 4.97-4.76 (m, 0.73H), 4.59 (s, 0.21H), 3.64-3.94 (m, 6.74H), 3.50-3.38 (m, 0.72H), 2.89-2.69 (m, 1H), 2.57-2.28 (m, 1H), 1.74-1.55 (m, 3H).

Example 252: (2,7-Dimethyl-3-(1-methyl-1H-indol-5-yl)-2,4,5,7-tetrahydro-6H-pyrazolo[3,4-c]pyridin-6-yl)(quinolin-6-yl)methanone

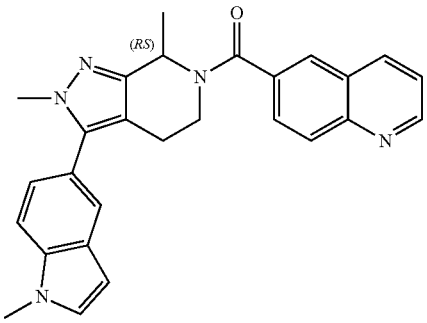 [SMILES: CC1c2nn(C)c(-c3ccc4c(ccn4C)c3)c2CCN1C(=O)c1ccc2ncccc2c1]

The title compound was prepared in a manner analogous to Example 98, using 2,7-dimethyl-6-(quinoline-6-carbonyl)-4,5,6,7-tetrahydro-2H-pyrazolo[3,4-c]pyridin-3-yl trifluoromethanesulfonate (Intermediate 11) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and N-methylindole-5-boronic acid instead of 3-(difluoromethoxy)phenylboronic acid. MS (ESI): mass calcd. for C$_{27}$H$_{25}$N$_5$O, 435.2; m/z found, 436.2 [M+H]$^+$. $^1$H NMR (500 MHz, CDCl$_3$) δ 8.97 (dd, J=4.2, 1.8 Hz, 1H), 8.22-8.13 (m, 2H), 7.94 (d, J=1.8 Hz, 1H), 7.78 (dd, J=8.6, 1.9 Hz, 1H), 7.59 (dd, J=1.6, 0.7 Hz, 1H), 7.48-7.40 (m, 2H), 7.21-7.12 (m, 2H), 6.55 (d, J=3.1 Hz, 1H), 5.94 (s, 0.42H), 5.16-4.82 (m, 0.7H), 3.94-3.68 (m, 6.65H), 3.44-3.11 (m, 1H), 2.98-2.70 (m, 1H), 2.59-2.36 (m, 1H), 1.74-1.51 (m, 3.23H).

Example 253: (2,7-Dimethyl-3-(1-methyl-1H-indol-7-yl)-2,4,5,7-tetrahydro-6H-pyrazolo[3,4-c]pyridin-6-yl)(quinolin-6-yl)methanone

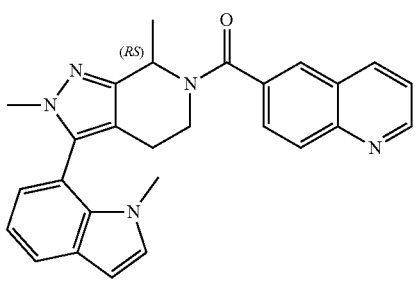 [SMILES: CC1c2nn(C)c(-c3cccc4ccn(C)c34)c2CCN1C(=O)c1ccc2ncccc2c1]

The title compound was prepared in a manner analogous to Example 106, using 1-methyl-7-(4,4,5,5-tetramethyl-1,3,2-dioxaborolan-2-yl)-1H-indole instead of 3,5-difluorophenylboronic acid in Step A. MS (ESI): mass calcd. for C$_{27}$H$_{25}$N$_5$O, 435.2; m/z found, 436.2 [M+H]$^+$. $^1$H NMR (500 MHz, CDCl$_3$) δ 8.97 (s, 1H), 8.23-8.11 (m, 2H), 7.91 (d, J=1.8 Hz, 1H), 7.72 (td, J=8.5, 1.5 Hz, 2H), 7.51-7.41 (m, 1H), 7.14 (t, J=7.5 Hz, 1H), 7.07-6.97 (m, 2H), 6.57 (d, J=3.2 Hz, 1H), 5.95 (s, 0.53H), 5.15-4.75 (m, 0.47H), 3.89-3.15 (m, 8H), 2.71-2.29 (m, 2H), 1.78-1.52 (m, 3H).

Example 254: (S)-(3-(3,5-Difluorophenyl)-2,7-dimethyl-5,7-dihydro-4H-pyrazolo[3,4-c]pyridin-6-yl]-[3-(2-fluoranylethoxy)-2-fluoro-phenyl]methanone

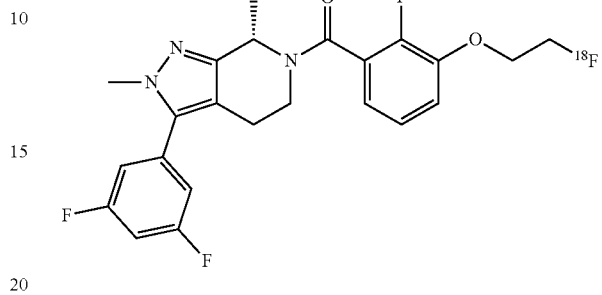

The title compound was prepared in a manner analogous to Example 140, using 2-fluoro-3-(2-(tosyloxy)ethoxy)benzoic acid (Intermediate 128) instead of 3-(2-(tosyloxy)ethoxy)benzoic acid in Step A.

Example 255: [2-Chloro-3-(2-fluoranylethoxy)phenyl]-[(7S)-3-(3,5-difluorophenyl)-2,7-dimethyl-5,7-dihydro-4H-pyrazolo[3,4-c]pyridin-6-yl]methanone

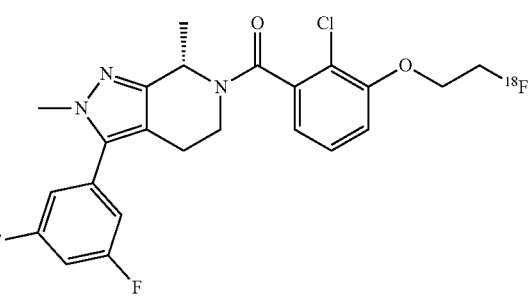

The title compound was prepared analogous to Example 151, using 2-chloro-3-(2-((tetrahydro-2H-pyran-2-yl)oxy)ethoxy)benzoic (Intermediate 129) instead of 1-(2-((tetrahydro-2H-pyran-2-yl)oxy)ethyl)-1H-indole-5-carboxylic acid in Step A.

Example 256: (S)-[3-(3,5-Difluorophenyl)-2,7-dimethyl-5,7-dihydro-4H-pyrazolo[3,4-c]pyridin-6-yl]-[3-(2-fluoranylethoxy)-5-fluoro-phenyl]methanone

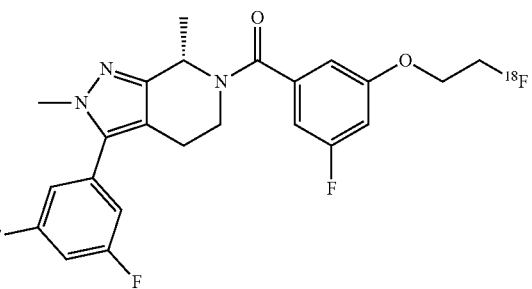

The title compound was prepared analogous to Example 140, using 3-fluoro-5-(2-(tosyloxy)ethoxy)benzoic acid (Intermediate 130) instead of 3-(2-(tosyloxy)ethoxy)benzoic acid in Step A.

Example 257: (3-Methoxyphenyl)-[(7S)-7-methyl-2,3-diphenyl-5,7-dihydro-4H-pyrazolo[3,4-c]pyridin-6-yl]methanone

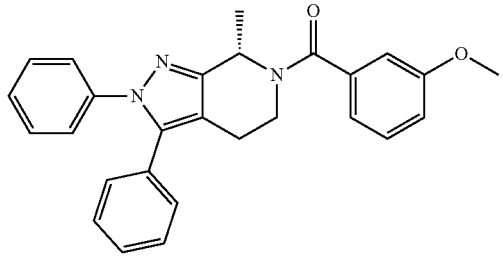 [SMILES: COc1cccc(C(=O)N2CCc3c(nn(-c4ccccc4)c3-c3ccccc3)[C@@H]2C)c1]

The title compound was prepared in a manner analogous to Example 288, using (S)-7-methyl-2,3-diphenyl-4,5,6,7-tetrahydro-2H-pyrazolo[3,4-c] pyridine (Intermediate 55) instead of (S)-2,7-dimethyl-3-(3,4,5-trifluorophenyl)-4,5,6,7-tetrahydro-2H-pyrazolo[3,4-c]pyridine and 3-methoxybenzoic acid instead of 2-fluoro-6-(2H-1,2,3-triazol-2-yl) benzoic acid. MS (ESI): mass calcd. for $C_{27}H_{25}N_3O_2$, 423.2; m/z found, 424 [M+H]$^+$. $^1$H NMR (400 MHz, DMSO-d$_6$) δ 7.43-7.27 (m, 7H), 7.27-7.11 (m, 4H), 7.10-6.93 (m, 3H), 5.66 (s, 1H), 3.80 (s, 3H), 2.84 (s, 2H), 2.54-2.51 (m, 2H), 1.55 (d, J=6.7 Hz, 3H).

Example 258: [(7S)-3-(3-Fluoro-5-methyl-phenyl)-2,7-dimethyl-5,7-dihydro-4H-pyrazolo[3,4-c]pyridin-6-yl]-(4-methoxyphenyl)methanone

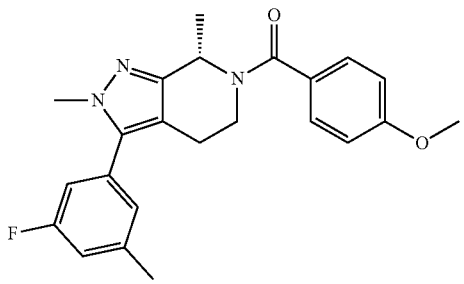 [SMILES: COc1ccc(C(=O)N2CCc3c(nn(C)c3-c3cc(C)cc(F)c3)[C@@H]2C)cc1]

The title compound was prepared in a manner analogous to Example 288, using 4-methoxybenzoic acid instead of 2-fluoro-6-(2H-1,2,3-triazol-2-yl) benzoic acid. MS (ESI): mass calcd. for $C_{23}H_{24}FN_3O_2$, 393.19; m/z found, 394.2 [M+H]$^+$. $^1$H NMR (400 MHz, DMSO-d$_6$) δ 7.45-7.35 (m, 2H), 7.20-7.06 (m, 3H), 7.04-6.95 (m, 2H), 5.45 (s, 1H), 4.18-3.91 (m, 1H), 3.84-3.74 (m, 6H), 3.17 (s, 1H), 2.80 (t, J=12.1 Hz, 1H), 2.43-2.26 (m, 4H), 1.45 (d, J=6.7 Hz, 3H).

Example 259: [(7S)-2,7-Dimethyl-3-(3,4,5-trifluorophenyl)-5,7-dihydro-4H-pyrazolo[3,4-c]pyridin-6-yl]-(2-methoxyphenyl)methanone

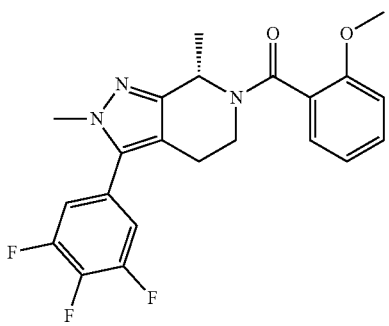 [SMILES: COc1ccccc1C(=O)N1CCc2c(nn(C)c2-c2cc(F)c(F)c(F)c2)[C@@H]1C]

The title compound was prepared in a manner analogous to Example 288, using 2-methoxybenzoic acid instead of 2-fluoro-6-(2H-1,2,3-triazol-2-yl)benzoic acid. MS (ESI): mass calcd. for $C_{22}H_{20}F_3N_3O_2$, 415.2; m/z found, 416.1 [M+H]$^+$. $^1$H NMR (600 MHz, DMSO-d$_6$) δ 7.57-7.48 (m, 2H), 7.44-7.38 (m, 1H), 7.28-7.13 (m, 1H), 7.12-6.95 (m, 2H), 5.61 (q, J=6.7 Hz, 0.38H), 5.56 (q, J=6.7 Hz, 0.32H), 4.73-4.65 (m, 0.28H), 4.58-4.52 (m, 0.16H), 4.51-4.45 (m, 0.13H), 3.85-3.71 (m, 5.65H), 3.58 (s, 0.36H), 3.45-3.36 (m, 0.80H), 3.25-3.11 (m, 0.72H), 3.05-2.93 (m, 0.27H), 2.75-2.54 (m, 1H), 2.37-2.31 (m, 0.31H), 2.27-2.21 (m, 0.37H), 1.47-1.24 (m, 3H). (Fractions of H's that overlap with DMSO and water may not be reported)

Example 260: [(7S)-2,7-Dimethyl-3-(3,4,5-trifluorophenyl)-5,7-dihydro-4H-pyrazolo[3,4-c]pyridin-6-yl]-(3-methoxyphenyl)methanone

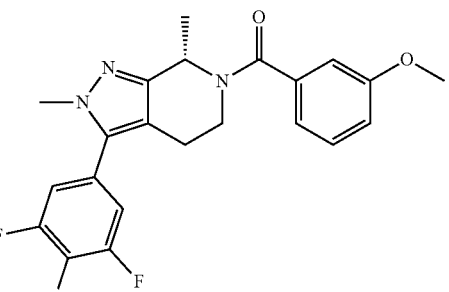

The title compound was prepared in a manner analogous to Example 288, using 3-methoxybenzoic acid instead of 2-fluoro-6-(2H-1,2,3-triazol-2-yl)benzoic acid. MS (ESI): mass calcd. for $C_{22}H_{20}F_3N_3O_2$, 415.2; m/z found, 416.1 [M+H]$^+$. $^1$H NMR (600 MHz, Methanol-d$_4$) δ 7.48-7.34 (m, 1H), 7.35-7.23 (m, 2H), 7.05 (dd, J=8.3, 2.5 Hz, 1H), 7.02-6.87 (m, 2H), 5.77-5.65 (m, 0.60H), 4.81-4.65 (m, 0.40H), 3.92-3.71 (m, 7H), 3.39-3.32 (m, 0.60H), 3.28-3.13 (m, 0.40H), 2.91-2.66 (m, 1H), 2.61-2.37 (m, 1H), 1.66-1.44 (m, 3H).

Example 261: [(7S)-2,7-Dimethyl-3-(3,4,5-trifluorophenyl)-5,7-dihydro-4H-pyrazolo[3,4-c]pyridin-6-yl]-(4-methoxyphenyl)methanone

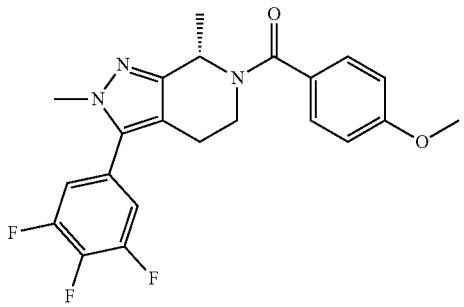 [SMILES: COc1ccc(C(=O)N2CCc3c(nn(C)c3-c3cc(F)c(F)c(F)c3)[C@@H]2C)cc1]

The title compound was prepared in a manner analogous to Example 288, using 4-methoxybenzoic acid instead of 2-fluoro-6-(2H-1,2,3-triazol-2-yl)benzoic acid. MS (ESI): mass calcd. for $C_{22}H_{20}F_3N_3O_2$, 415.2; m/z found, 416.1 [M+H]$^+$. $^1$H NMR (600 MHz, Methanol-d$_4$) δ 7.41 (d, J=8.2 Hz, 2H), 7.34-7.26 (m, 2H), 7.04-7.00 (m, 2H), 5.82-5.44 (m, 1H), 4.06-3.85 (m, 1H), 3.85 (s, 3H), 3.81 (s, 3H), 3.41-3.32 (m, 1H), 2.89-2.71 (m, 1H), 2.56-2.35 (m, 1H), 1.55 (d, J=6.8 Hz, 3H).

Example 262: [(7S)-2,7-Dimethyl-3-(3,4,5-trifluorophenyl)-5,7-dihydro-4H-pyrazolo[3,4-c]pyridin-6-yl]-[3-(trifluoromethoxy)phenyl]methanone

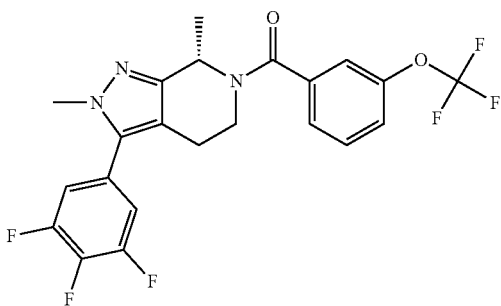 [SMILES: C[C@H]1c2nn(C)c(-c3cc(F)c(F)c(F)c3)c2CCN1C(=O)c1cccc(OC(F)(F)F)c1]

The title compound was prepared in a manner analogous to Example 288, using 3-(trifluoromethoxy)benzoic acid instead of 2-fluoro-6-(2H-1,2,3-triazol-2-yl)benzoic acid. MS (ESI): mass calcd. for $C_{22}H_{17}F_6N_3O_2$, 469.1; m/z found, 470.1 [M+H]$^+$. $^1$H NMR (500 MHz, Chloroform-d) δ 7.50-7.43 (m, 1H), 7.38-7.34 (m, 1H), 7.31-7.27 (m, 2H), 7.01-6.94 (m, 2H), 5.95-5.71 (m, 0.44H), 5.02-4.63 (m, 1H), 3.96-3.62 (m, 3.64H), 3.40-3.00 (m, 1H), 2.93-2.55 (m, 1H), 2.53-2.31 (m, 1H), 1.65-1.52 (m, 3H).

Example 263: [(7S)-2,7-Dimethyl-3-(3,4,5-trifluorophenyl)-5,7-dihydro-4H-pyrazolo[3,4-c]pyridin-6-yl]-[2-(trifluoromethoxy)phenyl]methanone.TFA salt

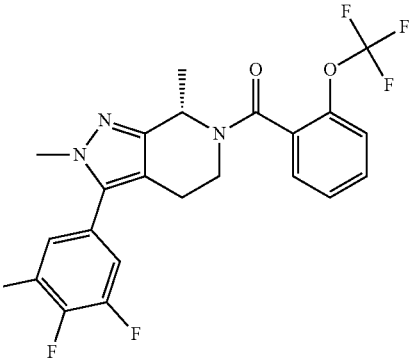

The title compound was prepared in a manner analogous to Example 288, using 2-(trifluoromethoxy)benzoic acid instead of 2-fluoro-6-(2H-1,2,3-triazol-2-yl)benzoic acid. MS (ESI): mass calcd. for $C_{22}H_{17}F_6N_3O_2$, 469.1; m/z found, 470.1 [M+H]$^+$. $^1$H NMR (500 MHz, Chloroform-d) δ 7.50-7.25 (m, 4H), 7.01-6.91 (m, 2H), 5.96-5.85 (m, 0.64H), 4.99-4.89 (m, 0.39H), 4.80-4.67 (m, 0.40H), 3.87-3.74 (m, 3H), 3.61-3.51 (m, 0.65H), 3.37-3.21 (m, 0.65H), 3.17-3.00 (m, 0.35H), 2.88-2.70 (m, 0.55H), 2.59-2.42 (m, 0.86H), 2.37-2.28 (m, 0.68H), 1.63-1.38 (m, 3H).

Example 264: [4-(Difluoromethoxy)phenyl]-[(7S)-2,7-dimethyl-3-(3,4,5-trifluorophenyl)-5,7-dihydro-4H-pyrazolo[3,4-c]pyridin-6-yl]methanone

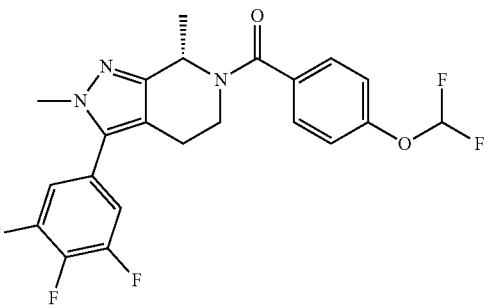

The title compound was prepared in a manner analogous to Example 288, using 4-(difluoromethoxy)benzoic acid of 2-fluoro-6-(2H-1,2,3-triazol-2-yl)benzoic acid. MS (ESI): mass calcd. for $C_{22}H_{18}F_5N_3O_2$, 451.1; m/z found, 452.0 [M+H]$^+$. $^1$H NMR (400 MHz, Methanol-d$_4$) δ 7.52 (s, 1H), 7.50 (s, 1H), 7.34-7.23 (m, 4H), 6.92 (t, J=73.6 Hz, 1H), 5.92-5.39 (m, 1H), 3.82 (s, 4H), 3.44-3.31 (m, 1H), 2.91-2.69 (m, 1H), 2.65-2.35 (m, 1H), 1.56 (d, J=6.8 Hz, 3H).

Example 265: [(7S)-2,7-Dimethyl-3-(3,4,5-trifluoro-phenyl)-5,7-dihydro-4H-pyrazolo[3,4-c]pyridin-6-yl]-(2-fluoro-4-methoxy-phenyl)methanone

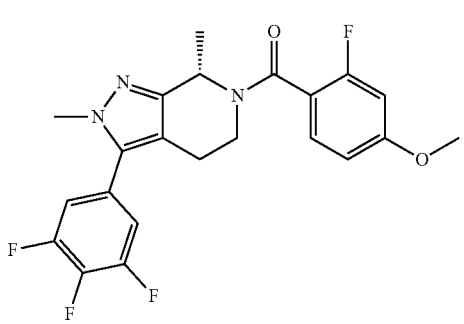 [SMILES: COc1ccc(C(=O)N2CCc3c(nn(C)c3-c3cc(F)c(F)c(F)c3)[C@@H]2C)c(F)c1]

The title compound was prepared in a manner analogous to Example 288, using 2-fluoro-4-methoxybenzoic acid instead of 2-fluoro-6-(2H-1,2,3-triazol-2-yl) benzoic acid. MS (ESI): mass calcd. for $C_{22}H_{19}F_4N_3O_2$, 433.14; m/z found, 434.1 [M+H]$^+$. $^1$H NMR (400 MHz, Methanol-d$_4$) δ 7.39-7.23 (m, 3H), 6.94-6.74 (m, 2H), 5.76 (q, J=6.8 Hz, 1H), 3.90-3.77 (m, 6H), 3.49-3.38 (m, 1H), 3.30-3.07 (m, 1H), 2.84-2.36 (m, 2H), 1.62-1.43 (m, 3H).

Example 266: 3-[(7S)-2,7-Dimethyl-3-(3,4,5-trifluoro-phenyl)-5,7-dihydro-4H-pyrazolo[3,4-c]pyridine-6-carbonyl]-N-methyl-benzamide

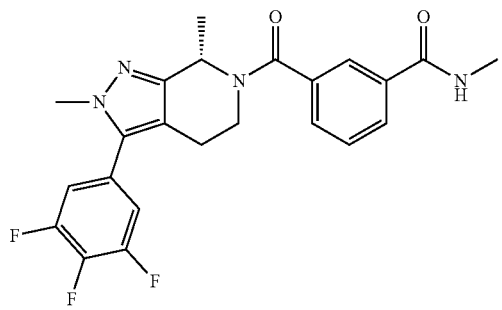 [SMILES: CNC(=O)c1cccc(C(=O)N2CCc3c(nn(C)c3-c3cc(F)c(F)c(F)c3)[C@@H]2C)c1]

The title compound was prepared in a manner analogous to Example 288, using 3-(methylcarbamoyl)benzoic acid instead of 2-fluoro-6-(2H-1,2,3-triazol-2-yl) benzoic acid. MS (ESI): mass calcd. for $C_{23}H_{21}F_3N_4O_2$, 442.2; m/z found, 443.1 [M+H]$^+$. $^1$H NMR (500 MHz, Chloroform-d) δ 7.85-7.79 (m, 2H), 7.57-7.53 (m, 1H), 7.52-7.47 (m, 1H), 7.01-6.94 (m, 2H), 6.16 (s, 1H), 5.84 (br s, 0.47H), 5.02-4.70 (m, 0.81H), 3.95-3.64 (m, 3.64H), 3.37-2.96 (m, 4H), 2.90-2.62 (m, 1H), 2.53-2.31 (m, 1H), 1.66-1.47 (m, 3H).

Example 267: [(7S)-2,7-Dimethyl-3-(3,4,5-trifluoro-phenyl)-5,7-dihydro-4H-pyrazolo[3,4-c]pyridin-6-yl]-(4-imidazol-1-ylphenyl)methanone

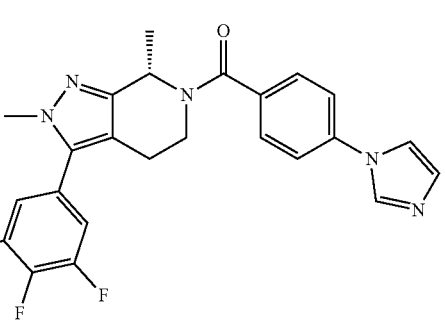

The title compound was prepared in a manner analogous to Example 288, using 4-(1H-imidazol-1-yl)benzoic acid instead of 2-fluoro-6-(2H-1,2,3-triazol-2-yl)benzoic acid. MS (ESI): mass calcd. for $C_{24}H_{20}F_3N_5O$, 451.2; m/z found, 452.1 [M+H]$^+$. $^1$H NMR (400 MHz, Methanol-d$_4$) δ 8.29-8.14 (m, 1H), 7.75-7.72 (m, 1H), 7.72-7.69 (m, 1H), 7.68-7.65 (m, 1H), 7.65-7.63 (m, 1H), 7.63-7.58 (m, 1H), 7.37-7.26 (m, 2H), 7.24-7.14 (m, 1H), 5.86-5.60 (m, 1H), 4.67-4.38 (m, 1H), 3.83 (s, 3H), 3.47-3.34 (m, 1H), 2.92-2.71 (m, 1H), 2.66-2.38 (m, 1H), 1.58 (d, J=6.8 Hz, 3H).

Example 268: [(7S)-2,7-Dimethyl-3-(3,4,5-trifluoro-phenyl)-5,7-dihydro-4H-pyrazolo[3,4-c]pyridin-6-yl]-[4-(1H-pyrazol-4-yl)phenyl]methanone

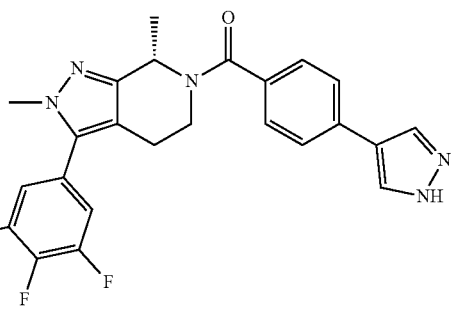

The title compound was prepared in a manner analogous to Example 288, using 4-(1H-pyrazol-4-yl)benzoic acid of 2-fluoro-6-(2H-1,2,3-triazol-2-yl)benzoic acid. MS (ESI): mass calcd. for $C_{24}H_{20}F_3N_5O$, 451.2; m/z found, 452.0 [M+H]$^+$. $^1$H NMR (400 MHz, Methanol-d$_4$) δ 8.12-7.91 (m, 2H), 7.77-7.66 (m, 2H), 7.52-7.42 (m, 2H), 7.36-7.25 (m, 2H), 5.85-5.56 (m, 1H), 4.04-3.73 (m, 4H), 3.44-3.34 (m, 1H), 2.91-2.74 (m, 1H), 2.69-2.32 (m, 1H), 1.57 (d, J=6.8 Hz, 3H).

Example 269: [(7S)-2,7-Dimethyl-3-(3,4,5-trifluoro-phenyl)-5,7-dihydro-4H-pyrazolo[3,4-c]pyridin-6-yl]-[4-(1H-pyrazol-5-yl)phenyl]methanone

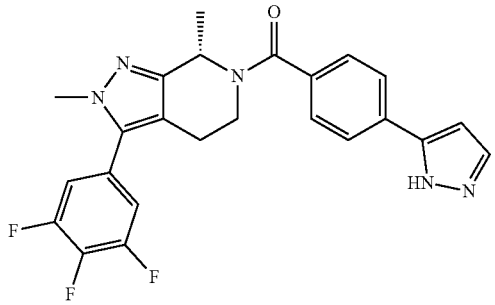 [SMILES: C[C@H]1c2nn(C)c(-c3cc(F)c(F)c(F)c3)c2CCN1C(=O)c1ccc(-c2ccn[nH]2)cc1]

The title compound was prepared in a manner analogous to Example 288, using 4-(1H-pyrazol-5-yl)benzoic acid of 2-fluoro-6-(2H-1,2,3-triazol-2-yl)benzoic acid. MS (ESI): mass calcd. for $C_{24}H_{20}F_3N_5O$, 451.2; m/z found, 452.0 [M+H]⁺. ¹H NMR (400 MHz, Methanol-$d_4$) δ 8.01-7.84 (m, 2H), 7.70 (s, 1H), 7.59-7.44 (m, 2H), 7.36-7.26 (m, 2H), 6.75 (d, J=2.3 Hz, 1H), 5.85-5.53 (m, 1H), 3.98-3.68 (m, 4H), 3.47-3.33 (m, 1H), 2.92-2.70 (m, 1H), 2.64-2.35 (m, 1H), 1.58 (d, J=6.8 Hz, 3H).

Example 270: [(7S)-2,7-Dimethyl-3-(3,4,5-trifluoro-phenyl)-5,7-dihydro-4H-pyrazolo[3,4-c]pyridin-6-yl]-[3-(1H-pyrazol-3-yl)phenyl]methanone

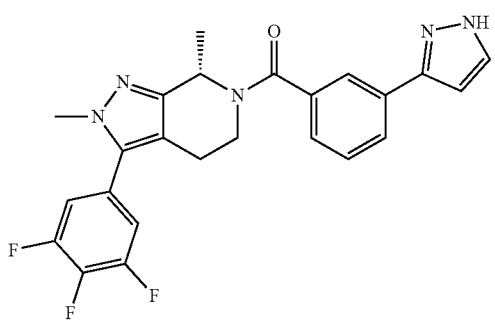 [SMILES: C[C@H]1c2nn(C)c(-c3cc(F)c(F)c(F)c3)c2CCN1C(=O)c1cccc(-c2cc[nH]n2)c1]

The title compound was prepared in a manner analogous to Example 288, using 3-(1H-pyrazol-3-yl)benzoic acid instead of 2-fluoro-6-(2H-1,2,3-triazol-2-yl)benzoic acid. MS (ESI): mass calcd. for $C_{24}H_{20}F_3N_5O$, 451.2; m/z found, 452.0 [M+H]⁺. ¹H NMR (400 MHz, Methanol-$d_4$) δ 7.98-7.89 (m, 1H), 7.89-7.80 (m, 1H), 7.79-7.63 (m, 1H), 7.62-7.48 (m, 1H), 7.46-7.35 (m, 1H), 7.35-7.19 (m, 1H), 6.74 (s, 1H), 5.85-5.63 (m, 1H), 4.01-3.70 (m, 4H), 3.46-3.32 (m, 1H), 2.95-2.69 (m, 1H), 2.61-2.32 (m, 1H), 1.68-1.45 (m, 3H). (The fraction of Hs that overlap with methanol or water are not reported).

Example 271: [(7S)-2,7-Dimethyl-3-(3,4,5-trifluoro-phenyl)-5,7-dihydro-4H-pyrazolo[3,4-c]pyridin-6-yl]-[4-methoxy-3-(1-methylpyrazol-3-yl)phenyl]methanone

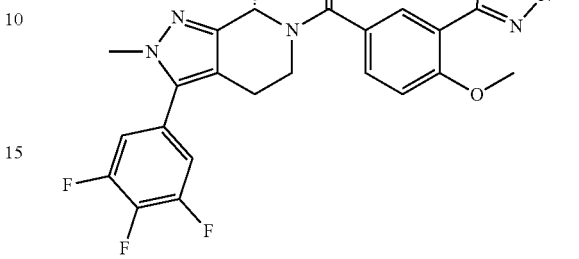

The title compound was prepared in a manner analogous to Example 288, using 4-methoxy-3-(1-methyl-1H-pyrazol-3-yl)benzoic acid instead of 2-fluoro-6-(2H-1,2,3-triazol-2-yl)benzoic acid. MS (ESI): mass calcd. for $C_{26}H_{24}F_3N_5O_2$, 495.2; m/z found, 496.0 [M+H]⁺. ¹H NMR (400 MHz, Methanol-$d_4$) δ 7.94 (d, J=2.2 Hz, 1H), 7.58 (d, J=2.3 Hz, 1H), 7.42 (dd, J=8.6, 2.2 Hz, 1H), 7.37-7.25 (m, 2H), 7.18 (d, J=8.6 Hz, 1H), 6.78 (d, J=2.3 Hz, 1H), 5.94-5.54 (m, 1H), 3.96 (s, 3H), 3.93 (s, 3H), 3.86-3.75 (m, 4H), 3.45-3.29 (m, 1H), 2.88-2.74 (m, 1H), 2.57-2.38 (m, 1H), 1.57 (d, J=6.8 Hz, 3H).

Example 272: [(7S)-2,7-Dimethyl-3-(3,4,5-trifluoro-phenyl)-5,7-dihydro-4H-pyrazolo[3,4-c]pyridin-6-yl]-[3-(1H-pyrazol-4-yl)phenyl]methanone

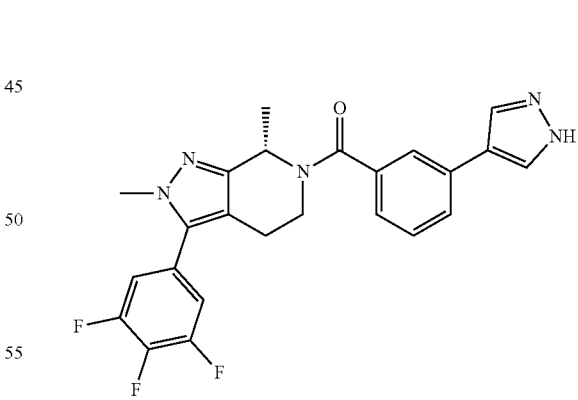

The title compound was prepared in a manner analogous to Example 288, using 3-(1H-pyrazol-4-yl)benzoic acid instead of 2-fluoro-6-(2H-1,2,3-triazol-2-yl)benzoic acid. MS (ESI): mass calcd. for $C_{24}H_{20}FN_5O$, 451.2; m/z found, 452.1 [M+H]⁺. ¹H NMR (400 MHz, Methanol-$d_4$) δ 8.13-7.92 (m, 2H), 7.77-7.69 (m, 1H), 7.68-7.60 (m, 1H), 7.49 (t, J=7.7 Hz, 1H), 7.38-7.18 (m, 3H), 5.83-5.64 (m, 1H), 3.84 (s, 3H), 3.79-3.73 (m, 1H), 3.45-3.34 (m, 1H), 2.89-2.71 (m, 1H), 2.61-2.37 (m, 1H), 1.65-1.50 (m, 3H).

Example 273: [(7S)-2,7-Dimethyl-3-(3,4,5-trifluoro-phenyl)-5,7-dihydro-4H-pyrazolo[3,4-c]pyridin-6-yl]-[3-(1-methylpyrazol-4-yl)phenyl]methanone Example 275: [(7S)-2,7-Dimethyl-3-(3,4,5-trifluoro-phenyl)-5,7-dihydro-4H-pyrazolo[3,4-c]pyridin-6-yl]-[3-(4-fluoropyrazol-1-yl)phenyl]methanone

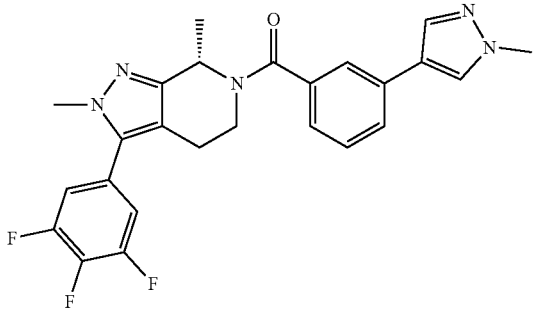 [SMILES: C[C@H]1c2nn(C)c(-c3cc(F)c(F)c(F)c3)c2CCN1C(=O)c1cccc(-c2cnn(C)c2)c1]

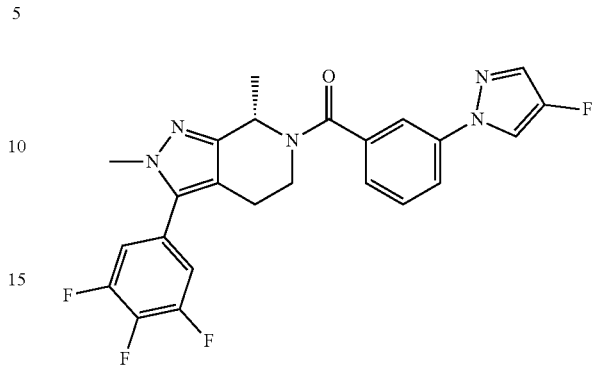

The title compound was prepared in a manner analogous to Example 288, using 3-(1-methyl-1H-pyrazol-4-yl)benzoic acid instead of 2-fluoro-6-(2H-1,2,3-triazol-2-yl)benzoic acid. MS (ESI): mass calcd. for $C_{25}H_{22}F_3N_5O$, 465.2; m/z found, 446.1 $[M+H]^+$. $^1H$ NMR (400 MHz, Chloroform-d) δ 7.76 (s, 1H), 7.62 (s, 1H), 7.54-7.49 (m, 2H), 7.40 (t, J=7.9 Hz, 1H), 7.27-7.21 (m, 1H), 7.02-6.92 (m, 2H), 5.86 (brs, 0.55), 5.14-4.74 (m, 1H), 3.95 (s, 3.20H), 3.81 (brs, 3.23H), 3.38-3.00 (m, 1.17H), 2.91-2.58 (m, 1.16H), 2.41 (brs, 1.17H), 1.58 (brs, 3H).

The title compound was prepared in a manner analogous to Example 296, using 3-(4-fluoro-1H-pyrazol-1-yl)benzoic acid (Intermediate 68) instead of 3-(1,2,4-triazol-4-yl)-5-(trifluoromethyl)benzoic acid. MS (ESI): mass calcd. for $C_{24}H_{19}F_4N_5O$, 469.2; m/z found, 470.2 $[M+H]^+$. $^1H$ NMR (300 MHz, DMSO-$d_6$) δ 8.84-8.76 (m, 1H), 7.98-7.74 (m, 3H), 7.67-7.47 (m, 3H), 7.43-7.29 (m, 1H), 5.69-5.47 (m, 1H), 3.81 (s, 3H), 3.73-3.50 (m, 1H), 3.42-3.00 (m, 1H), 2.90-2.71 (m, 1H), 2.65-2.22 (m, 1H), 1.59-1.33 (m, 3H).

Example 274: [(7S)-2,7-Dimethyl-3-(3,4,5-trifluoro-phenyl)-5,7-dihydro-4H-pyrazolo[3,4-c]pyridin-6-yl]-[2-fluoro-5-(1-methylpyrazol-4-yl)phenyl]methanone Example 276: [(7S)-2,7-Dimethyl-3-(3,4,5-trifluoro-phenyl)-5,7-dihydro-4H-pyrazolo[3,4-c]pyridin-6-yl]-[3-(3-methyl-1,2,4-triazol-1-yl)phenyl]methanone

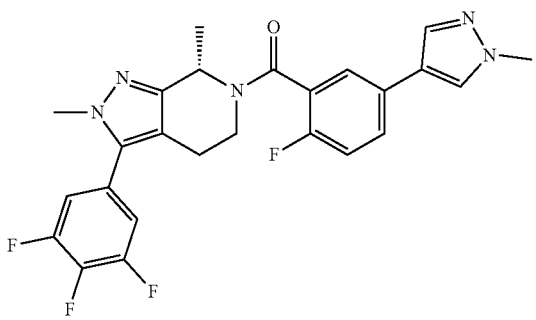 [SMILES: C[C@H]1c2nn(C)c(-c3cc(F)c(F)c(F)c3)c2CCN1C(=O)c1cc(-c2cnn(C)c2)ccc1F]

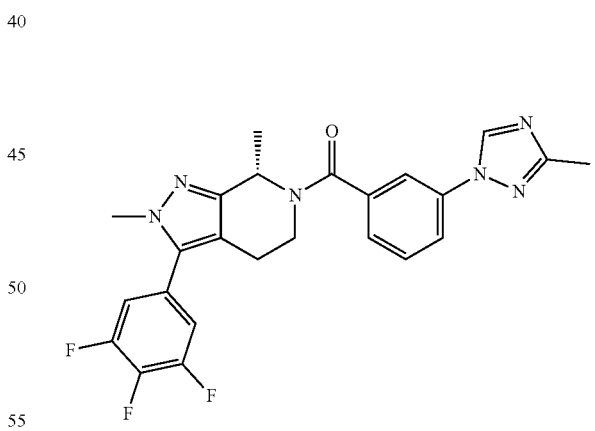

The title compound was prepared in a manner analogous to Example 288, using 2-fluoro-5-(1-methyl-1H-pyrazol-4-yl)benzoic acid instead of 2-fluoro-6-(2H-1,2,3-triazol-2-yl)benzoic acid. MS (ESI): mass calcd. for $C_{25}H_{21}F_4N_5O$, 483.2; m/z found, 484.4 $[M+H]^+$. $^1H$ NMR (400 MHz, Methanol-$d_4$) δ 7.99 (s, 1H), 7.88-7.74 (m, 1H), 7.72-7.64 (m, 1H), 7.58 (dd, J=6.3, 2.3 Hz, 1H), 7.35-7.18 (m, 3H), 5.88-5.66 (m, 1H), 3.92 (s, 3H), 3.83 (s, 2.1H), 3.77 (s, 0.90H), 3.76-3.68 (m, 1H), 3.57-3.35 (m, 0.70H), 3.25-3.18 (m, 0.30H), 2.92-2.61 (m, 1H), 2.61-2.51 (m, 0.30H), 2.49-2.36 (m, 0.70H), 1.59 (d, J=6.8 Hz, 2.1H), 1.48 (d, J=6.8 Hz, 0.90H).

The title compound was prepared in a manner analogous to Example 296, using 3-(3-methyl-1H-1,2,4-triazol-1-yl) benzoic acid (Intermediate 112) instead of 3-(1,2,4-triazol-4-yl)-5-(trifluoromethyl)benzoic acid. MS (ESI): mass calcd. for $C_{24}H_{21}F_3N_6O$, 466.2; m/z found, 467.2 $[M+H]^+$. $^1H$ NMR (500 MHz, DMSO-$d_6$) δ 9.24 (s, 1H), 7.98-7.90 (m, 1H), 7.89-7.79 (m, 1H), 7.64 (t, J=7.9 Hz, 1H), 7.59-7.50 (m, 2H), 7.47-7.37 (m, 1H), 5.64-5.51 (m, 1H), 3.82 (s, 3H), 3.68-3.57 (m, 1H), 3.36-3.23 (m, 1H), 2.87-2.76 (m, 1H), 2.36 (s, 3H), 2.38-2.25 (m, 1H), 1.53-1.42 (m, 3H).

Example 277: [(7S)-2,7-Dimethyl-3-(3,4,5-trifluorophenyl)-5,7-dihydro-4H-pyrazolo[3,4-c]pyridin-6-yl]-[3-fluoro-5-(1,2,4-triazol-1-yl)phenyl]methanone

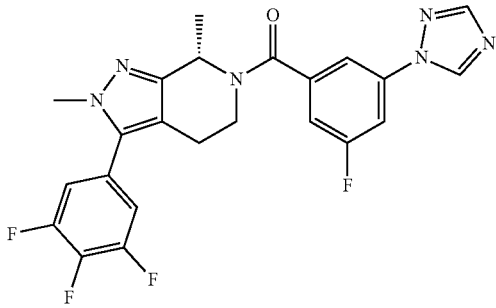 [SMILES: C[C@H]1c2nn(C)c(-c3cc(F)c(F)c(F)c3)c2CCN1C(=O)c1cc(F)cc(-n2cncn2)c1]

The title compound was prepared in a manner analogous to Example 296, using 3-fluoro-5-(1H-1,2,4-triazol-1-yl)benzoic acid (Intermediate 113) instead of 3-(1,2,4-triazol-4-yl)-5-(trifluoromethyl)benzoic acid. MS (ESI): mass calcd. for $C_{23}H_{18}F_4N_6O$, 470.2; m/z found, 471.2 [M+H]$^+$. $^1$H NMR (500 MHz, DMSO-d$_6$) δ 9.44 (s, 1H), 8.29 (s, 1H), 7.98-7.87 (m, 1H), 7.83-7.73 (m, 1H), 7.58-7.50 (m, 2H), 7.41-7.34 (m, 1H), 5.65-5.48 (m, 1H), 3.82 (s, 3H), 3.69-3.52 (m, 1H), 3.39-3.22 (m, 1H), 2.89-2.73 (m, 1H), 2.39-2.29 (m, 1H), 1.49 (d, J=6.9 Hz, 3H).

Example 278: [(7S)-2,7-Dimethyl-3-(3,4,5-trifluorophenyl)-5,7-dihydro-4H-pyrazolo[3,4-c]pyridin-6-yl]-[3-methoxy-5-(1,2,4-triazol-1-yl)phenyl]methanone

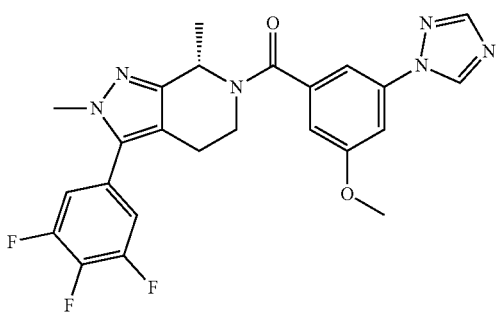 [SMILES: COc1cc(C(=O)N2CCc3c(nn(C)c3-c3cc(F)c(F)c(F)c3)[C@@H]2C)cc(-n2cncn2)c1]

The title compound was prepared in a manner analogous to Example 296, using 3-methoxy-5-(1H-1,2,4-triazol-1-yl)benzoic acid (Intermediate 114) instead of 3-(1,2,4-triazol-4-yl)-5-(trifluoromethyl)benzoic acid. MS (ESI): mass calcd. for $C_{24}H_{21}F_3N_6O_2$, 482.2; m/z found, 483.2 [M+H]$^+$. $^1$H NMR (500 MHz, DMSO-d$_6$) δ 9.40 (s, 1H), 8.25 (s, 1H), 7.60-7.51 (m, 3H), 7.49-7.44 (m, 1H), 7.04-6.93 (m, 1H), 5.67-5.48 (m, 1H), 3.89 (s, 3H), 3.82 (br s, 3H), 3.70-3.61 (m, 1H), 3.30-3.21 (m, 1H), 2.87-2.70 (m, 1H), 2.40-2.27 (m, 1H), 1.48 (d, J=6.9 Hz, 3H).

Example 279: [(7S)-2,7-Dimethyl-3-(3,4,5-trifluorophenyl)-5,7-dihydro-4H-pyrazolo[3,4-c]pyridin-6-yl]-[2-(1,2,4-triazol-1-yl)phenyl]methanone

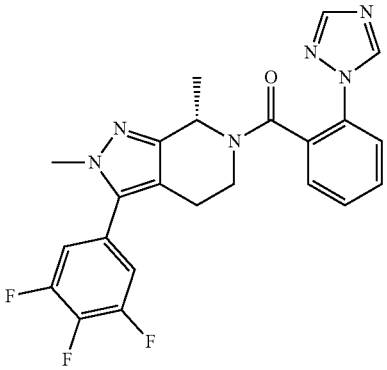 [SMILES: C[C@H]1c2nn(C)c(-c3cc(F)c(F)c(F)c3)c2CCN1C(=O)c1ccccc1-n1cncn1]

The title compound was prepared in a manner analogous to Example 296, using 2-(1H-1,2,4-triazol-1-yl)benzoic acid instead of 3-(1,2,4-triazol-4-yl)-5-(trifluoromethyl)benzoic acid. MS (ESI): mass calcd. for $C_{23}H_{19}F_3N_6O$, 452.2; m/z found, 453.2 [M+H]$^+$. $^1$H NMR (500 MHz, DMSO-d$_6$) δ 8.92 (s, 1H), 8.17 (s, 1H), 7.77-7.72 (m, 1H), 7.68-7.63 (m, 1H), 7.62-7.58 (m, 1H), 7.57-7.47 (m, 3H), 5.46 (q, J=6.7 Hz, 1H), 3.81 (s, 3H), 3.50-3.44 (m, 1H), 3.18-3.09 (m, 1H), 2.81-2.71 (m, 1H), 2.33-2.26 (m, 1H), 1.31 (d, J=6.8 Hz, 3H).

Example 280: [(7S)-2,7-Dimethyl-3-(3,4,5-trifluorophenyl)-5,7-dihydro-4H-pyrazolo[3,4-c]pyridin-6-yl]-[2-fluoro-6-(1,2,4-triazol-1-yl)phenyl]methanone

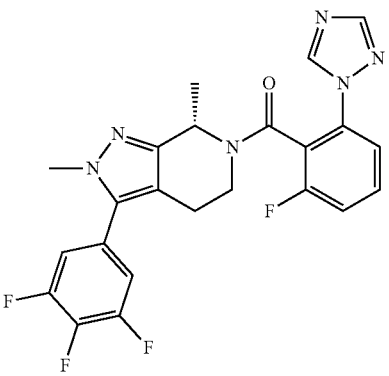 [SMILES: C[C@H]1c2nn(C)c(-c3cc(F)c(F)c(F)c3)c2CCN1C(=O)c1c(F)cccc1-n1cncn1]

The title compound was prepared in a manner analogous to Example 296, using 2-fluoro-6-(1H-1,2,4-triazol-1-yl)benzoic acid (Intermediate 115) instead of 3-(1,2,4-triazol-4-yl)-5-(trifluoromethyl)benzoic acid. MS (ESI): mass calcd. for $C_{23}H_{18}F_4N_6O$, 470.2; m/z found, 471.1 [M+H]$^+$. $^1$H NMR (500 MHz, DMSO-d$_6$) δ 9.01 (s, 1H), 8.17 (s, 1H), 7.73-7.46 (m, 5H), 5.44 (q, J=6.5 Hz, 1H), 3.78 (s, 3H), 3.56-3.49 (m, 1H), 3.23-3.16 (m, 1H), 2.68-2.59 (m, 1H), 2.41-2.35 (m, 1H), 1.31 (d, J=6.7 Hz, 3H).

Example 281: [(7S)-2,7-Dimethyl-3-(3,4,5-trifluorophenyl)-5,7-dihydro-4H-pyrazolo[3,4-c]pyridin-6-yl]-[5-fluoro-2-(1,2,4-triazol-1-yl)phenyl]methanone

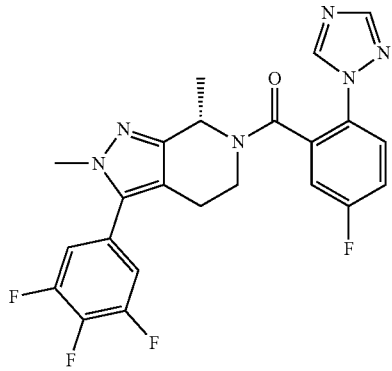 [SMILES: C[C@H]1c2nn(C)c(-c3cc(F)c(F)c(F)c3)c2CCN1C(=O)c1cc(F)ccc1-n1cncn1]

The title compound was prepared in a manner analogous to Example 296, using 5-fluoro-2-(1H-1,2,4-triazol-1-yl)benzoic acid (Intermediate 67) instead of 3-(1,2,4-triazol-4-yl)-5-(trifluoromethyl)benzoic acid. MS (ESI): mass calcd. for $C_{23}H_{18}F_4N_6O$, 470.2; m/z found, 471.1 [M+H]$^+$. $^1$H NMR (500 MHz, DMSO-d$_6$) δ 8.88 (s, 1H), 8.14 (s, 1H), 7.81-7.75 (m, 1H), 7.55-7.42 (m, 4H), 5.40 (q, J=6.7 Hz, 1H), 3.78 (s, 3H), 3.46 (dd, J=14.1, 5.2 Hz, 1H), 3.15-3.07 (m, 1H), 2.84-2.75 (m, 1H), 2.30-2.24 (m, 1H), 1.26 (d, J=6.7 Hz, 3H).

Example 282: [(7S)-2,7-Dimethyl-3-(3,4,5-trifluorophenyl)-5,7-dihydro-4H-pyrazolo[3,4-c]pyridin-6-yl]-[2-[3-(trifluoromethyl)-1,2,4-triazol-1-yl]phenyl]methanone

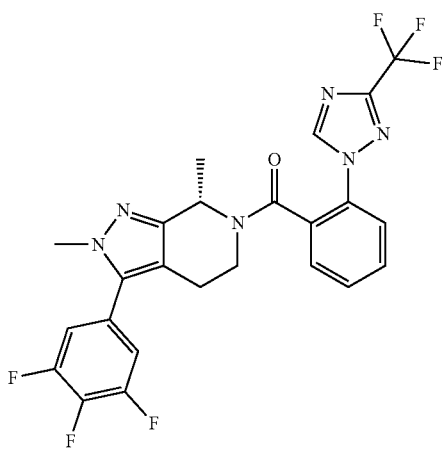 [SMILES: C[C@H]1c2nn(C)c(-c3cc(F)c(F)c(F)c3)c2CCN1C(=O)c1ccccc1-n1cnc(C(F)(F)F)n1]

The title compound was prepared in a manner analogous to Example 296, using 2-(3-(trifluoromethyl)-1H-1,2,4-triazol-1-yl)benzoic acid (Intermediate 66) instead of 3-(1,2,4-triazol-4-yl)-5-(trifluoromethyl)benzoic acid. MS (ESI): mass calcd. for $C_{24}H_{18}F_6N_6O$, 520.2; m/z found, 521.2 [M+H]$^+$. $^1$H NMR (300 MHz, DMSO-d$_6$) δ 9.33 (s, 1H), 7.94-7.22 (m, 6H), 5.53-5.31 (m, 1H), 3.81 (s, 3H), 3.61-3.49 (m, 1H), 2.95-2.76 (m, 1H), 2.63-2.19 (m, 2H), 1.29 (d, J=6.8 Hz, 3H).

Example 283: [(7S)-2,7-Dimethyl-3-(3,4,5-trifluorophenyl)-5,7-dihydro-4H-pyrazolo[3,4-c]pyridin-6-yl]-[3-(triazol-2-yl)phenyl]methanone

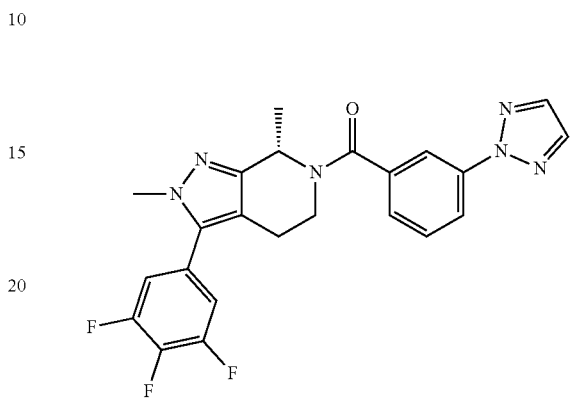

The title compound was prepared in a manner analogous to Example 296, using 3-(2H-1,2,3-triazol-2-yl)benzoic acid (Intermediate 65) instead of 3-(1,2,4-triazol-4-yl)-5-(trifluoromethyl)benzoic acid. MS (ESI): mass calcd. for $C_{23}H_{19}F_3N_6O$, 452.2; m/z found, 453.2 [M+H]$^+$. $^1$H NMR (300 MHz, DMSO-d$_6$) δ 8.17 (s, 2H), 8.15-7.93 (m, 2H), 7.74-7.41 (m, 4H), 5.70-5.49 (m, 1H), 3.81 (s, 3H), 3.76-3.57 (m, 1H), 3.25-3.00 (m, 1H), 2.90-2.69 (m, 1H), 2.60-2.30 (m, 1H), 1.49 (d, J=6.7 Hz, 3H).

Example 284: [(7S)-2,7-Dimethyl-3-(3,4,5-trifluorophenyl)-5,7-dihydro-4H-pyrazolo[3,4-c]pyridin-6-yl]-[3-fluoro-5-(triazol-2-yl)phenyl]methanone

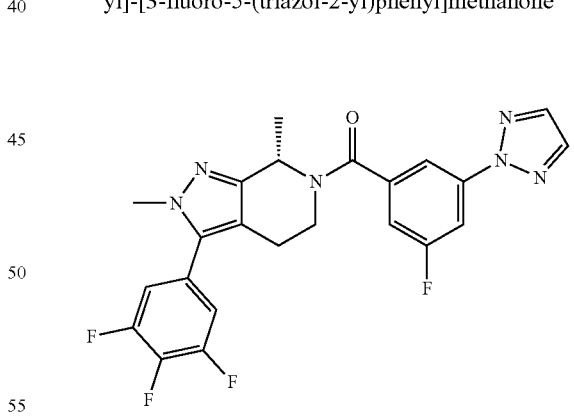

The title compound was prepared in a manner analogous to Example 296, using 3-fluoro-5-(triazol-2-yl)benzoic acid (Intermediate 111) instead of 3-(1,2,4-triazol-4-yl)-5-(trifluoromethyl)benzoic acid. MS (ESI): mass calcd. for $C_{23}H_{18}F_4N_6O$, 470.2; m/z found, 471.1 [M+H]$^+$. $^1$H NMR (500 MHz, DMSO-d$_6$) δ 8.19 (s, 2H), 7.93-7.87 (m, 1H), 7.86-7.76 (m, 1H), 7.57-7.48 (m, 2H), 7.41-7.35 (m, 1H), 5.66-5.41 (m, 1H), 3.79 (s, 3H), 3.69-3.56 (m, 1H), 3.33-3.21 (m, 1H), 2.84-2.72 (m, 1H), 2.39-2.24 (m, 1H), 1.46 (d, J=6.8 Hz, 3H).

Example 285: [(7S)-2,7-Dimethyl-3-(3,4,5-trifluoro-phenyl)-5,7-dihydro-4H-pyrazolo[3,4-c]pyridin-6-yl]-[2-fluoro-5-(triazol-2-yl)phenyl]methanone

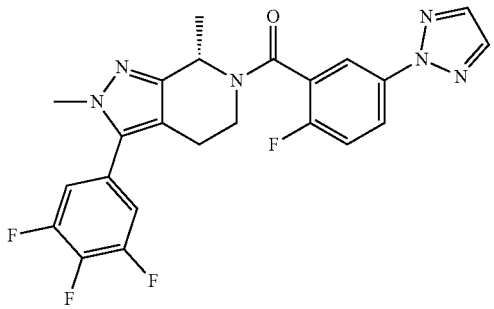 [SMILES: C[C@H]1c2nn(C)c(-c3cc(F)c(F)c(F)c3)c2CCN1C(=O)c1cc(-n2nccn2)ccc1F]

The title compound was prepared in a manner analogous to Example 296, using 2-fluoro-5-(2H-1,2,3-triazol-2-yl)benzoic acid (Intermediate 116) instead of 3-(1,2,4-triazol-4-yl)-5-(trifluoromethyl)benzoic acid. MS (ESI): mass calcd. for $C_{23}H_{18}F_4N_6O$, 470.2; m/z found, 471.2 [M+H]$^+$. $^1$H NMR (500 MHz, DMSO-d$_6$) δ 8.14 (s, 2H), 8.17-8.08 (m, 1H), 8.01-7.95 (m, 1H), 7.60-7.45 (m, 3H), 5.69-5.49 (m, 1H), 3.79 (s, 3H), 3.57 (dd, J=14.1, 5.0 Hz, 1H), 3.37-3.26 (m, 1H), 2.70-2.59 (m, 1H), 2.38-2.26 (m, 1H), 1.47 (d, J=6.7 Hz, 3H).

Example 286: [(7S)-2,7-Dimethyl-3-(3,4,5-trifluoro-phenyl)-5,7-dihydro-4H-pyrazolo[3,4-c]pyridin-6-yl]-[3-methyl-5-(triazol-2-yl)phenyl]methanone

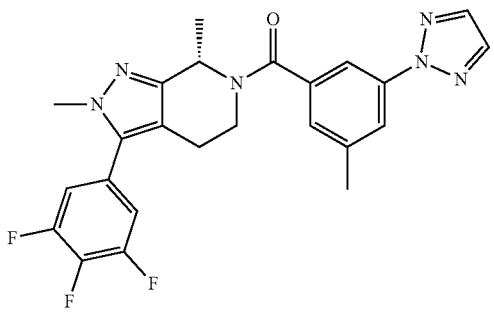 [SMILES: Cc1cc(C(=O)N2CCc3c(nn(C)c3-c3cc(F)c(F)c(F)c3)[C@@H]2C)cc(-n2nccn2)c1]

The title compound was prepared in a manner analogous to Example 296, using 3-methyl-5-(2H-1,2,3-triazol-2-yl)benzoic acid (Intermediate 117) instead of 3-(1,2,4-triazol-4-yl)-5-(trifluoromethyl)benzoic acid. MS (ESI): mass calcd. for $C_{24}H_{21}F_3N_6O$, 466.2; m/z found, 467.2 [M+H]$^+$. $^1$H NMR (500 MHz, DMSO-d$_6$) δ 8.13 (s, 2H), 7.97-7.91 (m, 1H), 7.80-7.72 (m, 1H), 7.57-7.48 (m, 2H), 7.30-7.23 (m, 1H), 5.66-5.48 (m, 1H), 3.79 (s, 3H), 3.82-3.59 (m, 1H), 3.35-3.18 (m, 1H), 2.81-2.68 (m, 1H), 2.45 (s, 3H), 2.43-2.25 (m, 1H), 1.52-1.37 (m, 3H).

Example 287: [(7S)-2,7-Dimethyl-3-(3,4,5-trifluoro-phenyl)-5,7-dihydro-4H-pyrazolo[3,4-c]pyridin-6-yl]-[3-(triazol-2-yl)-5-(trifluoromethyl)phenyl]methanone

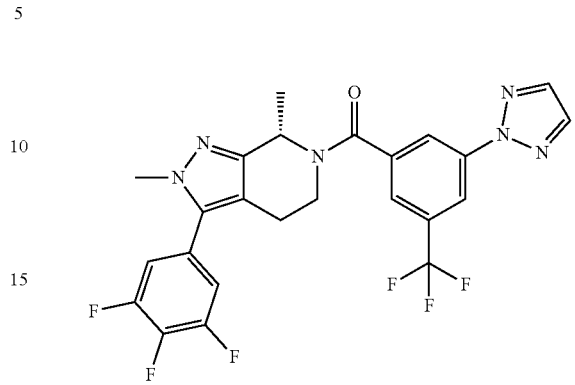

The title compound was prepared in a manner analogous to Example 296, using 3-(2H-1,2,3-triazol-2-yl)-5-(trifluoromethyl)benzoic acid (Intermediate 118) instead of 3-(1,2,4-triazol-4-yl)-5-(trifluoromethyl)benzoic acid. MS (ESI): mass calcd. for $C_{24}H_{18}F_6N_6O$, 520.2; m/z found, 521.1 [M+H]$^+$. $^1$H NMR (500 MHz, DMSO-d$_6$) δ 8.35-8.31 (m, 1H), 8.28-8.25 (m, 1H), 8.23 (s, 2H), 7.86-7.81 (m, 1H), 7.56-7.48 (m, 2H), 5.65-5.47 (m, 1H), 3.79 (s, 3H), 3.67-3.56 (m, 1H), 3.39-3.22 (m, 1H), 2.79-2.66 (m, 1H), 2.46-2.29 (m, 1H), 1.55-1.39 (m, 3H).

Example 288: [(7S)-2,7-Dimethyl-3-(3,4,5-trifluoro-phenyl)-5,7-dihydro-4H-pyrazolo[3,4-c]pyridin-6-yl]-[2-fluoro-6-(triazol-2-yl)phenyl]methanone

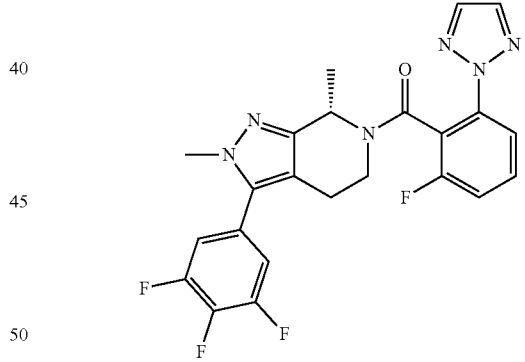

To a solution of (S)-2,7-dimethyl-3-(3,4,5-trifluorophenyl)-4,5,6,7-tetrahydro-2H-pyrazolo[3,4-c]pyridine (15 mg, 53.3 μmol) (Intermediate 40) in CH$_2$Cl$_2$ (0.48 mL) was added 2-fluoro-6-(2H-1,2,3-triazol-2-yl)benzoic acid (prepared according to methods described in Pat. Pub. No. WO2012145581, Oct. 26, 2012) (12.2 mg, 58.7 μmol), HATU (26.4 mg, 69.3 μmol), and N,N-diisopropylethylamine (27.6 μL, 0.16 mmol). After stirring at room temperature for 30 min, the mixture was concentrated in vacuo and purified by preparative HPLC (XBridge C18 column (5 μm, 100×4.6 mm), mobile phase of 5-95% ACN in 20 mM aqueous NH$_4$OH) to afford the title compound as a white powder (21 mg, 84% yield). MS (ESI): mass calcd. for $C_{23}H_{18}F_4N_6O$, 470.1; m/z found, 471.2 [M+H]$^+$. $^1$H NMR (600 MHz, DMSO-d$_6$) δ 8.19-8.05 (m, 1.62H), 7.93-7.90

(m, 0.40H), 7.87-7.83 (m, 0.91H), 7.74-7.66 (m, 1H), 7.59-7.38 (m, 3H), 5.59-5.49 (m, 0.74H), 4.73-4.62 (m, 0.28H), 4.57-4.51 (m, 0.17H), 3.81 (s, 2.26H), 3.76 (s, 0.22H), 3.70 (s, 0.52H), 3.64-3.52 (m, 0.72H), 3.38-3.17 (m, 0.73H), 3.07-3.00 (m, 0.22H), 2.84-2.76 (m, 0.15H), 2.71-2.60 (m, 0.63H), 2.45-2.22 (m, 1.47H), 1.47 (d, J=6.7 Hz, 2.28H), 1.35 (d, J=6.8 Hz, 0.6H).

Example 289: [(7S)-2,7-Dimethyl-3-(3,4,5-trifluorophenyl)-5,7-dihydro-4H-pyrazolo[3,4-c]pyridin-6-yl]-[5-methoxy-2-(triazol-2-yl)phenyl]methanone

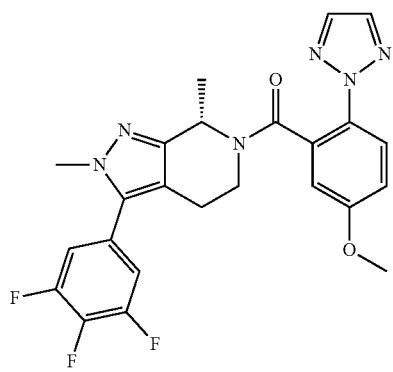 [SMILES: COc1ccc(-n2nccn2)c(C(=O)N2CCc3c(nn(C)c3-c3cc(F)c(F)c(F)c3)[C@@H]2C)c1]

The title compound was prepared in a manner analogous to Example 296, using 5-methoxy-2-(2H-1,2,3-triazol-2-yl)benzoic acid instead (Intermediate 63) of 3-(1,2,4-triazol-4-yl)-5-(trifluoromethyl)benzoic acid. MS (ESI): mass calcd. for $C_{24}H_{21}F_3N_6O_2$, 482.2; m/z found, 483.2 [M+H]$^+$. $^1$H NMR (500 MHz, DMSO-d$_6$) δ 8.01 (s, 2H), 7.82 (d, J=8.9 Hz, 1H), 7.58-7.49 (m, 2H), 7.19 (dd, J=8.9, 2.9 Hz, 1H), 6.99 (d, J=2.8 Hz, 1H), 5.47 (q, J=6.7 Hz, 1H), 3.86 (s, 3H), 3.81 (s, 3H), 3.52-3.46 (m, 1H), 3.12-3.04 (m, 1H), 2.81-2.73 (m, 1H), 2.32-2.26 (m, 1H), 1.38 (d, J=6.7 Hz, 3H).

Example 290: [(7S)-2,7-Dimethyl-3-(3,4,5-trifluorophenyl)-5,7-dihydro-4H-pyrazolo[3,4-c]pyridin-6-yl]-[3-(1,2,4-triazol-4-yl)phenyl]methanone

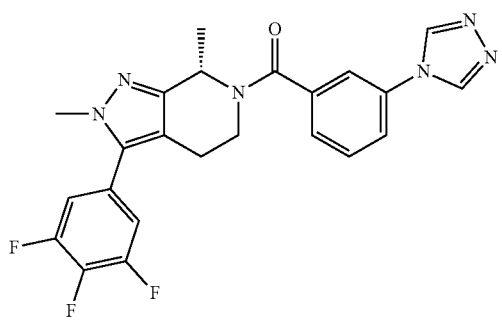 [SMILES: C[C@H]1c2nn(C)c(-c3cc(F)c(F)c(F)c3)c2CCN1C(=O)c1cccc(-n2cnnc2)c1]

The title compound was prepared in a manner analogous to Example 296, using 3-(4H-1,2,4-triazol-4-yl)benzoic acid instead of 3-(1,2,4-triazol-4-yl)-5-(trifluoromethyl)benzoic acid. MS (ESI): mass calcd. for $C_{23}H_{19}F_3N_6O$, 452.2; m/z found, 453.2 [M+H]$^+$. $^1$H NMR (300 MHz, DMSO-d$_6$) δ 9.21 (s, 2H), 7.91-7.38 (m, 6H), 5.68-5.49 (m, 1H), 3.82 (s, 3H), 3.69-3.55 (m, 1H), 2.93-2.75 (m, 1H), 2.62-2.29 (m, 2H), 1.49 (d, J=6.8 Hz, 3H).

Example 291: [(7S)-2,7-Dimethyl-3-(3,4,5-trifluorophenyl)-5,7-dihydro-4H-pyrazolo[3,4-c]pyridin-6-yl]-[4-fluoro-3-(1,2,4-triazol-4-yl)phenyl]methanone

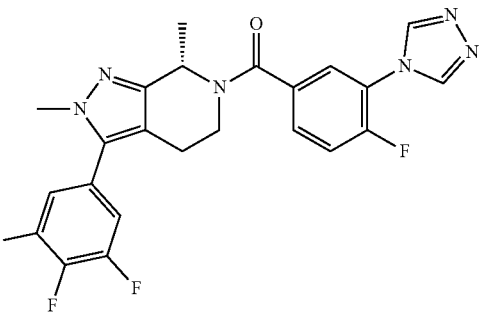

The title compound was prepared in a manner analogous to Example 296, using 4-fluoro-3-(4H-1,2,4-triazol-4-yl)benzoic acid (Intermediate 121) instead of 3-(1,2,4-triazol-4-yl)-5-(trifluoromethyl)benzoic acid. MS (ESI): mass calcd. for $C_{23}H_{18}F_4N_6O$, 470.2; m/z found, 471.2 [M+H]$^+$. $^1$H NMR (500 MHz, DMSO-d$_6$) δ 9.00 (s, 2H), 7.87-7.81 (m, 1H), 7.69-7.59 (m, 2H), 7.58-7.51 (m, 2H), 5.66-5.49 (m, 1H), 3.83 (s, 3H), 3.72-3.59 (m, 1H), 3.37-3.22 (m, 1H), 2.91-2.72 (m, 1H), 2.42-2.28 (m, 1H), 1.48 (d, J=6.8 Hz, 3H).

Example 292: [(7S)-2,7-Dimethyl-3-(3,4,5-trifluorophenyl)-5,7-dihydro-4H-pyrazolo[3,4-c]pyridin-6-yl]-[3-fluoro-5-(1,2,4-triazol-4-yl)phenyl]methanone

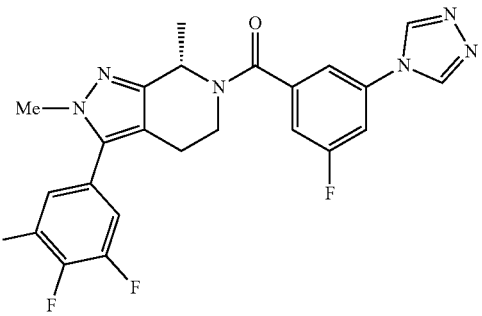

The title compound was prepared in a manner analogous to Example 288, using 3-fluoro-5-(4H-1,2,4-triazol-4-yl)benzoic acid (Intermediate 120) instead of 2-fluoro-6-(2H-1,2,3-triazol-2-yl)benzoic acid. MS (ESI): mass calcd. for $C_{23}H_{18}F_4N_6O$, 470.1; m/z found, 471.1 [M+H]$^+$. $^1$H NMR (600 MHz, Chloroform-d) δ 8.50 (s, 2H), 7.33-7.19 (m, 3H), 7.00-6.94 (m, 2H), 5.81 (brs, 0.46), 4.86 (d, J=46.3 Hz, 1H), 3.90-3.67 (m, 3.61H), 3.49-3.04 (m, 1.27H), 2.90-2.59 (m, 1.17H), 2.47 (brs, 1.11H), 1.59 (s, 3H).

Example 293: [(7S)-2,7-Dimethyl-3-(3,4,5-trifluoro-phenyl)-5,7-dihydro-4H-pyrazolo[3,4-c]pyridin-6-yl]-[3-methyl-5-(1,2,4-triazol-4-yl)phenyl]methanone

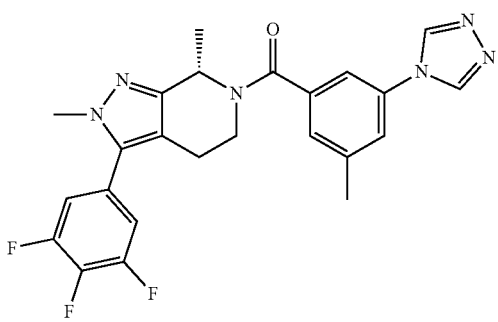

The title compound was prepared in a manner analogous to Example 296, using 3-methyl-5-(4H-1,2,4-triazol-4-yl)benzoic acid (Intermediate 122) instead of 3-(1,2,4-triazol-4-yl)-5-(trifluoromethyl)benzoic acid. MS (ESI): mass calcd. for $C_{24}H_{21}F_3N_6O$, 466.2; m/z found, 467.2 [M+H]$^+$. $^1$H NMR (500 MHz, DMSO-d$_6$) δ 9.18 (s, 2H), 7.73-7.66 (m, 1H), 7.61-7.57 (m, 1H), 7.56-7.50 (m, 2H), 7.36-7.19 (m, 1H), 5.61-5.53 (m, 1H), 3.82 (s, 3H), 3.68-3.58 (m, 1H), 3.34-3.22 (m, 1H), 2.87-2.74 (m, 1H), 2.44 (s, 3H), 2.38-2.30 (m, 1H), 1.48 (d, J=6.9 Hz, 3H).

Example 294: [(7S)-2,7-Dimethyl-3-(3,4,5-trifluoro-phenyl)-5,7-dihydro-4H-pyrazolo[3,4-c]pyridin-6-yl]-[4-methyl-3-(1,2,4-triazol-4-yl)phenyl]methanone

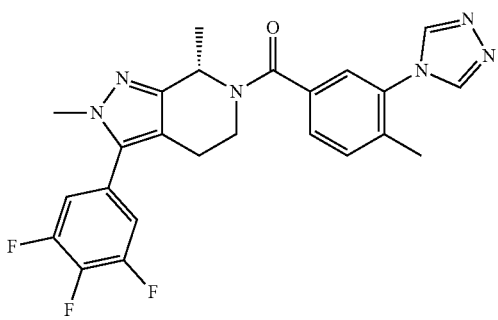 [SMILES: C[C@H]1c2nn(C)c(-c3cc(F)c(F)c(F)c3)c2CCN1C(=O)c1ccc(F)c(-n2cnnc2)c1]

The title compound was prepared in a manner analogous to Example 296, using 4-methyl-3-(4H-1,2,4-triazol-4-yl)benzoic acid (Intermediate 123) instead of 3-(1,2,4-triazol-4-yl)-5-(trifluoromethyl)benzoic acid. MS (ESI): mass calcd. for $C_{24}H_{21}F_3N_6O$, 466.2; m/z found, 467.2 [M+H]$^+$. $^1$H NMR (300 MHz, DMSO-d$_6$) δ 8.86 (s, 2H), 7.64-7.38 (m, 5H), 5.66-5.41 (m, 1H), 3.80 (s, 3H), 3.89-3.58 (m, 1H), 2.92-2.67 (m, 1H), 2.60-2.30 (m, 2H), 2.19 (s, 3H), 1.46 (d, J=6.8 Hz, 3H).

Example 295: [(7S)-2,7-Dimethyl-3-(3,4,5-trifluoro-phenyl)-5,7-dihydro-4H-pyrazolo[3,4-c]pyridin-6-yl]-[3-(1,2,4-triazol-4-yl)-4-(trifluoromethyl)phenyl]methanone

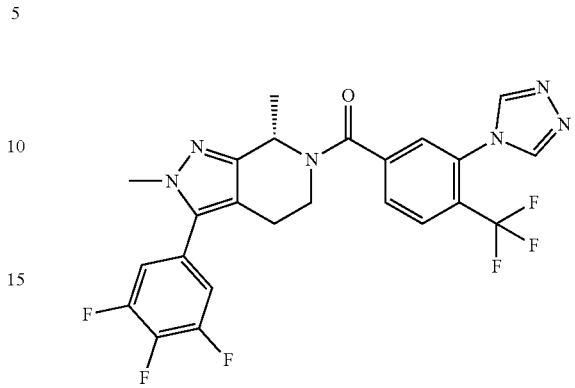

The title compound was prepared in a manner analogous to Example 296, using 3-(4H-1,2,4-triazol-4-yl)-4-(trifluoromethyl)benzoic acid (Intermediate 126) instead of 3-(1,2,4-triazol-4-yl)-5-(trifluoromethyl)benzoic acid. MS (ESI): mass calcd. for $C_{24}H_{18}F_6N_6O$, 520.2; m/z found, 521.2 [M+H]$^+$. $^1$H NMR (500 MHz, DMSO-d$_6$) δ 8.85 (s, 2H), 8.09 (d, J=8.1 Hz, 1H), 7.89-7.83 (m, 1H), 7.82-7.77 (m, 1H), 7.58-7.49 (m, 2H), 5.58 (q, J=6.7 Hz, 1H), 3.82 (s, 3H), 3.61 (dd, J=14.0, 5.0 Hz, 1H), 3.36-3.26 (m, 1H), 2.87-2.77 (m, 1H), 2.39-2.28 (m, 1H), 1.48 (d, J=7.0 Hz, 3H).

Example 296: [(7S)-2,7-Dimethyl-3-(3,4,5-trifluoro-phenyl)-5,7-dihydro-4H-pyrazolo[3,4-c]pyridin-6-yl]-[3-(1,2,4-triazol-4-yl)-5-(trifluoromethyl)phenyl]methanone

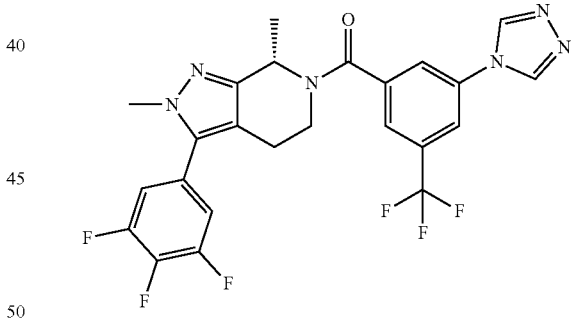

To a solution of(S)-2,7-dimethyl-3-(3,4,5-trifluorophenyl)-4,5,6,7-tetrahydro-2H-pyrazolo[3,4-c]pyridine (Intermediate 40, 25 mg, 0.0889 mmol) in dichloromethane (800 µL) was added 3-(4H-1,2,4-triazol-4-yl)-5-(trifluoromethyl)benzoic acid (Intermediate 127) (23 mg, 0.0894 mmol), O-(7-azabenzotriazol-1-yl)-N,N,N',N'-tetramethyluronium hexafluorophosphate (HATU, 37 mg, 0.0973 mmol, 0.19) and triethylamine (50 µL, 0.358 mmol, 0.725 g/mL). The reaction mixture was stirred at room temperature for 1 h. The mixture was diluted with dichloromethane (1 mL) and water (1 mL) and the layers were separated. The aqueous layer was extracted with dichloromethane (2×2 mL). The combined organic layers were washed with water (1×2 mL), dried over magnesium sulfate, filtered and evaporated. The crude product was purified by preparative HPLC to afford the title compound (30 mg, 0.058 mmol, 65%) as a white powder.

Optical rotation: [α]$_D^{25}$ −27.3° (c 0.19, MeOH). MS (ESI): mass calcd. for C$_{24}$H$_{18}$F$_6$N$_6$O, 520.2; m/z found, 521.2 [M+H]$^+$. $^1$H NMR (500 MHz, DMSO-d$_6$) δ 9.32 (s, 2H), 8.33-8.28 (m, 1H), 8.15-8.11 (m, 1H), 7.87-7.81 (m, 1H), 7.57-7.48 (m, 2H), 5.65-5.55 (m, 1H), 3.83 (s, 3H), 3.63-3.56 (m, 1H), 3.37-3.26 (m, 1H), 2.85-2.76 (m, 1H), 2.39-2.30 (m, 1H), 1.51 (d, J=6.7 Hz, 3H).

Example 297: [(7S)-2,7-Dimethyl-3-(3,4,5-trifluorophenyl)-5,7-dihydro-4H-pyrazolo[3,4-c]pyridin-6-yl]-[4-methoxy-3-(1,2,4-triazol-4-yl)phenyl]methanone

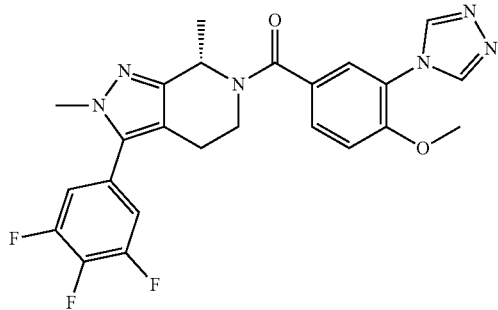 [SMILES: COc1ccc(C(=O)N2CCc3c(nn(C)c3-c3cc(F)c(F)c(F)c3)[C@@H]2C)cc1-n1cnnc1]

The title compound was prepared in a manner analogous to Example 296, using 4-methoxy-3-(4H-1,2,4-triazol-4-yl)benzoic acid (Intermediate 124) instead of 3-(1,2,4-triazol-4-yl)-5-(trifluoromethyl)benzoic acid. MS (ESI): mass calcd. for C$_{24}$H$_{21}$F$_3$N$_6$O$_2$, 482.2; m/z found, 483.2 [M+H]$^+$. $^1$H NMR (300 MHz, DMSO-d$_6$) δ 8.84 (s, 2H), 7.72-7.45 (m, 4H), 7.36 (d, J=8.4 Hz, 1H), 5.77-5.26 (m, 1H), 3.90 (s, 3H), 3.86-3.77 (m, 1H), 3.80 (s, 3H), 2.94-2.74 (m, 1H), 2.62-2.29 (m, 2H), 1.47 (d, J=6.8 Hz, 3H).

Example 298: [(7S)-2,7-Dimethyl-3-(3,4,5-trifluorophenyl)-5,7-dihydro-4H-pyrazolo[3,4-c]pyridin-6-yl]-[3-methoxy-5-(1,2,4-triazol-4-yl)phenyl]methanone

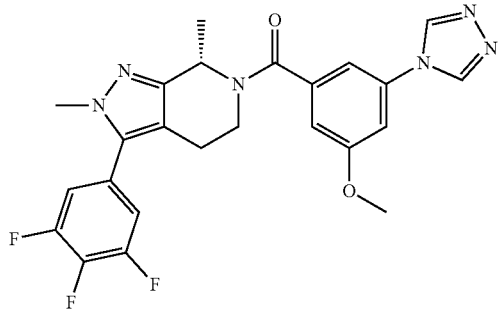 [SMILES: COc1cc(C(=O)N2CCc3c(nn(C)c3-c3cc(F)c(F)c(F)c3)[C@@H]2C)cc(-n2cnnc2)c1]

The title compound was prepared in a manner analogous to Example 296, using 3-methoxy-5-(4H-1,2,4-triazol-4-yl)benzoic acid (Intermediate 125) instead of 3-(1,2,4-triazol-4-yl)-5-(trifluoromethyl)benzoic acid. MS (ESI): mass calcd. for C$_{24}$H$_{21}$F$_3$N$_6$O$_2$, 482.2; m/z found, 483.2 [M+H]$^+$. $^1$H NMR (500 MHz, DMSO-d$_6$) δ 9.20 (s, 2H), 7.55-7.47 (m, 2H), 7.45-7.39 (m, 1H), 7.35-7.31 (m, 1H), 7.05-6.90 (m, 1H), 5.59-5.50 (m, 1H), 3.86 (s, 3H), 3.80 (s, 3H), 3.66-3.55 (m, 1H), 3.28-3.18 (m, 1H), 2.84-2.74 (m, 1H), 2.35-2.26 (m, 1H), 1.45 (d, J=6.8 Hz, 3H).

Example 299: [(7S)-2,7-Dimethyl-3-(3,4,5-trifluorophenyl)-5,7-dihydro-4H-pyrazolo[3,4-c]pyridin-6-yl]-[2-(1,2,4-triazol-4-yl)phenyl]methanone

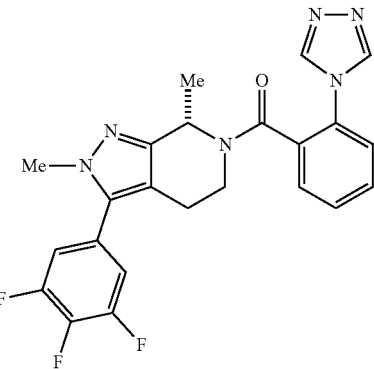

The title compound was prepared in a manner analogous to Example 288, using 2-(4H-1,2,4-triazol-4-yl)benzoic acid instead of 2-fluoro-6-(2H-1,2,3-triazol-2-yl)benzoic acid. MS (ESI): mass calcd. for C$_{23}$H$_{19}$F$_3$N$_6$O, 452.2; m/z found, 453.1 [M+H]$^+$. $^1$H NMR (500 MHz, Chloroform-d) δ 8.62-8.37 (m, 0.65H), 8.11 (s, 1.36H), 7.65-7.52 (m, 2.78H), 7.51-7.38 (m, 0.60H), 7.31 (d, J=7.6 Hz, 0.67H), 7.13-7.06 (m, 1.40H), 6.97-6.83 (m, 0.60H), 5.82-5.70 (m, 0.27H), 4.73 (dd, J=13.2, 5.6 Hz, 0.83H), 4.48 (q, J=6.8 Hz, 0.73H), 3.82-3.71 (m, 3.34H), 3.44-3.33 (m, 0.28H), 3.27-3.16 (m, 0.08H), 2.98 (td, J=12.7, 4.3 Hz, 1H), 2.58-2.10 (m, 2H), 1.44-1.27 (m, 2.60H).

Example 300: [(7S)-2,7-Dimethyl-3-(3,4,5-trifluorophenyl)-5,7-dihydro-4H-pyrazolo[3,4-c]pyridin-6-yl]-(6-methoxy-3-pyridyl)methanone

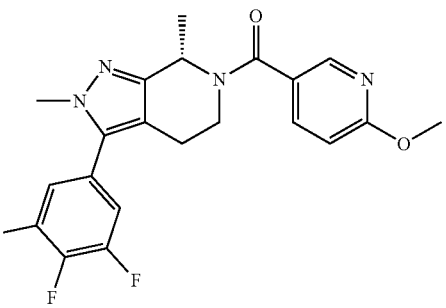

The title compound was prepared in a manner analogous to Example 288, using 6-methoxynicotinic acid instead of 2-fluoro-6-(2H-1,2,3-triazol-2-yl)benzoic acid. MS (ESI): mass calcd. for C$_{21}$H$_{19}$F$_3$N$_4$O$_2$, 416.1; m/z found, 417.0 [M+H]$^+$. $^1$H NMR (400 MHz, Methanol-d$_4$) δ 8.29 (d, J=2.4 Hz, 1H), 7.78 (dd, J=8.6, 2.4 Hz, 1H), 7.46-7.21 (m, 2H), 6.89 (dd, J=8.6, 0.8 Hz, 1H), 5.91-5.43 (m, 1H), 4.75-4.41 (m, 1H), 3.97 (s, 3H), 3.82 (s, 3H), 3.46-3.34 (m, 1H), 2.89-2.74 (m, 1H), 2.59-2.38 (m, 1H), 1.57 (d, J=6.8 Hz, 3H).

Example 301: [(7S)-2,7-Dimethyl-3-(3,4,5-trifluoro-phenyl)-5,7-dihydro-4H-pyrazolo[3,4-c]pyridin-6-yl]-(5-methoxy-2-pyridyl)methanone

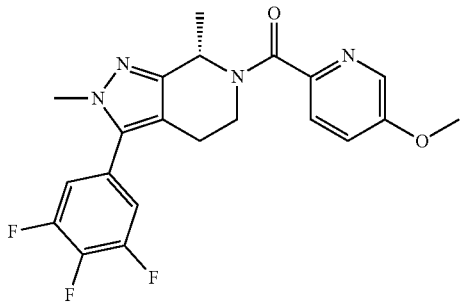 [SMILES: COc1ccc(C(=O)N2CCc3c(nn(C)c3-c3cc(F)c(F)c(F)c3)[C@@H]2C)nc1]

The title compound was prepared in a manner analogous to Example 288, using 5-methoxypicolinic acid instead of 2-fluoro-6-(2H-1,2,3-triazol-2-yl)benzoic acid. MS (ESI): mass calcd. for $C_{21}H_{16}F_3N_4O_2$, 416.1; m/z found, 417.0 [M+H]$^+$. $^1$H NMR (400 MHz, Methanol-d$_4$) δ 8.39-8.23 (m, 1H), 7.64 (d, J=8.6 Hz, 1H), 7.50 (dd, J=8.7, 2.9 Hz, 1H), 7.36-7.21 (m, 2H), 5.70 (q, J=6.8, 6.4 Hz, 0.70H), 5.28-5.11 (m, 0.30H), 4.83-4.58 (m, 0.30H), 4.01 (dd, J=13.5, 4.9 Hz, 0.70H), 3.93 (s, 3H), 3.83 (s, 2.1H), 3.77 (s, 0.90H), 3.42-3.32 (m, 0.70H), 3.26-3.14 (m, 0.30H), 3.04-2.85 (m, 0.70H), 2.86-2.70 (m, 0.30H), 2.61-2.49 (m, 0.30H), 2.48-2.32 (m, 0.70H), 1.68-1.50 (m, 3H).

Example 302: [(7S)-2,7-Dimethyl-3-(3,4,5-trifluoro-phenyl)-5,7-dihydro-4H-pyrazolo[3,4-c]pyridin-6-yl]-(6-methoxy-3-methyl-2-pyridyl)methanone

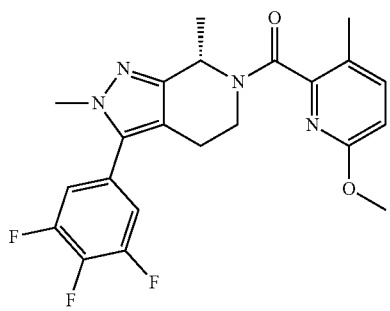 [SMILES: COc1ccc(C)c(C(=O)N2CCc3c(nn(C)c3-c3cc(F)c(F)c(F)c3)[C@@H]2C)n1]

The title compound was prepared in a manner analogous to Example 288, using 6-methoxy-3-methylpicolinic acid instead of 2-fluoro-6-(2H-1,2,3-triazol-2-yl)benzoic acid. MS (ESI): mass calcd. for $C_{22}H_{21}F_3N_4O_2$, 430.2; m/z found, 431.2 [M+H]$^+$. $^1$H NMR (500 MHz, DMSO-d$_6$) δ 7.67-7.62 (m, 1H), 7.60-7.49 (m, 2H), 6.86-6.79 (m, 1H), 5.60 (q, J=6.7 Hz, 0.70H), 4.71 (dd, J=13.0, 5.2 Hz, 0.33H), 4.48 (q, J=6.7 Hz, 0.35H), 3.88-3.71 (m, 6H), 3.26-3.18 (m, 0.68H), 3.03 (td, J=12.7, 3.9 Hz, 0.31H), 2.79-2.63 (m, 1H), 2.35-2.29 (m, 0.67H), 2.15 (s, 2H), 2.05 (s, 1H), 1.48 (d, J=6.7 Hz, 2H), 1.42 (d, J=6.7 Hz, 1H). (Fractions of H's that overlap with DMSO and water are not reported)

Example 303: [(7S)-2,7-Dimethyl-3-(3,4,5-trifluoro-phenyl)-5,7-dihydro-4H-pyrazolo[3,4-c]pyridin-6-yl]-(3-methoxy-2-pyridyl)methanone

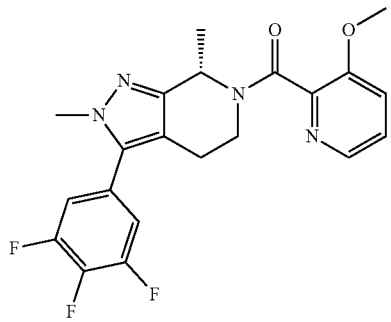

The title compound was prepared in a manner analogous to Example 288, using 3-methoxypicolinic acid instead of 2-fluoro-6-(2H-1,2,3-triazol-2-yl)benzoic acid. MS (ESI): mass calcd. for $C_{21}H_{19}F_3N_4O_2$, 416.1; m/z found, 417.2 [M+H]$^+$. $^1$H NMR (500 MHz, DMSO-d$_6$) δ 8.18-8.13 (m, 1H), 7.62-7.42 (m, 4H), 5.58 (q, J=6.7 Hz, 0.66H), 4.70 (dd, J=13.0, 5.3 Hz, 0.36H), 4.44 (q, J=6.7 Hz, 0.36H), 3.86-3.71 (m, 6H), 3.24-3.16 (m, 0.72H), 3.02 (td, J=12.7, 4.0 Hz, 0.36H), 2.73-2.55 (m, 1H), 2.33-2.25 (m, 0.67H), 1.45 (d, J=6.8 Hz, 2H), 1.32 (d, J=6.8 Hz, 1H). (Fractions of H's that overlap with DMSO and water may not be reported)

Example 304: [(7S)-2,7-Dimethyl-3-(3,4,5-trifluoro-phenyl)-5,7-dihydro-4H-pyrazolo[3,4-c]pyridin-6-yl]-[5-(methoxymethyl)-3-pyridyl]methanone

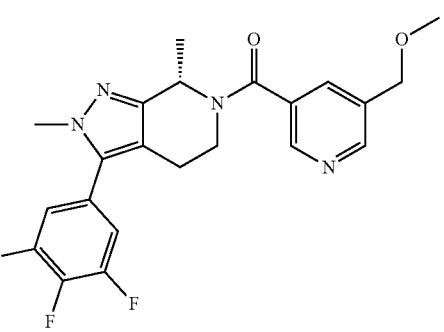

The title compound was prepared in a manner analogous to Example 288, using 5-(methoxymethyl)nicotinic acid instead of 2-fluoro-6-(2H-1,2,3-triazol-2-yl)benzoic acid. MS (ESI): mass calcd. for $C_{22}H_{21}F_3N_4O_2$, 430.2; m/z found, 431.2 [M+H]$^+$. $^1$H NMR (600 MHz, DMSO-d$_6$) δ 8.65-8.63 (m, 1H), 8.58 (s, 1H), 7.74-7.72 (m, 1H), 7.60-7.50 (m, 2H), 5.63-5.52 (m, 0.74H), 4.74-4.46 (m, 2.78H); 3.91-3.52 (m, 4H), 3.33 (s, 3H), 3.16-3.02 (m, 0.26H), 2.91-2.72 (m, 1H), 2.41-2.29 (0.78H), 1.54-1.41 (m, 3H). (Fractions of H's that overlap with DMSO and water may not be reported)

Example 305: [(7S)-2,7-Dimethyl-3-(3,4,5-trifluorophenyl)-5,7-dihydro-4H-pyrazolo[3,4-c]pyridin-6-yl]-(5-isopropoxy-3-pyridyl)methanone

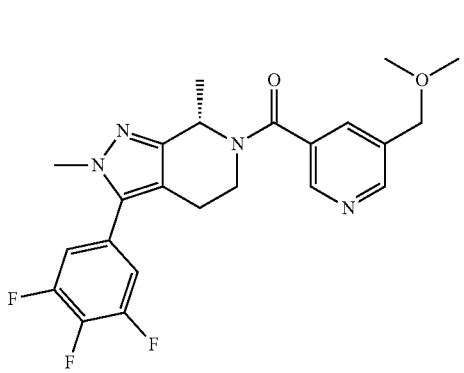

The title compound was prepared in a manner analogous to Example 288, using 5-isopropoxynicotinic acid instead of 2-fluoro-6-(2H-1,2,3-triazol-2-yl)benzoic acid. MS (ESI): mass calcd. for $C_{23}H_{23}F_3N_4O_2$, 444.2; m/z found, 445.2 [M+H]$^+$. $^1$H NMR (500 MHz, DMSO-d$_6$) δ 8.34 (d, J=2.8 Hz, 1H), 8.22-8.12 (m, 1H), 7.59-7.50 (m, 2H), 7.43-7.39 (m, 1H), 5.63-5.49 (m, 0.71H), 4.83-4.52 (m, 1.53H), 3.87-3.53 (m, 3.84H), 2.92-2.70 (m, 1H), 2.9-2.28 (m, 0.82H), 1.50-1.43 (m, 3H), 1.32-1.27 (m, 6H). (Fractions of H's that overlap with DMSO and water may not be reported)

Example 306: [(7S)-2,7-Dimethyl-3-(3,4,5-trifluorophenyl)-5,7-dihydro-4H-pyrazolo[3,4-c]pyridin-6-yl]-(6-methoxy-2-methyl-3-pyridyl)methanone

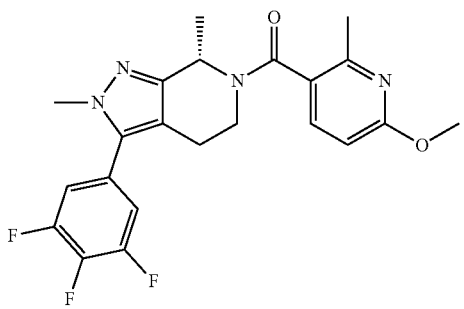

The title compound was prepared in a manner analogous to Example 288, using 6-methoxy-2-methylnicotinic acid instead of 2-fluoro-6-(2H-1,2,3-triazol-2-yl)benzoic acid. MS (ESI): mass calcd. for $C_{22}H_{21}F_3N_4O_2$, 430.2; m/z found, 431.2 [M+H]$^+$. $^1$H NMR (500 MHz, DMSO-d$_6$) δ 7.74-7.30 (m, 3H), 6.76-6.67 (m, 1H), 5.68-5.58 (m, 0.71H), 4.76-4.66 (m, 0.26H), 4.61-4.44 (s, 0.25H), 3.91-3.73 (m, 6H), 3.07-2.97 (m, 0.24H), 2.81-2.59 (m, 1H), 2.38-2.12 (m, 3.68H), 1.53-1.26 (m, 3H). (Fractions of H's that overlap with DMSO and water may not be reported)

Example 307: [(7S)-2,7-Dimethyl-3-(3,4,5-trifluorophenyl)-5,7-dihydro-4H-pyrazolo[3,4-c]pyridin-6-yl]-(4-methoxy-3-methyl-2-pyridyl)methanone.TFA salt

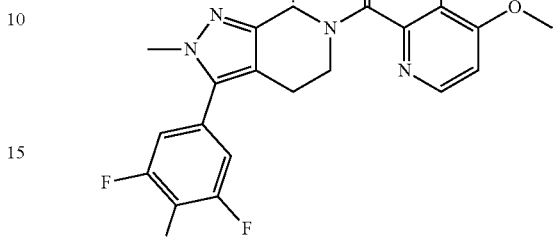

The title compound was prepared in a manner analogous to Example 288, using 4-methoxy-3-methylpicolinic acid instead of 2-fluoro-6-(2H-1,2,3-triazol-2-yl)benzoic acid. MS (ESI): mass calcd. for $C_{22}H_{21}F_3N_4O_2$, 430.2; m/z found, 431.2 [M+H]$^+$. $^1$H NMR (500 MHz, DMSO-d$_6$) δ 8.41-8.35 (m, 1H), 7.60-7.48 (m, 2H), 7.17-7.10 (m, 1H), 5.61 (q, J=6.7 Hz, 0.70H), 4.75-4.69 (m, 0.34H), 4.50 (q, J=6.7 Hz, 0.35H), 3.95-3.91 (m, 3H), 3.82 (s, 2H), 3.75 (s, 1H), 3.33-3.28 (m, 0.65H), 3.25-3.17 (m, 0.79H), 3.08-3.00 (m, 0.35H), 2.78-2.70 (m, 0.38H), 2.67-2.58 (m, 0.74H), 2.31-2.25 (m, 0.70H), 2.06 (s, 2H), 1.99 (s, 1H), 1.48 (d, J=6.8 Hz, 2H), 1.32 (d, J=6.8 Hz, 1H).

Example 308: [(7S)-2,7-Dimethyl-3-(3,4,5-trifluorophenyl)-5,7-dihydro-4H-pyrazolo[3,4-c]pyridin-6-yl]-(5-methoxy-2-methyl-3-pyridyl)methanone

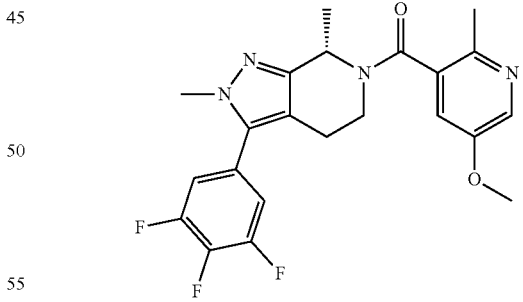

The title compound was prepared in a manner analogous to Example 288, using 5-methoxy-2-methylnicotinic acid instead of 2-fluoro-6-(2H-1,2,3-triazol-2-yl)benzoic acid. MS (ESI): mass calcd. for $C_{22}H_{21}F_3N_4O_2$, 430.2; m/z found, 431.2 [M+H]$^+$. $^1$H NMR (500 MHz, Chloroform-d) δ 8.25 (d, J=2.9 Hz, 1H), 7.06-6.87 (m, 3H), 5.92 (q, J=6.7 Hz, 0.58H), 4.96 (dd, J=13.2, 5.3 Hz, 0.43H), 4.88-4.59 (m, 0.45H), 3.90-3.75 (m, 6H), 3.63-3.47 (m, 0.58H), 3.36-3.22 (m, 0.59H), 3.10-2.99 (m, 0.39H), 2.84-2.73 (m, 0.40H), 2.63-2.24 (m, 4.64H), 1.66-1.38 (m, 3H).

Example 309: [(7S)-2,7-Dimethyl-3-(3,4,5-trifluoro-phenyl)-5,7-dihydro-4H-pyrazolo[3,4-c]pyridin-6-yl]-(4-methoxy-2-pyridyl)methanone

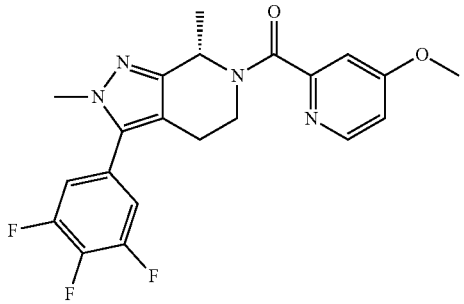

The title compound was prepared in a manner analogous to Example 288, using 4-methoxypicolinic acid instead of 2-fluoro-6-(2H-1,2,3-triazol-2-yl)benzoic acid. MS (ESI): mass calcd. for $C_{21}H_{19}F_3N_4O_2$, 416.1; m/z found, 417.2 [M+H]$^+$. $^1$H NMR (500 MHz, Chloroform-d) δ 8.43-8.38 (m, 1H), 7.18 (dd, J=20.1, 2.5 Hz, 1H), 7.02-6.92 (m, 2H), 6.89-6.83 (m, 1H), 5.85 (q, J=6.8 Hz, 0.55H), 5.28 (q, J=6.7 Hz, 0.45H), 4.87 (dd, J=13.1, 5.3 Hz, 0.46H), 4.08 (dd, J=13.6, 5.0 Hz, 0.57H), 3.94-3.72 (m, 6H), 3.31-3.22 (m, 0.56H), 3.10 (td, J=12.7, 4.0 Hz, 0.45H), 2.97-2.79 (m, 1H), 2.51-2.29 (m, 1H), 1.64-1.57 (m, 3H).

Example 310: [(7S)-2,7-Dimethyl-3-(3,4,5-trifluoro-phenyl)-5,7-dihydro-4H-pyrazolo[3,4-c]pyridin-6-yl]-(5-methoxy-6-methyl-3-pyridyl)methanone

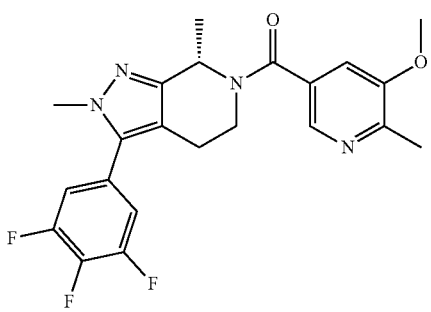 [SMILES: COc1cc(C(=O)N2CCc3c(nn(C)c3-c3cc(F)c(F)c(F)c3)[C@@H]2C)cnc1C]

The title compound was prepared in a manner analogous to Example 288, using 5-methoxy-6-methylnicotinic acid instead of 2-fluoro-6-(2H-1,2,3-triazol-2-yl)benzoic acid. MS (ESI): mass calcd. for $C_{22}H_{21}F_3N_4O_2$, 430.2; m/z found, 431.2 [M+H]$^+$. $^1$H NMR (500 MHz, DMSO-d$_6$) δ 8.07 (s, 1H), 7.59-7.50 (m, 2H), 7.35 (d, J=1.7 Hz, 1H), 5.55 (s, 0.69H), 4.83-4.50 (m, 0.53H), 3.91-3.60 (m, 7.24H), 2.92-2.74 (m, 1H), 2.43-2.30 (m, 4H), 1.48 (d, J=6.8 Hz, 3H). (Fractions of H's that overlap with DMSO and water may not be reported)

Example 311: [(7S)-2,7-Dimethyl-3-(3,4,5-trifluoro-phenyl)-5,7-dihydro-4H-pyrazolo[3,4-c]pyridin-6-yl]-(3-methoxy-4-pyridyl)methanone

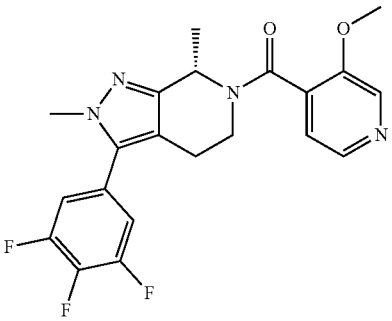 [SMILES: COc1cnccc1C(=O)N1CCc2c(nn(C)c2-c2cc(F)c(F)c(F)c2)[C@@H]1C]

The title compound was prepared in a manner analogous to Example 288, using 3-methoxyisonicotinic acid instead of 2-fluoro-6-(2H-1,2,3-triazol-2-yl)benzoic acid. MS (ESI): mass calcd. for $C_{21}H_{19}F_3N_4O_2$, 416.1; m/z found, 417.2 [M+H]$^+$. $^1$H NMR (500 MHz, DMSO-d$_6$) δ 8.57-8.44 (m, 1H), 8.34-8.23 (m, 1H), 7.60-7.46 (m, 2H), 7.39-7.06 (m, 1H), 5.64-5.51 (m, 0.73H), 4.72-4.63 (m, 0.29H), 4.53-4.37 (m, 0.34H), 3.99-3.89 (m, 2.60H), 3.84-3.70 (m, 3.30H), 3.10-2.95 (m, 0.26H), 2.79-2.56 (m, 1.18H), 2.41-2.21 (m, 0.72H), 1.50-1.26 (m, 3H). (Fractions of H's that overlap with DMSO and water may not be reported)

Example 312: [(7S)-2,7-Dimethyl-3-(3,4,5-trifluoro-phenyl)-5,7-dihydro-4H-pyrazolo[3,4-c]pyridin-6-yl]-(2-methoxy-4-pyridyl)methanone

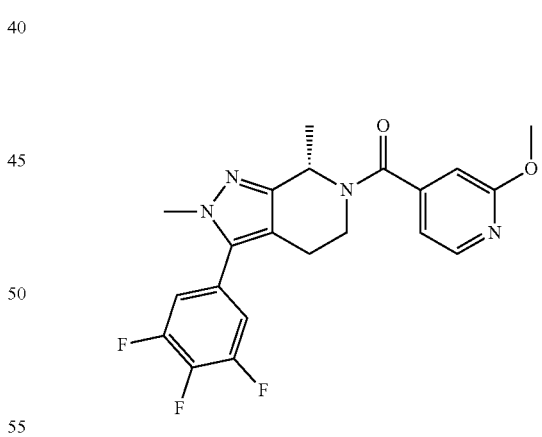

The title compound was prepared in a manner analogous to Example 288, using 2-methoxyisonicotinic acid instead of 2-fluoro-6-(2H-1,2,3-triazol-2-yl)benzoic acid. MS (ESI): mass calcd. for $C_{21}H_{19}F_3N_4O_2$, 416.1; m/z found, 417.2 [M+H]$^+$. $^1$H NMR (500 MHz, DMSO-d$_6$) δ 8.29-8.25 (m, 1H), 7.59-7.49 (m, 2H), 7.03-6.92 (m, 1H), 6.86-6.77 (m, 1H), 5.55 (q, J=6.7 Hz, 0.72H), 4.66-4.55 (m, 0.51H), 3.89 (s, 3H), 3.85-3.71 (m, 3H), 3.55-3.47 (m, 0.75H), 3.10-3.01 (m, 0.25H), 2.86-2.69 (m, 1H), 2.35-2.25 (m, 0.69H), 1.51-1.36 (m, 3H). (Fractions of H's that overlap with DMSO and water are not reported)

Example 313: [(7S)-2,7-Dimethyl-3-(3,4,5-trifluorophenyl)-5,7-dihydro-4H-pyrazolo[3,4-c]pyridin-6-yl]-(5-methoxy-4-methyl-3-pyridyl)methanone

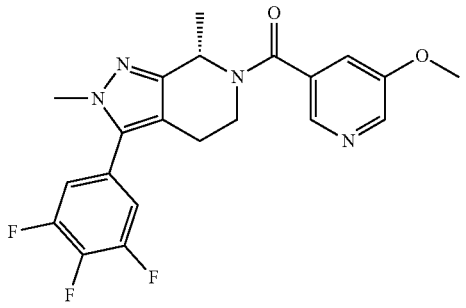

The title compound was prepared in a manner analogous to Example 288, using 5-methoxy-4-methylnicotinic acid instead of 2-fluoro-6-(2H-1,2,3-triazol-2-yl)benzoic acid. MS (ESI): mass calcd. for $C_{22}H_{21}F_3N_4O_2$, 430.2; m/z found, 431.2 [M+H]$^+$. $^1$H NMR (500 MHz, Chloroform-d) δ 8.26-7.93 (m, 2H), 7.02-6.89 (m, 2H), 6.00-5.88 (m, 0.58H), 5.03-4.92 (m, 0.46H), 4.87 (br s, 0.13H), 4.68-4.56 (m, 0.32H), 4.01-3.89 (m, 3H), 3.86-3.74 (m, 3H), 3.65-3.48 (m, 0.59H), 3.32-3.21 (m, 0.59H), 3.06 (td, J=12.7, 3.9 Hz, 0.43H), 2.86-2.73 (m, 0.42H), 2.66-2.44 (m, 1H), 2.36-1.98 (m, 3.66H), 1.67-1.33 (m, 3H).

Example 314: [(7S)-2,7-Dimethyl-3-(3,4,5-trifluorophenyl)-5,7-dihydro-4H-pyrazolo[3,4-c]pyridin-6-yl]-(2-methoxy-3-methyl-4-pyridyl)methanone

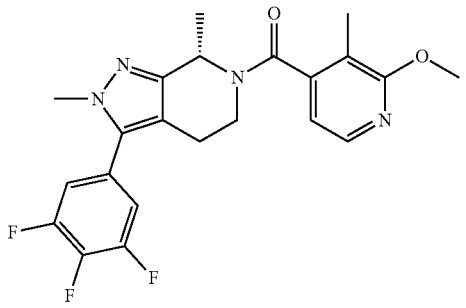 [SMILES: COc1nccc(C(=O)N2CCc3c(nn(C)c3-c3cc(F)c(F)c(F)c3)[C@@H]2C)c1C]

The title compound was prepared in a manner analogous to Example 288, using 2-methoxy-3-methylisonicotinic acid instead of 2-fluoro-6-(2H-1,2,3-triazol-2-yl)benzoic acid. MS (ESI): mass calcd. for $C_{22}H_{21}F_3N_4O_2$, 430.2; m/z found, 431.2 [M+H]$^+$. $^1$H NMR (500 MHz, DMSO-d$_6$) δ 8.15-8.02 (m, 1H), 7.60-7.46 (m, 2H), 7.00-6.60 (m, 1H), 5.62 (q, J=6.7 Hz, 0.76H), 4.76-4.55 (m, 0.37H), 4.45-4.36 (m, 0.17H), 3.94-3.88 (m, 3H), 3.81 (s, 2.25H), 3.76 (s, 0.76H), 3.10-2.98 (m, 0.25H), 2.81-2.61 (m, 0.80H), 2.34-2.23 (m, 0.76H), 2.14-1.82 (m, 3H), 1.52-1.26 (m, 3H). (Fractions of H's that overlap with DMSO and water may not be reported)

Example 315: [(7S)-2,7-Dimethyl-3-(3,4,5-trifluorophenyl)-5,7-dihydro-4H-pyrazolo[3,4-c]pyridin-6-yl]-(3-fluoro-2-methoxy-4-pyridyl)methanone

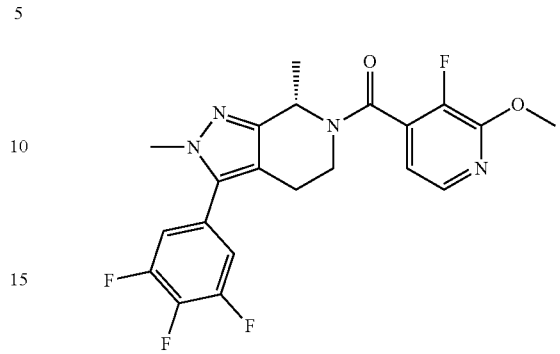

The title compound was prepared in a manner analogous to Example 288, using 3-fluoro-2-methoxyisonicotinic acid instead of 2-fluoro-6-(2H-1,2,3-triazol-2-yl)benzoic acid. MS (ESI): mass calcd. for $C_{21}H_{18}F_4N_4O_2$, 434.1; m/z found, 435.2 [M+H]$^+$. $^1$H NMR (500 MHz, DMSO-d$_6$) δ 8.07 (d, J=5.0 Hz, 1H), 7.59-7.49 (m, 2H), 7.08-6.98 (m, 1H), 5.59 (q, J=6.7 Hz, 0.76H), 4.67 (dd, J=13.2, 5.3 Hz, 0.29H), 4.59 (q, J=6.6 Hz, 0.28H), 4.01-3.95 (m, 3H), 3.81 (s, 2.24H), 3.76 (s, 0.83H), 3.54-3.47 (m, 0.79H), 3.13-3.05 (m, 0.27H), 2.77-2.62 (m, 1H), 2.33-2.28 (m, 0.68H), 1.47-1.37 (d, J=6.8 Hz, 2.27H), 1.37 (d, J=6.7 Hz, 0.80H). (Fractions of H's that overlap with DMSO and water are not reported)

Example 316: (3-Chloro-2-methoxy-4-pyridyl)-[(7S)-2,7-dimethyl-3-(3,4,5-trifluorophenyl)-5,7-dihydro-4H-pyrazolo[3,4-c]pyridin-6-yl]methanone

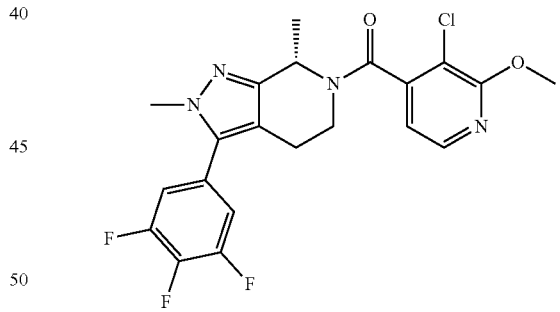

The title compound was prepared in a manner analogous to Example 288, using 3-chloro-2-methoxyisonicotinic acid instead of 2-fluoro-6-(2H-1,2,3-triazol-2-yl)benzoic acid. MS (ESI): mass calcd. for $C_{21}H_{18}ClF_3N_4O_2$, 450.1; m/z found, 451.2 [M+H]$^+$. $^1$H NMR (500 MHz, Chloroform-d) δ 8.16-8.10 (m, 0.87H), 8.06 (d, J=5.0 Hz, 0.12H), 7.02-6.91 (m, 2H), 6.89 (d, J=5.0 Hz, 0.25H), 6.83 (d, J=5.0 Hz, 0.62H), 6.71 (d, J=5.0 Hz, 0.12H), 5.92-5.85 (m, 0.62H), 4.94 (dd, J=13.1, 5.2 Hz, 0.41H), 4.75 (q, J=6.8 Hz, 0.14H), 4.63 (q, J=6.7 Hz, 0.26H), 4.08-4.02 (m, 3H), 3.85-3.76 (m, 3H), 3.54-3.44 (m, 0.63H), 3.43-3.33 (m, 0.39H), 3.31-3.22 (m, 0.23H), 3.11 (td, J=12.7, 4.1 Hz, 0.12H), 3.03 (td, J=12.7, 3.8 Hz, 0.24H), 2.87-2.74 (m, 0.61H), 2.57-2.45 (m, 0.77H), 2.37-2.28 (m, 0.62H), 1.65-1.39 (m, 3H).

Example 317: (3-Chloro-4-methoxy-2-pyridyl)-[(7S)-2,7-dimethyl-3-(3,4,5-trifluorophenyl)-5,7-dihydro-4H-pyrazolo[3,4-c]pyridin-6-yl]methanone

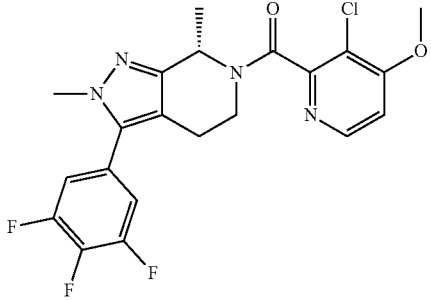 [SMILES: COc1ccnc(C(=O)N2CCc3c(nn(C)c3-c3cc(F)c(F)c(F)c3)[C@@H]2C)c1Cl]

The title compound was prepared in a manner analogous to Example 288, using 3-chloro-4-methoxypicolinic acid instead of 2-fluoro-6-(2H-1,2,3-triazol-2-yl)benzoic acid and DMF instead of DCM. MS (ESI): mass calcd. for $C_{21}H_{18}ClF_3N_4O_2$, 450.1; m/z found, 451.1 [M+H]$^+$. $^1$H NMR (500 MHz, Chloroform-d) δ 8.43-8.39 (m, 1H), 7.01-6.91 (m, 2H), 6.90-6.86 (m, 1H), 5.91 (q, J=6.8 Hz, 0.58H), 5.00-4.94 (m, 0.44H), 4.67 (q, J=6.7 Hz, 0.43H), 4.01-3.97 (m, 3H), 3.83 (s, 1.79H), 3.76 (s, 1.27H), 3.45-3.39 (m, 0.59H), 3.35-3.27 (m, 0.59H), 3.08 (td, J=12.7, 3.9 Hz, 0.42H), 2.88-2.72 (m, 1H), 2.52-2.46 (m, 0.42H), 2.31-2.23 (m, 0.59H), 1.64 (d, J=6.8 Hz, 1.79H), 1.49 (d, J=6.8 Hz, 1.32H).

Example 318: [(7S)-2,7-Dimethyl-3-(3,4,5-trifluorophenyl)-5,7-dihydro-4H-pyrazolo[3,4-c]pyridin-6-yl]-(5-pyrazol-1-yl-3-pyridyl)methanone

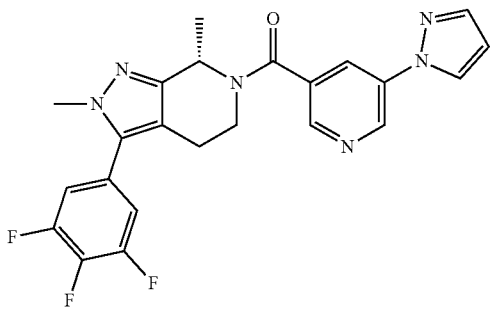 [SMILES: C[C@H]1c2nn(C)c(-c3cc(F)c(F)c(F)c3)c2CCN1C(=O)c1cncc(-n2cccn2)c1]

The title compound was prepared in a manner analogous to Example 296, using 5-(1H-pyrazol-1-yl)nicotinic acid (Intermediate 119) instead of 3-(1,2,4-triazol-4-yl)-5-(trifluoromethyl)benzoic acid. MS (ESI): mass calcd. for $C_{23}H_{19}F_3N_6O$, 452.2; m/z found, 453.2 [M+H]$^+$. $^1$H NMR (500 MHz, DMSO-d$_6$) δ 9.25 (d, J=2.5 Hz, 1H), 8.72 (d, J=2.6 Hz, 1H), 8.61-8.54 (m, 1H), 8.36-8.25 (m, 1H), 7.87 (d, J=1.8 Hz, 1H), 7.62-7.51 (m, 2H), 6.68-6.62 (m, 1H), 5.68-5.55 (m, 1H), 3.84 (s, 3H), 3.71-3.62 (m, 1H), 3.41-3.26 (m, 1H), 2.95-2.83 (m, 1H), 2.42-2.30 (m, 1H), 1.52 (d, J=6.9 Hz, 3H).

Example 319: [(7S)-2,7-Dimethyl-3-(3,4,5-trifluorophenyl)-5,7-dihydro-4H-pyrazolo[3,4-c]pyridin-6-yl]-[6-methyl-3-(triazol-2-yl)-2-pyridyl]methanone

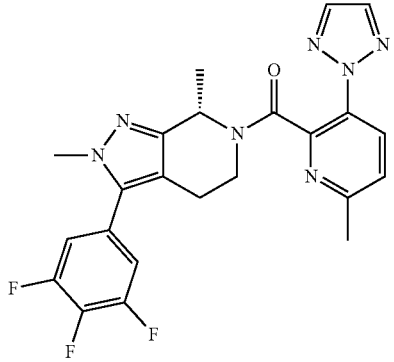 [SMILES: Cc1ccc(-n2nccn2)c(C(=O)N2CCc3c(nn(C)c3-c3cc(F)c(F)c(F)c3)[C@@H]2C)n1]

The title compound was prepared in a manner analogous to Example 296, using 6-methyl-3-(2H-1,2,3-triazol-2-yl)picolinic acid [prepared according to methods described in Pat. Pub. No. WO2016040789] instead of 3-(1,2,4-triazol-4-yl)-5-(trifluoromethyl)benzoic acid. MS (ESI): mass calcd. for $C_{23}H_{20}F_3N_7O$, 467.2; m/z found, 468.2 [M+H]$^+$. $^1$H NMR (500 MHz, DMSO-d$_6$) δ 8.26 (d, J=8.4 Hz, 1H), 8.11 (s, 2H), 7.60-7.48 (m, 3H), 5.47 (q, J=6.7 Hz, 1H), 3.82 (s, 3H), 3.52-3.46 (m, 1H), 3.26-3.18 (m, 1H), 2.70-2.61 (m, 1H), 2.58 (s, 3H), 2.33-2.27 (m, 1H), 1.47 (d, J=6.7 Hz, 3H).

Example 320: [(7S)-2,7-Dimethyl-3-(3,4,5-trifluorophenyl)-5,7-dihydro-4H-pyrazolo[3,4-c]pyridin-6-yl]-(6-pyrazol-1-yl-2-pyridyl)methanone

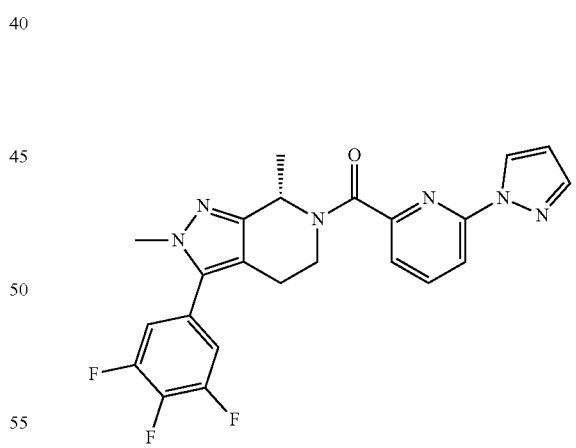

The title compound was prepared in a manner analogous to Example 296, using 6-(1H-pyrazol-1-yl)picolinic acid instead of 3-(1,2,4-triazol-4-yl)-5-(trifluoromethyl)benzoic acid. MS (ESI): mass calcd. for $C_{23}H_{19}F_3N_6O$, 452.2; m/z found, 453.2 [M+H]$^+$. $^1$H NMR (500 MHz, DMSO-d$_6$) δ 8.65 (d, J=2.6 Hz, 1H), 8.17-8.09 (m, 1H), 8.07-8.01 (m, 1H), 7.86 (d, J=1.5 Hz, 1H), 7.62-7.48 (m, 3H), 6.62-6.58 (m, 1H), 5.58 (q, J=6.7 Hz, 1H), 3.82 (s, 3H), 3.81-3.78 (m, 1H), 3.30-3.22 (m, 1H), 2.97-2.88 (m, 1H), 2.39-2.32 (m, 1H), 1.50 (d, J=6.8 Hz, 3H).

Example 321: [(7S)-2,7-Dimethyl-3-(3,4,5-trifluorophenyl)-5,7-dihydro-4H-pyrazolo[3,4-c]pyridin-6-yl]-(5-methyl-1-phenyl-1,2,4-triazol-3-yl)methanone

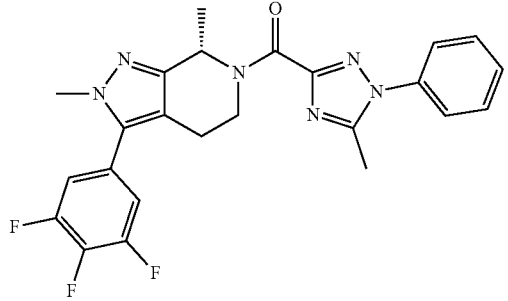 [SMILES: Cc1nc(C(=O)N2CCc3c(nn(C)c3-c3cc(F)c(F)c(F)c3)[C@@H]2C)nn1-c1ccccc1]

The title compound was prepared in a manner analogous to Example 288, using 5-methyl-1-phenyl-1H-1,2,4-triazole-3-carboxylic acid instead of 2-fluoro-6-(2H-1,2,3-triazol-2-yl)benzoic acid. MS (ESI): mass calcd. for $C_{24}H_{21}F_3N_6O$, 466.2; m/z found, 467.2 $[M+H]^+$. $^1H$ NMR (500 MHz, DMSO-$d_6$) δ 7.68-7.50 (m, 7H), 5.58 (q, J=6.7 Hz, 0.58H), 5.28 (q, J=6.7 Hz, 0.38H), 4.66 (dd, J=13.0, 5.2 Hz, 0.38H), 4.23 (dd, J=13.6, 5.0 Hz, 0.57H), 3.83-3.73 (m, 3H), 3.12-3.03 (m, 0.39H), 2.85-2.69 (m, 1H), 2.53-2.51 (m, 3H), 1.55-1.44 (m, 3H). (Fractions of H's that may overlap with DMSO and water are not reported)

Example 322: [(7S)-2,7-Dimethyl-3-(3,4,5-trifluorophenyl)-5,7-dihydro-4H-pyrazolo[3,4-c]pyridin-6-yl]-[1-(4-fluorophenyl)-5-methyl-1,2,4-triazol-3-yl]methanone

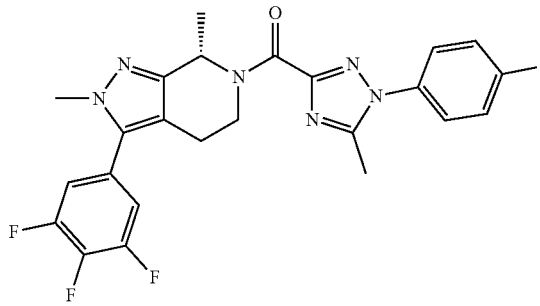

The title compound was prepared in a manner analogous to Example 288, using 1-(4-fluorophenyl)-5-methyl-1H-1,2,4-triazole-3-carboxylic acid instead of 2-fluoro-6-(2H-1,2,3-triazol-2-yl)benzoic acid. MS (ESI): mass calcd. for $C_{24}H_{20}F_4N_6O$, 484.2; m/z found, 485.1 $[M+H]^+$. $^1H$ NMR (500 MHz, DMSO-$d_6$) δ 7.74-7.68 (m, 2H), 7.59-7.51 (m, 2H), 7.48-7.41 (m, 2H), 5.58 (q, J=6.7 Hz, 0.59H), 5.27 (q, J=6.7 Hz, 0.39H), 4.65 (dd, J=13.0, 5.2 Hz, 0.38H), 4.22 (dd, J=13.7, 5.0 Hz, 0.57H), 3.84-3.73 (m, 3H), 3.11-3.03 (m, 0.40H), 2.84-2.69 (m, 1H), 1.55-1.43 (m, 3H). (Fractions of H's that may overlap with DMSO and water are not reported)

Example 323: [(7S)-2,7-Dimethyl-3-(3,4,5-trifluorophenyl)-5,7-dihydro-4H-pyrazolo[3,4-c]pyridin-6-yl]-[1-(2-pyridyl)-1,2,4-triazol-3-yl]methanone

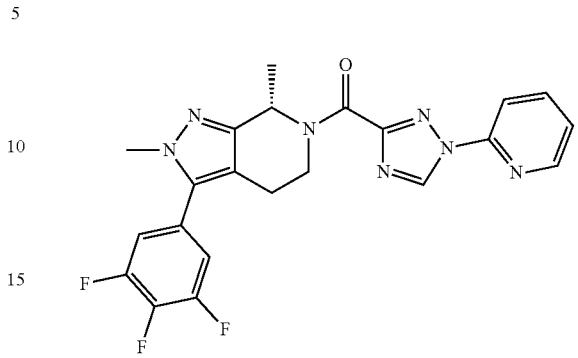

The title compound was prepared in a manner analogous to Example 288, using 1-(pyridin-2-yl)-1H-1,2,4-triazole-3-carboxylic acid instead of 2-fluoro-6-(2H-1,2,3-triazol-2-yl)benzoic acid. MS (ESI): mass calcd. for $C_{22}H_{18}F_3N_7O$, 453.2; m/z found, 454.1 $[M+H]^+$. $^1H$ NMR (500 MHz, DMSO-$d_6$) δ 9.52-9.49 (m, 1H), 8.61-8.57 (m, 1H), 8.14-8.09 (m, 1H), 7.94-7.88 (m, 1H), 7.60-7.51 (m, 3H), 5.60 (q, J=6.8 Hz, 0.63H), 5.19 (q, J=6.6 Hz, 0.38H), 4.68 (dd, J=13.0, 5.2 Hz, 0.41H), 4.12 (dd, J=13.8, 4.9 Hz, 0.58H), 3.85-3.73 (m, 3H), 3.12 (td, J=12.7, 4.0 Hz, 0.42H), 2.91-2.74 (m, 1H), 1.59-1.47 (m, 3H). (Fractions of H's that may overlap with DMSO and water are not reported)

Example 324: [(7S)-2,7-Dimethyl-3-(3,4,5-trifluorophenyl)-5,7-dihydro-4H-pyrazolo[3,4-c]pyridin-6-yl]-[1-(3-fluoro-2-pyridyl)-1,2,4-triazol-3-yl]methanone

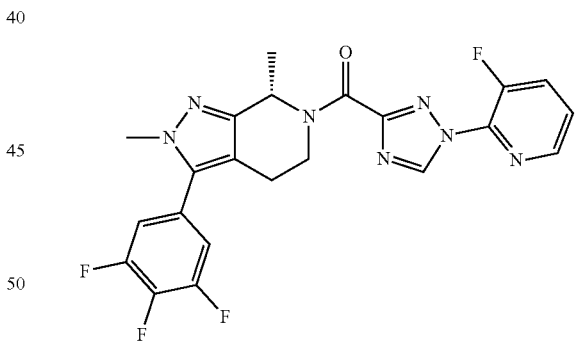

The title compound was prepared in a manner analogous to Example 288, using 1-(3-fluoropyridin-2-yl)-1H-1,2,4-triazole-3-carboxylic acid instead of 2-fluoro-6-(2H-1,2,3-triazol-2-yl)benzoic acid. MS (ESI): mass calcd. for $C_{22}H_{17}F_4N_7O$, 471.1; m/z found, 472.2 $[M+H]^+$. $^1H$ NMR (500 MHz, Chloroform-d) δ 9.01-8.97 (m, 1H), 8.41-8.36 (m, 1H), 7.75-7.69 (m, 1H), 7.47-7.42 (m, 1H), 7.02-6.92 (m, 2H), 5.89 (q, J=6.8 Hz, 0.52H), 5.52 (q, J=6.7 Hz, 0.46H), 4.93 (dd, J=13.1, 5.2 Hz, 0.48H), 4.39 (dd, J=13.8, 4.9 Hz, 0.54H), 3.84 (s, 1.58H), 3.77 (s, 1.36H), 3.40-3.32 (m, 0.52H), 3.18-3.10 (m, 0.46H), 3.02-2.93 (m, 0.53H), 2.89-2.80 (m, 0.45H), 2.50-2.39 (m, 1H), 1.72 (d, J=6.7 Hz, 1.40H), 1.63 (d, J=6.8 Hz, 1.62H).

Example 325: [(7S)-2,7-Dimethyl-3-(3,4,5-trifluorophenyl)-5,7-dihydro-4H-pyrazolo[3,4-c]pyridin-6-yl]-[5-(2-pyridyl)-2-thienyl]methanone

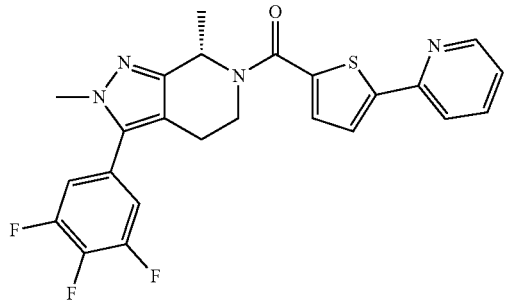 [SMILES: C[C@H]1c2nn(C)c(-c3cc(F)c(F)c(F)c3)c2CCN1C(=O)c1ccc(-c2ccccn2)s1]

The title compound was prepared in a manner analogous to Example 288, using 5-(pyridin-2-yl)thiophene-2-carboxylic acid instead of 2-fluoro-6-(2H-1,2,3-triazol-2-yl)benzoic acid and DMF instead of DCM. MS (ESI): mass calcd. for $C_{24}H_{19}F_3N_4OS$, 468.1; m/z found, 469.1 [M+H]$^+$. $^1$H NMR (500 MHz, DMSO-d$_6$) δ 8.59-8.54 (m, 1H), 8.03-7.99 (m, 1H), 7.88 (td, J=7.7, 1.8 Hz, 1H), 7.81 (d, J=3.9 Hz, 1H), 7.62-7.53 (m, 2H), 7.50 (d, J=3.9 Hz, 1H), 7.34 (ddd, J=7.5, 4.8, 1.1 Hz, 1H), 5.42 (br s, 1H), 4.30 (br s, 1H), 3.80 (s, 3H), 3.03-2.84 (m, 1H), 1.62-1.40 (m, 3H). (Fractions of Hs that may overlap with DMSO and water are not reported).

Example 326: [(7S)-2,7-Dimethyl-3-(3,4,5-trifluorophenyl)-5,7-dihydro-4H-pyrazolo[3,4-c]pyridin-6-yl]-(5-methoxypyrazin-2-yl)methanone

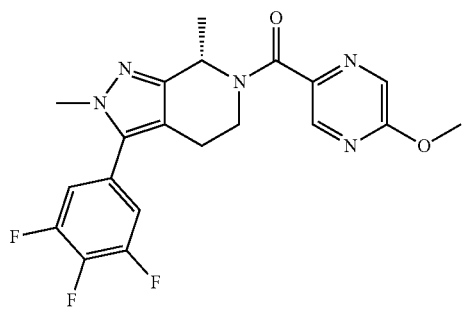 [SMILES: COc1cnc(C(=O)N2CCc3c(nn(C)c3-c3cc(F)c(F)c(F)c3)[C@@H]2C)cn1]

The title compound was prepared in a manner analogous to Example 288, using 5-methoxypyrazine-2-carboxylic acid instead of 2-fluoro-6-(2H-1,2,3-triazol-2-yl)benzoic acid. MS (ESI): mass calcd. for $C_{20}H_{18}F_3N_5O_2$, 417.1; m/z found, 418.0 [M+H]$^+$. $^1$H NMR (400 MHz, Methanol-d$_4$) δ 8.50 (d, J=1.4 Hz, 1H), 8.27-8.20 (m, 1H), 7.36-7.21 (m, 2H), 5.69 (q, J=6.7 Hz, 0.65H), 5.40-5.15 (m, 0.35H), 4.80-4.67 (m, 0.35H), 4.19-4.07 (m, 0.65H), 4.04 (s, 3H), 3.83 (s, 2H), 3.77 (s, 1H), 3.43-3.32 (m, 0.65H), 3.28-3.15 (m, 0.35H), 3.04-2.86 (m, 0.65H), 2.89-2.74 (m, 0.35H), 2.62-2.50 (m, 0.35H), 2.50-2.38 (m, 0.65H), 1.70-1.61 (m, 1H), 1.58 (d, J=6.7 Hz, 2H).

Example 327: (1,5-Dimethylpyrazol-4-yl)-[(7S)-3-(3-fluoro-5-methyl-phenyl)-2,7-dimethyl-5,7-dihydro-4H-pyrazolo[3,4-c]pyridin-6-yl]methanone

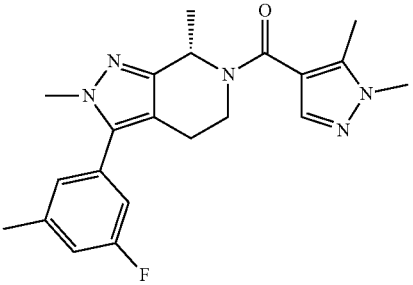

The title compound was prepared in a manner analogous to Example 288, using (S)-3-(3-fluoro-5-methylphenyl)-2,7-dimethyl-4,5,6,7-tetrahydro-2H-pyrazolo[3,4-c]pyridine (Intermediate 42) instead of (S)-2,7-dimethyl-3-(3,4,5-trifluorophenyl)-4,5,6,7-tetrahydro-2H-pyrazolo[3,4-c]pyridine (Intermediate 40) and 1,5-dimethyl-1H-pyrazole-4-carboxylic acid instead of 2-fluoro-6-(2H-1,2,3-triazol-2-yl)benzoic acid. MS (ESI): mass calcd. for $C_{21}H_{24}FN_5O$, 381.2; m/z found, 382.2 [M+H]$^+$. $^1$H NMR (400 MHz, DMSO-d$_6$) δ 7.54 (s, 1H), 7.22-7.06 (m, 3H), 5.38 (s, 1H), 4.33-3.92 (m, 1H), 3.76 (d, J=10.1 Hz, 6H), 3.26-3.13 (m, 1H), 2.80 (t, J=12.8 Hz, 1H), 2.43-2.33 (m, 4H), 2.30 (s, 3H), 1.44 (d, J=6.7 Hz, 3H).

Example 328: [(7S)-2,7-Dimethyl-3-(3,4,5-trifluorophenyl)-5,7-dihydro-4H-pyrazolo[3,4-c]pyridin-6-yl]-(5-isopropyl-1-methyl-pyrazol-4-yl)methanone

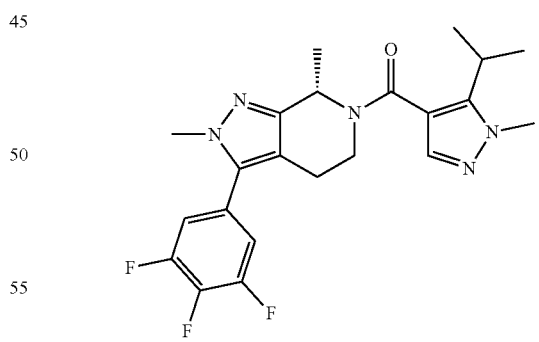

The title compound was prepared in a manner analogous to Example 288, using 5-isopropyl-1-methyl-1H-pyrazole-4-carboxylic acid instead of 2-fluoro-6-(2H-1,2,3-triazol-2-yl)benzoic acid. MS (ESI): mass calcd. for $C_{22}H_{24}F_3N_5O$, 431.2; m/z found, 432.1 [M+H]$^+$. $^1$H NMR (500 MHz, DMSO-d$_6$) δ 7.63-7.49 (m, 2H), 7.42 (s, 1H), 5.51 (s, 1H), 5.07-4.32 (m, 1H), 3.84-3.74 (m, 6H), 3.27-2.98 (m, 2H), 2.79 (s, 1H), 2.36 (d, J=15.7 Hz, 1H), 1.41 (d, J=6.7 Hz, 3H), 1.22 (dd, J=26.6, 5.8 Hz, 6H).

Example 329: [(7S)-2,7-Dimethyl-3-(3,4,5-trifluorophenyl)-5,7-dihydro-4H-pyrazolo[3,4-c]pyridin-6-yl]-[1-(trifluoromethyl)pyrazol-4-yl]methanone

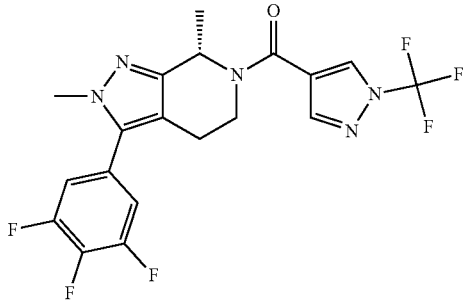 [SMILES: C[C@H]1c2nn(C)c(-c3cc(F)c(F)c(F)c3)c2CCN1C(=O)c1cnn(C(F)(F)F)c1]

The title compound was prepared in a manner analogous to Example 288, using 1-(trifluoromethyl)-1H-pyrazole-4-carboxylic acid instead of 2-fluoro-6-(2H-1,2,3-triazol-2-yl)benzoic acid. MS (ESI): mass calcd. for $C_{19}H_{15}F_6N_5O$, 443.1; m/z found, 444.2 [M+H]$^+$. $^1$H NMR (500 MHz, Chloroform-d) δ 8.15-8.12 (m, 1H), 7.94 (s, 1H), 7.00-6.92 (m, 2H), 5.93-5.05 (m, 1H), 4.95-4.00 (m, 1H), 3.81 (s, 3H), 3.53-2.99 (m, 1H), 2.86-2.68 (m, 1H), 2.58-2.38 (m, 1H), 1.62 (s, 3H).

Example 330: [5-(Difluoromethyl)-1-methyl-pyrazol-4-yl]-[(7S)-2,7-dimethyl-3-(3,4,5-trifluorophenyl)-5,7-dihydro-4H-pyrazolo[3,4-c]pyridin-6-yl]methanone

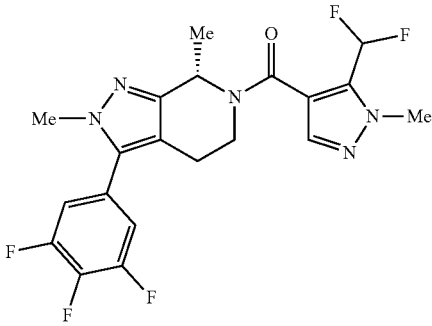 [SMILES: C[C@H]1c2nn(C)c(-c3cc(F)c(F)c(F)c3)c2CCN1C(=O)c1cnn(C)c1C(F)F]

The title compound was prepared in a manner analogous to Example 288, using 5-(difluoromethyl)-1-methyl-1H-pyrazole-4-carboxylic acid instead of 2-fluoro-6-(2H-1,2,3-triazol-2-yl)benzoic acid. MS (ESI): mass calcd. for $C_{20}H_{18}F_5N_5O$, 439.1; m/z found, 440.1 [M+H]$^+$. $^1$H NMR (400 MHz, Chloroform-d) δ 7.56 (brs, 1H), 7.29-6.93 (m, 3H), 5.87-5.25 (m, 1H), 5.01-4.00 (m, 4H), 3.80 (s, 3H), 3.55-3.00 (m, 1H), 2.84-2.67 (m, 1H), 2.54-2.40 (m, 1H), 1.59 (s, 3H).

Example 331: (1-Cyclopropylpyrazol-4-yl)-[(7S)-2,7-dimethyl-3-(3,4,5-trifluorophenyl)-5,7-dihydro-4H-pyrazolo[3,4-c]pyridin-6-yl]methanone

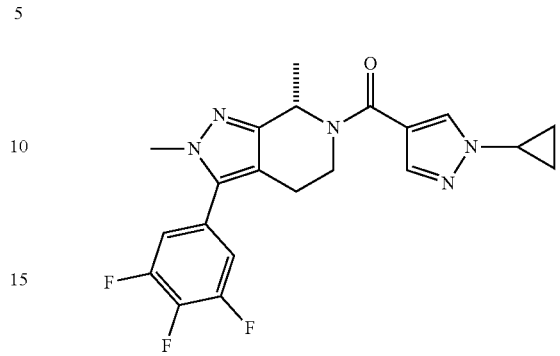

The title compound was prepared in a manner analogous to Example 288, using 1-cyclopropyl-1H-pyrazole-4-carboxylic acid instead of 2-fluoro-6-(2H-1,2,3-triazol-2-yl)benzoic acid. MS (ESI): mass calcd. for $C_{21}H_{20}F_3N_5O$, 415.2; m/z found, 416.1 [M+H]$^+$. $^1$H NMR (500 MHz, Chloroform-d) δ 7.81 (s, 1H), 7.66 (s, 1H), 7.01-6.91 (m, 2H), 5.54 (brs, 1H), 4.89-4.14 (m, 1H), 3.80 (s, 3H), 3.67-3.57 (m, 1H), 3.18 (brs, 1H), 2.83-2.68 (m, 1H), 2.54-2.38 (m, 1H), 1.61 (s, 3H), 1.19-1.00 (m, 4H).

Example 332: [1-Cyclopropyl-3-(trifluoromethyl)pyrazol-4-yl]-[(7S)-2,7-dimethyl-3-(3,4,5-trifluorophenyl)-5,7-dihydro-4H-pyrazolo[3,4-c]pyridin-6-yl]methanone

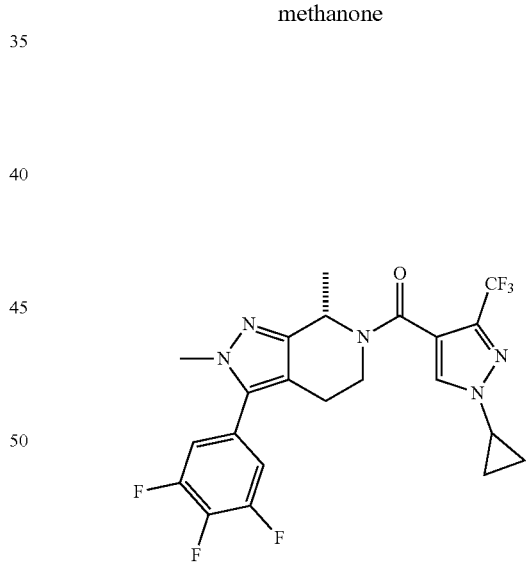

The title compound was prepared in a manner analogous to Example 288, using potassium 1-cyclopropyl-3-(trifluoromethyl)-1H-pyrazole-4-carboxylate (Intermediate 82) instead of 2-fluoro-6-(2H-1,2,3-triazol-2-yl)benzoic acid and DMF instead of DCM. MS (ESI): mass calcd. for $C_{22}H_{19}F_6N_5O$, 483.1; m/z found, 484.1 [M+H]$^+$. $^1$H NMR (500 MHz, Chloroform-d) δ 7.59 (s, 1H), 6.96 (t, J=6.9 Hz, 2H), 5.85 (brs, 0.51H), 4.92 (brs, 0.70H), 3.81 (s, 3H), 3.72-3.61 (m, 1H), 3.38-2.96 (m, 1H), 2.82-2.50 (m, 2.21H), 2.39 (brs, 1H), 1.78 (brs, 1H), 1.34-1.17 (m, 1.93H), 1.14-1.01 (m, 3.84H).

Example 333: (5-Cyclobutyl-1-methyl-pyrazol-4-yl)-[(7S)-2,7-dimethyl-3-(3,4,5-trifluorophenyl)-5,7-dihydro-4H-pyrazolo[3,4-c]pyridin-6-yl]methanone

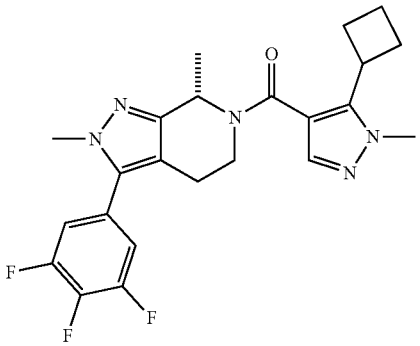 [SMILES: C[C@H]1c2nn(C)c(-c3cc(F)c(F)c(F)c3)c2CCN1C(=O)c1cnn(C)c1C1CCC1]

The title compound was prepared in a manner analogous to Example 288, using potassium 5-cyclobutyl-1-methyl-1H-pyrazole-4-carboxylate (Intermediate 80) instead of 2-fluoro-6-(2H-1,2,3-triazol-2-yl)benzoic acid and DMF instead of DCM. MS (ESI): mass calcd. for $C_{23}H_{24}F_3N_5O$, 443.2; m/z found, 444.1 [M+H]$^+$. $^1$H NMR (500 MHz, Chloroform-d) δ 7.36 (s, 1H), 7.00-6.92 (m, 2H), 5.81 (brs, 0.53H), 5.26-4.74 (m, 0.74H), 4.04 (brs, 0.56H), 3.86-3.73 (m, 6.27H), 3.72-3.56 (m, 1H), 3.40-2.88 (m, 1H), 2.68 (brs, 1H), 2.52-2.13 (m, 5H), 2.13-1.71 (m, 2H), 1.53 (s, 3H).

Example 334: [(7S)-2,7-Dimethyl-3-(3,4,5-trifluorophenyl)-5,7-dihydro-4H-pyrazolo[3,4-c]pyridin-6-yl]-[1-methyl-5-(1-methylcyclopropyl)pyrazol-4-yl]methanone

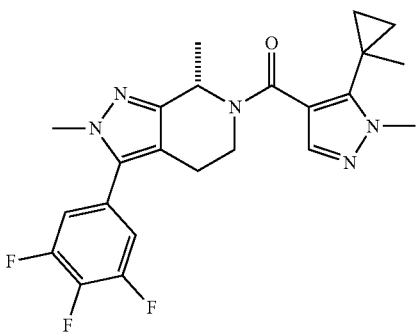 [SMILES: C[C@H]1c2nn(C)c(-c3cc(F)c(F)c(F)c3)c2CCN1C(=O)c1cnn(C)c1C1(C)CC1]

The title compound was prepared in a manner analogous to Example 288, using 1-methyl-5-(1-methylcyclopropyl)-1H-pyrazole-4-carboxylic acid (Intermediate 71) instead of 2-fluoro-6-(2H-1,2,3-triazol-2-yl)benzoic acid, stirring at 40° C. overnight. MS (ESI): mass calcd. for $C_{23}H_{24}F_3N_5O$, 443.2; m/z found, 444.3 [M+H]$^+$. $^1$H NMR (500 MHz, Chloroform-d) δ 7.39 (s, 1H), 7.00-6.92 (m, 2H), 6.09-4.55 (m, 1.48H), 4.23-3.72 (m, 7.90H), 3.17 (brs, 1.10H), 2.69 (brs, 1.09H), 2.41 (d, J=14.7 Hz, 1.14H), 1.57 (d, J=9.7 Hz, 4.93H), 1.40 (s, 3.28H).

Example 335: [(7S)-2,7-Dimethyl-3-(3,4,5-trifluorophenyl)-5,7-dihydro-4H-pyrazolo[3,4-c]pyridin-6-yl]-[5-(1-fluorocyclopropyl)-1-methyl-pyrazol-4-yl]methanone

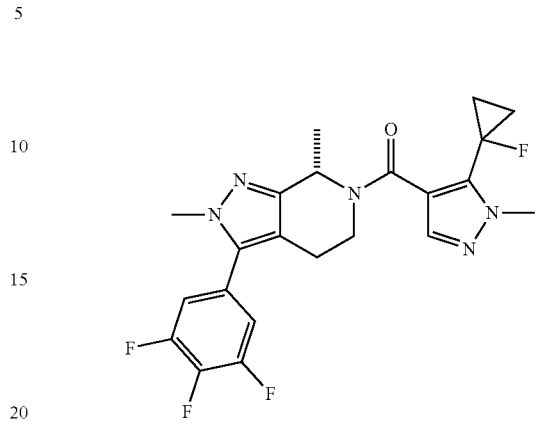

The title compound was prepared in a manner analogous to Example 288, using potassium 5-(1-fluorocyclopropyl)-1-methyl-1H-pyrazole-4-carboxylate (Intermediate 73) instead of 2-fluoro-6-(2H-1,2,3-triazol-2-yl)benzoic acid and DMF instead of DCM. MS (ESI): mass calcd. for $C_{22}H_{21}F_4N_5O$, 447.2; m/z found, 448.2 [M+H]$^+$. $^1$H NMR (500 MHz, Chloroform-d) δ 7.49 (s, 1H), 6.96 (t, J=6.9 Hz, 2H), 5.88 (s, 0.62H), 5.21-4.79 (m, 0.68H), 4.10-3.98 (m, 3.64H), 3.82 (s, 3H), 3.38-2.97 (m, 1H), 2.84-2.56 (m, 1H), 2.53-2.29 (m, 1H), 1.61-1.32 (m, 5H), 1.23-0.99 (m, 2H).

Example 336: (5-(2,2-Difluorocyclopropyl)-1-methyl-1H-pyrazol-4-yl)((S)-2,7-dimethyl-3-(3,4,5-trifluorophenyl)-4,5-dihydro-2H-pyrazolo[3,4-c]pyridin-6-yl)methanone

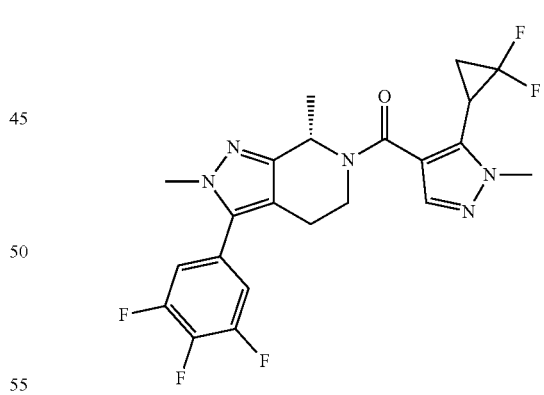

The title compound was prepared in a manner analogous to Example 288, using 5-(2,2-difluorocyclopropyl)-1-methyl-1H-pyrazole-4-carboxylic acid (Intermediate 75) instead of 2-fluoro-6-(2H-1,2,3-triazol-2-yl)benzoic acid. MS (ESI): mass calcd. for $C_{22}H_{20}F_5N_5O$, 465.2; m/z found, 466.2 [M+H]$^+$. $^1$H NMR (500 MHz, Chloroform-d) δ 7.49 (s, 1H), 7.00-6.93 (m, 2H), 5.76 (brs, 0.56H), 5.25-4.56 (m, 0.82H), 3.86 (d, J=52.3 Hz, 6.89H), 3.42-2.97 (m, 1H), 2.81-2.56 (m, 2.19H), 2.43 (m, 1H), 2.01 (brs, 1H), 1.58-1.54 (m, 3H), 1.14-1.06 (m, 0.69H).

Example 337: (5-((R*)-2,2-difluorocyclopropyl)-1-methyl-1H-pyrazol-4-yl)((S)-2,7-dimethyl-3-(3,4,5-trifluorophenyl)-2,4,5,7-tetrahydro-6H-pyrazolo[3,4-c]pyridin-6-yl)methanone

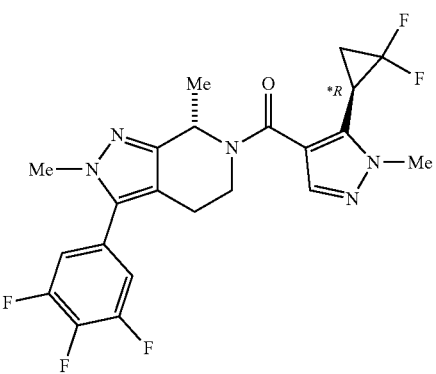 [SMILES: C[C@H]1c2nn(C)c(-c3cc(F)c(F)c(F)c3)c2CCN1C(=O)c1cnn(C)c1[C@H]1CC1(F)F]

The title compound was obtained as a single enantiomer by chiral SFC purification of racemic (5-(2,2-Difluorocyclopropyl)-1-methyl-1H-pyrazol-4-yl)((S)-2,7-dimethyl-3-(3,4,5-trifluorophenyl)-4,5-dihydro-2H-pyrazolo[3,4-c]pyridin-6-yl)methanone (Example 336) (stationary phase: Chiralcel OZ, 5 μm 250×21 mm; mobile phase: 40% MeOH with 0.2% TEA, 60% $CO_2$; flow rate: 42 mL/min). MS (ESI): mass calcd. for $C_{22}H_{20}F_5N_5O$, 465.2; m/z found, 466.2 $[M+H]^+$. $^1H$ NMR (500 MHz, Chloroform-d) δ 7.49 (s, 1H), 7.00-6.93 (m, 2H), 5.76 (brs, 0.56H), 5.25-4.56 (m, 0.82H), 3.86 (d, J=52.3 Hz, 6.89H), 3.42-2.97 (m, 1H), 2.81-2.56 (m, 2.19H), 2.43 (m, 1H), 2.01 (brs, 1H), 1.58-1.54 (m, 3H), 1.14-1.06 (m, 0.69H). (R*; absolute stereochemistry on cyclopropane was not determined).

Example 338: (5-((S*)-2,2-Difluorocyclopropyl)-1-methyl-1H-pyrazol-4-yl)((S)-2,7-dimethyl-3-(3,4,5-trifluorophenyl)-2,4,5,7-tetrahydro-6H-pyrazolo[3,4-c]pyridin-6-yl)methanone

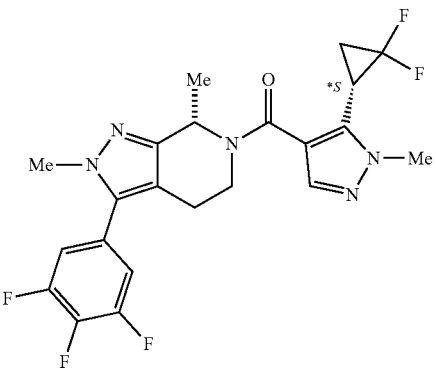 [SMILES: C[C@H]1c2nn(C)c(-c3cc(F)c(F)c(F)c3)c2CCN1C(=O)c1cnn(C)c1[C@@H]1CC1(F)F]

The title compound was obtained as a single enantiomer by chiral SFC purification of racemic (5-(2,2-Difluorocyclopropyl)-1-methyl-1H-pyrazol-4-yl)((S)-2,7-dimethyl-3-(3,4,5-trifluorophenyl)-4,5-dihydro-2H-pyrazolo[3,4-c]pyridin-6-yl)methanone (Example 336) (stationary phase: Chiralcel OZ, 5 μm 250×21 mm; mobile phase: 40% MeOH with 0.2% TEA, 60% $CO_2$; flow rate: 42 mL/min). MS (ESI): mass calcd. for $C_{22}H_{20}F_5N_5O$, 465.2; m/z found, 466.2 $[M+H]^+$. $^1H$ NMR (500 MHz, Chloroform-d) δ 7.48 (s, 1H), 7.01-6.93 (m, 2H), 5.80 (brs, 0.56H), 5.36-4.64 (m, 0.91H), 4.09 (brs, 0.63H), 3.90 (s, 3H), 3.81 (s, 3H), 3.39-2.97 (m, 1H), 2.81-2.54 (m, 2.78H), 2.47-2.33 (m, 1H), 1.93 (brs, 1H), 1.73-1.46 (m, 2.20H), 1.08 (t, J=7.2 Hz, 1H). (S*; absolute stereochemistry on cyclopropane was not determined).

Example 339: ((S)-2,7-Dimethyl-3-(3,4,5-trifluorophenyl)-2,4,5,7-tetrahydro-6H-pyrazolo[3,4-c]pyridin-6-yl)(cis-5-(2-fluorocyclopropyl)-1-methyl-1H-pyrazol-4-yl)methanone

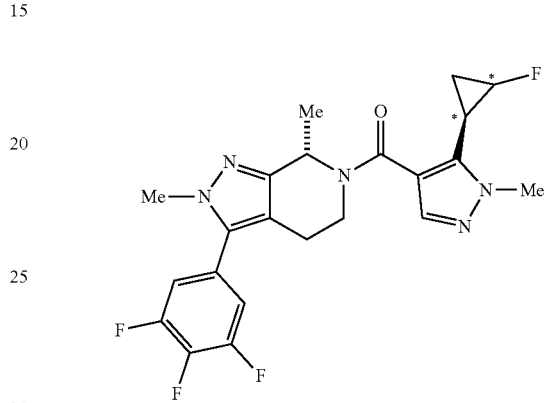

The title compound was prepared in a manner analogous to Example 288, using potassium cis-5-(2-fluorocyclopropyl)-1-methyl-1H-pyrazole-4-carboxylate (Intermediate 77) instead of 2-fluoro-6-(2H-1,2,3-triazol-2-yl)benzoic acid and DMF instead of DCM. MS (ESI): mass calcd. for $C_{22}H_{21}F_4N_5O$, 447.2; m/z found, 448.2 $[M+H]^+$. $^1H$ NMR (600 MHz, Chloroform-d) δ 7.46 (s, 1H), 7.02-6.90 (m, 2H), 5.81 (brs, 0.68H), 5.18 (brs, 0.33H), 5.00-4.72 (m, 1.48H), 4.04 (brs, 0.49H), 3.92 (s, 3H), 3.81 (s, 3H), 3.33-2.96 (m, 1H), 2.69 (brs, 1H), 2.40 (d, J=15.1 Hz, 1H), 1.98 (brs, 1H), 1.55 (s, 1.47H), 1.44-1.04 (m, 3.62H). (Mixture of isomers with relative cis-configuration at starred stereocenters).

Example 340: ((S)-2,7-Dimethyl-3-(3,4,5-trifluorophenyl)-2,4,5,7-tetrahydro-6H-pyrazolo[3,4-c]pyridin-6-yl)(trans-5-(2-fluorocyclopropyl)-1-methyl-1H-pyrazol-4-yl)methanone

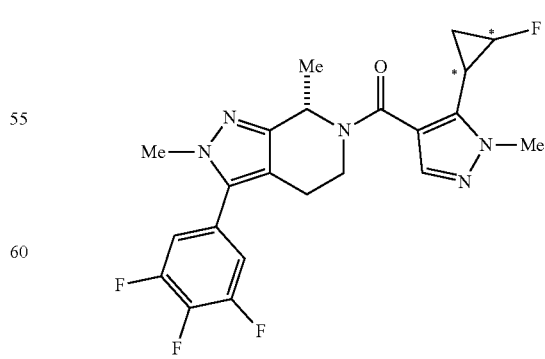

Method A: The title compound was prepared in a manner analogous to Example 288, using potassium trans-5-(2- fluorocyclopropyl)-1-methyl-1H-pyrazole-4-carboxylate (Intermediate 78) instead of 2-fluoro-6-(2H-1,2,3-triazol-2-yl)benzoic acid and DMF instead of DCM. MS (ESI): mass calcd. for C₂₂H₂₁F₄N₅O, 447.2; m/z found, 448.2 [M+H]⁺. ¹H NMR (500 MHz, Chloroform-d) δ 7.42 (d, J=3.3 Hz, 1H), 7.00-6.93 (m, 2H), 5.81 (brs, 0.53H), 5.20-4.64 (m, 1.84H), 4.17-3.86 (m, 3.45H), 3.81 (s, 3H), 3.42-2.96 (m, 1H), 2.69 (brs, 1H), 2.42 (d, J=15.1 Hz, 1H), 2.32-2.16 (m, 1H), 1.54 (s, 3.62H), 1.13 (m, 1.38H). (Mixture of isomers with relative trans-configuration at starred stereocenters).

Method B: The title compound was prepared in a manner analogous to Example 288, using trans-5-(2-fluorocyclopropyl)-1-methyl-1H-pyrazole-4-carboxylic acid (Intermediate 79) instead of 2-fluoro-6-(2H-1,2,3-triazol-2-yl)benzoic acid, stirring at 36° C. overnight.

Example 341: ((S)-2,7-Dimethyl-3-(3,4,5-trifluorophenyl)-2,4,5,7-tetrahydro-6H-pyrazolo[3,4-c]pyridin-6-yl)(1-methyl-cis-5-(2-methylcyclopropyl)-1H-pyrazol-4-yl)methanone

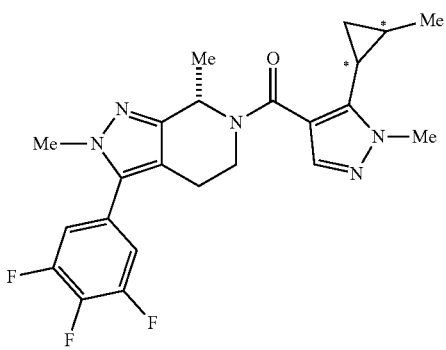 [SMILES: CC1CC1c1c(C(=O)N2CCc3c(nn(C)c3-c3cc(F)c(F)c(F)c3)[C@@H]2C)cnn1C]

Method A: The title compound was prepared in a manner analogous to Example 288, using potassium trans-5-(2-fluorocyclopropyl)-1-methyl-1H-pyrazole-4-carboxylate (Intermediate 78) instead of 2-fluoro-6-(2H-1,2,3-triazol-2-yl)benzoic acid and DMF instead of DCM. MS (ESI): mass calcd. for C₂₂H₂₁F₄N₅O, 447.2; m/z found, 448.2 [M+H]⁺. ¹H NMR (500 MHz, Chloroform-d) δ 7.42 (d, J=3.3 Hz, 1H), 7.00-6.93 (m, 2H), 5.81 (brs, 0.53H), 5.20-4.64 (m, 1.84H), 4.17-3.86 (m, 3.45H), 3.81 (s, 3H), 3.42-2.96 (m, 1H), 2.69 (brs, 1H), 2.42 (d, J=15.1 Hz, 1H), 2.32-2.16 (m, 1H), 1.54 (s, 3.62H), 1.13 (m, 1.38H). (Mixture of isomers with relative trans-configuration at starred stereocenters).

Method B: The title compound was prepared in a manner analogous to Example 288, using trans-5-(2-fluorocyclopropyl)-1-methyl-1H-pyrazole-4-carboxylic acid (Intermediate 79) instead of 2-fluoro-6-(2H-1,2,3-triazol-2-yl)benzoic acid, stirring at 36° C. overnight.

Example 342: (S*)-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone

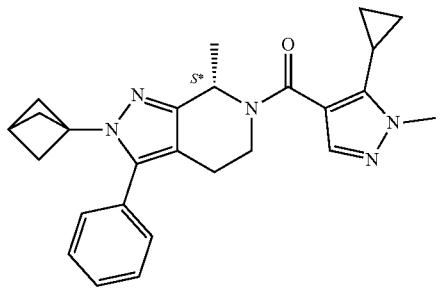

The title compound was isolated by SFC purification of racemic-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone (Example 615) (stationary phase: Chiralpak AD, 5 μm 250×30 mm; mobile phase: 20% MeOH with 0.2% TEA, 80% CO₂; flow rate: 85 mL/min). MS (ESI): mass calcd. for C₂₆H₂₉N₅O, 427.2; m/z found, 428.1 [M+H]⁺. ¹H NMR (500 MHz, Chloroform-d) δ 7.45-7.36 (m, 4H), 7.33-7.29 (m, 2H), 5.91 (brs, 0.41H), 5.16 (brs, 0.39H), 4.82 (brs, 0.42H), 3.98-3.82 (m, 3.37H), 3.39-2.94 (m, 1H), 2.56 (brs, 1H), 2.43-2.20 (m, 2H), 2.06 (s, 6H), 1.73 (s, 1H), 1.55 (brs, 3.16H), 1.07-0.54 (m, 4.34H). (S*: single enantiomer, but absolute configuration was not determined).

Example 343: (1,3-Dimethylpyrazol-4-yl)-[(7S)-2,7-dimethyl-3-(3,4,5-trifluorophenyl)-5,7-dihydro-4H-pyrazolo[3,4-c]pyridin-6-yl]methanone

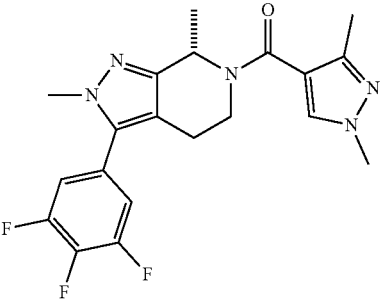 [SMILES: Cc1nn(C)cc1C(=O)N1CCc2c(nn(C)c2-c2cc(F)c(F)c(F)c2)[C@@H]1C]

The title compound was prepared in a manner analogous to Example 288, using 1,3-dimethyl-1H-pyrazole-4-carboxylic acid instead of 2-fluoro-6-(2H-1,2,3-triazol-2-yl)benzoic acid, stirring at 36° C. overnight. MS (ESI): mass calcd. for C₂₀H₂₀F₃N₅O, 403.2; m/z found, 404.1 [M+H]⁺. ¹H NMR (500 MHz, Chloroform-d) δ 7.42 (s, 1H), 7.01-6.93 (m, 2H), 5.55 (brs, 1H), 4.43 (brs, 1H), 3.85 (s, 3H), 3.81 (s, 3H), 3.18 (s, 1H), 2.76-2.63 (m, 1H), 2.47-2.37 (m, 1H), 2.31 (s, 3H), 1.55 (d, J=6.8 Hz, 3H).

Example 344: [(7S)-2,7-Dimethyl-3-(3,4,5-trifluorophenyl)-5,7-dihydro-4H-pyrazolo[3,4-c]pyridin-6-yl]-(1,3,5-trimethylpyrazol-4-yl)methanone

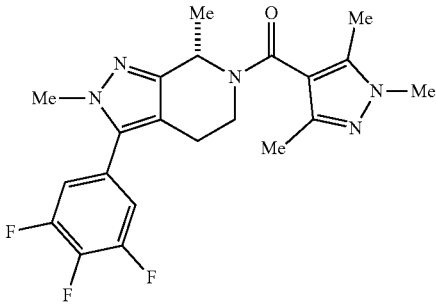 [SMILES: Cc1nn(C)c(C)c1C(=O)N1CCc2c(nn(C)c2-c2cc(F)c(F)c(F)c2)[C@@H]1C]

The title compound was prepared in a manner analogous to Example 288, using 1,3,5-trimethyl-1H-pyrazole-4-carboxylic acid instead of 2-fluoro-6-(2H-1,2,3-triazol-2-yl)benzoic acid, stirring overnight. MS (ESI): mass calcd. for $C_{21}H_{22}F_3N_5O$, 417.2; m/z found, 418.1 [M+H]$^+$. $^1$H NMR (500 MHz, Chloroform-d) δ 7.00-6.92 (m, 2H), 6.18-3.87 (m, 2H), 3.81 (s, 3H), 3.72 (s, 3H), 3.18 (brs, 1H), 2.62 (brs, 1H), 2.42 (d, J=14.3 Hz, 1H), 2.29-2.15 (m, 6H), 1.49 (s, 3H).

Example 345: (1,5-Dimethylpyrazol-4-yl)-[(7S)-2,7-dimethyl-3-(3,4,5-trifluorophenyl)-5,7-dihydro-4H-pyrazolo[3,4-c]pyridin-6-yl]methanone

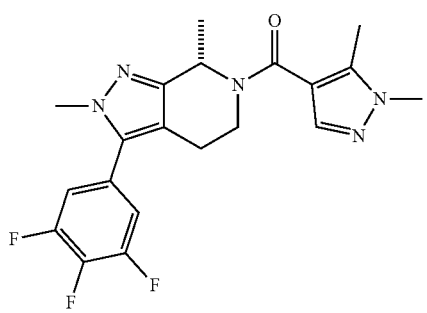 [SMILES: Cc1c(C(=O)N2CCc3c(nn(C)c3-c3cc(F)c(F)c(F)c3)[C@@H]2C)cnn1C]

The title compound was prepared in a manner analogous to Example 288, using 1,5-dimethyl-1H-pyrazole-4-carboxylic acid instead of 2-fluoro-6-(2H-1,2,3-triazol-2-yl)benzoic acid. MS (ESI): mass calcd. for $C_{20}H_{20}F_3N_5O$, 403.2; m/z found, 404.3 [M+H]$^+$. $^1$H NMR (500 MHz, Chloroform-d) δ 7.50 (s, 1H), 7.01-6.94 (m, 2H), 5.59 (brs, 1H), 4.46 (brs, 1H), 3.80 (d, J=5.3 Hz, 6H), 3.20 (brs, 1H), 2.85-2.69 (m, 1H), 2.46-2.36 (m, 4H), 1.58 (s, 3H).

Example 346: [1-Cyclopropyl-5-(trifluoromethyl)pyrazol-4-yl]-[(7S)-2,7-dimethyl-3-(3,4,5-trifluorophenyl)-5,7-dihydro-4H-pyrazolo[3,4-c]pyridin-6-yl]methanone

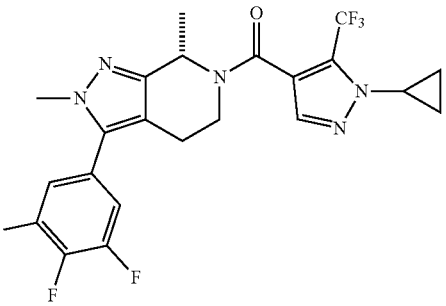

The title compound was prepared in a manner analogous to Example 288, using potassium 1-cyclopropyl-5-(trifluoromethyl)-1H-pyrazole-4-carboxylate (Intermediate 81) instead of 2-fluoro-6-(2H-1,2,3-triazol-2-yl)benzoic acid and DMF instead of DCM. MS (ESI): mass calcd. for $C_{22}H_{19}F_6N_5O$, 483.1; m/z found, 484.0 [M+H]$^+$. $^1$H NMR (500 MHz, Chloroform-d) δ 7.46-7.43 (m, 1H), 7.02-6.91 (m, 2H), 5.84 (q, J=6.7 Hz, 0.59H), 4.92-4.84 (m, 0.85H), 3.85-3.77 (m, 3H), 3.76-3.70 (m, 0.67H), 3.69-3.60 (m, 1H), 3.35-2.97 (m, 1H), 2.79-2.51 (m, 1H), 2.48-2.32 (m, 1H), 1.58-1.53 (m, 1.77H), 1.46 (d, J=6.7 Hz, 1.27H), 1.41-1.29 (m, 2H), 1.17-1.07 (m, 2H).

Example 347: [(7S)-2,7-Dimethyl-3-(3,4,5-trifluorophenyl)-5,7-dihydro-4H-pyrazolo[3,4-c]pyridin-6-yl]-[1-methyl-3-(1-methylcyclopropyl)pyrazol-4-yl]methanone

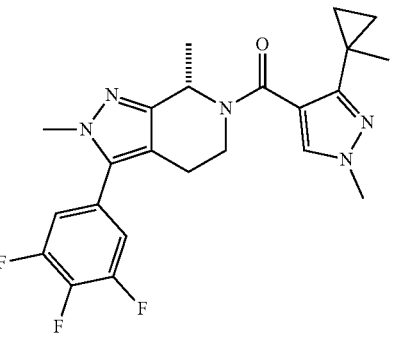

The title compound was prepared in a manner analogous to Example 288, using 1-methyl-3-(1-methylcyclopropyl)-1H-pyrazole-4-carboxylic acid (Intermediate 72) instead of 2-fluoro-6-(2H-1,2,3-triazol-2-yl)benzoic acid at 40° C. overnight. MS (ESI): mass calcd. for $C_{23}H_{24}F_3N_5O$, 443.2; m/z found, 444.3 [M+H]$^+$. $^1$H NMR (500 MHz, Chloroform-d) δ 7.31 (s, 1H), 7.00-6.92 (m, 2H), 6.15-3.71 (m, 9H), 3.17 (brs, 1H), 2.65 (brs, 1H), 2.40 (d, J=15.2 Hz, 1H), 1.71-1.30 (m, 5H), 1.08-0.87 (m, 2H), 0.61 (s, 2H).

Example 348: [(7S)-2,7-Dimethyl-3-(3,4,5-trifluorophenyl)-5,7-dihydro-4H-pyrazolo[3,4-c]pyridin-6-yl]-[3-(1-fluorocyclopropyl)-1-methyl-pyrazol-4-yl]methanone

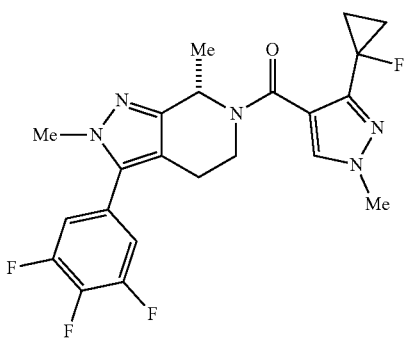 [SMILES: C[C@H]1c2nn(C)c(-c3cc(F)c(F)c(F)c3)c2CCN1C(=O)c1cn(C)nc1C1(F)CC1]

The title compound was prepared in a manner analogous to Example 288, using potassium 3-(1-fluorocyclopropyl)-1-methyl-1H-pyrazole-4-carboxylate (Intermediate 74) instead of 2-fluoro-6-(2H-1,2,3-triazol-2-yl)benzoic acid and DMF instead of DCM. MS (ESI): mass calcd. for $C_{22}H_{21}F_4N_5O$, 447.2; m/z found, 448.0 [M+H]$^+$. $^1$H NMR (500 MHz, Chloroform-d) δ 7.44 (s, 1H), 7.00-6.92 (m, 2H), 5.89 (brs, 0.76H), 5.27-4.72 (m, 1.05H), 4.14-3.98 (m, 0.53H), 3.93-3.76 (m, 6.13H), 3.44-2.95 (m, 1.41H), 2.64 (brs, 1.23H), 2.39 (brs, 1.22H), 1.58 (s, 1.55H), 1.44-1.22 (m, 2.19H), 1.21-1.09 (m, 2.13H).

Example 349: (R)-(5-cyclopropyl-1-methyl-1H-pyrazol-4-yl) (7-methyl-2,3-diphenyl-2,4,5,7-tetrahydro-6H-pyrazolo[3,4-c] pyridin-6-yl) methanone

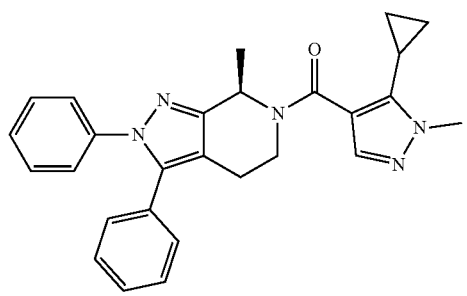 [SMILES: C[C@@H]1c2nn(-c3ccccc3)c(-c3ccccc3)c2CCN1C(=O)c1cnn(C)c1C1CC1]

The title compound was prepared in a manner analogous to Example 288, using (R)-7-methyl-2,3-diphenyl-4,5,6,7-tetrahydro-2H-pyrazolo[3,4-c]pyridine (Intermediate 56) instead of (S)-2,7-dimethyl-3-(3,4,5-trifluorophenyl)-4,5,6,7-tetrahydro-2H-pyrazolo[3,4-c]pyridine (Intermediate 40) and 5-cyclopropyl-1-methyl-1H-pyrazole-4-carboxylic acid instead of 2-fluoro-6-(2H-1,2,3-triazol-2-yl)benzoic acid. MS (ESI): mass calcd. for $C_{27}H_{27}N_5O$, 437.2; m/z found, 438.1 [M+H]$^+$. $^1$H NMR (400 MHz, DMSO-d$_6$) δ 7.45 (s, 1H), 7.40-7.28 (m, 6H), 7.24-7.15 (m, 4H), 5.81-5.54 (m, 1H), 5.03-4.47 (m, 1H), 3.85 (s, 4H), 2.87-2.68 (m, 1H), 2.49-2.31 (m, 1H), 1.87 (s, 1H), 1.51 (d, J=6.8 Hz, 3H), 0.92 (s, 2H), 0.62 (s, 2H).

Example 350: (S)-(5-cyclopropyl-1-methyl-1H-pyrazol-4-yl) (7-methyl-2,3-diphenyl-2,4,5,7-tetrahydro-6H-pyrazolo[3,4-c] pyridin-6-yl)methanone

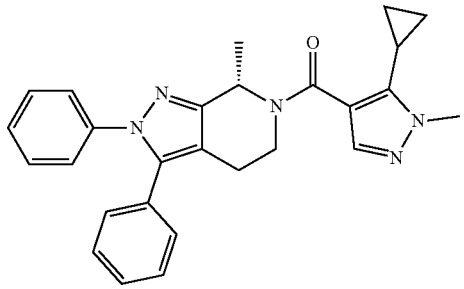 [SMILES: C[C@H]1c2nn(-c3ccccc3)c(-c3ccccc3)c2CCN1C(=O)c1cnn(C)c1C1CC1]

The title compound was prepared in a manner analogous to Example 288, using (S)-7-methyl-2,3-diphenyl-4,5,6,7-tetrahydro-2H-pyrazolo[3,4-c]pyridine (Intermediate 55) instead of (S)-2,7-dimethyl-3-(3,4,5-trifluorophenyl)-4,5,6,7-tetrahydro-2H-pyrazolo[3,4-c]pyridine (Intermediate 40) and 5-cyclopropyl-1-methyl-1H-pyrazole-4-carboxylic acid instead of 2-fluoro-6-(2H-1,2,3-triazol-2-yl)benzoic acid. MS (ESI): mass calcd. for $C_{27}H_{27}N_5O$, 437.2; m/z found, 438.1 [M+H]$^+$. $^1$H NMR (400 MHz, DMSO-d$_6$) δ 7.45 (s, 1H), 7.40-7.28 (m, 6H), 7.24-7.15 (m, 4H), 5.81-5.54 (m, 1H), 5.03-4.47 (m, 1H), 3.85 (s, 4H), 2.87-2.68 (m, 1H), 2.49-2.31 (m, 1H), 1.87 (s, 1H), 1.51 (d, J=6.8 Hz, 3H), 0.92 (s, 2H), 0.62 (s, 2H).

Example 351: (1,2-Dimethylpyrrol-3-yl)-[(7S)-2,7-dimethyl-3-(3,4,5-trifluorophenyl)-5,7-dihydro-4H-pyrazolo[3,4-c]pyridin-6-yl]methanone

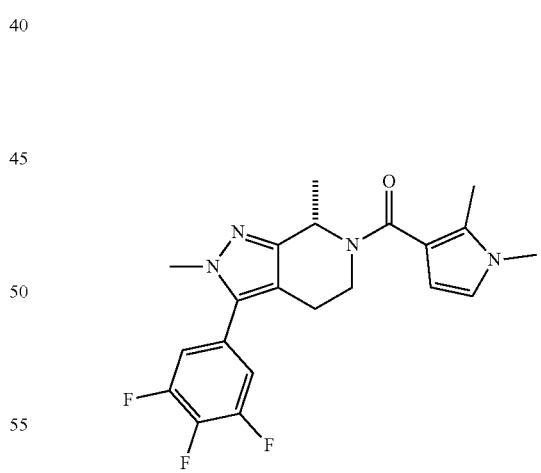

The title compound was prepared in a manner analogous to Example 288, using 1,2-dimethyl-1H-pyrrole-3-carboxylic acid instead of 2-fluoro-6-(2H-1,2,3-triazol-2-yl)benzoic acid. MS (ESI): mass calcd. for $C_{21}H_{21}F_3N_4O$, 402.2; m/z found, 403.2 [M+H]$^+$. $^1$H NMR (500 MHz, Chloroform-d) δ 7.01-6.93 (m, 2H), 6.47 (d, J=2.9 Hz, 1H), 6.13 (d, J=2.9 Hz, 1H), 5.61 (brs, 1H), 4.52 (brs, 1H), 3.80 (s, 3H), 3.51 (s, 3H), 3.15 (brs, 1H), 2.82-2.71 (m, 1H), 2.40 (dd, J=15.2, 3.9 Hz, 1H), 2.31 (s, 3H), 1.57-1.54 (m, 3H).

Example 352: (4,5-Dimethylisoxazol-3-yl)-[(7S)-2,7-dimethyl-3-(3,4,5-trifluorophenyl)-5,7-dihydro-4H-pyrazolo[3,4-c]pyridin-6-yl]methanone Example 354: [(7S)-2,7-Dimethyl-3-(3,4,5-trifluorophenyl)-5,7-dihydro-4H-pyrazolo[3,4-c]pyridin-6-yl]-(7-fluoro-1H-indol-4-yl)methanone

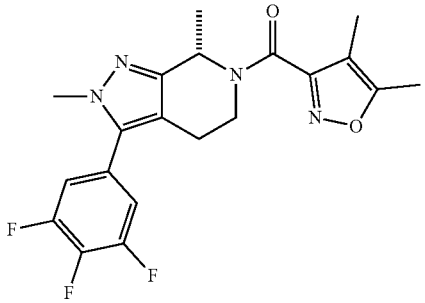 [SMILES: Cc1onc(C(=O)N2CCc3c(nn(C)c3-c3cc(F)c(F)c(F)c3)[C@@H]2C)c1C]

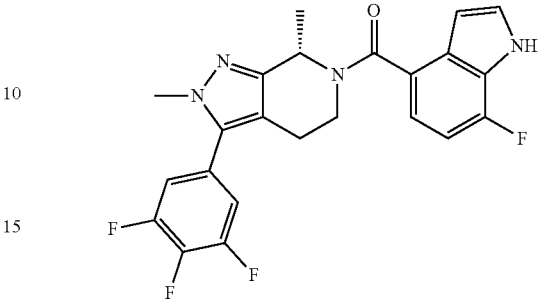

The title compound was prepared in a manner analogous to Example 288, using 4,5-dimethylisoxazole-3-carboxylic acid instead of 2-fluoro-6-(2H-1,2,3-triazol-2-yl)benzoic acid. MS (ESI): mass calcd. for $C_{20}H_{19}F_3N_4O_2$, 404.1; m/z found, 405.1 [M+H]$^+$. $^1$H NMR (500 MHz, Chloroform-d) δ 7.02-6.94 (m, 2H), 5.87 (q, J=6.8 Hz, 0.61H), 5.25 (q, J=6.7 Hz, 0.39H), 4.93-4.86 (m, 0.40H), 4.24-4.16 (m, 0.62H), 3.83 (s, 1.83H), 3.78 (s, 1.15H), 3.38-3.25 (m, 0.62H), 3.13-3.04 (m, 0.39H), 2.90-2.70 (m, 1H), 2.53-2.44 (m, 0.43H), 2.43-2.33 (m, 3.63H), 2.02 (s, 1.89H), 1.96 (s, 1.19H), 1.63-1.58 (m, 3H).

The title compound was prepared in a manner analogous to Example 288, using 7-fluoro-1H-indole-4-carboxylic acid instead of 2-fluoro-6-(2H-1,2,3-triazol-2-yl)benzoic acid. MS (ESI): mass calcd. for $C_{23}H_{18}F_4N_4O$, 442.1; m/z found, 443.2 [M+H]$^+$. $^1$H NMR (500 MHz, Chloroform-d) δ 8.49 (s, 1H), 7.30-7.24 (m, 1H), 7.07 (dd, J=8.0, 4.4 Hz, 1H), 7.01-6.89 (m, 3H), 6.56 (s, 1H), 6.15-5.76 (m, 0.37H), 5.29-4.68 (m, 0.62H), 3.97-3.63 (m, 3.64H), 3.20 (br s, 1H), 2.97-2.16 (m, 1.85H), 1.79-1.33 (m, 3H).

Example 353: [(7S)-2,7-Dimethyl-3-(3,4,5-trifluorophenyl)-5,7-dihydro-4H-pyrazolo[3,4-c]pyridin-6-yl]-(5-fluoro-1H-indol-6-yl)methanone Example 355: [(7S)-2,7-Dimethyl-3-(3,4,5-trifluorophenyl)-5,7-dihydro-4H-pyrazolo[3,4-c]pyridin-6-yl]-(5-fluoro-1H-indol-3-yl)methanone

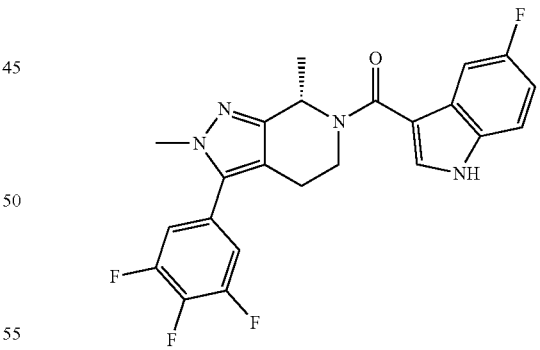

The title compound was prepared in a manner analogous to Example 288, using 5-fluoro-1H-indole-6-carboxylic acid instead of 2-fluoro-6-(2H-1,2,3-triazol-2-yl)benzoic acid. MS (ESI): mass calcd. for $C_{23}H_{18}F_4N_4O$, 426.1; m/z found, 427.1 [M+H]$^+$. $^1$H NMR (500 MHz, DMSO-d$_6$) δ 11.32 (s, 1H), 7.61-7.27 (m, 5H), 6.51-6.45 (m, 1H), 5.65 (br s, 0.66H), 4.77-4.62 (m, 0.59H), 3.86-3.70 (m, 3H), 3.63-3.55 (m, 0.68H), 3.12-3.01 (m, 0.31H), 2.82-2.58 (m, 1H), 2.38-2.26 (m, 0.71H), 1.54-1.30 (m, 3H). (Fractions of Hs that may overlap with DMSO and water are not reported).

The title compound was prepared in a manner analogous to Example 288, using 5-fluoro-1H-indole-3-carboxylic acid instead of 2-fluoro-6-(2H-1,2,3-triazol-2-yl)benzoic acid. MS (ESI): mass calcd. for $C_{23}H_{18}F_4N_4O$, 442.1; m/z found, 443.2 [M+H]$^+$. $^1$H NMR (500 MHz, DMSO-d$_6$) δ 11.71 (s, 1H), 7.82 (s, 1H), 7.60-7.52 (m, 2H), 7.46 (dd, J=8.8, 4.6 Hz, 1H), 7.42 (dd, J=10.1, 2.6 Hz, 1H), 7.02 (td, J=9.1, 2.6 Hz, 1H), 5.58-5.44 (m, 1H), 4.45-4.28 (m, 1H), 3.80 (s, 3H), 3.34-3.20 (m, 1H), 2.96-2.86 (m, 1H), 2.46-2.39 (m, 1H), 1.51 (d, J=6.7 Hz, 3H).

Example 356: [(7S)-2,7-Dimethyl-3-(3,4,5-trifluorophenyl)-5,7-dihydro-4H-pyrazolo[3,4-c]pyridin-6-yl]-(5-fluoro-1-methyl-indol-3-yl)methanone

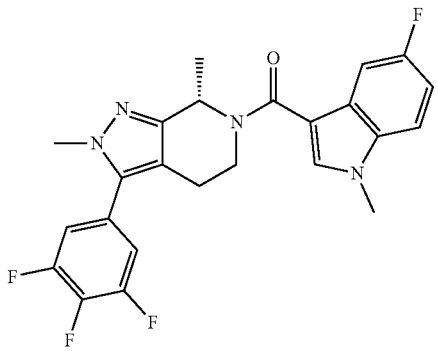 [SMILES: C[C@H]1c2nn(C)c(-c3cc(F)c(F)c(F)c3)c2CCN1C(=O)c1cn(C)c2ccc(F)cc12]

The title compound was prepared in a manner analogous to Example 288, using 5-fluoro-1-methyl-1H-indole-3-carboxylic acid instead of 2-fluoro-6-(2H-1,2,3-triazol-2-yl)benzoic acid and DMF instead of DCM. MS (ESI): mass calcd. for $C_{24}H_{20}F_4N_4O$, 456.2; m/z found, 457.2 $[M+H]^+$. $^1$H NMR (500 MHz, DMSO-$d_6$) δ 7.85 (s, 1H), 7.59-7.50 (m, 3H), 7.47 (dd, J=10.0, 2.6 Hz, 1H), 7.09 (td, J=9.2, 2.6 Hz, 1H), 5.55-5.46 (m, 1H), 4.45-4.31 (m, 1H), 3.87 (s, 3H), 3.80 (s, 3H), 2.96-2.83 (m, 1H), 2.47-2.41 (m, 1H), 1.51 (d, J=6.8 Hz, 3H). (Fractions of Hs that may overlap with DMSO and water are not reported).

Example 357: [(7S)-2,7-Dimethyl-3-(3,4,5-trifluorophenyl)-5,7-dihydro-4H-pyrazolo[3,4-c]pyridin-6-yl]-(4-fluoro-1H-indol-3-yl)methanone The title compound was prepared in a manner analogous to Example 288, using 4-fluoro-1H-indole-3-carboxylic acid instead of 2-fluoro-6-(2H-1,2,3-triazol-2-yl)benzoic acid and DMF instead of DCM. MS (ESI): mass calcd. for $C_{23}H_{18}F_4N_4O$, 442.1; m/z found, 443.2 $[M+H]^+$. $^1$H NMR (400 MHz, DMSO-$d_6$) δ 11.74 (s, 1H), 7.60 (s, 1H), 7.57-7.46 (m, 2H), 7.31-7.27 (m, 1H), 7.13 (td, J=8.0, 5.1 Hz, 1H), 6.83 (dd, J=11.0, 7.8 Hz, 1H), 5.77-5.32 (m, 1H), 4.25-3.71 (m, 4H), 3.29-3.13 (m, 1H), 2.75-2.62 (m, 1H), 2.41-2.28 (m, 1H), 1.43 (d, J=6.8 Hz, 3H).

Example 358: [(7S)-2,7-Dimethyl-3-(3,4,5-trifluorophenyl)-5,7-dihydro-4H-pyrazolo[3,4-c]pyridin-6-yl]-(6-fluoro-1H-indol-3-yl)methanone

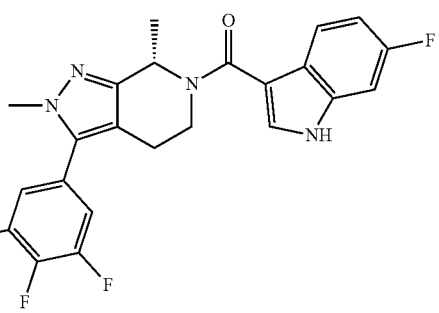

The title compound was prepared in a manner analogous to Example 288, using 6-fluoro-1H-indole-3-carboxylic acid instead of 2-fluoro-6-(2H-1,2,3-triazol-2-yl)benzoic acid. MS (ESI): mass calcd. for $C_{23}H_{18}F_4N_4O$, 442.1; m/z found, 443.1 $[M+H]^+$. $^1$H NMR (500 MHz, DMSO-$d_6$) δ 11.63 (s, 1H), 7.76-7.67 (m, 2H), 7.60-7.52 (m, 2H), 7.23 (dd, J=9.8, 2.4 Hz, 1H), 6.99-6.93 (m, 1H), 5.57-5.43 (m, 1H), 4.43-4.27 (m, 1H), 3.80 (s, 3H), 3.31-3.19 (m, 1H), 2.94-2.84 (m, 1H), 2.46-2.38 (m, 1H), 1.50 (d, J=6.8 Hz, 3H).

Example 359: [(7S)-2,7-Dimethyl-3-(3,4,5-trifluorophenyl)-5,7-dihydro-4H-pyrazolo[3,4-c]pyridin-6-yl]-(7-fluoro-1H-indol-3-yl)methanone

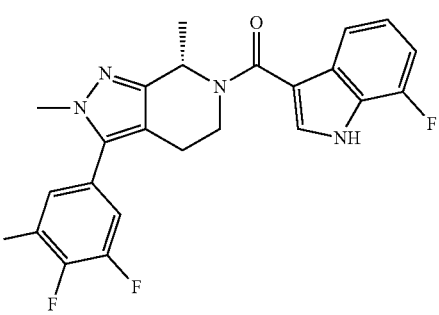

The title compound was prepared in a manner analogous to Example 288, using 7-fluoro-1H-indole-3-carboxylic acid instead of 2-fluoro-6-(2H-1,2,3-triazol-2-yl)benzoic acid. MS (ESI): mass calcd. for $C_{23}H_{18}F_4N_4O$, 442.1; m/z found, 443.1 $[M+H]^+$. $^1$H NMR (500 MHz, DMSO-$d_6$) δ 12.12 (s, 1H), 7.76 (s, 1H), 7.60-7.52 (m, 2H), 7.50 (d, J=7.9 Hz, 1H), 7.09-6.97 (m, 2H), 5.51 (br s, 1H), 4.31 (br s, 1H), 3.80 (s, 3H), 3.30-3.20 (m, 1H), 2.95-2.84 (m, 1H), 2.45-2.38 (m, 1H), 1.50 (d, J=6.8 Hz, 3H).

Example 360: [(7S)-2,7-Dimethyl-3-(3,4,5-trifluoro-phenyl)-5,7-dihydro-4H-pyrazolo[3,4-c]pyridin-6-yl]-(6-methyl-1H-indol-3-yl)methanone.TFA salt

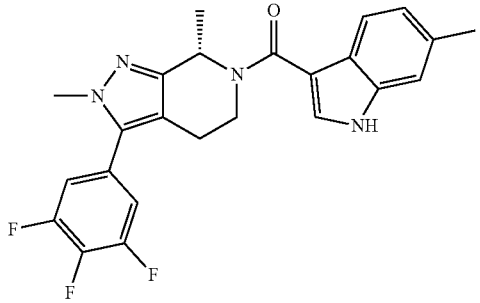 [SMILES: Cc1ccc2c(C(=O)N3CCc4c(nn(C)c4-c4cc(F)c(F)c(F)c4)[C@@H]3C)c[nH]c2c1]

The title compound was prepared in a manner analogous to Example 288, using 6-methyl-1H-indole-3-carboxylic acid instead of 2-fluoro-6-(2H-1,2,3-triazol-2-yl)benzoic acid. MS (ESI): mass calcd. for $C_{24}H_{21}F_3N_4O$, 438.2; m/z found, 439.1 $[M+H]^+$. $^1H$ NMR (500 MHz, DMSO-$d_6$) δ 11.44-11.39 (m, 1H), 7.62 (d, J=2.7 Hz, 1H), 7.59-7.52 (m, 3H), 7.25-7.21 (m, 1H), 6.95-6.89 (m, 1H), 5.56-5.47 (m, 1H), 4.40-4.29 (m, 1H), 3.79 (s, 3H), 3.29-3.18 (m, 1H), 2.92-2.82 (m, 1H), 2.45-2.37 (m, 4H), 1.49 (d, J=6.8 Hz, 3H).

Example 361: [(7S)-2,7-Dimethyl-3-(3,4,5-trifluoro-phenyl)-5,7-dihydro-4H-pyrazolo[3,4-c]pyridin-6-yl]-(1H-indazol-3-yl)methanone Example 362: [(7S)-2,7-Dimethyl-3-(3,4,5-trifluoro-phenyl)-5,7-dihydro-4H-pyrazolo[3,4-c]pyridin-6-yl]-(4-fluoro-1H-indazol-3-yl)methanone.TFA salt

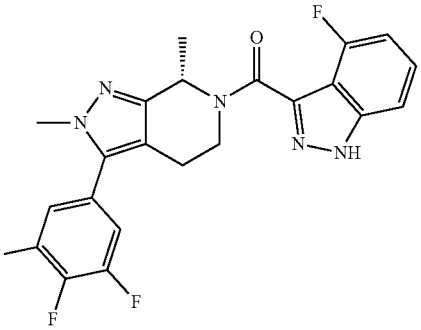

The title compound was prepared in a manner analogous to Example 288, using and 4-fluoro-1H-indazole-3-carbox-ylic acid instead of 2-fluoro-6-(2H-1,2,3-triazol-2-yl)ben-zoic acid. MS (ESI): mass calcd. for $C_{22}H_{17}F_4N_5O$, 443.1; m/z found, 444.1 $[M+H]^+$. $^1H$ NMR (500 MHz, DMSO-$d_6$) δ 13.76-13.66 (m, 1H), 7.60-7.50 (m, 2H), 7.47-7.38 (m, 2H), 6.98-6.91 (m, 1H), 5.68 (q, J=6.7 Hz, 0.64H), 5.08-5.01 (m, 0.36H), 4.79-4.72 (m, 0.39H), 3.84-3.72 (m, 3H), 3.15-3.07 (m, 0.42H), 2.81-2.67 (m, 1H), 2.39-2.32 (dd, J=3.7, 2.0 Hz, 0.57H), 1.51 (d, J=6.8 Hz, 2H), 1.45 (d, J=6.7 Hz, 1H). (Hs that may overlap with water and DMSO are not reported).

Example 363: [(7S)-2,7-Dimethyl-3-(3,4,5-trifluoro-phenyl)-5,7-dihydro-4H-pyrazolo[3,4-c]pyridin-6-yl]-(6-fluoro-1H-indazol-3-yl)methanone

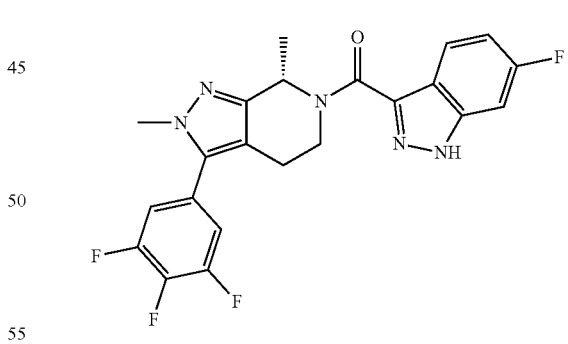

The title compound was prepared in a manner analogous to Example 288, using 1H-indazole-3-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.1 $[M+H]^+$. $^1H$ NMR (500 MHz, Chloroform-d) δ 10.44-10.11 (m, 1H), 8.18 (d, J=8.2 Hz, 1H), 7.54-7.48 (m, 1H), 7.47-7.39 (m, 1H), 7.31-7.22 (m, 1H), 7.03-6.93 (m, 2H), 6.17-5.91 (m, 1H), 5.05-4.87 (m, 1H), 3.92-3.72 (m, 3H), 3.40-3.10 (m, 1H), 3.04-2.82 (m, 1H), 2.57-2.39 (m, 1H), 1.78-1.61 (m, 3H).

The title compound was prepared in a manner analogous to Example 288, using and 6-fluoro-1H-indazole-3-carbox-ylic acid instead of 2-fluoro-6-(2H-1,2,3-triazol-2-yl)ben-zoic acid. MS (ESI): mass calcd. for $C_{22}H_{17}F_4N_5O$, 443.1; m/z found, 444.1 $[M+H]^+$. $^1H$ NMR (500 MHz, DMSO-$d_6$) δ 13.63 (s, 1H), 8.04-7.98 (m, 1H), 7.59-7.51 (m, 2H), 7.42 (dd, J=9.4, 2.2 Hz, 1H), 7.11 (td, J=9.2, 2.2 Hz, 1H), 6.09-5.96 (m, 0.38H), 5.75-5.63 (m, 0.56H), 5.00-4.69 (m, 1H), 3.86-3.71 (m, 3H), 3.16-3.04 (m, 0.43H), 2.94-2.74 (m, 1H), 1.63-1.46 (m, 3H). (Fractions of Hs that may overlap with DMSO and water are not reported).

Example 364: [(7S)-2,7-Dimethyl-3-(3,4,5-trifluorophenyl)-5,7-dihydro-4H-pyrazolo[3,4-c]pyridin-6-yl]-(5-fluoro-1H-indazol-3-yl)methanone

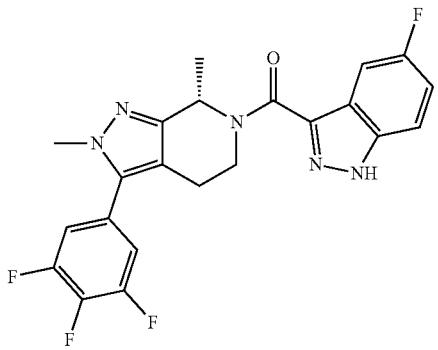

The title compound was prepared in a manner analogous to Example 288, using and 5-fluoro-1H-indazole-3-carboxylic acid instead of 2-fluoro-6-(2H-1,2,3-triazol-2-yl)benzoic acid and DMF instead of DCM. MS (ESI): mass calcd. for $C_{22}H_{17}F_4N_5O$, 443.1; m/z found, 444.2 [M+H]$^+$. $^1$H NMR (500 MHz, DMSO-d$_6$) δ 13.72 (s, 1H), 7.73-7.65 (m, 2H), 7.59-7.51 (m, 2H), 7.33 (td, J=9.1, 2.5 Hz, 1H), 6.19-6.07 (m, 0.36H), 5.74-7.63 (m, 0.53H), 5.10-5.00 (m, 0.53H), 4.80-4.69 (m, 0.40H), 3.86-3.72 (m, 3H), 3.16-3.03 (m, 0.42H), 2.95-2.74 (m, 1H), 1.67-1.45 (m, 3H). (Fractions of Hs that may overlap with DMSO and water are not reported).

Example 365: [(7S)-2,7-Dimethyl-3-(3,4,5-trifluorophenyl)-5,7-dihydro-4H-pyrazolo[3,4-c]pyridin-6-yl]-(2-methylindazol-3-yl)methanone

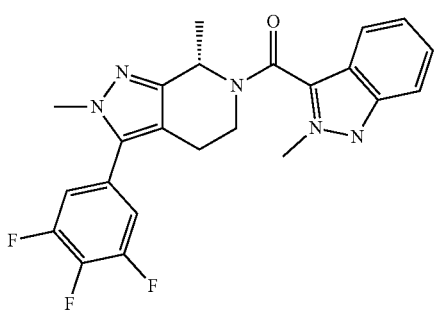

The title compound was prepared in a manner analogous to Example 288, using 2-methyl-2H-indazole-3-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (500 MHz, DMSO-d$_6$) δ 7.72-7.68 (m, 1H), 7.65-7.46 (m, 3H), 7.35-7.29 (m, 1H), 7.21-7.13 (m, 1H), 5.90-5.50 (m, 0.58H), 4.15 (s, 3H), 3.88-3.63 (m, 3.5H), 3.52-3.32 (m, 0.76H), 2.88-2.65 (m, 0.73H), 1.69-1.34 (m, 3H). (Fractions of Hs that may overlap with DMSO and water are not reported).

Example 366: [(7S)-2,7-Dimethyl-3-(3,4,5-trifluorophenyl)-5,7-dihydro-4H-pyrazolo[3,4-c]pyridin-6-yl]-(1-methylbenzimidazol-4-yl)methanone

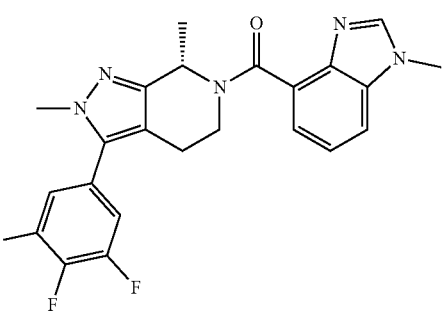

The title compound was prepared in a manner analogous to Example 288, using 1-methyl-1H-benzo[d]imidazole-4-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (400 MHz, Methanol-d$_4$) δ 9.30-9.04 (m, 1H), 8.05-7.90 (m, 1H), 7.76-7.68 (m, 1H), 7.68-7.61 (m, 1H), 7.34-7.24 (m, 2H), 6.00-5.71 (m, 1H), 4.13 (s, 3H), 3.98-3.59 (m, 4H), 3.49-3.34 (m, 1H), 3.07-2.73 (m, 1H), 2.64-2.29 (m, 1H), 1.65 (s, 3H).

Example 367: 1H-Benzotriazol-4-yl-[(7S)-2,7-dimethyl-3-(3,4,5-trifluorophenyl)-5,7-dihydro-4H-pyrazolo[3,4-c]pyridin-6-yl]methanone

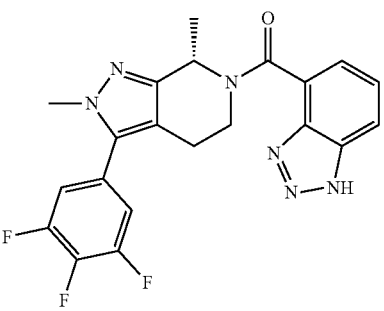 [SMILES: C[C@H]1c2nn(C)c(-c3cc(F)c(F)c(F)c3)c2CCN1C(=O)c1cccc2[nH]nnc12]

The title compound was prepared in a manner analogous to Example 288, using 1H-benzo[d][1,2,3]triazole-7-carboxylic acid instead of 2-fluoro-6-(2H-1,2,3-triazol-2-yl) benzoic acid. MS (ESI): mass calcd. for $C_{21}H_{17}F_3N_6O$, 426.1; m/z found, 427.0 [M+H]$^+$. $^1$H NMR (600 MHz, Methanol-d$_4$) δ 8.01-7.90 (m, 1H), 7.52 (dd, J=8.3, 7.0 Hz, 1H), 7.47-7.39 (m, 1H), 7.35-7.22 (m, 2H), 5.96-5.77 (m, 1H), 3.99-3.61 (m, 4H), 3.42-3.34 (m, 1H), 2.89-2.73 (m, 1H), 2.67-2.24 (m, 1H), 1.67 (s, 3H).

Example 368: [(7S)-2,7-Dimethyl-3-(3,4,5-trifluoro-phenyl)-5,7-dihydro-4H-pyrazolo[3,4-c]pyridin-6-yl]-(1H-pyrrolo[2,3-b]pyridin-5-yl)methanone

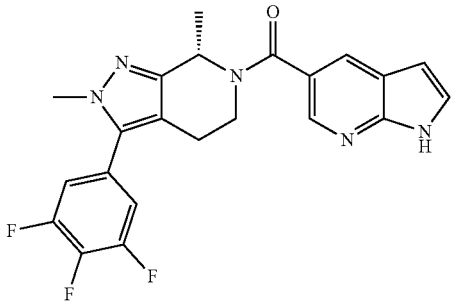

The title compound was prepared in a manner analogous to Example 288, using 1H-pyrrolo[2,3-b]pyridine-5-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.2 [M+H]$^+$. $^1$H NMR (500 MHz, DMSO-d$_6$) δ 11.89 (s, 1H), 8.32-8.26 (m, 1H), 8.06 (d, J=2.0 Hz, 1H), 7.61-7.51 (m, 3H), 6.56-6.51 (m, 1H), 5.55 (br s, 1H), 3.92-3.67 (m, 3.64H), 2.97-2.82 (m, 1H), 2.44-2.32 (m, 0.87H), 1.49 (d, J=6.8 Hz, 3H). (Fractions of Hs that may overlap with DMSO and water are not reported).

Example 369: [(7S)-2,7-Dimethyl-3-(3,4,5-trifluoro-phenyl)-5,7-dihydro-4H-pyrazolo[3,4-c]pyridin-6-yl]-(5-fluoro-1H-pyrrolo[2,3-b]pyridin-4-yl)methanone

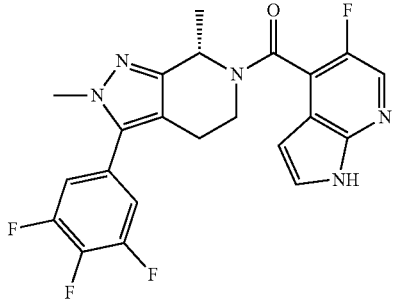 [SMILES: C[C@H]1c2nn(C)c(-c3cc(F)c(F)c(F)c3)c2CCN1C(=O)c1c(F)cnc2[nH]ccc12]

The title compound was prepared in a manner analogous to Example 288, using 5-fluoro-1H-pyrrolo[2,3-b]pyridine-4-carboxylic acid instead of 2-fluoro-6-(2H-1,2,3-triazol-2-yl)benzoic acid and DMF instead of DCM. MS (ESI): mass calcd. for $C_{22}H_{17}F_4N_5O$, 443.1; m/z found, 444.2 [M+H]$^+$. $^1$H NMR (500 MHz, Chloroform-d) δ 9.00-8.86 (m, 1H), 8.32-8.16 (m, 1H), 7.47-7.29 (m, 1H), 7.04-6.87 (m, 2H), 6.59-6.23 (m, 1H), 6.06-5.95 (m, 0.65H), 5.11-5.01 (m, 0.39H), 4.90-4.75 (s, 0.39H), 3.85 (s, 2H), 3.81-3.71 (m, 1H), 3.65 (dd, J=13.8, 5.1 Hz, 0.67H), 3.46-3.25 (m, 0.65H), 3.19-3.08 (m, 0.37H), 2.91-2.74 (m, 0.71H), 2.60-2.43 (m, 0.66H), 2.40-2.24 (m, 0.66H), 1.73-1.30 (m, 3H).

Example 370: [(7S)-2,7-Dimethyl-3-(3,4,5-trifluoro-phenyl)-5,7-dihydro-4H-pyrazolo[3,4-c]pyridin-6-yl]-(5-fluoro-1-methyl-pyrrolo[2,3-b]pyridin-4-yl)methanone

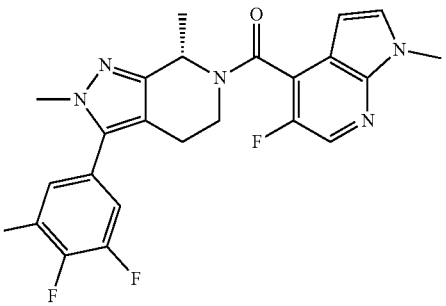

The title compound was prepared in a manner analogous to Example 288, using 5-fluoro-1-methyl-1H-pyrrolo[2,3-b]pyridine-4-carboxylic acid instead of 2-fluoro-6-(2H-1,2,3-triazol-2-yl)benzoic acid and DMF instead of DCM. MS (ESI): mass calcd. for $C_{23}H_{19}F_4N_5O$, 457.1; m/z found, 458.2 [M+H]$^+$. $^1$H NMR (500 MHz, DMSO-d$_6$) δ 8.43-8.30 (m, 1H), 7.75-7.47 (m, 3H), 6.46-6.13 (m, 1H), 5.71 (q, J=6.7 Hz, 0.63H), 4.85-4.75 (m, 0.33H), 4.64-4.51 (m, 0.34H), 3.90-3.68 (m, 6H), 3.51-3.41 (m, 0.74H), 3.18-3.05 (m, 0.33H), 2.98-2.87 (m, 0.33H), 2.79-2.69 (m, 0.15H), 2.37-2.24 (m, 0.64H), 1.60-1.21 (m, 3H). (Fractions of Hs that may overlap with DMSO and water are not reported).

Example 371: [(7S)-2,7-Dimethyl-3-(3,4,5-trifluoro-phenyl)-5,7-dihydro-4H-pyrazolo[3,4-c]pyridin-6-yl]-[5-(trifluoromethyl)-1H-pyrrolo[2,3-b]pyridin-4-yl] methanone.TFA salt

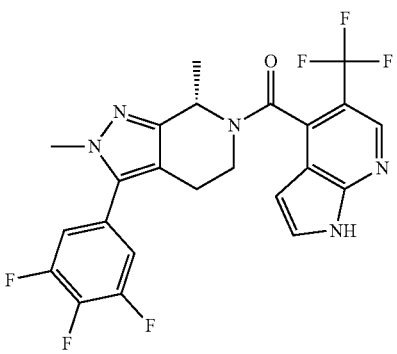 [SMILES: C[C@H]1c2nn(C)c(-c3cc(F)c(F)c(F)c3)c2CCN1C(=O)c1c(C(F)(F)F)cnc2[nH]ccc12]

Step A: (S)-(2,7-Dimethyl-3-(3,4,5-trifluorophenyl)-2,4,5,7-tetrahydro-6H-pyrazolo[3,4-c]pyridin-6-yl)(5-(trifluoromethyl)-1-((2-(trimethylsilyl)ethoxy)methyl)-1H-pyrrolo[2,3-b]pyridin-4-yl)methanone. The title compound was prepared in a manner analogous to Example 288, using 5-trifluoromethyl-1-((2-(trimethylsilyl)ethoxy)methyl)-1H-pyrrolo[2,3-b]pyridine-4-carboxylic acid (Intermediate 60) instead of 2-fluoro-6-(2H-1,2,3-triazol-2-yl)benzoic acid and DMF instead of DCM. MS (ESI): mass calcd. for $C_{29}H_{31}F_6N_5O_2Si$, 623.2; m/z found, 624.3 [M+H]$^+$.

Step B: (S)-[(7S)-2,7-Dimethyl-3-(3,4,5-trifluorophenyl)-5,7-dihydro-4H-pyrazolo[3,4-c]pyridin-6-yl]-[5-(trifluoromethyl)-1H-pyrrolo[2,3-b]pyridin-4-yl]methanone. TFA (0.09 mL, 1.3 mmol) was added to a mixture of (S)-(2,7-dimethyl-3-(3,4,5-trifluorophenyl)-2,4,5,7-tetrahydro-6H-pyrazolo[3,4-c]pyridin-6-yl)(5-(trifluoromethyl)-1-((2-(trimethylsilyl)ethoxy)methyl)-1H-pyrrolo[2,3-b]pyridin-4-yl)methanone (78.5 mg, 0.13 mmol) in DCM (1.7 mL). After 6 days, the reaction mixture was concentrated under reduced pressure and ammonia (7N in MeOH, 1.8 mL, 126 mmol) was added to the crude material. After completion, the reaction mixture was concentrated under reduce pressure. MeOH was added, the solids were filtered off. Purification of the filtrate (preparative HPLC, METHOD A followed by METHOD E) afforded the title compound. MS (ESI): mass calcd. for $C_{23}H_{17}F_6N_5O$, 493.1; m/z found, 494.2 [M+H]+.

Example 372: [(7S)-3-(3,5-Difluorophenyl)-2,7-dimethyl-5,7-dihydro-4H-pyrazolo[3,4-c]pyridin-6-yl]-[1-(2-fluoranylethyl)pyrrolo[2,3-b]pyridin-4-yl]methanone

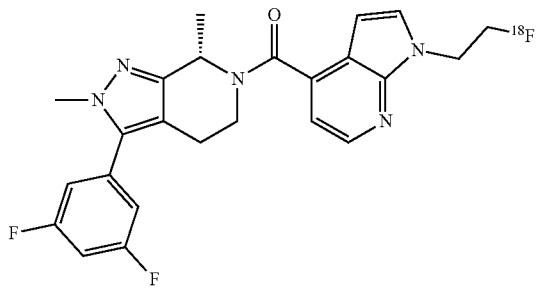 [SMILES: C[C@H]1c2nn(C)c(-c3cc(F)cc(F)c3)c2CCN1C(=O)c1ccnc2c1ccn2CC[18F]]

The title compound was prepared in a manner analogous to Example 140, using (S)-2-(4-(3-(3,5-difluorophenyl)-2,7-dimethyl-4,5,6,7-tetrahydro-2H-pyrazolo[3,4-c]pyridine-6-carbonyl)-1H-pyrrolo[2,3-b]pyridin-1-yl)ethyl 4-methylbenzenesulfonate (Intermediate 131) instead of (S)-2-(3-(3-(3,5-difluorophenyl)-2,7-dimethyl-4,5,6,7-tetrahydro-2H-pyrazolo[3,4-c]pyridine-6-carbonyl)phenoxy)ethyl 4-methylbenzenesulfonate in Step B.

Example 373: [(7S)-2,7-Dimethyl-3-(3,4,5-trifluorophenyl)-5,7-dihydro-4H-pyrazolo[3,4-c]pyridin-6-yl]-(1H-pyrrolo[2,3-b]pyridin-3-yl)methanone

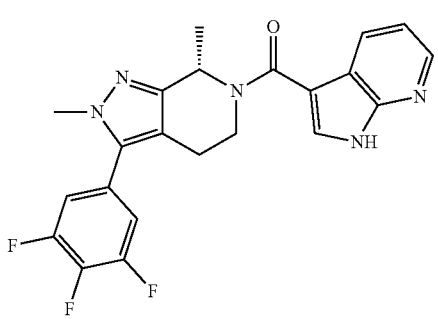 [SMILES: C[C@H]1c2nn(C)c(-c3cc(F)c(F)c(F)c3)c2CCN1C(=O)c1c[nH]c2ncccc12]

The title compound was prepared in a manner analogous to Example 288, using 1H-pyrrolo[2,3-b]pyridine-3-carboxylic acid instead of 2-fluoro-6-(2H-1,2,3-triazol-2-yl)benzoic acid and DMF instead of DCM. MS (ESI): mass calcd. for $C_{22}H_{18}F_3N_5O$, 425.1; m/z found, 426.2 [M+H]+. 1H NMR (500 MHz, DMSO-$d_6$) δ 12.18 (s, 1H), 8.29 (dd, J=4.7, 1.6 Hz, 1H), 8.10 (dd, J=7.9, 1.6 Hz, 1H), 7.87 (s, 1H), 7.60-7.52 (m, 2H), 7.16 (dd, J=7.9, 4.7 Hz, 1H), 5.58-5.44 (m, 1H), 4.43-4.27 (m, 1H), 3.80 (s, 3H), 2.98-2.86 (m, 1H), 1.51 (d, J=6.8 Hz, 3H). (Fractions of Hs that may overlap with DMSO and water are not reported).

Example 374: [(7S)-2,7-Dimethyl-3-(3,4,5-trifluorophenyl)-5,7-dihydro-4H-pyrazolo[3,4-c]pyridin-6-yl]-(5-fluoro-1H-pyrrolo[2,3-b]pyridin-3-yl)methanone

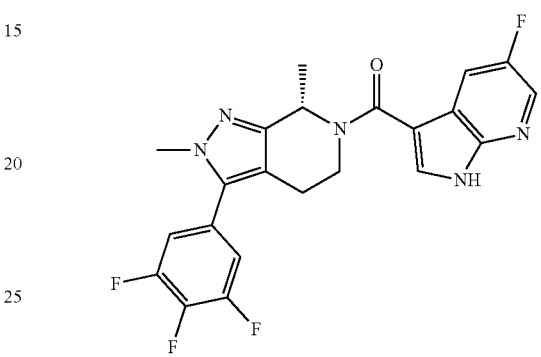

The title compound was prepared in a manner analogous to Example 288, using 5-fluoro-1H-pyrrolo[2,3-b]pyridine-3-carboxylic acid instead of 2-fluoro-6-(2H-1,2,3-triazol-2-yl)benzoic acid and DMF instead of DCM. MS (ESI): mass calcd. for $C_{22}H_{17}F_4N_5O$, 443.1; m/z found, 444.2 [M+H]+. 1H NMR (500 MHz, DMSO-$d_6$) δ 12.38 (s, 1H), 8.31-8.27 (m, 1H), 7.99 (s, 1H), 7.90 (dd, J=9.4, 2.8 Hz, 1H), 7.60-7.51 (m, 2H), 5.58-5.45 (m, 1H), 4.45-4.29 (m, 1H), 3.80 (s, 3H), 3.01-2.87 (m, 1H), 2.47-2.40 (m, 1H), 1.51 (d, J=6.8 Hz, 3H).

Example 375: [(7S)-2,7-Dimethyl-3-(3,4,5-trifluorophenyl)-5,7-dihydro-4H-pyrazolo[3,4-c]pyridin-6-yl]-(2-methyl-1H-pyrrolo[2,3-b]pyridin-3-yl)methanone

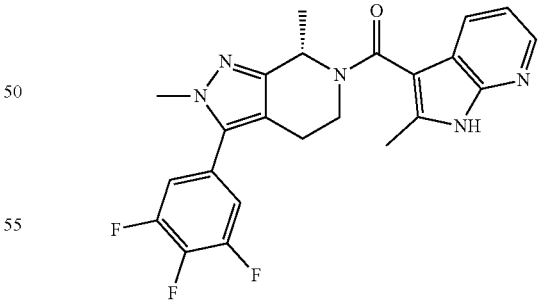

The title compound was prepared in a manner analogous to Example 288, using 2-methyl-1H-pyrrolo[2,3-b]pyridine-3-carboxylic acid instead of 2-fluoro-6-(2H-1,2,3-triazol-2-yl)benzoic acid and DMF instead of DCM. MS (ESI): mass calcd. for $C_{23}H_{20}F_3N_5O$, 439.2; m/z found, 440.2 [M+H]+. 1H NMR (500 MHz, DMSO-$d_6$) δ 11.93 (s, 1H), 8.18 (dd, J=4.7, 1.6 Hz, 1H), 7.74-7.64 (m, 1H), 7.59-7.49 (m, 2H), 7.08 (dd, J=7.9, 4.7 Hz, 1H), 5.53 (s, 1H), 4.07 (s, 1H), 3.80

(s, 3H), 2.72-2.62 (m, 1H), 2.44-2.32 (m, 4), 1.44 (d, J=6.8 Hz, 3H). (Fractions of Hs that may overlap with DMSO and water are not reported).

Example 376: [(7S)-2,7-Dimethyl-3-(3,4,5-trifluorophenyl)-5,7-dihydro-4H-pyrazolo[3,4-c]pyridin-6-yl]-(1H-pyrrolo[2,3-c]pyridin-7-yl)methanone

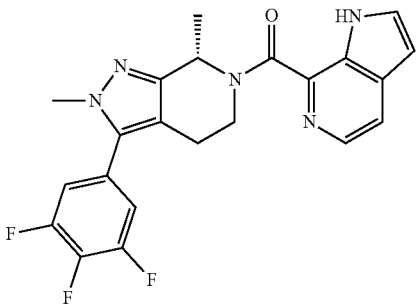 [SMILES: C[C@H]1c2nn(C)c(-c3cc(F)c(F)c(F)c3)c2CCN1C(=O)c1nccc2cc[nH]c12]

The title compound was prepared in a manner analogous to Example 288, using 1H-pyrrolo[2,3-c]pyridine-7-carboxylic acid instead of 2-fluoro-6-(2H-1,2,3-triazol-2-yl)benzoic acid, and 2,4,6-tripropyl-1,3,5,2,4,6-trioxatriphosphorinane-2,4,6-trioxide (T3P©) and DMF instead of HATU and DCM, respectively. MS (ESI): mass calcd. for $C_{22}H_{18}F_3N_5O$, 425.1; m/z found, 426.1 [M+H]$^+$.

Example 377: [(7S)-2,7-Dimethyl-3-(3,4,5-trifluorophenyl)-5,7-dihydro-4H-pyrazolo[3,4-c]pyridin-6-yl]-(3-fluoropyrazolo[1,5-a]pyridin-4-yl)methanone

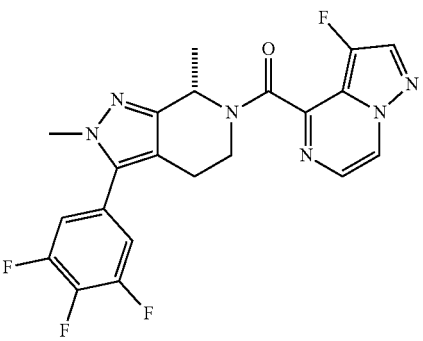 [SMILES: C[C@H]1c2nn(C)c(-c3cc(F)c(F)c(F)c3)c2CCN1C(=O)c1nccn2ncc(F)c12]

The title compound was prepared in a manner analogous to Example 288, using 3-fluoropyrazolo[1,5-a]pyridine-4-carboxylic acid (Intermediate 69) instead of 2-fluoro-6-(2H-1,2,3-triazol-2-yl)benzoic acid. MS (ESI): mass calcd. for $C_{22}H_{17}F_4N_5O$, 443.1; m/z found, 444.1 [M+H]$^+$. $^1$H NMR (500 MHz, Chloroform-d) δ 8.32 (d, J=7.0 Hz, 1H), 7.90-7.77 (m, 1H), 7.11-7.03 (m, 1H), 7.02-6.92 (m, 2H), 6.82-6.73 (m, 1H), 5.94 (q, J=6.7 Hz, 0.58H), 5.03-4.82 (m, 0.76H), 3.89-3.74 (m, 3H), 3.74-3.65 (m, 0.64H), 3.35 (t, J=14.3 Hz, 0.58H), 3.18-3.03 (m, 0.37H), 2.91-2.78 (m, 0.38H), 2.67-2.45 (m, 1H), 2.32 (d, J=14.7 Hz, 0.58H), 1.64 (d, J=6.7 Hz, 1.84H), 1.46 (d, J=6.1 Hz, 1.15H).

Example 378: [(7S)-2,7-Dimethyl-3-(3,4,5-trifluorophenyl)-5,7-dihydro-4H-pyrazolo[3,4-c]pyridin-6-yl]-(3-fluoropyrazolo[1,5-a]pyridin-5-yl)methanone

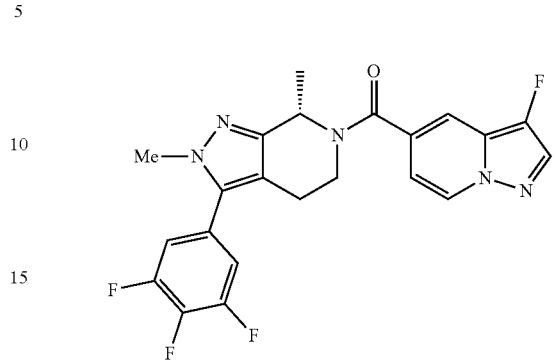

The title compound was prepared in a manner analogous to Example 288, using 3-fluoropyrazolo[1,5-a]pyridine-5-carboxylic acid (Intermediate 70) instead of 2-fluoro-6-(2H-1,2,3-triazol-2-yl)benzoic acid. MS (ESI): mass calcd. for $C_{22}H_{17}F_4N_5O$, 443.1; m/z found, 444.1 [M+H]$^+$. $^1$H NMR (500 MHz, DMSO-d$_6$) δ 8.70-8.61 (m, 1H), 8.20 (d, J=3.5 Hz, 1H), 7.77 (dd, J=1.8, 1.1 Hz, 1H), 7.60-7.48 (m, 2H), 6.90 (d, J=7.2 Hz, 1H), 5.56 (s, 1H), 4.72 (d, J=112.4 Hz, 1H), 3.90-3.62 (m, 4H), 2.86 (s, 1H), 2.42-2.32 (m, 1H), 1.48 (d, J=6.8 Hz, 3H).

Example 379: (3-Bromopyrazolo[1,5-a]pyridin-4-yl)-[(7S)-2,7-dimethyl-3-(3,4,5-trifluorophenyl)-5,7-dihydro-4H-pyrazolo[3,4-c]pyridin-6-yl]methanone

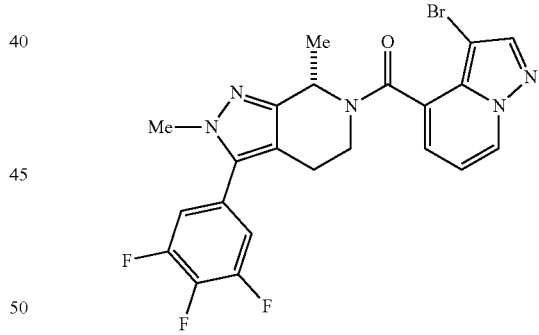

The title compound was prepared in a manner analogous to Example 288, using 3-bromopyrazolo[1,5-a]pyridine-4-carboxylic acid instead of 2-fluoro-6-(2H-1,2,3-triazol-2-yl)benzoic acid. MS (ESI): mass calcd. for $C_{22}H_{17}BrF_3N_5O$, 503.1; m/z found, 504.0 [M+H]$^+$. $^1$H NMR (500 MHz, Chloroform-d) δ 8.48 (d, J=7.0 Hz, 1H), 8.02-7.86 (m, 1H), 7.20-7.09 (m, 1H), 7.03-6.90 (m, 2H), 6.89-6.76 (m, 1H), 6.01-5.90 (m, 0.63H), 5.08-4.93 (m, 0.49H), 4.66 (q, J=6.7 Hz, 0.25H), 3.87-3.72 (m, 3H), 3.63 (dd, J=14.0, 4.6 Hz, 0.24H), 3.52 (dd, J=13.9, 4.8 Hz, 0.38H), 3.40-3.28 (m, 0.62H), 3.20-3.05 (m, 0.37H), 3.01-2.71 (m, 0.61H), 2.63-2.47 (m, 0.77H), 2.36-2.28 (m, 0.38H), 2.22-2.15 (m, 0.23H), 1.71 (d, J=6.8 Hz, 1.19H), 1.65 (d, J=6.8 Hz, 0.79H), 1.49-1.40 (m, 1.16H).

Example 380: [(7S)-2,7-Dimethyl-3-(3,4,5-trifluorophenyl)-5,7-dihydro-4H-pyrazolo[3,4-c]pyridin-6-yl]-(3-methylpyrazolo[1,5-a]pyridin-4-yl)methanone

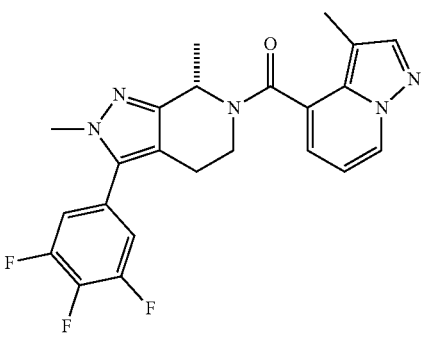 [SMILES: Cc1cnn2cccc(C(=O)N3CCc4c(nn(C)c4-c4cc(F)c(F)c(F)c4)[C@@H]3C)c12]

To a suspension of (S)-(3-bromopyrazolo[1,5-a]pyridin-4-yl)(2,7-dimethyl-3-(3,4,5-trifluorophenyl)-2,4,5,7-tetrahydro-6H-pyrazolo[3,4-c]pyridin-6-yl)methanone (Example 379) (81 mg, 0.16 mmol), potassium carbonate (67 mg, 0.48 mmol), and Pd(PPh$_3$)$_4$ (19 mg, 16.1 μmol), in DMF (0.36 mL) was added trimethylboroxine (51 μL, 0.36 mmol). The headspace was purged of air under vacuum and then backfilled with nitrogen three times, then the reaction heated to 100° C. for 16 h. After cooling to room temperature, EtOAc and H$_2$O were added, then the aqueous layer separated and extracted with EtOAc (×3). The combined organics were washed with brine (×5), dried over Na$_2$SO$_4$, filtered, and concentrated in vacuo. The material was purified by SFC (stationary phase: Chiralcel OZ, 5 μm 250×21 mm, mobile phase: 38% MeOH with 0.2% TEA, 62% CO$_2$) to afford the title compound in 20% yield. MS (ESI): mass calcd. for C$_{23}$H$_{20}$F$_3$N$_5$O, 439.2; m/z found, 440.1 [M+H]$^+$. $^1$H NMR (600 MHz, Chloroform-d) δ 8.48-8.41 (m, 1H), 7.86-7.68 (m, 1H), 7.10-6.83 (m, 3H), 6.80-6.64 (m, 1H), 5.95 (m, 0.59H), 5.30 (s, 0.21H), 5.12-4.97 (m, 0.51H), 4.73 (m, 0.29H), 3.91-3.70 (m, 3.20H), 3.62 (dd, J=14.0, 5.0 Hz, 0.43H), 3.36-3.21 (m, 0.59H), 3.09 (m, 0.39H), 2.81 (m, 0.38H), 2.70-2.39 (m, 0.93H), 2.38-2.21 (m, 2.17H), 2.14 (s, 0.47H), 2.04 (s, 0.96H), 1.69-1.61 (m, 1.78H), 1.48 (d, J=6.5 Hz, 0.93H), 1.32 (d, J=6.7 Hz, 0.31H).

Example 381: [(7S)-2,7-Dimethyl-3-(3,4,5-trifluorophenyl)-5,7-dihydro-4H-pyrazolo[3,4-c]pyridin-6-yl]-pyrazolo[1,5-a]pyridin-3-yl-methanone.TFA salt

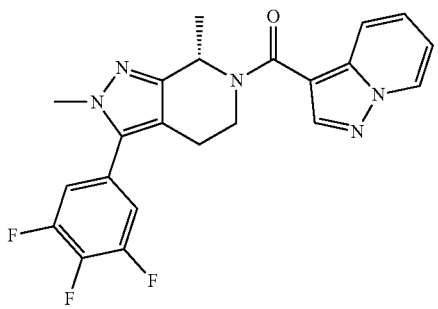 [SMILES: C[C@H]1c2nn(C)c(-c3cc(F)c(F)c(F)c3)c2CCN1C(=O)c1cnn2ccccc12]

The title compound was prepared in a manner analogous to Example 288, using pyrazolo[1,5-a]pyridine-3-carboxylic acid instead of 2-fluoro-6-(2H-1,2,3-triazol-2-yl)benzoic acid. MS (ESI): mass calcd. for C$_{22}$H$_{18}$F$_3$N$_5$O, 425.1; m/z found, 426.1 [M+H]$^+$. $^1$H NMR (500 MHz, DMSO-d$_6$) δ 8.82-8.78 (m, 1H), 8.33 (s, 1H), 7.94-7.90 (m, 1H), 7.61-7.53 (m, 2H), 7.47-7.41 (m, 1H), 7.07 (td, J=6.9, 1.4 Hz, 1H), 5.54-5.43 (m, 1H), 4.40-4.28 (m, 1H), 3.80 (s, 3H), 3.37-3.24 (m, 1H), 3.06-2.92 (m, 1H), 2.48-2.43 (m, 1H), 1.58-1.46 (m, 3H).

Example 382: [(7S)-2,7-Dimethyl-3-(3,4,5-trifluorophenyl)-5,7-dihydro-4H-pyrazolo[3,4-c]pyridin-6-yl]-(2-methylpyrazolo[1,5-a]pyridin-3-yl)methanone

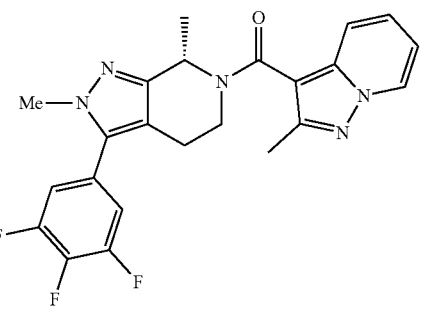

The title compound was prepared in a manner analogous to Example 288, using 2-methylpyrazolo[1,5-a]pyridine-3-carboxylic acid instead of 2-fluoro-6-(2H-1,2,3-triazol-2-yl) benzoic acid. MS (ESI): mass calcd. for C$_{23}$H$_{20}$F$_3$N$_5$O, 439.2; m/z found, 440.1 [M+H]$^+$. $^1$H NMR (500 MHz, DMSO-d$_6$) δ 8.70-8.60 (m, 1H), 7.60-7.51 (m, 2H), 7.45 (d, J=8.9 Hz, 1H), 7.37-7.30 (m, 1H), 7.00-6.90 (m, 1H), 4.08 (q, J=5.2 Hz, 1H), 3.81 (s, 3H), 3.17 (d, J=4.8 Hz, 2H), 2.76-2.63 (m, 1H), 2.40-2.35 (m, 4H), 1.45 (d, J=6.8 Hz, 3H).

Example 383: [(7S)-2,7-Dimethyl-3-(3,4,5-trifluorophenyl)-5,7-dihydro-4H-pyrazolo[3,4-c]pyridin-6-yl]-(5-methylpyrazolo[1,5-a]pyridin-3-yl)methanone

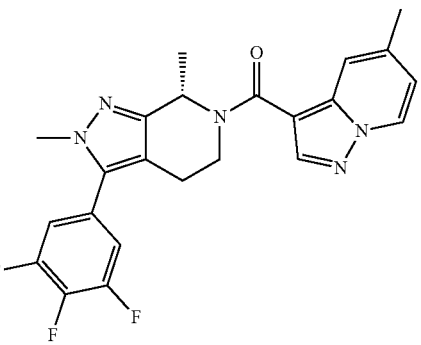

The title compound was prepared in a manner analogous to Example 288, using 5-methylpyrazolo[1,5-a]pyridine-3-carboxylic acid instead of 2-fluoro-6-(2H-1,2,3-triazol-2-yl) benzoic acid. MS (ESI): mass calcd. for C$_{23}$H$_{20}$F$_3$N$_5$O, 439.2; m/z found, 440.1 [M+H]$^+$. $^1$H NMR (500 MHz, DMSO-d$_6$) δ 8.69-8.66 (m, 1H), 8.25 (s, 1H), 7.72-7.70 (m, 1H), 7.60-7.53 (m, 2H), 6.91 (dd, J=7.0, 2.0 Hz, 1H), 5.54-5.42 (m, 1H), 4.41-4.26 (m, 1H), 3.80 (s, 3H), 3.04-

Example 384: [(7S)-2,7-Dimethyl-3-(3,4,5-trifluorophenyl)-5,7-dihydro-4H-pyrazolo[3,4-c]pyridin-6-yl]-(6-fluoropyrazolo[1,5-a]pyridin-3-yl)methanone

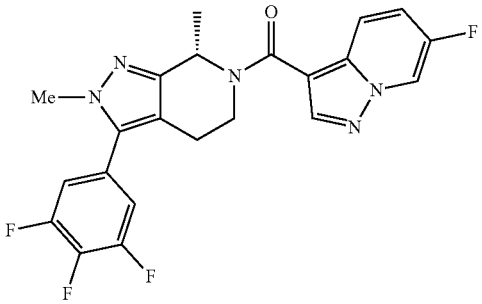 [SMILES: C[C@H]1c2nn(C)c(-c3cc(F)c(F)c(F)c3)c2CCN1C(=O)c1cnn2cc(F)ccc12]

The title compound was prepared in a manner analogous to Example 288, using 6-fluoropyrazolo[1,5-a]pyridine-3-carboxylic acid instead of 2-fluoro-6-(2H-1,2,3-triazol-2-yl)benzoic acid. MS (ESI): mass calcd. for $C_{22}H_{17}F_4N_5O$, 443.1; m/z found, 444.1 [M+H]$^+$. $^1$H NMR (500 MHz, DMSO-d$_6$) δ 9.18-9.09 (m, 1H), 8.36 (s, 1H), 8.03-7.85 (m, 1H), 7.63-7.48 (m, 3H), 5.49 (s, 1H), 4.34 (s, 1H), 3.80 (s, 3H), 2.99 (s, 1H), 2.49-2.29 (m, 2H), 1.53 (d, J=6.7 Hz, 3H).

Example 385: (2-Cyclopropyl-7-methyl-pyrazolo[1,5-a]pyridin-3-yl)-[(7S)-2,7-dimethyl-3-(3,4,5-trifluorophenyl)-5,7-dihydro-4H-pyrazolo[3,4-c]pyridin-6-yl]methanone

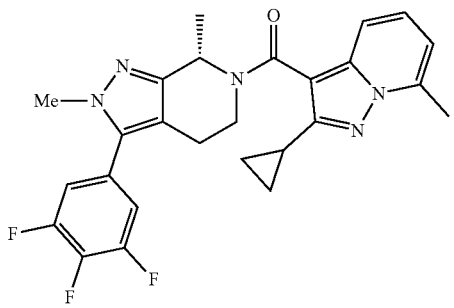 [SMILES: Cc1cccc2c(C(=O)N3CCc4c(nn(C)c4-c4cc(F)c(F)c(F)c4)[C@@H]3C)c(C3CC3)nn12]

The title compound was prepared in a manner analogous to Example 288, using 2-cyclopropyl-7-methylpyrazolo[1,5-a]pyridine-3-carboxylic acid (Intermediate 83) instead of 2-fluoro-6-(2H-1,2,3-triazol-2-yl)benzoic acid. MS (ESI): mass calcd. for $C_{26}H_{24}F_3N_5O$, 479.2; m/z found, 480.1 [M+H]$^+$. $^1$H NMR (500 MHz, DMSO-d$_6$) δ 7.54 (dd, J=8.7, 6.6 Hz, 2H), 7.37-7.20 (m, 2H), 6.89-6.78 (m, 1H), 5.55 (s, 1H), 4.16-4.01 (m, 1H), 3.80 (s, 3H), 3.24-3.18 (m, 1H), 2.62 (s, 4H), 2.44-2.28 (m, 1H), 2.15-1.94 (m, 1H), 1.45 (d, J=6.6 Hz, 3H), 1.04-0.93 (m, 4H).

Example 386: [(7S)-2,7-Dimethyl-3-(3,4,5-trifluorophenyl)-5,7-dihydro-4H-pyrazolo[3,4-c]pyridin-6-yl]-(7-methylpyrazolo[1,5-a]pyridin-3-yl)methanone

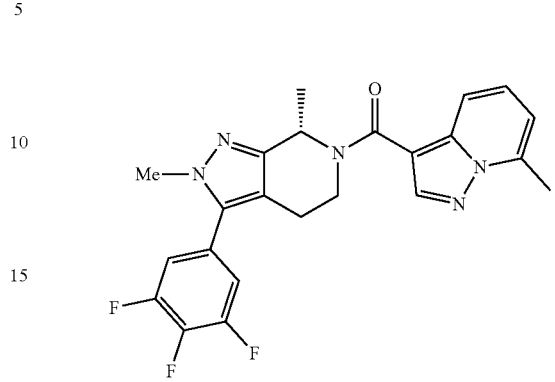

The title compound was prepared in a manner analogous to Example 288, using 7-methylpyrazolo[1,5-a]pyridine-3-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (500 MHz, DMSO-d$_6$) δ 8.35 (s, 1H), 7.88-7.75 (m, 1H), 7.63-7.51 (m, 2H), 7.39 (dd, J=8.9, 6.9 Hz, 1H), 7.03-6.94 (m, 1H), 5.60-5.42 (m, 1H), 4.45-4.25 (m, 1H), 3.80 (s, 3H), 3.29-3.16 (m, 1H), 3.05-2.89 (m, 1H), 2.73 (s, 3H), 2.49-2.41 (m, 1H), 1.53 (d, J=6.7 Hz, 3H).

Example 387: [(7S)-2,7-Dimethyl-3-(3,4,5-trifluorophenyl)-5,7-dihydro-4H-pyrazolo[3,4-c]pyridin-6-yl]-(7-methoxypyrazolo[1,5-a]pyridin-3-yl)methanone

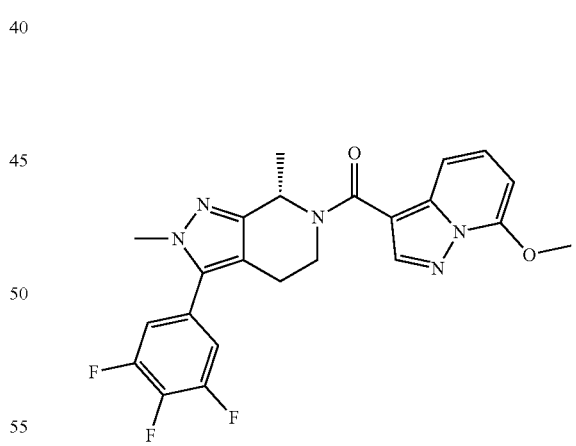

The title compound was prepared in a manner analogous to Example 288, using 7-methoxypyrazolo[1,5-a]pyridine-3-carboxylic acid instead of 2-fluoro-6-(2H-1,2,3-triazol-2-yl)benzoic acid. MS (ESI): mass calcd. for $C_{23}H_{20}F_3N_5O_2$, 455.2; m/z found, 456.2 [M+H]$^+$. $^1$H NMR (500 MHz, Chloroform-d) δ 8.15 (s, 1H), 7.68 (dd, J=8.8, 1.1 Hz, 1H), 7.32 (dd, J=8.9, 7.5 Hz, 1H), 7.02-6.95 (m, 2H), 6.26-6.22 (m, 1H), 5.76-5.61 (m, 1H), 4.66-4.50 (m, 1H), 4.18 (s, 3H), 3.81 (s, 3H), 3.38-3.19 (m, 1H), 2.91-2.81 (m, 1H), 2.54-2.45 (m, 1H), 1.67 (d, J=6.8 Hz, 3H).

Example 388: [(7S)-2,7-Dimethyl-3-(3,4,5-trifluorophenyl)-5,7-dihydro-4H-pyrazolo[3,4-c]pyridin-6-yl]-(6-methoxypyrazolo[1,5-a]pyridin-3-yl)methanone.TFA salt

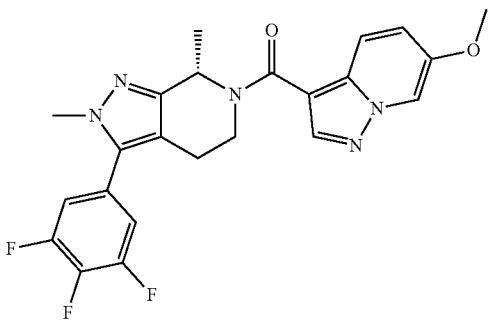 [SMILES: COc1ccc2c(C(=O)N3CCc4c(nn(C)c4-c4cc(F)c(F)c(F)c4)[C@@H]3C)cnn2c1]

The title compound was prepared in a manner analogous to Example 288, using 6-methoxypyrazolo[1,5-a]pyridine-3-carboxylic acid instead instead of 2-fluoro-6-(2H-1,2,3-triazol-2-yl)benzoic acid. MS (ESI): mass calcd. for $C_{23}H_{20}F_3N_5O_2$, 455.2; m/z found, 456.1 [M+H]$^+$. $^1$H NMR (500 MHz, DMSO-d$_6$) δ 8.53-8.51 (m, 1H), 8.23 (s, 1H), 7.86-7.82 (m, 1H), 7.60-7.53 (m, 2H), 7.25 (dd, J=9.6, 2.2 Hz, 1H), 5.53-5.43 (m, 1H), 4.42-4.31 (m, 1H), 3.85 (s, 3H), 3.80 (s, 3H), 3.37-3.22 (m, 1H), 3.05-2.92 (m, 1H), 2.48-2.42 (m, 1H), 1.59-1.46 (m, 3H).

Example 389: [(7S)-2,7-Dimethyl-3-(3,4,5-trifluorophenyl)-5,7-dihydro-4H-pyrazolo[3,4-c]pyridin-6-yl]-(5-methoxypyrazolo[1,5-a]pyridin-3-yl)methanone

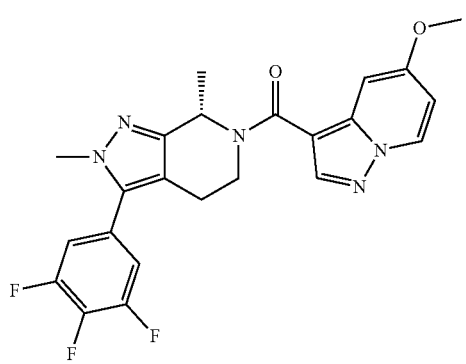 [SMILES: COc1ccn2ncc(C(=O)N3CCc4c(nn(C)c4-c4cc(F)c(F)c(F)c4)[C@@H]3C)c2c1]

The title compound was prepared in a manner analogous to Example 288, using 5-methoxypyrazolo[1,5-a]pyridine-3-carboxylic acid instead instead of 2-fluoro-6-(2H-1,2,3-triazol-2-yl)benzoic acid. MS (ESI): mass calcd. for $C_{23}H_{20}F_3N_5O_2$, 455.2; m/z found, 456.2 [M+H]$^+$. $^1$H NMR (500 MHz, DMSO-d$_6$) δ 8.65 (d, J=7.5 Hz, 1H), 8.23 (s, 1H), 7.61-7.52 (m, 2H), 7.25-7.21 (m, 1H), 6.74 (dd, J=7.5, 2.8 Hz, 1H), 5.51-5.42 (m, 1H), 4.42-4.31 (m, 1H), 3.86 (s, 3H), 3.80 (s, 3H), 3.06-2.94 (m, 1H), 1.58-1.46 (m, 3H). (Fractions of H's that overlap with DMSO and water may not be reported)

Example 390: [(7S)-2,7-Dimethyl-3-(3,4,5-trifluorophenyl)-5,7-dihydro-4H-pyrazolo[3,4-c] pyridin-6-yl]-(4-methoxypyrazolo[1,5-a]pyridin-3-yl)methanone

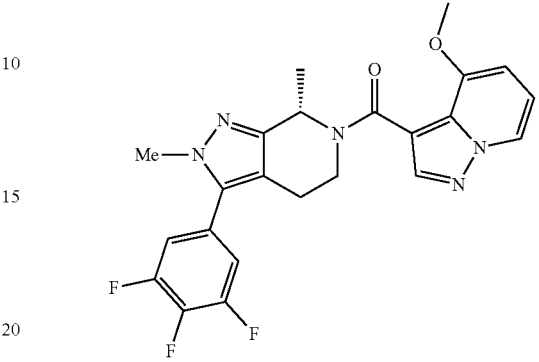

The title compound was prepared in a manner analogous to Example 288, using 4-methoxypyrazolo[1,5-a]pyridine-3-carboxylic acid instead of 2-fluoro-6-(2H-1,2,3-triazol-2-yl)benzoic acid. MS (ESI): mass calcd. for $C_{23}H_{20}F_3N_5O$, 455.2; m/z found, 456.1 [M+H]$^+$. $^1$H NMR (500 MHz, DMSO-d$_6$) δ 8.36 (d, J=6.8 Hz, 1H), 8.02 (s, 1H), 7.61-7.42 (m, 2H), 7.00-6.58 (m, 2H), 5.81-5.50 (m, 1H), 4.16-3.95 (m, 1H), 3.92-3.58 (m, 6H), 3.57-3.41 (m, 1H), 3.21-3.09 (m, 2H), 1.54-1.21 (m, 3H).

Example 391: [(7S)-2,7-Dimethyl-3-(3,4,5-trifluorophenyl)-5,7-dihydro-4H-pyrazolo[3,4-c]pyridin-6-yl]-imidazo[1,2-a]pyridin-6-yl-methanone

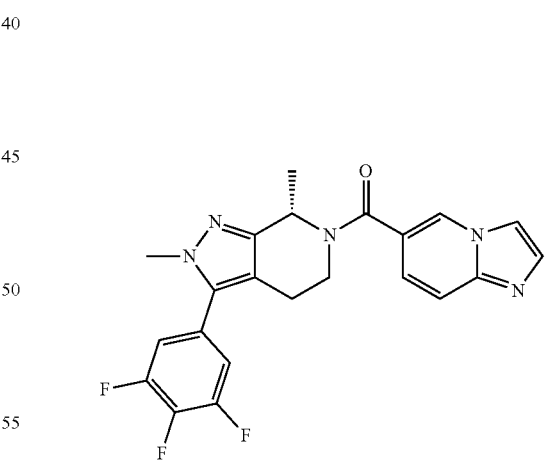

The title compound was prepared in a manner analogous to Example 288, using imidazo[1,2-a]pyridine-6-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.2 [M+H]$^+$. $^1$H NMR (500 MHz, Chloroform-d) δ 8.38 (s, 1H), 7.71 (d, J=1.0 Hz, 1H), 7.69-7.60 (m, 2H), 7.24-7.20 (m, 1H), 7.01-6.93 (m, 2H), 3.81 (s, 3H), 3.28 (brs, 1H), 2.79 (brs, 1H), 2.50-2.42 (m, 1H), 1.65-1.57 (m, 5H).

Example 392: [(7S)-2,7-Dimethyl-3-(3,4,5-trifluoro-phenyl)-5,7-dihydro-4H-pyrazolo[3,4-c]pyridin-6-yl]-imidazo[1,2-a]pyridin-8-yl-methanone

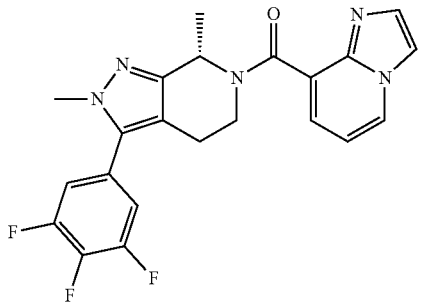 [SMILES: C[C@H]1c2nn(C)c(-c3cc(F)c(F)c(F)c3)c2CCN1C(=O)c1cccn2ccnc12]

The title compound was prepared in a manner analogous to Example 288, using imidazo[1,2-a]pyridine-8-carboxylic acid instead of 2-fluoro-6-(2H-1,2,3-triazol-2-yl)benzoic acid. MS (ESI): mass calcd. for $C_{22}H_{18}F_3N_5O$, 425.2; m/z found, 426.1 [M+H]$^+$. $^1$H NMR (400 MHz, DMSO-d$_6$) δ 8.69-8.56 (m, 1H), 8.08-7.98 (m, 1H), 7.63-7.46 (m, 3H), 7.28-7.18 (m, 1H), 6.96 (t, J=6.8 Hz, 1H), 5.66 (q, J=6.7 Hz, 1H), 4.85-4.55 (m, 1H), 3.86-3.69 (m, 3H), 3.25-3.00 (m, 1H), 2.83-2.63 (m, 1H), 2.33-2.14 (m, 1H), 1.42 (dd, J=68.2, 6.8 Hz, 3H).

Example 393: [(7S)-2,7-Dimethyl-3-(3,4,5-trifluoro-phenyl)-5,7-dihydro-4H-pyrazolo[3,4-c]pyridin-6-yl]-(7-fluoroimidazo[1,2-a]pyridin-3-yl)methanone

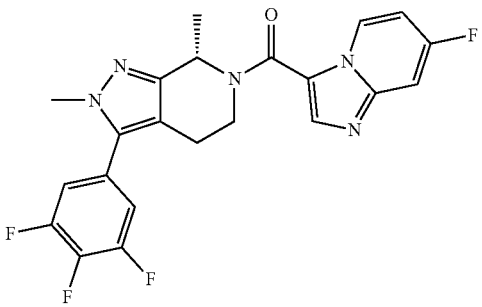 [SMILES: C[C@H]1c2nn(C)c(-c3cc(F)c(F)c(F)c3)c2CCN1C(=O)c1cnc2cc(F)ccn12]

The title compound was prepared in a manner analogous to Example 288, using 7-fluoroimidazo[1,2-a]pyridine-3-carboxylic acid (Intermediate 84) instead of 2-fluoro-6-(2H-1,2,3-triazol-2-yl)benzoic acid. MS (ESI): mass calcd. for $C_{22}H_{17}F_4N_5O$, 443.2; m/z found, 444.1 [M+H]$^+$. $^1$H NMR (400 MHz, DMSO-d$_6$) δ 9.01-8.90 (m, 1H), 8.09 (s, 1H), 7.66-7.47 (m, 3H), 7.25-7.02 (m, 1H), 5.60-4.39 (m, 3H), 3.85-3.73 (m, 3H), 3.48-3.34 (m, 1H), 3.15-2.95 (m, 1H), 1.56 (d, J=6.7 Hz, 3H).

Example 394: [(7S)-2,7-Dimethyl-3-(3,4,5-trifluoro-phenyl)-5,7-dihydro-4H-pyrazolo[3,4-c] pyridin-6-yl]-(2-methylimidazo[1,2-a]pyridin-5-yl)methanone

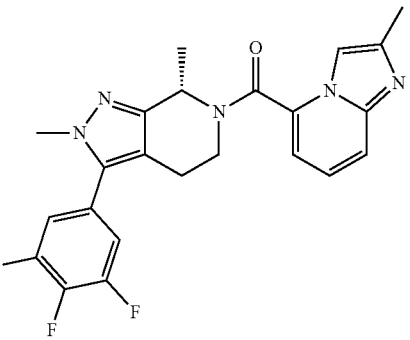

The title compound was prepared in a manner analogous to Example 288, using 2-methylimidazo[1,2-a]pyridine-5-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (400 MHz, DMSO-d$_6$) δ 7.61-7.45 (m, 4H), 7.32-7.21 (m, 1H), 7.00 (dd, J=6.9, 1.1 Hz, 1H), 5.70-5.50 (m, 1H), 4.96-4.16 (m, 1H), 3.91-3.55 (m, 4H), 2.96-2.73 (m, 1H), 2.44-2.23 (m, 4H), 1.55 (s, 3H).

Example 395: [(7S)-3-(3-Chloro-5-methoxy-phenyl)-2,7-dimethyl-5,7-dihydro-4H-pyrazolo[3,4-c] pyridin-6-yl]-(2-methylimidazo[1,2-a] pyridin-3-yl) methanone

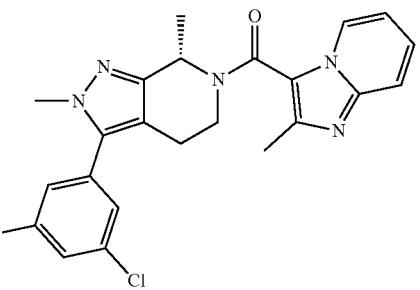

The title compound was prepared in a manner analogous to Example 288, using (S)-3-(3-chloro-5-methoxyphenyl)-2,7-dimethyl-4,5,6,7-tetrahydro-2H-pyrazolo[3,4-c]pyridine (Intermediate 41) instead of (S)-2,7-dimethyl-3-(3,4,5-trifluorophenyl)-4,5,6,7-tetrahydro-2H-pyrazolo[3,4-c] pyridine (Intermediate 40) and 2-methylimidazo[1,2-a] pyridine-3-carboxylic acid instead of 2-fluoro-6-(2H-1,2,3-triazol-2-yl)benzoic acid. MS (ESI): mass calcd. for $C_{24}H_{24}ClN_5O_2$, 449.2; m/z found, 450.1 [M+H]$^+$. $^1$H NMR (500 MHz, DMSO-d$_6$) δ 8.34 (d, J=6.9 Hz, 1H), 7.56 (dt, J=9.0, 1.2 Hz, 1H), 7.41-7.30 (m, 1H), 7.15-7.08 (m, 2H), 7.03-6.91 (m, 2H), 5.68-5.47 (m, 1H), 4.17-3.94 (m, 1H), 3.89-3.71 (m, 6H), 3.47-3.36 (m, 1H), 2.71 (d, J=12.0 Hz, 1H), 2.46-2.32 (m, 4H), 1.49 (d, J=6.8 Hz, 3H).

Example 396: [(7S)-3-(3-Fluoro-5-methyl-phenyl)-2,7-dimethyl-5,7-dihydro-4H-pyrazolo[3,4-c]pyridin-6-yl]-(2-methylimidazo[1,2-a]pyridin-3-yl)methanone

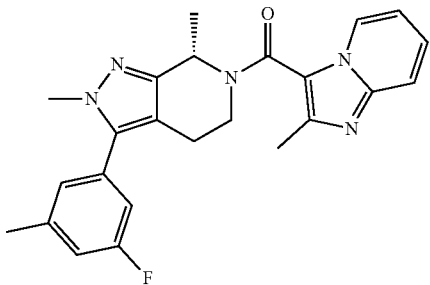 [SMILES: Cc1cc(F)cc(-c2c3c(nn2C)[C@H](C)N(C(=O)c2c(C)nc4ccccn24)CC3)c1]

The title compound was prepared in a manner analogous to Example 288, using (S)-3-(3-fluoro-5-methylphenyl)-2,7-dimethyl-4,5,6,7-tetrahydro-2H-pyrazolo[3,4-c]pyridine (Intermediate 42) instead of (S)-2,7-dimethyl-3-(3,4,5-trifluorophenyl)-4,5,6,7-tetrahydro-2H-pyrazolo[3,4-c]pyridine (Intermediate 40) and 2-methylimidazo[1,2-a]pyridine-3-carboxylic acid instead of 2-fluoro-6-(2H-1,2,3-triazol-2-yl)benzoic acid. MS (ESI): mass calcd. for $C_{24}H_{24}FN_5O$, 417.5; m/z found, 418.2 [M+H]$^+$. $^1$H NMR (500 MHz, DMSO-$d_6$) δ $^1$H NMR (400 MHz, DMSO-$d_6$) δ 8.39-8.28 (m, 1H), 7.61-7.50 (m, 1H), 7.37-7.29 (m, 1H), 7.21-7.06 (m, 3H), 7.03-6.90 (m, 1H), 5.68-5.50 (m, 1H), 4.14-3.95 (m, 1H), 3.80 (s, 3H), 3.46-3.34 (m, 1H), 2.69 (t, J=12.4 Hz, 1H), 2.47-2.41 (m, 1H), 2.39-2.33 (m, 6H), 1.49 (d, J=6.8 Hz, 3H).

Example 397: [(7S)-2,7-Dimethyl-3-(3,4,5-trifluorophenyl)-5,7-dihydro-4H-pyrazolo[3,4-c]pyridin-6-yl]-(2-methylimidazo[1,2-a]pyridin-3-yl)methanone

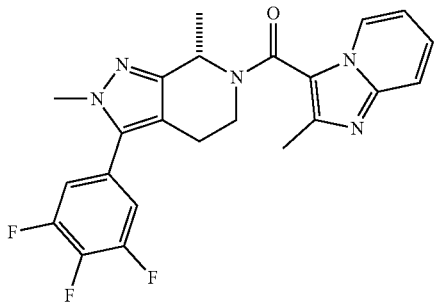 [SMILES: Cc1nc2ccccn2c1C(=O)N1CCc2c(nn(C)c2-c2cc(F)c(F)c(F)c2)[C@@H]1C]

The title compound was prepared in a manner analogous to Example 288, using 2-methylimidazo[1,2-a]pyridine-3-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (600 MHz, Chloroform-d) δ 8.38 (s, 1H), 7.56 (d, J=9.0 Hz, 1H), 7.26 (m, 1H), 6.97 (brs, 2H), 6.86 (t, J=6.1 Hz, 1H), 5.90 (brs, 1H), 4.89 (brs, 0.3H), 4.25 (brs, 0.78H), 3.84 (s, 3H), 3.42 (brs, 1H), 2.62 (m, 4.90H), 1.62 (s, 3H).

Example 398: [(7S)-2,7-Dimethyl-3-(3,4,5-trifluorophenyl)-5,7-dihydro-4H-pyrazolo[3,4-c]pyridin-6-yl]-(3-methylimidazo[1,2-a]pyridin-2-yl)methanone

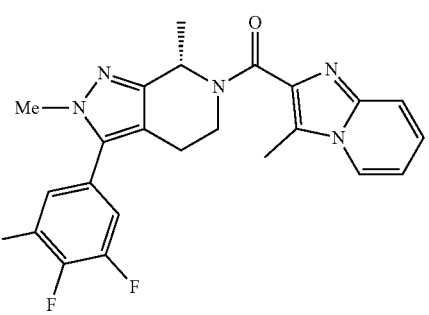

The title compound was prepared in a manner analogous to Example 288, using 3-methylimidazo[1,2-a]pyridine-2-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (500 MHz, DMSO-$d_6$) δ 8.33 (d, J=6.9 Hz, 1H), 7.66-7.49 (m, 3H), 7.41-7.27 (m, 1H), 7.10-6.98 (m, 1H), 5.98-5.58 (m, 1H), 4.82-4.65 (m, 1H), 3.88-3.69 (m, 3H), 3.10-2.67 (m, 2H), 2.58 (s, 3H), 2.45-2.34 (m, 1H), 1.58-1.42 (m, 3H).

Example 399: [(7S)-2,7-Dimethyl-3-(3,4,5-trifluorophenyl)-5,7-dihydro-4H-pyrazolo[3,4-c]pyridin-6-yl]-(7-methylimidazo[1,2-a]pyridin-3-yl)methanone

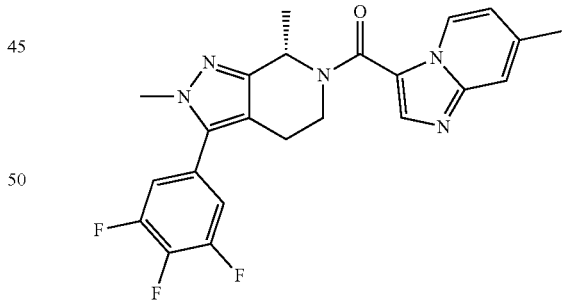

The title compound was prepared in a manner analogous to Example 288, using 7-methylimidazo[1,2-a]pyridine-3-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (400 MHz, DMSO-$d_6$) δ 8.84-8.80 (m, 1H), 8.02 (s, 1H), 7.62-7.53 (m, 2H), 7.52-7.49 (m, 1H), 6.95 (dd, J=7.2, 1.8 Hz, 1H), 5.51 (q, J=6.7 Hz, 1H), 4.49-4.40 (m, 1H), 3.81 (s, 3H), 3.12-2.97 (m, 1H), 2.42-2.39 (m, 3H), 1.55 (d, J=6.7 Hz, 3H). (Fractions of Hs that may overlap with DMSO and water are not reported).

Example 400: [(7S)-2,7-Dimethyl-3-(3,4,5-trifluoro-phenyl)-5,7-dihydro-4H-pyrazolo[3,4-c]pyridin-6-yl]-(6-methylimidazo[1,2-a]pyridin-3-yl)methanone

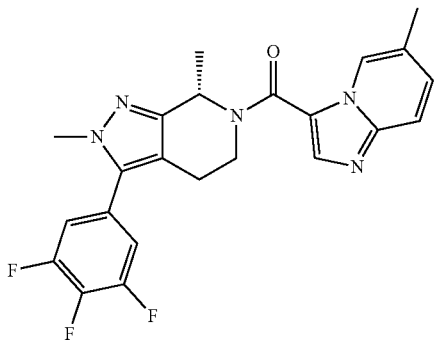 [SMILES: Cc1ccc2ncc(C(=O)N3CCc4c(nn(C)c4-c4cc(F)c(F)c(F)c4)[C@@H]3C)n2c1]

The title compound was prepared in a manner analogous to Example 288, using 6-methylimidazo[1,2-a]pyridine-3-carboxylic acid instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (500 MHz, DMSO-$d_6$) δ 8.76-8.68 (m, 1H), 8.03 (s, 1H), 7.67-7.53 (m, 3H), 7.32 (dd, J=9.2, 1.8 Hz, 1H), 5.57-5.45 (m, 1H), 4.51-4.38 (m, 1H), 3.81 (s, 3H), 3.20-2.99 (m, 2H), 2.49-2.45 (m, 1H), 2.37-2.30 (m, 3H), 1.56 (d, J=6.7 Hz, 3H).

Example 401: [(7S)-2,7-Dimethyl-3-(3,4,5-trifluoro-phenyl)-5,7-dihydro-4H-pyrazolo[3,4-c]pyridin-6-yl]-(5-methylimidazo[1,2-a]pyridin-3-yl)methanone

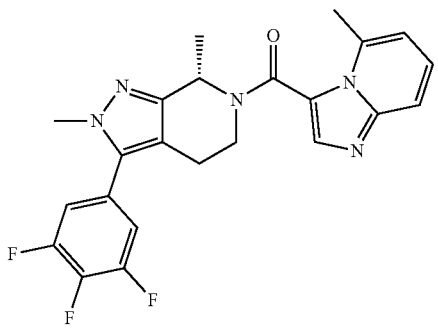 [SMILES: Cc1cccc2ncc(C(=O)N3CCc4c(nn(C)c4-c4cc(F)c(F)c(F)c4)[C@@H]3C)n12]

The title compound was prepared in a manner analogous to Example 288, using lithium (I) 5-methylimidazo[1,2-a]pyridine-3-carboxylate instead of 2-fluoro-6-(2H-1,2,3-triazol-2-yl)benzoic acid. MS (ESI): mass calcd. for $C_{23}H_{20}F_3N_5O$, 439.2; m/z found, 440.1 [M+H]$^+$. $^1$H NMR (500 MHz, DMSO-$d_6$) δ 7.91 (s, 1H), 7.63-7.53 (m, 3H), 7.36 (t, J=7.9 Hz, 1H), 6.90 (d, J=6.9 Hz, 1H), 5.58 (s, 1H), 4.09 (s, 1H), 3.80 (d, J=39.8 Hz, 3H), 3.21-2.72 (m, 3H), 2.54 (s, 2H), 2.40 (d, J=15.6 Hz, 1H), 1.51 (d, J=6.7 Hz, 3H).

Example 402: [(7S)-2,7-Dimethyl-3-(3,4,5-trifluoro-phenyl)-5,7-dihydro-4H-pyrazolo[3,4-c]pyridin-6-yl]-(7-fluoro-2-methyl-imidazo[1,2-a]pyridin-3-yl)methanone

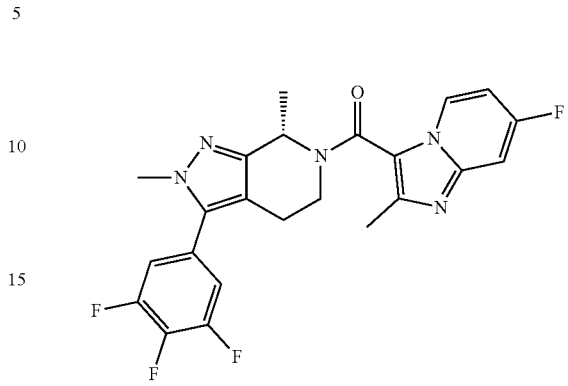

The title compound was prepared in a manner analogous to Example 288, using potassium 7-fluoro-2-methylimidazo[1,2-a]pyridine-3-carboxylate (Intermediate 85) instead of 2-fluoro-6-(2H-1,2,3-triazol-2-yl)benzoic acid. MS (ESI): mass calcd. for $C_{23}H_{19}F_4N_5O$, 457.2; m/z found, 458.1 [M+H]$^+$. $^1$H NMR (500 MHz, DMSO-$d_6$) δ 8.40 (dd, J=7.6, 5.8 Hz, 1H), 7.60-7.38 (m, 3H), 7.13-6.86 (m, 1H), 5.70-5.37 (m, 1H), 4.16-3.96 (m, 1H), 3.82 (s, 3H), 3.50-3.34 (m, 1H), 2.80-2.67 (m, 1H), 2.46-2.40 (m, 1H), 2.35 (s, 3H), 1.49 (d, J=6.8 Hz, 3H).

Example 403: (2,8-Dimethylimidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone

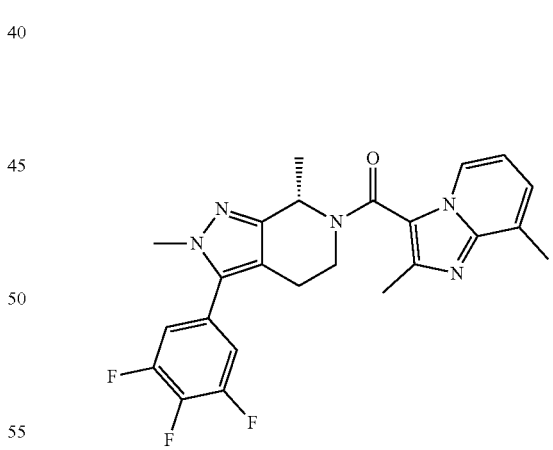

The title compound was prepared in a manner analogous to Example 288, using 2,8-dimethylimidazo[1,2-a]pyridine-3-carboxylic acid instead of 2-fluoro-6-(2H-1,2,3-triazol-2-yl)benzoic acid. MS (ESI): mass calcd. for $C_{24}H_{22}F_3N_5O$, 453.2; m/z found, 454.2 [M+H]$^+$. $^1$H NMR (400 MHz, DMSO-$d_6$) δ 8.17 (d, J=6.8 Hz, 1H), 7.55 (dd, J=8.7, 6.7 Hz, 2H), 7.16 (dt, J=6.9, 1.2 Hz, 1H), 6.88 (t, J=6.9 Hz, 1H), 5.57 (s, 1H), 4.17-3.94 (m, 1H), 3.81 (s, 3H), 3.46-3.35 (m, 1H), 2.81-2.63 (m, 1H), 2.49 (s, 3H), 2.37 (s, 4H), 1.48 (d, J=6.7 Hz, 3H).

Example 404: (2,7-Dimethylimidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone

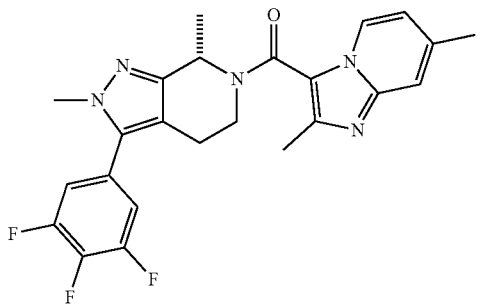 [SMILES: Cc1ccn2c(C(=O)N3CCc4c(nn(C)c4-c4cc(F)c(F)c(F)c4)[C@@H]3C)c(C)nc2c1]

The title compound was prepared in a manner analogous to Example 288, using 2,7-dimethylimidazo[1,2-a]pyridine-3-carboxylic acid instead of 2-fluoro-6-(2H-1,2,3-triazol-2-yl)benzoic acid. MS (ESI): mass calcd. for $C_{24}H_{22}F_3N_5O$, 453.2; m/z found, 454.2 [M+H]$^+$. $^1$H NMR (600 MHz, Chloroform-d) δ 8.28 (s, 1H), 7.29 (s, 1H), 6.97 (s, 2H), 6.69 (d, J=7.0 Hz, 1H), 6.22-4.02 (m, 1H), 3.84 (s, 3H), 3.41 (brs, 1H), 2.93-2.26 (m, 9H), 1.60 (brs, 3H).

Example 405: (2,6-Dimethylimidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone

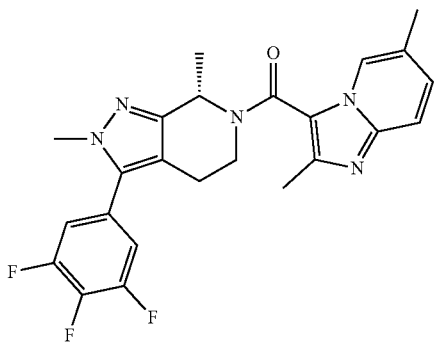 [SMILES: Cc1ccc2nc(C)c(C(=O)N3CCc4c(nn(C)c4-c4cc(F)c(F)c(F)c4)[C@@H]3C)n2c1]

The title compound was prepared in a manner analogous to Example 288, using 2,6-dimethylimidazo[1,2-a]pyridine-3-carboxylic acid instead of 2-fluoro-6-(2H-1,2,3-triazol-2-yl)benzoic acid. MS (ESI): mass calcd. for $C_{24}H_{22}F_3N_5O$, 453.2; m/z found, 454.2 [M+H]$^+$. $^1$H NMR (500 MHz, DMSO-d$_6$) δ 8.14 (s, 1H), 7.55 (dd, J=8.6, 6.5 Hz, 2H), 7.47 (dd, J=9.1, 0.9 Hz, 1H), 7.21 (dd, J=9.2, 1.7 Hz, 1H), 5.60 (s, 1H), 4.20-3.93 (m, 1H), 3.82 (s, 3H), 3.21-3.13 (m, 1H), 2.72 (s, 1H), 2.48-2.40 (m, 1H), 2.36-2.24 (m, 6H), 1.49 (d, J=6.8 Hz, 3H).

Example 406: [(7S)-3-(3-Chloro-5-methoxy-phenyl)-2,7-dimethyl-5,7-dihydro-4H-pyrazolo[3,4-c]pyridin-6-yl]-(6-fluoro-2-methyl-imidazo[1,2-a]pyridin-3-yl)methanone

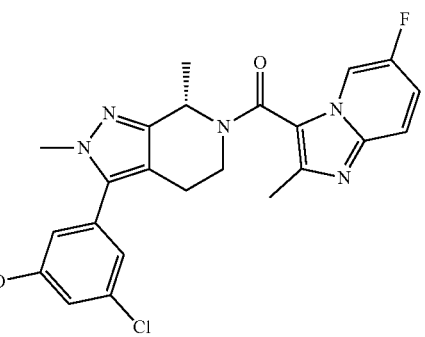

The title compound was prepared in a manner analogous to Example 288, using (S)-3-(3-chloro-5-methoxyphenyl)-2,7-dimethyl-4,5,6,7-tetrahydro-2H-pyrazolo[3,4-c] pyridine (Intermediate 41) instead of (S)-2,7-dimethyl-3-(3,4,5-trifluorophenyl)-4,5,6,7-tetrahydro-2H-pyrazolo[3,4-c] pyridine and 6-fluoro-2-methylimidazo[1,2-a]pyridine-3-carboxylic acid instead of 2-fluoro-6-(2H-1,2,3-triazol-2-yl)benzoic acid. MS (ESI): mass calcd. for $C_{24}H_{23}ClFN_5O_2$, 467.2; m/z found, 468.1 [M+H]$^+$. $^1$H NMR (500 MHz, DMSO-d$_6$) δ 8.45 (dd, J=4.7, 2.4 Hz, 1H), 7.69-7.60 (m, 1H), 7.53-7.38 (m, 1H), 7.18-7.05 (m, 2H), 6.99 (dd, J=2.3, 1.4 Hz, 1H), 5.70-5.48 (m, 1H), 4.17-3.98 (m, 1H), 3.86-3.75 (m, 6H), 3.47-3.37 (m, 1H), 2.72 (t, J=13.0 Hz, 1H), 2.46-2.34 (m, 4H), 1.50 (d, J=6.6 Hz, 3H).

Example 407: [(7S)-2,7-Dimethyl-3-(3,4,5-trifluorophenyl)-5,7-dihydro-4H-pyrazolo[3,4-c]pyridin-6-yl]-(6-fluoro-2-methyl-imidazo[1,2-a]pyridin-3-yl)methanone

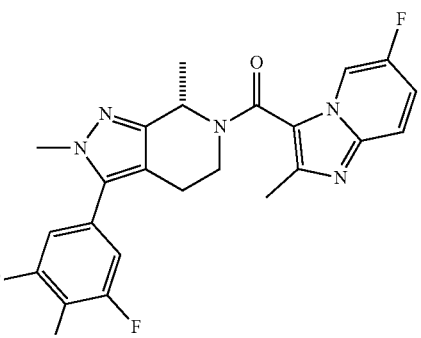

The title compound was prepared in a manner analogous to Example 288, using 6-fluoro-2-methylimidazo[1,2-a]pyridine-3-carboxylic acid instead of 2-fluoro-6-(2H-1,2,3-triazol-2-yl)benzoic acid. MS (ESI): mass calcd. for $C_{23}H_{19}F_4N_5O$, 457.2; m/z found, 458.1 [M+H]$^+$. $^1$H NMR (600 MHz, Chloroform-d) δ 8.38 (s, 1H), 7.53 (dd, J=9.8, 5.0 Hz, 1H), 7.23-7.17 (m, 1H), 6.98 (s, 2H), 6.22-3.94 (m, 2H), 3.84 (s, 3H), 3.43 (brs, 1H), 2.98-2.29 (m, 5H), 1.62 (brs, 3H).

Example 408: [(7S)-2,7-Dimethyl-3-(3,4,5-trifluorophenyl)-5,7-dihydro-4H-pyrazolo[3,4-c]pyridin-6-yl]-(6-fluoro-2,8-dimethyl-imidazo[1,2-a]pyridin-3-yl)methanone

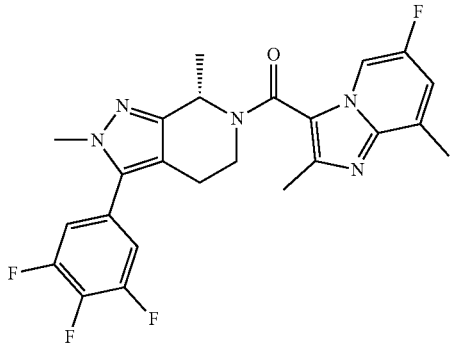 [SMILES: Cc1nc2c(C)cc(F)cn2c1C(=O)N1CCc2c(nn(C)c2-c2cc(F)c(F)c(F)c2)[C@@H]1C]

The title compound was prepared in a manner analogous to Example 288, using potassium 6-fluoro-2,8-dimethylimidazo[1,2-a]pyridine-3-carboxylate (Intermediate 86) instead of 2-fluoro-6-(2H-1,2,3-triazol-2-yl)benzoic acid. MS (ESI): mass calcd. for $C_{24}H_{21}F_4N_5O$, 471.2; m/z found, 472.2 [M+H]$^+$. $^1$H NMR (400 MHz, DMSO-d$_6$) δ 8.28 (dd, J=5.0, 2.4 Hz, 1H), 7.54 (dd, J=8.7, 6.6 Hz, 2H), 7.37-7.20 (m, 1H), 5.56 (s, 1H), 4.02 (d, J=22.7 Hz, 1H), 3.81 (s, 3H), 3.39 (t, J=12.7 Hz, 1H), 2.84-2.64 (m, 1H), 2.52 (s, 3H), 2.46-2.39 (m, 1H), 2.37 (s, 3H), 1.49 (d, J=6.7 Hz, 3H).

Example 409: [(7S)-2,7-Dimethyl-3-(3,4,5-trifluorophenyl)-5,7-dihydro-4H-pyrazolo[3,4-c]pyridin-6-yl]-(6-fluoro-2,7-dimethyl-imidazo[1,2-a]pyridin-3-yl)methanone

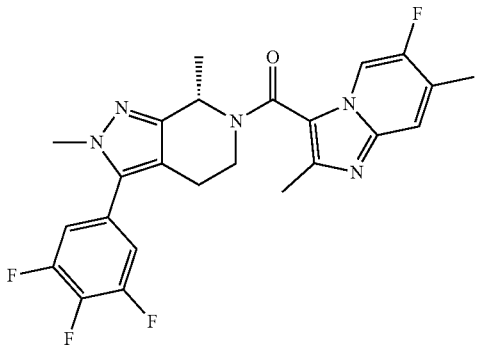 [SMILES: Cc1cc2nc(C)c(C(=O)N3CCc4c(nn(C)c4-c4cc(F)c(F)c(F)c4)[C@@H]3C)n2cc1F]

The title compound was prepared in a manner analogous to Example 288, using potassium 6-fluoro-2,7-dimethylimidazo[1,2-a]pyridine-3-carboxylate (Intermediate 87) instead of 2-fluoro-6-(2H-1,2,3-triazol-2-yl)benzoic acid. MS (ESI): mass calcd. for $C_{24}H_{21}F_4N_5O$, 471.2; m/z found, 472.2 [M+H]$^+$. $^1$H NMR (500 MHz, DMSO-d$_6$) δ 8.39 (d, J=5.2 Hz, 1H), 7.62-7.42 (m, 3H), 5.70-5.42 (m, 1H), 4.14-3.97 (m, 1H), 3.81 (s, 3H), 3.46-3.34 (m, 1H), 2.81-2.65 (m, 1H), 2.47-2.39 (m, 1H), 2.35 (d, J=2.1 Hz, 6H), 1.49 (d, J=6.8 Hz, 3H).

Example 410: (6,8-Difluoro-2-methyl-imidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone

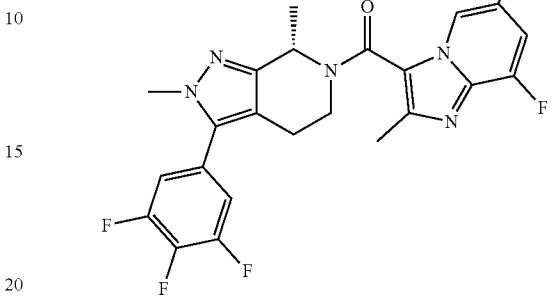

The title compound was prepared in a manner analogous to Example 288, using potassium 6,8-difluoro-2-methylimidazo[1,2-a] pyridine-3-carboxylate (Intermediate 88) instead of 2-fluoro-6-(2H-1,2,3-triazol-2-yl)benzoic acid. MS (ESI): mass calcd. for $C_{23}H_{18}F_5N_5O$, 475.2; m/z found, 476.1 [M+H]$^+$. $^1$H NMR (500 MHz, DMSO-d$_6$) δ 8.36 (d, J=2.9 Hz, 1H), 7.69-7.60 (m, 1H), 7.54 (dd, J=8.6, 6.6 Hz, 2H), 5.69-5.43 (m, 1H), 4.13-3.91 (m, 1H), 3.82 (s, 3H), 3.45-3.34 (m, 1H), 2.82-2.67 (m, 1H), 2.46-2.33 (m, 4H), 1.60-1.44 (m, 3H).

Example 411: [(7S)-2,7-Dimethyl-3-(3,4,5-trifluorophenyl)-5,7-dihydro-4H-pyrazolo[3,4-c]pyridin-6-yl]-(6-methoxy-2-methyl-imidazo[1,2-a]pyridin-3-yl)methanone

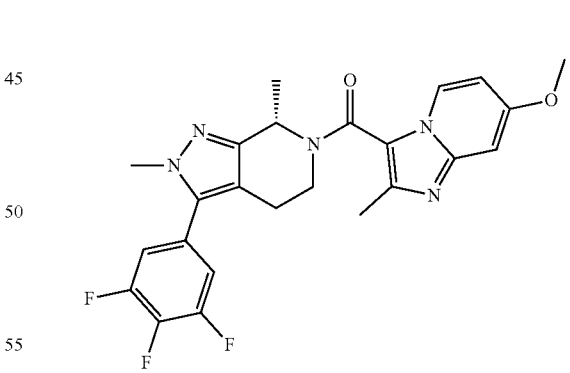

The title compound was prepared in a manner analogous to Example 288, using potassium 7-methoxy-2-methylimidazo[1,2-a]pyridine-3-carboxylate (Intermediate 89) instead of 2-fluoro-6-(2H-1,2,3-triazol-2-yl)benzoic acid. MS (ESI): mass calcd. for $C_{24}H_{22}F_3N_5O_2$, 469.2; m/z found, 470.1 [M+H]$^+$. $^1$H NMR (500 MHz, DMSO-d$_6$) δ 7.88-7.78 (m, 1H), 7.56-7.45 (m, 3H), 7.14 (dd, J=9.7, 2.4 Hz, 1H), 5.53 (s, 1H), 4.09 (s, 1H), 3.82 (s, 3H), 3.72 (s, 3H), 3.48-3.34 (m, 1H), 2.75 (d, J=12.9 Hz, 1H), 2.48-2.39 (m, 1H), 2.34 (s, 3H), 1.48 (d, J=6.8 Hz, 3H).

Example 412: [2-(Difluoromethyl)imidazo[1,2-a]pyridin-3-yl]-[(7S)-2,7-dimethyl-3-(3,4,5-trifluorophenyl)-5,7-dihydro-4H-pyrazolo[3,4-c]pyridin-6-yl]methanone

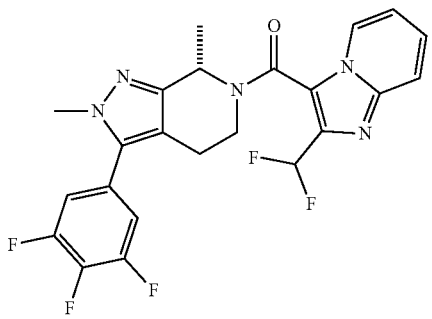 [SMILES: C[C@H]1c2nn(C)c(-c3cc(F)c(F)c(F)c3)c2CCN1C(=O)c1c(C(F)F)nc2ccccn12]

The title compound was prepared in a manner analogous to Example 288, using 2-(difluoromethyl)imidazo[1,2-a]pyridine-3-carboxylic acid instead of 2-fluoro-6-(2H-1,2,3-triazol-2-yl)benzoic acid. MS (ESI): mass calcd. for $C_{23}H_{18}F_5N_5O$, 475.1; m/z found, 476.1 [M+H]$^+$. $^1$H NMR (500 MHz, Chloroform-d) δ 8.18 (d, J=6.9 Hz, 1H), 7.71-7.66 (m, 1H), 7.39-7.32 (m, 1H), 7.03-6.87 (m, 4H), 5.78 (brs, 1H), 4.24 (brs, 1H), 3.83 (s, 3H), 3.39 (brs, 1H), 3.02-2.35 (m, 2H), 1.61 (d, J=6.6 Hz, 3H).

Example 413: [(7S)-2,7-Dimethyl-3-(3,4,5-trifluorophenyl)-5,7-dihydro-4H-pyrazolo[3,4-c]pyridin-6-yl]-[2-(trifluoromethyl) imidazo[1,2-a]pyridin-3-yl] methanone

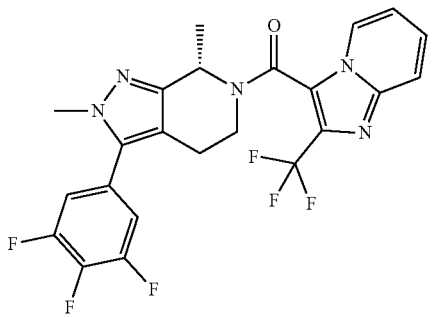 [SMILES: C[C@H]1c2nn(C)c(-c3cc(F)c(F)c(F)c3)c2CCN1C(=O)c1c(C(F)(F)F)nc2ccccn12]

The title compound was prepared in a manner analogous to Example 288, using 2-(trifluoromethyl)imidazo[1,2-a]pyridine-3-carboxylic acid instead of 2-fluoro-6-(2H-1,2,3-triazol-2-yl)benzoic acid. MS (ESI): mass calcd. for $C_{23}H_{17}F_6N_5O$, 493.1; m/z found, 494.1 [M+H]$^+$. $^1$H NMR (400 MHz, DMSO-d$_6$) δ 8.28 (d, J=67.0 Hz, 1H), 7.85-7.76 (m, 1H), 7.60-7.44 (m, 3H), 7.29-7.07 (m, 1H), 5.87-5.58 (m, 1H), 3.91-3.64 (m, 4H), 3.46-3.36 (m, 1H), 2.65-2.53 (m, 1H), 2.46-2.28 (m, 1H), 1.68-1.41 (m, 3H).

Example 414: [(7S)-2,7-Dimethyl-3-(3,4,5-trifluorophenyl)-5,7-dihydro-4H-pyrazolo[3,4-c]pyridin-6-yl]-[5-methyl-2-(trifluoromethyl)imidazo[1,2-a]pyridin-3-yl]methanone

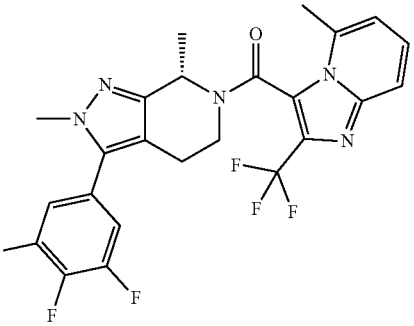

The title compound was prepared in a manner analogous to Example 288, using 5-methyl-2-(trifluoromethyl)imidazo[1,2-a]pyridine-3-carboxylic acid instead of 2-fluoro-6-(2H-1,2,3-triazol-2-yl)benzoic acid. MS (ESI): mass calcd. for $C_{24}H_{19}F_6N_5O$, 507.1; m/z found, 508.0 [M+H]$^+$. $^1$H NMR (400 MHz, DMSO-d$_6$) δ 8.28 (d, J=67.0 Hz, 1H), 7.85-7.76 (m, 1H), 7.60-7.44 (m, 3H), 7.29-7.07 (m, 1H), 5.87-5.58 (m, 1H), 3.91-3.64 (m, 4H), 3.46-3.36 (m, 1H), 2.65-2.53 (m, 1H), 2.46-2.28 (m, 1H), 1.68-1.41 (m, 3H).

Example 415: [(7S)-2,7-Dimethyl-3-(3,4,5-trifluorophenyl)-5,7-dihydro-4H-pyrazolo[3,4-c]pyridin-6-yl]-pyrrolo[1,2-a] pyrazin-1-yl-methanone

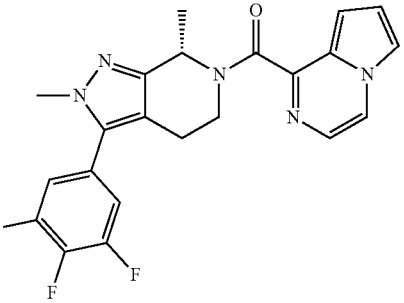

The title compound was prepared in a manner analogous to Example 288, using potassium pyrrolo[1,2-a]pyrazine-1-carboxylate (Intermediate 91) instead of 2-fluoro-6-(2H-1,2,3-triazol-2-yl)benzoic acid. MS (ESI): mass calcd. for $C_{22}H_{18}F_3N_5O$, 425.2; m/z found, 426.1 [M+H]$^+$. $^1$H NMR (400 MHz, DMSO-d$_6$) δ 8.38-8.28 (m, 1H), 7.93-7.78 (m, 1H), 7.61-7.39 (m, 3H), 7.02-6.84 (m, 1H), 6.77-6.56 (m, 1H), 5.74-5.51 (m, 1H), 4.84-4.63 (m, 1H), 3.86-3.68 (m, 3H), 3.25-2.98 (m, 1H), 2.89-2.58 (m, 1H), 2.40-2.24 (m, 1H), 1.62-1.32 (m, 3H).

Example 416: [(7S)-2,7-Dimethyl-3-(3,4,5-trifluoro-phenyl)-5,7-dihydro-4H-pyrazolo[3,4-c]pyridin-6-yl]-pyrrolo[1,2-a]pyrazin-8-yl-methanone

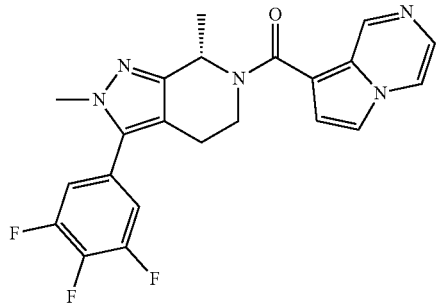 [SMILES: C[C@H]1c2nn(C)c(-c3cc(F)c(F)c(F)c3)c2CCN1C(=O)c1ccn2ccncc12]

The title compound was prepared in a manner analogous to Example 288, using pyrrolo[1,2-a]pyrazine-8-carboxylic acid instead of 2-fluoro-6-(2H-1,2,3-triazol-2-yl)benzoic acid. MS (ESI): mass calcd. for $C_{22}H_{18}F_3N_5O$, 425.2; m/z found, 426.1 [M+H]$^+$. $^1$H NMR (500 MHz, DMSO-d$_6$) δ 9.10-8.97 (m, 1H), 8.38 (dd, J=4.8, 1.6 Hz, 1H), 7.91-7.71 (m, 1H), 7.69-7.47 (m, 3H), 7.16 (d, J=2.7 Hz, 1H), 5.57-5.37 (m, 1H), 4.42-4.26 (m, 1H), 3.80 (s, 3H), 3.24-3.28 (m, 1H), 3.07-2.89 (m, 1H), 2.47-2.31 (m, 1H), 1.59-1.42 (m, 3H).

Example 417: (2,4-Dimethylpyrrolo[1,2-a] pyrimidin-8-yl)-[(7S)-2,7-dimethyl-3-(3,4,5-trifluorophe-nyl)-5,7-dihydro-4H-pyrazolo[3,4-c] pyridin-6-yl] methanone

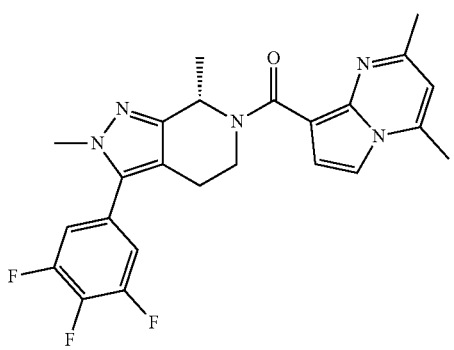 [SMILES: Cc1cc(C)n2ccc(C(=O)N3CCc4c(nn(C)c4-c4cc(F)c(F)c(F)c4)[C@@H]3C)c2n1]

The title compound was prepared in a manner analogous to Example 288, using 2,4-dimethylpyrrolo[1,2-a]pyrimi-dine-8-carboxylic acid instead of 2-fluoro-6-(2H-1,2,3-tri-azol-2-yl)benzoic acid. MS (ESI): mass calcd. for $C_{24}H_{22}F_3N_5O$, 453.2; m/z found, 454.1 [M+H]$^+$. $^1$H NMR (500 MHz, DMSO-d$_6$) δ 7.58-7.46 (m, 2H), 7.37 (d, J=3.2 Hz, 1H), 7.13-7.01 (m, 1H), 6.72-6.62 (m, 1H), 5.66-5.27 (m, 1H), 4.22-3.89 (m, 1H), 3.78 (s, 3H), 3.26-3.03 (m, 2H), 2.60-2.56 (m, 3H), 2.46-2.32 (m, 4H), 1.50 (s, 3H).

Example 418: [(7S)-2,7-Dimethyl-3-(3,4,5-trifluoro-phenyl)-5,7-dihydro-4H-pyrazolo[3,4-c]pyridin-6-yl]-(3-methylimidazo[1,5-a]pyridin-6-yl)methanone

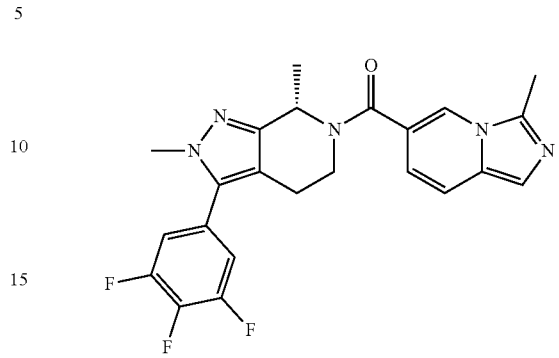

The title compound was prepared in a manner analogous to Example 288, using 3-methylimidazo[1,5-a]pyridine-6-carboxylic acid instead of 2-fluoro-6-(2H-1,2,3-triazol-2-yl) benzoic acid. MS (ESI): mass calcd. for $C_{23}H_{20}F_3N_5O$, 439.2; m/z found, 440.1 [M+H]$^+$. $^1$H NMR (400 MHz, DMSO-d$_6$) δ 8.28-8.07 (m, 1H), 7.61-7.48 (m, 3H), 7.40-7.26 (m, 1H), 6.72 (d, J=9.3 Hz, 1H), 5.67-5.33 (m, 1H), 4.25-3.84 (m, 1H), 3.80 (s, 3H), 3.27-3.05 (m, 1H), 2.93-2.73 (m, 1H), 2.62 (s, 3H), 2.45-2.32 (m, 1H), 1.58-1.29 (m, 3H).

Example 419: [(7S)-2,7-Dimethyl-3-(3,4,5-trifluoro-phenyl)-5,7-dihydro-4H-pyrazolo[3,4-c]pyridin-6-yl]-(7-methylimidazo[1,5-a]pyridin-1-yl)methanone

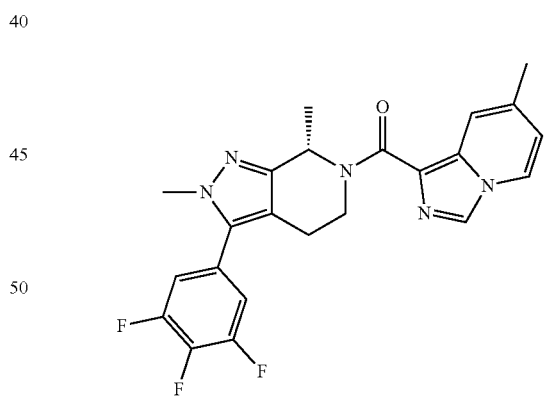

The title compound was prepared in a manner analogous to Example 288, using 7-methylimidazo[1,5-a]pyridine-1-carboxylic acid instead of 2-fluoro-6-(2H-1,2,3-triazol-2-yl) benzoic acid. MS (ESI): mass calcd. for $C_{23}H_{20}F_3N_5O$, 439.2; m/z found, 440.1 [M+H]$^+$. $^1$H NMR (500 MHz, DMSO-d$_6$) δ 8.42-8.35 (m, 2H), 7.90-7.86 (m, 1H), 7.58-7.49 (m, 2H), 6.74 (dd, J=7.1, 1.7 Hz, 1H), 6.68-6.50 (m, 0.32H), 5.73-5.46 (m, 1H), 4.79-4.57 (m, 0.32H), 3.79 (s, 3H), 3.10-2.67 (m, 1.45H), 2.46-2.40 (m, 1H), 2.34-2.31 (m, 3H), 1.67-1.40 (m, 3H). (Fractions of Hs that may overlap with DMSO and water are not reported).

Example 420: [(7S)-2,7-Dimethyl-3-(3,4,5-trifluorophenyl)-5,7-dihydro-4H-pyrazolo[3,4-c]pyridin-6-yl]-imidazo[1,5-a]pyridin-1-yl-methanone

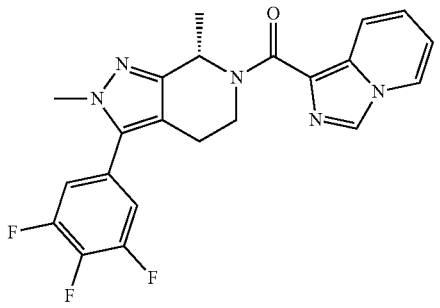 [SMILES: C[C@H]1c2nn(C)c(-c3cc(F)c(F)c(F)c3)c2CCN1C(=O)c1ncn2ccccc12]

The title compound was prepared in a manner analogous to Example 288, using imidazo[1,5-a]pyridine-1-carboxylic acid instead of 2-fluoro-6-(2H-1,2,3-triazol-2-yl)benzoic acid. MS (ESI): mass calcd. for $C_{22}H_{18}F_3N_5O$, 425.1; m/z found, 426.1 [M+H]$^+$. $^1$H NMR (500 MHz, Chloroform-d) δ 8.27 (d, J=9.3 Hz, 1H), 8.05-8.02 (m, 1H), 7.99 (dt, J=7.0, 1.1 Hz, 1H), 7.03-6.94 (m, 3H), 6.77-6.51 (m, 1.35H), 6.09-5.36 (m, 1H), 5.11-4.74 (m, 0.41H), 3.82 (s, 3H), 3.46-2.77 (m, 2H), 2.52-2.43 (m, 1H), 1.68 (br s, 3H).

Example 421: (3-Cyclopropylimidazo[1,5-a]pyridin-1-yl)-[(7S)-2,7-dimethyl-3-(3,4,5-trifluorophenyl)-5,7-dihydro-4H-pyrazolo[3,4-c]pyridin-6-yl]methanone

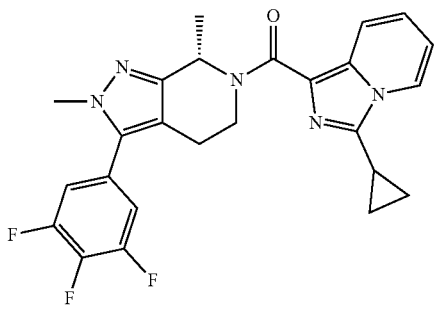 [SMILES: C[C@H]1c2nn(C)c(-c3cc(F)c(F)c(F)c3)c2CCN1C(=O)c1nc(C2CC2)n2ccccc12]

The title compound was prepared in a manner analogous to Example 288, using 3-cyclopropylimidazo[1,5-a]pyridine-1-carboxylic acid instead of 2-fluoro-6-(2H-1,2,3-triazol-2-yl)benzoic acid. MS (ESI): mass calcd. for $C_{25}H_{22}F_3N_5O$, 465.2; m/z found, 466.1 [M+H]$^+$. $^1$H NMR (400 MHz, DMSO-d$_6$) δ 8.58-8.42 (m, 1H), 8.15-7.95 (m, 1H), 7.63-7.46 (m, 2H), 7.13-7.01 (m, 1H), 6.97-6.88 (m, 1H), 6.80-6.20 (m, 1H), 5.86-4.33 (m, 1H), 3.78 (s, 3H), 3.23-2.67 (m, 2H), 2.49-2.34 (m, 2H), 1.52 (s, 3H), 1.18-0.90 (m, 4H).

Example 422: [(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-4-yl)methanone

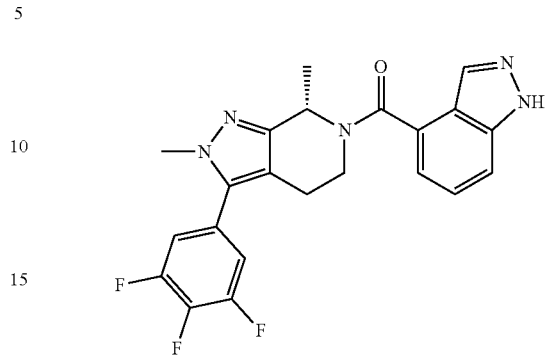

The title compound was prepared in a manner analogous to Example 288, using 1H-pyrazolo[3,4-b]pyridine-4-carboxylic acid instead of 2-fluoro-6-(2H-1,2,3-triazol-2-yl)benzoic acid and DMF instead of DCM. MS (ESI): mass calcd. for $C_{21}H_{17}F_3N_6O$, 426.1; m/z found, 427.1 [M+H]$^+$. $^1$H NMR (500 MHz, DMSO-d$_6$) δ 13.93 (s, 1H), 8.62 (d, J=4.6 Hz, 1H), 8.14-7.97 (m, 1H), 7.63-7.49 (m, 2H), 7.21 (d, J=4.6 Hz, 1H), 5.73-5.65 (m, 0.68H), 4.80-4.52 (m, 0.50H), 3.87-3.69 (m, 3H), 3.52-3.44 (m, 0.66H), 3.17-3.08 (m, 0.23H), 2.96-2.85 (s, 0.22H), 2.79-2.68 (m, 0.66H), 2.33-2.25 (m, 0.69H), 1.59-1.31 (m, 3H). (Fractions of Hs that may overlap with DMSO and water are not reported).

Example 423: [(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-5-yl)methanone.TFA salt

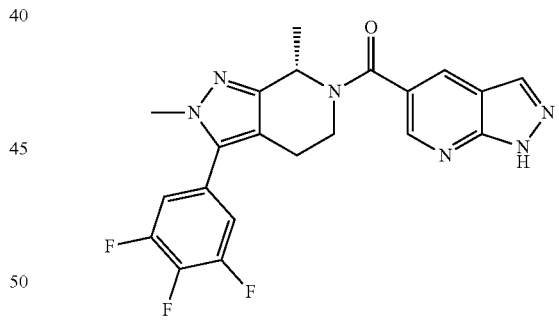

Step A: (S)-(2,7-Dimethyl-3-(3,4,5-trifluorophenyl)-4,5-dihydro-2H-pyrazolo[3,4-c]pyridin-6 (7H)-yl)(1-((2-(trimethylsilyl)ethoxy)methyl)-1H-pyrazolo[3,4-b]pyridin-5-yl) methanone. The title compound was prepared in a manner analogous to Example 288, using 1-((2-(trimethylsilyl)ethoxy)methyl)-1H-pyrazolo[3,4-b]pyridine-5-carboxylic acid (Intermediate 61) instead of 2-fluoro-6-(2H-1,2,3-triazol-2-yl)benzoic acid and DMF instead of DCM.

Step B: [(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-5-yl)methanone. The title compound was prepared in a manner analogous to Example 371, Step B. MS (ESI): mass calcd. for $C_{21}H_{17}F_3N_6O$, 426.1; m/z found, 427.2 [M+H]$^+$.

Example 424: (1,6-Dimethylpyrazolo[3,4-b]pyridin-4-yl)-[(7S)-2,7-dimethyl-3-(3,4,5-trifluorophenyl)-5,7-dihydro-4H-pyrazolo[3,4-c]pyridin-6-yl]methanone

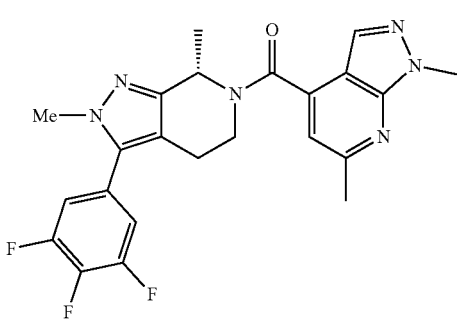 [SMILES: Cc1cc(C(=O)N2CCc3c(nn(C)c3-c3cc(F)c(F)c(F)c3)[C@@H]2C)c2cnn(C)c2n1]

The title compound was prepared in a manner analogous to Example 288, using 1,6-dimethyl-1H-pyrazolo[3,4-b]pyridine-4-carboxylic acid instead of 2-fluoro-6-(2H-1,2,3-triazol-2-yl)benzoic acid. MS (ESI): mass calcd. for $C_{23}H_{21}F_3N_6O$, 454.2; m/z found, 455.1 [M+H]$^+$. $^1$H NMR (400 MHz, DMSO-$d_6$) δ 8.08-7.78 (m, 1H), 7.65-7.43 (m, 2H), 7.12 (s, 1H), 5.75-5.51 (m, 1H), 4.87-4.43 (m, 1H), 4.05 (s, 3H), 3.87-3.67 (m, 3H), 3.55-3.34 (m, 1H), 3.30-3.07 (m, 1H), 2.66 (s, 3H), 2.39-2.21 (m, 1H), 1.61-1.27 (m, 3H).

Example 425: (1,3-Dimethylpyrazolo[3,4-b]pyridin-4-yl)-[(7S)-2,7-dimethyl-3-(3,4,5-trifluorophenyl)-5,7-dihydro-4H-pyrazolo[3,4-c]pyridin-6-yl]methanone

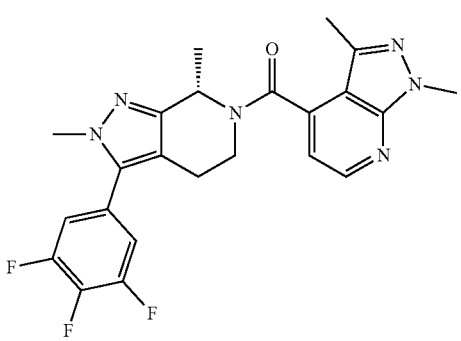 [SMILES: Cc1nn(C)c2nccc(C(=O)N3CCc4c(nn(C)c4-c4cc(F)c(F)c(F)c4)[C@@H]3C)c12]

The title compound was prepared in a manner analogous to Example 288, using 1,3-dimethyl-1H-pyrazolo[3,4-b]pyridine-4-carboxylic acid instead of 2-fluoro-6-(2H-1,2,3-triazol-2-yl)benzoic acid and DMF instead of DCM. MS (ESI): mass calcd. for $C_{23}H_{21}F_3N_6O$, 454.2; m/z found, 455.2 [M+H]$^+$. $^1$H NMR (600 MHz, DMSO-$d_6$) δ 8.64-8.69 (m, 1H), 7.58-7.49 (m, 2H), 7.25-7.10 (m, 1H), 5.71 (q, J=6.8 Hz, 0.78H), 4.83-4.77 (m, 0.24H), 4.41 (br s, 0.09H), 4.05-3.97 (m, 3H), 3.83 (s, 2.29H), 3.73 (s, 0.72H), 3.14 (td, J=12.7, 4.0 Hz, 0.31H), 2.84-2.69 (m, 0.73H), 2.59-2.55 (m, 0.32H), 2.46-2.10 (m, 4H), 1.54-1.28 (m, 3H). (Fractions of Hs that may overlap with DMSO and water are not reported).

Example 426: [(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-3-yl)methanone

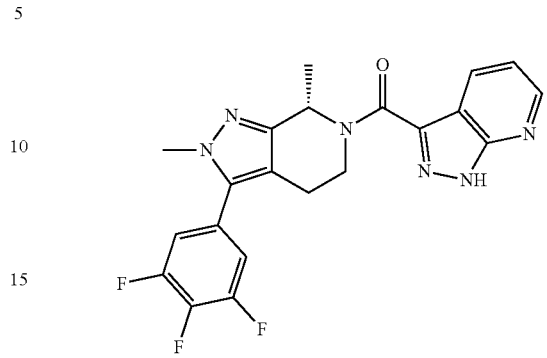

The title compound was prepared in a manner analogous to Example 288, using 1H-pyrazolo[3,4-b]pyridine-3-carboxylic acid instead of 2-fluoro-6-(2H-1,2,3-triazol-2-yl)benzoic acid. MS (ESI): mass calcd. for $C_{21}H_{17}F_3N_6O$, 426.1; m/z found, 427.1 [M+H]$^+$. $^1$H NMR (500 MHz, Chloroform-d) δ 12.11 (s, 0.48H), 11.17 (s, 0.43H), 8.67-8.54 (m, 2H), 7.33-7.25 (m, 1H), 7.04-6.94 (m, 2H), 6.44-6.35 (m, 0.48H), 6.00-5.89 (m, 0.42H), 5.24-5.13 (m, 0.46H), 5.04-4.92 (m, 0.53H), 3.92-3.82 (m, 3H), 3.43-3.32 (m, 0.45H), 3.25-3.14 (m, 0.52H), 3.07-3.82 (m, 1H), 2.57-2.46 (m, 1H), 1.90-1.60 (m, 3H).

Example 427: [(7S)-2,7-Dimethyl-3-(3,4,5-trifluorophenyl)-5,7-dihydro-4H-pyrazolo[3,4-c]pyridin-6-yl]-(1-methylpyrazolo[3,4-b]pyridin-3-yl)methanone

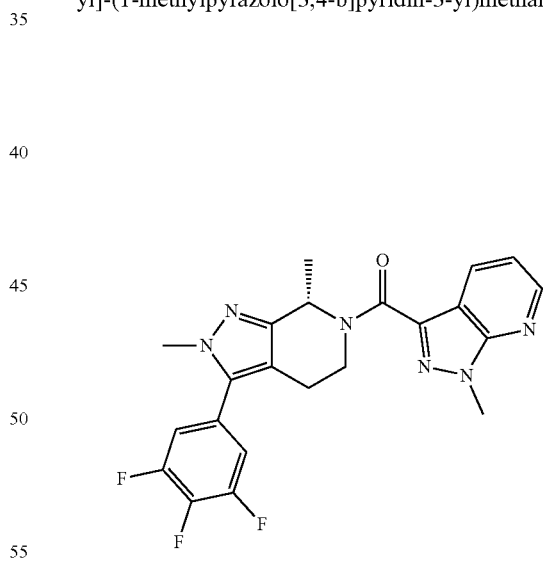

The title compound was prepared in a manner analogous to Example 288, using 1-methyl-1H-pyrazolo[3,4-b]pyridine-3-carboxylic acid instead of 2-fluoro-6-(2H-1,2,3-triazol-2-yl)benzoic acid. MS (ESI): mass calcd. for $C_{22}H_{19}F_3N_6O$, 440.2; m/z found, 441.2 [M+H]$^+$. $^1$H NMR (500 MHz, Chloroform-d) δ 8.61-8.53 (m, 2H), 7.26-7.19 (m, 1H), 7.04-6.92 (m, 2H), 6.43-6.34 (m, 0.46H), 5.99-5.88 (m, 0.45H), 5.31-5.18 (m, 0.49H), 5.02-4.89 (m, 0.53H), 4.21 (s, 3H), 3.90-3.75 (m, 3H), 3.43-3.31 (m, 0.47H), 3.21-3.10 (m, 0.49H), 3.04-2.79 (m, 1H), 2.55-2.45 (m, 1H), 1.80-1.60 (m, 3H).

Example 428: [(7S)-2,7-Dimethyl-3-(3,4,5-trifluorophenyl)-5,7-dihydro-4H-pyrazolo[3,4-c]pyridin-6-yl]-(5-fluoro-1H-pyrazolo[3,4-b]pyridin-3-yl)methanone.TFA salt

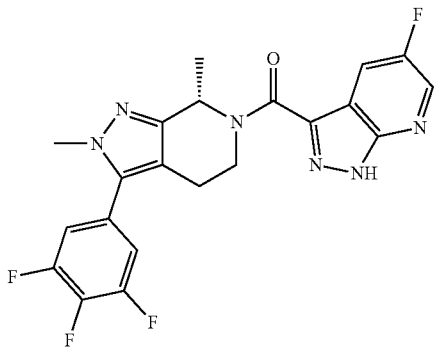 [SMILES: C[C@H]1c2nn(C)c(-c3cc(F)c(F)c(F)c3)c2CCN1C(=O)c1n[nH]c2ncc(F)cc12]

The title compound was prepared in a manner analogous to Example 288, using 5-fluoro-1H-pyrazolo[3,4-b]pyridine-3-carboxylic acid instead of 2-fluoro-6-(2H-1,2,3-triazol-2-yl)benzoic acid and DMF instead of DCM. MS (ESI): mass calcd. for $C_{21}H_{16}F_4N_6O$, 444.1; m/z found, 445.2 [M+H]$^+$. $^1$H NMR (500 MHz, DMSO-d$_6$) δ 14.45-14.31 (m, 1H), 8.68-8.65 (m, 1H), 8.23-8.16 (m, 1H), 7.59-7.50 (m, 2H), 6.22-6.11 (m, 0.40H), 5.73-5.61 (m, 0.58H), 5.15-5.02 (m, 0.59H), 4.79-4.69 (d, J=12.5 Hz, 0.44H), 3.86-3.72 (m, 3H), 3.17-3.06 (m, 0.43H), 2.96-2.72 (m, 1H), 1.66-1.46 (m, 3H). (Fractions of Hs that may overlap with DMSO and water are not reported).

Example 429: [(7S)-2,7-Dimethyl-3-(3,4,5-trifluorophenyl)-5,7-dihydro-4H-pyrazolo[3,4-c]pyridin-6-yl]-(2-methylpyrazolo[3,4-c]pyridin-7-yl)methanone

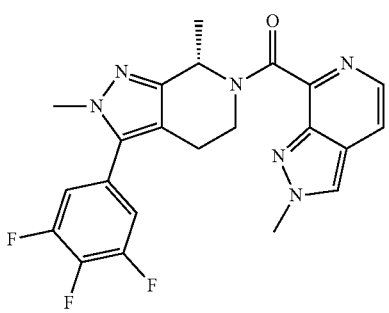 [SMILES: C[C@H]1c2nn(C)c(-c3cc(F)c(F)c(F)c3)c2CCN1C(=O)c1nccc2cn(C)nc12]

The title compound was prepared in a manner analogous to Example 206, using [(7S)-2,7-dimethyl-3-(3,4,5-trifluorophenyl)-5,7-dihydro-4H-pyrazolo[3,4-c]pyridin-6-yl]-(1H-pyrazolo[3,4-c]pyridin-7-yl)methanone (Example 432) instead of [(S)-(2,7-dimethyl-3-(3,4,5-trifluorophenyl)-2,4,5,7-tetrahydro-6H-pyrazolo[3,4-c]pyridin-6-yl)(1H-indol-7-yl)methanone] (Example 205) and DMF instead of THF. MS (ESI): mass calcd. for $C_{22}H_{19}F_3N_6O$, 440.2; m/z found, 441.0 [M+H]$^+$. $^1$H NMR (500 MHz, Methanol-d$_4$) δ 8.49-8.41 (m, 1H), 8.15-8.08 (m, 1H), 7.85-7.75 (m, 1H), 7.35-7.24 (m, 2H), 5.93-5.81 (m, 0.70H), 4.99-4.91 (m, 0.30H), 4.70-4.66 (m, 0.30H), 4.31 (s, 2.1H), 4.29 (s, 0.90H), 3.84 (s, 2.1H), 3.74 (s, 0.90H), 3.57-3.50 (m, 0.70H), 3.46-3.41 (m, 0.30H), 3.42-3.35 (m, 0.70H), 2.81-2.70 (m, 1H), 2.64-2.55 (m, 0.30H), 2.37-2.28 (m, 0.70H), 1.68 (d, J=6.8 Hz, 2.1H), 1.47 (d, J=6.8 Hz, 0.90H).

Example 430: [(7S)-2,7-Dimethyl-3-(3,4,5-trifluorophenyl)-5,7-dihydro-4H-pyrazolo[3,4-c]pyridin-6-yl]-(1H-pyrazolo[3,4-c]pyridin-3-yl)methanone

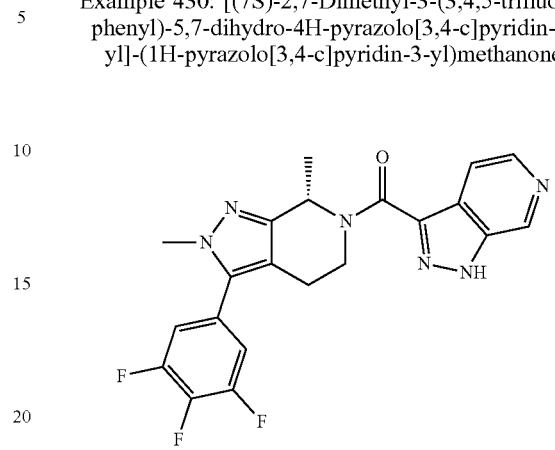

The title compound was prepared in a manner analogous to Example 288, using 1H-pyrazolo[3,4-c]pyridine-3-carboxylic acid instead of 2-fluoro-6-(2H-1,2,3-triazol-2-yl)benzoic acid. MS (ESI): mass calcd. for $C_{21}H_{17}F_3N_6O$, 426.1; m/z found, 427.1 [M+H]$^+$. $^1$H NMR (400 MHz, DMSO-d$_6$) δ 14.15 (s, 1H), 9.17-9.11 (m, 1H), 8.33 (d, J=5.6 Hz, 1H), 7.94 (dd, J=5.6, 1.3 Hz, 1H), 7.60-7.50 (m, 2H), 6.12-5.98 (m, 0.36H), 5.75-5.64 (m, 0.54H), 5.01-4.87 (m, 0.56H), 4.83-4.69 (m, 0.42H), 386-3.70 (m, 3H), 3.18-3.06 (m, 0.47H), 2.97-2.74 (m, 1H), 1.66-1.46 (m, 3H). (Fractions of Hs that may overlap with DMSO and water are not reported).

Example 431: [(7S)-2,7-Dimethyl-3-(3,4,5-trifluorophenyl)-5,7-dihydro-4H-pyrazolo[3,4-c]pyridin-6-yl]-(1-methylpyrazolo[3,4-c]pyridin-3-yl)methanone.TFA salt

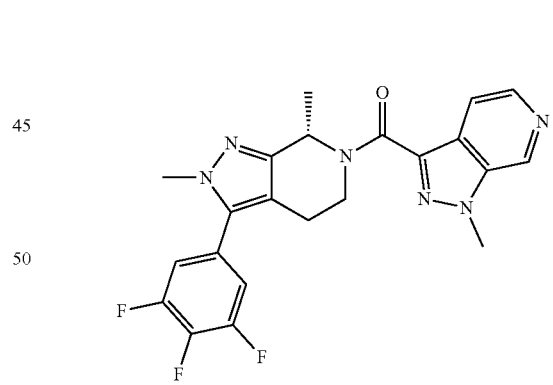

The title compound was prepared in a manner analogous to Example 288, using 1-methyl-1H-pyrazolo[3,4-c]pyridine-3-carboxylic acid instead of 2-fluoro-6-(2H-1,2,3-triazol-2-yl)benzoic acid and DMF instead of DCM. MS (ESI): mass calcd. for $C_{22}H_{19}F_3N_6O$, 440.2; m/z found, 441.2 [M+H]$^+$. $^1$H NMR (500 MHz, Chloroform-d) δ 9.46 (s, 1H), 8.54-8.36 (m, 2H), 7.04-6.93 (m, 2H), 6.29-6.21 (m, 0.51H), 5.96-5.89 (m, 0.42H), 5.15-5.07 (m, 0.46H), 4.99-4.91 (m, 0.56H), 4.35 (s, 3H), 3.88-3.77 (m, 3H), 3.47-3.38 (m, 0.44H), 3.25-3.15 (m, 0.56H), 3.03-2.79 (m, 1H), 2.57-2.51 (m, 1H), 1.82-1.62 (m, 3H).

Example 432: [(7S)-2,7-Dimethyl-3-(3,4,5-trifluorophenyl)-5,7-dihydro-4H-pyrazolo[3,4-c]pyridin-6-yl]-(1H-pyrazolo[3,4-c]pyridin-7-yl)methanone

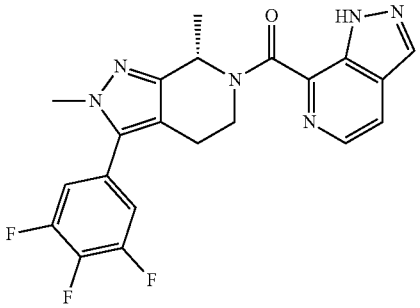 [SMILES: C[C@H]1c2nn(C)c(-c3cc(F)c(F)c(F)c3)c2CCN1C(=O)c1nccc2cn[nH]c12]

The title compound was prepared in a manner analogous to Example 288, using 1H-pyrazolo[3,4-c]pyridine-7-carboxylic acid instead of 2-fluoro-6-(2H-1,2,3-triazol-2-yl)benzoic acid. MS (ESI): mass calcd. for $C_{21}H_{17}F_3N_6O$, 426.1; m/z found, 427.0 $[M+H]^+$. $^1H$ NMR (500 MHz, Methanol-$d_4$) δ 8.35-8.27 (m, 1H), 8.26 (s, 1H), 7.96-7.86 (m, 1H), 7.37-7.25 (m, 2H), 5.86 (q, J=6.8 Hz, 0.65H), 5.62-5.47 (m, 0.35H), 4.99-4.88 (m, 0.35H), 4.41-4.29 (m, 0.65H), 3.85 (s, 2H), 3.76 (s, 1H), 3.47-3.36 (m, 0.65H), 3.31-3.23 (m, 0.35H), 2.98-2.86 (m, 1H), 2.65-2.55 (m, 0.35H), 2.49-2.39 (m, 0.65H), 1.67 (d, J=6.8 Hz, 2H), 1.61 (d, J=6.7 Hz, 1H).

Example 433: [(7S)-2,7-Dimethyl-3-(3,4,5-trifluorophenyl)-5,7-dihydro-4H-pyrazolo[3,4-c]pyridin-6-yl]-(1-methylpyrazolo[3,4-c]pyridin-7-yl)methanone

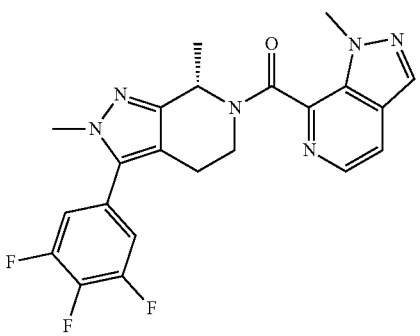 [SMILES: C[C@H]1c2nn(C)c(-c3cc(F)c(F)c(F)c3)c2CCN1C(=O)c1nccc2cnn(C)c12]

The title compound was prepared in a manner analogous to Example 206, using [(7S)-2,7-dimethyl-3-(3,4,5-trifluorophenyl)-5,7-dihydro-4H-pyrazolo[3,4-c]pyridin-6-yl]-(1H-pyrazolo[3,4-c]pyridin-7-yl)methanone Example 432 instead of [(S)-(2,7-dimethyl-3-(3,4,5-trifluorophenyl)-2,4,5,7-tetrahydro-6H-pyrazolo[3,4-c]pyridin-6-yl)(1H-indol-7-yl)methanone] (Example 205) and DMF instead of THF. MS (ESI): mass calcd. for $C_{22}H_{19}F_3N_6O$, 440.2; m/z found, 441.0 $[M+H]^+$. $^1H$ NMR (500 MHz, Methanol-$d_4$) δ 8.28 (d, J=5.6 Hz, 0.30H), 8.27 (d, J=5.6 Hz, 0.70H), 8.22 (s, 0.70H), 8.22 (s, 0.30H), 7.93-7.83 (m, 1H), 7.35-7.25 (m, 2H), 5.89 (q, J=6.8 Hz, 0.70H), 5.02-4.95 (m, 0.30H), 4.79-4.68 (m, 0.30H), 4.13 (s, 2.1H), 4.02 (s, 0.90H), 3.85 (s, 2.1H), 3.76 (s, 0.90H), 3.69-3.58 (m, 0.70H), 3.52-3.38 (m, 0.70H), 3.37-3.32 (m, 0.30H), 3.02-2.74 (m, 1H), 2.72-2.57 (m, 0.30H), 2.49-2.31 (m, 0.70H), 1.68 (d, J=6.8 Hz, 2.1H), 1.51 (d, J=6.8 Hz, 0.90H).

Example 434: [(7S)-2,7-Dimethyl-3-(3,4,5-trifluorophenyl)-5,7-dihydro-4H-pyrazolo[3,4-c]pyridin-6-yl]-(1H-pyrazolo[4,3-c]pyridin-7-yl)methanone

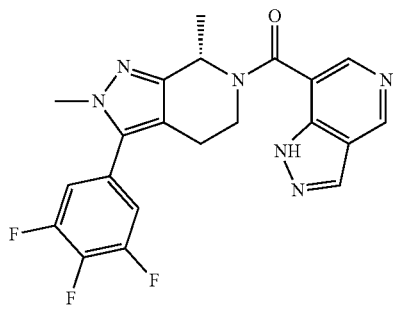 [SMILES: C[C@H]1c2nn(C)c(-c3cc(F)c(F)c(F)c3)c2CCN1C(=O)c1cncc2cn[nH]c12]

The title compound was prepared in a manner analogous to Example 288, using 1H-pyrazolo[4,3-c]pyridine-7-carboxylic acid instead of 2-fluoro-6-(2H-1,2,3-triazol-2-yl)benzoic acid. MS (ESI): mass calcd. for $C_{21}H_{17}F_3N_6O$, 426.1; m/z found, 427.0 $[M+H]^+$. $^1H$ NMR (400 MHz, Methanol-$d_4$) δ 9.56 (s, 1H), 8.80 (s, 1H), 8.65 (s, 1H), 7.44-7.17 (m, 2H), 6.05-5.58 (m, 1H), 4.04-3.67 (m, 4H), 3.58-3.40 (m, 1H), 2.99-2.72 (m, 1H), 2.66-2.34 (m, 1H), 1.66 (s, 3H).

Example 435: [(7S)-2,7-Dimethyl-3-(3,4,5-trifluorophenyl)-5,7-dihydro-4H-pyrazolo[3,4-c]pyridin-6-yl]-(1H-pyrazolo[4,3-c]pyridin-3-yl)methanone

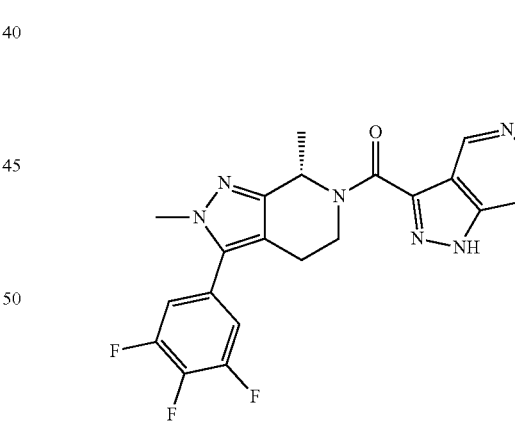

The title compound was prepared in a manner analogous to Example 288, using 1H-pyrazolo[4,3-c]pyridine-3-carboxylic acid instead of 2-fluoro-6-(2H-1,2,3-triazol-2-yl)benzoic acid. MS (ESI): mass calcd. for $C_{21}H_{17}F_3N_6O$, 426.1; m/z found, 427.1 $[M+H]^+$. $^1H$ NMR (500 MHz, Chloroform-d) δ 11.75-10.72 (m, 1H), 9.12-9.07 (m, 1H), 8.49-8.40 (m, 1H), 8.14-8.09 (m, 1H), 7.03-6.94 (m, 2H), 6.26-6.17 (m, 0.48H), 6.00-5.91 (m, 0.41H), 5.05-4.95 (m, 1H), 3.89-3.79 (m, 3H), 3.44-3.34 (m, 0.43H), 3.25-3.14 (m, 0.50H), 3.04-2.82 (m, 1H), 2.58-2.44 (m, 1H), 1.80-1.62 (m, 3H).

Example 436: [(7S)-2,7-Dimethyl-3-(3,4,5-trifluoro-phenyl)-5,7-dihydro-4H-pyrazolo[3,4-c]pyridin-6-yl]-(1H-pyrazolo[4,3-b]pyridin-3-yl)methanone

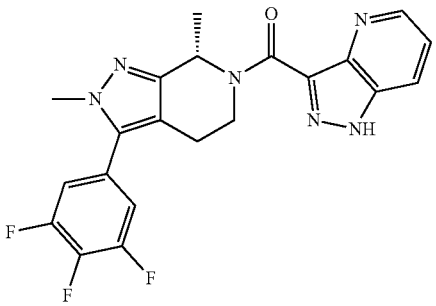

The title compound was prepared in a manner analogous to Example 288, using 1H-pyrazolo[4,3-b]pyridine-3-carboxylic acid instead of 2-fluoro-6-(2H-1,2,3-triazol-2-yl)benzoic acid. MS (ESI): mass calcd. for $C_{21}H_{17}F_3N_6O$, 426.1; m/z found, 427.1 [M+H]$^+$.

Example 437: [(7S)-2,7-Dimethyl-3-(3,4,5-trifluoro-phenyl)-5,7-dihydro-4H-pyrazolo[3,4-c]pyridin-6-yl]-([1,2,4]triazolo[4,3-a]pyridin-3-yl)methanone

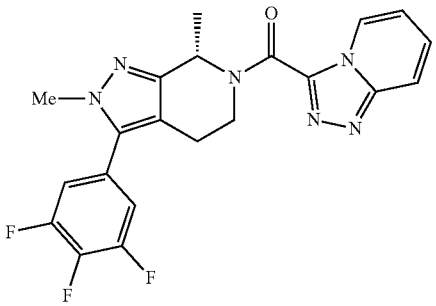 [SMILES: C[C@H]1c2nn(C)c(-c3cc(F)c(F)c(F)c3)c2CCN1C(=O)c1nnc2ccccn12]

The title compound was prepared in a manner analogous to Example 288, using potassium [1,2,4]triazolo[4,3-a]pyridine-3-carboxylate (Intermediate 92) instead of 2-fluoro-6-(2H-1,2,3-triazol-2-yl)benzoic acid. MS (ESI): mass calcd. for $C_{21}H_{17}F_3N_6O$, 426.1; m/z found, 427.2 [M+H]$^+$. $^1$H NMR (500 MHz, DMSO-$d_6$) δ 8.96 (dd, J=11.1, 7.1 Hz, 1H), 8.03-7.87 (m, 1H), 7.62-7.49 (m, 3H), 7.18 (t, J=6.8 Hz, 1H), 6.34-5.58 (m, 1H), 5.26-4.66 (m, 1H), 3.84-3.74 (m, 3H), 3.48-3.34 (m, 1H), 3.12-2.74 (m, 1H), 2.62-2.53 (m, 1H), 1.62-1.45 (m, 3H).

Example 438: [(7S)-2,7-Dimethyl-3-(3,4,5-trifluoro-phenyl)-5,7-dihydro-4H-pyrazolo[3,4-c]pyridin-6-yl]-([1,2,4]triazolo[4,3-a]pyridin-5-yl)methanone

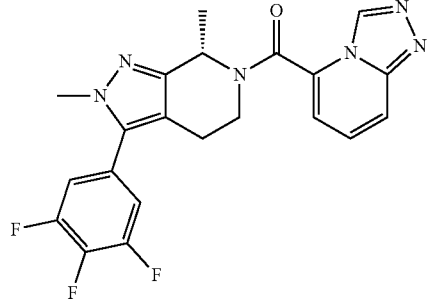 [SMILES: C[C@H]1c2nn(C)c(-c3cc(F)c(F)c(F)c3)c2CCN1C(=O)c1cccc2nncn12]

The title compound was prepared in a manner analogous to Example 288, using [1,2,4]triazolo[4,3-a]pyridine-5-carboxylic acid instead of 2-fluoro-6-(2H-1,2,3-triazol-2-yl)benzoic acid. MS (ESI): mass calcd. for $C_{21}H_{17}F_3N_6O$, 426.1; m/z found, 427.0 [M+H]$^+$. $^1$H NMR (400 MHz, DMSO-$d_6$) δ 9.15 (s, 1H), 8.00-7.84 (m, 1H), 7.62-7.41 (m, 3H), 7.25-7.15 (m, 1H), 5.70-5.36 (m, 1H), 5.11-4.33 (m, 1H), 4.03-3.72 (m, 4H), 3.06-2.83 (m, 1H), 2.46-2.31 (m, 1H), 1.61-1.49 (m, 3H).

Example 439: [(7S)-2,7-Dimethyl-3-(3,4,5-trifluoro-phenyl)-5,7-dihydro-4H-pyrazolo[3,4-c]pyridin-6-yl]-([1,2,4]triazolo[4,3-a]pyridin-6-yl)methanone

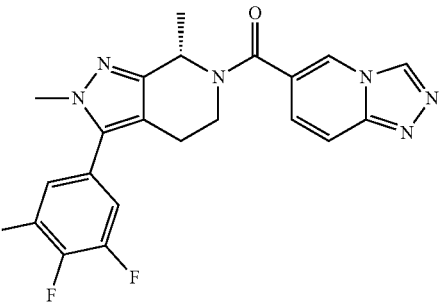

The title compound was prepared in a manner analogous to Example 288, using [1,2,4]triazolo[4,3-a]pyridine-6-carboxylic acid instead of 2-fluoro-6-(2H-1,2,3-triazol-2-yl)benzoic acid. MS (ESI): mass calcd. for $C_{21}H_{17}F_3N_6O$, 426.1; m/z found, 427.0 [M+H]$^+$. $^1$H NMR (400 MHz, DMSO-$d_6$) δ 9.26 (d, J=0.8 Hz, 1H), 8.78 (t, J=1.4 Hz, 1H), 7.91-7.65 (m, 1H), 7.64-7.52 (m, 2H), 7.47-7.29 (m, 1H), 5.61-5.31 (m, 1H), 4.77-4.20 (m, 1H), 4.00-3.74 (m, 4H), 2.95-2.78 (m, 1H), 2.47-2.32 (m, 1H), 1.49 (d, J=6.8 Hz, 3H).

Example 440: [3-(Difluoromethyl)-[1,2,4]triazolo[4,3-a]pyridin-6-yl]-[(7S)-2,7-dimethyl-3-(3,4,5-trifluo-rophenyl)-5,7-dihydro-4H-pyrazolo[3,4-c]pyridin-6-yl]methanone

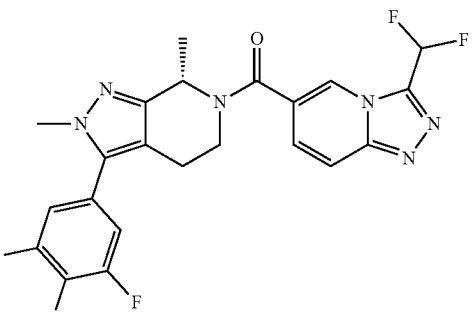

The title compound was prepared in a manner analogous to Example 288, using 3-(difluoromethyl)-[1,2,4]triazolo[4,3-a]pyridine-6-carboxylic acid instead of 2-fluoro-6-(2H-1,2,3-triazol-2-yl)benzoic acid. MS (ESI): mass calcd. for $C_{22}H_{17}F_5N_6O$, 476.1; m/z found, 477.1 [M+H]$^+$. $^1$H NMR (400 MHz, DMSO-$d_6$) δ 8.78 (s, 1H), 8.02 (dd, J=9.4, 1.1

Hz, 1H), 7.77 (t, J=51.7 Hz, 1H), 7.60-7.44 (m, 3H), 5.65-5.44 (m, 1H), 5.02-4.44 (m, 1H), 3.94-3.61 (m, 4H), 2.94-2.75 (m, 1H), 2.46-2.21 (m, 1H), 1.50 (d, J=6.7 Hz, 3H).

Example 441: [(7S)-2,7-Dimethyl-3-(3,4,5-trifluorophenyl)-5,7-dihydro-4H-pyrazolo[3,4-c]pyridin-6-yl]-(triazolo[1,5-a]pyridin-3-yl)methanone

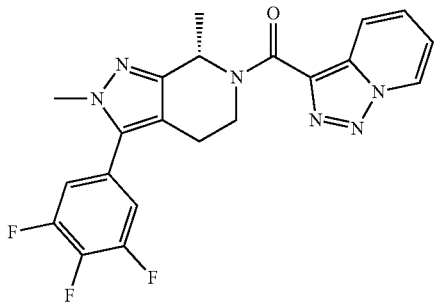 [SMILES: C[C@H]1c2nn(C)c(-c3cc(F)c(F)c(F)c3)c2CCN1C(=O)c1nnn2ccccc12]

The title compound was prepared in a manner analogous to Example 288, using [1,2,3]triazolo[1,5-a]pyridine-3-carboxylic acid instead of 2-fluoro-6-(2H-1,2,3-triazol-2-yl)benzoic acid. MS (ESI): mass calcd. for $C_{21}H_{17}F_3N_6O$, 426.1; m/z found, 427.1 [M+H]$^+$. $^1$H NMR (500 MHz, DMSO-d$_6$) δ 9.23 (dt, J=7.0, 1.0 Hz, 1H), 8.25 (dt, J=9.0, 1.2 Hz, 1H), 7.68-7.63 (m, 1H), 7.60-7.51 (m, 2H), 7.35 (td, J=6.8, 1.3 Hz, 1H), 6.48-6.42 (m, 0.37H), 5.75-5.61 (m, 0.55H), 5.43-5.29 (m, 0.55H), 4.82-4.66 (m, 0.39H), 3.88-3.73 (m, 3H), 3.19-2.72 (m, 1.58H), 1.72-1.44 (m, 3H). (Fractions of Hs that may overlap with DMSO and water are not reported).

Example 442: [(7S)-2,7-Dimethyl-3-(3,4,5-trifluorophenyl)-5,7-dihydro-4H-pyrazolo[3,4-c]pyridin-6-yl]-(2-methylpyrazolo[1,5-b] pyridazin-3-yl) methanone

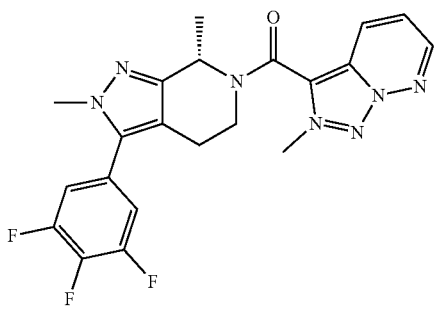

The title compound was prepared in a manner analogous to Example 288, using 2-methylpyrazolo[1,5-b]pyridazine-3-carboxylic acid instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]$^+$. $^1$H NMR (500 MHz, DMSO-d$_6$) δ 8.47 (dd, J=4.4, 1.9 Hz, 1H), 8.05 (dd, J=9.0, 1.8 Hz, 1H), 7.60-7.49 (m, 2H), 7.30 (dd, J=9.0, 4.5 Hz, 1H), 5.68-5.37 (m, 1H), 4.11-3.92 (m, 1H), 3.81 (s, 3H), 3.29-3.16 (m, 1H), 2.76-2.63 (m, 1H), 2.43 (s, 3H), 2.41-2.33 (m, 1H), 1.48-1.45 (m, 3H).

Example 443: [(7S)-2,7-Dimethyl-3-(3,4,5-trifluorophenyl)-5,7-dihydro-4H-pyrazolo[3,4-c]pyridin-6-yl]-(5-methylpyrazolo[1,5-b] pyridazin-3-yl) methanone

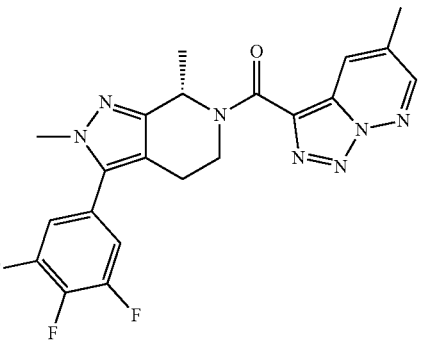

The title compound was prepared in a manner analogous to Example 288, using potassium 5-methylpyrazolo[1,5-b]pyridazine-3-carboxylate (Intermediate 93) instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]$^+$. $^1$H NMR (400 MHz, DMSO-d$_6$) δ 8.43 (d, J=4.6 Hz, 1H), 8.25 (s, 1H), 7.55 (dd, J=8.7, 6.7 Hz, 2H), 7.15 (d, J=4.5 Hz, 1H), 5.64 (s, 1H), 4.18-3.69 (m, 4H), 3.01-2.68 (m, 2H), 2.47-2.36 (m, 3H), 2.40-2.30 (m, 1H), 1.55-1.37 (m, 3H).

Example 444: (2-Cyclopropyl-4-methyl-pyrazolo[1,5-b]pyridazin-3-yl)-[(7S)-2,7-dimethyl-3-(3,4,5-trifluorophenyl)-5,7-dihydro-4H-pyrazolo[3,4-c]pyridin-6-yl]methanone

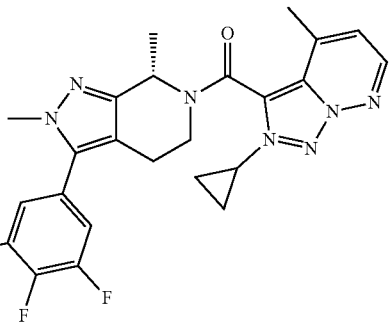

The title compound was prepared in a manner analogous to Example 288, using potassium 2-cyclopropyl-4-methylpyrazolo[1,5-b]pyridazine-3-carboxylate (Intermediate 108) instead of 2-fluoro-6-(2H-1,2,3-triazol-2-yl)benzoic acid. MS (ESI): mass calcd. for $C_{25}H_{23}F_3N_6O$, 480.2; m/z found, 481.3 [M+H]$^+$. $^1$H NMR (400 MHz, DMSO-d$_6$) δ 8.38-8.25 (m, 1H), 7.61-7.42 (m, 2H), 7.19-6.82 (m, 1H), 5.89-5.49 (m, 1H), 3.88-3.76 (m, 3H), 3.77-3.60 (m, 1H), 3.28-2.94 (m, 1H), 2.47-2.19 (m, 4H), 1.98-1.83 (m, 1H), 1.59-1.34 (m, 3H), 1.16-0.79 (m, 5H).

Example 445: (2-Cyclopropyl-5-methyl-pyrazolo[1,5-b]pyridazin-3-yl)-[(7S)-2,7-dimethyl-3-(3,4,5-trifluorophenyl)-5,7-dihydro-4H-pyrazolo[3,4-c]pyridin-6-yl]methanone

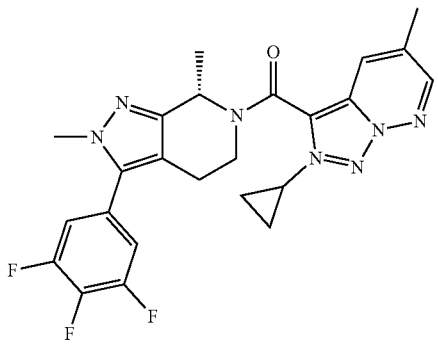

The title compound was prepared in a manner analogous to Example 288, using potassium 2-cyclopropyl-5-methylpyrazolo[1,5-b]pyridazine-3-carboxylate (Intermediate 109) instead of 2-fluoro-6-(2H-1,2,3-triazol-2-yl)benzoic acid. MS (ESI): mass calcd. for $C_{25}H_{23}F_3N_6O$, 480.2; m/z found, 481.3 [M+H]$^+$. $^1$H NMR (400 MHz, DMSO-d$_6$) δ 8.31 (d, J=2.4 Hz, 1H), 7.79 (t, J=1.8 Hz, 1H), 7.63-7.46 (m, 2H), 5.71-5.37 (m, 1H), 4.19-3.99 (m, 1H), 3.81 (s, 3H), 3.55-3.34 (m, 1H), 2.79-2.58 (m, 1H), 2.44-2.26 (m, 4H), 2.05-1.85 (m, 1H), 1.53-1.41 (m, 3H), 1.11-0.85 (m, 4H).

Example 446: (2,4-Dimethylpyrazolo[1,5-a]pyrazin-3-yl)-[(7S)-2,7-dimethyl-3-(3,4,5-trifluorophenyl)-5,7-dihydro-4H-pyrazolo[3,4-c]pyridin-6-yl]methanone

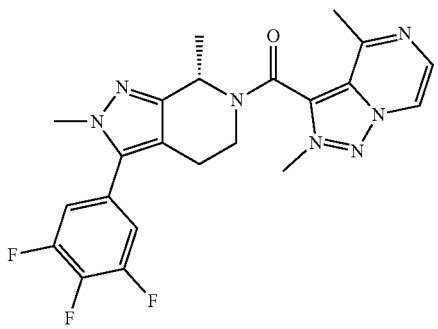

The title compound was prepared in a manner analogous to Example 288, using potassium 2,4-dimethylpyrazolo[1,5-a]pyrazine-3-carboxylate (Intermediate 94) instead of 2-fluoro-6-(2H-1,2,3-triazol-2-yl)benzoic acid. MS (ESI): mass calcd. for $C_{23}H_{21}F_3N_6O$, 454.2; m/z found, 455.1 [M+H]$^+$. $^1$H NMR (400 MHz, DMSO-d$_6$) δ 8.65-8.55 (m, 1H), 7.86-7.74 (m, 1H), 7.62-7.49 (m, 2H), 5.86-5.68 (m, 0.70H), 4.90-4.56 (m, 0.30H), 3.87-3.56 (m, 4H), 3.29-3.06 (m, 1H), 2.89-2.59 (m, 1H), 2.58-2.52 (m, 3H), 2.45-2.35 (m, 3H), 2.31-2.19 (m, 1H), 1.54-1.24 (m, 3H).

Example 447: (2-Cyclopropyl-4-methyl-pyrazolo[1,5-a]pyrazin-3-yl)-[(7S)-2,7-dimethyl-3-(3,4,5-trifluorophenyl)-5,7-dihydro-4H-pyrazolo[3,4-c]pyridin-6-yl]methanone

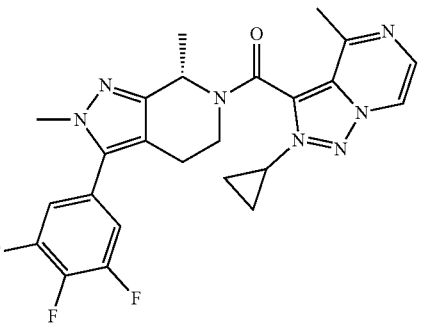

The title compound was prepared in a manner analogous to Example 288, using potassium 2-cyclopropyl-4-methylpyrazolo[1,5-a]pyrazine-3-carboxylate (Intermediate 95) instead of 2-fluoro-6-(2H-1,2,3-triazol-2-yl)benzoic acid. MS (ESI): mass calcd. for $C_{25}H_{23}F_3N_6O$, 480.2; m/z found, 481.2 [M+H]$^+$. $^1$H NMR (400 MHz, Methanol-d$_4$) δ 8.45-8.32 (m, 1H), 7.81-7.67 (m, 1H), 7.40-7.21 (m, 2H), 6.05-5.80 (m, 1H), 5.27-4.95 (m, 1H), 4.08-3.75 (m, 4H), 3.69-3.38 (m, 1H), 2.74-2.56 (m, 3H), 2.56-2.31 (m, 1H), 2.13-1.91 (m, 1H), 1.69-1.38 (m, 3H), 1.27-0.96 (m, 4H).

Example 448: [(7S)-2,7-Dimethyl-3-(3,4,5-trifluorophenyl)-5,7-dihydro-4H-pyrazolo[3,4-c]pyridin-6-yl]-pyrazolo[1,5-a]pyrimidin-3-yl-methanone

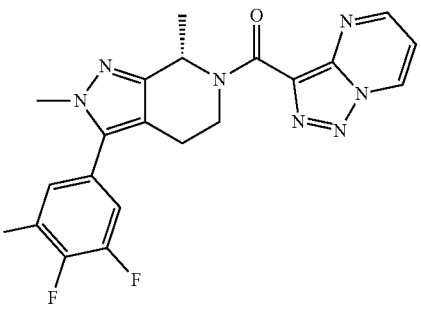

The title compound was prepared in a manner analogous to Example 288, using pyrazolo[1,5-a]pyrimidine-3-carboxylic acid instead of 2-fluoro-6-(2H-1,2,3-triazol-2-yl)benzoic acid and DMF instead of DCM. MS (ESI): mass calcd. for $C_{21}H_{17}F_3N_6O$, 426.1; m/z found, 427.2 [M+H]$^+$. $^1$H NMR (600 MHz, DMSO-d$_6$) δ 9.22 (dd, J=7.0, 1.7 Hz, 1H), 8.70 (dd, J=4.1, 1.8 Hz, 1H), 8.45 (s, 1H), 7.58-7.51 (m, 2H), 7.18 (dd, J=7.0, 4.1 Hz, 1H), 5.71-5.03 (m, 1.25H), 4.81-4.46 (m, 0.38H), 4.15-3.61 (m, 4H), 2.47-2.34 (m, 1H), 1.48 (d, J=6.7 Hz, 3H). (Fractions of Hs that overlap with DMSO and water are not reported).

Example 449: [(7S)-2,7-Dimethyl-3-(3,4,5-trifluorophenyl)-5,7-dihydro-4H-pyrazolo[3,4-c]pyridin-6-yl]-(2-methylpyrazolo[1,5-a]pyrimidin-3-yl)methanone

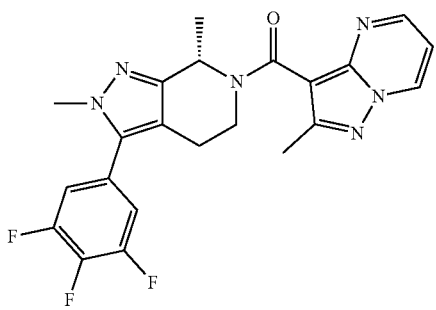 [SMILES: Cc1nn2cccnc2c1C(=O)N1CCc2c(nn(C)c2-c2cc(F)c(F)c(F)c2)[C@@H]1C]

The title compound was prepared in a manner analogous to Example 288, using 2-methylpyrazolo[1,5-a]pyrimidine-3-carboxylic acid instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]+. $^1$H NMR (400 MHz, DMSO-$d_6$) δ 9.08 (dd, J=7.0, 1.8 Hz, 1H), 8.61 (dd, J=4.2, 1.7 Hz, 1H), 7.63-7.48 (m, 2H), 7.08 (dd, J=7.0, 4.1 Hz, 1H), 5.71-5.61 (m, 1H), 5.04-4.69 (m, 1H), 3.93-3.69 (m, 4H), 2.97-2.75 (m, 1H), 2.48-2.23 (m, 4H), 1.57-1.25 (m, 3H)

Example 450: [(7S)-2,7-Dimethyl-3-(3,4,5-trifluorophenyl)-5,7-dihydro-4H-pyrazolo[3,4-c]pyridin-6-yl]-(7-methylpyrazolo[1,5-a]pyrimidin-3-yl)methanone

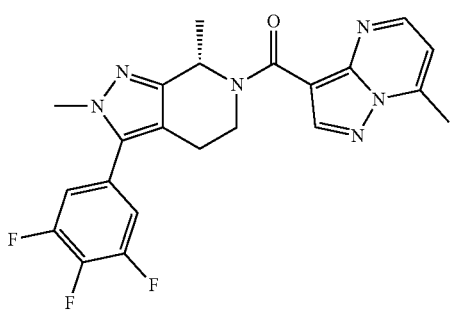 [SMILES: Cc1ccnc2c(C(=O)N3CCc4c(nn(C)c4-c4cc(F)c(F)c(F)c4)[C@@H]3C)cnn12]

The title compound was prepared in a manner analogous to Example 288, using 7-methylpyrazolo[1,5-a]pyrimidine-3-carboxylic acid instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]+. $^1$H NMR (500 MHz, DMSO-$d_6$) δ 8.60 (d, J=4.3 Hz, 1H), 8.46 (s, 1H), 7.54 (dd, J=8.6, 6.6 Hz, 2H), 7.14 (dd, J=4.3, 1.0 Hz, 1H), 5.59 (s, 1H), 4.13-3.91 (m, 1H), 3.79 (s, 3H), 3.24-2.93 (m, 2H), 2.83-2.74 (m, 3H), 2.46-2.32 (m, 1H), 1.48 (d, J=6.7 Hz, 3H).

Example 451: [(7S)-2,7-Dimethyl-3-(3,4,5-trifluorophenyl)-5,7-dihydro-4H-pyrazolo[3,4-c]pyridin-6-yl]-(6-methylpyrazolo[1,5-a]pyrimidin-3-yl)methanone

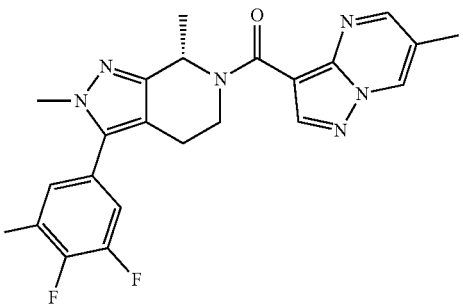

The title compound was prepared in a manner analogous to Example 288, using 6-methylpyrazolo[1,5-a]pyrimidine-3-carboxylic acid instead of 2-fluoro-6-(2H-1,2,3-triazol-2-yl)benzoic acid. MS (ESI): mass calcd. for $C_{22}H_{19}F_3N_6O$, 440.2; m/z found, 441.2 [M+H]+. $^1$H NMR (600 MHz, DMSO-$d_6$) δ 9.08-9.06 (m, 1H), 8.64-8.60 (m, 1H), 8.35 (s, 1H), 7.58-7.51 (m, 2H), 5.71-5.01 (m, 1.27H), 4.80-4.46 (m, 0.39H), 4.15-3.65 (m, 4H), 2.46-2.32 (m, 4H), 1.48 (d, J=6.7 Hz, 3H). (Fractions of H's that overlap with DMSO and water may not be reported)

Example 452: [(7S)-2,7-Dimethyl-3-(3,4,5-trifluorophenyl)-5,7-dihydro-4H-pyrazolo[3,4-c]pyridin-6-yl]-imidazo[1,2-b]pyridazin-6-yl-methanone

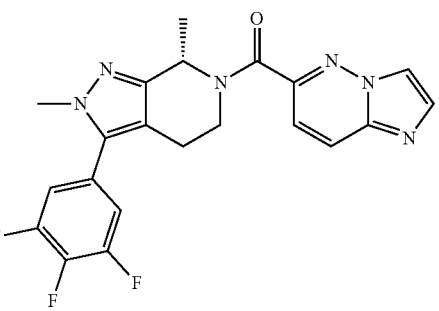

The title compound was prepared in a manner analogous to Example 288, using imidazo[1,2-b]pyridazine-6-carboxylic acid instead of 2-fluoro-6-(2H-1,2,3-triazol-2-yl)benzoic acid. MS (ESI): mass calcd. for $C_{21}H_{17}F_3N_6O$, 426.1; m/z found, 427.2 [M+H]+. $^1$H NMR (500 MHz, Chloroform-d) δ 8.08-8.01 (m, 1H), 8.01-7.97 (m, 1H), 7.87 (dd, J=3.9, 1.3 Hz, 1H), 7.39-7.33 (m, 1H), 7.02-6.93 (m, 2H), 5.86 (q, J=6.7 Hz, 0.51H), 5.34-5.27 (m, 0.64H), 4.88 (dd, J=13.1, 5.3 Hz, 0.43H), 4.12 (dd, J=13.8, 5.0 Hz, 0.51H), 3.84 (s, 1.53H), 3.77 (s, 1.33H), 3.44-3.32 (m, 0.51H), 3.24-3.13 (m, 0.44H), 3.01-2.79 (m, 1H), 2.58-2.40 (m, 1H), 1.71 (d, J=6.7 Hz, 1.35H), 1.65 (d, J=6.8 Hz, 1.65H).

Example 453: [(7S)-2,7-Dimethyl-3-(3,4,5-trifluorophenyl)-5,7-dihydro-4H-pyrazolo[3,4-c] pyridin-6-yl]-(2-methylimidazo[1,2-b]pyridazin-6-yl)methanone

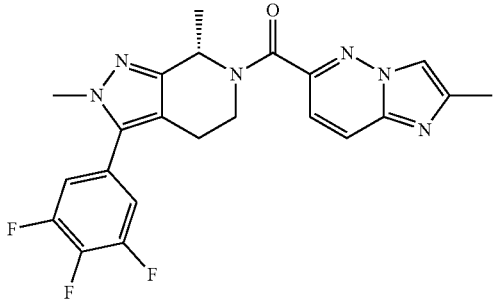 [SMILES: Cc1cn2nc(C(=O)N3CCc4c(nn(C)c4-c4cc(F)c(F)c(F)c4)[C@@H]3C)ccc2n1]

The title compound was prepared in a manner analogous to Example 288, using 2-methylimidazo[1,2-b]pyridazine-6-carboxylic acid (Intermediate 96) instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]$^+$. $^1$H NMR (500 MHz, DMSO-d$_6$) δ 8.19-8.03 (m, 2H), 7.60-7.50 (m, 2H), 7.35-7.20 (m, 1H), 5.66-4.85 (m, 2H), 3.93-3.53 (m, 4H), 2.92-2.69 (m, 1H), 2.46-2.31 (m, 4H), 1.55-1.40 (m, 3H).

Example 454: [(7S)-2,7-Dimethyl-3-(3,4,5-trifluorophenyl)-5,7-dihydro-4H-pyrazolo[3,4-c]pyridin-6-yl]-imidazo[1,2-b]pyridazin-3-yl-methanone

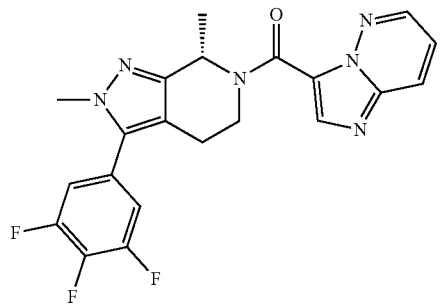 [SMILES: C[C@H]1c2nn(C)c(-c3cc(F)c(F)c(F)c3)c2CCN1C(=O)c1cnc2cccnn12]

The title compound was prepared in a manner analogous to Example 288, using imidazo[1,2-b]pyridazine-3-carboxylic acid instead of 2-fluoro-6-(2H-1,2,3-triazol-2-yl)benzoic acid. MS (ESI): mass calcd. for $C_{21}H_{17}F_3N_6O$, 426.1; m/z found, 427.1 [M+H]$^+$. $^1$H NMR (500 MHz, Chloroform-d) δ 8.46 (dd, J=4.4, 1.6 Hz, 1H), 8.03 (dd, J=9.2, 1.7 Hz, 1H), 7.98 (s, 1H), 7.15 (dd, J=9.2, 4.4 Hz, 1H), 7.02-6.94 (m, 2H), 6.14-4.60 (m, 1H), 4.24-3.68 (m, 4H), 3.34 (brs, 1H), 2.88 (brs, 1H), 2.46 (d, J=15.0 Hz, 1H), 1.66 (d, J=6.8 Hz, 3H).

Example 455: [(7S)-2,7-Dimethyl-3-(3,4,5-trifluorophenyl)-5,7-dihydro-4H-pyrazolo[3,4-c]pyridin-6-yl]-(2-methylimidazo[1,2-b]pyridazin-3-yl)methanone

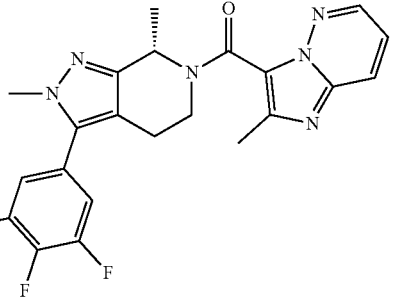

The title compound was prepared in a manner analogous to Example 288, using 2-methylimidazo[1,2-b]pyridazine-3-carboxylic acid hydrochloride instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]$^+$. $^1$H NMR (500 MHz, DMSO-d$_6$) δ 8.54 (s, 1H), 8.10 (dd, J=9.2, 1.6 Hz, 1H), 7.55 (d, J=8.0 Hz, 2H), 7.28 (dd, J=9.2, 4.5 Hz, 1H), 5.72-5.63 (m, 0.66H), 4.88-4.57 (m, 0.34H), 3.82 (s, 3H), 3.49-3.35 (m, 1H), 2.72 (d, J=25.5 Hz, 1H), 2.44-2.27 (m, 4H), 1.62-1.25 (m, 3H). (one proton under water peak).

Example 456: (2,8-Dimethylimidazo[1,2-b] pyridazin-3-yl)-[(7S)-2,7-dimethyl-3-(3,4,5-trifluorophenyl)-5,7-dihydro-4H-pyrazolo[3,4-c] pyridin-6-yl]methanone

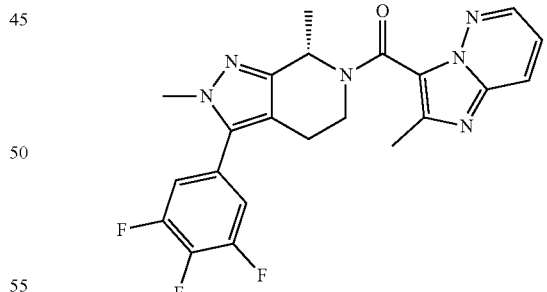

The title compound was prepared in a manner analogous to Example 288, using potassium 2,8-dimethylimidazo[1,2-b]pyridazine-3-carboxylate (Intermediate 97) instead of 2-fluoro-6-(2H-1,2,3-triazol-2-yl)benzoic acid. MS (ESI): mass calcd. for $C_{23}H_{21}F_3N_6O$, 454.2; m/z found, 455.1 [M+H]$^+$. $^1$H NMR (400 MHz, DMSO-d$_6$) δ 8.40 (d, J=4.7 Hz, 1H), 7.54 (t, J=7.5 Hz, 2H), 7.20-7.04 (m, 1H), 5.66 (s, 1H), 4.85-4.45 (m, 1H), 3.81 (s, 3H), 3.42 (s, 1H), 2.73 (s, 1H), 2.60-2.55 (m, 3H), 2.43-2.24 (m, 4H), 1.42 (d, J=72.4 Hz, 3H).

Example 457: (2,7-Dimethylimidazo[1,2-b]pyridazin-3-yl)-[(7S)-2,7-dimethyl-3-(3,4,5-trifluorophenyl)-5,7-dihydro-4H-pyrazolo[3,4-c] pyridin-6-yl] methanone

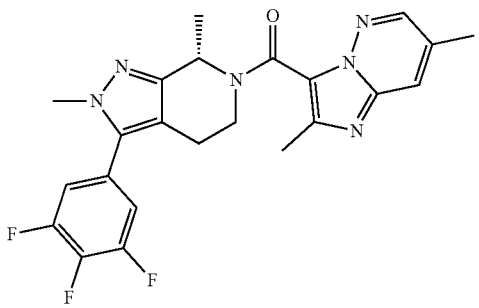 [SMILES: Cc1cnn2c(C(=O)N3CCc4c(nn(C)c4-c4cc(F)c(F)c(F)c4)[C@@H]3C)c(C)nc2c1]

The title compound was prepared in a manner analogous to Example 288, using potassium 2,7-dimethylimidazo[1,2-b]pyridazine-3-carboxylate (Intermediate 98) instead of 2-fluoro-6-(2H-1,2,3-triazol-2-yl)benzoic acid. MS (ESI): mass calcd. for $C_{23}H_{21}F_3N_6O$, 454.2; m/z found, 455.1 [M+H]$^+$. $^1$H NMR (500 MHz, DMSO-d$_6$) δ 8.43 (s, 1H), 7.88 (dd, J=2.1, 1.2 Hz, 1H), 7.54 (t, J=7.6 Hz, 2H), 5.65 (s, 1H), 4.85-4.53 (m, 1H), 3.81 (s, 3H), 3.54-3.40 (m, 1H), 3.23-3.01 (m, 1H), 2.86-2.65 (m, 1H), 2.40-2.38 (m, 3H), 2.37-2.31 (m, 3H), 1.50 (s, 3H).

Example 458: [(7S)-2,7-Dimethyl-3-(3,4,5-trifluorophenyl)-5,7-dihydro-4H-pyrazolo[3,4-c]pyridin-6-yl]-(2-methylimidazo[1,2-a]pyrimidin-3-yl)methanone

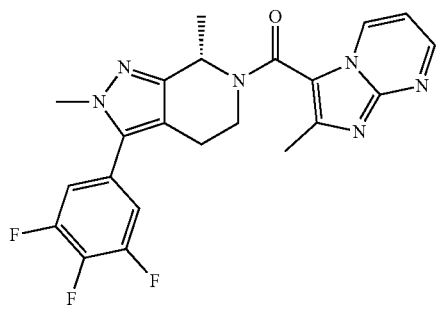 [SMILES: Cc1nc2ncccn2c1C(=O)N1CCc2c(nn(C)c2-c2cc(F)c(F)c(F)c2)[C@@H]1C]

The title compound was prepared in a manner analogous to Example 288, using 2-methylimidazo[1,2-a]pyrimidine-3-carboxylic acid instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]$^+$. $^1$H NMR (400 MHz, DMSO-d$_6$) δ 8.76 (dd, J=6.9, 2.0 Hz, 1H), 8.60 (dd, J=4.2, 2.0 Hz, 1H), 7.54 (dd, J=8.7, 6.6 Hz, 2H), 7.13 (dd, J=6.8, 4.2 Hz, 1H), 5.58 (s, 1H), 4.18-3.98 (m, 1H), 3.82 (s, 3H), 3.41 (t, J=12.7 Hz, 1H), 2.84-2.68 (m, 1H), 2.47-2.44 (m, 1H), 2.42 (s, 3H), 1.50 (d, J=6.7 Hz, 3H).

Example 459: [(7S)-2,7-Dimethyl-3-(3,4,5-trifluorophenyl)-5,7-dihydro-4H-pyrazolo[3,4-c]pyridin-6-yl]-(2,5,8-trimethylimidazo[1,2-a]pyrazin-3-yl) methanone

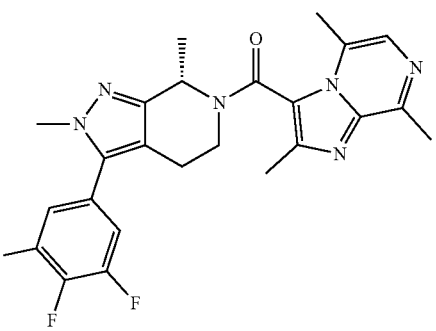

The title compound was prepared in a manner analogous to Example 288, using potassium 2,5,8-trimethylimidazo[1,2-a]pyrazine-3-carboxylate (Intermediate 99) instead of 2-fluoro-6-(2H-1,2,3-triazol-2-yl)benzoic acid. MS (ESI): mass calcd. for $C_{24}H_{23}F_3N_6O$, 468.1; m/z found, 469.2 [M+H]$^+$. $^1$H NMR (400 MHz, DMSO-d$_6$) δ 7.65-7.46 (m, 3H), 5.90-5.53 (m, 1H), 3.86-3.69 (m, 3H), 3.61-3.44 (m, 1H), 2.80-2.60 (m, 4H), 2.44 (m, 2H), 2.41-2.35 (m, 4H), 2.34-2.21 (m, 1H), 2.20-2.06 (m, 1H), 1.58-1.26 (m, 3H).

Example 460: [(7S)-2,7-Dimethyl-3-(3,4,5-trifluorophenyl)-5,7-dihydro-4H-pyrazolo[3,4-c] pyridin-6-yl]-(6-methylimidazo[1,5-a]pyrimidin-8-yl)methanone

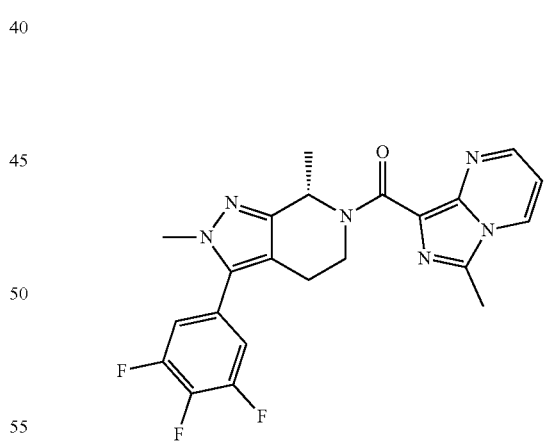

The title compound was prepared in a manner analogous to Example 288, using lithium 6-methylimidazo[1,5-a]pyrimidine-8-carboxylate instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]$^+$. $^1$H NMR (500 MHz, DMSO-d$_6$) δ 8.63 (dd, J=7.2, 1.7 Hz, 1H), 8.37-8.28 (m, 1H), 7.60-7.48 (m, 2H), 6.88 (dd, J=7.2, 3.7 Hz, 1H), 5.65-5.40 (m, 1H), 4.71-4.28 (m, 1H), 3.84-3.65 (m, 3H), 3.27-2.71 (m, 2H), 2.62 (s, 3H), 2.44-2.25 (m, 1H), 1.48 (s, 3H).

Example 461: [(7S)-2,7-Dimethyl-3-(3,4,5-trifluorophenyl)-5,7-dihydro-4H-pyrazolo[3,4-c] pyridin-6-yl]-(3-methylimidazo[1,5-a]pyrimidin-8-yl)methanone

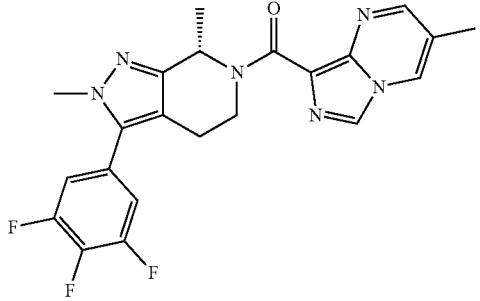 [SMILES: Cc1cnc2c(C(=O)N3CCc4c(nn(C)c4-c4cc(F)c(F)c(F)c4)[C@@H]3C)ncn2c1]

The title compound was prepared in a manner analogous to Example 288, using lithium 3-methylimidazo[1,5-a]pyrimidine-8-carboxylate instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]$^+$. $^1$H NMR (500 MHz, DMSO-$d_6$) δ 8.65-8.55 (m, 1H), 8.37-8.20 (m, 2H), 7.61-7.41 (m, 2H), 5.68-5.39 (m, 1H), 4.74-4.29 (m, 1H), 3.87-3.63 (m, 3H), 3.25-2.74 (m, 2H), 2.44-2.32 (m, 1H), 2.30-2.22 (m, 3H), 1.49 (s, 3H).

Example 462: [(7S)-2,7-Dimethyl-3-(3,4,5-trifluorophenyl)-5,7-dihydro-4H-pyrazolo[3,4-c] pyridin-6-yl]-(3-methylimidazo[1,5-a] pyrazin-1-yl) methanone

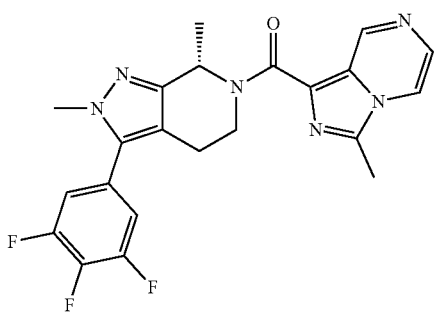 [SMILES: Cc1nc(C(=O)N2CCc3c(nn(C)c3-c3cc(F)c(F)c(F)c3)[C@@H]2C)c2cnccn12]

The title compound was prepared in a manner analogous to Example 288, using sodium 3-methylimidazo[1,5-a]pyrazine-1-carboxylate (Intermediate 100) instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]$^+$. $^1$H NMR (400 MHz, DMSO-$d_6$) δ 9.41 (d, J=1.6 Hz, 1H), 8.29 (dd, J=5.0, 1.6 Hz, 1H), 7.75 (d, J=4.9 Hz, 1H), 7.64-7.47 (m, 2H), 6.74-6.48 (m, 0.60H), 5.78-5.45 (m, 0.40H), 4.87-4.46 (m, 1H), 3.80 (s, 3H), 3.21-2.76 (m, 2H), 2.69 (s, 3H), 2.48-2.37 (m, 1H), 1.61-1.42 (m, 3H).

Example 463: [(7S)-2,7-Dimethyl-3-(3,4,5-trifluorophenyl)-5,7-dihydro-4H-pyrazolo[3,4-c]pyridin-6-yl]-[3-(trifluoromethyl) imidazo[1,5-a] pyrazin-1-yl] methanone

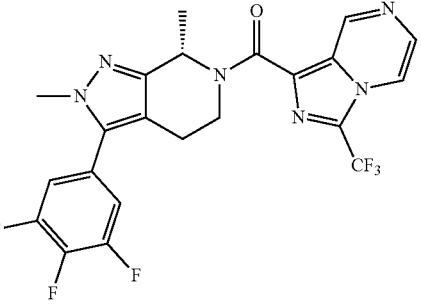

The title compound was prepared in a manner analogous to Example 288, using 3-(trifluoromethyl)imidazo[1,5-a]pyrazine-1-carboxylic acid instead of 2-fluoro-6-(2H-1,2,3-triazol-2-yl)benzoic acid. MS (ESI): mass calcd. for $C_{22}H_{16}F_6N_6O$, 494.1; m/z found, 495.1 [M+H]$^+$. $^1$H NMR (400 MHz, DMSO-$d_6$) δ 9.61 (d, J=1.6 Hz, 1H), 8.62-8.46 (m, 1H), 8.04 (d, J=5.0 Hz, 1H), 7.62-7.41 (m, 2H), 6.28-5.62 (m, 1H), 5.27-4.64 (m, 1H), 3.86-3.73 (m, 3H), 3.20-2.65 (m, 2H), 2.55-2.51 (m, 1H), 1.69-1.39 (m, 3H).

Example 464: [(7S)-2,7-Dimethyl-3-(3,4,5-trifluorophenyl)-5,7-dihydro-4H-pyrazolo[3,4-c]pyridin-6-yl]-(5-methyl-7H-pyrrolo[2,3-d]pyrimidin-4-yl) methanone

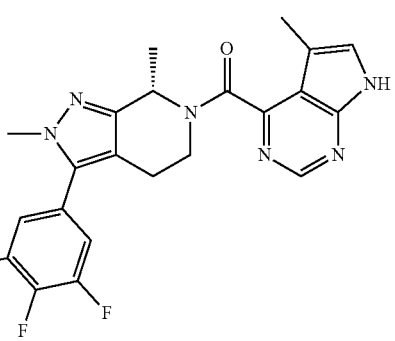

The title compound was prepared in a manner analogous to Example 288, using potassium 5-methyl-7H-pyrrolo[2,3-d]pyrimidine-4-carboxylate (Intermediate 101) instead of 2-fluoro-6-(2H-1,2,3-triazol-2-yl)benzoic acid. MS (ESI): mass calcd. for $C_{22}H_{19}F_3N_6O$, 440.2; m/z found, 441.1 [M+H]$^+$. $^1$H NMR (400 MHz, Methanol-$d_4$) δ 8.77 (d, J=4.8 Hz, 1H), 7.42-7.23 (m, 3H), 5.93-5.83 (m, 1H), 5.04-4.87 (m, 1H), 3.86-3.73 (m, 3H), 3.56-3.36 (m, 2H), 2.94-2.62 (m, 2H), 2.31-2.07 (m, 3H), 1.70-1.46 (m, 3H).

Example 465: [(7S)-3-(3-Fluoro-5-methyl-phenyl)-2,7-dimethyl-5,7-dihydro-4H-pyrazolo[3,4-c]pyridin-6-yl]-(7-methylpyrrolo[2,3-d] pyrimidin-4-yl)methanone

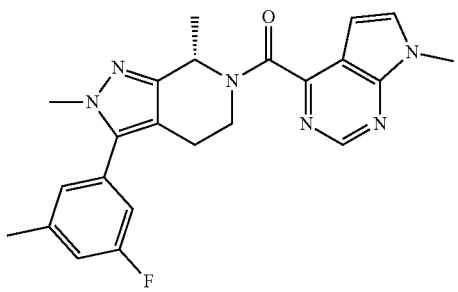

The title compound was prepared in a manner analogous to Example 288, using (S)-3-(3-fluoro-5-methylphenyl)-2,7-dimethyl-4,5,6,7-tetrahydro-2H-pyrazolo[3,4-c] pyridine (Intermediate 42) instead of (S)-2,7-dimethyl-3-(3,4,5-trifluorophenyl)-4,5,6,7-tetrahydro-2H-pyrazolo[3,4-c]pyridine and 7-methyl-7H-pyrrolo[2,3-d]pyrimidine-4-carboxylic acid instead of 2-fluoro-6-(2H-1,2,3-triazol-2-yl)benzoic acid. MS (ESI): mass calcd. for $C_{23}H_{23}FN_6O$, 418.2; m/z found, 419.1 $[M+H]^+$. $^1$H NMR (400 MHz, DMSO-$d_6$) δ 8.86 (d, J=5.4 Hz, 1H), 7.70 (dd, J=4.8, 3.5 Hz, 1H), 7.21-7.06 (m, 3H), 6.54 (dd, J=17.2, 3.5 Hz, 1H), 5.80-5.59 (m, 1H), 4.88-4.65 (m, 1H), 3.90-3.84 (m, 3H), 3.83-3.70 (m, 3H), 3.27-3.08 (m, 1H), 2.86-2.60 (m, 1H), 2.41-2.24 (m, 4H), 1.57-1.35 (m, 3H).

Example 466: [(7S)-2,7-Dimethyl-3-(3,4,5-trifluorophenyl)-5,7-dihydro-4H-pyrazolo[3,4-c]pyridin-6-yl]-(7-methylpyrrolo[2,3-d]pyrimidin-4-yl)methanone

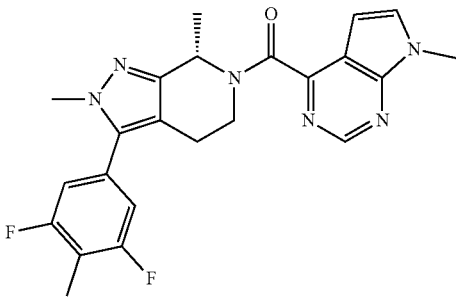 [SMILES: Cc1c(F)cc(-c2c3c(nn2C)[C@H](C)N(C(=O)c2ncnc4c2ccn4C)CC3)cc1F]

The title compound was prepared in a manner analogous to Example 288, using 7-methyl-7H-pyrrolo[2,3-d]pyrimidine-4-carboxylic acid instead of 2-fluoro-6-(2H-1,2,3-triazol-2-yl)benzoic acid. MS (ESI): mass calcd. for $C_{22}H_{19}F_3N_6O$, 440.2; m/z found, 441.1 $[M+H]^+$. $^1$H NMR (400 MHz, DMSO-$d_6$) δ 8.93-8.78 (m, 1H), 7.74-7.65 (m, 1H), 7.64-7.42 (m, 2H), 6.54 (dd, J=18.7, 3.5 Hz, 1H), 5.75-5.61 (m, 1H), 4.90-4.62 (m, 1H), 3.86 (s, 3H), 3.84-3.69 (m, 3H), 3.26-3.08 (m, 1H), 2.85-2.65 (m, 1H), 2.39-2.22 (m, 1H), 1.55-1.33 (m, 3H).

Example 467: (5,7-Dimethylpyrrolo[2,3-d] pyrimidin-4-yl)-[(7S)-2,7-dimethyl-3-(3,4,5-trifluorophenyl)-5,7-dihydro-4H-pyrazolo[3,4-c] pyridin-6-yl]methanone

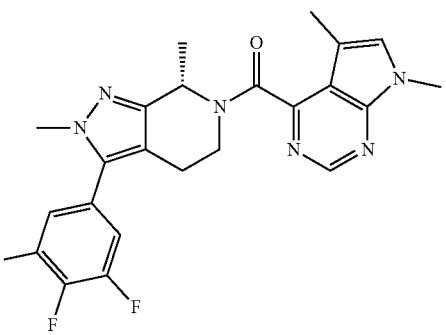

The title compound was prepared in a manner analogous to Example 288, using potassium 5,7-dimethyl-7H-pyrrolo[2,3-d]pyrimidine-4-carboxylate (Intermediate 102) instead of 2-fluoro-6-(2H-1,2,3-triazol-2-yl)benzoic acid. MS (ESI): mass calcd. for $C_{23}H_{21}F_3N_6O$, 454.2; m/z found, 455.1 $[M+H]^+$. $^1$H NMR (400 MHz, DMSO-$d_6$) δ 8.80 (d, J=5.2 Hz, 1H), 7.59-7.49 (m, 2H), 7.48-7.41 (m, 1H), 5.73-5.61 (m, 1H), 4.82-4.49 (m, 1H), 3.83-3.73 (m, 6H), 3.28-3.09 (m, 1H), 2.81-2.52 (m, 2H), 2.19-2.06 (m, 3H), 1.55-1.32 (m, 3H).

Example 468: [(7S)-2,7-Dimethyl-3-[3-(trifluoromethyl) phenyl]-5,7-dihydro-4H-pyrazolo[3,4-c] pyridin-6-yl]-(6-quinolyl)methanone

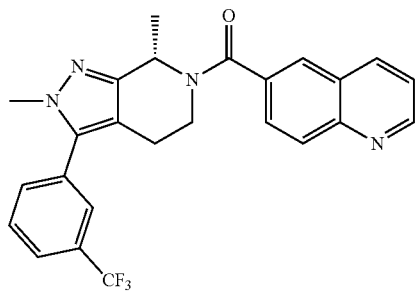 [SMILES: C[C@H]1c2nn(C)c(-c3cccc(C(F)(F)F)c3)c2CCN1C(=O)c1ccc2ncccc2c1]

The title compound was prepared in a manner analogous to Example 288, using (S)-2,7-dimethyl-3-(3-(trifluoromethyl)phenyl)-4,5,6,7-tetrahydro-2H-pyrazolo[3,4-c]pyridine (Intermediate 50) instead of (S)-2,7-dimethyl-3-(3,4,5-trifluorophenyl)-4,5,6,7-tetrahydro-2H-pyrazolo[3,4-c] pyridine and quinoline-6-carboxylic acid instead of 2-fluoro-6-(2H-1,2,3-triazol-2-yl) benzoic acid. MS (ESI): mass calcd. for $C_{25}H_{21}F_3N_4O$, 450.2; m/z found, 451.2 $[M+H]^+$. $^1$H NMR (400 MHz, DMSO-$d_6$) δ 8.98 (dd, J=4.2, 1.7 Hz, 1H), 8.48 (dd, J=8.2, 1.8 Hz, 1H), 8.10 (d, J=8.5 Hz, 2H), 7.90-7.73 (m, 5H), 7.67-7.53 (m, 1H), 5.78-5.50 (m, 1H), 4.90-4.38 (m, 1H), 3.98-3.58 (m, 4H), 3.01-2.75 (m, 1H), 2.46-2.21 (m, 1H), 1.58-1.43 (m, 3H).

Example 469: (6,7-Dimethylpyrrolo[2,3-d] pyrimidin-4-yl)-[(7S)-2,7-dimethyl-3-(3,4,5-trifluorophenyl)-5,7-dihydro-4H-pyrazolo[3,4-c] pyridin-6-yl]methanone

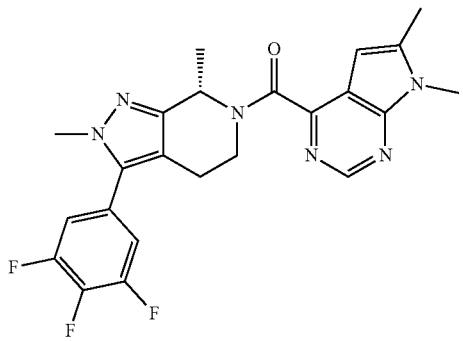 [SMILES: Cc1cc2c(C(=O)N3CCc4c(nn(C)c4-c4cc(F)c(F)c(F)c4)[C@@H]3C)ncnc2n1C]

The title compound was prepared in a manner analogous to Example 288, using 6,7-dimethyl-7H-pyrrolo[2,3-d]pyrimidine-4-carboxylic acid instead of 2-fluoro-6-(2H-1,2,3-triazol-2-yl)benzoic acid. MS (ESI): mass calcd. for $C_{23}H_{21}F_3N_6O$, 454.2; m/z found, 455.1 [M+H]$^+$. $^1$H NMR (500 MHz, DMSO-$d_6$) δ 8.76 (d, J=5.3 Hz, 1H), 7.61-7.45 (m, 2H), 6.38-6.23 (m, 1H), 5.73-5.56 (m, 1H), 5.03-4.40 (m, 1H), 3.86-3.73 (m, 6H), 3.70-3.60 (m, 1H), 3.28-3.06 (m, 1H), 2.84-2.63 (m, 1H), 2.49-2.46 (m, 3H), 1.63-1.32 (m, 3H).

Example 470: [(7S)-2,7-Dimethyl-3-(3,4,5-trifluorophenyl)-5,7-dihydro-4H-pyrazolo[3,4-c]pyridin-6-yl]-(7H-purin-6-yl)methanone

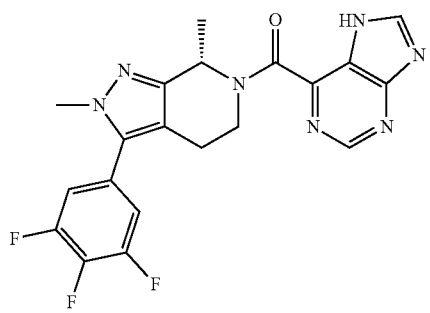 [SMILES: C[C@H]1c2nn(C)c(-c3cc(F)c(F)c(F)c3)c2CCN1C(=O)c1ncnc2nc[nH]c12]

The title compound was prepared in a manner analogous to Example 288, using 7H-purine-6-carboxylic acid instead of 2-fluoro-6-(2H-1,2,3-triazol-2-yl)benzoic acid and DMF instead of DCM. MS (ESI): mass calcd. for $C_{20}H_{16}F_3N_7O$, 427.2; m/z found, 428.1 [M+H]$^+$. $^1$H NMR (500 MHz, DMSO-$d_6$) δ 13.69 (s, 1H), 8.97-8.93 (m, 1H), 8.69-8.61 (m, 1H), 7.60-7.47 (m, 2H), 5.68 (q, J=6.7 Hz, 0.67H), 4.91-4.73 (m, 0.67H), 3.86-3.57 (m, 3.80H), 3.15 (td, J=12.7, 4.0 Hz, 0.44H), 2.84-2.69 (m, 1H), 2.59-2.53 (m, 0.38H), 2.35-2.25 (m, 0.64H), 1.54 (d, J=6.8 Hz, 2H), 1.40 (d, J=6.7 Hz, 1H). (Fractions of Hs that overlap with DMSO and water are not reported).

Example 471: [(7S)-2,7-Dimethyl-3-(3,4,5-trifluorophenyl)-5,7-dihydro-4H-pyrazolo[3,4-c]pyridin-6-yl]-(1-methylpyrazolo[3,4-d]pyrimidin-4-yl)methanone

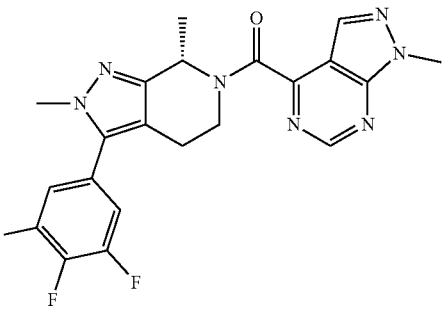

The title compound was prepared in a manner analogous to Example 288, using 1-methyl-1H-pyrazolo[3,4-d]pyrimidine-4-carboxylic acid instead of 2-fluoro-6-(2H-1,2,3-triazol-2-yl)benzoic acid. MS (ESI): mass calcd. for $C_{21}H_{18}F_3N_7O$, 441.2; m/z found, 442.1 [M+H]$^+$. $^1$H NMR (400 MHz, DMSO-$d_6$) δ 9.11 (d, J=6.5 Hz, 1H), 8.36 (d, J=22.2 Hz, 1H), 7.62-7.45 (m, 2H), 5.73-5.57 (m, 1H), 5.09-4.60 (m, 1H), 4.17-4.01 (m, 3H), 3.87-3.69 (m, 4H), 2.94-2.66 (m, 1H), 2.39-2.24 (m, 1H), 1.58-1.42 (m, 3H).

Example 472: [(7S)-2,7-Dimethyl-3-(3,4,5-trifluorophenyl)-5,7-dihydro-4H-pyrazolo[3,4-c]pyridin-6-yl]-(5-methyl-[1,2,4]triazolo[1,5-a]pyrimidin-7-yl)methanone

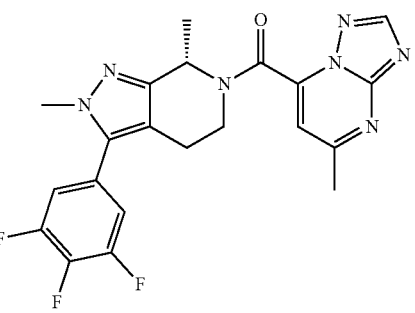

The title compound was prepared in a manner analogous to Example 288, using 5-methyl-[1,2,4]triazolo[1,5-a]pyrimidine-7-carboxylic acid instead of 2-fluoro-6-(2H-1,2,3-triazol-2-yl)benzoic acid and DMF instead of DCM. MS (ESI): mass calcd. for $C_{21}H_{18}F_3N_7O$, 441.2; m/z found, 442.2 [M+H]$^+$. $^1$H NMR (500 MHz, DMSO-$d_6$) δ 8.76 (s, 1H), 7.59-7.51 (m, 2H), 7.49-7.42 (m, 1H), 5.60 (q, J=6.7 Hz, 0.65H), 5.02 (q, J=6.7 Hz, 0.39H), 4.67 (dd, J=13.0, 5.3 Hz, 0.39H), 3.90-3.71 (m, 3.78H), 3.13 (td, J=12.6, 3.9 Hz, 0.43H), 2.87-2.72 (m, 4H), 2.38-2.30 (m, 0.71H), 1.53-1.48 (m, 3H). (Fractions of Hs that overlap with DMSO and water are not reported).

Example 473: [(7S)-2,7-Dimethyl-3-(3,4,5-trifluorophenyl)-5,7-dihydro-4H-pyrazolo[3,4-c] pyridin-6-yl]-(7-methylquinoxalin-6-yl) methanone

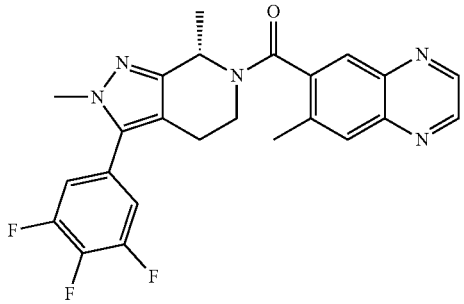 [SMILES: Cc1cc2nccnc2cc1C(=O)N1CCc2c(nn(C)c2-c2cc(F)c(F)c(F)c2)[C@@H]1C]

The title compound was prepared in a manner analogous to Example 288, using 7-methylquinoxaline-6-carboxylic acid instead of 2-fluoro-6-(2H-1,2,3-triazol-2-yl)benzoic acid. MS (ESI): mass calcd. for $C_{24}H_{20}F_3N_5O$, 451.2; m/z found, 452.1 [M+H]$^+$. $^1$H NMR (400 MHz, DMSO-d$_6$) δ 9.01-8.91 (m, 2H), 8.01 (d, J=34.5 Hz, 2H), 7.64-7.50 (m, 2H), 5.78-5.66 (m, 1H), 4.94-4.29 (m, 1H), 3.87-3.72 (m, 3H), 3.60-3.34 (m, 1H), 3.22-2.73 (m, 1H), 2.70-2.54 (m, 1H), 2.49-2.17 (m, 3H), 1.60-1.25 (m, 3H).

Example 474: [(7S)-2,7-Dimethyl-3-(3,4,5-trifluorophenyl)-5,7-dihydro-4H-pyrazolo[3,4-c] pyridin-6-yl]-(2-methylquinoxalin-5-yl)methanone

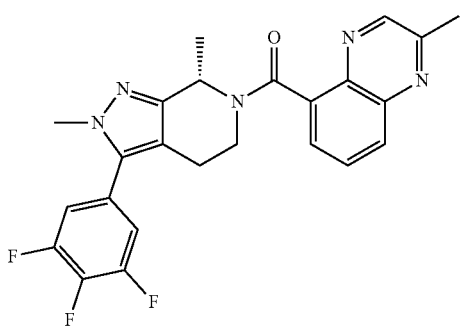 [SMILES: Cc1cnc2c(C(=O)N3CCc4c(nn(C)c4-c4cc(F)c(F)c(F)c4)[C@@H]3C)cccc2n1]

The title compound was prepared in a manner analogous to Example 288, using 2-methylquinoxaline-5-carboxylic acid instead of 2-fluoro-6-(2H-1,2,3-triazol-2-yl)benzoic acid and DMF instead of DCM. MS (ESI): mass calcd. for $C_{24}H_{20}F_3N_5O$, 451.2; m/z found, 452.1 [M+H]$^+$. $^1$H NMR (500 MHz, Chloroform-d) δ 8.79-8.63 (m, 1H), 8.13-8.07 (m, 1H), 7.79-7.58 (m, 2H), 7.03-6.87 (m, 2H), 6.12 (q, J=6.8 Hz, 0.24H), 6.05 (q, J=6.7 Hz, 0.30H), 5.18-5.08 (m, 0.44H), 4.73 (q, J=6.7 Hz, 0.20H), 4.54 (q, J=6.8 Hz, 0.23H), 3.85 (d, J=5.9 Hz, 1.73H), 3.74 (d, J=5.0 Hz, 1.29H), 3.48-3.32 (m, 0.57H), 3.29-3.17 (m, 0.77H), 3.15-3.01 (m, 0.44H), 2.92-2.81 (m, 0.21H), 2.80-2.66 (m, 2.58H), 2.59-2.48 (m, 0.74H), 2.39 (s, 0.67H), 2.25-2.19 (m, 0.30H), 2.15-2.08 (m, 0.25H), 1.75 (d, J=6.7 Hz, 0.93H), 1.67 (d, J=6.8 Hz, 0.76H), 1.39 (d, J=6.8 Hz, 0.66H), 1.34 (d, J=6.8 Hz, 0.58H).

Example 475: [(7S)-2,7-Dimethyl-3-(3,4,5-trifluorophenyl)-5,7-dihydro-4H-pyrazolo[3,4-c]pyridin-6-yl]-(3-methylquinoxalin-5-yl)methanone

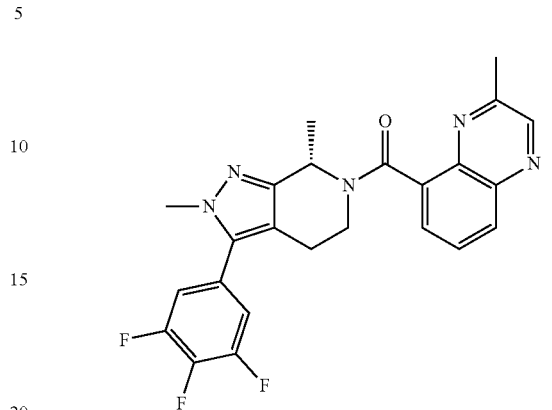

The title compound was prepared in a manner analogous to Example 288, using 3-methylquinoxaline-5-carboxylic acid instead of 2-fluoro-6-(2H-1,2,3-triazol-2-yl)benzoic acid and DMF instead of DCM. MS (ESI): mass calcd. for $C_{24}H_{20}F_3N_5O$, 451.2; m/z found, 452.2 [M+H]$^+$. $^1$H NMR (500 MHz, DMSO-d$_6$) δ 8.95-8.81 (m, 1H), 8.15-8.08 (m, 1H), 7.87-7.70 (m, 2H), 7.59-7.41 (m, 2H), 5.79-5.72 (m, 0.81H), 4.89-4.81 (m, 0.27H), 4.49-4.42 (m, 0.16H), 4.32-4.26 (m, 0.14H), 3.85-3.68 (m, 3H), 3.22-3.05 (m, 1.55H), 2.93-2.77 (m, 0.28H), 2.22-2.14 (m, 0.75H), 1.61-1.50 (m, 2H), 1.32-1.20 (m, 1H). (Fractions of Hs that overlap with DMSO and water are not reported).

Example 476: (2,3-Dimethylquinoxalin-6-yl)-[(7S)-2,7-dimethyl-3-(3,4,5-trifluorophenyl)-5,7-dihydro-4H-pyrazolo[3,4-c]pyridin-6-yl]methanone

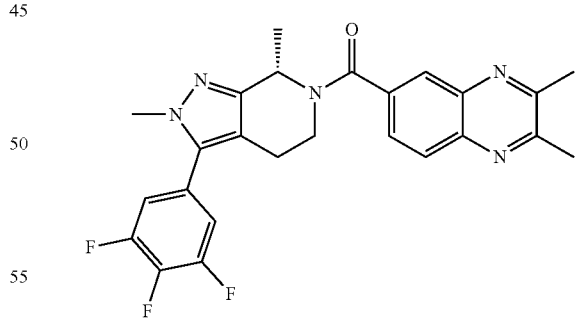

The title compound was prepared in a manner analogous to Example 288, using 2,3-dimethylquinoxaline-6-carboxylic acid (Intermediate 103) instead of 2-fluoro-6-(2H-1,2,3-triazol-2-yl)benzoic acid. MS (ESI): mass calcd. for $C_{25}H_{22}F_3N_5O$, 465.2; m/z found, 466.0 [M+H]$^+$. $^1$H NMR (400 MHz, DMSO-d$_6$) δ 8.04 (d, J=8.5 Hz, 1H), 7.97 (s, 1H), 7.74 (d, J=8.4 Hz, 1H), 7.63-7.49 (m, 2H), 5.73-5.47 (m, 1H), 4.95-4.15 (m, 1H), 3.96-3.50 (m, 4H), 3.09-2.78 (m, 1H), 2.78-2.59 (m, 6H), 2.39-2.20 (m, 1H), 1.50 (s, 3H).

Example 477: [(7S)-2,7-Dimethyl-3-(3,4,5-trifluorophenyl)-5,7-dihydro-4H-pyrazolo[3,4-c]pyridin-6-yl]-quinoxalin-2-yl-methanone

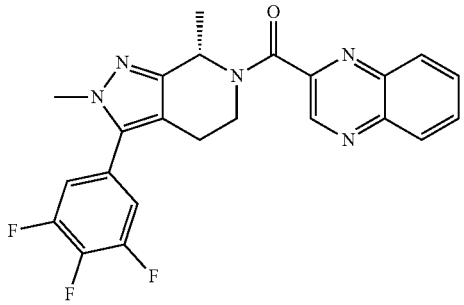 [SMILES: C[C@H]1c2nn(C)c(-c3cc(F)c(F)c(F)c3)c2CCN1C(=O)c1cnc2ccccc2n1]

The title compound was prepared in a manner analogous to Example 288, using quinoxaline-2-carboxylic acid instead of 2-fluoro-6-(2H-1,2,3-triazol-2-yl)benzoic acid. MS (ESI): mass calcd. for $C_{23}H_{18}F_3N_5O$, 437.1; m/z found, 438.1 [M+H]$^+$. $^1$H NMR (500 MHz, DMSO-d$_6$) δ 9.15-9.13 (m, 1H), 8.20-8.13 (m, 2H), 8.00-7.93 (m, 2H), 7.60-7.52 (m, 2H), 5.66 (q, J=6.8 Hz, 0.71H), 5.18 (q, J=6.7 Hz, 0.35H), 4.77-4.71 (m, 0.35H), 4.02-3.96 (m, 0.76H), 3.83 (s, 2H), 3.75 (s, 1H), 3.01-2.92 (m, 0.72H), 2.87-2.78 (m, 0.36H), 2.41-2.35 (m, 0.75H), 1.60 (d, J=6.7 Hz, 1H), 1.55 (d, J=6.8 Hz, 2H). (Fractions of Hs that overlap with DMSO and water are not reported).

Example 478: Cinnolin-3-yl-[(7S)-2,7-dimethyl-3-(3,4,5-trifluorophenyl)-5,7-dihydro-4H-pyrazolo[3,4-c]pyridin-6-yl]methanone

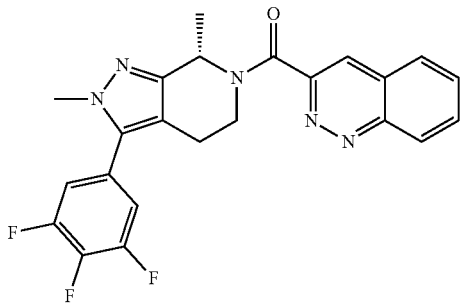 [SMILES: C[C@H]1c2nn(C)c(-c3cc(F)c(F)c(F)c3)c2CCN1C(=O)c1cc2ccccc2nn1]

The title compound was prepared in a manner analogous to Example 288, using cinnoline-3-carboxylic acid instead of 2-fluoro-6-(2H-1,2,3-triazol-2-yl)benzoic acid. MS (ESI): mass calcd. for $C_{23}H_{18}F_3N_5O$, 437.1; m/z found, 438.1 [M+H]$^+$. $^1$H NMR (400 MHz, DMSO-d$_6$) δ 8.59-8.51 (m, 2H), 8.21-8.16 (m, 1H), 8.10-8.03 (m, 1H), 8.00-7.94 (m, 1H), 7.60-7.51 (m, 2H), 5.72 (q, J=6.8 Hz, 0.64H), 4.97 (q, J=6.6 Hz, 0.32H), 4.82-4.75 (m, 0.32H), 3.87-3.70 (m, 3.68H), 2.97-2.79 (m, 1H), 2.40-2.30 (m, 0.71H), 1.60-1.51 (m, 3H). (Fractions of H's that overlap with DMSO and water may not be reported)

Example 479: [(7S)-2,7-Dimethyl-3-(3,4,5-trifluorophenyl)-5,7-dihydro-4H-pyrazolo[3,4-c]pyridin-6-yl]-quinazolin-6-yl-methanone

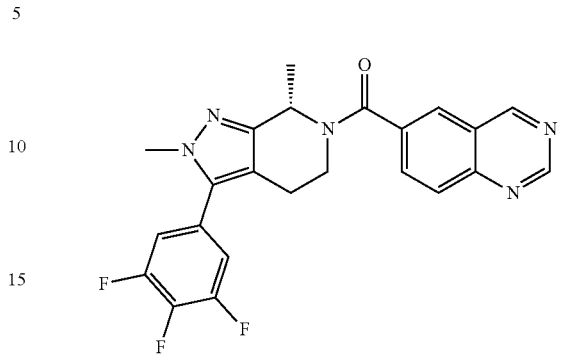

The title compound was prepared in a manner analogous to Example 288, using quinazoline-6-carboxylic acid instead of 2-fluoro-6-(2H-1,2,3-triazol-2-yl)benzoic acid. MS (ESI): mass calcd. for $C_{23}H_{18}F_3N_5O$, 437.1; m/z found, 438.1 [M+H]$^+$. $^1$H NMR (400 MHz, DMSO-d$_6$) δ 9.71 (s, 1H), 9.37 (s, 1H), 8.31-8.24 (m, 1H), 8.14-8.01 (m, 2H), 7.60-7.50 (m, 2H), 5.70-5.54 (m, 0.65H), 4.82-4.59 (s, 0.39H), 3.91-3.59 (m, 3.80H), 2.96-2.77 (s, 1H), 1.59-1.41 (m, 3H). (Fractions of Hs that overlap with DMSO and water are not reported).

Example 480: [(7S)-2,7-Dimethyl-3-(3,4,5-trifluorophenyl)-5,7-dihydro-4H-pyrazolo[3,4-c]pyridin-6-yl]-quinazolin-7-yl-methanone

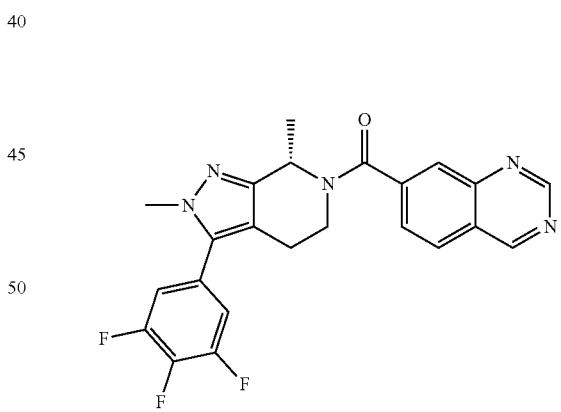

The title compound was prepared in a manner analogous to Example 288, using quinazoline-7-carboxylic acid instead of 2-fluoro-6-(2H-1,2,3-triazol-2-yl)benzoic acid. MS (ESI): mass calcd. for $C_{23}H_{18}F_3N_5O$, 437.1; m/z found, 438.1 [M+H]$^+$. $^1$H NMR (500 MHz, DMSO-d$_6$) δ 9.72-9.78 (m, 1H), 9.39-9.36 (m, 1H), 8.31-8.27 (m, 1H), 8.06-7.96 (m, 1H), 7.83-7.71 (m, 1H), 7.60-7.52 (m, 2H), 5.69-5.59 (m, 0.66H), 4.76-4.60 (m, 0.44H), 3.89-3.66 (m, 3H), 3.64-3.52 (m, 0.72H), 2.94-2.77 (m, 1H), 2.35-2.25 (m, 0.67H), 1.58-1.39 (m, 3H). (Fractions of Hs that overlap with DMSO and water are not reported).

Example 481: [(7S)-2,7-Dimethyl-3-(3,4,5-trifluorophenyl)-5,7-dihydro-4H-pyrazolo[3,4-c]pyridin-6-yl]-(8-fluoroquinazolin-4-yl)methanone

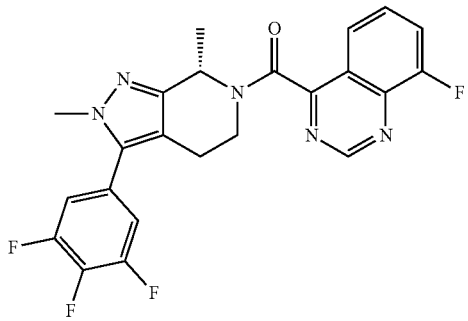 [SMILES: C[C@H]1c2nn(C)c(-c3cc(F)c(F)c(F)c3)c2CCN1C(=O)c1ncnc2c(F)cccc12]

The title compound was prepared in a manner analogous to Example 288, using 8-fluoroquinazoline-4-carboxylic acid instead of 2-fluoro-6-(2H-1,2,3-triazol-2-yl)benzoic acid. MS (ESI): mass calcd. for $C_{23}H_{17}F_4N_5O$, 455.1; m/z found, 456.2 [M+H]$^+$. $^1$H NMR (500 MHz, DMSO-$d_6$) δ 9.44-9.40 (m, 1H), 8.01-7.91 (m, 1H), 7.85-7.72 (m, 2H), 7.62-7.49 (m, 2H), 5.74 (q, J=6.7 Hz, 0.76H), 4.83 (dd, J=13.0, 5.2 Hz, 0.36H), 4.60 (q, J=6.6 Hz, 0.37H), 3.83 (s, 2H), 3.72 (s, 1H), 3.47-3.40 (m, 0.80H), 2.97-2.88 (m, 0.36H), 2.67-2.54 (m, 1.19H), 2.30-2.23 (m, 0.72H), 1.60 (d, J=6.8 Hz, 2H), 1.38 (d, J=6.7 Hz, 1H). (Fractions of Hs that overlap with DMSO and water are not reported).

Example 482: [(7S)-2,7-Dimethyl-3-(3,4,5-trifluorophenyl)-5,7-dihydro-4H-pyrazolo[3,4-c]pyridin-6-yl]-quinazolin-4-yl-methanone

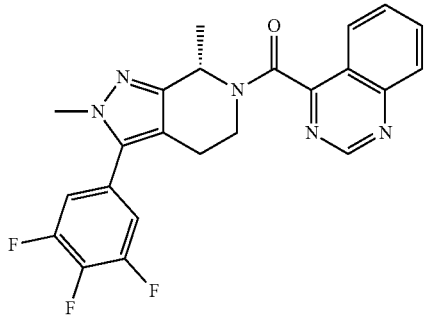 [SMILES: C[C@H]1c2nn(C)c(-c3cc(F)c(F)c(F)c3)c2CCN1C(=O)c1ncnc2ccccc12]

The title compound was prepared in a manner analogous to Example 288, using lithium quinazoline-4-carboxylate instead of 2-fluoro-6-(2H-1,2,3-triazol-2-yl)benzoic acid. MS (ESI): mass calcd. for $C_{23}H_{18}F_3N_5O$, 437.2; m/z found, 438.1 [M+H]$^+$. $^1$H NMR (500 MHz, DMSO-$d_6$) δ 9.36 (d, J=5.3 Hz, 1H), 8.20-8.04 (m, 2H), 7.99-7.74 (m, 2H), 7.64-7.40 (m, 2H), 5.83-5.63 (m, 1H), 4.93-4.39 (m, 1H), 3.87-3.66 (m, 3H), 3.45-3.33 (m, 1H), 3.25-2.87 (m, 1H), 2.71-2.55 (m, 1H), 1.65-1.33 (m, 3H).

Example 483: (2-Deuterioquinoxalin-6-yl)-[(7S)-2,7-dimethyl-3-(3,4,5-trifluorophenyl)-5,7-dihydro-4H-pyrazolo[3,4-c]pyridin-6-yl]methanone

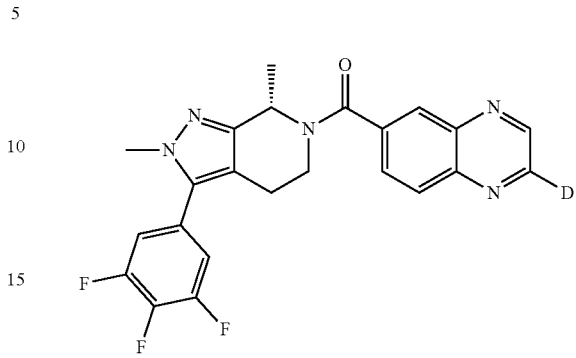

The title compound was prepared in a manner analogous to Example 288, using lithium(I) quinoxaline-6-carboxylate-2-d (Intermediate 104) instead of 2-fluoro-6-(2H-1,2,3-triazol-2-yl)benzoic acid. MS (ESI): mass calcd. for $C_{23}H_{17}F_3N_5O$, 438.2; m/z found, 439.0 [M+H]$^+$. $^1$H NMR (500 MHz, DMSO-$d_6$) δ 9.09-8.98 (m, 1H), 8.25-8.10 (m, 2H), 7.98-7.84 (m, 1H), 7.57 (dd, J=8.7, 6.7 Hz, 2H), 5.73-5.53 (m, 1H), 4.83-4.58 (m, 1H), 3.91-3.58 (m, 4H), 3.02-2.78 (m, 1H), 2.45-2.21 (m, 1H), 1.52 (s, 3H).

Example 484: [(7S)-2,7-Dimethyl-3-(3,4,5-trifluorophenyl)-5,7-dihydro-4H-pyrazolo[3,4-c]pyridin-6-yl]-pyrido[4,3-d]pyrimidin-5-yl-methanone

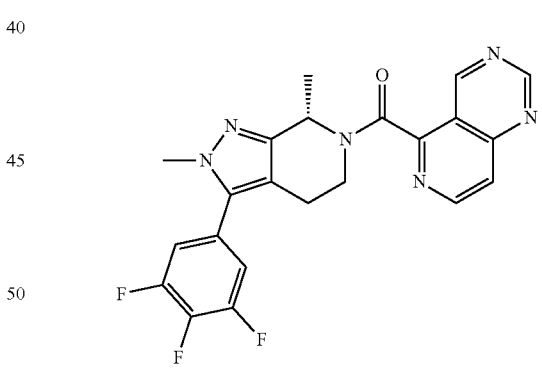

The title compound was prepared in a manner analogous to Example 288, using pyrido[4,3-d]pyrimidine-5-carboxylic acid instead of 2-fluoro-6-(2H-1,2,3-triazol-2-yl)benzoic acid. MS (ESI): mass calcd. for $C_{22}H_{17}F_3N_6O$, 438.1; m/z found, 439.1 [M+H]$^+$. $^1$H NMR (400 MHz, DMSO-$d_6$) δ 9.64-9.54 (m, 2H), 9.01-8.96 (m, 1H), 8.07-8.03 (m, 1H), 7.62-7.49 (m, 2H), 5.75 (q, J=6.7 Hz, 0.67H), 4.87-4.80 (m, 0.34H), 4.72 (q, J=6.6 Hz, 0.36H), 3.83 (s, 2H), 3.73 (s, 1H), 3.60-3.52 (m, 0.66H), 3.24-3.15 (m, 0.47H), 3.06-2.93 (m, 0.49H), 2.81-2.69 (m, 0.81H), 2.58-2.51 (m, 0.36H), 2.33-2.26 (m, 0.72H), 1.61 (d, J=6.8 Hz, 2H), 1.44 (d, J=6.7 Hz, 1H). (Fractions of Hs that overlap with DMSO and water are not reported).

Example 485: [(7S)-2,7-Dimethyl-3-(3,4,5-trifluoro-phenyl)-5,7-dihydro-4H-pyrazolo[3,4-c]pyridin-6-yl]-(1,5-naphthyridin-4-yl)methanone

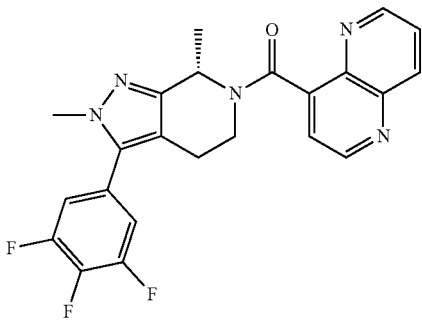 [SMILES: C[C@H]1c2nn(C)c(-c3cc(F)c(F)c(F)c3)c2CCN1C(=O)c1ccnc2cccnc12]

The title compound was prepared in a manner analogous to Example 288, using 1,5-naphthyridine-4-carboxylic acid instead of 2-fluoro-6-(2H-1,2,3-triazol-2-yl)benzoic acid. MS (ESI): mass calcd. for $C_{23}H_{18}F_3N_5O$, 437.2; m/z found, 438.1 [M+H]$^+$. $^1$H NMR (400 MHz, DMSO-$d_6$) δ 9.11-9.02 (m, 2H), 8.57-8.46 (m, 1H), 7.94-7.73 (m, 2H), 7.61-7.45 (m, 3H), 5.81-5.54 (m, 1H), 3.86-3.78 (m, 3H), 3.78-3.67 (m, 1H), 2.73-2.57 (m, 1H), 2.26-2.09 (m, 1H), 1.56 (dd, J=15.5, 6.8 Hz, 3H)

Example 486: [(7S)-2,7-Dimethyl-3-(3,4,5-trifluoro-phenyl)-5,7-dihydro-4H-pyrazolo[3,4-c]pyridin-6-yl]-(1,6-naphthyridin-5-1 methanone

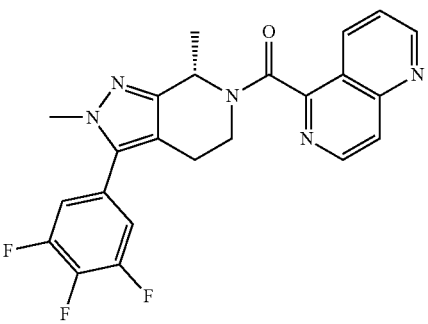 [SMILES: C[C@H]1c2nn(C)c(-c3cc(F)c(F)c(F)c3)c2CCN1C(=O)c1nccc2ncccc12]

The title compound was prepared in a manner analogous to Example 288, using 1,6-naphthyridine-5-carboxylic acid instead of 2-fluoro-6-(2H-1,2,3-triazol-2-yl)benzoic acid. MS (ESI): mass calcd. for $C_{23}H_{18}F_3N_5O$, 437.1; m/z found, 438.2 [M+H]$^+$. $^1$H NMR (500 MHz, DMSO-$d_6$) δ 9.22-9.17 (m, 1H), 8.79-8.75 (m, 1H), 8.36-8.31 (m, 1H), 8.06-8.00 (m, 1H), 7.75 (dd, J=8.5, 4.2 Hz, 0.68H), 7.71 (dd, J=8.5, 4.2 Hz, 0.34H), 7.62-7.48 (m, 2H), 5.77 (q, J=6.7 Hz, 0.69H), 4.86 (dd, J=12.9, 5.2 Hz, 0.34H), 4.54 (q, J=6.7 Hz, 0.35H), 3.83 (s, 2H), 3.72 (s, 1H), 3.17 (td, J=12.7, 3.9 Hz, 0.36H), 2.96-2.88 (m, 0.34H), 2.69-2.60 (m, 0.73H), 2.30-2.23 (m, 0.68H), 1.60 (d, J=6.8 Hz, 2H), 1.36 (d, J=6.8 Hz, 1H). (Fractions of Hs that overlap with DMSO and water are not reported).

Example 487: [(7S)-2,7-Dimethyl-3-(3,4,5-trifluoro-phenyl)-5,7-dihydro-4H-pyrazolo[3,4-c]pyridin-6-yl]-(2-methyl-1,6-naphthyridin-5-yl)methanone

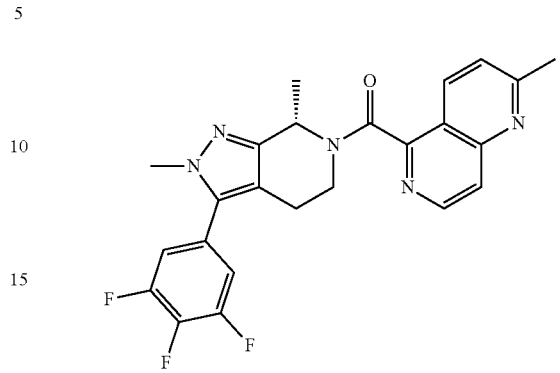

The title compound was prepared in a manner analogous to Example 288, using 2-methyl-1,6-naphthyridine-5-carboxylic acid instead of 2-fluoro-6-(2H-1,2,3-triazol-2-yl) benzoic acid and DMF instead of DCM. MS (ESI): mass calcd. for $C_{24}H_{20}F_3N_5O$, 451.2; m/z found, 452.1 [M+H]$^+$. $^1$H NMR (500 MHz, DMSO-$d_6$) δ 8.73-8.68 (m, 1H), 8.22-8.17 (m, 1H), 7.93-7.89 (m, 1H), 7.64-7.48 (m, 3H), 5.76 (q, J=6.7 Hz, 0.70H), 4.84 (dd, J=12.9, 5.2 Hz, 0.37H), 4.51 (q, J=6.7 Hz, 0.38H), 3.83 (s, 2H), 3.72 (s, 1H), 3.20-3.12 (m, 0.38H), 2.95-2.87 (m, 0.36H), 2.76-2.70 (m, 3H), 2.29-2.22 (m, 0.66H), 1.58 (d, J=6.7 Hz, 2H), 1.34 (d, J=6.7 Hz, 1H). (Fractions of Hs that overlap with DMSO or water are not reported).

Example 488: [(7S)-2,7-Dimethyl-3-(3,4,5-trifluoro-phenyl)-5,7-dihydro-4H-pyrazolo[3,4-c]pyridin-6-yl]-(1,6-naphthyridin-3-yl)methanone

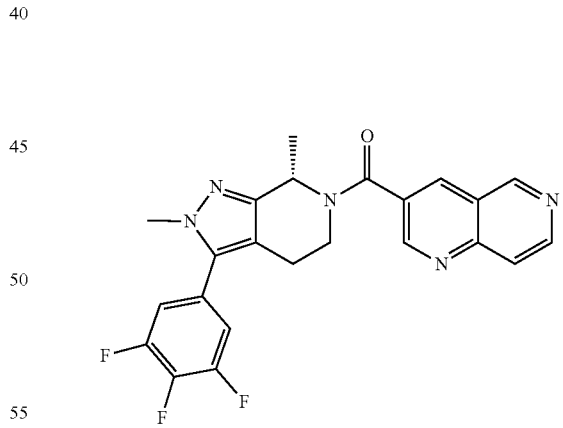

The title compound was prepared in a manner analogous to Example 288, using 1,6-naphthyridine-3-carboxylic acid instead of 2-fluoro-6-(2H-1,2,3-triazol-2-yl)benzoic acid. MS (ESI): mass calcd. for $C_{23}H_{18}F_3N_5O$, 437.2; m/z found, 438.1 [M+H]$^+$. $^1$H NMR (400 MHz, DMSO-$d_6$) δ 9.51 (d, J=1.0 Hz, 1H), 9.23-9.11 (m, 1H), 8.82 (d, J=5.9 Hz, 1H), 8.72 (dd, J=2.2, 0.9 Hz, 1H), 7.99 (dt, J=5.9, 1.0 Hz, 1H), 7.56 (dd, J=8.7, 6.6 Hz, 2H), 5.74-4.56 (m, 2H), 3.91-3.62 (m, 4H), 2.94 (s, 1H), 2.38 (d, J=15.7 Hz, 1H), 1.53 (d, J=6.7 Hz, 3H).

Example 489: [(7S)-2,7-Dimethyl-3-(3,4,5-trifluorophenyl)-5,7-dihydro-4H-pyrazolo[3,4-c]pyridin-6-yl]-(1,7-naphthyridin-5-yl)methanone

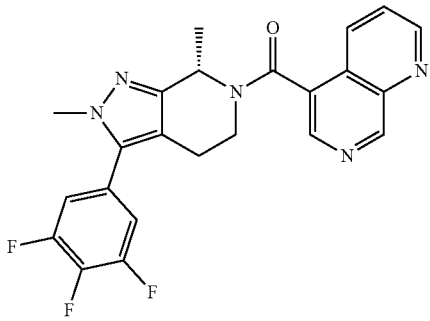 [SMILES: C[C@H]1c2nn(C)c(-c3cc(F)c(F)c(F)c3)c2CCN1C(=O)c1cncc2ncccc12]

The title compound was prepared in a manner analogous to Example 288, using 1,7-naphthyridine-5-carboxylic acid instead of 2-fluoro-6-(2H-1,2,3-triazol-2-yl)benzoic acid. MS (ESI): mass calcd. for $C_{23}H_{18}F_3N_5O$, 437.1; m/z found, 438.1 [M+H]$^+$. $^1$H NMR (500 MHz, DMSO-d$_6$) δ 9.52-9.47 (m, 1H), 9.18-9.10 (m, 1H), 8.79-8.57 (m, 1H), 8.26-8.03 (m, 1H), 7.93-8.75 (d, J=40.3 Hz, 1H), 7.63-7.44 (m, 2H), 5.82-5.73 (m, 0.72H), 4.89-4.79 (m, 0.23H), 4.54-4.36 (m, 0.12H), 3.84 (s, 2.32H), 3.71 (s, 0.71H), 3.06-2.81 (m, 0.74H), 2.31-2.21 (m, 0.78H), 1.67-1.32 (m, 3H). (Fractions of Hs that overlap with DMSO and water are not reported).

Example 490: [(7S)-2,7-Dimethyl-3-(3,4,5-trifluorophenyl)-5,7-dihydro-4H-pyrazolo[3,4-c]pyridin-6-yl]-(1,8-naphthyridin-3-yl)methanone

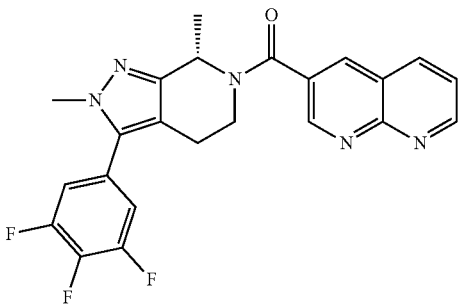

The title compound was prepared in a manner analogous to Example 288, using 1,8-naphthyridine-3-carboxylic acid instead of 2-fluoro-6-(2H-1,2,3-triazol-2-yl)benzoic acid. MS (ESI): mass calcd. for $C_{23}H_{18}F_3N_5O$, 437.1; m/z found, 438.1 [M+H]$^+$. $^1$H NMR (500 MHz, DMSO-d$_6$) δ 9.17 (dd, J=4.2, 2.0 Hz, 1H), 9.13 (s, 1H), 8.62 (d, J=2.4 Hz, 1H), 8.60-8.55 (m, 1H), 7.73 (dd, J=8.1, 4.2 Hz, 1H), 7.60-7.52 (m, 2H), 5.70-5.58 (m, 0.70H), 4.88-4.61 (m, 0.37H), 3.92-3.62 (m, 3.88H), 3.02-2.76 (m, 1H), 1.58-1.44 (m, 3H). (Fractions of Hs that overlap with DMSO and water are not reported).

Example 491: [(7S)-2,7-Dimethyl-3-(3,4,5-trifluorophenyl)-5,7-dihydro-4H-pyrazolo[3,4-c]pyridin-6-yl]-(1,8-naphthyridin-4-yl)methanone

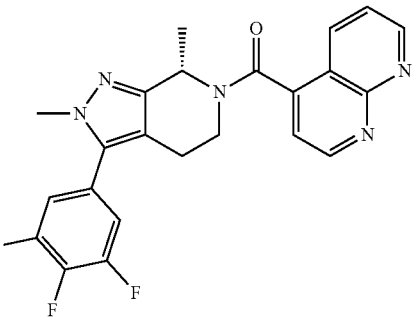

The title compound was prepared in a manner analogous to Example 288, using 1,8-naphthyridine-4-carboxylic acid instead of 2-fluoro-6-(2H-1,2,3-triazol-2-yl)benzoic acid. MS (ESI): mass calcd. for $C_{23}H_{11}F_3N_5O$, 437.1; m/z found, 438.1 [M+H]$^+$. $^1$H NMR (500 MHz, DMSO-d$_6$) δ 9.22-9.08 (m, 2H), 8.41-8.02 (m, 1H), 7.81-7.40 (m, 4H), 5.83-5.70 (s, 0.72H), 4.90-4.77 (m, 0.24H), 4.70-4.59 (m, 0.04H), 4.41-4.26 (m, 0.14H), 3.87-3.64 (m, 3H), 1.68-1.34 (m, 3H). (Fractions of Hs that overlap with DMSO and water are not reported).

Example 492: [(7S)-2,7-Dimethyl-3-(o-tolyl)-5,7-dihydro-4H-pyrazolo[3,4-c]pyridin-6-yl]-(6-quinolyl)methanone

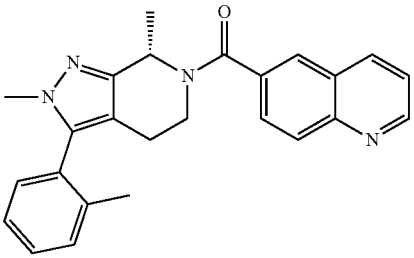 [SMILES: Cc1ccccc1-c1c2c(nn1C)[C@H](C)N(C(=O)c1ccc3ncccc3c1)CC2]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and o-tolylboronic acid instead of 3-(difluoromethoxy)phenylboronic acid. MS (ESI): mass calcd. for $C_{25}H_{24}N_4O$, 396.2; m/z found, 397.2 [M+H]$^+$. $^1$H NMR (500 MHz, DMSO-d$_6$) δ 8.90 (d, J=3.4 Hz, 1H), 8.34 (d, J=8.2 Hz, 1H), 8.06 (d, J=8.2 Hz, 1H), 7.99 (s, 1H), 7.71 (d, J=8.7 Hz, 1H), 7.51 (dd, J=8.2, 4.0 Hz, 1H), 7.37-7.29 (m, 2H), 7.28-7.14 (m, 2H), 5.72-5.51 (m, 1H), 3.86-3.64 (m, 1H), 3.62-3.44 (m, 3H), 3.37-3.16 (m, 1H), 2.70-2.55 (m, 1H), 2.35-2.12 (m, 4H), 1.56 (d, J=5.8 Hz, 3H).

Example 493: [(7S)-2,7-Dimethyl-3-[2-(trifluoromethyl)phenyl]-5,7-dihydro-4H-pyrazolo[3,4-c]pyridin-6-yl]-(6-quinolyl)methanone

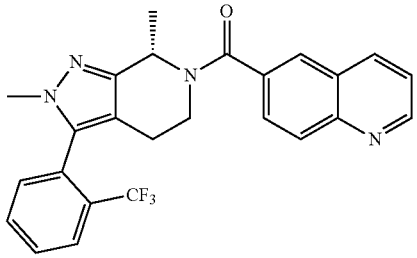 [SMILES: C[C@H]1c2nn(C)c(-c3ccccc3C(F)(F)F)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (2-(trifluoromethyl)phenyl)boronic acid instead of 3-(difluoromethoxy)phenylboronic acid. MS (ESI): mass calcd. for $C_{25}H_{21}F_3N_4O$, 450.2; m/z found, 451.2 [M+H]$^+$. $^1$H NMR (500 MHz, DMSO-$d_6$) δ 8.92-8.88 (m, 1H), 8.37-8.31 (m, 1H), 8.09-8.02 (m, 2H), 7.97 (d, J=9.2 Hz, 1H), 7.85 (t, J=9.3 Hz, 1H), 7.79-7.73 (m, 1H), 7.71-7.67 (m, 1H), 7.53-7.49 (m, 1H), 7.48-7.41 (m, 1H), 5.68-3.71 (m, 1H), 3.61-3.46 (m, 3H), 3.45-3.27 (m, 1H), 3.27-3.12 (m, 1H), 2.98-2.93 (m, 1H), 2.30-2.10 (m, 1H), 1.56 (d, J=6.9 Hz, 3H).

Example 494: [(7S)-2,7-Dimethyl-3-[4-(trifluoromethyl)phenyl]-5,7-dihydro-4H-pyrazolo[3,4-c]pyridin-6-yl]-(6-quinolyl)methanone

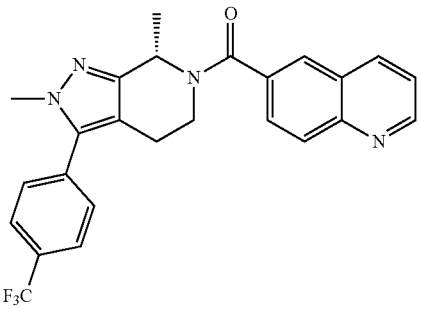 [SMILES: C[C@H]1c2nn(C)c(-c3ccc(C(F)(F)F)cc3)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (4-(trifluoromethyl)phenyl)boronic acid instead of 3-(difluoromethoxy)phenylboronic acid. MS (ESI): mass calcd. for $C_{25}H_{21}F_3N_4O$, 450.2; m/z found, 451.0 [M+H]$^+$. $^1$H NMR (500 MHz, DMSO-$d_6$) δ 8.94-8.89 (m, 1H), 8.37 (d, J=8.2 Hz, 1H), 8.08 (d, J=8.6 Hz, 1H), 8.02 (s, 1H), 7.79 (d, J=8.1 Hz, 1H), 7.74 (d, J=8.6 Hz, 1H), 7.66 (d, J=8.0 Hz, 2H), 7.56-7.50 (m, 1H), 5.80-4.49 (m, 1H), 4.15-3.62 (m, 4H), 3.47-3.11 (m, 1H), 2.97-2.85 (m, 1H), 2.48-2.32 (m, 1H), 1.59-1.53 (m, 3H). (Fractions of Hs that overlap with DMSO or water are not reported).

Example 495: [(7S)-3-(3-Methoxyphenyl)-2,7-dimethyl-5,7-dihydro-4H-pyrazolo[3,4-c]pyridin-6-yl]-(6-quinolyl)methanone

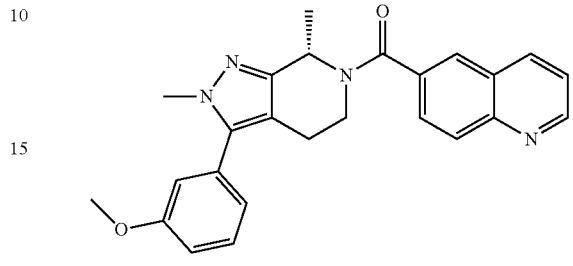

The title compound was prepared in a manner analogous to Example 288, using (S)-3-(3-methoxyphenyl)-2,7-dimethyl-4,5,6,7-tetrahydro-2H-pyrazolo[3,4-c]pyridine (Intermediate 48) instead of (S)-2,7-dimethyl-3-(3,4,5-trifluorophenyl)-4,5,6,7-tetrahydro-2H-pyrazolo[3,4-c]pyridine and quinoline-6-carboxylic acid instead of 2-fluoro-6-(2H-1,2,3-triazol-2-yl) benzoic acid. MS (ESI): mass calcd. for $C_{25}H_{24}N_4O_2$, 412.2; m/z found, 413.1 $^1$H NMR (400 MHz, DMSO-$d_6$) δ 8.98 (dd, J=4.2, 1.7 Hz, 1H), 8.57-8.40 (m, 1H), 8.14-8.03 (m, 2H), 7.80 (d, J=8.7 Hz, 1H), 7.61 (dd, J=8.3, 4.2 Hz, 1H), 7.43 (dd, J=8.9, 7.5 Hz, 1H), 7.11-6.89 (m, 3H), 5.63 (s, 1H), 4.93-4.36 (m, 1H), 3.87-3.75 (m, 6H), 3.62 (s, 1H), 2.98-2.73 (m, 1H), 2.47-2.22 (m, 1H), 1.57-1.43 (m, 3H).

Example 496: [(7S)-3-(2-Methoxyphenyl)-2,7-dimethyl-5,7-dihydro-4H-pyrazolo[3,4-c]pyridin-6-yl]-(6-quinolyl)methanone

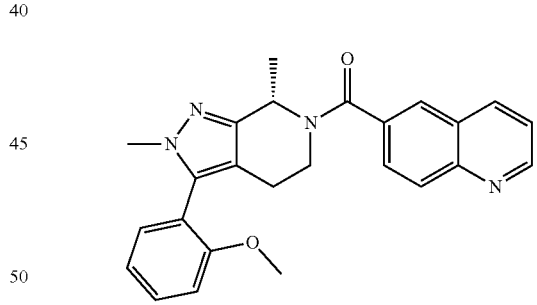

The title compound was prepared in a manner analogous to Example 288, using (S)-3-(2-methoxyphenyl)-2,7-dimethyl-4,5,6,7-tetrahydro-2H-pyrazolo[3,4-c]pyridine (Intermediate 47) instead of (S)-2,7-dimethyl-3-(3,4,5-trifluorophenyl)-4,5,6,7-tetrahydro-2H-pyrazolo[3,4-c]pyridine and quinoline-6-carboxylic acid instead of 2-fluoro-6-(2H-1,2,3-triazol-2-yl) benzoic acid. MS (ESI): mass calcd. for $C_{25}H_{24}N_4O_2$, 412.2; m/z found, 413.1 [M+H]$^+$. $^1$H NMR (400 MHz, DMSO-$d_6$) δ 8.97 (dd, J=4.3, 1.7 Hz, 1H), 8.55-8.36 (m, 1H), 8.17-8.06 (m, 2H), 7.78 (dd, J=8.7, 1.9 Hz, 1H), 7.60 (dd, J=8.3, 4.2 Hz, 1H), 7.53-7.43 (m, 1H), 7.29 (dd, J=7.5, 1.8 Hz, 1H), 7.24-7.12 (m, 1H), 7.11-7.01 (m, 1H), 5.73-5.42 (m, 1H), 4.83-4.59 (m, 1H), 3.81 (s, 3H), 3.63 (s, 3H), 3.27-3.03 (m, 1H), 2.76-2.58 (m, 1H), 2.42-2.13 (m, 1H), 1.62-1.42 (m, 3H).

Example 497: [(7S)-3-(4-Ethoxyphenyl)-2,7-dimethyl-5,7-dihydro-4H-pyrazolo[3,4-c]pyridin-6-yl]-(6-quinolyl)methanone

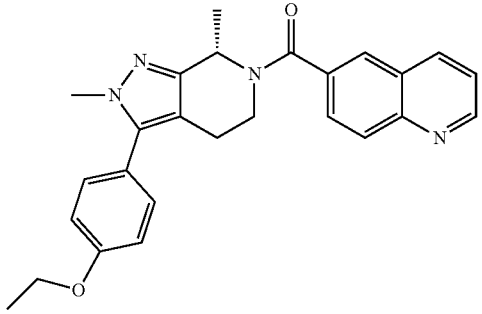 [SMILES: CCOc1ccc(-c2c3c(nn2C)[C@H](C)N(C(=O)c2ccc4ncccc4c2)CC3)cc1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (4-ethoxyphenyl)boronic acid instead of 3-(difluoromethoxy)phenylboronic acid. MS (ESI): mass calcd. for $C_{26}H_{26}N_4O_2$, 426.2; m/z found, 427.2 [M+H]$^+$. $^1$H NMR (500 MHz, DMSO-$d_6$) δ 8.90 (d, J=4.0 Hz, 1H), 8.36 (d, J=8.1 Hz, 1H), 8.07 (d, J=8.6 Hz, 1H), 8.00 (s, 1H), 7.72 (d, J=8.5 Hz, 1H), 7.52 (dd, J=8.2, 4.1 Hz, 1H), 7.29 (d, J=8.4 Hz, 1H), 6.96 (d, J=8.3 Hz, 1H), 5.69-5.53 (m, 1H), 4.07 (q, J=6.8 Hz, 2H), 3.77 (s, 4H), 3.35-3.22 (m, 1H), 2.87-2.78 (m, 1H), 2.41-2.29 (m, 1H), 1.53 (bs, 3H), 1.42 (t, J=6.9 Hz, 3H). (Fractions of Hs that overlap with DMSO or water are not reported).

Example 498: [(7S)-3-(3-Isopropoxyphenyl)-2,7-dimethyl-5,7-dihydro-4H-pyrazolo[3,4-c]pyridin-6-yl]-(6-quinolyl)methanone

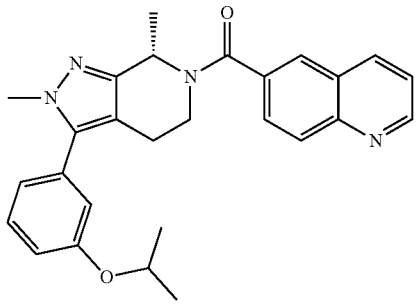 [SMILES: CC(C)Oc1cccc(-c2c3c(nn2C)[C@H](C)N(C(=O)c2ccc4ncccc4c2)CC3)c1]

The title compound was prepared in a manner analogous to Example 288, using (S)-3-(3-isopropoxyphenyl)-2,7-dimethyl-4,5,6,7-tetrahydro-2H-pyrazolo[3,4-c]pyridine (Intermediate 46) instead of (S)-2,7-dimethyl-3-(3,4,5-trifluorophenyl)-4,5,6,7-tetrahydro-2H-pyrazolo[3,4-c]pyridine and quinoline-6-carboxylic acid instead of 2-fluoro-6-(2H-1,2,3-triazol-2-yl) benzoic acid. MS (ESI): mass calcd. for $C_{27}H_{28}N_4O_2$, 440.2; m/z found, 441.1 [M+H]$^+$. $^1$H NMR (400 MHz, DMSO-$d_6$) δ 8.98 (dd, J=4.2, 1.8 Hz, 1H), 8.54-8.41 (m, 1H), 8.17-8.04 (m, 2H), 7.80 (d, J=8.6 Hz, 1H), 7.61 (dd, J=8.3, 4.2 Hz, 1H), 7.45-7.34 (m, 1H), 7.06-6.92 (m, 3H), 5.76-5.54 (m, 1H), 4.75-4.59 (m, 1H), 3.92-3.58 (m, 4H), 3.26-3.08 (m, 1H), 2.91-2.77 (m, 1H), 2.43-2.24 (m, 1H), 1.51 (s, 3H), 1.28 (d, J=6.0 Hz, 6H).

Example 499: [(7S)-3-[3-(Difluoromethoxy)phenyl]-2,7-dimethyl-5,7-dihydro-4H-pyrazolo[3,4-c]pyridin-6-yl]-(6-quinolyl)methanone

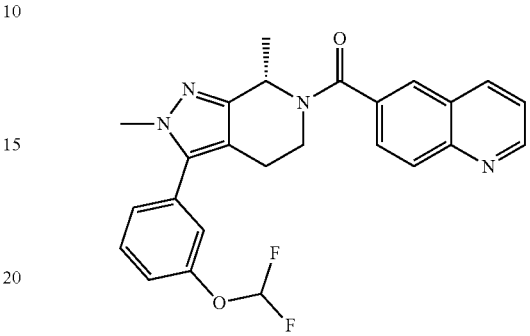

The title compound was prepared in a manner analogous to Example 288, using (S)-3-(3-(difluoromethoxy)phenyl)-2,7-dimethyl-4,5,6,7-tetrahydro-2H-pyrazolo[3,4-c]pyridine (Intermediate 45) instead of (S)-2,7-dimethyl-3-(3,4,5-trifluorophenyl)-4,5,6,7-tetrahydro-2H-pyrazolo[3,4-c]pyridine and quinoline-6-carboxylic acid instead of 2-fluoro-6-(2H-1,2,3-triazol-2-yl) benzoic acid. MS (ESI): mass calcd. for $C_{25}H_{22}F_2N_4O_2$, 448.2; m/z found, 449.1 [M+H]$^+$. $^1$H NMR (400 MHz, DMSO-$d_6$) δ 8.98 (dd, J=4.3, 1.7 Hz, 1H), 8.52-8.35 (m, 1H), 8.18-8.03 (m, 2H), 7.87-7.68 (m, 1H), 7.64-7.46 (m, 2H), 7.43-7.07 (m, 4H), 5.83-5.40 (m, 1H), 4.88-4.53 (m, 1H), 3.91-3.59 (m, 4H), 3.00-2.70 (m, 1H), 2.43-2.25 (m, 1H), 1.61-1.36 (m, 3H).

Example 500: [(7S)-2,7-Dimethyl-3-[4-(trifluoromethoxy)phenyl]-5,7-dihydro-4H-pyrazolo[3,4-c]pyridin-6-yl]-(6-quinolyl)methanone

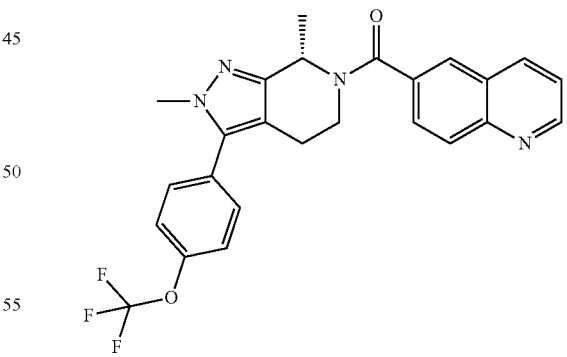

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (4-(trifluoromethoxy)phenyl)boronic acid instead of 3-(difluoromethoxy)phenylboronic acid. MS (ESI): mass calcd. for $C_{25}H_{21}F_3N_4O_2$, 466.2; m/z found, 467.2 [M+H]⁺. ¹H NMR (400 MHz, DMSO-d₆) δ 9.01-8.97 (m, 1H), 8.53-8.47 (m, 1H), 8.14-8.07 (m, 2H), 7.84-7.77 (m, 1H), 7.67-7.61 (m, 3H), 7.54-7.48 (m, 2H), 5.68-5.56 (m, 1H), 3.92-3.75 (m, 3H), 3.73-3.58 (m, 1H), 3.33-3.23 (m, 1H), 2.90-2.79 (m, 1H), 2.45-2.33 (m, 1H), 1.57-1.45 (m, 3H).

Example 501: [(7S)-2,7-Dimethyl-3-[3-(trifluoromethoxy)phenyl]-5,7-dihydro-4H-pyrazolo[3,4-c]pyridin-6-yl]-(6-quinolyl)methanone

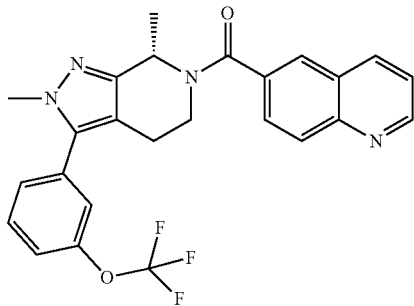 [SMILES: C[C@H]1c2nn(C)c(-c3cccc(OC(F)(F)F)c3)c2CCN1C(=O)c1ccc2ncccc2c1]

The title compound was prepared in a manner analogous to Example 288, using (S)-2,7-dimethyl-3-(3-(trifluoromethoxy)phenyl)-4,5,6,7-tetrahydro-2H-pyrazolo[3,4-c]pyridine (Intermediate 44) instead of (S)-2,7-dimethyl-3-(3,4,5-trifluorophenyl)-4,5,6,7-tetrahydro-2H-pyrazolo[3,4-c]pyridine and quinoline-6-carboxylic acid instead of 2-fluoro-6-(2H-1,2,3-triazol-2-yl) benzoic acid. MS (ESI): mass calcd. for C₂₅H₂₁F₃N₄O₂, 466.2; m/z found, 467.1 [M+H]⁺. ¹H NMR (400 MHz, DMSO-d₆) δ 8.98 (dd, J=4.3, 1.7 Hz, 1H), 8.48 (dd, J=8.4, 1.7 Hz, 1H), 8.16-8.04 (m, 2H), 7.86-7.75 (m, 1H), 7.71-7.42 (m, 5H), 5.77-5.47 (m, 1H), 4.92-4.50 (m, 1H), 3.94-3.60 (m, 4H), 2.99-2.73 (m, 1H), 2.46-2.26 (m, 1H), 1.61-1.42 (m, 3H).

Example 502: [(7S)-3-(2,4-Difluorophenyl)-2,7-dimethyl-5,7-dihydro-4H-pyrazolo[3,4-c]pyridin-6-yl]-(6-quinolyl)methanone

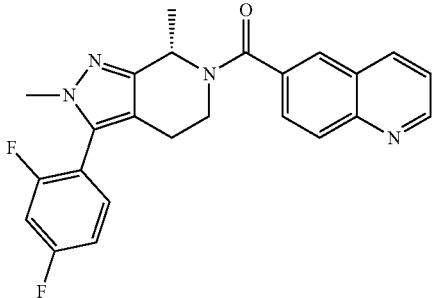 [SMILES: C[C@H]1c2nn(C)c(-c3ccc(F)cc3F)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (2,4-difluorophenyl)boronic acid instead of 3-(difluoromethoxy)phenylboronic acid. MS (ESI): mass calcd. for C₂₄H₂₀F₂N₄O, 418.2; m/z found, 419.2 [M+H]⁺. ¹H NMR (500 MHz, DMSO-d₆) δ 8.90 (d, J=3.1 Hz, 1H), 8.35 (d, J=8.1 Hz, 1H), 8.07 (d, J=8.5 Hz, 1H), 7.99 (s, 1H), 7.72 (d, J=8.5 Hz, 1H), 7.55-7.45 (m, 2H), 7.19-7.09 (m, 2H), 5.75-5.56 (m, 1H), 3.71 (s, 4H), 3.36-3.18 (m, 1H), 2.78-2.67 (m, 1H), 2.36-2.21 (m, 1H), 1.56 (d, J=5.5 Hz, 3H).

Example 503: [(7S)-3-(2,3-Difluorophenyl)-2,7-dimethyl-5,7-dihydro-4H-pyrazolo[3,4-c]pyridin-6-yl]-(6-quinolyl)methanone

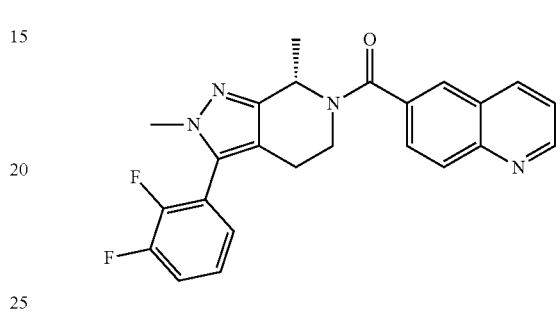

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (2,3-difluorophenyl)boronic acid instead of 3-(difluoromethoxy)phenylboronic acid. MS (ESI): mass calcd. for C₂₄H₂₀F₂N₄O, 418.2; m/z found, 419.2 [M+H]⁺. ¹H NMR (500 MHz, DMSO-d₆) δ 8.90 (d, J=3.9 Hz, 1H), 8.35 (d, J=8.2 Hz, 1H), 8.07 (d, J=8.6 Hz, 1H), 7.51 (dd, J=8.2, 4.1 Hz, 1H), 7.47-7.36 (m, 1H), 7.35-7.27 (m, 1H), 7.26-7.16 (m, 1H), 5.75-5.51 (m, 1H), 3.94-3.43 (m, 4H), 3.36-3.14 (m, 1H), 2.83-2.69 (m, 1H), 2.42-2.24 (m, 1H), 1.56 (d, J=6.0 Hz, 3H). (Fraction of Hs that overlap with DMSO or water are not reported).

Example 504: [(7S)-3-(4-Chloro-3-fluoro-phenyl)-2,7-dimethyl-5,7-dihydro-4H-pyrazolo[3,4-c]pyridin-6-yl]-(6-quinolyl)methanone

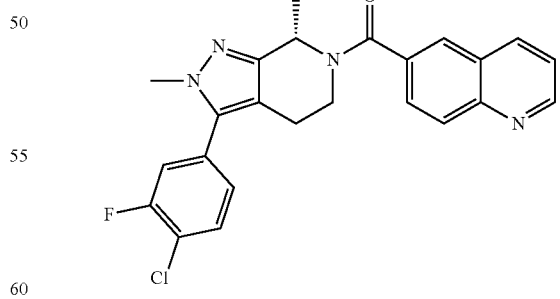

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (4-chloro-3-fluorophenyl)boronic acid instead of 3-(difluoromethoxy)phenylboronic acid. MS (ESI): mass calcd. for $C_{24}H_{20}ClFN_4O$, 434.1; m/z found, 435.0 [M+H]⁺. ¹H NMR (500 MHz, CD₃OD) δ 8.98-8.93 (m, 1H), 8.49 (d, J=8.4 Hz, 1H), 8.16 (d, J=8.7 Hz, 1H), 8.10 (s, 1H), 7.89-7.80 (m, 1H), 7.68-7.61 (m, 2H), 7.43 (d, J=9.8 Hz, 1H), 7.29 (d, J=8.3 Hz, 1H), 5.87-5.71 (m, 1H), 3.92-3.81 (m, 3H), 3.81-3.71 (m, 1H), 3.57-3.37 (m, 1H), 2.92-2.83 (m, 1H), 2.62-2.40 (m, 1H), 1.69-1.56 (m, 3H).

Example 505: [(7S)-3-(3-Chloro-4-fluoro-phenyl)-2,7-dimethyl-5,7-dihydro-4H-pyrazolo[3,4-c]pyridin-6-yl]-(6-quinolyl)methanone

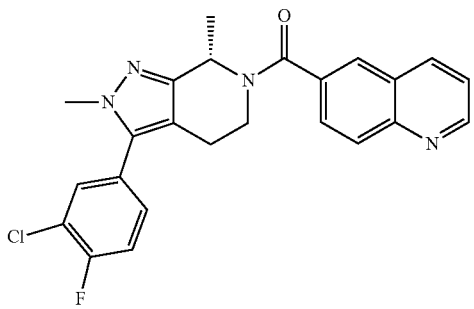 [SMILES: C[C@H]1c2nn(C)c(-c3ccc(F)c(Cl)c3)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (3-chloro-4-fluorophenyl)boronic acid instead of 3-(difluoromethoxy)phenylboronic acid. MS (ESI): mass calcd. for $C_{24}H_{20}ClFN_4O$, 434.1; m/z found, 435.2 [M+H]⁺. ¹H NMR (500 MHz, CD₃OD) δ 8.98-8.93 (m, 1H), 8.48 (d, J=8.3 Hz, 1H), 8.16 (d, J=8.6 Hz, 1H), 8.09 (s, 1H), 7.88-7.81 (m, 1H), 7.66-7.61 (m, 2H), 7.46-7.40 (m, 2H), 5.88-5.71 (m, 1H), 3.88-3.78 (m, 3H), 3.78-3.67 (m, 1H), 3.52-3.36 (m, 1H), 2.90-2.81 (m, 1H), 2.54-2.36 (m, 1H), 1.67-1.56 (m, 3H).

Example 506: [(7S)-3-(2-Chloro-4-fluoro-phenyl)-2,7-dimethyl-5,7-dihydro-4H-pyrazolo[3,4-c]pyridin-6-yl]-(6-quinolyl)methanone

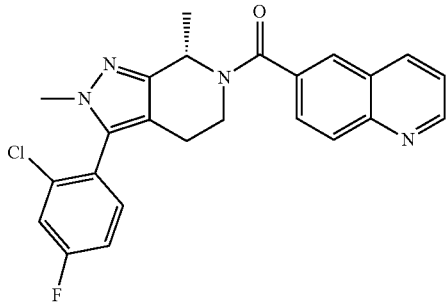 [SMILES: C[C@H]1c2nn(C)c(-c3ccc(F)cc3Cl)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (2-chloro-4-fluorophenyl)boronic acid instead of 3-(difluoromethoxy)phenylboronic acid. MS (ESI): mass calcd. for $C_{24}H_{20}ClFN_4O$, 434.1; m/z found, 435.0 [M+H]⁺. ¹H NMR (500 MHz, CD₃OD) δ 8.96 (s, 1H), 8.51 (d, J=8.4 Hz, 1H), 8.16 (d, J=8.5 Hz, 1H), 8.10 (s, 1H), 7.85 (dd, J=8.7, 1.9 Hz, 1H), 7.68-7.61 (m, 1H), 7.53-7.43 (m, 2H), 7.30-7.24 (m, 1H), 5.94-5.74 (m, 1H), 3.92-3.72 (m, 1H), 3.72-3.58 (m, 3H), 3.55-3.35 (m, 1H), 2.79-2.63 (m, 1H), 2.49-2.24 (m, 1H), 1.68-1.56 (m, 3H).

Example 507: [(7S)-3-(3,4-Dichlorophenyl)-2,7-dimethyl-5,7-dihydro-4H-pyrazolo[3,4-c]pyridin-6-yl]-(6-quinolyl)methanone

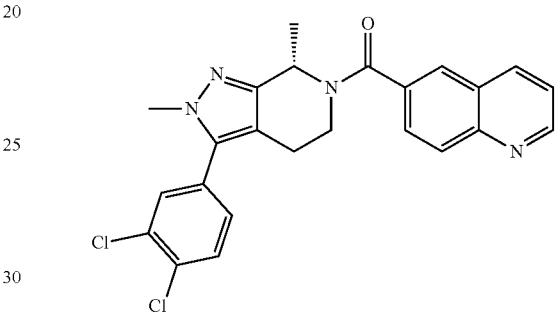

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (3,4-dichlorophenyl)boronic acid instead of 3-(difluoromethoxy)phenylboronic acid. MS (ESI): mass calcd. for $C_{24}H_{20}Cl_2N_4O$, 450.1; m/z found, 451.0 [M+H]⁺. ¹H NMR (500 MHz, CD₃OD) δ 8.97-8.94 (m, 1H), 8.50 (d, J=8.7 Hz, 1H), 8.17 (d, J=8.7 Hz, 1H), 8.10 (s, 1H), 7.89-7.83 (m, 1H), 7.72-7.62 (m, 3H), 7.44-7.38 (m, 1H), 5.92-5.70 (m, 1H), 3.92-3.79 (m, 3H), 3.79-3.64 (m, 1H), 3.49-3.37 (m, 1H), 2.89-2.82 (m, 1H), 2.61-2.39 (m, 1H), 1.70-1.55 (m, 3H).

Example 508: [(7S)-3-(5-Fluoro-2-methoxy-phenyl)-2,7-dimethyl-5,7-dihydro-4H-pyrazolo[3,4-c]pyridin-6-yl]-(6-quinolyl)methanone

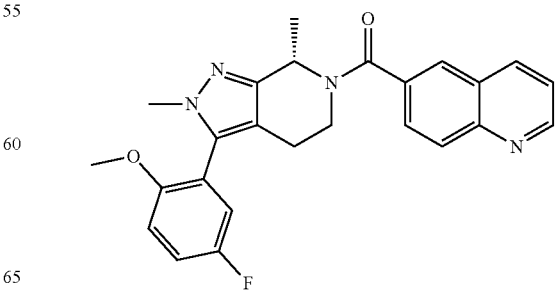

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (5-fluoro-2-methoxyphenyl)boronic acid instead of 3-(difluoromethoxy)phenylboronic acid. MS (ESI): mass calcd. for $C_{25}H_{23}FN_4O_2$, 430.2; m/z found, 431.2 [M+H]$^+$. $^1$H NMR (400 MHz, CDCl$_3$) δ 8.97-8.91 (m, 1H), 8.17 (d, J=8.3 Hz, 1H), 8.13 (d, J=8.6 Hz, 1H), 7.93-7.88 (m, 1H), 7.74 (d, J=8.8 Hz, 1H), 7.43 (dd, J=8.3, 4.2 Hz, 1H), 7.14-7.04 (m, 1H), 6.96-6.88 (m, 2H), 5.91-4.82 (m, 1H), 3.80 (s, 3H), 3.71-3.59 (m, 3H), 3.40-3.12 (m, 1H), 2.95-2.60 (m, 1H), 2.47-2.22 (m, 1H), 1.90-1.65 (m, 1H), 1.65-1.39 (m, 3H).

Example 509: [(7S)-3-(4-Fluoro-3-methoxy-phenyl)-2,7-dimethyl-5,7-dihydro-4H-pyrazolo[3,4-c]pyridin-6-yl]-(6-quinolyl)methanone

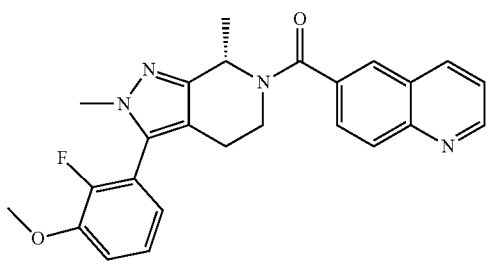 [SMILES: COc1cccc(-c2c3c(nn2C)[C@H](C)N(C(=O)c2ccc4ncccc4c2)CC3)c1F]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (2-fluoro-3-methoxyphenyl)boronic acid instead of 3-(difluoromethoxy)phenylboronic acid. MS (ESI): mass calcd. for $C_{25}H_{23}FN_4O_2$, 430.2; m/z found, 431.2 [M+H]$^+$. $^1$H NMR (500 MHz, DMSO-d$_6$) δ 8.90 (d, J=3.8 Hz, 1H), 8.36 (d, J=8.1 Hz, 1H), 8.07 (d, J=8.5 Hz, 1H), 8.00 (s, 1H), 7.72 (d, J=8.3 Hz, 1H), 7.51 (dd, J=8.2, 4.1 Hz, 1H), 7.23-7.11 (m, 2H), 6.91 (t, J=6.5 Hz, 1H), 5.73-5.55 (m, 1H), 3.92 (s, 3H), 3.81-3.65 (m, 3H), 3.37-3.12 (m, 2H), 2.78-2.71 (m, 1H), 2.37-2.28 (m, 1H), 1.55 (d, J=5.2 Hz, 3H).

Example 510: [(7S)-3-(2-Fluoro-3-methoxy-phenyl)-2,7-dimethyl-5,7-dihydro-4H-pyrazolo[3,4-c]pyridin-6-yl]-(6-quinolyl)methanone

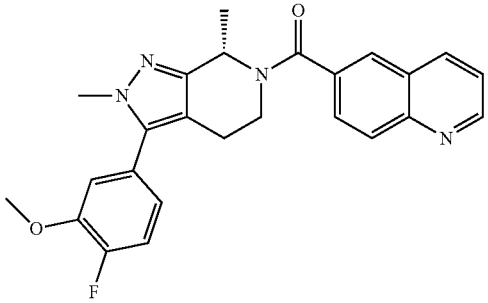 [SMILES: COc1cc(-c2c3c(nn2C)[C@H](C)N(C(=O)c2ccc4ncccc4c2)CC3)ccc1F]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (4-fluoro-3-methoxyphenyl)boronic acid instead of 3-(difluoromethoxy)phenylboronic acid. MS (ESI): mass calcd. for $C_{25}H_{23}FN_4O_2$, 430.2; m/z found, 431.0 [M+H]$^+$. $^1$H NMR (400 MHz, CDCl$_3$) δ 8.95 (d, J=4.2 Hz, 1H), 8.18 (bs, 1H), 8.14 (d, J=8.6 Hz, 1H), 7.91 (s, 1H), 7.73 (d, J=8.6 Hz, 1H), 7.44 (dd, J=8.3, 4.2 Hz, 1H), 7.16 (m, 1H), 6.89 (d, J=9.5 Hz, 1H), 6.87-6.78 (m, 1H), 6.03-5.70 (m, 1H), 5.08-4.70 (m, 1H), 3.89 (s, 3H), 3.83-3.69 (m, 3H), 3.37-3.05 (m, 1H), 2.92-2.60 (m, 1H), 2.54-2.27 (m, 1H), 1.80 (s, 3H).

Example 511: [(7S)-3-(3-Fluoro-5-methyl-phenyl)-2,7-dimethyl-5,7-dihydro-4H-pyrazolo[3,4-c]pyridin-6-yl]-(6-quinolyl)methanone The title compound was prepared in a manner analogous to Example 288, using (S)-3-(3-fluoro-5-methylphenyl)-2,7-dimethyl-4,5,6,7-tetrahydro-2H-pyrazolo[3,4-c] pyridine (Intermediate 42) instead of (S)-2,7-dimethyl-3-(3,4,5-trifluorophenyl)-4,5,6,7-tetrahydro-2H-pyrazolo[3,4-c]pyridine and quinoline-6-carboxylic acid instead of 2-fluoro-6-(2H-1,2,3-triazol-2-yl) benzoic acid. MS (ESI): mass calcd. for $C_{25}H_{23}FN_4O$, 414.2; m/z found, 415.1 [M+H]$^+$. $^1$H NMR (400 MHz, DMSO-d$_6$) δ 8.98 (dd, J=4.2, 1.7 Hz, 1H), 8.54-8.44 (m, 1H), 8.17-8.03 (m, 2H), 7.80 (d, J=8.7 Hz, 1H), 7.61 (dd, J=8.3, 4.2 Hz, 1H), 7.20-7.07 (m, 3H), 5.71-5.55 (m, 1H), 4.79-4.60 (m, 1H), 3.89-3.64 (m, 4H), 2.96-2.78 (m, 1H), 2.43-2.29 (m, 4H), 1.51 (d, J=6.6 Hz, 3H).

Example 512: [(7S)-3-(4-Methoxy-3-methyl-phenyl)-2,7-dimethyl-5,7-dihydro-4H-pyrazolo[3,4-c]pyridin-6-yl]-(6-quinolyl)methanone

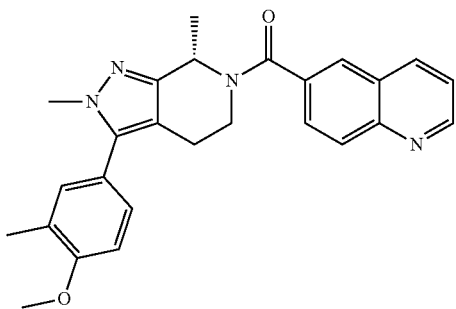 [SMILES: COc1ccc(-c2c3c(nn2C)[C@H](C)N(C(=O)c2ccc4ncccc4c2)CC3)cc1C]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (4-methoxy-3-methylphenyl)boronic acid instead of 3-(difluoromethoxy)phenylboronic acid. MS (ESI): mass calcd. for $C_{26}H_{26}N_4O_2$, 426.2; m/z found, 427.2 [M+H]$^+$. $^1$H NMR (500 MHz, CD$_3$OD) δ 8.95 (s, 1H), 8.49 (d, J=8.3 Hz, 1H), 8.16 (d, J=8.7 Hz, 1H), 8.09 (s, 1H), 7.85 (d, J=8.8 Hz, 1H), 7.66-7.60 (m, 1H), 7.23 (d, J=8.4 Hz, 1H), 7.19 (s, 1H), 7.04 (d, J=7.7 Hz, 1H), 5.86-5.70 (m, 1H), 3.88 (s, 3H), 3.80 (s, 3H), 3.76-3.65 (m, 1H), 3.48-3.36 (m, 1H), 2.86-2.77 (m, 1H), 2.50-2.33 (m, 1H), 2.25 (s, 3H), 1.66-1.54 (m, 3H).

Example 513: [(7S)-3-(3-Chloro-5-methoxy-phenyl)-2,7-dimethyl-5,7-dihydro-4H-pyrazolo[3,4-c]pyridin-6-yl]-(6-quinolyl)methanone

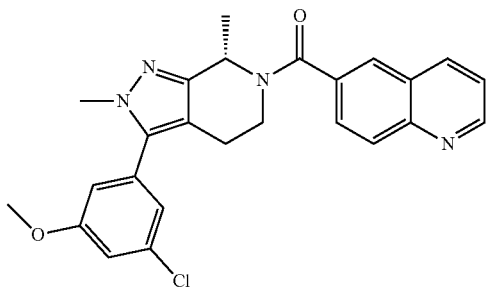 [SMILES: COc1cc(Cl)cc(-c2c3c(nn2C)[C@H](C)N(C(=O)c2ccc4ncccc4c2)CC3)c1]

The title compound was prepared in a manner analogous to Example 288, using (S)-3-(3-chloro-5-methoxyphenyl)-2,7-dimethyl-4,5,6,7-tetrahydro-2H-pyrazolo[3,4-c]pyridine (Intermediate 41) instead of (S)-2,7-dimethyl-3-(3,4,5-trifluorophenyl)-4,5,6,7-tetrahydro-2H-pyrazolo[3,4-c]pyridine and quinoline-6-carboxylic acid instead of 2-fluoro-6-(2H-1,2,3-triazol-2-yl) benzoic acid. MS (ESI): mass calcd. for $C_{25}H_{23}ClN_4O_2$, 446.2; m/z found, 447.1 [M+H]$^+$. $^1$H NMR (500 MHz, DMSO-d$_6$) δ 8.98 (dd, J=4.2, 1.8 Hz, 1H), 8.58-8.38 (m, 1H), 8.23-8.02 (m, 2H), 7.85-7.75 (m, 1H), 7.61 (dd, J=8.3, 4.2 Hz, 1H), 7.16-7.09 (m, 2H), 7.02 (t, J=1.8 Hz, 1H), 5.72-5.49 (m, 1H), 4.89-3.95 (m, 2H), 3.87-3.64 (m, 6H), 2.97-2.72 (m, 1H), 2.37-2.31 (m, 1H), 1.57-1.43 (m, 3H).

Example 514: [(7S)-3-(4-Chloro-2,3-difluoro-phenyl)-2,7-dimethyl-5,7-dihydro-4H-pyrazolo[3,4-c]pyridin-6-yl]-(6-quinolyl)methanone

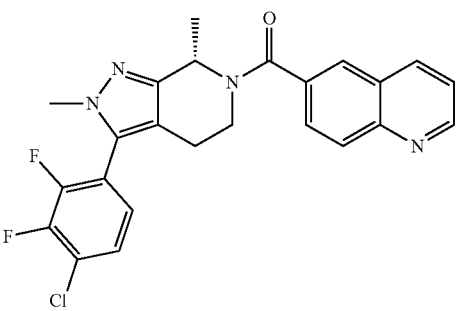 [SMILES: C[C@H]1c2nn(C)c(-c3ccc(Cl)c(F)c3F)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (4-chloro-2,3-difluorophenyl)boronic acid instead of 3-(difluoromethoxy)phenylboronic acid. MS (ESI): mass calcd. for $C_{24}H_{19}ClF_2N_4O$, 452.1; m/z found, 453.0 [M+H]$^+$. $^1$H NMR (500 MHz, CD$_3$OD) δ 8.95 (s, 1H), 8.49 (d, J=8.4 Hz, 1H), 8.16 (d, J=8.7 Hz, 1H), 8.10 (s, 1H), 7.85 (d, J=8.7 Hz, 1H), 7.52-7.46 (m, 1H), 7.32-7.25 (m, 1H), 5.93-5.73 (m, 1H), 3.90-3.67 (m, 4H), 2.99-2.70 (m, 2H), 2.54-2.36 (m, 1H), 1.68-1.57 (m, 3H). (Fraction of Hs that overlap with methanol or water are not reported).

Example 515: [(7S)-2,7-Dimethyl-3-(2,3,4-trifluorophenyl)-5,7-dihydro-4H-pyrazolo[3,4-c]pyridin-6-yl]-(6-quinolyl)methanone

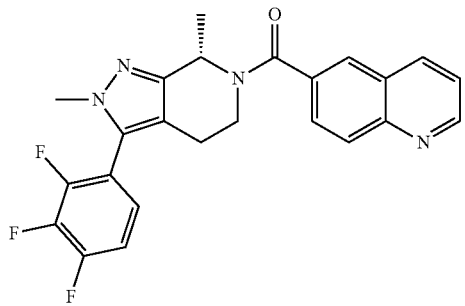 [SMILES: C[C@H]1c2nn(C)c(-c3ccc(F)c(F)c3F)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (2,3,4-trifluorophenyl)boronic acid instead of 3-(difluoromethoxy)phenylboronic acid. MS (ESI): mass calcd. for C$_{24}$H$_{19}$F$_3$N$_4$O, 436.2; m/z found, 437.2 [M+H]$^+$. $^1$H NMR (500 MHz, DMSO-d$_6$) δ 8.91 (d, J=3.8 Hz, 1H), 8.35 (d, J=8.2 Hz, 1H), 8.07 (d, J=8.6 Hz, 1H), 8.00 (s, 1H), 7.72 (d, J=8.6 Hz, 1H), 7.52 (dd, J=8.3, 4.1 Hz, 1H), 7.36-7.27 (m, 2H), 5.76-5.56 (m, 1H), 3.73 (s, 4H), 3.40-3.22 (m, 1H), 2.80-2.69 (m, 1H), 2.35-2.31 (m, 1H), 1.55 (d, J=6.1 Hz, 3H).

Example 516: [(7S)-2,7-Dimethyl-3-(3,4,5-trifluorophenyl)-5,7-dihydro-4H-pyrazolo[3,4-c]pyridin-6-yl]-(1-oxidoquinolin-1-ium-6-yl)methanone

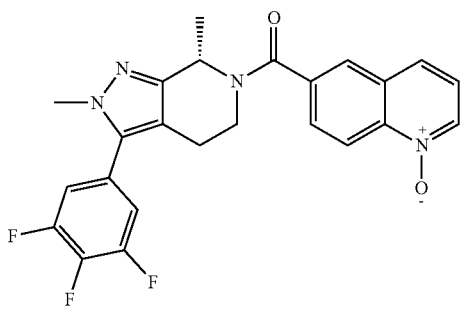

To an ice-cold solution of (S)-(2,7-dimethyl-3-(3,4,5-trifluorophenyl)-2,4,5,7-tetrahydro-6H-pyrazolo[3,4-c]pyridin-6-yl)(quinolin-6-yl)methanone (Example 234, 160 mg, 0.37 mmol) in DCM (5.0 mL) was added 3-chlorobenzoperoxoic acid (95 mg, 0.55 mmol) portion wise, at 0° C. over a period of 10 minutes and the mixture was slowly warmed to rt. After stirring for 1 h, the reaction mixture was quenched with a saturated aqueous solution of NaHCO$_3$ and extracted with DCM (2×). The combined organics were washed with brine, dried over Na$_2$SO$_4$, filtered, and concentrated in vacuo. The crude product was purified by reverse-phase (Method A) to afford the title compound as a white solid (121 mg, 72% yield). MS (ESI): mass calcd. for C$_{24}$H$_{19}$F$_3$N$_4$O$_2$, 452.2; m/z found, 453.1 [M+H]$^+$. $^1$H NMR (400 MHz, DMSO-d$_6$) δ 8.67-8.54 (m, 2H), 8.20 (s, 1H), 8.03 (d, J=8.5 Hz, 1H), 7.83 (d, J=9.1 Hz, 1H), 7.60-7.44 (m, 3H), 5.70-5.50 (m, 1H), 4.86-4.39 (m, 1H), 3.87-3.56 (m, 4H), 2.95-2.77 (m, 1H), 2.45-2.26 (m, 1H), 1.57-1.43 (m, 3H).

Example 517: [(7S)-2,7-Dimethyl-3-(3,4,5-trifluorophenyl)-5,7-dihydro-4H-pyrazolo[3,4-c]pyridin-6-yl]-(2-hydroxy-6-quinolyl)methanone

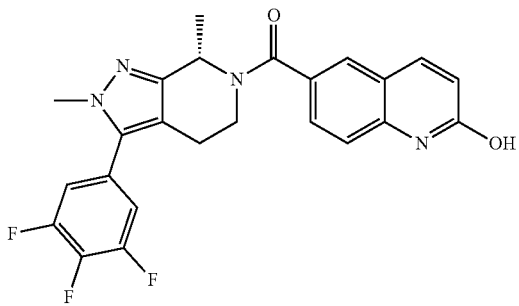 [SMILES: C[C@H]1c2nn(C)c(-c3cc(F)c(F)c(F)c3)c2CCN1C(=O)c1ccc2nc(O)ccc2c1]

The title compound was prepared in a manner analogous to Example 288, using 2-hydroxyquinoline-6-carboxylic acid instead of 2-fluoro-6-(2H-1,2,3-triazol-2-yl)benzoic acid. MS (ESI): mass calcd. for C$_{24}$H$_{19}$F$_3$N$_4$O$_2$, 452.1; m/z found, 453.0 [M+H]$^+$. $^1$H NMR (600 MHz, DMSO-d$_6$) δ 11.91 (s, 1H), 7.98 (d, J=9.5 Hz, 1H), 7.83-7.69 (m, 1H), 7.62-7.48 (m, 3H), 7.37 (d, J=8.4 Hz, 1H), 6.56 (d, J=9.6 Hz, 1H), 5.53 (s, 1H), 4.95-4.30 (m, 1H), 3.89-3.64 (m, 4H), 3.28 (s, 1H), 2.38 (s, 1H), 1.54-1.39 (m, 3H).

Example 518: [(7S)-2,7-Dimethyl-3-(3,4,5-trifluorophenyl)-5,7-dihydro-4H-pyrazolo[3,4-c]pyridin-6-yl]-(4-hydroxy-6-quinolyl)methanone

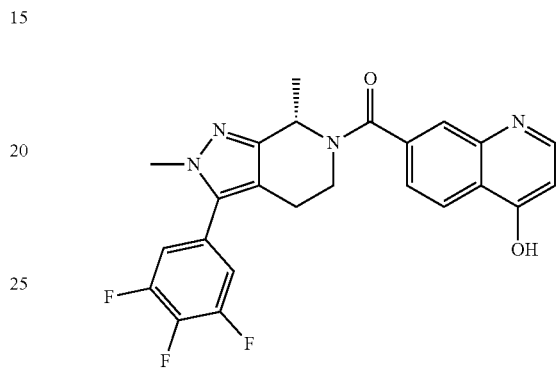

The title compound was prepared in a manner analogous to Example 288, using 4-hydroxyquinoline-7-carboxylic acid instead of 2-fluoro-6-(2H-1,2,3-triazol-2-yl)benzoic acid. MS (ESI): mass calcd. for C$_{24}$H$_{19}$F$_3$N$_4$O$_2$, 452.2; m/z found, 453.1 [M+H]$^+$. $^1$H NMR (400 MHz, DMSO-d$_6$) δ 12.52-11.29 (m, 1H), 8.08 (s, 1H), 7.96 (d, J=7.4 Hz, 1H), 7.70 (dd, J=8.5, 2.0 Hz, 1H), 7.67-7.48 (m, 3H), 6.08 (d, J=7.4 Hz, 1H), 5.56 (s, 1H), 5.00-4.31 (m, 1H), 3.95-3.63 (m, 4H), 2.88-2.71 (m, 1H), 2.46-2.29 (m, 1H), 1.57-1.40 (m, 3H).

Example 519: [(7S)-2,7-Dimethyl-3-(6-methyl-3-pyridyl)-5,7-dihydro-4H-pyrazolo[3,4-c]pyridin-6-yl]-(6-quinolyl)methanone

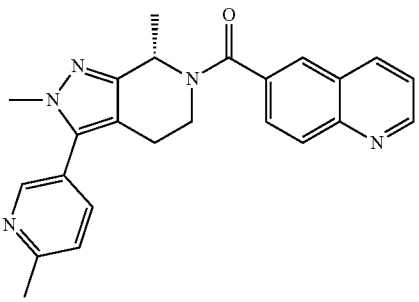 [SMILES: Cc1ccc(-c2c3c(nn2C)[C@H](C)N(C(=O)c2ccc4ncccc4c2)CC3)cn1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-methyl-5-(4,4,5,5-tetramethyl-1,3,2-dioxaborolan-2-yl)pyridine instead of 3-(difluoromethoxy)

phenylboronic acid. MS (ESI): mass calcd. for $C_{24}H_{23}N_5O$, 397.2; m/z found, 398.2 [M+H]$^+$. $^1$H NMR (500 MHz, DMSO-d$_6$) δ 8.91 (d, J=4.0 Hz, 1H), 8.48 (s, 1H), 8.36 (d, J=8.2 Hz, 1H), 8.07 (d, J=8.6 Hz, 1H), 8.00 (s, 1H), 7.77-7.68 (m, 1H), 7.52 (dd, J=8.2, 4.1 Hz, 1H), 7.31 (d, J=8.0 Hz, 1H), 5.73-5.55 (m, 1H), 3.80 (s, 4H), 3.36-3.20 (m, 1H), 2.94-2.82 (m, 1H), 2.56 (s, 3H), 2.44-2.31 (m, 1H), 1.55 (d, J=5.8 Hz, 3H).

Example 520: [(7S)-2,7-Dimethyl-3-(2-methyl-4-pyridyl)-5,7-dihydro-4H-pyrazolo[3,4-c]pyridin-6-yl]-(6-quinolyl)methanone

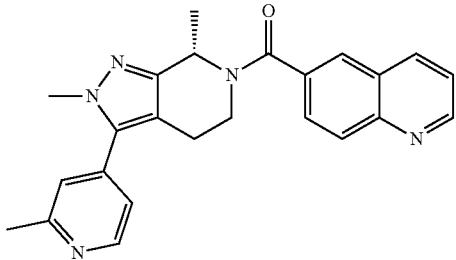 [SMILES: Cc1cc(-c2c3c(nn2C)[C@H](C)N(C(=O)c2ccc4ncccc4c2)CC3)ccn1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-methyl-4-(4,4,5,5-tetramethyl-1,3,2-dioxaborolan-2-yl)pyridine instead of 3-(difluoromethoxy)phenylboronic acid. MS (ESI): mass calcd. for $C_{24}H_{23}N_5O$, 397.2; m/z found, 398.2 [M+H]$^+$. $^1$H NMR (500 MHz, CDCl$_3$) δ 9.00 (d, J=4.1 Hz, 1H), 8.63 (d, J=4.7 Hz, 1H), 8.21 (d, J=8.2 Hz, 1H), 8.18 (d, J=8.7 Hz, 1H), 7.95 (s, 1H), 7.77 (d, J=8.6 Hz, 1H), 7.48 (dd, J=8.2, 4.2 Hz, 1H), 7.14 (s, 1H), 7.09 (d, J=5.0 Hz, 1H), 6.04-5.80 (m, 1H), 5.11-4.80 (m, 1H), 3.93-3.76 (m, 3H), 3.37-3.11 (m, 1H), 3.03-2.77 (m, 1H), 2.62 (s, 3H), 2.56-2.34 (m, 1H), 1.61 (s, 3H).

Example 521: [(7S)-3-[6-(Difluoromethyl)-3-pyridyl]-2,7-dimethyl-5,7-dihydro-4H-pyrazolo[3,4-c]pyridin-6-yl]-(6-quinolyl)methanone

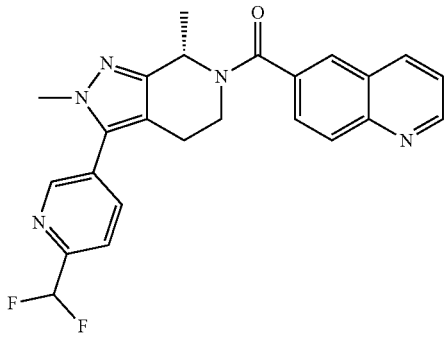 [SMILES: C[C@H]1c2nn(C)c(-c3ccc(C(F)F)nc3)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) 20 and 2-difluoromethyl-5-(4,4,5,5-tetramethyl-1,3,2-dioxaborolan-2-yl)pyridine instead of 3-(difluoromethoxy)phenylboronic acid. MS (ESI): mass calcd. for $C_{24}H_{21}F_2N_5O$, 433.2; m/z found, 434.2 [M+H]$^+$. $^1$H NMR (500 MHz, DMSO-d$_6$) δ 8.91 (d, J=3.9 Hz, 1H), 8.75 (s, 1H), 8.37 (d, J=8.3 Hz, 1H), 8.08 (t, J=7.3 Hz, 1H), 8.02 (s, 1H), 7.80 (d, J=8.1 Hz, 1H), 7.74 (d, J=8.3 Hz, 1H), 7.52 (dd, J=8.3, 4.2 Hz, 1H), 6.80 (t, J=55.1 Hz, 1H), 5.71-5.59 (m, 1H), 3.96-3.70 (m, 4H), 3.39-3.21 (m, 1H), 2.96-2.90 (m, 1H), 2.47-2.37 (m, 1H), 1.56 (d, J=6.1 Hz, 3H). (Fraction of Hs that overlap with DMSO or water are not reported).

Example 522: [(7S)-2,7-Dimethyl-3-[6-(trifluoromethyl)-3-pyridyl]-5,7-dihydro-4H-pyrazolo[3,4-c]pyridin-6-yl]-(6-quinolyl)methanone

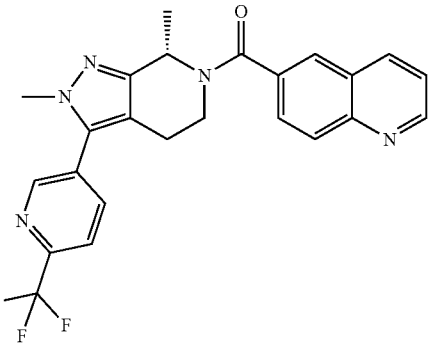

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-trifluoromethyl-5-(4,4,5,5-tetramethyl-1,3,2-dioxaborolan-2-yl)pyridine instead of 3-(difluoromethoxy)phenylboronic acid. MS (ESI): mass calcd. for $C_{24}H_{20}F_3N_5O$, 451.2; m/z found, 452.0 [M+H]$^+$. $^1$H NMR (400 MHz, DMSO-d$_6$) δ 9.01-8.92 (m, 2H), 8.48 (d, J=8.1 Hz, 1H), 8.27 (d, J=8.0 Hz, 1H), 8.15-8.02 (m, 3H), 7.80 (d, J=7.5 Hz, 1H), 7.61 (dd, J=8.1, 4.1 Hz, 1H), 5.86-5.51 (m, 1H), 3.97-3.62 (m, 4H), 3.28-3.05 (m, 1H), 3.02-2.84 (m, 1H), 2.45-2.31 (m, 1H), 1.53 (d, J=3.3 Hz, 3H).

Example 523: [(7S)-2,7-Dimethyl-3-[2-(trifluoromethyl)-4-pyridyl]-5,7-dihydro-4H-pyrazolo[3,4-c]pyridin-6-yl]-(6-quinolyl)methanone

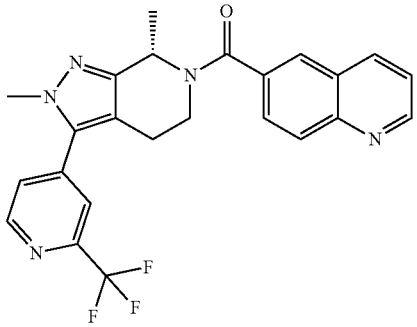 [SMILES: C[C@H]1c2nn(C)c(-c3ccnc(C(F)(F)F)c3)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-trifluoromethyl-4-(4,4,5,5-tetramethyl-1,3,2-dioxaborolan-2-yl)pyridine instead of 3-(difluoromethoxy)phenylboronic acid. MS (ESI): mass calcd. for $C_{24}H_{20}F_3N_5O$, 451.2; m/z found, 452.2 [M+H]+. $^1$H NMR (400 MHz, CDCl$_3$) δ 8.99-8.93 (m, 1H), 8.86-8.81 (m, 1H), 8.21-8.16 (m, 1H), 8.15 (d, J=8.7 Hz, 1H), 7.94-7.89 (m, 1H), 7.77-7.69 (m, 1H), 7.63 (s, 1H), 7.49-7.41 (m, 2H), 6.08-4.90 (m, 1H), 3.93-3.81 (m, 3H), 3.42-3.09 (m, 2H), 3.03-2.74 (m, 1H), 2.56-2.36 (m, 1H), 1.91-1.44 (m, 3H).

Example 524: [(7S)-2,7-Dimethyl-3-[5-(trifluoromethyl)-3-thienyl]-5,7-dihydro-4H-pyrazolo[3,4-c]pyridin-6-yl]-(6-quinolyl)methanone

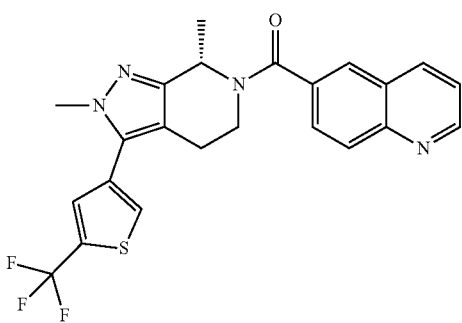 [SMILES: C[C@H]1c2nn(C)c(-c3csc(C(F)(F)F)c3)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and (5-(trifluoromethyl)thiophen-3-yl)boronic acid instead of 3-(difluoromethoxy)phenylboronic acid. MS (ESI): mass calcd. for $C_{23}H_{19}F_3N_4OS$, 456.1; m/z found, 457.2 [M+H]+. $^1$H NMR (500 MHz, DMSO-d$_6$) δ 8.93-8.89 (m, 1H), 8.38-8.35 (m, 1H), 8.10-8.06 (m, 1H), 8.02-7.98 (m, 2H), 7.75-7.71 (m, 2H), 7.54-7.50 (m, 1H), 5.72-4.64 (m, 1H), 4.06-3.64 (m, 4H), 3.36-3.11 (m, 1H), 2.98-2.85 (m, 2H), 2.47-2.35 (m, 1H), 1.53 (d, J=6.7 Hz, 3H).

Example 525: [(7S)-3-(6-Methoxy-3-pyridyl)-2,7-dimethyl-5,7-dihydro-4H-pyrazolo[3,4-c]pyridin-6-yl]-(6-quinolyl)methanone

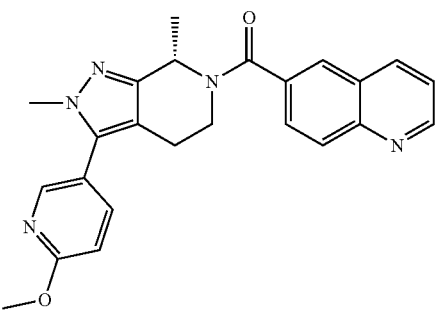 [SMILES: COc1ccc(-c2c3c(nn2C)[C@H](C)N(C(=O)c2ccc4ncccc4c2)CC3)cn1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-methoxy-5-(4,4,5,5-tetramethyl-1,3,2-dioxaborolan-2-yl)pyridine instead of 3-(difluoromethoxy)phenylboronic acid. MS (ESI): mass calcd. for $C_{24}H_{23}N_5O_2$, 413.2; m/z found, 414.1 [M+H]+. $^1$H NMR (500 MHz, DMSO-d$_6$) δ 8.91 (d, J=4.0 Hz, 1H), 8.36 (d, J=8.2 Hz, 1H), 8.19 (s, 1H), 8.07 (d, J=8.5 Hz, 1H), 8.00 (s, 1H), 7.76-7.69 (m, 2H), 7.52 (dd, J=8.2, 4.1 Hz, 1H), 6.86 (d, J=8.5 Hz, 1H), 5.70-5.54 (m, 1H), 3.93 (s, 3H), 3.79 (s, 4H), 3.33-3.21 (m, 1H), 2.93-2.81 (m, 1H), 2.44-2.32 (m, 1H), 1.54 (d, J=5.9 Hz, 3H).

Example 526: [(7S)-3-(2-Methoxy-4-pyridyl)-2,7-dimethyl-5,7-dihydro-4H-pyrazolo[3,4-c]pyridin-6-yl]-(6-quinolyl)methanone

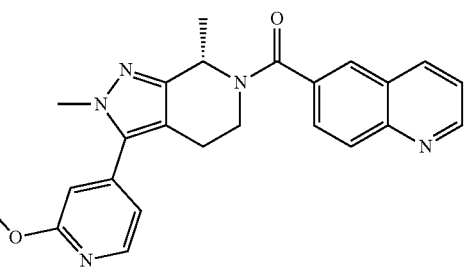

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-methoxy-4-(4,4,5,5-tetramethyl-1,3,2-dioxaborolan-2-yl)pyridine instead of 3-(difluoromethoxy)phenylboronic acid. MS (ESI): mass calcd. for $C_{24}H_{23}N_5O_2$, 413.2; m/z found, 414.2 [M+H]⁺. ¹H NMR (400 MHz, CDCl₃) δ 8.98 (m, 1H), 8.25 (d, J=5.1 Hz, 1H), 8.22 (d, J=8.5 Hz, 1H), 8.18 (d, J=8.7 Hz, 1H), 7.93 (s, 1H), 7.75 (dd, J=8.6, 1.4 Hz, 1H), 7.48 (dd, J=8.1, 4.2 Hz, 1H), 6.83 (d, J=5.1 Hz, 1H), 6.69 (s, 1H), 6.11-5.71 (m, 1H), 5.05-4.75 (m, 1H), 3.97 (s, 3H), 3.91-3.79 (m, 3H), 3.32-3.02 (m, 1H), 2.97-2.72 (m, 1H), 2.50 (d, J=25.1 Hz, 1H), 1.69-1.48 (m, 3H).

Example 527: [(7S)-3-[6-(Difluoromethoxy)-3-pyridyl]-2,7-dimethyl-5,7-dihydro-4H-pyrazolo[3,4-c]pyridin-6-yl]-(6-quinolyl)methanone

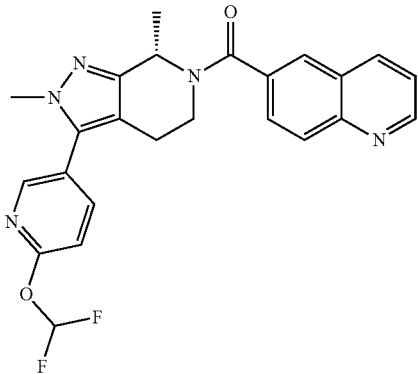 [SMILES: C[C@H]1c2nn(C)c(-c3ccc(OC(F)F)nc3)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-difluoromethoxy-5-(4,4,5,5-tetramethyl-1,3,2-dioxaborolan-2-yl)pyridine instead of 3-(difluoromethoxy)phenylboronic acid. MS (ESI): mass calcd. for C₂₄H₂₁F₂N₅O₂, 449.2; m/z found, 450.1 [M+H]⁺. ¹H NMR (400 MHz, CDCl₃) δ 8.95 (dd, J=4.1, 1.4 Hz, 1H), 8.23-8.15 (m, 2H), 8.14 (d, J=8.8 Hz, 1H), 7.91 (s, 1H), 7.79-7.68 (m, 2H), 7.67-7.29 (m, 2H), 7.02 (d, J=8.4 Hz, 1H), 6.10-5.68 (m, 1H), 5.13-4.74 (m, 1H), 3.78 (s, 3H), 3.35-3.09 (m, 1H), 2.95-2.65 (m, 1H), 2.51-2.27 (m, 1H), 1.60 (s, 3H).

Example 528: [(7S)-3-[5-(Difluoromethoxy)-3-pyridyl]-2,7-dimethyl-5,7-dihydro-4H-pyrazolo[3,4-c]pyridin-6-yl]-(6-quinolyl)methanone

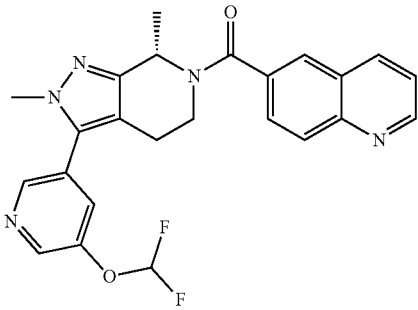 [SMILES: C[C@H]1c2nn(C)c(-c3cncc(OC(F)F)c3)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 3-difluoromethoxy-5-(4,4,5,5-tetramethyl-1,3,2-dioxaborolan-2-yl)pyridine instead of 3-(difluoromethoxy)phenylboronic acid. MS (ESI): mass calcd. for C₂₄H₂₁F₂N₅O₂, 449.2; m/z found, 450.2 [M+H]⁺. ¹H NMR (500 MHz, DMSO-d₆) δ 8.91 (d, J=2.8 Hz, 1H), 8.51 (s, 1H), 8.46 (s, 1H), 8.37 (d, J=8.0 Hz, 1H), 8.08 (d, J=8.6 Hz, 1H), 8.01 (s, 1H), 7.79-7.69 (m, 2H), 7.52 (d, J=8.2, 4.1 Hz, 1H), 7.26 (t, J=73.1 Hz, 1H), 5.72-5.56 (m, 1H), 3.95-3.71 (m, 4H), 3.38-3.21 (m, 1H), 2.96-2.85 (m, 1H), 2.45-2.29 (m, 1H), 1.55 (br s, 3H).

Example 529: [(7S)-3-(6-Methoxy-5-methyl-3-pyridyl)-2,7-dimethyl-5,7-dihydro-4H-pyrazolo[3,4-c]pyridin-6-yl]-(6-quinolyl)methanone

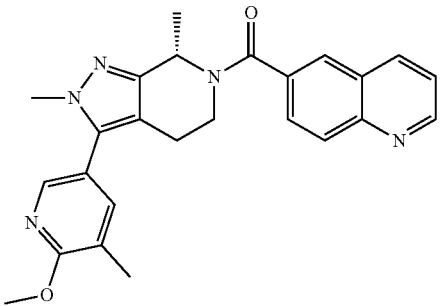 [SMILES: COc1ncc(-c2c3c(nn2C)[C@H](C)N(C(=O)c2ccc4ncccc4c2)CC3)cc1C]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-methoxy-3-methyl-5-(4,4,5,5-tetramethyl-1,3,2-dioxaborolan-2-yl)pyridine instead of 3-(difluoromethoxy)phenylboronic acid. MS (ESI): mass calcd. for C₂₅H₂₅N₅O₂, 427.2; m/z found, 428.2 [M+H]⁺. ¹H NMR (400 MHz, CDCl₃) δ 8.98-8.92 (m, 1H), 8.20-8.10 (m, 2H), 8.00-7.95 (m, 1H), 7.93-7.88 (m, 1H), 7.77-7.70 (m, 1H), 7.48-7.40 (m, 1H), 7.36-7.31 (m, 1H), 5.91-4.83 (m, 1H), 3.99 (s, 3H), 3.84-3.71 (m, 4H), 3.41-3.08 (m, 1H), 2.94-2.63 (m, 1H), 2.52-2.28 (m, 1H), 2.22 (s, 3H), 1.84-1.39 (m, 3H).

Example 530: [(7S)-3-[6-Methoxy-5-(trifluoromethyl)-3-pyridyl]-2,7-dimethyl-5,7-dihydro-4H-pyrazolo[3,4-c]pyridin-6-yl]-(6-quinolyl)methanone

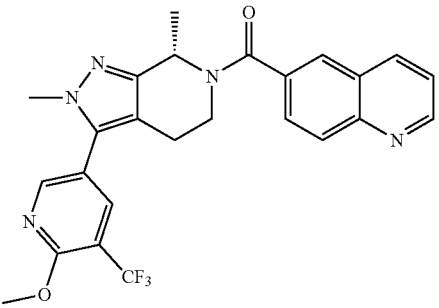 [SMILES: COc1ncc(-c2c3c(nn2C)[C@H](C)N(C(=O)c2ccc4ncccc4c2)CC3)cc1C(F)(F)F]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-methoxy-5-(4,4,5,5-tetramethyl-1,3,2-dioxaborolan-2-yl)-3-(trifluoromethyl)pyridine instead of 3-(difluoromethoxy)phenylboronic acid. MS (ESI): mass calcd. for $C_{25}H_{22}F_3N_5O_2$, 481.2; m/z found, 482.1 [M+H]$^+$. $^1$H NMR (500 MHz, DMSO-d$_6$) δ 8.93-8.89 (m, 1H), 8.47 (s, 1H), 8.36 (d, J=8.1 Hz, 1H), 8.08 (d, J=8.7 Hz, 1H), 8.04 (s, 1H), 8.01 (s, 1H), 7.73 (d, J=8.8 Hz, 1H), 7.52 (dd, J=8.3, 4.1 Hz, 1H), 5.64 (s, 1H), 4.09 (s, 3H), 3.81 (s, 4H), 3.39-3.11 (m, 1H), 2.95-2.83 (m, 1H), 2.43-2.27 (m, 1H), 1.55 (s, 3H).

Example 531: [(7S)-3-(1H-Indol-7-yl)-2,7-dimethyl-5,7-dihydro-4H-pyrazolo[3,4-c]pyridin-6-yl]-(6-quinolyl)methanone

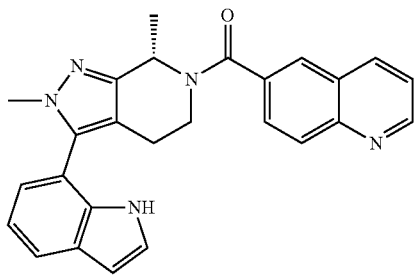 [SMILES: C[C@H]1c2nn(C)c(-c3cccc4cc[nH]c34)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 7-(4,4,5,5-tetramethyl-1,3,2-dioxaborolan-2-yl)-1H-indole instead of 3-(difluoromethoxy)phenylboronic acid. MS (ESI): mass calcd. for $C_{26}H_{23}N_5O$, 421.2; m/z found, 422.1 [M+H]$^+$. $^1$H NMR (500 MHz, DMSO-d$_6$) δ 10.87 (d, J=13.1 Hz, 1H), 8.90 (s, 1H), 8.35 (d, J=7.3 Hz, 1H), 8.13-7.95 (m, 2H), 7.75 (dd, J=23.2, 10.5 Hz, 1H), 7.59 (d, J=7.8 Hz, 1H), 7.51 (d, J=4.6 Hz, 1H), 7.23 (d, J=29.8 Hz, 1H), 7.13-6.96 (m, 2H), 6.47 (s, 1H), 5.71 (d, J=37.9 Hz, 1H), 3.86-3.58 (m, 4H), 3.34-3.20 (m, 1H), 2.88-2.71 (m, 1H), 2.30-2.12 (m, 1H), 1.61 (br s, 3H).

Example 532: [(7S)-3-(Benzofuran-6-yl)-2,7-dimethyl-5,7-dihydro-4H-pyrazolo[3,4-c]pyridin-6-yl]-(6-quinolyl)methanone

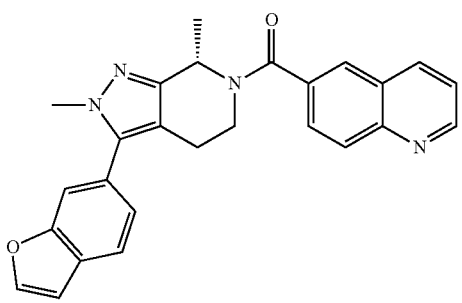 [SMILES: C[C@H]1c2nn(C)c(-c3ccc4ccoc4c3)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-(benzofuran-6-yl)-4,4,5,5-tetramethyl-1,3,2-dioxaborolane instead of 3-(difluoromethoxy)phenylboronic acid. MS (ESI): mass calcd. for $C_{26}H_{22}N_4O_2$, 422.2; m/z found, 423.2 [M+H]$^+$. $^1$H NMR (500 MHz, DMSO-d$_6$) δ 8.93-8.88 (m, 1H), 8.37 (d, J=8.3 Hz, 1H), 8.07 (d, J=8.6 Hz, 1H), 8.01 (s, 1H), 7.90-7.86 (m, 1H), 7.76-7.69 (m, 2H), 7.59 (s, 1H), 7.54-7.49 (m, 1H), 7.27 (d, J=8.1 Hz, 1H), 6.93-6.89 (m, 1H), 5.75-4.65 (m, 1H), 3.84 (s, 3H), 3.39-3.11 (m, 1H), 2.95-2.85 (m, 1H), 2.49-2.31 (m, 2H), 1.60-1.50 (m, 3H).

Example 533: [(7S)-3-(Benzofuran-5-yl)-2,7-dimethyl-5,7-dihydro-4H-pyrazolo[3,4-c]pyridin-6-yl]-(6-quinolyl)methanone

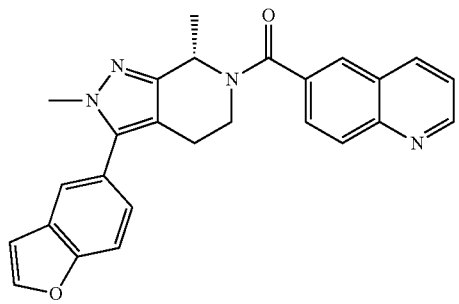 [SMILES: C[C@H]1c2nn(C)c(-c3ccc4occc4c3)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-(benzofuran-5-yl)-4,4,5,5-tetramethyl-1,3,2-dioxaborolane instead of 3-(difluoromethoxy)phenylboronic acid. MS (ESI): mass calcd. for $C_{26}H_{22}N_4O_2$, 422.2; m/z found, 423.2 [M+H]⁺. ¹H NMR (500 MHz, DMSO-d₆) δ 8.93-8.88 (m, 1H), 8.36 (d, J=8.2 Hz, 1H), 8.07 (d, J=8.6 Hz, 1H), 8.01 (s, 1H), 7.89-7.85 (m, 1H), 7.73 (d, J=8.6 Hz, 1H), 7.68-7.64 (m, 1H), 7.62 (d, J=8.5 Hz, 1H), 7.54-7.49 (m, 1H), 7.35-7.31 (m, 1H), 6.93-6.89 (m, 1H), 5.70-4.66 (m, 1H), 3.96-3.59 (m, 4H), 3.41-3.16 (m, 1H), 2.91-2.82 (m, 1H), 2.45-2.31 (m, 1H), 1.56 (d, J=6.7 Hz, 3H).

Example 534: [(7S)-3-(Benzofuran-7-yl)-2,7-dimethyl-5,7-dihydro-4H-pyrazolo[3,4-c]pyridin-6-yl]-(6-quinolyl)methanone

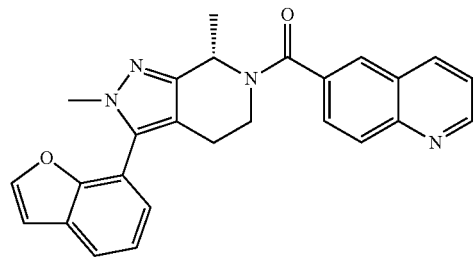 [SMILES: C[C@H]1c2nn(C)c(-c3cccc4ccoc34)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-(benzofuran-7-yl)-4,4,5,5-tetramethyl-1,3,2-dioxaborolane instead of 3-(difluoromethoxy)phenylboronic acid. MS (ESI): mass calcd. for $C_{26}H_{22}N_4O_2$, 422.2; m/z found, 423.2 [M+H]⁺. ¹H NMR (500 MHz, DMSO-d₆) δ 8.90 (d, J=3.5 Hz, 1H), 8.36 (d, J=8.2 Hz, 1H), 8.07 (d, J=8.1 Hz, 1H), 8.01 (s, 1H), 7.89 (s, 1H), 7.73 (d, J=8.6 Hz, 1H), 7.70 (d, J=7.5 Hz, 1H), 7.51 (dd, J=8.2, 4.1 Hz, 1H), 7.34 (t, J=7.5 Hz, 1H), 7.29 (d, J=7.3 Hz, 1H), 6.94 (s, 1H), 5.76-5.58 (m, 1H), 3.77 (s, 4H), 3.43-3.23 (m, 1H), 2.86-2.76 (m, 1H), 2.41-2.29 (m, 1H), 1.58 (br s, 3H).

Example 535: [(7S)-3-(Benzofuran-4-yl)-2,7-dimethyl-5,7-dihydro-4H-pyrazolo[3,4-c]pyridin-6-yl]-(6-quinolyl)methanone

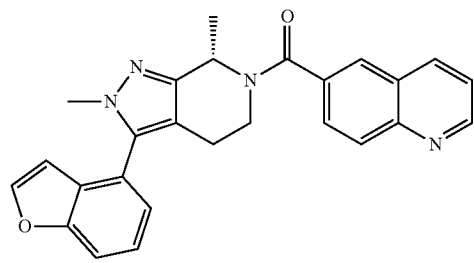 [SMILES: C[C@H]1c2nn(C)c(-c3cccc4occc34)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-(benzofuran-4-yl)-4,4,5,5-tetramethyl-1,3,2-dioxaborolane instead of 3-(difluoromethoxy)phenylboronic acid. MS (ESI): mass calcd. for $C_{26}H_{22}N_4O_2$, 422.2; m/z found, 423.0 [M+H]⁺. ¹H NMR (500 MHz, CD₃OD) δ 8.95 (s, 1H), 8.51 (d, J=8.3 Hz, 1H), 8.16 (d, J=8.5 Hz, 1H), 8.12 (s, 1H), 7.92-7.85 (m, 2H), 7.69-7.61 (m, 2H), 7.49-7.42 (m, 1H), 7.31-7.24 (m, 1H), 6.85-6.68 (m, 1H), 5.93-5.75 (m, 1H), 3.85-3.70 (m, 3H), 3.70-3.57 (m, 1H), 3.54-3.35 (m, 1H), 2.86-2.69 (m, 1H), 2.48-2.29 (m, 1H), 1.73-1.59 (m, 3H).

Example 536: [(7S)-3-(5-Fluorobenzofuran-7-yl)-2,7-dimethyl-5,7-dihydro-4H-pyrazolo[3,4-c]pyridin-6-yl]-(6-quinolyl)methanone

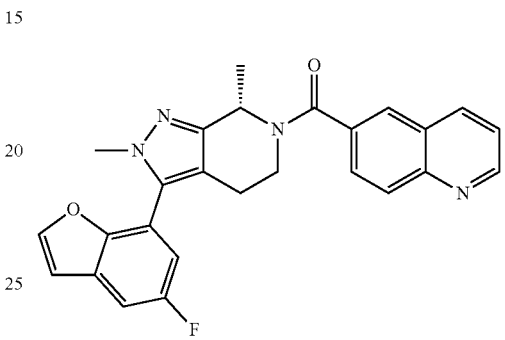

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-(5-fluorobenzofuran-7-yl)-4,4,5,5-tetramethyl-1,3,2-dioxaborolane instead of 3-(difluoromethoxy)phenylboronic acid. MS (ESI): mass calcd. for $C_{26}H_{21}FN_4O_2$, 440.2; m/z found, 441.0 [M+H]⁺. ¹H NMR (500 MHz, CD₃OD) δ 8.94 (s, 1H), 8.48 (d, J=8.3 Hz, 1H), 8.15 (d, J=8.7 Hz, 1H), 8.11-8.07 (m, 1H), 7.94-7.90 (m, 1H), 7.88-7.82 (m, 1H), 7.68-7.61 (m, 1H), 7.51-7.46 (m, 1H), 7.19 (dd, J=9.5, 2.2 Hz, 1H), 6.98 (s, 1H), 5.96-5.76 (m, 1H), 3.90-3.75 (m, 3H), 3.75-3.62 (m, 1H), 3.54-3.33 (m, 1H), 2.92-2.77 (m, 1H), 2.55-2.34 (m, 1H), 1.69-1.53 (m, 3H).

Example 537: [(7S)-3-(1,3-Benzothiazol-4-yl)-2,7-dimethyl-5,7-dihydro-4H-pyrazolo[3,4-c]pyridin-6-yl]-(6-quinolyl)methanone

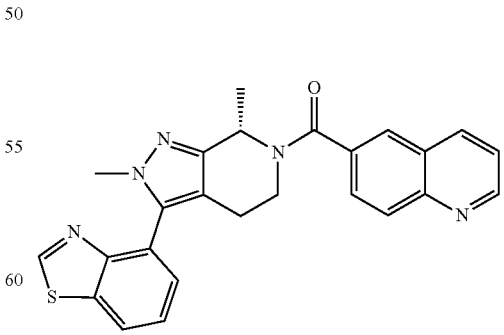

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of

[2-methyl-6-(quinoline-6-carbonyl)-4,5,6,7-tetrahydro-2H-pyrazolo[3,4-c]pyridin-3-yl trifluoromethanesulfonate] (Intermediate 10) and 4-(4,4,5,5-tetramethyl-1,3,2-dioxaborolan-2-yl)benzo[d]thiazole instead of 3-(difluoromethoxy)phenylboronic acid. MS (ESI): mass calcd. for $C_{25}H_{21}N_5OS$, 439.1; m/z found, 440.2 [M+H]$^+$. $^1$H NMR (500 MHz, CDCl$_3$) δ 9.09 (s, 1H), 8.98 (s, 1H), 8.22 (d, J=8.5 Hz, 1H), 8.19 (d, J=9.6 Hz, 1H), 8.09 (d, J=8.1 Hz, 1H), 7.96 (s, 1H), 7.80 (d, J=7.6 Hz, 1H), 7.58 (t, J=7.7 Hz, 1H), 7.50-7.46 (m, 2H), 6.09-5.89 (m, 1H), 5.10-4.89 (m, 1H), 3.81 (s, 3H), 3.40-3.19 (m, 1H), 2.95-2.74 (m, 1H), 2.50-2.32 (m, 1H), 1.71 (s, 3H).

Example 538: [(7S)-3-(2,1,3-Benzoxadiazol-4-yl)-2,7-dimethyl-5,7-dihydro-4H-pyrazolo[3,4-c]pyridin-6-yl]-(6-quinolyl)methanone

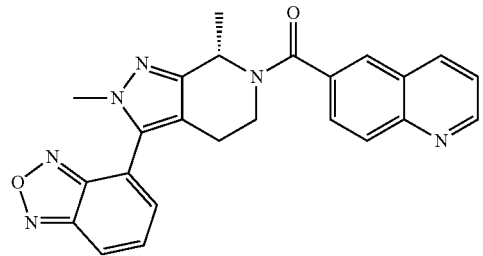 [SMILES: C[C@H]1c2nn(C)c(-c3cccc4nonc34)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and benzo[c][1,2,5]oxadiazol-4-ylboronic acid instead of 3-(difluoromethoxy)phenylboronic acid. MS (ESI): mass calcd. for $C_{24}H_{20}N_6O_2$, 424.2; m/z found, 425.0 [M+H]$^+$. $^1$H NMR (500 MHz, DMSO-d$_6$) δ 8.91 (d, J=4.1 Hz, 1H), 8.36 (d, J=8.3 Hz, 1H), 8.07 (d, J=8.6 Hz, 1H), 8.05-8.00 (m, 2H), 7.76-7.72 (m, 1H), 7.72-7.66 (m, 1H), 7.63 (d, J=6.6 Hz, 1H), 7.55-7.49 (m, 1H), 5.75-4.76 (m, 1H), 4.01-3.61 (m, 4H), 3.40-3.20 (m, 1H), 2.91-2.82 (m, 1H), 2.47-2.34 (m, 1H), 1.59 (d, J=6.7 Hz, 3H).

Example 539: [(7S)-3-(2,3-Dihydrobenzofuran-7-yl)-2,7-dimethyl-5,7-dihydro-4H-pyrazolo[3,4-c]pyridin-6-yl]-(6-quinolyl)methanone

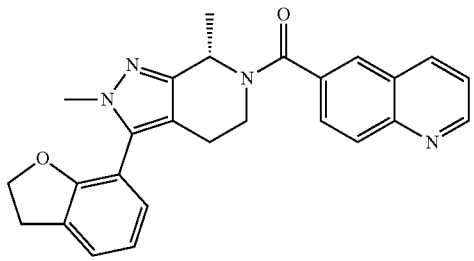 [SMILES: C[C@H]1c2nn(C)c(-c3cccc4c3OCO4)c2CCN1C(=O)c1ccc2ncccc2c1]

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-(2,3-dihydrobenzofuran-7-yl)-4,4,5,5-tetramethyl-1,3,2-dioxaborolane instead of 3-(difluoromethoxy)phenylboronic acid. MS (ESI): mass calcd. for $C_{26}H_{24}N_4O_2$, 424.2; m/z found, 425.0 [M+H]$^+$. $^1$H NMR (500 MHz, CD$_3$OD) δ 8.96-8.92 (m, 1H), 8.50-8.44 (m, 1H), 8.18-8.12 (m, 1H), 8.10-8.06 (m, 1H), 7.86-7.81 (m, 1H), 7.65-7.59 (m, 1H), 7.34-7.29 (m, 1H), 7.13-7.08 (m, 1H), 7.00-6.92 (m, 1H), 5.89-5.71 (m, 1H), 4.67-4.56 (m, 2H), 3.87-3.69 (m, 3H), 3.69-3.53 (m, 1H), 3.49-3.32 (m, 1H), 3.30-3.20 (m, 2H), 2.86-2.69 (m, 1H), 2.56-2.35 (m, 1H), 1.68-1.53 (m, 3H).

Example 540: [(7S)-3-(1,3-Benzodioxol-5-yl)-2,7-dimethyl-5,7-dihydro-4H-pyrazolo[3,4-c]pyridin-6-yl]-(6-quinolyl)methanone

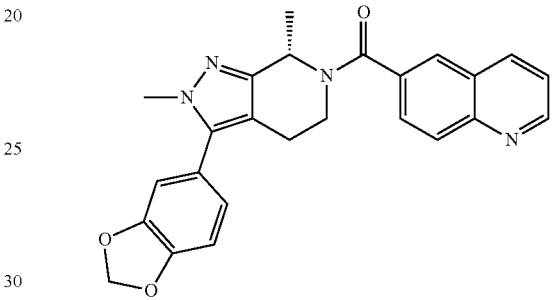

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-(benzo[d][1,3]dioxol-5-yl)-4,4,5,5-tetramethyl-1,3,2-dioxaborolane instead of 3-(difluoromethoxy)phenylboronic acid. MS (ESI): mass calcd. for $C_{25}H_{22}N_4O_3$, 426.2; m/z found, 427.0 [M+H]$^+$. $^1$H NMR (500 MHz, DMSO-d$_6$) δ 8.90 (d, J=4.0 Hz, 1H), 8.36 (d, J=8.2 Hz, 1H), 8.07 (d, J=8.6 Hz, 1H), 8.00 (s, 1H), 7.72 (d, J=8.4 Hz, 1H), 7.52 (dd, J=8.2, 4.2 Hz, 1H), 6.99-6.90 (m, 2H), 6.85 (d, J=8.0 Hz, 1H), 6.05 (s, 2H), 5.69-5.54 (m, 1H), 3.90-3.63 (m, 4H), 3.33-3.22 (m, 1H), 2.88-2.79 (m, 1H), 2.41-2.29 (m, 1H), 1.53 (d, J=5.2 Hz, 3H).

Example 541: [(7S)-3-(1,3-Benzodioxol-4-yl)-2,7-dimethyl-5,7-dihydro-4H-pyrazolo[3,4-c]pyridin-6-yl]-(6-quinolyl)methanone

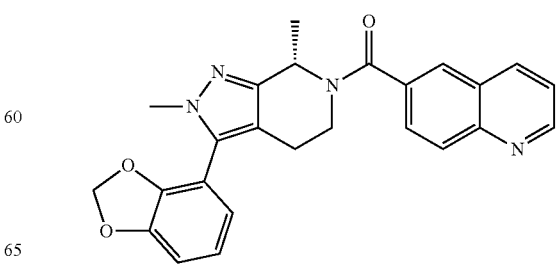

The title compound was prepared in a manner analogous to Example 98, using (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 49) instead of [2-methyl-6-(quinoline-6-carbonyl)-4,5,6,7-tetrahydro-2H-pyrazolo[3,4-c]pyridin-3-yl trifluoromethanesulfonate] (Intermediate 10) and 2-(benzo[d][1,3]dioxol-4-yl)-4,4,5,5-tetramethyl-1,3,2-dioxaborolane instead of 3-(difluoromethoxy)phenylboronic acid. MS (ESI): mass calcd. for $C_{25}H_{22}N_4O_3$, 426.2; m/z found, 427.2 [M+H]$^+$. $^1$H NMR (500 MHz, DMSO-d$_6$) δ 8.90 (d, J=3.9 Hz, 1H), 8.36 (d, J=8.2 Hz, 1H), 8.07 (d, J=8.5 Hz, 1H), 8.00 (s, 1H), 7.72 (d, J=8.6 Hz, 1H), 7.51 (dd, J=8.2, 4.1 Hz, 1H), 6.94-6.87 (m, 2H), 6.82 (d, J=7.4 Hz, 1H), 6.07 (s, 1H), 6.04 (s, 1H), 5.71-5.54 (m, 1H), 3.77 (s, 4H), 3.33-3.23 (m, 1H), 2.82-2.73 (m, 1H), 2.41-2.32 (m, 1H), 1.54 (br s, 3H).

Example 542: [(7S)-3-(2,2-Difluoro-1,3-benzodioxol-4-yl)-2,7-dimethyl-5,7-dihydro-4H-pyrazolo[3,4-c]pyridin-6-yl]-(6-quinolyl)methanone

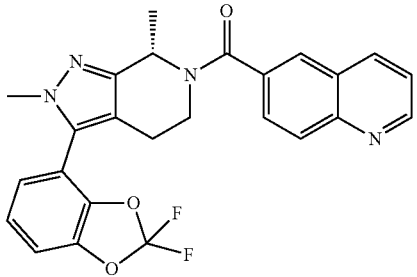 [SMILES: C[C@H]1c2nn(C)c(-c3cccc4c3OC(F)(F)O4)c2CCN1C(=O)c1ccc2ncccc2c1]

The title compound was prepared in a manner analogous to Example 288, using (S)-3-(2,2-difluorobenzo[d][1,3]dioxol-4-yl)-2,7-dimethyl-4,5,6,7-tetrahydro-2H-pyrazolo[3,4-c]pyridine (Intermediate 43) instead of (S)-2,7-dimethyl-3-(3,4,5-trifluorophenyl)-4,5,6,7-tetrahydro-2H-pyrazolo[3,4-c]pyridine and quinoline-6-carboxylic acid instead of 2-fluoro-6-(2H-1,2,3-triazol-2-yl) benzoic acid. MS (ESI): mass calcd. for $C_{25}H_{20}F_2N_4O_3$, 462.1; m/z found, 463.0 [M+H]$^+$. $^1$H NMR (500 MHz, DMSO-d$_6$) δ 9.03-8.91 (m, 1H), 8.47 (d, J=8.3 Hz, 1H), 8.16-8.05 (m, 2H), 7.79 (dd, J=8.6, 1.9 Hz, 1H), 7.64-7.50 (m, 2H), 7.41-7.31 (m, 2H), 5.77-5.49 (m, 1H), 4.88-4.47 (m, 1H), 3.87-3.65 (m, 4H), 2.85-2.69 (m, 1H), 2.43-2.29 (m, 1H), 1.63-1.40 (m, 3H).

Example 543: [(7S)-2,7-Dimethyl-3-(3,4,5-trifluorophenyl)-5,7-dihydro-4H-pyrazolo[3,4-c]pyridin-6-yl]-(5-isoquinolyl)methanone

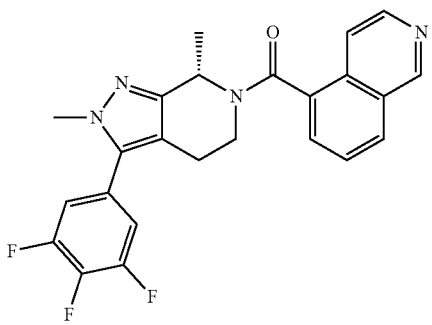 [SMILES: C[C@H]1c2nn(C)c(-c3cc(F)c(F)c(F)c3)c2CCN1C(=O)c1cccc2cnccc12]

The title compound was prepared in a manner analogous to Example 288, using isoquinoline-5-carboxylic acid instead of 2-fluoro-6-(2H-1,2,3-triazol-2-yl)benzoic acid. MS (ESI): mass calcd. for $C_{24}H_{19}F_3N_4O$, 436.2; m/z found, 437.1 [M+H]$^+$. $^1$H NMR (500 MHz, DMSO-d$_6$) δ 9.44-9.38 (m, 1H), 8.65-8.38 (m, 1H), 8.27-8.19 (m, 1H), 7.94-7.40 (m, 5H), 5.87-5.72 (m, 0.75H), 4.93-4.78 (m, 0.28H), 4.71-4.58 (m, 0.07H), 4.38-4.25 (m, 0.17H), 3.89-3.63 (m, 3H), 3.18-2.93 (m, 0.43H), 2.84-2.71 (s, 0.48H), 2.29-2.18 (m, 0.72H), 1.69-1.30 (m, 3H). (Fractions of Hs that overlap with DMSO and water are not reported).

Example 544: [(7S)-2,7-Dimethyl-3-(3,4,5-trifluorophenyl)-5,7-dihydro-4H-pyrazolo[3,4-c]pyridin-6-yl]-(6-isoquinolyl)methanone

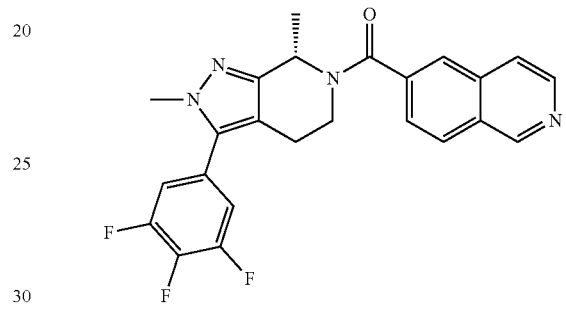

The title compound was prepared in a manner analogous to Example 288, using isoquinoline-6-carboxylic acid instead of 2-fluoro-6-(2H-1,2,3-triazol-2-yl) benzoic acid. MS (ESI): mass calcd. for $C_{24}H_{19}F_3N_4O$, 436.1; m/z found, 437.3 [M+H]$^+$. $^1$H NMR (400 MHz, DMSO-d$_6$) δ 9.40 (d, J=1.0 Hz, 1H), 8.58 (d, J=5.7 Hz, 1H), 8.24 (d, J=8.4 Hz, 1H), 8.12-7.88 (m, 2H), 7.77-7.65 (m, 1H), 7.60-7.41 (m, 2H), 5.74-5.47 (m, 1H), 3.88-3.56 (m, 4H), 2.93-2.66 (m, 2H), 2.39-2.22 (m, 1H), 1.60-1.26 (m, 3H).

Example 545: [(7S)-2,7-Dimethyl-3-(3,4,5-trifluorophenyl)-5,7-dihydro-4H-pyrazolo[3,4-c]pyridin-6-yl]-(5-fluoro-3-quinolyl)methanone

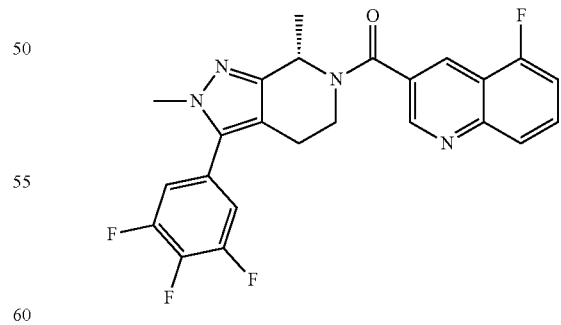

The title compound was prepared in a manner analogous to Example 288, using 5-fluoroquinoline-3-carboxylic acid instead of 2-fluoro-6-(2H-1,2,3-triazol-2-yl) benzoic acid. MS (ESI): mass calcd. for $C_{24}H_{18}F_4N_4O$, 454.1; m/z found, 455.0 [M+H]$^+$. $^1$H NMR (400 MHz, DMSO-d$_6$) δ 9.03 (s, 1H), 8.54 (s, 1H), 8.02-7.75 (m, 2H), 7.66-7.41 (m, 3H), 5.74-5.46 (m, 1H), 4.94-4.35 (m, 1H), 3.96-3.63 (m, 4H), 2.97-2.79 (m, 1H), 2.41-2.29 (m, 1H), 1.62-1.45 (m, 3H).

Example 546: [(7S)-2,7-Dimethyl-3-(3,4,5-trifluorophenyl)-5,7-dihydro-4H-pyrazolo[3,4-c]pyridin-6-yl]-(8-fluoro-4-isoquinolyl)methanone

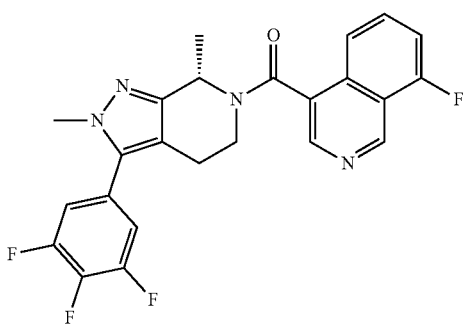 [SMILES: C[C@H]1c2nn(C)c(-c3cc(F)c(F)c(F)c3)c2CCN1C(=O)c1cncc2c(F)cccc12]

The title compound was prepared in a manner analogous to Example 288, using 8-fluoroisoquinoline-4-carboxylic acid instead of 2-fluoro-6-(2H-1,2,3-triazol-2-yl)benzoic acid. MS (ESI): mass calcd. for $C_{24}H_{18}F_4N_4O$, 454.1; m/z found, 455.1 [M+H]$^+$. $^1$H NMR (600 MHz, DMSO-d$_6$) δ 9.59-9.52 (m, 1H), 8.78-8.39 (m, 1H), 7.97-7.40 (m, 5H), 5.83-5.74 (d, J=17.8 Hz, 0.78H), 4.92-4.63 (m, 0.53H), 4.42-4.32 (s, 0.23H), 3.88-3.65 (m, 3.32H), 3.05-2.80 (m, 0.88H), 2.44-2.33 (m, 0.21H), 2.30-2.20 (m, 0.82H), 1.67-1.37 (m, 3H). (Fraction of Hs that overlap with DMSO and water are not reported).

Example 547: (4-Bromo-6-quinolyl)-[(7S)-2,7-dimethyl-3-(3,4,5-trifluorophenyl)-5,7-dihydro-4H-pyrazolo[3,4-c]pyridin-6-yl]methanone

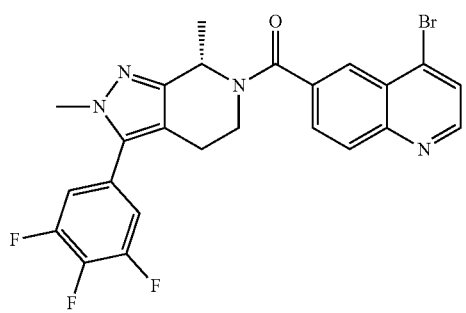 [SMILES: C[C@H]1c2nn(C)c(-c3cc(F)c(F)c(F)c3)c2CCN1C(=O)c1ccc2nccc(Br)c2c1]

The title compound was prepared in a manner analogous to Example 288, using 4-bromoquinoline-6-carboxylic acid instead of 2-fluoro-6-(2H-1,2,3-triazol-2-yl) benzoic acid. MS (ESI): mass calcd. for $C_{24}H_{18}BrF_3N_4O$, 514.1; m/z found, 515.0 [M+H]$^+$. $^1$H NMR (500 MHz, DMSO-d$_6$) δ 8.81 (d, J=4.6 Hz, 1H), 8.24-8.13 (m, 2H), 8.04 (d, J=4.7 Hz, 1H), 7.95-7.83 (m, 1H), 7.64-7.49 (m, 2H), 5.75-5.45 (m, 1H), 4.88-4.49 (m, 1H), 3.91-3.57 (m, 4H), 2.91-2.79 (m, 1H), 2.46-2.28 (m, 1H), 1.53 (d, J=6.8 Hz, 3H).

Example 548: [(7S)-2,7-Dimethyl-3-(3,4,5-trifluorophenyl)-5,7-dihydro-4H-pyrazolo[3,4-c]pyridin-6-yl]-(2-methyl-6-quinolyl)methanone

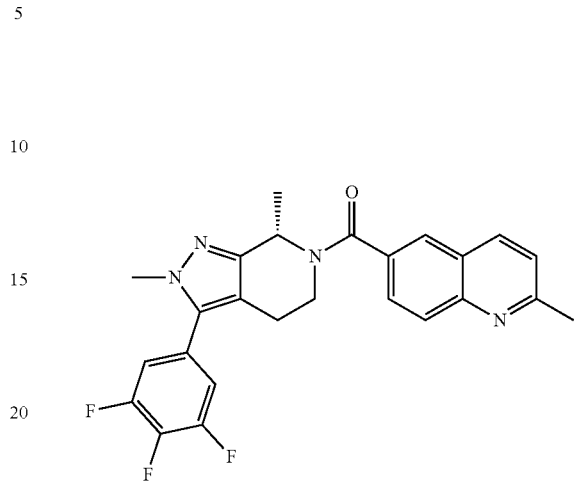

The title compound was prepared in a manner analogous to Example 288, using 2-methylquinoline-6-carboxylic acid instead of 2-fluoro-6-(2H-1,2,3-triazol-2-yl) benzoic acid. MS (ESI): mass calcd. for $C_{25}H_{21}F_3N_4O$, 450.2; m/z found, 451.2 [M+H]$^+$. $^1$H NMR (400 MHz, DMSO-d$_6$) δ 8.35 (d, J=8.4 Hz, 1H), 8.08-7.94 (m, 2H), 7.79-7.67 (m, 1H), 7.65-7.44 (m, 3H), 5.73-5.48 (m, 0.60H), 4.82-4.52 (m, 0.40H), 3.91-3.59 (m, 4H), 3.27-2.76 (m, 2H), 2.69 (s, 3H), 2.46-2.18 (m, 1H), 1.56-1.39 (m, 3H).

Example 549: [(7S)-2,7-Dimethyl-3-(3,4,5-trifluorophenyl)-5,7-dihydro-4H-pyrazolo[3,4-c]pyridin-6-yl]-(4-methyl-6-quinolyl)methanone

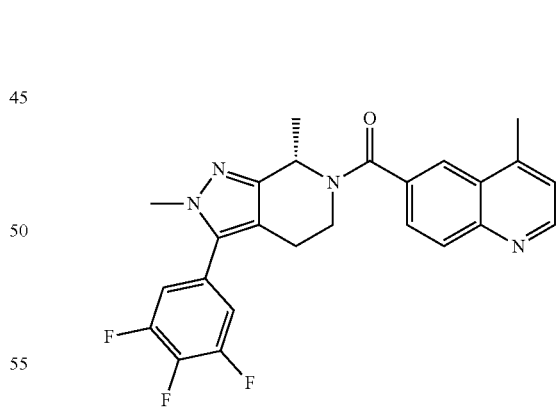

The title compound was prepared in a manner analogous to Example 288, using 4-methylquinoline-6-carboxylic acid instead of 2-fluoro-6-(2H-1,2,3-triazol-2-yl) benzoic acid. MS (ESI): mass calcd. for $C_{25}H_{21}F_3N_4O$, 450.2; m/z found, 451.0 [M+H]$^+$. $^1$H NMR (400 MHz, DMSO-d$_6$) δ 8.83 (d, J=4.3 Hz, 1H), 8.18-8.02 (m, 2H), 7.83-7.69 (m, 1H), 7.63-7.41 (m, 3H), 5.72-5.51 (m, 1H), 4.86-4.54 (m, 1H), 3.89-3.55 (m, 4H), 3.18-2.77 (m, 1H), 2.76-2.64 (m, 3H), 2.43-2.26 (m, 1H), 1.52 (d, J=6.7 Hz, 3H).

Example 550: [(7S)-2,7-Dimethyl-3-(3,4,5-trifluorophenyl)-5,7-dihydro-4H-pyrazolo[3,4-c]pyridin-6-yl]-(8-methoxy-4-quinolyl)methanone

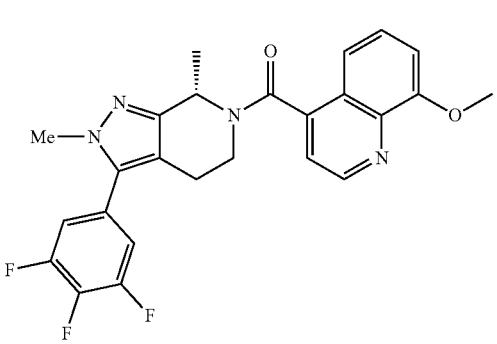 [SMILES: COc1cccc2c(C(=O)N3CCc4c(nn(C)c4-c4cc(F)c(F)c(F)c4)[C@@H]3C)ccnc12]

The title compound was prepared in a manner analogous to Example 288, using 8-methoxyquinoline-4-carboxylic acid instead of 2-fluoro-6-(2H-1,2,3-triazol-2-yl) benzoic acid. MS (ESI): mass calcd. for $C_{25}H_{21}F_3N_4O_2$, 466.2; m/z found, 467.1 [M+H]$^+$. $^1$H NMR (400 MHz, DMSO-d$_6$) δ 8.92 (d, J=4.2 Hz, 1H), 7.69-7.42 (m, 4H), 7.32-7.11 (m, 2H), 5.86-5.68 (m, 1H), 4.92-4.21 (m, 1H), 3.99 (d, J=6.0 Hz, 3H), 3.76 (d, J=54.2 Hz, 3H), 3.21 (d, J=7.1 Hz, 2H), 2.84-2.60 (m, 1H), 2.41-2.17 (m, 1H), 1.64-1.52 (m, 2H).

Example 551: 5,6-Dihydro-4H-pyrrolo[1,2-b]pyrazol-3-yl-[(7S)-2,7-dimethyl-3-(3,4,5-trifluorophenyl)-5,7-dihydro-4H-pyrazolo[3,4-c]pyridin-6-yl]methanone

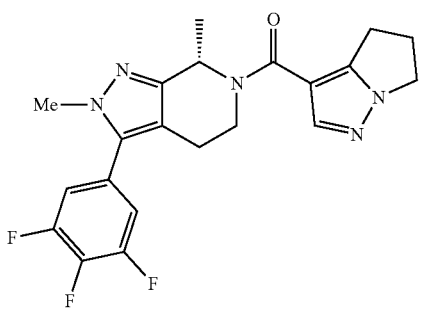 [SMILES: C[C@H]1c2nn(C)c(-c3cc(F)c(F)c(F)c3)c2CCN1C(=O)c1cnn2c1CCC2]

The title compound was prepared in a manner analogous to Example 288, using 5,6-dihydro-4H-pyrrolo[1,2-b]pyrazole-3-carboxylic acid instead of 2-fluoro-6-(2H-1,2,3-triazol-2-yl) benzoic acid. MS (ESI): mass calcd. for $C_{21}H_{20}F_3N_5O$, 415.2; m/z found, 416.1 [M+H]$^+$. $^1$H NMR (400 MHz, DMSO-d$_6$) δ 7.71 (s, 1H), 7.60-7.47 (m, 2H), 5.40 (s, 1H), 4.36-4.19 (m, 1H), 4.09 (t, J=7.3 Hz, 2H), 3.79 (s, 3H), 3.29-3.13 (m, 1H), 3.01-2.79 (m, 3H), 2.62-2.53 (m, 2H), 2.48-2.35 (m, 1H), 1.53-1.35 (m, 3H).

Example 552: [(7S)-2,7-Dimethyl-3-(3,4,5-trifluorophenyl)-5,7-dihydro-4H-pyrazolo[3,4-c]pyridin-6-yl]-(4,5,6,7-tetrahydropyrazolo[1,5-a]pyridin-3-yl)methanone

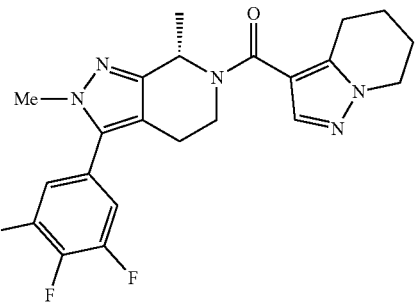

The title compound was prepared in a manner analogous to Example 288, using 4,5,6,7-tetrahydropyrazolo[1,5-a]pyridine-3-carboxylic acid instead of 2-fluoro-6-(2H-1,2,3-triazol-2-yl) benzoic acid. MS (ESI): mass calcd. for $C_{22}H_{22}F_3N_5O$, 429.2; m/z found, 430.2 [M+H]$^+$. $^1$H NMR (500 MHz, DMSO-d$_6$) δ 7.61 (s, 1H), 7.59-7.50 (m, 2H), 5.52-5.24 (m, 1H), 4.26-3.99 (m, 3H), 3.79 (s, 3H), 3.26-3.14 (m, 1H), 2.95-2.66 (m, 3H), 2.46-2.30 (m, 1H), 2.03-1.89 (m, 2H), 1.87-1.68 (m, 2H), 1.49-1.36 (m, 3H).

Example 553: 6,7-Dihydro-5H-pyrazolo[5,1-b][1,3]oxazin-2-yl-[(7S)-2,7-dimethyl-3-(3,4,5-trifluorophenyl)-5,7-dihydro-4H-pyrazolo[3,4-c]pyridin-6-yl]methanone

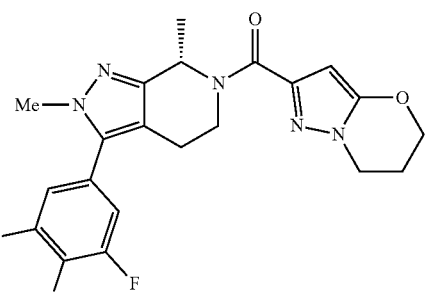

The title compound was prepared in a manner analogous to Example 288, using 6,7-dihydro-5H-pyrazolo[5,1-b][1,3]oxazine-2-carboxylic acid instead of 2-fluoro-6-(2H-1,2,3-triazol-2-yl) benzoic acid. MS (ESI): mass calcd. for $C_{21}H_{20}F_3N_5O$, 431.2; m/z found, 432.1 [M+H]$^+$. $^1$H NMR (400 MHz, DMSO-d$_6$) δ 7.61-7.45 (m, 2H), 5.90-5.74 (m, 1H), 5.61-5.30 (m, 1H), 4.84-4.53 (m, 1H), 4.38-4.23 (m, 2H), 4.22-4.06 (m, 2H), 3.84-3.67 (m, 3H), 3.27-2.60 (m, 2H), 2.39 (d, J=15.6 Hz, 1H), 2.27-2.14 (m, 2H), 1.54-1.35 (m, 3H).

Example 554: 6,7-Dihydro-5H-pyrazolo[5,1-b][1,3]oxazin-3-yl-[(7S)-2,7-dimethyl-3-(3,4,5-trifluorophenyl)-5,7-dihydro-4H-pyrazolo[3,4-c]pyridin-6-yl]methanone

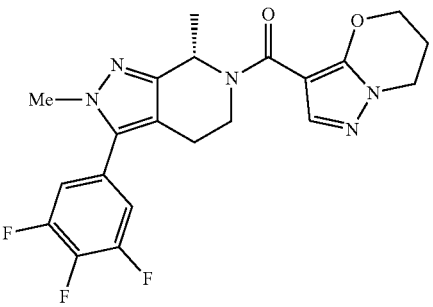 [SMILES: C[C@H]1c2nn(C)c(-c3cc(F)c(F)c(F)c3)c2CCN1C(=O)c1cnn2c1OCCC2]

The title compound was prepared in a manner analogous to Example 288, using 6,7-dihydro-5H-pyrazolo[5,1-b][1,3]oxazine-3-carboxylic acid instead of 2-fluoro-6-(2H-1,2,3-triazol-2-yl) benzoic acid. MS (ESI): mass calcd. for $C_{21}H_{20}F_3N_5O$, 431.2; m/z found, 432.1 [M+H]$^+$. $^1$H NMR (400 MHz, DMSO-$d_6$) δ 7.61-7.51 (m, 2H), 7.48 (s, 1H), 5.42-5.20 (m, 1H), 4.49-4.26 (m, 2H), 4.18-4.02 (m, 3H), 3.78 (s, 3H), 3.27-3.05 (m, 1H), 2.80 (t, J=12.6 Hz, 1H), 2.45-2.31 (m, 1H), 2.28-2.06 (m, 2H), 1.52-1.27 (m, 3H).

Example 555: [(7S)-2,7-Dimethyl-3-(3,4,5-trifluorophenyl)-5,7-dihydro-4H-pyrazolo[3,4-c]pyridin-6-yl]-(3-methyl-6,7-dihydro-5H-pyrazolo[5,1-b][1,3]oxazin-2-yl)methanone

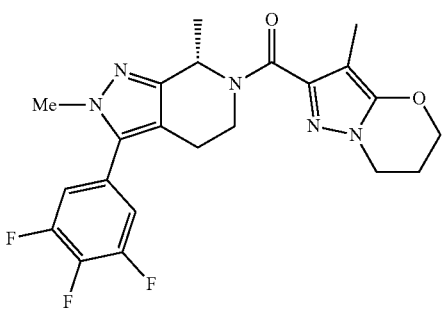 [SMILES: Cc1c(C(=O)N2CCc3c(nn(C)c3-c3cc(F)c(F)c(F)c3)[C@@H]2C)nn2c1OCCC2]

The title compound was prepared in a manner analogous to Example 288, using 3-methyl-6,7-dihydro-5H-pyrazolo[5,1-b][1,3]oxazine-2-carboxylic acid instead of 2-fluoro-6-(2H-1,2,3-triazol-2-yl) benzoic acid. MS (ESI): mass calcd. for $C_{22}H_{22}F_3N_5O_2$, 445.2; m/z found, 446.1 [M+H]$^+$. $^1$H NMR (400 MHz, DMSO-$d_6$) δ 7.54 (dd, J=8.7, 6.7 Hz, 2H), 5.56 (q, J=6.7 Hz, 1H), 4.68-4.37 (m, 1H), 4.30 (t, J=5.2 Hz, 2H), 4.15-4.01 (m, 2H), 3.84-3.72 (m, 3H), 3.17-2.65 (m, 2H), 2.48-2.30 (m, 1H), 2.25-2.10 (m, 2H), 1.84 (s, 3H), 1.49-1.35 (m, 3H).

Example 556: [(7S)-2,7-Dimethyl-3-(3,4,5-trifluorophenyl)-5,7-dihydro-4H-pyrazolo[3,4-c]pyridin-6-yl]-(2,6,6-trimethyl-4,7-dihydropyrazolo[5,1-c][1,4]oxazin-3-yl)methanone

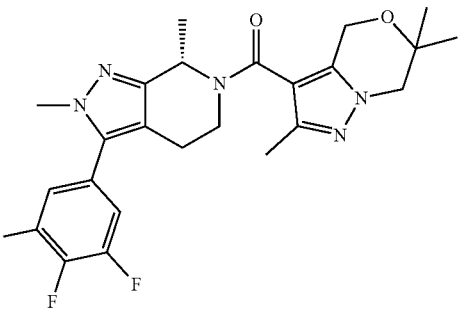

The title compound was prepared in a manner analogous to Example 288, using 2,6,6-trimethyl-6,7-dihydro-4H-pyrazolo[5,1-c][1,4]oxazine-3-carboxylic acid (Intermediate 105) instead of 2-fluoro-6-(2H-1,2,3-triazol-2-yl) benzoic acid. MS (ESI): mass calcd. for $C_{24}H_{26}F_3N_5O_2$, 473.2; m/z found, 474.1 [M+H]$^+$. $^1$H NMR (500 MHz, DMSO-$d_6$) δ 7.62-7.45 (m, 2H), 5.53-5.35 (m, 1H), 4.70 (q, J=16.1 Hz, 2H), 3.92-3.84 (m, 2H), 3.80 (s, 3H), 3.28-3.09 (m, 2H), 2.71-2.56 (m, 1H), 2.43-2.30 (m, 1H), 2.13 (s, 3H), 1.38 (d, J=6.8 Hz, 3H), 1.27 (d, J=3.4 Hz, 6H).

Example 557: [(7S)-2,7-Dimethyl-3-(3,4,5-trifluorophenyl)-5,7-dihydro-4H-pyrazolo[3,4-c]pyridin-6-yl]-(3,6,6-trimethyl-4,7-dihydropyrazolo[5,1-c][1,4]oxazin-2-yl)methanone

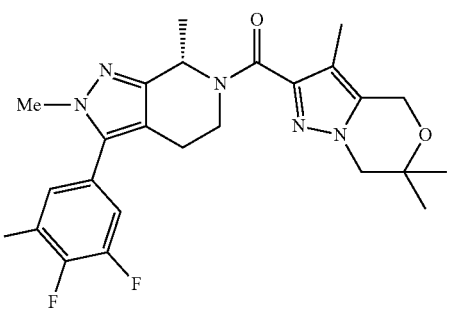

The title compound was prepared in a manner analogous to Example 288, using ethyl 3,6,6-trimethyl-6,7-dihydro-4H-pyrazolo[5,1-c][1,4]oxazine-2-carboxylate (Intermediate 106) instead of 2-fluoro-6-(2H-1,2,3-triazol-2-yl) benzoic acid. MS (ESI): mass calcd. for $C_{24}H_{26}F_3N_5O_2$, 473.2; m/z found, 474.1 [M+H]$^+$. $^1$H NMR (500 MHz, DMSO-$d_6$) δ 7.59-7.47 (m, 2H), 5.66-5.40 (m, 1H), 4.77 (s, 2H), 4.68-4.29 (m, 1H), 3.97-3.88 (m, 2H), 3.84-3.72 (m, 3H), 3.28-3.10 (m, 1H), 3.09-2.58 (m, 1H), 2.47-2.30 (m, 1H), 1.99-1.85 (m, 3H), 1.50-1.37 (m, 3H), 1.34-1.23 (m, 6H).

Example 558: ((S)-2,7-Dimethyl-3-(3,4,5-trifluorophenyl)-4,5-dihydro-2H-pyrazolo[3,4-c]pyridin-6(7H)-yl)(7-(trifluoromethyl)-4,5,6,7-tetrahydropyrazolo[1,5-a]pyrimidin-3-yl)methanone

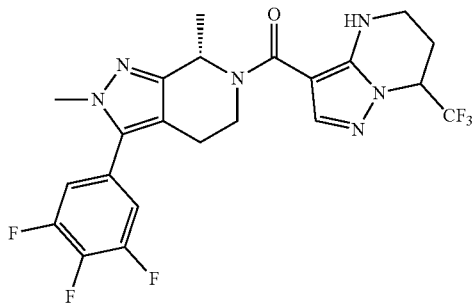 [SMILES: C[C@H]1c2nn(C)c(-c3cc(F)c(F)c(F)c3)c2CCN1C(=O)c1cnn2c1NCCC2C(F)(F)F]

The title compound was prepared in a manner analogous to Example 288, using 7-(trifluoromethyl)-4,5,6,7-tetrahydropyrazolo[1,5-a]pyrimidine-3-carboxylic acid instead of 2-fluoro-6-(2H-1,2,3-triazol-2-yl) benzoic acid. MS (ESI): mass calcd. for $C_{22}H_{20}F_6N_6O$, 498.2; m/z found, 499.0 [M+H]$^+$. $^1$H NMR (400 MHz, DMSO-$d_6$) δ 7.61 (d, J=3.2 Hz, 1H), 7.59-7.48 (m, 2H), 7.16-7.04 (m, 1H), 5.44-5.28 (m, 1H), 5.23-5.05 (m, 1H), 4.40-4.06 (m, 1H), 3.83-3.71 (m, 3H), 3.52-3.35 (m, 1H), 3.21-3.10 (m, 2H), 2.94-2.73 (m, 1H), 2.48-2.37 (m, 1H), 2.37-2.07 (m, 2H), 1.53-1.38 (m, 3H).

Example 559: 6,7-Dihydro-5H-pyrrolo[1,2-a]imidazol-3-yl-[(7S)-2,7-dimethyl-3-(3,4,5-trifluorophenyl)-5,7-dihydro-4H-pyrazolo[3,4-c]pyridin-6-yl]methanone

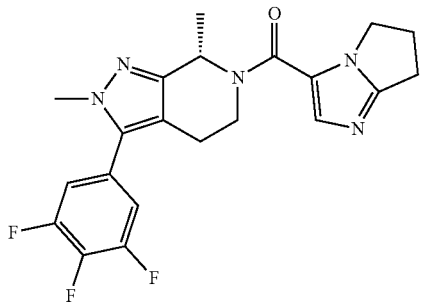 [SMILES: C[C@H]1c2nn(C)c(-c3cc(F)c(F)c(F)c3)c2CCN1C(=O)c1cnc2n1CCC2]

The title compound was prepared in a manner analogous to Example 288, using 6,7-dihydro-5H-pyrrolo[1,2-a]imidazole-3-carboxylic acid hydrochloride instead of 2-fluoro-6-(2H-1,2,3-triazol-2-yl)benzoic acid. MS (ESI): mass calcd. for $C_{21}H_{20}F_3N_5O$, 415.2; m/z found, 416.2 [M+H]$^+$. $^1$H NMR (500 MHz, Chloroform-d) δ 7.59-7.52 (m, 2H), 7.40 (s, 1H), 5.44 (q, J=6.7 Hz, 1H), 4.46-4.36 (m, 1H), 4.21-4.13 (m, 1H), 4.02-3.94 (m, 1H), 3.79 (s, 3H), 2.96-2.70 (m, 3H), 1.56-1.38 (m, 3H). (Fractions of Hs that overlap with DMSO and water are not reported).

Example 560: [(7S)-2,7-Dimethyl-3-(3,4,5-trifluorophenyl)-5,7-dihydro-4H-pyrazolo[3,4-c]pyridin-6-yl]-(5,6,7,8-tetrahydroimidazo[1,2-a]pyridin-3-yl)methanone

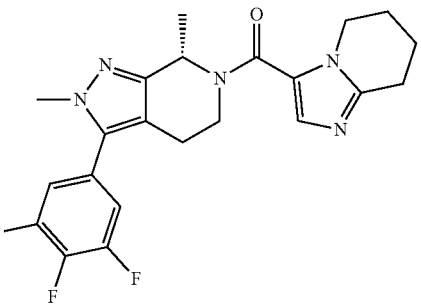

The title compound was prepared in a manner analogous to Example 288, using 5,6,7,8-tetrahydroimidazo[1,2-a]pyridine-3-carboxylic acid instead of 2-fluoro-6-(2H-1,2,3-triazol-2-yl) benzoic acid. MS (ESI): mass calcd. for $C_{22}H_{22}F_3N_5O$, 429.2; m/z found, 430.1 [M+H]$^+$. $^1$H NMR (500 MHz, DMSO-$d_6$) δ 7.56 (dd, J=8.7, 6.6 Hz, 2H), 7.24 (s, 1H), 5.51-5.32 (m, 1H), 4.42-4.20 (m, 1H), 4.20-4.06 (m, 1H), 3.96-3.82 (m, 1H), 3.80 (s, 3H), 3.17 (s, 1H), 2.97-2.84 (m, 1H), 2.84-2.71 (m, 2H), 2.46-2.34 (m, 1H), 1.95-1.77 (m, 4H), 1.52-1.38 (m, 3H).

Example 561: [2-(Difluoromethyl)-5,6,7,8-tetrahydroimidazo[1,2-a]pyridin-3-yl]-[(7S)-2,7-dimethyl-3-(3,4,5-trifluorophenyl)-5,7-dihydro-4H-pyrazolo[3,4-c]pyridin-6-yl]methanone

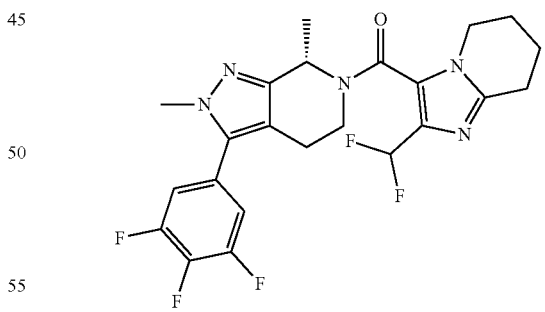

The title compound was prepared in a manner analogous to Example 288, using 2-(difluoromethyl)-5,6,7,8-tetrahydroimidazo[1,2-a]pyridine-3-carboxylic acid instead of 2-fluoro-6-(2H-1,2,3-triazol-2-yl) benzoic acid. MS (ESI): mass calcd. for $C_{23}H_{22}F_5N_5O$, 479.2; m/z found, 480.1 [M+H]$^+$. $^1$H NMR (500 MHz, DMSO-$d_6$) δ 7.56 (dd, J=8.7, 6.6 Hz, 2H), 7.24 (s, 1H), 5.51-5.32 (m, 1H), 4.42-4.20 (m, 1H), 4.20-4.06 (m, 1H), 3.96-3.82 (m, 1H), 3.80 (s, 3H), 3.17 (s, 1H), 2.97-2.84 (m, 1H), 2.84-2.71 (m, 2H), 2.46-2.34 (m, 1H), 1.95-1.77 (m, 4H), 1.52-1.38 (m, 3H).

Example 562: 6,8-Dihydro-5H-imidazo[2,1-c][1,4]oxazin-3-yl-[(7S)-2,7-dimethyl-3-(3,4,5-trifluorophenyl)-5,7-dihydro-4H-pyrazolo[3,4-c]pyridin-6-yl]methanone

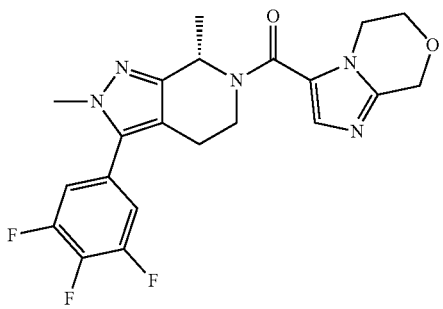 [SMILES: C[C@H]1c2nn(C)c(-c3cc(F)c(F)c(F)c3)c2CCN1C(=O)c1cnc2n1CCOC2]

The title compound was prepared in a manner analogous to Example 288, using 5,6-dihydro-8H-imidazo[2,1-c][1,4]oxazine-3-carboxylic acid hydrochloride instead of 2-fluoro-6-(2H-1,2,3-triazol-2-yl)benzoic acid and DMF instead of DCM. MS (ESI): mass calcd. for $C_{21}H_{20}F_3N_5O_2$, 431.2; m/z found, 432.2 [M+H]$^+$. $^1$H NMR (500 MHz, DMSO-d$_6$) δ 7.60-7.51 (m, 2H), 7.36 (s, 1H), 5.48-5.38 (m, 1H), 4.84-4.71 (m, 2H), 4.41-4.28 (m, 1H), 4.26-4.17 (m, 1H), 4.09-3.89 (m, 3H), 3.80 (s, 3H), 3.01-2.85 (m, 1H), 2.48-2.42 (m, 1H), 1.55-1.42 (m, 3H). (Fractions of Hs that overlap with DMSO and water are not reported).

Example 563: 3,4-Dihydro-2H-pyrano[2,3-b]pyridin-6-yl-[(7S)-2,7-dimethyl-3-(3,4,5-trifluorophenyl)-5,7-dihydro-4H-pyrazolo[3,4-c]pyridin-6-yl]methanone

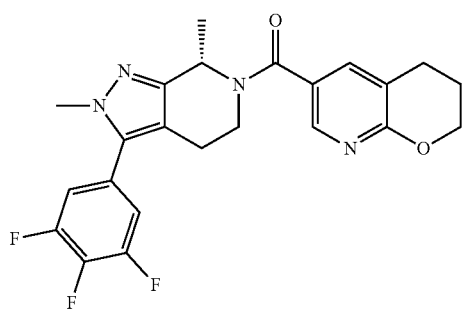 [SMILES: C[C@H]1c2nn(C)c(-c3cc(F)c(F)c(F)c3)c2CCN1C(=O)c1cnc2c(c1)CCCO2]

The title compound was prepared in a manner analogous to Example 288, using 3,4-dihydro-2H-pyrano[2,3-b]pyridine-6-carboxylic acid instead of 2-fluoro-6-(2H-1,2,3-triazol-2-yl)benzoic acid. MS (ESI): mass calcd. for $C_{23}H_{21}F_3N_4O_2$, 442.2; m/z found, 443.1 [M+H]$^+$. $^1$H NMR (500 MHz, DMSO-d$_6$) δ 8.10-8.06 (m, 1H), 7.62-7.52 (m, 3H), 5.61-5.37 (m, 0.78H), 4.34-4.29 (m, 2H), 3.8-3.67 (m, 3.85H), 2.92-2.75 (m, 3H), 1.97-1.89 (m, 2H), 1.45 (d, J=6.8 Hz, 3H). (Fractions of Hs that overlap with DMSO and water are not reported).

Example 564: 3,4-Dihydro-2H-pyrano[2,3-b]pyridin-5-yl-[(7S)-2,7-dimethyl-3-(3,4,5-trifluorophenyl)-5,7-dihydro-4H-pyrazolo[3,4-c]pyridin-6-yl]methanone

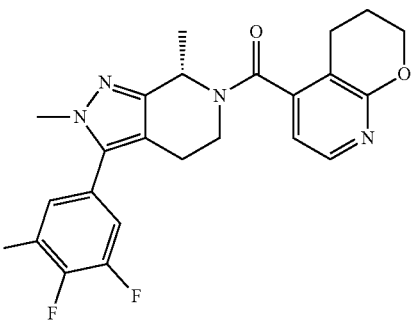

The title compound was prepared in a manner analogous to Example 288, using 3,4-dihydro-2H-pyrano[2,3-b]pyridine-5-carboxylic acid (Intermediate 58) instead of 2-fluoro-6-(2H-1,2,3-triazol-2-yl) benzoic acid. MS (ESI): mass calcd. for $C_{23}H_{21}F_3N_4O_2$, 442.2; m/z found, 443.2 [M+H]$^+$. $^1$H NMR (500 MHz, Chloroform-d) δ 8.20-8.05 (m, 1H), 7.02-6.90 (m, 2H), 6.86-6.60 (m, 1H), 5.93-5.84 (m, 0.57H), 4.97-4.87 (m, 0.49H), 4.69-4.59 (m, 0.28H), 4.46-4.25 (m, 2H), 3.86-3.76 (m, 3H), 3.67-3.47 (m, 0.63H), 3.32-3.22 (m, 0.56H), 3.08-2.91 (m, 1H), 2.89-2.22 (m, 3H), 2.12-1.86 (m, 2H), 1.64-1.34 (m, 3H).

Example 565: 6,8-Dihydro-5H-pyrano[3,4-b]pyridin-4-yl-[(7S)-2,7-dimethyl-3-(3,4,5-trifluorophenyl)-5,7-dihydro-4H-pyrazolo[3,4-c]pyridin-6-yl]methanone

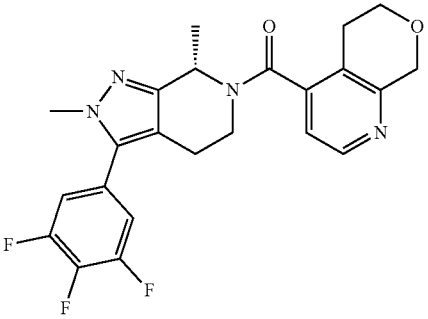 [SMILES: C[C@H]1c2nn(C)c(-c3cc(F)c(F)c(F)c3)c2CCN1C(=O)c1ccnc2c1CCOC2]

The title compound was prepared in a manner analogous to Example 288, using 5,8-dihydro-6H-pyrano[3,4-b]pyridine-4-carboxylic acid (Intermediate 57) instead of 2-fluoro-6-(2H-1,2,3-triazol-2-yl) benzoic acid and DMF instead of DCM. MS (ESI): mass calcd. for $C_{23}H_{21}F_3N_4O_2$, 442.1; m/z found, 443.2 [M+H]$^+$.

Example 566: 6,8-Dihydro-5H-pyrano[3,4-b]pyridin-2-yl-[(7S)-2,7-dimethyl-3-(3,4,5-trifluorophenyl)-5,7-dihydro-4H-pyrazolo[3,4-c]pyridin-6-yl]methanone

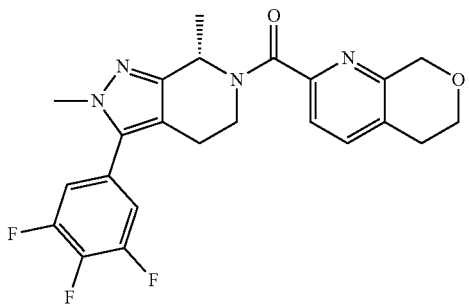 [SMILES: C[C@H]1c2nn(C)c(-c3cc(F)c(F)c(F)c3)c2CCN1C(=O)c1ccc2c(n1)COCC2]

The title compound was prepared in a manner analogous to Example 288, using 5,8-dihydro-6H-pyrano[3,4-b]pyridine-2-carboxylic acid (Intermediate 59) instead of 2-fluoro-6-(2H-1,2,3-triazol-2-yl)benzoic acid. MS (ESI): mass calcd. for $C_{23}H_{21}F_3N_4O_2$, 442.2; m/z found, 443.2 [M+H]$^+$. $^1$H NMR (500 MHz, DMSO-d$_6$) δ 7.73-7.69 (m, 1H), 7.58-7.50 (m, 2H), 7.42-7.38 (m, 1H), 5.56 (q, J=6.7 Hz, 0.63H), 4.89 (q, J=6.6 Hz, 0.42H), 4.73-4.59 (m, 2.56H), 3.99-3.71 (m, 6H), 3.07-2.99 (m, 0.41H), 2.92-2.85 (m, 2H), 2.81-2.70 (m, 1H), 2.35-2.28 (m, 0.59H), 1.49-1.43 (m, 3H). (Fractions of Hs that overlap with DMSO and water are not reported).

Example 567: 7,8-Dihydro-5H-pyrano[4,3-b]pyridin-3-yl-[(7S)-2,7-dimethyl-3-(3,4,5-trifluorophenyl)-5,7-dihydro-4H-pyrazolo[3,4-c]pyridin-6-yl]methanone

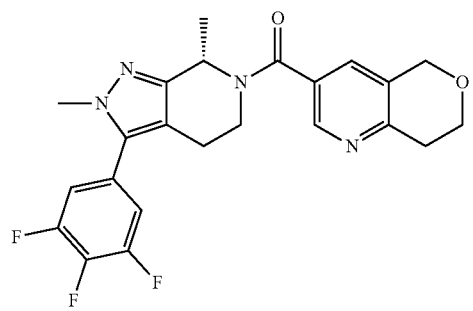 [SMILES: C[C@H]1c2nn(C)c(-c3cc(F)c(F)c(F)c3)c2CCN1C(=O)c1cnc2c(c1)COCC2]

The title compound was prepared in a manner analogous to Example 288, using 7,8-dihydro-5H-pyrano[4,3-b]pyridine-3-carboxylic acid instead of 2-fluoro-6-(2H-1,2,3-triazol-2-yl) benzoic acid. MS (ESI): mass calcd. for $C_{23}H_{21}F_3N_4O_2$, 442.2; m/z found, 443.2 [M+H]$^+$. $^1$H NMR (500 MHz, Chloroform-d) δ 8.52 (s, 1H), 7.41 (s, 1H), 7.01-6.92 (m, 2H), 5.82 (s, 0.46H), 5.03-4.66 (m, 3H), 4.10 (t, J=5.8 Hz, 2H), 3.89-3.70 (m, 3.59H), 3.45-2.97 (m, 3H), 2.90-2.60 (m, 1H), 2.53-2.32 (m, 1H), 1.66-1.51 (m, 3H).

Example 568: 3,4-Dihydro-2H-pyrano[3,2-b]pyridin-8-yl-[(7S)-2,7-dimethyl-3-(3,4,5-trifluorophenyl)-5,7-dihydro-4H-pyrazolo[3,4-c]pyridin-6-yl]methanone

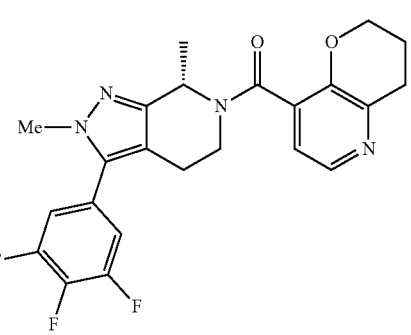

The title compound was prepared in a manner analogous to Example 288, using 3,4-dihydro-2H-pyrano[3,2-b]pyridine-8-carboxylic acid instead of 2-fluoro-6-(2H-1,2,3-triazol-2-yl) benzoic acid. MS (ESI): mass calcd. for $C_{23}H_{21}F_3N_4O_2$, 442.2; m/z found, 443.1 [M+H]$^+$. $^1$H NMR (500 MHz, DMSO-d$_6$) δ 8.11 (d, J=4.7 Hz, 1H), 7.58-7.40 (m, 2H), 7.17-6.89 (m, 1H), 5.71-5.35 (m, 0.70H), 4.76-4.41 (m, 0.30H), 4.31-4.14 (m, 2H), 3.86-3.72 (m, 3H), 3.48-3.35 (m, 1H), 3.29-3.12 (m, 1H), 3.00-2.80 (m, 2H), 2.71-2.54 (m, 1H), 2.46-2.16 (m, 1H), 2.12-1.95 (m, 2H), 1.51-1.29 (m, 3H).

Example 569: 2,3-Dihydro-[1,4]dioxino[2,3-b]pyridin-8-yl-[(7S)-2,7-dimethyl-3-(3,4,5-trifluorophenyl)-5,7-dihydro-4H-pyrazolo[3,4-c]pyridin-6-yl]methanone

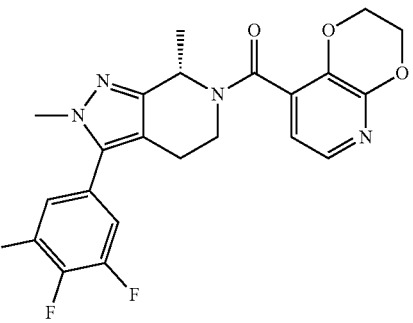

The title compound was prepared in a manner analogous to Example 288, using 2,3-dihydro-[1,4]dioxino[2,3-b]pyridine-8-carboxylic acid instead of 2-fluoro-6-(2H-1,2,3-triazol-2-yl)benzoic acid. MS (ESI): mass calcd. for $C_{22}H_{19}F_3N_4O_3$, 444.1; m/z found, 445.2 [M+H]$^+$. $^1$H NMR (500 MHz, DMSO-d$_6$) δ 7.85-7.72 (m, 1H), 7.58-7.46 (m, 2H), 7.01-6.67 (m, 1H), 5.63-5.49 (m, 0.76H), 4.72-4.23 (m, 4.56H), 4.19-4.05 (m, 0.25H), 3.85-3.69 (m, 3H), 3.56-3.44 (m, 0.81H), 3.10-2.96 (m, 0.26H), 2.77-2.57 (m, 1H), 2.42-2.23 (m, 0.72H), 1.50-1.29 (m, 3H). (Fractions of Hs that overlap with DMSO and water are not reported).

Example 570: 2,3-Dihydro-[1,4]dioxino[2,3-b]pyridin-7-yl-[(7S)-2,7-dimethyl-3-(3,4,5-trifluorophenyl)-5,7-dihydro-4H-pyrazolo[3,4-c]pyridin-6-yl]methanone

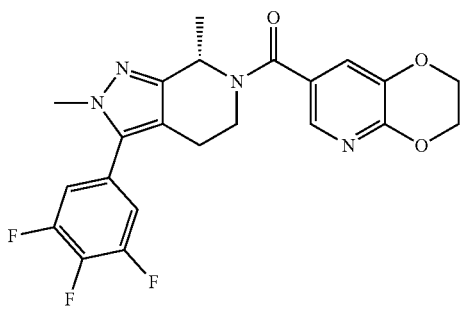 [SMILES: C[C@H]1c2nn(C)c(-c3cc(F)c(F)c(F)c3)c2CCN1C(=O)c1cnc2c(c1)OCCO2]

The title compound was prepared in a manner analogous to Example 288, using 2,3-dihydro-[1,4]dioxino[2,3-b]pyridine-7-carboxylic acid instead of 2-fluoro-6-(2H-1,2,3-triazol-2-yl)benzoic acid. MS (ESI): mass calcd. for $C_{22}H_{19}F_3N_4O_3$, 444.1; m/z found, 445.2 [M+H]$^+$. $^1$H NMR (500 MHz, DMSO-$d_6$) δ 7.84 (s, 1H), 7.59-7.51 (m, 2H), 7.36 (s, 1H), 5.50 (br s, 0.74H), 4.97-4.39 (m, 2.82H), 4.36-4.23 (m, 2.25H), 3.89-3.61 (m, 4H), 2.87 (br s, 1H), 2.42-2.28 (m, 0.88H), 1.45 (d, J=6.7 Hz, 3H). (Fractions of Hs that overlap with DMSO and water are not reported).

Example 571: 3,4-Dihydro-2H-pyrido[3,2-b][1,4]oxazin-7-yl-[(7S)-2,7-dimethyl-3-(3,4,5-trifluorophenyl)-5,7-dihydro-4H-pyrazolo[3,4-c]pyridin-6-yl]methanone

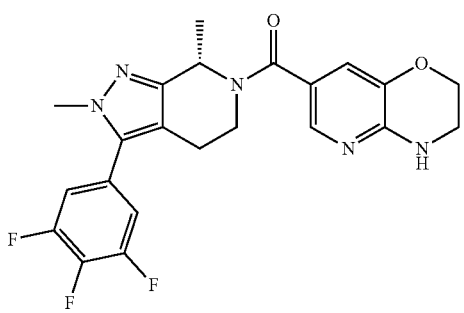 [SMILES: C[C@H]1c2nn(C)c(-c3cc(F)c(F)c(F)c3)c2CCN1C(=O)c1cnc2c(c1)OCCN2]

The title compound was prepared in a manner analogous to Example 288, using 3,4-dihydro-2H-pyrido[3,2-b][1,4]oxazine-7-carboxylic acid instead of 2-fluoro-6-(2H-1,2,3-triazol-2-yl) benzoic acid. MS (ESI): mass calcd. for $C_{22}H_{20}F_3N_5O_2$, 443.2; m/z found, 444.2 [M+H]$^+$. $^1$H NMR (500 MHz, Chloroform-d) δ 7.84 (d, J=1.9 Hz, 1H), 7.11-7.07 (m, 1H), 7.00-6.93 (m, 2H), 5.47 (br s, 1H), 5.03 (s, 1H), 4.71-4.03 (m, 3H), 3.80 (s, 3H), 3.64-3.55 (m, 2H), 3.20 (s, 1H), 2.84-2.71 (m, 1H), 2.45-2.36 (m, 1H), 1.58 (d, J=6.8 Hz, 3H).

Example 572: [(7S)-2,7-Dimethyl-3-(3,4,5-trifluorophenyl)-5,7-dihydro-4H-pyrazolo[3,4-c]pyridin-6-yl]-(4-methyl-2,3-dihydropyrido[3,2-b][1,4]oxazin-7-yl)methanone The title compound was prepared in a manner analogous to Example 288, using 4-methyl-3,4-dihydro-2H-pyrido[3,2-b][1,4]oxazine-7-carboxylic acid instead of 2-fluoro-6-(2H-1,2,3-triazol-2-yl) benzoic acid. MS (ESI): mass calcd. for $C_{23}H_{22}F_3N_5O_2$, 457.2; m/z found, 458.2 [M+H]$^+$. $^1$H NMR (500 MHz, Chloroform-d) δ 7.91 (d, J=1.9 Hz, 1H), 7.04 (d, J=1.9 Hz, 1H), 7.00-6.93 (m, 2H), 5.48 (br s, 1H), 4.57-4.16 (m, 3H), 3.80 (s, 3H), 3.54-3.46 (m, 2H), 3.29-3.11 (m, 4H), 2.85-2.75 (m, 1H), 2.44-2.37 (m, 1H), 1.58 (d, J=6.8 Hz, 3H).

Example 573: 3,4-Dihydro-2H-pyrano[2,3-c]pyridin-6-yl-[(7S)-2,7-dimethyl-3-(3,4,5-trifluorophenyl)-5,7-dihydro-4H-pyrazolo[3,4-c]pyridin-6-yl]methanone

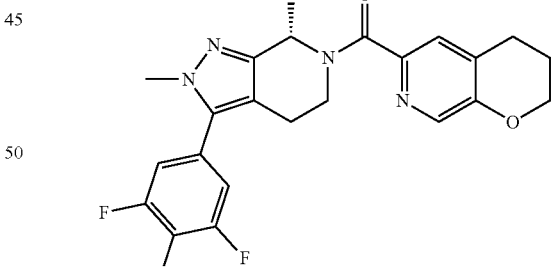

The title compound was prepared in a manner analogous to Example 288, using 3,4-dihydro-2H-pyrano[2,3-c]pyridine-6-carboxylic acid instead of 2-fluoro-6-(2H-1,2,3-triazol-2-yl) benzoic acid. MS (ESI): mass calcd. for $C_{23}H_{21}F_3N_4O_2$, 442.2; m/z found, 443.1 [M+H]$^+$. $^1$H NMR (400 MHz, Chloroform-d) δ 8.09 (s, 1H), 7.50-7.40 (m, 1H), 7.04-6.90 (m, 2H), 5.87-5.77 (m, 0.52H), 5.51-5.41 (m, 0.42H), 4.88-4.77 (m, 0.46H), 4.34-7.22 (m, 2.60H), 3.87-3.73 (m, 3H), 3.31-3.19 (m, 0.55H), 3.15-2.91 (m, 1H), 2.90-2.71 (m, 2.49H), 2.49-2.29 (m, 1H), 2.10-1.99 (m, 2H), 1.66-1.56 (m, 3H).

Example 574: [(7S)-2,7-Dimethyl-3-(3,4,5-trifluoro-phenyl)-5,7-dihydro-4H-pyrazolo[3,4-c]pyridin-6-yl]-(1,2,3,4-tetrahydroisoquinolin-5-yl)methanone

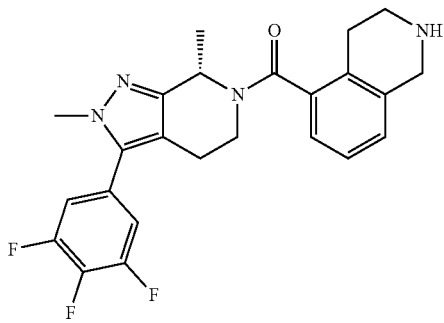 [SMILES: C[C@H]1c2nn(C)c(-c3cc(F)c(F)c(F)c3)c2CCN1C(=O)c1cccc2c1CCNC2]

Step A: tert-Butyl (S)-5-(2,7-dimethyl-3-(3,4,5-trifluoro-phenyl)-4,5,6,7-tetrahydro-2H-pyrazolo[3,4-c]pyridine-6-carbonyl)-3,4-dihydroisoquinoline-2 (1H)-carboxylate. The title compound was prepared in a manner analogous to Example 288, using 2-(tert-butoxycarbonyl)-1,2,3,4-tetrahydroisoquinoline-5-carboxylic acid instead of 2-fluoro-6-(2H-1,2,3-triazol-2-yl) benzoic acid. MS (ESI): mass calcd. for $C_{29}H_{31}F_3N_4O$, 540.2; m/z found, 541.2 [M+H]$^+$.

Step B: [(7S)-2,7-Dimethyl-3-(3,4,5-trifluorophenyl)-5,7-dihydro-4H-pyrazolo[3,4-c]pyridin-6-yl]-(1,2,3,4-tetrahydroisoquinolin-5-yl)methanone. TFA (0.24 mL, 3.1 mmol) was added to a mixture of tert-butyl (S)-5-(2,7-dimethyl-3-(3,4,5-trifluorophenyl)-4,5,6,7-tetrahydro-2H-pyrazolo[3,4-c]pyridine-6-carbonyl)-3,4-dihydroisoquinoline-2 (1H)-carboxylate (85.1 mg, 0.16 mmol) in DCM (2.2 mL). Upon completion, volatiles were removed. Purification of the filtrate (preparative HPLC, METHOD A followed by METHOD E) afforded the title compound (46 mg, 66%). MS (ESI): mass calcd. for $C_{24}H_{23}F_3N_4O$, 440.2; m/z found, 441.1 [M+H]$^+$. $^1$H NMR (500 MHz, Chloroform-d) δ 7.24-6.89 (m, 5H), 5.98-5.88 (m, 0.58H), 5.03-4.92 (m, 0.52H), 4.67 (q, J=6.7 Hz, 0.30H), 4.10-3.97 (m, 2H), 3.87-3.74 (m, 3H), 3.73-3.65 (m, 0.20H), 3.56 (dd, J=13.5, 5.1 Hz, 0.43H), 3.27-2.90 (m, 3.65H), 2.86-2.43 (m, 2.48H), 2.35-2.21 (m, 0.88H), 1.61-1.33 (m, 3H).

Example 575: [(7S)-2,7-Dimethyl-3-(3,4,5-trifluoro-phenyl)-5,7-dihydro-4H-pyrazolo[3,4-c]pyridin-6-yl]-(1,2,3,4-tetrahydroisoquinolin-8-yl)methanone

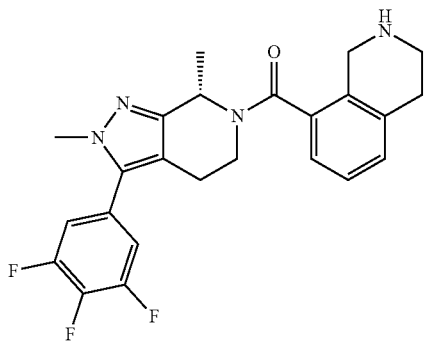 [SMILES: C[C@H]1c2nn(C)c(-c3cc(F)c(F)c(F)c3)c2CCN1C(=O)c1cccc2c1CNCC2]

The title compound was prepared in a manner analogous to Example 574 using 2-(tert-butoxycarbonyl)-1,2,3,4-tetrahydroisoquinoline-8-carboxylic acid in Step A. MS (ESI): mass calcd. for $C_{24}H_{23}F_3N_4O$, 440.2; m/z found, 441.1 [M+H]$^+$.

Example 576: [(7S)-2,7-Dimethyl-3-(3,4,5-trifluoro-phenyl)-5,7-dihydro-4H-pyrazolo[3,4-c]pyridin-6-yl]-isochroman-5-yl-methanone

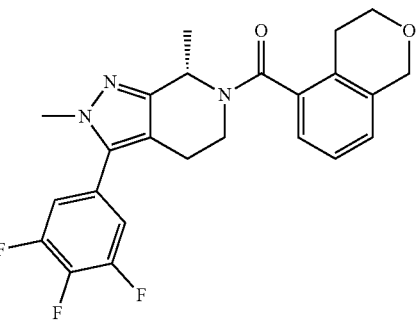

The title compound was prepared in a manner analogous to Example 288, using isochromane-5-carboxylic acid instead of 2-fluoro-6-(2H-1,2,3-triazol-2-yl) benzoic acid. MS (ESI): mass calcd. for $C_{24}H_{22}F_3N_3O_2$, 441.2; m/z found, 442.2 [M+H]$^+$.

Example 577: [(7S)-2,7-Dimethyl-3-(3,4,5-trifluoro-phenyl)-5,7-dihydro-4H-pyrazolo[3,4-c]pyridin-6-yl]-isochroman-7-yl-methanone

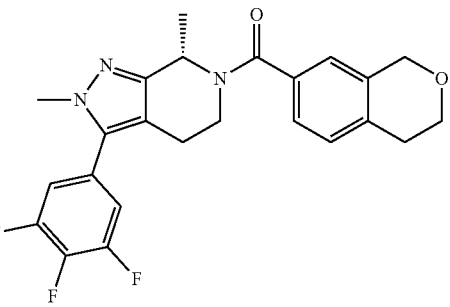

The title compound was prepared in a manner analogous to Example 288, using isochromane-7-carboxylic acid instead of 2-fluoro-6-(2H-1,2,3-triazol-2-yl) benzoic acid. MS (ESI): mass calcd. for $C_{24}H_{22}F_3N_3O_2$, 441.2; m/z found, 442.1 [M+H]$^+$. $^1$H NMR (500 MHz, Chloroform-d) δ 7.23-7.19 (m, 1H), 7.18-7.14 (m, 1H), 7.06 (s, 1H), 7.01-6.93 (m, 2H), 5.82 (br s, 0.46H), 5.13-4.68 (m, 3H), 3.98 (t, J=5.7 Hz, 2H), 3.89-3.72 (m, 3.5H), 3.35-2.97 (m, 1H), 2.92-2.56 (m, 3H), 2.50-2.29 (m, 1H), 1.62-1.49 (m, 3H).

Example 578: [(7S)-2,7-Dimethyl-3-(3,4,5-trifluorophenyl)-5,7-dihydro-4H-pyrazolo[3,4-c]pyridin-6-yl]-isochroman-6-yl-methanone

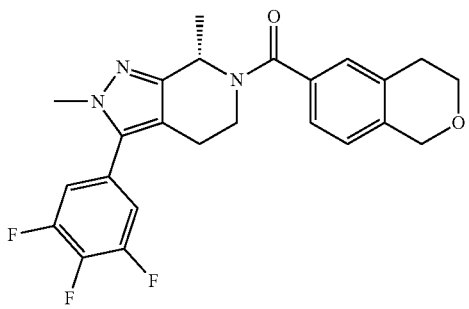 [SMILES: C[C@H]1c2nn(C)c(-c3cc(F)c(F)c(F)c3)c2CCN1C(=O)c1ccc2c(c1)CCOC2]

The title compound was prepared in a manner analogous to Example 288, using isochromane-6-carboxylic acid instead of 2-fluoro-6-(2H-1,2,3-triazol-2-yl) benzoic acid. MS (ESI): mass calcd. for $C_{24}H_{22}F_3N_3O_2$, 441.2; m/z found, 442.2 $[M+H]^+$. $^1$H NMR (500 MHz, Chloroform-d) δ 7.22-7.17 (m, 2H), 7.04-6.93 (m, 3H), 5.93-5.72 (m, 0.45H), 5.13-4.72 (m, 3H), 3.98 (t, J=5.7 Hz, 2H), 3.92-3.69 (m, 3.52H), 3.35-2.97 (m, 1H), 2.94-2.57 (m, 3H), 2.40 (s, 1H), 1.65-1.46 (m, 3H).

Example 579: [(7S)-2,7-Dimethyl-3-(3,4,5-trifluorophenyl)-5,7-dihydro-4H-pyrazolo[3,4-c]pyridin-6-yl]-isochroman-8-yl-methanone

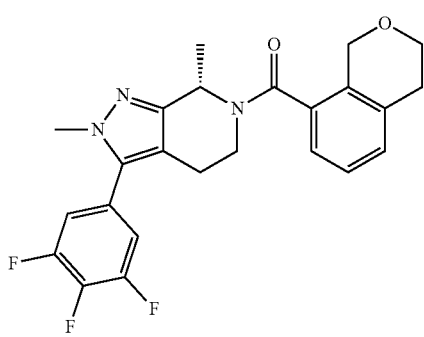 [SMILES: C[C@H]1c2nn(C)c(-c3cc(F)c(F)c(F)c3)c2CCN1C(=O)c1cccc2c1COCC2]

The title compound was prepared in a manner analogous to Example 288, using isochromane-8-carboxylic acid instead of 2-fluoro-6-(2H-1,2,3-triazol-2-yl) benzoic acid. MS (ESI): mass calcd. for $C_{24}H_{22}F_3N_3O_2$, 441.2; m/z found, 442.1 $[M+H]^+$.

Example 580: Chroman-6-yl-[(7S)-2,7-dimethyl-3-(3,4,5-trifluorophenyl)-5,7-dihydro-4H-pyrazolo[3,4-c]pyridin-6-yl]methanone

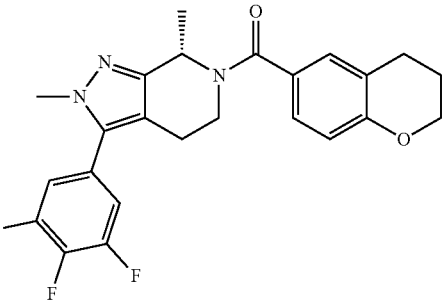

The title compound was prepared in a manner analogous to Example 288, using chromane-6-carboxylic acid instead of 2-fluoro-6-(2H-1,2,3-triazol-2-yl) benzoic acid. MS (ESI): mass calcd. for $C_{24}H_{22}F_3N_3O_2$, 441.2; m/z found, 442.2 $[M+H]^+$. $^1$H NMR (500 MHz, Chloroform-d) δ 7.18-7.13 (m, 2H), 7.01-6.93 (m, 2H), 6.79 (d, J=8.2 Hz, 1H), 5.93-3.61 (m, 7H), 3.17 (br s, 1H), 2.87-2.65 (m, 3H), 2.44-2.34 (m, 1H), 2.06-1.96 (m, 2H), 1.58-1.52 (s, 3H).

Example 581: Chroman-5-yl-[(7S)-2,7-dimethyl-3-(3,4,5-trifluorophenyl)-5,7-dihydro-4H-pyrazolo[3,4-c]pyridin-6-yl]methanone

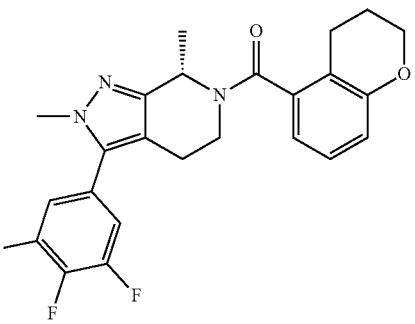

The title compound was prepared in a manner analogous to Example 288, using chromane-5-carboxylic acid instead of 2-fluoro-6-(2H-1,2,3-triazol-2-yl) benzoic acid. MS (ESI): mass calcd. for $C_{24}H_{22}F_3N_3O_2$, 441.2; m/z found, 442.1 $[M+H]^+$. $^1$H NMR (500 MHz, Chloroform-d) δ 7.18-6.60 (m, 5H), 5.98-5.87 (m, 0.57H), 5.07-4.91 (m, 0.54H), 4.77-4.68 (m, 0.29H), 4.30-4.07 (m, 2H), 3.86-3.69 (m, 3H), 3.61 (dd, J=13.6, 5.1 Hz, 0.41H), 3.22 (td, J=12.9, 3.6 Hz, 0.58H), 3.06-2.89 (m, 1H), 2.87-2.69 (m, 0.71H), 2.66-2.40 (m, 2H), 2.38-2.18 (m, 0.86H), 2.11-1.83 (m, 2H), 1.63-1.32 (m, 3H).

Example 582: Chroman-7-yl-[(7S)-2,7-dimethyl-3-(3,4,5-trifluorophenyl)-5,7-dihydro-4H-pyrazolo[3,4-c]pyridin-6-yl]methanone

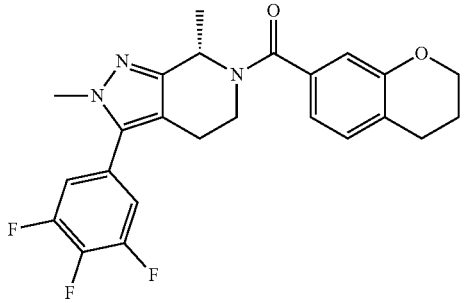 [SMILES: C[C@H]1c2nn(C)c(-c3cc(F)c(F)c(F)c3)c2CCN1C(=O)c1ccc2c(c1)OCCC2]

The title compound was prepared in a manner analogous to Example 288, using chromane-7-carboxylic acid instead of 2-fluoro-6-(2H-1,2,3-triazol-2-yl) benzoic acid. MS (ESI): mass calcd. for $C_{24}H_{22}F_3N_3O_2$, 441.2; m/z found, 442.1 [M+H]$^+$. $^1$H NMR (500 MHz, Chloroform-d) δ 7.09-7.03 (m, 1H), 7.00-6.93 (m, 2H), 6.90-6.85 (m, 1H), 6.84-6.80 (m, 1H), 5.81 (br s, 0.46H), 5.13-4.67 (m, 1H), 4.24-4.15 (m, 2H), 3.99-3.68 (m, 3.62H), 3.33-2.95 (m, 1H), 2.88-2.58 (m, 3H), 2.38 (br s, 1H), 2.05-1.98 (m, 2H), 1.63-1.45 (m, 3H).

Example 583: Chroman-8-yl-[(7S)-2,7-dimethyl-3-(3,4,5-trifluorophenyl)-5,7-dihydro-4H-pyrazolo[3,4-c]pyridin-6-yl]methanone

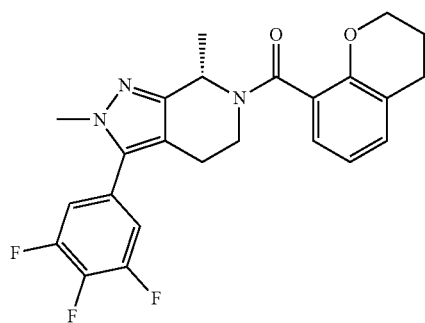 [SMILES: C[C@H]1c2nn(C)c(-c3cc(F)c(F)c(F)c3)c2CCN1C(=O)c1cccc2c1OCCC2]

The title compound was prepared in a manner analogous to Example 288, using chromane-8-carboxylic acid instead of 2-fluoro-6-(2H-1,2,3-triazol-2-yl) benzoic acid. MS (ESI): mass calcd. for $C_{24}H_{22}F_3N_3O_2$, 441.2; m/z found, 442.1 [M+H]$^+$. $^1$H NMR (500 MHz, Chloroform-d) δ 7.10-6.77 (m, 5H), 5.94-5.87 (m, 0.55H), 5.01-4.92 (m, 0.48H), 4.91-4.85 (m, 0.28H), 4.82-4.76 (m, 0.22H), 4.30-4.10 (m, 1.69H), 4.06-3.98 (m, 0.21H), 3.94-3.87 (m, 0.22H), 3.85-3.72 (m, 3H), 3.70-3.60 (m, 0.61H), 3.32-3.14 (m, 0.60H), 3.09-2.93 (m, 0.47H), 2.88-2.67 (m, 2.74H), 2.56-2.39 (m, 0.76H), 2.33-2.22 (m, 0.59H), 2.12-1.85 (m, 2.18H), 1.62-1.34 (m, 3H).

Example 584: 4-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one

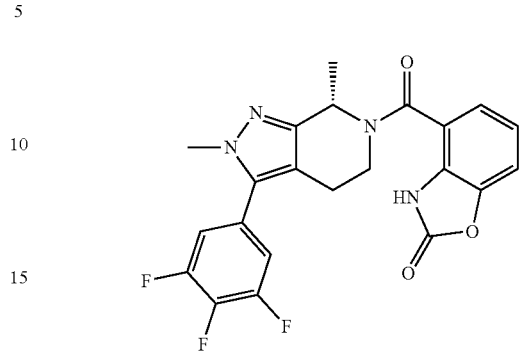

The title compound was prepared in a manner analogous to Example 288, using 2-oxo-2,3-dihydrobenzo[d]oxazole-4-carboxylic acid instead of 2-fluoro-6-(2H-1,2,3-triazol-2-yl)benzoic acid. MS (ESI): mass calcd. for $C_{22}H_{17}F_3N_4O_3$, 442.1; m/z found, 443.0 [M+H]$^+$. $^1$H NMR (400 MHz, Methanol-d$_4$) δ 7.32-7.26 (m, 3H), 7.20-7.14 (m, 2H), 5.97-5.59 (m, 1H), 3.82 (s, 4H), 3.47-3.34 (m, 1H), 2.89-2.69 (m, 1H), 2.58-2.37 (m, 1H), 1.38-1.32 (m, 3H).

Example 585: 4-[(7S)-2,7-Dimethyl-3-(3,4,5-trifluorophenyl)-5,7-dihydro-4H-pyrazolo[3,4-c]pyridine-6-carbonyl]-3-methyl-1,3-benzoxazol-2-one

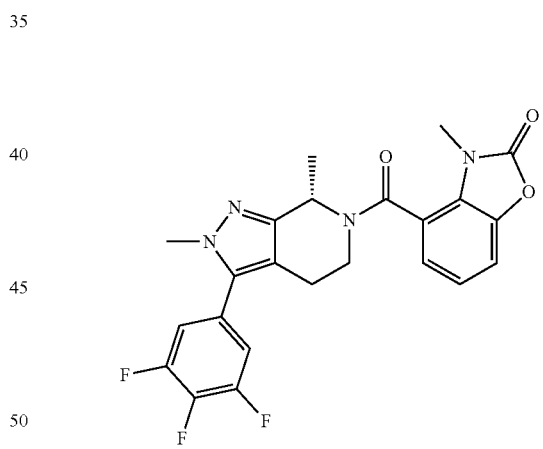

The title compound was prepared in a manner analogous to Example 206, using 4-[(7S)-2,7-dimethyl-3-(3,4,5-trifluorophenyl)-5,7-dihydro-4H-pyrazolo[3,4-c]pyridine-6-carbonyl]-3H-1,3-benzoxazol-2-one (Example 584) instead of [(S)-(2,7-dimethyl-3-(3,4,5-trifluorophenyl)-2,4,5,7-tetrahydro-6H-pyrazolo[3,4-c]pyridin-6-yl)(1H-indol-7-yl)methanone] (Example 205). MS (ESI): mass calcd. for $C_{23}H_{19}F_3N_4O_3$, 456.1; m/z found, 457.0 [M+H]$^+$. $^1$H NMR (400 MHz, Methanol-d$_4$) δ 7.46-7.11 (m, 5H), 5.98-5.84 (m, 0.30H), 5.77 (q, J=6.6 Hz, 0.70H), 3.84 (s, 2.1H), 3.77 (s, 0.90H), 3.73 (dd, J=14.1, 5.3 Hz, 0.30H), 3.48-3.36 (m, 3.70H), 3.30-3.25 (m, 0.30H), 3.20-3.09 (m, 0.70H), 2.90-2.71 (m, 1H), 2.60 (dd, J=15.6, 4.0 Hz, 0.30H), 2.47-2.36 (m, 0.70H), 1.61 (d, J=6.8 Hz, 2.1H), 1.53 (d, J=6.6 Hz, 0.90H).

Example 586: 5-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one

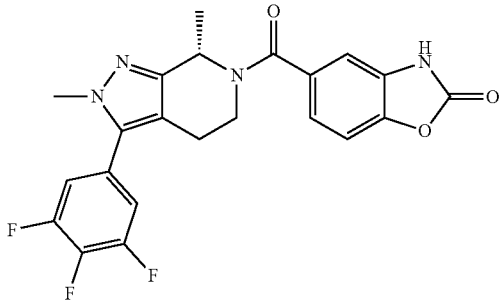 [SMILES: C[C@H]1c2nn(C)c(-c3cc(F)c(F)c(F)c3)c2CCN1C(=O)c1ccc2oc(=O)[nH]c2c1]

The title compound was prepared in a manner analogous to Example 288, using 2-oxo-2,3-dihydrobenzo[d]oxazole-5-carboxylic acid instead of 2-fluoro-6-(2H-1,2,3-triazol-2-yl)benzoic acid. MS (ESI): mass calcd. for $C_{22}H_{17}F_3N_4O_3$, 442.1; m/z found, 443.0 [M+H]$^+$. $^1$H NMR (400 MHz, Methanol-d$_4$) δ 7.43-7.21 (m, 3H), 7.22-7.06 (m, 2H), 5.98-5.51 (m, 1H), 4.16-3.68 (m, 4H), 3.39-3.19 (m, 1H), 2.90-2.71 (m, 1H), 2.56-2.42 (m, 1H), 1.56 (d, J=6.8 Hz, 3H).

Example 587: 7-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one

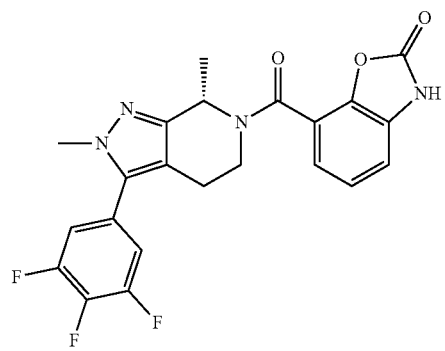 [SMILES: C[C@H]1c2nn(C)c(-c3cc(F)c(F)c(F)c3)c2CCN1C(=O)c1cccc2[nH]c(=O)oc12]

The title compound was prepared in a manner analogous to Example 288, using 2-oxo-2,3-dihydrobenzo[d]oxazole-7-carboxylic acid instead of 2-fluoro-6-(2H-1,2,3-triazol-2-yl)benzoic acid. MS (ESI): mass calcd. for $C_{22}H_{17}F_3N_4O_3$, 442.1; m/z found, 443.1 [M+H]$^+$. $^1$H NMR (400 MHz, DMSO-d$_6$) δ 11.84 (s, 1H), 7.61-7.47 (m, 2H), 7.26-7.14 (m, 2H), 7.12-7.01 (m, 1H), 5.61 (q, J=6.7 Hz, 0.69H), 4.74-4.62 (m, 0.52H), 3.85-3.70 (m, 3H), 3.66-3.55 (m, 0.72H), 2.81-2.64 (m, 1H), 2.40-2.27 (m, 0.77H), 1.54-1.34 (m, 3H). (Fractions of Hs that overlap with DMSO and water are not reported).

Example 588: 6-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one

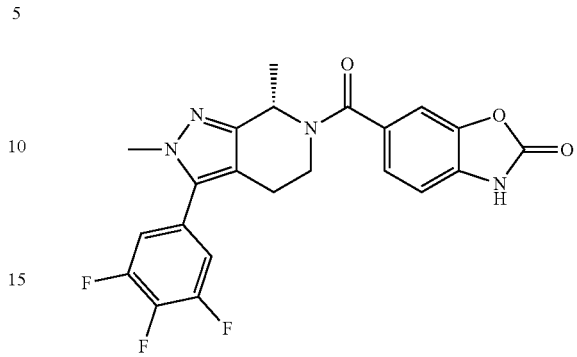

The title compound was prepared in a manner analogous to Example 288, using 2-oxo-2,3-dihydrobenzo[d]oxazole-6-carboxylic acid instead of 2-fluoro-6-(2H-1,2,3-triazol-2-yl)benzoic acid. MS (ESI): mass calcd. for $C_{22}H_{17}F_3N_4O_3$, 442.1; m/z found, 443.1 [M+H]$^+$. $^1$H NMR (500 MHz, DMSO-d$_6$) δ 11.83 (br s, 1H), 7.59-7.50 (m, 2H), 7.36 (s, 1H), 7.24-7.18 (m, 1H), 7.16-7.11 (m, 1H), 5.63-5.30 (m, 0.55H), 3.90-3.59 (m, 4H), 2.93-2.75 (m, 1H), 2.41-2.30 (m, 1H), 1.45 (d, J=6.7 Hz, 3H). (Fractions of Hs that overlap with DMSO and water are not reported).

Example 589: 7-[(7S)-2,7-dimethyl-3-(3,4,5-trifluorophenyl)-5,7-dihydro-4H-pyrazolo[3,4-c]pyridine-6-carbonyl]-3-methyl-1,3-benzoxazol-2-one

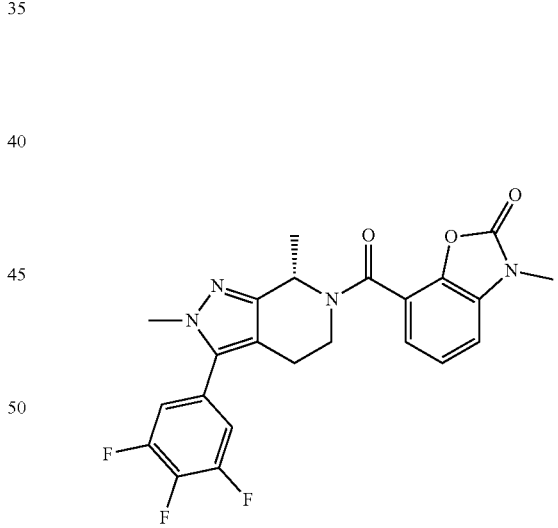

The title compound was prepared in a manner analogous to Example 288, using 3-methyl-2-oxo-2,3-dihydrobenzo[d]oxazole-7-carboxylic acid instead of 2-fluoro-6-(2H-1,2,3-triazol-2-yl)benzoic acid. MS (ESI): mass calcd. for $C_{23}H_{19}F_3N_4O_3$, 456.1; m/z found, 457.2 [M+H]$^+$. $^1$H NMR (500 MHz, DMSO-d$_6$) δ 7.61-7.48 (m, 2H), 7.38-7.28 (m, 2H), 7.17-7.06 (m, 1H), 5.62 (q, J=6.7 Hz, 0.71H), 4.74-4.64 (m, 0.58H), 3.85-3.71 (m, 3H), 3.63-3.56 (m, 0.73H), 3.36 (s, 3H), 3.14-3.04 (m, 0.27H), 2.82-2.65 (m, 1H), 2.38-2.29 (m, 0.68H), 1.55-1.33 (m, 3H). (Fractions of Hs that overlap with DMSO and water are not reported).

Example 590: 7-[(7S)-2,7-Dimethyl-3-(3,4,5-trifluorophenyl)-5,7-dihydro-4H-pyrazolo[3,4-c]pyridine-6-carbonyl]-4-methyl-1,4-benzoxazin-3-one.TFA salt

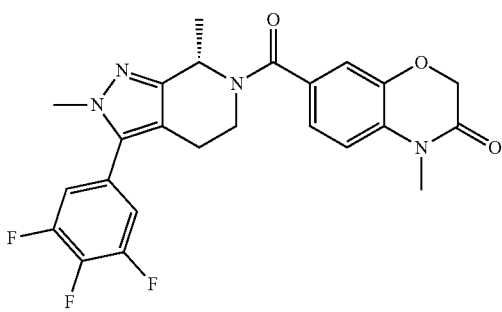 [SMILES: C[C@H]1c2nn(C)c(-c3cc(F)c(F)c(F)c3)c2CCN1C(=O)c1ccc2c(c1)OCC(=O)N2C]

The title compound was prepared in a manner analogous to Example 288, using 4-methyl-3-oxo-3,4-dihydro-2H-benzo[b][1,4]oxazine-7-carboxylic acid instead of 2-fluoro-6-(2H-1,2,3-triazol-2-yl)benzoic acid. MS (ESI): mass calcd. for $C_{24}H_{21}F_3N_4O_3$, 470.2; m/z found, 471.2 [M+H]$^+$. $^1$H NMR (500 MHz, Chloroform-d) δ 7.16-7.12 (m, 1H), 7.09-7.07 (m, 1H), 7.03-6.94 (m, 3H), 5.84 (br s, 0.37H), 5.16-4.59 (m, 3H), 4.01-3.70 (m, 3.48H), 3.43-3.01 (m, 4H), 2.75 (s, 1H), 2.50-2.33 (m, 1H), 1.63-1.49 (m, 3H).

Example 591: [(7S)-2,7-8-[(7S)-2,7-Dimethyl-3-(3,4,5-trifluorophenyl)-5,7-dihydro-4H-pyrazolo[3,4-c]pyridine-6-carbonyl]-4-methyl-1,4-benzoxazin-3-one.TFA salt

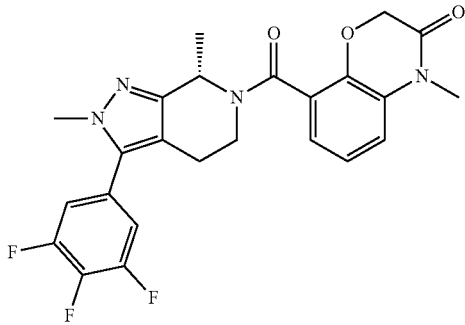 [SMILES: C[C@H]1c2nn(C)c(-c3cc(F)c(F)c(F)c3)c2CCN1C(=O)c1cccc2c1OCC(=O)N2C]

The title compound was prepared in a manner analogous to Example 288, using 4-methyl-3-oxo-3,4-dihydro-2H-benzo[b][1,4]oxazine-8-carboxylic acid instead of 2-fluoro-6-(2H-1,2,3-triazol-2-yl)benzoic acid and DMF instead of DCM. MS (ESI): mass calcd. for $C_{24}H_{21}F_3N_4O_3$, 470.2; m/z found, 471.1 [M+H]$^+$. $^1$H NMR (500 MHz, Chloroform-d) δ 7.16-6.84 (m, 5H), 5.91 (q, J=6.7 Hz, 0.53H), 5.00-4.56 (m, 2.58H), 4.44 (q, J=15.1 Hz, 0.54H), 3.86-3.74 (m, 3H), 3.63 (dd, J=13.8, 5.1 Hz, 0.54H), 3.43-3.21 (m, 3.59H), 3.14-2.99 (m, 0.45H), 2.86-2.66 (m, 0.73H), 2.59-2.43 (m, 0.75H), 2.36-2.27 (m, 0.57H), 1.63-1.36 (m, 3H).

Example 592: 3,4-Dihydro-2H-1,4-benzoxazin-8-yl-[(7S)-2,7-dimethyl-3-(3,4,5-trifluorophenyl)-5,7-dihydro-4H-pyrazolo[3,4-c]pyridin-6-yl]methanone

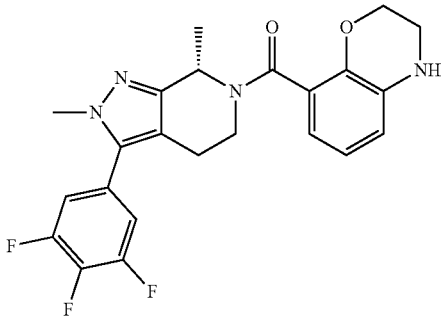 [SMILES: C[C@H]1c2nn(C)c(-c3cc(F)c(F)c(F)c3)c2CCN1C(=O)c1cccc2c1OCCN2]

The title compound was prepared in a manner analogous to Example 288, using 4-methyl-3-oxo-3,4-dihydro-2H-benzo[b][1,4]oxazine-8-carboxylic acid instead of 2-fluoro-6-(2H-1,2,3-triazol-2-yl)benzoic acid. MS (ESI): mass calcd. for $C_{23}H_{21}F_3N_4O_2$, 442.2; m/z found, 443.2 [M+H]$^+$. $^1$H NMR (500 MHz, Chloroform-d) δ 7.01-6.90 (m, 2H), 6.82-6.68 (m, 1H), 6.66-6.46 (m, 2H), 5.91 (p, J=6.8 Hz, 0.56H), 5.01-4.83 (m, 0.88H), 4.37-4.19 (m, 1.66H), 4.13-3.99 (m, 0.36H), 3.88-3.69 (m, 4.56H), 3.54-3.15 (m, 2.56H), 3.08-2.93 (m, 0.39H), 2.86-2.66 (m, 0.67H), 2.58-2.49 (m, 0.28H), 2.48-2.39 (m, 0.41H), 2.35-2.23 (m, 0.56H), 1.63-1.36 (m, 3H).

Example 593: [(7S)-3-[3-(Difluoromethyl)-4-fluorophenyl]-2,7-dimethyl-5,7-dihydro-4H-pyrazolo[3,4-c]pyridin-6-yl]-(2-methoxy-3-methyl-4-pyridyl)methanone

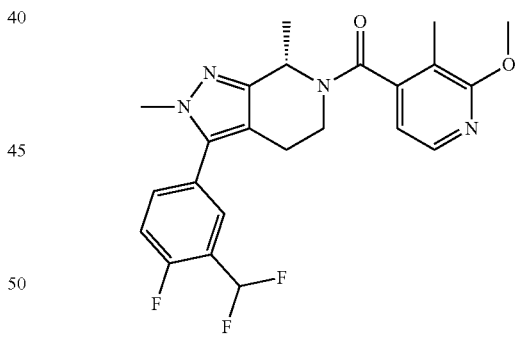

Step A: (S)-6-(2-Methoxy-3-methylisonicotinoyl)-2,7-dimethyl-4,5,6,7-tetrahydro-2H-pyrazolo[3,4-c]pyridin-3-yl trifluoromethanesulfonate. 2,4,6-Tripropyl-1,3,5,2,4,6-trioxatriphosphorinane-2,4,6-trioxide (T3P©) (50% w/w solution in DCM, 1.7 g, 2.6 mmol) was added to a mixture of tert-butyl (S)-2,7-dimethyl-3-(((trifluoromethyl)sulfonyl)oxy)-2,4,5,7-tetrahydro-6H-pyrazolo[3,4-c]pyridine-6-carboxylate (Intermediate 8, 260 mg, 0.9 mmol), 2-methoxy-3-methylisonicotinic acid (166 mg, 1.0 mmol) and DIPEA (0.45 mL, 2.6 mmol) in DMF (3 mL) at room temperature. Upon completion, saturated aqueous NaHCO$_3$ (20 mL) was added and the mixture was extracted using EtOAc (3×30 mL). The combined organics were dried over MgSO$_4$, filtered and concentrated under reduced pressure to afford the title compound (309 mg, 79%). MS (ESI): mass calcd. for $C_{17}H_{19}F_3N_4O_5S$, 448.1; m/z found, 449.2 [M+H]$^+$.

Step B: [(7S)-3-[3-(Difluoromethyl)-4-fluoro-phenyl]-2,7-dimethyl-5,7-dihydro-4H-pyrazolo[3,4-c]pyridin-6-yl]-(2-methoxy-3-methyl-4-pyridyl)methanone. The title compound was prepared in a manner analogous to Example 106, Step A, using 2-(3-(difluoromethyl)-4-fluorophenyl)-4,4,5,5-tetramethyl-1,3,2-dioxaborolane instead of 3,5-difluorophenylboronic acid. MS (ESI): mass calcd. for $C_{23}H_{23}F_3N_4O_2$, 444.2; m/z found, 445.2 [M+H]$^+$. $^1$H NMR (500 MHz, DMSO-d$_6$) δ 8.16-8.01 (m, 1H), 7.79-7.65 (m, 2H), 7.59-7.47 (m, 1H), 7.37-7.31 (m, 0.25H), 7.27-7.19 (m, 0.50H), 7.16-7.09 (m, 0.25H), 6.96 (d, J=5.1 Hz, 0.15H), 6.90 (d, J=5.1 Hz, 0.50H), 6.82 (d, J=5.1 Hz, 0.23H), 6.71-6.66 (m, 0.07H), 5.63 (q, J=6.7 Hz, 0.74H), 4.75-4.67 (m, 0.28H), 4.65-4.57 (m, 0.12H), 4.46-4.38 (m, 0.19H), 3.96-3.85 (m, 3H), 3.79 (s, 2.2H), 3.74 (s, 0.8H), 3.11-3.01 (m, 0.28H), 2.33-2.21 (m, 0.74H), 2.14-1.83 (m, 3H). (Fractions of Hs that overlap with DMSO and water are not reported).

Example 594: [(7S)-3-[3-(1,1-Difluoroethyl)phenyl]-2,7-dimethyl-5,7-dihydro-4H-pyrazolo[3,4-c]pyridin-6-yl]-(2-methoxy-3-methyl-4-pyridyl)methanone

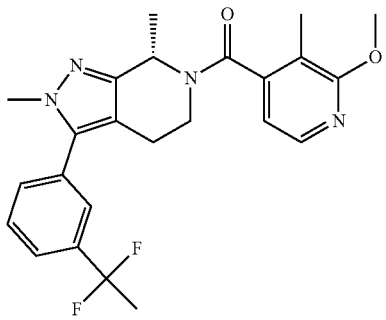 [SMILES: COc1nccc(C(=O)N2CCc3c(nn(C)c3-c3cccc(C(C)(F)F)c3)[C@@H]2C)c1C]

The title compound was prepared in a manner analogous to Example 593, using 2-(3-(1,1-difluoroethyl)phenyl)-4,4,5,5-tetramethyl-1,3,2-dioxaborolane instead of 2-(3-(difluoromethyl)-4-fluorophenyl)-4,4,5,5-tetramethyl-1,3,2-dioxaborolane in Step B. MS (ESI): mass calcd. for $C_{24}H_{26}F_2N_4O_2$, 440.2; m/z found, 441.3 [M+H]$^+$. $^1$H NMR (500 MHz, Chloroform-d) δ 8.12-7.97 (m, 1H), 7.59-7.34 (m, 4H), 6.82-6.60 (m, 1H), 5.98-5.88 (m, 0.57H), 4.95 (dd, J=13.1, 5.3 Hz, 0.44H), 4.89-4.80 (m, 0.15H), 4.66 (q, J=6.8 Hz, 0.31H), 4.03-3.93 (m, 3H), 3.85 (s, 1.73H), 3.79 (s, 1.27H), 3.60-3.46 (m, 0.59H), 3.32-3.22 (m, 0.59H), 3.11-3.00 (m, 0.44H), 2.88-2.76 (m, 0.45H), 2.64-2.46 (m, 1H), 2.39-2.29 (m, 0.62H), 2.25-2.12 (m, 2.17H), 2.04-1.89 (m, 3.88H), 1.66-1.38 (m, 3H).

Example 595: [(7S)-3-[3-(Difluoromethoxy)-4-fluoro-phenyl]-2,7-dimethyl-5,7-dihydro-4H-pyrazolo[3,4-c]pyridin-6-yl]-(2-methoxy-3-methyl-4-pyridyl)methanone

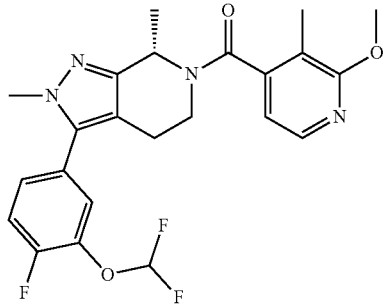 [SMILES: COc1nccc(C(=O)N2CCc3c(nn(C)c3-c3ccc(F)c(OC(F)F)c3)[C@@H]2C)c1C]

The title compound was prepared in a manner analogous to Example 593, using 2-(3-(difluoromethoxy)-4-fluorophenyl)-4,4,5,5-tetramethyl-1,3,2-dioxaborolane instead of 2-(3-(difluoromethyl)-4-fluorophenyl)-4,4,5,5-tetramethyl-1,3,2-dioxaborolane in Step B. MS (ESI): mass calcd. for $C_{23}H_{23}F_3N_4O_3$, 460.2; m/z found, 461.3 [M+H]$^+$. $^1$H NMR (500 MHz, DMSO-d$_6$) δ 8.15-8.01 (m, 1H), 7.60-7.13 (m, 4H), 6.98-6.65 (m, 1H), 5.62 (q, J=6.7 Hz, 0.75H), 4.75-4.67 (m, 0.30H), 4.64-4.55 (m, 0.14H), 4.45-4.38 (m, 0.20H), 3.95-3.87 (m, 3H), 3.82-3.71 (m, 3H), 3.11-3.00 (m, 0.30H), 2.78-2.68 (m, 0.33H), 2.35-2.22 (m, 0.76H), 2.13-1.83 (m, 3H), 1.51-1.25 (m, 3H). (Fractions of Hs that overlap with DMSO and water are not reported).

Example 596: Chroman-7-yl-[(7S)-3-[3-(difluoromethoxy)-5-fluoro-phenyl]-2,7-dimethyl-5,7-dihydro-4H-pyrazolo[3,4-c]pyridin-6-yl]methanone

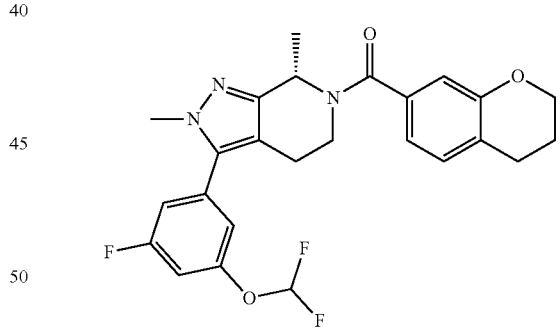

The title compound was prepared in a manner analogous to Example 106, using 2-(3-(difluoromethoxy)-5-fluorophenyl)-4,4,5,5-tetramethyl-1,3,2-dioxaborolane instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and chromane-7-carboxylic acid instead of quinoline 6-carboxylic acid in Step C. DMF was used in Step C. MS (ESI): mass calcd. for $C_{25}H_{24}F_3N_3O_3$, 471.2; m/z found, 472.3 [M+H]$^+$. $^1$H NMR (400 MHz, Chloroform-d) δ 7.09-7.03 (m, 1H), 6.96-6.81 (m, 5H), 6.56 (t, J=72.7 Hz, 1H), 5.82 (br s, 0.49H), 5.17-4.65 (m, 1H), 4.24-4.14 (m, 2H), 4.00-3.69 (m, 3.64H), 3.35-2.98 (m, 1H), 2.91-2.60 (m, 3H), 2.53-2.30 (m, 1H), 2.08-1.96 (m, 2H), 1.61-1.48 (m, 3H).

Example 597: [(7S)-3-[3-(Difluoromethoxy)-5-fluoro-phenyl]-2,7-dimethyl-5,7-dihydro-4H-pyrazolo[3,4-c]pyridin-6-yl]-(2-methoxy-3-methyl-4-pyridyl)methanone

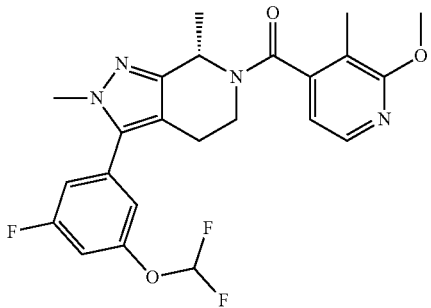 [SMILES: COc1nccc(C(=O)N2CCc3c(nn(C)c3-c3cc(F)cc(OC(F)F)c3)[C@@H]2C)c1C]

The title compound was prepared in a manner analogous to Example 106, using 2-(3-(difluoromethoxy)-5-fluorophenyl)-4,4,5,5-tetramethyl-1,3,2-dioxaborolane instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 2-methoxy-3-methylisonicotinic acid instead of quinoline 6-carboxylic acid in Step C. DMF was used in Step C. MS (ESI): mass calcd. for $C_{23}H_{23}F_3N_4O_3$, 460.2; m/z found, 461.3 [M+H]$^+$. $^1$H NMR (600 MHz, Chloroform-d) δ 8.11-7.98 (m, 1H), 6.97-6.87 (m, 3H), 6.81-6.42 (m, 2H), 5.96-5.87 (m, 0.58H), 4.96 (dd, J=13.1, 5.3 Hz, 0.41H), 4.87-4.79 (m, 0.12H), 4.65 (q, J=6.7 Hz, 0.25H), 4.02-3.93 (m, 3H), 3.86 (s, 1.79H), 3.80 (s, 1.27H), 3.60-3.47 (m, 0.55H), 3.30-3.21 (m, 0.56H), 3.09-3.00 (m, 0.38H), 2.86-2.75 (m, 0.38H), 2.62-2.49 (m, 1H), 2.39-2.30 (m, 0.58H), 2.25-2.13 (m, 2.10H), 1.99 (s, 0.77H), 1.65-1.35 (m, 3H).

Example 598: [(7S)-3-(4-Fluoro-3-methyl-phenyl)-2,7-dimethyl-5,7-dihydro-4H-pyrazolo[3,4-c]pyridin-6-yl]-(2-methoxy-3-methyl-4-pyridyl)methanone

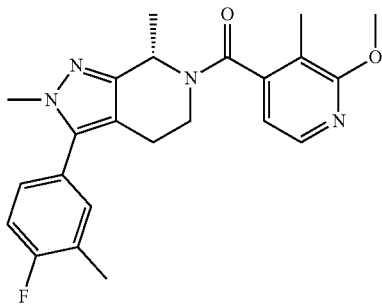 [SMILES: COc1nccc(C(=O)N2CCc3c(nn(C)c3-c3ccc(F)c(C)c3)[C@@H]2C)c1C]

The title compound was prepared in a manner analogous to Example 106, using 2-(4-fluoro-3-methylphenyl)-4,4,5,5-tetramethyl-1,3,2-dioxaborolane instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 2-methoxy-3-methylisonicotinic acid instead of quinoline 6-carboxylic acid in Step C. MS (ESI): mass calcd. for $C_{23}H_{25}FN_4O_2$, 408.2; m/z found, 409.3 [M+H]$^+$. $^1$H NMR (500 MHz, Chloroform-d) δ 8.11-7.97 (m, 1H), 7.19-7.05 (m, 3H), 6.82-6.59 (m, 1H), 5.95-5.87 (m, 0.57H), 4.93 (dd, J=13.0, 5.3 Hz, 0.43H), 4.87-4.80 (m, 0.13H), 4.67-4.60 (m, 0.27H), 4.01-3.93 (m, 3H), 3.80 (s, 1.71H), 3.75 (s, 1.29H), 3.58-3.44 (m, 0.60H), 3.31-3.19 (m, 0.58H), 3.10-2.99 (m, 0.43H), 2.83-2.71 (m, 0.42H), 2.59-2.43 (m, 1H), 2.37-1.95 (m, 6.84H), 1.66-1.35 (m, 3H).

Example 599: [(7S)-2,7-Dimethyl-3-(3,4,5-trifluoro-phenyl)-5,7-dihydro-4H-pyrazolo[3,4-c]pyridin-6-yl]-(3-methoxy-2-methyl-4-pyridyl)methanone

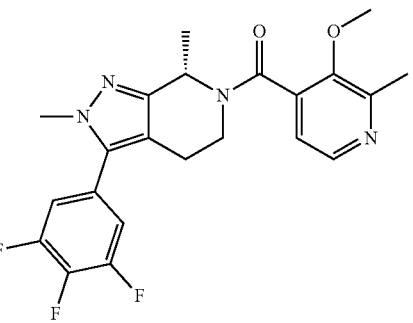

The title compound was prepared in a manner analogous to Example 106, using 2-(4-fluoro-3-methylphenyl)-4,4,5,5-tetramethyl-1,3,2-dioxaborolane instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 3-methoxy-2-methylisonicotinic acid instead of quinoline 6-carboxylic acid in Step C. MS (ESI): mass calcd. for $C_{22}H_{21}F_3N_4O_2$, 430.2; m/z found, 431.2 [M+H]$^+$. $^1$H NMR (500 MHz, Chloroform-d) δ 8.36-8.22 (m, 1H), 7.10-6.88 (m, 3H), 5.89 (q, J=6.8 Hz, 0.64H), 5.00-4.89 (m, 0.35H), 4.73-4.63 (m, 0.35H), 3.91-3.68 (m, 6H), 3.54-3.45 (m, 1H), 3.37-3.27 (m, 0.38H), 3.25-3.17 (m, 0.25H), 3.15-2.98 (m, 0.33H), 2.85-2.71 (m, 0.60H), 2.62-2.45 (m, 3.74H), 2.34-2.27 (m, 0.64H), 1.57 (s, 3H).

Example 600: [(7S)-2,7-Dimethyl-3-(3,4,5-trifluorophenyl)-5,7-dihydro-4H-pyrazolo[3,4-c]pyridin-6-yl]-(1-methyl-4-phenyl-imidazol-2-yl)methanone

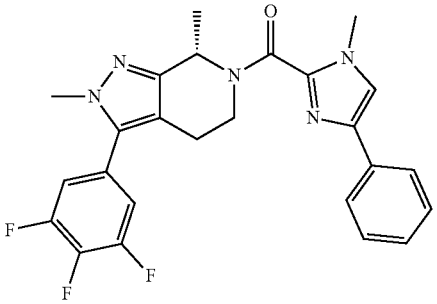 [SMILES: C[C@H]1c2nn(C)c(-c3cc(F)c(F)c(F)c3)c2CCN1C(=O)c1nc(-c2ccccc2)cn1C]

The title compound was prepared in a manner analogous to Example 106, using 3,4,5-trifluorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and lithium 1-methyl-4-phenyl-1H-imidazole-2-carboxylate instead of quinoline-6-carboxylic acid in Step C. DMF was used instead of DCM in Step C. MS (ESI): mass calcd. for $C_{25}H_{22}F_3N_5O$, 465.2; m/z found, 466.2 [M+H]$^+$. $^1$H NMR (500 MHz, DMSO-d$_6$) δ 7.86-7.74 (m, 3H), 7.60-7.51 (m, 2H), 7.44-7.34 (m, 2H), 7.28-7.21 (m, 1H), 5.90 (q, J=6.6 Hz, 0.4H), 5.58 (q, J=6.7 Hz, 0.56H), 4.81 (dd, J=13.4, 4.9 Hz, 0.59H), 4.65 (dd, J=12.9, 5.2 Hz, 0.44H), 3.85-3.73 (m, 6H), 3.12-3.03 (m, 0.42H), 2.99-2.89 (m, 0.60H), 2.80-2.71 (m, 0.46H), 1.66 (d, J=6.7 Hz, 1.24H), 1.49 (d, J=6.8 Hz, 1.73H). (Fractions of Hs that overlap with DMSO and water are not reported).

Example 601: [(7S)-2,7-Dimethyl-3-(3,4,5-trifluorophenyl)-5,7-dihydro-4H-pyrazolo[3,4-c]pyridin-6-yl]-(1-phenylimidazol-4-yl)methanone

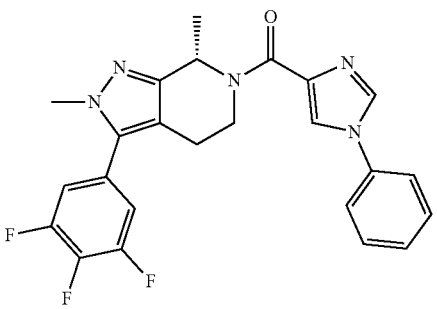 [SMILES: C[C@H]1c2nn(C)c(-c3cc(F)c(F)c(F)c3)c2CCN1C(=O)c1cn(-c2ccccc2)cn1]

The title compound was prepared in a manner analogous to Example 106, using 3,4,5-trifluorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 1-phenyl-1H-imidazole-4-carboxylic acid instead of quinoline-6-carboxylic acid in Step C. DMF was used instead of DCM in Step C. MS (ESI): mass calcd. for $C_{24}H_{20}F_3N_5O$, 451.2; m/z found, 452.2 [M+H]$^+$. $^1$H NMR (600 MHz, DMSO-d$_6$) δ 8.41-8.34 (m, 1H), 8.24 (d, J=1.5 Hz, 1H), 7.77-7.71 (m, 2H), 7.59-7.50 (m, 4H), 7.44-7.39 (m, 1H), 6.29 (s, 0.40H), 5.57 (s, 0.55H), 5.31-5.16 (m, 0.55H), 4.72-4.55 (s, 0.39H), 3.87-3.71 (m, 3H), 3.09-2.65 (m, 1.42H), 2.47-2.40 (m, 1H), 1.66-1.37 (m, 3H). (Fractions of Hs that overlap with DMSO and water are not reported).

Example 602: [(7S)-2,7-Dimethyl-3-(3,4,5-trifluorophenyl)-5,7-dihydro-4H-pyrazolo[3,4-c]pyridin-6-yl]-[3-methyl-2-(2-pyridyl)imidazol-4-yl]methanone

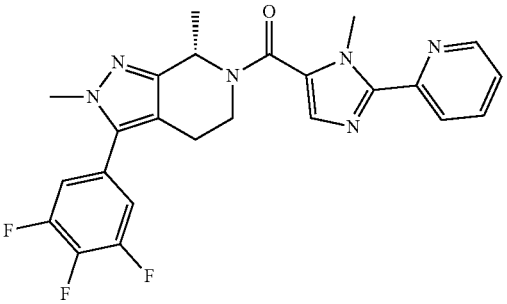 [SMILES: C[C@H]1c2nn(C)c(-c3cc(F)c(F)c(F)c3)c2CCN1C(=O)c1cnc(-c2ccccn2)n1C]

The title compound was prepared in a manner analogous to Example 106, using 3,4,5-trifluorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 1-methyl-2-(pyridin-2-yl)-1H-imidazole-5-carboxylic acid instead of quinoline-6-carboxylic acid in Step C. DMF was used instead of DCM in Step C. MS (ESI): mass calcd. for $C_{24}H_{21}F_3N_6O$, 466.2; m/z found, 467.2 [M+H]$^+$. $^1$H NMR (600 MHz, DMSO-d$_6$) δ 8.69-8.65 (m, 1H), 8.10 (dt, J=8.0, 1.1 Hz, 1H), 7.95 (td, J=7.8, 1.8 Hz, 1H), 7.61-7.54 (m, 2H), 7.44 (ddd, J=7.5, 4.9, 1.2 Hz, 1H), 7.41 (s, 1H), 5.66-5.22 (m, 1H), 4.47-3.73 (m, 7H), 3.03-2.83 (m, 1H), 2.48-2.42 (m, 1H), 1.50 (d, J=6.8 Hz, 3H). (Fractions of Hs that overlap with DMSO and water are not reported).

Example 603: [(7S)-2,7-Dimethyl-3-(3,4,5-trifluorophenyl)-5,7-dihydro-4H-pyrazolo[3,4-c]pyridin-6-yl]-(2-fluoro-6-pyrazol-1-yl-phenyl)methanone

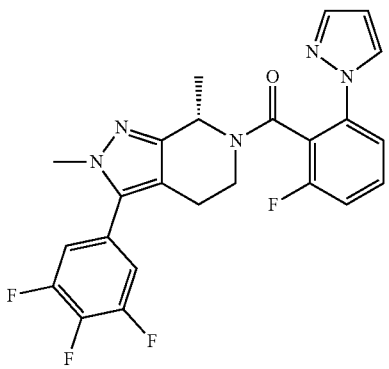 [SMILES: C[C@H]1c2nn(C)c(-c3cc(F)c(F)c(F)c3)c2CCN1C(=O)c1c(F)cccc1-n1cccn1]

The title compound was prepared in a manner analogous to Example 106, using 3,4,5-trifluorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 2-fluoro-6-(1H-pyrazol-1-yl)benzoic acid instead of quinoline 6-carboxylic acid in Step C. DMF was used instead of DCM in Step C. MS (ESI): mass calcd. for $C_{24}H_{19}F_4N_5O$, 469.2; m/z found, 470.2 [M+H]$^+$.

Example 604: [(7S)-2,7-Dimethyl-3-(3,4,5-trifluorophenyl)-5,7-dihydro-4H-pyrazolo[3,4-c]pyridin-6-yl]-spiro[3,4-dihydro-1,4-benzoxazine-2,1'-cyclopropane]-8-yl-methanone

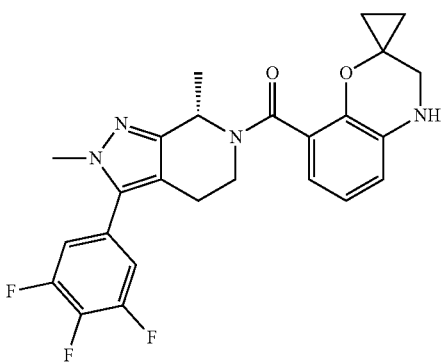 [SMILES: C[C@H]1c2nn(C)c(-c3cc(F)c(F)c(F)c3)c2CCN1C(=O)c1cccc2c1OC1(CC1)CN2]

The title compound was prepared in a manner analogous to Example 106, using 3,4,5-trifluorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 3,4-dihydrospiro[benzo[b][1,4]oxazine-2,1'-cyclopropane]-8-carboxylic acid instead of quinoline 6-carboxylic acid in Step C. DMF was used instead of DCM in Step C. MS (ESI): mass calcd. for $C_{25}H_{23}F_3N_4O_2$, 468.2; m/z found, 469.1 [M+H]$^+$. $^1$H NMR (500 MHz, Chloroform-d) δ 7.00-6.89 (m, 2H), 6.85-6.71 (m, 1H), 6.69-6.46 (m, 2H), 5.92-5.81 (m, 0.53H), 5.02-4.94 (m, 0.15H), 4.91 (dd, J=13.1, 5.3 Hz, 0.47H), 4.81 (q, J=6.8 Hz, 0.31H), 4.02-3.86 (m, 1H), 3.85-3.65 (m, 3.64H), 3.57 (d, J=11.5 Hz, 0.30H), 3.50-3.37 (m, 0.67H), 3.32-3.13 (m, 1.22H), 3.05-2.85 (m, 0.76H), 2.80-2.65 (m, 0.62H), 2.56-2.46 (m, 0.36H), 2.46-2.36 (m, 0.46H), 2.33-2.22 (m, 0.53H), 1.57-1.36 (m, 3H), 1.15-1.01 (m, 0.82H), 1.00-0.86 (m, 0.59H), 0.75-0.53 (m, 2H), 0.41-0.32 (m, 0.60H).

Example 605: [(7S)-2,7-Dimethyl-3-(3,4,5-trifluorophenyl)-5,7-dihydro-4H-pyrazolo[3,4-c]pyridin-6-yl]-(3-fluoro-1H-pyrrolo[2,3-b]pyridin-4-yl)methanone

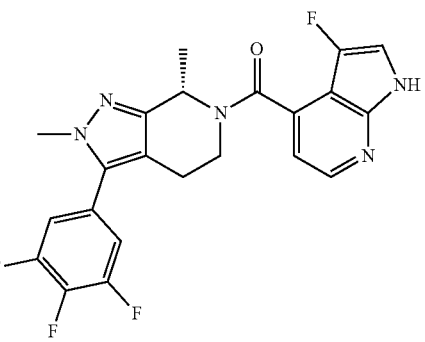

The title compound was prepared in a manner analogous to Example 371 using 3-fluoro-1-((2-(trimethylsilyl)ethoxy)methyl)-1H-pyrrolo[2,3-b]pyridine-4-carboxylic acid (Intermediate 62) instead of 5-trifluoromethyl-1-((2-(trimethylsilyl)ethoxy)methyl)-1H-pyrrolo[2,3-b]pyridine-4-carboxylic acid (Intermediate 60) in Step A. MS (ESI): mass calcd. for $C_{22}H_{17}F_4N_5O$, 443.1; m/z found, 444.2 [M+H]$^+$. $^1$H NMR (500 MHz, Chloroform-d) δ 8.79-8.62 (m, 1H), 8.43-8.34 (m, 1H), 7.17-6.89 (m, 4H), 5.99 (q, J=6.8 Hz, 0.58H), 5.03 (dd, J=13.0, 5.2 Hz, 0.39H), 4.81 (q, J=6.7 Hz, 0.39H), 3.84 (s, 1.85H), 3.76 (s, 1.15H), 3.68-3.58 (m, 0.59H), 3.39-3.27 (m, 0.58H), 3.10 (td, J=12.7, 3.9 Hz, 0.36H), 2.91-2.81 (m, 0.37H), 2.65-2.47 (m, 1H), 2.32-2.22 (m, 0.56H), 1.71-1.39 (m, 3H).

Example 606: [(7S)-2,7-Dimethyl-3-(3,4,5-trifluorophenyl)-5,7-dihydro-4H-pyrazolo[3,4-c]pyridin-6-yl]-(9-methylpurin-6-yl)methanone

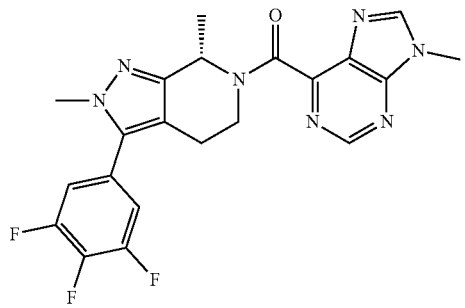 [SMILES: C[C@H]1c2nn(C)c(-c3cc(F)c(F)c(F)c3)c2CCN1C(=O)c1ncnc2c1ncn2C]

The title compound was prepared in a manner analogous to Example 106, using 3,4,5-trifluorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 9-methyl-9H-purine-6-carboxylic acid instead of quinoline 6-carboxylic acid in Step C. DMF was used instead of DCM in Step C. MS (ESI): mass calcd. for $C_{21}H_{18}F_3N_7O$, 441.2; m/z found, 442.2 [M+H]$^+$. $^1$H NMR (500 MHz, Chloroform-d) δ 9.06-9.01 (m, 1H), 8.15-8.09 (m, 1H), 7.00-6.92 (m, 2H), 5.99 (q, J=6.8 Hz, 0.54H), 5.04 (dd, J=13.1, 5.4 Hz, 0.50H), 4.89 (q, J=6.8 Hz, 0.49H), 3.98-3.91 (m, 3H), 3.86-3.71 (m, 3H), 3.68-3.62 (m, 0.57H), 3.40-3.31 (m, 0.55H), 3.17 (td, J=12.7, 4.0 Hz, 0.43H), 2.98-2.85 (m, 1H), 2.54-2.48 (m, 0.42H), 2.30-2.23 (m, 0.53H), 1.74-1.47 (m, 3H).

Example 607: [(7S)-2,7-Dimethyl-3-(3,4,5-trifluorophenyl)-5,7-dihydro-4H-pyrazolo[3,4-c]pyridin-6-yl]-(3-fluoro-5-methoxy-4-pyridyl)methanone

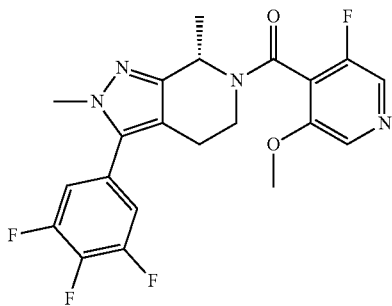 [SMILES: COc1cncc(F)c1C(=O)N1CCc2c(nn(C)c2-c2cc(F)c(F)c(F)c2)[C@@H]1C]

The title compound was prepared in a manner analogous to Example 106, using 3,4,5-trifluorophenylboronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 3-fluoro-5-methoxyisonicotinic acid (Intermediate 107) instead of quinoline 6-carboxylic acid in Step C. DMF was used instead of DCM in Step C. MS (ESI): mass calcd. for $C_{21}H_{18}F_4N_4O_2$, 434.1; m/z found, 435.2 [M+H]$^+$. $^1$H NMR (600 MHz, Chloroform-d) δ 8.29-8.16 (m, 2H), 7.02-6.91 (m, 2H), 5.91 (p, J=6.8 Hz, 0.59H), 5.01-4.93 (m, 0.40H), 4.70 (q, J=6.8 Hz, 0.20H), 4.65 (q, J=6.8 Hz, 0.17H), 4.03-3.94 (m, 2.47H), 3.86-3.76 (m, 3.62H), 3.55-3.47 (m, 0.58H), 3.37-3.30 (m, 0.58H), 3.11-3.02 (m, 0.37H), 2.82-2.75 (m, 0.37H), 2.68-2.57 (m, 0.58H), 2.52-2.46 (m, 0.38H), 2.39-2.31 (m, 0.58H), 1.63-1.42 (m, 3H).

Example 608: (3-Chloro-4-methoxy-2-pyridyl)-[(7S)-3-[3-(difluoromethyl)-5-fluoro-phenyl]-2,7-dimethyl-5,7-dihydro-4H-pyrazolo[3,4-c]pyridin-6-yl]methanone

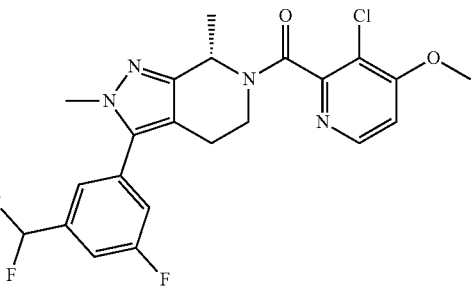

The title compound was prepared in a manner analogous to Example 106, using 2-(3-(difluoromethyl)-5-fluorophenyl)-4,4,5,5-tetramethyl-1,3,2-dioxaborolane instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 3-chloro-4-methoxypicolinic acid instead of quinoline 6-carboxylic acid in Step C. DMF was used instead of DCM in Step C. MS (ESI): mass calcd. for $C_{22}H_{20}ClF_3N_4O_2$, 464.1; m/z found, 465.2 [M+H]$^+$. $^1$H NMR (500 MHz, Chloroform-d) δ 8.43-8.39 (m, 1H), 7.31-7.22 (m, 2H), 7.19-7.12 (m, 1H), 6.89-6.86 (m, 1H), 6.81-6.54 (m, 1H), 5.93 (q, J=6.8 Hz, 0.59H), 5.01-4.94 (m, 0.45H), 4.68 (q, J=6.8 Hz, 0.44H), 4.01-3.97 (m, 3H), 3.87-3.77 (m, 3H), 3.46-3.38 (m, 0.59H), 3.36-3.28 (m, 0.59H), 3.09 (td, J=12.7, 3.9 Hz, 0.42H), 2.92-2.75 (m, 1H), 2.54-2.47 (m, 0.42H), 2.33-2.26 (m, 0.58H), 1.69-1.46 (m, 3H).

Example 609: [(7S)-3-[3-(Difluoromethyl)-5-fluoro-phenyl]-2,7-dimethyl-5,7-dihydro-4H-pyrazolo[3,4-c]pyridin-6-yl]-(2-methoxy-3-methyl-4-pyridyl)methanone

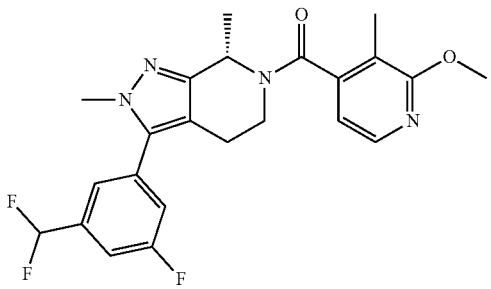 [SMILES: COc1nccc(C(=O)N2CCc3c(nn(C)c3-c3cc(F)cc(C(F)F)c3)[C@@H]2C)c1C]

The title compound was prepared in a manner analogous to Example 106, using 2-(3-(difluoromethyl)-5-fluorophenyl)-4,4,5,5-tetramethyl-1,3,2-dioxaborolane instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 2-methoxy-3-methylisonicotinic acid instead of quinoline 6-carboxylic acid in Step C. DMF was used instead of DCM in Step C. MS (ESI): mass calcd. for $C_{23}H_{23}F_3N_4O_2$, 444.2; m/z found, 445.2 [M+H]$^+$. $^1$H NMR (500 MHz, Chloroform-d) δ 8.12-7.96 (m, 1H), 7.32-7.11 (m, 3H), 6.82-6.54 (m, 2H), 5.96-5.88 (m, 0.55H), 4.96 (dd, J=13.1, 5.3 Hz, 0.43H), 4.87-4.80 (m, 0.14H), 4.69-4.61 (m, 0.27H), 4.02-3.94 (m, 3H), 3.87-3.77 (m, 3H), 3.61-3.48 (m, 0.56H), 3.32-3.21 (m, 0.55H), 3.10-2.99 (m, 0.39H), 2.87-2.75 (m, 0.39H), 2.64-2.48 (m, 1H), 2.38-2.29 (m, 0.57H), 2.25-1.96 (m, 3H), 1.66-1.36 (m, 3H).

Example 610: Chroman-7-yl-[(7S)-3-[3-(difluoromethyl)-5-fluoro-phenyl]-2,7-dimethyl-5,7-dihydro-4H-pyrazolo[3,4-c]pyridin-6-yl]methanone

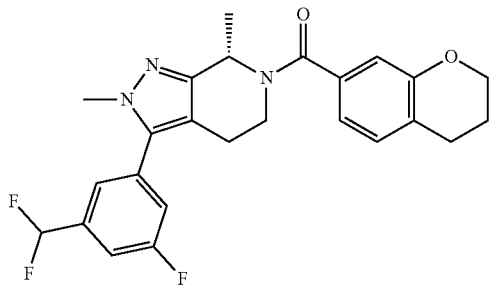 [SMILES: C[C@H]1c2nn(C)c(-c3cc(F)cc(C(F)F)c3)c2CCN1C(=O)c1ccc2c(c1)OCCC2]

The title compound was prepared in a manner analogous to Example 106, using 2-(3-(difluoromethyl)-5-fluorophenyl)-4,4,5,5-tetramethyl-1,3,2-dioxaborolane instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and chromane-7-carboxylic acid instead of quinoline 6-carboxylic acid in Step C. DMF was used instead of DCM in Step C. MS (ESI): mass calcd. for $C_{25}H_{24}F_3N_3O_2$, 455.2; m/z found, 456.3 [M+H]$^+$. $^1$H NMR (500 MHz, Chloroform-d) δ 7.30-7.26 (m, 2H), 7.19-7.14 (m, 1H), 7.09-7.04 (m, 1H), 6.91-6.85 (m, 1H), 6.84-6.81 (m, 1H), 6.68 (t, J=56.1 Hz, 1H), 5.87 (br s, 0.44H), 5.17-4.66 (m, 1H), 4.24-4.15 (m, 2H), 3.99-3.71 (m, 3.55H), 3.34-2.97 (m, 1H), 2.91-2.63 (m, 3H), 2.51-2.29 (m, 1H), 2.06-1.96 (m, 2H), 1.69-1.43 (m, 3H).

Example 611: Chroman-7-yl-[(7S)-3-(3-fluoro-5-methoxy-phenyl)-2,7-dimethyl-5,7-dihydro-4H-pyrazolo[3,4-c]pyridin-6-yl]methanone

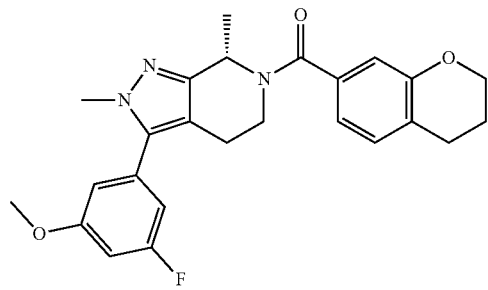 [SMILES: COc1cc(F)cc(-c2c3c(nn2C)[C@H](C)N(C(=O)c2ccc4c(c2)OCCC4)CC3)c1]

The title compound was prepared in a manner analogous to Example 106, using (3-fluoro-5-methoxyphenyl)boronic acid instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and chromane-7-carboxylic acid instead of quinoline 6-carboxylic acid in Step C. DMF was used instead of DCM in Step C. MS (ESI): mass calcd. for $C_{25}H_{26}FN_3O_3$, 435.2; m/z found, 436.3 [M+H]$^+$. $^1$H NMR (500 MHz, Chloroform-d) δ 7.09-7.02 (m, 1H), 6.91-6.79 (m, 2H), 6.70-6.59 (m, 3H), 5.82 (br s, 0.47H), 5.16-4.70 (m, 1H), 4.24-4.13 (m, 2H), 3.96-3.71 (m, 6.44H), 3.35-2.96 (m, 1H), 2.90-2.61 (m, 3H), 2.53-2.31 (m, 1H), 2.06-1.96 (m, 2H), 1.67-1.44 (m, 3H).

Example 612: (3-Chloro-4-methoxy-2-pyridyl)-[(7S)-3-[3-(difluoromethoxy)-5-fluoro-phenyl]-2,7-dimethyl-5,7-dihydro-4H-pyrazolo[3,4-c]pyridin-6-yl]methanone

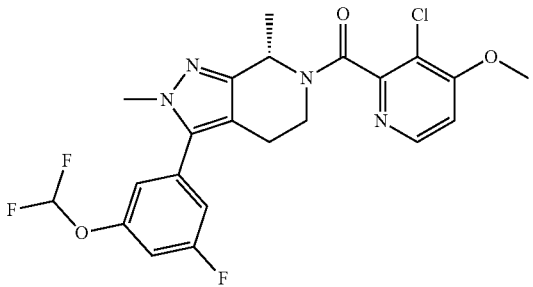 [SMILES: COc1ccnc(C(=O)N2CCc3c(nn(C)c3-c3cc(F)cc(OC(F)F)c3)[C@@H]2C)c1Cl]

The title compound was prepared in a manner analogous to Example 106, using 2-(3-(difluoromethoxy)-5-fluorophenyl)-4,4,5,5-tetramethyl-1,3,2-dioxaborolane instead of 3,5-difluorophenylboronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 7) in Step A, and 3-chloro-4-methoxypicolinic acid instead of quinoline 6-carboxylic acid in Step C. DMF was used instead of DCM in Step C. MS (ESI): mass calcd. for $C_{22}H_{20}ClF_3N_4O_3$, 480.1; m/z found, 481.2 [M+H]$^+$. $^1$H NMR (600 MHz, Chloroform-d) δ 8.44-8.38 (m, 1H), 6.96-6.85 (m, 4H), 6.71-6.41 (m, 1H), 5.92 (q, J=6.8 Hz, 0.57H), 5.00-4.95 (m, 0.42H), 4.68 (q, J=6.8 Hz, 0.40H), 4.01-3.96 (m, 3H), 3.87-3.77 (m, 3H), 3.45-3.40 (m, 0.57H), 3.36-3.29 (m, 0.58H), 3.08 (td, J=12.7, 3.9 Hz, 0.41H), 2.91-2.83 (m, 0.42H), 2.82-2.74 (m, 0.58H), 2.54-2.48 (m, 0.41H), 2.34-2.28 (m, 0.57H), 1.68-1.44 (m, 3H).

Example 613: [(7S)-3-(3-Fluoro-5-methoxy-phenyl)-2,7-dimethyl-5,7-dihydro-4H-pyrazolo[3,4-c]pyridin-6-yl]-(2-methoxy-3-methyl-4-pyridyl)methanone

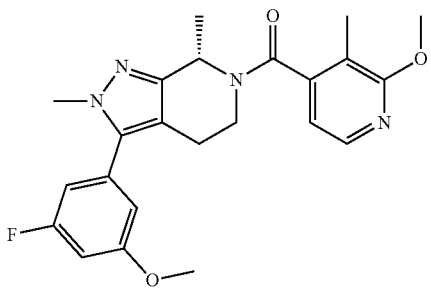

The title compound was prepared in a manner analogous to Example 106, using (3-fluoro-5-methoxyphenyl)boronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-((((trifluoromethyl)sulfonyl)oxy)-2,4,5,7-tetrahydro-6H-pyrazolo[3,4-c]pyridine-6-carboxylate (Intermediate 7) in Step A, and 2-methoxy-3-methylisonicotinic acid instead of quinoline 6-carboxylic acid in Step C. DMF was used instead of DCM in Step C. MS (ESI): mass calcd. for $C_{23}H_{25}FN_4O_3$, 424.2; m/z found, 425.3 [M+H]$^+$. $^1$H NMR (600 MHz, Chloroform-d) δ 8.11-7.97 (m, 1H), 6.82-6.57 (m, 4H), 5.95-5.87 (m, 0.58H), 4.94 (dd, J=13.1, 5.3 Hz, 0.42H), 4.86-4.80 (m, 0.13H), 4.64 (q, J=6.7 Hz, 0.26H), 4.01-3.93 (m, 3H), 3.87-3.76 (m, 6H), 3.58-3.46 (m, 0.60H), 3.30-3.20 (m, 0.58H), 3.10-3.00 (m, 0.41H), 2.85-2.74 (m, 0.40H), 2.60-2.48 (m, 1H), 2.39-2.31 (m, 0.58H), 2.24-1.96 (m, 3H), 1.65-1.36 (m, 3H).

Example 614: (3-Chloro-4-methoxy-2-pyridyl)-[(7S)-3-(3-fluoro-5-methoxy-phenyl)-2,7-dimethyl-5,7-dihydro-4H-pyrazolo[3,4-c]pyridin-6-yl]methanone

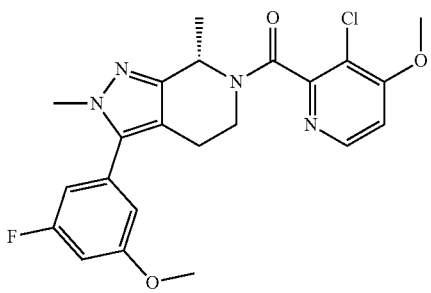 [SMILES: COc1cc(F)cc(-c2c3c(nn2C)[C@H](C)N(C(=O)c2nccc(OC)c2Cl)CC3)c1]

The title compound was prepared in a manner analogous to Example 106, using (3-fluoro-5-methoxyphenyl)boronic acid and (S)-tert-butyl 2,7-dimethyl-3-(((trifluoromethyl)sulfonyl)oxy)-2,4,5,7-tetrahydro-6H-pyrazolo[3,4-c]pyridine-6-carboxylate (Intermediate 8) instead of racemic tert-butyl 2,7-dimethyl-3-((((trifluoromethyl)sulfonyl)oxy)-2,4,5,7-tetrahydro-6H-pyrazolo[3,4-c]pyridine-6-carboxylate (Intermediate 7) in Step A, and 3-chloro-4-methoxypicolinic acid instead of quinoline 6-carboxylic acid in Step C. DMF was used instead of DCM in Step C. MS (ESI): mass calcd. for $C_{22}H_{22}ClFN_4O_3$, 444.1; m/z found, 445.2 [M+H]$^+$. $^1$H NMR (500 MHz, Chloroform-d) δ 8.43-8.39 (m, 1H), 6.89-6.85 (m, 1H), 6.69-6.60 (m, 3H), 5.92 (q, J=6.8 Hz, 0.56H), 4.99-4.93 (m, 0.44H), 4.68 (q, J=6.8 Hz, 0.43H), 4.01-3.96 (m, 3H), 3.86-3.76 (m, 6H), 3.43-3.37 (m, 0.56H), 3.36-3.28 (m, 0.57H), 3.08 (td, J=12.7, 3.9 Hz, 0.43H), 2.90-2.82 (m, 0.43H), 2.81-2.73 (m, 0.56H), 2.56-2.49 (m, 0.42H), 2.35-2.28 (m, 0.56H), 1.69-1.46 (m, 3H).

Example 615: racemic-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone

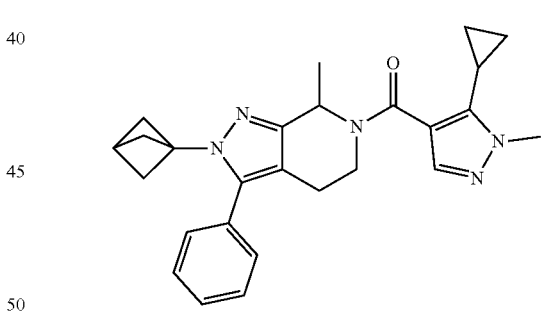

The title compound was prepared in a manner analogous to Example 288, using 2-(bicyclo[1.1.1]pentan-1-yl)-7-methyl-3-phenyl-4,5,6,7-tetrahydro-2H-pyrazolo[3,4-c]pyridine (Intermediate 51) instead of (S)-2,7-dimethyl-3-(3,4,5-trifluorophenyl)-4,5,6,7-tetrahydro-2H-pyrazolo[3,4-c]pyridine (Intermediate 40) and 5-cyclopropyl-1-methyl-1H-pyrazole-4-carboxylic acid instead of 2-fluoro-6-(2H-1,2,3-triazol-2-yl)benzoic acid. MS (ESI): mass calcd. for $C_{26}H_{29}N_5O$, 427.2; m/z found, 428.1 [M+H]$^+$. $^1$H NMR (500 MHz, Chloroform-d) δ 7.45-7.36 (m, 4H), 7.33-7.29 (m, 2H), 5.91 (brs, 0.41H), 5.16 (brs, 0.39H), 4.82 (brs, 0.42H), 3.98-3.82 (m, 3.37H), 3.39-2.94 (m, 1H), 2.56 (brs, 1H), 2.43-2.20 (m, 2H), 2.06 (s, 6H), 1.73 (s, 1H), 1.55 (brs, 3.16H), 1.07-0.54 (m, 4.34H).

Example 616: (R*)-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone

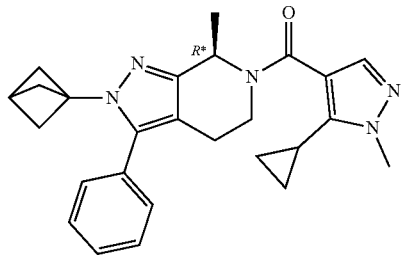 [SMILES: C[C@@H]1c2nn(C34CC(C3)C4)c(-c3ccccc3)c2CCN1C(=O)c1cnn(C)c1C1CC1]

The title compound was isolated by SFC purification of racemic-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone (Example 615) (stationary phase: Chiralpak AD, 5 μm 250×30 mm; mobile phase: 20% MeOH with 0.2% TEA, 80% $CO_2$; flow rate: 85 mL/min). MS (ESI): mass calcd. for $C_{26}H_{29}N_5O$, 427.2; m/z found, 428.1 $[M+H]^+$. (R*: single enantiomer, but absolute configuration was not determined).

Example 617: (S)-(1,6-Dimethyl-1H-pyrazolo[3,4-d]pyrimidin-4-yl)(2,7-dimethyl-3-(3,4,5-trifluorophenyl)-2,4,5,7-tetrahydro-6H-pyrazolo[3,4-c]pyridin-6-yl)methanone

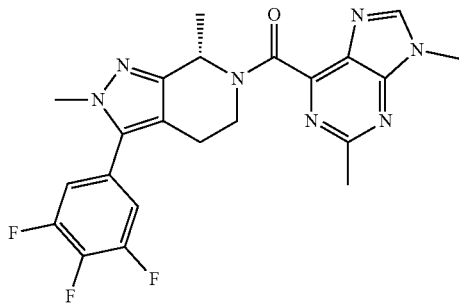 [SMILES: Cc1nc(C(=O)N2CCc3c(nn(C)c3-c3cc(F)c(F)c(F)c3)[C@@H]2C)c2ncn(C)c2n1]

The title compound was prepared in a manner analogous to Example 288, using 1,6-dimethyl-1H-pyrazolo[3,4-d]pyrimidine-4-carboxylic acid (Intermediate 110) instead of 2-fluoro-6-(2H-1,2,3-triazol-2-yl)benzoic acid. MS (ESI): mass calcd. for $C_{22}H_{20}F_3N_7O$, 455.2; m/z found, 456.1 $[M+H]^+$. $^1$H NMR (400 MHz, DMSO-$d_6$) δ 8.25 (d, J=22.1 Hz, 1H), 7.63-7.46 (m, 2H), 5.66 (q, J=6.7 Hz, 1H), 5.03-4.66 (m, 1H), 4.15-4.00 (m, 3H), 3.92-3.64 (m, 4H), 3.20-3.09 (m, 1H), 2.81-2.74 (m, 3H), 2.37-2.21 (m, 1H), 1.50 (dd, J=32.3, 6.7 Hz, 3H).

Example 618: Cyclopropyl-2-methyl-imidazo[1,2-a]pyridin-3-yl)-[(7S)-2,7-dimethyl-3-(3,4,5-trifluorophenyl)-5,7-dihydro-4H-pyrazolo[3,4-c] pyridin-6-yl] methanone

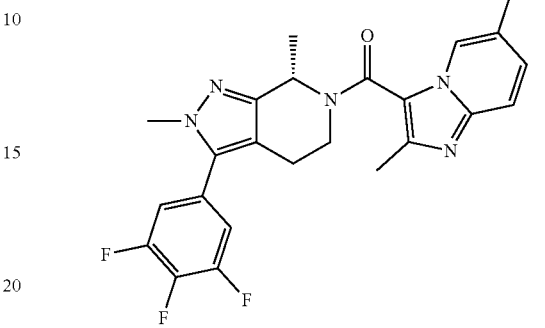

The title compound was prepared in a manner analogous to Example 288, using potassium 6-cyclopropyl-2-methyl-imidazo[1,2-a]pyridine-3-carboxylate (Intermediate 90) instead of 2-fluoro-6-(2H-1,2,3-triazol-2-yl)benzoic acid. MS (ESI): mass calcd. for $C_{26}H_{24}F_3N_5O$, 479.2; m/z found, 480.1 $[M+H]^+$. $^1$H NMR (500 MHz, DMSO-$d_6$) δ 8.12 (s, 1H), 7.54 (dd, J=8.7, 6.6 Hz, 2H), 7.46 (dd, J=9.3, 0.9 Hz, 1H), 7.03 (dd, J=9.3, 1.8 Hz, 1H), 5.65-5.46 (m, 1H), 4.19-3.96 (m, 1H), 3.82 (s, 3H), 3.47-3.34 (m, 1H), 2.84-2.68 (m, 1H), 2.45-2.39 (m, 1H), 2.37-2.29 (m, 3H), 2.08-1.92 (m, 1H), 1.48 (d, J=6.8 Hz, 3H), 1.00-0.87 (m, 2H), 0.64 (t, J=5.1 Hz, 2H).

Biological Data

The assay used to measure the in vitro activity of MGL is adapted from the assay used for another serine hydrolase (FAAH) described in Wilson et al., 2003 (A high-throughput-compatible assay for determining the activity of fatty acid amide hydrolase. Wilson S J, Lovenberg T W, Barbier A J. Anal Biochem. 2003 Jul. 15; 318(2):270-5.). The assay consists of combining endogenously expressed MGL from HeLa cells with test compounds, adding [glycerol-1,3-$^3$H]-oleyl glycerol, incubating for one hour, and then measuring the amount of cleaved [1,3-$^3$H]-glycerol that passes through an activated carbon filter. The amount of cleaved, tritiated glycerol passing through the carbon filter is proportional to the activity of the MGL enzyme in a particular well/test condition.

Standard conditions for this assay combine 300 nM [Glycerol-1,3-$^3$H]-oleyl glycerol with human MGL from HeLa cells and test compounds for one hour, after which the reaction is filtered through activated carbon and tritium is measured in the flow through. The test compound concentration in screening mode is 10 uM, while the highest compound concentration in $IC_{50}$ assays is determined empirically. MGL is the predominant hydrolase in HeLa cells/cell homogenates.

TABLE 4

| Ex # | Compound Name | MGL $IC_{50}$ (nM) |
|---|---|---|
| 1 | (2-Methyl-3-phenyl-2,4,5,7-tetrahydro-6H-pyrazolo[3,4-c]pyridin-6-yl)(naphthalen-1-yl)methanone; | 13.00 |
| 2 | (3-Cyclopropyl-2-methyl-2,4,5,7-tetrahydro-6H-pyrazolo[3,4-c]pyridin-6-yl)(2,3-dichlorophenyl)methanone; | 4600.44 |

TABLE 4-continued

| Ex # | Compound Name | MGL IC$_{50}$ (nM) |
|---|---|---|
| 3 | (3-Cyclopropyl-2-methyl-2,4,5,7-tetrahydro-6H-pyrazolo[3,4-c]pyridin-6-yl)(naphthalen-1-yl)methanone; | 799.47 |
| 4 | (2-Fluoro-3-(trifluoromethoxy)phenyl)(2-methyl-3-phenyl-2,4,5,7-tetrahydro-6H-pyrazolo[3,4-c]pyridin-6-yl)methanone; | 432.81 |
| 5 | (2-Methoxy-6-(trifluoromethyl)phenyl)(2-methyl-3-phenyl-2,4,5,7-tetrahydro-6H-pyrazolo[3,4-c]pyridin-6-yl)methanone; | >10000 |
| 6 | (3-Methoxy-5-(trifluoromethyl)phenyl)(2-methyl-3-phenyl-2,4,5,7-tetrahydro-6H-pyrazolo[3,4-c]pyridin-6-yl)methanone; | 364.75 |
| 7 | (2-Methoxy-3-methylphenyl)(2-methyl-3-phenyl-2,4,5,7-tetrahydro-6H-pyrazolo[3,4-c]pyridin-6-yl)methanone; | 112.72 |
| 8 | (2-Ethyl-3-methoxyphenyl)(2-methyl-3-phenyl-2,4,5,7-tetrahydro-6H-pyrazolo[3,4-c]pyridin-6-yl)methanone; | 1840.77 |
| 9 | (3,4-Dimethoxyphenyl)(2-methyl-3-phenyl-2,4,5,7-tetrahydro-6H-pyrazolo[3,4-c]pyridin-6-yl)methanone; | 440.56 |
| 10 | (2,6-Dimethoxyphenyl)(2-methyl-3-phenyl-2,4,5,7-tetrahydro-6H-pyrazolo[3,4-c]pyridin-6-yl)methanone; | >10000 |
| 11 | (3,5-Dimethoxyphenyl)-(2-methyl-3-phenyl-5,7-dihydro-4H-pyrazolo[3,4-c]pyridin-6-yl)methanone; | 187.28 |
| 12 | (2-Chloro-3-hydroxyphenyl)(2-methyl-3-phenyl-2,4,5,7-tetrahydro-6H-pyrazolo[3,4-c]pyridin-6-yl)methanone; | 3415.07 |
| 13 | (2-Chloro-3-methoxyphenyl)(2-methyl-3-phenyl-2,4,5,7-tetrahydro-6H-pyrazolo[3,4-c]pyridin-6-yl)methanone; | 16.77 |
| 14 | (3-Chloro-2-methoxy-phenyl)-(2-methyl-3-phenyl-5,7-dihydro-4H-pyrazolo[3,4-c]pyridin-6-yl)methanone; | 2585.83 |
| 15 | (2-Chloro-6-methoxyphenyl)(2-methyl-3-phenyl-2,4,5,7-tetrahydro-6H-pyrazolo[3,4-c]pyridin-6-yl)methanone; | 10000.00 |
| 16 | (3-Chloro-5-methoxyphenyl)(2-methyl-3-phenyl-2,4,5,7-tetrahydro-6H-pyrazolo[3,4-c]pyridin-6-yl)methanone; | 77.89 |
| 17 | (2-Amino-3-methylphenyl)(2-methyl-3-phenyl-2,4,5,7-tetrahydro-6H-pyrazolo[3,4-c]pyridin-6-yl)methanone; | 1399.91 |
| 18 | (2-(1H-1,2,4-Triazol-1-yl)phenyl)(2-methyl-3-phenyl-2,4,5,7-tetrahydro-6H-pyrazolo[3,4-c]pyridin-6-yl)methanone; | 670.97 |
| 19 | (2-Methyl-3-morpholinophenyl)(2-methyl-3-phenyl-2,4,5,7-tetrahydro-6H-pyrazolo[3,4-c]pyridin-6-yl)methanone; | 4818.37 |
| 20 | (5-Chloro-1-methyl-1H-pyrazol-4-yl)(2-methyl-3-phenyl-2,4,5,7-tetrahydro-6H-pyrazolo[3,4-c]pyridin-6-yl)methanone; | 2094.60 |
| 21 | (1,5-Dimethyl-1H-pyrazol-4-yl)(2-methyl-3-phenyl-2,4,5,7-tetrahydro-6H-pyrazolo[3,4-c]pyridin-6-yl)methanone; | 10000.00 |
| 22 | (5-Cyclopropyl-1-methyl-1H-pyrazol-4-yl)(2-methyl-3-phenyl-2,4,5,7-tetrahydro-6H-pyrazolo[3,4-c]pyridin-6-yl)methanone; | 683.28 |
| 23 | (2-Methyl-3-phenyl-2,4,5,7-tetrahydro-6H-pyrazolo[3,4-c]pyridin-6-yl)(1-phenyl-1H-1,2,4-triazol-3-yl)methanone; | 846.64 |
| 24 | (6-(Difluoromethoxy)pyridin-2-yl)(2-methyl-3-phenyl-2,4,5,7-tetrahydro-6H-pyrazolo[3,4-c]pyridin-6-yl)methanone; | 2556.82 |
| 25 | (2-Methyl-3-phenyl-2,4,5,7-tetrahydro-6H-pyrazolo[3,4-c]pyridin-6-yl)(6-(trifluoromethoxy)pyridin-2-yl)methanone; | 2427.73 |
| 26 | 5-(2-Methyl-3-phenyl-4,5,6,7-tetrahydro-2H-pyrazolo[3,4-c]pyridine-6-carbonyl)-2H-benzo[b][1,4]oxazin-3(4H)-one; | 2456.97 |
| 27 | (4-Methyl-3,4-dihydro-2H-benzo[b][1,4]oxazin-7-yl)(2-methyl-3-phenyl-2,4,5,7-tetrahydro-6H-pyrazolo[3,4-c]pyridin-6-yl)methanone; | 290.07 |
| 28 | Benzo[d][1,3]dioxol-4-yl(2-methyl-3-phenyl-2,4,5,7-tetrahydro-6H-pyrazolo[3,4-c]pyridin-6-yl)methanone; | 4004.98 |
| 29 | Benzo[d][1,3]dioxol-5-yl(2-methyl-3-phenyl-2,4,5,7-tetrahydro-6H-pyrazolo[3,4-c]pyridin-6-yl)methanone; | 1948.95 |
| 30 | (2,2-Difluorobenzo[d][1,3]dioxol-4-yl)(2-methyl-3-phenyl-2,4,5,7-tetrahydro-6H-pyrazolo[3,4-c]pyridin-6-yl)methanone; | 1036.33 |
| 31 | (2-Methyl-3-phenyl-2,4,5,7-tetrahydro-6H-pyrazolo[3,4-c]pyridin-6-yl)(4H-thieno[3,2-b]pyrrol-2-yl)methanone; | 1229.99 |
| 32 | (2-Methyl-3-phenyl-2,4,5,7-tetrahydro-6H-pyrazolo[3,4-c]pyridin-6-yl)(6-methylimidazo[2,1-b]thiazol-5-yl)methanone; | 1085.93 |
| 33 | Benzofuran-7-yl(2-methyl-3-phenyl-2,4,5,7-tetrahydro-6H-pyrazolo[3,4-c]pyridin-6-yl)methanone; | 89.93 |
| 34 | Benzofuran-4-yl(2-methyl-3-phenyl-2,4,5,7-tetrahydro-6H-pyrazolo[3,4-c]pyridin-6-yl)methanone; | 299.99 |
| 35 | Benzofuran-5-yl(2-methyl-3-phenyl-2,4,5,7-tetrahydro-6H-pyrazolo[3,4-c]pyridin-6-yl)methanone; | 482.06 |
| 36 | Benzofuran-3-yl(2-methyl-3-phenyl-2,4,5,7-tetrahydro-6H-pyrazolo[3,4-c]pyridin-6-yl)methanone; | 749.89 |
| 37 | Benzo[b]thiophen-7-yl(2-methyl-3-phenyl-2,4,5,7-tetrahydro-6H-pyrazolo[3,4-c]pyridin-6-yl)methanone; | 47.84 |
| 38 | Benzo[b]thiophen-4-yl(2-methyl-3-phenyl-2,4,5,7-tetrahydro-6H-pyrazolo[3,4-c]pyridin-6-yl)methanone; | 68.00 |
| 39 | Benzo[b]thiophen-5-yl(2-methyl-3-phenyl-2,4,5,7-tetrahydro-6H-pyrazolo[3,4-c]pyridin-6-yl)methanone; | 136.30 |
| 40 | Benzo[b]thiophen-3-yl(2-methyl-3-phenyl-2,4,5,7-tetrahydro-6H-pyrazolo[3,4-c]pyridin-6-yl)methanone; | 140.51 |

TABLE 4-continued

| Ex # | Compound Name | MGL IC$_{50}$ (nM) |
|---|---|---|
| 41 | (3-Chlorobenzo[b]thiophen-2-yl)(2-methyl-3-phenyl-2,4,5,7-tetrahydro-6H-pyrazolo[3,4-c]pyridin-6-yl)methanone; | 64.58 |
| 42 | (1H-Indol-4-yl)(2-methyl-3-phenyl-2,4,5,7-tetrahydro-6H-pyrazolo[3,4-c]pyridin-6-yl)methanone; | 23.65 |
| 43 | (1H-Indol-5-yl)(2-methyl-3-phenyl-2,4,5,7-tetrahydro-6H-pyrazolo[3,4-c]pyridin-6-yl)methanone; | 64.71 |
| 44 | (1H-Indol-3-yl)(2-methyl-3-phenyl-2,4,5,7-tetrahydro-6H-pyrazolo[3,4-c]pyridin-6-yl)methanone; | 319.37 |
| 45 | (1H-Indol-7-yl)(2-methyl-3-phenyl-2,4,5,7-tetrahydro-6H-pyrazolo[3,4-c]pyridin-6-yl)methanone; | 1463.86 |
| 46 | (1H-Indol-6-yl)(2-methyl-3-phenyl-2,4,5,7-tetrahydro-6H-pyrazolo[3,4-c]pyridin-6-yl)methanone; | 358.67 |
| 47 | (5-Fluoro-1H-indol-4-yl)(2-methyl-3-phenyl-2,4,5,7-tetrahydro-6H-pyrazolo[3,4-c]pyridin-6-yl)methanone; | 70.15 |
| 48 | (7-Chloro-1H-indol-3-yl)(2-methyl-3-phenyl-2,4,5,7-tetrahydro-6H-pyrazolo[3,4-c]pyridin-6-yl)methanone; | 102.59 |
| 49 | (4-Chloro-1H-indol-3-yl)(2-methyl-3-phenyl-2,4,5,7-tetrahydro-6H-pyrazolo[3,4-c]pyridin-6-yl)methanone; | 461.21 |
| 50 | (7-Methyl-1H-indol-2-yl)(2-methyl-3-phenyl-2,4,5,7-tetrahydro-6H-pyrazolo[3,4-c]pyridin-6-yl)methanone; | 1999.86 |
| 51 | (1-Methyl-1H-indol-4-yl)(2-methyl-3-phenyl-2,4,5,7-tetrahydro-6H-pyrazolo[3,4-c]pyridin-6-yl)methanone; | 15.63 |
| 52 | (1-Methyl-1H-indol-3-yl)(2-methyl-3-phenyl-2,4,5,7-tetrahydro-6H-pyrazolo[3,4-c]pyridin-6-yl)methanone; | 138.10 |
| 53 | Benzo[d]isoxazol-3-yl(2-methyl-3-phenyl-2,4,5,7-tetrahydro-6H-pyrazolo[3,4-c]pyridin-6-yl)methanone; | 32.15 |
| 54 | (6-Chlorobenzo[d]isoxazol-3-yl)(2-methyl-3-phenyl-2,4,5,7-tetrahydro-6H-pyrazolo[3,4-c]pyridin-6-yl)methanone; | 1116.09 |
| 55 | Benzo[c]isoxazol-3-yl(2-methyl-3-phenyl-2,4,5,7-tetrahydro-6H-pyrazolo[3,4-c]pyridin-6-yl)methanone; | 225.68 |
| 56 | Benzo[d]oxazol-6-yl(2-methyl-3-phenyl-2,4,5,7-tetrahydro-6H-pyrazolo[3,4-c]pyridin-6-yl)methanone; | 292.69 |
| 57 | Benzo[d]oxazol-2-yl(2-methyl-3-phenyl-2,4,5,7-tetrahydro-6H-pyrazolo[3,4-c]pyridin-6-yl)methanone; | 1683.84 |
| 58 | Benzo[d]oxazol-5-yl(2-methyl-3-phenyl-2,4,5,7-tetrahydro-6H-pyrazolo[3,4-c]pyridin-6-yl)methanone; | 4181.19 |
| 59 | Benzo[d]thiazol-7-yl(2-methyl-3-phenyl-2,4,5,7-tetrahydro-6H-pyrazolo[3,4-c]pyridin-6-yl)methanone; | 402.53 |
| 60 | Benzo[d]thiazol-5-yl(2-methyl-3-phenyl-2,4,5,7-tetrahydro-6H-pyrazolo[3,4-c]pyridin-6-yl)methanone; | 550.05 |
| 61 | Benzo[d]thiazol-4-yl(2-methyl-3-phenyl-2,4,5,7-tetrahydro-6H-pyrazolo[3,4-c]pyridin-6-yl)methanone; | 754.92 |
| 62 | Benzo[d]thiazol-2-yl(2-methyl-3-phenyl-2,4,5,7-tetrahydro-6H-pyrazolo[3,4-c]pyridin-6-yl)methanone; | 1636.82 |
| 63 | Benzo[d]isothiazol-3-yl(2-methyl-3-phenyl-2,4,5,7-tetrahydro-6H-pyrazolo[3,4-c]pyridin-6-yl)methanone; | 48.96 |
| 64 | (1H-Indazol-5-yl)(2-methyl-3-phenyl-2,4,5,7-tetrahydro-6H-pyrazolo[3,4-c]pyridin-6-yl)methanone; | 56.22 |
| 65 | (1H-Indazol-4-yl)(2-methyl-3-phenyl-2,4,5,7-tetrahydro-6H-pyrazolo[3,4-c]pyridin-6-yl)methanone; | 101.30 |
| 66 | (1H-Indazol-3-yl)(2-methyl-3-phenyl-2,4,5,7-tetrahydro-6H-pyrazolo[3,4-c]pyridin-6-yl)methanone; | 299.99 |
| 67 | (1H-Indazol-7-yl)(2-methyl-3-phenyl-2,4,5,7-tetrahydro-6H-pyrazolo[3,4-c]pyridin-6-yl)methanone; | 1627.80 |
| 68 | (1H-Indazol-6-yl)(2-methyl-3-phenyl-2,4,5,7-tetrahydro-6H-pyrazolo[3,4-c]pyridin-6-yl)methanone; | 2192.81 |
| 69 | (7-Chloro-1H-indazol-3-yl)(2-methyl-3-phenyl-2,4,5,7-tetrahydro-6H-pyrazolo[3,4-c]pyridin-6-yl)methanone; | 661.76 |
| 70 | (1-Methyl-1H-indazol-3-yl)(2-methyl-3-phenyl-2,4,5,7-tetrahydro-6H-pyrazolo[3,4-c]pyridin-6-yl)methanone; | 379.67 |
| 71 | (1H-Benzo[d]imidazol-5-yl)(2-methyl-3-phenyl-2,4,5,7-tetrahydro-6H-pyrazolo[3,4-c]pyridin-6-yl)methanone; | 1009.02 |
| 72 | (2-Methyl-3-phenyl-2,4,5,7-tetrahydro-6H-pyrazolo[3,4-c]pyridin-6-yl)(2-(trifluoromethyl)-1H-benzo[d]imidazol-4-yl)methanone; | 2324.88 |
| 73 | (2-Methyl-3-phenyl-2,4,5,7-tetrahydro-6H-pyrazolo[3,4-c]pyridin-6-yl)(pyrazolo[1,5-a]pyridin-5-yl)methanone; | 2499.77 |
| 74 | (2-Methyl-3-phenyl-2,4,5,7-tetrahydro-6H-pyrazolo[3,4-c]pyridin-6-yl)(pyrazolo[1,5-a]pyridin-3-yl)methanone; | 612.77 |
| 75 | (2-Methyl-3-phenyl-2,4,5,7-tetrahydro-6H-pyrazolo[3,4-c]pyridin-6-yl)(pyrazolo[1,5-a]pyridin-7-yl)methanone; | 1800.11 |
| 76 | Imidazo[1,5-a]pyridin-1-yl(2-methyl-3-phenyl-2,4,5,7-tetrahydro-6H-pyrazolo[3,4-c]pyridin-6-yl)methanone; | 6112.23 |
| 77 | Imidazo[1,5-a]pyridin-6-yl(2-methyl-3-phenyl-2,4,5,7-tetrahydro-6H-pyrazolo[3,4-c]pyridin-6-yl)methanone; | 5158.22 |
| 78 | Imidazo[1,5-a]pyridin-7-yl(2-methyl-3-phenyl-2,4,5,7-tetrahydro-6H-pyrazolo[3,4-c]pyridin-6-yl)methanone; | 1999.86 |

TABLE 4-continued

| Ex # | Compound Name | MGL IC$_{50}$ (nM) |
|---|---|---|
| 79 | Imidazo[1,5-a]pyridin-5-yl(2-methyl-3-phenyl-2,4,5,7-tetrahydro-6H-pyrazolo[3,4-c]pyridin-6-yl)methanone; | 1193.99 |
| 80 | Imidazo[1,2-a]pyridin-5-yl(2-methyl-3-phenyl-2,4,5,7-tetrahydro-6H-pyrazolo[3,4-c]pyridin-6-yl)methanone; | 2331.85 |
| 81 | Imidazo[1,2-a]pyridin-3-yl(2-methyl-3-phenyl-2,4,5,7-tetrahydro-6H-pyrazolo[3,4-c]pyridin-6-yl)methanone; | 1316.13 |
| 82 | (5-Chloro-2-methylimidazo[1,2-a]pyridin-3-yl)(2-methyl-3-phenyl-2,4,5,7-tetrahydro-6H-pyrazolo[3,4-c]pyridin-6-yl)methanone; | 4812.83 |
| 83 | (2-Methyl-3-phenyl-2,4,5,7-tetrahydro-6H-pyrazolo[3,4-c]pyridin-6-yl)(1H-pyrrolo[3,2-c]pyridin-3-yl)methanone; | 1504.87 |
| 84 | (1-Methyl-1H-pyrrolo[2,3-b]pyridin-4-yl)(2-methyl-3-phenyl-2,4,5,7-tetrahydro-6H-pyrazolo[3,4-c]pyridin-6-yl)methanone; | 48.35 |
| 85 | [1,2,4]Triazolo[1,5-a]pyridin-5-yl(2-methyl-3-phenyl-2,4,5,7-tetrahydro-6H-pyrazolo[3,4-c]pyridin-6-yl)methanone; | 7135.10 |
| 86 | (2-Methyl-3-phenyl-2,4,5,7-tetrahydro-6H-pyrazolo[3,4-c]pyridin-6-yl)(quinolin-4-yl)methanone; | 32.36 |
| 87 | Isoquinolin-4-yl(2-methyl-3-phenyl-2,4,5,7-tetrahydro-6H-pyrazolo[3,4-c]pyridin-6-yl)methanone; | 39.77 |
| 88 | Isoquinolin-1-yl(2-methyl-3-phenyl-2,4,5,7-tetrahydro-6H-pyrazolo[3,4-c]pyridin-6-yl)methanone; | 47.29 |
| 89 | (2-Methyl-3-phenyl-2,4,5,7-tetrahydro-6H-pyrazolo[3,4-c]pyridin-6-yl)(quinolin-5-yl)methanone; | 56.04 |
| 90 | (2-Methyl-3-phenyl-2,4,5,7-tetrahydro-6H-pyrazolo[3,4-c]pyridin-6-yl)(quinolin-6-yl)methanone; | 226.67 |
| 91 | (2-Ethyl-3-phenyl-2,4,5,7-tetrahydro-6H-pyrazolo[3,4-c]pyridin-6-yl)(quinolin-6-yl)methanone; | 780.91 |
| 92 | Isoquinolin-5-yl(2-methyl-3-phenyl-2,4,5,7-tetrahydro-6H-pyrazolo[3,4-c]pyridin-6-yl)methanone; | 107.70 |
| 93 | (2-Methyl-3-phenyl-2,4,5,7-tetrahydro-6H-pyrazolo[3,4-c]pyridin-6-yl)(quinolin-8-yl)methanone; | 125.98 |
| 94 | (2-Methyl-3-phenyl-2,4,5,7-tetrahydro-6H-pyrazolo[3,4-c]pyridin-6-yl)(quinolin-2-yl)methanone; | 282.23 |
| 95 | (2-Methyl-3-phenyl-2,4,5,7-tetrahydro-6H-pyrazolo[3,4-c]pyridin-6-yl)(quinolin-3-yl)methanone; | 983.56 |
| 96 | (8-Fluoroquinolin-4-yl)(2-methyl-3-phenyl-2,4,5,7-tetrahydro-6H-pyrazolo[3,4-c]pyridin-6-yl)methanone; | 257.69 |
| 97 | (2-Methyl-3-phenyl-2,4,5,7-tetrahydro-6H-pyrazolo[3,4-c]pyridin-6-yl)(quinoxalin-5-yl)methanone; | 4256.96 |
| 98 | (3-(3-(Difluoromethoxy)phenyl)-2-methyl-2,4,5,7-tetrahydro-6H-pyrazolo[3,4-c]pyridin-6-yl)(quinolin-6-yl)methanone; | 972.75 |
| 99 | (3-(3-Chlorophenyl)-2-methyl-2,4,5,7-tetrahydro-6H-pyrazolo[3,4-c]pyridin-6-yl)(quinolin-6-yl)methanone; | 268.23 |
| 100 | (3-(3-Fluorophenyl)-2-methyl-2,4,5,7-tetrahydro-6H-pyrazolo[3,4-c]pyridin-6-yl)(quinolin-6-yl)methanone; | 124.71 |
| 101 | (3-(3,5-Difluorophenyl)-2-methyl-2,4,5,7-tetrahydro-6H-pyrazolo[3,4-c]pyridin-6-yl)(quinolin-6-yl)methanone; | 52.36 |
| 102 | Benzo[d]isoxazol-3-yl(2-methyl-3-(5-methylthiophen-2-yl)-2,4,5,7-tetrahydro-6H-pyrazolo[3,4-c]pyridin-6-yl)methanone; | 158.09 |
| 103 | (2-Methyl-3-(5-(trifluoromethyl)thiophen-2-yl)-2,4,5,7-tetrahydro-6H-pyrazolo[3,4-c]pyridin-6-yl)(quinolin-6-yl)methanone; | 264.48 |
| 104 | (3-(1H-Indol-2-yl)-2-methyl-2,4,5,7-tetrahydro-6H-pyrazolo[3,4-c]pyridin-6-yl)(quinolin-6-yl)methanone; | 790.86 |
| 105 | (2-Methyl-3-(1-methyl-1H-indol-2-yl)-2,4,5,7-tetrahydro-6H-pyrazolo[3,4-c]pyridin-6-yl)(quinolin-6-yl)methanone; | 405.98 |
| 106 | (3-(3,5-Difluorophenyl)-2,7-dimethyl-2,4,5,7-tetrahydro-6H-pyrazolo[3,4-c]pyridin-6-yl)(quinolin-6-yl)methanone; | 7.36 |
| 107 | (S)-(2,7-Dimethyl-3-(5-methylfuran-2-yl)-2,4,5,7-tetrahydro-6H-pyrazolo[3,4-c]pyridin-6-yl)(quinoxalin-6-yl)methanone; | 260.92 |
| 108 | (S)-(2,7-Dimethyl-3-(pyridin-3-yl)-2,4,5,7-tetrahydro-6H-pyrazolo[3,4-c]pyridin-6-yl)(quinoxalin-6-yl)methanone; | 1304.97 |
| 109 | (S)-(3-(5-Fluoropyridin-3-yl)-2,7-dimethyl-2,4,5,7-tetrahydro-6H-pyrazolo[3,4-c]pyridin-6-yl)(quinoxalin-6-yl)methanone; | 721.44 |
| 110 | (2,7-Dimethyl-3-phenyl-2,4,5,7-tetrahydro-6H-pyrazolo[3,4-c]pyridin-6-yl)(quinolin-6-yl)methanone; | 19.94 |
| 111 | (R)-(2,7-Dimethyl-3-phenyl-2,4,5,7-tetrahydro-6H-pyrazolo[3,4-c]pyridin-6-yl)(quinolin-6-yl)methanone; | 8239.49 |
| 112 | (S)-(2,7-Dimethyl-3-phenyl-2,4,5,7-tetrahydro-6H-pyrazolo[3,4-c]pyridin-6-yl)(quinolin-6-yl)methanone; | 6.96 |
| 113 | (7-Methyl-2,3-diphenyl-2,4,5,7-tetrahydro-6H-pyrazolo[3,4-c]pyridin-6-yl)(quinolin-6-yl)methanone; | 235.61 |
| 114 | (R)-(7-Methyl-2,3-diphenyl-2,4,5,7-tetrahydro-6H-pyrazolo[3,4-c]pyridin-6-yl)(quinolin-6-yl)methanone; | 10000.00 |
| 115 | (S)-(7-Methyl-2,3-diphenyl-2,4,5,7-tetrahydro-6H-pyrazolo[3,4-c]pyridin-6-yl)(quinolin-6-yl)methanone; | 44.25 |
| 116 | (S)-(3-Chloro-5-(trifluoromethoxy)phenyl)(3-(3-chlorophenyl)-2,7-dimethyl-2,4,5,7-tetrahydro-6H-pyrazolo[3,4-c]pyridin-6-yl)methanone; | 198.79 |

TABLE 4-continued

| Ex # | Compound Name | MGL IC$_{50}$ (nM) |
|---|---|---|
| 117 | (S)-(3-(3-Chlorophenyl)-2,7-dimethyl-2,4,5,7-tetrahydro-6H-pyrazolo[3,4-c]pyridin-6-yl)(1-phenyl-1H-1,2,4-triazol-3-yl)methanone; | 56.66 |
| 118 | (S)-(3-(3-Chlorophenyl)-2,7-dimethyl-2,4,5,7-tetrahydro-6H-pyrazolo[3,4-c]pyridin-6-yl)(5-ethyl-1-(2-fluorophenyl)-1H-1,2,4-triazol-3-yl)methanone; | 13.84 |
| 119 | (S)-(3-(3-Chlorophenyl)-2,7-dimethyl-2,4,5,7-tetrahydro-6H-pyrazolo[3,4-c]pyridin-6-yl)(4-(hydroxymethyl)pyridin-2-yl)methanone; | 398.20 |
| 120 | (S)-(3-(3-Chlorophenyl)-2,7-dimethyl-2,4,5,7-tetrahydro-6H-pyrazolo[3,4-c]pyridin-6-yl)(5-(methoxymethyl)pyridin-3-yl)methanone; | 173.70 |
| 121 | (S)-(3-(3-Chlorophenyl)-2,7-dimethyl-2,4,5,7-tetrahydro-6H-pyrazolo[3,4-c]pyridin-6-yl)(6-isopropoxypyridin-3-yl)methanone; | 329.53 |
| 122 | (S)-(3-(3-Chlorophenyl)-2,7-dimethyl-2,4,5,7-tetrahydro-6H-pyrazolo[3,4-c]pyridin-6-yl)(5-isopropoxypyridin-3-yl)methanone; | 78.23 |
| 123 | (S)-Benzo[d][1,3]dioxol-4-yl(3-(3-chlorophenyl)-2,7-dimethyl-2,4,5,7-tetrahydro-6H-pyrazolo[3,4-c]pyridin-6-yl)methanone; | 45.13 |
| 124 | (S)-6-(3-(3-Chlorophenyl)-2,7-dimethyl-4,5,6,7-tetrahydro-2H-pyrazolo[3,4-c]pyridine-6-carbonyl)benzo[d]oxazol-2(3H)-one | 19.70 |
| 125 | (S)-(3-(3-Chlorophenyl)-2,7-dimethyl-2,4,5,7-tetrahydro-6H-pyrazolo[3,4-c]pyridin-6-yl)(2-methylbenzo[d]oxazol-6-yl)methanone; | 9.52 |
| 126 | (3-(3-Chlorophenyl)-2,7-dimethyl-2,4,5,7-tetrahydro-6H-pyrazolo[3,4-c]pyridin-6-yl)(furo[3,2-b]pyridin-6-yl)methanone; | 129.99 |
| 127 | (R)-(3-(3-Chlorophenyl)-2,7-dimethyl-2,4,5,7-tetrahydro-6H-pyrazolo[3,4-c]pyridin-6-yl)(furo[3,2-b]pyridin-6-yl)methanone; | >10000 |
| 128 | (S)-(3-(3-Chlorophenyl)-2,7-dimethyl-2,4,5,7-tetrahydro-6H-pyrazolo[3,4-c]pyridin-6-yl)(furo[3,2-b]pyridin-6-yl)methanone; | 26.29 |
| 129 | (S)-(3-(3-Chlorophenyl)-2,7-dimethyl-2,4,5,7-tetrahydro-6H-pyrazolo[3,4-c]pyridin-6-yl)(furo[3,2-b]pyridin-2-yl)methanone; | 47.18 |
| 130 | (S)-(3-(3-Chlorophenyl)-2,7-dimethyl-2,4,5,7-tetrahydro-6H-pyrazolo[3,4-c]pyridin-6-yl)(1H-pyrrolo[2,3-b]pyridin-6-yl)methanone; | 273.59 |
| 131 | (S)-(3-(3-Chlorophenyl)-2,7-dimethyl-2,4,5,7-tetrahydro-6H-pyrazolo[3,4-c]pyridin-6-yl)(1,5-naphthyridin-2-yl)methanone; | 46.17 |
| 132 | (3-(3-Chlorophenyl)-2,7-dimethyl-2,4,5,7-tetrahydro-6H-pyrazolo[3,4-c]pyridin-6-yl)(quinoxalin-6-yl)methanone; | 18.37 |
| 133 | (R)-(3-(3-Chlorophenyl)-2,7-dimethyl-2,4,5,7-tetrahydro-6H-pyrazolo[3,4-c]pyridin-6-yl)(quinoxalin-6-yl)methanone; | >10000 |
| 134 | (S)-(3-(3-Chlorophenyl)-2,7-dimethyl-2,4,5,7-tetrahydro-6H-pyrazolo[3,4-c]pyridin-6-yl)(quinoxalin-6-yl)methanone; | 4.27 |
| 135 | (S)-(8-Bromoquinoxalin-6-yl)(3-(3-chlorophenyl)-2,7-dimethyl-2,4,5,7-tetrahydro-6H-pyrazolo[3,4-c]pyridin-6-yl)methanone; | 10.60 |
| 136 | (7-Ethyl-3-(3-fluorophenyl)-2-methyl-2,4,5,7-tetrahydro-6H-pyrazolo[3,4-c]pyridin-6-yl)(quinolin-6-yl)methanone; | 31.39 |
| 137 | [(7S)-3-(3,5-Difluorophenyl)-2,7-dimethyl-5,7-dihydro-4H-pyrazolo[3,4-c]pyridin-6-yl]-[2-(2-fluoroethoxy)phenyl]methanone; | 240.49 |
| 138 | (S)-(3-(3,5-Difluorophenyl)-2,7-dimethyl-2,4,5,7-tetrahydro-6H-pyrazolo[3,4-c]pyridin-6-yl)(4-(2-fluoroethoxy)phenyl)methanone; | 39.53 |
| 139 | (S)-(3-(3,5-Difluorophenyl)-2,7-dimethyl-2,4,5,7-tetrahydro-6H-pyrazolo[3,4-c]pyridin-6-yl)(3-(2-fluoroethoxy)phenyl)methanone; | 9.80 |
| 140 | (S)-(3-(3,5-Difluorophenyl)-2,7-dimethyl-2,4,5,7-tetrahydro-6H-pyrazolo[3,4-c]pyridin-6-yl)(3-(2-(fluoro-$^{18}$F)ethoxy)phenyl)methanone; | NT |
| 141 | (S)-(3-(3,5-Difluorophenyl)-2,7-dimethyl-2,4,5,7-tetrahydro-6H-pyrazolo[3,4-c]pyridin-6-yl)(2-fluoro-3-(2-fluoroethoxy)phenyl)methanone; | 1.72 |
| 142 | (S)-(3-(3,5-Difluorophenyl)-2,7-dimethyl-2,4,5,7-tetrahydro-6H-pyrazolo[3,4-c]pyridin-6-yl)(2-fluoro-5-(2-fluoroethoxy)phenyl)methanone; | 3.70 |
| 143 | (S)-(3-(3,5-Difluorophenyl)-2,7-dimethyl-2,4,5,7-tetrahydro-6H-pyrazolo[3,4-c]pyridin-6-yl)(3-fluoro-5-(2-fluoroethoxy)phenyl)methanone; | 4.21 |
| 144 | (S)-(3-(3,5-Difluorophenyl)-2,7-dimethyl-2,4,5,7-tetrahydro-6H-pyrazolo[3,4-c]pyridin-6-yl)(4-fluoro-3-(2-fluoroethoxy)phenyl)methanone; | 55.02 |
| 145 | [2-Chloro-3-(2-fluoroethoxy)phenyl]-[(7S)-3-(3,5-difluorophenyl)-2,7-dimethyl-5,7-dihydro-4H-pyrazolo[3,4-c]pyridin-6-yl]methanone; | 2.13 |
| 146 | [(2-Chloro-5-(2-fluoroethoxy)phenyl](3-(3,5-difluorophenyl)-2,7-dimethyl-2,4,5,7-tetrahydro-6H-pyrazolo[3,4-c]pyridin-6-yl)methanone; | 3.73 |
| 147 | (S)-(2-(2H-1,2,3-Triazol-2-yl)phenyl)(3-(3,5-difluorophenyl)-2,7-dimethyl-2,4,5,7-tetrahydro-6H-pyrazolo[3,4-c]pyridin-6-yl)methanone; | 71.75 |

TABLE 4-continued

| Ex # | Compound Name | MGL IC$_{50}$ (nM) |
|---|---|---|
| 148 | (3-(3,5-Difluorophenyl)-2,7-dimethyl-2,4,5,7-tetrahydro-6H-pyrazolo[3,4-c]pyridin-6-yl)(1-phenyl-1H-1,2,4-triazol-3-yl)methanone; | 67.08 |
| 149 | (S)-(3-(3,5-Difluorophenyl)-2,7-dimethyl-2,4,5,7-tetrahydro-6H-pyrazolo[3,4-c]pyridin-6-yl)(5-ethyl-1-phenyl-1H-1,2,4-triazol-3-yl)methanone; | 11.95 |
| 150 | (S)-(3-(3,5-Difluorophenyl)-2,7-dimethyl-2,4,5,7-tetrahydro-6H-pyrazolo[3,4-c]pyridin-6-yl)(1-(2-fluoroethyl)-1H-indol-4-yl)methanone; | 0.67 |
| 151 | [(7S)-3-(3,5-Difluorophenyl)-2,7-dimethyl-5,7-dihydro-4H-pyrazolo[3,4-c]pyridin-6-yl]-[1-(2-fluoranylethyl)indol-5-yl]methanone; | NT |
| 152 | (S)-(3-(3,5-Difluorophenyl)-2,7-dimethyl-2,4,5,7-tetrahydro-6H-pyrazolo[3,4-c]pyridin-6-yl)(1-(2-fluoroethyl)-1H-pyrrolo[2,3-b]pyridin-4-yl)methanone; | 1.63 |
| 153 | (S)-(3-(3,5-Difluorophenyl)-2,7-dimethyl-2,4,5,7-tetrahydro-6H-pyrazolo[3,4-c]pyridin-6-yl)(furo[3,2-b]pyridin-6-yl)methanone; | 15.42 |
| 154 | (R)-(3-(3,5-Difluorophenyl)-2,7-dimethyl-2,4,5,7-tetrahydro-6H-pyrazolo[3,4-c]pyridin-6-yl)(furo[3,2-b]pyridin-6-yl)methanone; | 6553.91 |
| 155 | (2-(Difluoromethyl)-3-(3,5-difluorophenyl)-7-methyl-2,4,5,7-tetrahydro-6H-pyrazolo[3,4-c]pyridin-6-yl)(quinolin-6-yl)methanone; | 4.63 |
| 156 | (3-(3,5-Difluorophenyl)-7-methyl-2-(trifluoromethyl)-2,4,5,7-tetrahydro-6H-pyrazolo[3,4-c]pyridin-6-yl)(quinolin-6-yl)methanone; | 17.00 |
| 157 | (3-(3,5-Difluorophenyl)-7-methyl-2-(methyl-d3)-2,4,5,7-tetrahydro-6H-pyrazolo[3,4-c]pyridin-6-yl)(quinolin-6-yl)methanone; | 13.78 |
| 158 | (R)-(3-(3,5-Difluorophenyl)-2,7-dimethyl-2,4,5,7-tetrahydro-6H-pyrazolo[3,4-c]pyridin-6-yl)(quinolin-6-yl)methanone; | 10000.00 |
| 159 | (S)-(3-(3,5-Difluorophenyl)-2,7-dimethyl-2,4,5,7-tetrahydro-6H-pyrazolo[3,4-c]pyridin-6-yl)(quinolin-6-yl)methanone; | 7.30 |
| 160 | (3-(3,5-Difluorophenyl)-2,7-dimethyl-2,4,5,7-tetrahydro-6H-pyrazolo[3,4-c]pyridin-6-yl)(isoquinolin-3-yl)methanone; | 259.60 |
| 161 | (3-(3,5-Difluorophenyl)-2,7-dimethyl-2,4,5,7-tetrahydro-6H-pyrazolo[3,4-c]pyridin-6-yl)(isoquinolin-7-yl)methanone; | 260.02 |
| 162 | (4-Bromoquinolin-6-yl)(3-(3,5-difluorophenyl)-2,7-dimethyl-2,4,5,7-tetrahydro-6H-pyrazolo[3,4-c]pyridin-6-yl)methanone; | 11.27 |
| 163 | (5-Chloroquinolin-6-yl)(3-(3,5-difluorophenyl)-2,7-dimethyl-2,4,5,7-tetrahydro-6H-pyrazolo[3,4-c]pyridin-6-yl)methanone; | 11.82 |
| 164 | (S)-(3-(3,5-Difluorophenyl)-2,7-dimethyl-2,4,5,7-tetrahydro-6H-pyrazolo[3,4-c]pyridin-6-yl)(8-(trifluoromethyl)quinolin-6-yl)methanone; | 38.44 |
| 165 | (S)-(3-(3,5-Difluorophenyl)-2,7-dimethyl-2,4,5,7-tetrahydro-6H-pyrazolo[3,4-c]pyridin-6-yl)(3-(trifluoromethyl)quinolin-6-yl)methanone; | 103.40 |
| 166 | (S)-(3-(3,5-Difluorophenyl)-2,7-dimethyl-2,4,5,7-tetrahydro-6H-pyrazolo[3,4-c]pyridin-6-yl)(3-(2-fluoroethoxy)quinolin-6-yl)methanone; | 11.27 |
| 167 | (3-(3,5-Difluorophenyl)-2,7-dimethyl-2,4,5,7-tetrahydro-6H-pyrazolo[3,4-c]pyridin-6-yl)(quinoxalin-6-yl)methanone; | 25.11 |
| 168 | (S)-(3-(3,5-Difluorophenyl)-2,7-dimethyl-2,4,5,7-tetrahydro-6H-pyrazolo[3,4-c]pyridin-6-yl)(quinoxalin-6-yl)methanone; | 7.04 |
| 169 | (R)-(3-(3,5-Difluorophenyl)-2,7-dimethyl-2,4,5,7-tetrahydro-6H-pyrazolo[3,4-c]pyridin-6-yl)(quinoxalin-6-yl)methanone; | 3736.80 |
| 170 | (S)-(3-(3,5-Difluorophenyl)-2,7-dimethyl-2,4,5,7-tetrahydro-6H-pyrazolo[3,4-c]pyridin-6-yl)(1,5-naphthyridin-2-yl)methanone; | 23.20 |
| 171 | (S)-(3-(3,5-Difluorophenyl)-2,7-dimethyl-2,4,5,7-tetrahydro-6H-pyrazolo[3,4-c]pyridin-6-yl)(7-fluoroquinoxalin-6-yl)methanone; | 13.00 |
| 172 | (S)-(3-(3,5-Dichlorophenyl)-2,7-dimethyl-2,4,5,7-tetrahydro-6H-pyrazolo[3,4-c]pyridin-6-yl)(2-methylbenzo[d]oxazol-6-yl)methanone; | 4.89 |
| 173 | (S)-(3-(3,5-Dichlorophenyl)-2,7-dimethyl-2,4,5,7-tetrahydro-6H-pyrazolo[3,4-c]pyridin-6-yl)(1-methyl-1H-pyrazolo[3,4-b]pyridin-3-yl)methanone; | 18.01 |
| 174 | (S)-(3-(3,5-Dichlorophenyl)-2,7-dimethyl-2,4,5,7-tetrahydro-6H-pyrazolo[3,4-c]pyridin-6-yl)(quinolin-6-yl)methanone; | 2.62 |
| 175 | (S)-(3-(3,5-Dichlorophenyl)-2,7-dimethyl-2,4,5,7-tetrahydro-6H-pyrazolo[3,4-c]pyridin-6-yl)(quinoxalin-6-yl)methanone; | 6.24 |
| 176 | (S)-(3-(3,5-Dichlorophenyl)-2,7-dimethyl-2,4,5,7-tetrahydro-6H-pyrazolo[3,4-c]pyridin-6-yl)(2-methylquinoxalin-6-yl)methanone; | 8.49 |
| 177 | (3-(3-Chloro-5-fluorophenyl)-2,7-dimethyl-2,4,5,7-tetrahydro-6H-pyrazolo[3,4-c]pyridin-6-yl)(quinolin-6-yl)methanone; | 15.92 |
| 178 | (S)-(3-(3-Chloro-5-fluorophenyl)-2,7-dimethyl-2,4,5,7-tetrahydro-6H-pyrazolo[3,4-c]pyridin-6-yl)(quinolin-6-yl)methanone; | 4.16 |
| 179 | (R)-(3-(3-Chloro-5-fluorophenyl)-2,7-dimethyl-2,4,5,7-tetrahydro-6H-pyrazolo[3,4-c]pyridin-6-yl)(quinolin-6-yl)methanone; | 592.65 |

TABLE 4-continued

| Ex # | Compound Name | MGL IC$_{50}$ (nM) |
|---|---|---|
| 180 | (3-(3-Chloro-5-fluorophenyl)-2,7-dimethyl-2,4,5,7-tetrahydro-6H-pyrazolo[3,4-c]pyridin-6-yl)(quinoxalin-6-yl)methanone; | 31.31 |
| 181 | (S)-(3-(3-Chloro-5-fluorophenyl)-2,7-dimethyl-2,4,5,7-tetrahydro-6H-pyrazolo[3,4-c]pyridin-6-yl)(quinoxalin-6-yl)methanone; | 6.37 |
| 182 | (R)-(3-(3-Chloro-5-fluorophenyl)-2,7-dimethyl-2,4,5,7-tetrahydro-6H-pyrazolo[3,4-c]pyridin-6-yl)(quinoxalin-6-yl)methanone; | >10000 |
| 183 | (S)-(3-(3-Chloro-4-methylphenyl)-2,7-dimethyl-2,4,5,7-tetrahydro-6H-pyrazolo[3,4-c]pyridin-6-yl)(quinoxalin-6-yl)methanone; | 26.93 |
| 184 | (S)-(3-(3-Fluoro-5-(trifluoromethyl)phenyl)-2,7-dimethyl-2,4,5,7-tetrahydro-6H-pyrazolo[3,4-c]pyridin-6-yl)(quinoxalin-6-yl)methanone; | 136.40 |
| 185 | (S)-(3-(3-Fluoro-4-methoxyphenyl)-2,7-dimethyl-2,4,5,7-tetrahydro-6H-pyrazolo[3,4-c]pyridin-6-yl)(quinoxalin-6-yl)methanone; | 386.46 |
| 186 | (S)-(3-(3-Fluoro-5-methoxyphenyl)-2,7-dimethyl-2,4,5,7-tetrahydro-6H-pyrazolo[3,4-c]pyridin-6-yl)(quinoxalin-6-yl)methanone; | 46.02 |
| 187 | (S)-(3-(3-Fluoro-5-methoxyphenyl)-2,7-dimethyl-2,4,5,7-tetrahydro-6H-pyrazolo[3,4-c]pyridin-6-yl)(7-fluoroquinoxalin-6-yl)methanone; | 41.68 |
| 188 | (S)-(3-(3-Chloro-4-methoxyphenyl)-2,7-dimethyl-2,4,5,7-tetrahydro-6H-pyrazolo[3,4-c]pyridin-6-yl)(quinoxalin-6-yl)methanone; | 104.59 |
| 189 | (S)-(3-(4-(Difluoromethoxy)-3-fluorophenyl)-2,7-dimethyl-2,4,5,7-tetrahydro-6H-pyrazolo[3,4-c]pyridin-6-yl)(quinoxalin-6-yl)methanone; | 102.00 |
| 190 | (S)-(3-(3,5-Difluoro-4-methylphenyl)-2,7-dimethyl-2,4,5,7-tetrahydro-6H-pyrazolo[3,4-c]pyridin-6-yl)(quinoxalin-6-yl)methanone; | 133.29 |
| 191 | (S)-(2-Chloro-3-methoxyphenyl)(2,7-dimethyl-3-(3,4,5-trifluorophenyl)-2,4,5,7-tetrahydro-6H-pyrazolo[3,4-c]pyridin-6-yl)methanone; | 2.56 |
| 192 | (S)-(3-Chloro-5-methoxyphenyl)(2,7-dimethyl-3-(3,4,5-trifluorophenyl)-2,4,5,7-tetrahydro-6H-pyrazolo[3,4-c]pyridin-6-yl)methanone; | 6.78 |
| 193 | (S)-(2,7-Dimethyl-3-(3,4,5-trifluorophenyl)-2,4,5,7-tetrahydro-6H-pyrazolo[3,4-c]pyridin-6-yl)(5-fluoro-2-(1H-pyrazol-1-yl)phenyl)methanone; | 75.46 |
| 194 | (S)-(3-(1H-1,2,4-Triazol-1-yl)phenyl)(2,7-dimethyl-3-(3,4,5-trifluorophenyl)-2,4,5,7-tetrahydro-6H-pyrazolo[3,4-c]pyridin-6-yl)methanone; | 14.83 |
| 195 | (S)-(2,7-Dimethyl-3-(3,4,5-trifluorophenyl)-2,4,5,7-tetrahydro-6H-pyrazolo[3,4-c]pyridin-6-yl)(3-fluoro-2-(2H-1,2,3-triazol-2-yl)phenyl)methanone; | 309.17 |
| 196 | (S)-(2,7-Dimethyl-3-(3,4,5-trifluorophenyl)-2,4,5,7-tetrahydro-6H-pyrazolo[3,4-c]pyridin-6-yl)(4-fluoro-2-(2H-1,2,3-triazol-2-yl)phenyl)methanone; | 307.47 |
| 197 | (S)-(2,7-Dimethyl-3-(3,4,5-trifluorophenyl)-2,4,5,7-tetrahydro-6H-pyrazolo[3,4-c]pyridin-6-yl)(5-methyl-2-(2H-1,2,3-triazol-2-yl)phenyl)methanone; | 60.02 |
| 198 | (S)-(2,7-Dimethyl-3-(3,4,5-trifluorophenyl)-2,4,5,7-tetrahydro-6H-pyrazolo[3,4-c]pyridin-6-yl)(1-methyl-5-(trifluoromethyl)-1H-pyrazol-4-yl)methanone; | 14.01 |
| 199 | (S)-(1-(tert-Butyl)-5-(trifluoromethyl)-1H-pyrazol-4-yl)(2,7-dimethyl-3-(3,4,5-trifluorophenyl)-2,4,5,7-tetrahydro-6H-pyrazolo[3,4-c]pyridin-6-yl)methanone; | 171.59 |
| 200 | (S)-(2,7-Dimethyl-3-(3,4,5-trifluorophenyl)-2,4,5,7-tetrahydro-6H-pyrazolo[3,4-c]pyridin-6-yl)(5-methoxy-1-methyl-1H-pyrazol-3-yl)methanone; | 295.12 |
| 201 | (S)-(5-Cyclopropyl-1-methyl-1H-pyrazol-4-yl)(2,7-dimethyl-3-(3,4,5-trifluorophenyl)-2,4,5,7-tetrahydro-6H-pyrazolo[3,4-c]pyridin-6-yl)methanone; | 6.26 |
| 202 | (S)-(2,7-Dimethyl-3-(3,4,5-trifluorophenyl)-2,4,5,7-tetrahydro-6H-pyrazolo[3,4-c]pyridin-6-yl)(5-ethyl-1-phenyl-1H-1,2,4-triazol-3-yl)methanone; | 7.39 |
| 203 | (S)-(2,7-Dimethyl-3-(3,4,5-trifluorophenyl)-2,4,5,7-tetrahydro-6H-pyrazolo[3,4-c]pyridin-6-yl)(5-methoxypyridin-3-yl)methanone; | 67.50 |
| 204 | (S)-6-(2,7-Dimethyl-3-(3,4,5-trifluorophenyl)-4,5,6,7-tetrahydro-2H-pyrazolo[3,4-c]pyridine-6-carbonyl)-4-methyl-2H-benzo[b][1,4]oxazin-3(4H)-one; | 17.73 |
| 205 | (S)-(2,7-Dimethyl-3-(3,4,5-trifluorophenyl)-2,4,5,7-tetrahydro-6H-pyrazolo[3,4-c]pyridin-6-yl)(1H-indol-7-yl)methanone; | 33.32 |
| 206 | (S)-(2,7-Dimethyl-3-(3,4,5-trifluorophenyl)-2,4,5,7-tetrahydro-6H-pyrazolo[3,4-c]pyridin-6-yl)(1-methyl-1H-indol-7-yl)methanone; | 4.91 |
| 207 | (S)-(2,7-Dimethyl-3-(3,4,5-trifluorophenyl)-2,4,5,7-tetrahydro-6H-pyrazolo[3,4-c]pyridin-6-yl)(1-methyl-1H-indol-4-yl)methanone; | 0.22 |

TABLE 4-continued

| Ex # | Compound Name | MGL IC$_{50}$ (nM) |
|---|---|---|
| 208 | (S)-(2,7-Dimethyl-3-(3,4,5-trifluorophenyl)-2,4,5,7-tetrahydro-6H-pyrazolo[3,4-c]pyridin-6-yl)(1H-indazol-7-yl)methanone; | 34.20 |
| 209 | (S)-(2,7-Dimethyl-3-(3,4,5-trifluorophenyl)-2,4,5,7-tetrahydro-6H-pyrazolo[3,4-c]pyridin-6-yl)(1-methyl-1H-indazol-7-yl)methanone; | 11.08 |
| 210 | (S)-(2,7-Dimethyl-3-(3,4,5-trifluorophenyl)-2,4,5,7-tetrahydro-6H-pyrazolo[3,4-c]pyridin-6-yl)(7-methyl-1H-indazol-5-yl)methanone; | 0.60 |
| 211 | (S)-(2,7-Dimethyl-3-(3,4,5-trifluorophenyl)-2,4,5,7-tetrahydro-6H-pyrazolo[3,4-c]pyridin-6-yl)(1-methyl-1H-indazol-5-yl)methanone; | 72.18 |
| 212 | (S)-(2,7-Dimethyl-3-(3,4,5-trifluorophenyl)-2,4,5,7-tetrahydro-6H-pyrazolo[3,4-c]pyridin-6-yl)(imidazo[1,5-a]pyridin-8-yl)methanone; | 5.56 |
| 213 | (S)-(2,7-Dimethyl-3-(3,4,5-trifluorophenyl)-2,4,5,7-tetrahydro-6H-pyrazolo[3,4-c]pyridin-6-yl)(imidazo[1,2-a]pyridin-3-yl)methanone; | 25.61 |
| 214 | (S)-(2,7-Dimethyl-3-(3,4,5-trifluorophenyl)-2,4,5,7-tetrahydro-6H-pyrazolo[3,4-c]pyridin-6-yl)(furo[3,2-c]pyridin-4-yl)methanone; | 23.54 |
| 215 | (S)-Benzo[d]isoxazol-3-yl(2,7-dimethyl-3-(3,4,5-trifluorophenyl)-2,4,5,7-tetrahydro-6H-pyrazolo[3,4-c]pyridin-6-yl)methanone; | 3.17 |
| 216 | (S)-(2,7-Dimethyl-3-(3,4,5-trifluorophenyl)-2,4,5,7-tetrahydro-6H-pyrazolo[3,4-c]pyridin-6-yl)(1H-pyrrolo[3,2-c]pyridin-4-yl)methanone; | 26.21 |
| 217 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[3,2-c]pyridin-4-yl)methanone; | 5.07 |
| 218 | (S)-(2,7-Dimethyl-3-(3,4,5-trifluorophenyl)-2,4,5,7-tetrahydro-6H-pyrazolo[3,4-c]pyridin-6-yl)(1H-pyrrolo[3,2-c]pyridin-3-yl)methanone; | 35.15 |
| 219 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[3,2-c]pyridin-3-yl)methanone; | 28.57 |
| 220 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[3,2-b]pyridin-3-yl)methanone; | 129.81 |
| 221 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-c]pyridin-3-yl)methanone; | 78.89 |
| 222 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-2-yl)methanone; | 64.73 |
| 223 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-3-yl)methanone; | 87.58 |
| 224 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-c]pyridin-4-yl)methanone; | 2.55 |
| 225 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-4-yl)methanone; | 0.64 |
| 226 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-5-yl)methanone; | 16.15 |
| 227 | (S)-(2,7-Dimethyl-3-(3,4,5-trifluorophenyl)-2,4,5,7-tetrahydro-6H-pyrazolo[3,4-c]pyridin-6-yl)(pyrazolo[1,5-a]pyridin-4-yl)methanone; | 9.51 |
| 228 | (S)-(2,7-Dimethyl-3-(3,4,5-trifluorophenyl)-2,4,5,7-tetrahydro-6H-pyrazolo[3,4-c]pyridin-6-yl)(pyrazolo[1,5-a]pyridin-5-yl)methanone; | 48.10 |
| 229 | (S)-(2,7-Dimethyl-3-(3,4,5-trifluorophenyl)-2,4,5,7-tetrahydro-6H-pyrazolo[3,4-c]pyridin-6-yl)(pyrazolo[1,5-a]pyrazin-3-yl)methanone; | 40.73 |
| 230 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrazolo[3,4-b]pyridin-3-yl)methanone; | 23.00 |
| 231 | (S)-(2,7-Dimethyl-3-(3,4,5-trifluorophenyl)-2,4,5,7-tetrahydro-6H-pyrazolo[3,4-c]pyridin-6-yl)(1-methyl-1H-pyrazolo[3,4-b]pyridin-5-yl)methanone; | 124.19 |
| 232 | (S)-(2-(Difluoromethyl)-7-methyl-3-(3,4,5-trifluorophenyl)-2,4,5,7-tetrahydro-6H-pyrazolo[3,4-c]pyridin-6-yl)(quinolin-6-yl)methanone; | 5.57 |
| 233 | (R)-(2-(Difluoromethyl)-7-methyl-3-(3,4,5-trifluorophenyl)-2,4,5,7-tetrahydro-6H-pyrazolo[3,4-c]pyridin-6-yl)(quinolin-6-yl)methanone; | 550.05 |
| 234 | (S)-(2,7-Dimethyl-3-(3,4,5-trifluorophenyl)-2,4,5,7-tetrahydro-6H-pyrazolo[3,4-c]pyridin-6-yl)(quinolin-6-yl)methanone; | 4.71 |
| 235 | (R)-(2,7-Dimethyl-3-(3,4,5-trifluorophenyl)-2,4,5,7-tetrahydro-6H-pyrazolo[3,4-c]pyridin-6-yl)(quinolin-6-yl)methanone; | 3661.85 |

TABLE 4-continued

| Ex # | Compound Name | MGL IC$_{50}$ (nM) |
| --- | --- | --- |
| 236 | (S)-(2,7-Dimethyl-3-(3,4,5-trifluorophenyl)-2,4,5,7-tetrahydro-6H-pyrazolo[3,4-c]pyridin-6-yl)(quinolin-8-yl)methanone; | 5.79 |
| 237 | (S)-(2,7-Dimethyl-3-(3,4,5-trifluorophenyl)-2,4,5,7-tetrahydro-6H-pyrazolo[3,4-c]pyridin-6-yl)(isoquinolin-1-yl)methanone; | 1.89 |
| 238 | (S)-(2,7-Dimethyl-3-(3,4,5-trifluorophenyl)-2,4,5,7-tetrahydro-6H-pyrazolo[3,4-c]pyridin-6-yl)(8-fluoroquinolin-4-yl)methanone; | 2.69 |
| 239 | (S)-(2,7-Dimethyl-3-(3,4,5-trifluorophenyl)-2,4,5,7-tetrahydro-6H-pyrazolo[3,4-c]pyridin-6-yl)(2-methylquinolin-4-yl)methanone; | 3.74 |
| 240 | (S)-(2,7-Dimethyl-3-(3,4,5-trifluorophenyl)-2,4,5,7-tetrahydro-6H-pyrazolo[3,4-c]pyridin-6-yl)(2-methoxyquinolin-4-yl)methanone; | 0.69 |
| 241 | (S)-(2,7-Dimethyl-3-(3,4,5-trifluorophenyl)-2,4,5,7-tetrahydro-6H-pyrazolo[3,4-c]pyridin-6-yl)(8-fluoro-2-methylquinolin-4-yl)methanone; | 6.56 |
| 242 | (S)-(2,7-Dimethyl-3-(3,4,5-trifluorophenyl)-2,4,5,7-tetrahydro-6H-pyrazolo[3,4-c]pyridin-6-yl)(quinoxalin-6-yl)methanone; | 22.30 |
| 243 | (S)-(2,7-Dimethyl-3-(3,4,5-trifluorophenyl)-2,4,5,7-tetrahydro-6H-pyrazolo[3,4-c]pyridin-6-yl)(2-methylquinoxalin-6-yl)methanone; | 25.03 |
| 244 | (S)-(2,7-Dimethyl-3-(3,4,5-trifluorophenyl)-2,4,5,7-tetrahydro-6H-pyrazolo[3,4-c]pyridin-6-yl)(1,5-naphthyridin-2-yl)methanone; | 14.13 |
| 245 | (S)-(2,7-Dimethyl-3-(3,4,5-trifluorophenyl)-2,4,5,7-tetrahydro-6H-pyrazolo[3,4-c]pyridin-6-yl)(1,5-naphthyridin-3-yl)methanone; | 121.51 |
| 246 | (S)-(2,7-Dimethyl-3-(3,4,5-trifluorophenyl)-2,4,5,7-tetrahydro-6H-pyrazolo[3,4-c]pyridin-6-yl)(1,6-naphthyridin-8-yl)methanone; | 20.00 |
| 247 | (S)-(2,7-Dimethyl-3-(5-(trifluoromethyl)furan-2-yl)-2,4,5,7-tetrahydro-6H-pyrazolo[3,4-c]pyridin-6-yl)(quinoxalin-6-yl)methanone; | 185.99 |
| 248 | (S)-(2,7-Dimethyl-3-(5-(trifluoromethyl)pyridin-3-yl)-2,4,5,7-tetrahydro-6H-pyrazolo[3,4-c]pyridin-6-yl)(quinoxalin-6-yl)methanone; | 2228.95 |
| 249 | (2,7-Dimethyl-3-(1-methyl-1H-indol-4-yl)-2,4,5,7-tetrahydro-6H-pyrazolo[3,4-c]pyridin-6-yl)(quinolin-6-yl)methanone; | 1525.11 |
| 250 | (2,7-Dimethyl-3-(1-methyl-1H-indol-2-yl)-2,4,5,7-tetrahydro-6H-pyrazolo[3,4-c]pyridin-6-yl)(quinolin-6-yl)methanone; | 206.40 |
| 251 | (2,7-Dimethyl-3-(1-methyl-1H-indol-3-yl)-2,4,5,7-tetrahydro-6H-pyrazolo[3,4-c]pyridin-6-yl)(quinolin-6-yl)methanone; | 1887.99 |
| 252 | (2,7-Dimethyl-3-(1-methyl-1H-indol-5-yl)-2,4,5,7-tetrahydro-6H-pyrazolo[3,4-c]pyridin-6-yl)(quinolin-6-yl)methanone; | 630.52 |
| 253 | (2,7-Dimethyl-3-(1-methyl-1H-indol-7-yl)-2,4,5,7-tetrahydro-6H-pyrazolo[3,4-c]pyridin-6-yl)(quinolin-6-yl)methanone. | 1605.83 |
| 254 | (S)-(3-(3,5-Difluorophenyl)-2,7-dimethyl-5,7-dihydro-4H-pyrazolo[3,4-c]pyridin-6-yl]-[3-(2-fluoranylethoxy)-2-fluoro-phenyl]methanone; | NT |
| 255 | [2-Chloro-3-(2-fluoranylethoxy)phenyl]-[(7S)-3-(3,5-difluorophenyl)-2,7-dimethyl-5,7-dihydro-4H-pyrazolo[3,4-c]pyridin-6-yl]methanone; | NT |
| 256 | (S)-[3-(3,5-Difluorophenyl)-2,7-dimethyl-5,7-dihydro-4H-pyrazolo[3,4-c]pyridin-6-yl]-[3-(2-fluoranylethoxy)-5-fluoro-phenyl]methanone; | NT |
| 257 | (3-Methoxyphenyl)-[(7S)-7-methyl-2,3-diphenyl-5,7-dihydro-4H-pyrazolo[3,4-c]pyridin-6-yl]methanone; | 100.69 |
| 258 | [(7S)-3-(3-Fluoro-5-methyl-phenyl)-2,7-dimethyl-5,7-dihydro-4H-pyrazolo[3,4-c]pyridin-6-yl]-(4-methoxyphenyl)methanone; | 68.52 |
| 259 | [(7S)-2,7-Dimethyl-3-(3,4,5-trifluorophenyl)-5,7-dihydro-4H-pyrazolo[3,4-c]pyridin-6-yl]-(2-methoxyphenyl)methanone; | 12.63 |
| 260 | [(7S)-2,7-Dimethyl-3-(3,4,5-trifluorophenyl)-5,7-dihydro-4H-pyrazolo[3,4-c]pyridin-6-yl]-(3-methoxyphenyl)methanone; | 7.25 |
| 261 | [(7S)-2,7-Dimethyl-3-(3,4,5-trifluorophenyl)-5,7-dihydro-4H-pyrazolo[3,4-c]pyridin-6-yl]-(4-methoxyphenyl)methanone; | 29.42 |
| 262 | [(7S)-2,7-Dimethyl-3-(3,4,5-trifluorophenyl)-5,7-dihydro-4H-pyrazolo[3,4-c]pyridin-6-yl]-[3-(trifluoromethoxy)phenyl]methanone; | 52.83 |
| 263 | [(7S)-2,7-Dimethyl-3-(3,4,5-trifluorophenyl)-5,7-dihydro-4H-pyrazolo[3,4-c]pyridin-6-yl]-[2-(trifluoromethoxy)phenyl]methanone; | 28.34 |
| 264 | [4-(Difluoromethoxy)phenyl]-[(7S)-2,7-dimethyl-3-(3,4,5-trifluorophenyl)-5,7-dihydro-4H-pyrazolo[3,4-c]pyridin-6-yl]methanone; | 213.30 |
| 265 | [(7S)-2,7-Dimethyl-3-(3,4,5-trifluorophenyl)-5,7-dihydro-4H-pyrazolo[3,4-c]pyridin-6-yl]-(2-fluoro-4-methoxy-phenyl)methanone; | 35.02 |
| 266 | 3-[(7S)-2,7-Dimethyl-3-(3,4,5-trifluorophenyl)-5,7-dihydro-4H-pyrazolo[3,4-c]pyridine-6-carbonyl]-N-methyl-benzamide; | 131.80 |
| 267 | [(7S)-2,7-Dimethyl-3-(3,4,5-trifluorophenyl)-5,7-dihydro-4H-pyrazolo[3,4-c]pyridin-6-yl]-(4-imidazol-1-ylphenyl)methanone; | 575.84 |
| 268 | [(7S)-2,7-Dimethyl-3-(3,4,5-trifluorophenyl)-5,7-dihydro-4H-pyrazolo[3,4-c]pyridin-6-yl]-[4-(1H-pyrazol-4-yl)phenyl]methanone; | 24.20 |

TABLE 4-continued

| Ex # | Compound Name | MGL IC$_{50}$ (nM) |
|---|---|---|
| 269 | [(7S)-2,7-Dimethyl-3-(3,4,5-trifluorophenyl)-5,7-dihydro-4H-pyrazolo[3,4-c]pyridin-6-yl]-[4-(1H-pyrazol-5-yl)phenyl]methanone; | 8.92 |
| 270 | [(7S)-2,7-Dimethyl-3-(3,4,5-trifluorophenyl)-5,7-dihydro-4H-pyrazolo[3,4-c]pyridin-6-yl]-[3-(1H-pyrazol-3-yl)phenyl]methanone; | 9.07 |
| 271 | [(7S)-2,7-Dimethyl-3-(3,4,5-trifluorophenyl)-5,7-dihydro-4H-pyrazolo[3,4-c]pyridin-6-yl]-[4-methoxy-3-(1-methylpyrazol-3-yl)phenyl]methanone; | 182.10 |
| 272 | [(7S)-2,7-Dimethyl-3-(3,4,5-trifluorophenyl)-5,7-dihydro-4H-pyrazolo[3,4-c]pyridin-6-yl]-[3-(1H-pyrazol-4-yl)phenyl]methanone; | 14.63 |
| 273 | [(7S)-2,7-Dimethyl-3-(3,4,5-trifluorophenyl)-5,7-dihydro-4H-pyrazolo[3,4-c]pyridin-6-yl]-[3-(1-methylpyrazol-4-yl)phenyl]methanone; | 93.09 |
| 274 | [(7S)-2,7-Dimethyl-3-(3,4,5-trifluorophenyl)-5,7-dihydro-4H-pyrazolo[3,4-c]pyridin-6-yl]-[2-fluoro-5-(1-methylpyrazol-4-yl)phenyl]methanone; | 13.74 |
| 275 | [(7S)-2,7-Dimethyl-3-(3,4,5-trifluorophenyl)-5,7-dihydro-4H-pyrazolo[3,4-c]pyridin-6-yl]-[3-(4-fluoropyrazol-1-yl)phenyl]methanone; | 67.30 |
| 276 | [(7S)-2,7-Dimethyl-3-(3,4,5-trifluorophenyl)-5,7-dihydro-4H-pyrazolo[3,4-c]pyridin-6-yl]-[3-(3-methyl-1,2,4-triazol-1-yl)phenyl]methanone; | 144.61 |
| 277 | [(7S)-2,7-Dimethyl-3-(3,4,5-trifluorophenyl)-5,7-dihydro-4H-pyrazolo[3,4-c]pyridin-6-yl]-[3-fluoro-5-(1,2,4-triazol-1-yl)phenyl]methanone; | 22.01 |
| 278 | [(7S)-2,7-Dimethyl-3-(3,4,5-trifluorophenyl)-5,7-dihydro-4H-pyrazolo[3,4-c]pyridin-6-yl]-[3-methoxy-5-(1,2,4-triazol-1-yl)phenyl]methanone; | 3.24 |
| 279 | [(7S)-2,7-Dimethyl-3-(3,4,5-trifluorophenyl)-5,7-dihydro-4H-pyrazolo[3,4-c]pyridin-6-yl]-[2-(1,2,4-triazol-1-yl)phenyl]methanone; | 7.34 |
| 280 | [(7S)-2,7-Dimethyl-3-(3,4,5-trifluorophenyl)-5,7-dihydro-4H-pyrazolo[3,4-c]pyridin-6-yl]-[2-fluoro-6-(1,2,4-triazol-1-yl)phenyl]methanone; | 7.77 |
| 281 | [(7S)-2,7-Dimethyl-3-(3,4,5-trifluorophenyl)-5,7-dihydro-4H-pyrazolo[3,4-c]pyridin-6-yl]-[5-fluoro-2-(1,2,4-triazol-1-yl)phenyl]methanone; | 9.01 |
| 282 | [(7S)-2,7-Dimethyl-3-(3,4,5-trifluorophenyl)-5,7-dihydro-4H-pyrazolo[3,4-c]pyridin-6-yl]-[2-[3-(trifluoromethyl)-1,2,4-triazol-1-yl]phenyl]methanone; | 1865.09 |
| 283 | [(7S)-2,7-Dimethyl-3-(3,4,5-trifluorophenyl)-5,7-dihydro-4H-pyrazolo[3,4-c]pyridin-6-yl]-[3-(triazol-2-yl)phenyl]methanone; | 19.14 |
| 284 | [(7S)-2,7-Dimethyl-3-(3,4,5-trifluorophenyl)-5,7-dihydro-4H-pyrazolo[3,4-c]pyridin-6-yl]-[3-fluoro-5-(triazol-2-yl)phenyl]methanone; | 15.58 |
| 285 | [(7S)-2,7-Dimethyl-3-(3,4,5-trifluorophenyl)-5,7-dihydro-4H-pyrazolo[3,4-c]pyridin-6-yl]-[2-fluoro-5-(triazol-2-yl)phenyl]methanone; | 18.65 |
| 286 | [(7S)-2,7-Dimethyl-3-(3,4,5-trifluorophenyl)-5,7-dihydro-4H-pyrazolo[3,4-c]pyridin-6-yl]-[3-methyl-5-(triazol-2-yl)phenyl]methanone; | 2.27 |
| 287 | [(7S)-2,7-Dimethyl-3-(3,4,5-trifluorophenyl)-5,7-dihydro-4H-pyrazolo[3,4-c]pyridin-6-yl]-[3-(triazol-2-yl)-5-(trifluoromethyl)phenyl]methanone; | 60.42 |
| 288 | [(7S)-2,7-Dimethyl-3-(3,4,5-trifluorophenyl)-5,7-dihydro-4H-pyrazolo[3,4-c]pyridin-6-yl]-[2-fluoro-6-(triazol-2-yl)phenyl]methanone; | 59.81 |
| 289 | [(7S)-2,7-Dimethyl-3-(3,4,5-trifluorophenyl)-5,7-dihydro-4H-pyrazolo[3,4-c]pyridin-6-yl]-[5-methoxy-2-(triazol-2-yl)phenyl]methanone; | 19.82 |
| 290 | [(7S)-2,7-Dimethyl-3-(3,4,5-trifluorophenyl)-5,7-dihydro-4H-pyrazolo[3,4-c]pyridin-6-yl]-[3-(1,2,4-triazol-4-yl)phenyl]methanone; | 71.80 |
| 291 | [(7S)-2,7-Dimethyl-3-(3,4,5-trifluorophenyl)-5,7-dihydro-4H-pyrazolo[3,4-c]pyridin-6-yl]-[4-fluoro-3-(1,2,4-triazol-4-yl)phenyl]methanone; | 1395.08 |
| 292 | [(7S)-2,7-Dimethyl-3-(3,4,5-trifluorophenyl)-5,7-dihydro-4H-pyrazolo[3,4-c]pyridin-6-yl]-[3-fluoro-5-(1,2,4-triazol-4-yl)phenyl]methanone; | 245.19 |
| 293 | [(7S)-2,7-Dimethyl-3-(3,4,5-trifluorophenyl)-5,7-dihydro-4H-pyrazolo[3,4-c]pyridin-6-yl]-[3-methyl-5-(1,2,4-triazol-4-yl)phenyl]methanone; | 63.04 |
| 294 | [(7S)-2,7-Dimethyl-3-(3,4,5-trifluorophenyl)-5,7-dihydro-4H-pyrazolo[3,4-c]pyridin-6-yl]-[4-methyl-3-(1,2,4-triazol-4-yl)phenyl]methanone; | 1661.88 |

TABLE 4-continued

| Ex # | Compound Name | MGL IC$_{50}$ (nM) |
|---|---|---|
| 295 | [(7S)-2,7-Dimethyl-3-(3,4,5-trifluorophenyl)-5,7-dihydro-4H-pyrazolo[3,4-c]pyridin-6-yl]-[3-(1,2,4-triazol-4-yl)-4-(trifluoromethyl)phenyl]methanone; | NT |
| 296 | [(7S)-2,7-Dimethyl-3-(3,4,5-trifluorophenyl)-5,7-dihydro-4H-pyrazolo[3,4-c]pyridin-6-yl]-[3-(1,2,4-triazol-4-yl)-5-(trifluoromethyl)phenyl]methanone; | 608.42 |
| 297 | [(7S)-2,7-Dimethyl-3-(3,4,5-trifluorophenyl)-5,7-dihydro-4H-pyrazolo[3,4-c]pyridin-6-yl]-[4-methoxy-3-(1,2,4-triazol-4-yl)phenyl]methanone; | 923.00 |
| 298 | [(7S)-2,7-Dimethyl-3-(3,4,5-trifluorophenyl)-5,7-dihydro-4H-pyrazolo[3,4-c]pyridin-6-yl]-[3-methoxy-5-(1,2,4-triazol-4-yl)phenyl]methanone; | 18.71 |
| 299 | [(7S)-2,7-Dimethyl-3-(3,4,5-trifluorophenyl)-5,7-dihydro-4H-pyrazolo[3,4-c]pyridin-6-yl]-[2-(1,2,4-triazol-4-yl)phenyl]methanone; | NT |
| 300 | [(7S)-2,7-Dimethyl-3-(3,4,5-trifluorophenyl)-5,7-dihydro-4H-pyrazolo[3,4-c]pyridin-6-yl]-(6-methoxy-3-pyridyl)methanone; | 262.79 |
| 301 | [(7S)-2,7-Dimethyl-3-(3,4,5-trifluorophenyl)-5,7-dihydro-4H-pyrazolo[3,4-c]pyridin-6-yl]-(5-methoxy-2-pyridyl)methanone; | 248.31 |
| 302 | [(7S)-2,7-Dimethyl-3-(3,4,5-trifluorophenyl)-5,7-dihydro-4H-pyrazolo[3,4-c]pyridin-6-yl]-(6-methoxy-3-methyl-2-pyridyl)methanone; | 311.67 |
| 303 | [(7S)-2,7-Dimethyl-3-(3,4,5-trifluorophenyl)-5,7-dihydro-4H-pyrazolo[3,4-c]pyridin-6-yl]-(3-methoxy-2-pyridyl)methanone; | 112.80 |
| 304 | [(7S)-2,7-Dimethyl-3-(3,4,5-trifluorophenyl)-5,7-dihydro-4H-pyrazolo[3,4-c]pyridin-6-yl]-[5-(methoxymethyl)-3-pyridyl]methanone; | 577.70 |
| 305 | [(7S)-2,7-Dimethyl-3-(3,4,5-trifluorophenyl)-5,7-dihydro-4H-pyrazolo[3,4-c]pyridin-6-yl]-(5-isopropoxy-3-pyridyl)methanone; | 228.82 |
| 306 | [(7S)-2,7-Dimethyl-3-(3,4,5-trifluorophenyl)-5,7-dihydro-4H-pyrazolo[3,4-c]pyridin-6-yl]-(6-methoxy-2-methyl-3-pyridyl)methanone; | 189.02 |
| 307 | [(7S)-2,7-Dimethyl-3-(3,4,5-trifluorophenyl)-5,7-dihydro-4H-pyrazolo[3,4-c]pyridin-6-yl]-(4-methoxy-3-methyl-2-pyridyl)methanone; | 180.88 |
| 308 | [(7S)-2,7-Dimethyl-3-(3,4,5-trifluorophenyl)-5,7-dihydro-4H-pyrazolo[3,4-c]pyridin-6-yl]-(5-methoxy-2-methyl-3-pyridyl)methanone; | 114.79 |
| 309 | [(7S)-2,7-Dimethyl-3-(3,4,5-trifluorophenyl)-5,7-dihydro-4H-pyrazolo[3,4-c]pyridin-6-yl]-(4-methoxy-2-pyridyl)methanone; | 219.38 |
| 310 | [(7S)-2,7-Dimethyl-3-(3,4,5-trifluorophenyl)-5,7-dihydro-4H-pyrazolo[3,4-c]pyridin-6-yl]-(5-methoxy-6-methyl-3-pyridyl)methanone; | 96.27 |
| 311 | [(7S)-2,7-Dimethyl-3-(3,4,5-trifluorophenyl)-5,7-dihydro-4H-pyrazolo[3,4-c]pyridin-6-yl]-(3-methoxy-4-pyridyl)methanone; | 87.12 |
| 312 | [(7S)-2,7-Dimethyl-3-(3,4,5-trifluorophenyl)-5,7-dihydro-4H-pyrazolo[3,4-c]pyridin-6-yl]-(2-methoxy-4-pyridyl)methanone; | 81.66 |
| 313 | [(7S)-2,7-Dimethyl-3-(3,4,5-trifluorophenyl)-5,7-dihydro-4H-pyrazolo[3,4-c]pyridin-6-yl]-(5-methoxy-4-methyl-3-pyridyl)methanone; | 37.96 |
| 314 | [(7S)-2,7-Dimethyl-3-(3,4,5-trifluorophenyl)-5,7-dihydro-4H-pyrazolo[3,4-c]pyridin-6-yl]-(2-methoxy-3-methyl-4-pyridyl)methanone; | 20.60 |
| 315 | [(7S)-2,7-Dimethyl-3-(3,4,5-trifluorophenyl)-5,7-dihydro-4H-pyrazolo[3,4-c]pyridin-6-yl]-(3-fluoro-2-methoxy-4-pyridyl)methanone; | 42.42 |
| 316 | (3-Chloro-2-methoxy-4-pyridyl)-[(7S)-2,7-dimethyl-3-(3,4,5-trifluorophenyl)-5,7-dihydro-4H-pyrazolo[3,4-c]pyridin-6-yl]methanone; | 17.20 |
| 317 | (3-Chloro-4-methoxy-2-pyridyl)-[(7S)-2,7-dimethyl-3-(3,4,5-trifluorophenyl)-5,7-dihydro-4H-pyrazolo[3,4-c]pyridin-6-yl]methanone; | 30.07 |
| 318 | [(7S)-2,7-Dimethyl-3-(3,4,5-trifluorophenyl)-5,7-dihydro-4H-pyrazolo[3,4-c]pyridin-6-yl]-(5-pyrazol-1-yl-3-pyridyl)methanone; | 177.58 |
| 319 | [(7S)-2,7-Dimethyl-3-(3,4,5-trifluorophenyl)-5,7-dihydro-4H-pyrazolo[3,4-c]pyridin-6-yl]-[6-methyl-3-(triazol-2-yl)-2-pyridyl]methanone; | 255.27 |
| 320 | [(7S)-2,7-Dimethyl-3-(3,4,5-trifluorophenyl)-5,7-dihydro-4H-pyrazolo[3,4-c]pyridin-6-yl]-(6-pyrazol-1-yl-2-pyridyl)methanone; | 79.05 |
| 321 | [(7S)-2,7-Dimethyl-3-(3,4,5-trifluorophenyl)-5,7-dihydro-4H-pyrazolo[3,4-c]pyridin-6-yl]-(5-methyl-1-phenyl-1,2,4-triazol-3-yl)methanone; | 14.84 |
| 322 | [(7S)-2,7-Dimethyl-3-(3,4,5-trifluorophenyl)-5,7-dihydro-4H-pyrazolo[3,4-c]pyridin-6-yl]-[1-(4-fluorophenyl)-5-methyl-1,2,4-triazol-3-yl]methanone; | 34.56 |

TABLE 4-continued

| Ex # | Compound Name | MGL IC$_{50}$ (nM) |
| --- | --- | --- |
| 323 | [(7S)-2,7-Dimethyl-3-(3,4,5-trifluorophenyl)-5,7-dihydro-4H-pyrazolo[3,4-c]pyridin-6-yl]-[1-(2-pyridyl)-1,2,4-triazol-3-yl]methanone; | 65.64 |
| 324 | [(7S)-2,7-Dimethyl-3-(3,4,5-trifluorophenyl)-5,7-dihydro-4H-pyrazolo[3,4-c]pyridin-6-yl]-[1-(3-fluoro-2-pyridyl)-1,2,4-triazol-3-yl]methanone; | 41.66 |
| 325 | [(7S)-2,7-Dimethyl-3-(3,4,5-trifluorophenyl)-5,7-dihydro-4H-pyrazolo[3,4-c]pyridin-6-yl]-[5-(2-pyridyl)-2-thienyl]methanone; | 7.90 |
| 326 | [(7S)-2,7-Dimethyl-3-(3,4,5-trifluorophenyl)-5,7-dihydro-4H-pyrazolo[3,4-c]pyridin-6-yl]-(5-methoxypyrazin-2-yl)methanone; | 522.16 |
| 327 | (1,5-Dimethylpyrazol-4-yl)-[(7S)-3-(3-fluoro-5-methyl-phenyl)-2,7-dimethyl-5,7-dihydro-4H-pyrazolo[3,4-c]pyridin-6-yl]methanone; | 55.30 |
| 328 | [(7S)-2,7-Dimethyl-3-(3,4,5-trifluorophenyl)-5,7-dihydro-4H-pyrazolo[3,4-c]pyridin-6-yl]-(5-isopropyl-1-methyl-pyrazol-4-yl)methanone; | 1085.93 |
| 329 | [(7S)-2,7-Dimethyl-3-(3,4,5-trifluorophenyl)-5,7-dihydro-4H-pyrazolo[3,4-c]pyridin-6-yl]-[1-(trifluoromethyl)pyrazol-4-yl]methanone; | 5075.75 |
| 330 | [5-(Difluoromethyl)-1-methyl-pyrazol-4-yl]-[(7S)-2,7-dimethyl-3-(3,4,5-trifluorophenyl)-5,7-dihydro-4H-pyrazolo[3,4-c]pyridin-6-yl]methanone; | 101.60 |
| 331 | (1-Cyclopropylpyrazol-4-yl)-[(7S)-2,7-dimethyl-3-(3,4,5-trifluorophenyl)-5,7-dihydro-4H-pyrazolo[3,4-c]pyridin-6-yl]methanone; | 249.92 |
| 332 | [1-Cyclopropyl-3-(trifluoromethyl)pyrazol-4-yl]-[(7S)-2,7-dimethyl-3-(3,4,5-trifluorophenyl)-5,7-dihydro-4H-pyrazolo[3,4-c]pyridin-6-yl]methanone; | 143.19 |
| 333 | (5-Cyclobutyl-1-methyl-pyrazol-4-yl)-[(7S)-2,7-dimethyl-3-(3,4,5-trifluorophenyl)-5,7-dihydro-4H-pyrazolo[3,4-c]pyridin-6-yl]methanone; | 25.39 |
| 334 | [(7S)-2,7-Dimethyl-3-(3,4,5-trifluorophenyl)-5,7-dihydro-4H-pyrazolo[3,4-c]pyridin-6-yl]-[1-methyl-5-(1-methylcyclopropyl)pyrazol-4-yl]methanone; | 2791.26 |
| 335 | [(7S)-2,7-Dimethyl-3-(3,4,5-trifluorophenyl)-5,7-dihydro-4H-pyrazolo[3,4-c]pyridin-6-yl]-[5-(1-fluorocyclopropyl)-1-methyl-pyrazol-4-yl]methanone; | 32.06 |
| 336 | (5-(2,2-Difluorocyclopropyl)-1-methyl-1H-pyrazol-4-yl)((S)-2,7-dimethyl-3-(3,4,5-trifluorophenyl)-4,5-dihydro-2H-pyrazolo[3,4-c]pyridin-6-yl)methanone; | 8.70 |
| 337 | (5-((R*)-2,2-difluorocyclopropyl)-1-methyl-1H-pyrazol-4-yl)((S)-2,7-dimethyl-3-(3,4,5-trifluorophenyl)-2,4,5,7-tetrahydro-6H-pyrazolo[3,4-c]pyridin-6-yl)methanone; | 8.07 |
| 338 | (5-((S*)-2,2-Difluorocyclopropyl)-1-methyl-1H-pyrazol-4-yl)((S)-2,7-dimethyl-3-(3,4,5-trifluorophenyl)-2,4,5,7-tetrahydro-6H-pyrazolo[3,4-c]pyridin-6-yl)methanone; | 14.25 |
| 339 | ((S)-2,7-Dimethyl-3-(3,4,5-trifluorophenyl)-2,4,5,7-tetrahydro-6H-pyrazolo[3,4-c]pyridin-6-yl)(cis-5-(2-fluorocyclopropyl)-1-methyl-1H-pyrazol-4-yl)methanone; | 3.01 |
| 340 | ((S)-2,7-Dimethyl-3-(3,4,5-trifluorophenyl)-2,4,5,7-tetrahydro-6H-pyrazolo[3,4-c]pyridin-6-yl)(trans-5-(2-fluorocyclopropyl)-1-methyl-1H-pyrazol-4-yl)methanone; | 32.49 |
| 341 | ((S)-2,7-Dimethyl-3-(3,4,5-trifluorophenyl)-2,4,5,7-tetrahydro-6H-pyrazolo[3,4-c]pyridin-6-yl)(1-methyl-cis-5-(2-methylcyclopropyl)-1H-pyrazol-4-yl)methanone; | 9.53 |
| 342 | (S*)-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone; | 254.51 |
| 343 | (1,3-Dimethylpyrazol-4-yl)-[(7S)-2,7-dimethyl-3-(3,4,5-trifluorophenyl)-5,7-dihydro-4H-pyrazolo[3,4-c]pyridin-6-yl]methanone; | 308.18 |
| 344 | [(7S)-2,7-Dimethyl-3-(3,4,5-trifluorophenyl)-5,7-dihydro-4H-pyrazolo[3,4-c]pyridin-6-yl]-(1,3,5-trimethylpyrazol-4-yl)methanone; | 58.13 |
| 345 | (1,5-Dimethylpyrazol-4-yl)-[(7S)-2,7-dimethyl-3-(3,4,5-trifluorophenyl)-5,7-dihydro-4H-pyrazolo[3,4-c]pyridin-6-yl]methanone; | 52.75 |
| 346 | [1-Cyclopropyl-5-(trifluoromethyl)pyrazol-4-yl]-[(7S)-2,7-dimethyl-3-(3,4,5-trifluorophenyl)-5,7-dihydro-4H-pyrazolo[3,4-c]pyridin-6-yl]methanone; | 22.44 |
| 347 | [(7S)-2,7-Dimethyl-3-(3,4,5-trifluorophenyl)-5,7-dihydro-4H-pyrazolo[3,4-c]pyridin-6-yl]-[1-methyl-3-(1-methylcyclopropyl)pyrazol-4-yl]methanone; | 2492.87 |
| 348 | [(7S)-2,7-Dimethyl-3-(3,4,5-trifluorophenyl)-5,7-dihydro-4H-pyrazolo[3,4-c]pyridin-6-yl]-[3-(1-fluorocyclopropyl)-1-methyl-pyrazol-4-yl]methanone; | 848.20 |

TABLE 4-continued

| Ex # | Compound Name | MGL IC$_{50}$ (nM) |
|---|---|---|
| 349 | (R)-(5-cyclopropyl-1-methyl-1H-pyrazol-4-yl) (7-methyl-2,3-diphenyl-2,4,5,7-tetrahydro-6H-pyrazolo[3,4-c] pyridin-6-yl)methanone; | 1077.95 |
| 350 | (S)-(5-cyclopropyl-1-methyl-1H-pyrazol-4-yl) (7-methyl-2,3-diphenyl-2,4,5,7-tetrahydro-6H-pyrazolo[3,4-c] pyridin-6-yl)methanone; | 27.64 |
| 351 | (1,2-Dimethylpyrrol-3-yl)-[(7S)-2,7-dimethyl-3-(3,4,5-trifluorophenyl)-5,7-dihydro-4H-pyrazolo[3,4-c]pyridin-6-yl]methanone; | 8.90 |
| 352 | (4,5-Dimethylisoxazol-3-yl)-[(7S)-2,7-dimethyl-3-(3,4,5-trifluorophenyl)-5,7-dihydro-4H-pyrazolo[3,4-c]pyridin-6-yl]methanone; | 30.54 |
| 353 | [(7S)-2,7-Dimethyl-3-(3,4,5-trifluorophenyl)-5,7-dihydro-4H-pyrazolo[3,4-c]pyridin-6-yl]-(5-fluoro-1H-indol-6-yl)methanone; | 48.53 |
| 354 | [(7S)-2,7-Dimethyl-3-(3,4,5-trifluorophenyl)-5,7-dihydro-4H-pyrazolo[3,4-c]pyridin-6-yl]-(7-fluoro-1H-indol-4-yl)methanone; | 2.23 |
| 355 | [(7S)-2,7-Dimethyl-3-(3,4,5-trifluorophenyl)-5,7-dihydro-4H-pyrazolo[3,4-c]pyridin-6-yl]-(5-fluoro-1H-indol-3-yl)methanone; | 22.82 |
| 356 | [(7S)-2,7-Dimethyl-3-(3,4,5-trifluorophenyl)-5,7-dihydro-4H-pyrazolo[3,4-c]pyridin-6-yl]-(5-fluoro-1-methyl-indol-3-yl)methanone; | 18.65 |
| 357 | [(7S)-2,7-Dimethyl-3-(3,4,5-trifluorophenyl)-5,7-dihydro-4H-pyrazolo[3,4-c]pyridin-6-yl]-(4-fluoro-1H-indol-3-yl)methanone; | 8.88 |
| 358 | [(7S)-2,7-Dimethyl-3-(3,4,5-trifluorophenyl)-5,7-dihydro-4H-pyrazolo[3,4-c]pyridin-6-yl]-(6-fluoro-1H-indol-3-yl)methanone; | 37.61 |
| 359 | [(7S)-2,7-Dimethyl-3-(3,4,5-trifluorophenyl)-5,7-dihydro-4H-pyrazolo[3,4-c]pyridin-6-yl]-(7-fluoro-1H-indol-3-yl)methanone; | 31.05 |
| 360 | [(7S)-2,7-Dimethyl-3-(3,4,5-trifluorophenyl)-5,7-dihydro-4H-pyrazolo[3,4-c]pyridin-6-yl]-(6-methyl-1H-indol-3-yl)methanone; | 46.78 |
| 361 | [(7S)-2,7-Dimethyl-3-(3,4,5-trifluorophenyl)-5,7-dihydro-4H-pyrazolo[3,4-c]pyridin-6-yl]-(1H-indazol-3-yl)methanone; | 14.63 |
| 362 | [(7S)-2,7-Dimethyl-3-(3,4,5-trifluorophenyl)-5,7-dihydro-4H-pyrazolo[3,4-c]pyridin-6-yl]-(4-fluoro-1H-indazol-3-yl)methanone; | 2.74 |
| 363 | [(7S)-2,7-Dimethyl-3-(3,4,5-trifluorophenyl)-5,7-dihydro-4H-pyrazolo[3,4-c]pyridin-6-yl]-(6-fluoro-1H-indazol-3-yl)methanone; | 44.14 |
| 364 | [(7S)-2,7-Dimethyl-3-(3,4,5-trifluorophenyl)-5,7-dihydro-4H-pyrazolo[3,4-c]pyridin-6-yl]-(5-fluoro-1H-indazol-3-yl)methanone; | 20.34 |
| 365 | [(7S)-2,7-Dimethyl-3-(3,4,5-trifluorophenyl)-5,7-dihydro-4H-pyrazolo[3,4-c]pyridin-6-yl]-(2-methylindazol-3-yl)methanone; | 66.37 |
| 366 | [(7S)-2,7-Dimethyl-3-(3,4,5-trifluorophenyl)-5,7-dihydro-4H-pyrazolo[3,4-c]pyridin-6-yl]-(1-methylbenzimidazol-4-yl)methanone; | 51.87 |
| 367 | 1H-Benzotriazol-4-yl-[(7S)-2,7-dimethyl-3-(3,4,5-trifluorophenyl)-5,7-dihydro-4H-pyrazolo[3,4-c]pyridin-6-yl]methanone; | 658.26 |
| 368 | [(7S)-2,7-Dimethyl-3-(3,4,5-trifluorophenyl)-5,7-dihydro-4H-pyrazolo[3,4-c]pyridin-6-yl]-(1H-pyrrolo[2,3-b]pyridin-5-yl)methanone; | 9.36 |
| 369 | [(7S)-2,7-Dimethyl-3-(3,4,5-trifluorophenyl)-5,7-dihydro-4H-pyrazolo[3,4-c]pyridin-6-yl]-(5-fluoro-1H-pyrrolo[2,3-b]pyridin-4-yl)methanone; | 1.88 |
| 370 | [(7S)-2,7-Dimethyl-3-(3,4,5-trifluorophenyl)-5,7-dihydro-4H-pyrazolo[3,4-c]pyridin-6-yl]-(5-fluoro-1-methyl-pyrrolo[2,3-b]pyridin-4-yl)methanone; | 0.30 |
| 371 | [(7S)-2,7-Dimethyl-3-(3,4,5-trifluorophenyl)-5,7-dihydro-4H-pyrazolo[3,4-c]pyridin-6-yl]-[5-(trifluoromethyl)-1H-pyrrolo[2,3-b]pyridin-4-yl] methanone; | 135.80 |
| 372 | [(7S)-3-(3,5-Difluorophenyl)-2,7-dimethyl-5,7-dihydro-4H-pyrazolo[3,4-c]pyridin-6-yl]-[1-(2-fluoranylethyl)pyrrolo[2,3-b]pyridin-4-yl]methanone; | NT |
| 373 | [(7S)-2,7-Dimethyl-3-(3,4,5-trifluorophenyl)-5,7-dihydro-4H-pyrazolo[3,4-c]pyridin-6-yl]-(1H-pyrrolo[2,3-b]pyridin-3-yl)methanone; | 23.23 |
| 374 | [(7S)-2,7-Dimethyl-3-(3,4,5-trifluorophenyl)-5,7-dihydro-4H-pyrazolo[3,4-c]pyridin-6-yl]-(5-fluoro-1H-pyrrolo[2,3-b]pyridin-3-yl)methanone; | 21.03 |
| 375 | [(7S)-2,7-Dimethyl-3-(3,4,5-trifluorophenyl)-5,7-dihydro-4H-pyrazolo[3,4-c]pyridin-6-yl]-(2-methyl-1H-pyrrolo[2,3-b]pyridin-3-yl)methanone; | 30.32 |
| 376 | [(7S)-2,7-Dimethyl-3-(3,4,5-trifluorophenyl)-5,7-dihydro-4H-pyrazolo[3,4-c]pyridin-6-yl]-(1H-pyrrolo[2,3-c]pyridin-7-yl)methanone; | 598.83 |
| 377 | [(7S)-2,7-Dimethyl-3-(3,4,5-trifluorophenyl)-5,7-dihydro-4H-pyrazolo[3,4-c]pyridin-6-yl]-(3-fluoropyrazolo[1,5-a]pyridin-4-yl)methanone; | 4.68 |
| 378 | [(7S)-2,7-Dimethyl-3-(3,4,5-trifluorophenyl)-5,7-dihydro-4H-pyrazolo[3,4-c]pyridin-6-yl]-(3-fluoropyrazolo[1,5-a]pyridin-5-yl)methanone; | 38.79 |

TABLE 4-continued

| Ex # | Compound Name | MGL IC$_{50}$ (nM) |
|---|---|---|
| 379 | (3-Bromopyrazolo[1,5-a]pyridin-4-yl)-[(7S)-2,7-dimethyl-3-(3,4,5-trifluorophenyl)-5,7-dihydro-4H-pyrazolo[3,4-c]pyridin-6-yl]methanone; | 45.53 |
| 380 | [(7S)-2,7-Dimethyl-3-(3,4,5-trifluorophenyl)-5,7-dihydro-4H-pyrazolo[3,4-c]pyridin-6-yl]-(3-methylpyrazolo[1,5-a]pyridin-4-yl)methanone; | 43.99 |
| 381 | [(7S)-2,7-Dimethyl-3-(3,4,5-trifluorophenyl)-5,7-dihydro-4H-pyrazolo[3,4-c]pyridin-6-yl]-pyrazolo[1,5-a]pyridin-3-yl-methanone; | 10.69 |
| 382 | [(7S)-2,7-Dimethyl-3-(3,4,5-trifluorophenyl)-5,7-dihydro-4H-pyrazolo[3,4-c]pyridin-6-yl]-(2-methylpyrazolo[1,5-a]pyridin-3-yl)methanone; | 4.26 |
| 383 | [(7S)-2,7-Dimethyl-3-(3,4,5-trifluorophenyl)-5,7-dihydro-4H-pyrazolo[3,4-c]pyridin-6-yl]-(5-methylpyrazolo[1,5-a]pyridin-3-yl)methanone; | 6.39 |
| 384 | [(7S)-2,7-Dimethyl-3-(3,4,5-trifluorophenyl)-5,7-dihydro-4H-pyrazolo[3,4-c]pyridin-6-yl]-(6-fluoropyrazolo[1,5-a]pyridin-3-yl)methanone; | 43.99 |
| 385 | (2-Cyclopropyl-7-methyl-pyrazolo[1,5-a]pyridin-3-yl)-[(7S)-2,7-dimethyl-3-(3,4,5-trifluorophenyl)-5,7-dihydro-4H-pyrazolo[3,4-c]pyridin-6-yl]methanone; | 120.39 |
| 386 | [(7S)-2,7-Dimethyl-3-(3,4,5-trifluorophenyl)-5,7-dihydro-4H-pyrazolo[3,4-c] pyridin-6-yl]-(7-methylpyrazolo[1,5-a] pyridin-3-yl)methanone; | 11.67 |
| 387 | [(7S)-2,7-Dimethyl-3-(3,4,5-trifluorophenyl)-5,7-dihydro-4H-pyrazolo[3,4-c]pyridin-6-yl]-(7-methoxypyrazolo[1,5-a]pyridin-3-yl)methanone; | 26.38 |
| 388 | [(7S)-2,7-Dimethyl-3-(3,4,5-trifluorophenyl)-5,7-dihydro-4H-pyrazolo[3,4-c]pyridin-6-yl]-(6-methoxypyrazolo[1,5-a]pyridin-3-yl)methanone; | 60.67 |
| 389 | [(7S)-2,7-Dimethyl-3-(3,4,5-trifluorophenyl)-5,7-dihydro-4H-pyrazolo[3,4-c]pyridin-6-yl]-(5-methoxypyrazolo[1,5-a]pyridin-3-yl)methanone; | 9.94 |
| 390 | [(7S)-2,7-Dimethyl-3-(3,4,5-trifluorophenyl)-5,7-dihydro-4H-pyrazolo[3,4-c] pyridin-6-yl]-(4-methoxypyrazolo[1,5-a]pyridin-3-yl)methanone; | 12.60 |
| 391 | [(7S)-2,7-Dimethyl-3-(3,4,5-trifluorophenyl)-5,7-dihydro-4H-pyrazolo[3,4-c]pyridin-6-yl]-imidazo[1,2-a]pyridin-6-yl-methanone; | 103.49 |
| 392 | [(7S)-2,7-Dimethyl-3-(3,4,5-trifluorophenyl)-5,7-dihydro-4H-pyrazolo[3,4-c]pyridin-6-yl]-imidazo[1,2-a]pyridin-8-yl-methanone; | 710.56 |
| 393 | [(7S)-2,7-Dimethyl-3-(3,4,5-trifluorophenyl)-5,7-dihydro-4H-pyrazolo[3,4-c]pyridin-6-yl]-(7-fluoroimidazo[1,2-a]pyridin-3-yl)methanone; | 252.17 |
| 394 | [(7S)-2,7-Dimethyl-3-(3,4,5-trifluorophenyl)-5,7-dihydro-4H-pyrazolo[3,4-c] pyridin-6-yl]-(2-methylimidazo[1,2-a]pyridin-5-yl)methanone; | 140.31 |
| 395 | [(7S)-3-(3-Chloro-5-methoxy-phenyl)-2,7-dimethyl-5,7-dihydro-4H-pyrazolo[3,4-c] pyridin-6-yl]-(2-methylimidazo[1,2-a] pyridin-3-yl) methanone; | 6.73 |
| 396 | [(7S)-3-(3-Fluoro-5-methyl-phenyl)-2,7-dimethyl-5,7-dihydro-4H-pyrazolo[3,4-c] pyridin-6-yl]-(2-methylimidazo[1,2-a] pyridin-3-yl)methanone; | 5.04 |
| 397 | [(7S)-2,7-Dimethyl-3-(3,4,5-trifluorophenyl)-5,7-dihydro-4H-pyrazolo[3,4-c]pyridin-6-yl]-(2-methylimidazo[1,2-a]pyridin-3-yl)methanone; | 10.25 |
| 398 | [(7S)-2,7-Dimethyl-3-(3,4,5-trifluorophenyl)-5,7-dihydro-4H-pyrazolo[3,4-c]pyridin-6-yl]-(3-methylimidazo[1,2-a]pyridin-2-yl)methanone; | 247.97 |
| 399 | [(7S)-2,7-Dimethyl-3-(3,4,5-trifluorophenyl)-5,7-dihydro-4H-pyrazolo[3,4-c]pyridin-6-yl]-(7-methylimidazo[1,2-a]pyridin-3-yl)methanone; | 63.23 |
| 400 | [(7S)-2,7-Dimethyl-3-(3,4,5-trifluorophenyl)-5,7-dihydro-4H-pyrazolo[3,4-c]pyridin-6-yl]-(6-methylimidazo[1,2-a]pyridin-3-yl)methanone; | 52.26 |
| 401 | [(7S)-2,7-Dimethyl-3-(3,4,5-trifluorophenyl)-5,7-dihydro-4H-pyrazolo[3,4-c]pyridin-6-yl]-(5-methylimidazo[1,2-a]pyridin-3-yl)methanone; | 14.47 |
| 402 | [(7S)-2,7-Dimethyl-3-(3,4,5-trifluorophenyl)-5,7-dihydro-4H-pyrazolo[3,4-c]pyridin-6-yl]-(7-fluoro-2-methyl-imidazo[1,2-a]pyridin-3-yl)methanone; | 21.64 |
| 403 | (2,8-Dimethylimidazo[1,2-a] pyridin-3-yl)-[(7S)-2,7-dimethyl-3-(3,4,5-trifluorophenyl)-5,7-dihydro-4H-pyrazolo[3,4-c] pyridin-6-yl]methanone; | 43.58 |

TABLE 4-continued

| Ex # | Compound Name | MGL IC$_{50}$ (nM) |
| --- | --- | --- |
| 404 | (2,7-Dimethylimidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone; | 50.48 |
| 405 | (2,6-Dimethylimidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone; | 279.90 |
| 406 | [(7S)-3-(3-Chloro-5-methoxy-phenyl)-2,7-dimethyl-5,7-dihydro-4H-pyrazolo[3,4-c]pyridin-6-yl]-(6-fluoro-2-methyl-imidazo[1,2-a]pyridin-3-yl)methanone; | 22.59 |
| 407 | [(7S)-2,7-Dimethyl-3-(3,4,5-trifluorophenyl)-5,7-dihydro-4H-pyrazolo[3,4-c]pyridin-6-yl]-(6-fluoro-2-methyl-imidazo[1,2-a]pyridin-3-yl)methanone; | 21.33 |
| 408 | [(7S)-2,7-Dimethyl-3-(3,4,5-trifluorophenyl)-5,7-dihydro-4H-pyrazolo[3,4-c]pyridin-6-yl]-(6-fluoro-2,8-dimethyl-imidazo[1,2-a]pyridin-3-yl)methanone; | 26.96 |
| 409 | [(7S)-2,7-Dimethyl-3-(3,4,5-trifluorophenyl)-5,7-dihydro-4H-pyrazolo[3,4-c]pyridin-6-yl]-(6-fluoro-2,7-dimethyl-imidazo[1,2-a]pyridin-3-yl)methanone; | 76.59 |
| 410 | (6,8-Difluoro-2-methyl-imidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone; | 172.58 |
| 411 | [(7S)-2,7-Dimethyl-3-(3,4,5-trifluorophenyl)-5,7-dihydro-4H-pyrazolo[3,4-c]pyridin-6-yl]-(6-methoxy-2-methyl-imidazo[1,2-a]pyridin-3-yl)methanone; | 203.70 |
| 412 | [2-(Difluoromethyl)imidazo[1,2-a]pyridin-3-yl]-[(7S)-2,7-dimethyl-3-(3,4,5-trifluorophenyl)-5,7-dihydro-4H-pyrazolo[3,4-c]pyridin-6-yl]methanone; | 12.94 |
| 413 | [(7S)-2,7-Dimethyl-3-(3,4,5-trifluorophenyl)-5,7-dihydro-4H-pyrazolo[3,4-c] pyridin-6-yl]-[2-(trifluoromethyl) imidazo[1,2-a]pyridin-3-yl]methanone; | 23.00 |
| 414 | [(7S)-2,7-Dimethyl-3-(3,4,5-trifluorophenyl)-5,7-dihydro-4H-pyrazolo[3,4-c]pyridin-6-yl]-[5-methyl-2-(trifluoromethyl)imidazo[1,2-a]pyridin-3-yl]methanone; | 20.43 |
| 415 | [(7S)-2,7-Dimethyl-3-(3,4,5-trifluorophenyl)-5,7-dihydro-4H-pyrazolo[3,4-c] pyridin-6-yl]-pyrrolo[1,2-a] pyrazin-1-yl-methanone; | 13.28 |
| 416 | [(7S)-2,7-Dimethyl-3-(3,4,5-trifluorophenyl)-5,7-dihydro-4H-pyrazolo[3,4-c] pyridin-6-yl]-pyrrolo[1,2-a]pyrazin-8-yl-methanone; | 7.18 |
| 417 | (2,4-Dimethylpyrrolo[1,2-a] pyrimidin-8-yl)-[(7S)-2,7-dimethyl-3-(3,4,5-trifluorophenyl)-5,7-dihydro-4H-pyrazolo[3,4-c] pyridin-6-yl] methanone; | 126.21 |
| 418 | [(7S)-2,7-Dimethyl-3-(3,4,5-trifluorophenyl)-5,7-dihydro-4H-pyrazolo[3,4-c]pyridin-6-yl]-(3-methylimidazo[1,5-a]pyridin-6-yl)methanone; | 14.58 |
| 419 | [(7S)-2,7-Dimethyl-3-(3,4,5-trifluorophenyl)-5,7-dihydro-4H-pyrazolo[3,4-c] pyridin-6-yl]-(7-methylimidazo[1,5-a]pyridin-1-yl)methanone; | 192.00 |
| 420 | [(7S)-2,7-Dimethyl-3-(3,4,5-trifluorophenyl)-5,7-dihydro-4H-pyrazolo[3,4-c]pyridin-6-yl]-imidazo[1,5-a]pyridin-1-yl-methanone; | 59.09 |
| 421 | (3-Cyclopropylimidazo[1,5-a]pyridin-1-yl)-[(7S)-2,7-dimethyl-3-(3,4,5-trifluorophenyl)-5,7-dihydro-4H-pyrazolo[3,4-c]pyridin-6-yl]methanone; | 6.66 |
| 422 | [(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-4-yl)methanone; | 45.88 |
| 423 | [(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-5-yl)methanone; | 41.00 |
| 424 | (1,6-Dimethylpyrazolo[3,4-b]pyridin-4-yl)-[(7S)-2,7-dimethyl-3-(3,4,5-trifluorophenyl)-5,7-dihydro-4H-pyrazolo[3,4-c]pyridin-6-yl]methanone; | 10.73 |
| 425 | (1,3-Dimethylpyrazolo[3,4-b]pyridin-4-yl)-[(7S)-2,7-dimethyl-3-(3,4,5-trifluorophenyl)-5,7-dihydro-4H-pyrazolo[3,4-c]pyridin-6-yl]methanone; | 68.09 |
| 426 | [(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-3-yl)methanone; | 14.46 |
| 427 | [(7S)-2,7-Dimethyl-3-(3,4,5-trifluorophenyl)-5,7-dihydro-4H-pyrazolo[3,4-c]pyridin-6-yl]-(1-methylpyrazolo[3,4-b]pyridin-3-yl)methanone; | 28.55 |
| 428 | [(7S)-2,7-Dimethyl-3-(3,4,5-trifluorophenyl)-5,7-dihydro-4H-pyrazolo[3,4-c]pyridin-6-yl]-(5-fluoro-1H-pyrazolo[3,4-b]pyridin-3-yl)methanone; | 23.00 |

TABLE 4-continued

| Ex # | Compound Name | MGL IC$_{50}$ (nM) |
| --- | --- | --- |
| 429 | [(7S)-2,7-Dimethyl-3-(3,4,5-trifluorophenyl)-5,7-dihydro-4H-pyrazolo[3,4-c]pyridin-6-yl]-(2-methylpyrazolo[3,4-c]pyridin-7-yl)methanone; | 411.81 |
| 430 | [(7S)-2,7-Dimethyl-3-(3,4,5-trifluorophenyl)-5,7-dihydro-4H-pyrazolo[3,4-c]pyridin-6-yl]-(1H-pyrazolo[3,4-c]pyridin-3-yl)methanone; | 56.10 |
| 431 | [(7S)-2,7-Dimethyl-3-(3,4,5-trifluorophenyl)-5,7-dihydro-4H-pyrazolo[3,4-c]pyridin-6-yl]-(1-methylpyrazolo[3,4-c]pyridin-3-yl)methanone; | 95.30 |
| 432 | [(7S)-2,7-Dimethyl-3-(3,4,5-trifluorophenyl)-5,7-dihydro-4H-pyrazolo[3,4-c]pyridin-6-yl]-(1H-pyrazolo[3,4-c]pyridin-7-yl)methanone; | 274.28 |
| 433 | [(7S)-2,7-Dimethyl-3-(3,4,5-trifluorophenyl)-5,7-dihydro-4H-pyrazolo[3,4-c]pyridin-6-yl]-(1-methylpyrazolo[3,4-c]pyridin-7-yl)methanone; | 104.30 |
| 434 | [(7S)-2,7-Dimethyl-3-(3,4,5-trifluorophenyl)-5,7-dihydro-4H-pyrazolo[3,4-c]pyridin-6-yl]-(1H-pyrazolo[4,3-c]pyridin-7-yl)methanone; | 276.57 |
| 435 | [(7S)-2,7-Dimethyl-3-(3,4,5-trifluorophenyl)-5,7-dihydro-4H-pyrazolo[3,4-c]pyridin-6-yl]-(1H-pyrazolo[4,3-c]pyridin-3-yl)methanone; | 40.22 |
| 436 | [(7S)-2,7-Dimethyl-3-(3,4,5-trifluorophenyl)-5,7-dihydro-4H-pyrazolo[3,4-c] pyridin-6-yl]-(1H-pyrazolo[4,3-b]pyridin-3-yl)methanone; | 174.78 |
| 437 | [(7S)-2,7-Dimethyl-3-(3,4,5-trifluorophenyl)-5,7-dihydro-4H-pyrazolo[3,4-c]pyridin-6-yl]-([1,2,4]triazolo[4,3-a]pyridin-3-yl)methanone; | 186.98 |
| 438 | [(7S)-2,7-Dimethyl-3-(3,4,5-trifluorophenyl)-5,7-dihydro-4H-pyrazolo[3,4-c]pyridin-6-yl]-([1,2,4]triazolo[4,3-a]pyridin-5-yl)methanone; | 513.45 |
| 439 | [(7S)-2,7-Dimethyl-3-(3,4,5-trifluorophenyl)-5,7-dihydro-4H-pyrazolo[3,4-c]pyridin-6-yl]-([1,2,4]triazolo[4,3-a]pyridin-6-yl)methanone; | 9274.70 |
| 440 | [3-(Difluoromethyl)-[1,2,4]triazolo[4,3-a]pyridin-6-yl]-[(7S)-2,7-dimethyl-3-(3,4,5-trifluorophenyl)-5,7-dihydro-4H-pyrazolo[3,4-c]pyridin-6-yl]methanone; | 865.17 |
| 441 | [(7S)-2,7-Dimethyl-3-(3,4,5-trifluorophenyl)-5,7-dihydro-4H-pyrazolo[3,4-c]pyridin-6-yl]-(triazolo[1,5-a]pyridin-3-yl)methanone; | 24.08 |
| 442 | [(7S)-2,7-Dimethyl-3-(3,4,5-trifluorophenyl)-5,7-dihydro-4H-pyrazolo[3,4-c] pyridin-6-yl]-(2-methylpyrazolo[1,5-b] pyridazin-3-yl) methanone; | 43.93 |
| 443 | [(7S)-2,7-Dimethyl-3-(3,4,5-trifluorophenyl)-5,7-dihydro-4H-pyrazolo[3,4-c] pyridin-6-yl]-(5-methylpyrazolo[1,5-b] pyridazin-3-yl) methanone; | 12.39 |
| 444 | (2-Cyclopropyl-4-methyl-pyrazolo[1,5-b]pyridazin-3-yl)-[(7S)-2,7-dimethyl-3-(3,4,5-trifluorophenyl)-5,7-dihydro-4H-pyrazolo[3,4-c]pyridin-6-yl]methanone; | 2380.13 |
| 445 | (2-Cyclopropyl-5-methyl-pyrazolo[1,5-b]pyridazin-3-yl)-[(7S)-2,7-dimethyl-3-(3,4,5-trifluorophenyl)-5,7-dihydro-4H-pyrazolo[3,4-c]pyridin-6-yl]methanone; | 525.05 |
| 446 | (2,4-Dimethylpyrazolo[1,5-a] pyrazin-3-yl)-[(7S)-2,7-dimethyl-3-(3,4,5-trifluorophenyl)-5,7-dihydro-4H-pyrazolo[3,4-c] pyridin-6-yl] methanone; | 34.06 |
| 447 | (2-Cyclopropyl-4-methyl-pyrazolo[1,5-a]pyrazin-3-yl)-[(7S)-2,7-dimethyl-3-(3,4,5-trifluorophenyl)-5,7-dihydro-4H-pyrazolo[3,4-c]pyridin-6-yl]methanone; | 392.10 |
| 448 | [(7S)-2,7-Dimethyl-3-(3,4,5-trifluorophenyl)-5,7-dihydro-4H-pyrazolo[3,4-c] pyridin-6-yl]-pyrazolo[1,5-a]pyrimidin-3-yl-methanone; | 113.19 |
| 449 | [(7S)-2,7-Dimethyl-3-(3,4,5-trifluorophenyl)-5,7-dihydro-4H-pyrazolo[3,4-c]pyridin-6-yl]-(2-methylpyrazolo[1,5-a]pyrimidin-3-yl)methanone; | 49.00 |
| 450 | [(7S)-2,7-Dimethyl-3-(3,4,5-trifluorophenyl)-5,7-dihydro-4H-pyrazolo[3,4-c] pyridin-6-yl]-(7-methylpyrazolo[1,5-a] pyrimidin-3-yl) methanone; | 171.59 |
| 451 | [(7S)-2,7-Dimethyl-3-(3,4,5-trifluorophenyl)-5,7-dihydro-4H-pyrazolo[3,4-c]pyridin-6-yl]-(6-methylpyrazolo[1,5-a]pyrimidin-3-yl)methanone; | 199.11 |
| 452 | [(7S)-2,7-Dimethyl-3-(3,4,5-trifluorophenyl)-5,7-dihydro-4H-pyrazolo[3,4-c]pyridin-6-yl]-imidazo[1,2-b]pyridazin-6-yl-methanone; | 275.99 |
| 453 | [(7S)-2,7-Dimethyl-3-(3,4,5-trifluorophenyl)-5,7-dihydro-4H-pyrazolo[3,4-c] pyridin-6-yl]-(2-methylimidazo[1,2-b]pyridazin-6-yl)methanone; | 164.51 |

TABLE 4-continued

| Ex # | Compound Name | MGL IC$_{50}$ (nM) |
|---|---|---|
| 454 | [(7S)-2,7-Dimethyl-3-(3,4,5-trifluorophenyl)-5,7-dihydro-4H-pyrazolo[3,4-c]pyridin-6-yl]-imidazo[1,2-b]pyridazin-3-yl-methanone; | 24.90 |
| 455 | [(7S)-2,7-Dimethyl-3-(3,4,5-trifluorophenyl)-5,7-dihydro-4H-pyrazolo[3,4-c]pyridin-6-yl]-(2-methylimidazo[1,2-b]pyridazin-3-yl)methanone; | 23.17 |
| 456 | (2,8-Dimethylimidazo[1,2-b] pyridazin-3-yl)-[(7S)-2,7-dimethyl-3-(3,4,5-trifluorophenyl)-5,7-dihydro-4H-pyrazolo[3,4-c] pyridin-6-yl]methanone; | 25.39 |
| 457 | (2,7-Dimethylimidazo[1,2-b] pyridazin-3-yl)-[(7S)-2,7-dimethyl-3-(3,4,5-trifluorophenyl)-5,7-dihydro-4H-pyrazolo[3,4-c] pyridin-6-yl] methanone; | 39.40 |
| 458 | [(7S)-2,7-Dimethyl-3-(3,4,5-trifluorophenyl)-5,7-dihydro-4H-pyrazolo[3,4-c] pyridin-6-yl]-(2-methylimidazo[1,2-a]pyrimidin-3-yl)methanone; | 163.08 |
| 459 | [(7S)-2,7-Dimethyl-3-(3,4,5-trifluorophenyl)-5,7-dihydro-4H-pyrazolo[3,4-c]pyridin-6-yl]-(2,5,8-trimethylimidazo[1,2-a]pyrazin-3-yl)methanone; | 312.39 |
| 460 | [(7S)-2,7-Dimethyl-3-(3,4,5-trifluorophenyl)-5,7-dihydro-4H-pyrazolo[3,4-c] pyridin-6-yl]-(6-methylimidazo[1,5-a]pyrimidin-8-yl)methanone; | 521.68 |
| 461 | [(7S)-2,7-Dimethyl-3-(3,4,5-trifluorophenyl)-5,7-dihydro-4H-pyrazolo[3,4-c] pyridin-6-yl]-(3-methylimidazo[1,5-a]pyrimidin-8-yl)methanone; | 1012.05 |
| 462 | [(7S)-2,7-Dimethyl-3-(3,4,5-trifluorophenyl)-5,7-dihydro-4H-pyrazolo[3,4-c] pyridin-6-yl]-(3-methylimidazo[1,5-a] pyrazin-1-yl) methanone; | 35.39 |
| 463 | [(7S)-2,7-Dimethyl-3-(3,4,5-trifluorophenyl)-5,7-dihydro-4H-pyrazolo[3,4-c] pyridin-6-yl]-[3-(trifluoromethyl) imidazo[1,5-a] pyrazin-1-yl]methanone; | 19.75 |
| 464 | [(7S)-2,7-Dimethyl-3-(3,4,5-trifluorophenyl)-5,7-dihydro-4H-pyrazolo[3,4-c]pyridin-6-yl]-(5-methyl-7H-pyrrolo[2,3-d]pyrimidin-4-yl)methanone; | 31.44 |
| 465 | [(7S)-3-(3-Fluoro-5-methyl-phenyl)-2,7-dimethyl-5,7-dihydro-4H-pyrazolo[3,4-c]pyridin-6-yl]-(7-methylpyrrolo[2,3-d] pyrimidin-4-yl) methanone; | 8.46 |
| 466 | [(7S)-2,7-Dimethyl-3-(3,4,5-trifluorophenyl)-5,7-dihydro-4H-pyrazolo[3,4-c]pyridin-6-yl]-(7-methylpyrrolo[2,3-d]pyrimidin-4-yl)methanone; | 5.86 |
| 467 | (5,7-Dimethylpyrrolo[2,3-d] pyrimidin-4-yl)-[(7S)-2,7-dimethyl-3-(3,4,5-trifluorophenyl)-5,7-dihydro-4H-pyrazolo[3,4-c] pyridin-6-yl] methanone; | 36.13 |
| 468 | [(7S)-2,7-Dimethyl-3-[3-(trifluoromethyl) phenyl]-5,7-dihydro-4H-pyrazolo[3,4-c] pyridin-6-yl]-(6-quinolyl)methanone; | 50.72 |
| 469 | (6,7-Dimethylpyrrolo[2,3-d] pyrimidin-4-yl)-[(7S)-2,7-dimethyl-3-(3,4,5-trifluorophenyl)-5,7-dihydro-4H-pyrazolo[3,4-c] pyridin-6-yl]methanone; | 36.41 |
| 470 | [(7S)-2,7-Dimethyl-3-(3,4,5-trifluorophenyl)-5,7-dihydro-4H-pyrazolo[3,4-c]pyridin-6-yl]-(7H-purin-6-yl)methanone; | 3347.34 |
| 471 | [(7S)-2,7-Dimethyl-3-(3,4,5-trifluorophenyl)-5,7-dihydro-4H-pyrazolo[3,4-c] pyridin-6-yl]-(1-methylpyrazolo[3,4-d]pyrimidin-4-yl)methanone; | 32.51 |
| 472 | [(7S)-2,7-Dimethyl-3-(3,4,5-trifluorophenyl)-5,7-dihydro-4H-pyrazolo[3,4-c]pyridin-6-yl]-(5-methyl-[1,2,4]triazolo[1,5-a]pyrimidin-7-yl)methanone; | 1557.04 |
| 473 | [(7S)-2,7-Dimethyl-3-(3,4,5-trifluorophenyl)-5,7-dihydro-4H-pyrazolo[3,4-c] pyridin-6-yl]-(7-methylquinoxalin-6-yl) methanone; | 30.66 |
| 474 | [(7S)-2,7-Dimethyl-3-(3,4,5-trifluorophenyl)-5,7-dihydro-4H-pyrazolo[3,4-c] pyridin-6-yl]-(2-methylquinoxalin-5-yl)methanone; | 85.31 |
| 475 | [(7S)-2,7-Dimethyl-3-(3,4,5-trifluorophenyl)-5,7-dihydro-4H-pyrazolo[3,4-c]pyridin-6-yl]-(3-methylquinoxalin-5-yl)methanone; | 73.62 |
| 476 | (2,3-Dimethylquinoxalin-6-yl)-[(7S)-2,7-dimethyl-3-(3,4,5-trifluorophenyl)-5,7-dihydro-4H-pyrazolo[3,4-c]pyridin-6-yl]methanone; | 25.43 |
| 477 | [(7S)-2,7-Dimethyl-3-(3,4,5-trifluorophenyl)-5,7-dihydro-4H-pyrazolo[3,4-c]pyridin-6-yl]-quinoxalin-2-yl-methanone; | 126.50 |
| 478 | Cinnolin-3-yl-[(7S)-2,7-dimethyl-3-(3,4,5-trifluorophenyl)-5,7-dihydro-4H-pyrazolo[3,4-c]pyridin-6-yl]methanone; | 112.41 |
| 479 | [(7S)-2,7-Dimethyl-3-(3,4,5-trifluorophenyl)-5,7-dihydro-4H-pyrazolo[3,4-c]pyridin-6-yl]-quinazolin-6-yl-methanone; | 189.19 |
| 480 | [(7S)-2,7-Dimethyl-3-(3,4,5-trifluorophenyl)-5,7-dihydro-4H-pyrazolo[3,4-c]pyridin-6-yl]-quinazolin-7-yl-methanone; | 206.73 |
| 481 | [(7S)-2,7-Dimethyl-3-(3,4,5-trifluorophenyl)-5,7-dihydro-4H-pyrazolo[3,4-c]pyridin-6-yl]-(8-fluoroquinazolin-4-yl)methanone; | 5.20 |

TABLE 4-continued

| Ex # | Compound Name | MGL IC$_{50}$ (nM) |
|---|---|---|
| 482 | [(7S)-2,7-Dimethyl-3-(3,4,5-trifluorophenyl)-5,7-dihydro-4H-pyrazolo[3,4-c]pyridin-6-yl]-quinazolin-4-yl-methanone; | 6.22 |
| 483 | (2-Deuteroquinoxalin-6-yl)-[(7S)-2,7-dimethyl-3-(3,4,5-trifluorophenyl)-5,7-dihydro-4H-pyrazolo[3,4-c]pyridin-6-yl]methanone; | 10.23 |
| 484 | [(7S)-2,7-Dimethyl-3-(3,4,5-trifluorophenyl)-5,7-dihydro-4H-pyrazolo[3,4-c]pyridin-6-yl]-pyrido[4,3-d]pyrimidin-5-yl-methanone; | 62.23 |
| 485 | [(7S)-2,7-Dimethyl-3-(3,4,5-trifluorophenyl)-5,7-dihydro-4H-pyrazolo[3,4-c]pyridin-6-yl]-(1,5-naphthyridin-4-yl)methanone; | 33.22 |
| 486 | [(7S)-2,7-Dimethyl-3-(3,4,5-trifluorophenyl)-5,7-dihydro-4H-pyrazolo[3,4-c]pyridin-6-yl]-(1,6-naphthyridin-5-yl)methanone; | 13.66 |
| 487 | [(7S)-2,7-Dimethyl-3-(3,4,5-trifluorophenyl)-5,7-dihydro-4H-pyrazolo[3,4-c]pyridin-6-yl]-(2-methyl-1,6-naphthyridin-5-yl)methanone; | 35.33 |
| 488 | [(7S)-2,7-Dimethyl-3-(3,4,5-trifluorophenyl)-5,7-dihydro-4H-pyrazolo[3,4-c]pyridin-6-yl]-(1,6-naphthyridin-3-yl)methanone; | 226.88 |
| 489 | [(7S)-2,7-Dimethyl-3-(3,4,5-trifluorophenyl)-5,7-dihydro-4H-pyrazolo[3,4-c]pyridin-6-yl]-(1,7-naphthyridin-5-yl)methanone; | 30.00 |
| 490 | [(7S)-2,7-Dimethyl-3-(3,4,5-trifluorophenyl)-5,7-dihydro-4H-pyrazolo[3,4-c]pyridin-6-yl]-(1,8-naphthyridin-3-yl)methanone; | 226.20 |
| 491 | [(7S)-2,7-Dimethyl-3-(3,4,5-trifluorophenyl)-5,7-dihydro-4H-pyrazolo[3,4-c]pyridin-6-yl]-(1,8-naphthyridin-4-yl)methanone; | 140.99 |
| 492 | [(7S)-2,7-Dimethyl-3-(o-tolyl)-5,7-dihydro-4H-pyrazolo[3,4-c]pyridin-6-yl]-(6-quinolyl)methanone; | 219.99 |
| 493 | [(7S)-2,7-Dimethyl-3-[2-(trifluoromethyl)phenyl]-5,7-dihydro-4H-pyrazolo[3,4-c]pyridin-6-yl]-(6-quinolyl)methanone; | 2362.11 |
| 494 | [(7S)-2,7-Dimethyl-3-[4-(trifluoromethyl)phenyl]-5,7-dihydro-4H-pyrazolo[3,4-c]pyridin-6-yl]-(6-quinolyl)methanone; | 54.89 |
| 495 | [(7S)-3-(3-Methoxyphenyl)-2,7-dimethyl-5,7-dihydro-4H-pyrazolo[3,4-c]pyridin-6-yl]-(6-quinolyl)methanone; | 47.08 |
| 496 | [(7S)-3-(2-Methoxyphenyl)-2,7-dimethyl-5,7-dihydro-4H-pyrazolo[3,4-c]pyridin-6-yl]-(6-quinolyl)methanone; | 54.40 |
| 497 | [(7S)-3-(4-Ethoxyphenyl)-2,7-dimethyl-5,7-dihydro-4H-pyrazolo[3,4-c]pyridin-6-yl]-(6-quinolyl)methanone; | 313.18 |
| 498 | [(7S)-3-(3-Isopropoxyphenyl)-2,7-dimethyl-5,7-dihydro-4H-pyrazolo[3,4-c]pyridin-6-yl]-(6-quinolyl)methanone; | 361.49 |
| 499 | [(7S)-3-[3-(Difluoromethoxy)phenyl]-2,7-dimethyl-5,7-dihydro-4H-pyrazolo[3,4-c]pyridin-6-yl]-(6-quinolyl)methanone; | 44.40 |
| 500 | [(7S)-2,7-Dimethyl-3-[4-(trifluoromethoxy)phenyl]-5,7-dihydro-4H-pyrazolo[3,4-c]pyridin-6-yl]-(6-quinolyl)methanone; | 75.68 |
| 501 | [(7S)-2,7-Dimethyl-3-[3-(trifluoromethoxy)phenyl]-5,7-dihydro-4H-pyrazolo[3,4-c]pyridin-6-yl]-(6-quinolyl)methanone; | 58.64 |
| 502 | [(7S)-3-(2,4-Difluorophenyl)-2,7-dimethyl-5,7-dihydro-4H-pyrazolo[3,4-c]pyridin-6-yl]-(6-quinolyl)methanone; | 106.29 |
| 503 | [(7S)-3-(2,3-Difluorophenyl)-2,7-dimethyl-5,7-dihydro-4H-pyrazolo[3,4-c]pyridin-6-yl]-(6-quinolyl)methanone; | 21.99 |
| 504 | [(7S)-3-(4-Chloro-3-fluoro-phenyl)-2,7-dimethyl-5,7-dihydro-4H-pyrazolo[3,4-c]pyridin-6-yl]-(6-quinolyl)methanone; | 25.27 |
| 505 | [(7S)-3-(3-Chloro-4-fluoro-phenyl)-2,7-dimethyl-5,7-dihydro-4H-pyrazolo[3,4-c]pyridin-6-yl]-(6-quinolyl)methanone; | 7.38 |
| 506 | [(7S)-3-(2-Chloro-4-fluoro-phenyl)-2,7-dimethyl-5,7-dihydro-4H-pyrazolo[3,4-c]pyridin-6-yl]-(6-quinolyl)methanone; | 346.82 |
| 507 | [(7S)-3-(3,4-Dichlorophenyl)-2,7-dimethyl-5,7-dihydro-4H-pyrazolo[3,4-c]pyridin-6-yl]-(6-quinolyl)methanone; | 15.19 |
| 508 | [(7S)-3-(5-Fluoro-2-methoxy-phenyl)-2,7-dimethyl-5,7-dihydro-4H-pyrazolo[3,4-c]pyridin-6-yl]-(6-quinolyl)methanone; | 70.03 |
| 509 | [(7S)-3-(4-Fluoro-3-methoxy-phenyl)-2,7-dimethyl-5,7-dihydro-4H-pyrazolo[3,4-c]pyridin-6-yl]-(6-quinolyl)methanone; | 59.55 |
| 510 | [(7S)-3-(2-Fluoro-3-methoxy-phenyl)-2,7-dimethyl-5,7-dihydro-4H-pyrazolo[3,4-c]pyridin-6-yl]-(6-quinolyl)methanone; | 231.69 |
| 511 | [(7S)-3-(3-Fluoro-5-methyl-phenyl)-2,7-dimethyl-5,7-dihydro-4H-pyrazolo[3,4-c]pyridin-6-yl]-(6-quinolyl)methanone; | 6.58 |
| 512 | [(7S)-3-(4-Methoxy-3-methyl-phenyl)-2,7-dimethyl-5,7-dihydro-4H-pyrazolo[3,4-c]pyridin-6-yl]-(6-quinolyl)methanone; | 185.31 |
| 513 | [(7S)-3-(3-Chloro-5-methoxy-phenyl)-2,7-dimethyl-5,7-dihydro-4H-pyrazolo[3,4-c]pyridin-6-yl]-(6-quinolyl)methanone; | 10.49 |
| 514 | [(7S)-3-(4-Chloro-2,3-difluoro-phenyl)-2,7-dimethyl-5,7-dihydro-4H-pyrazolo[3,4-c]pyridin-6-yl]-(6-quinolyl)methanone; | NT |
| 515 | [(7S)-2,7-Dimethyl-3-(2,3,4-trifluorophenyl)-5,7-dihydro-4H-pyrazolo[3,4-c]pyridin-6-yl]-(6-quinolyl)methanone; | 52.20 |
| 516 | [(7S)-2,7-Dimethyl-3-(3,4,5-trifluorophenyl)-5,7-dihydro-4H-pyrazolo[3,4-c]pyridin-6-yl]-(1-oxidoquinolin-1-ium-6-yl)methanone; | 140.70 |
| 517 | [(7S)-2,7-Dimethyl-3-(3,4,5-trifluorophenyl)-5,7-dihydro-4H-pyrazolo[3,4-c]pyridin-6-yl]-(2-hydroxy-6-quinolyl)methanone; | 80.74 |

TABLE 4-continued

| Ex # | Compound Name | MGL IC$_{50}$ (nM) |
|---|---|---|
| 518 | [(7S)-2,7-Dimethyl-3-(3,4,5-trifluorophenyl)-5,7-dihydro-4H-pyrazolo[3,4-c]pyridin-6-yl]-(4-hydroxy-6-quinolyl)methanone; | 70.79 |
| 519 | [(7S)-2,7-Dimethyl-3-(6-methyl-3-pyridyl)-5,7-dihydro-4H-pyrazolo[3,4-c]pyridin-6-yl]-(6-quinolyl)methanone; | 1451.11 |
| 520 | [(7S)-2,7-Dimethyl-3-(2-methyl-4-pyridyl)-5,7-dihydro-4H-pyrazolo[3,4-c]pyridin-6-yl]-(6-quinolyl)methanone; | 1114.04 |
| 521 | [(7S)-3-[6-(Difluoromethyl)-3-pyridyl]-2,7-dimethyl-5,7-dihydro-4H-pyrazolo[3,4-c]pyridin-6-yl]-(6-quinolyl)methanone; | 766.13 |
| 522 | [(7S)-2,7-Dimethyl-3-[6-(trifluoromethyl)-3-pyridyl]-5,7-dihydro-4H-pyrazolo[3,4-c]pyridin-6-yl]-(6-quinolyl)methanone; | 266.81 |
| 523 | [(7S)-2,7-Dimethyl-3-[2-(trifluoromethyl)-4-pyridyl]-5,7-dihydro-4H-pyrazolo[3,4-c]pyridin-6-yl]-(6-quinolyl)methanone; | 417.16 |
| 524 | [(7S)-2,7-Dimethyl-3-[5-(trifluoromethyl)-3-thienyl]-5,7-dihydro-4H-pyrazolo[3,4-c]pyridin-6-yl]-(6-quinolyl)methanone; | 7.23 |
| 525 | [(7S)-3-(6-Methoxy-3-pyridyl)-2,7-dimethyl-5,7-dihydro-4H-pyrazolo[3,4-c]pyridin-6-yl]-(6-quinolyl)methanone; | 601.59 |
| 526 | [(7S)-3-(2-Methoxy-4-pyridyl)-2,7-dimethyl-5,7-dihydro-4H-pyrazolo[3,4-c]pyridin-6-yl]-(6-quinolyl)methanone; | 502.00 |
| 527 | [(7S)-3-[6-(Difluoromethoxy)-3-pyridyl]-2,7-dimethyl-5,7-dihydro-4H-pyrazolo[3,4-c]pyridin-6-yl]-(6-quinolyl)methanone; | 277.78 |
| 528 | [(7S)-3-[5-(Difluoromethoxy)-3-pyridyl]-2,7-dimethyl-5,7-dihydro-4H-pyrazolo[3,4-c]pyridin-6-yl]-(6-quinolyl)methanone; | 396.55 |
| 529 | [(7S)-3-(6-Methoxy-5-methyl-3-pyridyl)-2,7-dimethyl-5,7-dihydro-4H-pyrazolo[3,4-c]pyridin-6-yl]-(6-quinolyl)methanone; | 319.67 |
| 530 | [(7S)-3-[6-Methoxy-5-(trifluoromethyl)-3-pyridyl]-2,7-dimethyl-5,7-dihydro-4H-pyrazolo[3,4-c]pyridin-6-yl]-(6-quinolyl)methanone; | 129.81 |
| 531 | [(7S)-3-(1H-Indol-7-yl)-2,7-dimethyl-5,7-dihydro-4H-pyrazolo[3,4-c]pyridin-6-yl]-(6-quinolyl)methanone; | 22.91 |
| 532 | [(7S)-3-(Benzofuran-6-yl)-2,7-dimethyl-5,7-dihydro-4H-pyrazolo[3,4-c]pyridin-6-yl]-(6-quinolyl)methanone; | 65.00 |
| 533 | [(7S)-3-(Benzofuran-5-yl)-2,7-dimethyl-5,7-dihydro-4H-pyrazolo[3,4-c]pyridin-6-yl]-(6-quinolyl)methanone; | 17.40 |
| 534 | [(7S)-3-(Benzofuran-7-yl)-2,7-dimethyl-5,7-dihydro-4H-pyrazolo[3,4-c]pyridin-6-yl]-(6-quinolyl)methanone; | 25.12 |
| 535 | [(7S)-3-(Benzofuran-4-yl)-2,7-dimethyl-5,7-dihydro-4H-pyrazolo[3,4-c]pyridin-6-yl]-(6-quinolyl)methanone; | 18.14 |
| 536 | [(7S)-3-(5-Fluorobenzofuran-7-yl)-2,7-dimethyl-5,7-dihydro-4H-pyrazolo[3,4-c]pyridin-6-yl]-(6-quinolyl)methanone; | 19.99 |
| 537 | [(7S)-3-(1,3-Benzothiazol-4-yl)-2,7-dimethyl-5,7-dihydro-4H-pyrazolo[3,4-c]pyridin-6-yl]-(6-quinolyl)methanone; | 32.98 |
| 538 | [(7S)-3-(2,1,3-Benzoxadiazol-4-yl)-2,7-dimethyl-5,7-dihydro-4H-pyrazolo[3,4-c]pyridin-6-yl]-(6-quinolyl)methanone; | 72.58 |
| 539 | [(7S)-3-(2,3-Dihydrobenzofuran-7-yl)-2,7-dimethyl-5,7-dihydro-4H-pyrazolo[3,4-c]pyridin-6-yl]-(6-quinolyl)methanone; | 55.18 |
| 540 | [(7S)-3-(1,3-Benzodioxol-5-yl)-2,7-dimethyl-5,7-dihydro-4H-pyrazolo[3,4-c]pyridin-6-yl]-(6-quinolyl)methanone; | 133.11 |
| 541 | [(7S)-3-(1,3-Benzodioxol-4-yl)-2,7-dimethyl-5,7-dihydro-4H-pyrazolo[3,4-c]pyridin-6-yl]-(6-quinolyl)methanone; | 2.17 |
| 542 | [(7S)-3-(2,2-Difluoro-1,3-benzodioxol-4-yl)-2,7-dimethyl-5,7-dihydro-4H-pyrazolo[3,4-c]pyridin-6-yl]-(6-quinolyl)methanone; | 81.15 |
| 543 | [(7S)-2,7-Dimethyl-3-(3,4,5-trifluorophenyl)-5,7-dihydro-4H-pyrazolo[3,4-c]pyridin-6-yl]-(5-isoquinolyl)methanone; | 4.92 |
| 544 | [(7S)-2,7-Dimethyl-3-(3,4,5-trifluorophenyl)-5,7-dihydro-4H-pyrazolo[3,4-c]pyridin-6-yl]-(6-isoquinolyl)methanone; | 10.22 |
| 545 | [(7S)-2,7-Dimethyl-3-(3,4,5-trifluorophenyl)-5,7-dihydro-4H-pyrazolo[3,4-c]pyridin-6-yl]-(5-fluoro-3-quinolyl)methanone; | 11.66 |
| 546 | [(7S)-2,7-Dimethyl-3-(3,4,5-trifluorophenyl)-5,7-dihydro-4H-pyrazolo[3,4-c]pyridin-6-yl]-(8-fluoro-4-isoquinolyl)methanone; | 5.06 |
| 547 | (4-Bromo-6-quinolyl)-[(7S)-2,7-dimethyl-3-(3,4,5-trifluorophenyl)-5,7-dihydro-4H-pyrazolo[3,4-c]pyridin-6-yl]methanone; | 5.62 |
| 548 | [(7S)-2,7-Dimethyl-3-(3,4,5-trifluorophenyl)-5,7-dihydro-4H-pyrazolo[3,4-c]pyridin-6-yl]-(2-methyl-6-quinolyl)methanone; | 16.18 |
| 549 | [(7S)-2,7-Dimethyl-3-(3,4,5-trifluorophenyl)-5,7-dihydro-4H-pyrazolo[3,4-c]pyridin-6-yl]-(4-methyl-6-quinolyl)methanone; | 1.99 |
| 550 | [(7S)-2,7-Dimethyl-3-(3,4,5-trifluorophenyl)-5,7-dihydro-4H-pyrazolo[3,4-c]pyridin-6-yl]-(8-methoxy-4-quinolyl)methanone; | 48.27 |
| 551 | 5,6-Dihydro-4H-pyrrolo[1,2-b]pyrazol-3-yl-[(7S)-2,7-dimethyl-3-(3,4,5-trifluorophenyl)-5,7-dihydro-4H-pyrazolo[3,4-c]pyridin-6-yl]methanone; | 122.49 |
| 552 | [(7S)-2,7-Dimethyl-3-(3,4,5-trifluorophenyl)-5,7-dihydro-4H-pyrazolo[3,4-c]pyridin-6-yl]-(4,5,6,7-tetrahydropyrazolo[1,5-a]pyridin-3-yl)methanone; | 40.43 |
| 553 | 6,7-Dihydro-5H-pyrazolo[5,1-b][1,3]oxazin-2-yl-[(7S)-2,7-dimethyl-3-(3,4,5-trifluorophenyl)-5,7-dihydro-4H-pyrazolo[3,4-c]pyridin-6-yl]methanone; | 285.37 |

TABLE 4-continued

| Ex # | Compound Name | MGL IC$_{50}$ (nM) |
|---|---|---|
| 554 | 6,7-Dihydro-5H-pyrazolo[5,1-b][1,3]oxazin-3-yl-[(7S)-2,7-dimethyl-3-(3,4,5-trifluorophenyl)-5,7-dihydro-4H-pyrazolo[3,4-c]pyridin-6-yl]methanone; | 57.58 |
| 555 | [(7S)-2,7-Dimethyl-3-(3,4,5-trifluorophenyl)-5,7-dihydro-4H-pyrazolo[3,4-c]pyridin-6-yl]-(3-methyl-6,7-dihydro-5H-pyrazolo[5,1-b][1,3]oxazin-2-yl)methanone; | 182.81 |
| 556 | [(7S)-2,7-Dimethyl-3-(3,4,5-trifluorophenyl)-5,7-dihydro-4H-pyrazolo[3,4-c]pyridin-6-yl]-(2,6,6-trimethyl-4,7-dihydropyrazolo[5,1-c][1,4]oxazin-3-yl)methanone; | 803.16 |
| 557 | [(7S)-2,7-Dimethyl-3-(3,4,5-trifluorophenyl)-5,7-dihydro-4H-pyrazolo[3,4-c]pyridin-6-yl]-(3,6,6-trimethyl-4,7-dihydropyrazolo[5,1-c][1,4]oxazin-2-yl)methanone; | 1837.81 |
| 558 | ((S)-2,7-Dimethyl-3-(3,4,5-trifluorophenyl)-4,5-dihydro-2H-pyrazolo[3,4-c]pyridin-6(7H)-yl)(7-(trifluoromethyl)-4,5,6,7-tetrahydropyrazolo[1,5-a]pyrimidin-3-yl)methanone; | 1796.80 |
| 559 | 6,7-Dihydro-5H-pyrrolo[1,2-a]imidazol-3-yl-[(7S)-2,7-dimethyl-3-(3,4,5-trifluorophenyl)-5,7-dihydro-4H-pyrazolo[3,4-c]pyridin-6-yl]methanone; | 294.17 |
| 560 | [(7S)-2,7-Dimethyl-3-(3,4,5-trifluorophenyl)-5,7-dihydro-4H-pyrazolo[3,4-c]pyridin-6-yl]-(5,6,7,8-tetrahydroimidazo[1,2-a]pyridin-3-yl)methanone; | 120.09 |
| 561 | [2-(Difluoromethyl)-5,6,7,8-tetrahydroimidazo[1,2-a]pyridin-3-yl]-[(7S)-2,7-dimethyl-3-(3,4,5-trifluorophenyl)-5,7-dihydro-4H-pyrazolo[3,4-c]pyridin-6-yl]methanone; | 326.36 |
| 562 | 6,8-Dihydro-5H-imidazo[2,1-c][1,4]oxazin-3-yl-[(7S)-2,7-dimethyl-3-(3,4,5-trifluorophenyl)-5,7-dihydro-4H-pyrazolo[3,4-c]pyridin-6-yl]methanone; | 716.64 |
| 563 | 3,4-Dihydro-2H-pyrano[2,3-b]pyridin-6-yl-[(7S)-2,7-dimethyl-3-(3,4,5-trifluorophenyl)-5,7-dihydro-4H-pyrazolo[3,4-c]pyridin-6-yl]methanone; | 328.70 |
| 564 | 3,4-Dihydro-2H-pyrano[2,3-b]pyridin-5-yl-[(7S)-2,7-dimethyl-3-(3,4,5-trifluorophenyl)-5,7-dihydro-4H-pyrazolo[3,4-c]pyridin-6-yl]methanone; | 58.74 |
| 565 | 6,8-Dihydro-5H-pyrano[3,4-b]pyridin-4-yl-[(7S)-2,7-dimethyl-3-(3,4,5-trifluorophenyl)-5,7-dihydro-4H-pyrazolo[3,4-c]pyridin-6-yl]methanone; | 108.47 |
| 566 | 6,8-Dihydro-5H-pyrano[3,4-b]pyridin-2-yl-[(7S)-2,7-dimethyl-3-(3,4,5-trifluorophenyl)-5,7-dihydro-4H-pyrazolo[3,4-c]pyridin-6-yl]methanone; | 533.21 |
| 567 | 7,8-Dihydro-5H-pyrano[4,3-b]pyridin-3-yl-[(7S)-2,7-dimethyl-3-(3,4,5-trifluorophenyl)-5,7-dihydro-4H-pyrazolo[3,4-c]pyridin-6-yl]methanone; | 1050.03 |
| 568 | 3,4-Dihydro-2H-pyrano[3,2-b]pyridin-8-yl-[(7S)-2,7-dimethyl-3-(3,4,5-trifluorophenyl)-5,7-dihydro-4H-pyrazolo[3,4-c]pyridin-6-yl]methanone; | 9.68 |
| 569 | 2,3-Dihydro-[1,4]dioxino[2,3-b]pyridin-8-yl-[(7S)-2,7-dimethyl-3-(3,4,5-trifluorophenyl)-5,7-dihydro-4H-pyrazolo[3,4-c]pyridin-6-yl]methanone; | 28.68 |
| 570 | 2,3-Dihydro-[1,4]dioxino[2,3-b]pyridin-7-yl-[(7S)-2,7-dimethyl-3-(3,4,5-trifluorophenyl)-5,7-dihydro-4H-pyrazolo[3,4-c]pyridin-6-yl]methanone; | 136.40 |
| 571 | 3,4-Dihydro-2H-pyrido[3,2-b][1,4]oxazin-7-yl-[(7S)-2,7-dimethyl-3-(3,4,5-trifluorophenyl)-5,7-dihydro-4H-pyrazolo[3,4-c]pyridin-6-yl]methanone; | 12.67 |
| 572 | [(7S)-2,7-Dimethyl-3-(3,4,5-trifluorophenyl)-5,7-dihydro-4H-pyrazolo[3,4-c]pyridin-6-yl]-(4-methyl-2,3-dihydropyrido[3,2-b][1,4]oxazin-7-yl)methanone; | 51.94 |
| 573 | 3,4-Dihydro-2H-pyrano[2,3-c]pyridin-6-yl-[(7S)-2,7-dimethyl-3-(3,4,5-trifluorophenyl)-5,7-dihydro-4H-pyrazolo[3,4-c]pyridin-6-yl]methanone; | 241.66 |
| 574 | [(7S)-2,7-Dimethyl-3-(3,4,5-trifluorophenyl)-5,7-dihydro-4H-pyrazolo[3,4-c]pyridin-6-yl]-(1,2,3,4-tetrahydroisoquinolin-5-yl)methanone; | 330.07 |
| 575 | [(7S)-2,7-Dimethyl-3-(3,4,5-trifluorophenyl)-5,7-dihydro-4H-pyrazolo[3,4-c]pyridin-6-yl]-(1,2,3,4-tetrahydroisoquinolin-8-yl)methanone; | 72.69 |
| 576 | [(7S)-2,7-Dimethyl-3-(3,4,5-trifluorophenyl)-5,7-dihydro-4H-pyrazolo[3,4-c]pyridin-6-yl]-isochroman-5-yl-methanone; | 18.87 |
| 577 | [(7S)-2,7-Dimethyl-3-(3,4,5-trifluorophenyl)-5,7-dihydro-4H-pyrazolo[3,4-c]pyridin-6-yl]-isochroman-7-yl-methanone; | 32.16 |
| 578 | [(7S)-2,7-Dimethyl-3-(3,4,5-trifluorophenyl)-5,7-dihydro-4H-pyrazolo[3,4-c]pyridin-6-yl]-isochroman-6-yl-methanone; | 27.42 |
| 579 | [(7S)-2,7-Dimethyl-3-(3,4,5-trifluorophenyl)-5,7-dihydro-4H-pyrazolo[3,4-c]pyridin-6-yl]-isochroman-8-yl-methanone; | 8.18 |
| 580 | Chroman-6-yl-[(7S)-2,7-dimethyl-3-(3,4,5-trifluorophenyl)-5,7-dihydro-4H-pyrazolo[3,4-c]pyridin-6-yl]methanone; | 19.63 |

TABLE 4-continued

| Ex # | Compound Name | MGL IC$_{50}$ (nM) |
|---|---|---|
| 581 | Chroman-5-yl-[(7S)-2,7-dimethyl-3-(3,4,5-trifluorophenyl)-5,7-dihydro-4H-pyrazolo[3,4-c]pyridin-6-yl]methanone; | 15.60 |
| 582 | Chroman-7-yl-[(7S)-2,7-dimethyl-3-(3,4,5-trifluorophenyl)-5,7-dihydro-4H-pyrazolo[3,4-c]pyridin-6-yl]methanone; | 7.52 |
| 583 | Chroman-8-yl-[(7S)-2,7-dimethyl-3-(3,4,5-trifluorophenyl)-5,7-dihydro-4H-pyrazolo[3,4-c]pyridin-6-yl]methanone; | 1.42 |
| 584 | 4-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one; | 299.99 |
| 585 | 4-[(7S)-2,7-Dimethyl-3-(3,4,5-trifluorophenyl)-5,7-dihydro-4H-pyrazolo[3,4-c]pyridine-6-carbonyl]-3-methyl-1,3-benzoxazol-2-one; | 25.42 |
| 586 | 5-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one; | 1000.00 |
| 587 | 7-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one; | 13.44 |
| 588 | 6-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one; | 11.26 |
| 589 | 7-[(7S)-2,7-dimethyl-3-(3,4,5-trifluorophenyl)-5,7-dihydro-4H-pyrazolo[3,4-c]pyridine-6-carbonyl]-3-methyl-1,3-benzoxazol-2-one; | 1.84 |
| 590 | 7-[(7S)-2,7-Dimethyl-3-(3,4,5-trifluorophenyl)-5,7-dihydro-4H-pyrazolo[3,4-c]pyridine-6-carbonyl]-4-methyl-1,4-benzoxazin-3-one; | 172.78 |
| 591 | [(7S)-2,7-8-[(7S)-2,7-Dimethyl-3-(3,4,5-trifluorophenyl)-5,7-dihydro-4H-pyrazolo[3,4-c]pyridine-6-carbonyl]-4-methyl-1,4-benzoxazin-3-one; | 4.18 |
| 592 | 3,4-Dihydro-2H-1,4-benzoxazin-8-yl-[(7S)-2,7-dimethyl-3-(3,4,5-trifluorophenyl)-5,7-dihydro-4H-pyrazolo[3,4-c]pyridin-6-yl]methanone; | 7.31 |
| 593 | [(7S)-3-[3-(Difluoromethyl)-4-fluoro-phenyl]-2,7-dimethyl-5,7-dihydro-4H-pyrazolo[3,4-c]pyridin-6-yl]-(2-methoxy-3-methyl-4-pyridyl)methanone; | 56.96 |
| 594 | [(7S)-3-[3-(1,1-Difluoroethyl)phenyl]-2,7-dimethyl-5,7-dihydro-4H-pyrazolo[3,4-c]pyridin-6-yl]-(2-methoxy-3-methyl-4-pyridyl)methanone; | 334.58 |
| 595 | [(7S)-3-[3-(Difluoromethoxy)-4-fluoro-phenyl]-2,7-dimethyl-5,7-dihydro-4H-pyrazolo[3,4-c]pyridin-6-yl]-(2-methoxy-3-methyl-4-pyridyl)methanone; | 106.39 |
| 596 | Chroman-7-yl-[(7S)-3-[3-(difluoromethoxy)-5-fluoro-phenyl]-2,7-dimethyl-5,7-dihydro-4H-pyrazolo[3,4-c]pyridin-6-yl]methanone; | 28.68 |
| 597 | [(7S)-3-[3-(Difluoromethoxy)-5-fluoro-phenyl]-2,7-dimethyl-5,7-dihydro-4H-pyrazolo[3,4-c]pyridin-6-yl]-(2-methoxy-3-methyl-4-pyridyl)methanone; | 25.00 |
| 598 | [(7S)-3-(4-Fluoro-3-methyl-phenyl)-2,7-dimethyl-5,7-dihydro-4H-pyrazolo[3,4-c]pyridin-6-yl]-(2-methoxy-3-methyl-4-pyridyl)methanone; | 29.89 |
| 599 | [(7S)-2,7-Dimethyl-3-(3,4,5-trifluorophenyl)-5,7-dihydro-4H-pyrazolo[3,4-c]pyridin-6-yl]-(3-methoxy-2-methyl-4-pyridyl)methanone; | 71.43 |
| 600 | [(7S)-2,7-Dimethyl-3-(3,4,5-trifluorophenyl)-5,7-dihydro-4H-pyrazolo[3,4-c]pyridin-6-yl]-(1-methyl-4-phenyl-imidazol-2-yl)methanone; | 109.60 |
| 601 | [(7S)-2,7-Dimethyl-3-(3,4,5-trifluorophenyl)-5,7-dihydro-4H-pyrazolo[3,4-c]pyridin-6-yl]-(1-phenylimidazol-4-yl)methanone; | 252.29 |
| 602 | [(7S)-2,7-Dimethyl-3-(3,4,5-trifluorophenyl)-5,7-dihydro-4H-pyrazolo[3,4-c]pyridin-6-yl]-[3-methyl-2-(2-pyridyl)imidazol-4-yl]methanone; | 459.83 |
| 603 | [(7S)-2,7-Dimethyl-3-(3,4,5-trifluorophenyl)-5,7-dihydro-4H-pyrazolo[3,4-c]pyridin-6-yl]-(2-fluoro-6-pyrazol-1-yl-phenyl)methanone; | 113.61 |
| 604 | [(7S)-2,7-Dimethyl-3-(3,4,5-trifluorophenyl)-5,7-dihydro-4H-pyrazolo[3,4-c]pyridin-6-yl]-spiro[3,4-dihydro-1,4-benzoxazine-2,1'-cyclopropane]-8-yl-methanone; | 101.91 |
| 605 | [(7S)-2,7-Dimethyl-3-(3,4,5-trifluorophenyl)-5,7-dihydro-4H-pyrazolo[3,4-c]pyridin-6-yl]-(3-fluoro-1H-pyrrolo[2,3-b]pyridin-4-yl)methanone; | 1.10 |
| 606 | [(7S)-2,7-Dimethyl-3-(3,4,5-trifluorophenyl)-5,7-dihydro-4H-pyrazolo[3,4-c]pyridin-6-yl]-(9-methylpurin-6-yl)methanone; | 724.44 |
| 607 | [(7S)-2,7-Dimethyl-3-(3,4,5-trifluorophenyl)-5,7-dihydro-4H-pyrazolo[3,4-c]pyridin-6-yl]-(3-fluoro-5-methoxy-4-pyridyl)methanone; | 18.23 |
| 608 | (3-Chloro-4-methoxy-2-pyridyl)-[(7S)-3-[3-(difluoromethyl)-5-fluoro-phenyl]-2,7-dimethyl-5,7-dihydro-4H-pyrazolo[3,4-c]pyridin-6-yl]methanone; | 21.66 |
| 609 | [(7S)-3-[3-(Difluoromethyl)-5-fluoro-phenyl]-2,7-dimethyl-5,7-dihydro-4H-pyrazolo[3,4-c]pyridin-6-yl]-(2-methoxy-3-methyl-4-pyridyl)methanone; | 22.74 |

TABLE 4-continued

| Ex # | Compound Name | MGL IC$_{50}$ (nM) |
|---|---|---|
| 610 | Chroman-7-yl-[(7S)-3-[3-(difluoromethyl)-5-fluoro-phenyl]-2,7-dimethyl-5,7-dihydro-4H-pyrazolo[3,4-c]pyridin-6-yl]methanone; | 29.44 |
| 611 | Chroman-7-yl-[(7S)-3-(3-fluoro-5-methoxy-phenyl)-2,7-dimethyl-5,7-dihydro-4H-pyrazolo[3,4-c]pyridin-6-yl]methanone; | 25.57 |
| 612 | (3-Chloro-4-methoxy-2-pyridyl)-[(7S)-3-[3-(difluoromethoxy)-5-fluoro-phenyl]-2,7-dimethyl-5,7-dihydro-4H-pyrazolo[3,4-c]pyridin-6-yl]methanone; | 29.78 |
| 613 | [(7S)-3-(3-Fluoro-5-methoxy-phenyl)-2,7-dimethyl-5,7-dihydro-4H-pyrazolo[3,4-c]pyridin-6-yl]-(2-methoxy-3-methyl-4-pyridyl)methanone; | 27.82 |
| 614 | (3-Chloro-4-methoxy-2-pyridyl)-[(7S)-3-(3-fluoro-5-methoxy-phenyl)-2,7-dimethyl-5,7-dihydro-4H-pyrazolo[3,4-c]pyridin-6-yl]methanone; | 35.90 |
| 615 | racemic-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone; | 820.73 |
| 616 | (R*)-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone; | NT |
| 617 | (S)-(1,6-Dimethyl-1H-pyrazolo[3,4-d]pyrimidin-4-yl)(2,7-dimethyl-3-(3,4,5-trifluorophenyl)-2,4,5,7-tetrahydro-6H-pyrazolo[3,4-c]pyridin-6-yl)methanone; and | 32.44 |
| 618 | Cyclopropyl-2-methyl-imidazo[1,2-a] pyridin-3-yl)-[(7S)-2,7-dimethyl-3-(3,4,5-trifluorophenyl)-5,7-dihydro-4H-pyrazolo[3,4-c]pyridin-6-yl] methanone. | 18.22 |

NT means not tested.

What is claimed:
1. A compound of Formula (I),

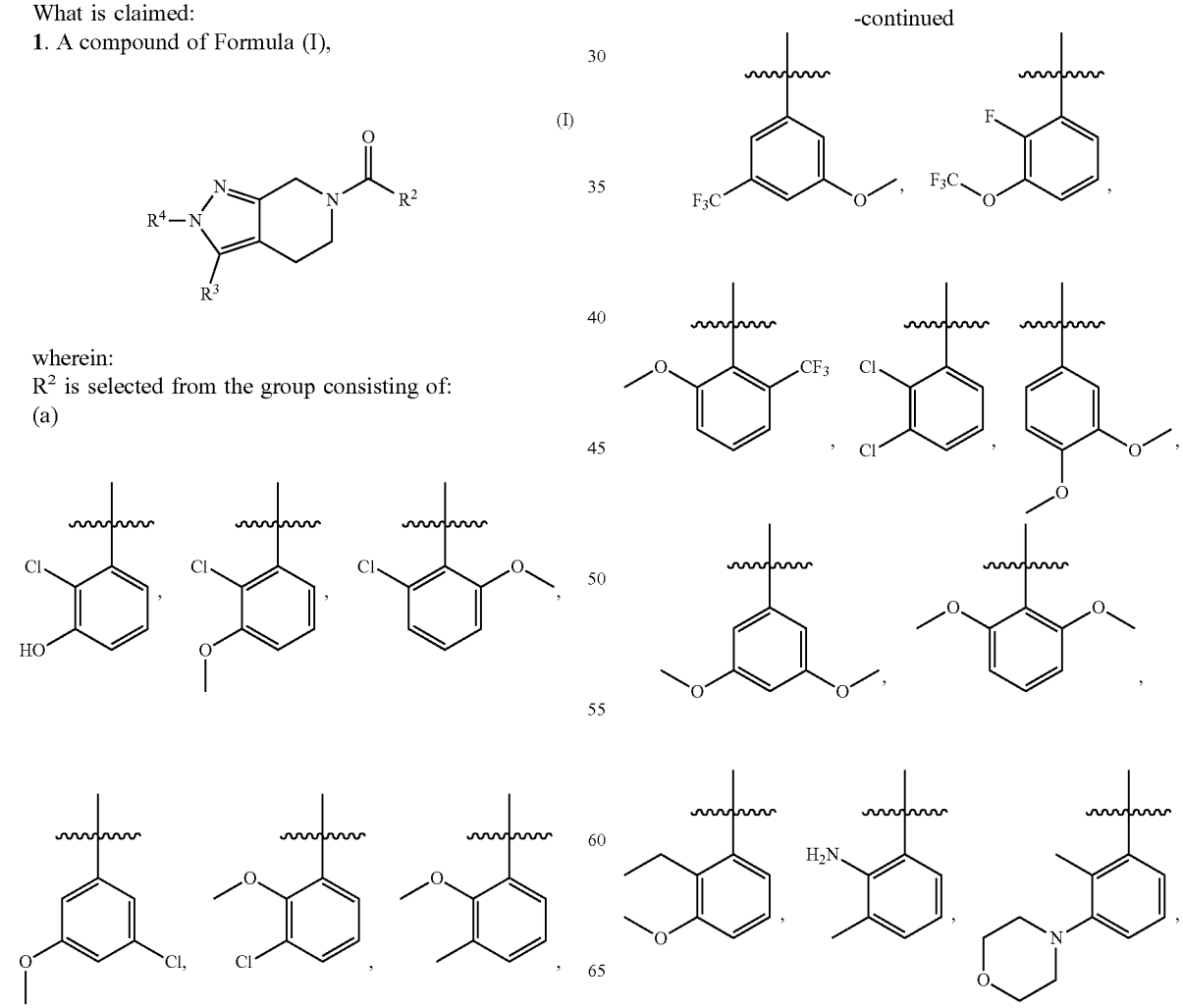

wherein:
R² is selected from the group consisting of:
(a)

-continued
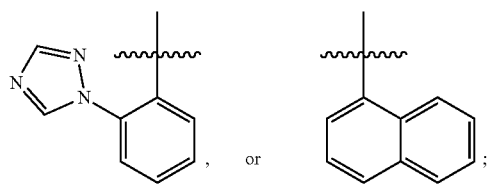, or ;
(b) pyridyl substituted with $OC_{1-4}$haloalkyl;
(c) pyrazole or 1H-1,2,4-triazole each substituted with one or two members each independently selected from the group consisting of: H, Cl, $C_{1-4}$alkyl, cyclopropyl and phenyl;
(d)
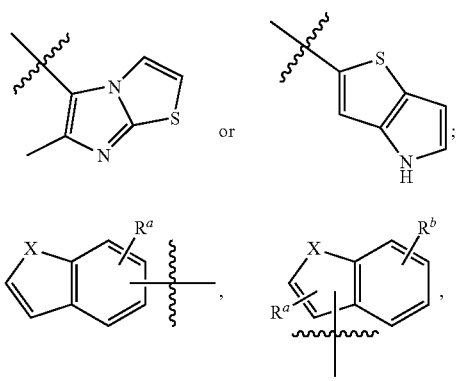 or ;
(e)
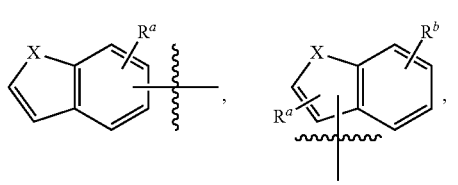,
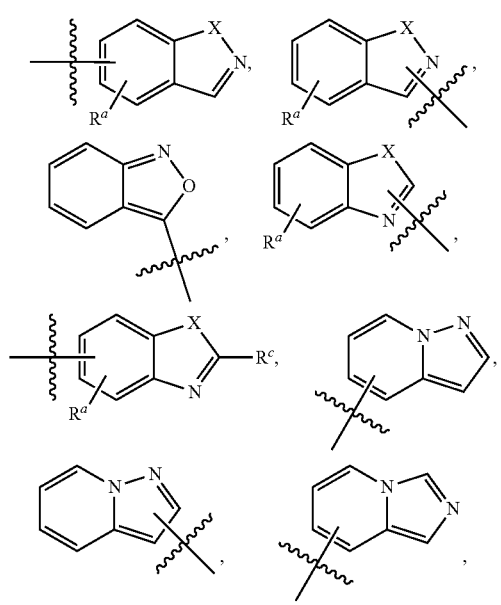
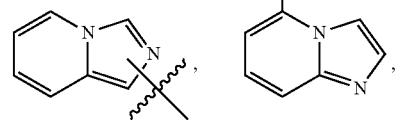,
-continued
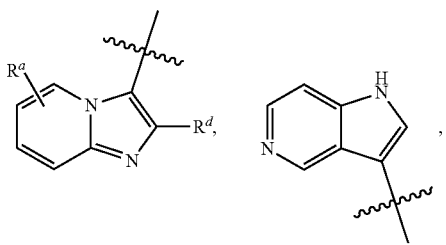,
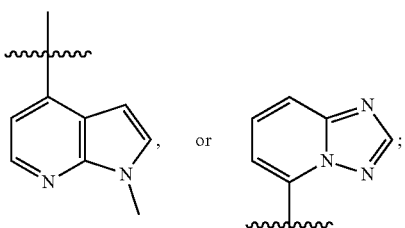 or ;
(f)
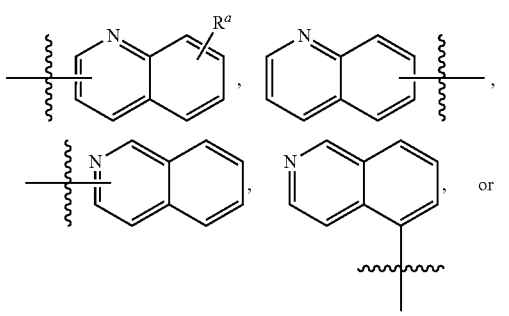, or
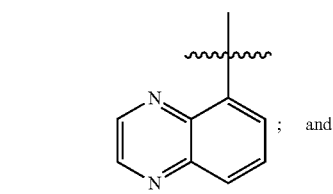; and
(g)
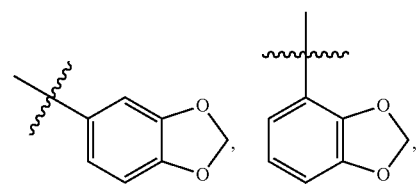,
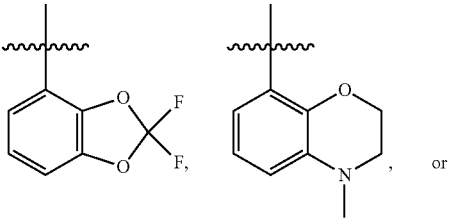, or
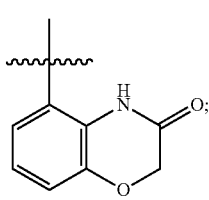;

where X is selected from the group consisting of: O, S, NH, and NCH$_3$;

R$^a$ is H or halo;

R$^b$ is selected from the group consisting of: H, halo and CH$_3$;

R$^c$ is H or CF$_3$; and

R$^d$ is H or CH$_3$;

R$^3$ is selected from the group consisting of:

(a) Phenyl; or phenyl independently substituted with one or two members selected from the group consisting of: halo and OC$_{1-4}$haloalkyl;

(b)

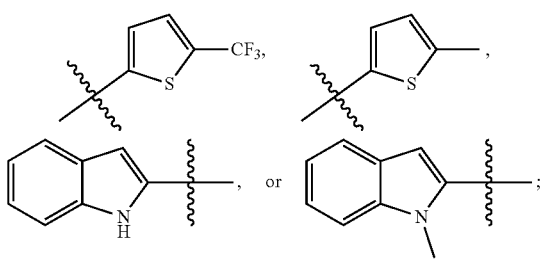

and (c) C$_{3-4}$cycloalkyl; and

R$^4$ is selected from the group consisting of: C$_{1-4}$alkyl;

with the proviso that when R$^2$ is

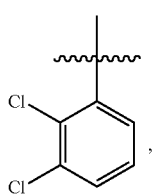 [SMILES: *c1cccc(Cl)c1Cl]

then R$^3$ is cyclopropyl, and pharmaceutically acceptable salts, isotopes, N-oxides, and stereoisomers thereof.

2. A compound as claimed in claim 1, wherein R$^2$ is

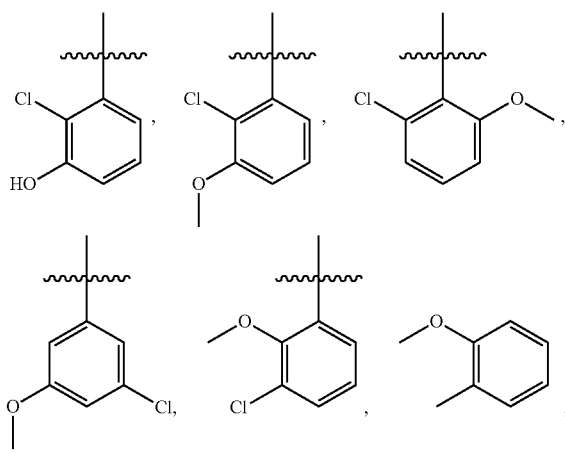

-continued

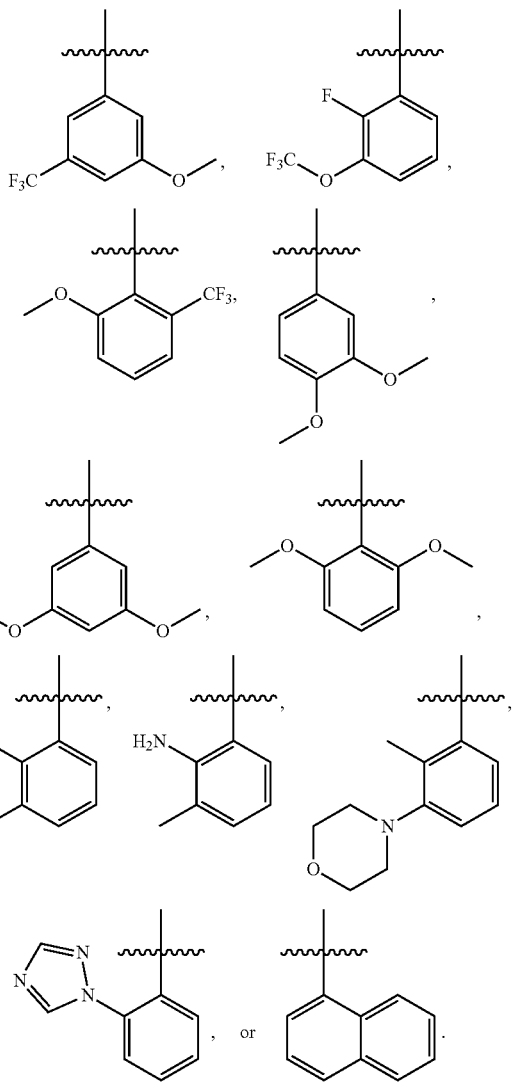

3. A compound as claimed in claim 1, wherein R$^2$ is

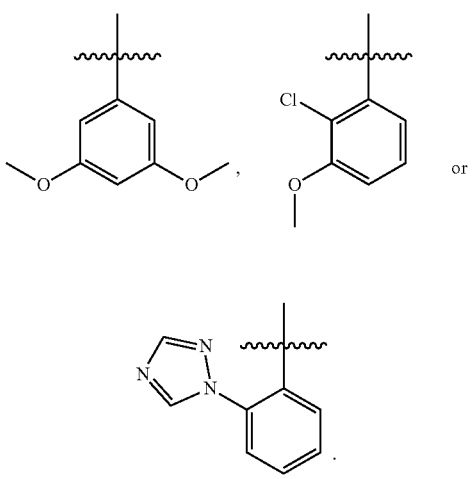

4. A compound as claimed in claim 1, wherein R² is
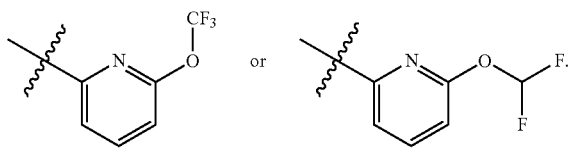 [SMILES: *c1cccc(OC(F)(F)F)n1 ; *c1cccc(OC(F)F)n1] or
5. A compound as claimed in claim 1, wherein R² is
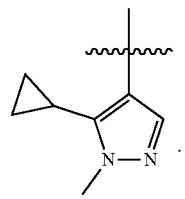 [SMILES: *c1cnn(C)c1C1CC1]
6. A compound as claimed in claim 1, wherein R² is
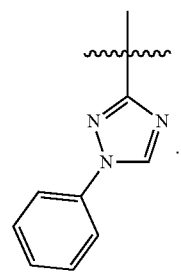 [SMILES: *c1ncn(-c2ccccc2)n1]
7. A compound as claimed in claim 1, wherein R² is
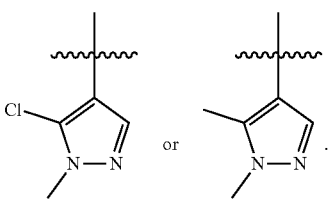 or
8. A compound as claimed in claim 1, wherein R² is
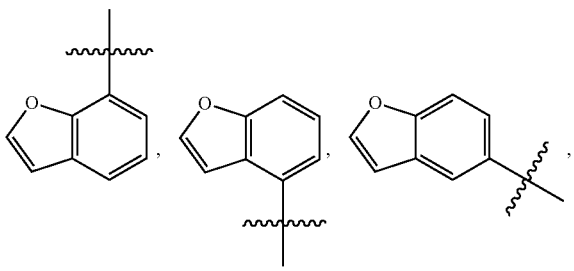
-continued
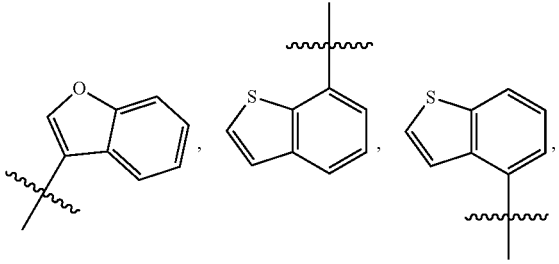
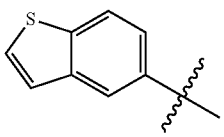 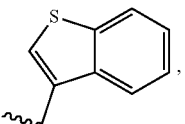
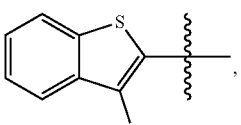
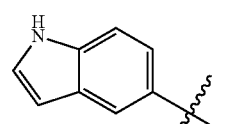 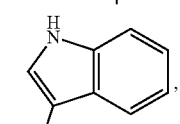
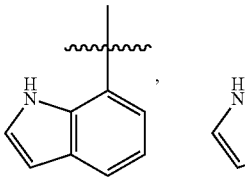 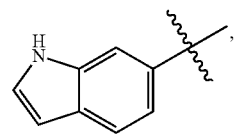
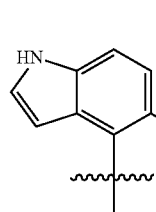 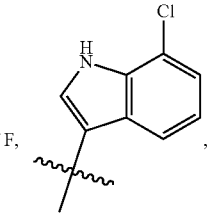
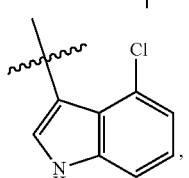 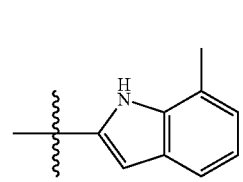
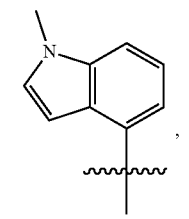 or 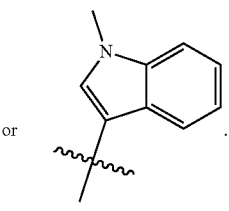

9. A compound as claimed in claim 1, wherein $R^2$ is
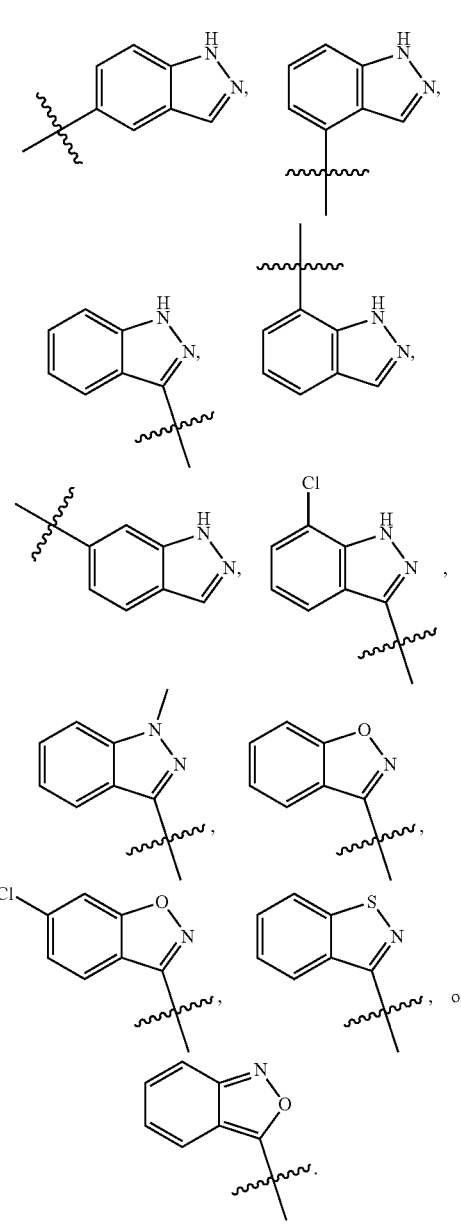
10. A compound as claimed in claim 1, wherein $R^2$ is
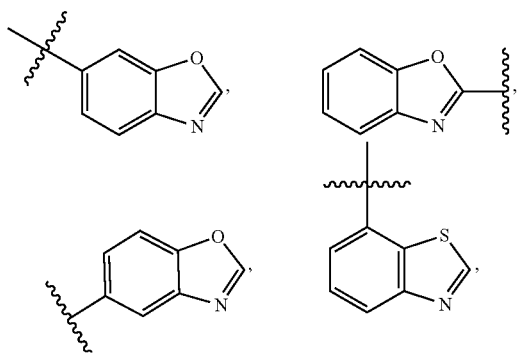
11. A compound as claimed in claim 1, wherein $R^2$ is
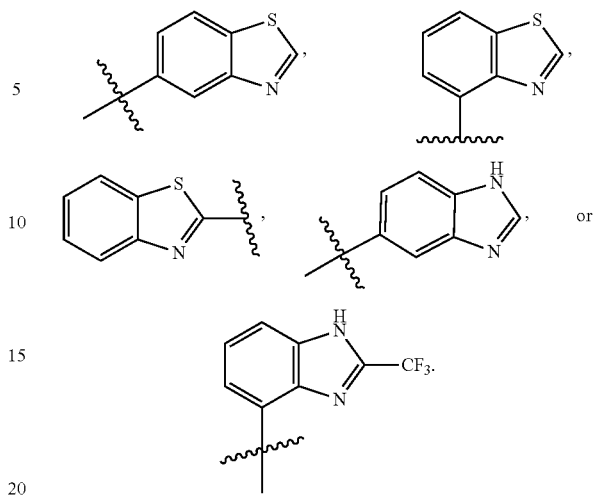
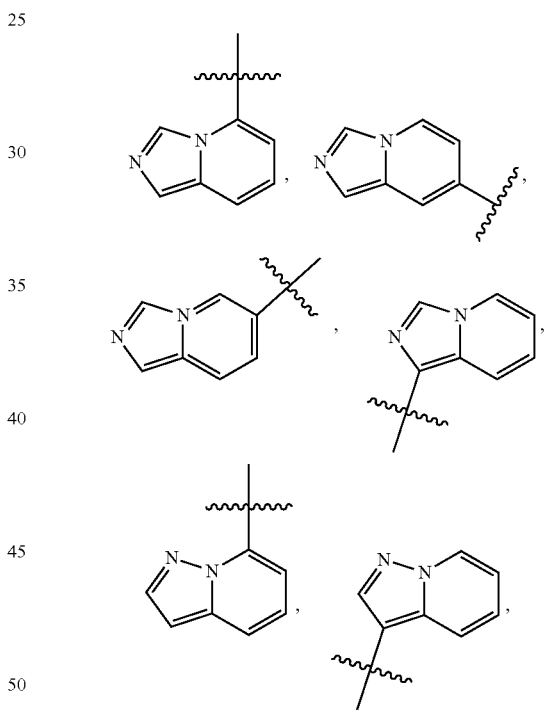
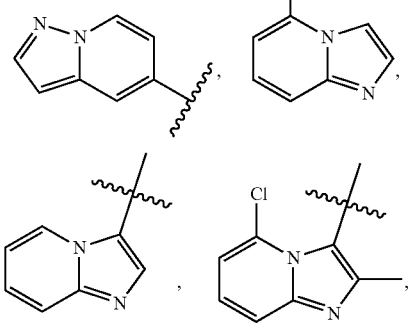

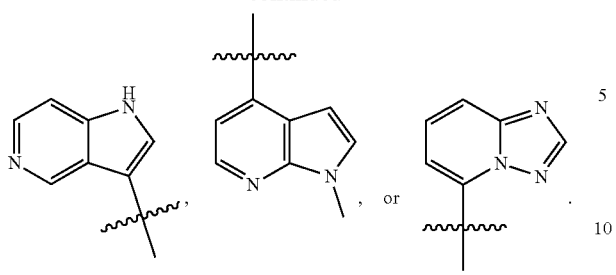

12. A compound as claimed in claim 1, wherein R² is

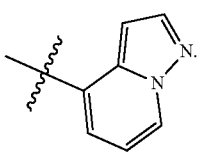 [SMILES: *c1cccn2nccc12]

13. A compound as claimed in claim 1, wherein R² is

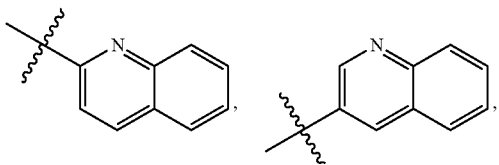

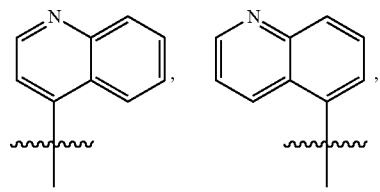

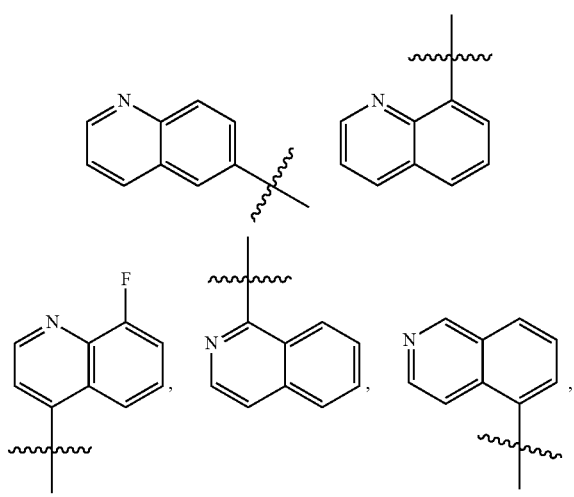

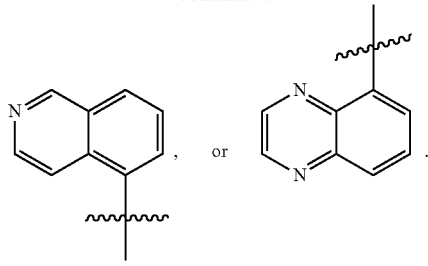

14. A compound as claimed in claim 1, wherein R³ is phenyl, 3,5-difluorophenyl, 3-chlorophenyl, 3-fluorophenyl, or 3-(difluoromethoxy)phenyl.

15. A compound as claimed in claim 1, wherein R³ is cyclopropyl.

16. A compound as claimed in claim 1, wherein R⁴ is CH₃.

17. A compound as claimed in claim 1, wherein X is O.

18. A compound as claimed in claim 1, wherein X is S.

19. A compound as claimed in claim 1, wherein X is NH or NCH₃.

20. A compound selected from the group consisting of:
- (2-Methyl-3-phenyl-2,4,5,7-tetrahydro-6H-pyrazolo[3,4-c]pyridin-6-yl)(naphthalen-1-yl)methanone;
- (3-Cyclopropyl-2-methyl-2,4,5,7-tetrahydro-6H-pyrazolo[3,4-c]pyridin-6-yl)(2,3-dichlorophenyl)methanone;
- (3-Cyclopropyl-2-methyl-2,4,5,7-tetrahydro-6H-pyrazolo[3,4-c]pyridin-6-yl)(naphthalen-1-yl)methanone;
- (2-Fluoro-3-(trifluoromethoxy)phenyl)(2-methyl-3-phenyl-2,4,5,7-tetrahydro-6H-pyrazolo[3,4-c]pyridin-6-yl)methanone;
- (2-Methoxy-6-(trifluoromethyl)phenyl)(2-methyl-3-phenyl-2,4,5,7-tetrahydro-6H-pyrazolo[3,4-c]pyridin-6-yl)methanone;
- (3-Methoxy-5-(trifluoromethyl)phenyl)(2-methyl-3-phenyl-2,4,5,7-tetrahydro-6H-pyrazolo[3,4-c]pyridin-6-yl)methanone;
- (2-Methoxy-3-methylphenyl)(2-methyl-3-phenyl-2,4,5,7-tetrahydro-6H-pyrazolo[3,4-c]pyridin-6-yl)methanone;
- (2-Ethyl-3-methoxyphenyl)(2-methyl-3-phenyl-2,4,5,7-tetrahydro-6H-pyrazolo[3,4-c]pyridin-6-yl)methanone;
- (3,4-Dimethoxyphenyl)(2-methyl-3-phenyl-2,4,5,7-tetrahydro-6H-pyrazolo[3,4-c]pyridin-6-yl)methanone;
- (2,6-Dimethoxyphenyl)(2-methyl-3-phenyl-2,4,5,7-tetrahydro-6H-pyrazolo[3,4-c]pyridin-6-yl)methanone;
- (3,5-Dimethoxyphenyl)-(2-methyl-3-phenyl-5,7-dihydro-4H-pyrazolo[3,4-c]pyridin-6-yl)methanone;
- (2-Chloro-3-hydroxyphenyl)(2-methyl-3-phenyl-2,4,5,7-tetrahydro-6H-pyrazolo[3,4-c]pyridin-6-yl)methanone;
- (2-Chloro-3-methoxyphenyl)(2-methyl-3-phenyl-2,4,5,7-tetrahydro-6H-pyrazolo[3,4-c]pyridin-6-yl)methanone;
- (3-Chloro-2-methoxy-phenyl)-(2-methyl-3-phenyl-5,7-dihydro-4H-pyrazolo[3,4-c]pyridin-6-yl)methanone;
- (2-Chloro-6-methoxyphenyl)(2-methyl-3-phenyl-2,4,5,7-tetrahydro-6H-pyrazolo[3,4-c]pyridin-6-yl)methanone;
- (3-Chloro-5-methoxyphenyl)(2-methyl-3-phenyl-2,4,5,7-tetrahydro-6H-pyrazolo[3,4-c]pyridin-6-yl)methanone;

(2-Amino-3-methylphenyl)(2-methyl-3-phenyl-2,4,5,7-tetrahydro-6H-pyrazolo[3,4-c]pyridin-6-yl)methanone;
(2-(1H-1,2,4-Triazol-1-yl)phenyl)(2-methyl-3-phenyl-2,4,5,7-tetrahydro-6H-pyrazolo[3,4-c]pyridin-6-yl)methanone;
(2-Methyl-3-morpholinophenyl)(2-methyl-3-phenyl-2,4,5,7-tetrahydro-6H-pyrazolo[3,4-c]pyridin-6-yl)methanone;
(5-Chloro-1-methyl-1H-pyrazol-4-yl)(2-methyl-3-phenyl-2,4,5,7-tetrahydro-6H-pyrazolo[3,4-c]pyridin-6-yl)methanone;
(1,5-Dimethyl-1H-pyrazol-4-yl)(2-methyl-3-phenyl-2,4,5,7-tetrahydro-6H-pyrazolo[3,4-c]pyridin-6-yl)methanone;
(5-Cyclopropyl-1-methyl-1H-pyrazol-4-yl)(2-methyl-3-phenyl-2,4,5,7-tetrahydro-6H-pyrazolo[3,4-c]pyridin-6-yl)methanone;
(2-Methyl-3-phenyl-2,4,5,7-tetrahydro-6H-pyrazolo[3,4-c]pyridin-6-yl)(1-phenyl-1H-1,2,4-triazol-3-yl)methanone;
(6-(Difluoromethoxy)pyridin-2-yl)(2-methyl-3-phenyl-2,4,5,7-tetrahydro-6H-pyrazolo[3,4-c]pyridin-6-yl)methanone;
(2-Methyl-3-phenyl-2,4,5,7-tetrahydro-6H-pyrazolo[3,4-c]pyridin-6-yl)(6-(trifluoromethoxy)pyridin-2-yl)methanone;
5-(2-Methyl-3-phenyl-4,5,6,7-tetrahydro-2H-pyrazolo[3,4-c]pyridine-6-carbonyl)-2H-benzo[b][1,4]oxazin-3(4H)-one;
(4-Methyl-3,4-dihydro-2H-benzo[b][1,4]oxazin-7-yl)(2-methyl-3-phenyl-2,4,5,7-tetrahydro-6H-pyrazolo[3,4-c]pyridin-6-yl)methanone;
Benzo[d][1,3]dioxol-4-yl(2-methyl-3-phenyl-2,4,5,7-tetrahydro-6H-pyrazolo[3,4-c]pyridin-6-yl)methanone;
Benzo[d][1,3]dioxol-5-yl(2-methyl-3-phenyl-2,4,5,7-tetrahydro-6H-pyrazolo[3,4-c]pyridin-6-yl)methanone;
(2,2-Difluorobenzo[d][1,3]dioxol-4-yl)(2-methyl-3-phenyl-2,4,5,7-tetrahydro-6H-pyrazolo[3,4-c]pyridin-6-yl)methanone;
(2-Methyl-3-phenyl-2,4,5,7-tetrahydro-6H-pyrazolo[3,4-c]pyridin-6-yl)(4H-thieno[3,2-b]pyrrol-2-yl)methanone;
(2-Methyl-3-phenyl-2,4,5,7-tetrahydro-6H-pyrazolo[3,4-c]pyridin-6-yl)(6-methylimidazo[2,1-b]thiazol-5-yl)methanone;
Benzofuran-7-yl(2-methyl-3-phenyl-2,4,5,7-tetrahydro-6H-pyrazolo[3,4-c]pyridin-6-yl)methanone;
Benzofuran-4-yl(2-methyl-3-phenyl-2,4,5,7-tetrahydro-6H-pyrazolo[3,4-c]pyridin-6-yl)methanone;
Benzofuran-5-yl(2-methyl-3-phenyl-2,4,5,7-tetrahydro-6H-pyrazolo[3,4-c]pyridin-6-yl)methanone;
Benzofuran-3-yl(2-methyl-3-phenyl-2,4,5,7-tetrahydro-6H-pyrazolo[3,4-c]pyridin-6-yl)methanone;
Benzo[b]thiophen-7-yl(2-methyl-3-phenyl-2,4,5,7-tetrahydro-6H-pyrazolo[3,4-c]pyridin-6-yl)methanone;
Benzo[b]thiophen-4-yl(2-methyl-3-phenyl-2,4,5,7-tetrahydro-6H-pyrazolo[3,4-c]pyridin-6-yl)methanone;
Benzo[b]thiophen-5-yl(2-methyl-3-phenyl-2,4,5,7-tetrahydro-6H-pyrazolo[3,4-c]pyridin-6-yl)methanone;
Benzo[b]thiophen-3-yl(2-methyl-3-phenyl-2,4,5,7-tetrahydro-6H-pyrazolo[3,4-c]pyridin-6-yl)methanone;
(3-Chlorobenzo[b]thiophen-2-yl)(2-methyl-3-phenyl-2,4,5,7-tetrahydro-6H-pyrazolo[3,4-c]pyridin-6-yl)methanone;
(1H-Indol-4-yl)(2-methyl-3-phenyl-2,4,5,7-tetrahydro-6H-pyrazolo[3,4-c]pyridin-6-yl)methanone;
(1H-Indol-5-yl)(2-methyl-3-phenyl-2,4,5,7-tetrahydro-6H-pyrazolo[3,4-c]pyridin-6-yl)methanone;
(1H-Indol-3-yl)(2-methyl-3-phenyl-2,4,5,7-tetrahydro-6H-pyrazolo[3,4-c]pyridin-6-yl)methanone;
(1H-Indol-7-yl)(2-methyl-3-phenyl-2,4,5,7-tetrahydro-6H-pyrazolo[3,4-c]pyridin-6-yl)methanone;
(1H-Indol-6-yl)(2-methyl-3-phenyl-2,4,5,7-tetrahydro-6H-pyrazolo[3,4-c]pyridin-6-yl)methanone;
(5-Fluoro-1H-indol-4-yl)(2-methyl-3-phenyl-2,4,5,7-tetrahydro-6H-pyrazolo[3,4-c]pyridin-6-yl)methanone;
(7-Chloro-1H-indol-3-yl)(2-methyl-3-phenyl-2,4,5,7-tetrahydro-6H-pyrazolo[3,4-c]pyridin-6-yl)methanone;
(4-Chloro-1H-indol-3-yl)(2-methyl-3-phenyl-2,4,5,7-tetrahydro-6H-pyrazolo[3,4-c]pyridin-6-yl)methanone;
(7-Methyl-1H-indol-2-yl)(2-methyl-3-phenyl-2,4,5,7-tetrahydro-6H-pyrazolo[3,4-c]pyridin-6-yl)methanone;
(1-Methyl-1H-indol-4-yl)(2-methyl-3-phenyl-2,4,5,7-tetrahydro-6H-pyrazolo[3,4-c]pyridin-6-yl)methanone;
(1-Methyl-1H-indol-3-yl)(2-methyl-3-phenyl-2,4,5,7-tetrahydro-6H-pyrazolo[3,4-c]pyridin-6-yl)methanone;
Benzo[d]isoxazol-3-yl(2-methyl-3-phenyl-2,4,5,7-tetrahydro-6H-pyrazolo[3,4-c]pyridin-6-yl)methanone;
(6-Chlorobenzo[d]isoxazol-3-yl)(2-methyl-3-phenyl-2,4,5,7-tetrahydro-6H-pyrazolo[3,4-c]pyridin-6-yl)methanone;
Benzo[c]isoxazol-3-yl(2-methyl-3-phenyl-2,4,5,7-tetrahydro-6H-pyrazolo[3,4-c]pyridin-6-yl)methanone;
Benzo[d]oxazol-6-yl(2-methyl-3-phenyl-2,4,5,7-tetrahydro-6H-pyrazolo[3,4-c]pyridin-6-yl)methanone;
Benzo[d]oxazol-2-yl(2-methyl-3-phenyl-2,4,5,7-tetrahydro-6H-pyrazolo[3,4-c]pyridin-6-yl)methanone;
Benzo[d]oxazol-5-yl(2-methyl-3-phenyl-2,4,5,7-tetrahydro-6H-pyrazolo[3,4-c]pyridin-6-yl)methanone;
Benzo[d]thiazol-7-yl(2-methyl-3-phenyl-2,4,5,7-tetrahydro-6H-pyrazolo[3,4-c]pyridin-6-yl)methanone;
Benzo[d]thiazol-5-yl(2-methyl-3-phenyl-2,4,5,7-tetrahydro-6H-pyrazolo[3,4-c]pyridin-6-yl)methanone;
Benzo[d]thiazol-4-yl(2-methyl-3-phenyl-2,4,5,7-tetrahydro-6H-pyrazolo[3,4-c]pyridin-6-yl)methanone;
Benzo[d]thiazol-2-yl(2-methyl-3-phenyl-2,4,5,7-tetrahydro-6H-pyrazolo[3,4-c]pyridin-6-yl)methanone;
Benzo[d]isothiazol-3-yl(2-methyl-3-phenyl-2,4,5,7-tetrahydro-6H-pyrazolo[3,4-c]pyridin-6-yl)methanone;
(1H-Indazol-5-yl)(2-methyl-3-phenyl-2,4,5,7-tetrahydro-6H-pyrazolo[3,4-c]pyridin-6-yl)methanone;
(1H-Indazol-4-yl)(2-methyl-3-phenyl-2,4,5,7-tetrahydro-6H-pyrazolo[3,4-c]pyridin-6-yl)methanone;
(1H-Indazol-3-yl)(2-methyl-3-phenyl-2,4,5,7-tetrahydro-6H-pyrazolo[3,4-c]pyridin-6-yl)methanone;
(1H-Indazol-7-yl)(2-methyl-3-phenyl-2,4,5,7-tetrahydro-6H-pyrazolo[3,4-c]pyridin-6-yl)methanone;
(1H-Indazol-6-yl)(2-methyl-3-phenyl-2,4,5,7-tetrahydro-6H-pyrazolo[3,4-c]pyridin-6-yl)methanone;
(7-Chloro-1H-indazol-3-yl)(2-methyl-3-phenyl-2,4,5,7-tetrahydro-6H-pyrazolo[3,4-c]pyridin-6-yl)methanone;
(1-Methyl-1H-indazol-3-yl)(2-methyl-3-phenyl-2,4,5,7-tetrahydro-6H-pyrazolo[3,4-c]pyridin-6-yl)methanone;
(1H-Benzo[d]imidazol-5-yl)(2-methyl-3-phenyl-2,4,5,7-tetrahydro-6H-pyrazolo[3,4-c]pyridin-6-yl)methanone;
(2-Methyl-3-phenyl-2,4,5,7-tetrahydro-6H-pyrazolo[3,4-c]pyridin-6-yl)(2-(trifluoromethyl)-1H-benzo[d]imidazol-4-yl)methanone;

(2-Methyl-3-phenyl-2,4,5,7-tetrahydro-6H-pyrazolo[3,4-c]pyridin-6-yl)(pyrazolo[1,5-a]pyridin-5-yl)methanone;
(2-Methyl-3-phenyl-2,4,5,7-tetrahydro-6H-pyrazolo[3,4-c]pyridin-6-yl)(pyrazolo[1,5-a]pyridin-3-yl)methanone;
(2-Methyl-3-phenyl-2,4,5,7-tetrahydro-6H-pyrazolo[3,4-c]pyridin-6-yl)(pyrazolo[1,5-a]pyridin-7-yl)methanone;
Imidazo[1,5-a]pyridin-1-yl(2-methyl-3-phenyl-2,4,5,7-tetrahydro-6H-pyrazolo[3,4-c]pyridin-6-yl)methanone;
Imidazo[1,5-a]pyridin-6-yl(2-methyl-3-phenyl-2,4,5,7-tetrahydro-6H-pyrazolo[3,4-c]pyridin-6-yl)methanone;
Imidazo[1,5-a]pyridin-7-yl(2-methyl-3-phenyl-2,4,5,7-tetrahydro-6H-pyrazolo[3,4-c]pyridin-6-yl)methanone;
Imidazo[1,5-a]pyridin-5-yl(2-methyl-3-phenyl-2,4,5,7-tetrahydro-6H-pyrazolo[3,4-c]pyridin-6-yl)methanone;
Imidazo[1,2-a]pyridin-5-yl(2-methyl-3-phenyl-2,4,5,7-tetrahydro-6H-pyrazolo[3,4-c]pyridin-6-yl)methanone;
Imidazo[1,2-a]pyridin-3-yl(2-methyl-3-phenyl-2,4,5,7-tetrahydro-6H-pyrazolo[3,4-c]pyridin-6-yl)methanone;
(5-Chloro-2-methylimidazo[1,2-a]pyridin-3-yl)(2-methyl-3-phenyl-2,4,5,7-tetrahydro-6H-pyrazolo[3,4-c]pyridin-6-yl)methanone;
(2-Methyl-3-phenyl-2,4,5,7-tetrahydro-6H-pyrazolo[3,4-c]pyridin-6-yl)(1H-pyrrolo[3,2-c]pyridin-3-yl)methanone;
(1-Methyl-1H-pyrrolo[2,3-b]pyridin-4-yl)(2-methyl-3-phenyl-2,4,5,7-tetrahydro-6H-pyrazolo[3,4-c]pyridin-6-yl)methanone;
[1,2,4]Triazolo[1,5-a]pyridin-5-yl(2-methyl-3-phenyl-2,4,5,7-tetrahydro-6H-pyrazolo[3,4-c]pyridin-6-yl)methanone;
(2-Methyl-3-phenyl-2,4,5,7-tetrahydro-6H-pyrazolo[3,4-c]pyridin-6-yl)(quinolin-4-yl)methanone;
Isoquinolin-4-yl(2-methyl-3-phenyl-2,4,5,7-tetrahydro-6H-pyrazolo[3,4-c]pyridin-6-yl)methanone;
Isoquinolin-1-yl(2-methyl-3-phenyl-2,4,5,7-tetrahydro-6H-pyrazolo[3,4-c]pyridin-6-yl)methanone;
(2-Methyl-3-phenyl-2,4,5,7-tetrahydro-6H-pyrazolo[3,4-c]pyridin-6-yl)(quinolin-5-yl)methanone;
(2-Methyl-3-phenyl-2,4,5,7-tetrahydro-6H-pyrazolo[3,4-c]pyridin-6-yl)(quinolin-6-yl)methanone;
(2-Ethyl-3-phenyl-2,4,5,7-tetrahydro-6H-pyrazolo[3,4-c]pyridin-6-yl)(quinolin-6-yl)methanone;
Isoquinolin-5-yl(2-methyl-3-phenyl-2,4,5,7-tetrahydro-6H-pyrazolo[3,4-c]pyridin-6-yl)methanone;
(2-Methyl-3-phenyl-2,4,5,7-tetrahydro-6H-pyrazolo[3,4-c]pyridin-6-yl)(quinolin-8-yl)methanone;
(2-Methyl-3-phenyl-2,4,5,7-tetrahydro-6H-pyrazolo[3,4-c]pyridin-6-yl)(quinolin-2-yl)methanone;
(2-Methyl-3-phenyl-2,4,5,7-tetrahydro-6H-pyrazolo[3,4-c]pyridin-6-yl)(quinolin-3-yl)methanone;
(8-Fluoroquinolin-4-yl)(2-methyl-3-phenyl-2,4,5,7-tetrahydro-6H-pyrazolo[3,4-c]pyridin-6-yl)methanone;
(2-Methyl-3-phenyl-2,4,5,7-tetrahydro-6H-pyrazolo[3,4-c]pyridin-6-yl)(quinoxalin-5-yl)methanone;
(3-(3-(Difluoromethoxy)phenyl)-2-methyl-2,4,5,7-tetrahydro-6H-pyrazolo[3,4-c]pyridin-6-yl)(quinolin-6-yl)methanone;
(3-(3-Chlorophenyl)-2-methyl-2,4,5,7-tetrahydro-6H-pyrazolo[3,4-c]pyridin-6-yl)(quinolin-6-yl)methanone;
(3-(3-Fluorophenyl)-2-methyl-2,4,5,7-tetrahydro-6H-pyrazolo[3,4-c]pyridin-6-yl)(quinolin-6-yl)methanone;
(3-(3,5-Difluorophenyl)-2-methyl-2,4,5,7-tetrahydro-6H-pyrazolo[3,4-c]pyridin-6-yl)(quinolin-6-yl)methanone;
Benzo[d]isoxazol-3-yl(2-methyl-3-(5-methylthiophen-2-yl)-2,4,5,7-tetrahydro-6H-pyrazolo[3,4-c]pyridin-6-yl)methanone;
(2-Methyl-3-(5-(trifluoromethyl)thiophen-2-yl)-2,4,5,7-tetrahydro-6H-pyrazolo[3,4-c]pyridin-6-yl)(quinolin-6-yl)methanone;
(3-(1H-Indol-2-yl)-2-methyl-2,4,5,7-tetrahydro-6H-pyrazolo[3,4-c]pyridin-6-yl)(quinolin-6-yl)methanone; and
(2-Methyl-3-(1-methyl-1H-indol-2-yl)-2,4,5,7-tetrahydro-6H-pyrazolo[3,4-c]pyridin-6-yl)(quinolin-6-yl)methanone;

and pharmaceutically acceptable salts, isotopes, N-oxides, and stereoisomers thereof.

21. A pharmaceutical composition comprising:

(A) at least one compound of Formula (I):

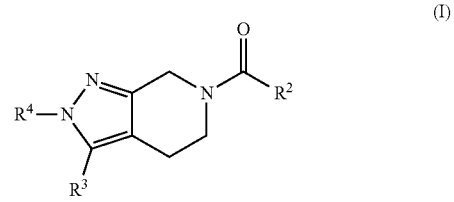

(I)

wherein:

$R^2$ is selected from the group consisting of:

(a)

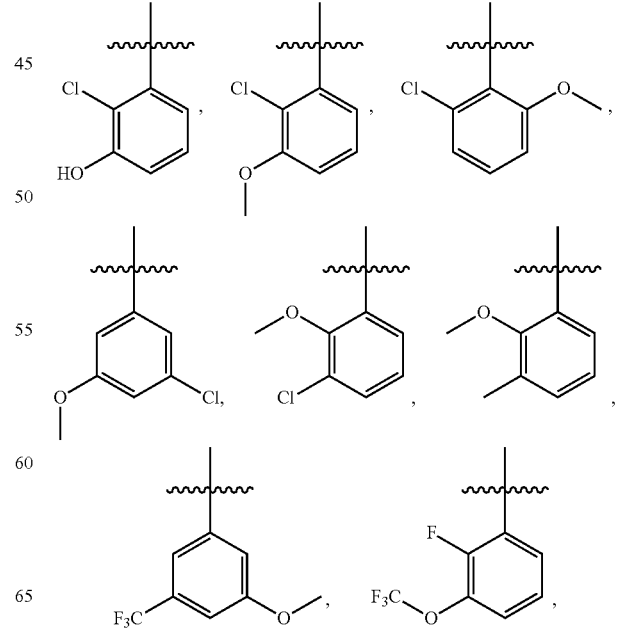

-continued
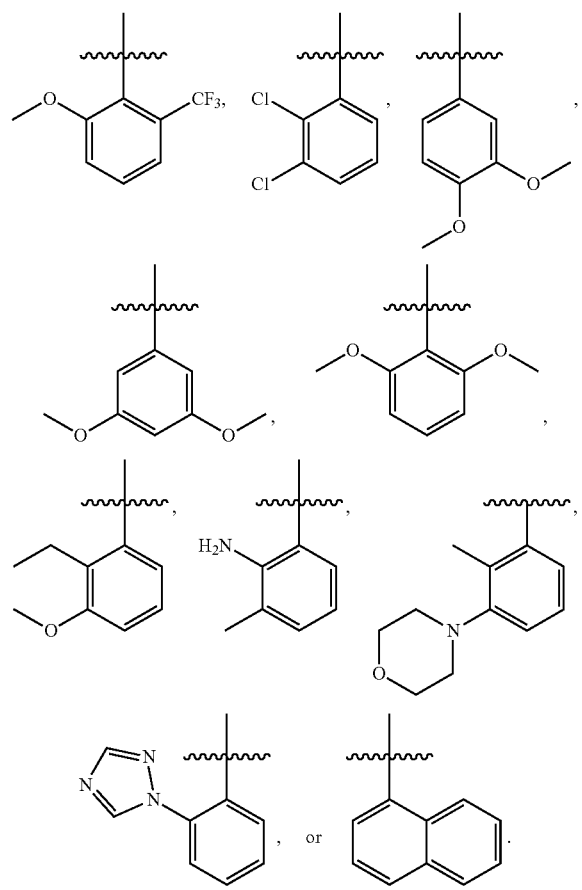
(b) pyridyl substituted with $OC_{1-4}$haloalkyl;
(c) pyrazole or 1H-1,2,4-triazole each substituted with one or two members each independently selected from the group consisting of: H, Cl, $C_{1-4}$alkyl, cyclopropyl and phenyl;
(d)
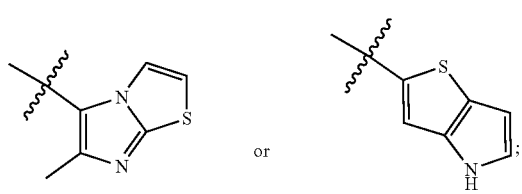
(e)
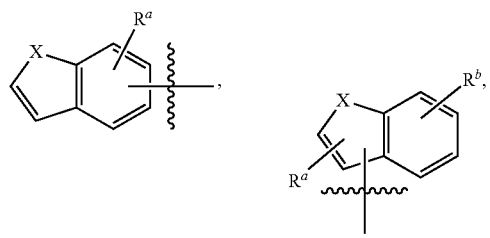
-continued
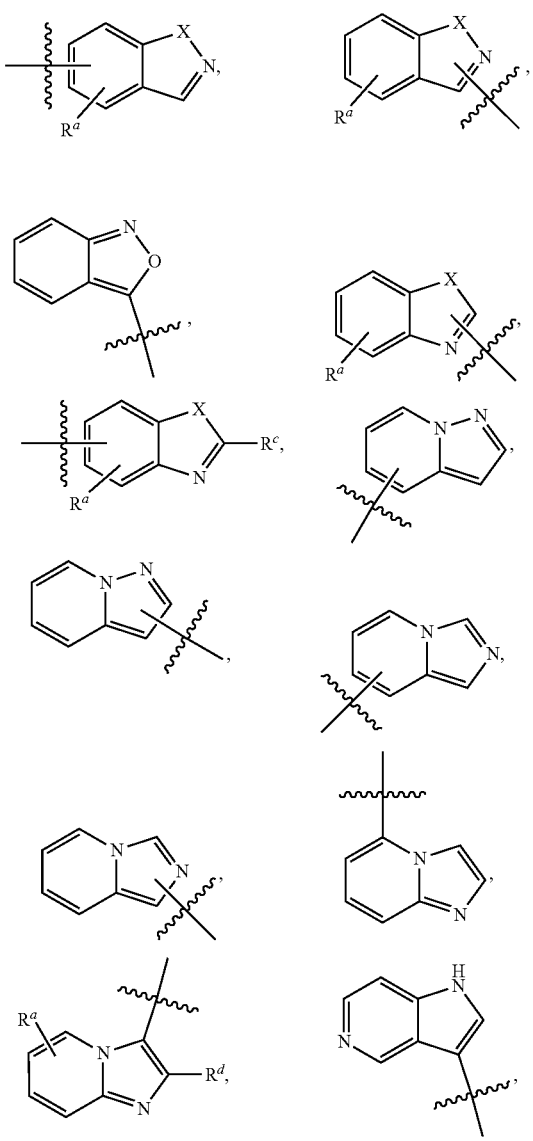
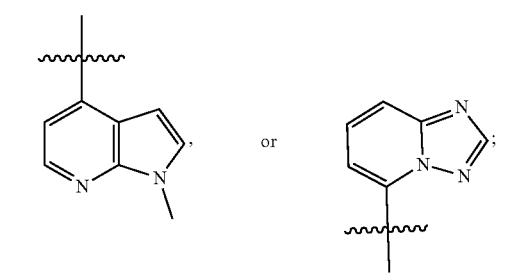
(f)
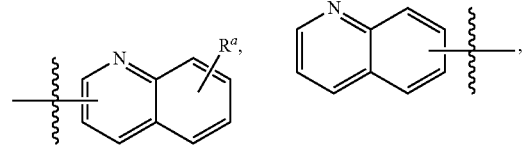

-continued

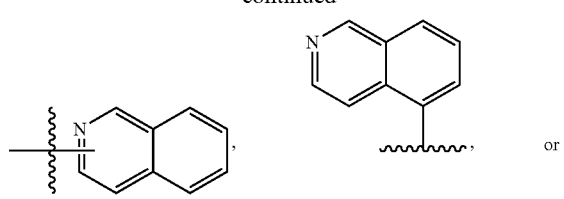

or

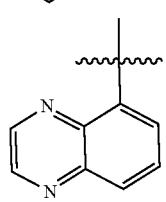

and (g)

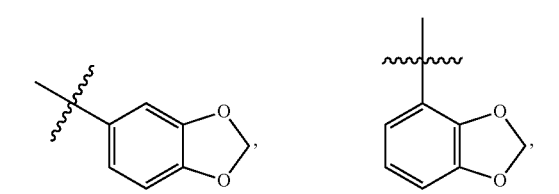

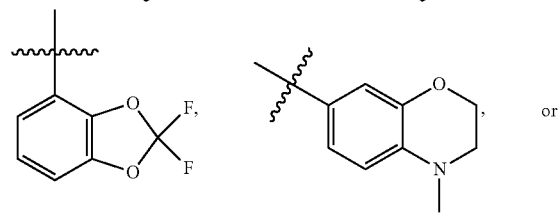

or

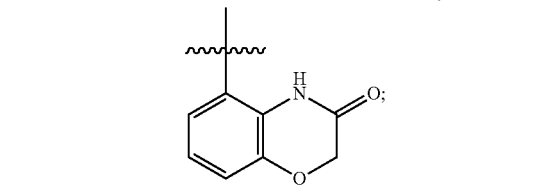

where X is selected from the group consisting of: O, S, NH, and NCH$_3$;

$R^a$ is H or halo;

$R^b$ is selected from the group consisting of: H, halo and CH$_3$;

$R^c$ is H or CF$_3$; and $R^d$ is H or CH$_3$;

$R^3$ is selected from the group consisting of:

(h) Phenyl; or phenyl independently substituted with one or two members selected from the group consisting of: halo and OC$_{1-4}$haloalkyl;

(i)

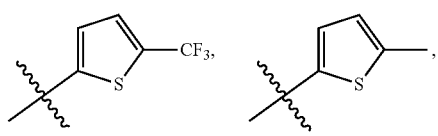

-continued

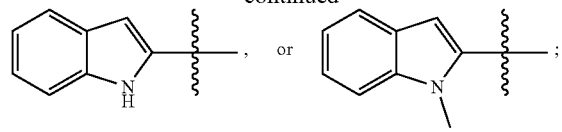

(j) C$_{3-4}$cycloalkyl; and $R^4$ is selected from the group consisting of: C$_{1-4}$alkyl;

with the proviso that when $R^2$ is

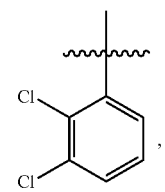 [SMILES: *c1cccc(Cl)c1Cl]

then $R^3$ is cyclopropyl;

and pharmaceutically acceptable salts, isotopes, N-oxides, and stereoisomers of compounds of Formula (I);

(B) at least one pharmaceutically acceptable excipient.

22. A pharmaceutical composition comprising at least one compound of claim 20 and at least one pharmaceutically acceptable excipient.

23. A compound, having the structure of Formula (II):

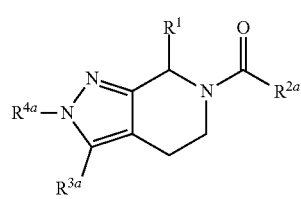

(II)

wherein $R^1$ is C$_{1-4}$alkyl;

$R^{2a}$ is selected from the group consisting of:

(a)

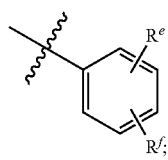

(b) 6-Membered heteroaryl selected from the group consisting of:

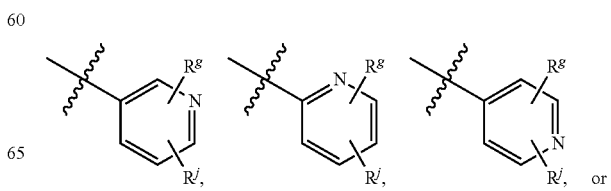

or

-continued
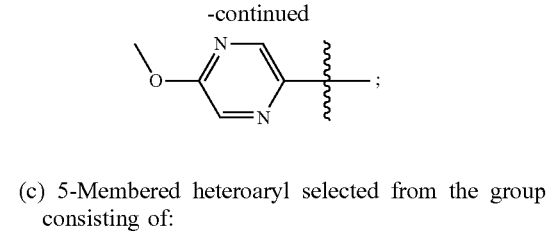
(c) 5-Membered heteroaryl selected from the group consisting of:
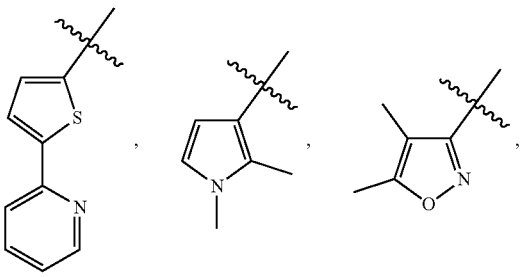
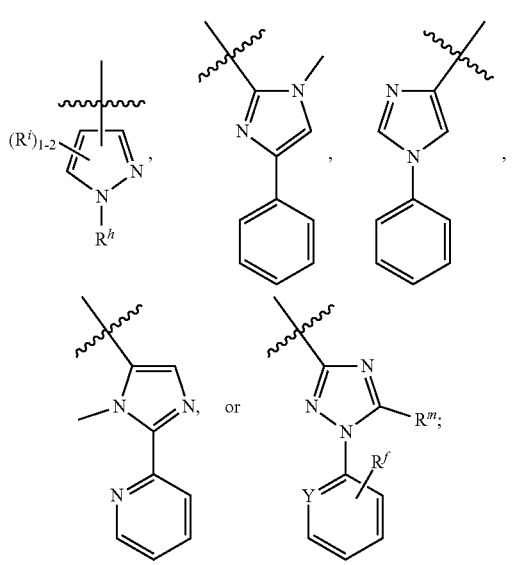
(d) 5,6-Fused or 6,5-fused heteroaryl selected from the group consisting of:
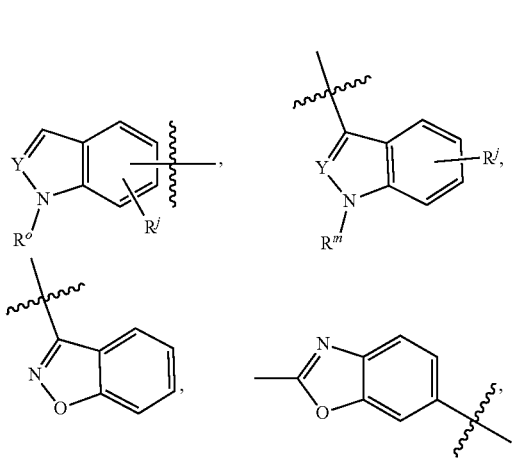
-continued
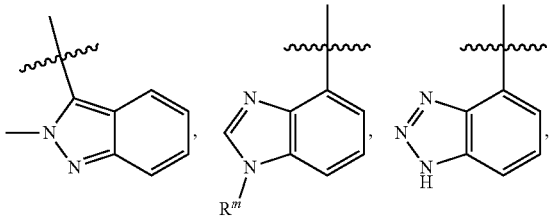
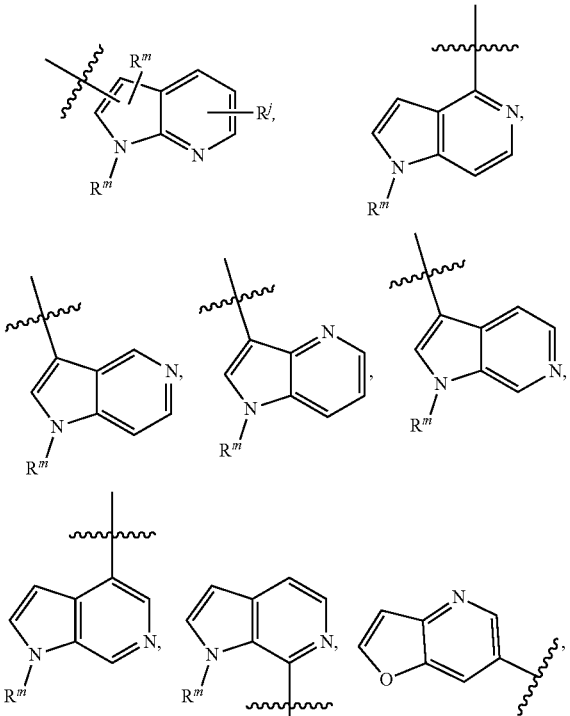
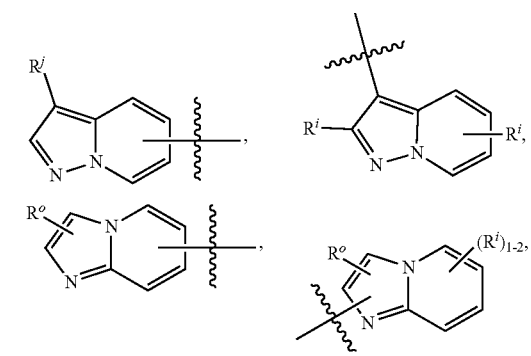

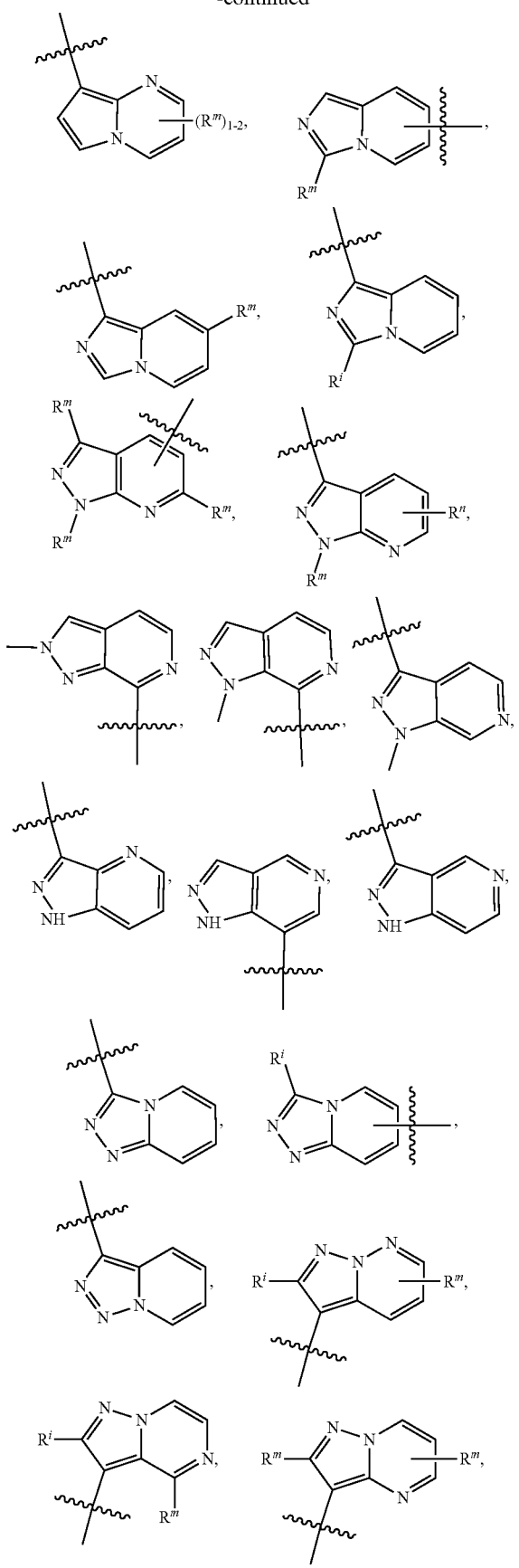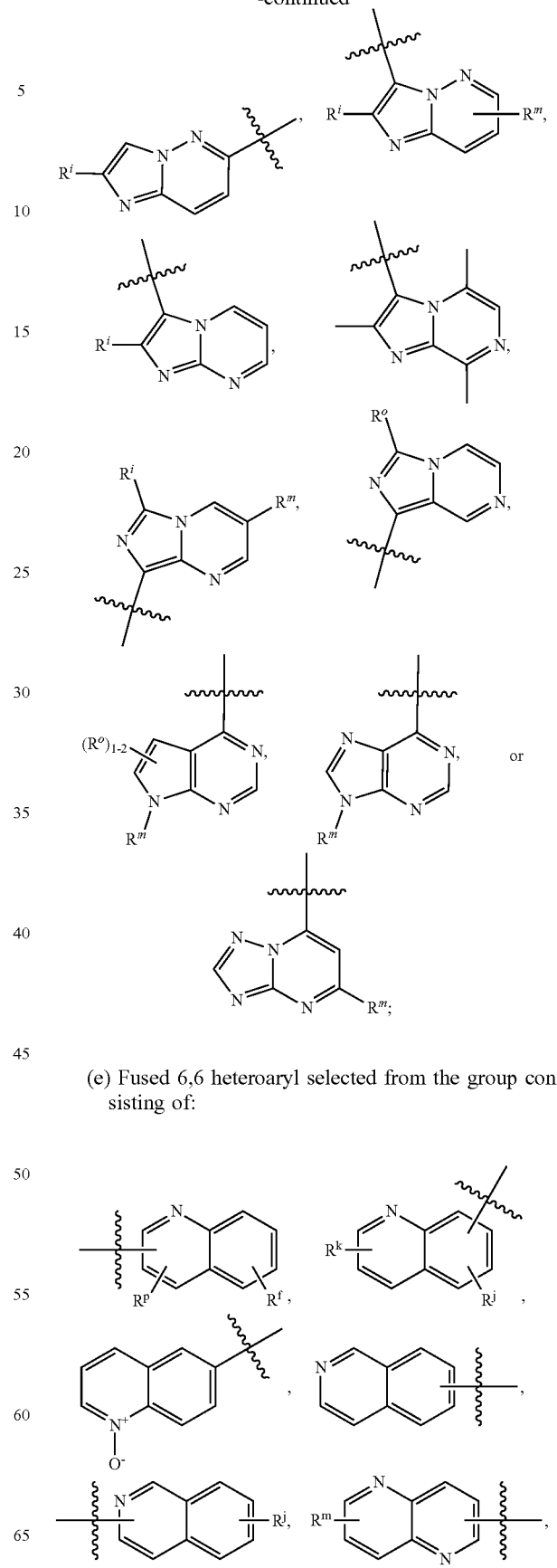
(e) Fused 6,6 heteroaryl selected from the group consisting of:

-continued
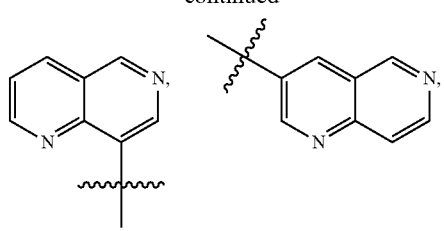
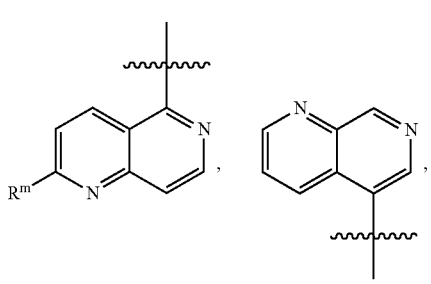
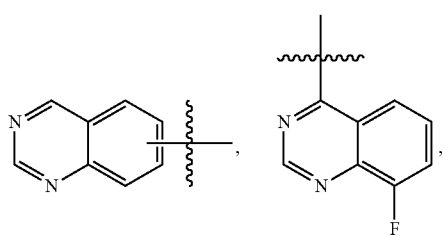
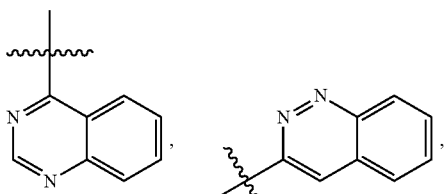
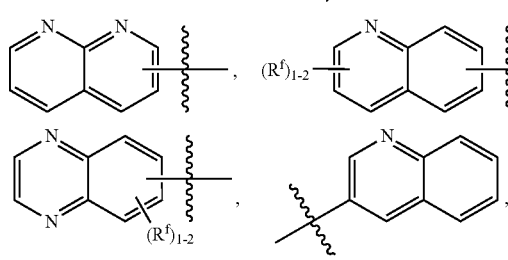
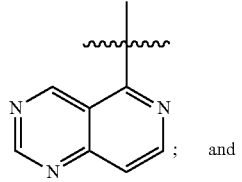
; and
(f) Heterocycloalkyl selected from the group consisting of:
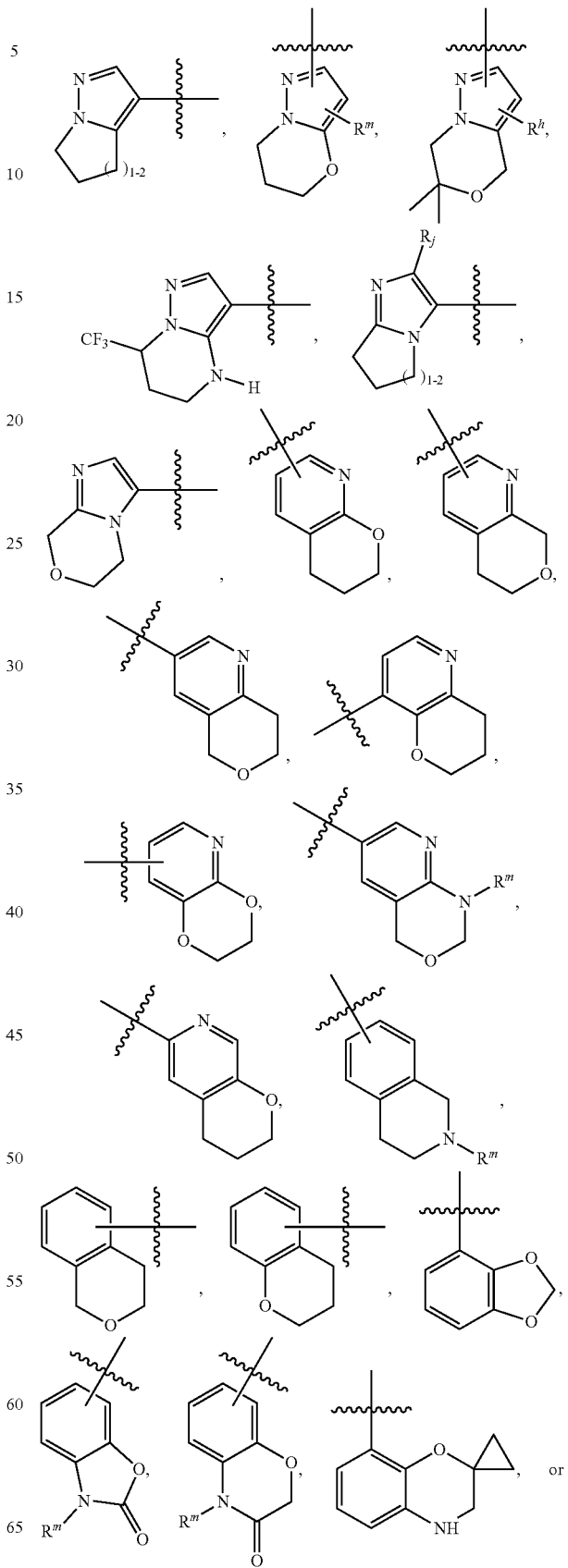

-continued

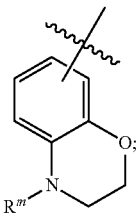

$R^{3a}$ is selected from the group consisting of:
(a) Phenyl; or phenyl substituted with one, two, or three members each independently selected from the group consisting of: halo, $C_{1-4}$alkyl, $C_{1-4}$haloalkyl, $OC_{1-4}$alkyl, and $OC_{1-6}$haloalkyl;
(b) 5-Membered heteroaryl selected from the group consisting of:

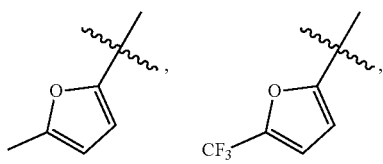

and

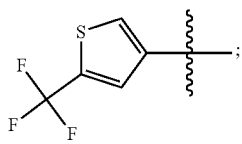

(c) 6-Membered heteroaryl selected from the group consisting of:

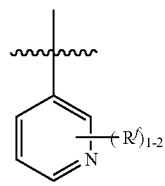

and

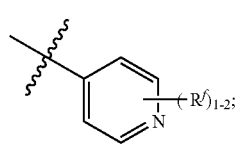

(d) 5,6-Fused or 6,5-fused heteroaryl selected from the group consisting of:

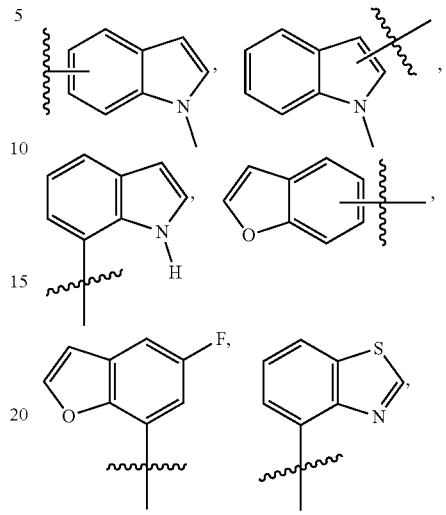

and

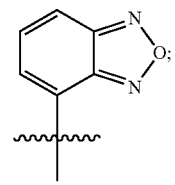 [SMILES: *c1cccc2nonc12]

and
(e) Heterocycloalkyl selected from the group consisting of:

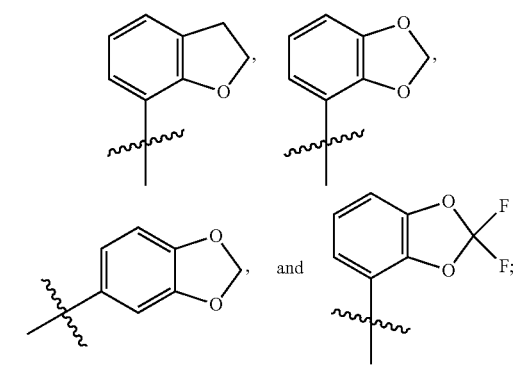

$R^e$ is selected from the group consisting of: $OC_{1-4}$alkyl, $OC_{1-4}$haloalkyl, $(C{=}O)NHCH_3$, and 5-membered heteroaryl ring containing two or three nitrogen members, wherein the 5-membered heteroaryl ring is optionally substituted with one $R^f$ member;

$R^f$ is selected from the group consisting of: H, halo, $C_{1-4}$alkyl, $C_{1-4}$haloalkyl, $OC_{1-4}$alkyl, and $OC_{1-4}$haloalkyl;

$R^g$ is selected from the group consisting of: $OC_{1-4}$alkyl, $OC_{1-4}$haloalkyl, $CH_2OCH_3$, $CH_2OH$,

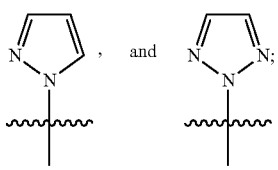 [SMILES: *n1cccn1 ; *n1nccn1]

$R^h$ is selected from the group consisting of: H, $C_{1-4}$alkyl, $C_{1-4}$haloalkyl, and $C_{3-6}$cycloalkyl;

$R^i$ is selected from the group consisting of: H, halo, $C_{1-4}$alkyl, $C_{1-4}$haloalkyl, $OC_{1-4}$alkyl, $C_{3-6}$cycloalkyl, and $C_{3-6}$cycloalkyl substituted with one or two members independently selected from: F and $CH_3$;

$R^j$ is selected from the group consisting of: H, halo, $C_{1-4}$alkyl and $C_{1-4}$haloalkyl;

$R^k$ is selected from the group consisting of: H, halo, OH, $C_{1-4}$alkyl, $C_{1-4}$haloalkyl, $OC_{1-4}$alkyl, and $OC_{1-4}$haloalkyl;

$R^m$ is H or $C_{1-4}$alkyl;

$R^n$ is selected from the group consisting of: H, halo and $OC_{1-4}$alkyl;

$R^o$ is selected from the group consisting of: H, $C_{1-4}$alkyl, and $C_{1-4}$haloalkyl;

$R^p$ is selected from the group consisting of: H, $C_{1-4}$alkyl, and $OC_{1-4}$alkyl;

Y is CH or N; and $R^{4a}$ is selected from the group consisting of: $CH_3$, $CF_2H$, $CF_3$, $C_{3-6}$cycloalkyl, and phenyl;

and pharmaceutically acceptable salts, isotopes, N-oxides, and stereoisomers thereof.

24. A compound as claimed in claim 23, wherein $R^1$ is $CH_3$.

25. A compound as claimed in claim 23, wherein $R^1$ is $CH_2CH_3$.

26. A compound as claimed in claim 23, wherein $R^{2a}$ is

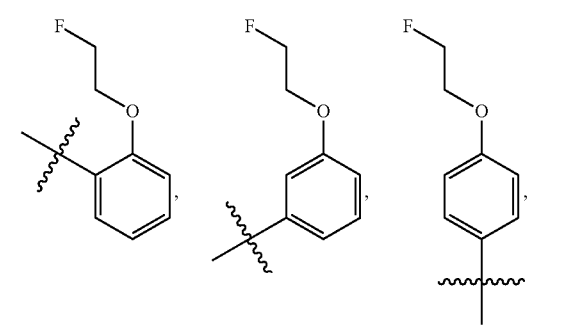

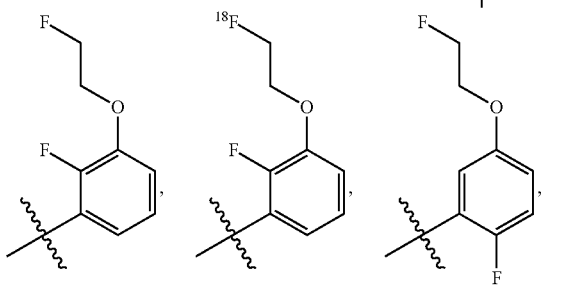

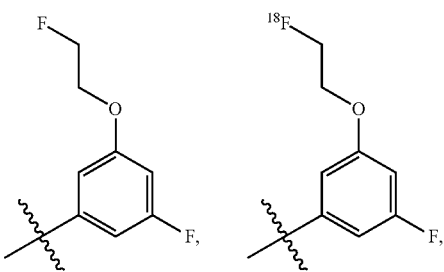

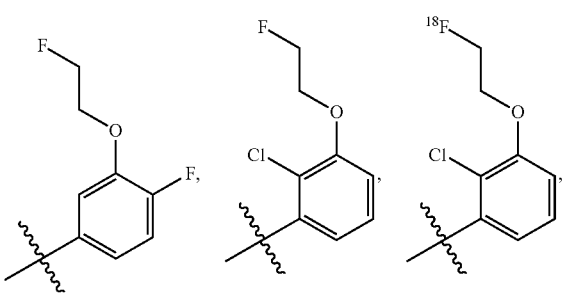

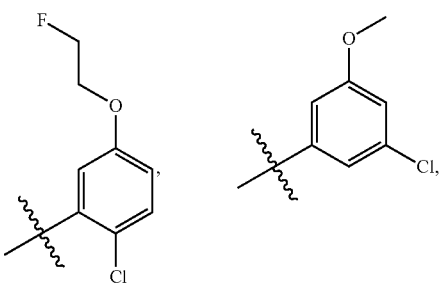

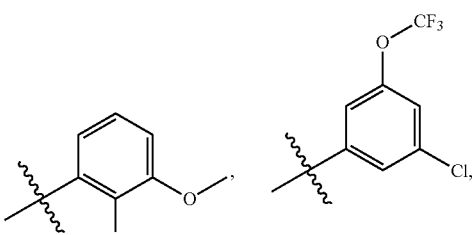

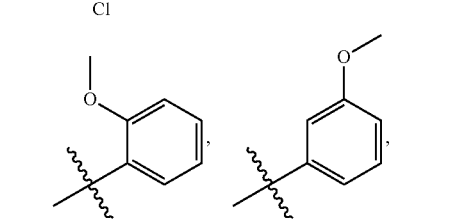

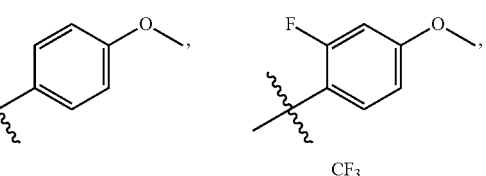

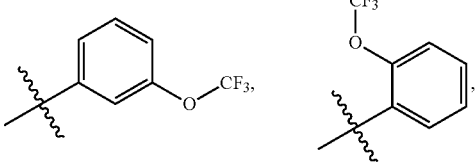

-continued
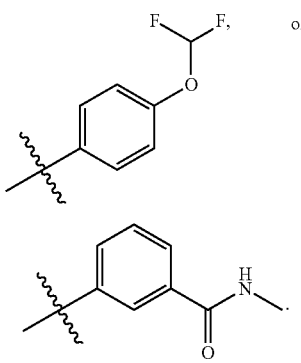
27. A compound as claimed in claim 23, wherein $R^{2a}$ is
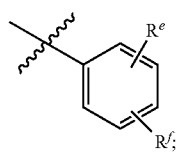
where $R^e$ is
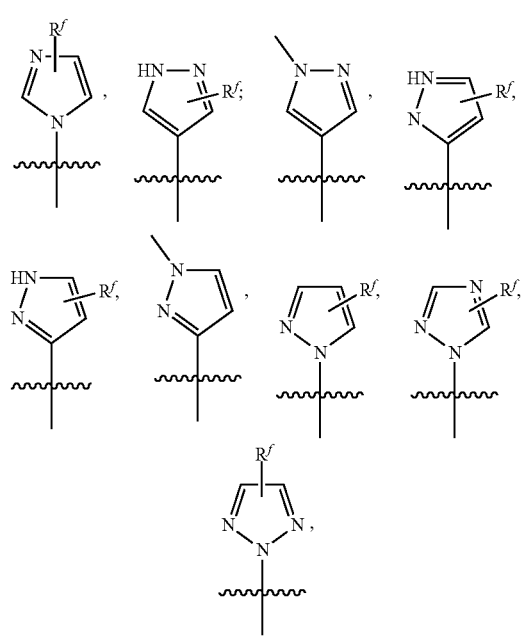
or
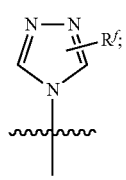
and $R^f$ is H, F, $CH_3$, $CF_3$, or $OCH_3$.
28. A compound as claimed in claim 23, wherein $R^e$ is
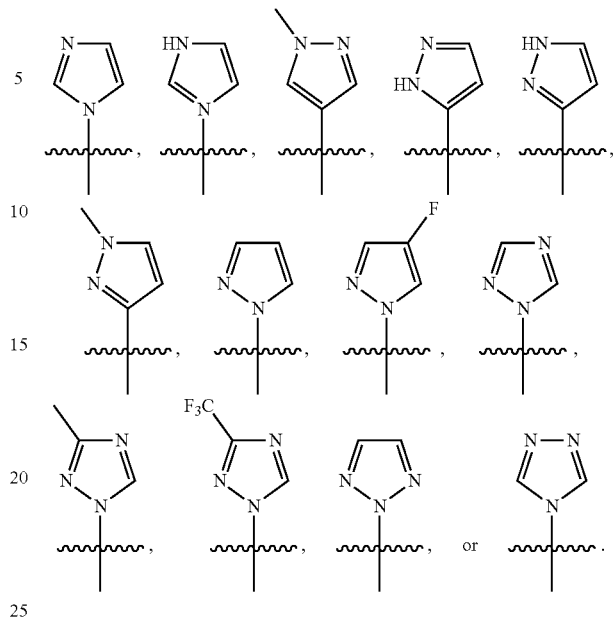
29. A compound as claimed in claim 23, wherein $R^{2a}$ is
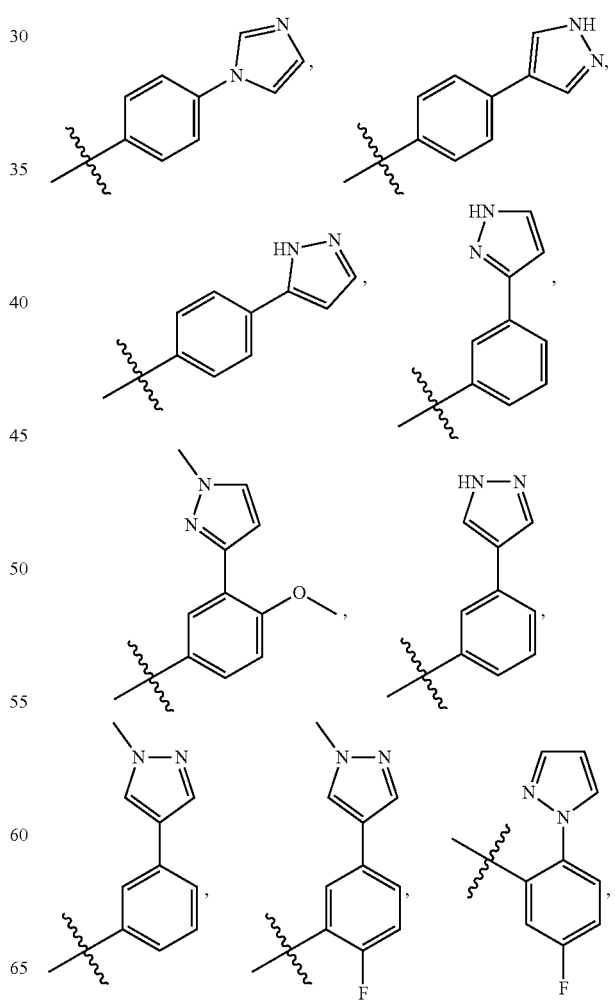

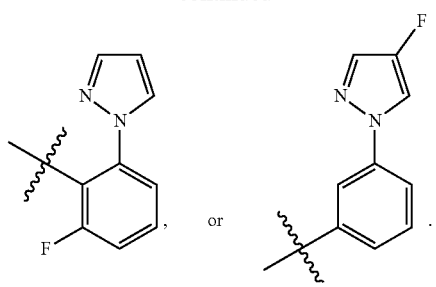
or
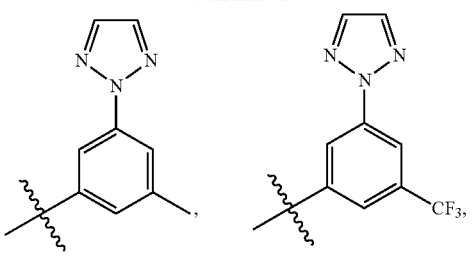
30. A compound as claimed in claim 23, wherein $R^{2a}$ is
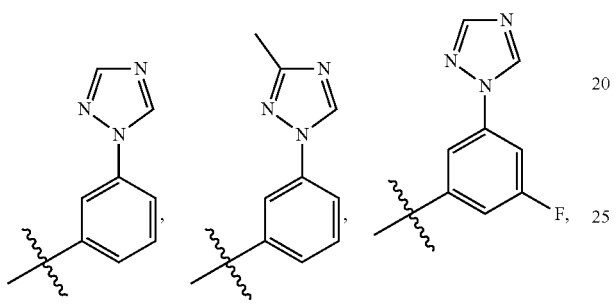
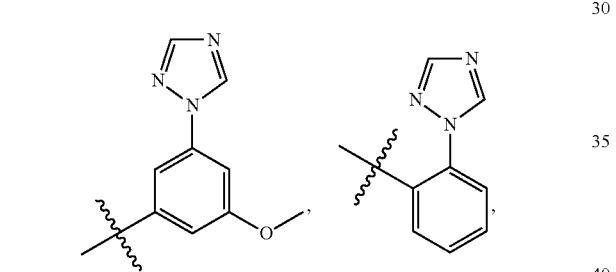
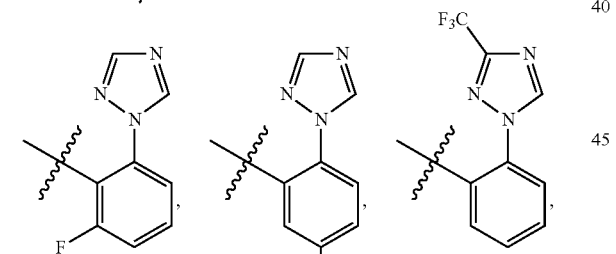
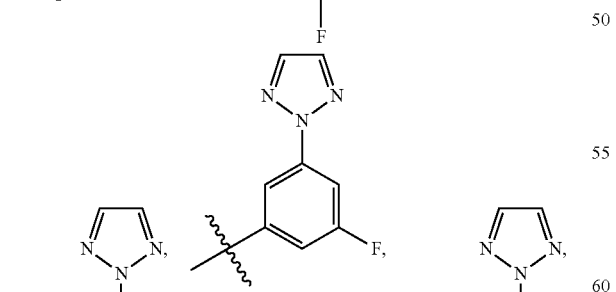
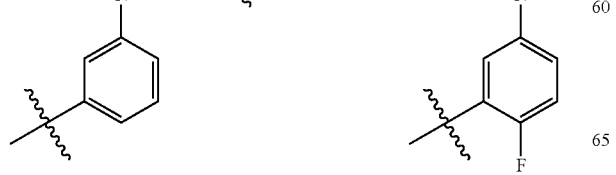
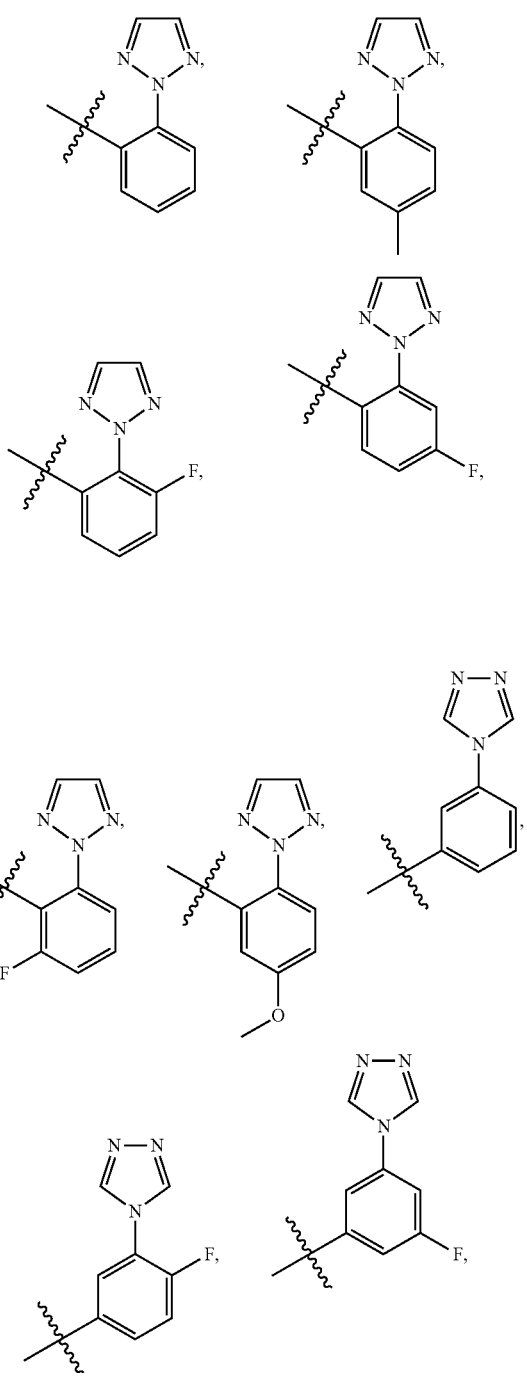

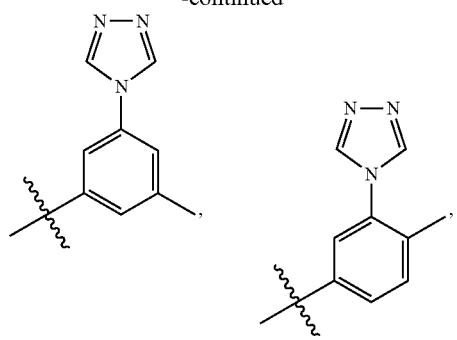
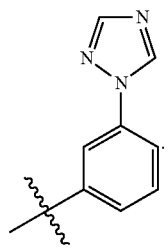
31. A compound as claimed in claim 23, wherein R²ᵃ is
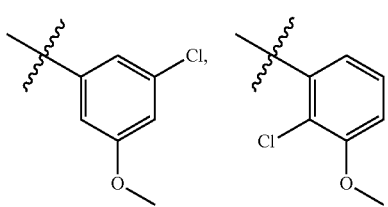
or
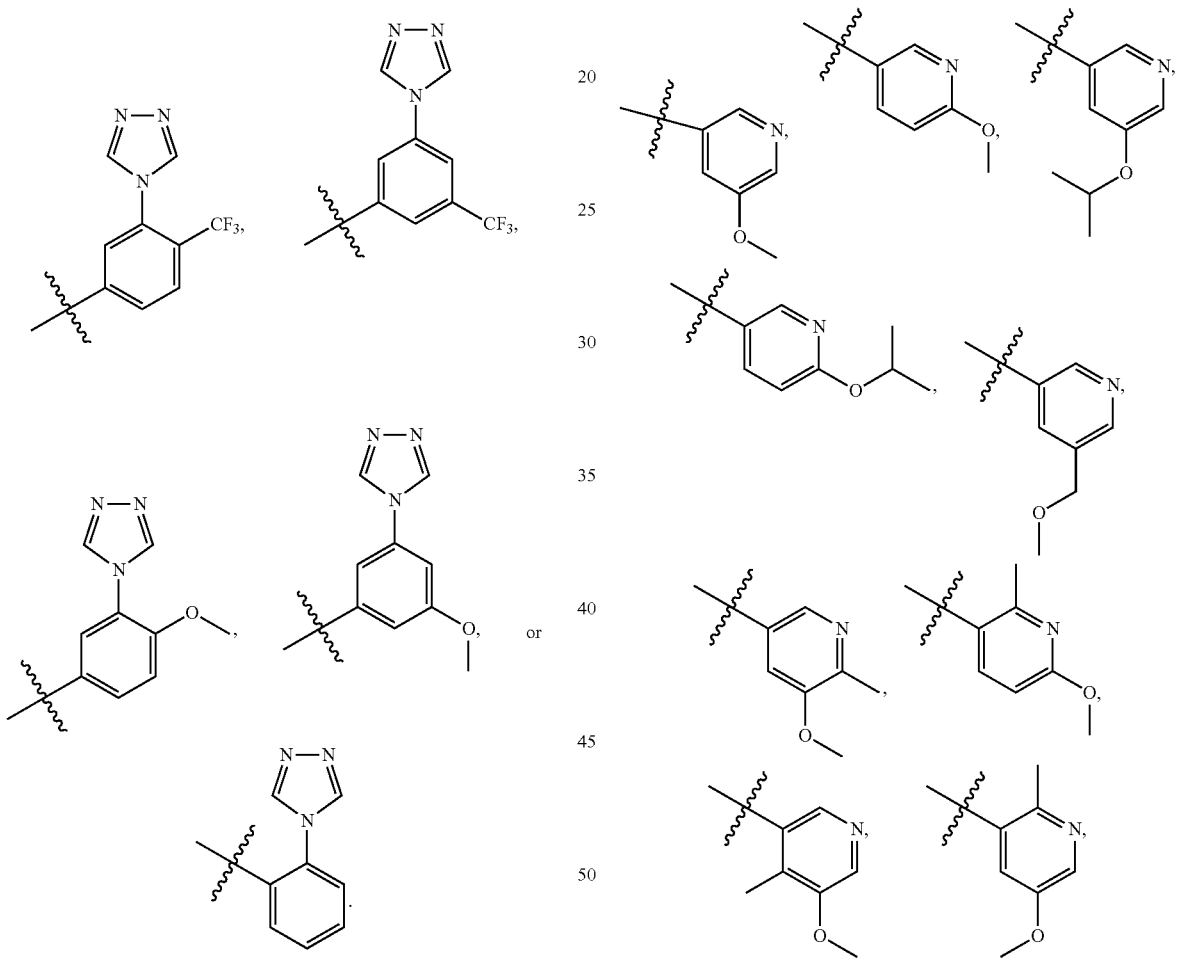
32. A compound as claimed in claim 23, wherein R²ᵃ is
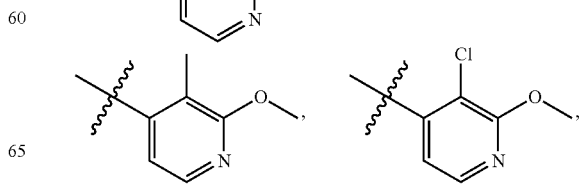

-continued
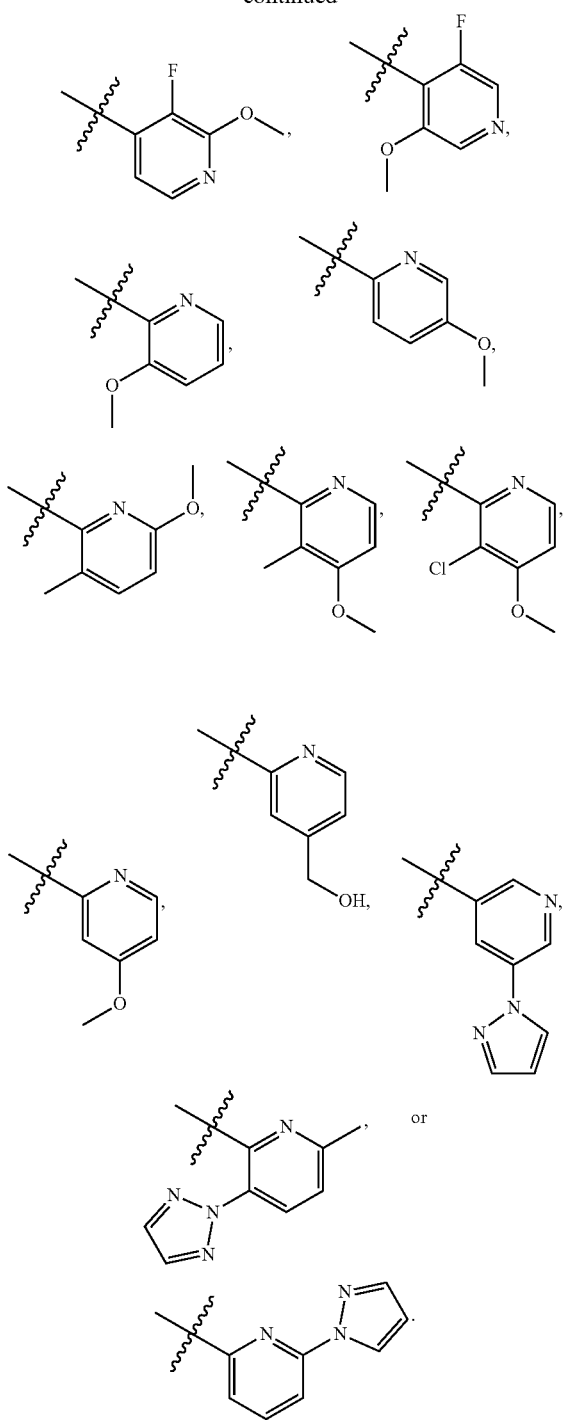
33. A compound as claimed in claim 23, wherein $R^{2a}$ is
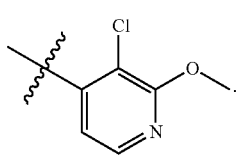 [SMILES: *c1ccnc(OC)c1Cl]
34. A compound as claimed in claim 23, wherein $R^{2a}$ is
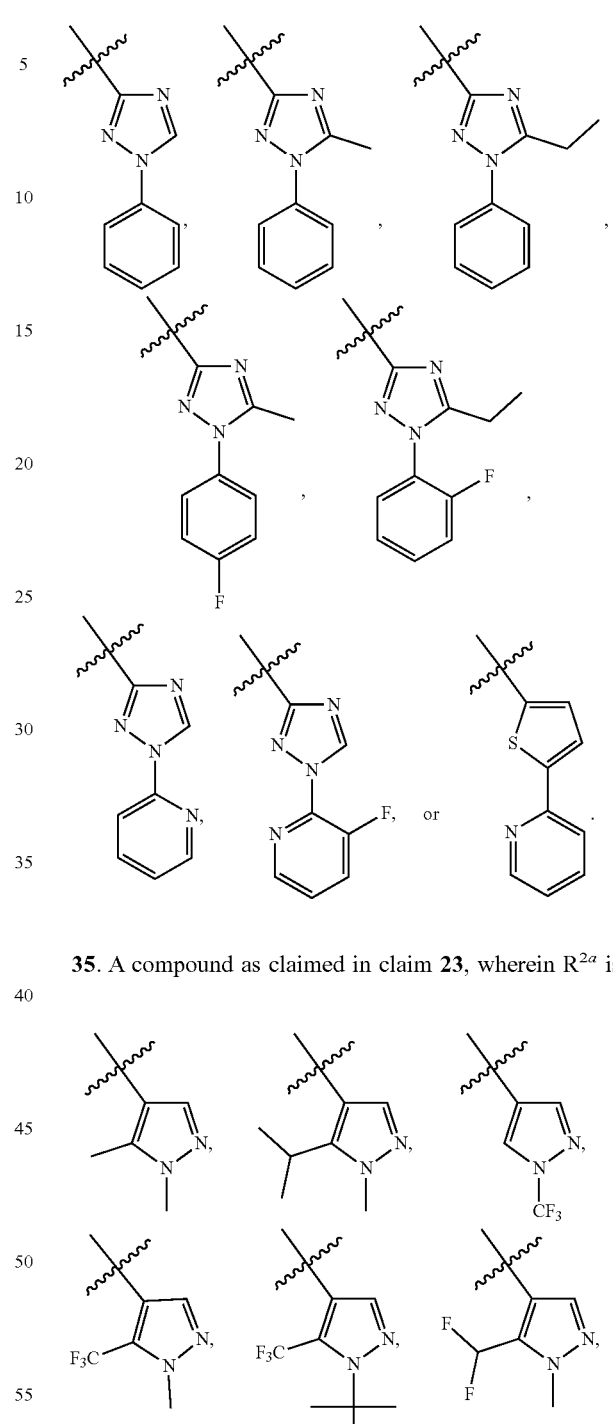
35. A compound as claimed in claim 23, wherein $R^{2a}$ is
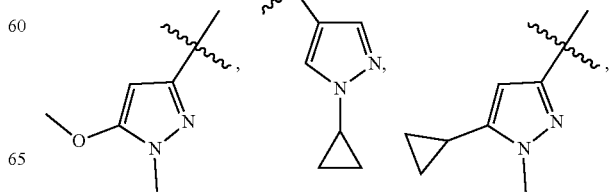

-continued
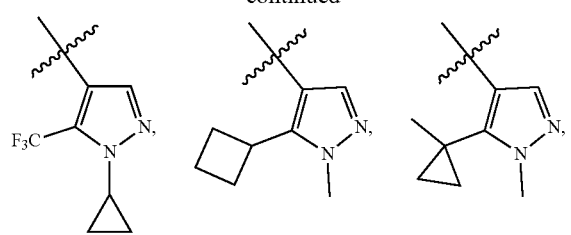
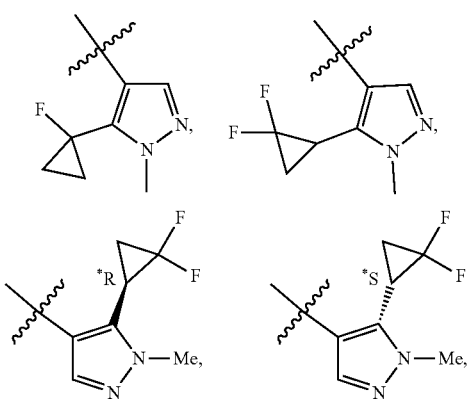
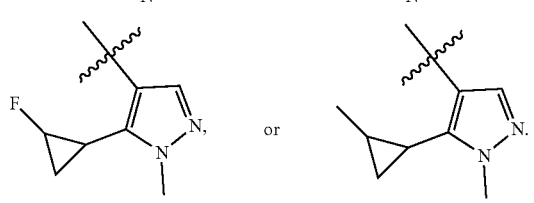
36. A compound as claimed in claim 23, wherein $R^{2a}$ is
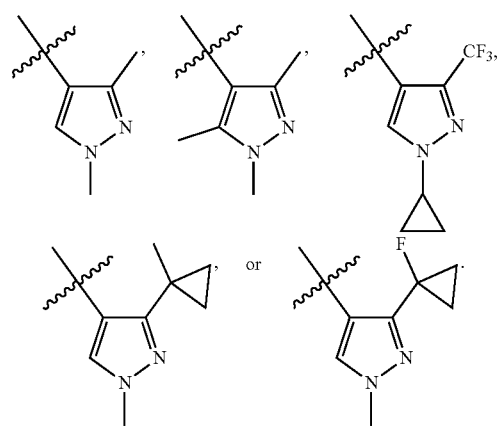
37. A compound as claimed in claim 23, wherein $R^{2a}$ is
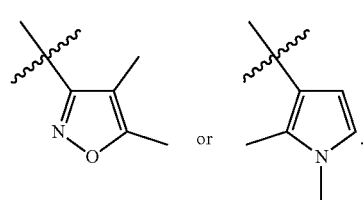
38. A compound as claimed in claim 23, wherein $R^{2a}$ is
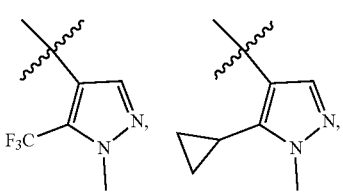
or
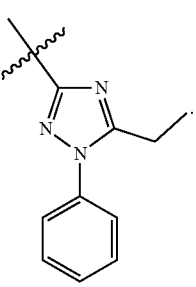 [SMILES: *c1nc(CC)n(-c2ccccc2)n1]
39. A compound as claimed in claim 23, wherein $R^{2a}$ is
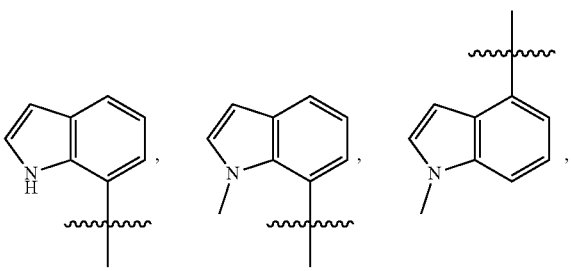
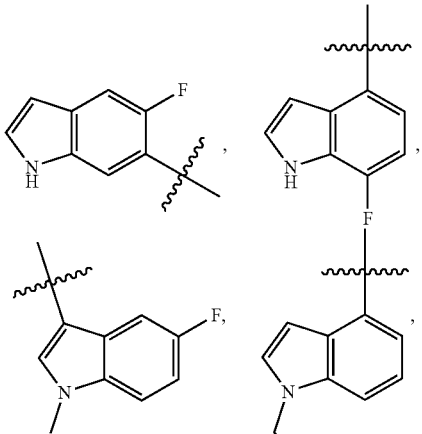
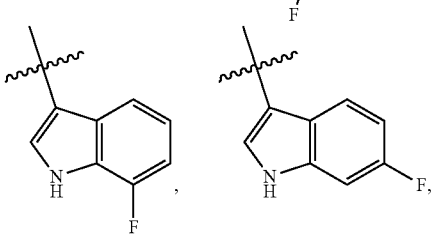

-continued
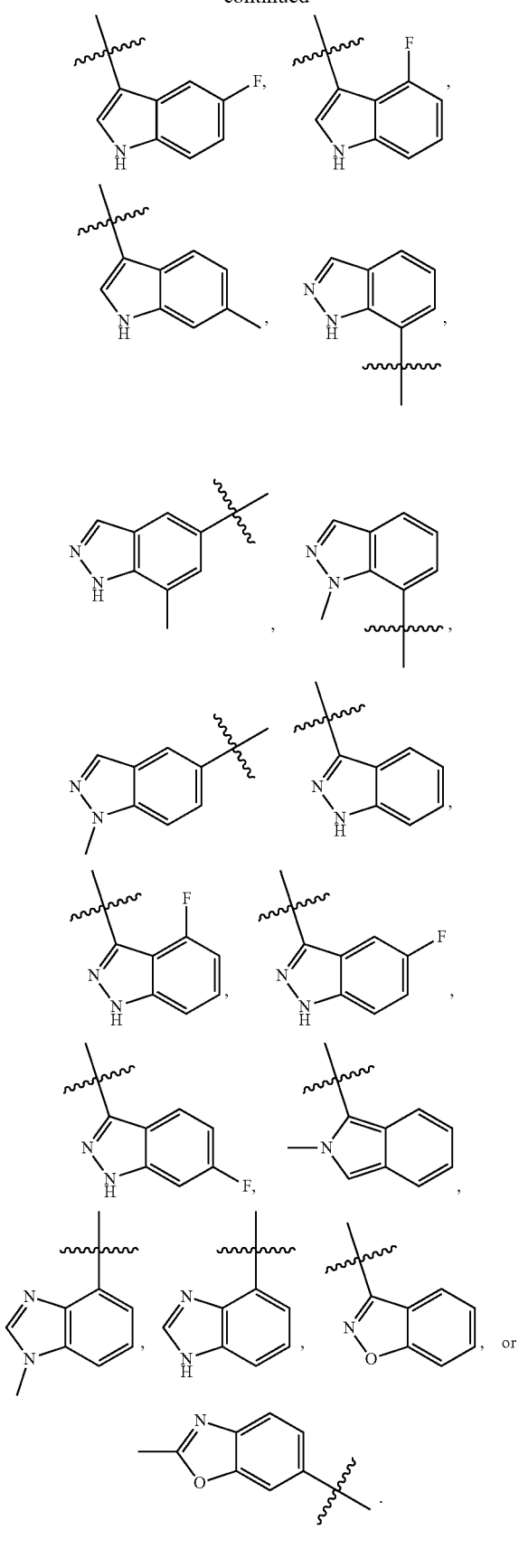
40. A compound as claimed in claim 23, wherein $R^{2a}$ is
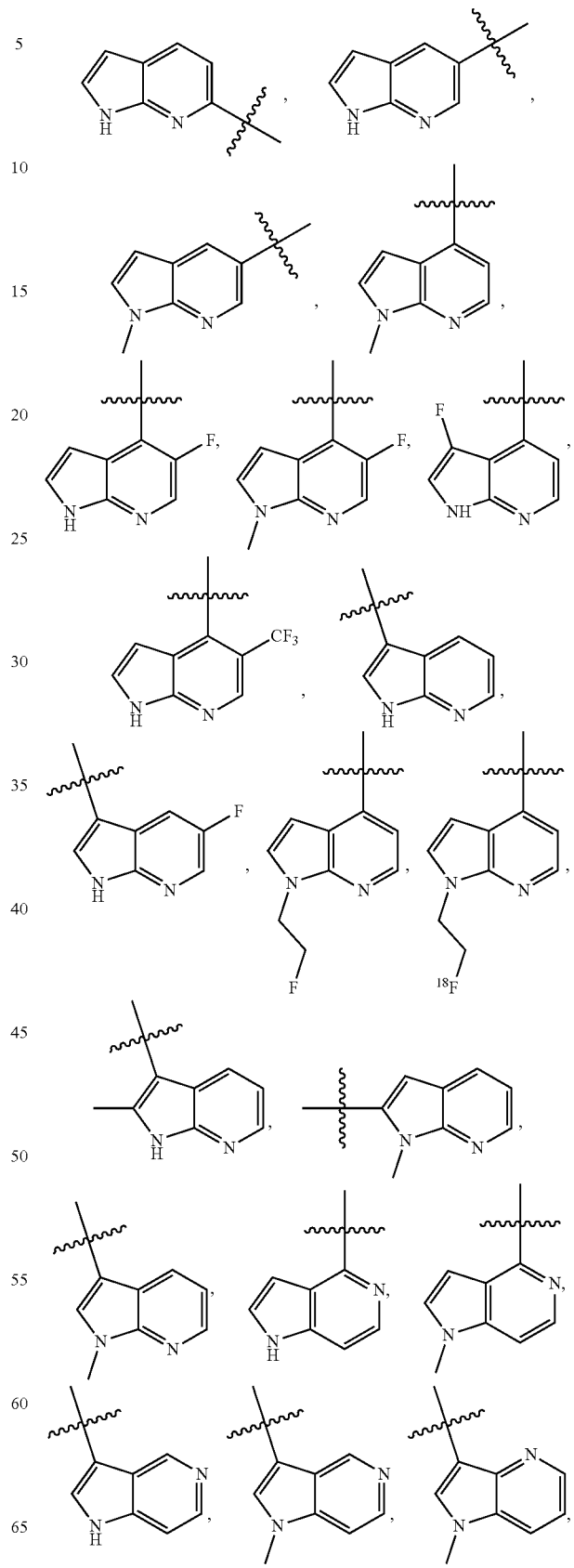

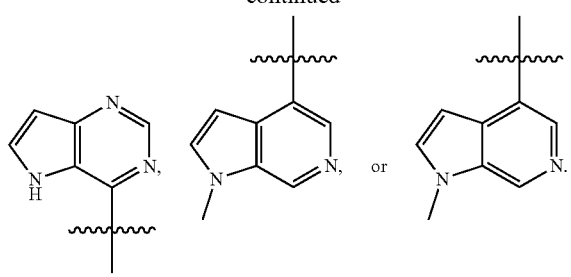
41. A compound as claimed in claim 23, wherein $R^{2a}$ is
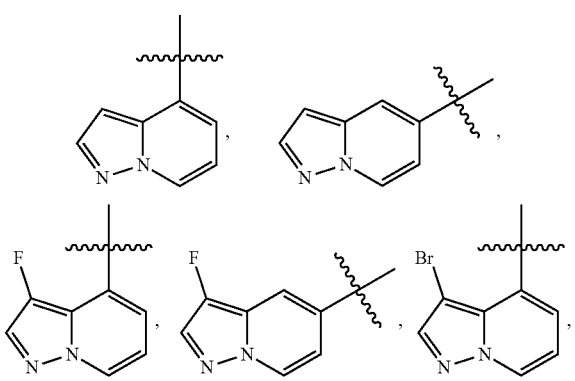
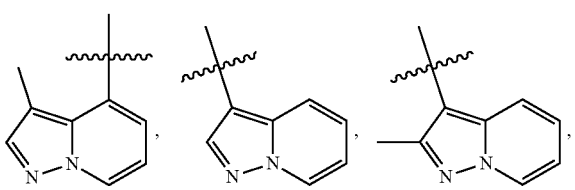
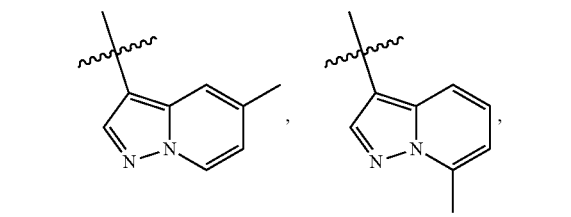
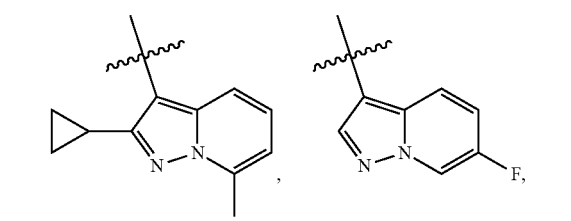
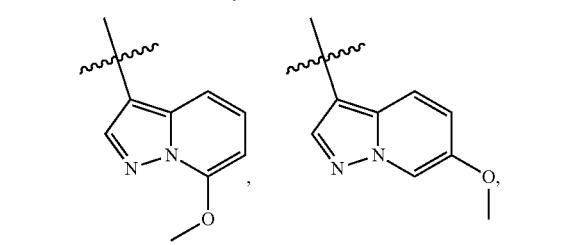
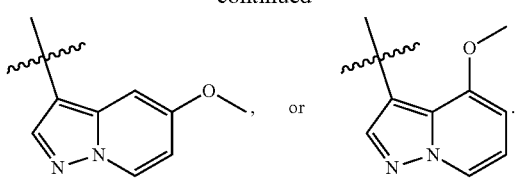
42. A compound as claimed in claim 23, wherein $R^{2a}$ is
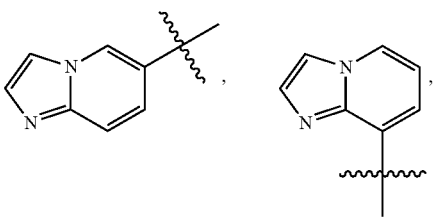
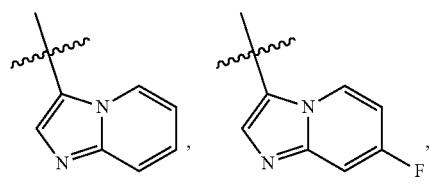
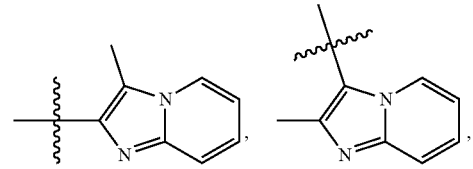
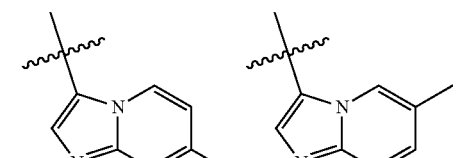
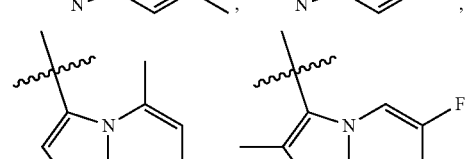
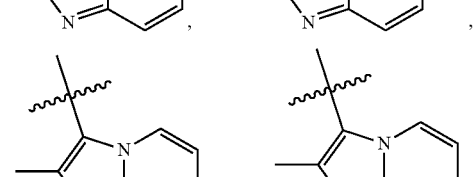
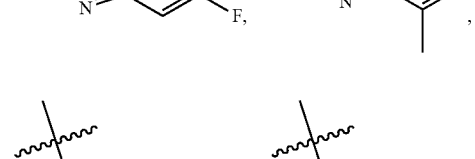

-continued
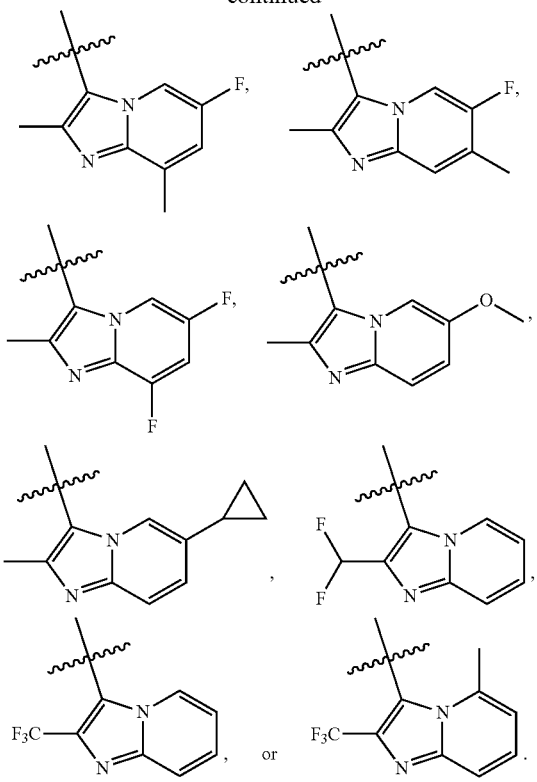
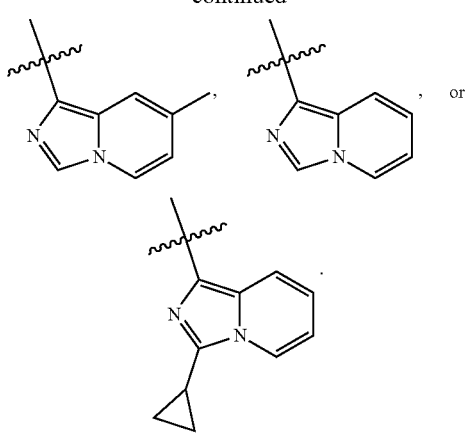
43. A compound as claimed in claim 23, wherein $R^{2a}$ is
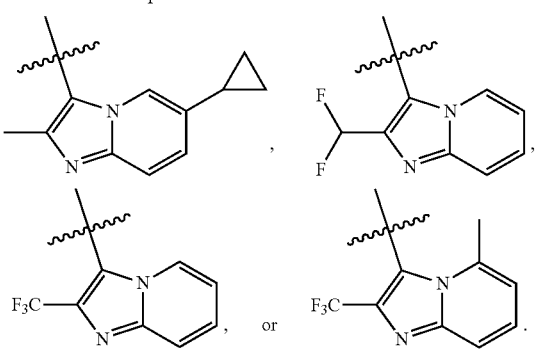
or
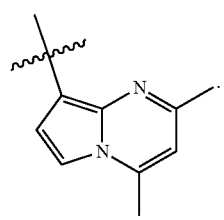 [SMILES: *c1ccn2c(C)cc(C)nc12]
44. A compound as claimed in claim 23, wherein $R^{2a}$ is
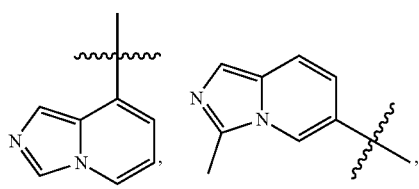
45. A compound as claimed in claim 23, wherein $R^{2a}$ is
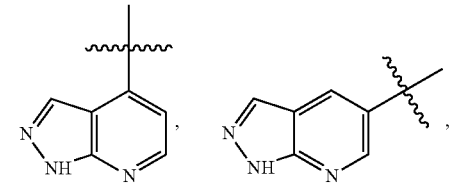
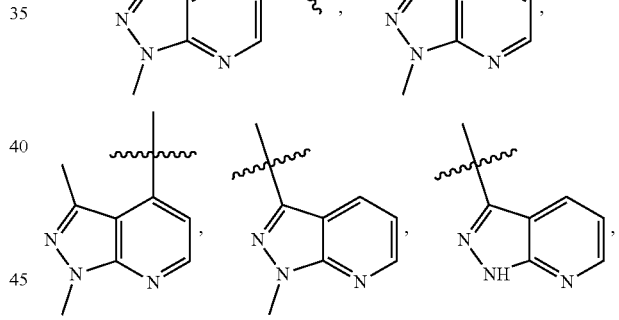
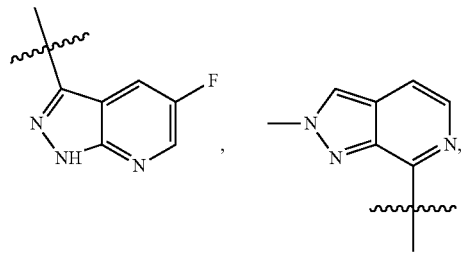
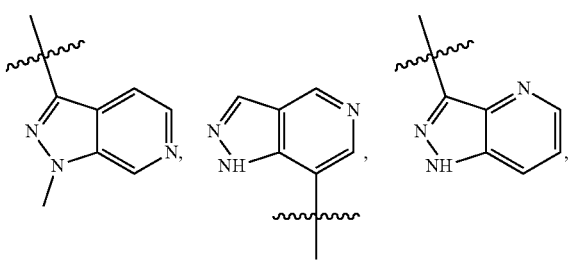

-continued
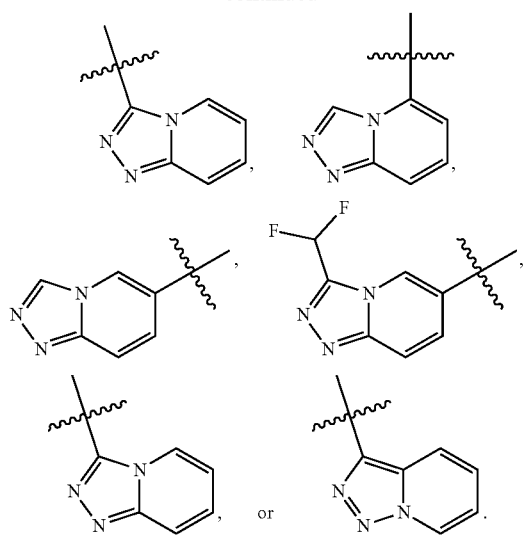
46. A compound as claimed in claim 23, wherein $R^{2a}$ is
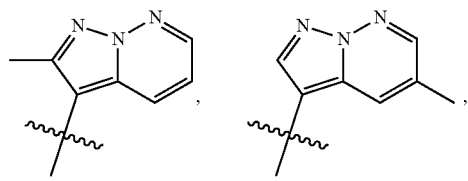
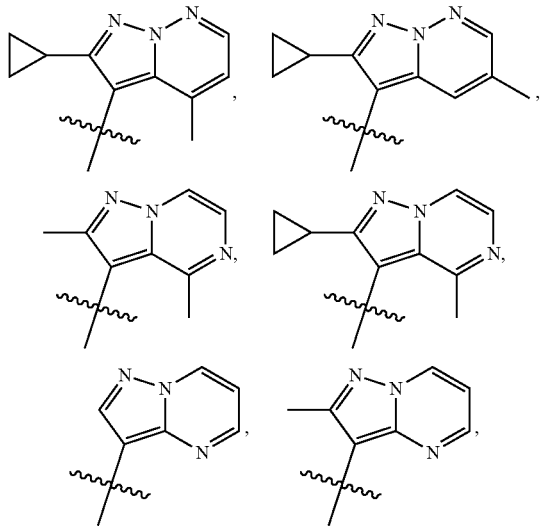
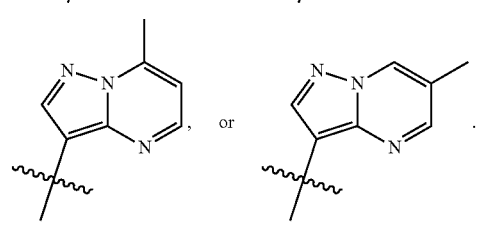
47. A compound as claimed in claim 23, wherein $R^{2a}$ is
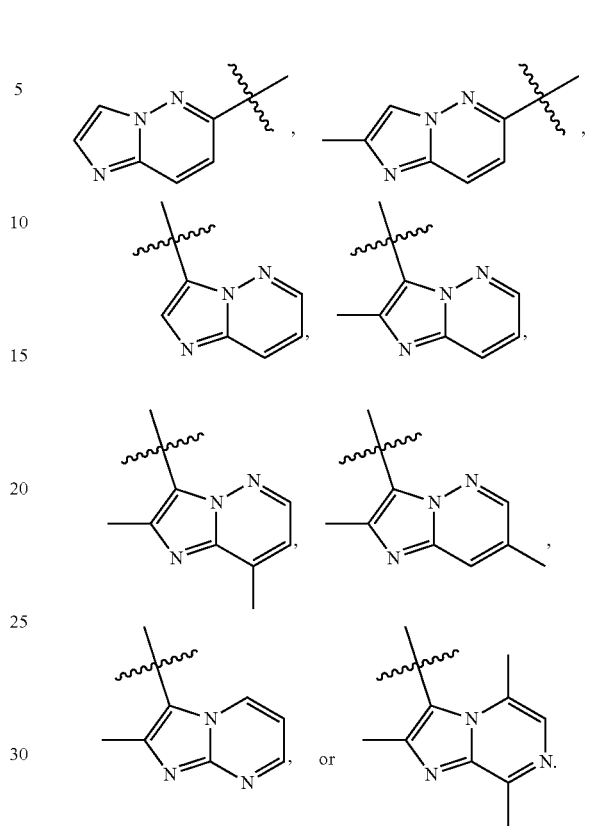
48. A compound as claimed in claim 23, wherein $R^{2a}$ is
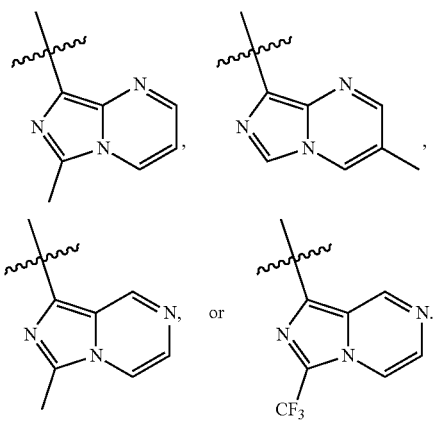
49. A compound as claimed in claim 23, wherein $R^{2a}$ is
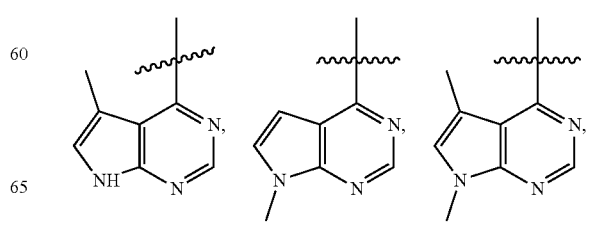

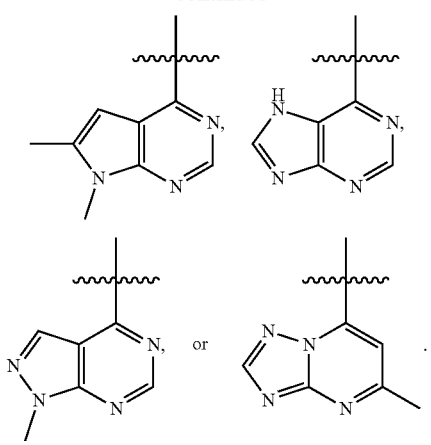
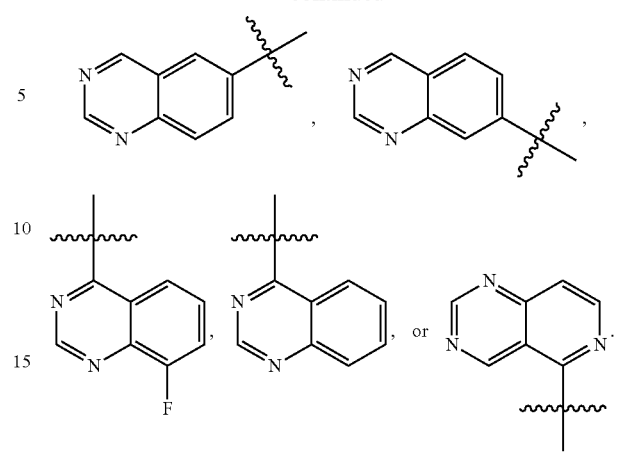
50. A compound as claimed in claim 23, wherein $R^{2a}$ is
52. A compound as claimed in claim 23, wherein $R^{2a}$ is
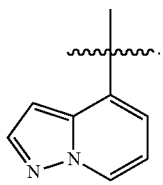 [SMILES: *c1cccn2nccc12]
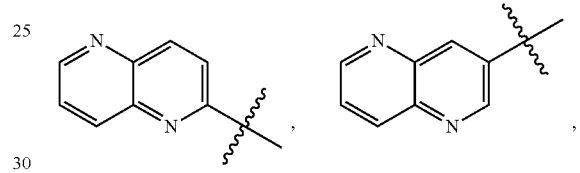
51. A compound as claimed in claim 23, wherein $R^{2a}$ is
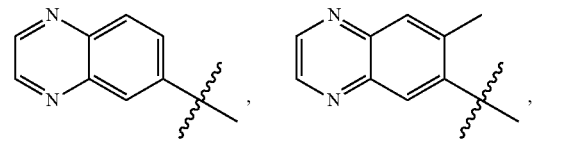
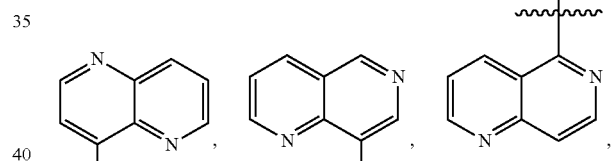
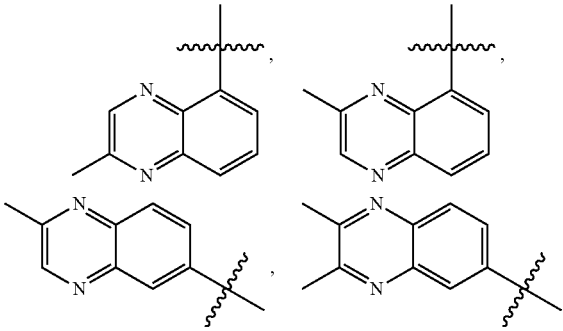
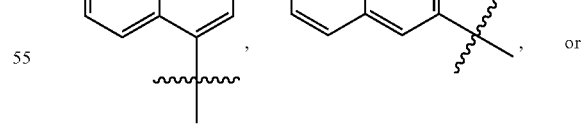
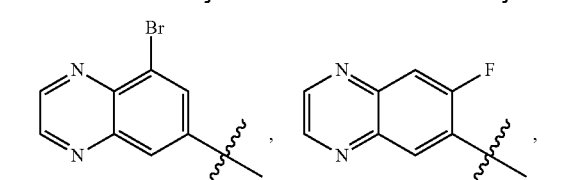
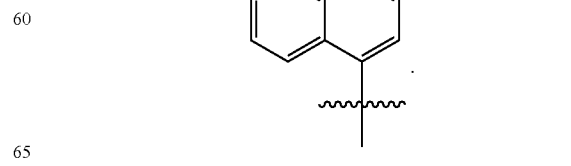
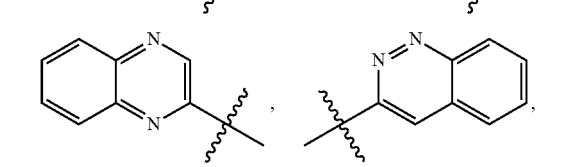

53. A compound as claimed in claim 23, wherein $R^{2a}$ is
54. A compound as claimed in claim 23, wherein $R^{2a}$ is
55. A compound as claimed in claim 23, wherein $R^{2a}$ is
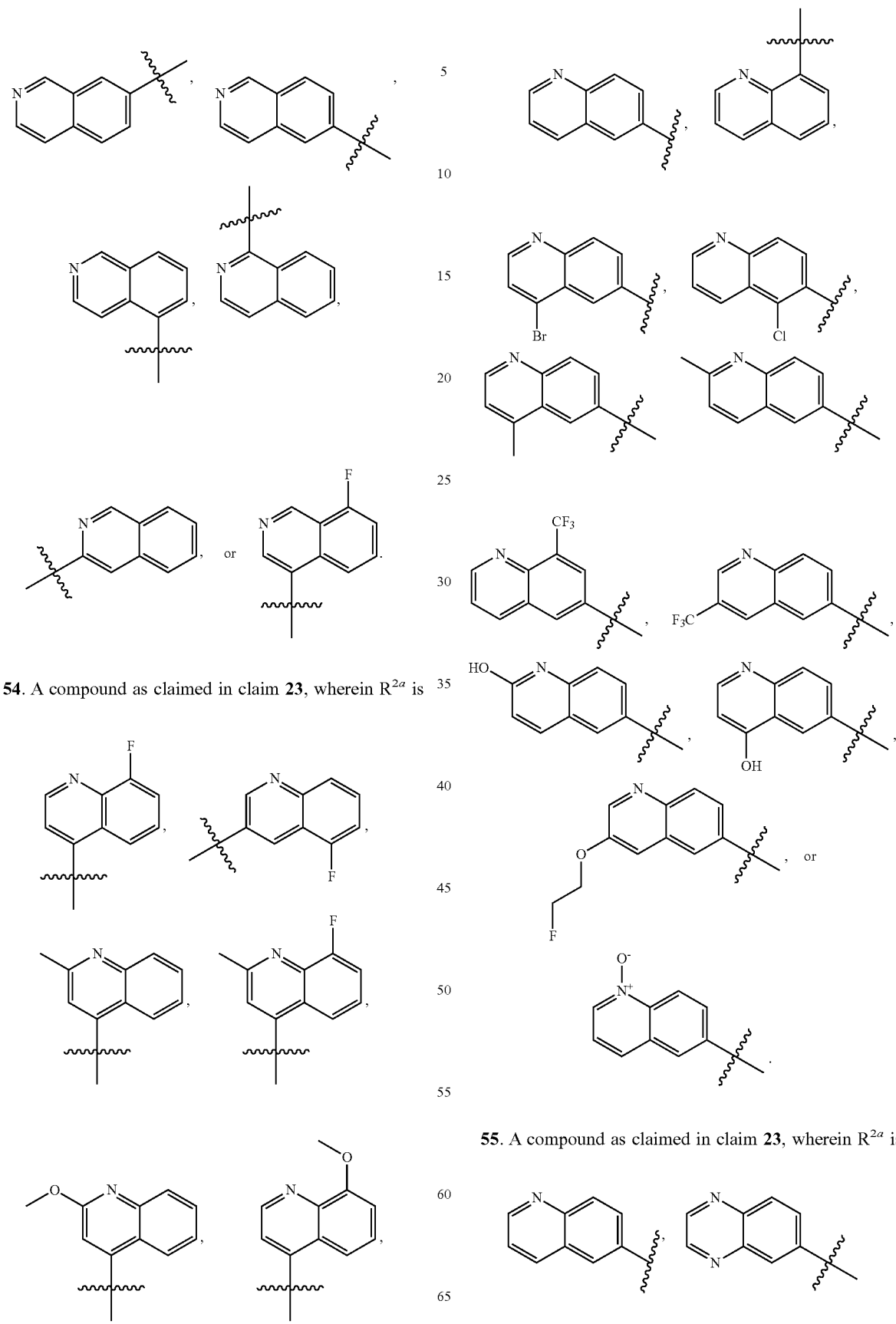

or
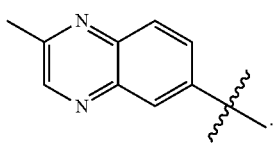 [SMILES: *c1ccc2nc(C)cnc2c1]
56. A compound as claimed in claim 23, wherein $R^{2a}$ is
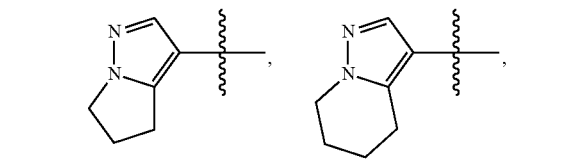
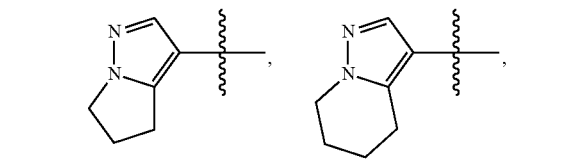
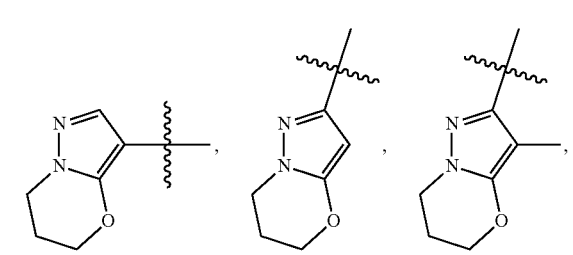
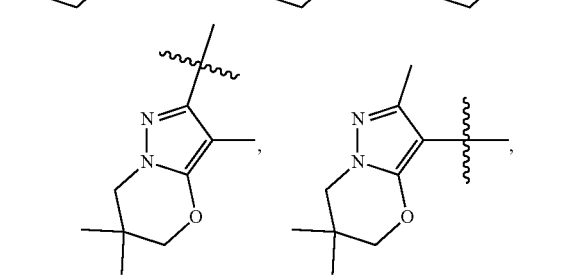
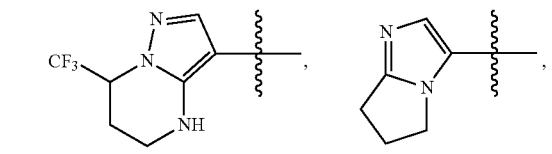
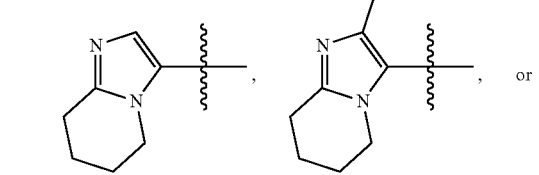
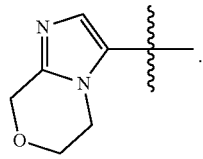
57. A compound as claimed in claim 23, wherein $R^{2a}$ is
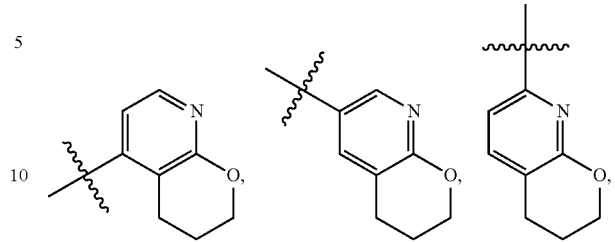
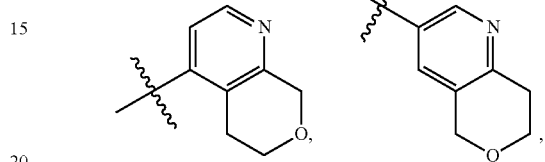
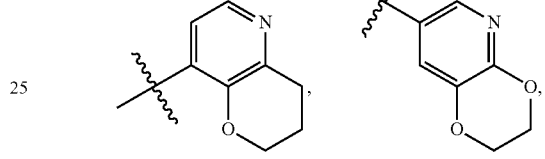
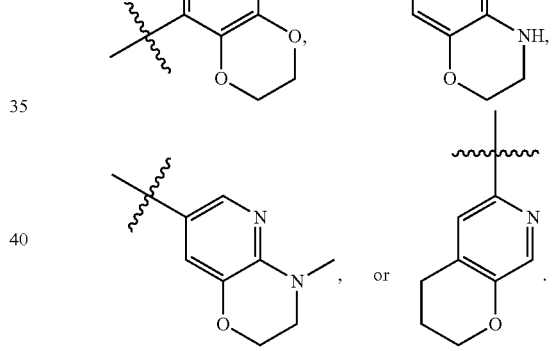
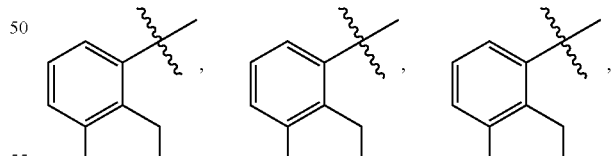
58. A compound as claimed in claim 23, wherein $R^{2a}$ is
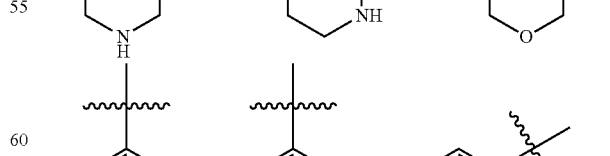

-continued

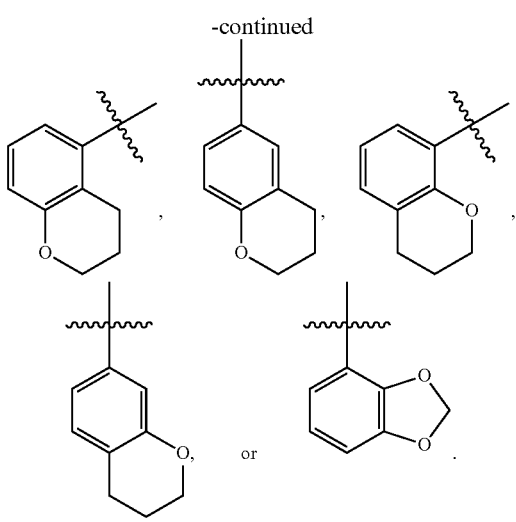

59. A compound as claimed in claim 23, wherein $R^{2a}$ is

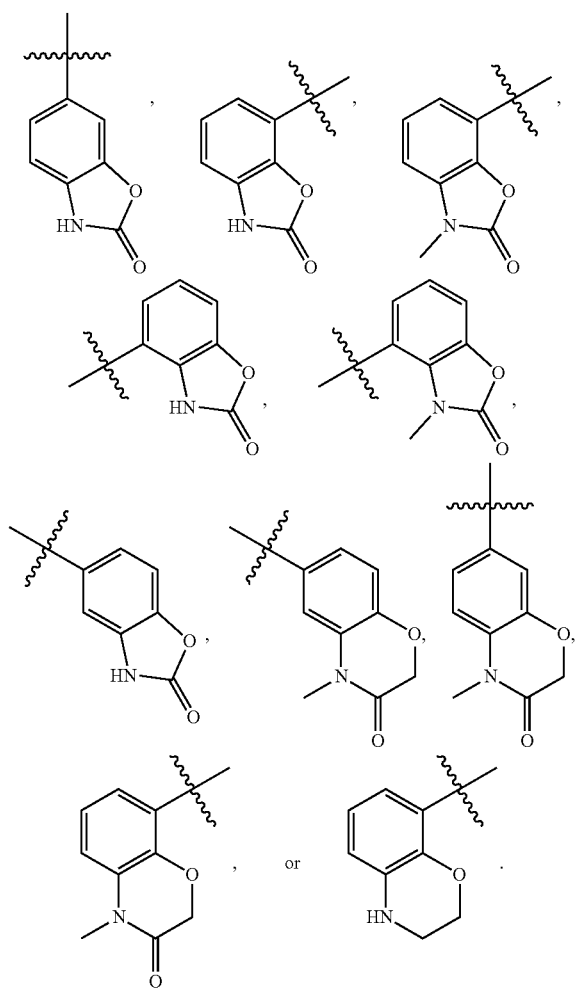

60. A compound as claimed in claim 23, wherein $R^{3a}$ is Phenyl; or phenyl substituted with one member selected from the group consisting of: F, Cl, OCH$_3$, OCH$_2$CH$_3$, OCH(CH$_3$)$_2$, OCHF$_2$, CF$_3$, CF$_2$CH$_3$, OCF$_2$H, and OCF$_3$.

61. A compound as claimed in claim 23, wherein $R^{3a}$ is phenyl substituted with two or three members independently selected from the group consisting of: F, Cl, CH$_3$, CF$_2$H, OCF$_2$H and OCH$_3$.

62. A compound as claimed in claim 23, wherein $R^{3a}$ is 3,5-difluorophenyl, 3,5-dichlorophenyl, 3-chloro-5-fluorophenyl, 3-fluoro-5-methoxyphenyl, 3-chloro-4-methoxyphenyl, 3-fluoro-4-methoxyphenyl, or 3,4,5-trifluorophenyl.

63. A compound as claimed in claim 23, wherein $R^{3a}$ is

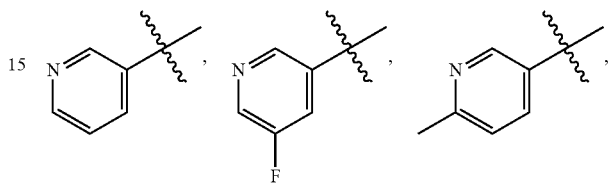

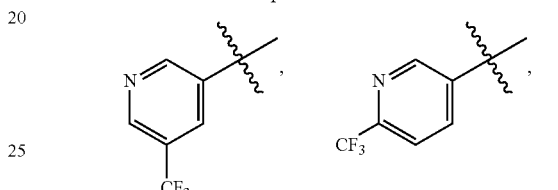

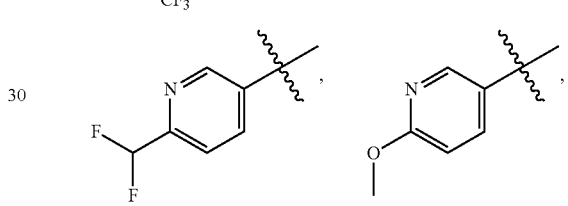

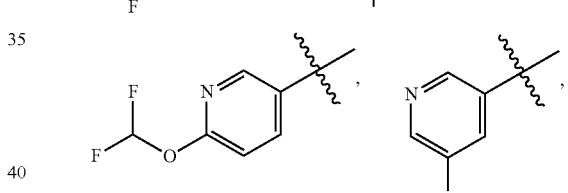

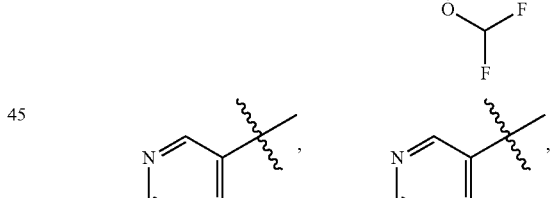

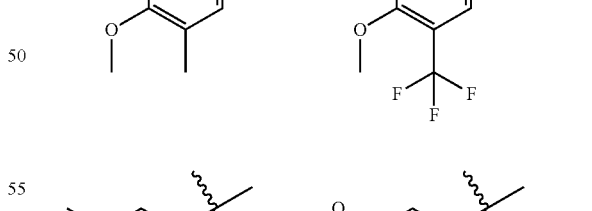

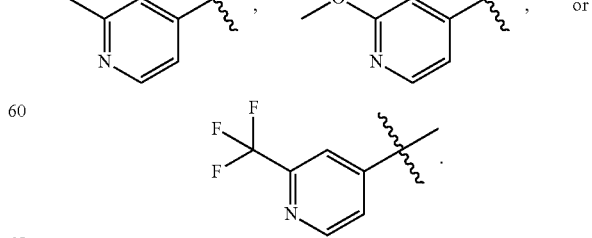

64. A compound as claimed in claim 23, wherein $R^{3a}$ is

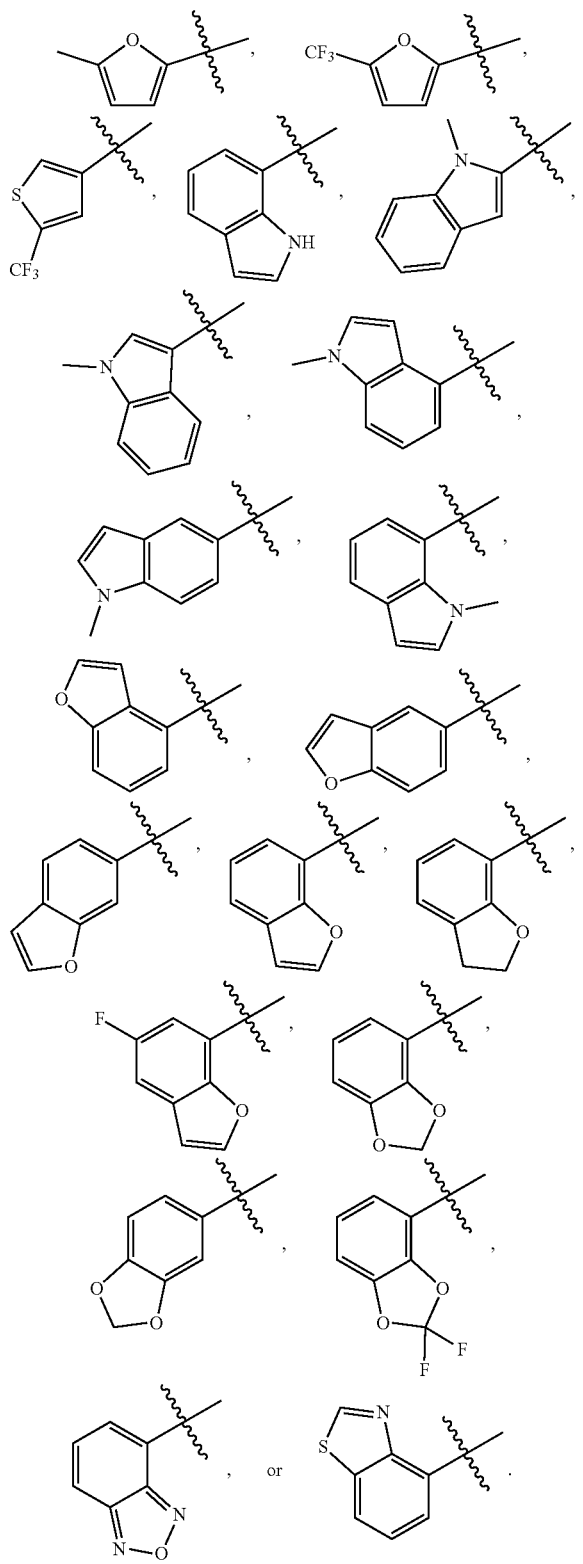

65. A compound as claimed in claim 23, wherein $R^{4a}$ is $CH_3$.

66. A compound as claimed in claim 23, wherein $R^{4a}$ is $CF_3$.

67. A compound as claimed in claim 23, wherein $R^{4a}$ is $CF_2H$.

68. A compound as claimed in claim 23, wherein $R^{4a}$ is phenyl.

69. The compound of claim 23, having the structure of Formula (IIA):

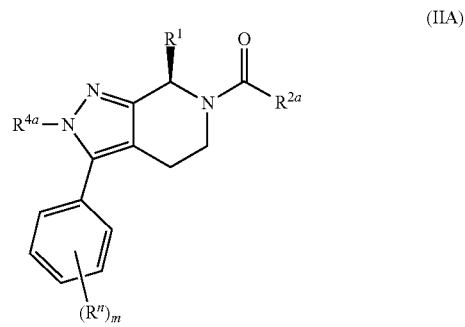

(IIA)

and pharmaceutically acceptable salts, isotopes, N-oxides, and stereoisomers thereof, wherein
$R^1$ is $CH_3$;
$R^{2a}$ is selected from the group consisting of:

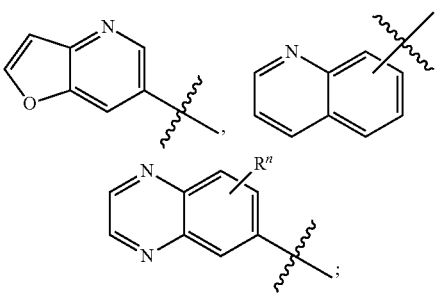

$R^{4a}$ is $CH_3$ or phenyl; and
each $R^n$ is independently selected from the group consisting of: H, Cl and F; and
m is 1, 2, or 3.

70. The compound of claim 23, having the structure of Formula (IIB):

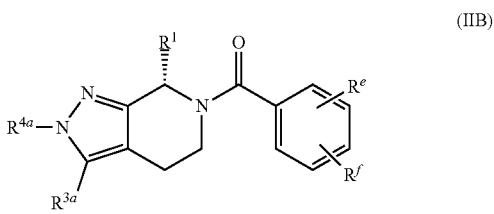

(IIB)

and pharmaceutically acceptable salts, isotopes, N-oxides, and stereoisomers thereof, wherein
$R^1$ is $CH_3$ or $CH_2CH_3$;
$R^e$ is selected from the group consisting of: $OC_{1-4}$alkyl, $OC_{1-4}$haloalkyl, (C=O)NHCH$_3$, and 5-membered heteroaryl ring containing two or three nitrogen members, wherein the 5-membered heteroaryl ring is optionally substituted with one $R^f$ member;
$R^f$ is selected from the group consisting of: H, halo, $C_{1-4}$alkyl, $C_{1-4}$haloalkyl, $OC_{1-4}$alkyl, and $OC_{1-4}$haloalkyl;

R[3a] is phenyl substituted with one, two, or three members independently selected from halo or $C_{1-4}$alkyl; and R[4a] is $CH_3$.

71. A compound of claim 70, wherein

R[1] is $CH_3$;

R[e] is selected from the group consisting of: $OC_{1-4}$alkyl, $OC_{1-4}$haloalkyl, (C=O)NHCH$_3$, and 5-membered heteroaryl ring containing two or three nitrogen members, wherein the 5-membered heteroaryl ring is optionally substituted with one R[f] member;

R[f] is selected from the group consisting of: H, halo, $C_{1-4}$alkyl, $C_{1-4}$haloalkyl, $OC_{1-4}$alkyl, and $OC_{1-4}$haloalkyl;

R[3a] is 3-chlorophenyl, 3,5-difluorophenyl, 3-fluoro-5-methyl-phenyl, or 3,4,5-trifluorophenyl; and R[4a] is $CH_3$.

72. The compound of claim 23, having the structure of Formula (IIC):

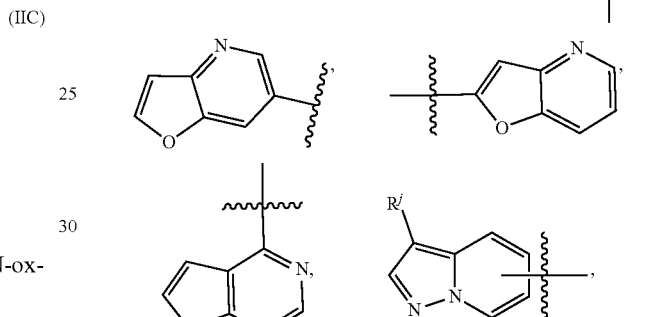

(IIC)

and pharmaceutically acceptable salts, isotopes, N-oxides, and stereoisomers thereof, wherein R[1] is $CH_3$;

R[2a] is selected from the group consisting of:

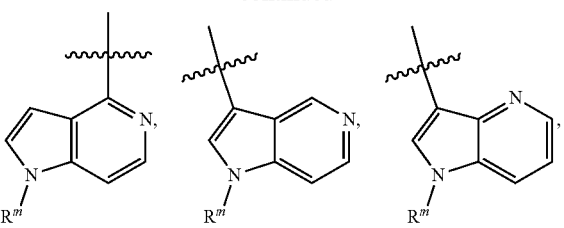

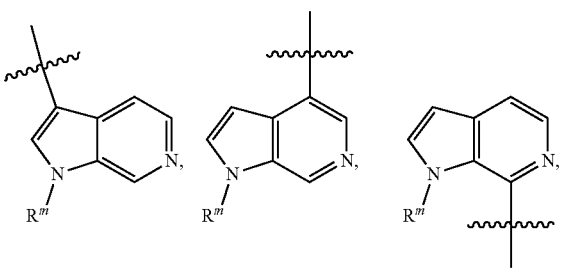

-continued

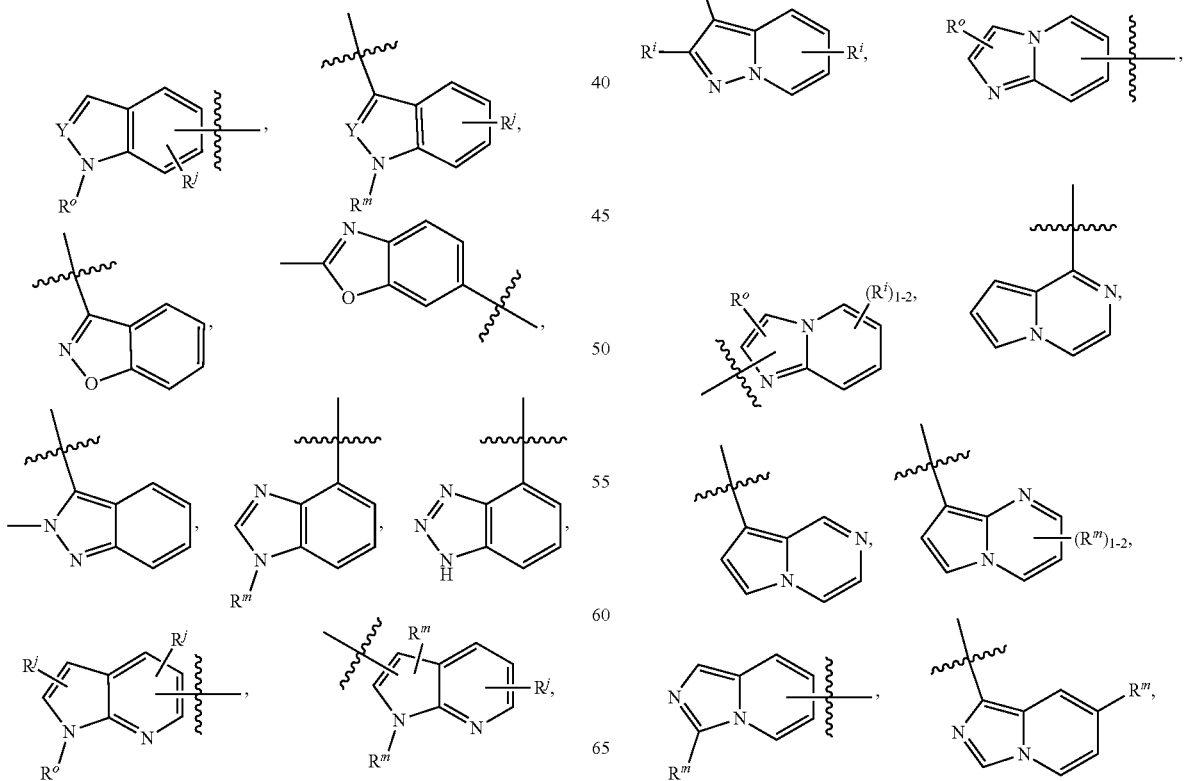

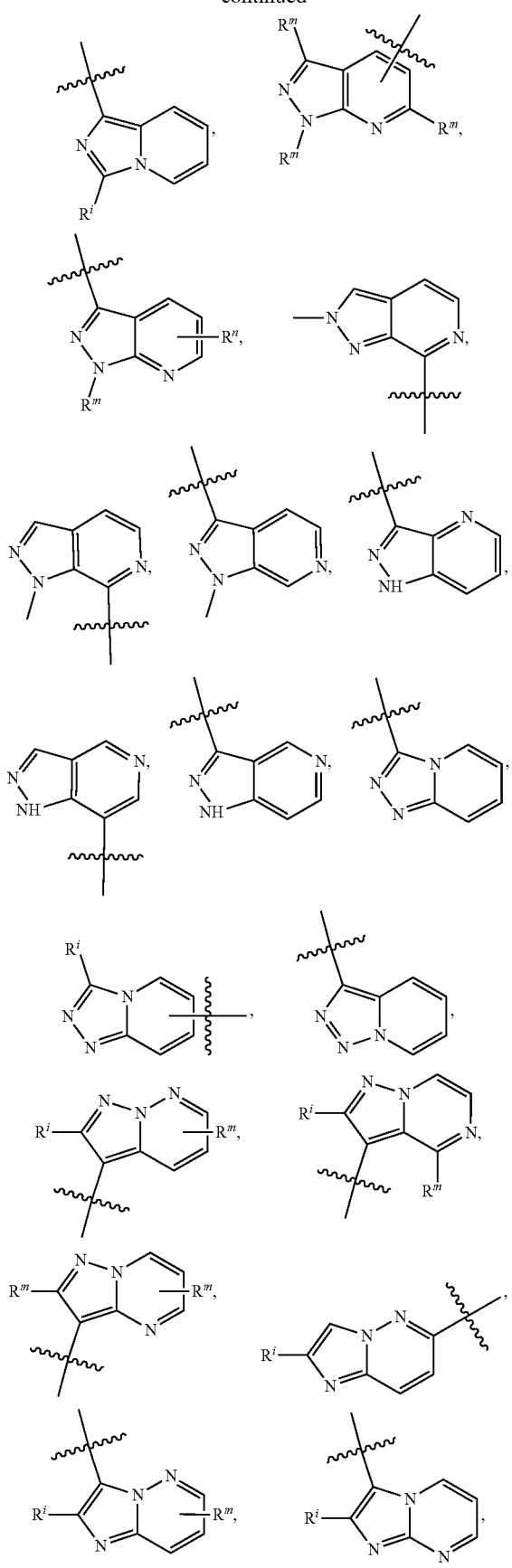
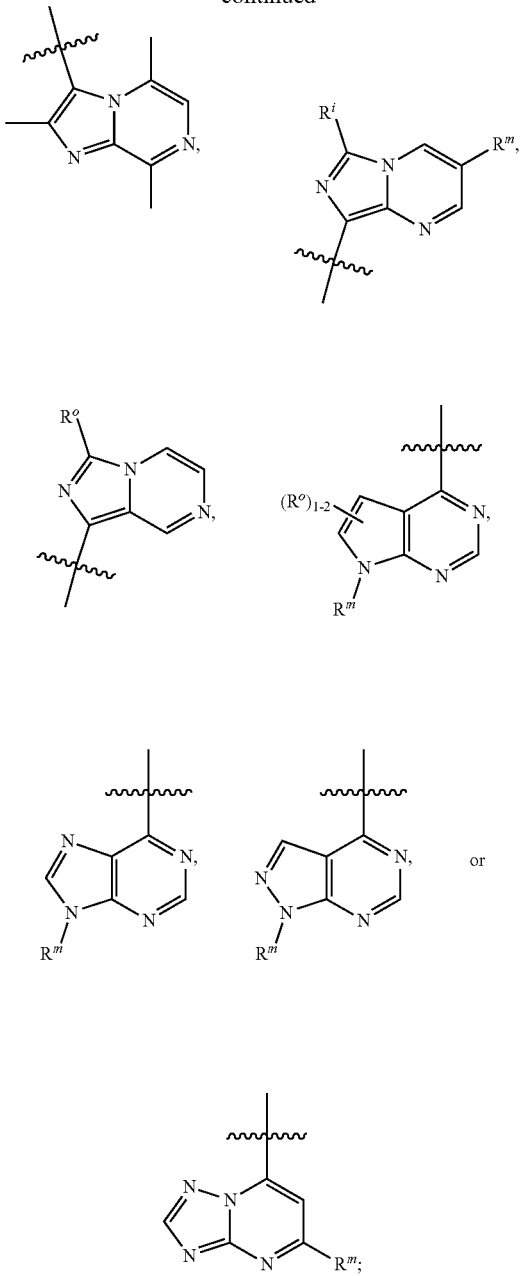

R$^i$ is selected from the group consisting of: H, F, CH$_3$, CF$_3$, CF$_2$H, OCH$_3$, and cyclopropyl;

R$^j$ is selected from the group consisting of: H, Br, F, CH$_3$, and CF$_3$;

R$^m$ is H or CH$_3$;

R$^n$ is selected from the group consisting of: H, halo and OCH$_3$;

R$^o$ is selected from the group consisting of: H, CH$_3$, CF$_3$, CF$_2$H, and CH$_2$CH$_2$F;

Y is CH or N;

and

R$^{3a}$ is phenyl substituted with one, two or three members each independently selected from the group consisting of: Cl, F, CH$_3$, and OCH$_3$.

73. A compound of claim 72, wherein
R[1] is CH$_3$;
R[2a] is
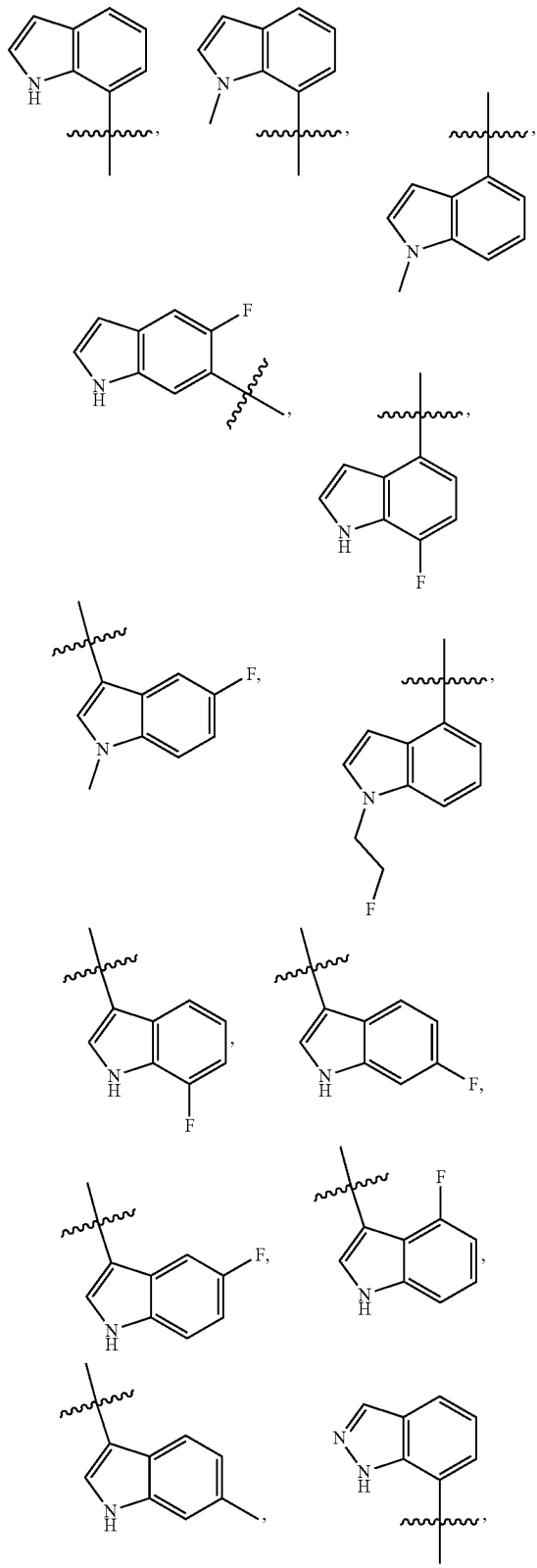
-continued
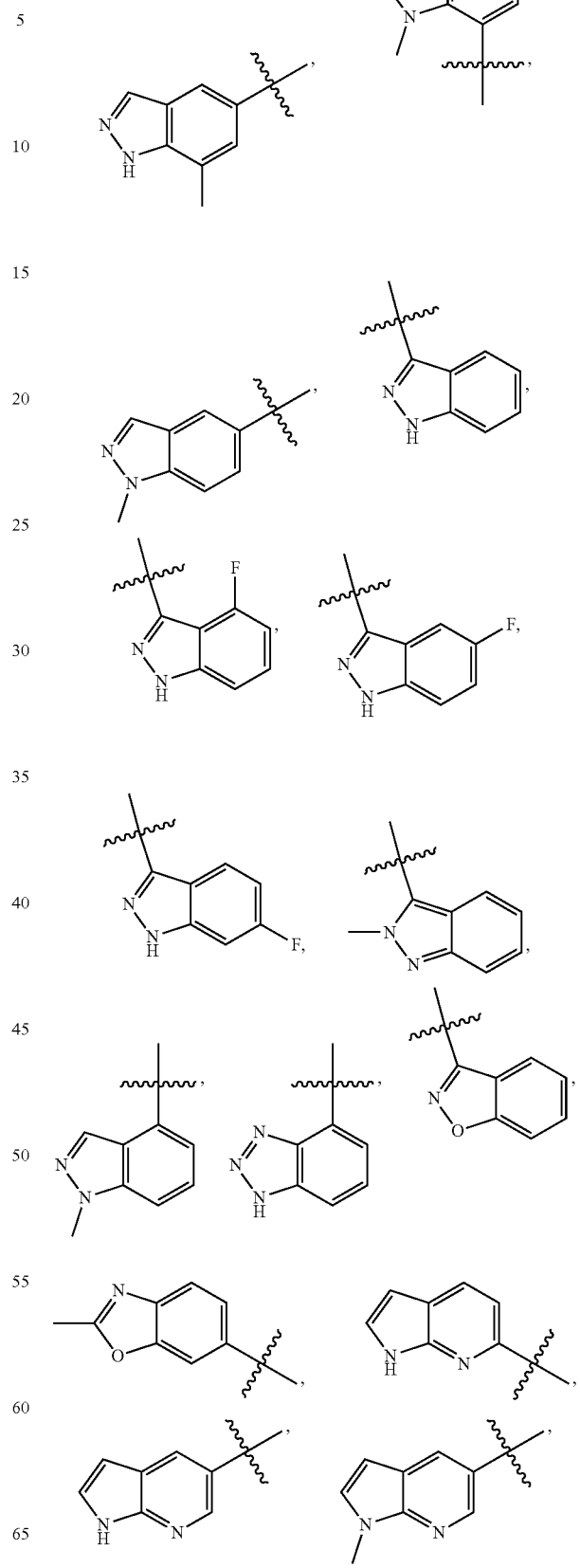

669
-continued
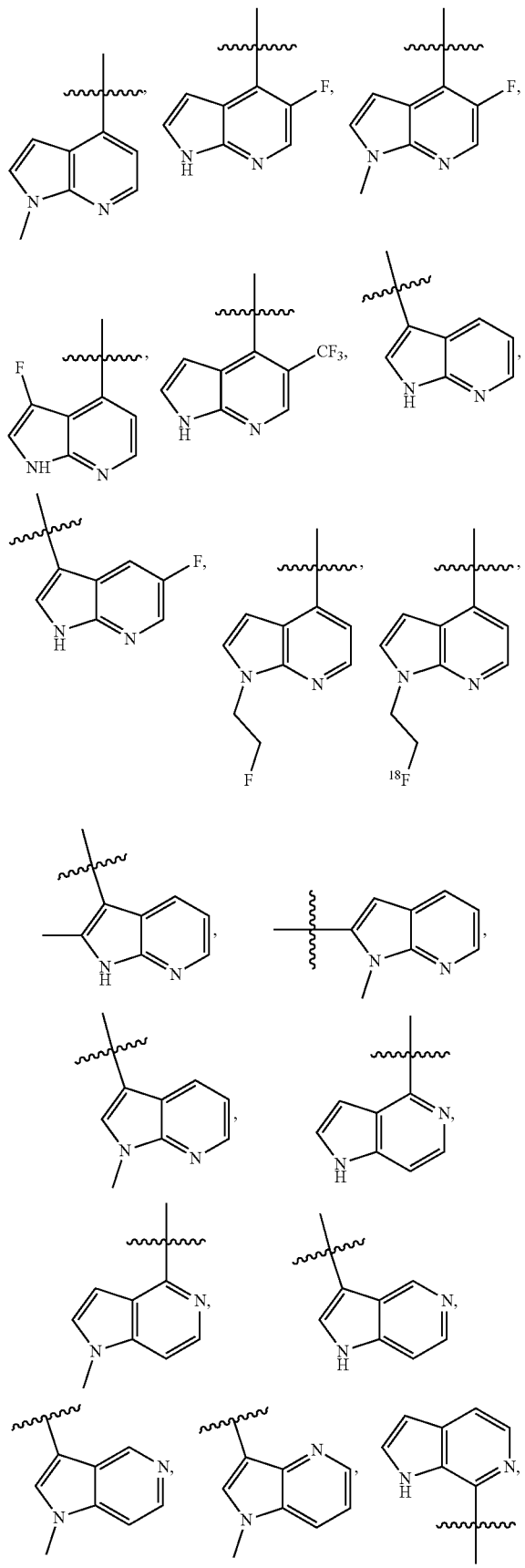
670
-continued
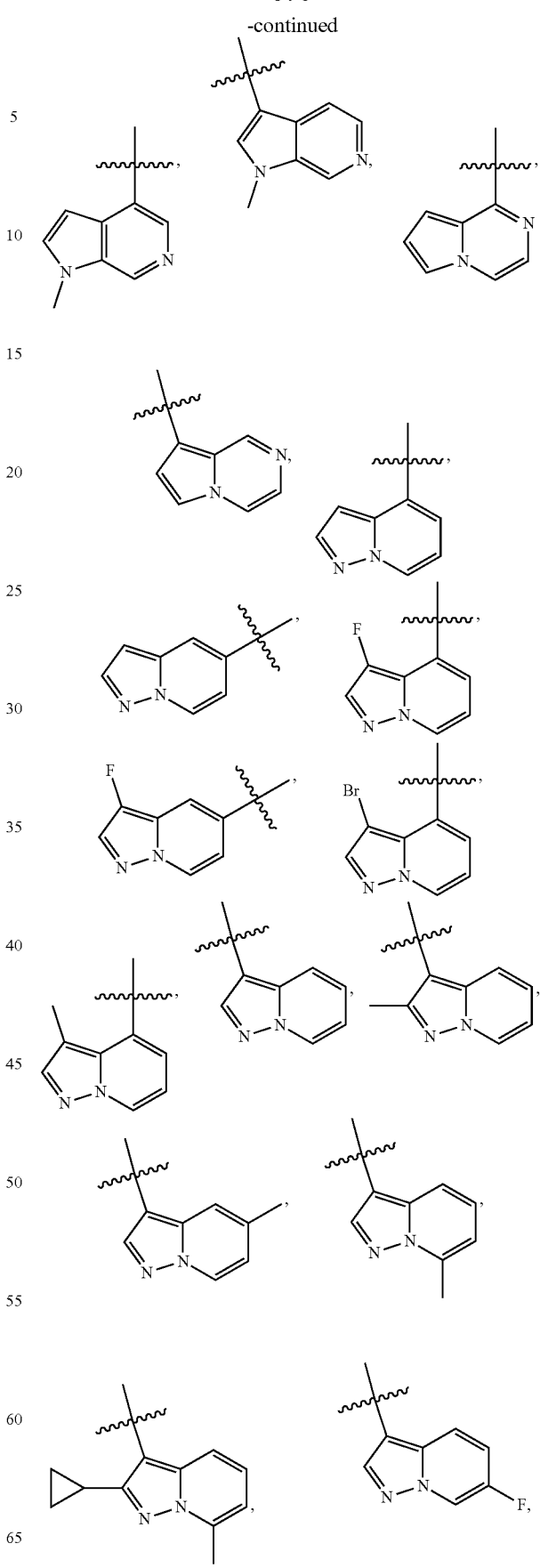

671
-continued
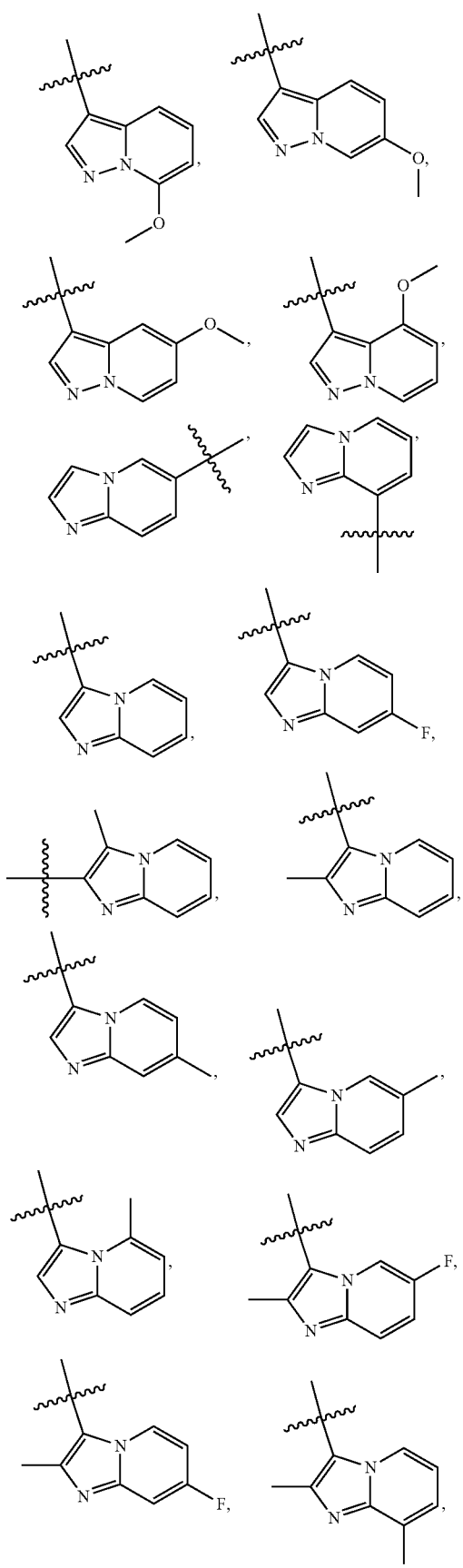
672
-continued
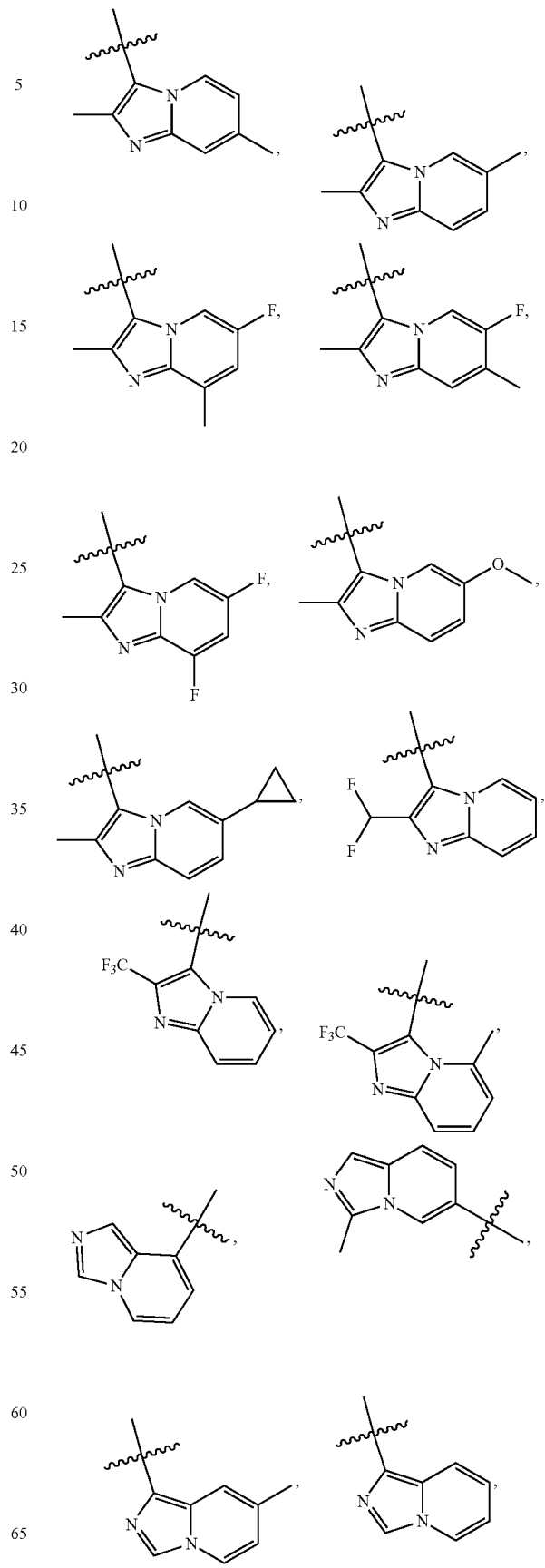

673
-continued
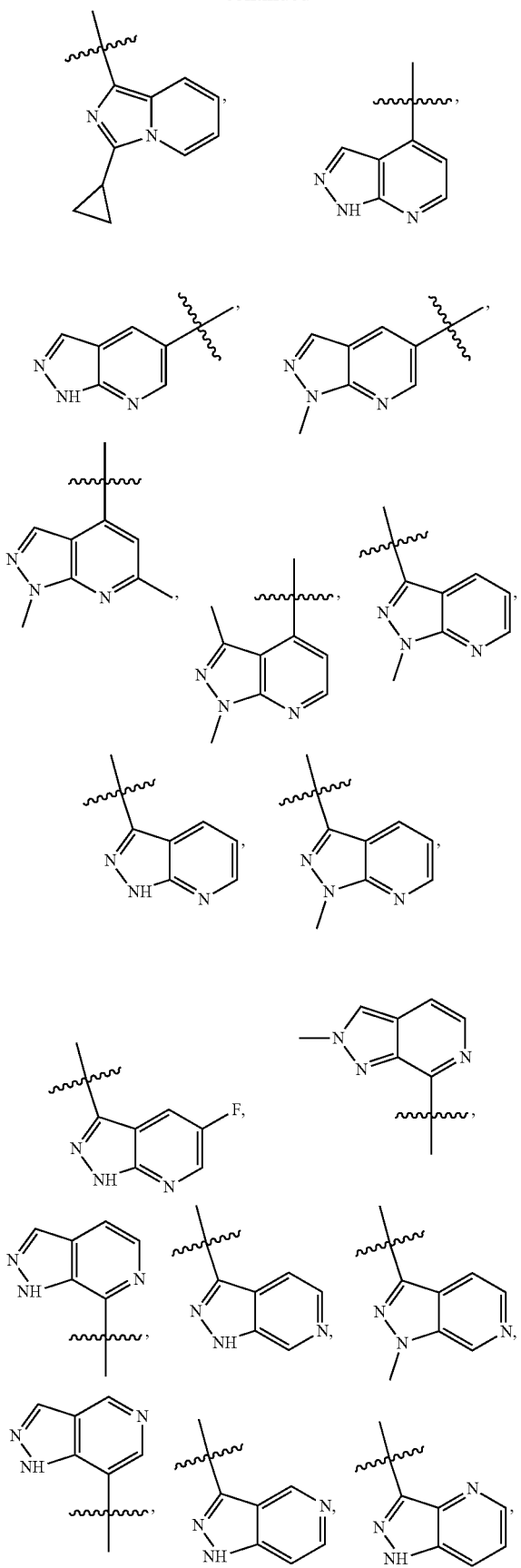
674
-continued
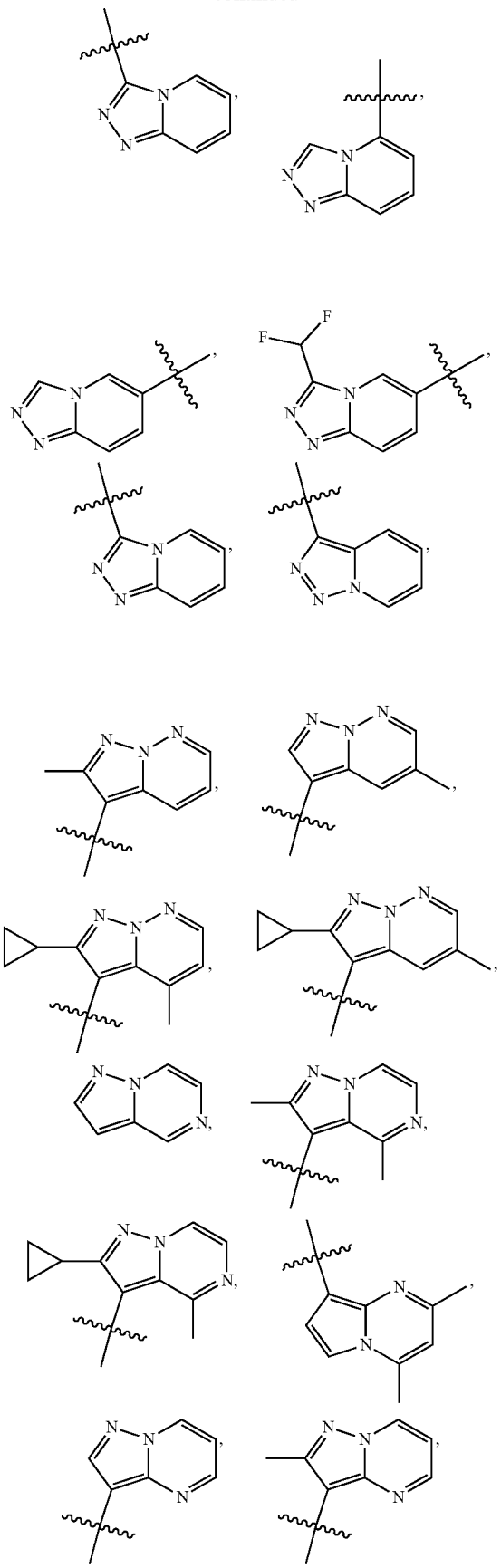

675
-continued
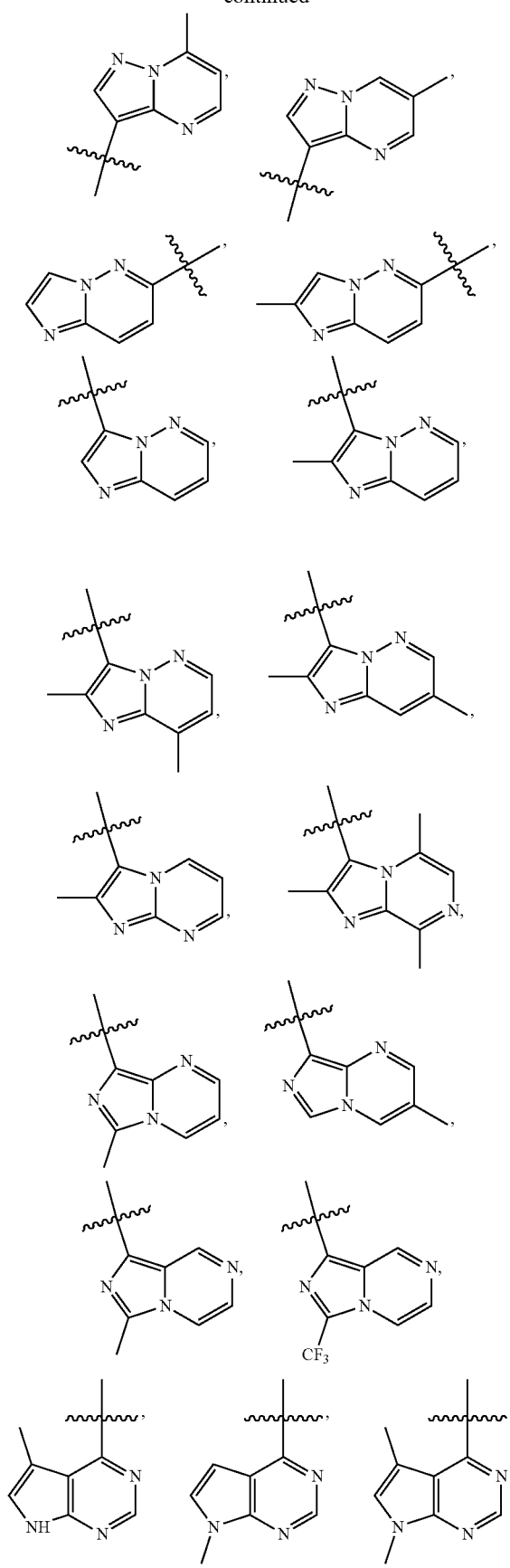
676
-continued
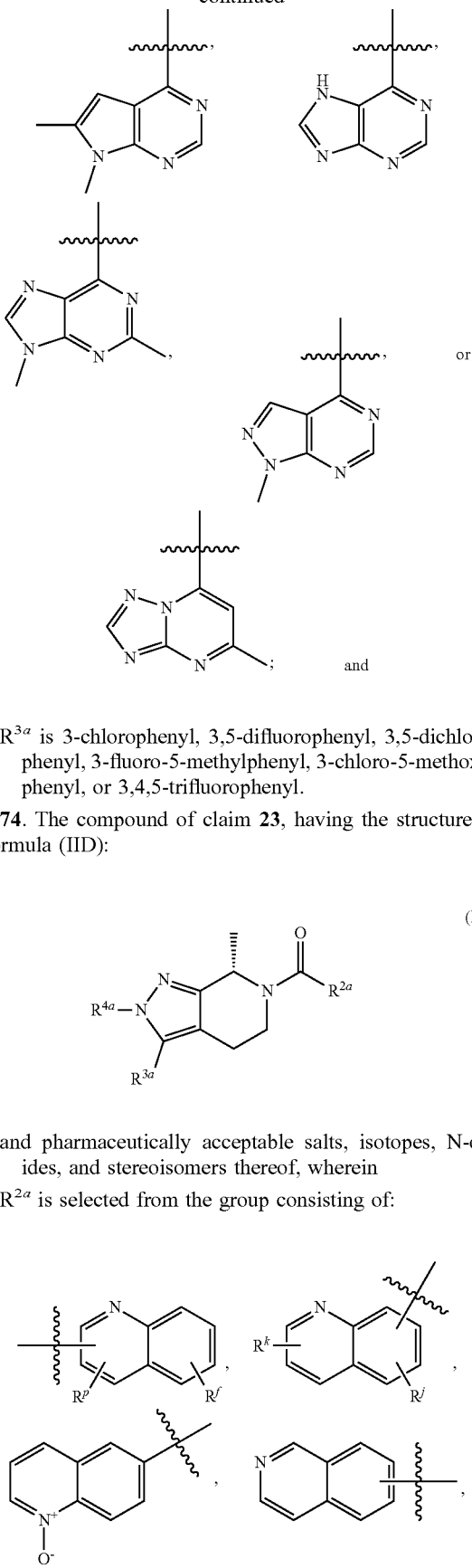
$R^{3a}$ is 3-chlorophenyl, 3,5-difluorophenyl, 3,5-dichlorophenyl, 3-fluoro-5-methylphenyl, 3-chloro-5-methoxyphenyl, or 3,4,5-trifluorophenyl.
74. The compound of claim 23, having the structure of Formula (IID):
(IID)
and pharmaceutically acceptable salts, isotopes, N-oxides, and stereoisomers thereof, wherein
$R^{2a}$ is selected from the group consisting of:

-continued

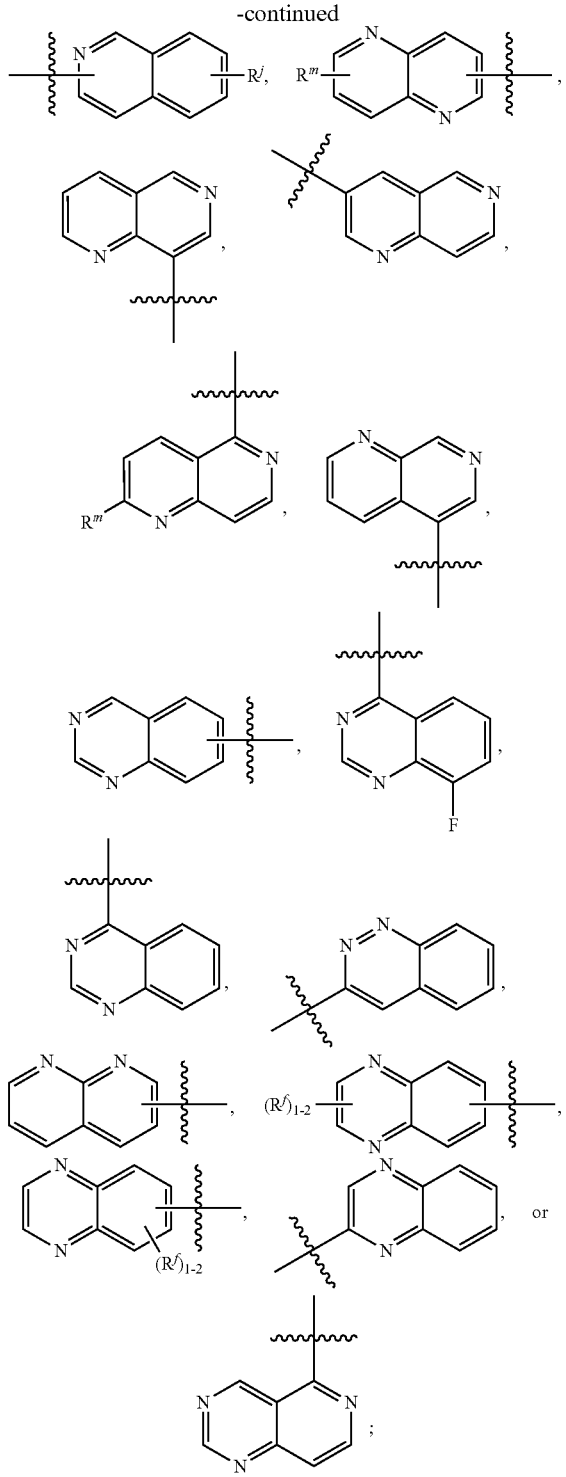

$R^f$ is selected from the group consisting of: H, F and OCH$_3$;
$R^j$ is selected from the group consisting of: H, Cl, F and CF$_3$;
$R^k$ is selected from the group consisting of: H, Br, CH$_3$, CF$_3$, OH, and OCH$_2$CH$_2$F;
$R^m$ is H or CH$_3$; and
$R^p$ is selected from the group consisting of: H, CH$_3$, and OCH$_3$;

$R^{3a}$ is selected from the group consisting of:
(a) Phenyl; or phenyl substituted with one, two or three members each independently selected from the group consisting of: Cl, F, C$_{1-4}$alkyl, CF$_3$, OC$_{1-4}$alkyl, OCF$_3$, and OCF$_2$H; and
(b)

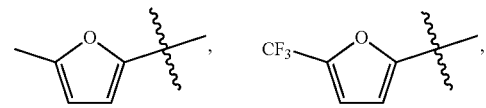

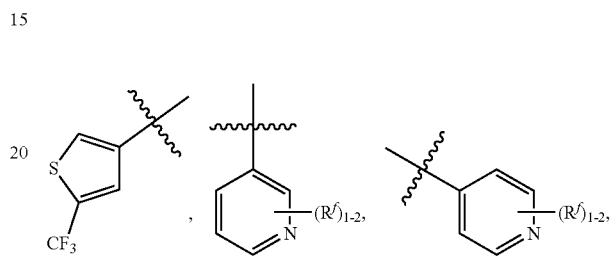

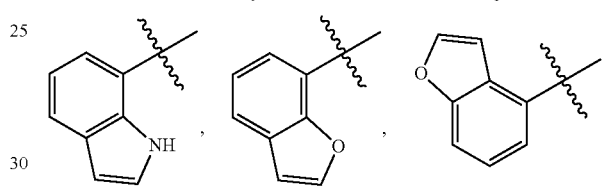

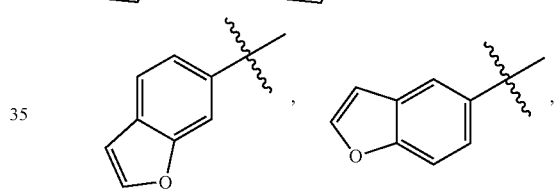

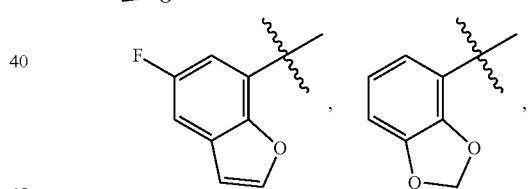

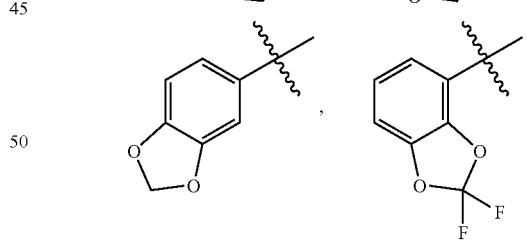

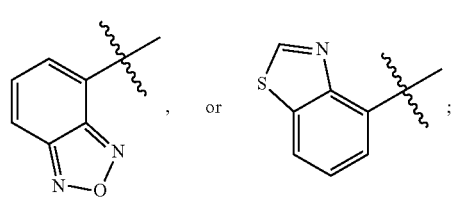

where $R^f$ is H, F, CH$_3$, CF$_2$H, CF$_3$, OCH$_3$, OCF$_2$H; and
$R^{4a}$ is CH$_3$ or CF$_2$H.

75. The compound of claim 23, wherein R$^{2a}$ is
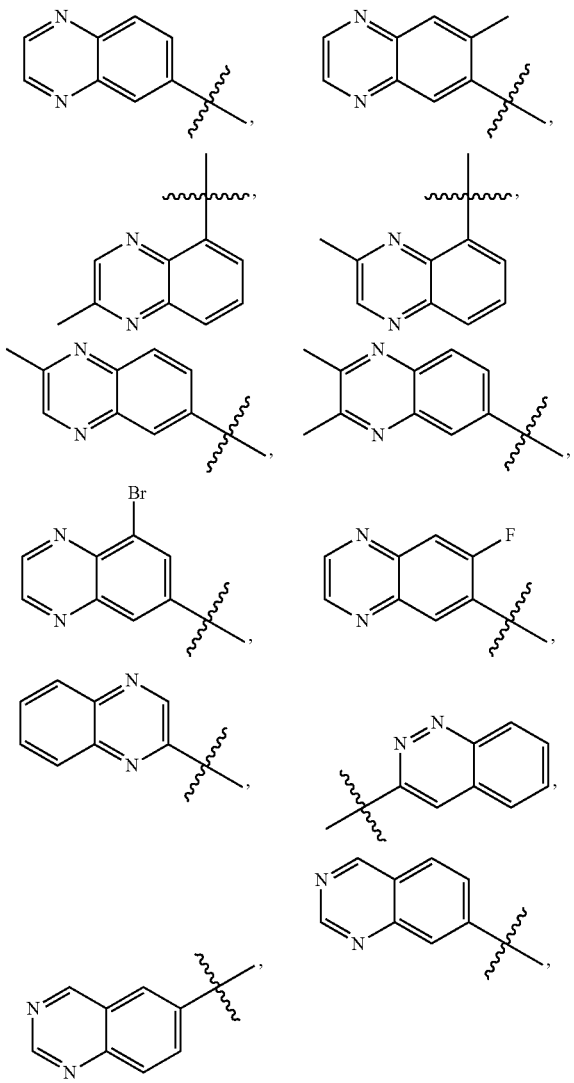
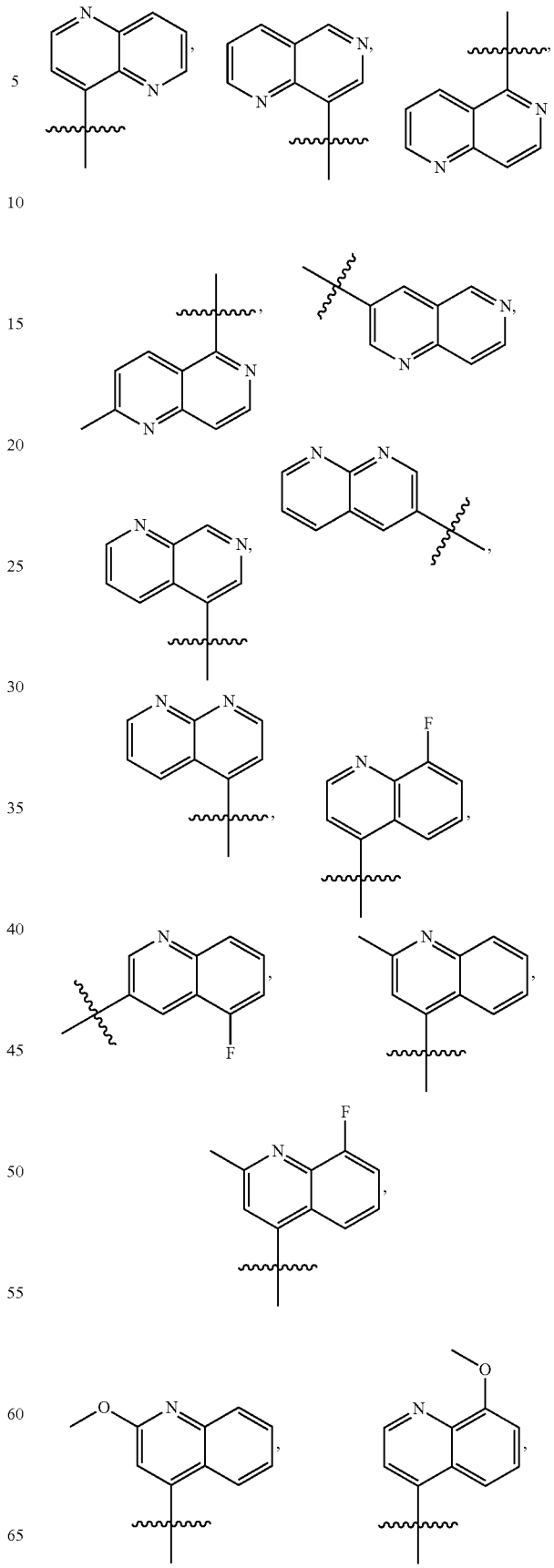

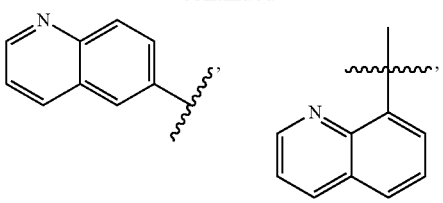

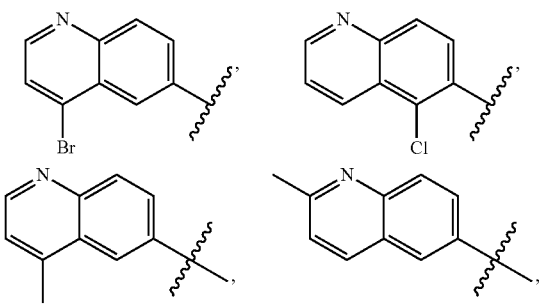

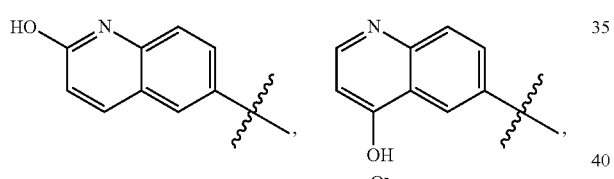

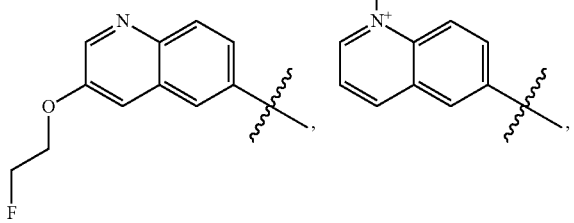

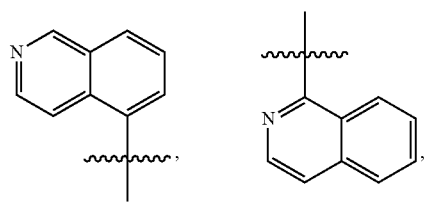

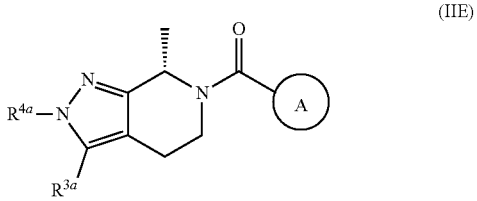

R$^{3a}$ is 5-methylfuran-2-yl, 5-(trifluoromethyl)furan-2-yl, pyridin-3-yl, 5-fluoropyridin-3-yl, 5-(trifluoromethyl)pyridin-3-yl, phenyl, 3-chlorophenyl, 3,5-difluorophenyl, 3,5-dichlorophenyl, 3-chloro-5-fluorophenyl, 3-fluoro-4-methoxyphenyl, 4-(difluoromethoxy)-3-fluorophenyl, 3-fluoro-5-(trifluoromethyl)phenyl, 3-chloro-4-methoxyphenyl, 3-fluoro-5-methoxyphenyl, 3-chloro-4-methylphenyl, 3,5-difluoro-4-methylphenyl, or 3,4,5-trifluorophenyl; and R$^{4a}$ is CH$_3$.

76. The compound of claim 23, having the structure of Formula (IIE):

(IIE)

and pharmaceutically acceptable salts, isotopes, N-oxides, and stereoisomers thereof, wherein ring

A is selected from the group consisting of:

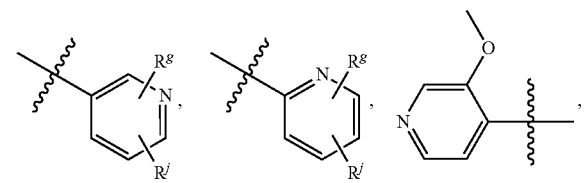

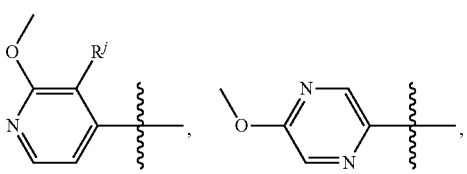

-continued

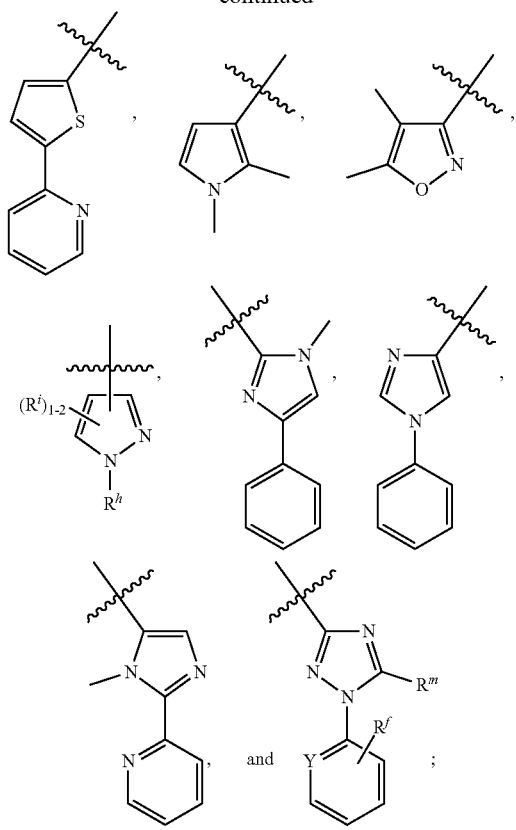

where
Y is CH or N;
$R^f$ is H or F;
$R^g$ is selected from the group consisting of: $OC_{1-4}$alkyl, $CH_2OCH_3$, $CH_2OH$,

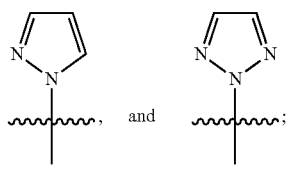 [SMILES: *n1cccn1 ; *n1nccn1]

$R^h$ is selected from the group consisting of: $C_{1-4}$alkyl, $CF_3$, and cyclopropyl;
$R^i$ is selected from the group consisting of: H, halo, $C_{1-4}$alkyl, $CF_2H$, $CF_3$, $OCH_3$, cyclopropyl, cyclobutyl, and cyclopropyl substituted with one or two members independently selected from: F and $CH_3$;
$R^j$ is selected from the group consisting of: H, Cl, F, and $CH_3$;
$R^m$ is H, $CH_3$, or $CH_2CH_3$;
$R^{3a}$ is selected from the group consisting of: phenyl, 3-fluoro-5-methyl-phenyl, and 3,4,5-trifluorophenyl; and
$R^{4a}$ is selected from the group consisting of: $CH_3$, $C_{3-6}$cycloalkyl, and phenyl.

77. The compound of claim 23, having the structure of Formula (IIF):

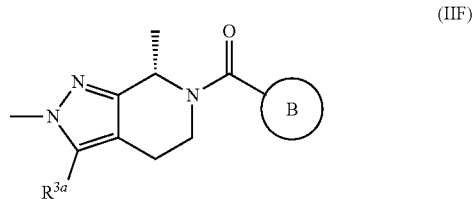

and pharmaceutically acceptable salts, isotopes, N-oxides, and stereoisomers thereof, wherein ring

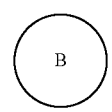

is selected from the group consisting of:

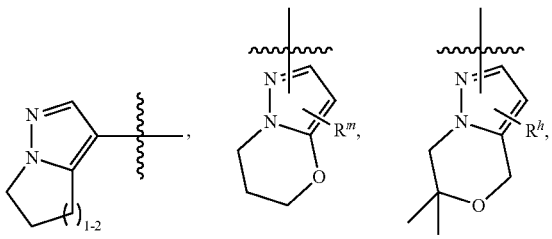

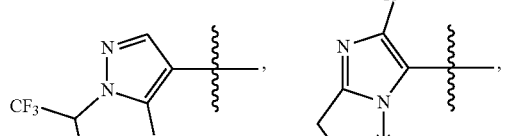

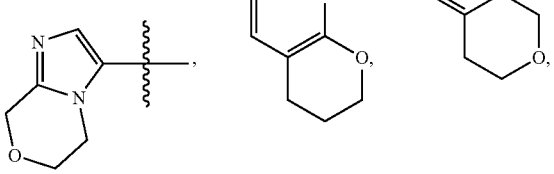

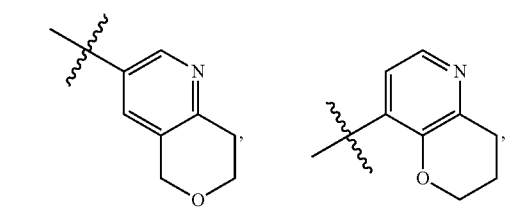

-continued where
R$^h$ is CH$_3$;
R$^j$ is H or CF$_2$H;
R$^m$ is H or CH$_3$.
R$^{3a}$ is 3-chlorophenyl or 3,4,5-trifluorophenyl.

78. A compound selected from the group consisting of:
(3-(3,5-Difluorophenyl)-2,7-dimethyl-2,4,5,7-tetrahydro-6H-pyrazolo[3,4-c]pyridin-6-yl)(quinolin-6-yl)methanone;
(S)-(2,7-Dimethyl-3-(5-methylfuran-2-yl)-2,4,5,7-tetrahydro-6H-pyrazolo[3,4-c]pyridin-6-yl)(quinoxalin-6-yl)methanone;
(S)-(2,7-Dimethyl-3-(pyridin-3-yl)-2,4,5,7-tetrahydro-6H-pyrazolo[3,4-c]pyridin-6-yl)(quinoxalin-6-yl)methanone;
(S)-(3-(5-Fluoropyridin-3-yl)-2,7-dimethyl-2,4,5,7-tetrahydro-6H-pyrazolo[3,4-c]pyridin-6-yl)(quinoxalin-6-yl)methanone;
(2,7-Dimethyl-3-phenyl-2,4,5,7-tetrahydro-6H-pyrazolo[3,4-c]pyridin-6-yl)(quinolin-6-yl)methanone;
(R)-(2,7-Dimethyl-3-phenyl-2,4,5,7-tetrahydro-6H-pyrazolo[3,4-c]pyridin-6-yl)(quinolin-6-yl)methanone;
(S)-(2,7-Dimethyl-3-phenyl-2,4,5,7-tetrahydro-6H-pyrazolo[3,4-c]pyridin-6-yl)(quinolin-6-yl)methanone;
(7-Methyl-2,3-diphenyl-2,4,5,7-tetrahydro-6H-pyrazolo[3,4-c]pyridin-6-yl)(quinolin-6-yl)methanone;
(R)-(7-Methyl-2,3-diphenyl-2,4,5,7-tetrahydro-6H-pyrazolo[3,4-c]pyridin-6-yl)(quinolin-6-yl)methanone;
(S)-(7-Methyl-2,3-diphenyl-2,4,5,7-tetrahydro-6H-pyrazolo[3,4-c]pyridin-6-yl)(quinolin-6-yl)methanone;
(S)-(3-Chloro-5-(trifluoromethoxy)phenyl)(3-(3-chlorophenyl)-2,7-dimethyl-2,4,5,7-tetrahydro-6H-pyrazolo[3,4-c]pyridin-6-yl)methanone;
(S)-(3-(3-Chlorophenyl)-2,7-dimethyl-2,4,5,7-tetrahydro-6H-pyrazolo[3,4-c]pyridin-6-yl)(1-phenyl-1H-1,2,4-triazol-3-yl)methanone;
(S)-(3-(3-Chlorophenyl)-2,7-dimethyl-2,4,5,7-tetrahydro-6H-pyrazolo[3,4-c]pyridin-6-yl)(5-ethyl-1-(2-fluorophenyl)-1H-1,2,4-triazol-3-yl)methanone;
(S)-(3-(3-Chlorophenyl)-2,7-dimethyl-2,4,5,7-tetrahydro-6H-pyrazolo[3,4-c]pyridin-6-yl)(4-(hydroxymethyl)pyridin-2-yl)methanone;
(S)-(3-(3-Chlorophenyl)-2,7-dimethyl-2,4,5,7-tetrahydro-6H-pyrazolo[3,4-c]pyridin-6-yl)(5-(methoxymethyl)pyridin-3-yl)methanone;
(S)-(3-(3-Chlorophenyl)-2,7-dimethyl-2,4,5,7-tetrahydro-6H-pyrazolo[3,4-c]pyridin-6-yl)(6-isopropoxypyridin-3-yl)methanone;
(S)-(3-(3-Chlorophenyl)-2,7-dimethyl-2,4,5,7-tetrahydro-6H-pyrazolo[3,4-c]pyridin-6-yl)(5-isopropoxypyridin-3-yl)methanone;
(S)-Benzo[d][1,3]dioxol-4-yl(3-(3-chlorophenyl)-2,7-dimethyl-2,4,5,7-tetrahydro-6H-pyrazolo[3,4-c]pyridin-6-yl)methanone;
(S)-6-(3-(3-Chlorophenyl)-2,7-dimethyl-4,5,6,7-tetrahydro-2H-pyrazolo[3,4-c]pyridine-6-carbonyl)benzo[d]oxazol-2(3H)-one;
(S)-(3-(3-Chlorophenyl)-2,7-dimethyl-2,4,5,7-tetrahydro-6H-pyrazolo[3,4-c]pyridin-6-yl)(2-methylbenzo[d]oxazol-6-yl)methanone;
(3-(3-Chlorophenyl)-2,7-dimethyl-2,4,5,7-tetrahydro-6H-pyrazolo[3,4-c]pyridin-6-yl)(furo[3,2-b]pyridin-6-yl)methanone;
(R)-(3-(3-Chlorophenyl)-2,7-dimethyl-2,4,5,7-tetrahydro-6H-pyrazolo[3,4-c]pyridin-6-yl)(furo[3,2-b]pyridin-6-yl)methanone;
(S)-(3-(3-Chlorophenyl)-2,7-dimethyl-2,4,5,7-tetrahydro-6H-pyrazolo[3,4-c]pyridin-6-yl)(furo[3,2-b]pyridin-6-yl)methanone;
(S)-(3-(3-Chlorophenyl)-2,7-dimethyl-2,4,5,7-tetrahydro-6H-pyrazolo[3,4-c]pyridin-6-yl)(furo[3,2-b]pyridin-2-yl)methanone;
(S)-(3-(3-Chlorophenyl)-2,7-dimethyl-2,4,5,7-tetrahydro-6H-pyrazolo[3,4-c]pyridin-6-yl)(1H-pyrrolo[2,3-b]pyridin-6-yl)methanone;
(S)-(3-(3-Chlorophenyl)-2,7-dimethyl-2,4,5,7-tetrahydro-6H-pyrazolo[3,4-c]pyridin-6-yl)(1,5-naphthyridin-2-yl)methanone;
(3-(3-Chlorophenyl)-2,7-dimethyl-2,4,5,7-tetrahydro-6H-pyrazolo[3,4-c]pyridin-6-yl)(quinoxalin-6-yl)methanone;
(R)-(3-(3-Chlorophenyl)-2,7-dimethyl-2,4,5,7-tetrahydro-6H-pyrazolo[3,4-c]pyridin-6-yl)(quinoxalin-6-yl)methanone;
(S)-(3-(3-Chlorophenyl)-2,7-dimethyl-2,4,5,7-tetrahydro-6H-pyrazolo[3,4-c]pyridin-6-yl)(quinoxalin-6-yl)methanone;
(S)-(8-Bromoquinoxalin-6-yl)(3-(3-chlorophenyl)-2,7-dimethyl-2,4,5,7-tetrahydro-6H-pyrazolo[3,4-c]pyridin-6-yl)methanone;

(7-Ethyl-3-(3-fluorophenyl)-2-methyl-2,4,5,7-tetrahydro-6H-pyrazolo[3,4-c]pyridin-6-yl)(quinolin-6-yl)methanone;

[(7S)-3-(3,5-Difluorophenyl)-2,7-dimethyl-5,7-dihydro-4H-pyrazolo[3,4-c]pyridin-6-yl]-[2-(2-fluoroethoxy)phenyl]methanone;

(S)-(3-(3,5-Difluorophenyl)-2,7-dimethyl-2,4,5,7-tetrahydro-6H-pyrazolo[3,4-c]pyridin-6-yl)(4-(2-fluoroethoxy)phenyl)methanone;

(S)-(3-(3,5-Difluorophenyl)-2,7-dimethyl-2,4,5,7-tetrahydro-6H-pyrazolo[3,4-c]pyridin-6-yl)(3-(2-fluoroethoxy)phenyl)methanone;

(S)-(3-(3,5-Difluorophenyl)-2,7-dimethyl-2,4,5,7-tetrahydro-6H-pyrazolo[3,4-c]pyridin-6-yl)(2-fluoro-3-(2-fluoroethoxy)phenyl)methanone;

(S)-(3-(3,5-Difluorophenyl)-2,7-dimethyl-2,4,5,7-tetrahydro-6H-pyrazolo[3,4-c]pyridin-6-yl)(2-fluoro-5-(2-fluoroethoxy)phenyl)methanone;

(S)-(3-(3,5-Difluorophenyl)-2,7-dimethyl-2,4,5,7-tetrahydro-6H-pyrazolo[3,4-c]pyridin-6-yl)(3-fluoro-5-(2-fluoroethoxy)phenyl)methanone;

(S)-(3-(3,5-Difluorophenyl)-2,7-dimethyl-2,4,5,7-tetrahydro-6H-pyrazolo[3,4-c]pyridin-6-yl)(4-fluoro-3-(2-fluoroethoxy)phenyl)methanone;

[2-Chloro-3-(2-fluoroethoxy)phenyl]-[(7S)-3-(3,5-difluorophenyl)-2,7-dimethyl-5,7-dihydro-4H-pyrazolo[3,4-c]pyridin-6-yl]methanone;

(S)-(2-(2H-1,2,3-Triazol-2-yl)phenyl)(3-(3,5-difluorophenyl)-2,7-dimethyl-2,4,5,7-tetrahydro-6H-pyrazolo[3,4-c]pyridin-6-yl)methanone;

(3-(3,5-Difluorophenyl)-2,7-dimethyl-2,4,5,7-tetrahydro-6H-pyrazolo[3,4-c]pyridin-6-yl)(1-phenyl-1H-1,2,4-triazol-3-yl)methanone;

(S)-(3-(3,5-Difluorophenyl)-2,7-dimethyl-2,4,5,7-tetrahydro-6H-pyrazolo[3,4-c]pyridin-6-yl)(5-ethyl-1-phenyl-1H-1,2,4-triazol-3-yl)methanone;

(S)-(3-(3,5-Difluorophenyl)-2,7-dimethyl-2,4,5,7-tetrahydro-6H-pyrazolo[3,4-c]pyridin-6-yl)(1-(2-fluoroethyl)-1H-indol-4-yl)methanone;

(S)-(3-(3,5-Difluorophenyl)-2,7-dimethyl-2,4,5,7-tetrahydro-6H-pyrazolo[3,4-c]pyridin-6-yl)(1-(2-(fluoro-$^{18}$F)ethyl)-1H-indol-5-yl);

(S)-(3-(3,5-Difluorophenyl)-2,7-dimethyl-2,4,5,7-tetrahydro-6H-pyrazolo[3,4-c]pyridin-6-yl)(1-(2-fluoroethyl)-1H-pyrrolo[2,3-b]pyridin-4-yl)methanone;

(S)-(3-(3,5-Difluorophenyl)-2,7-dimethyl-2,4,5,7-tetrahydro-6H-pyrazolo[3,4-c]pyridin-6-yl)(furo[3,2-b]pyridin-6-yl)methanone;

(R)-(3-(3,5-Difluorophenyl)-2,7-dimethyl-2,4,5,7-tetrahydro-6H-pyrazolo[3,4-c]pyridin-6-yl)(furo[3,2-b]pyridin-6-yl)methanone;

(2-(Difluoromethyl)-3-(3,5-difluorophenyl)-7-methyl-2,4,5,7-tetrahydro-6H-pyrazolo[3,4-c]pyridin-6-yl)(quinolin-6-yl)methanone;

(3-(3,5-Difluorophenyl)-7-methyl-2-(trifluoromethyl)-2,4,5,7-tetrahydro-6H-pyrazolo[3,4-c]pyridin-6-yl)(quinolin-6-yl)methanone;

(3-(3,5-Difluorophenyl)-7-methyl-2-(methyl-d$_3$)-2,4,5,7-tetrahydro-6H-pyrazolo[3,4-c]pyridin-6-yl)(quinolin-6-yl)methanone;

(R)-(3-(3,5-Difluorophenyl)-2,7-dimethyl-2,4,5,7-tetrahydro-6H-pyrazolo[3,4-c]pyridin-6-yl)(quinolin-6-yl)methanone;

(S)-(3-(3,5-Difluorophenyl)-2,7-dimethyl-2,4,5,7-tetrahydro-6H-pyrazolo[3,4-c]pyridin-6-yl)(quinolin-6-yl)methanone;

(3-(3,5-Difluorophenyl)-2,7-dimethyl-2,4,5,7-tetrahydro-6H-pyrazolo[3,4-c]pyridin-6-yl)(isoquinolin-3-yl)methanone;

(3-(3,5-Difluorophenyl)-2,7-dimethyl-2,4,5,7-tetrahydro-6H-pyrazolo[3,4-c]pyridin-6-yl)(isoquinolin-7-yl)methanone;

(4-Bromoquinolin-6-yl)(3-(3,5-difluorophenyl)-2,7-dimethyl-2,4,5,7-tetrahydro-6H-pyrazolo[3,4-c]pyridin-6-yl)methanone;

(5-Chloroquinolin-6-yl)(3-(3,5-difluorophenyl)-2,7-dimethyl-2,4,5,7-tetrahydro-6H-pyrazolo[3,4-c]pyridin-6-yl)methanone;

(S)-(3-(3,5-Difluorophenyl)-2,7-dimethyl-2,4,5,7-tetrahydro-6H-pyrazolo[3,4-c]pyridin-6-yl)(8-(trifluoromethyl)quinolin-6-yl)methanone;

(S)-(3-(3,5-Difluorophenyl)-2,7-dimethyl-2,4,5,7-tetrahydro-6H-pyrazolo[3,4-c]pyridin-6-yl)(3-(trifluoromethyl)quinolin-6-yl)methanone;

(S)-(3-(3,5-Difluorophenyl)-2,7-dimethyl-2,4,5,7-tetrahydro-6H-pyrazolo[3,4-c]pyridin-6-yl)(3-(2-fluoroethoxy)quinolin-6-yl)methanone;

(3-(3,5-Difluorophenyl)-2,7-dimethyl-2,4,5,7-tetrahydro-6H-pyrazolo[3,4-c]pyridin-6-yl)(quinoxalin-6-yl)methanone;

(S)-(3-(3,5-Difluorophenyl)-2,7-dimethyl-2,4,5,7-tetrahydro-6H-pyrazolo[3,4-c]pyridin-6-yl)(quinoxalin-6-yl)methanone;

(R)-(3-(3,5-Difluorophenyl)-2,7-dimethyl-2,4,5,7-tetrahydro-6H-pyrazolo[3,4-c]pyridin-6-yl)(quinoxalin-6-yl)methanone;

(S)-(3-(3,5-Difluorophenyl)-2,7-dimethyl-2,4,5,7-tetrahydro-6H-pyrazolo[3,4-c]pyridin-6-yl)(1,5-naphthyridin-2-yl)methanone;

(S)-(3-(3,5-Difluorophenyl)-2,7-dimethyl-2,4,5,7-tetrahydro-6H-pyrazolo[3,4-c]pyridin-6-yl)(7-fluoroquinoxalin-6-yl)methanone;

(S)-(3-(3,5-Dichlorophenyl)-2,7-dimethyl-2,4,5,7-tetrahydro-6H-pyrazolo[3,4-c]pyridin-6-yl)(2-methylbenzo[d]oxazol-6-yl)methanone;

(S)-(3-(3,5-Dichlorophenyl)-2,7-dimethyl-2,4,5,7-tetrahydro-6H-pyrazolo[3,4-c]pyridin-6-yl)(1-methyl-1H-pyrazolo[3,4-b]pyridin-3-yl)methanone;

(S)-(3-(3,5-Dichlorophenyl)-2,7-dimethyl-2,4,5,7-tetrahydro-6H-pyrazolo[3,4-c]pyridin-6-yl)(quinolin-6-yl)methanone;

(S)-(3-(3,5-Dichlorophenyl)-2,7-dimethyl-2,4,5,7-tetrahydro-6H-pyrazolo[3,4-c]pyridin-6-yl)(quinoxalin-6-yl)methanone;

(S)-(3-(3,5-Dichlorophenyl)-2,7-dimethyl-2,4,5,7-tetrahydro-6H-pyrazolo[3,4-c]pyridin-6-yl)(2-methylquinoxalin-6-yl)methanone;

(3-(3-Chloro-5-fluorophenyl)-2,7-dimethyl-2,4,5,7-tetrahydro-6H-pyrazolo[3,4-c]pyridin-6-yl)(quinolin-6-yl)methanone;

(S)-(3-(3-Chloro-5-fluorophenyl)-2,7-dimethyl-2,4,5,7-tetrahydro-6H-pyrazolo[3,4-c]pyridin-6-yl)(quinolin-6-yl)methanone;

(R)-(3-(3-Chloro-5-fluorophenyl)-2,7-dimethyl-2,4,5,7-tetrahydro-6H-pyrazolo[3,4-c]pyridin-6-yl)(quinolin-6-yl)methanone;

(3-(3-Chloro-5-fluorophenyl)-2,7-dimethyl-2,4,5,7-tetrahydro-6H-pyrazolo[3,4-c]pyridin-6-yl)(quinoxalin-6-yl)methanone;

(S)-(3-(3-Chloro-5-fluorophenyl)-2,7-dimethyl-2,4,5,7-tetrahydro-6H-pyrazolo[3,4-c]pyridin-6-yl)(quinoxalin-6-yl)methanone;

(R)-(3-(3-Chloro-5-fluorophenyl)-2,7-dimethyl-2,4,5,7-tetrahydro-6H-pyrazolo[3,4-c]pyridin-6-yl)(quinoxalin-6-yl)methanone;

(S)-(3-(3-Chloro-4-methylphenyl)-2,7-dimethyl-2,4,5,7-tetrahydro-6H-pyrazolo[3,4-c]pyridin-6-yl)(quinoxalin-6-yl)methanone;

(S)-(3-(3-Fluoro-5-(trifluoromethyl)phenyl)-2,7-dimethyl-2,4,5,7-tetrahydro-6H-pyrazolo[3,4-c]pyridin-6-yl)(quinoxalin-6-yl)methanone;

(S)-(3-(3-Fluoro-4-methoxyphenyl)-2,7-dimethyl-2,4,5,7-tetrahydro-6H-pyrazolo[3,4-c]pyridin-6-yl)(quinoxalin-6-yl)methanone;

(S)-(3-(3-Fluoro-5-methoxyphenyl)-2,7-dimethyl-2,4,5,7-tetrahydro-6H-pyrazolo[3,4-c]pyridin-6-yl)(quinoxalin-6-yl)methanone;

(S)-(3-(3-Fluoro-5-methoxyphenyl)-2,7-dimethyl-2,4,5,7-tetrahydro-6H-pyrazolo[3,4-c]pyridin-6-yl)(7-fluoroquinoxalin-6-yl)methanone;

(S)-(3-(3-Chloro-4-methoxyphenyl)-2,7-dimethyl-2,4,5,7-tetrahydro-6H-pyrazolo[3,4-c]pyridin-6-yl)(quinoxalin-6-yl)methanone;

(S)-(3-(4-(Difluoromethoxy)-3-fluorophenyl)-2,7-dimethyl-2,4,5,7-tetrahydro-6H-pyrazolo[3,4-c]pyridin-6-yl)(quinoxalin-6-yl)methanone;

(S)-(3-(3,5-Difluoro-4-methylphenyl)-2,7-dimethyl-2,4,5,7-tetrahydro-6H-pyrazolo[3,4-c]pyridin-6-yl)(quinoxalin-6-yl)methanone;

(S)-(2-Chloro-3-methoxyphenyl)(2,7-dimethyl-3-(3,4,5-trifluorophenyl)-2,4,5,7-tetrahydro-6H-pyrazolo[3,4-c]pyridin-6-yl)methanone;

(S)-(3-Chloro-5-methoxyphenyl)(2,7-dimethyl-3-(3,4,5-trifluorophenyl)-2,4,5,7-tetrahydro-6H-pyrazolo[3,4-c]pyridin-6-yl)methanone;

(S)-(2,7-Dimethyl-3-(3,4,5-trifluorophenyl)-2,4,5,7-tetrahydro-6H-pyrazolo[3,4-c]pyridin-6-yl)(5-fluoro-2-(1H-pyrazol-1-yl)phenyl)methanone;

(S)-(3-(1H-1,2,4-Triazol-1-yl)phenyl)(2,7-dimethyl-3-(3,4,5-trifluorophenyl)-2,4,5,7-tetrahydro-6H-pyrazolo[3,4-c]pyridin-6-yl)methanone;

(S)-(2,7-Dimethyl-3-(3,4,5-trifluorophenyl)-2,4,5,7-tetrahydro-6H-pyrazolo[3,4-c]pyridin-6-yl)(3-fluoro-2-(2H-1,2,3-triazol-2-yl)phenyl)methanone;

(S)-(2,7-Dimethyl-3-(3,4,5-trifluorophenyl)-2,4,5,7-tetrahydro-6H-pyrazolo[3,4-c]pyridin-6-yl)(4-fluoro-2-(2H-1,2,3-triazol-2-yl)phenyl)methanone;

(S)-(2,7-Dimethyl-3-(3,4,5-trifluorophenyl)-2,4,5,7-tetrahydro-6H-pyrazolo[3,4-c]pyridin-6-yl)(5-methyl-2-(2H-1,2,3-triazol-2-yl)phenyl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-5-(trifluoromethyl)-1H-pyrazol-4-yl)methanone;

(S)-(1-(tert-Butyl)-5-(trifluoromethyl)-1H-pyrazol-4-yl)(2,7-dimethyl-3-(3,4,5-trifluorophenyl)-2,4,5,7-tetrahydro-6H-pyrazolo[3,4-c]pyridin-6-yl)methanone;

(S)-(2,7-Dimethyl-3-(3,4,5-trifluorophenyl)-2,4,5,7-tetrahydro-6H-pyrazolo[3,4-c]pyridin-6-yl)(5-methoxy-1-methyl-1H-pyrazol-3-yl)methanone;

(S)-(5-Cyclopropyl-1-methyl-1H-pyrazol-4-yl)(2,7-dimethyl-3-(3,4,5-trifluorophenyl)-2,4,5,7-tetrahydro-6H-pyrazolo[3,4-c]pyridin-6-yl)methanone;

(S)-(2,7-Dimethyl-3-(3,4,5-trifluorophenyl)-2,4,5,7-tetrahydro-6H-pyrazolo[3,4-c]pyridin-6-yl)(5-ethyl-1-phenyl-1H-1,2,4-triazol-3-yl)methanone;

(S)-(2,7-Dimethyl-3-(3,4,5-trifluorophenyl)-2,4,5,7-tetrahydro-6H-pyrazolo[3,4-c]pyridin-6-yl)(5-methoxypyridin-3-yl)methanone;

(S)-6-(2,7-Dimethyl-3-(3,4,5-trifluorophenyl)-4,5,6,7-tetrahydro-2H-pyrazolo[3,4-c]pyridine-6-carbonyl)-4-methyl-2H-benzo[b][1,4]oxazin-3 (4H)-one;

(S)-(2,7-Dimethyl-3-(3,4,5-trifluorophenyl)-2,4,5,7-tetrahydro-6H-pyrazolo[3,4-c]pyridin-6-yl)(1H-indol-7-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-indol-7-yl)methanone;

(S)-(2,7-dimethyl-3-(3,4,5-trifluorophenyl)-2,4,5,7-tetrahydro-6H-pyrazolo[3,4-c]pyridin-6-yl)(1-methyl-1H-indol-4-yl)methanone;

(S)-(2,7-Dimethyl-3-(3,4,5-trifluorophenyl)-2,4,5,7-tetrahydro-6H-pyrazolo[3,4-c]pyridin-6-yl)(1H-indazol-7-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-indazol-7-yl)methanone;

(S)-(2,7-Dimethyl-3-(3,4,5-trifluorophenyl)-2,4,5,7-tetrahydro-6H-pyrazolo[3,4-c]pyridin-6-yl)(7-methyl-1H-indazol-5-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-indazol-5-yl)methanone;

(S)-(2,7-Dimethyl-3-(3,4,5-trifluorophenyl)-2,4,5,7-tetrahydro-6H-pyrazolo[3,4-c]pyridin-6-yl)(imidazo[1,5-a]pyridin-8-yl)methanone;

(S)-(2,7-Dimethyl-3-(3,4,5-trifluorophenyl)-2,4,5,7-tetrahydro-6H-pyrazolo[3,4-c]pyridin-6-yl)(imidazo[1,2-a]pyridin-3-yl)methanone;

(S)-(2,7-Dimethyl-3-(3,4,5-trifluorophenyl)-2,4,5,7-tetrahydro-6H-pyrazolo[3,4-c]pyridin-6-yl)(furo[3,2-c]pyridin-4-yl)methanone;

(S)-Benzo[d]isoxazol-3-yl(2,7-dimethyl-3-(3,4,5-trifluorophenyl)-2,4,5,7-tetrahydro-6H-pyrazolo[3,4-c]pyridin-6-yl)methanone;

(S)-(2,7-Dimethyl-3-(3,4,5-trifluorophenyl)-2,4,5,7-tetrahydro-6H-pyrazolo[3,4-c]pyridin-6-yl)(1H-pyrrolo[3,2-c]pyridin-4-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[3,2-c]pyridin-4-yl)methanone;

(S)-(2,7-Dimethyl-3-(3,4,5-trifluorophenyl)-2,4,5,7-tetrahydro-6H-pyrazolo[3,4-c]pyridin-6-yl)(1H-pyrrolo[3,2-c]pyridin-3-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[3,2-c]pyridin-3-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[3,2-b]pyridin-3-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-c]pyridin-3-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-2-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-3-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-c]pyridin-4-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-4-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-pyrrolo[2,3-b]pyridin-5-yl)methanone;

(S)-(2,7-Dimethyl-3-(3,4,5-trifluorophenyl)-2,4,5,7-tetrahydro-6H-pyrazolo[3,4-c]pyridin-6-yl)(pyrazolo[1,5-a]pyridin-4-yl)methanone;

(S)-(2,7-Dimethyl-3-(3,4,5-trifluorophenyl)-2,4,5,7-tetrahydro-6H-pyrazolo[3,4-c]pyridin-6-yl)(pyrazolo[1,5-a]pyridin-5-yl)methanone;

(S)-(2,7-Dimethyl-3-(3,4,5-trifluorophenyl)-2,4,5,7-tetrahydro-6H-pyrazolo[3,4-c]pyridin-6-yl)(pyrazolo[1,5-a]pyrazin-3-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-pyrazolo[3,4-b]pyridin-3-yl)methanone;

(S)-(2,7-Dimethyl-3-(3,4,5-trifluorophenyl)-2,4,5,7-tetrahydro-6H-pyrazolo[3,4-c]pyridin-6-yl)(1-methyl-1H-pyrazolo[3,4-b]pyridin-5-yl)methanone;

(S)-(2-(Difluoromethyl)-7-methyl-3-(3,4,5-trifluorophenyl)-2,4,5,7-tetrahydro-6H-pyrazolo[3,4-c]pyridin-6-yl)(quinolin-6-yl)methanone;

(R)-(2-(Difluoromethyl)-7-methyl-3-(3,4,5-trifluorophenyl)-2,4,5,7-tetrahydro-6H-pyrazolo[3,4-c]pyridin-6-yl)(quinolin-6-yl)methanone;

(S)-(2,7-Dimethyl-3-(3,4,5-trifluorophenyl)-2,4,5,7-tetrahydro-6H-pyrazolo[3,4-c]pyridin-6-yl)(quinolin-6-yl)methanone;

(R)-(2,7-Dimethyl-3-(3,4,5-trifluorophenyl)-2,4,5,7-tetrahydro-6H-pyrazolo[3,4-c]pyridin-6-yl)(quinolin-6-yl)methanone;

(S)-(2,7-dimethyl-3-(3,4,5-trifluorophenyl)-2,4,5,7-tetrahydro-6H-pyrazolo[3,4-c]pyridin-6-yl)(quinolin-8-yl)methanone;

(S)-(2,7-Dimethyl-3-(3,4,5-trifluorophenyl)-2,4,5,7-tetrahydro-6H-pyrazolo[3,4-c]pyridin-6-yl)(isoquinolin-1-yl)methanone;

(S)-(2,7-Dimethyl-3-(3,4,5-trifluorophenyl)-2,4,5,7-tetrahydro-6H-pyrazolo[3,4-c]pyridin-6-yl)(8-fluoroquinolin-4-yl)methanone;

(S)-(2,7-Dimethyl-3-(3,4,5-trifluorophenyl)-2,4,5,7-tetrahydro-6H-pyrazolo[3,4-c]pyridin-6-yl)(2-methylquinolin-4-yl)methanone;

(S)-(2,7-Dimethyl-3-(3,4,5-trifluorophenyl)-2,4,5,7-tetrahydro-6H-pyrazolo[3,4-c]pyridin-6-yl)(2-methoxyquinolin-4-yl)methanone;

(S)-(2,7-Dimethyl-3-(3,4,5-trifluorophenyl)-2,4,5,7-tetrahydro-6H-pyrazolo[3,4-c]pyridin-6-yl)(8-fluoro-2-methylquinolin-4-yl)methanone;

(S)-(2,7-Dimethyl-3-(3,4,5-trifluorophenyl)-2,4,5,7-tetrahydro-6H-pyrazolo[3,4-c]pyridin-6-yl)(quinoxalin-6-yl)methanone;

(S)-(2,7-Dimethyl-3-(3,4,5-trifluorophenyl)-2,4,5,7-tetrahydro-6H-pyrazolo[3,4-c]pyridin-6-yl)(2-methylquinoxalin-6-yl)methanone;

(S)-(2,7-Dimethyl-3-(3,4,5-trifluorophenyl)-2,4,5,7-tetrahydro-6H-pyrazolo[3,4-c]pyridin-6-yl)(1,5-naphthyridin-2-yl)methanone;

(S)-(2,7-Dimethyl-3-(3,4,5-trifluorophenyl)-2,4,5,7-tetrahydro-6H-pyrazolo[3,4-c]pyridin-6-yl)(1,5-naphthyridin-3-yl)methanone;

(S)-(2,7-Dimethyl-3-(3,4,5-trifluorophenyl)-2,4,5,7-tetrahydro-6H-pyrazolo[3,4-c]pyridin-6-yl)(1,6-naphthyridin-8-yl)methanone;

(S)-(2,7-Dimethyl-3-(5-(trifluoromethyl)furan-2-yl)-2,4,5,7-tetrahydro-6H-pyrazolo[3,4-c]pyridin-6-yl)(quinoxalin-6-yl)methanone;

(S)-(2,7-Dimethyl-3-(5-(trifluoromethyl)pyridin-3-yl)-2,4,5,7-tetrahydro-6H-pyrazolo[3,4-c]pyridin-6-yl)(quinoxalin-6-yl)methanone;

(2,7-Dimethyl-3-(1-methyl-1H-indol-4-yl)-2,4,5,7-tetrahydro-6H-pyrazolo[3,4-c]pyridin-6-yl)(quinolin-6-yl)methanone;

(2,7-Dimethyl-3-(1-methyl-1H-indol-2-yl)-2,4,5,7-tetrahydro-6H-pyrazolo[3,4-c]pyridin-6-yl)(quinolin-6-yl)methanone;

(2,7-Dimethyl-3-(1-methyl-1H-indol-3-yl)-2,4,5,7-tetrahydro-6H-pyrazolo[3,4-c]pyridin-6-yl)(quinolin-6-yl)methanone;

(2,7-Dimethyl-3-(1-methyl-1H-indol-5-yl)-2,4,5,7-tetrahydro-6H-pyrazolo[3,4-c]pyridin-6-yl)(quinolin-6-yl)methanone; and (2,7-Dimethyl-3-(1-methyl-1H-indol-7-yl)-2,4,5,7-tetrahydro-6H-pyrazolo[3,4-c]pyridin-6-yl)(quinolin-6-yl)methanone;

(S)-(3-(3,5-Difluorophenyl)-2,7-dimethyl-5,7-dihydro-4H-pyrazolo[3,4-c]pyridin-6-yl]-[3-(2-fluoranylethoxy)-2-fluoro-phenyl]methanone;

[2-Chloro-3-(2-fluoranylethoxy)phenyl]-[(7S)-3-(3,5-difluorophenyl)-2,7-dimethyl-5,7-dihydro-4H-pyrazolo[3,4-c]pyridin-6-yl]methanone;

(S)-[3-(3,5-Difluorophenyl)-2,7-dimethyl-5,7-dihydro-4H-pyrazolo[3,4-c]pyridin-6-yl]-[3-(2-fluoranylethoxy)-5-fluoro-phenyl]methanone;

(3-Methoxyphenyl)-[(7S)-7-methyl-2,3-diphenyl-5,7-dihydro-4H-pyrazolo[3,4-c]pyridin-6-yl]methanone;

[(7S)-3-(3-Fluoro-5-methyl-phenyl)-2,7-dimethyl-5,7-dihydro-4H-pyrazolo[3,4-c]pyridin-6-yl]-(4-methoxyphenyl)methanone;

[(7S)-2,7-Dimethyl-3-(3,4,5-trifluorophenyl)-5,7-dihydro-4H-pyrazolo[3,4-c]pyridin-6-yl]-(2-methoxyphenyl)methanone;

[(7S)-2,7-Dimethyl-3-(3,4,5-trifluorophenyl)-5,7-dihydro-4H-pyrazolo[3,4-c]pyridin-6-yl]-(3-methoxyphenyl)methanone;

[(7S)-2,7-Dimethyl-3-(3,4,5-trifluorophenyl)-5,7-dihydro-4H-pyrazolo[3,4-c]pyridin-6-yl]-(4-methoxyphenyl)methanone;

[(7S)-2,7-Dimethyl-3-(3,4,5-trifluorophenyl)-5,7-dihydro-4H-pyrazolo[3,4-c]pyridin-6-yl]-[3-(trifluoromethoxy)phenyl]methanone;

[(7S)-2,7-Dimethyl-3-(3,4,5-trifluorophenyl)-5,7-dihydro-4H-pyrazolo[3,4-c]pyridin-6-yl]-[2-(trifluoromethoxy)phenyl]methanone;

[4-(Difluoromethoxy)phenyl]-[(7S)-2,7-dimethyl-3-(3,4,5-trifluorophenyl)-5,7-dihydro-4H-pyrazolo[3,4-c]pyridin-6-yl]methanone;

[(7S)-2,7-Dimethyl-3-(3,4,5-trifluorophenyl)-5,7-dihydro-4H-pyrazolo[3,4-c]pyridin-6-yl]-(2-fluoro-4-methoxy-phenyl)methanone;

3-[(7S)-2,7-Dimethyl-3-(3,4,5-trifluorophenyl)-5,7-dihydro-4H-pyrazolo[3,4-c] pyridine-6-carbonyl]-N-methyl-benzamide;

[(7S)-2,7-Dimethyl-3-(3,4,5-trifluorophenyl)-5,7-dihydro-4H-pyrazolo[3,4-c]pyridin-6-yl]-(4-imidazol-1-ylphenyl)methanone;

[(7S)-2,7-Dimethyl-3-(3,4,5-trifluorophenyl)-5,7-dihydro-4H-pyrazolo[3,4-c]pyridin-6-yl]-[4-(1H-pyrazol-4-yl)phenyl]methanone;

[(7S)-2,7-Dimethyl-3-(3,4,5-trifluorophenyl)-5,7-dihydro-4H-pyrazolo[3,4-c]pyridin-6-yl]-[4-(1H-pyrazol-5-yl)phenyl]methanone;

[(7S)-2,7-Dimethyl-3-(3,4,5-trifluorophenyl)-5,7-dihydro-4H-pyrazolo[3,4-c]pyridin-6-yl]-[3-(1H-pyrazol-3-yl)phenyl]methanone;
[(7S)-2,7-Dimethyl-3-(3,4,5-trifluorophenyl)-5,7-dihydro-4H-pyrazolo[3,4-c]pyridin-6-yl]-[4-methoxy-3-(1-methylpyrazol-3-yl)phenyl]methanone;
[(7S)-2,7-Dimethyl-3-(3,4,5-trifluorophenyl)-5,7-dihydro-4H-pyrazolo[3,4-c]pyridin-6-yl]-[3-(1H-pyrazol-4-yl)phenyl]methanone;
[(7S)-2,7-Dimethyl-3-(3,4,5-trifluorophenyl)-5,7-dihydro-4H-pyrazolo[3,4-c]pyridin-6-yl]-[3-(1-methylpyrazol-4-yl)phenyl]methanone;
[(7S)-2,7-Dimethyl-3-(3,4,5-trifluorophenyl)-5,7-dihydro-4H-pyrazolo[3,4-c]pyridin-6-yl]-[2-fluoro-5-(1-methylpyrazol-4-yl)phenyl]methanone;
[(7S)-2,7-Dimethyl-3-(3,4,5-trifluorophenyl)-5,7-dihydro-4H-pyrazolo[3,4-c]pyridin-6-yl]-[3-(4-fluoropyrazol-1-yl)phenyl]methanone;
[(7S)-2,7-Dimethyl-3-(3,4,5-trifluorophenyl)-5,7-dihydro-4H-pyrazolo[3,4-c]pyridin-6-yl]-[3-(3-methyl-1,2,4-triazol-1-yl)phenyl]methanone;
[(7S)-2,7-Dimethyl-3-(3,4,5-trifluorophenyl)-5,7-dihydro-4H-pyrazolo[3,4-c]pyridin-6-yl]-[3-fluoro-5-(1,2,4-triazol-1-yl)phenyl]methanone;
[(7S)-2,7-Dimethyl-3-(3,4,5-trifluorophenyl)-5,7-dihydro-4H-pyrazolo[3,4-c]pyridin-6-yl]-[3-methoxy-5-(1,2,4-triazol-1-yl)phenyl]methanone;
[(7S)-2,7-Dimethyl-3-(3,4,5-trifluorophenyl)-5,7-dihydro-4H-pyrazolo[3,4-c]pyridin-6-yl]-[2-(1,2,4-triazol-1-yl)phenyl]methanone;
[(7S)-2,7-Dimethyl-3-(3,4,5-trifluorophenyl)-5,7-dihydro-4H-pyrazolo[3,4-c]pyridin-6-yl]-[2-fluoro-6-(1,2,4-triazol-1-yl)phenyl]methanone;
[(7S)-2,7-Dimethyl-3-(3,4,5-trifluorophenyl)-5,7-dihydro-4H-pyrazolo[3,4-c]pyridin-6-yl]-[5-fluoro-2-(1,2,4-triazol-1-yl)phenyl]methanone;
[(7S)-2,7-Dimethyl-3-(3,4,5-trifluorophenyl)-5,7-dihydro-4H-pyrazolo[3,4-c]pyridin-6-yl]-[2-[3-(trifluoromethyl)-1,2,4-triazol-1-yl]phenyl]methanone;
[(7S)-2,7-Dimethyl-3-(3,4,5-trifluorophenyl)-5,7-dihydro-4H-pyrazolo[3,4-c]pyridin-6-yl]-[3-(triazol-2-yl)phenyl]methanone;
[(7S)-2,7-Dimethyl-3-(3,4,5-trifluorophenyl)-5,7-dihydro-4H-pyrazolo[3,4-c]pyridin-6-yl]-[3-fluoro-5-(triazol-2-yl)phenyl]methanone;
[(7S)-2,7-Dimethyl-3-(3,4,5-trifluorophenyl)-5,7-dihydro-4H-pyrazolo[3,4-c]pyridin-6-yl]-[2-fluoro-5-(triazol-2-yl)phenyl]methanone;
[(7S)-2,7-Dimethyl-3-(3,4,5-trifluorophenyl)-5,7-dihydro-4H-pyrazolo[3,4-c]pyridin-6-yl]-[3-methyl-5-(triazol-2-yl)phenyl]methanone;
[(7S)-2,7-Dimethyl-3-(3,4,5-trifluorophenyl)-5,7-dihydro-4H-pyrazolo[3,4-c]pyridin-6-yl]-[3-(triazol-2-yl)-5-(trifluoromethyl)phenyl]methanone;
[(7S)-2,7-Dimethyl-3-(3,4,5-trifluorophenyl)-5,7-dihydro-4H-pyrazolo[3,4-c]pyridin-6-yl]-[2-fluoro-6-(triazol-2-yl)phenyl]methanone;
[(7S)-2,7-Dimethyl-3-(3,4,5-trifluorophenyl)-5,7-dihydro-4H-pyrazolo[3,4-c]pyridin-6-yl]-[5-methoxy-2-(triazol-2-yl)phenyl]methanone;
[(7S)-2,7-Dimethyl-3-(3,4,5-trifluorophenyl)-5,7-dihydro-4H-pyrazolo[3,4-c]pyridin-6-yl]-[3-(1,2,4-triazol-4-yl)phenyl]methanone;
[(7S)-2,7-Dimethyl-3-(3,4,5-trifluorophenyl)-5,7-dihydro-4H-pyrazolo[3,4-c]pyridin-6-yl]-[4-fluoro-3-(1,2,4-triazol-4-yl)phenyl]methanone;
[(7S)-2,7-Dimethyl-3-(3,4,5-trifluorophenyl)-5,7-dihydro-4H-pyrazolo[3,4-c]pyridin-6-yl]-[3-fluoro-5-(1,2,4-triazol-4-yl)phenyl]methanone;
[(7S)-2,7-Dimethyl-3-(3,4,5-trifluorophenyl)-5,7-dihydro-4H-pyrazolo[3,4-c]pyridin-6-yl]-[3-methyl-5-(1,2,4-triazol-4-yl)phenyl]methanone;
[(7S)-2,7-Dimethyl-3-(3,4,5-trifluorophenyl)-5,7-dihydro-4H-pyrazolo[3,4-c]pyridin-6-yl]-[4-methyl-3-(1,2,4-triazol-4-yl)phenyl]methanone;
[(7S)-2,7-Dimethyl-3-(3,4,5-trifluorophenyl)-5,7-dihydro-4H-pyrazolo[3,4-c]pyridin-6-yl]-[3-(1,2,4-triazol-4-yl)-4-(trifluoromethyl)phenyl]methanone;
[(7S)-2,7-Dimethyl-3-(3,4,5-trifluorophenyl)-5,7-dihydro-4H-pyrazolo[3,4-c]pyridin-6-yl]-[3-(1,2,4-triazol-4-yl)-5-(trifluoromethyl)phenyl]methanone;
[(7S)-2,7-Dimethyl-3-(3,4,5-trifluorophenyl)-5,7-dihydro-4H-pyrazolo[3,4-c]pyridin-6-yl]-[4-methoxy-3-(1,2,4-triazol-4-yl)phenyl]methanone;
[(7S)-2,7-Dimethyl-3-(3,4,5-trifluorophenyl)-5,7-dihydro-4H-pyrazolo[3,4-c]pyridin-6-yl]-[3-methoxy-5-(1,2,4-triazol-4-yl)phenyl]methanone;
[(7S)-2,7-Dimethyl-3-(3,4,5-trifluorophenyl)-5,7-dihydro-4H-pyrazolo[3,4-c]pyridin-6-yl]-[2-(1,2,4-triazol-4-yl)phenyl]methanone;
[(7S)-2,7-Dimethyl-3-(3,4,5-trifluorophenyl)-5,7-dihydro-4H-pyrazolo[3,4-c]pyridin-6-yl]-(6-methoxy-3-pyridyl)methanone;
[(7S)-2,7-Dimethyl-3-(3,4,5-trifluorophenyl)-5,7-dihydro-4H-pyrazolo[3,4-c]pyridin-6-yl]-(5-methoxy-2-pyridyl)methanone;
[(7S)-2,7-Dimethyl-3-(3,4,5-trifluorophenyl)-5,7-dihydro-4H-pyrazolo[3,4-c]pyridin-6-yl]-(6-methoxy-3-methyl-2-pyridyl)methanone;
[(7S)-2,7-Dimethyl-3-(3,4,5-trifluorophenyl)-5,7-dihydro-4H-pyrazolo[3,4-c]pyridin-6-yl]-(3-methoxy-2-pyridyl)methanone;
[(7S)-2,7-Dimethyl-3-(3,4,5-trifluorophenyl)-5,7-dihydro-4H-pyrazolo[3,4-c]pyridin-6-yl]-[5-(methoxymethyl)-3-pyridyl]methanone;
[(7S)-2,7-Dimethyl-3-(3,4,5-trifluorophenyl)-5,7-dihydro-4H-pyrazolo[3,4-c]pyridin-6-yl]-(5-isopropoxy-3-pyridyl)methanone;
[(7S)-2,7-Dimethyl-3-(3,4,5-trifluorophenyl)-5,7-dihydro-4H-pyrazolo[3,4-c]pyridin-6-yl]-(6-methoxy-2-methyl-3-pyridyl)methanone;
[(7S)-2,7-Dimethyl-3-(3,4,5-trifluorophenyl)-5,7-dihydro-4H-pyrazolo[3,4-c]pyridin-6-yl]-(4-methoxy-3-methyl-2-pyridyl)methanone;
[(7S)-2,7-Dimethyl-3-(3,4,5-trifluorophenyl)-5,7-dihydro-4H-pyrazolo[3,4-c]pyridin-6-yl]-(5-methoxy-2-methyl-3-pyridyl)methanone;
[(7S)-2,7-Dimethyl-3-(3,4,5-trifluorophenyl)-5,7-dihydro-4H-pyrazolo[3,4-c]pyridin-6-yl]-(4-methoxy-2-pyridyl)methanone;
[(7S)-2,7-Dimethyl-3-(3,4,5-trifluorophenyl)-5,7-dihydro-4H-pyrazolo[3,4-c]pyridin-6-yl]-(5-methoxy-6-methyl-3-pyridyl)methanone;
[(7S)-2,7-Dimethyl-3-(3,4,5-trifluorophenyl)-5,7-dihydro-4H-pyrazolo[3,4-c]pyridin-6-yl]-(3-methoxy-4-pyridyl)methanone;
[(7S)-2,7-Dimethyl-3-(3,4,5-trifluorophenyl)-5,7-dihydro-4H-pyrazolo[3,4-c]pyridin-6-yl]-(2-methoxy-4-pyridyl)methanone;
[(7S)-2,7-Dimethyl-3-(3,4,5-trifluorophenyl)-5,7-dihydro-4H-pyrazolo[3,4-c]pyridin-6-yl]-(5-methoxy-4-methyl-3-pyridyl)methanone;

[(7S)-2,7-Dimethyl-3-(3,4,5-trifluorophenyl)-5,7-dihydro-4H-pyrazolo[3,4-c]pyridin-6-yl]-(2-methoxy-3-methyl-4-pyridyl)methanone;
[(7S)-2,7-Dimethyl-3-(3,4,5-trifluorophenyl)-5,7-dihydro-4H-pyrazolo[3,4-c]pyridin-6-yl]-(3-fluoro-2-methoxy-4-pyridyl)methanone;
(3-Chloro-2-methoxy-4-pyridyl)-[(7S)-2,7-dimethyl-3-(3,4,5-trifluorophenyl)-5,7-dihydro-4H-pyrazolo[3,4-c]pyridin-6-yl]methanone;
(3-Chloro-4-methoxy-2-pyridyl)-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-(5-pyrazol-1-yl-3-pyridyl)methanone;
[(7S)-2,7-Dimethyl-3-(3,4,5-trifluorophenyl)-5,7-dihydro-4H-pyrazolo[3,4-c]pyridin-6-yl]-[6-methyl-3-(triazol-2-yl)-2-pyridyl]methanone;
[(7S)-2,7-Dimethyl-3-(3,4,5-trifluorophenyl)-5,7-dihydro-4H-pyrazolo[3,4-c]pyridin-6-yl]-(6-pyrazol-1-yl-2-pyridyl)methanone;
[(7S)-2,7-Dimethyl-3-(3,4,5-trifluorophenyl)-5,7-dihydro-4H-pyrazolo[3,4-c]pyridin-6-yl]-(5-methyl-1-phenyl-1,2,4-triazol-3-yl)methanone;
[(7S)-2,7-Dimethyl-3-(3,4,5-trifluorophenyl)-5,7-dihydro-4H-pyrazolo[3,4-c]pyridin-6-yl]-[1-(4-fluorophenyl)-5-methyl-1,2,4-triazol-3-yl]methanone;
[(7S)-2,7-Dimethyl-3-(3,4,5-trifluorophenyl)-5,7-dihydro-4H-pyrazolo[3,4-c]pyridin-6-yl]-[1-(2-pyridyl)-1,2,4-triazol-3-yl]methanone;
[(7S)-2,7-Dimethyl-3-(3,4,5-trifluorophenyl)-5,7-dihydro-4H-pyrazolo[3,4-c]pyridin-6-yl]-[1-(3-fluoro-2-pyridyl)-1,2,4-triazol-3-yl]methanone;
[(7S)-2,7-Dimethyl-3-(3,4,5-trifluorophenyl)-5,7-dihydro-4H-pyrazolo[3,4-c]pyridin-6-yl]-[5-(2-pyridyl)-2-thienyl]methanone;
[(7S)-2,7-Dimethyl-3-(3,4,5-trifluorophenyl)-5,7-dihydro-4H-pyrazolo[3,4-c]pyridin-6-yl]-(5-methoxypyrazin-2-yl)methanone;
(1,5-Dimethylpyrazol-4-yl)-[(7S)-3-(3-fluoro-5-methylphenyl)-2,7-dimethyl-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-(5-isopropyl-1-methyl-pyrazol-4-yl)methanone;
[(7S)-2,7-Dimethyl-3-(3,4,5-trifluorophenyl)-5,7-dihydro-4H-pyrazolo[3,4-c]pyridin-6-yl]-[1-(trifluoromethyl)pyrazol-4-yl]methanone;
[5-(Difluoromethyl)-1-methyl-pyrazol-4-yl]-[(7S)-2,7-dimethyl-3-(3,4,5-trifluorophenyl)-5,7-dihydro-4H-pyrazolo[3,4-c]pyridin-6-yl]methanone;
(1-Cyclopropylpyrazol-4-yl)-[(7S)-2,7-dimethyl-3-(3,4,5-trifluorophenyl)-5,7-dihydro-4H-pyrazolo[3,4-c]pyridin-6-yl]methanone;
[1-Cyclopropyl-3-(trifluoromethyl)pyrazol-4-yl]-[(7S)-2,7-dimethyl-3-(3,4,5-trifluorophenyl)-5,7-dihydro-4H-pyrazolo[3,4-c]pyridin-6-yl]methanone;
(5-Cyclobutyl-1-methyl-pyrazol-4-yl)-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-[1-methyl-5-(1-methylcyclopropyl)pyrazol-4-yl]methanone;
[(7S)-2,7-Dimethyl-3-(3,4,5-trifluorophenyl)-5,7-dihydro-4H-pyrazolo[3,4-c]pyridin-6-yl]-[5-(1-fluorocyclopropyl)-1-methyl-pyrazol-4-yl]methanone;
(5-(2,2-Difluorocyclopropyl)-1-methyl-1H-pyrazol-4-yl)((S)-2,7-dimethyl-3-(3,4,5-trifluorophenyl)-4,5-dihydro-2H-pyrazolo[3,4-c]pyridin-6-yl)methanone;
(5-((R-2,2-difluorocyclopropyl)-1-methyl-1H-pyrazol-4-yl)((S)-2,7-dimethyl-3-(3,4,5-trifluorophenyl)-2,4,5,7-tetrahydro-6H-pyrazolo[3,4-c]pyridin-6-yl)methanone;
(5-((S*i)-2,2-Difluorocyclopropyl)-1-methyl-1H-pyrazol-4-yl)((S)-2,7-dimethyl-3-(3,4,5-trifluorophenyl)-2,4,5,7-tetrahydro-6H-pyrazolo[3,4-c]pyridin-6-yl)methanone;
((S)-2,7-Dimethyl-3-(3,4,5-trifluorophenyl)-2,4,5,7-tetrahydro-6H-pyrazolo[3,4-c]pyridin-6-yl)(cis-5-(2-fluorocyclopropyl)-1-methyl-1H-pyrazol-4-yl)methanone;
((S)-2,7-Dimethyl-3-(3,4,5-trifluorophenyl)-2,4,5,7-tetrahydro-6H-pyrazolo[3,4-c]pyridin-6-yl)(trans-5-(2-fluorocyclopropyl)-1-methyl-1H-pyrazol-4-yl)methanone;
((S)-2,7-Dimethyl-3-(3,4,5-trifluorophenyl)-2,4,5,7-tetrahydro-6H-pyrazolo[3,4-c]pyridin-6-yl)(1-methyl-cis-5-(2-methylcyclopropyl)-1H-pyrazol-4-yl)methanone;
(S)-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone;
(1,3-Dimethylpyrazol-4-yl)-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-(1,3,5-trimethylpyrazol-4-yl)methanone;
(1,5-Dimethylpyrazol-4-yl)-[(7S)-2,7-dimethyl-3-(3,4,5-trifluorophenyl)-5,7-dihydro-4H-pyrazolo[3,4-c]pyridin-6-yl]methanone;
[1-Cyclopropyl-5-(trifluoromethyl)pyrazol-4-yl]-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-[1-methyl-3-(1-methylcyclopropyl)pyrazol-4-yl]methanone;
[(7S)-2,7-Dimethyl-3-(3,4,5-trifluorophenyl)-5,7-dihydro-4H-pyrazolo[3,4-c]pyridin-6-yl]-[3-(1-fluorocyclopropyl)-1-methyl-pyrazol-4-yl]methanone;
(R)-(5-cyclopropyl-1-methyl-1H-pyrazol-4-yl)(7-methyl-2,3-diphenyl-2,4,5,7-tetrahydro-6H-pyrazolo[3,4-c] pyridin-6-yl) methanone;
(S)-(5-cyclopropyl-1-methyl-1H-pyrazol-4-yl)(7-methyl-2,3-diphenyl-2,4,5,7-tetrahydro-6H-pyrazolo[3,4-c] pyridin-6-yl)methanone;
(1,2-Dimethylpyrrol-3-yl)-[(7S)-2,7-dimethyl-3-(3,4,5-trifluorophenyl)-5,7-dihydro-4H-pyrazolo[3,4-c]pyridin-6-yl]methanone;
(4,5-Dimethylisoxazol-3-yl)-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-(5-fluoro-1H-indol-6-yl)methanone;
[(7S)-2,7-Dimethyl-3-(3,4,5-trifluorophenyl)-5,7-dihydro-4H-pyrazolo[3,4-c]pyridin-6-yl]-(7-fluoro-1H-indol-4-yl)methanone;
[(7S)-2,7-Dimethyl-3-(3,4,5-trifluorophenyl)-5,7-dihydro-4H-pyrazolo[3,4-c]pyridin-6-yl]-(5-fluoro-1H-indol-3-yl)methanone;
[(7S)-2,7-Dimethyl-3-(3,4,5-trifluorophenyl)-5,7-dihydro-4H-pyrazolo[3,4-c]pyridin-6-yl]-(5-fluoro-1-methyl-indol-3-yl)methanone;

[(7S)-2,7-Dimethyl-3-(3,4,5-trifluorophenyl)-5,7-dihydro-4H-pyrazolo[3,4-c]pyridin-6-yl]-(4-fluoro-1H-indol-3-yl)methanone;
[(7S)-2,7-Dimethyl-3-(3,4,5-trifluorophenyl)-5,7-dihydro-4H-pyrazolo[3,4-c]pyridin-6-yl]-(6-fluoro-1H-indol-3-yl)methanone;
[(7S)-2,7-Dimethyl-3-(3,4,5-trifluorophenyl)-5,7-dihydro-4H-pyrazolo[3,4-c]pyridin-6-yl]-(7-fluoro-1H-indol-3-yl)methanone;
[(7S)-2,7-Dimethyl-3-(3,4,5-trifluorophenyl)-5,7-dihydro-4H-pyrazolo[3,4-c]pyridin-6-yl]-(6-methyl-1H-indol-3-yl)methanone;
[(7S)-2,7-Dimethyl-3-(3,4,5-trifluorophenyl)-5,7-dihydro-4H-pyrazolo[3,4-c]pyridin-6-yl]-(1H-indazol-3-yl)methanone;
[(7S)-2,7-Dimethyl-3-(3,4,5-trifluorophenyl)-5,7-dihydro-4H-pyrazolo[3,4-c]pyridin-6-yl]-(4-fluoro-1H-indazol-3-yl)methanone;
[(7S)-2,7-Dimethyl-3-(3,4,5-trifluorophenyl)-5,7-dihydro-4H-pyrazolo[3,4-c]pyridin-6-yl]-(6-fluoro-1H-indazol-3-yl)methanone;
[(7S)-2,7-Dimethyl-3-(3,4,5-trifluorophenyl)-5,7-dihydro-4H-pyrazolo[3,4-c]pyridin-6-yl]-(5-fluoro-1H-indazol-3-yl)methanone;
[(7S)-2,7-Dimethyl-3-(3,4,5-trifluorophenyl)-5,7-dihydro-4H-pyrazolo[3,4-c]pyridin-6-yl]-(2-methylindazol-3-yl)methanone;
[(7S)-2,7-Dimethyl-3-(3,4,5-trifluorophenyl)-5,7-dihydro-4H-pyrazolo[3,4-c]pyridin-6-yl]-(1-methylbenzimidazol-4-yl)methanone;
1H-Benzotriazol-4-yl-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-(1H-pyrrolo[2,3-b]pyridin-5-yl)methanone;
[(7S)-2,7-Dimethyl-3-(3,4,5-trifluorophenyl)-5,7-dihydro-4H-pyrazolo[3,4-c]pyridin-6-yl]-(5-fluoro-1H-pyrrolo[2,3-b]pyridin-4-yl)methanone;
[(7S)-2,7-Dimethyl-3-(3,4,5-trifluorophenyl)-5,7-dihydro-4H-pyrazolo[3,4-c]pyridin-6-yl]-(5-fluoro-1-methyl-pyrrolo[2,3-b]pyridin-4-yl)methanone;
[(7S)-2,7-Dimethyl-3-(3,4,5-trifluorophenyl)-5,7-dihydro-4H-pyrazolo[3,4-c]pyridin-6-yl]-[5-(trifluoromethyl)-1H-pyrrolo[2,3-b]pyridin-4-yl] methanone;
[(7S)-3-(3,5-Difluorophenyl)-2,7-dimethyl-5,7-dihydro-4H-pyrazolo[3,4-c]pyridin-6-yl]-[1-(2-fluoranylethyl)pyrrolo[2,3-b]pyridin-4-yl]methanone;
[(7S)-2,7-Dimethyl-3-(3,4,5-trifluorophenyl)-5,7-dihydro-4H-pyrazolo[3,4-c]pyridin-6-yl]-(1H-pyrrolo[2,3-b]pyridin-3-yl)methanone;
[(7S)-2,7-Dimethyl-3-(3,4,5-trifluorophenyl)-5,7-dihydro-4H-pyrazolo[3,4-c]pyridin-6-yl]-(5-fluoro-1H-pyrrolo[2,3-b]pyridin-3-yl)methanone;
[(7S)-2,7-Dimethyl-3-(3,4,5-trifluorophenyl)-5,7-dihydro-4H-pyrazolo[3,4-c]pyridin-6-yl]-(2-methyl-1H-pyrrolo[2,3-b]pyridin-3-yl)methanone;
[(7S)-2,7-Dimethyl-3-(3,4,5-trifluorophenyl)-5,7-dihydro-4H-pyrazolo[3,4-c]pyridin-6-yl]-(1H-pyrrolo[2,3-c]pyridin-7-yl)methanone;
[(7S)-2,7-Dimethyl-3-(3,4,5-trifluorophenyl)-5,7-dihydro-4H-pyrazolo[3,4-c]pyridin-6-yl]-(3-fluoropyrazolo[1,5-a]pyridin-4-yl)methanone;
[(7S)-2,7-Dimethyl-3-(3,4,5-trifluorophenyl)-5,7-dihydro-4H-pyrazolo[3,4-c]pyridin-6-yl]-(3-fluoropyrazolo[1,5-a]pyridin-5-yl)methanone;
(3-Bromopyrazolo[1,5-a]pyridin-4-yl)-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-(3-methylpyrazolo[1,5-a]pyridin-4-yl)methanone;
[(7S)-2,7-Dimethyl-3-(3,4,5-trifluorophenyl)-5,7-dihydro-4H-pyrazolo[3,4-c]pyridin-6-yl]-pyrazolo[1,5-a]pyridin-3-yl-methanone;
[(7S)-2,7-Dimethyl-3-(3,4,5-trifluorophenyl)-5,7-dihydro-4H-pyrazolo[3,4-c]pyridin-6-yl]-(2-methylpyrazolo[1,5-a]pyridin-3-yl)methanone;
[(7S)-2,7-Dimethyl-3-(3,4,5-trifluorophenyl)-5,7-dihydro-4H-pyrazolo[3,4-c]pyridin-6-yl]-(5-methylpyrazolo[1,5-a]pyridin-3-yl)methanone;
[(7S)-2,7-Dimethyl-3-(3,4,5-trifluorophenyl)-5,7-dihydro-4H-pyrazolo[3,4-c]pyridin-6-yl]-(6-fluoropyrazolo[1,5-a]pyridin-3-yl)methanone;
(2-Cyclopropyl-7-methyl-pyrazolo[1,5-a]pyridin-3-yl)-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c] pyridin-6-yl]-(7-methylpyrazolo[1,5-a] pyridin-3-yl)methanone;
[(7S)-2,7-Dimethyl-3-(3,4,5-trifluorophenyl)-5,7-dihydro-4H-pyrazolo[3,4-c]pyridin-6-yl]-(7-methoxypyrazolo[1,5-a]pyridin-3-yl)methanone;
[(7S)-2,7-Dimethyl-3-(3,4,5-trifluorophenyl)-5,7-dihydro-4H-pyrazolo[3,4-c]pyridin-6-yl]-(6-methoxypyrazolo[1,5-a]pyridin-3-yl)methanone;
[(7S)-2,7-Dimethyl-3-(3,4,5-trifluorophenyl)-5,7-dihydro-4H-pyrazolo[3,4-c]pyridin-6-yl]-(5-methoxypyrazolo[1,5-a]pyridin-3-yl)methanone;
[(7S)-2,7-Dimethyl-3-(3,4,5-trifluorophenyl)-5,7-dihydro-4H-pyrazolo[3,4-c] pyridin-6-yl]-(4-methoxypyrazolo[1,5-a]pyridin-3-yl)methanone;
[(7S)-2,7-Dimethyl-3-(3,4,5-trifluorophenyl)-5,7-dihydro-4H-pyrazolo[3,4-c]pyridin-6-yl]-imidazo[1,2-a]pyridin-6-yl-methanone;
[(7S)-2,7-Dimethyl-3-(3,4,5-trifluorophenyl)-5,7-dihydro-4H-pyrazolo[3,4-c]pyridin-6-yl]-imidazo[1,2-a]pyridin-8-yl-methanone;
[(7S)-2,7-Dimethyl-3-(3,4,5-trifluorophenyl)-5,7-dihydro-4H-pyrazolo[3,4-c]pyridin-6-yl]-(7-fluoroimidazo[1,2-a]pyridin-3-yl)methanone;
[(7S)-2,7-Dimethyl-3-(3,4,5-trifluorophenyl)-5,7-dihydro-4H-pyrazolo[3,4-c] pyridin-6-yl]-(2-methylimidazo[1,2-a]pyridin-5-yl)methanone;
[(7S)-3-(3-Chloro-5-methoxy-phenyl)-2,7-dimethyl-5,7-dihydro-4H-pyrazolo[3,4-c] pyridin-6-yl]-(2-methylimidazo[1,2-a] pyridin-3-yl) methanone;
[(7S)-3-(3-Fluoro-5-methyl-phenyl)-2,7-dimethyl-5,7-dihydro-4H-pyrazolo[3,4-c] pyridin-6-yl]-(2-methylimidazo[1,2-a] pyridin-3-yl)methanone;
[(7S)-2,7-Dimethyl-3-(3,4,5-trifluorophenyl)-5,7-dihydro-4H-pyrazolo[3,4-c]pyridin-6-yl]-(2-methylimidazo[1,2-a]pyridin-3-yl)methanone;
[(7S)-2,7-Dimethyl-3-(3,4,5-trifluorophenyl)-5,7-dihydro-4H-pyrazolo[3,4-c]pyridin-6-yl]-(3-methylimidazo[1,2-a]pyridin-2-yl)methanone;
[(7S)-2,7-Dimethyl-3-(3,4,5-trifluorophenyl)-5,7-dihydro-4H-pyrazolo[3,4-c]pyridin-6-yl]-(7-methylimidazo[1,2-a]pyridin-3-yl)methanone;
[(7S)-2,7-Dimethyl-3-(3,4,5-trifluorophenyl)-5,7-dihydro-4H-pyrazolo[3,4-c]pyridin-6-yl]-(6-methylimidazo[1,2-a]pyridin-3-yl)methanone;

[(7S)-2,7-Dimethyl-3-(3,4,5-trifluorophenyl)-5,7-dihydro-4H-pyrazolo[3,4-c]pyridin-6-yl]-(5-methylimidazo[1,2-a]pyridin-3-yl)methanone;

[(7S)-2,7-Dimethyl-3-(3,4,5-trifluorophenyl)-5,7-dihydro-4H-pyrazolo[3,4-c]pyridin-6-yl]-(7-fluoro-2-methyl-imidazo[1,2-a]pyridin-3-yl)methanone;

(2,8-Dimethylimidazo[1,2-a] pyridin-3-yl)-[(7S)-2,7-dimethyl-3-(3,4,5-trifluorophenyl)-5,7-dihydro-4H-pyrazolo[3,4-c] pyridin-6-yl]methanone;

(2,7-Dimethylimidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone;

(2,6-Dimethylimidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone;

[(7S)-3-(3-Chloro-5-methoxy-phenyl)-2,7-dimethyl-5,7-dihydro-4H-pyrazolo[3,4-c]pyridin-6-yl]-(6-fluoro-2-methyl-imidazo[1,2-a]pyridin-3-yl)methanone;

[(7S)-2,7-Dimethyl-3-(3,4,5-trifluorophenyl)-5,7-dihydro-4H-pyrazolo[3,4-c]pyridin-6-yl]-(6-fluoro-2-methyl-imidazo[1,2-a]pyridin-3-yl)methanone;

[(7S)-2,7-Dimethyl-3-(3,4,5-trifluorophenyl)-5,7-dihydro-4H-pyrazolo[3,4-c]pyridin-6-yl]-(6-fluoro-2,8-dimethyl-imidazo[1,2-a]pyridin-3-yl)methanone;

[(7S)-2,7-Dimethyl-3-(3,4,5-trifluorophenyl)-5,7-dihydro-4H-pyrazolo[3,4-c]pyridin-6-yl]-(6-fluoro-2,7-dimethyl-imidazo[1,2-a]pyridin-3-yl)methanone;

(6,8-Difluoro-2-methyl-imidazo[1,2-a]pyridin-3-yl)-[(7S)-2,7-dimethyl-3-(3,4,5-trifluorophenyl)-5,7-dihydro-4H-pyrazolo[3,4-c]pyridin-6-yl]methanone;

[(7S)-2,7-Dimethyl-3-(3,4,5-trifluorophenyl)-5,7-dihydro-4H-pyrazolo[3,4-c]pyridin-6-yl]-(6-methoxy-2-methyl-imidazo[1,2-a]pyridin-3-yl)methanone;

[2-(Difluoromethyl)imidazo[1,2-a]pyridin-3-yl]-[(7S)-2,7-dimethyl-3-(3,4,5-trifluorophenyl)-5,7-dihydro-4H-pyrazolo[3,4-c]pyridin-6-yl]methanone;

[(7S)-2,7-Dimethyl-3-(3,4,5-trifluorophenyl)-5,7-dihydro-4H-pyrazolo[3,4-c] pyridin-6-yl]-[2-(trifluoromethyl) imidazo[1,2-a]pyridin-3-yl]methanone;

[(7S)-2,7-Dimethyl-3-(3,4,5-trifluorophenyl)-5,7-dihydro-4H-pyrazolo[3,4-c]pyridin-6-yl]-[5-methyl-2-(trifluoromethyl)imidazo[1,2-a]pyridin-3-yl]methanone;

[(7S)-2,7-Dimethyl-3-(3,4,5-trifluorophenyl)-5,7-dihydro-4H-pyrazolo[3,4-c] pyridin-6-yl]-pyrrolo[1,2-a] pyrazin-1-yl-methanone;

[(7S)-2,7-Dimethyl-3-(3,4,5-trifluorophenyl)-5,7-dihydro-4H-pyrazolo[3,4-c] pyridin-6-yl]-pyrrolo[1,2-a] pyrazin-8-yl-methanone;

(2,4-Dimethylpyrrolo[1,2-a] pyrimidin-8-yl)-[(7S)-2,7-dimethyl-3-(3,4,5-trifluorophenyl)-5,7-dihydro-4H-pyrazolo[3,4-c] pyridin-6-yl] methanone;

[(7S)-2,7-Dimethyl-3-(3,4,5-trifluorophenyl)-5,7-dihydro-4H-pyrazolo[3,4-c]pyridin-6-yl]-(3-methylimidazo[1,5-a]pyridin-6-yl)methanone;

[(7S)-2,7-Dimethyl-3-(3,4,5-trifluorophenyl)-5,7-dihydro-4H-pyrazolo[3,4-c] pyridin-6-yl]-(7-methylimidazo[1,5-a]pyridin-1-yl)methanone;

[(7S)-2,7-Dimethyl-3-(3,4,5-trifluorophenyl)-5,7-dihydro-4H-pyrazolo[3,4-c]pyridin-6-yl]-imidazo[1,5-a]pyridin-1-yl-methanone;

(3-Cyclopropylimidazo[1,5-a]pyridin-1-yl)-[(7S)-2,7-dimethyl-3-(3,4,5-trifluorophenyl)-5,7-dihydro-4H-pyrazolo[3,4-c]pyridin-6-yl]methanone;

[(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-4-yl)methanone;

[(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-5-yl)methanone;

(1,6-Dimethylpyrazolo[3,4-b]pyridin-4-yl)-[(7S)-2,7-dimethyl-3-(3,4,5-trifluorophenyl)-5,7-dihydro-4H-pyrazolo[3,4-c]pyridin-6-yl]methanone;

(1,3-Dimethylpyrazolo[3,4-b]pyridin-4-yl)-[(7S)-2,7-dimethyl-3-(3,4,5-trifluorophenyl)-5,7-dihydro-4H-pyrazolo[3,4-c]pyridin-6-yl]methanone;

[(7S)-2,7-Dimethyl-3-(3,4,5-trifluorophenyl)-5,7-dihydro-4H-pyrazolo[3,4-c]pyridin-6-yl]-(1H-pyrazolo[3,4-b]pyridin-3-yl)methanone;

[(7S)-2,7-Dimethyl-3-(3,4,5-trifluorophenyl)-5,7-dihydro-4H-pyrazolo[3,4-c]pyridin-6-yl]-(1-methylpyrazolo[3,4-b]pyridin-3-yl)methanone;

[(7S)-2,7-Dimethyl-3-(3,4,5-trifluorophenyl)-5,7-dihydro-4H-pyrazolo[3,4-c]pyridin-6-yl]-(5-fluoro-1H-pyrazolo[3,4-b]pyridin-3-yl)methanone;

[(7S)-2,7-Dimethyl-3-(3,4,5-trifluorophenyl)-5,7-dihydro-4H-pyrazolo[3,4-c]pyridin-6-yl]-(2-methylpyrazolo[3,4-c]pyridin-7-yl)methanone;

[(7S)-2,7-Dimethyl-3-(3,4,5-trifluorophenyl)-5,7-dihydro-4H-pyrazolo[3,4-c]pyridin-6-yl]-(1H-pyrazolo[3,4-c]pyridin-3-yl)methanone;

[(7S)-2,7-Dimethyl-3-(3,4,5-trifluorophenyl)-5,7-dihydro-4H-pyrazolo[3,4-c]pyridin-6-yl]-(1-methylpyrazolo[3,4-c]pyridin-3-yl)methanone;

[(7S)-2,7-Dimethyl-3-(3,4,5-trifluorophenyl)-5,7-dihydro-4H-pyrazolo[3,4-c]pyridin-6-yl]-(1H-pyrazolo[3,4-c]pyridin-7-yl)methanone;

[(7S)-2,7-Dimethyl-3-(3,4,5-trifluorophenyl)-5,7-dihydro-4H-pyrazolo[3,4-c]pyridin-6-yl]-(1-methylpyrazolo[3,4-c]pyridin-7-yl)methanone;

[(7S)-2,7-Dimethyl-3-(3,4,5-trifluorophenyl)-5,7-dihydro-4H-pyrazolo[3,4-c]pyridin-6-yl]-(1H-pyrazolo[4,3-c]pyridin-7-yl)methanone;

[(7S)-2,7-Dimethyl-3-(3,4,5-trifluorophenyl)-5,7-dihydro-4H-pyrazolo[3,4-c]pyridin-6-yl]-(1H-pyrazolo[4,3-c]pyridin-3-yl)methanone;

[(7S)-2,7-Dimethyl-3-(3,4,5-trifluorophenyl)-5,7-dihydro-4H-pyrazolo[3,4-c] pyridin-6-yl]-(1H-pyrazolo[4,3-b]pyridin-3-yl)methanone;

[(7S)-2,7-Dimethyl-3-(3,4,5-trifluorophenyl)-5,7-dihydro-4H-pyrazolo[3,4-c]pyridin-6-yl]-([1,2,4]triazolo[4,3-a]pyridin-3-yl)methanone;

[(7S)-2,7-Dimethyl-3-(3,4,5-trifluorophenyl)-5,7-dihydro-4H-pyrazolo[3,4-c]pyridin-6-yl]-([1,2,4]triazolo[4,3-a]pyridin-5-yl)methanone;

[(7S)-2,7-Dimethyl-3-(3,4,5-trifluorophenyl)-5,7-dihydro-4H-pyrazolo[3,4-c]pyridin-6-yl]-([1,2,4]triazolo[4,3-a]pyridin-6-yl)methanone;

[3-(Difluoromethyl)-[1,2,4]triazolo[4,3-a]pyridin-6-yl]-[(7S)-2,7-dimethyl-3-(3,4,5-trifluorophenyl)-5,7-dihydro-4H-pyrazolo[3,4-c]pyridin-6-yl]methanone;

[(7S)-2,7-Dimethyl-3-(3,4,5-trifluorophenyl)-5,7-dihydro-4H-pyrazolo[3,4-c]pyridin-6-yl]-(triazolo[1,5-a]pyridin-3-yl)methanone;

[(7S)-2,7-Dimethyl-3-(3,4,5-trifluorophenyl)-5,7-dihydro-4H-pyrazolo[3,4-c] pyridin-6-yl]-(2-methylpyrazolo[1,5-b] pyridazin-3-yl) methanone;

[(7S)-2,7-Dimethyl-3-(3,4,5-trifluorophenyl)-5,7-dihydro-4H-pyrazolo[3,4-c] pyridin-6-yl]-(5-methylpyrazolo[1,5-b] pyridazin-3-yl) methanone;

(2-Cyclopropyl-4-methyl-pyrazolo[1,5-b]pyridazin-3-yl)-[(7S)-2,7-dimethyl-3-(3,4,5-trifluorophenyl)-5,7-dihydro-4H-pyrazolo[3,4-c]pyridin-6-yl]methanone;

(2-Cyclopropyl-5-methyl-pyrazolo[1,5-b]pyridazin-3-yl)-[(7S)-2,7-dimethyl-3-(3,4,5-trifluorophenyl)-5,7-dihydro-4H-pyrazolo[3,4-c]pyridin-6-yl]methanone;

(2,4-Dimethylpyrazolo[1,5-a] pyrazin-3-yl)-[(7S)-2,7-dimethyl-3-(3,4,5-trifluorophenyl)-5,7-dihydro-4H-pyrazolo[3,4-c] pyridin-6-yl] methanone;

(2-Cyclopropyl-4-methyl-pyrazolo[1,5-a]pyrazin-3-yl)-[(7S)-2,7-dimethyl-3-(3,4,5-trifluorophenyl)-5,7-dihydro-4H-pyrazolo[3,4-c]pyridin-6-yl]methanone;

[(7S)-2,7-Dimethyl-3-(3,4,5-trifluorophenyl)-5,7-dihydro-4H-pyrazolo[3,4-c] pyridin-6-yl]-pyrazolo[1,5-a]pyrimidin-3-yl-methanone;

[(7S)-2,7-Dimethyl-3-(3,4,5-trifluorophenyl)-5,7-dihydro-4H-pyrazolo[3,4-c]pyridin-6-yl]-(2-methylpyrazolo[1,5-a]pyrimidin-3-yl)methanone;

[(7S)-2,7-Dimethyl-3-(3,4,5-trifluorophenyl)-5,7-dihydro-4H-pyrazolo[3,4-c] pyridin-6-yl]-(7-methylpyrazolo[1,5-a] pyrimidin-3-yl) methanone;

[(7S)-2,7-Dimethyl-3-(3,4,5-trifluorophenyl)-5,7-dihydro-4H-pyrazolo[3,4-c]pyridin-6-yl]-(6-methylpyrazolo[1,5-a]pyrimidin-3-yl)methanone;

[(7S)-2,7-Dimethyl-3-(3,4,5-trifluorophenyl)-5,7-dihydro-4H-pyrazolo[3,4-c]pyridin-6-yl]-imidazo[1,2-b]pyridazin-6-yl-methanone;

[(7S)-2,7-Dimethyl-3-(3,4,5-trifluorophenyl)-5,7-dihydro-4H-pyrazolo[3,4-c] pyridin-6-yl]-(2-methylimidazo[1,2-b]pyridazin-6-yl)methanone;

[(7S)-2,7-Dimethyl-3-(3,4,5-trifluorophenyl)-5,7-dihydro-4H-pyrazolo[3,4-c]pyridin-6-yl]-imidazo[1,2-b]pyridazin-3-yl-methanone;

[(7S)-2,7-Dimethyl-3-(3,4,5-trifluorophenyl)-5,7-dihydro-4H-pyrazolo[3,4-c]pyridin-6-yl]-(2-methylimidazo[1,2-b]pyridazin-3-yl)methanone;

(2,8-Dimethylimidazo[1,2-b] pyridazin-3-yl)-[(7S)-2,7-dimethyl-3-(3,4,5-trifluorophenyl)-5,7-dihydro-4H-pyrazolo[3,4-c] pyridin-6-yl]methanone;

(2,7-Dimethylimidazo[1,2-b] pyridazin-3-yl)-[(7S)-2,7-dimethyl-3-(3,4,5-trifluorophenyl)-5,7-dihydro-4H-pyrazolo[3,4-c] pyridin-6-yl] methanone;

[(7S)-2,7-Dimethyl-3-(3,4,5-trifluorophenyl)-5,7-dihydro-4H-pyrazolo[3,4-c] pyridin-6-yl]-(2-methylimidazo[1,2-a]pyrimidin-3-yl)methanone;

[(7S)-2,7-Dimethyl-3-(3,4,5-trifluorophenyl)-5,7-dihydro-4H-pyrazolo[3,4-c]pyridin-6-yl]-(2,5,8-trimethylimidazo[1,2-a]pyrazin-3-yl)methanone;

[(7S)-2,7-Dimethyl-3-(3,4,5-trifluorophenyl)-5,7-dihydro-4H-pyrazolo[3,4-c] pyridin-6-yl]-(6-methylimidazo[1,5-a]pyrimidin-8-yl)methanone;

[(7S)-2,7-Dimethyl-3-(3,4,5-trifluorophenyl)-5,7-dihydro-4H-pyrazolo[3,4-c] pyridin-6-yl]-(3-methylimidazo[1,5-a]pyrimidin-8-yl)methanone;

[(7S)-2,7-Dimethyl-3-(3,4,5-trifluorophenyl)-5,7-dihydro-4H-pyrazolo[3,4-c]pyridin-6-yl]-(3-methylimidazo[1,5-a] pyrazin-1-yl) methanone;

[(7S)-2,7-Dimethyl-3-(3,4,5-trifluorophenyl)-5,7-dihydro-4H-pyrazolo[3,4-c] pyridin-6-yl]-[3-(trifluoromethyl) imidazo[1,5-a] pyrazin-1-yl]methanone;

[(7S)-2,7-Dimethyl-3-(3,4,5-trifluorophenyl)-5,7-dihydro-4H-pyrazolo[3,4-c]pyridin-6-yl]-(5-methyl-7H-pyrrolo[2,3-d]pyrimidin-4-yl)methanone;

[(7S)-3-(3-Fluoro-5-methyl-phenyl)-2,7-dimethyl-5,7-dihydro-4H-pyrazolo[3,4-c] pyridin-6-yl]-(7-methylpyrrolo[2,3-d] pyrimidin-4-yl) methanone;

[(7S)-2,7-Dimethyl-3-(3,4,5-trifluorophenyl)-5,7-dihydro-4H-pyrazolo[3,4-c]pyridin-6-yl]-(7-methylpyrrolo[2,3-d]pyrimidin-4-yl)methanone;

(5,7-Dimethylpyrrolo[2,3-d] pyrimidin-4-yl)-[(7S)-2,7-dimethyl-3-(3,4,5-trifluorophenyl)-5,7-dihydro-4H-pyrazolo[3,4-c] pyridin-6-yl] methanone;

[(7S)-2,7-Dimethyl-3-[3-(trifluoromethyl) phenyl]-5,7-dihydro-4H-pyrazolo[3,4-c] pyridin-6-yl]-(6-quinolyl) methanone;

(6,7-Dimethylpyrrolo[2,3-d] pyrimidin-4-yl)-[(7S)-2,7-dimethyl-3-(3,4,5-trifluorophenyl)-5,7-dihydro-4H-pyrazolo[3,4-c] pyridin-6-yl] methanone;

[(7S)-2,7-Dimethyl-3-(3,4,5-trifluorophenyl)-5,7-dihydro-4H-pyrazolo[3,4-c]pyridin-6-yl]-(7H-purin-6-yl)methanone;

[(7S)-2,7-Dimethyl-3-(3,4,5-trifluorophenyl)-5,7-dihydro-4H-pyrazolo[3,4-c] pyridin-6-yl]-(1-methylpyrazolo[3,4-d]pyrimidin-4-yl)methanone;

[(7S)-2,7-Dimethyl-3-(3,4,5-trifluorophenyl)-5,7-dihydro-4H-pyrazolo[3,4-c]pyridin-6-yl]-(5-methyl-[1,2,4]triazolo[1,5-a]pyrimidin-7-yl)methanone;

[(7S)-2,7-Dimethyl-3-(3,4,5-trifluorophenyl)-5,7-dihydro-4H-pyrazolo[3,4-c] pyridin-6-yl]-(7-methylquinoxalin-6-yl) methanone;

[(7S)-2,7-Dimethyl-3-(3,4,5-trifluorophenyl)-5,7-dihydro-4H-pyrazolo[3,4-c] pyridin-6-yl]-(2-methylquinoxalin-5-yl)methanone;

[(7S)-2,7-Dimethyl-3-(3,4,5-trifluorophenyl)-5,7-dihydro-4H-pyrazolo[3,4-c]pyridin-6-yl]-(3-methylquinoxalin-5-yl)methanone;

(2,3-Dimethylquinoxalin-6-yl)-[(7S)-2,7-dimethyl-3-(3,4,5-trifluorophenyl)-5,7-dihydro-4H-pyrazolo[3,4-c] pyridin-6-yl]methanone;

[(7S)-2,7-Dimethyl-3-(3,4,5-trifluorophenyl)-5,7-dihydro-4H-pyrazolo[3,4-c]pyridin-6-yl]-quinoxalin-2-yl-methanone;

Cinnolin-3-yl-[(7S)-2,7-dimethyl-3-(3,4,5-trifluorophenyl)-5,7-dihydro-4H-pyrazolo[3,4-c]pyridin-6-yl] methanone;

[(7S)-2,7-Dimethyl-3-(3,4,5-trifluorophenyl)-5,7-dihydro-4H-pyrazolo[3,4-c]pyridin-6-yl]-quinazolin-6-yl-methanone;

[(7S)-2,7-Dimethyl-3-(3,4,5-trifluorophenyl)-5,7-dihydro-4H-pyrazolo[3,4-c]pyridin-6-yl]-quinazolin-7-yl-methanone;

[(7S)-2,7-Dimethyl-3-(3,4,5-trifluorophenyl)-5,7-dihydro-4H-pyrazolo[3,4-c]pyridin-6-yl]-(8-fluoroquinazolin-4-yl)methanone;

[(7S)-2,7-Dimethyl-3-(3,4,5-trifluorophenyl)-5,7-dihydro-4H-pyrazolo[3,4-c]pyridin-6-yl]-quinazolin-4-yl-methanone;

(2-Deuterioquinoxalin-6-yl)-[(7S)-2,7-dimethyl-3-(3,4,5-trifluorophenyl)-5,7-dihydro-4H-pyrazolo[3,4-c]pyridin-6-yl]methanone;

[(7S)-2,7-Dimethyl-3-(3,4,5-trifluorophenyl)-5,7-dihydro-4H-pyrazolo[3,4-c]pyridin-6-yl]-pyrido[4,3-d]pyrimidin-5-yl-methanone;

[(7S)-2,7-Dimethyl-3-(3,4,5-trifluorophenyl)-5,7-dihydro-4H-pyrazolo[3,4-c]pyridin-6-yl]-(1,5-naphthyridin-4-yl)methanone;

[(7S)-2,7-Dimethyl-3-(3,4,5-trifluorophenyl)-5,7-dihydro-4H-pyrazolo[3,4-c]pyridin-6-yl]-(1,6-naphthyridin-5-yl)methanone;

[(7S)-2,7-Dimethyl-3-(3,4,5-trifluorophenyl)-5,7-dihydro-4H-pyrazolo[3,4-c]pyridin-6-yl]-(2-methyl-1,6-naphthyridin-5-yl)methanone;

[(7S)-2,7-Dimethyl-3-(3,4,5-trifluorophenyl)-5,7-dihydro-4H-pyrazolo[3,4-c]pyridin-6-yl]-(1,6-naphthyridin-3-yl)methanone;

[(7S)-2,7-Dimethyl-3-(3,4,5-trifluorophenyl)-5,7-dihydro-4H-pyrazolo[3,4-c]pyridin-6-yl]-(1,7-naphthyridin-5-yl)methanone;
[(7S)-2,7-Dimethyl-3-(3,4,5-trifluorophenyl)-5,7-dihydro-4H-pyrazolo[3,4-c]pyridin-6-yl]-(1,8-naphthyridin-3-yl)methanone;
[(7S)-2,7-Dimethyl-3-(3,4,5-trifluorophenyl)-5,7-dihydro-4H-pyrazolo[3,4-c]pyridin-6-yl]-(1,8-naphthyridin-4-yl)methanone;
[(7S)-2,7-Dimethyl-3-(o-tolyl)-5,7-dihydro-4H-pyrazolo[3,4-c]pyridin-6-yl]-(6-quinolyl)methanone;
[(7S)-2,7-Dimethyl-3-[2-(trifluoromethyl)phenyl]-5,7-dihydro-4H-pyrazolo[3,4-c]pyridin-6-yl]-(6-quinolyl)methanone;
[(7S)-2,7-Dimethyl-3-[4-(trifluoromethyl)phenyl]-5,7-dihydro-4H-pyrazolo[3,4-c]pyridin-6-yl]-(6-quinolyl)methanone;
[(7S)-3-(3-Methoxyphenyl)-2,7-dimethyl-5,7-dihydro-4H-pyrazolo[3,4-c]pyridin-6-yl]-(6-quinolyl)methanone;
[(7S)-3-(2-Methoxyphenyl)-2,7-dimethyl-5,7-dihydro-4H-pyrazolo[3,4-c]pyridin-6-yl]-(6-quinolyl)methanone;
[(7S)-3-(4-Ethoxyphenyl)-2,7-dimethyl-5,7-dihydro-4H-pyrazolo[3,4-c]pyridin-6-yl]-(6-quinolyl)methanone;
[(7S)-3-(3-Isopropoxyphenyl)-2,7-dimethyl-5,7-dihydro-4H-pyrazolo[3,4-c]pyridin-6-yl]-(6-quinolyl)methanone;
[(7S)-3-[3-(Difluoromethoxy)phenyl]-2,7-dimethyl-5,7-dihydro-4H-pyrazolo[3,4-c]pyridin-6-yl]-(6-quinolyl)methanone;
[(7S)-2,7-Dimethyl-3-[4-(trifluoromethoxy)phenyl]-5,7-dihydro-4H-pyrazolo[3,4-c]pyridin-6-yl]-(6-quinolyl)methanone;
[(7S)-2,7-Dimethyl-3-[3-(trifluoromethoxy)phenyl]-5,7-dihydro-4H-pyrazolo[3,4-c]pyridin-6-yl]-(6-quinolyl)methanone;
[(7S)-3-(2,4-Difluorophenyl)-2,7-dimethyl-5,7-dihydro-4H-pyrazolo[3,4-c]pyridin-6-yl]-(6-quinolyl)methanone;
[(7S)-3-(2,3-Difluorophenyl)-2,7-dimethyl-5,7-dihydro-4H-pyrazolo[3,4-c]pyridin-6-yl]-(6-quinolyl)methanone;
[(7S)-3-(4-Chloro-3-fluoro-phenyl)-2,7-dimethyl-5,7-dihydro-4H-pyrazolo[3,4-c]pyridin-6-yl]-(6-quinolyl)methanone;
[(7S)-3-(3-Chloro-4-fluoro-phenyl)-2,7-dimethyl-5,7-dihydro-4H-pyrazolo[3,4-c]pyridin-6-yl]-(6-quinolyl)methanone;
[(7S)-3-(2-Chloro-4-fluoro-phenyl)-2,7-dimethyl-5,7-dihydro-4H-pyrazolo[3,4-c]pyridin-6-yl]-(6-quinolyl)methanone;
[(7S)-3-(3,4-Dichlorophenyl)-2,7-dimethyl-5,7-dihydro-4H-pyrazolo[3,4-c]pyridin-6-yl]-(6-quinolyl)methanone;
[(7S)-3-(5-Fluoro-2-methoxy-phenyl)-2,7-dimethyl-5,7-dihydro-4H-pyrazolo[3,4-c]pyridin-6-yl]-(6-quinolyl)methanone;
[(7S)-3-(4-Fluoro-3-methoxy-phenyl)-2,7-dimethyl-5,7-dihydro-4H-pyrazolo[3,4-c]pyridin-6-yl]-(6-quinolyl)methanone;
[(7S)-3-(2-Fluoro-3-methoxy-phenyl)-2,7-dimethyl-5,7-dihydro-4H-pyrazolo[3,4-c]pyridin-6-yl]-(6-quinolyl)methanone;
[(7S)-3-(3-Fluoro-5-methyl-phenyl)-2,7-dimethyl-5,7-dihydro-4H-pyrazolo[3,4-c]pyridin-6-yl]-(6-quinolyl)methanone;
[(7S)-3-(4-Methoxy-3-methyl-phenyl)-2,7-dimethyl-5,7-dihydro-4H-pyrazolo[3,4-c]pyridin-6-yl]-(6-quinolyl)methanone;
[(7S)-3-(3-Chloro-5-methoxy-phenyl)-2,7-dimethyl-5,7-dihydro-4H-pyrazolo[3,4-c]pyridin-6-yl]-(6-quinolyl)methanone;
[(7S)-3-(4-Chloro-2,3-difluoro-phenyl)-2,7-dimethyl-5,7-dihydro-4H-pyrazolo[3,4-c]pyridin-6-yl]-(6-quinolyl)methanone;
[(7S)-2,7-Dimethyl-3-(2,3,4-trifluorophenyl)-5,7-dihydro-4H-pyrazolo[3,4-c]pyridin-6-yl]-(6-quinolyl)methanone;
[(7S)-2,7-Dimethyl-3-(3,4,5-trifluorophenyl)-5,7-dihydro-4H-pyrazolo[3,4-c]pyridin-6-yl]-(1-oxidoquinolin-1-ium-6-yl)methanone;
[(7S)-2,7-Dimethyl-3-(3,4,5-trifluorophenyl)-5,7-dihydro-4H-pyrazolo[3,4-c]pyridin-6-yl]-(2-hydroxy-6-quinolyl)methanone;
[(7S)-2,7-Dimethyl-3-(3,4,5-trifluorophenyl)-5,7-dihydro-4H-pyrazolo[3,4-c]pyridin-6-yl]-(4-hydroxy-6-quinolyl)methanone;
[(7S)-2,7-Dimethyl-3-(6-methyl-3-pyridyl)-5,7-dihydro-4H-pyrazolo[3,4-c]pyridin-6-yl]-(6-quinolyl)methanone;
[(7S)-2,7-Dimethyl-3-(2-methyl-4-pyridyl)-5,7-dihydro-4H-pyrazolo[3,4-c]pyridin-6-yl]-(6-quinolyl)methanone;
[(7S)-3-[6-(Difluoromethyl)-3-pyridyl]-2,7-dimethyl-5,7-dihydro-4H-pyrazolo[3,4-c]pyridin-6-yl]-(6-quinolyl)methanone;
[(7S)-2,7-Dimethyl-3-[6-(trifluoromethyl)-3-pyridyl]-5,7-dihydro-4H-pyrazolo[3,4-c]pyridin-6-yl]-(6-quinolyl)methanone;
[(7S)-2,7-Dimethyl-3-[2-(trifluoromethyl)-4-pyridyl]-5,7-dihydro-4H-pyrazolo[3,4-c]pyridin-6-yl]-(6-quinolyl)methanone;
[(7S)-2,7-Dimethyl-3-[5-(trifluoromethyl)-3-thienyl]-5,7-dihydro-4H-pyrazolo[3,4-c]pyridin-6-yl]-(6-quinolyl)methanone;
[(7S)-3-(6-Methoxy-3-pyridyl)-2,7-dimethyl-5,7-dihydro-4H-pyrazolo[3,4-c]pyridin-6-yl]-(6-quinolyl)methanone;
[(7S)-3-(2-Methoxy-4-pyridyl)-2,7-dimethyl-5,7-dihydro-4H-pyrazolo[3,4-c]pyridin-6-yl]-(6-quinolyl)methanone;
[(7S)-3-[6-(Difluoromethoxy)-3-pyridyl]-2,7-dimethyl-5,7-dihydro-4H-pyrazolo[3,4-c]pyridin-6-yl]-(6-quinolyl)methanone;
[(7S)-3-[5-(Difluoromethoxy)-3-pyridyl]-2,7-dimethyl-5,7-dihydro-4H-pyrazolo[3,4-c]pyridin-6-yl]-(6-quinolyl)methanone;
[(7S)-3-(6-Methoxy-5-methyl-3-pyridyl)-2,7-dimethyl-5,7-dihydro-4H-pyrazolo[3,4-c]pyridin-6-yl]-(6-quinolyl)methanone;
[(7S)-3-[6-Methoxy-5-(trifluoromethyl)-3-pyridyl]-2,7-dimethyl-5,7-dihydro-4H-pyrazolo[3,4-c]pyridin-6-yl]-(6-quinolyl)methanone;
[(7S)-3-(1H-Indol-7-yl)-2,7-dimethyl-5,7-dihydro-4H-pyrazolo[3,4-c]pyridin-6-yl]-(6-quinolyl)methanone;
[(7S)-3-(Benzofuran-6-yl)-2,7-dimethyl-5,7-dihydro-4H-pyrazolo[3,4-c]pyridin-6-yl]-(6-quinolyl)methanone;
[(7S)-3-(Benzofuran-5-yl)-2,7-dimethyl-5,7-dihydro-4H-pyrazolo[3,4-c]pyridin-6-yl]-(6-quinolyl)methanone;
[(7S)-3-(Benzofuran-7-yl)-2,7-dimethyl-5,7-dihydro-4H-pyrazolo[3,4-c]pyridin-6-yl]-(6-quinolyl)methanone;
[(7S)-3-(Benzofuran-4-yl)-2,7-dimethyl-5,7-dihydro-4H-pyrazolo[3,4-c]pyridin-6-yl]-(6-quinolyl)methanone;

[(7S)-3-(5-Fluorobenzofuran-7-yl)-2,7-dimethyl-5,7-dihydro-4H-pyrazolo[3,4-c]pyridin-6-yl]-(6-quinolyl)methanone;
[(7S)-3-(1,3-Benzothiazol-4-yl)-2,7-dimethyl-5,7-dihydro-4H-pyrazolo[3,4-c]pyridin-6-yl]-(6-quinolyl)methanone;
[(7S)-3-(2,1,3-Benzoxadiazol-4-yl)-2,7-dimethyl-5,7-dihydro-4H-pyrazolo[3,4-c]pyridin-6-yl]-(6-quinolyl)methanone;
[(7S)-3-(2,3-Dihydrobenzofuran-7-yl)-2,7-dimethyl-5,7-dihydro-4H-pyrazolo[3,4-c]pyridin-6-yl]-(6-quinolyl)methanone;
[(7S)-3-(1,3-Benzodioxol-5-yl)-2,7-dimethyl-5,7-dihydro-4H-pyrazolo[3,4-c]pyridin-6-yl]-(6-quinolyl)methanone;
[(7S)-3-(1,3-Benzodioxol-4-yl)-2,7-dimethyl-5,7-dihydro-4H-pyrazolo[3,4-c]pyridin-6-yl]-(6-quinolyl)methanone;
[(7S)-3-(2,2-Difluoro-1,3-benzodioxol-4-yl)-2,7-dimethyl-5,7-dihydro-4H-pyrazolo[3,4-c]pyridin-6-yl]-(6-quinolyl)methanone;
[(7S)-2,7-Dimethyl-3-(3,4,5-trifluorophenyl)-5,7-dihydro-4H-pyrazolo[3,4-c]pyridin-6-yl]-(5-isoquinolyl)methanone;
[(7S)-2,7-Dimethyl-3-(3,4,5-trifluorophenyl)-5,7-dihydro-4H-pyrazolo[3,4-c]pyridin-6-yl]-(6-isoquinolyl)methanone;
[(7S)-2,7-Dimethyl-3-(3,4,5-trifluorophenyl)-5,7-dihydro-4H-pyrazolo[3,4-c]pyridin-6-yl]-(5-fluoro-3-quinolyl)methanone;
[(7S)-2,7-Dimethyl-3-(3,4,5-trifluorophenyl)-5,7-dihydro-4H-pyrazolo[3,4-c]pyridin-6-yl]-(8-fluoro-4-isoquinolyl)methanone;
(4-Bromo-6-quinolyl)-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-(2-methyl-6-quinolyl)methanone;
[(7S)-2,7-Dimethyl-3-(3,4,5-trifluorophenyl)-5,7-dihydro-4H-pyrazolo[3,4-c]pyridin-6-yl]-(4-methyl-6-quinolyl)methanone;
[(7S)-2,7-Dimethyl-3-(3,4,5-trifluorophenyl)-5,7-dihydro-4H-pyrazolo[3,4-c]pyridin-6-yl]-(8-methoxy-4-quinolyl)methanone;
5,6-Dihydro-4H-pyrrolo[1,2-b]pyrazol-3-yl-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-(4,5,6,7-tetrahydropyrazolo[1,5-a]pyridin-3-yl)methanone;
6,7-Dihydro-5H-pyrazolo[5,1-b][1,3]oxazin-2-yl-[(7S)-2,7-dimethyl-3-(3,4,5-trifluorophenyl)-5,7-dihydro-4H-pyrazolo[3,4-c]pyridin-6-yl]methanone;
6,7-Dihydro-5H-pyrazolo[5,1-b][1,3]oxazin-3-yl-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-(3-methyl-6,7-dihydro-5H-pyrazolo[5,1-b][1,3]oxazin-2-yl)methanone;
[(7S)-2,7-Dimethyl-3-(3,4,5-trifluorophenyl)-5,7-dihydro-4H-pyrazolo[3,4-c]pyridin-6-yl]-(2,6,6-trimethyl-4,7-dihydropyrazolo[5,1-c][1,4]oxazin-3-yl)methanone;
[(7S)-2,7-Dimethyl-3-(3,4,5-trifluorophenyl)-5,7-dihydro-4H-pyrazolo[3,4-c]pyridin-6-yl]-(3,6,6-trimethyl-4,7-dihydropyrazolo[5,1-c][1,4]oxazin-2-yl)methanone;
((S)-2,7-Dimethyl-3-(3,4,5-trifluorophenyl)-4,5-dihydro-2H-pyrazolo[3,4-c]pyridin-6 (7H)-yl)(7-(trifluoromethyl)-4,5,6,7-tetrahydropyrazolo[1,5-a]pyrimidin-3-yl)methanone;
6,7-Dihydro-5H-pyrrolo[1,2-a]imidazol-3-yl-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-(5,6,7,8-tetrahydroimidazo[1,2-a]pyridin-3-yl)methanone;
[2-(Difluoromethyl)-5,6,7,8-tetrahydroimidazo[1,2-a]pyridin-3-yl]-[(7S)-2,7-dimethyl-3-(3,4,5-trifluorophenyl)-5,7-dihydro-4H-pyrazolo[3,4-c]pyridin-6-yl]methanone;
6,8-Dihydro-5H-imidazo[2,1-c][1,4]oxazin-3-yl-[(7S)-2,7-dimethyl-3-(3,4,5-trifluorophenyl)-5,7-dihydro-4H-pyrazolo[3,4-c]pyridin-6-yl]methanone;
3,4-Dihydro-2H-pyrano[2,3-b]pyridin-6-yl-[(7S)-2,7-dimethyl-3-(3,4,5-trifluorophenyl)-5,7-dihydro-4H-pyrazolo[3,4-c]pyridin-6-yl]methanone;
3,4-Dihydro-2H-pyrano[2,3-b]pyridin-5-yl-[(7S)-2,7-dimethyl-3-(3,4,5-trifluorophenyl)-5,7-dihydro-4H-pyrazolo[3,4-c]pyridin-6-yl]methanone;
6,8-Dihydro-5H-pyrano[3,4-b]pyridin-4-yl-[(7S)-2,7-dimethyl-3-(3,4,5-trifluorophenyl)-5,7-dihydro-4H-pyrazolo[3,4-c]pyridin-6-yl]methanone;
6,8-Dihydro-5H-pyrano[3,4-b]pyridin-2-yl-[(7S)-2,7-dimethyl-3-(3,4,5-trifluorophenyl)-5,7-dihydro-4H-pyrazolo[3,4-c]pyridin-6-yl]methanone;
7,8-Dihydro-5H-pyrano[4,3-b]pyridin-3-yl-[(7S)-2,7-dimethyl-3-(3,4,5-trifluorophenyl)-5,7-dihydro-4H-pyrazolo[3,4-c]pyridin-6-yl]methanone;
3,4-Dihydro-2H-pyrano[3,2-b]pyridin-8-yl-[(7S)-2,7-dimethyl-3-(3,4,5-trifluorophenyl)-5,7-dihydro-4H-pyrazolo[3,4-c]pyridin-6-yl]methanone;
2,3-Dihydro-[1,4]dioxino[2,3-b]pyridin-8-yl-[(7S)-2,7-dimethyl-3-(3,4,5-trifluorophenyl)-5,7-dihydro-4H-pyrazolo[3,4-c]pyridin-6-yl]methanone;
2,3-Dihydro-[1,4]dioxino[2,3-b]pyridin-7-yl-[(7S)-2,7-dimethyl-3-(3,4,5-trifluorophenyl)-5,7-dihydro-4H-pyrazolo[3,4-c]pyridin-6-yl]methanone;
3,4-Dihydro-2H-pyrido[3,2-b][1,4]oxazin-7-yl-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-(4-methyl-2,3-dihydropyrido[3,2-b][1,4]oxazin-7-yl)methanone;
3,4-Dihydro-2H-pyrano[2,3-c]pyridin-6-yl-[(7S)-2,7-dimethyl-3-(3,4,5-trifluorophenyl)-5,7-dihydro-4H-pyrazolo[3,4-c]pyridin-6-yl]methanone;
[(7S)-2,7-Dimethyl-3-(3,4,5-trifluorophenyl)-5,7-dihydro-4H-pyrazolo[3,4-c]pyridin-6-yl]-(1,2,3,4-tetrahydroisoquinolin-5-yl)methanone;
[(7S)-2,7-Dimethyl-3-(3,4,5-trifluorophenyl)-5,7-dihydro-4H-pyrazolo[3,4-c]pyridin-6-yl]-(1,2,3,4-tetrahydroisoquinolin-8-yl)methanone;
[(7S)-2,7-Dimethyl-3-(3,4,5-trifluorophenyl)-5,7-dihydro-4H-pyrazolo[3,4-c]pyridin-6-yl]-isochroman-5-yl-methanone;
[(7S)-2,7-Dimethyl-3-(3,4,5-trifluorophenyl)-5,7-dihydro-4H-pyrazolo[3,4-c]pyridin-6-yl]-isochroman-7-yl-methanone;

[(7S)-2,7-Dimethyl-3-(3,4,5-trifluorophenyl)-5,7-dihydro-4H-pyrazolo[3,4-c]pyridin-6-yl]-isochroman-6-yl-methanone;
[(7S)-2,7-Dimethyl-3-(3,4,5-trifluorophenyl)-5,7-dihydro-4H-pyrazolo[3,4-c]pyridin-6-yl]-isochroman-8-yl-methanone;
Chroman-6-yl-[(7S)-2,7-dimethyl-3-(3,4,5-trifluorophenyl)-5,7-dihydro-4H-pyrazolo[3,4-c]pyridin-6-yl] methanone;
Chroman-5-yl-[(7S)-2,7-dimethyl-3-(3,4,5-trifluorophenyl)-5,7-dihydro-4H-pyrazolo[3,4-c]pyridin-6-yl] methanone;
Chroman-7-yl-[(7S)-2,7-dimethyl-3-(3,4,5-trifluorophenyl)-5,7-dihydro-4H-pyrazolo[3,4-c]pyridin-6-yl] methanone;
Chroman-8-yl-[(7S)-2,7-dimethyl-3-(3,4,5-trifluorophenyl)-5,7-dihydro-4H-pyrazolo[3,4-c]pyridin-6-yl] methanone;
4-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one;
4-[(7S)-2,7-Dimethyl-3-(3,4,5-trifluorophenyl)-5,7-dihydro-4H-pyrazolo[3,4-c]pyridine-6-carbonyl]-3-methyl-1,3-benzoxazol-2-one;
5-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one;
7-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one;
6-[(7S)-2,7-Dimethyl-3-(3,4,5-trifluorophenyl)-5,7-dihydro-4H-pyrazolo[3,4-c]pyridine-6-carbonyl]-3H-1,3-benzoxazol-2-one;
7-[(7S)-2,7-dimethyl-3-(3,4,5-trifluorophenyl)-5,7-dihydro-4H-pyrazolo[3,4-c]pyridine-6-carbonyl]-3-methyl-1,3-benzoxazol-2-one;
7-[(7S)-2,7-Dimethyl-3-(3,4,5-trifluorophenyl)-5,7-dihydro-4H-pyrazolo[3,4-c]pyridine-6-carbonyl]-4-methyl-1,4-benzoxazin-3-one;
3,4-Dihydro-2H-1,4-benzoxazin-8-yl-[(7S)-2,7-dimethyl-3-(3,4,5-trifluorophenyl)-5,7-dihydro-4H-pyrazolo[3,4-c]pyridin-6-yl]methanone;
[(7S)-3-[3-(Difluoromethyl)-4-fluoro-phenyl]-2,7-dimethyl-5,7-dihydro-4H-pyrazolo[3,4-c]pyridin-6-yl]-(2-methoxy-3-methyl-4-pyridyl)methanone;
[(7S)-3-[3-(1,1-Difluoroethyl)phenyl]-2,7-dimethyl-5,7-dihydro-4H-pyrazolo[3,4-c]pyridin-6-yl]-(2-methoxy-3-methyl-4-pyridyl)methanone;
[(7S)-3-[3-(Difluoromethoxy)-4-fluoro-phenyl]-2,7-dimethyl-5,7-dihydro-4H-pyrazolo[3,4-c]pyridin-6-yl]-(2-methoxy-3-methyl-4-pyridyl)methanone;
Chroman-7-yl-[(7S)-3-[3-(difluoromethoxy)-5-fluoro-phenyl]-2,7-dimethyl-5,7-dihydro-4H-pyrazolo[3,4-c]pyridin-6-yl]methanone;
[(7S)-3-[3-(Difluoromethoxy)-5-fluoro-phenyl]-2,7-dimethyl-5,7-dihydro-4H-pyrazolo[3,4-c]pyridin-6-yl]-(2-methoxy-3-methyl-4-pyridyl)methanone;
[(7S)-3-(4-Fluoro-3-methyl-phenyl)-2,7-dimethyl-5,7-dihydro-4H-pyrazolo[3,4-c]pyridin-6-yl]-(2-methoxy-3-methyl-4-pyridyl)methanone;
[(7S)-2,7-Dimethyl-3-(3,4,5-trifluorophenyl)-5,7-dihydro-4H-pyrazolo[3,4-c]pyridin-6-yl]-(3-methoxy-2-methyl-4-pyridyl)methanone;
[(7S)-2,7-Dimethyl-3-(3,4,5-trifluorophenyl)-5,7-dihydro-4H-pyrazolo[3,4-c]pyridin-6-yl]-(1-methyl-4-phenyl-imidazol-2-yl)methanone;
[(7S)-2,7-Dimethyl-3-(3,4,5-trifluorophenyl)-5,7-dihydro-4H-pyrazolo[3,4-c]pyridin-6-yl]-(1-phenylimidazol-4-yl)methanone;
[(7S)-2,7-Dimethyl-3-(3,4,5-trifluorophenyl)-5,7-dihydro-4H-pyrazolo[3,4-c]pyridin-6-yl]-[3-methyl-2-(2-pyridyl)imidazol-4-yl]methanone;
[(7S)-2,7-Dimethyl-3-(3,4,5-trifluorophenyl)-5,7-dihydro-4H-pyrazolo[3,4-c]pyridin-6-yl]-(2-fluoro-6-pyrazol-1-yl-phenyl)methanone;
[(7S)-2,7-Dimethyl-3-(3,4,5-trifluorophenyl)-5,7-dihydro-4H-pyrazolo[3,4-c]pyridin-6-yl]-spiro[3,4-dihydro-1,4-benzoxazine-2,1'-cyclopropane]-8-yl-methanone;
[(7S)-2,7-Dimethyl-3-(3,4,5-trifluorophenyl)-5,7-dihydro-4H-pyrazolo[3,4-c]pyridin-6-yl]-(3-fluoro-1H-pyrrolo[2,3-b]pyridin-4-yl)methanone;
[(7S)-2,7-Dimethyl-3-(3,4,5-trifluorophenyl)-5,7-dihydro-4H-pyrazolo[3,4-c]pyridin-6-yl]-(9-methylpurin-6-yl)methanone;
[(7S)-2,7-Dimethyl-3-(3,4,5-trifluorophenyl)-5,7-dihydro-4H-pyrazolo[3,4-c]pyridin-6-yl]-(3-fluoro-5-methoxy-4-pyridyl)methanone;
(3-Chloro-4-methoxy-2-pyridyl)-[(7S)-3-[3-(difluoromethyl)-5-fluoro-phenyl]-2,7-dimethyl-5,7-dihydro-4H-pyrazolo[3,4-c]pyridin-6-yl]methanone;
[(7S)-3-[3-(Difluoromethyl)-5-fluoro-phenyl]-2,7-dimethyl-5,7-dihydro-4H-pyrazolo[3,4-c]pyridin-6-yl]-(2-methoxy-3-methyl-4-pyridyl)methanone;
Chroman-7-yl-[(7S)-3-[3-(difluoromethyl)-5-fluoro-phenyl]-2,7-dimethyl-5,7-dihydro-4H-pyrazolo[3,4-c]pyridin-6-yl]methanone;
Chroman-7-yl-[(7S)-3-(3-fluoro-5-methoxy-phenyl)-2,7-dimethyl-5,7-dihydro-4H-pyrazolo[3,4-c]pyridin-6-yl]methanone;
(3-Chloro-4-methoxy-2-pyridyl)-[(7S)-3-[3-(difluoromethoxy)-5-fluoro-phenyl]-2,7-dimethyl-5,7-dihydro-4H-pyrazolo[3,4-c]pyridin-6-yl]methanone;
[(7S)-3-(3-Fluoro-5-methoxy-phenyl)-2,7-dimethyl-5,7-dihydro-4H-pyrazolo[3,4-c]pyridin-6-yl]-(2-methoxy-3-methyl-4-pyridyl)methanone;
(3-Chloro-4-methoxy-2-pyridyl)-[(7S)-3-(3-fluoro-5-methoxy-phenyl)-2,7-dimethyl-5,7-dihydro-4H-pyrazolo[3,4-c]pyridin-6-yl]methanone;
racemic-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone; and
(R)-(2-(Bicyclo[1.1.1]pentan-1-yl)-7-methyl-3-phenyl-2,4,5,7-tetrahydro-6H-pyrazolo[3,4-c]pyridin-6-yl)(5-cyclopropyl-1-methyl-1H-pyrazol-4-yl)methanone;
and pharmaceutically acceptable salts, isotopes, N-oxides, and stereoisomers thereof.

79. A compound selected from the group consisting of:

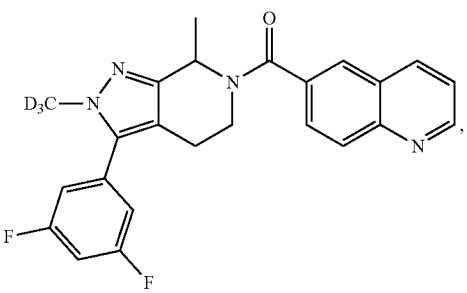

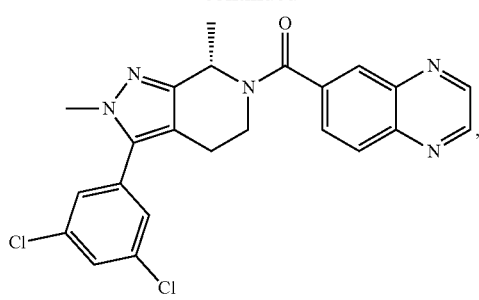
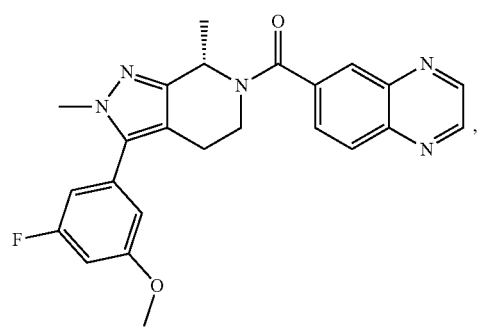
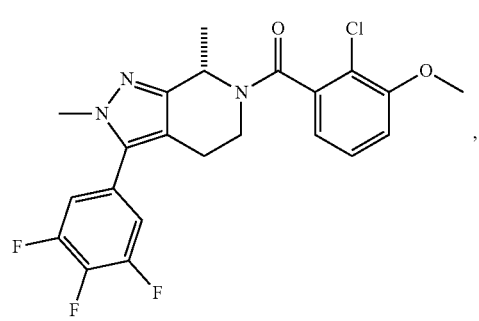
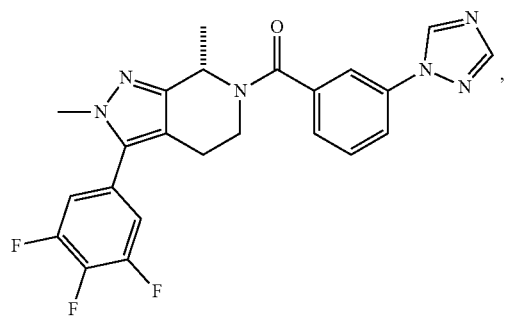
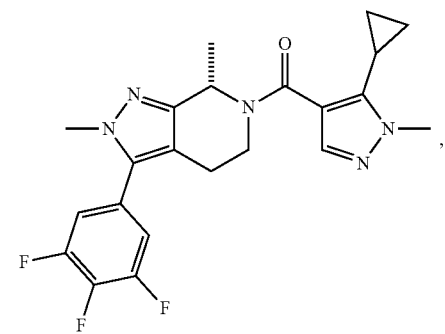
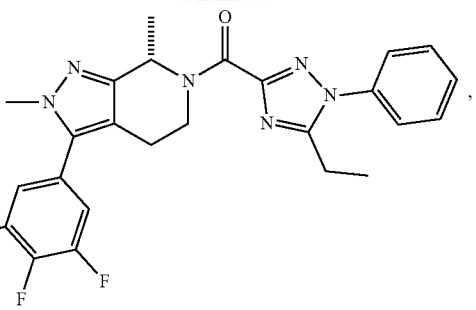
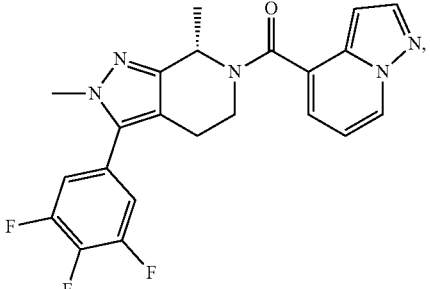
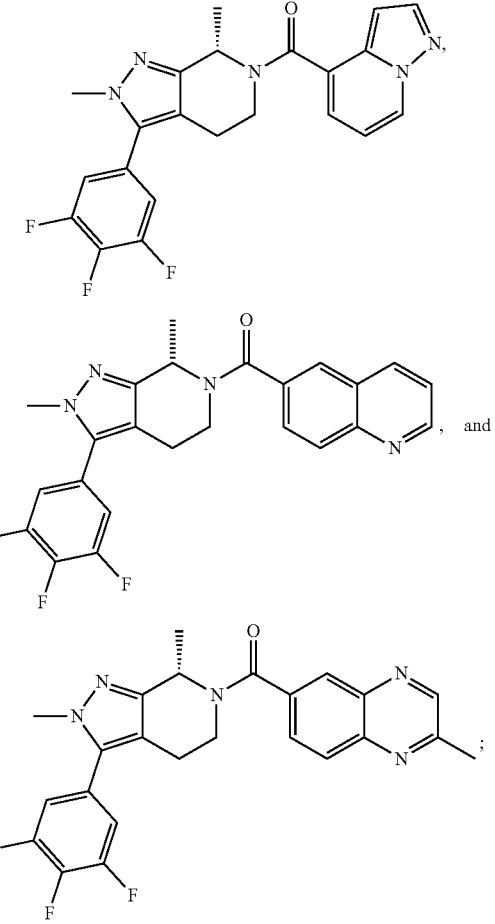
and pharmaceutically acceptable salts, isotopes, N-oxides, and stereoisomers.
80. A pharmaceutical composition comprising:
(A) at least one compound of Formula (II):
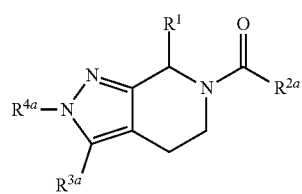

wherein
R¹ is $C_{1-4}$alkyl;
$R^{2a}$ is selected from the group consisting of:
(a)
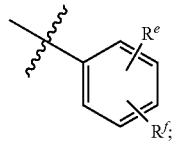
(b) 6-Membered heteroaryl selected from the group consisting of:
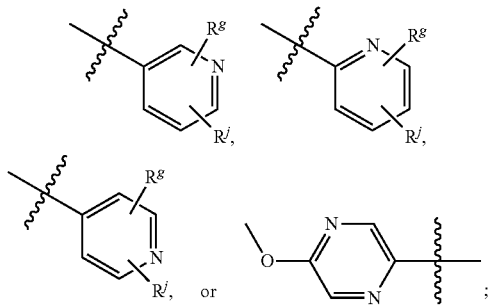
(c) 5-Membered heteroaryl selected from the group consisting of:
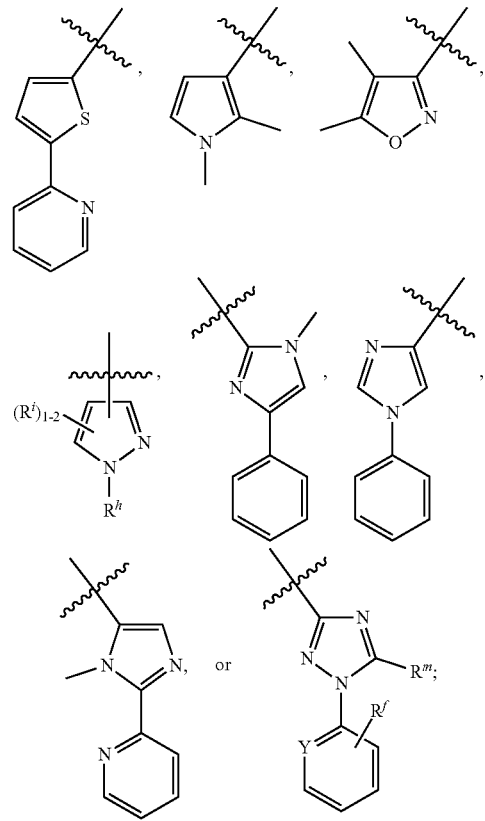
(d) 5,6-Fused or 6,5-fused heteroaryl selected from the group consisting of:
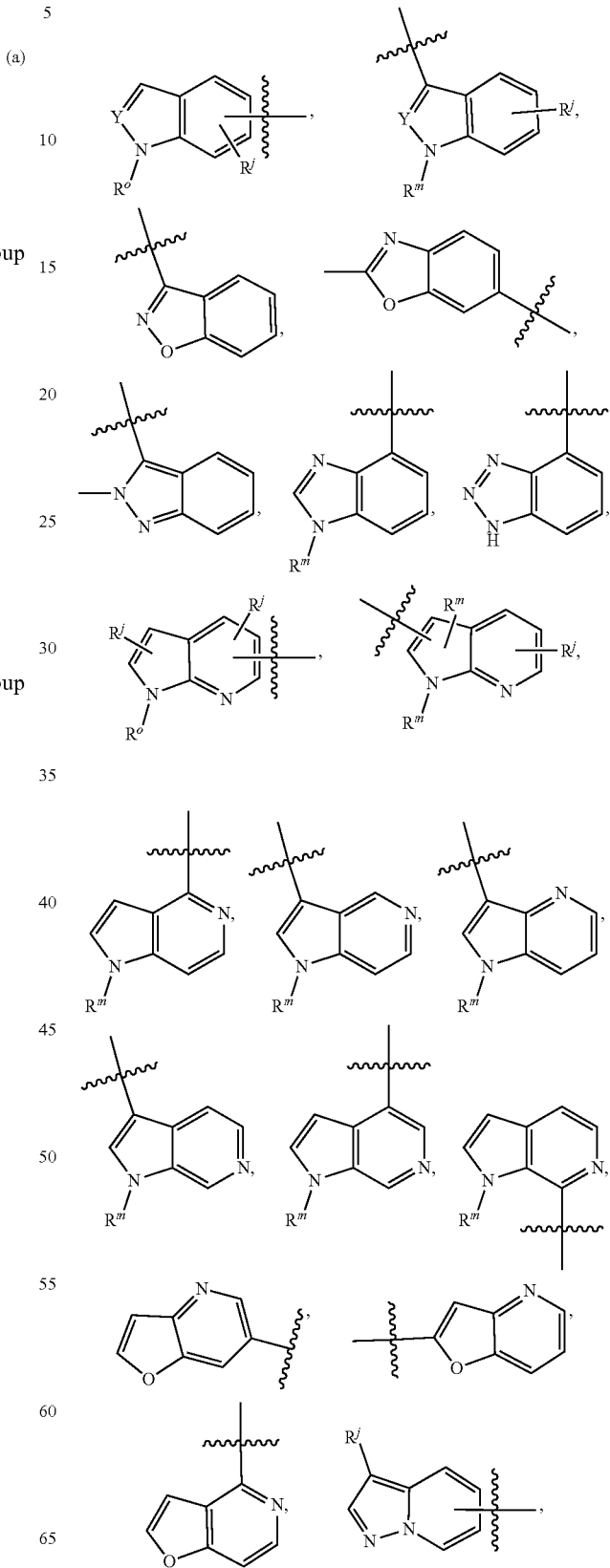

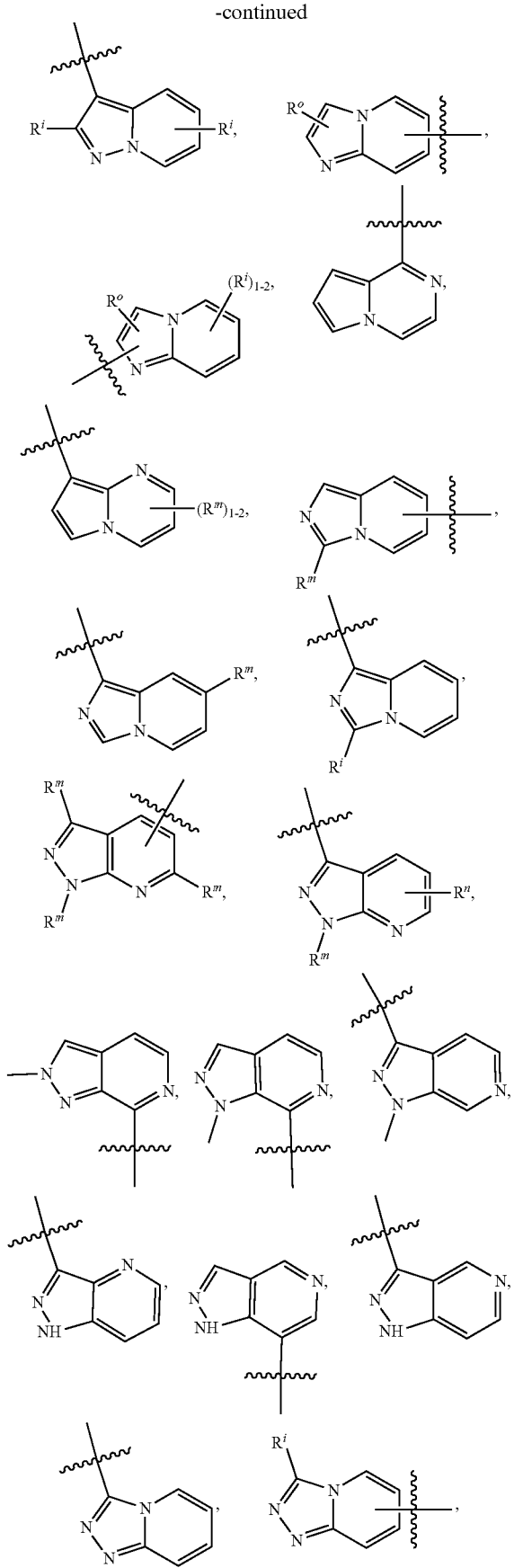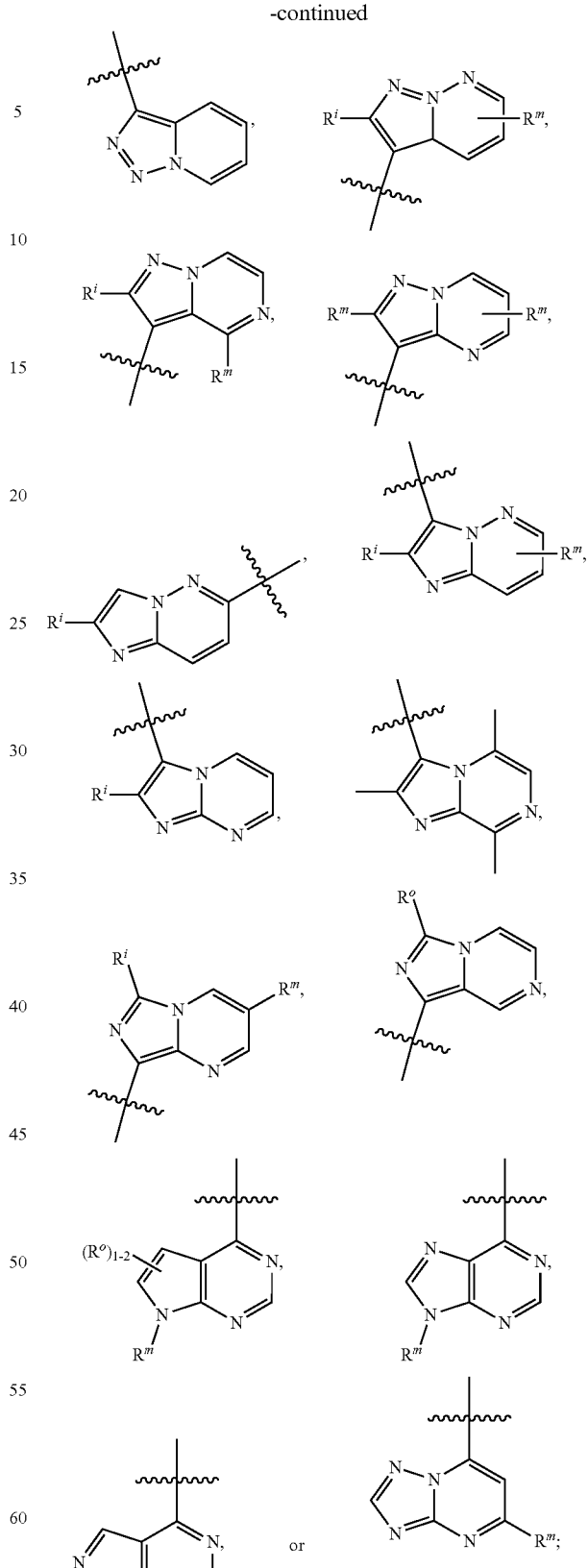

(e) Fused 6,6 heteroaryl selected from the group consisting of:
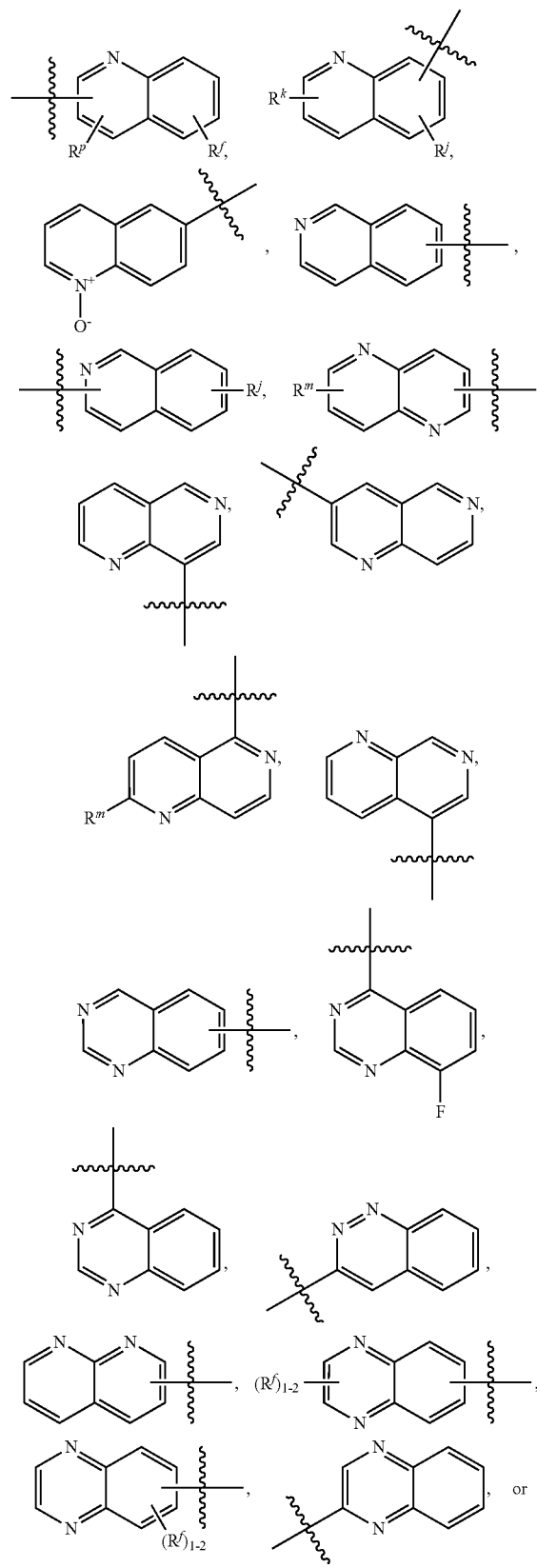
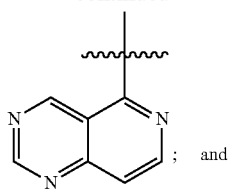
; and
(f) Heterocycloalkyl selected from the group consisting of:
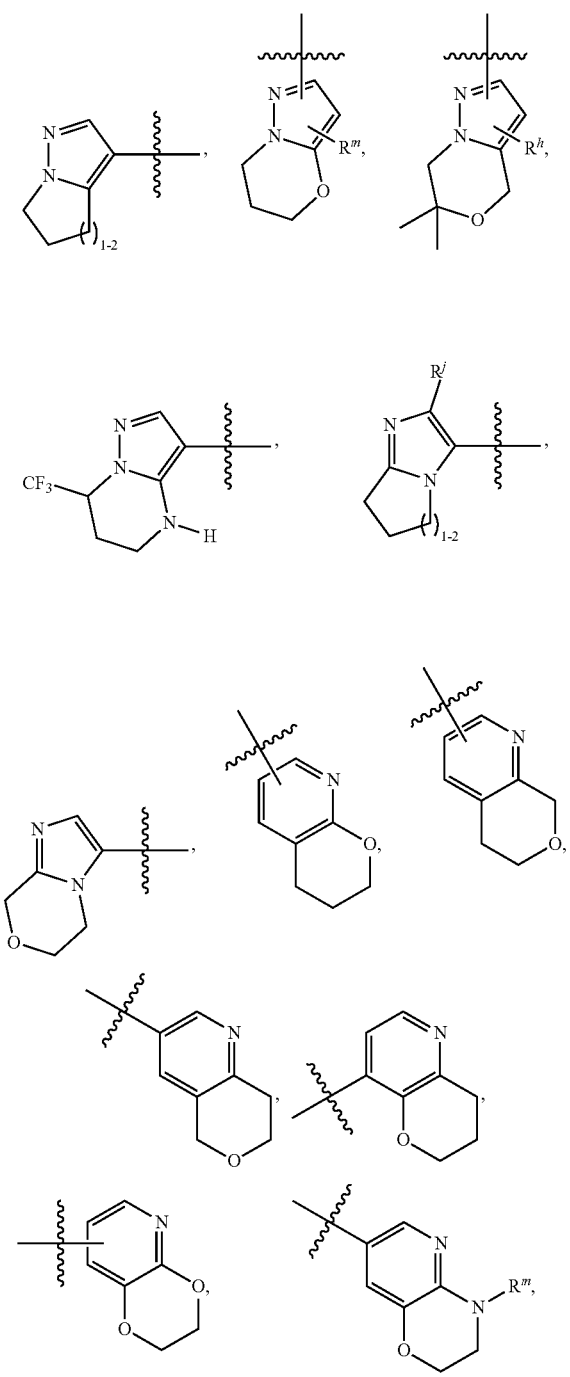

-continued

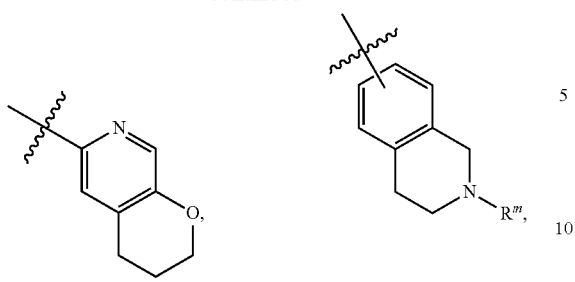

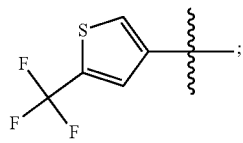

and

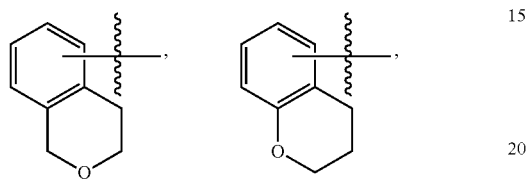

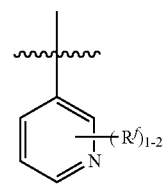

(c) 6-Membered heteroaryl selected from the group consisting of:

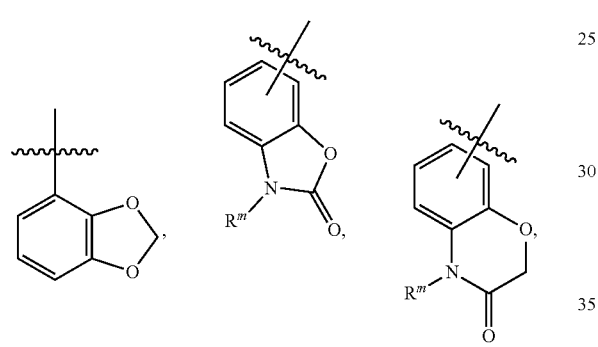

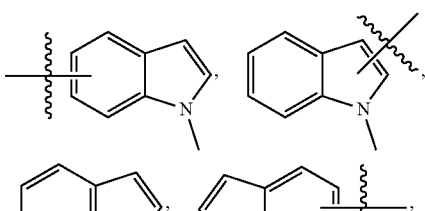

and

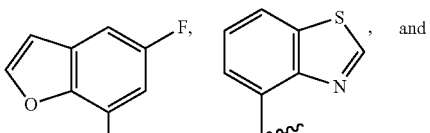

(d) 5,6-Fused or 6,5-fused heteroaryl selected from the group consisting of:

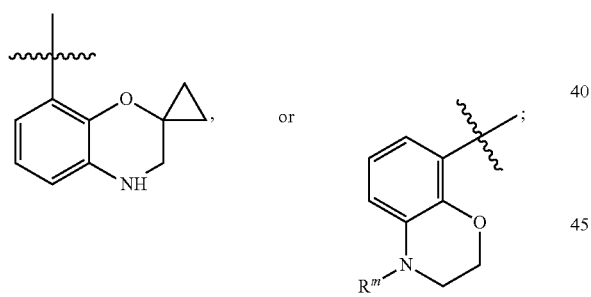

$R^{3a}$ is selected from the group consisting of:

(a) Phenyl; or phenyl substituted with one, two, or three members each independently selected from the group consisting of: halo, $C_{1-4}$alkyl, $C_{1-4}$haloalkyl, $OC_{1-4}$alkyl, and $OC_{1-6}$haloalkyl;

(b) 5-Membered heteroaryl selected from the group consisting of:

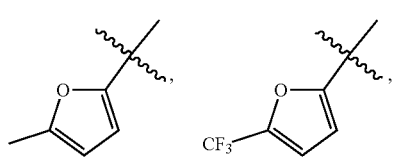

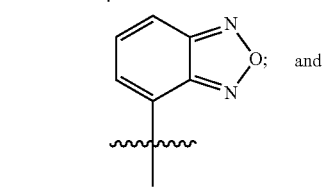

and (e) Heterocycloalkyl selected from the group consisting of:

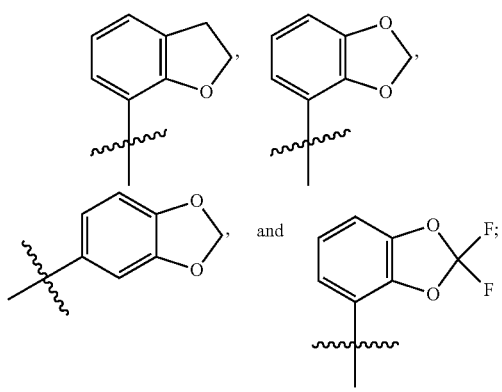

$R^e$ is selected from the group consisting of: $OC_{1-4}$alkyl, $OC_{1-4}$haloalkyl, (C=O)NHCH$_3$, and 5-membered heteroaryl ring containing two or three nitrogen members, wherein the 5-membered heteroaryl ring is optionally substituted with one $R^f$ member;

$R^f$ is selected from the group consisting of: H, halo, $C_{1-4}$alkyl, $C_{1-4}$haloalkyl, $OC_{1-4}$alkyl, and $OC_{1-4}$haloalkyl;

$R^g$ is selected from the group consisting of: $OC_{1-4}$alkyl, $OC_{1-4}$haloalkyl, $CH_2OCH_3$, $CH_2OH$,

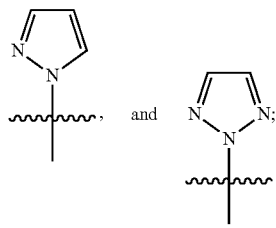 [SMILES: *n1cccn1 ; *n1nccn1]

$R^h$ is selected from the group consisting of: H, $C_{1-4}$alkyl, $C_{1-4}$haloalkyl, and $C_{3-6}$cycloalkyl;

$R^i$ is selected from the group consisting of: H, halo, $C_{1-4}$alkyl, $C_{1-4}$haloalkyl, $OC_{1-4}$alkyl, $C_{3-6}$cycloalkyl, and $C_{3-6}$cycloalkyl substituted with one or two members independently selected from: F and $CH_3$;

$R^j$ is selected from the group consisting of: H, halo, $C_{1-4}$alkyl and $C_{1-4}$haloalkyl;

$R^k$ is selected from the group consisting of: H, halo, OH, $C_{1-4}$alkyl, $C_{1-4}$haloalkyl, $OC_{1-4}$alkyl, and $OC_{1-4}$haloalkyl;

$R^m$ is H or $C_{1-4}$alkyl;

$R^n$ is selected from the group consisting of: H, halo and $OC_{1-4}$alkyl;

$R^o$ is selected from the group consisting of: H, $C_{1-4}$alkyl, and $C_{1-4}$haloalkyl;

$R^p$ is selected from the group consisting of: H, $C_{1-4}$alkyl, and $OC_{1-4}$alkyl;

Y is CH or N; and $R^{4a}$ is selected from the group consisting of: $CH_3$, $CF_2H$, $CF_3$, $C_{3-6}$cycloalkyl, and phenyl;

and pharmaceutically acceptable salts, isotopes, N-oxides, and stereoisomers of compounds of Formula (II); and (B) at least one pharmaceutically acceptable excipient.

81. A pharmaceutical composition comprising at least one compound of claim 78 and at least one pharmaceutically acceptable excipient.

82. A pharmaceutical composition comprising at least one compound of claim 79 and at least one pharmaceutically acceptable excipient.

83. A compound, having the structure of Formula (II):

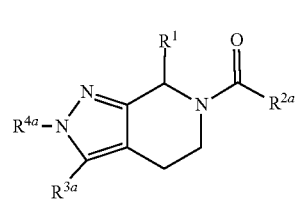

(II)

wherein $R^1$ is —$CH_3$;

$R^{2a}$ is a fused 6,6 heteroaryl selected from the group consisting of:

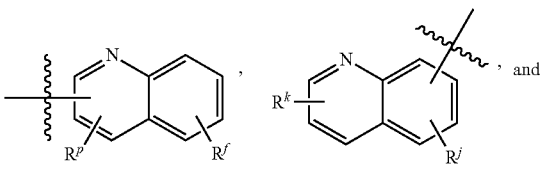

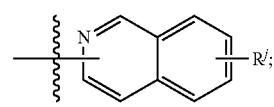

and $R^{3a}$ is

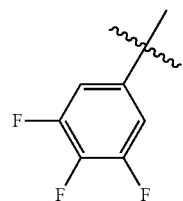 [SMILES: *c1cc(F)c(F)c(F)c1]

$R^f$ is selected from the group consisting of: H and F;

$R^j$ is selected from the group consisting of: H;

$R^k$ is selected from the group consisting of: H;

$R^p$ is selected from the group consisting of: H, —$CH_3$ and —$OCH_3$;

$R^{4a}$ is —$CH_3$;

and pharmaceutically acceptable salts thereof.

84. The compound of claim 83, wherein the compound is:

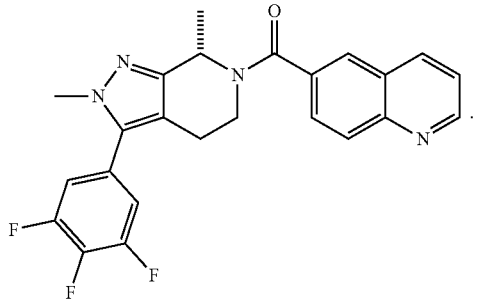 [SMILES: C[C@H]1c2nn(C)c(-c3cc(F)c(F)c(F)c3)c2CCN1C(=O)c1ccc2ncccc2c1 ; "."]

and pharmaceutically acceptable salts thereof.

85. The compound of claim 84, wherein the compound is a free base.

86. The compound of claim 83, wherein the compound is:

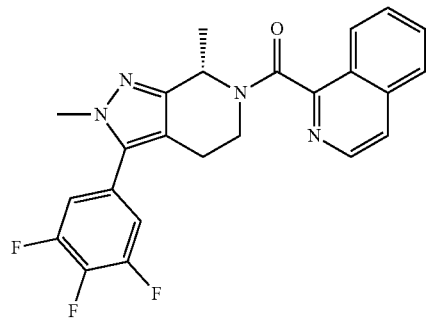

and pharmaceutically acceptable salts thereof.

87. The compound of claim 86, wherein the compound is a free base.

88. The compound of claim 83, wherein the compound is:

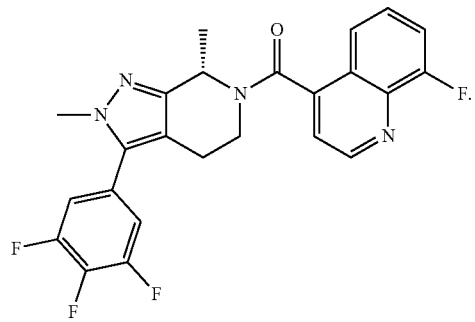 [SMILES: C[C@H]1c2nn(C)c(-c3cc(F)c(F)c(F)c3)c2CCN1C(=O)c1ccnc2c(F)cccc12]

and pharmaceutically acceptable salts thereof.

89. The compound of claim 88, wherein the compound is a free base.

90. The compound of claim 83, wherein the compound is:

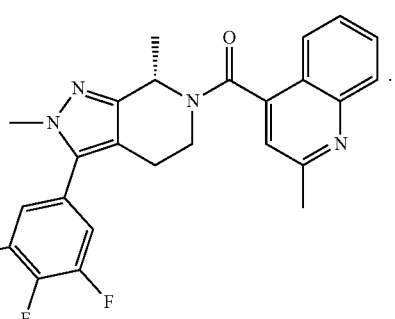

and pharmaceutically acceptable salts thereof.

91. The compound of claim 90, wherein the compound is a free base.

92. The compound of claim 83, wherein the compound is:

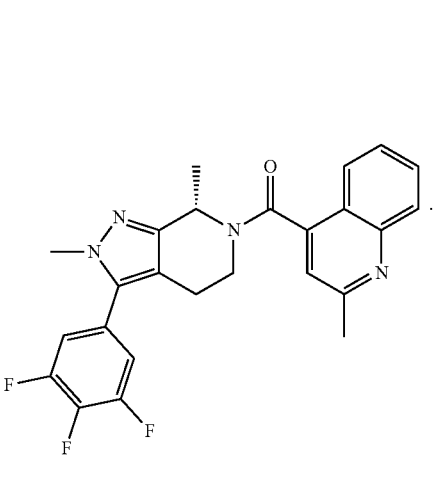 [SMILES: Cc1cc(C(=O)N2CCc3c(nn(C)c3-c3cc(F)c(F)c(F)c3)[C@@H]2C)c2ccccc2n1 ; "."]

and pharmaceutically acceptable salts thereof.

93. The compound of claim 92, wherein the compound is a free base.

* * * * *